US012053517B2

(12) United States Patent
Li et al.

(10) Patent No.: US 12,053,517 B2
(45) Date of Patent: Aug. 6, 2024

(54) HIV VACCINES AND METHODS OF USING

(71) Applicant: Gilead Sciences, Inc., Foster City, CA (US)

(72) Inventors: Jiani Li, San Francisco, CA (US); Xinan Liu, Shanghai (CN); Azure T. Makadzange, Half Moon Bay, CA (US); Stephen R. Martin, Tiburon, CA (US); Hesham Shehata, Sunnyvale, CA (US); Evguenia Svarovskaia, Redwood City, CA (US)

(73) Assignee: GILEAD SCIENCES, INC., Foster City, CA (US)

( * ) Notice: Subject to any disclaimer, the term of this patent is extended or adjusted under 35 U.S.C. 154(b) by 274 days.

(21) Appl. No.: 17/574,465

(22) Filed: Jan. 12, 2022

(65) Prior Publication Data

US 2022/0218813 A1 Jul. 14, 2022

Related U.S. Application Data

(60) Provisional application No. 63/170,900, filed on Apr. 5, 2021, provisional application No. 63/149,820, filed on Feb. 16, 2021, provisional application No. 63/137,521, filed on Jan. 14, 2021.

(51) Int. Cl.

| | |
|---|---|
| ***A61K 39/12*** | (2006.01) |
| ***A61P 31/18*** | (2006.01) |
| ***C07K 14/005*** | (2006.01) |
| ***C07K 16/10*** | (2006.01) |
| ***C07K 16/28*** | (2006.01) |
| ***C12N 15/10*** | (2006.01) |
| ***C12N 15/86*** | (2006.01) |
| *A61K 39/00* | (2006.01) |

(52) U.S. Cl.

CPC .............. *A61K 39/12* (2013.01); *A61P 31/18* (2018.01); *C07K 14/005* (2013.01); *C07K 16/1045* (2013.01); *C07K 16/2818* (2013.01); *C07K 16/2827* (2013.01); *C12N 15/1082* (2013.01); *C12N 15/86* (2013.01); *A61K 2039/53* (2013.01); *A61K 2039/70* (2013.01); *C12N 2710/10343* (2013.01); *C12N 2710/16143* (2013.01); *C12N 2740/15034* (2013.01); *C12N 2740/16022* (2013.01); *C12N 2740/16034* (2013.01); *C12N 2740/16134* (2013.01); *C12N 2740/16234* (2013.01); *C12N 2760/10043* (2013.01)

(58) Field of Classification Search

None

See application file for complete search history.

(56) References Cited

U.S. PATENT DOCUMENTS

| | | | |
|---|---|---|---|
| 6,303,334 | B1 | 10/2001 | Holler et al. |
| 6,440,730 | B1 | 8/2002 | Von Laer et al. |
| 6,610,476 | B1 | 8/2003 | Chang et al. |
| 7,153,509 | B2 | 12/2006 | Haynes et al. |
| 7,172,761 | B2 | 2/2007 | Haynes et al. |
| 7,195,768 | B2 | 3/2007 | Haynes et al. |
| 7,425,611 | B2 | 9/2008 | Lal et al. |
| 7,488,485 | B2 | 2/2009 | Narayan et al. |
| 7,612,173 | B2 | 11/2009 | Abrecht et al. |
| 7,618,642 | B2 | 11/2009 | zur Megede et al. |
| 7,655,235 | B2 | 2/2010 | Ertl |
| 7,820,786 | B2 | 10/2010 | Thomson et al. |
| 7,935,805 | B1 | 5/2011 | Barnett et al. |
| 7,943,375 | B2 | 5/2011 | Barnett et al. |
| 7,951,377 | B2 | 5/2011 | Korber et al. |
| 7,981,430 | B2 | 7/2011 | Hanke et al. |
| 8,000,900 | B2 | 8/2011 | Heckerman et al. |
| 8,071,107 | B2 | 12/2011 | Haynes et al. |
| 8,119,140 | B2 | 2/2012 | Korber et al. |
| 8,119,144 | B2 | 2/2012 | Gupta et al. |
| 8,263,394 | B2 | 9/2012 | zur Megede et al. |
| 8,452,541 | B2 | 5/2013 | Kirovski et al. |
| 8,452,542 | B2 | 5/2013 | Zemla et al. |
| 8,478,535 | B2 | 7/2013 | Jojic et al. |
| 8,541,230 | B2 | 9/2013 | Barnett et al. |
| 8,592,205 | B2 | 11/2013 | Pinschewer et al. |
| 8,697,084 | B2 | 4/2014 | Weiner et al. |

(Continued)

FOREIGN PATENT DOCUMENTS

| | | |
|---|---|---|
| CN | 108064181 A | 5/2018 |
| EP | 1456376 A2 | 9/2004 |

(Continued)

OTHER PUBLICATIONS

Abbink P et al. (2018), "Rapid Cloning of Novel Rhesus Adenoviral Vaccine Vectors", Journal of Virology, vol. 92, Issue 6, e01924-17.

Abdul-Jawad S et al. (2016), "Increased Valency of Conserved-mosaic Vaccines Enhances the Breadth and Depth of Epitope Recognition", Molecular Therapy, vol. 24(2), pp. 375-384.

Amacker M et al. (2020), "New GMP manufacturing processes to obtain thermostable HIV-1 gp41 virosomes under solid forms for various mucosal vaccination routes", npj Vaccines 5:41.

Andean Manual for the Patent Examination; first edition, Aug. 12, 2022; author(s) Pimentel Juan R.; Vazquez Karla F.; published Aug. 2022.

(Continued)

*Primary Examiner* — Nicole Kinsey White

(57) ABSTRACT

Provided are HIV-1 fusion polypeptides, polynucleotides encoding such fusion polypeptides, vectors expressing such fusion polypeptides for use in eliciting an immune response against HIV-1; pharmaceutical and immunogenic compositions and kits comprising such fusion polypeptides, polynucleotides or vectors, and methods of use in treating and/or preventing HIV-1. Further provided are methods for design of antiviral vaccines, including vaccines to elicit an immune response against HIV-1.

12 Claims, 98 Drawing Sheets

Specification includes a Sequence Listing.

(56) References Cited

U.S. PATENT DOCUMENTS

| | | | |
|---|---|---|---|
| 8,735,542 | B2 | 5/2014 | Gupta et al. |
| 8,795,685 | B2 | 8/2014 | Renard et al. |
| 9,011,873 | B2 | 4/2015 | Korber et al. |
| 9,011,875 | B2 | 4/2015 | Korber et al. |
| 9,017,691 | B2 | 4/2015 | Barouch et al. |
| 9,044,445 | B2 | 6/2015 | Korber et al. |
| 9,309,289 | B2 | 4/2016 | Pinschewer et al. |
| 9,342,786 | B2 | 5/2016 | Krause et al. |
| 9,376,471 | B2 | 6/2016 | Weiner et al. |
| 9,492,532 | B2 | 11/2016 | Korber et al. |
| 9,501,614 | B2 | 11/2016 | Ortoleva |
| 9,670,253 | B2 | 6/2017 | Barouch et al. |
| 9,725,768 | B2 | 8/2017 | Santos et al. |
| 9,732,121 | B2 | 8/2017 | Foung et al. |
| 9,821,053 | B2 | 11/2017 | Korber et al. |
| 9,833,506 | B2 | 12/2017 | Lambkin-Williams et al. |
| 9,844,589 | B2 | 12/2017 | Haynes et al. |
| 9,844,590 | B2 | 12/2017 | Korber et al. |
| 9,855,329 | B2 | 1/2018 | Korber et al. |
| 9,913,895 | B2 | 3/2018 | Yamamoto |
| 9,944,952 | B2 | 4/2018 | Pinschewer et al. |
| 9,988,425 | B2 | 6/2018 | Brander et al. |
| 10,004,800 | B2 | 6/2018 | Haynes et al. |
| 10,010,606 | B2 | 7/2018 | Korber et al. |
| 10,285,942 | B2 | 5/2019 | Luo |
| 10,722,564 | B2 | 7/2020 | Pinschewer et al. |
| 11,230,572 | B2 | 1/2022 | Barouch et al. |
| 11,254,712 | B2 | 2/2022 | Chappell et al. |
| 11,795,210 | B2 | 10/2023 | Liu et al. |
| 2007/0077257 | A1 | 4/2007 | Emini et al. |
| 2010/0047276 | A1 | 2/2010 | Heeney et al. |
| 2014/0234399 | A1 | 8/2014 | Bourguignon et al. |
| 2017/0319679 | A1 | 11/2017 | Bruening et al. |

FOREIGN PATENT DOCUMENTS

| | | | |
|---|---|---|---|
| EP | 1921146 | A1 | 5/2008 |
| EP | 1682666 | B1 | 12/2008 |
| EP | 1667523 | B1 | 11/2012 |
| EP | 2604695 | A1 | 6/2013 |
| EP | 2238255 | B1 | 9/2013 |
| EP | 3218504 | B1 | 7/2020 |
| GB | 2406336 | A | 3/2005 |
| JP | 2018-527366 | A | 9/2018 |
| WO | WO-03/053338 | A2 | 7/2003 |
| WO | WO-2005/028634 | A2 | 3/2005 |
| WO | WO-2009/083210 | A1 | 7/2009 |
| WO | WO-2010/059732 | A1 | 5/2010 |
| WO | WO-2011/019932 | A2 | 2/2011 |
| WO | WO-2014/160747 | A2 | 10/2014 |
| WO | WO-2015/048785 | A2 | 4/2015 |
| WO | WO-2016/049287 | A1 | 3/2016 |
| WO | WO-2016/054654 | A1 | 4/2016 |
| WO | WO-2016/075250 | A1 | 5/2016 |
| WO | WO-2017/044850 | A1 | 3/2017 |
| WO | WO-2017/048727 | A1 | 3/2017 |
| WO | WO-2017/106638 | A1 | 6/2017 |
| WO | WO-2017/198726 | A1 | 11/2017 |
| WO | WO-2018/075559 | A1 | 4/2018 |
| WO | WO-2018/098362 | A1 | 5/2018 |
| WO | WO-2018/195357 | A1 | 10/2018 |
| WO | WO-2018/208856 | A1 | 11/2018 |
| WO | WO-2018/227030 | A1 | 12/2018 |
| WO | WO-2019/036688 | A1 | 2/2019 |
| WO | WO-2019/050994 | A1 | 3/2019 |
| WO | WO-2019/070730 | A1 | 4/2019 |
| WO | WO-2019/075112 | A1 | 4/2019 |
| WO | WO-2019/104203 | A1 | 5/2019 |
| WO | WO-2019/133853 | A1 | 7/2019 |
| WO | WO-2021/003348 | A1 | 1/2021 |
| WO | WO-2021/011544 | A1 | 1/2021 |
| WO | WO-2021/081437 | A2 | 4/2021 |
| WO | WO-2022/006095 | A2 | 1/2022 |
| WO | WO-2023/064424 | A2 | 4/2023 |

OTHER PUBLICATIONS

Apostolico J et al. (2016), "Adjuvants: Classification, Modus Operandi, and Licensing", Journal of Immunology Research, vol. 2016, Article ID 1459394, 16 pgs.

Bahbouhi B et al. (2002), "Effects of L- and D-REKR amino acid-containing peptides on HIV and SIV envelope glycoprotein precursor maturation and HIV and SIV replication", Biochem. J. 366, 863-872.

Bajracharya R et al. (2019), "Recent Advancements in Non-Invasive Formulations for Protein Drug Delivery", Computational and Structural Biotechnolgy Journal 17: 1290-1308.

Barouch D H et al. (2013), "Protective Efficacy of a Global HIV-1 Mosaic Vaccine against Heterologous SHIV Challenges in Rhesus Monkeys", Cell 155, 531-539.

Boopathy a V et al. (2022), "Flt3 Agonist Enhances Immunogenicity of Arenavirus-Based Vaccine Vector in Macaques", PowePoint Presentation for AIDS 2022, Jul. 29-Aug. 2, Montreal, Quebec, Canada.

Boopathy A V et al. (2022), "Immunogenicity and Prophylactic Efficacy of Arenavirus-Based SIV Vaccine in Macaques", Poster presented at Virtual CROI 2022, Feb 12-16.

Boopathy A V et al. (2023), "Immunogenic arenavirus vector SIV vaccine reduces setpoint viral load in SIV-challenged rhesus monkeys", npj Vaccines 8:175, 1-12.

Chen X et al. (2013), "Fusion Protein Linkers: Property, Design and Functionality", Adv Drug Deliv Rev. 65(10): 1357-1369.

Chng J et al. (2015), "Cleavage efficient 2A peptides for high level monoclonal antibody expression in CHO cells", mAbs 7:2, 403-412.

Decision dated Nov. 16, 2023 for Taiwanese Application No. 111101389.

Donnelly M L L et al. (2001), "The 'cleavage' activities of foot-and-mouth disease virus 2A site-directed mutants and naturally occurring '2A-like' sequences", Journal of General Virology, 82, 1027-1041.

Dorta-Estremera S et al. (2017), "Minimally invasive monitoring of CD4 T cells at multiple mucosal tissues after intranasal vaccination in rhesus macaques", PLoS ONE 12(12): e0188807.

Fischer W et al. (2007), "Polyvalent vaccines for optimal coverage of potential T-cell epitopes in global HIV-1 variants", Nature Medicine, vol. 13, No. 1, pp. 100-106.

Gaiha G D et al. (2019), "Structural topology defines protective CD8+ T cell epitopes in the HIV proteome", Science 364, 480-484.

Guo J et al. (2018), "Development of novel vaccine vectors: Chimpanzee adenoviral vectors", Human Vaccines & Immunotherapeutics 2018, vol. 14, No. 7, 1679-1685.

Hamid M A et al. (2019), "Enriched HLA-E and CD94/NKG2A interaction limits antitumor $CD8^+$tumor-infiltrating T lymphocyte responses", Cancer Immunol Res, vol. 7, Issue 8.

Hepler N L et al. (2014), "IDEPI: Rapid Prediction of HIV-1 Antibody Epitopes and Other Phenotypic Features from Sequence Data Using a Flexible Machine Learning Platform", Plos Comput Biol, vol. 10, No. 9, article No. e1003842 (pp. 1-10).

International Preliminary Report on Patentability and Written Opinion dated Jul. 4, 2023 for International Application No. PCT/US2022/012195.

International Search Report and Written Opinion dated Jun. 15, 2022 for International Application No. PCT/US2022/012195 (19 pages).

Karpenko L I et al. (2012), "Attenuated *Salmonella enteritidis* E23 as a vehicle for the rectal delivery of DNA vaccine coding for HIV-1 polyepitope CTL immunogen", Microbial Biotechnology 5(2), 241-250.

Liu H et al. (2017), "Introducing a cleavable signal peptide enhances the packaging efficiency of lentiviral vectors pseudotyped with Japanese encephalitis virus envelope proteins", Virus Research 229, 9-16.

Martins M A et al. (2017), "Vaccine-induced immune responses against both Gag and Env improve control of simian immunodeficiency virus replication in rectally challenged rhesus macaques", PLoS Pathog 13(7): e1006529.

McMichael A J et al. (2019), "Topological perspective on HIV escape", Science 364 (6439), 438-439.

(56) References Cited

OTHER PUBLICATIONS

Ndhlovu Z M et al. (2019), "Augmentation of HIV-specific T cell function by immediate treatment of hyperacute HIV-1 infection", Sci. Transl. Med. 11, eaau0528.
Oconnor G M et al. (2015), "Peptide-Dependent Recognition of HLA-B57:01 by KIR3DS1", Journal of Virology, vol. 89, No. 10, 5213-5221.
Office Action and Search Report dated May 10, 2023 for Taiwanese Application No. 111101389.
Ondondo B et al. (2016), "Novel Conserved-region T-cell Mosaic Vaccine With High Global HIV-1 Coverage is Recognized by Protective Responses in Untreated Infection", Molecular Therapy, vol. 24, No. 4, pp. 832-842.
Opposition dated Oct. 31, 2023 for Colombian Application No. NC2023-0009285.
Patterson L J et al. (2012), "Replicating Adenovirus-Simian Immunodeficiency Virus (SIV) Vectors Efficiently Prime SIV-Specific Systemic and Mucosal Immune Responses by Targeting Myeloid Dendritic Cells and Persisting in Rectal Macrophages, Regardless of Immunization Route", Clinical and Vaccine Immunology, vol. 19, No. 5, p. 629-637.
Sanchez-Trincado, J L et al. (2017), "Fundamentals and Methods for T- and B-Cell Epitope Prediction", Journal of Immunology Research, vol. 2017, Article ID 2680160, 14 pgs.
Shah R R et al. (2017), "Overview of Vaccine Adjuvants: Introduction, History, and Current Status", Chapter 1, in Vaccine Adjuvants: Methods and Protocols, Methods in Molecular Biology, vol. 1494.
Theiler J et al. (2016), "Epigraph: A Vaccine Design Tool Applied to an HIV Therapeutic Vaccine and a Pan-Filovirus Vaccine", Sci Rep, vol. 6(33987), https://doi.org/10.1038/srep33987.
Trolle T et al. (2016), "The length distribution of class I restricted T cell epitopes is determined by both peptide supply and MHC allele specific binding preference", J Immunol. 196(4): 1480-1487.
Tuyishime S et al. (2018), "Correlates of Protection Against $SIV_{mac251}$ Infection in Rhesus Macaques Immunized With Chimpanzee-Derived Adenovirus Vectors", EBioMedicine 31:25-35.
Wallis J et al. (2019), "Novel approaches for the design, delivery and administration of vaccine technologies", Clinical and Experimental Immunology, 196: 189-204.
Wee E G et al. (2017), "HIV-1 Conserved Mosaics Delivered by Regimens with Integration-Deficient DC-Targeting Lentiviral Vector Induce Robust T Cells", Molecular Therapy, vol. 25, No. 2, 494-503.
Woodberry T et al. (1999), "Immunogenicity of a Human Immunodeficiency Virus (HIV) Polytope Vaccine Containing Multiple HLA A2 HIV CD8+ Cytotoxic T-Cell Epitopes", Journal of Virology, The American Society for Microbiology, vol. 73, No. 7, 5320-5325.
Xu H et al. (2017), "Mucosal Vaccination with Heterologous Viral Vectored Vaccine Targeting Subdominant SIV Accessory Antigens Strongly Inhibits Early Viral Replication", EBioMedicine 18:204-215.
Zou C et al. (2019), "Effective Suppression of HIV-1 Replication by Cytotoxic T Lymphocytes Specific for Pol Epitopes in Conserved Mosaic Vaccine Immunogens", Journal of Virology, vol. 93, Issue 7, e02142-18.

INPUT: Viral Sequence Data Set

↓

1: Identify conserved regions

↓

2: Build multivalent (bivalent) sequences in conserved regions

↓

3: Rearrange epitopes and conserved region sequences to reduce or eliminate creation of neoepitope at junctions

Figure 2:
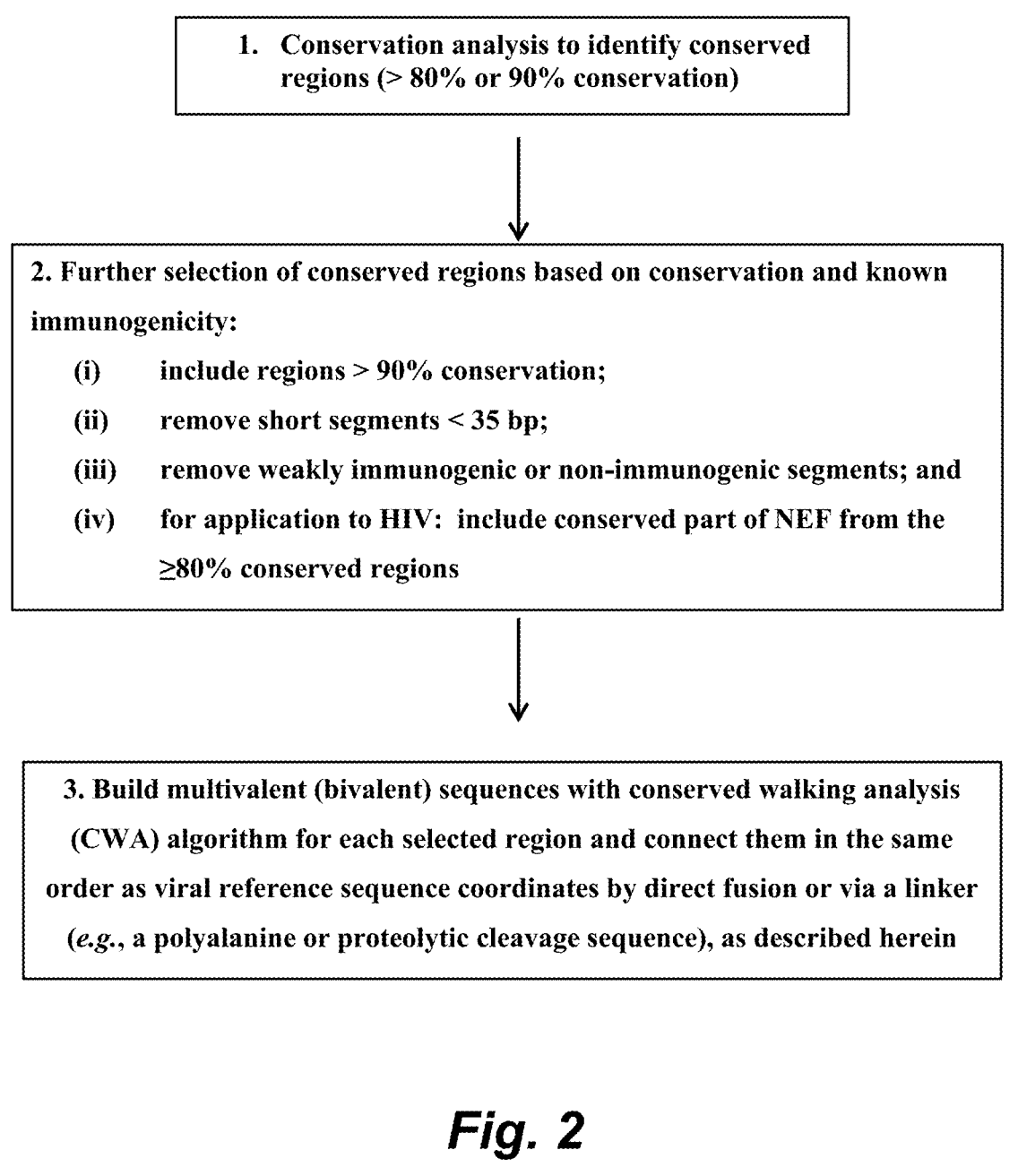

1. Conservation analysis to identify conserved regions (> 80% or 90% conservation)

↓

2. Further selection of conserved regions based on conservation and known immunogenicity:

- (i) include regions > 90% conservation;
- (ii) remove short segments < 35 bp;
- (iii) remove weakly immunogenic or non-immunogenic segments; and
- (iv) for application to HIV: include conserved part of NEF from the ≥80% conserved regions

↓

**3. Build multivalent (bivalent) sequences with conserved walking analysis (CWA) algorithm for each selected region and connect them in the same order as viral reference sequence coordinates by direct fusion or via a linker (*e.g.*, a polyalanine or proteolytic cleavage sequence), as described herein**

| HIV Peptide | HLA Allele | Human Protein 9-mer | Human Protein |
|---|---|---|---|
| HPPQAGPVA | B07:02 | VPLQAGPVQ | sp\|P15822\|ZEP1 |
| | | MPGQAGPVG | sp\|P35247\|SFTPD |
| | | QYRQAGPVI | sp\|Q8NCI6\|GLBL3 |

Fig. 6

1. Conservation Walking Algorithm (CWA) analysis to identify conserved regions within fusion polypeptides of immunogen version 1 (> 80% conservation).

2. Build multivalent (bivalent) sequences with CWA for each conserved region.

3. Identify intra-patient 9-mer variants within conserved regions using deep sequencing data from N=238 subjects.

4. Identify conserved regions of Pol, Gag, and Nef where >70% of subjects' sequence variants were covered by the bivalent vaccine sequences based on deep sequencing data (intrapatient conservation).

5. Regions with > 1 known immunogenic epitopes from LANL databases or defined epitopes from *in vitro* ELISPOT Assay.

6. Arrange bi-valent vaccine sequence segments to reduce possible junction response based on HLA binding prediction and cross conservation with human peptides. Place Nef segment at the C-terminus of the bi-valent sequence segments.

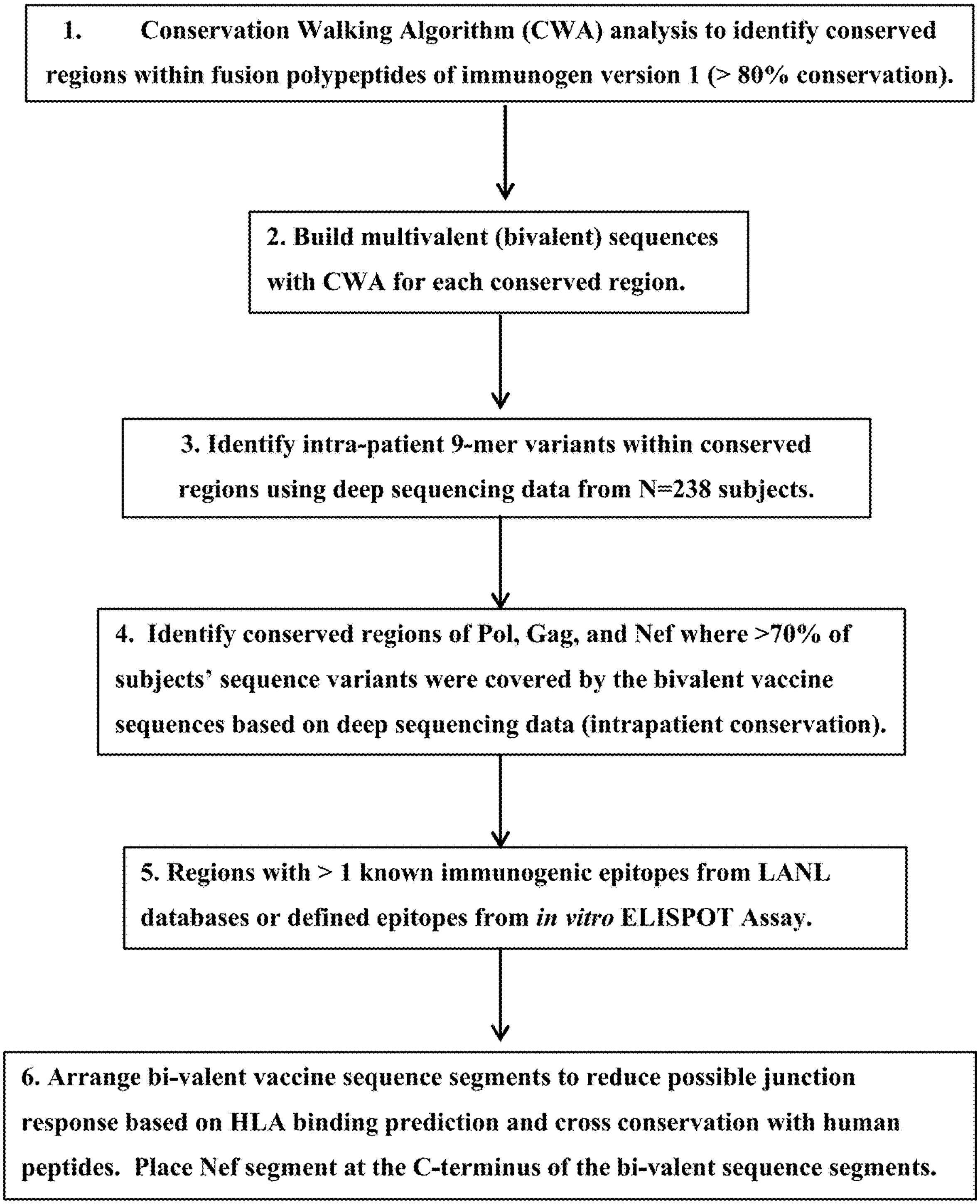

*Fig. 9*

1. Conservation Walking Algorithm (CWA) analysis to identify conserved regions within immunogen version 1 (> 90% conservation). Conservation filter for immunogen 3 was only applied to Pol. Gag p24 and Nef:64-76 were kept because of their high immunogenicity 2. Build multivalent (bivalent) sequences with CWA for each conserved region 3. Identify conserved regions where >75% of subjects' sequence variants were covered by the bivalent vaccine sequences based on deep sequencing data. (Intra-patient conservation filter for immunogen 3 was only applied to Pol. Gag p24 and Nef:64-76 were kept because of their high immunogenicity).

4. Regions with > 1 known immunogenic epitopes from LANL databases or defined epitopes from *in vitro* ELISPOT Assay.

5. Arrange bi-valent vaccine sequence segments to reduce possible junction response based on HLA binding prediction and cross conservation with human peptides. Place Nef segment at the C-terminus of the bi-valent sequence segments.

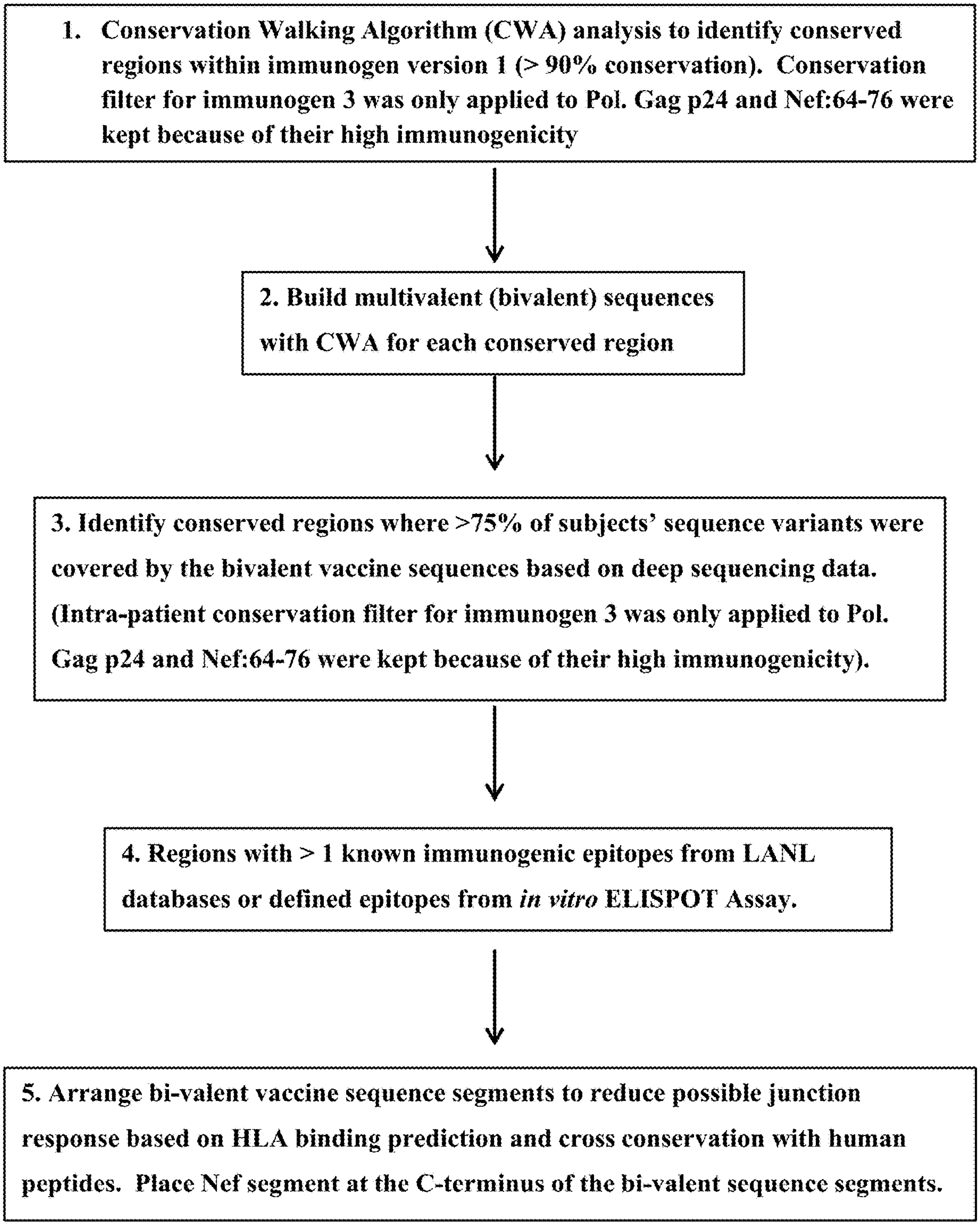

*Fig. 13*

MGARASVLSGGELDRWEKIRLRPGGKKKYKLKHIVWASRELERFAVNPGLLETSEGCRQILGQLQPSLQTGSEELRSLYNTVAT
MAARASVLSGGELDRWEKIRLRPGGKKKYRLKHIVWASRELERFAVNPGLLET
MAARASILSGGKLDKWEKIRLRPGGRKKYKLKHLVWASRELERFALNPGLLET

LYCVHQRIEIKDTKEALDKIEEEQNKSKKKAQQAAADTGHSNQVSQNYPIVQNIQGQMVHQAISPRTLNAWVKVVEEKAFSPEV
ISPRTLNAWVKVVEEKAFSPEV
LSPRTLNAWVKVIEEKAFSPEV

IPMFSALSEGATPQDLNTMLNTVGGHQAAMQMLKETINEEAAEWDRVHPVHAGPIAPGQMREPRGSDIAGTTSTLQEQIGWMTN
IPMFSALSEGATPQDLNTMLNTVGGHQAAMQMLKETINEEAAEWDRLHPVHAGPIAPGQMREPRGSDIAGTTSTLQEQIGWMTN
IPMFTALSEGATPHDLNTMLNTIGGHQAAMQMLKDTINEEAAEWDRVHPVHAGPVAPGQMRDPRGSDIAGSTSTLQEQIAWMTN

NPPIPVGEIYKRWIILGLNKIVRMYSPTSILDIRQGPKEPFRDYVDRFYKTLRAEQASQEVKNWMTETLLVQNANPDCKTILKA
NPPIPVGEIYKRWIILGLNKIVRMYSPTSILDIRQGPKEPFRDYVDRFYKTLRAEQASQEVKNWMTETLLVQNANPDCKTILKA
NPPIPVGDIYKRWIIMGLNKIVRMYSPVSILDIKQGPKEPFRDYVDRFYRTLRAEQASQDVKNWMTETLLVQNSNPDCKTILKA

LGPAATLEEMMTACQGVGGPGHKARVLAEAMSQVTNSATIMMQRGNFRNQRKIVKCFNCGKEGHTARNCRAPRKKGCWKCGKEG
LGPAATLEEMMTACQGVGGPGHKARVLAEAMSQ
LGPGATLEEMMSACQGVGGPSHKARVLAEAMCQ

HQMKDCTERQANFLGKIWPSYKGRPGNFLQSRPEPTAPPEESFRSGVETTTPPQKQEPIDKELYPLTSLRSLFGNDPSSQ

*Fig. 16*

```
FFREDLAFLQGKAREFSSEQTRANSPTRRELQVWGRDNNSPSEAGADRQGTVSFNFPQVTLWQRPLVTIKIGGQLKEA
                                                             FPQITLWQRPLVTIKIGGQLKEA
                                                             LPQITLWQRPIVTIKIGGQIKEA

LLDTGADDTVLEEMSLPGRWKPKMIGGIGGFIKVRQYDQILIEICGHKAIGTVLVGPTPVNIIGRNLLTQIGCTLNFP
LLDTGADDTVLEEMNLPGRWKPKMIGGIGGFIKVRQYDQ          GTVLVGPTPVNIIGRNLLTQIGCTLNFP
LLDTGADDTVLEDMNLPGKWKPKMIGGIGGFIKVKQYDQ          GTVLIGPTPVNIIGRNLLTQLGCTLNFP

ISPIETVPVKLKPGMDGPKVKQWPLTEEKIKALVEICTEMEKEGKISKIGPENPYNTPVFAIKKKDSTKWRKLVDFRE
ISPIETVPVKLKPGMDGPKVKQWPLTEEKIKALVEICTEMEKEGKISKIGPENPYNTPVFAIKKKDSTKWRKLVDFRE
ISPIDTVPVKLKPGMDGPRVKQWPLTEEKIKALIEICTEMEKEGKISRIGPENPYNTPIFAIKKKDGTKWRKLVDFRE

LNKRTQDFWEVQLGIPHPAGLKKKKSVTVLDVGDAYFSVPLDEDFRKYTAFTIPSINNETPGIRYQYNVLPQGWKGSP
LNKRTQDFWEVQLGIPHPAGLKKKKSVTVLDVGDAYFSVPLDKDFRKYTAFTIPSINNETPGIRYQYNVLPQGWKGSP
LNKKTQDFWEVQLGIPHPSGLKKKKSVTVLDIGDAYFSVPLDKEFRKYTAFTVPSTNNETPGVRYQYNVLPMGWKGSP

AIFQSSMTKILEPFRKQNPDIVIYQYMDDLYVGSDLEIGQHRTKIEELRQHLLRWGLTTPDKKHQKEPPFLWMGYELH
AIFQSSMT                                                  WGFTTPDKKHQKEPPFLWMGYELH
AIFQCSMT                                                  WGLTTPDKKHQKDPPFLWMGYELH
```

*Fig. 17A*

```
PDKWTVQPIVLPEKDSWTVNDIQKLVGKLNWASQIYPGIKVRQLCKLLRGTKALTEVIPLTEEAELELAENREILKEP
PDKWTVQPIVLPEKDSWTVNDIQKLVGKLNWASQIYPGIKV
PDRWTVQPIELPEKESWTVNDIQKLIGKLNWASQIYAGIKV

VHGVYYDPSKDLIAEIQKQGQGQWTYQIYQEPFKNLKTGKYARMRGAHTNDVKQLTEAVQKITTESIVIWGKTPKFKL
                                                                         PKFKL
                                                                         PKFRL

PIQKETWETWWTEYWQATWIPEWEFVNTPPLVKLWYQLEKEPIVGAETFYVDGAANRETKLGKAGYVTNRGRQKVVTL
PIQKETWETWWTEYWQATWIPEWEFVNTPPLVKLWYQLEKEPIVGAETFYVDGAANRETK
PIQKETWDTWWTDYWQATWIPEWEFTNTPPLVKLWYQLETEPIAGVETFYVDGASNRETK
                                      KEPIVGAETFYVDGAANRETK
                                      TEPIAGVETFYVDGASNRETK

TDTTNQKTELQAIYLALQDSGLEVNIVTDSQYALGIIQAQPDQSESELVNQIIEQLIKKEKVYLAWVPAHKGIGGNEQ
                                                           KEKVYLAWVPAHKGIGGNEQ
                                                           KEKIYLAWVPAHKGIGGNEQ

VDKLVSAGIRKVLFLDGIDKAQDEHEKYHSNWRAMASDFNLPPVVAKEIVASCDKCQLKGEAMHGQVDCSPGIWQLDC
VDKLVS                                      VAKEIVASCDKCQLKGEAMHGQVDCSPGIWQLDC
IDKLVS                                      VAKEIVACCDKCQLKGEAIHGQVDCSPGVWQLDC
```

Fig. 17B

```
THLEGKVILVAVHVASGYIEAEVIPAETGQETAYFLLKLAGRWPVKTIHTDNGSNFTGATVRAACWWAGIKQEFGIPY
THLEGKIILVAVHVASGYIEAEVIPAETGQETAYFLLKLAGRWPVKT            TVKAACWWAGIKQEFGIPY
THLEGKVILVAVHVASGYIEAEIIPTETGQETAYFILKLAGRWPVTT            AVKAACWWAGVKQEFGIPY
                                                           TVKAACWWAGIKQEFGIPY
                                                           AVKAACWWAGVKQEFGIPY

NPQSQGVVESMNKELKKIIGQVRDQAEHLKTAVQMAVFIHNFKRKGGIGGYSAGERIVDIIATDIQTKELQKQITKIQ
NPQSQGVVESMNKELKKIIGQVRDQAEHLKTAVQMAVFIHNFKRKGGIGGYSAGERIVDIIA           ITKIQ
NTQSQGVVESMNNELKKIIGQIRDQAEHLKTAVQMAVLIHNFKRKGGIGEYSAGERIIDIIA           ITKLQ
NTQSQGVVESMNNELKKIIGQIRDQAEHLKTAVQMAVLIHNFKRKGGIGE
NTQSQGVVESMNNELKKIIGQIRDQAEHLKTAVQMAVLIHNFKRKGGIGE

NFRVYYRDSRNPLWKGPAKLLWKGEGAVVIQDNSDIKVVPRRKAKIIRDYGKQMAGDDCVASRQDED
NFRVYYRDSRDPLWKGPAKLLWKGEGAVVIQDNSDIKVVPRRKAKIIRDYGKQMAGDDCVASRQDED
NFRVYYRDNRDPLWKGPARLLWKGEGAVVIQDNSEIKVVPRRKVKIIRDYGKRMAGDDCVAGRQDED
```

Fig. 17C

```
MGGKWSKSSVIGWPTVRERMRRAEPAADRVGAASRDLEKHGAITSSNTAATNAACAWLEAQEEEEVGFPVTPQVPLRP
                                                               EEVGFPVKPQVPLRP
                                                               EEVGFPVRPQVPLRP
                                                               EEVGFPVKPQVPL
                                                               EEVGFPVRPQVPL

MTYKAAVDLSHFLKEKGGLEGLIHSQRRQDILDLWIYHTQGYFPDWQNYTPGPGVRYPLTFGWCYKLVPVEPDKIEEA
MTFKGALDLSHFLREKGGLEG                 TQGYFPDWQNYTPGPGTRYPLTFGWCFKLVPV
MTYKGALDLSHFLKEKGGLEG                 TQGFFPDWQNYTPGPGIRFPLTFGWCFKLVPL

NKGENTSLLHPVSLHGMDDPEREVLEWRFDSRLAFHHVARELHPEYFKNC
```

*Homologous vector prime-boost*

*Single vector immunogenicity*

*Homologous vector prime-boost*
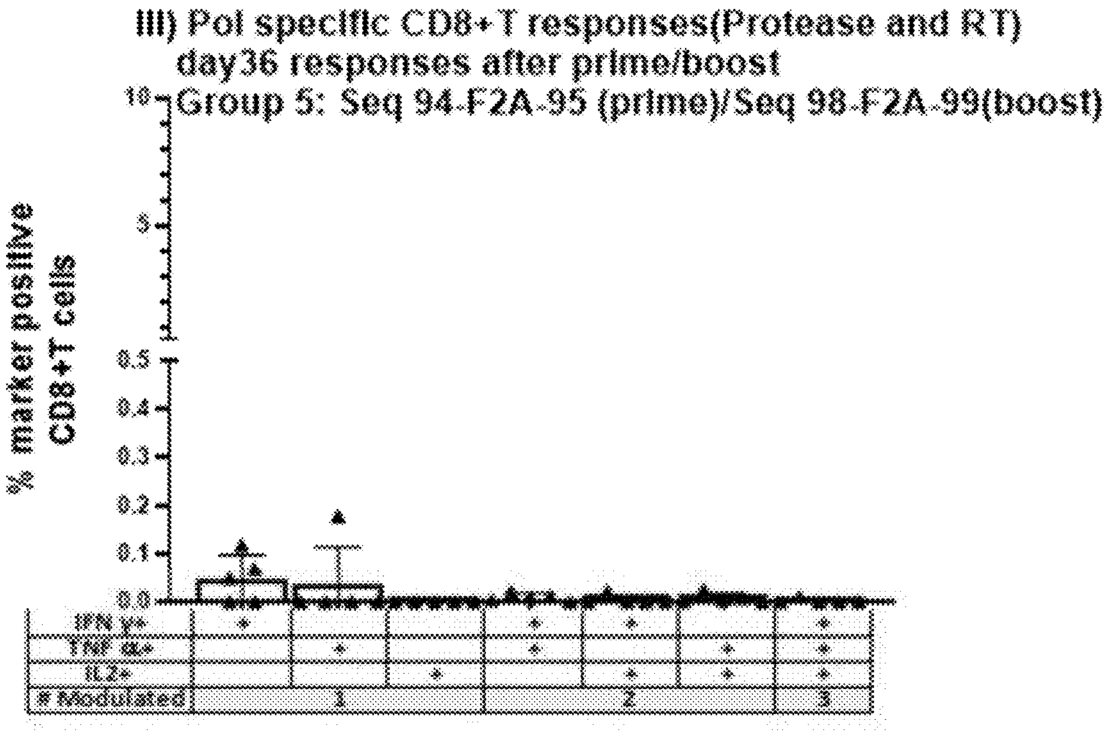
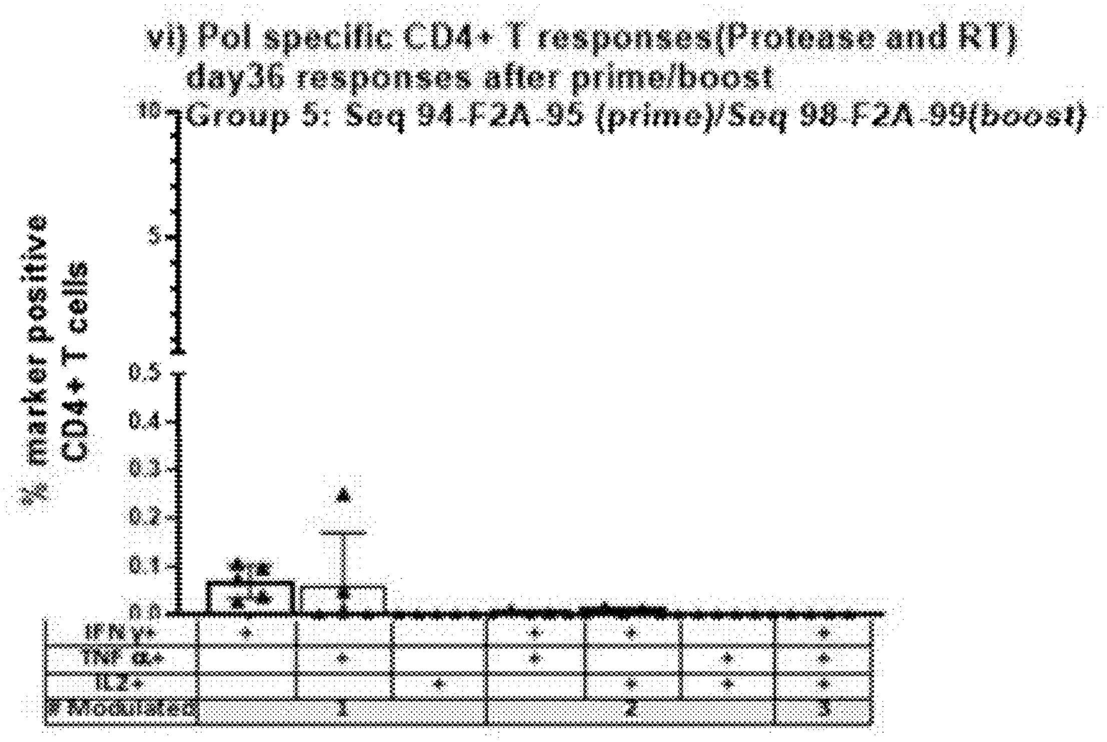
*Fig. 33C*

Homologous vector prime-boost
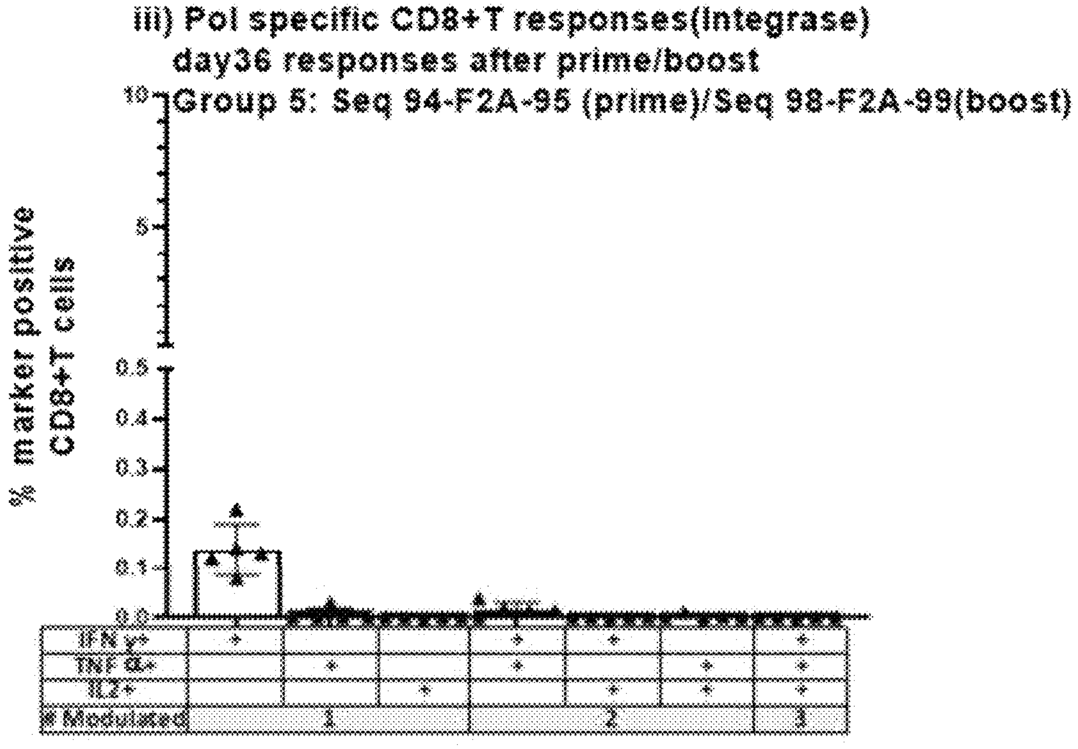
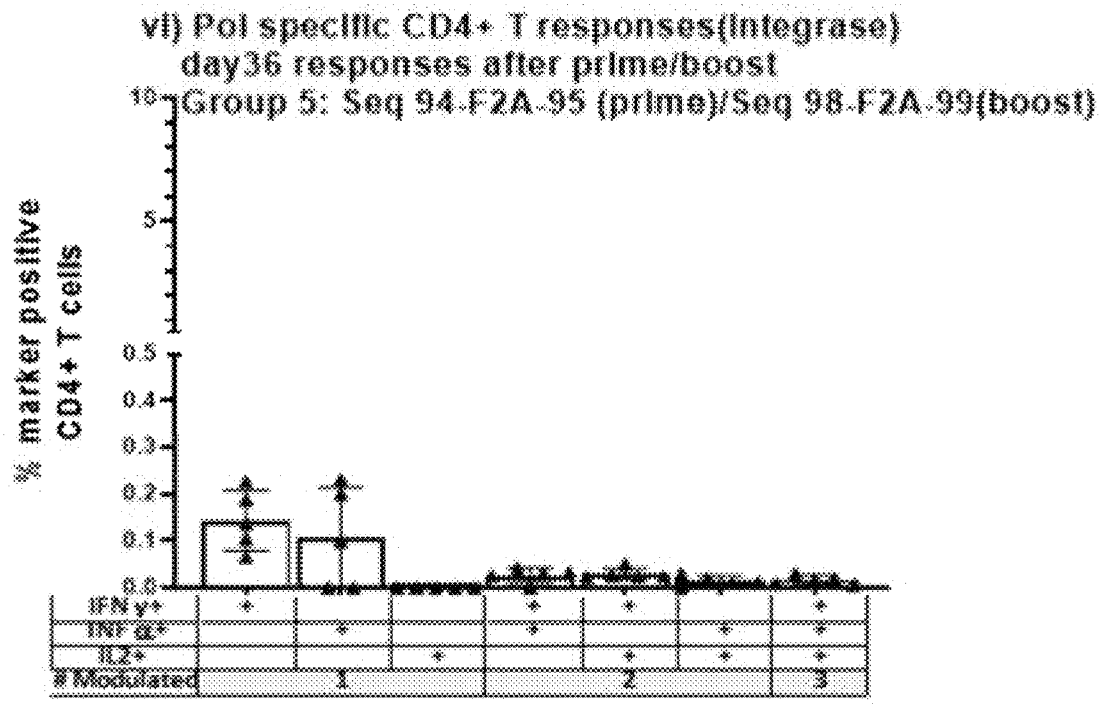
*Fig. 34C*

*Homologous vector prime-boost*
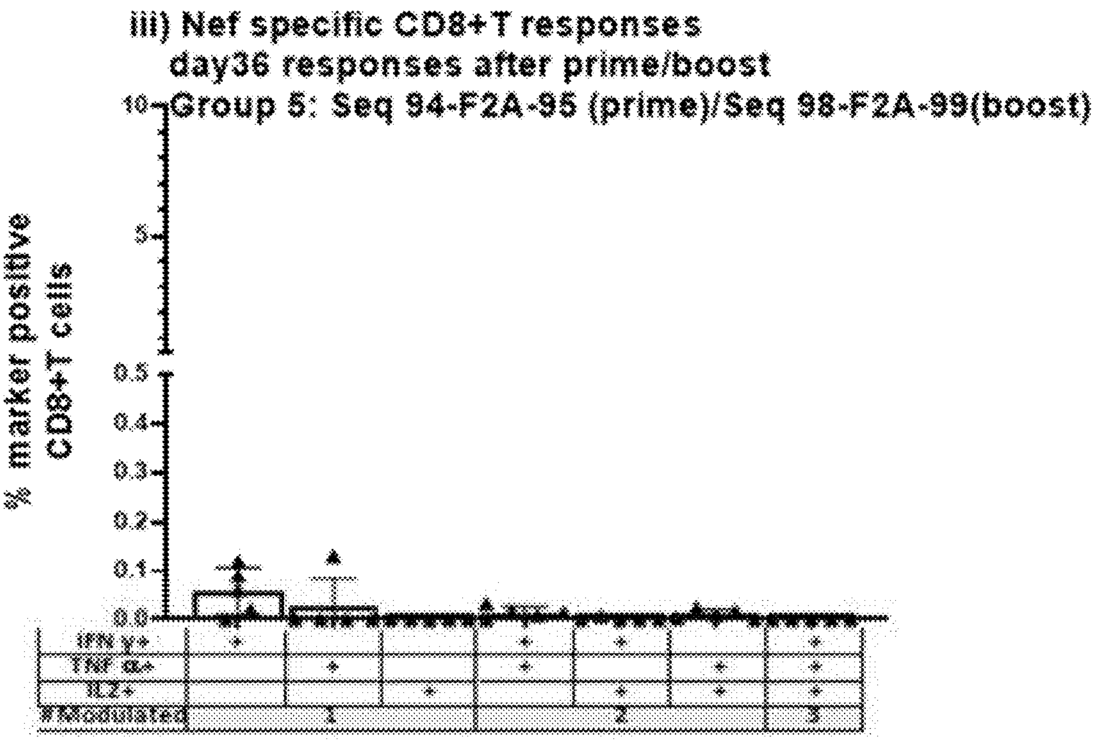
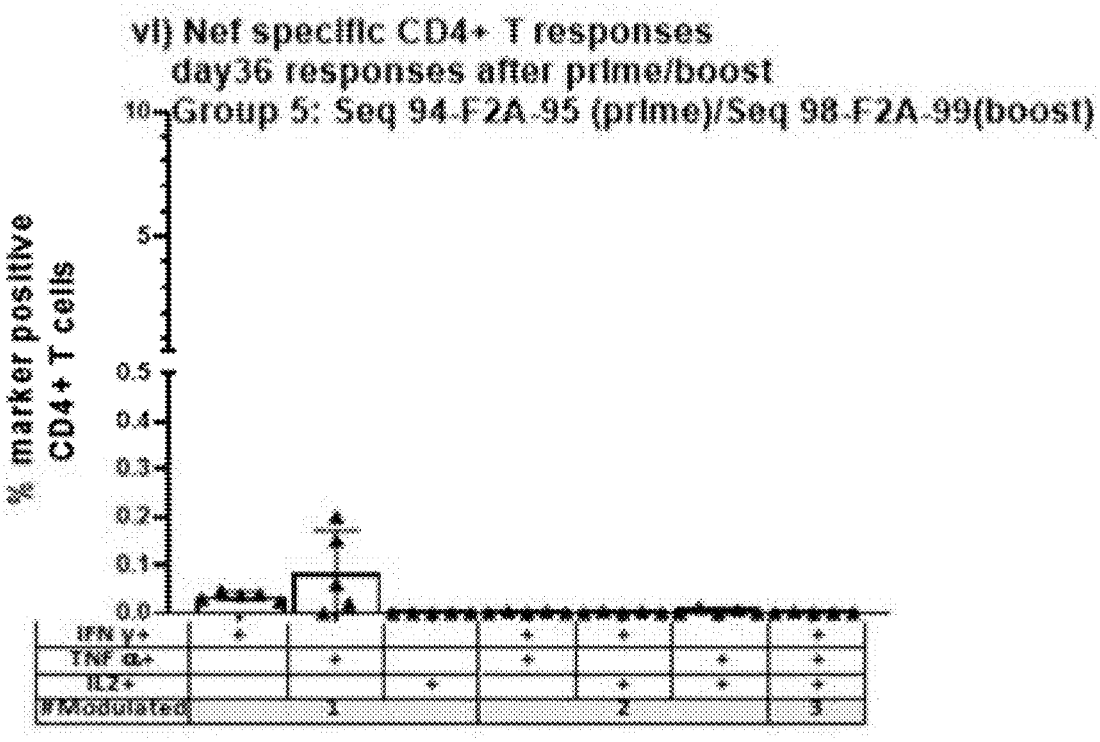
*Fig. 35C*

*Single vector immunogenicity*

*Homologous vector prime-boost*
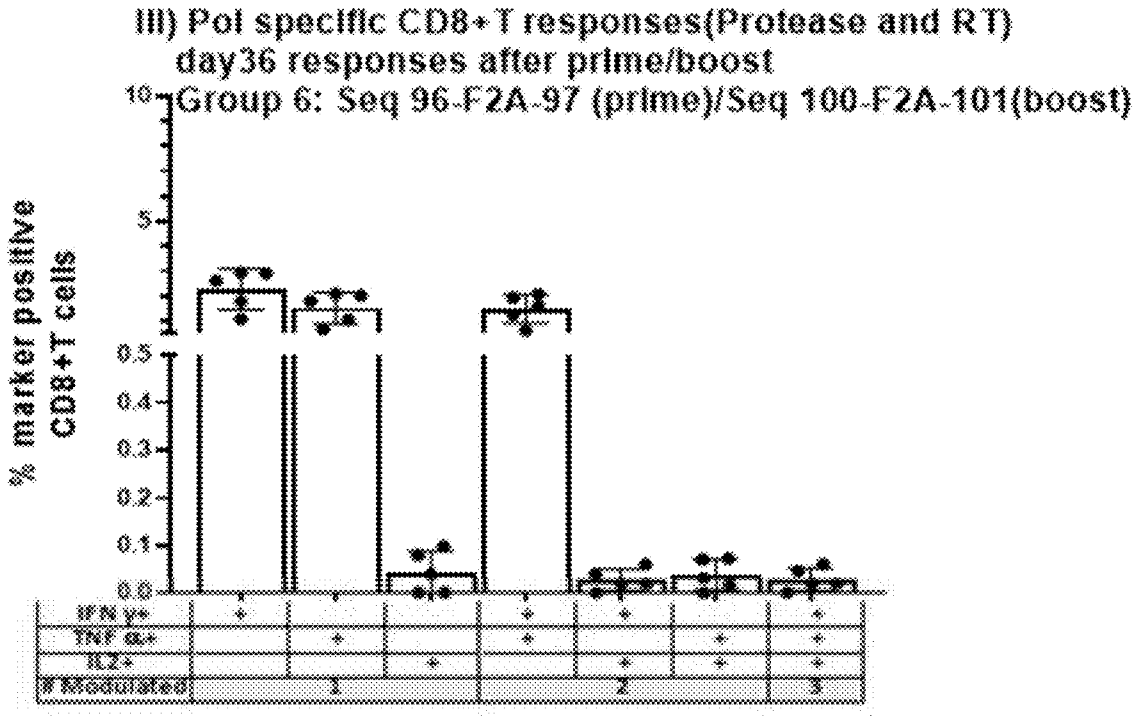
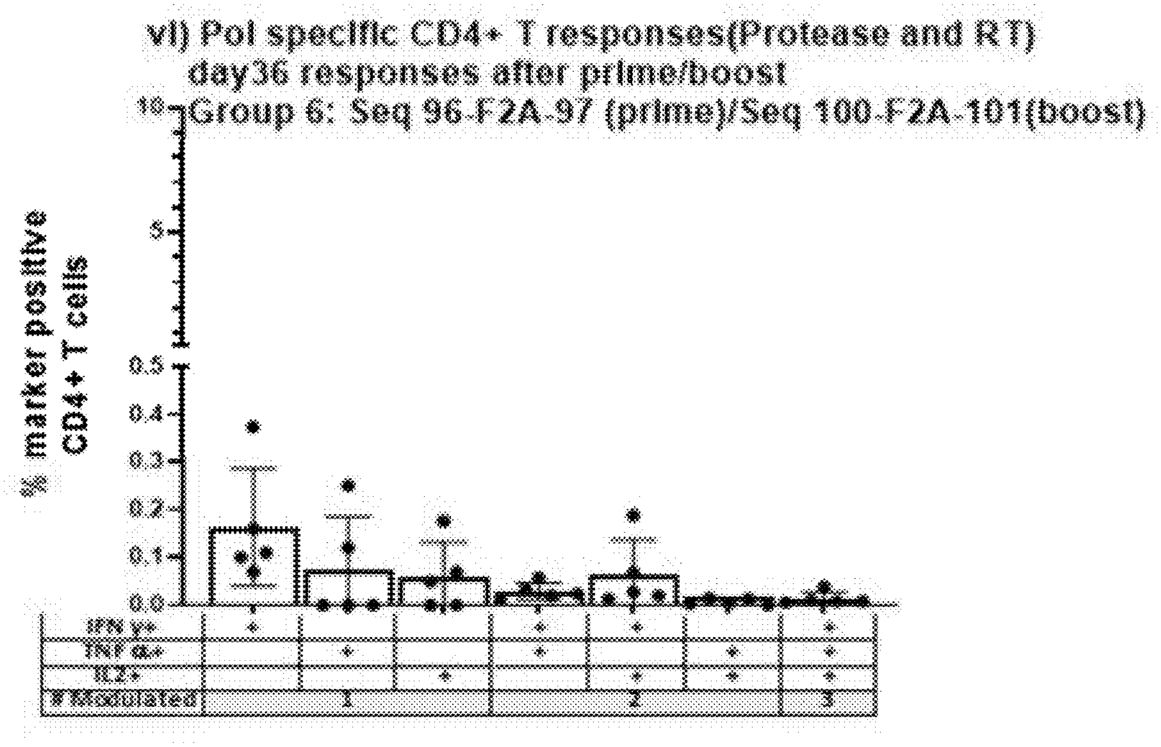
*Fig. 36C*

Homologous vector prime-boost
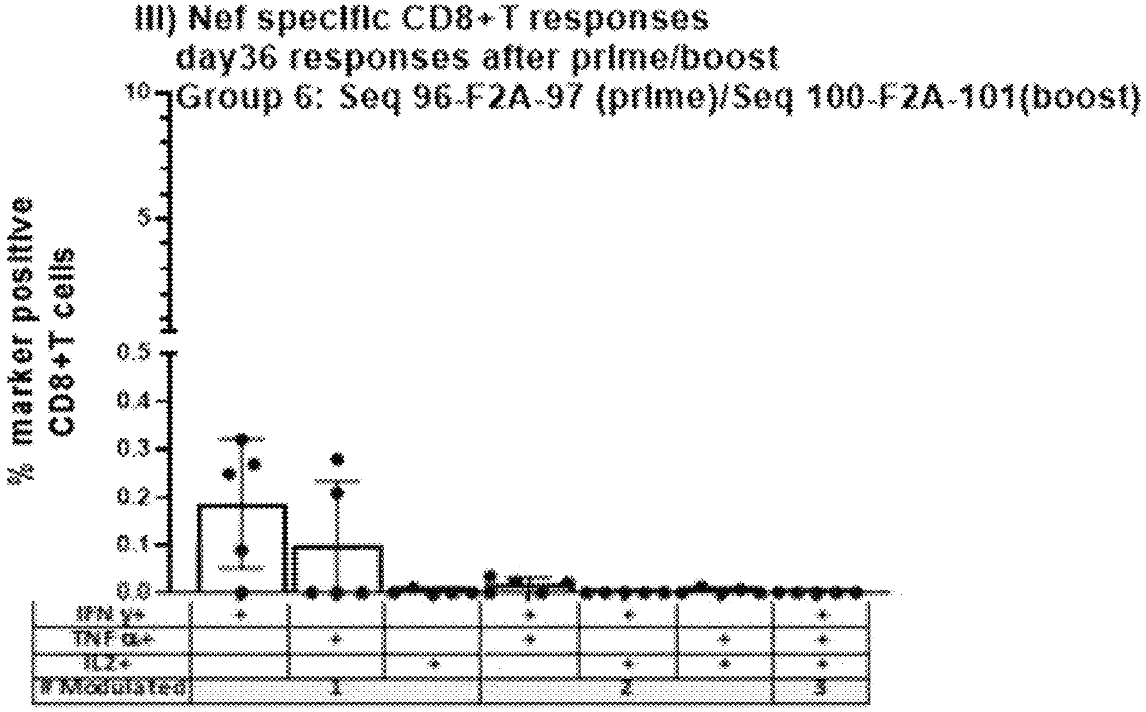
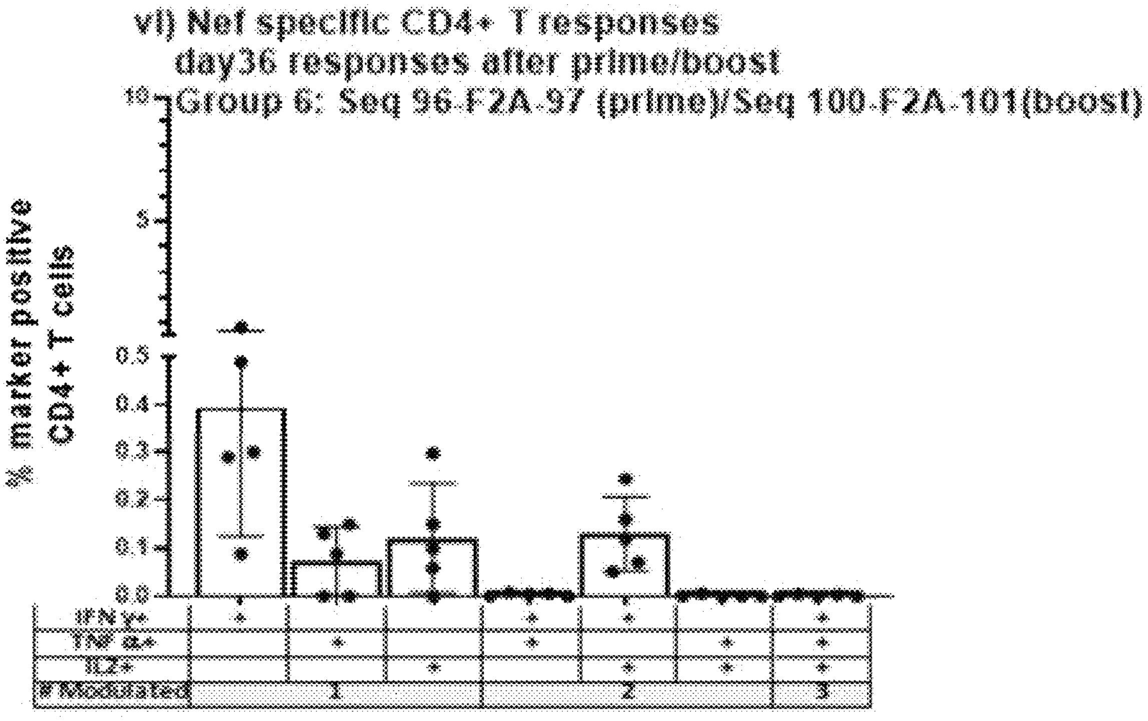
*Fig. 38C*

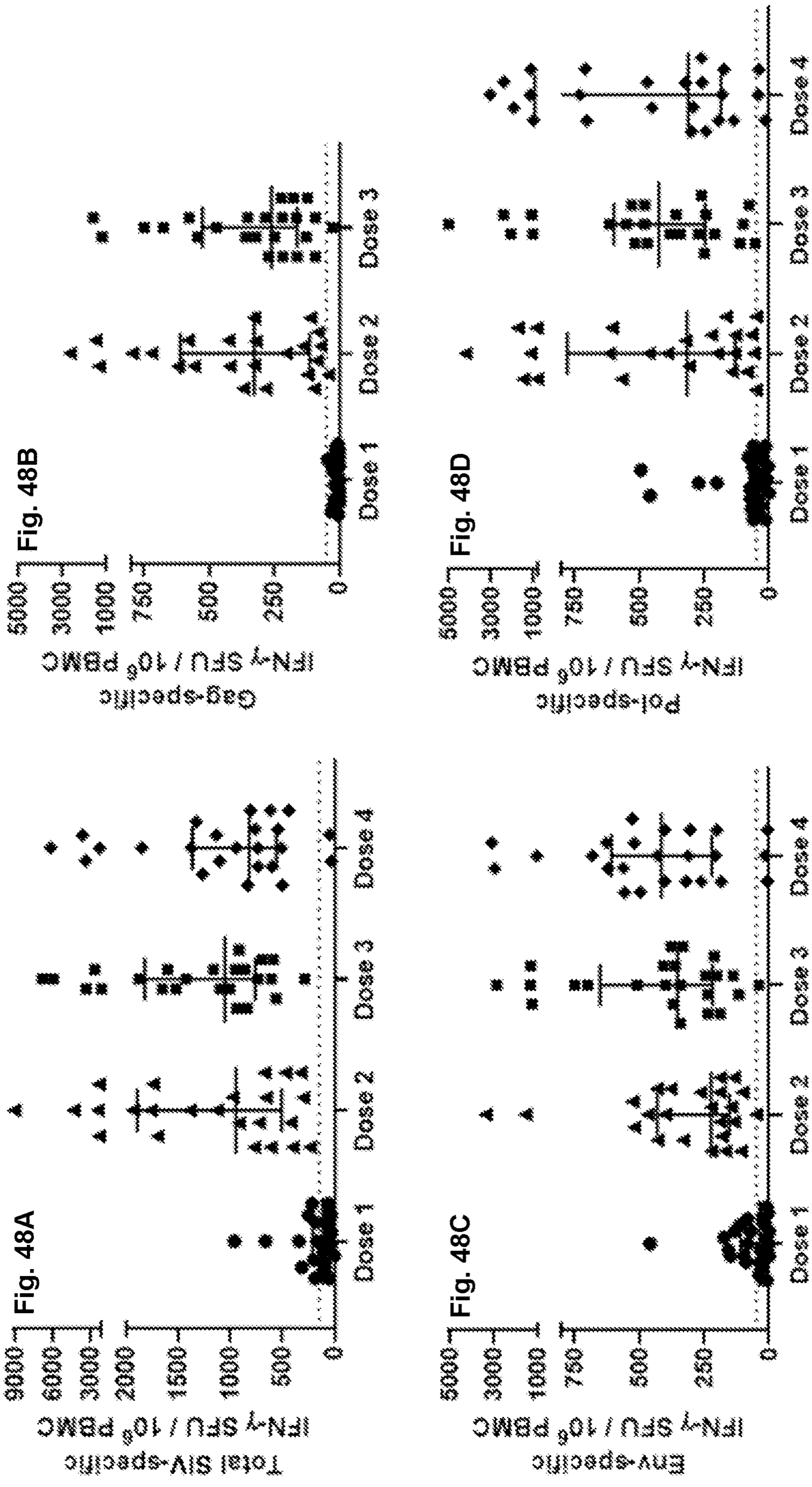
Fig. 48A-D

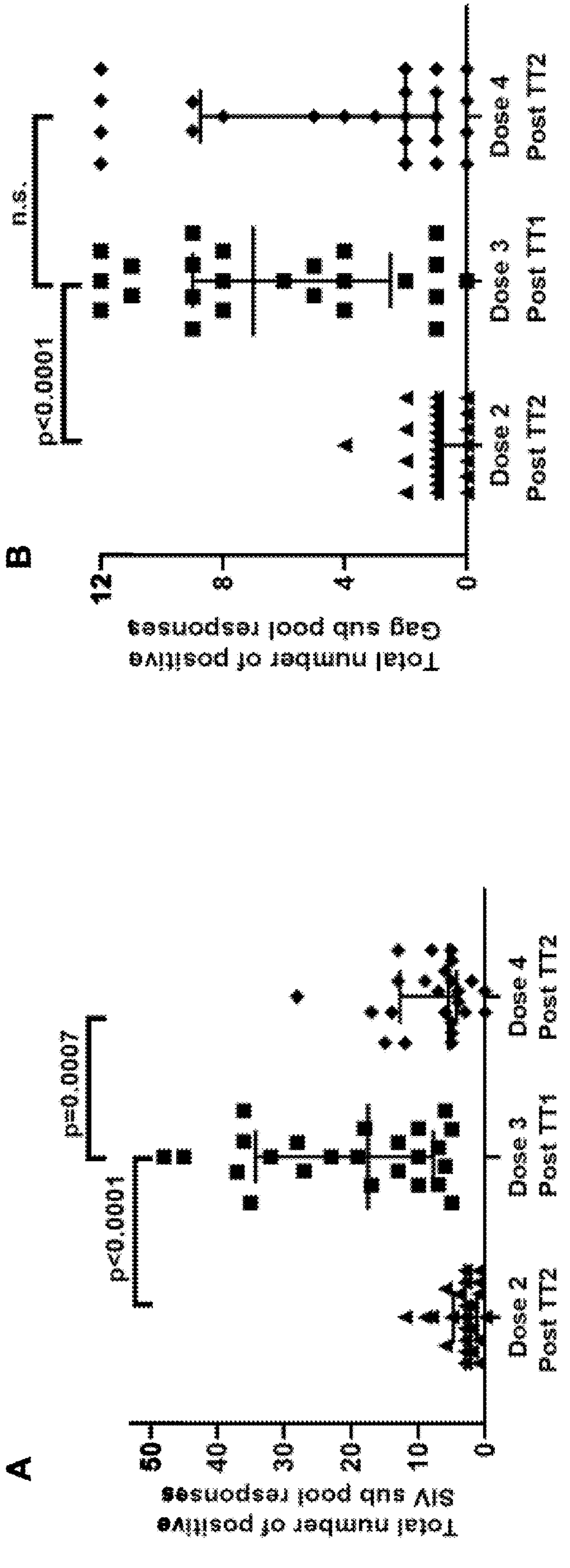
Fig. 49A-B

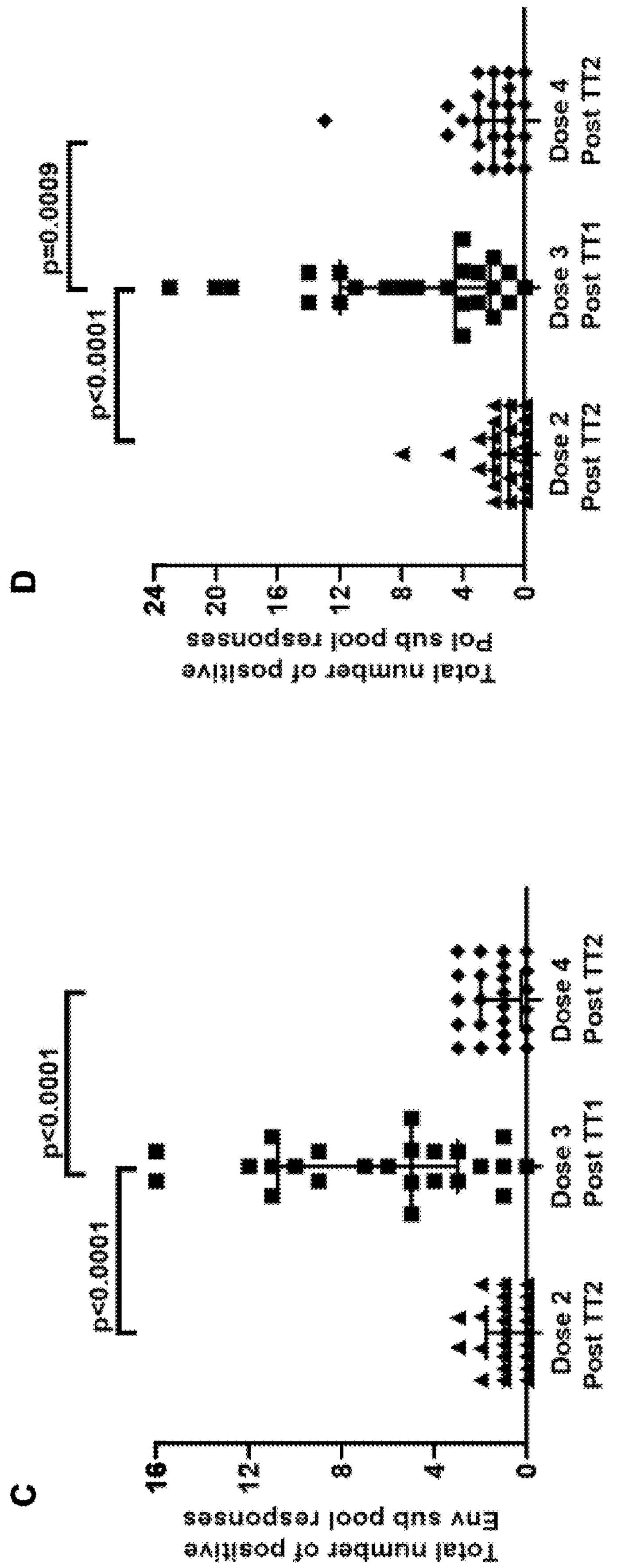
*Fig. 49C-D*

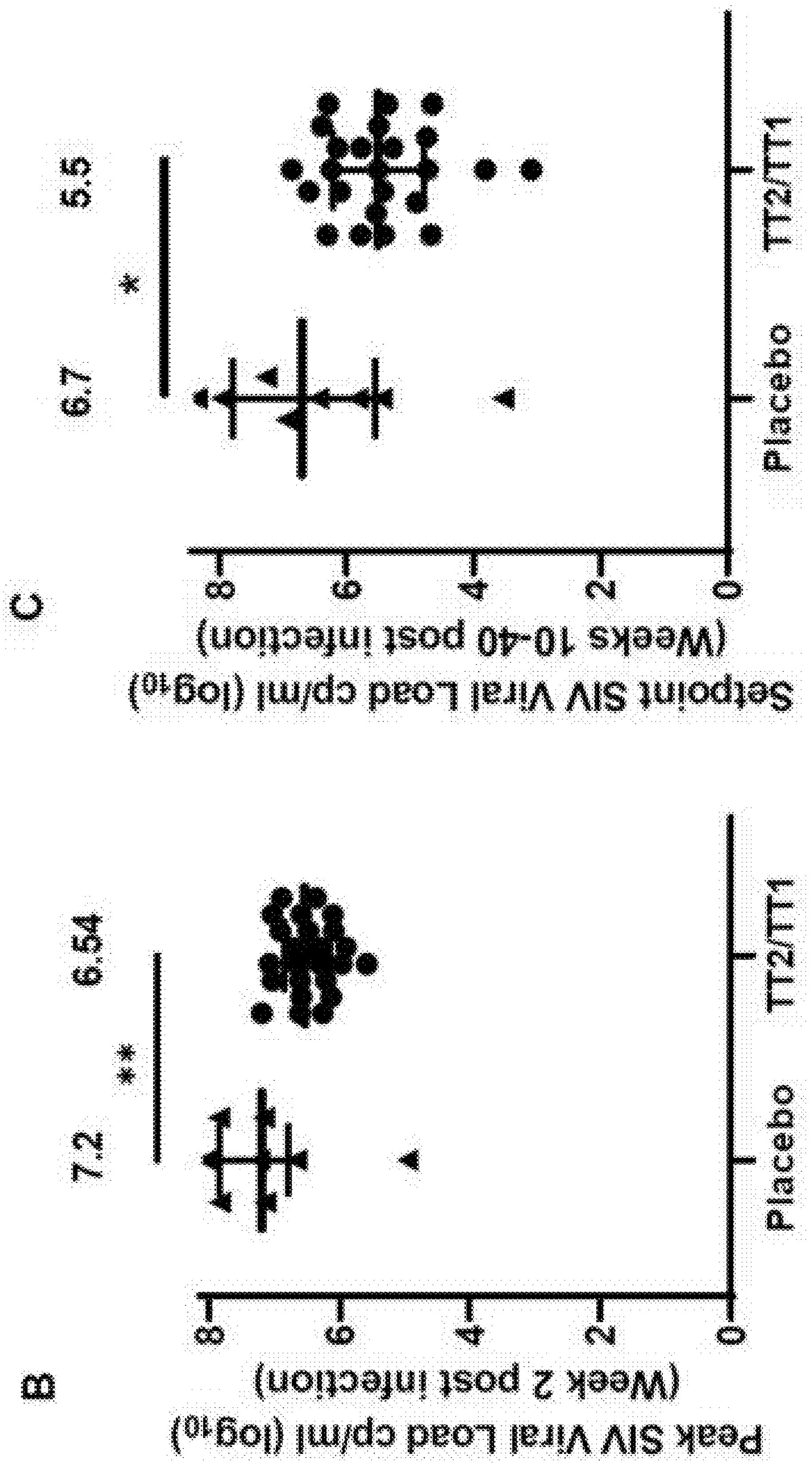
*Fig. 50B-C*

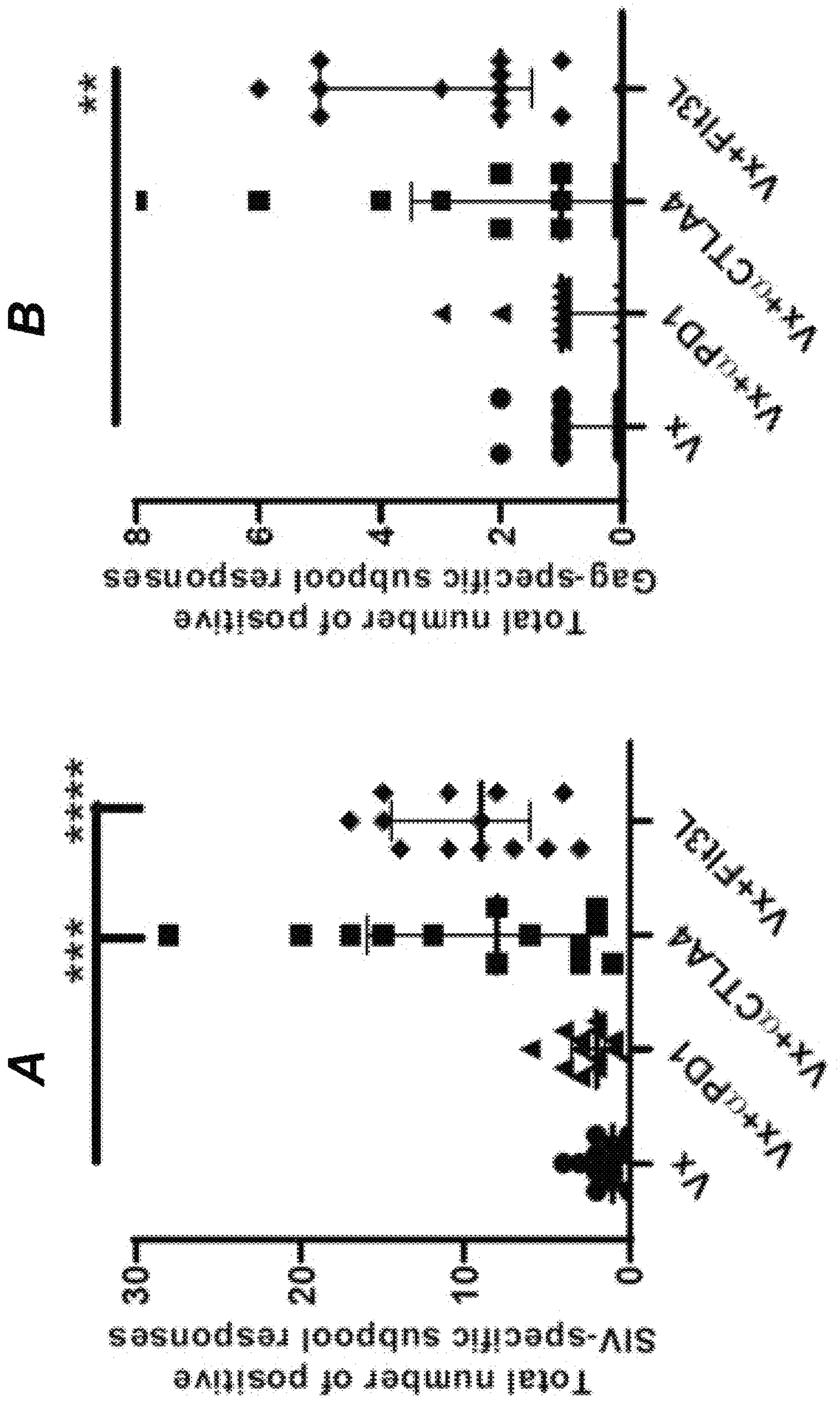
Fig. 64A-B

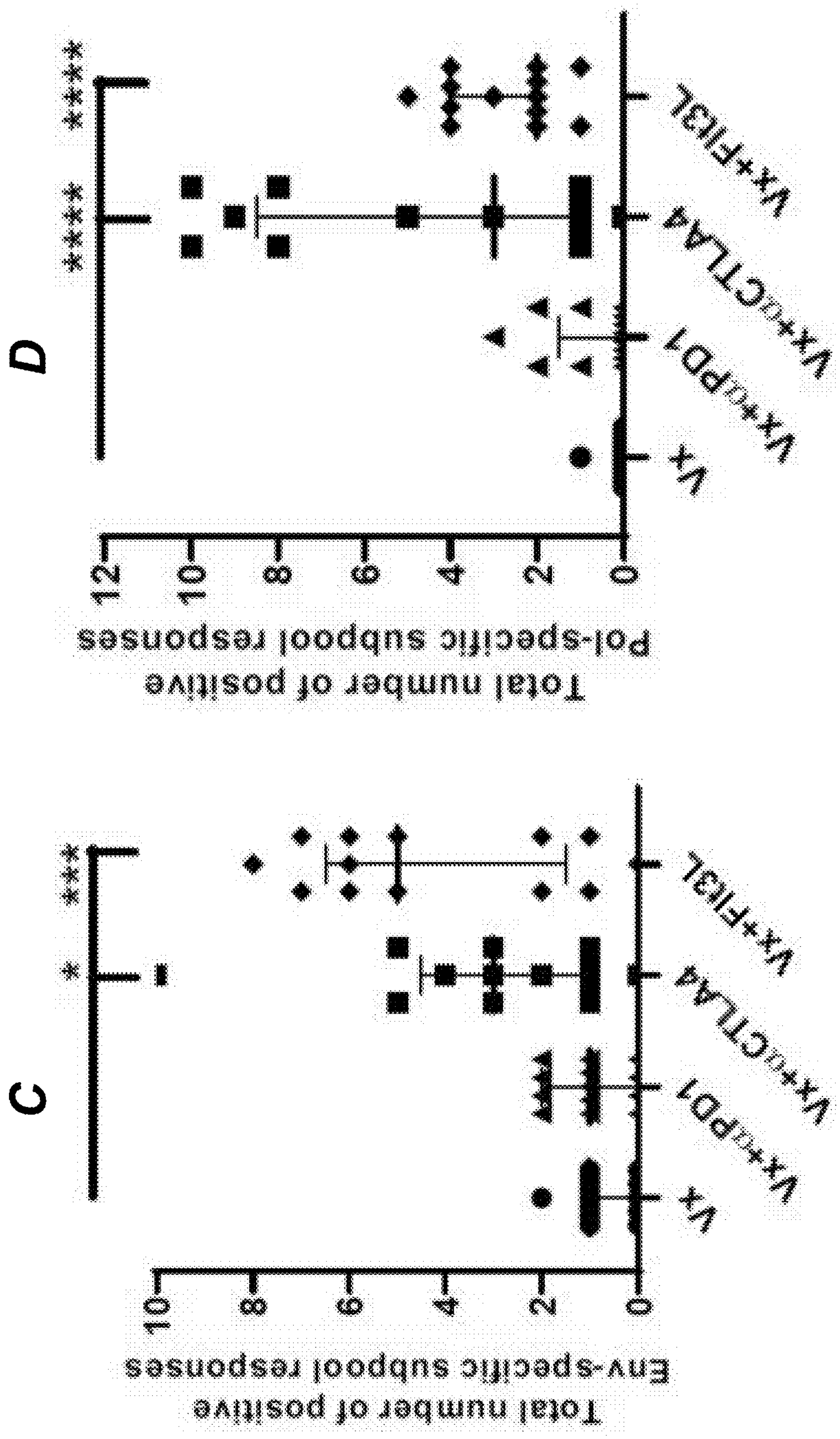
Fig. 64C-D

SEQUENCE LISTING

<160> NUMBER OF SEQ ID NOS: 231

<210> SEQ ID NO 1
<211> LENGTH: 500
<212> TYPE: PRT
<213> ORGANISM: Human immunodeficiency virus 1

<400> SEQUENCE: 1

```
Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Asn Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365
```

```
Gln Val Thr Asn Ser Ala Thr Ile Met Met Gln Arg Gly Asn Phe Arg
    370                 375                 380

Asn Gln Arg Lys Ile Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Tyr Lys Gly Arg Pro Gly Asn Phe
        435                 440                 445

Leu Gln Ser Arg Pro Glu Pro Thr Ala Pro Pro Glu Glu Ser Phe Arg
    450                 455                 460

Ser Gly Val Glu Thr Thr Thr Pro Pro Gln Lys Gln Glu Pro Ile Asp
465                 470                 475                 480

Lys Glu Leu Tyr Pro Leu Thr Ser Leu Arg Ser Leu Phe Gly Asn Asp
                485                 490                 495

Pro Ser Ser Gln
            500


<210> SEQ ID NO 2
<211> LENGTH: 1003
<212> TYPE: PRT
<213> ORGANISM: Human immunodeficiency virus 1

<400> SEQUENCE: 2

Phe Phe Arg Glu Asp Leu Ala Phe Leu Gln Gly Lys Ala Arg Glu Phe
1               5                   10                  15

Ser Ser Glu Gln Thr Arg Ala Asn Ser Pro Thr Arg Arg Glu Leu Gln
            20                  25                  30

Val Trp Gly Arg Asp Asn Asn Ser Pro Ser Glu Ala Gly Ala Asp Arg
        35                  40                  45

Gln Gly Thr Val Ser Phe Asn Phe Pro Gln Val Thr Leu Trp Gln Arg
    50                  55                  60

Pro Leu Val Thr Ile Lys Ile Gly Gly Gln Leu Lys Glu Ala Leu Leu
65                  70                  75                  80

Asp Thr Gly Ala Asp Asp Thr Val Leu Glu Glu Met Ser Leu Pro Gly
                85                  90                  95

Arg Trp Lys Pro Lys Met Ile Gly Gly Ile Gly Gly Phe Ile Lys Val
            100                 105                 110

Arg Gln Tyr Asp Gln Ile Leu Ile Glu Ile Cys Gly His Lys Ala Ile
        115                 120                 125

Gly Thr Val Leu Val Gly Pro Thr Pro Val Asn Ile Ile Gly Arg Asn
    130                 135                 140

Leu Leu Thr Gln Ile Gly Cys Thr Leu Asn Phe Pro Ile Ser Pro Ile
145                 150                 155                 160

Glu Thr Val Pro Val Lys Leu Lys Pro Gly Met Asp Gly Pro Lys Val
                165                 170                 175

Lys Gln Trp Pro Leu Thr Glu Glu Lys Ile Lys Ala Leu Val Glu Ile
            180                 185                 190

Cys Thr Glu Met Glu Lys Glu Gly Lys Ile Ser Lys Ile Gly Pro Glu
        195                 200                 205

Asn Pro Tyr Asn Thr Pro Val Phe Ala Ile Lys Lys Lys Asp Ser Thr
    210                 215                 220

Lys Trp Arg Lys Leu Val Asp Phe Arg Glu Leu Asn Lys Arg Thr Gln
225                 230                 235                 240
```

```
Asp Phe Trp Glu Val Gln Leu Gly Ile Pro His Pro Ala Gly Leu Lys
                245                 250                 255

Lys Lys Lys Ser Val Thr Val Leu Asp Val Gly Asp Ala Tyr Phe Ser
            260                 265                 270

Val Pro Leu Asp Glu Asp Phe Arg Lys Tyr Thr Ala Phe Thr Ile Pro
        275                 280                 285

Ser Ile Asn Asn Glu Thr Pro Gly Ile Arg Tyr Gln Tyr Asn Val Leu
    290                 295                 300

Pro Gln Gly Trp Lys Gly Ser Pro Ala Ile Phe Gln Ser Ser Met Thr
305                 310                 315                 320

Lys Ile Leu Glu Pro Phe Arg Lys Gln Asn Pro Asp Ile Val Ile Tyr
                325                 330                 335

Gln Tyr Met Asp Asp Leu Tyr Val Gly Ser Asp Leu Glu Ile Gly Gln
            340                 345                 350

His Arg Thr Lys Ile Glu Glu Leu Arg Gln His Leu Leu Arg Trp Gly
        355                 360                 365

Leu Thr Thr Pro Asp Lys Lys His Gln Lys Glu Pro Pro Phe Leu Trp
    370                 375                 380

Met Gly Tyr Glu Leu His Pro Asp Lys Trp Thr Val Gln Pro Ile Val
385                 390                 395                 400

Leu Pro Glu Lys Asp Ser Trp Thr Val Asn Asp Ile Gln Lys Leu Val
                405                 410                 415

Gly Lys Leu Asn Trp Ala Ser Gln Ile Tyr Pro Gly Ile Lys Val Arg
            420                 425                 430

Gln Leu Cys Lys Leu Leu Arg Gly Thr Lys Ala Leu Thr Glu Val Ile
        435                 440                 445

Pro Leu Thr Glu Glu Ala Glu Leu Glu Leu Ala Glu Asn Arg Glu Ile
    450                 455                 460

Leu Lys Glu Pro Val His Gly Val Tyr Tyr Asp Pro Ser Lys Asp Leu
465                 470                 475                 480

Ile Ala Glu Ile Gln Lys Gln Gly Gln Gly Gln Trp Thr Tyr Gln Ile
                485                 490                 495

Tyr Gln Glu Pro Phe Lys Asn Leu Lys Thr Gly Lys Tyr Ala Arg Met
            500                 505                 510

Arg Gly Ala His Thr Asn Asp Val Lys Gln Leu Thr Glu Ala Val Gln
        515                 520                 525

Lys Ile Thr Thr Glu Ser Ile Val Ile Trp Gly Lys Thr Pro Lys Phe
    530                 535                 540

Lys Leu Pro Ile Gln Lys Glu Thr Trp Glu Thr Trp Trp Thr Glu Tyr
545                 550                 555                 560

Trp Gln Ala Thr Trp Ile Pro Glu Trp Glu Phe Val Asn Thr Pro Pro
                565                 570                 575

Leu Val Lys Leu Trp Tyr Gln Leu Glu Lys Glu Pro Ile Val Gly Ala
            580                 585                 590

Glu Thr Phe Tyr Val Asp Gly Ala Ala Asn Arg Glu Thr Lys Leu Gly
        595                 600                 605

Lys Ala Gly Tyr Val Thr Asn Arg Gly Arg Gln Lys Val Val Thr Leu
    610                 615                 620

Thr Asp Thr Thr Asn Gln Lys Thr Glu Leu Gln Ala Ile Tyr Leu Ala
625                 630                 635                 640

Leu Gln Asp Ser Gly Leu Glu Val Asn Ile Val Thr Asp Ser Gln Tyr
                645                 650                 655
```

Ala Leu Gly Ile Ile Gln Ala Gln Pro Asp Gln Ser Glu Ser Glu Leu
660 665 670

Val Asn Gln Ile Ile Glu Gln Leu Ile Lys Lys Glu Lys Val Tyr Leu
675 680 685

Ala Trp Val Pro Ala His Lys Gly Ile Gly Gly Asn Glu Gln Val Asp
690 695 700

Lys Leu Val Ser Ala Gly Ile Arg Lys Val Leu Phe Leu Asp Gly Ile
705 710 715 720

Asp Lys Ala Gln Asp Glu His Glu Lys Tyr His Ser Asn Trp Arg Ala
725 730 735

Met Ala Ser Asp Phe Asn Leu Pro Pro Val Val Ala Lys Glu Ile Val
740 745 750

Ala Ser Cys Asp Lys Cys Gln Leu Lys Gly Glu Ala Met His Gly Gln
755 760 765

Val Asp Cys Ser Pro Gly Ile Trp Gln Leu Asp Cys Thr His Leu Glu
770 775 780

Gly Lys Val Ile Leu Val Ala Val His Val Ala Ser Gly Tyr Ile Glu
785 790 795 800

Ala Glu Val Ile Pro Ala Glu Thr Gly Gln Glu Thr Ala Tyr Phe Leu
805 810 815

Leu Lys Leu Ala Gly Arg Trp Pro Val Lys Thr Ile His Thr Asp Asn
820 825 830

Gly Ser Asn Phe Thr Gly Ala Thr Val Arg Ala Ala Cys Trp Trp Ala
835 840 845

Gly Ile Lys Gln Glu Phe Gly Ile Pro Tyr Asn Pro Gln Ser Gln Gly
850 855 860

Val Val Glu Ser Met Asn Lys Glu Leu Lys Lys Ile Ile Gly Gln Val
865 870 875 880

Arg Asp Gln Ala Glu His Leu Lys Thr Ala Val Gln Met Ala Val Phe
885 890 895

Ile His Asn Phe Lys Arg Lys Gly Gly Ile Gly Gly Tyr Ser Ala Gly
900 905 910

Glu Arg Ile Val Asp Ile Ile Ala Thr Asp Ile Gln Thr Lys Glu Leu
915 920 925

Gln Lys Gln Ile Thr Lys Ile Gln Asn Phe Arg Val Tyr Tyr Arg Asp
930 935 940

Ser Arg Asn Pro Leu Trp Lys Gly Pro Ala Lys Leu Leu Trp Lys Gly
945 950 955 960

Glu Gly Ala Val Val Ile Gln Asp Asn Ser Asp Ile Lys Val Val Pro
965 970 975

Arg Arg Lys Ala Lys Ile Ile Arg Asp Tyr Gly Lys Gln Met Ala Gly
980 985 990

Asp Asp Cys Val Ala Ser Arg Gln Asp Glu Asp
995 1000

<210> SEQ ID NO 3
<211> LENGTH: 206
<212> TYPE: PRT
<213> ORGANISM: Human immunodeficiency virus 1

<400> SEQUENCE: 3

Met Gly Gly Lys Trp Ser Lys Ser Ser Val Ile Gly Trp Pro Thr Val
1 5 10 15

Arg Glu Arg Met Arg Arg Ala Glu Pro Ala Ala Asp Arg Val Gly Ala
20 25 30

```
Ala Ser Arg Asp Leu Glu Lys His Gly Ala Ile Thr Ser Ser Asn Thr
        35                  40                  45

Ala Ala Thr Asn Ala Ala Cys Ala Trp Leu Glu Ala Gln Glu Glu Glu
    50                  55                  60

Glu Val Gly Phe Pro Val Thr Pro Gln Val Pro Leu Arg Pro Met Thr
65                  70                  75                  80

Tyr Lys Ala Ala Val Asp Leu Ser His Phe Leu Lys Glu Lys Gly Gly
                85                  90                  95

Leu Glu Gly Leu Ile His Ser Gln Arg Arg Gln Asp Ile Leu Asp Leu
            100                 105                 110

Trp Ile Tyr His Thr Gln Gly Tyr Phe Pro Asp Trp Gln Asn Tyr Thr
        115                 120                 125

Pro Gly Pro Gly Val Arg Tyr Pro Leu Thr Phe Gly Trp Cys Tyr Lys
    130                 135                 140

Leu Val Pro Val Glu Pro Asp Lys Ile Glu Glu Ala Asn Lys Gly Glu
145                 150                 155                 160

Asn Thr Ser Leu Leu His Pro Val Ser Leu His Gly Met Asp Asp Pro
                165                 170                 175

Glu Arg Glu Val Leu Glu Trp Arg Phe Asp Ser Arg Leu Ala Phe His
            180                 185                 190

His Val Ala Arg Glu Leu His Pro Glu Tyr Phe Lys Asn Cys
        195                 200                 205


<210> SEQ ID NO 4
<211> LENGTH: 53
<212> TYPE: PRT
<213> ORGANISM: Human immunodeficiency virus 1

<400> SEQUENCE: 4

Met Ala Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Arg Leu Lys
            20                  25                  30

His Ile Val Trp Ala Ser Arg Glu Leu Glu Arg Phe Ala Val Asn Pro
        35                  40                  45

Gly Leu Leu Glu Thr
    50


<210> SEQ ID NO 5
<211> LENGTH: 53
<212> TYPE: PRT
<213> ORGANISM: Human immunodeficiency virus 1

<400> SEQUENCE: 5

Met Ala Ala Arg Ala Ser Ile Leu Ser Gly Gly Lys Leu Asp Lys Trp
1               5                   10                  15

Glu Lys Ile Arg Leu Arg Pro Gly Gly Arg Lys Lys Tyr Lys Leu Lys
            20                  25                  30

His Leu Val Trp Ala Ser Arg Glu Leu Glu Arg Phe Ala Leu Asn Pro
        35                  40                  45

Gly Leu Leu Glu Thr
    50


<210> SEQ ID NO 6
<211> LENGTH: 223
<212> TYPE: PRT
<213> ORGANISM: Human immunodeficiency virus 1
```

<400> SEQUENCE: 6

Ile Ser Pro Arg Thr Leu Asn Ala Trp Val Lys Val Val Glu Glu Lys
1               5                   10                  15

Ala Phe Ser Pro Glu Val Ile Pro Met Phe Ser Ala Leu Ser Glu Gly
            20                  25                  30

Ala Thr Pro Gln Asp Leu Asn Thr Met Leu Asn Thr Val Gly Gly His
        35                  40                  45

Gln Ala Ala Met Gln Met Leu Lys Glu Thr Ile Asn Glu Glu Ala Ala
    50                  55                  60

Glu Trp Asp Arg Leu His Pro Val His Ala Gly Pro Ile Ala Pro Gly
65                  70                  75                  80

Gln Met Arg Glu Pro Arg Gly Ser Asp Ile Ala Gly Thr Thr Ser Thr
                85                  90                  95

Leu Gln Glu Gln Ile Gly Trp Met Thr Asn Asn Pro Pro Ile Pro Val
            100                 105                 110

Gly Glu Ile Tyr Lys Arg Trp Ile Ile Leu Gly Leu Asn Lys Ile Val
        115                 120                 125

Arg Met Tyr Ser Pro Thr Ser Ile Leu Asp Ile Arg Gln Gly Pro Lys
    130                 135                 140

Glu Pro Phe Arg Asp Tyr Val Asp Arg Phe Tyr Lys Thr Leu Arg Ala
145                 150                 155                 160

Glu Gln Ala Ser Gln Glu Val Lys Asn Trp Met Thr Glu Thr Leu Leu
                165                 170                 175

Val Gln Asn Ala Asn Pro Asp Cys Lys Thr Ile Leu Lys Ala Leu Gly
            180                 185                 190

Pro Ala Ala Thr Leu Glu Glu Met Met Thr Ala Cys Gln Gly Val Gly
        195                 200                 205

Gly Pro Gly His Lys Ala Arg Val Leu Ala Glu Ala Met Ser Gln
    210                 215                 220

<210> SEQ ID NO 7
<211> LENGTH: 223
<212> TYPE: PRT
<213> ORGANISM: Human immunodeficiency virus 1

<400> SEQUENCE: 7

Leu Ser Pro Arg Thr Leu Asn Ala Trp Val Lys Val Ile Glu Glu Lys
1               5                   10                  15

Ala Phe Ser Pro Glu Val Ile Pro Met Phe Thr Ala Leu Ser Glu Gly
            20                  25                  30

Ala Thr Pro His Asp Leu Asn Thr Met Leu Asn Thr Ile Gly Gly His
        35                  40                  45

Gln Ala Ala Met Gln Met Leu Lys Asp Thr Ile Asn Glu Glu Ala Ala
    50                  55                  60

Glu Trp Asp Arg Val His Pro Val His Ala Gly Pro Val Ala Pro Gly
65                  70                  75                  80

Gln Met Arg Asp Pro Arg Gly Ser Asp Ile Ala Gly Ser Thr Ser Thr
                85                  90                  95

Leu Gln Glu Gln Ile Ala Trp Met Thr Asn Asn Pro Pro Ile Pro Val
            100                 105                 110

Gly Asp Ile Tyr Lys Arg Trp Ile Ile Met Gly Leu Asn Lys Ile Val
        115                 120                 125

Arg Met Tyr Ser Pro Val Ser Ile Leu Asp Ile Lys Gln Gly Pro Lys
    130                 135                 140

Glu Pro Phe Arg Asp Tyr Val Asp Arg Phe Tyr Arg Thr Leu Arg Ala
145 150 155 160

Glu Gln Ala Ser Gln Asp Val Lys Asn Trp Met Thr Glu Thr Leu Leu
165 170 175

Val Gln Asn Ser Asn Pro Asp Cys Lys Thr Ile Leu Lys Ala Leu Gly
180 185 190

Pro Gly Ala Thr Leu Glu Glu Met Met Ser Ala Cys Gln Gly Val Gly
195 200 205

Gly Pro Ser His Lys Ala Arg Val Leu Ala Glu Ala Met Cys Gln
210 215 220

<210> SEQ ID NO 8
<211> LENGTH: 62
<212> TYPE: PRT
<213> ORGANISM: Human immunodeficiency virus 1

<400> SEQUENCE: 8

Phe Pro Gln Ile Thr Leu Trp Gln Arg Pro Leu Val Thr Ile Lys Ile
1 5 10 15

Gly Gly Gln Leu Lys Glu Ala Leu Leu Asp Thr Gly Ala Asp Asp Thr
20 25 30

Val Leu Glu Glu Met Asn Leu Pro Gly Arg Trp Lys Pro Lys Met Ile
35 40 45

Gly Gly Ile Gly Gly Phe Ile Lys Val Arg Gln Tyr Asp Gln
50 55 60

<210> SEQ ID NO 9
<211> LENGTH: 62
<212> TYPE: PRT
<213> ORGANISM: Human immunodeficiency virus 1

<400> SEQUENCE: 9

Leu Pro Gln Ile Thr Leu Trp Gln Arg Pro Ile Val Thr Ile Lys Ile
1 5 10 15

Gly Gly Gln Ile Lys Glu Ala Leu Leu Asp Thr Gly Ala Asp Asp Thr
20 25 30

Val Leu Glu Asp Met Asn Leu Pro Gly Lys Trp Lys Pro Lys Met Ile
35 40 45

Gly Gly Ile Gly Gly Phe Ile Lys Val Lys Gln Tyr Asp Gln
50 55 60

<210> SEQ ID NO 10
<211> LENGTH: 192
<212> TYPE: PRT
<213> ORGANISM: Human immunodeficiency virus 1

<400> SEQUENCE: 10

Gly Thr Val Leu Val Gly Pro Thr Pro Val Asn Ile Ile Gly Arg Asn
1 5 10 15

Leu Leu Thr Gln Ile Gly Cys Thr Leu Asn Phe Pro Ile Ser Pro Ile
20 25 30

Glu Thr Val Pro Val Lys Leu Lys Pro Gly Met Asp Gly Pro Lys Val
35 40 45

Lys Gln Trp Pro Leu Thr Glu Glu Lys Ile Lys Ala Leu Val Glu Ile
50 55 60

Cys Thr Glu Met Glu Lys Glu Gly Lys Ile Ser Lys Ile Gly Pro Glu
65 70 75 80

```
Asn Pro Tyr Asn Thr Pro Val Phe Ala Ile Lys Lys Lys Asp Ser Thr
                85                  90                  95

Lys Trp Arg Lys Leu Val Asp Phe Arg Glu Leu Asn Lys Arg Thr Gln
            100                 105                 110

Asp Phe Trp Glu Val Gln Leu Gly Ile Pro His Pro Ala Gly Leu Lys
        115                 120                 125

Lys Lys Lys Ser Val Thr Val Leu Asp Val Gly Asp Ala Tyr Phe Ser
    130                 135                 140

Val Pro Leu Asp Lys Asp Phe Arg Lys Tyr Thr Ala Phe Thr Ile Pro
145                 150                 155                 160

Ser Ile Asn Asn Glu Thr Pro Gly Ile Arg Tyr Gln Tyr Asn Val Leu
                165                 170                 175

Pro Gln Gly Trp Lys Gly Ser Pro Ala Ile Phe Gln Ser Ser Met Thr
            180                 185                 190


<210> SEQ ID NO 11
<211> LENGTH: 192
<212> TYPE: PRT
<213> ORGANISM: Human immunodeficiency virus 1

<400> SEQUENCE: 11

Gly Thr Val Leu Ile Gly Pro Thr Pro Val Asn Ile Ile Gly Arg Asn
1               5                   10                  15

Leu Leu Thr Gln Leu Gly Cys Thr Leu Asn Phe Pro Ile Ser Pro Ile
            20                  25                  30

Asp Thr Val Pro Val Lys Leu Lys Pro Gly Met Asp Gly Pro Arg Val
        35                  40                  45

Lys Gln Trp Pro Leu Thr Glu Glu Lys Ile Lys Ala Leu Ile Glu Ile
    50                  55                  60

Cys Thr Glu Met Glu Lys Glu Gly Lys Ile Ser Arg Ile Gly Pro Glu
65                  70                  75                  80

Asn Pro Tyr Asn Thr Pro Ile Phe Ala Ile Lys Lys Lys Asp Gly Thr
                85                  90                  95

Lys Trp Arg Lys Leu Val Asp Phe Arg Glu Leu Asn Lys Lys Thr Gln
            100                 105                 110

Asp Phe Trp Glu Val Gln Leu Gly Ile Pro His Pro Ser Gly Leu Lys
        115                 120                 125

Lys Lys Lys Ser Val Thr Val Leu Asp Ile Gly Asp Ala Tyr Phe Ser
    130                 135                 140

Val Pro Leu Asp Lys Glu Phe Arg Lys Tyr Thr Ala Phe Thr Val Pro
145                 150                 155                 160

Ser Thr Asn Asn Glu Thr Pro Gly Val Arg Tyr Gln Tyr Asn Val Leu
                165                 170                 175

Pro Met Gly Trp Lys Gly Ser Pro Ala Ile Phe Gln Cys Ser Met Thr
            180                 185                 190


<210> SEQ ID NO 12
<211> LENGTH: 65
<212> TYPE: PRT
<213> ORGANISM: Human immunodeficiency virus 1

<400> SEQUENCE: 12

Trp Gly Phe Thr Thr Pro Asp Lys Lys His Gln Lys Glu Pro Pro Phe
1               5                   10                  15

Leu Trp Met Gly Tyr Glu Leu His Pro Asp Lys Trp Thr Val Gln Pro
            20                  25                  30
```

Ile Val Leu Pro Glu Lys Asp Ser Trp Thr Val Asn Asp Ile Gln Lys
35 40 45

Leu Val Gly Lys Leu Asn Trp Ala Ser Gln Ile Tyr Pro Gly Ile Lys
50 55 60

Val
65

<210> SEQ ID NO 13
<211> LENGTH: 65
<212> TYPE: PRT
<213> ORGANISM: Human immunodeficiency virus 1

<400> SEQUENCE: 13

Trp Gly Leu Thr Thr Pro Asp Lys Lys His Gln Lys Asp Pro Pro Phe
1 5 10 15

Leu Trp Met Gly Tyr Glu Leu His Pro Asp Arg Trp Thr Val Gln Pro
20 25 30

Ile Glu Leu Pro Glu Lys Glu Ser Trp Thr Val Asn Asp Ile Gln Lys
35 40 45

Leu Ile Gly Lys Leu Asn Trp Ala Ser Gln Ile Tyr Ala Gly Ile Lys
50 55 60

Val
65

<210> SEQ ID NO 14
<211> LENGTH: 65
<212> TYPE: PRT
<213> ORGANISM: Human immunodeficiency virus 1

<400> SEQUENCE: 14

Pro Lys Phe Lys Leu Pro Ile Gln Lys Glu Thr Trp Glu Thr Trp Trp
1 5 10 15

Thr Glu Tyr Trp Gln Ala Thr Trp Ile Pro Glu Trp Glu Phe Val Asn
20 25 30

Thr Pro Pro Leu Val Lys Leu Trp Tyr Gln Leu Glu Lys Glu Pro Ile
35 40 45

Val Gly Ala Glu Thr Phe Tyr Val Asp Gly Ala Ala Asn Arg Glu Thr
50 55 60

Lys
65

<210> SEQ ID NO 15
<211> LENGTH: 65
<212> TYPE: PRT
<213> ORGANISM: Human immunodeficiency virus 1

<400> SEQUENCE: 15

Pro Lys Phe Arg Leu Pro Ile Gln Lys Glu Thr Trp Asp Thr Trp Trp
1 5 10 15

Thr Asp Tyr Trp Gln Ala Thr Trp Ile Pro Glu Trp Glu Phe Thr Asn
20 25 30

Thr Pro Pro Leu Val Lys Leu Trp Tyr Gln Leu Glu Thr Glu Pro Ile
35 40 45

Ala Gly Val Glu Thr Phe Tyr Val Asp Gly Ala Ser Asn Arg Glu Thr
50 55 60

Lys
65

<210> SEQ ID NO 16
<211> LENGTH: 21
<212> TYPE: PRT
<213> ORGANISM: Human immunodeficiency virus 1

<400> SEQUENCE: 16

```
Lys Glu Pro Ile Val Gly Ala Glu Thr Phe Tyr Val Asp Gly Ala Ala
1               5                   10                  15

Asn Arg Glu Thr Lys
            20
```

<210> SEQ ID NO 17
<211> LENGTH: 21
<212> TYPE: PRT
<213> ORGANISM: Human immunodeficiency virus 1

<400> SEQUENCE: 17

```
Thr Glu Pro Ile Ala Gly Val Glu Thr Phe Tyr Val Asp Gly Ala Ser
1               5                   10                  15

Asn Arg Glu Thr Lys
            20
```

<210> SEQ ID NO 18
<211> LENGTH: 26
<212> TYPE: PRT
<213> ORGANISM: Human immunodeficiency virus 1

<400> SEQUENCE: 18

```
Lys Glu Lys Val Tyr Leu Ala Trp Val Pro Ala His Lys Gly Ile Gly
1               5                   10                  15

Gly Asn Glu Gln Val Asp Lys Leu Val Ser
            20                  25
```

<210> SEQ ID NO 19
<211> LENGTH: 26
<212> TYPE: PRT
<213> ORGANISM: Human immunodeficiency virus 1

<400> SEQUENCE: 19

```
Lys Glu Lys Ile Tyr Leu Ala Trp Val Pro Ala His Lys Gly Ile Gly
1               5                   10                  15

Gly Asn Glu Gln Ile Asp Lys Leu Val Ser
            20                  25
```

<210> SEQ ID NO 20
<211> LENGTH: 81
<212> TYPE: PRT
<213> ORGANISM: Human immunodeficiency virus 1

<400> SEQUENCE: 20

```
Val Ala Lys Glu Ile Val Ala Ser Cys Asp Lys Cys Gln Leu Lys Gly
1               5                   10                  15

Glu Ala Met His Gly Gln Val Asp Cys Ser Pro Gly Ile Trp Gln Leu
            20                  25                  30

Asp Cys Thr His Leu Glu Gly Lys Ile Ile Leu Val Ala Val His Val
        35                  40                  45

Ala Ser Gly Tyr Ile Glu Ala Glu Val Ile Pro Ala Glu Thr Gly Gln
    50                  55                  60

Glu Thr Ala Tyr Phe Leu Leu Lys Leu Ala Gly Arg Trp Pro Val Lys
65                  70                  75                  80

Thr
```

<210> SEQ ID NO 21
<211> LENGTH: 81
<212> TYPE: PRT
<213> ORGANISM: Human immunodeficiency virus 1

<400> SEQUENCE: 21

Val Ala Lys Glu Ile Val Ala Cys Cys Asp Lys Cys Gln Leu Lys Gly
1 5 10 15

Glu Ala Ile His Gly Gln Val Asp Cys Ser Pro Gly Val Trp Gln Leu
20 25 30

Asp Cys Thr His Leu Glu Gly Lys Val Ile Leu Val Ala Val His Val
35 40 45

Ala Ser Gly Tyr Ile Glu Ala Glu Ile Ile Pro Thr Glu Thr Gly Gln
50 55 60

Glu Thr Ala Tyr Phe Ile Leu Lys Leu Ala Gly Arg Trp Pro Val Thr
65 70 75 80

Thr

<210> SEQ ID NO 22
<211> LENGTH: 69
<212> TYPE: PRT
<213> ORGANISM: Human immunodeficiency virus 1

<400> SEQUENCE: 22

Thr Val Lys Ala Ala Cys Trp Trp Ala Gly Ile Lys Gln Glu Phe Gly
1 5 10 15

Ile Pro Tyr Asn Pro Gln Ser Gln Gly Val Val Glu Ser Met Asn Lys
20 25 30

Glu Leu Lys Lys Ile Ile Gly Gln Val Arg Asp Gln Ala Glu His Leu
35 40 45

Lys Thr Ala Val Gln Met Ala Val Phe Ile His Asn Phe Lys Arg Lys
50 55 60

Gly Gly Ile Gly Gly
65

<210> SEQ ID NO 23
<211> LENGTH: 69
<212> TYPE: PRT
<213> ORGANISM: Human immunodeficiency virus 1

<400> SEQUENCE: 23

Ala Val Lys Ala Ala Cys Trp Trp Ala Gly Val Lys Gln Glu Phe Gly
1 5 10 15

Ile Pro Tyr Asn Thr Gln Ser Gln Gly Val Val Glu Ser Met Asn Asn
20 25 30

Glu Leu Lys Lys Ile Ile Gly Gln Ile Arg Asp Gln Ala Glu His Leu
35 40 45

Lys Thr Ala Val Gln Met Ala Val Leu Ile His Asn Phe Lys Arg Lys
50 55 60

Gly Gly Ile Gly Glu
65

<210> SEQ ID NO 24
<211> LENGTH: 81
<212> TYPE: PRT
<213> ORGANISM: Human immunodeficiency virus 1

<400> SEQUENCE: 24

Thr Val Lys Ala Ala Cys Trp Trp Ala Gly Ile Lys Gln Glu Phe Gly
1               5                   10                  15

Ile Pro Tyr Asn Pro Gln Ser Gln Gly Val Val Glu Ser Met Asn Lys
            20                  25                  30

Glu Leu Lys Lys Ile Ile Gly Gln Val Arg Asp Gln Ala Glu His Leu
        35                  40                  45

Lys Thr Ala Val Gln Met Ala Val Phe Ile His Asn Phe Lys Arg Lys
    50                  55                  60

Gly Gly Ile Gly Gly Tyr Ser Ala Gly Glu Arg Ile Val Asp Ile Ile
65                  70                  75                  80

Ala

<210> SEQ ID NO 25
<211> LENGTH: 81
<212> TYPE: PRT
<213> ORGANISM: Human immunodeficiency virus 1

<400> SEQUENCE: 25

Ala Val Lys Ala Ala Cys Trp Trp Ala Gly Val Lys Gln Glu Phe Gly
1               5                   10                  15

Ile Pro Tyr Asn Thr Gln Ser Gln Gly Val Val Glu Ser Met Asn Asn
            20                  25                  30

Glu Leu Lys Lys Ile Ile Gly Gln Ile Arg Asp Gln Ala Glu His Leu
        35                  40                  45

Lys Thr Ala Val Gln Met Ala Val Leu Ile His Asn Phe Lys Arg Lys
    50                  55                  60

Gly Gly Ile Gly Glu Tyr Ser Ala Gly Glu Arg Ile Ile Asp Ile Ile
65                  70                  75                  80

Ala

<210> SEQ ID NO 26
<211> LENGTH: 72
<212> TYPE: PRT
<213> ORGANISM: Human immunodeficiency virus 1

<400> SEQUENCE: 26

Ile Thr Lys Ile Gln Asn Phe Arg Val Tyr Tyr Arg Asp Ser Arg Asp
1               5                   10                  15

Pro Leu Trp Lys Gly Pro Ala Lys Leu Leu Trp Lys Gly Glu Gly Ala
            20                  25                  30

Val Val Ile Gln Asp Asn Ser Asp Ile Lys Val Val Pro Arg Arg Lys
        35                  40                  45

Ala Lys Ile Ile Arg Asp Tyr Gly Lys Gln Met Ala Gly Asp Asp Cys
    50                  55                  60

Val Ala Ser Arg Gln Asp Glu Asp
65                  70

<210> SEQ ID NO 27
<211> LENGTH: 72
<212> TYPE: PRT
<213> ORGANISM: Human immunodeficiency virus 1

<400> SEQUENCE: 27

Ile Thr Lys Leu Gln Asn Phe Arg Val Tyr Tyr Arg Asp Asn Arg Asp
1               5                   10                  15

Pro Leu Trp Lys Gly Pro Ala Arg Leu Leu Trp Lys Gly Glu Gly Ala
            20                  25                  30

```
Val Val Ile Gln Asp Asn Ser Glu Ile Lys Val Val Pro Arg Arg Lys
        35                  40                  45

Val Lys Ile Ile Arg Asp Tyr Gly Lys Arg Met Ala Gly Asp Asp Cys
    50                  55                  60

Val Ala Gly Arg Gln Asp Glu Asp
65                  70


<210> SEQ ID NO 28
<211> LENGTH: 13
<212> TYPE: PRT
<213> ORGANISM: Human immunodeficiency virus 1

<400> SEQUENCE: 28

Glu Glu Val Gly Phe Pro Val Lys Pro Gln Val Pro Leu
1               5                   10


<210> SEQ ID NO 29
<211> LENGTH: 13
<212> TYPE: PRT
<213> ORGANISM: Human immunodeficiency virus 1

<400> SEQUENCE: 29

Glu Glu Val Gly Phe Pro Val Arg Pro Gln Val Pro Leu
1               5                   10


<210> SEQ ID NO 30
<211> LENGTH: 36
<212> TYPE: PRT
<213> ORGANISM: Human immunodeficiency virus 1

<400> SEQUENCE: 30

Glu Glu Val Gly Phe Pro Val Lys Pro Gln Val Pro Leu Arg Pro Met
1               5                   10                  15

Thr Phe Lys Gly Ala Leu Asp Leu Ser His Phe Leu Arg Glu Lys Gly
            20                  25                  30

Gly Leu Glu Gly
        35


<210> SEQ ID NO 31
<211> LENGTH: 36
<212> TYPE: PRT
<213> ORGANISM: Human immunodeficiency virus 1

<400> SEQUENCE: 31

Glu Glu Val Gly Phe Pro Val Arg Pro Gln Val Pro Leu Arg Pro Met
1               5                   10                  15

Thr Tyr Lys Gly Ala Leu Asp Leu Ser His Phe Leu Lys Glu Lys Gly
            20                  25                  30

Gly Leu Glu Gly
        35


<210> SEQ ID NO 32
<211> LENGTH: 32
<212> TYPE: PRT
<213> ORGANISM: Human immunodeficiency virus 1

<400> SEQUENCE: 32

Thr Gln Gly Tyr Phe Pro Asp Trp Gln Asn Tyr Thr Pro Gly Pro Gly
1               5                   10                  15

Thr Arg Tyr Pro Leu Thr Phe Gly Trp Cys Phe Lys Leu Val Pro Val
            20                  25                  30
```

<210> SEQ ID NO 33
<211> LENGTH: 32
<212> TYPE: PRT
<213> ORGANISM: Human immunodeficiency virus 1

<400> SEQUENCE: 33

Thr Gln Gly Phe Phe Pro Asp Trp Gln Asn Tyr Thr Pro Gly Pro Gly
1 5 10 15

Ile Arg Phe Pro Leu Thr Phe Gly Trp Cys Phe Lys Leu Val Pro Leu
20 25 30

<210> SEQ ID NO 34

<400> SEQUENCE: 34

000

<210> SEQ ID NO 35
<211> LENGTH: 92
<212> TYPE: PRT
<213> ORGANISM: Human immunodeficiency virus 1

<400> SEQUENCE: 35

Glu Gly Cys Arg Gln Ile Leu Gly Gln Leu Gln Pro Ser Leu Gln Thr
1 5 10 15

Gly Ser Glu Glu Leu Arg Ser Leu Tyr Asn Thr Val Ala Thr Leu Tyr
20 25 30

Cys Val His Gln Arg Ile Glu Ile Lys Asp Thr Lys Glu Ala Leu Asp
35 40 45

Lys Ile Glu Glu Glu Gln Asn Lys Ser Lys Lys Lys Ala Gln Gln Ala
50 55 60

Ala Ala Asp Thr Gly His Ser Asn Gln Val Ser Gln Asn Tyr Pro Ile
65 70 75 80

Val Gln Asn Ile Gln Gly Gln Met Val His Gln Ala
85 90

<210> SEQ ID NO 36
<211> LENGTH: 131
<212> TYPE: PRT
<213> ORGANISM: Human immunodeficiency virus 1

<400> SEQUENCE: 36

Val Thr Asn Ser Ala Thr Ile Met Met Gln Arg Gly Asn Phe Arg Asn
1 5 10 15

Gln Arg Lys Ile Val Lys Cys Phe Asn Cys Gly Lys Glu Gly His Thr
20 25 30

Ala Arg Asn Cys Arg Ala Pro Arg Lys Lys Gly Cys Trp Lys Cys Gly
35 40 45

Lys Glu Gly His Gln Met Lys Asp Cys Thr Glu Arg Gln Ala Asn Phe
50 55 60

Leu Gly Lys Ile Trp Pro Ser Tyr Lys Gly Arg Pro Gly Asn Phe Leu
65 70 75 80

Gln Ser Arg Pro Glu Pro Thr Ala Pro Pro Glu Glu Ser Phe Arg Ser
85 90 95

Gly Val Glu Thr Thr Thr Pro Pro Gln Lys Gln Glu Pro Ile Asp Lys
100 105 110

Glu Leu Tyr Pro Leu Thr Ser Leu Arg Ser Leu Phe Gly Asn Asp Pro
115 120 125

```
Ser Ser Gln
    130


<210> SEQ ID NO 37
<211> LENGTH: 55
<212> TYPE: PRT
<213> ORGANISM: Human immunodeficiency virus 1

<400> SEQUENCE: 37

Phe Phe Arg Glu Asp Leu Ala Phe Leu Gln Gly Lys Ala Arg Glu Phe
1               5                   10                  15

Ser Ser Glu Gln Thr Arg Ala Asn Ser Pro Thr Arg Arg Glu Leu Gln
            20                  25                  30

Val Trp Gly Arg Asp Asn Asn Ser Pro Ser Glu Ala Gly Ala Asp Arg
        35                  40                  45

Gln Gly Thr Val Ser Phe Asn
    50                  55


<210> SEQ ID NO 38
<211> LENGTH: 11
<212> TYPE: PRT
<213> ORGANISM: Human immunodeficiency virus 1

<400> SEQUENCE: 38

Ile Leu Ile Glu Ile Cys Gly His Lys Ala Ile
1               5                   10


<210> SEQ ID NO 39
<211> LENGTH: 46
<212> TYPE: PRT
<213> ORGANISM: Human immunodeficiency virus 1

<400> SEQUENCE: 39

Lys Ile Leu Glu Pro Phe Arg Lys Gln Asn Pro Asp Ile Val Ile Tyr
1               5                   10                  15

Gln Tyr Met Asp Asp Leu Tyr Val Gly Ser Asp Leu Glu Ile Gly Gln
            20                  25                  30

His Arg Thr Lys Ile Glu Glu Leu Arg Gln His Leu Leu Arg
        35                  40                  45


<210> SEQ ID NO 40
<211> LENGTH: 109
<212> TYPE: PRT
<213> ORGANISM: Human immunodeficiency virus 1

<400> SEQUENCE: 40

Gln Leu Cys Lys Leu Leu Arg Gly Thr Lys Ala Leu Thr Glu Val Ile
1               5                   10                  15

Pro Leu Thr Glu Glu Ala Glu Leu Glu Leu Ala Glu Asn Arg Glu Ile
            20                  25                  30

Leu Lys Glu Pro Val His Gly Val Tyr Tyr Asp Pro Ser Lys Asp Leu
        35                  40                  45

Ile Ala Glu Ile Gln Lys Gln Gly Gln Gly Gln Trp Thr Tyr Gln Ile
    50                  55                  60

Tyr Gln Glu Pro Phe Lys Asn Leu Lys Thr Gly Lys Tyr Ala Arg Met
65                  70                  75                  80

Arg Gly Ala His Thr Asn Asp Val Lys Gln Leu Thr Glu Ala Val Gln
                85                  90                  95

Lys Ile Thr Thr Glu Ser Ile Val Ile Trp Gly Lys Thr
```

100                 105

<210> SEQ ID NO 41
<211> LENGTH: 75
<212> TYPE: PRT
<213> ORGANISM: Human immunodeficiency virus 1

<400> SEQUENCE: 41

Gly Lys Ala Gly Tyr Val Thr Asn Arg Gly Arg Gln Lys Val Val Thr
1               5                   10                  15

Leu Thr Asp Thr Thr Asn Gln Lys Thr Glu Leu Gln Ala Ile Tyr Leu
            20                  25                  30

Ala Leu Gln Asp Ser Gly Leu Glu Val Asn Ile Val Thr Asp Ser Gln
        35                  40                  45

Tyr Ala Leu Gly Ile Ile Gln Ala Gln Pro Asp Gln Ser Glu Ser Glu
    50                  55                  60

Leu Val Asn Gln Ile Ile Glu Gln Leu Ile Lys
65                  70                  75

<210> SEQ ID NO 42
<211> LENGTH: 38
<212> TYPE: PRT
<213> ORGANISM: Human immunodeficiency virus 1

<400> SEQUENCE: 42

Ala Gly Ile Arg Lys Val Leu Phe Leu Asp Gly Ile Asp Lys Ala Gln
1               5                   10                  15

Asp Glu His Glu Lys Tyr His Ser Asn Trp Arg Ala Met Ala Ser Asp
            20                  25                  30

Phe Asn Leu Pro Pro Val
        35

<210> SEQ ID NO 43
<211> LENGTH: 12
<212> TYPE: PRT
<213> ORGANISM: Human immunodeficiency virus 1

<400> SEQUENCE: 43

Ile His Thr Asp Asn Gly Ser Asn Phe Thr Gly Ala
1               5                   10

<210> SEQ ID NO 44
<211> LENGTH: 11
<212> TYPE: PRT
<213> ORGANISM: Human immunodeficiency virus 1

<400> SEQUENCE: 44

Thr Asp Ile Gln Thr Lys Glu Leu Gln Lys Gln
1               5                   10

<210> SEQ ID NO 45
<211> LENGTH: 63
<212> TYPE: PRT
<213> ORGANISM: Human immunodeficiency virus 1

<400> SEQUENCE: 45

Met Gly Gly Lys Trp Ser Lys Ser Ser Val Ile Gly Trp Pro Thr Val
1               5                   10                  15

Arg Glu Arg Met Arg Arg Ala Glu Pro Ala Ala Asp Arg Val Gly Ala
            20                  25                  30

Ala Ser Arg Asp Leu Glu Lys His Gly Ala Ile Thr Ser Ser Asn Thr

```
        35                  40                  45

Ala Ala Thr Asn Ala Ala Cys Ala Trp Leu Glu Ala Gln Glu Glu
    50                  55                  60


<210> SEQ ID NO 46
<211> LENGTH: 17
<212> TYPE: PRT
<213> ORGANISM: Human immunodeficiency virus 1

<400> SEQUENCE: 46

Leu Ile His Ser Gln Arg Arg Gln Asp Ile Leu Asp Leu Trp Ile Tyr
1               5                   10                  15

His


<210> SEQ ID NO 47
<211> LENGTH: 57
<212> TYPE: PRT
<213> ORGANISM: Human immunodeficiency virus 1

<400> SEQUENCE: 47

Pro Asp Lys Ile Glu Glu Ala Asn Lys Gly Glu Asn Thr Ser Leu Leu
1               5                   10                  15

His Pro Val Ser Leu His Gly Met Asp Asp Pro Glu Arg Glu Val Leu
            20                  25                  30

Glu Trp Arg Phe Asp Ser Arg Leu Ala Phe His His Val Ala Arg Glu
        35                  40                  45

Leu His Pro Glu Tyr Phe Lys Asn Cys
    50                  55


<210> SEQ ID NO 48
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Ala Ala
1


<210> SEQ ID NO 49
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Ala Tyr
1


<210> SEQ ID NO 50
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
```

<400> SEQUENCE: 50

Ala Ala Xaa
1

<210> SEQ ID NO 51
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 51

Gln Glu Glu
1

<210> SEQ ID NO 52
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 52

Lys Ile Leu
1

<210> SEQ ID NO 53
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 53

Leu Ile Lys
1

<210> SEQ ID NO 54
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 54

Pro Pro Val
1

<210> SEQ ID NO 55
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 55

Ser Glu Gly
1

<210> SEQ ID NO 56

<400> SEQUENCE: 56

000

<210> SEQ ID NO 57
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 57

Gly Gly Ser
1

<210> SEQ ID NO 58
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 58

Gly Ser Gly
1

<210> SEQ ID NO 59
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 59

Gly Gly Gly Ser
1

<210> SEQ ID NO 60
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 60

Arg Ala Lys Arg
1

<210> SEQ ID NO 61
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 61

Arg Glu Lys Arg
1

<210> SEQ ID NO 62
<211> LENGTH: 4
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 62

Arg Arg Lys Arg
1

<210> SEQ ID NO 63
<211> LENGTH: 19
<212> TYPE: PRT
<213> ORGANISM: Porcine teschovirus 1

<400> SEQUENCE: 63

Ala Thr Asn Phe Ser Leu Leu Lys Gln Ala Gly Asp Val Glu Glu Asn
1 5 10 15

Pro Gly Pro

<210> SEQ ID NO 64
<211> LENGTH: 24
<212> TYPE: PRT
<213> ORGANISM: Foot-and-mouth disease virus

<400> SEQUENCE: 64

Ala Pro Val Lys Gln Thr Leu Asn Phe Asp Leu Leu Lys Leu Ala Gly
1 5 10 15

Asp Val Glu Ser Asn Pro Gly Pro
20

<210> SEQ ID NO 65
<211> LENGTH: 28
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 65

Arg Ala Lys Arg Ala Pro Val Lys Gln Thr Leu Asn Phe Asp Leu Leu
1 5 10 15

Lys Leu Ala Gly Asp Val Glu Ser Asn Pro Gly Pro
20 25

<210> SEQ ID NO 66
<211> LENGTH: 20
<212> TYPE: PRT
<213> ORGANISM: Equine rhinitis A virus

<400> SEQUENCE: 66

Gln Cys Thr Asn Tyr Ala Leu Leu Lys Leu Ala Gly Asp Val Glu Ser
1 5 10 15

Asn Pro Gly Pro
20

<210> SEQ ID NO 67
<211> LENGTH: 18
<212> TYPE: PRT
<213> ORGANISM: Thosea asigna virus

<400> SEQUENCE: 67

Glu Gly Arg Gly Ser Leu Leu Thr Cys Gly Asp Val Glu Glu Asn Pro
1 5 10 15

Gly Pro

<210> SEQ ID NO 68

<400> SEQUENCE: 68

000

<210> SEQ ID NO 69

<400> SEQUENCE: 69

000

<210> SEQ ID NO 70
<211> LENGTH: 337
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Ile Ser Pro Arg Thr Leu Asn Ala Trp Val Lys Val Val Glu Glu Lys
1               5                   10                  15

Ala Phe Ser Pro Glu Val Ile Pro Met Phe Ser Ala Leu Ser Glu Gly
            20                  25                  30

Ala Thr Pro Gln Asp Leu Asn Thr Met Leu Asn Thr Val Gly Gly His
        35                  40                  45

Gln Ala Ala Met Gln Met Leu Lys Glu Thr Ile Asn Glu Glu Ala Ala
    50                  55                  60

Glu Trp Asp Arg Leu His Pro Val His Ala Gly Pro Ile Ala Pro Gly
65                  70                  75                  80

Gln Met Arg Glu Pro Arg Gly Ser Asp Ile Ala Gly Thr Thr Ser Thr
                85                  90                  95

Leu Gln Glu Gln Ile Gly Trp Met Thr Asn Asn Pro Pro Ile Pro Val
            100                 105                 110

Gly Glu Ile Tyr Lys Arg Trp Ile Ile Leu Gly Leu Asn Lys Ile Val
        115                 120                 125

Arg Met Tyr Ser Pro Thr Ser Ile Leu Asp Ile Arg Gln Gly Pro Lys
    130                 135                 140

Glu Pro Phe Arg Asp Tyr Val Asp Arg Phe Tyr Lys Thr Leu Arg Ala
145                 150                 155                 160

Glu Gln Ala Ser Gln Glu Val Lys Asn Trp Met Thr Glu Thr Leu Leu
                165                 170                 175

Val Gln Asn Ala Asn Pro Asp Cys Lys Thr Ile Leu Lys Ala Leu Gly
            180                 185                 190

Pro Ala Ala Thr Leu Glu Glu Met Met Thr Ala Cys Gln Gly Val Gly
        195                 200                 205

Gly Pro Gly His Lys Ala Arg Val Leu Ala Glu Ala Met Ser Gln Met
    210                 215                 220

Ala Ala Arg Ala Ser Val Leu Ser Gly Gly Glu Leu Asp Arg Trp Glu
225                 230                 235                 240

Lys Ile Arg Leu Arg Pro Gly Gly Lys Lys Lys Tyr Arg Leu Lys His
                245                 250                 255

Ile Val Trp Ala Ser Arg Glu Leu Glu Arg Phe Ala Val Asn Pro Gly
            260                 265                 270

Leu Leu Glu Thr Ala Ala Ala Lys Glu Lys Val Tyr Leu Ala Trp Val
        275                 280                 285
```

Pro Ala His Lys Gly Ile Gly Gly Asn Glu Gln Val Asp Lys Leu Val
    290                 295                 300

Ser Thr Gln Gly Tyr Phe Pro Asp Trp Gln Asn Tyr Thr Pro Gly Pro
305                 310                 315                 320

Gly Thr Arg Tyr Pro Leu Thr Phe Gly Trp Cys Phe Lys Leu Val Pro
                325                 330                 335

Val

<210> SEQ ID NO 71
<211> LENGTH: 339
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 71

Leu Ser Pro Arg Thr Leu Asn Ala Trp Val Lys Val Ile Glu Glu Lys
1               5                   10                  15

Ala Phe Ser Pro Glu Val Ile Pro Met Phe Thr Ala Leu Ser Glu Gly
            20                  25                  30

Ala Thr Pro His Asp Leu Asn Thr Met Leu Asn Thr Ile Gly Gly His
        35                  40                  45

Gln Ala Ala Met Gln Met Leu Lys Asp Thr Ile Asn Glu Glu Ala Ala
    50                  55                  60

Glu Trp Asp Arg Val His Pro Val His Ala Gly Pro Val Ala Pro Gly
65                  70                  75                  80

Gln Met Arg Asp Pro Arg Gly Ser Asp Ile Ala Gly Ser Thr Ser Thr
                85                  90                  95

Leu Gln Glu Gln Ile Ala Trp Met Thr Asn Asn Pro Pro Ile Pro Val
            100                 105                 110

Gly Asp Ile Tyr Lys Arg Trp Ile Ile Met Gly Leu Asn Lys Ile Val
        115                 120                 125

Arg Met Tyr Ser Pro Val Ser Ile Leu Asp Ile Lys Gln Gly Pro Lys
    130                 135                 140

Glu Pro Phe Arg Asp Tyr Val Asp Arg Phe Tyr Arg Thr Leu Arg Ala
145                 150                 155                 160

Glu Gln Ala Ser Gln Asp Val Lys Asn Trp Met Thr Glu Thr Leu Leu
                165                 170                 175

Val Gln Asn Ser Asn Pro Asp Cys Lys Thr Ile Leu Lys Ala Leu Gly
            180                 185                 190

Pro Gly Ala Thr Leu Glu Glu Met Met Ser Ala Cys Gln Gly Val Gly
        195                 200                 205

Gly Pro Ser His Lys Ala Arg Val Leu Ala Glu Ala Met Cys Gln Ala
    210                 215                 220

Ala Met Ala Ala Arg Ala Ser Ile Leu Ser Gly Gly Lys Leu Asp Lys
225                 230                 235                 240

Trp Glu Lys Ile Arg Leu Arg Pro Gly Gly Arg Lys Lys Tyr Lys Leu
                245                 250                 255

Lys His Leu Val Trp Ala Ser Arg Glu Leu Glu Arg Phe Ala Leu Asn
            260                 265                 270

Pro Gly Leu Leu Glu Thr Thr Gln Gly Phe Phe Pro Asp Trp Gln Asn
        275                 280                 285

Tyr Thr Pro Gly Pro Gly Ile Arg Phe Pro Leu Thr Phe Gly Trp Cys
    290                 295                 300

```
Phe Lys Leu Val Pro Leu Leu Ile Lys Lys Glu Lys Ile Tyr Leu Ala
305                 310                 315                 320

Trp Val Pro Ala His Lys Gly Ile Gly Gly Asn Glu Gln Ile Asp Lys
                325                 330                 335

Leu Val Ser


<210> SEQ ID NO 72
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Trp Gly Phe Thr Thr Pro Asp Lys Lys His Gln Lys Glu Pro Pro Phe
1               5                   10                  15

Leu Trp Met Gly Tyr Glu Leu His Pro Asp Lys Trp Thr Val Gln Pro
            20                  25                  30

Ile Val Leu Pro Glu Lys Asp Ser Trp Thr Val Asn Asp Ile Gln Lys
        35                  40                  45

Leu Val Gly Lys Leu Asn Trp Ala Ser Gln Ile Tyr Pro Gly Ile Lys
    50                  55                  60

Val Ala Ala Gln Glu Glu Glu Glu Val Gly Phe Pro Val Lys Pro Gln
65                  70                  75                  80

Val Pro Leu Arg Pro Met Thr Phe Lys Gly Ala Leu Asp Leu Ser His
                85                  90                  95

Phe Leu Arg Glu Lys Gly Gly Leu Glu Gly Phe Pro Gln Ile Thr Leu
            100                 105                 110

Trp Gln Arg Pro Leu Val Thr Ile Lys Ile Gly Gly Gln Leu Lys Glu
        115                 120                 125

Ala Leu Leu Asp Thr Gly Ala Asp Asp Thr Val Leu Glu Glu Met Asn
    130                 135                 140

Leu Pro Gly Arg Trp Lys Pro Lys Met Ile Gly Gly Ile Gly Gly Phe
145                 150                 155                 160

Ile Lys Val Arg Gln Tyr Asp Gln Gly Thr Val Leu Val Gly Pro Thr
                165                 170                 175

Pro Val Asn Ile Ile Gly Arg Asn Leu Leu Thr Gln Ile Gly Cys Thr
            180                 185                 190

Leu Asn Phe Pro Ile Ser Pro Ile Glu Thr Val Pro Val Lys Leu Lys
        195                 200                 205

Pro Gly Met Asp Gly Pro Lys Val Lys Gln Trp Pro Leu Thr Glu Glu
    210                 215                 220

Lys Ile Lys Ala Leu Val Glu Ile Cys Thr Glu Met Glu Lys Glu Gly
225                 230                 235                 240

Lys Ile Ser Lys Ile Gly Pro Glu Asn Pro Tyr Asn Thr Pro Val Phe
                245                 250                 255

Ala Ile Lys Lys Lys Asp Ser Thr Lys Trp Arg Lys Leu Val Asp Phe
            260                 265                 270

Arg Glu Leu Asn Lys Arg Thr Gln Asp Phe Trp Glu Val Gln Leu Gly
        275                 280                 285

Ile Pro His Pro Ala Gly Leu Lys Lys Lys Lys Ser Val Thr Val Leu
    290                 295                 300

Asp Val Gly Asp Ala Tyr Phe Ser Val Pro Leu Asp Lys Asp Phe Arg
305                 310                 315                 320
```

```
Lys Tyr Thr Ala Phe Thr Ile Pro Ser Ile Asn Asn Glu Thr Pro Gly
            325                 330                 335

Ile Arg Tyr Gln Tyr Asn Val Leu Pro Gln Gly Trp Lys Gly Ser Pro
        340                 345                 350

Ala Ile Phe Gln Ser Ser Met Thr
    355                 360
```

<210> SEQ ID NO 73
<211> LENGTH: 356
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 73

```
Leu Pro Gln Ile Thr Leu Trp Gln Arg Pro Ile Val Thr Ile Lys Ile
1               5                   10                  15

Gly Gly Gln Ile Lys Glu Ala Leu Leu Asp Thr Gly Ala Asp Asp Thr
            20                  25                  30

Val Leu Glu Asp Met Asn Leu Pro Gly Lys Trp Lys Pro Lys Met Ile
        35                  40                  45

Gly Gly Ile Gly Gly Phe Ile Lys Val Lys Gln Tyr Asp Gln Glu Glu
    50                  55                  60

Val Gly Phe Pro Val Arg Pro Gln Val Pro Leu Arg Pro Met Thr Tyr
65                  70                  75                  80

Lys Gly Ala Leu Asp Leu Ser His Phe Leu Lys Glu Lys Gly Gly Leu
                85                  90                  95

Glu Gly Trp Gly Leu Thr Thr Pro Asp Lys Lys His Gln Lys Asp Pro
            100                 105                 110

Pro Phe Leu Trp Met Gly Tyr Glu Leu His Pro Asp Arg Trp Thr Val
        115                 120                 125

Gln Pro Ile Glu Leu Pro Glu Lys Glu Ser Trp Thr Val Asn Asp Ile
    130                 135                 140

Gln Lys Leu Ile Gly Lys Leu Asn Trp Ala Ser Gln Ile Tyr Ala Gly
145                 150                 155                 160

Ile Lys Val Lys Gly Thr Val Leu Ile Gly Pro Thr Pro Val Asn Ile
                165                 170                 175

Ile Gly Arg Asn Leu Leu Thr Gln Leu Gly Cys Thr Leu Asn Phe Pro
            180                 185                 190

Ile Ser Pro Ile Asp Thr Val Pro Val Lys Leu Lys Pro Gly Met Asp
        195                 200                 205

Gly Pro Arg Val Lys Gln Trp Pro Leu Thr Glu Glu Lys Ile Lys Ala
    210                 215                 220

Leu Ile Glu Ile Cys Thr Glu Met Glu Lys Glu Gly Lys Ile Ser Arg
225                 230                 235                 240

Ile Gly Pro Glu Asn Pro Tyr Asn Thr Pro Ile Phe Ala Ile Lys Lys
                245                 250                 255

Lys Asp Gly Thr Lys Trp Arg Lys Leu Val Asp Phe Arg Glu Leu Asn
            260                 265                 270

Lys Lys Thr Gln Asp Phe Trp Glu Val Gln Leu Gly Ile Pro His Pro
        275                 280                 285

Ser Gly Leu Lys Lys Lys Lys Ser Val Thr Val Leu Asp Ile Gly Asp
    290                 295                 300

Ala Tyr Phe Ser Val Pro Leu Asp Lys Glu Phe Arg Lys Tyr Thr Ala
305                 310                 315                 320
```

Phe Thr Val Pro Ser Thr Asn Asn Glu Thr Pro Gly Val Arg Tyr Gln
325 330 335

Tyr Asn Val Leu Pro Met Gly Trp Lys Gly Ser Pro Ala Ile Phe Gln
340 345 350

Cys Ser Met Thr
355

<210> SEQ ID NO 74
<211> LENGTH: 335
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

Pro Lys Phe Lys Leu Pro Ile Gln Lys Glu Thr Trp Glu Thr Trp Trp
1 5 10 15

Thr Glu Tyr Trp Gln Ala Thr Trp Ile Pro Glu Trp Glu Phe Val Asn
20 25 30

Thr Pro Pro Leu Val Lys Leu Trp Tyr Gln Leu Glu Lys Glu Pro Ile
35 40 45

Val Gly Ala Glu Thr Phe Tyr Val Asp Gly Ala Ala Asn Arg Glu Thr
50 55 60

Lys Ile Thr Lys Ile Gln Asn Phe Arg Val Tyr Tyr Arg Asp Ser Arg
65 70 75 80

Asp Pro Leu Trp Lys Gly Pro Ala Lys Leu Leu Trp Lys Gly Glu Gly
85 90 95

Ala Val Val Ile Gln Asp Asn Ser Asp Ile Lys Val Val Pro Arg Arg
100 105 110

Lys Ala Lys Ile Ile Arg Asp Tyr Gly Lys Gln Met Ala Gly Asp Asp
115 120 125

Cys Val Ala Ser Arg Gln Asp Glu Asp Val Ala Lys Glu Ile Val Ala
130 135 140

Ser Cys Asp Lys Cys Gln Leu Lys Gly Glu Ala Met His Gly Gln Val
145 150 155 160

Asp Cys Ser Pro Gly Ile Trp Gln Leu Asp Cys Thr His Leu Glu Gly
165 170 175

Lys Ile Ile Leu Val Ala Val His Val Ala Ser Gly Tyr Ile Glu Ala
180 185 190

Glu Val Ile Pro Ala Glu Thr Gly Gln Glu Thr Ala Tyr Phe Leu Leu
195 200 205

Lys Leu Ala Gly Arg Trp Pro Val Lys Thr Glu Glu Val Gly Phe Pro
210 215 220

Val Lys Pro Gln Val Pro Leu Arg Pro Met Thr Phe Lys Gly Ala Leu
225 230 235 240

Asp Leu Ser His Phe Leu Arg Glu Lys Gly Gly Leu Glu Gly Thr Val
245 250 255

Lys Ala Ala Cys Trp Trp Ala Gly Ile Lys Gln Glu Phe Gly Ile Pro
260 265 270

Tyr Asn Pro Gln Ser Gln Gly Val Val Glu Ser Met Asn Lys Glu Leu
275 280 285

Lys Lys Ile Ile Gly Gln Val Arg Asp Gln Ala Glu His Leu Lys Thr
290 295 300

Ala Val Gln Met Ala Val Phe Ile His Asn Phe Lys Arg Lys Gly Gly

```
305                 310                 315                 320

Ile Gly Gly Tyr Ser Ala Gly Glu Arg Ile Val Asp Ile Ile Ala
                325                 330                 335


<210> SEQ ID NO 75
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Pro Lys Phe Arg Leu Pro Ile Gln Lys Glu Thr Trp Asp Thr Trp Trp
1               5                   10                  15

Thr Asp Tyr Trp Gln Ala Thr Trp Ile Pro Glu Trp Glu Phe Thr Asn
            20                  25                  30

Thr Pro Pro Leu Val Lys Leu Trp Tyr Gln Leu Glu Thr Glu Pro Ile
        35                  40                  45

Ala Gly Val Glu Thr Phe Tyr Val Asp Gly Ala Ser Asn Arg Glu Thr
    50                  55                  60

Lys Glu Glu Val Gly Phe Pro Val Arg Pro Gln Val Pro Leu Arg Pro
65                  70                  75                  80

Met Thr Tyr Lys Gly Ala Leu Asp Leu Ser His Phe Leu Lys Glu Lys
                85                  90                  95

Gly Gly Leu Glu Gly Val Ala Lys Glu Ile Val Ala Cys Cys Asp Lys
            100                 105                 110

Cys Gln Leu Lys Gly Glu Ala Ile His Gly Gln Val Asp Cys Ser Pro
        115                 120                 125

Gly Val Trp Gln Leu Asp Cys Thr His Leu Glu Gly Lys Val Ile Leu
    130                 135                 140

Val Ala Val His Val Ala Ser Gly Tyr Ile Glu Ala Glu Ile Ile Pro
145                 150                 155                 160

Thr Glu Thr Gly Gln Glu Thr Ala Tyr Phe Ile Leu Lys Leu Ala Gly
                165                 170                 175

Arg Trp Pro Val Thr Thr Ile Thr Lys Leu Gln Asn Phe Arg Val Tyr
            180                 185                 190

Tyr Arg Asp Asn Arg Asp Pro Leu Trp Lys Gly Pro Ala Arg Leu Leu
        195                 200                 205

Trp Lys Gly Glu Gly Ala Val Val Ile Gln Asp Asn Ser Glu Ile Lys
    210                 215                 220

Val Val Pro Arg Arg Lys Val Lys Ile Ile Arg Asp Tyr Gly Lys Arg
225                 230                 235                 240

Met Ala Gly Asp Asp Cys Val Ala Gly Arg Gln Asp Glu Asp Ala Val
                245                 250                 255

Lys Ala Ala Cys Trp Trp Ala Gly Val Lys Gln Glu Phe Gly Ile Pro
            260                 265                 270

Tyr Asn Thr Gln Ser Gln Gly Val Val Glu Ser Met Asn Asn Glu Leu
        275                 280                 285

Lys Lys Ile Ile Gly Gln Ile Arg Asp Gln Ala Glu His Leu Lys Thr
    290                 295                 300

Ala Val Gln Met Ala Val Leu Ile His Asn Phe Lys Arg Lys Gly Gly
305                 310                 315                 320

Ile Gly Glu Tyr Ser Ala Gly Glu Arg Ile Ile Asp Ile Ile Ala
                325                 330                 335
```

<210> SEQ ID NO 76
<211> LENGTH: 340
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 76

```
Thr Gln Gly Tyr Phe Pro Asp Trp Gln Asn Tyr Thr Pro Gly Pro Gly
1               5                   10                  15

Thr Arg Tyr Pro Leu Thr Phe Gly Trp Cys Phe Lys Leu Val Pro Val
            20                  25                  30

Lys Glu Lys Val Tyr Leu Ala Trp Val Pro Ala His Lys Gly Ile Gly
        35                  40                  45

Gly Asn Glu Gln Val Asp Lys Leu Val Ser Ala Ala Tyr Met Ala Ala
    50                  55                  60

Arg Ala Ser Val Leu Ser Gly Gly Glu Leu Asp Arg Trp Glu Lys Ile
65                  70                  75                  80

Arg Leu Arg Pro Gly Gly Lys Lys Lys Tyr Arg Leu Lys His Ile Val
                85                  90                  95

Trp Ala Ser Arg Glu Leu Glu Arg Phe Ala Val Asn Pro Gly Leu Leu
            100                 105                 110

Glu Thr Ser Glu Gly Ile Ser Pro Arg Thr Leu Asn Ala Trp Val Lys
        115                 120                 125

Val Val Glu Glu Lys Ala Phe Ser Pro Glu Val Ile Pro Met Phe Ser
    130                 135                 140

Ala Leu Ser Glu Gly Ala Thr Pro Gln Asp Leu Asn Thr Met Leu Asn
145                 150                 155                 160

Thr Val Gly Gly His Gln Ala Ala Met Gln Met Leu Lys Glu Thr Ile
                165                 170                 175

Asn Glu Glu Ala Ala Glu Trp Asp Arg Leu His Pro Val His Ala Gly
            180                 185                 190

Pro Ile Ala Pro Gly Gln Met Arg Glu Pro Arg Gly Ser Asp Ile Ala
        195                 200                 205

Gly Thr Thr Ser Thr Leu Gln Glu Gln Ile Gly Trp Met Thr Asn Asn
    210                 215                 220

Pro Pro Ile Pro Val Gly Glu Ile Tyr Lys Arg Trp Ile Ile Leu Gly
225                 230                 235                 240

Leu Asn Lys Ile Val Arg Met Tyr Ser Pro Thr Ser Ile Leu Asp Ile
                245                 250                 255

Arg Gln Gly Pro Lys Glu Pro Phe Arg Asp Tyr Val Asp Arg Phe Tyr
            260                 265                 270

Lys Thr Leu Arg Ala Glu Gln Ala Ser Gln Glu Val Lys Asn Trp Met
        275                 280                 285

Thr Glu Thr Leu Leu Val Gln Asn Ala Asn Pro Asp Cys Lys Thr Ile
    290                 295                 300

Leu Lys Ala Leu Gly Pro Ala Ala Thr Leu Glu Glu Met Met Thr Ala
305                 310                 315                 320

Cys Gln Gly Val Gly Gly Pro Gly His Lys Ala Arg Val Leu Ala Glu
                325                 330                 335

Ala Met Ser Gln
            340
```

<210> SEQ ID NO 77

<211> LENGTH: 334
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 77

Leu Ser Pro Arg Thr Leu Asn Ala Trp Val Lys Val Ile Glu Glu Lys
1 5 10 15

Ala Phe Ser Pro Glu Val Ile Pro Met Phe Thr Ala Leu Ser Glu Gly
20 25 30

Ala Thr Pro His Asp Leu Asn Thr Met Leu Asn Thr Ile Gly Gly His
35 40 45

Gln Ala Ala Met Gln Met Leu Lys Asp Thr Ile Asn Glu Glu Ala Ala
50 55 60

Glu Trp Asp Arg Val His Pro Val His Ala Gly Pro Val Ala Pro Gly
65 70 75 80

Gln Met Arg Asp Pro Arg Gly Ser Asp Ile Ala Gly Ser Thr Ser Thr
85 90 95

Leu Gln Glu Gln Ile Ala Trp Met Thr Asn Asn Pro Pro Ile Pro Val
100 105 110

Gly Asp Ile Tyr Lys Arg Trp Ile Ile Met Gly Leu Asn Lys Ile Val
115 120 125

Arg Met Tyr Ser Pro Val Ser Ile Leu Asp Ile Lys Gln Gly Pro Lys
130 135 140

Glu Pro Phe Arg Asp Tyr Val Asp Arg Phe Tyr Arg Thr Leu Arg Ala
145 150 155 160

Glu Gln Ala Ser Gln Asp Val Lys Asn Trp Met Thr Glu Thr Leu Leu
165 170 175

Val Gln Asn Ser Asn Pro Asp Cys Lys Thr Ile Leu Lys Ala Leu Gly
180 185 190

Pro Gly Ala Thr Leu Glu Glu Met Met Ser Ala Cys Gln Gly Val Gly
195 200 205

Gly Pro Ser His Lys Ala Arg Val Leu Ala Glu Ala Met Cys Gln Thr
210 215 220

Gln Gly Phe Phe Pro Asp Trp Gln Asn Tyr Thr Pro Gly Pro Gly Ile
225 230 235 240

Arg Phe Pro Leu Thr Phe Gly Trp Cys Phe Lys Leu Val Pro Leu Met
245 250 255

Ala Ala Arg Ala Ser Ile Leu Ser Gly Gly Lys Leu Asp Lys Trp Glu
260 265 270

Lys Ile Arg Leu Arg Pro Gly Gly Arg Lys Lys Tyr Lys Leu Lys His
275 280 285

Leu Val Trp Ala Ser Arg Glu Leu Glu Arg Phe Ala Leu Asn Pro Gly
290 295 300

Leu Leu Glu Thr Lys Glu Lys Ile Tyr Leu Ala Trp Val Pro Ala His
305 310 315 320

Lys Gly Ile Gly Gly Asn Glu Gln Ile Asp Lys Leu Val Ser
325 330

<210> SEQ ID NO 78
<211> LENGTH: 360
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 78

Phe Pro Gln Ile Thr Leu Trp Gln Arg Pro Leu Val Thr Ile Lys Ile
1 5 10 15

Gly Gly Gln Leu Lys Glu Ala Leu Leu Asp Thr Gly Ala Asp Asp Thr
20 25 30

Val Leu Glu Glu Met Asn Leu Pro Gly Arg Trp Lys Pro Lys Met Ile
35 40 45

Gly Gly Ile Gly Gly Phe Ile Lys Val Arg Gln Tyr Asp Gln Ala Ala
50 55 60

Tyr Glu Glu Val Gly Phe Pro Val Lys Pro Gln Val Pro Leu Arg Pro
65 70 75 80

Met Thr Phe Lys Gly Ala Leu Asp Leu Ser His Phe Leu Arg Glu Lys
85 90 95

Gly Gly Leu Glu Gly Ala Ala Trp Gly Phe Thr Thr Pro Asp Lys Lys
100 105 110

His Gln Lys Glu Pro Pro Phe Leu Trp Met Gly Tyr Glu Leu His Pro
115 120 125

Asp Lys Trp Thr Val Gln Pro Ile Val Leu Pro Glu Lys Asp Ser Trp
130 135 140

Thr Val Asn Asp Ile Gln Lys Leu Val Gly Lys Leu Asn Trp Ala Ser
145 150 155 160

Gln Ile Tyr Pro Gly Ile Lys Val Gly Thr Val Leu Val Gly Pro Thr
165 170 175

Pro Val Asn Ile Ile Gly Arg Asn Leu Leu Thr Gln Ile Gly Cys Thr
180 185 190

Leu Asn Phe Pro Ile Ser Pro Ile Glu Thr Val Pro Val Lys Leu Lys
195 200 205

Pro Gly Met Asp Gly Pro Lys Val Lys Gln Trp Pro Leu Thr Glu Glu
210 215 220

Lys Ile Lys Ala Leu Val Glu Ile Cys Thr Glu Met Glu Lys Glu Gly
225 230 235 240

Lys Ile Ser Lys Ile Gly Pro Glu Asn Pro Tyr Asn Thr Pro Val Phe
245 250 255

Ala Ile Lys Lys Lys Asp Ser Thr Lys Trp Arg Lys Leu Val Asp Phe
260 265 270

Arg Glu Leu Asn Lys Arg Thr Gln Asp Phe Trp Glu Val Gln Leu Gly
275 280 285

Ile Pro His Pro Ala Gly Leu Lys Lys Lys Lys Ser Val Thr Val Leu
290 295 300

Asp Val Gly Asp Ala Tyr Phe Ser Val Pro Leu Asp Lys Asp Phe Arg
305 310 315 320

Lys Tyr Thr Ala Phe Thr Ile Pro Ser Ile Asn Asn Glu Thr Pro Gly
325 330 335

Ile Arg Tyr Gln Tyr Asn Val Leu Pro Gln Gly Trp Lys Gly Ser Pro
340 345 350

Ala Ile Phe Gln Ser Ser Met Thr
355 360

<210> SEQ ID NO 79
<211> LENGTH: 358
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 79

Trp Gly Leu Thr Thr Pro Asp Lys Lys His Gln Lys Asp Pro Pro Phe
1 5 10 15

Leu Trp Met Gly Tyr Glu Leu His Pro Asp Arg Trp Thr Val Gln Pro
20 25 30

Ile Glu Leu Pro Glu Lys Glu Ser Trp Thr Val Asn Asp Ile Gln Lys
35 40 45

Leu Ile Gly Lys Leu Asn Trp Ala Ser Gln Ile Tyr Ala Gly Ile Lys
50 55 60

Val Glu Glu Val Gly Phe Pro Val Arg Pro Gln Val Pro Leu Arg Pro
65 70 75 80

Met Thr Tyr Lys Gly Ala Leu Asp Leu Ser His Phe Leu Lys Glu Lys
85 90 95

Gly Gly Leu Glu Gly Leu Pro Gln Ile Thr Leu Trp Gln Arg Pro Ile
100 105 110

Val Thr Ile Lys Ile Gly Gly Gln Ile Lys Glu Ala Leu Leu Asp Thr
115 120 125

Gly Ala Asp Asp Thr Val Leu Glu Asp Met Asn Leu Pro Gly Lys Trp
130 135 140

Lys Pro Lys Met Ile Gly Gly Ile Gly Gly Phe Ile Lys Val Lys Gln
145 150 155 160

Tyr Asp Gln Ala Ala Ala Gly Thr Val Leu Ile Gly Pro Thr Pro Val
165 170 175

Asn Ile Ile Gly Arg Asn Leu Leu Thr Gln Leu Gly Cys Thr Leu Asn
180 185 190

Phe Pro Ile Ser Pro Ile Asp Thr Val Pro Val Lys Leu Lys Pro Gly
195 200 205

Met Asp Gly Pro Arg Val Lys Gln Trp Pro Leu Thr Glu Glu Lys Ile
210 215 220

Lys Ala Leu Ile Glu Ile Cys Thr Glu Met Glu Lys Glu Gly Lys Ile
225 230 235 240

Ser Arg Ile Gly Pro Glu Asn Pro Tyr Asn Thr Pro Ile Phe Ala Ile
245 250 255

Lys Lys Lys Asp Gly Thr Lys Trp Arg Lys Leu Val Asp Phe Arg Glu
260 265 270

Leu Asn Lys Lys Thr Gln Asp Phe Trp Glu Val Gln Leu Gly Ile Pro
275 280 285

His Pro Ser Gly Leu Lys Lys Lys Lys Ser Val Thr Val Leu Asp Ile
290 295 300

Gly Asp Ala Tyr Phe Ser Val Pro Leu Asp Lys Glu Phe Arg Lys Tyr
305 310 315 320

Thr Ala Phe Thr Val Pro Ser Thr Asn Asn Glu Thr Pro Gly Val Arg
325 330 335

Tyr Gln Tyr Asn Val Leu Pro Met Gly Trp Lys Gly Ser Pro Ala Ile
340 345 350

Phe Gln Cys Ser Met Thr
355

<210> SEQ ID NO 80
<211> LENGTH: 342
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 80

Ile Thr Lys Ile Gln Asn Phe Arg Val Tyr Tyr Arg Asp Ser Arg Asp
1 5 10 15

Pro Leu Trp Lys Gly Pro Ala Lys Leu Leu Trp Lys Gly Glu Gly Ala
20 25 30

Val Val Ile Gln Asp Asn Ser Asp Ile Lys Val Val Pro Arg Arg Lys
35 40 45

Ala Lys Ile Ile Arg Asp Tyr Gly Lys Gln Met Ala Gly Asp Asp Cys
50 55 60

Val Ala Ser Arg Gln Asp Glu Asp Ala Ala Tyr Glu Glu Glu Glu Val
65 70 75 80

Gly Phe Pro Val Lys Pro Gln Val Pro Leu Arg Pro Met Thr Phe Lys
85 90 95

Gly Ala Leu Asp Leu Ser His Phe Leu Arg Glu Lys Gly Gly Leu Glu
100 105 110

Gly Leu Ile Pro Lys Phe Lys Leu Pro Ile Gln Lys Glu Thr Trp Glu
115 120 125

Thr Trp Trp Thr Glu Tyr Trp Gln Ala Thr Trp Ile Pro Glu Trp Glu
130 135 140

Phe Val Asn Thr Pro Pro Leu Val Lys Leu Trp Tyr Gln Leu Glu Lys
145 150 155 160

Glu Pro Ile Val Gly Ala Glu Thr Phe Tyr Val Asp Gly Ala Ala Asn
165 170 175

Arg Glu Thr Lys Val Ala Lys Glu Ile Val Ala Ser Cys Asp Lys Cys
180 185 190

Gln Leu Lys Gly Glu Ala Met His Gly Gln Val Asp Cys Ser Pro Gly
195 200 205

Ile Trp Gln Leu Asp Cys Thr His Leu Glu Gly Lys Ile Ile Leu Val
210 215 220

Ala Val His Val Ala Ser Gly Tyr Ile Glu Ala Glu Val Ile Pro Ala
225 230 235 240

Glu Thr Gly Gln Glu Thr Ala Tyr Phe Leu Leu Lys Leu Ala Gly Arg
245 250 255

Trp Pro Val Lys Thr Thr Val Lys Ala Ala Cys Trp Trp Ala Gly Ile
260 265 270

Lys Gln Glu Phe Gly Ile Pro Tyr Asn Pro Gln Ser Gln Gly Val Val
275 280 285

Glu Ser Met Asn Lys Glu Leu Lys Lys Ile Ile Gly Gln Val Arg Asp
290 295 300

Gln Ala Glu His Leu Lys Thr Ala Val Gln Met Ala Val Phe Ile His
305 310 315 320

Asn Phe Lys Arg Lys Gly Gly Ile Gly Gly Tyr Ser Ala Gly Glu Arg
325 330 335

Ile Val Asp Ile Ile Ala
340

<210> SEQ ID NO 81
<211> LENGTH: 335
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 81

Glu Glu Val Gly Phe Pro Val Arg Pro Gln Val Pro Leu Arg Pro Met
1 5 10 15

Thr Tyr Lys Gly Ala Leu Asp Leu Ser His Phe Leu Lys Glu Lys Gly
20 25 30

Gly Leu Glu Gly Ile Thr Lys Leu Gln Asn Phe Arg Val Tyr Tyr Arg
35 40 45

Asp Asn Arg Asp Pro Leu Trp Lys Gly Pro Ala Arg Leu Leu Trp Lys
50 55 60

Gly Glu Gly Ala Val Val Ile Gln Asp Asn Ser Glu Ile Lys Val Val
65 70 75 80

Pro Arg Arg Lys Val Lys Ile Ile Arg Asp Tyr Gly Lys Arg Met Ala
85 90 95

Gly Asp Asp Cys Val Ala Gly Arg Gln Asp Glu Asp Pro Lys Phe Arg
100 105 110

Leu Pro Ile Gln Lys Glu Thr Trp Asp Thr Trp Trp Thr Asp Tyr Trp
115 120 125

Gln Ala Thr Trp Ile Pro Glu Trp Glu Phe Thr Asn Thr Pro Pro Leu
130 135 140

Val Lys Leu Trp Tyr Gln Leu Glu Thr Glu Pro Ile Ala Gly Val Glu
145 150 155 160

Thr Phe Tyr Val Asp Gly Ala Ser Asn Arg Glu Thr Lys Ala Val Lys
165 170 175

Ala Ala Cys Trp Trp Ala Gly Val Lys Gln Glu Phe Gly Ile Pro Tyr
180 185 190

Asn Thr Gln Ser Gln Gly Val Val Glu Ser Met Asn Asn Glu Leu Lys
195 200 205

Lys Ile Ile Gly Gln Ile Arg Asp Gln Ala Glu His Leu Lys Thr Ala
210 215 220

Val Gln Met Ala Val Leu Ile His Asn Phe Lys Arg Lys Gly Gly Ile
225 230 235 240

Gly Glu Tyr Ser Ala Gly Glu Arg Ile Ile Asp Ile Ile Ala Val Ala
245 250 255

Lys Glu Ile Val Ala Cys Cys Asp Lys Cys Gln Leu Lys Gly Glu Ala
260 265 270

Ile His Gly Gln Val Asp Cys Ser Pro Gly Val Trp Gln Leu Asp Cys
275 280 285

Thr His Leu Glu Gly Lys Val Ile Leu Val Ala Val His Val Ala Ser
290 295 300

Gly Tyr Ile Glu Ala Glu Ile Ile Pro Thr Glu Thr Gly Gln Glu Thr
305 310 315 320

Ala Tyr Phe Ile Leu Lys Leu Ala Gly Arg Trp Pro Val Thr Thr
325 330 335

<210> SEQ ID NO 82
<211> LENGTH: 353
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 82

Thr Val Lys Ala Ala Cys Trp Trp Ala Gly Ile Lys Gln Glu Phe Gly

-continued 1 5 10 15

Ile Pro Tyr Asn Pro Gln Ser Gln Gly Val Val Glu Ser Met Asn Lys
20 25 30

Glu Leu Lys Lys Ile Ile Gly Gln Val Arg Asp Gln Ala Glu His Leu
35 40 45

Lys Thr Ala Val Gln Met Ala Val Phe Ile His Asn Phe Lys Arg Lys
50 55 60

Gly Gly Ile Gly Gly Tyr Ser Ala Gly Glu Arg Ile Val Asp Ile Ile
65 70 75 80

Ala Ile Ser Pro Arg Thr Leu Asn Ala Trp Val Lys Val Val Glu Glu
85 90 95

Lys Ala Phe Ser Pro Glu Val Ile Pro Met Phe Ser Ala Leu Ser Glu
100 105 110

Gly Ala Thr Pro Gln Asp Leu Asn Thr Met Leu Asn Thr Val Gly Gly
115 120 125

His Gln Ala Ala Met Gln Met Leu Lys Glu Thr Ile Asn Glu Glu Ala
130 135 140

Ala Glu Trp Asp Arg Leu His Pro Val His Ala Gly Pro Ile Ala Pro
145 150 155 160

Gly Gln Met Arg Glu Pro Arg Gly Ser Asp Ile Ala Gly Thr Thr Ser
165 170 175

Thr Leu Gln Glu Gln Ile Gly Trp Met Thr Asn Asn Pro Pro Ile Pro
180 185 190

Val Gly Glu Ile Tyr Lys Arg Trp Ile Ile Leu Gly Leu Asn Lys Ile
195 200 205

Val Arg Met Tyr Ser Pro Thr Ser Ile Leu Asp Ile Arg Gln Gly Pro
210 215 220

Lys Glu Pro Phe Arg Asp Tyr Val Asp Arg Phe Tyr Lys Thr Leu Arg
225 230 235 240

Ala Glu Gln Ala Ser Gln Glu Val Lys Asn Trp Met Thr Glu Thr Leu
245 250 255

Leu Val Gln Asn Ala Asn Pro Asp Cys Lys Thr Ile Leu Lys Ala Leu
260 265 270

Gly Pro Ala Ala Thr Leu Glu Glu Met Met Thr Ala Cys Gln Gly Val
275 280 285

Gly Gly Pro Gly His Lys Ala Arg Val Leu Ala Glu Ala Met Ser Gln
290 295 300

Lys Glu Pro Ile Val Gly Ala Glu Thr Phe Tyr Val Asp Gly Ala Ala
305 310 315 320

Asn Arg Glu Thr Lys Ala Ala Lys Glu Lys Val Tyr Leu Ala Trp Val
325 330 335

Pro Ala His Lys Gly Ile Gly Gly Asn Glu Gln Val Asp Lys Leu Val
340 345 350

Ser

<210> SEQ ID NO 83
<211> LENGTH: 351
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 83

Leu Ser Pro Arg Thr Leu Asn Ala Trp Val Lys Val Ile Glu Glu Lys

-continued

```
1               5                   10                  15

Ala Phe Ser Pro Glu Val Ile Pro Met Phe Thr Ala Leu Ser Glu Gly
            20                  25                  30

Ala Thr Pro His Asp Leu Asn Thr Met Leu Asn Thr Ile Gly Gly His
        35                  40                  45

Gln Ala Ala Met Gln Met Leu Lys Asp Thr Ile Asn Glu Glu Ala Ala
    50                  55                  60

Glu Trp Asp Arg Val His Pro Val His Ala Gly Pro Val Ala Pro Gly
65                  70                  75                  80

Gln Met Arg Asp Pro Arg Gly Ser Asp Ile Ala Gly Ser Thr Ser Thr
                85                  90                  95

Leu Gln Glu Gln Ile Ala Trp Met Thr Asn Asn Pro Pro Ile Pro Val
            100                 105                 110

Gly Asp Ile Tyr Lys Arg Trp Ile Ile Met Gly Leu Asn Lys Ile Val
        115                 120                 125

Arg Met Tyr Ser Pro Val Ser Ile Leu Asp Ile Lys Gln Gly Pro Lys
    130                 135                 140

Glu Pro Phe Arg Asp Tyr Val Asp Arg Phe Tyr Arg Thr Leu Arg Ala
145                 150                 155                 160

Glu Gln Ala Ser Gln Asp Val Lys Asn Trp Met Thr Glu Thr Leu Leu
                165                 170                 175

Val Gln Asn Ser Asn Pro Asp Cys Lys Thr Ile Leu Lys Ala Leu Gly
            180                 185                 190

Pro Gly Ala Thr Leu Glu Glu Met Met Ser Ala Cys Gln Gly Val Gly
        195                 200                 205

Gly Pro Ser His Lys Ala Arg Val Leu Ala Glu Ala Met Cys Gln Lys
    210                 215                 220

Glu Lys Ile Tyr Leu Ala Trp Val Pro Ala His Lys Gly Ile Gly Gly
225                 230                 235                 240

Asn Glu Gln Ile Asp Lys Leu Val Ser Thr Glu Pro Ile Ala Gly Val
                245                 250                 255

Glu Thr Phe Tyr Val Asp Gly Ala Ser Asn Arg Glu Thr Lys Ala Val
            260                 265                 270

Lys Ala Ala Cys Trp Trp Ala Gly Val Lys Gln Glu Phe Gly Ile Pro
        275                 280                 285

Tyr Asn Thr Gln Ser Gln Gly Val Val Glu Ser Met Asn Asn Glu Leu
    290                 295                 300

Lys Lys Ile Ile Gly Gln Ile Arg Asp Gln Ala Glu His Leu Lys Thr
305                 310                 315                 320

Ala Val Gln Met Ala Val Leu Ile His Asn Phe Lys Arg Lys Gly Gly
                325                 330                 335

Ile Gly Glu Tyr Ser Ala Gly Glu Arg Ile Ile Asp Ile Ile Ala
            340                 345                 350
```

<210> SEQ ID NO 84
<211> LENGTH: 358
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 84

```
Thr Val Lys Ala Ala Cys Trp Trp Ala Gly Ile Lys Gln Glu Phe Gly
1               5                   10                  15
```

-continued

Ile Pro Tyr Asn Pro Gln Ser Gln Gly Val Val Glu Ser Met Asn Lys
20 25 30

Glu Leu Lys Lys Ile Ile Gly Gln Val Arg Asp Gln Ala Glu His Leu
35 40 45

Lys Thr Ala Val Gln Met Ala Val Phe Ile His Asn Phe Lys Arg Lys
50 55 60

Gly Gly Ile Gly Gly Tyr Ser Ala Gly Glu Arg Ile Val Asp Ile Ile
65 70 75 80

Ala Lys Glu Pro Ile Val Gly Ala Glu Thr Phe Tyr Val Asp Gly Ala
85 90 95

Ala Asn Arg Glu Thr Lys Ala Ala Ala Ile Ser Pro Arg Thr Leu Asn
100 105 110

Ala Trp Val Lys Val Val Glu Glu Lys Ala Phe Ser Pro Glu Val Ile
115 120 125

Pro Met Phe Ser Ala Leu Ser Glu Gly Ala Thr Pro Gln Asp Leu Asn
130 135 140

Thr Met Leu Asn Thr Val Gly Gly His Gln Ala Ala Met Gln Met Leu
145 150 155 160

Lys Glu Thr Ile Asn Glu Glu Ala Ala Glu Trp Asp Arg Leu His Pro
165 170 175

Val His Ala Gly Pro Ile Ala Pro Gly Gln Met Arg Glu Pro Arg Gly
180 185 190

Ser Asp Ile Ala Gly Thr Thr Ser Thr Leu Gln Glu Gln Ile Gly Trp
195 200 205

Met Thr Asn Asn Pro Pro Ile Pro Val Gly Glu Ile Tyr Lys Arg Trp
210 215 220

Ile Ile Leu Gly Leu Asn Lys Ile Val Arg Met Tyr Ser Pro Thr Ser
225 230 235 240

Ile Leu Asp Ile Arg Gln Gly Pro Lys Glu Pro Phe Arg Asp Tyr Val
245 250 255

Asp Arg Phe Tyr Lys Thr Leu Arg Ala Glu Gln Ala Ser Gln Glu Val
260 265 270

Lys Asn Trp Met Thr Glu Thr Leu Leu Val Gln Asn Ala Asn Pro Asp
275 280 285

Cys Lys Thr Ile Leu Lys Ala Leu Gly Pro Ala Ala Thr Leu Glu Glu
290 295 300

Met Met Thr Ala Cys Gln Gly Val Gly Gly Pro Gly His Lys Ala Arg
305 310 315 320

Val Leu Ala Glu Ala Met Ser Gln Ala Ala Ala Lys Glu Lys Val Tyr
325 330 335

Leu Ala Trp Val Pro Ala His Lys Gly Ile Gly Gly Asn Glu Gln Val
340 345 350

Asp Lys Leu Val Ser Leu
355

<210> SEQ ID NO 85
<211> LENGTH: 353
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 85

Leu Ser Pro Arg Thr Leu Asn Ala Trp Val Lys Val Ile Glu Glu Lys
1 5 10 15

```
Ala Phe Ser Pro Glu Val Ile Pro Met Phe Thr Ala Leu Ser Glu Gly
            20                  25                  30

Ala Thr Pro His Asp Leu Asn Thr Met Leu Asn Thr Ile Gly Gly His
        35                  40                  45

Gln Ala Ala Met Gln Met Leu Lys Asp Thr Ile Asn Glu Glu Ala Ala
    50                  55                  60

Glu Trp Asp Arg Val His Pro Val His Ala Gly Pro Val Ala Pro Gly
65                  70                  75                  80

Gln Met Arg Asp Pro Arg Gly Ser Asp Ile Ala Gly Ser Thr Ser Thr
                85                  90                  95

Leu Gln Glu Gln Ile Ala Trp Met Thr Asn Asn Pro Pro Ile Pro Val
            100                 105                 110

Gly Asp Ile Tyr Lys Arg Trp Ile Ile Met Gly Leu Asn Lys Ile Val
        115                 120                 125

Arg Met Tyr Ser Pro Val Ser Ile Leu Asp Ile Lys Gln Gly Pro Lys
    130                 135                 140

Glu Pro Phe Arg Asp Tyr Val Asp Arg Phe Tyr Arg Thr Leu Arg Ala
145                 150                 155                 160

Glu Gln Ala Ser Gln Asp Val Lys Asn Trp Met Thr Glu Thr Leu Leu
                165                 170                 175

Val Gln Asn Ser Asn Pro Asp Cys Lys Thr Ile Leu Lys Ala Leu Gly
            180                 185                 190

Pro Gly Ala Thr Leu Glu Glu Met Met Ser Ala Cys Gln Gly Val Gly
        195                 200                 205

Gly Pro Ser His Lys Ala Arg Val Leu Ala Glu Ala Met Cys Gln Ala
    210                 215                 220

Val Lys Ala Ala Cys Trp Trp Ala Gly Val Lys Gln Glu Phe Gly Ile
225                 230                 235                 240

Pro Tyr Asn Thr Gln Ser Gln Gly Val Val Glu Ser Met Asn Asn Glu
                245                 250                 255

Leu Lys Lys Ile Ile Gly Gln Ile Arg Asp Gln Ala Glu His Leu Lys
            260                 265                 270

Thr Ala Val Gln Met Ala Val Leu Ile His Asn Phe Lys Arg Lys Gly
        275                 280                 285

Gly Ile Gly Glu Tyr Ser Ala Gly Glu Arg Ile Ile Asp Ile Ile Ala
    290                 295                 300

Thr Glu Pro Ile Ala Gly Val Glu Thr Phe Tyr Val Asp Gly Ala Ser
305                 310                 315                 320

Asn Arg Glu Thr Lys Ala Ala Lys Glu Lys Ile Tyr Leu Ala Trp Val
                325                 330                 335

Pro Ala His Lys Gly Ile Gly Gly Asn Glu Gln Ile Asp Lys Leu Val
            340                 345                 350

Ser
```

<210> SEQ ID NO 86
<211> LENGTH: 361
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 86

```
Ile Thr Lys Ile Gln Asn Phe Arg Val Tyr Tyr Arg Asp Ser Arg Asp
1               5                   10                  15
```

Pro Leu Trp Lys Gly Pro Ala Lys Leu Leu Trp Lys Gly Glu Gly Ala
20 25 30

Val Val Ile Gln Asp Asn Ser Asp Ile Lys Val Val Pro Arg Arg Lys
35 40 45

Ala Lys Ile Ile Arg Asp Tyr Gly Lys Gln Met Ala Gly Asp Asp Cys
50 55 60

Val Ala Ser Arg Gln Asp Glu Asp Val Ala Lys Glu Ile Val Ala Ser
65 70 75 80

Cys Asp Lys Cys Gln Leu Lys Gly Glu Ala Met His Gly Gln Val Asp
85 90 95

Cys Ser Pro Gly Ile Trp Gln Leu Asp Cys Thr His Leu Glu Gly Lys
100 105 110

Ile Ile Leu Val Ala Val His Val Ala Ser Gly Tyr Ile Glu Ala Glu
115 120 125

Val Ile Pro Ala Glu Thr Gly Gln Glu Thr Ala Tyr Phe Leu Leu Lys
130 135 140

Leu Ala Gly Arg Trp Pro Val Lys Thr Gly Thr Val Leu Val Gly Pro
145 150 155 160

Thr Pro Val Asn Ile Ile Gly Arg Asn Leu Leu Thr Gln Ile Gly Cys
165 170 175

Thr Leu Asn Phe Pro Ile Ser Pro Ile Glu Thr Val Pro Val Lys Leu
180 185 190

Lys Pro Gly Met Asp Gly Pro Lys Val Lys Gln Trp Pro Leu Thr Glu
195 200 205

Glu Lys Ile Lys Ala Leu Val Glu Ile Cys Thr Glu Met Glu Lys Glu
210 215 220

Gly Lys Ile Ser Lys Ile Gly Pro Glu Asn Pro Tyr Asn Thr Pro Val
225 230 235 240

Phe Ala Ile Lys Lys Lys Asp Ser Thr Lys Trp Arg Lys Leu Val Asp
245 250 255

Phe Arg Glu Leu Asn Lys Arg Thr Gln Asp Phe Trp Glu Val Gln Leu
260 265 270

Gly Ile Pro His Pro Ala Gly Leu Lys Lys Lys Lys Ser Val Thr Val
275 280 285

Leu Asp Val Gly Asp Ala Tyr Phe Ser Val Pro Leu Asp Lys Asp Phe
290 295 300

Arg Lys Tyr Thr Ala Phe Thr Ile Pro Ser Ile Asn Asn Glu Thr Pro
305 310 315 320

Gly Ile Arg Tyr Gln Tyr Asn Val Leu Pro Gln Gly Trp Lys Gly Ser
325 330 335

Pro Ala Ile Phe Gln Ser Ser Met Thr Gln Glu Glu Glu Glu Val Gly
340 345 350

Phe Pro Val Lys Pro Gln Val Pro Leu
355 360

<210> SEQ ID NO 87
<211> LENGTH: 364
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 87

Val Ala Lys Glu Ile Val Ala Cys Cys Asp Lys Cys Gln Leu Lys Gly

```
1               5                   10                  15

Glu Ala Ile His Gly Gln Val Asp Cys Ser Pro Gly Val Trp Gln Leu
            20                  25                  30

Asp Cys Thr His Leu Glu Gly Lys Val Ile Leu Val Ala Val His Val
        35                  40                  45

Ala Ser Gly Tyr Ile Glu Ala Glu Ile Ile Pro Thr Glu Thr Gly Gln
    50                  55                  60

Glu Thr Ala Tyr Phe Ile Leu Lys Leu Ala Gly Arg Trp Pro Val Thr
65                  70                  75                  80

Thr Ile Thr Lys Leu Gln Asn Phe Arg Val Tyr Tyr Arg Asp Asn Arg
                85                  90                  95

Asp Pro Leu Trp Lys Gly Pro Ala Arg Leu Leu Trp Lys Gly Glu Gly
            100                 105                 110

Ala Val Val Ile Gln Asp Asn Ser Glu Ile Lys Val Val Pro Arg Arg
        115                 120                 125

Lys Val Lys Ile Ile Arg Asp Tyr Gly Lys Arg Met Ala Gly Asp Asp
    130                 135                 140

Cys Val Ala Gly Arg Gln Asp Glu Asp Gly Thr Val Leu Ile Gly Pro
145                 150                 155                 160

Thr Pro Val Asn Ile Ile Gly Arg Asn Leu Leu Thr Gln Leu Gly Cys
                165                 170                 175

Thr Leu Asn Phe Pro Ile Ser Pro Ile Asp Thr Val Pro Val Lys Leu
            180                 185                 190

Lys Pro Gly Met Asp Gly Pro Arg Val Lys Gln Trp Pro Leu Thr Glu
        195                 200                 205

Glu Lys Ile Lys Ala Leu Ile Glu Ile Cys Thr Glu Met Glu Lys Glu
    210                 215                 220

Gly Lys Ile Ser Arg Ile Gly Pro Glu Asn Pro Tyr Asn Thr Pro Ile
225                 230                 235                 240

Phe Ala Ile Lys Lys Lys Asp Gly Thr Lys Trp Arg Lys Leu Val Asp
                245                 250                 255

Phe Arg Glu Leu Asn Lys Lys Thr Gln Asp Phe Trp Glu Val Gln Leu
            260                 265                 270

Gly Ile Pro His Pro Ser Gly Leu Lys Lys Lys Lys Ser Val Thr Val
        275                 280                 285

Leu Asp Ile Gly Asp Ala Tyr Phe Ser Val Pro Leu Asp Lys Glu Phe
    290                 295                 300

Arg Lys Tyr Thr Ala Phe Thr Val Pro Ser Thr Asn Asn Glu Thr Pro
305                 310                 315                 320

Gly Val Arg Tyr Gln Tyr Asn Val Leu Pro Met Gly Trp Lys Gly Ser
                325                 330                 335

Pro Ala Ile Phe Gln Cys Ser Met Thr Lys Ile Leu Gln Glu Glu Glu
            340                 345                 350

Glu Val Gly Phe Pro Val Arg Pro Gln Val Pro Leu
        355                 360
```

<210> SEQ ID NO 88
<211> LENGTH: 365
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 88

```
Ile Thr Lys Ile Gln Asn Phe Arg Val Tyr Tyr Arg Asp Ser Arg Asp
1               5                   10                  15

Pro Leu Trp Lys Gly Pro Ala Lys Leu Leu Trp Lys Gly Glu Gly Ala
            20                  25                  30

Val Val Ile Gln Asp Asn Ser Asp Ile Lys Val Val Pro Arg Arg Lys
        35                  40                  45

Ala Lys Ile Ile Arg Asp Tyr Gly Lys Gln Met Ala Gly Asp Asp Cys
    50                  55                  60

Val Ala Ser Arg Gln Asp Glu Asp Ala Ala Ala Ile Gly Thr Val Leu
65                  70                  75                  80

Val Gly Pro Thr Pro Val Asn Ile Ile Gly Arg Asn Leu Leu Thr Gln
                85                  90                  95

Ile Gly Cys Thr Leu Asn Phe Pro Ile Ser Pro Ile Glu Thr Val Pro
            100                 105                 110

Val Lys Leu Lys Pro Gly Met Asp Gly Pro Lys Val Lys Gln Trp Pro
        115                 120                 125

Leu Thr Glu Glu Lys Ile Lys Ala Leu Val Glu Ile Cys Thr Glu Met
    130                 135                 140

Glu Lys Glu Gly Lys Ile Ser Lys Ile Gly Pro Glu Asn Pro Tyr Asn
145                 150                 155                 160

Thr Pro Val Phe Ala Ile Lys Lys Lys Asp Ser Thr Lys Trp Arg Lys
                165                 170                 175

Leu Val Asp Phe Arg Glu Leu Asn Lys Arg Thr Gln Asp Phe Trp Glu
            180                 185                 190

Val Gln Leu Gly Ile Pro His Pro Ala Gly Leu Lys Lys Lys Lys Ser
        195                 200                 205

Val Thr Val Leu Asp Val Gly Asp Ala Tyr Phe Ser Val Pro Leu Asp
    210                 215                 220

Lys Asp Phe Arg Lys Tyr Thr Ala Phe Thr Ile Pro Ser Ile Asn Asn
225                 230                 235                 240

Glu Thr Pro Gly Ile Arg Tyr Gln Tyr Asn Val Leu Pro Gln Gly Trp
                245                 250                 255

Lys Gly Ser Pro Ala Ile Phe Gln Ser Ser Met Thr Val Ala Lys Glu
            260                 265                 270

Ile Val Ala Ser Cys Asp Lys Cys Gln Leu Lys Gly Glu Ala Met His
        275                 280                 285

Gly Gln Val Asp Cys Ser Pro Gly Ile Trp Gln Leu Asp Cys Thr His
    290                 295                 300

Leu Glu Gly Lys Ile Ile Leu Val Ala Val His Val Ala Ser Gly Tyr
305                 310                 315                 320

Ile Glu Ala Glu Val Ile Pro Ala Glu Thr Gly Gln Glu Thr Ala Tyr
                325                 330                 335

Phe Leu Leu Lys Leu Ala Gly Arg Trp Pro Val Lys Thr Gln Glu Glu
            340                 345                 350

Glu Glu Val Gly Phe Pro Val Lys Pro Gln Val Pro Leu
        355                 360                 365
```

<210> SEQ ID NO 89
<211> LENGTH: 363
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

```
Gly Thr Val Leu Ile Gly Pro Thr Pro Val Asn Ile Ile Gly Arg Asn
1               5                   10                  15

Leu Leu Thr Gln Leu Gly Cys Thr Leu Asn Phe Pro Ile Ser Pro Ile
            20                  25                  30

Asp Thr Val Pro Val Lys Leu Lys Pro Gly Met Asp Gly Pro Arg Val
        35                  40                  45

Lys Gln Trp Pro Leu Thr Glu Glu Lys Ile Lys Ala Leu Ile Glu Ile
    50                  55                  60

Cys Thr Glu Met Glu Lys Glu Gly Lys Ile Ser Arg Ile Gly Pro Glu
65                  70                  75                  80

Asn Pro Tyr Asn Thr Pro Ile Phe Ala Ile Lys Lys Lys Asp Gly Thr
                85                  90                  95

Lys Trp Arg Lys Leu Val Asp Phe Arg Glu Leu Asn Lys Lys Thr Gln
            100                 105                 110

Asp Phe Trp Glu Val Gln Leu Gly Ile Pro His Pro Ser Gly Leu Lys
        115                 120                 125

Lys Lys Lys Ser Val Thr Val Leu Asp Ile Gly Asp Ala Tyr Phe Ser
    130                 135                 140

Val Pro Leu Asp Lys Glu Phe Arg Lys Tyr Thr Ala Phe Thr Val Pro
145                 150                 155                 160

Ser Thr Asn Asn Glu Thr Pro Gly Val Arg Tyr Gln Tyr Asn Val Leu
                165                 170                 175

Pro Met Gly Trp Lys Gly Ser Pro Ala Ile Phe Gln Cys Ser Met Thr
            180                 185                 190

Ile Thr Lys Leu Gln Asn Phe Arg Val Tyr Tyr Arg Asp Asn Arg Asp
        195                 200                 205

Pro Leu Trp Lys Gly Pro Ala Arg Leu Leu Trp Lys Gly Glu Gly Ala
    210                 215                 220

Val Val Ile Gln Asp Asn Ser Glu Ile Lys Val Val Pro Arg Arg Lys
225                 230                 235                 240

Val Lys Ile Ile Arg Asp Tyr Gly Lys Arg Met Ala Gly Asp Asp Cys
                245                 250                 255

Val Ala Gly Arg Gln Asp Glu Asp Val Ala Lys Glu Ile Val Ala Cys
            260                 265                 270

Cys Asp Lys Cys Gln Leu Lys Gly Glu Ala Ile His Gly Gln Val Asp
        275                 280                 285

Cys Ser Pro Gly Val Trp Gln Leu Asp Cys Thr His Leu Glu Gly Lys
    290                 295                 300

Val Ile Leu Val Ala Val His Val Ala Ser Gly Tyr Ile Glu Ala Glu
305                 310                 315                 320

Ile Ile Pro Thr Glu Thr Gly Gln Glu Thr Ala Tyr Phe Ile Leu Lys
                325                 330                 335

Leu Ala Gly Arg Trp Pro Val Thr Thr Ala Ala Gln Glu Glu Glu Glu
            340                 345                 350

Val Gly Phe Pro Val Arg Pro Gln Val Pro Leu
        355                 360
```

<210> SEQ ID NO 90
<211> LENGTH: 391
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 90

Thr Val Lys Ala Ala Cys Trp Trp Ala Gly Ile Lys Gln Glu Phe Gly
1               5                   10                  15

Ile Pro Tyr Asn Pro Gln Ser Gln Gly Val Val Glu Ser Met Asn Lys
            20                  25                  30

Glu Leu Lys Lys Ile Ile Gly Gln Val Arg Asp Gln Ala Glu His Leu
        35                  40                  45

Lys Thr Ala Val Gln Met Ala Val Phe Ile His Asn Phe Lys Arg Lys
    50                  55                  60

Gly Gly Ile Gly Gly Ala Ala Ile Ser Pro Arg Thr Leu Asn Ala Trp
65                  70                  75                  80

Val Lys Val Val Glu Glu Lys Ala Phe Ser Pro Glu Val Ile Pro Met
                85                  90                  95

Phe Ser Ala Leu Ser Glu Gly Ala Thr Pro Gln Asp Leu Asn Thr Met
            100                 105                 110

Leu Asn Thr Val Gly Gly His Gln Ala Ala Met Gln Met Leu Lys Glu
        115                 120                 125

Thr Ile Asn Glu Glu Ala Ala Glu Trp Asp Arg Leu His Pro Val His
    130                 135                 140

Ala Gly Pro Ile Ala Pro Gly Gln Met Arg Glu Pro Arg Gly Ser Asp
145                 150                 155                 160

Ile Ala Gly Thr Thr Ser Thr Leu Gln Glu Gln Ile Gly Trp Met Thr
                165                 170                 175

Asn Asn Pro Pro Ile Pro Val Gly Glu Ile Tyr Lys Arg Trp Ile Ile
            180                 185                 190

Leu Gly Leu Asn Lys Ile Val Arg Met Tyr Ser Pro Thr Ser Ile Leu
        195                 200                 205

Asp Ile Arg Gln Gly Pro Lys Glu Pro Phe Arg Asp Tyr Val Asp Arg
    210                 215                 220

Phe Tyr Lys Thr Leu Arg Ala Glu Gln Ala Ser Gln Glu Val Lys Asn
225                 230                 235                 240

Trp Met Thr Glu Thr Leu Leu Val Gln Asn Ala Asn Pro Asp Cys Lys
                245                 250                 255

Thr Ile Leu Lys Ala Leu Gly Pro Ala Ala Thr Leu Glu Glu Met Met
            260                 265                 270

Thr Ala Cys Gln Gly Val Gly Gly Pro Gly His Lys Ala Arg Val Leu
        275                 280                 285

Ala Glu Ala Met Ser Gln Val Ala Lys Glu Ile Val Ala Ser Cys Asp
    290                 295                 300

Lys Cys Gln Leu Lys Gly Glu Ala Met His Gly Gln Val Asp Cys Ser
305                 310                 315                 320

Pro Gly Ile Trp Gln Leu Asp Cys Thr His Leu Glu Gly Lys Ile Ile
                325                 330                 335

Leu Val Ala Val His Val Ala Ser Gly Tyr Ile Glu Ala Glu Val Ile
            340                 345                 350

Pro Ala Glu Thr Gly Gln Glu Thr Ala Tyr Phe Leu Leu Lys Leu Ala
        355                 360                 365

Gly Arg Trp Pro Val Lys Thr Gln Glu Glu Glu Glu Val Gly Phe Pro
    370                 375                 380

Val Lys Pro Gln Val Pro Leu
385                 390

<210> SEQ ID NO 91

<211> LENGTH: 393
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 91

```
Ala Val Lys Ala Ala Cys Trp Trp Ala Gly Val Lys Gln Glu Phe Gly
1               5                   10                  15

Ile Pro Tyr Asn Thr Gln Ser Gln Gly Val Val Glu Ser Met Asn Asn
            20                  25                  30

Glu Leu Lys Lys Ile Ile Gly Gln Ile Arg Asp Gln Ala Glu His Leu
        35                  40                  45

Lys Thr Ala Val Gln Met Ala Val Leu Ile His Asn Phe Lys Arg Lys
    50                  55                  60

Gly Gly Ile Gly Glu Leu Ser Pro Arg Thr Leu Asn Ala Trp Val Lys
65                  70                  75                  80

Val Ile Glu Glu Lys Ala Phe Ser Pro Glu Val Ile Pro Met Phe Thr
                85                  90                  95

Ala Leu Ser Glu Gly Ala Thr Pro His Asp Leu Asn Thr Met Leu Asn
            100                 105                 110

Thr Ile Gly Gly His Gln Ala Ala Met Gln Met Leu Lys Asp Thr Ile
        115                 120                 125

Asn Glu Glu Ala Ala Glu Trp Asp Arg Val His Pro Val His Ala Gly
    130                 135                 140

Pro Val Ala Pro Gly Gln Met Arg Asp Pro Arg Gly Ser Asp Ile Ala
145                 150                 155                 160

Gly Ser Thr Ser Thr Leu Gln Glu Gln Ile Ala Trp Met Thr Asn Asn
                165                 170                 175

Pro Pro Ile Pro Val Gly Asp Ile Tyr Lys Arg Trp Ile Ile Met Gly
            180                 185                 190

Leu Asn Lys Ile Val Arg Met Tyr Ser Pro Val Ser Ile Leu Asp Ile
        195                 200                 205

Lys Gln Gly Pro Lys Glu Pro Phe Arg Asp Tyr Val Asp Arg Phe Tyr
    210                 215                 220

Arg Thr Leu Arg Ala Glu Gln Ala Ser Gln Asp Val Lys Asn Trp Met
225                 230                 235                 240

Thr Glu Thr Leu Leu Val Gln Asn Ser Asn Pro Asp Cys Lys Thr Ile
                245                 250                 255

Leu Lys Ala Leu Gly Pro Gly Ala Thr Leu Glu Glu Met Met Ser Ala
            260                 265                 270

Cys Gln Gly Val Gly Gly Pro Ser His Lys Ala Arg Val Leu Ala Glu
        275                 280                 285

Ala Met Cys Gln Val Thr Val Ala Lys Glu Ile Val Ala Cys Cys Asp
    290                 295                 300

Lys Cys Gln Leu Lys Gly Glu Ala Ile His Gly Gln Val Asp Cys Ser
305                 310                 315                 320

Pro Gly Val Trp Gln Leu Asp Cys Thr His Leu Glu Gly Lys Val Ile
                325                 330                 335

Leu Val Ala Val His Val Ala Ser Gly Tyr Ile Glu Ala Glu Ile Ile
            340                 345                 350

Pro Thr Glu Thr Gly Gln Glu Thr Ala Tyr Phe Ile Leu Lys Leu Ala
        355                 360                 365

Gly Arg Trp Pro Val Thr Thr Ala Ala Gln Glu Glu Glu Glu Val Gly
```

```
    370                 375                 380

Phe Pro Val Arg Pro Gln Val Pro Leu
385                 390


<210> SEQ ID NO 92
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Thr Val Lys Ala Ala Cys Trp Trp Ala Gly Ile Lys Gln Glu Phe Gly
1               5                   10                  15

Ile Pro Tyr Asn Pro Gln Ser Gln Gly Val Val Glu Ser Met Asn Lys
            20                  25                  30

Glu Leu Lys Lys Ile Ile Gly Gln Val Arg Asp Gln Ala Glu His Leu
        35                  40                  45

Lys Thr Ala Val Gln Met Ala Val Phe Ile His Asn Phe Lys Arg Lys
    50                  55                  60

Gly Gly Ile Gly Gly Val Ala Lys Glu Ile Val Ala Ser Cys Asp Lys
65                  70                  75                  80

Cys Gln Leu Lys Gly Glu Ala Met His Gly Gln Val Asp Cys Ser Pro
                85                  90                  95

Gly Ile Trp Gln Leu Asp Cys Thr His Leu Glu Gly Lys Ile Ile Leu
            100                 105                 110

Val Ala Val His Val Ala Ser Gly Tyr Ile Glu Ala Glu Val Ile Pro
        115                 120                 125

Ala Glu Thr Gly Gln Glu Thr Ala Tyr Phe Leu Leu Lys Leu Ala Gly
    130                 135                 140

Arg Trp Pro Val Lys Thr Ala Ala Ile Ser Pro Arg Thr Leu Asn Ala
145                 150                 155                 160

Trp Val Lys Val Val Glu Glu Lys Ala Phe Ser Pro Glu Val Ile Pro
                165                 170                 175

Met Phe Ser Ala Leu Ser Glu Gly Ala Thr Pro Gln Asp Leu Asn Thr
            180                 185                 190

Met Leu Asn Thr Val Gly Gly His Gln Ala Ala Met Gln Met Leu Lys
        195                 200                 205

Glu Thr Ile Asn Glu Glu Ala Ala Glu Trp Asp Arg Leu His Pro Val
    210                 215                 220

His Ala Gly Pro Ile Ala Pro Gly Gln Met Arg Glu Pro Arg Gly Ser
225                 230                 235                 240

Asp Ile Ala Gly Thr Thr Ser Thr Leu Gln Glu Gln Ile Gly Trp Met
                245                 250                 255

Thr Asn Asn Pro Pro Ile Pro Val Gly Glu Ile Tyr Lys Arg Trp Ile
            260                 265                 270

Ile Leu Gly Leu Asn Lys Ile Val Arg Met Tyr Ser Pro Thr Ser Ile
        275                 280                 285

Leu Asp Ile Arg Gln Gly Pro Lys Glu Pro Phe Arg Asp Tyr Val Asp
    290                 295                 300

Arg Phe Tyr Lys Thr Leu Arg Ala Glu Gln Ala Ser Gln Glu Val Lys
305                 310                 315                 320

Asn Trp Met Thr Glu Thr Leu Leu Val Gln Asn Ala Asn Pro Asp Cys
                325                 330                 335
```

Lys Thr Ile Leu Lys Ala Leu Gly Pro Ala Ala Thr Leu Glu Glu Met
340 345 350

Met Thr Ala Cys Gln Gly Val Gly Gly Pro Gly His Lys Ala Arg Val
355 360 365

Leu Ala Glu Ala Met Ser Gln Gln Glu Glu Glu Glu Val Gly Phe Pro
370 375 380

Val Lys Pro Gln Val Pro Leu
385 390

<210> SEQ ID NO 93
<211> LENGTH: 394
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 93

Leu Ser Pro Arg Thr Leu Asn Ala Trp Val Lys Val Ile Glu Glu Lys
1 5 10 15

Ala Phe Ser Pro Glu Val Ile Pro Met Phe Thr Ala Leu Ser Glu Gly
20 25 30

Ala Thr Pro His Asp Leu Asn Thr Met Leu Asn Thr Ile Gly Gly His
35 40 45

Gln Ala Ala Met Gln Met Leu Lys Asp Thr Ile Asn Glu Glu Ala Ala
50 55 60

Glu Trp Asp Arg Val His Pro Val His Ala Gly Pro Val Ala Pro Gly
65 70 75 80

Gln Met Arg Asp Pro Arg Gly Ser Asp Ile Ala Gly Ser Thr Ser Thr
85 90 95

Leu Gln Glu Gln Ile Ala Trp Met Thr Asn Asn Pro Pro Ile Pro Val
100 105 110

Gly Asp Ile Tyr Lys Arg Trp Ile Ile Met Gly Leu Asn Lys Ile Val
115 120 125

Arg Met Tyr Ser Pro Val Ser Ile Leu Asp Ile Lys Gln Gly Pro Lys
130 135 140

Glu Pro Phe Arg Asp Tyr Val Asp Arg Phe Tyr Arg Thr Leu Arg Ala
145 150 155 160

Glu Gln Ala Ser Gln Asp Val Lys Asn Trp Met Thr Glu Thr Leu Leu
165 170 175

Val Gln Asn Ser Asn Pro Asp Cys Lys Thr Ile Leu Lys Ala Leu Gly
180 185 190

Pro Gly Ala Thr Leu Glu Glu Met Met Ser Ala Cys Gln Gly Val Gly
195 200 205

Gly Pro Ser His Lys Ala Arg Val Leu Ala Glu Ala Met Cys Gln Pro
210 215 220

Val Val Ala Lys Glu Ile Val Ala Cys Cys Asp Lys Cys Gln Leu Lys
225 230 235 240

Gly Glu Ala Ile His Gly Gln Val Asp Cys Ser Pro Gly Val Trp Gln
245 250 255

Leu Asp Cys Thr His Leu Glu Gly Lys Val Ile Leu Val Ala Val His
260 265 270

Val Ala Ser Gly Tyr Ile Glu Ala Glu Ile Ile Pro Thr Glu Thr Gly
275 280 285

Gln Glu Thr Ala Tyr Phe Ile Leu Lys Leu Ala Gly Arg Trp Pro Val
290 295 300

Thr Thr Ala Ala Tyr Ala Val Lys Ala Ala Cys Trp Trp Ala Gly Val
305 310 315 320

Lys Gln Glu Phe Gly Ile Pro Tyr Asn Thr Gln Ser Gln Gly Val Val
325 330 335

Glu Ser Met Asn Asn Glu Leu Lys Lys Ile Ile Gly Gln Ile Arg Asp
340 345 350

Gln Ala Glu His Leu Lys Thr Ala Val Gln Met Ala Val Leu Ile His
355 360 365

Asn Phe Lys Arg Lys Gly Gly Ile Gly Glu Gln Glu Glu Glu Glu Val
370 375 380

Gly Phe Pro Val Arg Pro Gln Val Pro Leu
385 390

<210> SEQ ID NO 94
<211> LENGTH: 499
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 94

Thr Val Lys Ala Ala Cys Trp Trp Ala Gly Ile Lys Gln Glu Phe Gly
1 5 10 15

Ile Pro Tyr Asn Pro Gln Ser Gln Gly Val Val Glu Ser Met Asn Lys
20 25 30

Glu Leu Lys Lys Ile Ile Gly Gln Val Arg Asp Gln Ala Glu His Leu
35 40 45

Lys Thr Ala Val Gln Met Ala Val Phe Ile His Asn Phe Lys Arg Lys
50 55 60

Gly Gly Ile Gly Gly Tyr Ser Ala Gly Glu Arg Ile Val Asp Ile Ile
65 70 75 80

Ala Ile Ser Pro Arg Thr Leu Asn Ala Trp Val Lys Val Val Glu Glu
85 90 95

Lys Ala Phe Ser Pro Glu Val Ile Pro Met Phe Ser Ala Leu Ser Glu
100 105 110

Gly Ala Thr Pro Gln Asp Leu Asn Thr Met Leu Asn Thr Val Gly Gly
115 120 125

His Gln Ala Ala Met Gln Met Leu Lys Glu Thr Ile Asn Glu Glu Ala
130 135 140

Ala Glu Trp Asp Arg Leu His Pro Val His Ala Gly Pro Ile Ala Pro
145 150 155 160

Gly Gln Met Arg Glu Pro Arg Gly Ser Asp Ile Ala Gly Thr Thr Ser
165 170 175

Thr Leu Gln Glu Gln Ile Gly Trp Met Thr Asn Asn Pro Pro Ile Pro
180 185 190

Val Gly Glu Ile Tyr Lys Arg Trp Ile Ile Leu Gly Leu Asn Lys Ile
195 200 205

Val Arg Met Tyr Ser Pro Thr Ser Ile Leu Asp Ile Arg Gln Gly Pro
210 215 220

Lys Glu Pro Phe Arg Asp Tyr Val Asp Arg Phe Tyr Lys Thr Leu Arg
225 230 235 240

Ala Glu Gln Ala Ser Gln Glu Val Lys Asn Trp Met Thr Glu Thr Leu
245 250 255

Leu Val Gln Asn Ala Asn Pro Asp Cys Lys Thr Ile Leu Lys Ala Leu

```
            260                 265                 270

Gly Pro Ala Ala Thr Leu Glu Glu Met Met Thr Ala Cys Gln Gly Val
        275                 280                 285

Gly Gly Pro Gly His Lys Ala Arg Val Leu Ala Glu Ala Met Ser Gln
    290                 295                 300

Met Ala Ala Arg Ala Ser Val Leu Ser Gly Gly Glu Leu Asp Arg Trp
305                 310                 315                 320

Glu Lys Ile Arg Leu Arg Pro Gly Gly Lys Lys Lys Tyr Arg Leu Lys
                325                 330                 335

His Ile Val Trp Ala Ser Arg Glu Leu Glu Arg Phe Ala Val Asn Pro
            340                 345                 350

Gly Leu Leu Glu Thr Pro Pro Val Val Ala Lys Glu Ile Val Ala Ser
        355                 360                 365

Cys Asp Lys Cys Gln Leu Lys Gly Glu Ala Met His Gly Gln Val Asp
    370                 375                 380

Cys Ser Pro Gly Ile Trp Gln Leu Asp Cys Thr His Leu Glu Gly Lys
385                 390                 395                 400

Ile Ile Leu Val Ala Val His Val Ala Ser Gly Tyr Ile Glu Ala Glu
                405                 410                 415

Val Ile Pro Ala Glu Thr Gly Gln Glu Thr Ala Tyr Phe Leu Leu Lys
            420                 425                 430

Leu Ala Gly Arg Trp Pro Val Lys Thr Lys Glu Lys Val Tyr Leu Ala
        435                 440                 445

Trp Val Pro Ala His Lys Gly Ile Gly Gly Asn Glu Gln Val Asp Lys
    450                 455                 460

Leu Val Ser Thr Gln Gly Tyr Phe Pro Asp Trp Gln Asn Tyr Thr Pro
465                 470                 475                 480

Gly Pro Gly Thr Arg Tyr Pro Leu Thr Phe Gly Trp Cys Phe Lys Leu
                485                 490                 495

Val Pro Val


<210> SEQ ID NO 95
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Leu Ser Pro Arg Thr Leu Asn Ala Trp Val Lys Val Ile Glu Glu Lys
1               5                   10                  15

Ala Phe Ser Pro Glu Val Ile Pro Met Phe Thr Ala Leu Ser Glu Gly
            20                  25                  30

Ala Thr Pro His Asp Leu Asn Thr Met Leu Asn Thr Ile Gly Gly His
        35                  40                  45

Gln Ala Ala Met Gln Met Leu Lys Asp Thr Ile Asn Glu Glu Ala Ala
    50                  55                  60

Glu Trp Asp Arg Val His Pro Val His Ala Gly Pro Val Ala Pro Gly
65                  70                  75                  80

Gln Met Arg Asp Pro Arg Gly Ser Asp Ile Ala Gly Ser Thr Ser Thr
                85                  90                  95

Leu Gln Glu Gln Ile Ala Trp Met Thr Asn Asn Pro Pro Ile Pro Val
            100                 105                 110

Gly Asp Ile Tyr Lys Arg Trp Ile Ile Met Gly Leu Asn Lys Ile Val
```

-continued 115 120 125

Arg Met Tyr Ser Pro Val Ser Ile Leu Asp Ile Lys Gln Gly Pro Lys
130 135 140

Glu Pro Phe Arg Asp Tyr Val Asp Arg Phe Tyr Arg Thr Leu Arg Ala
145 150 155 160

Glu Gln Ala Ser Gln Asp Val Lys Asn Trp Met Thr Glu Thr Leu Leu
165 170 175

Val Gln Asn Ser Asn Pro Asp Cys Lys Thr Ile Leu Lys Ala Leu Gly
180 185 190

Pro Gly Ala Thr Leu Glu Glu Met Met Ser Ala Cys Gln Gly Val Gly
195 200 205

Gly Pro Ser His Lys Ala Arg Val Leu Ala Glu Ala Met Cys Gln Val
210 215 220

Ala Lys Glu Ile Val Ala Cys Cys Asp Lys Cys Gln Leu Lys Gly Glu
225 230 235 240

Ala Ile His Gly Gln Val Asp Cys Ser Pro Gly Val Trp Gln Leu Asp
245 250 255

Cys Thr His Leu Glu Gly Lys Val Ile Leu Val Ala Val His Val Ala
260 265 270

Ser Gly Tyr Ile Glu Ala Glu Ile Ile Pro Thr Glu Thr Gly Gln Glu
275 280 285

Thr Ala Tyr Phe Ile Leu Lys Leu Ala Gly Arg Trp Pro Val Thr Thr
290 295 300

Met Ala Ala Arg Ala Ser Ile Leu Ser Gly Gly Lys Leu Asp Lys Trp
305 310 315 320

Glu Lys Ile Arg Leu Arg Pro Gly Gly Arg Lys Lys Tyr Lys Leu Lys
325 330 335

His Leu Val Trp Ala Ser Arg Glu Leu Glu Arg Phe Ala Leu Asn Pro
340 345 350

Gly Leu Leu Glu Thr Ala Ala Ala Val Lys Ala Ala Cys Trp Trp Ala
355 360 365

Gly Val Lys Gln Glu Phe Gly Ile Pro Tyr Asn Thr Gln Ser Gln Gly
370 375 380

Val Val Glu Ser Met Asn Asn Glu Leu Lys Lys Ile Ile Gly Gln Ile
385 390 395 400

Arg Asp Gln Ala Glu His Leu Lys Thr Ala Val Gln Met Ala Val Leu
405 410 415

Ile His Asn Phe Lys Arg Lys Gly Gly Ile Gly Glu Tyr Ser Ala Gly
420 425 430

Glu Arg Ile Ile Asp Ile Ile Ala Thr Gln Gly Phe Phe Pro Asp Trp
435 440 445

Gln Asn Tyr Thr Pro Gly Pro Gly Ile Arg Phe Pro Leu Thr Phe Gly
450 455 460

Trp Cys Phe Lys Leu Val Pro Leu Leu Ile Lys Lys Glu Lys Ile Tyr
465 470 475 480

Leu Ala Trp Val Pro Ala His Lys Gly Ile Gly Gly Asn Glu Gln Ile
485 490 495

Asp Lys Leu Val Ser
500

<210> SEQ ID NO 96
<211> LENGTH: 494
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 96

```
Phe Pro Gln Ile Thr Leu Trp Gln Arg Pro Leu Val Thr Ile Lys Ile
1               5                   10                  15

Gly Gly Gln Leu Lys Glu Ala Leu Leu Asp Thr Gly Ala Asp Asp Thr
            20                  25                  30

Val Leu Glu Glu Met Asn Leu Pro Gly Arg Trp Lys Pro Lys Met Ile
        35                  40                  45

Gly Gly Ile Gly Gly Phe Ile Lys Val Arg Gln Tyr Asp Gln Glu Glu
    50                  55                  60

Val Gly Phe Pro Val Lys Pro Gln Val Pro Leu Arg Pro Met Thr Phe
65                  70                  75                  80

Lys Gly Ala Leu Asp Leu Ser His Phe Leu Arg Glu Lys Gly Gly Leu
                85                  90                  95

Glu Gly Leu Ile Pro Lys Phe Lys Leu Pro Ile Gln Lys Glu Thr Trp
            100                 105                 110

Glu Thr Trp Trp Thr Glu Tyr Trp Gln Ala Thr Trp Ile Pro Glu Trp
        115                 120                 125

Glu Phe Val Asn Thr Pro Pro Leu Val Lys Leu Trp Tyr Gln Leu Glu
    130                 135                 140

Lys Glu Pro Ile Val Gly Ala Glu Thr Phe Tyr Val Asp Gly Ala Ala
145                 150                 155                 160

Asn Arg Glu Thr Lys Trp Gly Phe Thr Thr Pro Asp Lys Lys His Gln
                165                 170                 175

Lys Glu Pro Pro Phe Leu Trp Met Gly Tyr Glu Leu His Pro Asp Lys
            180                 185                 190

Trp Thr Val Gln Pro Ile Val Leu Pro Glu Lys Asp Ser Trp Thr Val
        195                 200                 205

Asn Asp Ile Gln Lys Leu Val Gly Lys Leu Asn Trp Ala Ser Gln Ile
    210                 215                 220

Tyr Pro Gly Ile Lys Val Ile Thr Lys Ile Gln Asn Phe Arg Val Tyr
225                 230                 235                 240

Tyr Arg Asp Ser Arg Asp Pro Leu Trp Lys Gly Pro Ala Lys Leu Leu
                245                 250                 255

Trp Lys Gly Glu Gly Ala Val Val Ile Gln Asp Asn Ser Asp Ile Lys
            260                 265                 270

Val Val Pro Arg Arg Lys Ala Lys Ile Ile Arg Asp Tyr Gly Lys Gln
        275                 280                 285

Met Ala Gly Asp Asp Cys Val Ala Ser Arg Gln Asp Glu Asp Gly Thr
    290                 295                 300

Val Leu Val Gly Pro Thr Pro Val Asn Ile Ile Gly Arg Asn Leu Leu
305                 310                 315                 320

Thr Gln Ile Gly Cys Thr Leu Asn Phe Pro Ile Ser Pro Ile Glu Thr
                325                 330                 335

Val Pro Val Lys Leu Lys Pro Gly Met Asp Gly Pro Lys Val Lys Gln
            340                 345                 350

Trp Pro Leu Thr Glu Glu Lys Ile Lys Ala Leu Val Glu Ile Cys Thr
        355                 360                 365

Glu Met Glu Lys Glu Gly Lys Ile Ser Lys Ile Gly Pro Glu Asn Pro
    370                 375                 380

Tyr Asn Thr Pro Val Phe Ala Ile Lys Lys Lys Asp Ser Thr Lys Trp
```

385 390 395 400

Arg Lys Leu Val Asp Phe Arg Glu Leu Asn Lys Arg Thr Gln Asp Phe
405 410 415

Trp Glu Val Gln Leu Gly Ile Pro His Pro Ala Gly Leu Lys Lys Lys
420 425 430

Lys Ser Val Thr Val Leu Asp Val Gly Asp Ala Tyr Phe Ser Val Pro
435 440 445

Leu Asp Lys Asp Phe Arg Lys Tyr Thr Ala Phe Thr Ile Pro Ser Ile
450 455 460

Asn Asn Glu Thr Pro Gly Ile Arg Tyr Gln Tyr Asn Val Leu Pro Gln
465 470 475 480

Gly Trp Lys Gly Ser Pro Ala Ile Phe Gln Ser Ser Met Thr
485 490

<210> SEQ ID NO 97
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 97

Leu Pro Gln Ile Thr Leu Trp Gln Arg Pro Ile Val Thr Ile Lys Ile
1 5 10 15

Gly Gly Gln Ile Lys Glu Ala Leu Leu Asp Thr Gly Ala Asp Asp Thr
20 25 30

Val Leu Glu Asp Met Asn Leu Pro Gly Lys Trp Lys Pro Lys Met Ile
35 40 45

Gly Gly Ile Gly Gly Phe Ile Lys Val Lys Gln Tyr Asp Gln Trp Gly
50 55 60

Leu Thr Thr Pro Asp Lys Lys His Gln Lys Asp Pro Pro Phe Leu Trp
65 70 75 80

Met Gly Tyr Glu Leu His Pro Asp Arg Trp Thr Val Gln Pro Ile Glu
85 90 95

Leu Pro Glu Lys Glu Ser Trp Thr Val Asn Asp Ile Gln Lys Leu Ile
100 105 110

Gly Lys Leu Asn Trp Ala Ser Gln Ile Tyr Ala Gly Ile Lys Val Ala
115 120 125

Ala Gln Glu Glu Glu Glu Val Gly Phe Pro Val Arg Pro Gln Val Pro
130 135 140

Leu Arg Pro Met Thr Tyr Lys Gly Ala Leu Asp Leu Ser His Phe Leu
145 150 155 160

Lys Glu Lys Gly Gly Leu Glu Gly Ile Thr Lys Leu Gln Asn Phe Arg
165 170 175

Val Tyr Tyr Arg Asp Asn Arg Asp Pro Leu Trp Lys Gly Pro Ala Arg
180 185 190

Leu Leu Trp Lys Gly Glu Gly Ala Val Val Ile Gln Asp Asn Ser Glu
195 200 205

Ile Lys Val Val Pro Arg Arg Lys Val Lys Ile Ile Arg Asp Tyr Gly
210 215 220

Lys Arg Met Ala Gly Asp Asp Cys Val Ala Gly Arg Gln Asp Glu Asp
225 230 235 240

Pro Lys Phe Arg Leu Pro Ile Gln Lys Glu Thr Trp Asp Thr Trp Trp
245 250 255

Thr Asp Tyr Trp Gln Ala Thr Trp Ile Pro Glu Trp Glu Phe Thr Asn
260 265 270

Thr Pro Pro Leu Val Lys Leu Trp Tyr Gln Leu Glu Thr Glu Pro Ile
275 280 285

Ala Gly Val Glu Thr Phe Tyr Val Asp Gly Ala Ser Asn Arg Glu Thr
290 295 300

Lys Ala Ala Gly Thr Val Leu Ile Gly Pro Thr Pro Val Asn Ile Ile
305 310 315 320

Gly Arg Asn Leu Leu Thr Gln Leu Gly Cys Thr Leu Asn Phe Pro Ile
325 330 335

Ser Pro Ile Asp Thr Val Pro Val Lys Leu Lys Pro Gly Met Asp Gly
340 345 350

Pro Arg Val Lys Gln Trp Pro Leu Thr Glu Glu Lys Ile Lys Ala Leu
355 360 365

Ile Glu Ile Cys Thr Glu Met Glu Lys Glu Gly Lys Ile Ser Arg Ile
370 375 380

Gly Pro Glu Asn Pro Tyr Asn Thr Pro Ile Phe Ala Ile Lys Lys Lys
385 390 395 400

Asp Gly Thr Lys Trp Arg Lys Leu Val Asp Phe Arg Glu Leu Asn Lys
405 410 415

Lys Thr Gln Asp Phe Trp Glu Val Gln Leu Gly Ile Pro His Pro Ser
420 425 430

Gly Leu Lys Lys Lys Lys Ser Val Thr Val Leu Asp Ile Gly Asp Ala
435 440 445

Tyr Phe Ser Val Pro Leu Asp Lys Glu Phe Arg Lys Tyr Thr Ala Phe
450 455 460

Thr Val Pro Ser Thr Asn Asn Glu Thr Pro Gly Val Arg Tyr Gln Tyr
465 470 475 480

Asn Val Leu Pro Met Gly Trp Lys Gly Ser Pro Ala Ile Phe Gln Cys
485 490 495

Ser Met Thr

<210> SEQ ID NO 98
<211> LENGTH: 504
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 98

Val Ala Lys Glu Ile Val Ala Ser Cys Asp Lys Cys Gln Leu Lys Gly
1 5 10 15

Glu Ala Met His Gly Gln Val Asp Cys Ser Pro Gly Ile Trp Gln Leu
20 25 30

Asp Cys Thr His Leu Glu Gly Lys Ile Ile Leu Val Ala Val His Val
35 40 45

Ala Ser Gly Tyr Ile Glu Ala Glu Val Ile Pro Ala Glu Thr Gly Gln
50 55 60

Glu Thr Ala Tyr Phe Leu Leu Lys Leu Ala Gly Arg Trp Pro Val Lys
65 70 75 80

Thr Thr Gln Gly Tyr Phe Pro Asp Trp Gln Asn Tyr Thr Pro Gly Pro
85 90 95

Gly Thr Arg Tyr Pro Leu Thr Phe Gly Trp Cys Phe Lys Leu Val Pro
100 105 110

Val Thr Val Lys Ala Ala Cys Trp Trp Ala Gly Ile Lys Gln Glu Phe
115 120 125

Gly Ile Pro Tyr Asn Pro Gln Ser Gln Gly Val Val Glu Ser Met Asn
130 135 140

Lys Glu Leu Lys Lys Ile Ile Gly Gln Val Arg Asp Gln Ala Glu His
145 150 155 160

Leu Lys Thr Ala Val Gln Met Ala Val Phe Ile His Asn Phe Lys Arg
165 170 175

Lys Gly Gly Ile Gly Gly Tyr Ser Ala Gly Glu Arg Ile Val Asp Ile
180 185 190

Ile Ala Ala Ala Met Ala Ala Arg Ala Ser Val Leu Ser Gly Gly Glu
195 200 205

Leu Asp Arg Trp Glu Lys Ile Arg Leu Arg Pro Gly Gly Lys Lys Lys
210 215 220

Tyr Arg Leu Lys His Ile Val Trp Ala Ser Arg Glu Leu Glu Arg Phe
225 230 235 240

Ala Val Asn Pro Gly Leu Leu Glu Thr Ser Glu Gly Ile Ser Pro Arg
245 250 255

Thr Leu Asn Ala Trp Val Lys Val Val Glu Glu Lys Ala Phe Ser Pro
260 265 270

Glu Val Ile Pro Met Phe Ser Ala Leu Ser Glu Gly Ala Thr Pro Gln
275 280 285

Asp Leu Asn Thr Met Leu Asn Thr Val Gly Gly His Gln Ala Ala Met
290 295 300

Gln Met Leu Lys Glu Thr Ile Asn Glu Glu Ala Ala Glu Trp Asp Arg
305 310 315 320

Leu His Pro Val His Ala Gly Pro Ile Ala Pro Gly Gln Met Arg Glu
325 330 335

Pro Arg Gly Ser Asp Ile Ala Gly Thr Thr Ser Thr Leu Gln Glu Gln
340 345 350

Ile Gly Trp Met Thr Asn Asn Pro Pro Ile Pro Val Gly Glu Ile Tyr
355 360 365

Lys Arg Trp Ile Ile Leu Gly Leu Asn Lys Ile Val Arg Met Tyr Ser
370 375 380

Pro Thr Ser Ile Leu Asp Ile Arg Gln Gly Pro Lys Glu Pro Phe Arg
385 390 395 400

Asp Tyr Val Asp Arg Phe Tyr Lys Thr Leu Arg Ala Glu Gln Ala Ser
405 410 415

Gln Glu Val Lys Asn Trp Met Thr Glu Thr Leu Leu Val Gln Asn Ala
420 425 430

Asn Pro Asp Cys Lys Thr Ile Leu Lys Ala Leu Gly Pro Ala Ala Thr
435 440 445

Leu Glu Glu Met Met Thr Ala Cys Gln Gly Val Gly Gly Pro Gly His
450 455 460

Lys Ala Arg Val Leu Ala Glu Ala Met Ser Gln Ala Ala Ala Lys Glu
465 470 475 480

Lys Val Tyr Leu Ala Trp Val Pro Ala His Lys Gly Ile Gly Gly Asn
485 490 495

Glu Gln Val Asp Lys Leu Val Ser
500

<210> SEQ ID NO 99
<211> LENGTH: 499
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 99

```
Leu Ser Pro Arg Thr Leu Asn Ala Trp Val Lys Val Ile Glu Glu Lys
1               5                   10                  15

Ala Phe Ser Pro Glu Val Ile Pro Met Phe Thr Ala Leu Ser Glu Gly
            20                  25                  30

Ala Thr Pro His Asp Leu Asn Thr Met Leu Asn Thr Ile Gly Gly His
        35                  40                  45

Gln Ala Ala Met Gln Met Leu Lys Asp Thr Ile Asn Glu Glu Ala Ala
    50                  55                  60

Glu Trp Asp Arg Val His Pro Val His Ala Gly Pro Val Ala Pro Gly
65                  70                  75                  80

Gln Met Arg Asp Pro Arg Gly Ser Asp Ile Ala Gly Ser Thr Ser Thr
                85                  90                  95

Leu Gln Glu Gln Ile Ala Trp Met Thr Asn Asn Pro Pro Ile Pro Val
            100                 105                 110

Gly Asp Ile Tyr Lys Arg Trp Ile Ile Met Gly Leu Asn Lys Ile Val
        115                 120                 125

Arg Met Tyr Ser Pro Val Ser Ile Leu Asp Ile Lys Gln Gly Pro Lys
    130                 135                 140

Glu Pro Phe Arg Asp Tyr Val Asp Arg Phe Tyr Arg Thr Leu Arg Ala
145                 150                 155                 160

Glu Gln Ala Ser Gln Asp Val Lys Asn Trp Met Thr Glu Thr Leu Leu
                165                 170                 175

Val Gln Asn Ser Asn Pro Asp Cys Lys Thr Ile Leu Lys Ala Leu Gly
            180                 185                 190

Pro Gly Ala Thr Leu Glu Glu Met Met Ser Ala Cys Gln Gly Val Gly
        195                 200                 205

Gly Pro Ser His Lys Ala Arg Val Leu Ala Glu Ala Met Cys Gln Ala
    210                 215                 220

Val Lys Ala Ala Cys Trp Trp Ala Gly Val Lys Gln Glu Phe Gly Ile
225                 230                 235                 240

Pro Tyr Asn Thr Gln Ser Gln Gly Val Val Glu Ser Met Asn Asn Glu
                245                 250                 255

Leu Lys Lys Ile Ile Gly Gln Ile Arg Asp Gln Ala Glu His Leu Lys
            260                 265                 270

Thr Ala Val Gln Met Ala Val Leu Ile His Asn Phe Lys Arg Lys Gly
        275                 280                 285

Gly Ile Gly Glu Tyr Ser Ala Gly Glu Arg Ile Ile Asp Ile Ile Ala
    290                 295                 300

Lys Glu Lys Ile Tyr Leu Ala Trp Val Pro Ala His Lys Gly Ile Gly
305                 310                 315                 320

Gly Asn Glu Gln Ile Asp Lys Leu Val Ser Ala Ala Tyr Met Ala Ala
                325                 330                 335

Arg Ala Ser Ile Leu Ser Gly Gly Lys Leu Asp Lys Trp Glu Lys Ile
            340                 345                 350

Arg Leu Arg Pro Gly Gly Arg Lys Lys Tyr Lys Leu Lys His Leu Val
        355                 360                 365

Trp Ala Ser Arg Glu Leu Glu Arg Phe Ala Leu Asn Pro Gly Leu Leu
    370                 375                 380
```

```
Glu Thr Thr Gln Gly Phe Phe Pro Asp Trp Gln Asn Tyr Thr Pro Gly
385                 390                 395                 400

Pro Gly Ile Arg Phe Pro Leu Thr Phe Gly Trp Cys Phe Lys Leu Val
                405                 410                 415

Pro Leu Val Ala Lys Glu Ile Val Ala Cys Cys Asp Lys Cys Gln Leu
            420                 425                 430

Lys Gly Glu Ala Ile His Gly Gln Val Asp Cys Ser Pro Gly Val Trp
        435                 440                 445

Gln Leu Asp Cys Thr His Leu Glu Gly Lys Val Ile Leu Val Ala Val
    450                 455                 460

His Val Ala Ser Gly Tyr Ile Glu Ala Glu Ile Ile Pro Thr Glu Thr
465                 470                 475                 480

Gly Gln Glu Thr Ala Tyr Phe Ile Leu Lys Leu Ala Gly Arg Trp Pro
                485                 490                 495

Val Thr Thr


<210> SEQ ID NO 100
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Ile Thr Lys Ile Gln Asn Phe Arg Val Tyr Tyr Arg Asp Ser Arg Asp
1               5                   10                  15

Pro Leu Trp Lys Gly Pro Ala Lys Leu Leu Trp Lys Gly Glu Gly Ala
            20                  25                  30

Val Val Ile Gln Asp Asn Ser Asp Ile Lys Val Val Pro Arg Arg Lys
        35                  40                  45

Ala Lys Ile Ile Arg Asp Tyr Gly Lys Gln Met Ala Gly Asp Asp Cys
    50                  55                  60

Val Ala Ser Arg Gln Asp Glu Asp Ala Ala Tyr Glu Glu Glu Glu Val
65                  70                  75                  80

Gly Phe Pro Val Lys Pro Gln Val Pro Leu Arg Pro Met Thr Phe Lys
                85                  90                  95

Gly Ala Leu Asp Leu Ser His Phe Leu Arg Glu Lys Gly Gly Leu Glu
            100                 105                 110

Gly Ala Ala Trp Gly Phe Thr Thr Pro Asp Lys Lys His Gln Lys Glu
        115                 120                 125

Pro Pro Phe Leu Trp Met Gly Tyr Glu Leu His Pro Asp Lys Trp Thr
    130                 135                 140

Val Gln Pro Ile Val Leu Pro Glu Lys Asp Ser Trp Thr Val Asn Asp
145                 150                 155                 160

Ile Gln Lys Leu Val Gly Lys Leu Asn Trp Ala Ser Gln Ile Tyr Pro
                165                 170                 175

Gly Ile Lys Val Pro Lys Phe Lys Leu Pro Ile Gln Lys Glu Thr Trp
            180                 185                 190

Glu Thr Trp Trp Thr Glu Tyr Trp Gln Ala Thr Trp Ile Pro Glu Trp
        195                 200                 205

Glu Phe Val Asn Thr Pro Pro Leu Val Lys Leu Trp Tyr Gln Leu Glu
    210                 215                 220

Lys Glu Pro Ile Val Gly Ala Glu Thr Phe Tyr Val Asp Gly Ala Ala
225                 230                 235                 240
```

```
Asn Arg Glu Thr Lys Phe Pro Gln Ile Thr Leu Trp Gln Arg Pro Leu
                245                 250                 255

Val Thr Ile Lys Ile Gly Gly Gln Leu Lys Glu Ala Leu Leu Asp Thr
            260                 265                 270

Gly Ala Asp Asp Thr Val Leu Glu Glu Met Asn Leu Pro Gly Arg Trp
        275                 280                 285

Lys Pro Lys Met Ile Gly Gly Ile Gly Gly Phe Ile Lys Val Arg Gln
    290                 295                 300

Tyr Asp Gln Gly Thr Val Leu Val Gly Pro Thr Pro Val Asn Ile Ile
305                 310                 315                 320

Gly Arg Asn Leu Leu Thr Gln Ile Gly Cys Thr Leu Asn Phe Pro Ile
                325                 330                 335

Ser Pro Ile Glu Thr Val Pro Val Lys Leu Lys Pro Gly Met Asp Gly
            340                 345                 350

Pro Lys Val Lys Gln Trp Pro Leu Thr Glu Glu Lys Ile Lys Ala Leu
        355                 360                 365

Val Glu Ile Cys Thr Glu Met Glu Lys Glu Gly Lys Ile Ser Lys Ile
    370                 375                 380

Gly Pro Glu Asn Pro Tyr Asn Thr Pro Val Phe Ala Ile Lys Lys Lys
385                 390                 395                 400

Asp Ser Thr Lys Trp Arg Lys Leu Val Asp Phe Arg Glu Leu Asn Lys
                405                 410                 415

Arg Thr Gln Asp Phe Trp Glu Val Gln Leu Gly Ile Pro His Pro Ala
            420                 425                 430

Gly Leu Lys Lys Lys Lys Ser Val Thr Val Leu Asp Val Gly Asp Ala
        435                 440                 445

Tyr Phe Ser Val Pro Leu Asp Lys Asp Phe Arg Lys Tyr Thr Ala Phe
    450                 455                 460

Thr Ile Pro Ser Ile Asn Asn Glu Thr Pro Gly Ile Arg Tyr Gln Tyr
465                 470                 475                 480

Asn Val Leu Pro Gln Gly Trp Lys Gly Ser Pro Ala Ile Phe Gln Ser
                485                 490                 495

Ser Met Thr


<210> SEQ ID NO 101
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Pro Lys Phe Arg Leu Pro Ile Gln Lys Glu Thr Trp Asp Thr Trp Trp
1               5                   10                  15

Thr Asp Tyr Trp Gln Ala Thr Trp Ile Pro Glu Trp Glu Phe Thr Asn
            20                  25                  30

Thr Pro Pro Leu Val Lys Leu Trp Tyr Gln Leu Glu Thr Glu Pro Ile
        35                  40                  45

Ala Gly Val Glu Thr Phe Tyr Val Asp Gly Ala Ser Asn Arg Glu Thr
    50                  55                  60

Lys Glu Glu Val Gly Phe Pro Val Arg Pro Gln Val Pro Leu Arg Pro
65                  70                  75                  80

Met Thr Tyr Lys Gly Ala Leu Asp Leu Ser His Phe Leu Lys Glu Lys
                85                  90                  95
```

-continued

```
Gly Gly Leu Glu Gly Leu Pro Gln Ile Thr Leu Trp Gln Arg Pro Ile
            100                 105                 110

Val Thr Ile Lys Ile Gly Gly Gln Ile Lys Glu Ala Leu Leu Asp Thr
        115                 120                 125

Gly Ala Asp Asp Thr Val Leu Glu Asp Met Asn Leu Pro Gly Lys Trp
    130                 135                 140

Lys Pro Lys Met Ile Gly Gly Ile Gly Gly Phe Ile Lys Val Lys Gln
145                 150                 155                 160

Tyr Asp Gln Ile Thr Lys Leu Gln Asn Phe Arg Val Tyr Tyr Arg Asp
                165                 170                 175

Asn Arg Asp Pro Leu Trp Lys Gly Pro Ala Arg Leu Leu Trp Lys Gly
            180                 185                 190

Glu Gly Ala Val Val Ile Gln Asp Asn Ser Glu Ile Lys Val Val Pro
        195                 200                 205

Arg Arg Lys Val Lys Ile Ile Arg Asp Tyr Gly Lys Arg Met Ala Gly
    210                 215                 220

Asp Asp Cys Val Ala Gly Arg Gln Asp Glu Asp Trp Gly Leu Thr Thr
225                 230                 235                 240

Pro Asp Lys Lys His Gln Lys Asp Pro Pro Phe Leu Trp Met Gly Tyr
                245                 250                 255

Glu Leu His Pro Asp Arg Trp Thr Val Gln Pro Ile Glu Leu Pro Glu
            260                 265                 270

Lys Glu Ser Trp Thr Val Asn Asp Ile Gln Lys Leu Ile Gly Lys Leu
        275                 280                 285

Asn Trp Ala Ser Gln Ile Tyr Ala Gly Ile Lys Val Lys Gly Thr Val
    290                 295                 300

Leu Ile Gly Pro Thr Pro Val Asn Ile Ile Gly Arg Asn Leu Leu Thr
305                 310                 315                 320

Gln Leu Gly Cys Thr Leu Asn Phe Pro Ile Ser Pro Ile Asp Thr Val
                325                 330                 335

Pro Val Lys Leu Lys Pro Gly Met Asp Gly Pro Arg Val Lys Gln Trp
            340                 345                 350

Pro Leu Thr Glu Glu Lys Ile Lys Ala Leu Ile Glu Ile Cys Thr Glu
        355                 360                 365

Met Glu Lys Glu Gly Lys Ile Ser Arg Ile Gly Pro Glu Asn Pro Tyr
    370                 375                 380

Asn Thr Pro Ile Phe Ala Ile Lys Lys Lys Asp Gly Thr Lys Trp Arg
385                 390                 395                 400

Lys Leu Val Asp Phe Arg Glu Leu Asn Lys Lys Thr Gln Asp Phe Trp
                405                 410                 415

Glu Val Gln Leu Gly Ile Pro His Pro Ser Gly Leu Lys Lys Lys Lys
            420                 425                 430

Ser Val Thr Val Leu Asp Ile Gly Asp Ala Tyr Phe Ser Val Pro Leu
        435                 440                 445

Asp Lys Glu Phe Arg Lys Tyr Thr Ala Phe Thr Val Pro Ser Thr Asn
    450                 455                 460

Asn Glu Thr Pro Gly Val Arg Tyr Gln Tyr Asn Val Leu Pro Met Gly
465                 470                 475                 480

Trp Lys Gly Ser Pro Ala Ile Phe Gln Cys Ser Met Thr
                485                 490
```

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105
<211> LENGTH: 1028
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 105

```
Thr Val Lys Ala Ala Cys Trp Trp Ala Gly Ile Lys Gln Glu Phe Gly
1               5                   10                  15

Ile Pro Tyr Asn Pro Gln Ser Gln Gly Val Val Glu Ser Met Asn Lys
            20                  25                  30

Glu Leu Lys Lys Ile Ile Gly Gln Val Arg Asp Gln Ala Glu His Leu
        35                  40                  45

Lys Thr Ala Val Gln Met Ala Val Phe Ile His Asn Phe Lys Arg Lys
    50                  55                  60

Gly Gly Ile Gly Gly Tyr Ser Ala Gly Glu Arg Ile Val Asp Ile Ile
65                  70                  75                  80

Ala Ile Ser Pro Arg Thr Leu Asn Ala Trp Val Lys Val Val Glu Glu
                85                  90                  95

Lys Ala Phe Ser Pro Glu Val Ile Pro Met Phe Ser Ala Leu Ser Glu
            100                 105                 110

Gly Ala Thr Pro Gln Asp Leu Asn Thr Met Leu Asn Thr Val Gly Gly
        115                 120                 125

His Gln Ala Ala Met Gln Met Leu Lys Glu Thr Ile Asn Glu Glu Ala
    130                 135                 140

Ala Glu Trp Asp Arg Leu His Pro Val His Ala Gly Pro Ile Ala Pro
145                 150                 155                 160

Gly Gln Met Arg Glu Pro Arg Gly Ser Asp Ile Ala Gly Thr Thr Ser
                165                 170                 175

Thr Leu Gln Glu Gln Ile Gly Trp Met Thr Asn Asn Pro Pro Ile Pro
            180                 185                 190

Val Gly Glu Ile Tyr Lys Arg Trp Ile Ile Leu Gly Leu Asn Lys Ile
        195                 200                 205

Val Arg Met Tyr Ser Pro Thr Ser Ile Leu Asp Ile Arg Gln Gly Pro
    210                 215                 220

Lys Glu Pro Phe Arg Asp Tyr Val Asp Arg Phe Tyr Lys Thr Leu Arg
225                 230                 235                 240

Ala Glu Gln Ala Ser Gln Glu Val Lys Asn Trp Met Thr Glu Thr Leu
                245                 250                 255

Leu Val Gln Asn Ala Asn Pro Asp Cys Lys Thr Ile Leu Lys Ala Leu
            260                 265                 270
```

```
Gly Pro Ala Ala Thr Leu Glu Glu Met Met Thr Ala Cys Gln Gly Val
        275                 280                 285

Gly Gly Pro Gly His Lys Ala Arg Val Leu Ala Glu Ala Met Ser Gln
    290                 295                 300

Met Ala Ala Arg Ala Ser Val Leu Ser Gly Gly Glu Leu Asp Arg Trp
305                 310                 315                 320

Glu Lys Ile Arg Leu Arg Pro Gly Gly Lys Lys Lys Tyr Arg Leu Lys
                325                 330                 335

His Ile Val Trp Ala Ser Arg Glu Leu Glu Arg Phe Ala Val Asn Pro
            340                 345                 350

Gly Leu Leu Glu Thr Pro Pro Val Val Ala Lys Glu Ile Val Ala Ser
        355                 360                 365

Cys Asp Lys Cys Gln Leu Lys Gly Glu Ala Met His Gly Gln Val Asp
    370                 375                 380

Cys Ser Pro Gly Ile Trp Gln Leu Asp Cys Thr His Leu Glu Gly Lys
385                 390                 395                 400

Ile Ile Leu Val Ala Val His Val Ala Ser Gly Tyr Ile Glu Ala Glu
                405                 410                 415

Val Ile Pro Ala Glu Thr Gly Gln Glu Thr Ala Tyr Phe Leu Leu Lys
            420                 425                 430

Leu Ala Gly Arg Trp Pro Val Lys Thr Lys Glu Lys Val Tyr Leu Ala
        435                 440                 445

Trp Val Pro Ala His Lys Gly Ile Gly Gly Asn Glu Gln Val Asp Lys
    450                 455                 460

Leu Val Ser Thr Gln Gly Tyr Phe Pro Asp Trp Gln Asn Tyr Thr Pro
465                 470                 475                 480

Gly Pro Gly Thr Arg Tyr Pro Leu Thr Phe Gly Trp Cys Phe Lys Leu
                485                 490                 495

Val Pro Val Arg Ala Lys Arg Ala Pro Val Lys Gln Thr Leu Asn Phe
            500                 505                 510

Asp Leu Leu Lys Leu Ala Gly Asp Val Glu Ser Asn Pro Gly Pro Leu
        515                 520                 525

Ser Pro Arg Thr Leu Asn Ala Trp Val Lys Val Ile Glu Glu Lys Ala
    530                 535                 540

Phe Ser Pro Glu Val Ile Pro Met Phe Thr Ala Leu Ser Glu Gly Ala
545                 550                 555                 560

Thr Pro His Asp Leu Asn Thr Met Leu Asn Thr Ile Gly Gly His Gln
                565                 570                 575

Ala Ala Met Gln Met Leu Lys Asp Thr Ile Asn Glu Glu Ala Ala Glu
            580                 585                 590

Trp Asp Arg Val His Pro Val His Ala Gly Pro Val Ala Pro Gly Gln
        595                 600                 605

Met Arg Asp Pro Arg Gly Ser Asp Ile Ala Gly Ser Thr Ser Thr Leu
    610                 615                 620

Gln Glu Gln Ile Ala Trp Met Thr Asn Asn Pro Pro Ile Pro Val Gly
625                 630                 635                 640

Asp Ile Tyr Lys Arg Trp Ile Ile Met Gly Leu Asn Lys Ile Val Arg
                645                 650                 655

Met Tyr Ser Pro Val Ser Ile Leu Asp Ile Lys Gln Gly Pro Lys Glu
            660                 665                 670

Pro Phe Arg Asp Tyr Val Asp Arg Phe Tyr Arg Thr Leu Arg Ala Glu
        675                 680                 685

Gln Ala Ser Gln Asp Val Lys Asn Trp Met Thr Glu Thr Leu Leu Val
```

690 695 700

Gln Asn Ser Asn Pro Asp Cys Lys Thr Ile Leu Lys Ala Leu Gly Pro
705 710 715 720

Gly Ala Thr Leu Glu Glu Met Met Ser Ala Cys Gln Gly Val Gly Gly
725 730 735

Pro Ser His Lys Ala Arg Val Leu Ala Glu Ala Met Cys Gln Val Ala
740 745 750

Lys Glu Ile Val Ala Cys Cys Asp Lys Cys Gln Leu Lys Gly Glu Ala
755 760 765

Ile His Gly Gln Val Asp Cys Ser Pro Gly Val Trp Gln Leu Asp Cys
770 775 780

Thr His Leu Glu Gly Lys Val Ile Leu Val Ala Val His Val Ala Ser
785 790 795 800

Gly Tyr Ile Glu Ala Glu Ile Ile Pro Thr Glu Thr Gly Gln Glu Thr
805 810 815

Ala Tyr Phe Ile Leu Lys Leu Ala Gly Arg Trp Pro Val Thr Thr Met
820 825 830

Ala Ala Arg Ala Ser Ile Leu Ser Gly Gly Lys Leu Asp Lys Trp Glu
835 840 845

Lys Ile Arg Leu Arg Pro Gly Gly Arg Lys Lys Tyr Lys Leu Lys His
850 855 860

Leu Val Trp Ala Ser Arg Glu Leu Glu Arg Phe Ala Leu Asn Pro Gly
865 870 875 880

Leu Leu Glu Thr Ala Ala Ala Val Lys Ala Ala Cys Trp Trp Ala Gly
885 890 895

Val Lys Gln Glu Phe Gly Ile Pro Tyr Asn Thr Gln Ser Gln Gly Val
900 905 910

Val Glu Ser Met Asn Asn Glu Leu Lys Lys Ile Ile Gly Gln Ile Arg
915 920 925

Asp Gln Ala Glu His Leu Lys Thr Ala Val Gln Met Ala Val Leu Ile
930 935 940

His Asn Phe Lys Arg Lys Gly Gly Ile Gly Glu Tyr Ser Ala Gly Glu
945 950 955 960

Arg Ile Ile Asp Ile Ile Ala Thr Gln Gly Phe Phe Pro Asp Trp Gln
965 970 975

Asn Tyr Thr Pro Gly Pro Gly Ile Arg Phe Pro Leu Thr Phe Gly Trp
980 985 990

Cys Phe Lys Leu Val Pro Leu Leu Ile Lys Lys Glu Lys Ile Tyr Leu
995 1000 1005

Ala Trp Val Pro Ala His Lys Gly Ile Gly Gly Asn Glu Gln Ile
1010 1015 1020

Asp Lys Leu Val Ser
1025

<210> SEQ ID NO 106
<211> LENGTH: 1028
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 106

Leu Ser Pro Arg Thr Leu Asn Ala Trp Val Lys Val Ile Glu Glu Lys
1 5 10 15

-continued

```
Ala Phe Ser Pro Glu Val Ile Pro Met Phe Thr Ala Leu Ser Glu Gly
            20                  25                  30

Ala Thr Pro His Asp Leu Asn Thr Met Leu Asn Thr Ile Gly Gly His
        35                  40                  45

Gln Ala Ala Met Gln Met Leu Lys Asp Thr Ile Asn Glu Glu Ala Ala
    50                  55                  60

Glu Trp Asp Arg Val His Pro Val His Ala Gly Pro Val Ala Pro Gly
65                  70                  75                  80

Gln Met Arg Asp Pro Arg Gly Ser Asp Ile Ala Gly Ser Thr Ser Thr
                85                  90                  95

Leu Gln Glu Gln Ile Ala Trp Met Thr Asn Asn Pro Pro Ile Pro Val
            100                 105                 110

Gly Asp Ile Tyr Lys Arg Trp Ile Ile Met Gly Leu Asn Lys Ile Val
        115                 120                 125

Arg Met Tyr Ser Pro Val Ser Ile Leu Asp Ile Lys Gln Gly Pro Lys
    130                 135                 140

Glu Pro Phe Arg Asp Tyr Val Asp Arg Phe Tyr Arg Thr Leu Arg Ala
145                 150                 155                 160

Glu Gln Ala Ser Gln Asp Val Lys Asn Trp Met Thr Glu Thr Leu Leu
                165                 170                 175

Val Gln Asn Ser Asn Pro Asp Cys Lys Thr Ile Leu Lys Ala Leu Gly
            180                 185                 190

Pro Gly Ala Thr Leu Glu Glu Met Met Ser Ala Cys Gln Gly Val Gly
        195                 200                 205

Gly Pro Ser His Lys Ala Arg Val Leu Ala Glu Ala Met Cys Gln Val
    210                 215                 220

Ala Lys Glu Ile Val Ala Cys Cys Asp Lys Cys Gln Leu Lys Gly Glu
225                 230                 235                 240

Ala Ile His Gly Gln Val Asp Cys Ser Pro Gly Val Trp Gln Leu Asp
                245                 250                 255

Cys Thr His Leu Glu Gly Lys Val Ile Leu Val Ala Val His Val Ala
            260                 265                 270

Ser Gly Tyr Ile Glu Ala Glu Ile Ile Pro Thr Glu Thr Gly Gln Glu
        275                 280                 285

Thr Ala Tyr Phe Ile Leu Lys Leu Ala Gly Arg Trp Pro Val Thr Thr
    290                 295                 300

Met Ala Ala Arg Ala Ser Ile Leu Ser Gly Gly Lys Leu Asp Lys Trp
305                 310                 315                 320

Glu Lys Ile Arg Leu Arg Pro Gly Gly Arg Lys Lys Tyr Lys Leu Lys
                325                 330                 335

His Leu Val Trp Ala Ser Arg Glu Leu Glu Arg Phe Ala Leu Asn Pro
            340                 345                 350

Gly Leu Leu Glu Thr Ala Ala Ala Val Lys Ala Ala Cys Trp Trp Ala
        355                 360                 365

Gly Val Lys Gln Glu Phe Gly Ile Pro Tyr Asn Thr Gln Ser Gln Gly
    370                 375                 380

Val Val Glu Ser Met Asn Asn Glu Leu Lys Lys Ile Ile Gly Gln Ile
385                 390                 395                 400

Arg Asp Gln Ala Glu His Leu Lys Thr Ala Val Gln Met Ala Val Leu
                405                 410                 415

Ile His Asn Phe Lys Arg Lys Gly Gly Ile Gly Glu Tyr Ser Ala Gly
            420                 425                 430

Glu Arg Ile Ile Asp Ile Ile Ala Thr Gln Gly Phe Phe Pro Asp Trp
```

-continued

```
        435                 440                 445

Gln Asn Tyr Thr Pro Gly Pro Gly Ile Arg Phe Pro Leu Thr Phe Gly
    450                 455                 460

Trp Cys Phe Lys Leu Val Pro Leu Leu Ile Lys Lys Glu Lys Ile Tyr
465                 470                 475                 480

Leu Ala Trp Val Pro Ala His Lys Gly Ile Gly Gly Asn Glu Gln Ile
                485                 490                 495

Asp Lys Leu Val Ser Arg Ala Lys Arg Ala Pro Val Lys Gln Thr Leu
            500                 505                 510

Asn Phe Asp Leu Leu Lys Leu Ala Gly Asp Val Glu Ser Asn Pro Gly
        515                 520                 525

Pro Thr Val Lys Ala Ala Cys Trp Trp Ala Gly Ile Lys Gln Glu Phe
    530                 535                 540

Gly Ile Pro Tyr Asn Pro Gln Ser Gln Gly Val Val Glu Ser Met Asn
545                 550                 555                 560

Lys Glu Leu Lys Lys Ile Ile Gly Gln Val Arg Asp Gln Ala Glu His
                565                 570                 575

Leu Lys Thr Ala Val Gln Met Ala Val Phe Ile His Asn Phe Lys Arg
            580                 585                 590

Lys Gly Gly Ile Gly Gly Tyr Ser Ala Gly Glu Arg Ile Val Asp Ile
        595                 600                 605

Ile Ala Ile Ser Pro Arg Thr Leu Asn Ala Trp Val Lys Val Val Glu
    610                 615                 620

Glu Lys Ala Phe Ser Pro Glu Val Ile Pro Met Phe Ser Ala Leu Ser
625                 630                 635                 640

Glu Gly Ala Thr Pro Gln Asp Leu Asn Thr Met Leu Asn Thr Val Gly
                645                 650                 655

Gly His Gln Ala Ala Met Gln Met Leu Lys Glu Thr Ile Asn Glu Glu
            660                 665                 670

Ala Ala Glu Trp Asp Arg Leu His Pro Val His Ala Gly Pro Ile Ala
        675                 680                 685

Pro Gly Gln Met Arg Glu Pro Arg Gly Ser Asp Ile Ala Gly Thr Thr
    690                 695                 700

Ser Thr Leu Gln Glu Gln Ile Gly Trp Met Thr Asn Asn Pro Pro Ile
705                 710                 715                 720

Pro Val Gly Glu Ile Tyr Lys Arg Trp Ile Ile Leu Gly Leu Asn Lys
                725                 730                 735

Ile Val Arg Met Tyr Ser Pro Thr Ser Ile Leu Asp Ile Arg Gln Gly
            740                 745                 750

Pro Lys Glu Pro Phe Arg Asp Tyr Val Asp Arg Phe Tyr Lys Thr Leu
        755                 760                 765

Arg Ala Glu Gln Ala Ser Gln Glu Val Lys Asn Trp Met Thr Glu Thr
    770                 775                 780

Leu Leu Val Gln Asn Ala Asn Pro Asp Cys Lys Thr Ile Leu Lys Ala
785                 790                 795                 800

Leu Gly Pro Ala Ala Thr Leu Glu Glu Met Met Thr Ala Cys Gln Gly
                805                 810                 815

Val Gly Gly Pro Gly His Lys Ala Arg Val Leu Ala Glu Ala Met Ser
            820                 825                 830

Gln Met Ala Ala Arg Ala Ser Val Leu Ser Gly Gly Glu Leu Asp Arg
        835                 840                 845

Trp Glu Lys Ile Arg Leu Arg Pro Gly Gly Lys Lys Lys Tyr Arg Leu
    850                 855                 860
```

Lys His Ile Val Trp Ala Ser Arg Glu Leu Glu Arg Phe Ala Val Asn
865 870 875 880

Pro Gly Leu Leu Glu Thr Pro Pro Val Val Ala Lys Glu Ile Val Ala
885 890 895

Ser Cys Asp Lys Cys Gln Leu Lys Gly Glu Ala Met His Gly Gln Val
900 905 910

Asp Cys Ser Pro Gly Ile Trp Gln Leu Asp Cys Thr His Leu Glu Gly
915 920 925

Lys Ile Ile Leu Val Ala Val His Val Ala Ser Gly Tyr Ile Glu Ala
930 935 940

Glu Val Ile Pro Ala Glu Thr Gly Gln Glu Thr Ala Tyr Phe Leu Leu
945 950 955 960

Lys Leu Ala Gly Arg Trp Pro Val Lys Thr Lys Glu Lys Val Tyr Leu
965 970 975

Ala Trp Val Pro Ala His Lys Gly Ile Gly Gly Asn Glu Gln Val Asp
980 985 990

Lys Leu Val Ser Thr Gln Gly Tyr Phe Pro Asp Trp Gln Asn Tyr Thr
995 1000 1005

Pro Gly Pro Gly Thr Arg Tyr Pro Leu Thr Phe Gly Trp Cys Phe
1010 1015 1020

Lys Leu Val Pro Val
1025

<210> SEQ ID NO 107
<211> LENGTH: 1022
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 107

Phe Pro Gln Ile Thr Leu Trp Gln Arg Pro Leu Val Thr Ile Lys Ile
1 5 10 15

Gly Gly Gln Leu Lys Glu Ala Leu Leu Asp Thr Gly Ala Asp Asp Thr
20 25 30

Val Leu Glu Glu Met Asn Leu Pro Gly Arg Trp Lys Pro Lys Met Ile
35 40 45

Gly Gly Ile Gly Gly Phe Ile Lys Val Arg Gln Tyr Asp Gln Glu Glu
50 55 60

Val Gly Phe Pro Val Lys Pro Gln Val Pro Leu Arg Pro Met Thr Phe
65 70 75 80

Lys Gly Ala Leu Asp Leu Ser His Phe Leu Arg Glu Lys Gly Gly Leu
85 90 95

Glu Gly Leu Ile Pro Lys Phe Lys Leu Pro Ile Gln Lys Glu Thr Trp
100 105 110

Glu Thr Trp Trp Thr Glu Tyr Trp Gln Ala Thr Trp Ile Pro Glu Trp
115 120 125

Glu Phe Val Asn Thr Pro Pro Leu Val Lys Leu Trp Tyr Gln Leu Glu
130 135 140

Lys Glu Pro Ile Val Gly Ala Glu Thr Phe Tyr Val Asp Gly Ala Ala
145 150 155 160

Asn Arg Glu Thr Lys Trp Gly Phe Thr Thr Pro Asp Lys Lys His Gln
165 170 175

Lys Glu Pro Pro Phe Leu Trp Met Gly Tyr Glu Leu His Pro Asp Lys

```
            180                 185                 190

Trp Thr Val Gln Pro Ile Val Leu Pro Glu Lys Asp Ser Trp Thr Val
        195                 200                 205

Asn Asp Ile Gln Lys Leu Val Gly Lys Leu Asn Trp Ala Ser Gln Ile
    210                 215                 220

Tyr Pro Gly Ile Lys Val Ile Thr Lys Ile Gln Asn Phe Arg Val Tyr
225                 230                 235                 240

Tyr Arg Asp Ser Arg Asp Pro Leu Trp Lys Gly Pro Ala Lys Leu Leu
                245                 250                 255

Trp Lys Gly Glu Gly Ala Val Val Ile Gln Asp Asn Ser Asp Ile Lys
            260                 265                 270

Val Val Pro Arg Arg Lys Ala Lys Ile Ile Arg Asp Tyr Gly Lys Gln
        275                 280                 285

Met Ala Gly Asp Asp Cys Val Ala Ser Arg Gln Asp Glu Asp Gly Thr
    290                 295                 300

Val Leu Val Gly Pro Thr Pro Val Asn Ile Ile Gly Arg Asn Leu Leu
305                 310                 315                 320

Thr Gln Ile Gly Cys Thr Leu Asn Phe Pro Ile Ser Pro Ile Glu Thr
                325                 330                 335

Val Pro Val Lys Leu Lys Pro Gly Met Asp Gly Pro Lys Val Lys Gln
            340                 345                 350

Trp Pro Leu Thr Glu Glu Lys Ile Lys Ala Leu Val Glu Ile Cys Thr
        355                 360                 365

Glu Met Glu Lys Glu Gly Lys Ile Ser Lys Ile Gly Pro Glu Asn Pro
    370                 375                 380

Tyr Asn Thr Pro Val Phe Ala Ile Lys Lys Lys Asp Ser Thr Lys Trp
385                 390                 395                 400

Arg Lys Leu Val Asp Phe Arg Glu Leu Asn Lys Arg Thr Gln Asp Phe
                405                 410                 415

Trp Glu Val Gln Leu Gly Ile Pro His Pro Ala Gly Leu Lys Lys Lys
            420                 425                 430

Lys Ser Val Thr Val Leu Asp Val Gly Asp Ala Tyr Phe Ser Val Pro
        435                 440                 445

Leu Asp Lys Asp Phe Arg Lys Tyr Thr Ala Phe Thr Ile Pro Ser Ile
    450                 455                 460

Asn Asn Glu Thr Pro Gly Ile Arg Tyr Gln Tyr Asn Val Leu Pro Gln
465                 470                 475                 480

Gly Trp Lys Gly Ser Pro Ala Ile Phe Gln Ser Ser Met Thr Arg Ala
                485                 490                 495

Lys Arg Ala Pro Val Lys Gln Thr Leu Asn Phe Asp Leu Leu Lys Leu
            500                 505                 510

Ala Gly Asp Val Glu Ser Asn Pro Gly Pro Asn Leu Pro Gln Ile Thr
        515                 520                 525

Leu Trp Gln Arg Pro Ile Val Thr Ile Lys Ile Gly Gly Gln Ile Lys
    530                 535                 540

Glu Ala Leu Leu Asp Thr Gly Ala Asp Asp Thr Val Leu Glu Asp Met
545                 550                 555                 560

Asn Leu Pro Gly Lys Trp Lys Pro Lys Met Ile Gly Gly Ile Gly Gly
                565                 570                 575

Phe Ile Lys Val Lys Gln Tyr Asp Gln Trp Gly Leu Thr Thr Pro Asp
            580                 585                 590

Lys Lys His Gln Lys Asp Pro Pro Phe Leu Trp Met Gly Tyr Glu Leu
        595                 600                 605
```

-continued

```
His Pro Asp Arg Trp Thr Val Gln Pro Ile Glu Leu Pro Glu Lys Glu
    610                 615                 620

Ser Trp Thr Val Asn Asp Ile Gln Lys Leu Ile Gly Lys Leu Asn Trp
625                 630                 635                 640

Ala Ser Gln Ile Tyr Ala Gly Ile Lys Val Ala Ala Gln Glu Glu Glu
                645                 650                 655

Glu Val Gly Phe Pro Val Arg Pro Gln Val Pro Leu Arg Pro Met Thr
            660                 665                 670

Tyr Lys Gly Ala Leu Asp Leu Ser His Phe Leu Lys Glu Lys Gly Gly
        675                 680                 685

Leu Glu Gly Ile Thr Lys Leu Gln Asn Phe Arg Val Tyr Tyr Arg Asp
    690                 695                 700

Asn Arg Asp Pro Leu Trp Lys Gly Pro Ala Arg Leu Leu Trp Lys Gly
705                 710                 715                 720

Glu Gly Ala Val Val Ile Gln Asp Asn Ser Glu Ile Lys Val Val Pro
                725                 730                 735

Arg Arg Lys Val Lys Ile Ile Arg Asp Tyr Gly Lys Arg Met Ala Gly
            740                 745                 750

Asp Asp Cys Val Ala Gly Arg Gln Asp Glu Asp Pro Lys Phe Arg Leu
        755                 760                 765

Pro Ile Gln Lys Glu Thr Trp Asp Thr Trp Trp Thr Asp Tyr Trp Gln
    770                 775                 780

Ala Thr Trp Ile Pro Glu Trp Glu Phe Thr Asn Thr Pro Pro Leu Val
785                 790                 795                 800

Lys Leu Trp Tyr Gln Leu Glu Thr Glu Pro Ile Ala Gly Val Glu Thr
                805                 810                 815

Phe Tyr Val Asp Gly Ala Ser Asn Arg Glu Thr Lys Ala Ala Gly Thr
            820                 825                 830

Val Leu Ile Gly Pro Thr Pro Val Asn Ile Ile Gly Arg Asn Leu Leu
        835                 840                 845

Thr Gln Leu Gly Cys Thr Leu Asn Phe Pro Ile Ser Pro Ile Asp Thr
    850                 855                 860

Val Pro Val Lys Leu Lys Pro Gly Met Asp Gly Pro Arg Val Lys Gln
865                 870                 875                 880

Trp Pro Leu Thr Glu Glu Lys Ile Lys Ala Leu Ile Glu Ile Cys Thr
                885                 890                 895

Glu Met Glu Lys Glu Gly Lys Ile Ser Arg Ile Gly Pro Glu Asn Pro
            900                 905                 910

Tyr Asn Thr Pro Ile Phe Ala Ile Lys Lys Lys Asp Gly Thr Lys Trp
        915                 920                 925

Arg Lys Leu Val Asp Phe Arg Glu Leu Asn Lys Lys Thr Gln Asp Phe
    930                 935                 940

Trp Glu Val Gln Leu Gly Ile Pro His Pro Ser Gly Leu Lys Lys Lys
945                 950                 955                 960

Lys Ser Val Thr Val Leu Asp Ile Gly Asp Ala Tyr Phe Ser Val Pro
                965                 970                 975

Leu Asp Lys Glu Phe Arg Lys Tyr Thr Ala Phe Thr Val Pro Ser Thr
            980                 985                 990

Asn Asn Glu Thr Pro Gly Val Arg  Tyr Gln Tyr Asn Val  Leu Pro Met
        995                 1000                1005

Gly Trp  Lys Gly Ser Pro Ala  Ile Phe Gln Cys Ser  Met Thr
    1010                 1015                1020
```

<210> SEQ ID NO 108
<211> LENGTH: 1021
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 108

Leu Pro Gln Ile Thr Leu Trp Gln Arg Pro Ile Val Thr Ile Lys Ile
1 5 10 15

Gly Gly Gln Ile Lys Glu Ala Leu Leu Asp Thr Gly Ala Asp Asp Thr
20 25 30

Val Leu Glu Asp Met Asn Leu Pro Gly Lys Trp Lys Pro Lys Met Ile
35 40 45

Gly Gly Ile Gly Gly Phe Ile Lys Val Lys Gln Tyr Asp Gln Trp Gly
50 55 60

Leu Thr Thr Pro Asp Lys Lys His Gln Lys Asp Pro Pro Phe Leu Trp
65 70 75 80

Met Gly Tyr Glu Leu His Pro Asp Arg Trp Thr Val Gln Pro Ile Glu
85 90 95

Leu Pro Glu Lys Glu Ser Trp Thr Val Asn Asp Ile Gln Lys Leu Ile
100 105 110

Gly Lys Leu Asn Trp Ala Ser Gln Ile Tyr Ala Gly Ile Lys Val Ala
115 120 125

Ala Gln Glu Glu Glu Glu Val Gly Phe Pro Val Arg Pro Gln Val Pro
130 135 140

Leu Arg Pro Met Thr Tyr Lys Gly Ala Leu Asp Leu Ser His Phe Leu
145 150 155 160

Lys Glu Lys Gly Gly Leu Glu Gly Ile Thr Lys Leu Gln Asn Phe Arg
165 170 175

Val Tyr Tyr Arg Asp Asn Arg Asp Pro Leu Trp Lys Gly Pro Ala Arg
180 185 190

Leu Leu Trp Lys Gly Glu Gly Ala Val Val Ile Gln Asp Asn Ser Glu
195 200 205

Ile Lys Val Val Pro Arg Arg Lys Val Lys Ile Ile Arg Asp Tyr Gly
210 215 220

Lys Arg Met Ala Gly Asp Asp Cys Val Ala Gly Arg Gln Asp Glu Asp
225 230 235 240

Pro Lys Phe Arg Leu Pro Ile Gln Lys Glu Thr Trp Asp Thr Trp Trp
245 250 255

Thr Asp Tyr Trp Gln Ala Thr Trp Ile Pro Glu Trp Glu Phe Thr Asn
260 265 270

Thr Pro Pro Leu Val Lys Leu Trp Tyr Gln Leu Glu Thr Glu Pro Ile
275 280 285

Ala Gly Val Glu Thr Phe Tyr Val Asp Gly Ala Ser Asn Arg Glu Thr
290 295 300

Lys Ala Ala Gly Thr Val Leu Ile Gly Pro Thr Pro Val Asn Ile Ile
305 310 315 320

Gly Arg Asn Leu Leu Thr Gln Leu Gly Cys Thr Leu Asn Phe Pro Ile
325 330 335

Ser Pro Ile Asp Thr Val Pro Val Lys Leu Lys Pro Gly Met Asp Gly
340 345 350

Pro Arg Val Lys Gln Trp Pro Leu Thr Glu Glu Lys Ile Lys Ala Leu
355 360 365

-continued

```
Ile Glu Ile Cys Thr Glu Met Glu Lys Glu Gly Lys Ile Ser Arg Ile
    370                 375                 380

Gly Pro Glu Asn Pro Tyr Asn Thr Pro Ile Phe Ala Ile Lys Lys Lys
385                 390                 395                 400

Asp Gly Thr Lys Trp Arg Lys Leu Val Asp Phe Arg Glu Leu Asn Lys
                405                 410                 415

Lys Thr Gln Asp Phe Trp Glu Val Gln Leu Gly Ile Pro His Pro Ser
            420                 425                 430

Gly Leu Lys Lys Lys Lys Ser Val Thr Val Leu Asp Ile Gly Asp Ala
        435                 440                 445

Tyr Phe Ser Val Pro Leu Asp Lys Glu Phe Arg Lys Tyr Thr Ala Phe
    450                 455                 460

Thr Val Pro Ser Thr Asn Asn Glu Thr Pro Gly Val Arg Tyr Gln Tyr
465                 470                 475                 480

Asn Val Leu Pro Met Gly Trp Lys Gly Ser Pro Ala Ile Phe Gln Cys
                485                 490                 495

Ser Met Thr Arg Ala Lys Arg Ala Pro Val Lys Gln Thr Leu Asn Phe
            500                 505                 510

Asp Leu Leu Lys Leu Ala Gly Asp Val Glu Ser Asn Pro Gly Pro Phe
        515                 520                 525

Pro Gln Ile Thr Leu Trp Gln Arg Pro Leu Val Thr Ile Lys Ile Gly
    530                 535                 540

Gly Gln Leu Lys Glu Ala Leu Leu Asp Thr Gly Ala Asp Asp Thr Val
545                 550                 555                 560

Leu Glu Glu Met Asn Leu Pro Gly Arg Trp Lys Pro Lys Met Ile Gly
                565                 570                 575

Gly Ile Gly Gly Phe Ile Lys Val Arg Gln Tyr Asp Gln Glu Glu Val
            580                 585                 590

Gly Phe Pro Val Lys Pro Gln Val Pro Leu Arg Pro Met Thr Phe Lys
        595                 600                 605

Gly Ala Leu Asp Leu Ser His Phe Leu Arg Glu Lys Gly Gly Leu Glu
    610                 615                 620

Gly Leu Ile Pro Lys Phe Lys Leu Pro Ile Gln Lys Glu Thr Trp Glu
625                 630                 635                 640

Thr Trp Trp Thr Glu Tyr Trp Gln Ala Thr Trp Ile Pro Glu Trp Glu
                645                 650                 655

Phe Val Asn Thr Pro Pro Leu Val Lys Leu Trp Tyr Gln Leu Glu Lys
            660                 665                 670

Glu Pro Ile Val Gly Ala Glu Thr Phe Tyr Val Asp Gly Ala Ala Asn
        675                 680                 685

Arg Glu Thr Lys Trp Gly Phe Thr Thr Pro Asp Lys Lys His Gln Lys
    690                 695                 700

Glu Pro Pro Phe Leu Trp Met Gly Tyr Glu Leu His Pro Asp Lys Trp
705                 710                 715                 720

Thr Val Gln Pro Ile Val Leu Pro Glu Lys Asp Ser Trp Thr Val Asn
                725                 730                 735

Asp Ile Gln Lys Leu Val Gly Lys Leu Asn Trp Ala Ser Gln Ile Tyr
            740                 745                 750

Pro Gly Ile Lys Val Ile Thr Lys Ile Gln Asn Phe Arg Val Tyr Tyr
        755                 760                 765

Arg Asp Ser Arg Asp Pro Leu Trp Lys Gly Pro Ala Lys Leu Leu Trp
    770                 775                 780
```

Lys Gly Glu Gly Ala Val Val Ile Gln Asp Asn Ser Asp Ile Lys Val
785 790 795 800

Val Pro Arg Arg Lys Ala Lys Ile Ile Arg Asp Tyr Gly Lys Gln Met
805 810 815

Ala Gly Asp Asp Cys Val Ala Ser Arg Gln Asp Glu Asp Gly Thr Val
820 825 830

Leu Val Gly Pro Thr Pro Val Asn Ile Ile Gly Arg Asn Leu Leu Thr
835 840 845

Gln Ile Gly Cys Thr Leu Asn Phe Pro Ile Ser Pro Ile Glu Thr Val
850 855 860

Pro Val Lys Leu Lys Pro Gly Met Asp Gly Pro Lys Val Lys Gln Trp
865 870 875 880

Pro Leu Thr Glu Glu Lys Ile Lys Ala Leu Val Glu Ile Cys Thr Glu
885 890 895

Met Glu Lys Glu Gly Lys Ile Ser Lys Ile Gly Pro Glu Asn Pro Tyr
900 905 910

Asn Thr Pro Val Phe Ala Ile Lys Lys Lys Asp Ser Thr Lys Trp Arg
915 920 925

Lys Leu Val Asp Phe Arg Glu Leu Asn Lys Arg Thr Gln Asp Phe Trp
930 935 940

Glu Val Gln Leu Gly Ile Pro His Pro Ala Gly Leu Lys Lys Lys Lys
945 950 955 960

Ser Val Thr Val Leu Asp Val Gly Asp Ala Tyr Phe Ser Val Pro Leu
965 970 975

Asp Lys Asp Phe Arg Lys Tyr Thr Ala Phe Thr Ile Pro Ser Ile Asn
980 985 990

Asn Glu Thr Pro Gly Ile Arg Tyr Gln Tyr Asn Val Leu Pro Gln Gly
995 1000 1005

Trp Lys Gly Ser Pro Ala Ile Phe Gln Ser Ser Met Thr
1010 1015 1020

<210> SEQ ID NO 109
<211> LENGTH: 1034
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

Val Ala Lys Glu Ile Val Ala Ser Cys Asp Lys Cys Gln Leu Lys Gly
1 5 10 15

Glu Ala Met His Gly Gln Val Asp Cys Ser Pro Gly Ile Trp Gln Leu
20 25 30

Asp Cys Thr His Leu Glu Gly Lys Ile Ile Leu Val Ala Val His Val
35 40 45

Ala Ser Gly Tyr Ile Glu Ala Glu Val Ile Pro Ala Glu Thr Gly Gln
50 55 60

Glu Thr Ala Tyr Phe Leu Leu Lys Leu Ala Gly Arg Trp Pro Val Lys
65 70 75 80

Thr Thr Gln Gly Tyr Phe Pro Asp Trp Gln Asn Tyr Thr Pro Gly Pro
85 90 95

Gly Thr Arg Tyr Pro Leu Thr Phe Gly Trp Cys Phe Lys Leu Val Pro
100 105 110

Val Thr Val Lys Ala Ala Cys Trp Trp Ala Gly Ile Lys Gln Glu Phe
115 120 125

```
Gly Ile Pro Tyr Asn Pro Gln Ser Gln Gly Val Val Glu Ser Met Asn
    130                 135                 140

Lys Glu Leu Lys Lys Ile Ile Gly Gln Val Arg Asp Gln Ala Glu His
145                 150                 155                 160

Leu Lys Thr Ala Val Gln Met Ala Val Phe Ile His Asn Phe Lys Arg
                165                 170                 175

Lys Gly Gly Ile Gly Gly Tyr Ser Ala Gly Glu Arg Ile Val Asp Ile
            180                 185                 190

Ile Ala Ala Ala Met Ala Ala Arg Ala Ser Val Leu Ser Gly Gly Glu
        195                 200                 205

Leu Asp Arg Trp Glu Lys Ile Arg Leu Arg Pro Gly Gly Lys Lys Lys
    210                 215                 220

Tyr Arg Leu Lys His Ile Val Trp Ala Ser Arg Glu Leu Glu Arg Phe
225                 230                 235                 240

Ala Val Asn Pro Gly Leu Leu Glu Thr Ser Glu Gly Ile Ser Pro Arg
                245                 250                 255

Thr Leu Asn Ala Trp Val Lys Val Val Glu Glu Lys Ala Phe Ser Pro
            260                 265                 270

Glu Val Ile Pro Met Phe Ser Ala Leu Ser Glu Gly Ala Thr Pro Gln
        275                 280                 285

Asp Leu Asn Thr Met Leu Asn Thr Val Gly Gly His Gln Ala Ala Met
    290                 295                 300

Gln Met Leu Lys Glu Thr Ile Asn Glu Glu Ala Ala Glu Trp Asp Arg
305                 310                 315                 320

Leu His Pro Val His Ala Gly Pro Ile Ala Pro Gly Gln Met Arg Glu
                325                 330                 335

Pro Arg Gly Ser Asp Ile Ala Gly Thr Thr Ser Thr Leu Gln Glu Gln
            340                 345                 350

Ile Gly Trp Met Thr Asn Asn Pro Pro Ile Pro Val Gly Glu Ile Tyr
        355                 360                 365

Lys Arg Trp Ile Ile Leu Gly Leu Asn Lys Ile Val Arg Met Tyr Ser
    370                 375                 380

Pro Thr Ser Ile Leu Asp Ile Arg Gln Gly Pro Lys Glu Pro Phe Arg
385                 390                 395                 400

Asp Tyr Val Asp Arg Phe Tyr Lys Thr Leu Arg Ala Glu Gln Ala Ser
                405                 410                 415

Gln Glu Val Lys Asn Trp Met Thr Glu Thr Leu Leu Val Gln Asn Ala
            420                 425                 430

Asn Pro Asp Cys Lys Thr Ile Leu Lys Ala Leu Gly Pro Ala Ala Thr
        435                 440                 445

Leu Glu Glu Met Met Thr Ala Cys Gln Gly Val Gly Gly Pro Gly His
    450                 455                 460

Lys Ala Arg Val Leu Ala Glu Ala Met Ser Gln Ala Ala Ala Lys Glu
465                 470                 475                 480

Lys Val Tyr Leu Ala Trp Val Pro Ala His Lys Gly Ile Gly Gly Asn
                485                 490                 495

Glu Gln Val Asp Lys Leu Val Ser Arg Ala Lys Arg Ala Pro Val Lys
            500                 505                 510

Gln Thr Leu Asn Phe Asp Leu Leu Lys Leu Ala Gly Asp Val Glu Ser
        515                 520                 525

Asn Pro Gly Pro His Gln Ala Leu Ser Pro Arg Thr Leu Asn Ala Trp
    530                 535                 540
```

-continued

```
Val Lys Val Ile Glu Glu Lys Ala Phe Ser Pro Glu Val Ile Pro Met
545                 550                 555                 560

Phe Thr Ala Leu Ser Glu Gly Ala Thr Pro His Asp Leu Asn Thr Met
                565                 570                 575

Leu Asn Thr Ile Gly Gly His Gln Ala Ala Met Gln Met Leu Lys Asp
            580                 585                 590

Thr Ile Asn Glu Glu Ala Ala Glu Trp Asp Arg Val His Pro Val His
        595                 600                 605

Ala Gly Pro Val Ala Pro Gly Gln Met Arg Asp Pro Arg Gly Ser Asp
    610                 615                 620

Ile Ala Gly Ser Thr Ser Thr Leu Gln Glu Gln Ile Ala Trp Met Thr
625                 630                 635                 640

Asn Asn Pro Pro Ile Pro Val Gly Asp Ile Tyr Lys Arg Trp Ile Ile
                645                 650                 655

Met Gly Leu Asn Lys Ile Val Arg Met Tyr Ser Pro Val Ser Ile Leu
            660                 665                 670

Asp Ile Lys Gln Gly Pro Lys Glu Pro Phe Arg Asp Tyr Val Asp Arg
        675                 680                 685

Phe Tyr Arg Thr Leu Arg Ala Glu Gln Ala Ser Gln Asp Val Lys Asn
    690                 695                 700

Trp Met Thr Glu Thr Leu Leu Val Gln Asn Ser Asn Pro Asp Cys Lys
705                 710                 715                 720

Thr Ile Leu Lys Ala Leu Gly Pro Gly Ala Thr Leu Glu Glu Met Met
                725                 730                 735

Ser Ala Cys Gln Gly Val Gly Gly Pro Ser His Lys Ala Arg Val Leu
            740                 745                 750

Ala Glu Ala Met Cys Gln Ala Val Lys Ala Ala Cys Trp Trp Ala Gly
        755                 760                 765

Val Lys Gln Glu Phe Gly Ile Pro Tyr Asn Thr Gln Ser Gln Gly Val
    770                 775                 780

Val Glu Ser Met Asn Asn Glu Leu Lys Lys Ile Ile Gly Gln Ile Arg
785                 790                 795                 800

Asp Gln Ala Glu His Leu Lys Thr Ala Val Gln Met Ala Val Leu Ile
                805                 810                 815

His Asn Phe Lys Arg Lys Gly Gly Ile Gly Glu Tyr Ser Ala Gly Glu
            820                 825                 830

Arg Ile Ile Asp Ile Ile Ala Lys Glu Lys Ile Tyr Leu Ala Trp Val
        835                 840                 845

Pro Ala His Lys Gly Ile Gly Gly Asn Glu Gln Ile Asp Lys Leu Val
    850                 855                 860

Ser Ala Ala Tyr Met Ala Ala Arg Ala Ser Ile Leu Ser Gly Gly Lys
865                 870                 875                 880

Leu Asp Lys Trp Glu Lys Ile Arg Leu Arg Pro Gly Gly Arg Lys Lys
                885                 890                 895

Tyr Lys Leu Lys His Leu Val Trp Ala Ser Arg Glu Leu Glu Arg Phe
            900                 905                 910

Ala Leu Asn Pro Gly Leu Leu Glu Thr Thr Gln Gly Phe Phe Pro Asp
        915                 920                 925

Trp Gln Asn Tyr Thr Pro Gly Pro Gly Ile Arg Phe Pro Leu Thr Phe
    930                 935                 940

Gly Trp Cys Phe Lys Leu Val Pro Leu Val Ala Lys Glu Ile Val Ala
945                 950                 955                 960

Cys Cys Asp Lys Cys Gln Leu Lys Gly Glu Ala Ile His Gly Gln Val
```

```
                965                 970                 975

Asp Cys Ser Pro Gly Val Trp Gln Leu Asp Cys Thr His Leu Glu Gly
            980                 985                 990

Lys Val Ile Leu Val Ala Val His  Val Ala Ser Gly Tyr  Ile Glu Ala
        995                 1000                1005

Glu Ile  Ile Pro Thr Glu Thr  Gly Gln Glu Thr Ala  Tyr Phe Ile
    1010                1015                1020

Leu Lys  Leu Ala Gly Arg Trp  Pro Val Thr Thr
    1025                1030


<210> SEQ ID NO 110
<211> LENGTH: 1031
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Leu Ser Pro Arg Thr Leu Asn Ala Trp Val Lys Val Ile Glu Glu Lys
1               5                   10                  15

Ala Phe Ser Pro Glu Val Ile Pro Met Phe Thr Ala Leu Ser Glu Gly
            20                  25                  30

Ala Thr Pro His Asp Leu Asn Thr Met Leu Asn Thr Ile Gly Gly His
        35                  40                  45

Gln Ala Ala Met Gln Met Leu Lys Asp Thr Ile Asn Glu Glu Ala Ala
    50                  55                  60

Glu Trp Asp Arg Val His Pro Val His Ala Gly Pro Val Ala Pro Gly
65                  70                  75                  80

Gln Met Arg Asp Pro Arg Gly Ser Asp Ile Ala Gly Ser Thr Ser Thr
                85                  90                  95

Leu Gln Glu Gln Ile Ala Trp Met Thr Asn Asn Pro Pro Ile Pro Val
            100                 105                 110

Gly Asp Ile Tyr Lys Arg Trp Ile Ile Met Gly Leu Asn Lys Ile Val
        115                 120                 125

Arg Met Tyr Ser Pro Val Ser Ile Leu Asp Ile Lys Gln Gly Pro Lys
    130                 135                 140

Glu Pro Phe Arg Asp Tyr Val Asp Arg Phe Tyr Arg Thr Leu Arg Ala
145                 150                 155                 160

Glu Gln Ala Ser Gln Asp Val Lys Asn Trp Met Thr Glu Thr Leu Leu
                165                 170                 175

Val Gln Asn Ser Asn Pro Asp Cys Lys Thr Ile Leu Lys Ala Leu Gly
            180                 185                 190

Pro Gly Ala Thr Leu Glu Glu Met Met Ser Ala Cys Gln Gly Val Gly
        195                 200                 205

Gly Pro Ser His Lys Ala Arg Val Leu Ala Glu Ala Met Cys Gln Ala
    210                 215                 220

Val Lys Ala Ala Cys Trp Trp Ala Gly Val Lys Gln Glu Phe Gly Ile
225                 230                 235                 240

Pro Tyr Asn Thr Gln Ser Gln Gly Val Val Glu Ser Met Asn Asn Glu
                245                 250                 255

Leu Lys Lys Ile Ile Gly Gln Ile Arg Asp Gln Ala Glu His Leu Lys
            260                 265                 270

Thr Ala Val Gln Met Ala Val Leu Ile His Asn Phe Lys Arg Lys Gly
        275                 280                 285
```

```
Gly Ile Gly Glu Tyr Ser Ala Gly Glu Arg Ile Ile Asp Ile Ile Ala
    290                 295                 300

Lys Glu Lys Ile Tyr Leu Ala Trp Val Pro Ala His Lys Gly Ile Gly
305                 310                 315                 320

Gly Asn Glu Gln Ile Asp Lys Leu Val Ser Ala Ala Tyr Met Ala Ala
                325                 330                 335

Arg Ala Ser Ile Leu Ser Gly Gly Lys Leu Asp Lys Trp Glu Lys Ile
            340                 345                 350

Arg Leu Arg Pro Gly Gly Arg Lys Lys Tyr Lys Leu Lys His Leu Val
        355                 360                 365

Trp Ala Ser Arg Glu Leu Glu Arg Phe Ala Leu Asn Pro Gly Leu Leu
    370                 375                 380

Glu Thr Thr Gln Gly Phe Phe Pro Asp Trp Gln Asn Tyr Thr Pro Gly
385                 390                 395                 400

Pro Gly Ile Arg Phe Pro Leu Thr Phe Gly Trp Cys Phe Lys Leu Val
                405                 410                 415

Pro Leu Val Ala Lys Glu Ile Val Ala Cys Cys Asp Lys Cys Gln Leu
            420                 425                 430

Lys Gly Glu Ala Ile His Gly Gln Val Asp Cys Ser Pro Gly Val Trp
        435                 440                 445

Gln Leu Asp Cys Thr His Leu Glu Gly Lys Val Ile Leu Val Ala Val
    450                 455                 460

His Val Ala Ser Gly Tyr Ile Glu Ala Glu Ile Ile Pro Thr Glu Thr
465                 470                 475                 480

Gly Gln Glu Thr Ala Tyr Phe Ile Leu Lys Leu Ala Gly Arg Trp Pro
                485                 490                 495

Val Thr Thr Arg Ala Lys Arg Ala Pro Val Lys Gln Thr Leu Asn Phe
            500                 505                 510

Asp Leu Leu Lys Leu Ala Gly Asp Val Glu Ser Asn Pro Gly Pro Val
        515                 520                 525

Ala Lys Glu Ile Val Ala Ser Cys Asp Lys Cys Gln Leu Lys Gly Glu
    530                 535                 540

Ala Met His Gly Gln Val Asp Cys Ser Pro Gly Ile Trp Gln Leu Asp
545                 550                 555                 560

Cys Thr His Leu Glu Gly Lys Ile Ile Leu Val Ala Val His Val Ala
                565                 570                 575

Ser Gly Tyr Ile Glu Ala Glu Val Ile Pro Ala Glu Thr Gly Gln Glu
            580                 585                 590

Thr Ala Tyr Phe Leu Leu Lys Leu Ala Gly Arg Trp Pro Val Lys Thr
        595                 600                 605

Thr Gln Gly Tyr Phe Pro Asp Trp Gln Asn Tyr Thr Pro Gly Pro Gly
    610                 615                 620

Thr Arg Tyr Pro Leu Thr Phe Gly Trp Cys Phe Lys Leu Val Pro Val
625                 630                 635                 640

Thr Val Lys Ala Ala Cys Trp Trp Ala Gly Ile Lys Gln Glu Phe Gly
                645                 650                 655

Ile Pro Tyr Asn Pro Gln Ser Gln Gly Val Val Glu Ser Met Asn Lys
            660                 665                 670

Glu Leu Lys Lys Ile Ile Gly Gln Val Arg Asp Gln Ala Glu His Leu
        675                 680                 685

Lys Thr Ala Val Gln Met Ala Val Phe Ile His Asn Phe Lys Arg Lys
    690                 695                 700

Gly Gly Ile Gly Gly Tyr Ser Ala Gly Glu Arg Ile Val Asp Ile Ile
```

-continued

```
705                 710                 715                 720

Ala Ala Ala Met Ala Ala Arg Ala Ser Val Leu Ser Gly Gly Glu Leu
                725                 730                 735

Asp Arg Trp Glu Lys Ile Arg Leu Arg Pro Gly Gly Lys Lys Lys Tyr
            740                 745                 750

Arg Leu Lys His Ile Val Trp Ala Ser Arg Glu Leu Glu Arg Phe Ala
        755                 760                 765

Val Asn Pro Gly Leu Leu Glu Thr Ser Glu Gly Ile Ser Pro Arg Thr
    770                 775                 780

Leu Asn Ala Trp Val Lys Val Val Glu Glu Lys Ala Phe Ser Pro Glu
785                 790                 795                 800

Val Ile Pro Met Phe Ser Ala Leu Ser Glu Gly Ala Thr Pro Gln Asp
                805                 810                 815

Leu Asn Thr Met Leu Asn Thr Val Gly Gly His Gln Ala Ala Met Gln
            820                 825                 830

Met Leu Lys Glu Thr Ile Asn Glu Glu Ala Ala Glu Trp Asp Arg Leu
        835                 840                 845

His Pro Val His Ala Gly Pro Ile Ala Pro Gly Gln Met Arg Glu Pro
    850                 855                 860

Arg Gly Ser Asp Ile Ala Gly Thr Thr Ser Thr Leu Gln Glu Gln Ile
865                 870                 875                 880

Gly Trp Met Thr Asn Asn Pro Pro Ile Pro Val Gly Glu Ile Tyr Lys
                885                 890                 895

Arg Trp Ile Ile Leu Gly Leu Asn Lys Ile Val Arg Met Tyr Ser Pro
            900                 905                 910

Thr Ser Ile Leu Asp Ile Arg Gln Gly Pro Lys Glu Pro Phe Arg Asp
        915                 920                 925

Tyr Val Asp Arg Phe Tyr Lys Thr Leu Arg Ala Glu Gln Ala Ser Gln
    930                 935                 940

Glu Val Lys Asn Trp Met Thr Glu Thr Leu Leu Val Gln Asn Ala Asn
945                 950                 955                 960

Pro Asp Cys Lys Thr Ile Leu Lys Ala Leu Gly Pro Ala Ala Thr Leu
                965                 970                 975

Glu Glu Met Met Thr Ala Cys Gln Gly Val Gly Gly Pro Gly His Lys
            980                 985                 990

Ala Arg Val Leu Ala Glu Ala Met  Ser Gln Ala Ala Ala  Lys Glu Lys
        995                 1000                 1005

Val Tyr  Leu Ala Trp Val Pro  Ala His Lys Gly Ile  Gly Gly Asn
    1010                 1015                 1020

Glu Gln  Val Asp Lys Leu Val  Ser
    1025                 1030


<210> SEQ ID NO 111
<211> LENGTH: 1020
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Ile Thr Lys Ile Gln Asn Phe Arg Val Tyr Tyr Arg Asp Ser Arg Asp
1               5                   10                  15

Pro Leu Trp Lys Gly Pro Ala Lys Leu Leu Trp Lys Gly Glu Gly Ala
            20                  25                  30
```

-continued

```
Val Val Ile Gln Asp Asn Ser Asp Ile Lys Val Val Pro Arg Arg Lys
        35                  40                  45

Ala Lys Ile Ile Arg Asp Tyr Gly Lys Gln Met Ala Gly Asp Asp Cys
    50                  55                  60

Val Ala Ser Arg Gln Asp Glu Asp Ala Ala Tyr Glu Glu Glu Glu Val
65                  70                  75                  80

Gly Phe Pro Val Lys Pro Gln Val Pro Leu Arg Pro Met Thr Phe Lys
                85                  90                  95

Gly Ala Leu Asp Leu Ser His Phe Leu Arg Glu Lys Gly Gly Leu Glu
            100                 105                 110

Gly Ala Ala Trp Gly Phe Thr Thr Pro Asp Lys Lys His Gln Lys Glu
        115                 120                 125

Pro Pro Phe Leu Trp Met Gly Tyr Glu Leu His Pro Asp Lys Trp Thr
    130                 135                 140

Val Gln Pro Ile Val Leu Pro Glu Lys Asp Ser Trp Thr Val Asn Asp
145                 150                 155                 160

Ile Gln Lys Leu Val Gly Lys Leu Asn Trp Ala Ser Gln Ile Tyr Pro
                165                 170                 175

Gly Ile Lys Val Pro Lys Phe Lys Leu Pro Ile Gln Lys Glu Thr Trp
            180                 185                 190

Glu Thr Trp Trp Thr Glu Tyr Trp Gln Ala Thr Trp Ile Pro Glu Trp
        195                 200                 205

Glu Phe Val Asn Thr Pro Pro Leu Val Lys Leu Trp Tyr Gln Leu Glu
    210                 215                 220

Lys Glu Pro Ile Val Gly Ala Glu Thr Phe Tyr Val Asp Gly Ala Ala
225                 230                 235                 240

Asn Arg Glu Thr Lys Phe Pro Gln Ile Thr Leu Trp Gln Arg Pro Leu
                245                 250                 255

Val Thr Ile Lys Ile Gly Gly Gln Leu Lys Glu Ala Leu Leu Asp Thr
            260                 265                 270

Gly Ala Asp Asp Thr Val Leu Glu Glu Met Asn Leu Pro Gly Arg Trp
        275                 280                 285

Lys Pro Lys Met Ile Gly Gly Ile Gly Gly Phe Ile Lys Val Arg Gln
    290                 295                 300

Tyr Asp Gln Gly Thr Val Leu Val Gly Pro Thr Pro Val Asn Ile Ile
305                 310                 315                 320

Gly Arg Asn Leu Leu Thr Gln Ile Gly Cys Thr Leu Asn Phe Pro Ile
                325                 330                 335

Ser Pro Ile Glu Thr Val Pro Val Lys Leu Lys Pro Gly Met Asp Gly
            340                 345                 350

Pro Lys Val Lys Gln Trp Pro Leu Thr Glu Glu Lys Ile Lys Ala Leu
        355                 360                 365

Val Glu Ile Cys Thr Glu Met Glu Lys Glu Gly Lys Ile Ser Lys Ile
    370                 375                 380

Gly Pro Glu Asn Pro Tyr Asn Thr Pro Val Phe Ala Ile Lys Lys Lys
385                 390                 395                 400

Asp Ser Thr Lys Trp Arg Lys Leu Val Asp Phe Arg Glu Leu Asn Lys
                405                 410                 415

Arg Thr Gln Asp Phe Trp Glu Val Gln Leu Gly Ile Pro His Pro Ala
            420                 425                 430

Gly Leu Lys Lys Lys Lys Ser Val Thr Val Leu Asp Val Gly Asp Ala
        435                 440                 445

Tyr Phe Ser Val Pro Leu Asp Lys Asp Phe Arg Lys Tyr Thr Ala Phe
```

-continued 450 455 460

Thr Ile Pro Ser Ile Asn Asn Glu Thr Pro Gly Ile Arg Tyr Gln Tyr
465 470 475 480

Asn Val Leu Pro Gln Gly Trp Lys Gly Ser Pro Ala Ile Phe Gln Ser
485 490 495

Ser Met Thr Arg Ala Lys Arg Ala Pro Val Lys Gln Thr Leu Asn Phe
500 505 510

Asp Leu Leu Lys Leu Ala Gly Asp Val Glu Ser Asn Pro Gly Pro Pro
515 520 525

Lys Phe Arg Leu Pro Ile Gln Lys Glu Thr Trp Asp Thr Trp Trp Thr
530 535 540

Asp Tyr Trp Gln Ala Thr Trp Ile Pro Glu Trp Glu Phe Thr Asn Thr
545 550 555 560

Pro Pro Leu Val Lys Leu Trp Tyr Gln Leu Glu Thr Glu Pro Ile Ala
565 570 575

Gly Val Glu Thr Phe Tyr Val Asp Gly Ala Ser Asn Arg Glu Thr Lys
580 585 590

Glu Glu Val Gly Phe Pro Val Arg Pro Gln Val Pro Leu Arg Pro Met
595 600 605

Thr Tyr Lys Gly Ala Leu Asp Leu Ser His Phe Leu Lys Glu Lys Gly
610 615 620

Gly Leu Glu Gly Leu Pro Gln Ile Thr Leu Trp Gln Arg Pro Ile Val
625 630 635 640

Thr Ile Lys Ile Gly Gly Gln Ile Lys Glu Ala Leu Leu Asp Thr Gly
645 650 655

Ala Asp Asp Thr Val Leu Glu Asp Met Asn Leu Pro Gly Lys Trp Lys
660 665 670

Pro Lys Met Ile Gly Gly Ile Gly Gly Phe Ile Lys Val Lys Gln Tyr
675 680 685

Asp Gln Ile Thr Lys Leu Gln Asn Phe Arg Val Tyr Tyr Arg Asp Asn
690 695 700

Arg Asp Pro Leu Trp Lys Gly Pro Ala Arg Leu Leu Trp Lys Gly Glu
705 710 715 720

Gly Ala Val Val Ile Gln Asp Asn Ser Glu Ile Lys Val Val Pro Arg
725 730 735

Arg Lys Val Lys Ile Ile Arg Asp Tyr Gly Lys Arg Met Ala Gly Asp
740 745 750

Asp Cys Val Ala Gly Arg Gln Asp Glu Asp Trp Gly Leu Thr Thr Pro
755 760 765

Asp Lys Lys His Gln Lys Asp Pro Pro Phe Leu Trp Met Gly Tyr Glu
770 775 780

Leu His Pro Asp Arg Trp Thr Val Gln Pro Ile Glu Leu Pro Glu Lys
785 790 795 800

Glu Ser Trp Thr Val Asn Asp Ile Gln Lys Leu Ile Gly Lys Leu Asn
805 810 815

Trp Ala Ser Gln Ile Tyr Ala Gly Ile Lys Val Lys Gly Thr Val Leu
820 825 830

Ile Gly Pro Thr Pro Val Asn Ile Ile Gly Arg Asn Leu Leu Thr Gln
835 840 845

Leu Gly Cys Thr Leu Asn Phe Pro Ile Ser Pro Ile Asp Thr Val Pro
850 855 860

Val Lys Leu Lys Pro Gly Met Asp Gly Pro Arg Val Lys Gln Trp Pro
865 870 875 880

Leu Thr Glu Glu Lys Ile Lys Ala Leu Ile Glu Ile Cys Thr Glu Met
885 890 895

Glu Lys Glu Gly Lys Ile Ser Arg Ile Gly Pro Glu Asn Pro Tyr Asn
900 905 910

Thr Pro Ile Phe Ala Ile Lys Lys Lys Asp Gly Thr Lys Trp Arg Lys
915 920 925

Leu Val Asp Phe Arg Glu Leu Asn Lys Lys Thr Gln Asp Phe Trp Glu
930 935 940

Val Gln Leu Gly Ile Pro His Pro Ser Gly Leu Lys Lys Lys Lys Ser
945 950 955 960

Val Thr Val Leu Asp Ile Gly Asp Ala Tyr Phe Ser Val Pro Leu Asp
965 970 975

Lys Glu Phe Arg Lys Tyr Thr Ala Phe Thr Val Pro Ser Thr Asn Asn
980 985 990

Glu Thr Pro Gly Val Arg Tyr Gln Tyr Asn Val Leu Pro Met Gly Trp
995 1000 1005

Lys Gly Ser Pro Ala Ile Phe Gln Cys Ser Met Thr
1010 1015 1020

<210> SEQ ID NO 112
<211> LENGTH: 1020
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 112

Pro Lys Phe Arg Leu Pro Ile Gln Lys Glu Thr Trp Asp Thr Trp Trp
1 5 10 15

Thr Asp Tyr Trp Gln Ala Thr Trp Ile Pro Glu Trp Glu Phe Thr Asn
20 25 30

Thr Pro Pro Leu Val Lys Leu Trp Tyr Gln Leu Glu Thr Glu Pro Ile
35 40 45

Ala Gly Val Glu Thr Phe Tyr Val Asp Gly Ala Ser Asn Arg Glu Thr
50 55 60

Lys Glu Glu Val Gly Phe Pro Val Arg Pro Gln Val Pro Leu Arg Pro
65 70 75 80

Met Thr Tyr Lys Gly Ala Leu Asp Leu Ser His Phe Leu Lys Glu Lys
85 90 95

Gly Gly Leu Glu Gly Leu Pro Gln Ile Thr Leu Trp Gln Arg Pro Ile
100 105 110

Val Thr Ile Lys Ile Gly Gly Gln Ile Lys Glu Ala Leu Leu Asp Thr
115 120 125

Gly Ala Asp Asp Thr Val Leu Glu Asp Met Asn Leu Pro Gly Lys Trp
130 135 140

Lys Pro Lys Met Ile Gly Gly Ile Gly Gly Phe Ile Lys Val Lys Gln
145 150 155 160

Tyr Asp Gln Ile Thr Lys Leu Gln Asn Phe Arg Val Tyr Tyr Arg Asp
165 170 175

Asn Arg Asp Pro Leu Trp Lys Gly Pro Ala Arg Leu Leu Trp Lys Gly
180 185 190

Glu Gly Ala Val Val Ile Gln Asp Asn Ser Glu Ile Lys Val Val Pro
195 200 205

Arg Arg Lys Val Lys Ile Ile Arg Asp Tyr Gly Lys Arg Met Ala Gly

-continued

```
    210                 215                 220

Asp Asp Cys Val Ala Gly Arg Gln Asp Glu Asp Trp Gly Leu Thr Thr
225                 230                 235                 240

Pro Asp Lys Lys His Gln Lys Asp Pro Pro Phe Leu Trp Met Gly Tyr
                245                 250                 255

Glu Leu His Pro Asp Arg Trp Thr Val Gln Pro Ile Glu Leu Pro Glu
            260                 265                 270

Lys Glu Ser Trp Thr Val Asn Asp Ile Gln Lys Leu Ile Gly Lys Leu
        275                 280                 285

Asn Trp Ala Ser Gln Ile Tyr Ala Gly Ile Lys Val Lys Gly Thr Val
    290                 295                 300

Leu Ile Gly Pro Thr Pro Val Asn Ile Ile Gly Arg Asn Leu Leu Thr
305                 310                 315                 320

Gln Leu Gly Cys Thr Leu Asn Phe Pro Ile Ser Pro Ile Asp Thr Val
                325                 330                 335

Pro Val Lys Leu Lys Pro Gly Met Asp Gly Pro Arg Val Lys Gln Trp
            340                 345                 350

Pro Leu Thr Glu Glu Lys Ile Lys Ala Leu Ile Glu Ile Cys Thr Glu
        355                 360                 365

Met Glu Lys Glu Gly Lys Ile Ser Arg Ile Gly Pro Glu Asn Pro Tyr
    370                 375                 380

Asn Thr Pro Ile Phe Ala Ile Lys Lys Lys Asp Gly Thr Lys Trp Arg
385                 390                 395                 400

Lys Leu Val Asp Phe Arg Glu Leu Asn Lys Lys Thr Gln Asp Phe Trp
                405                 410                 415

Glu Val Gln Leu Gly Ile Pro His Pro Ser Gly Leu Lys Lys Lys Lys
            420                 425                 430

Ser Val Thr Val Leu Asp Ile Gly Asp Ala Tyr Phe Ser Val Pro Leu
        435                 440                 445

Asp Lys Glu Phe Arg Lys Tyr Thr Ala Phe Thr Val Pro Ser Thr Asn
    450                 455                 460

Asn Glu Thr Pro Gly Val Arg Tyr Gln Tyr Asn Val Leu Pro Met Gly
465                 470                 475                 480

Trp Lys Gly Ser Pro Ala Ile Phe Gln Cys Ser Met Thr Arg Ala Lys
                485                 490                 495

Arg Ala Pro Val Lys Gln Thr Leu Asn Phe Asp Leu Leu Lys Leu Ala
            500                 505                 510

Gly Asp Val Glu Ser Asn Pro Gly Pro Ile Thr Lys Ile Gln Asn Phe
        515                 520                 525

Arg Val Tyr Tyr Arg Asp Ser Arg Asp Pro Leu Trp Lys Gly Pro Ala
    530                 535                 540

Lys Leu Leu Trp Lys Gly Glu Gly Ala Val Val Ile Gln Asp Asn Ser
545                 550                 555                 560

Asp Ile Lys Val Val Pro Arg Arg Lys Ala Lys Ile Ile Arg Asp Tyr
                565                 570                 575

Gly Lys Gln Met Ala Gly Asp Asp Cys Val Ala Ser Arg Gln Asp Glu
            580                 585                 590

Asp Ala Ala Tyr Glu Glu Glu Glu Val Gly Phe Pro Val Lys Pro Gln
        595                 600                 605

Val Pro Leu Arg Pro Met Thr Phe Lys Gly Ala Leu Asp Leu Ser His
    610                 615                 620

Phe Leu Arg Glu Lys Gly Gly Leu Glu Gly Ala Ala Trp Gly Phe Thr
625                 630                 635                 640
```

```
Thr Pro Asp Lys Lys His Gln Lys Glu Pro Pro Phe Leu Trp Met Gly
                645                 650                 655

Tyr Glu Leu His Pro Asp Lys Trp Thr Val Gln Pro Ile Val Leu Pro
            660                 665                 670

Glu Lys Asp Ser Trp Thr Val Asn Asp Ile Gln Lys Leu Val Gly Lys
        675                 680                 685

Leu Asn Trp Ala Ser Gln Ile Tyr Pro Gly Ile Lys Val Pro Lys Phe
    690                 695                 700

Lys Leu Pro Ile Gln Lys Glu Thr Trp Glu Thr Trp Trp Thr Glu Tyr
705                 710                 715                 720

Trp Gln Ala Thr Trp Ile Pro Glu Trp Glu Phe Val Asn Thr Pro Pro
                725                 730                 735

Leu Val Lys Leu Trp Tyr Gln Leu Glu Lys Glu Pro Ile Val Gly Ala
            740                 745                 750

Glu Thr Phe Tyr Val Asp Gly Ala Ala Asn Arg Glu Thr Lys Phe Pro
        755                 760                 765

Gln Ile Thr Leu Trp Gln Arg Pro Leu Val Thr Ile Lys Ile Gly Gly
    770                 775                 780

Gln Leu Lys Glu Ala Leu Leu Asp Thr Gly Ala Asp Asp Thr Val Leu
785                 790                 795                 800

Glu Glu Met Asn Leu Pro Gly Arg Trp Lys Pro Lys Met Ile Gly Gly
                805                 810                 815

Ile Gly Gly Phe Ile Lys Val Arg Gln Tyr Asp Gln Gly Thr Val Leu
            820                 825                 830

Val Gly Pro Thr Pro Val Asn Ile Ile Gly Arg Asn Leu Leu Thr Gln
        835                 840                 845

Ile Gly Cys Thr Leu Asn Phe Pro Ile Ser Pro Ile Glu Thr Val Pro
    850                 855                 860

Val Lys Leu Lys Pro Gly Met Asp Gly Pro Lys Val Lys Gln Trp Pro
865                 870                 875                 880

Leu Thr Glu Glu Lys Ile Lys Ala Leu Val Glu Ile Cys Thr Glu Met
                885                 890                 895

Glu Lys Glu Gly Lys Ile Ser Lys Ile Gly Pro Glu Asn Pro Tyr Asn
            900                 905                 910

Thr Pro Val Phe Ala Ile Lys Lys Lys Asp Ser Thr Lys Trp Arg Lys
        915                 920                 925

Leu Val Asp Phe Arg Glu Leu Asn Lys Arg Thr Gln Asp Phe Trp Glu
    930                 935                 940

Val Gln Leu Gly Ile Pro His Pro Ala Gly Leu Lys Lys Lys Lys Ser
945                 950                 955                 960

Val Thr Val Leu Asp Val Gly Asp Ala Tyr Phe Ser Val Pro Leu Asp
                965                 970                 975

Lys Asp Phe Arg Lys Tyr Thr Ala Phe Thr Ile Pro Ser Ile Asn Asn
            980                 985                 990

Glu Thr Pro Gly Ile Arg Tyr Gln  Tyr Asn Val Leu Pro  Gln Gly Trp
        995                 1000                1005

Lys Gly  Ser Pro Ala Ile Phe  Gln Ser Ser Met Thr
    1010                1015                1020
```

<210> SEQ ID NO 113

<400> SEQUENCE: 113

000

<210> SEQ ID NO 114

<400> SEQUENCE: 114

000

<210> SEQ ID NO 115
<211> LENGTH: 16
<212> TYPE: PRT
<213> ORGANISM: Unknown
<220> FEATURE:
<223> OTHER INFORMATION: Description of Unknown:
CD74 sequence

<400> SEQUENCE: 115

Met His Arg Arg Arg Ser Arg Ser Cys Arg Glu Asp Gln Lys Pro Val
1 5 10 15

<210> SEQ ID NO 116
<211> LENGTH: 16
<212> TYPE: PRT
<213> ORGANISM: Vesicular stomatitis virus

<400> SEQUENCE: 116

Met Lys Cys Leu Leu Tyr Leu Ala Phe Leu Phe Ile Gly Val Asn Cys
1 5 10 15

<210> SEQ ID NO 117
<211> LENGTH: 17
<212> TYPE: PRT
<213> ORGANISM: Unknown
<220> FEATURE:
<223> OTHER INFORMATION: Description of Unknown:
albumin sequence

<400> SEQUENCE: 117

Lys Trp Val Thr Phe Ile Ser Leu Leu Phe Leu Phe Ser Ser Ala Tyr
1 5 10 15

Ser

<210> SEQ ID NO 118
<211> LENGTH: 17
<212> TYPE: PRT
<213> ORGANISM: Unknown
<220> FEATURE:
<223> OTHER INFORMATION: Description of Unknown:
calreticulin sequence

<400> SEQUENCE: 118

Met Leu Leu Ser Val Pro Leu Leu Leu Gly Leu Leu Gly Leu Ala Val
1 5 10 15

Ala

<210> SEQ ID NO 119
<211> LENGTH: 18
<212> TYPE: PRT
<213> ORGANISM: Unknown
<220> FEATURE:
<223> OTHER INFORMATION: Description of Unknown:
CSF2, GM-CSF sequence

<400> SEQUENCE: 119

Met Trp Leu Gln Ser Leu Leu Leu Leu Gly Thr Val Ala Cys Ser Ile
1 5 10 15

Ser Val

<210> SEQ ID NO 120
<211> LENGTH: 21
<212> TYPE: PRT
<213> ORGANISM: Unknown
<220> FEATURE:
<223> OTHER INFORMATION: Description of Unknown:
CXCL10, IP-10 sequence

<400> SEQUENCE: 120

Met Asn Gln Thr Ala Ile Leu Ile Cys Cys Leu Ile Phe Leu Thr Leu
1 5 10 15

Ser Gly Ile Gln Gly
20

<210> SEQ ID NO 121
<211> LENGTH: 23
<212> TYPE: PRT
<213> ORGANISM: Unknown
<220> FEATURE:
<223> OTHER INFORMATION: Description of Unknown:
PLAT, t-PA sequence

<400> SEQUENCE: 121

Met Asp Ala Met Lys Arg Gly Leu Cys Cys Val Leu Leu Leu Cys Gly
1 5 10 15

Ala Val Phe Val Ser Ala Arg
20

<210> SEQ ID NO 122
<211> LENGTH: 31
<212> TYPE: PRT
<213> ORGANISM: Unknown
<220> FEATURE:
<223> OTHER INFORMATION: Description of Unknown:
Beta-catenin sequence

<400> SEQUENCE: 122

Met Arg Lys Ala Ala Val Ser His Trp Gln Gln Gln Ser Tyr Leu Asp
1 5 10 15

Ser Gly Ile His Ser Gly Ala Thr Thr Thr Ala Pro Ser Leu Ser
20 25 30

<210> SEQ ID NO 123
<211> LENGTH: 76
<212> TYPE: PRT
<213> ORGANISM: Unknown
<220> FEATURE:
<223> OTHER INFORMATION: Description of Unknown:
ubiquitin sequence

<400> SEQUENCE: 123

Met Gln Ile Phe Val Lys Thr Leu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Phe Ala Gly Lys
35 40 45

Gln Leu Glu Asp Gly Arg Thr Leu Ser Asp Tyr Asn Ile Gln Lys Glu
50 55 60

Ser Thr Leu His Leu Val Leu Arg Leu Arg Gly Gly
65 70 75

<210> SEQ ID NO 124
<211> LENGTH: 23
<212> TYPE: PRT
<213> ORGANISM: Unknown
<220> FEATURE:
<223> OTHER INFORMATION: Description of Unknown:
CCL7, MCP-3 sequence

<400> SEQUENCE: 124

```
Met Lys Ala Ser Ala Ala Leu Leu Cys Leu Leu Leu Thr Ala Ala Ala
1               5                   10                  15

Phe Ser Pro Gln Gly Leu Ala
            20
```

<210> SEQ ID NO 125
<211> LENGTH: 384
<212> TYPE: PRT
<213> ORGANISM: Unknown
<220> FEATURE:
<223> OTHER INFORMATION: Description of Unknown:
LAMP-1 N-terminal sequence

<400> SEQUENCE: 125

```
Met Ala Pro Arg Ser Ala Arg Arg Pro Leu Leu Leu Leu Leu Leu Leu
1               5                   10                  15

Leu Leu Leu Gly Leu Met His Cys Ala Ser Ala Ala Met Phe Met Val
            20                  25                  30

Lys Asn Gly Asn Gly Thr Ala Cys Ile Met Ala Asn Phe Ser Ala Ala
        35                  40                  45

Phe Ser Val Asn Tyr Asp Thr Lys Ser Gly Pro Lys Asn Met Thr Leu
    50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Pro Ser Pro Ser
        195                 200                 205

Pro Ser Pro Val Pro Lys Ser Pro Ser Val Asp Lys Tyr Asn Val Ser
    210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
                245                 250                 255

Ile Asn Pro Asn Lys Thr Ser Ala Ser Gly Ser Cys Gly Ala His Leu
            260                 265                 270
```

Val Thr Leu Glu Leu His Ser Glu Gly Thr Thr Val Leu Leu Phe Gln
        275                 280                 285

Phe Gly Met Asn Ala Ser Ser Ser Arg Phe Phe Leu Gln Gly Ile Gln
    290                 295                 300

Leu Asn Thr Leu Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
        355                 360                 365

Gly Ser Val Glu Glu Cys Leu Leu Asp Glu Asn Ser Leu Glu Asp Ile
    370                 375                 380

<210> SEQ ID NO 126
<211> LENGTH: 39
<212> TYPE: PRT
<213> ORGANISM: Unknown
<220> FEATURE:
<223> OTHER INFORMATION: Description of Unknown:
      LAMP-1 C-terminal sequence

<400> SEQUENCE: 126

Gly Ser Glu Phe Thr Leu Ile Pro Ile Ala Val Gly Gly Ala Leu Ala
1               5                   10                  15

Gly Leu Val Ile Val Leu Ile Ala Tyr Leu Val Gly Arg Lys Arg Ser
            20                  25                  30

His Ala Gly Tyr Gln Thr Ile
        35

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130
<211> LENGTH: 1497
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130
acagtgaagg cagcttgttg gtgggccgga attaaacagg agtttggcat cccttataat     60
cctcagtctc agggagtggt ggagtctatg aacaaggagc tgaagaagat catcggccag    120
gtgagagatc aggcagaaca tctgaagaca gcagtgcaga tggccgtgtt tatccacaac    180

```
ttcaagagga agggcggcat tggaggatat agcgcaggag aaagaatcgt ggacatcatc    240
gccatctctc ctagaacact gaacgcttgg gtgaaagtgg tggaggagaa agcctttagc    300
ccagaagtga tccctatgtt ctcagctctg tcagaaggag ctacacctca ggatctgaac    360
accatgctga ataccgtggg aggacatcag gcagctatgc agatgctgaa ggagacaatt    420
aacgaggaag cagccgagtg ggatagactg catccagtgc acgcaggacc tattgctcca    480
ggacagatga gagagcctag aggaagcgat attgccggca caacatctac actgcaggaa    540
cagatcggtt ggatgaccaa caatcctcct atcccagtgg gcgaaatcta caaacgctgg    600
atcatcctgg gcctgaataa gatcgtgaga atgtacagcc ccacaagcat cctggatatc    660
agacagggac ctaaggaacc tttcagggat tacgtggacc ggttctacaa gacactgaga    720
gcagaacagg catctcagga ggtgaagaat tggatgaccg agacactgct ggtgcagaac    780
gctaatccag attgcaagac cattctgaaa gctctgggac cagcagctac actggaagag    840
atgatgacag cttgtcaggg agtgggagga ccaggacata aagctagagt gctggcagaa    900
gctatgtctc agatggcagc tagagcttca gtgctgtcag gaggagaact cgataggtgg    960
gagaagatca gactgagacc aggaggcaag aagaagtaca gactgaagca catcgtgtgg   1020
gcttctagag aactggagag atttgccgtg aatccaggac tcctggaaac acctccagtg   1080
gtggctaaag agattgtggc ttcttgcgat aagtgccagc tgaaaggaga ggctatgcac   1140
ggacaggtgg attgttctcc aggaatttgg cagctggatt gtacacacct ggagggaaag   1200
attattctgg tggcagtgca cgtggcatca ggatatattg aggccgaagt gattccagca   1260
gaaacaggac aggagacagc ttactttctg ctcaaactgg caggtcgctg gccagtgaaa   1320
accaaggaga aggtgtacct ggcttgggtg ccagctcata aaggaattgg cggaaacgag   1380
caggtggata aactggtgtc tacacagggc tacttcccag attggcagaa ttacacacca   1440
ggaccaggca caagatatcc tctgacattc ggttggtgtt tcaagctggt gcccgtg      1497
```

<210> SEQ ID NO 131
<211> LENGTH: 1497
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 131

```
acagtgaaag cagcttgttg gtgggcagga atcaagcagg agtttggcat cccttacaat     60
cctcagtctc agggagtggt ggaatctatg aacaaggagc tgaagaagat catcggccag    120
gtgagagatc aggcagaaca tctgaagaca gcagtgcaga tggcagtgtt tatccacaat    180
ttcaagagaa agggcggcat tggcggatat agcgccggag agagaatcgt ggatatcatc    240
gccatctctc ctagaacact gaacgcttgg gtgaaagtgg tggaagagaa agccttctct    300
ccagaggtga tccctatgtt tagcgctctg tcagaaggag ctacacctca ggatctgaat    360
accatgctga ataccgtggg cggacatcag gcagctatgc agatgctgaa agagacaatc    420
aacgaagaag cagccgagtg ggatagactg catccagtgc acgcaggacc tattgctcca    480
ggacagatga gagaacctag aggatcagac attgccggaa caacatctac actgcaggag    540
cagatcggtt ggatgacaaa caaccctcca atcccagtgg gagagatcta caagagatgg    600
atcatcctgg gcctgaataa gatcgtgaga atgtacagcc ccacaagcat cctggatatc    660
agacagggac ctaaggagcc tttcagagat tacgtggaca ggttctacaa gaccctgaga    720
```

-continued

```
gcagaacagg cttctcagga ggtgaaaaat tggatgaccg aaacactgct ggtgcagaac    780

gctaatcccg attgcaagac catcctgaaa gctctgggac cagcagctac actggaagag    840

atgatgacag cttgtcaggg agtgggagga ccaggacata aagctagagt gctggcagaa    900

gctatgtctc agatggcagc tagagcttca gtgctgtcag gaggagaact cgatagatgg    960

gaaaagatca gactgagacc aggaggaaag aagaagtaca ggctgaagca catcgtctgg   1020

gcttctagag aactggagag atttgccgtg aatccaggac tcctggaaac acctccagtg   1080

gtggctaaag agattgtggc ttcttgcgac aagtgtcagc tgaaaggaga ggctatgcac   1140

ggacaggtgg attgttctcc aggaatttgg cagctggatt gcacacatct ggaaggaaag   1200

attattctgg tggcagtgca cgtggcatct ggatatatcg aggccgaggt gattccagcc   1260

gaaacaggac aggaaacagc ctactttctc ctgaaactgg caggtaggtg gccagtgaag   1320

acaaaggaga aggtgtacct ggcttgggtg ccagcccata aaggaattgg aggcaatgag   1380

caggtggata aactggtgtc aacacagggc tacttcccag attggcagaa ttacacccca   1440

ggaccaggaa caagatatcc tctgacattc ggttggtgct ttaaactggt gcccgtg      1497
```

<210> SEQ ID NO 132
<211> LENGTH: 1503
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132

```
ctgtctccta gaacactgaa cgcttgggtg aaggtgatcg aagagaaggc ctttagccca     60

gaagtgatcc ctatgttcac agctctgtca gaaggagcta cacctcatga cctgaacacc    120

atgctgaata ccatcggagg acatcaggca gctatgcaga tgctgaagga taccatcaac    180

gaagaagcag ccgagtggga tagagtgcat ccagtgcacg caggaccagt ggctccagga    240

cagatgagag atcctagagg aagcgatatt gccggctcta catctacact gcaggaacag    300

atcgcttgga tgaccaacaa tcctcctatc ccagtgggcg atatctacaa acgctggatc    360

atcatgggcc tgaacaagat cgtgaggatg tacagcccag tgtctatcct ggatatcaag    420

cagggcccta aagaaccttt cagggattac gtggaccggt tctacagaac actgagagca    480

gaacaggcct cacaggatgt gaagaattgg atgaccgaga cactgctggt gcagaacagc    540

aaccccgatt gcaagaccat tctgaaagct ctgggaccag gagctacact ggaagagatg    600

atgtcagctt gtcagggagt gggaggacca tctcataaag ctagagtgct ggccgaagct    660

atgtgtcagg tggctaaaga gatcgtggct tgttgcgaca agtgtcagct gaaaggagag    720

gctattcacg gacaggtgga ttgttctcca ggagtctggc agctggattg tacacacctg    780

gagggaaagg tgattctggt ggcagtgcac gtggcatcag gatatattga ggccgagatc    840

attcctacag aaacaggaca ggagaccgct tacttcatcc tgaaactggc aggtaggtgg    900

ccagtgacaa caatggcagc tagagcttct atcctgagcg gaggaaaact cgacaagtgg    960

gagaagatca gactgagacc aggaggcaga aagaagtaca agctgaagca tctcgtctgg   1020

gcttctagag agctggaaag attcgctctg aatccaggtc tgctggaaac agcagcagca   1080

gtgaaagcag cttgttggtg ggcaggagtg aaacaggaat ttggcatccc ttacaataca   1140

cagtctcagg gagtggtgga gagcatgaac aacgagctga agaagatcat cggccagatc   1200

agagatcagg cagaacatct gaagacagca gtgcagatgg cagtgctgat ccacaacttc   1260
```

aagaggaagg gcggaatcgg agaatatagc gccggcgaga gaattatcga tatcatcgcc 1320
acacagggct ttttcccaga ttggcagaac tatacaccag gaccaggaat caggttccct 1380
ctgacattcg gttggtgttt caagctggtg cctctgctga tcaagaagga gaaaatctat 1440
ctggcttggg tgccagctca caaaggaatt ggcggaaacg agcagatcga taagctggtg 1500
tct 1503

<210> SEQ ID NO 133
<211> LENGTH: 1503
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 133
ctgtctccta gaacactgaa cgcttgggtg aaggtgattg aggagaaagc cttcagccca 60
gaagtgatcc ctatgtttac agccctgagc gaaggagcta cacctcacga tctgaatacc 120
atgctgaata caatcggcgg acatcaggca gccatgcaga tgctgaagga tacaatcaac 180
gaagaagcag ccgagtggga tagagtgcat ccagtgcacg caggaccagt ggctccagga 240
cagatgagag atcctagagg aagcgatatc gccggatcta catctacact gcaggaacag 300
atcgcttgga tgacaaataa ccccccctatc ccagtgggag atatctataa gcgctggatc 360
atcatgggcc tgaacaagat cgtgaggatg tacagcccag tgagcatcct ggatatcaag 420
cagggaccta aggagccttt cagagattac gtggacaggt tctacagaac cctgagagca 480
gaacaggctt ctcaggacgt gaagaattgg atgaccgaaa cactgctggt gcagaatagc 540
aaccccgatt gcaagaccat cctgaaagct ctgggaccag gagctacact ggaagaaatg 600
atgagcgctt gtcagggagt gggaggacca tctcataagg ctagagtgct ggcagaagct 660
atgtgtcagg tggctaagga gattgtggct tgttgcgaca agtgtcagct gaaaggagag 720
gctattcacg gacaggtgga ttgttctcca ggagtctggc agctggattg tacacatctg 780
gagggaaaag tgattctggt ggcagtgcac gtggcatcag gatatattga ggccgaaatc 840
atccctacag agacaggaca ggagacagcc tactttatcc tgaaactggc aggcagatgg 900
ccagtgacaa caatggcagc tagagcttct atcctgagcg gaggaaagct ggataagtgg 960
gaaaagatca gactgagacc aggaggaagg aagaagtaca agctgaagca cctggtctgg 1020
gcttctagag aactggaaag attcgccctg aatccaggtc tgctggaaac agcagcagca 1080
gtgaaagcag cttgttggtg ggcaggagtg aaacaggagt tcggaatccc ctacaacaca 1140
cagtctcagg gagtggtgga atctatgaac aacgagctga agaagatcat cggccagatc 1200
agagaccagg ccgaacatct gaagacagca gtgcagatgg cagtgctgat tcacaatttc 1260
aagagaaagg gcggcatcgg agagtatagc gccggagaga gaatcatcga tatcatcgct 1320
acacagggct tcttccccga ttggcagaat tacaccccag gcccaggcat tagattccct 1380
ctgacattcg gttggtgctt caaactggtg cctctgctga tcaagaagga gaagatctac 1440
ctggcttggg tgccagctca taaaggaatc ggaggaaacg agcagatcga taagctggtg 1500
tct 1503

<210> SEQ ID NO 134
<211> LENGTH: 1482
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 134

```
tttcctcaga tcactctctg gcagagacca ctggtgacaa tcaagatcgg aggacagctg     60

aaagaagctc tgctggatac aggagcagac gatacagtgc tggaagagat gaatctgcca    120

ggtcgctgga aacctaagat gattggaggc attggcggct ttatcaaggt gagacagtac    180

gaccaggagg aagtgggatt tccagtgaaa cctcaggtgc ctctgagacc tatgacattt    240

aagggcgctc tggacctgtc tcactttctg agagagaagg gaggactgga aggactgatc    300

cctaagttca agctgcctat ccagaaggag acttgggaaa cttggtggac agagtattgg    360

caggctactt ggattcccga gtgggaattt gtgaacacac ctcctctggt gaagctgtgg    420

tatcagctgg aaaaggagcc tattgtgggc gcagaaacat tctacgtgga cggagcagct    480

aacagagaaa ctaagtgggg attcaccacc ccagataaga agcaccagaa ggagccacca    540

tttctctgga tgggatacga actgcaccca gataagtgga cagtccagcc tattgtgctg    600

ccagaaaagg actcttggac cgtgaacgat atccagaagc tggtgggaaa gctgaattgg    660

gcttctcaga tctacccagg aatcaaggtg atcaccaaga tccagaactt cagggtgtac    720

tacagagaca gcagagatcc tctctggaag ggaccagcta aactcctctg gaaaggagaa    780

ggagcagtgg tgatccagga taacagcgac atcaaggtgg tgcctagaag aaaggccaag    840

atcatcaggg actacggcaa acagatggca ggagacgatt gcgtggcttc tagacaggac    900

gaagacggaa cagtcctggt gggacctaca ccagtgaata tcatcggcag aaatctcctg    960

acacagatcg gttgtaccct gaacttccct atcagcccta tcgagacagt gccagtgaaa   1020

ctgaagccag gaatggacgg acctaaagtc aagcagtggc ctctgacaga agagaagatc   1080

aaggccctgg tggagatttg cacagagatg gagaaggagg gaaagatcag caagatcggc   1140

ccagagaatc cttacaacac cccagtgttc gccatcaaga agaaggatag caccaagtgg   1200

agaaagctgg tggatttcag ggagctgaac aagagaaccc aggacttttg ggaagtgcag   1260

ctgggcatcc cccatccagc aggactgaag aagaagaaga gcgtgacagt gctggacgtg   1320

ggagacgctt attttagcgt gcctctggac aaggacttca gaaagtacac cgccttcacc   1380

atcccttcta tcaacaacga gaccccaggc atcagatacc agtataacgt gctgcctcag   1440

ggttggaaag gatctccagc aatctttcag tctagcatga cc                      1482
```

<210> SEQ ID NO 135
<211> LENGTH: 1482
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 135

```
ttccctcaga ttactctctg gcagaggcca ctggtgacaa ttaagatcgg aggacagctg     60

aaagaagctc tgctggatac aggagcagac gatacagtgc tggaggaaat gaacctgcca    120

ggtcgctgga aacctaaaat gatcggagga atcggcggct ttattaaggt gagacagtac    180

gatcaggagg aagtgggatt tccagtgaaa cctcaggtgc ctctgagacc tatgacattt    240

aagggcgctc tggatctgag ccactttctg agagagaaag gaggactgga aggactgatc    300

cctaagttca agctgcccat ccagaaggag acttgggaaa cttggtggac cgagtattgg    360

caggcaactt ggattcccga gtgggaattt gtgaacacac ctcctctggt gaagctgtgg    420
```

```
tatcagctgg aaaaggagcc tatcgtggga gccgaaacat tttacgtgga cggagcagcc    480

aacagagaaa ctaagtgggg attcaccacc ccagataaga agcaccagaa agagcctccc    540

tttctctgga tgggatacga actgcaccca gataagtgga cagtccagcc tattgtgctg    600

ccagaaaagg actcttggac agtgaacgac atccagaagc tggtgggaaa gctgaattgg    660

gcctctcaga tttacccagg aatcaaggtg atcaccaaga tccagaactt cagggtgtac    720

tacagggata gcagagatcc tctctggaag ggaccagcta aactcctctg gaaaggagaa    780

ggagcagtgg tgatccagga taatagcgac atcaaggtgg tgcctagaag aaaggctaag    840

atcatccggg actacggcaa acagatggca ggagacgatt gcgtggcttc tagacaggat    900

gaagacggaa cagtcctggt gggacctaca ccagtgaaca tcatcggcag aaacctgctg    960

acacagatcg gttgtaccct gaacttccct atctctccta tcgaaacagt gccagtgaag   1020

ctgaagccag gaatggacgg acctaaagtc aagcagtggc ctctgacaga agagaagatc   1080

aaggctctgg tggagatttg caccgaaatg gagaaggagg gcaagatcag caagatcgga   1140

ccagagaatc cttacaatac cccagtgttc gccatcaaga agaaggacag caccaagtgg   1200

agaaagctgg tggatttcag ggaactgaac aagaggaccc aggacttttg ggaagtgcag   1260

ctgggcatcc cccatccagc aggactgaag aagaagaaga gcgtgacagt gctggacgtg   1320

ggagacgctt attttagcgt gcctctggac aaggacttca gaaagtacac cgccttcacc   1380

atccctagca tcaataacga gaccccaggc atcagatacc agtataacgt gctgccacag   1440

ggctggaaag gatctccagc aatctttcag agctctatga ca                      1482
```

<210> SEQ ID NO 136
<211> LENGTH: 1497
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 136

```
ctgcctcaga ttaccctgtg gcagagacct atcgtgacca tcaagatcgg aggacagatc     60

aaagaagctc tgctggatac aggagcagac gatacagtgc tggaggatat gaacctgcca    120

ggtaagtgga agcctaagat gatcggcgga attggcggct ttatcaaggt caagcagtac    180

gatcagtggg gactgacaac accagacaag aagcaccaga aggacccccc tttcctctgg    240

atgggatacg aactgcatcc agataggtgg acagtgcagc caattgagct gccagaaaag    300

gagtcttgga cagtgaacga catccagaag ctgatcggca agctgaattg ggcttctcag    360

atctacgccg gaattaaggt ggcagctcag gaagaagaag aagtgggatt tccagtgaga    420

cctcaggtgc ctctgagacc tatgacatac aagggagctc tggatctgag ccactttctg    480

aaagagaagg gaggactgga gggaattacc aagctgcaga acttcagggt gtactacagg    540

gacaacagag atcctctgtg gaaaggacca gctagactcc tctggaaagg agaaggagca    600

gtggtgattc aggacaatag cgagatcaag gtggtgccta gaagaaaggt gaagatcatc    660

cgggactacg gcaaaagaat ggcaggagac gattgcgtgg caggaagaca ggacgaggac    720

cccaaattca gactgcctat ccagaaggag acttgggaca cttggtggac agattattgg    780

caggcaactt ggattcccga gtgggaattt accaataccc ctcctctggt caagctctgg    840

tatcagctgg aaacagagcc tatcgcagga gtggaaacat tctacgtgga cggagcctct    900

aatagagaga caaaagccgc aggaacagtg ctgattggac ctacaccagt gaacatcatc    960
```

gggagaaacc tgctgacaca gctgggttgt acactgaact tccctatcag ccctatcgat 1020
acagtgccag tgaaactgaa gccaggaatg gacggaccta gagtgaaaca gtggcctctg 1080
acagaagaga agatcaaggc cctgatcgag atttgtacag agatggagaa ggagggcaag 1140
atctctagaa ttggcccaga gaacccctac aatacccta tctttgccat caagaagaag 1200
gacggcacca agtggagaaa gctggtggat ttcagggagc tgaacaagaa gacccaggac 1260
ttttgggaag tgcagctggg catcccccac cctagcggac tgaaaaagaa gaagagcgtg 1320
accgtgctgg atattggaga cgcctatttt agcgtgccac tggataagga gttcagaaag 1380
tacaccgcct ttaccgtgcc ttctaccaat aacgagacac caggagtgag ataccagtac 1440
aacgtgctgc ctatgggttg gaagggatca ccagccatct ttcagtgtag catgaca 1497

<210> SEQ ID NO 137
<211> LENGTH: 1497
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 137
ctgcctcaga ttactctctg gcagaggcct attgtgacaa tcaagatcgg cggacagatc 60
aaagaagccc tgctggatac aggagcagac gatacagtgc tggaggatat gaacctgcca 120
ggcaagtgga aacctaagat gatcggagga atcggcggat ttatcaaggt gaagcagtac 180
gatcagtggg gactgacaac accagataag aagcaccaga aggacccccc attcctgtgg 240
atgggatacg aactgcatcc agataggtgg acagtgcagc caatcgaact gccagaaaag 300
gagtcttgga ccgtgaacga catccagaaa ctgatcggca agctgaattg ggccagccag 360
atttacgccg gaatcaaagt ggcagctcag gaagaagagg aagtgggatt tccagtgaga 420
cctcaggtgc ctctgagacc tatgacatac aaaggcgctc tggatctgag ccactttctg 480
aaagagaagg gaggactgga gggaattaca aagctgcaga acttccgggt gtactacaga 540
gacaacagag accctctctg gaaaggacca gctagactcc tctggaaagg agaaggagca 600
gtggtgatcc aggataatag cgagatcaag gtggtgccta ggagaaaggt gaagatcatc 660
agggattacg gcaaaagaat ggccggagac gattgcgtgg caggaagaca ggacgaagat 720
cccaagttca gactgcctat ccagaaggag acttgggaca cttggtggac cgattattgg 780
caggcaactt ggattcccga gtgggaattt accaacacac ctcctctggt gaagctgtgg 840
tatcagctgg aaacagagcc tattgccgga gtggaaacat tctacgtgga cggagccagc 900
aacagagaga caaaagccgc cggaacagtg ctgattggac ctacacccgt gaatatcatc 960
ggaagaaatc tgctgacaca gctgggttgt accctgaatt tccctatcag ccccatcgat 1020
acagtgccag tgaaactgaa gccaggaatg gacggaccta gagtcaaaca gtggcctctg 1080
acagaagaga agatcaaggc cctgatcgag atttgtaccg agatggagaa ggagggaaag 1140
atcagcagaa tcggcccaga gaatccttac aacaccccca tcttcgccat caagaagaaa 1200
gacggaacca agtggagaaa gctggtggat ttcagggagc tgaacaagaa gacccaggac 1260
ttttgggaag tgcagctggg catcccccac cctagcggcc tgaagaagaa aaagagcgtg 1320
acagtgctgg acattggaga cgcttatttc agcgtgccac tggataagga gttcagaaag 1380
tacaccgcct ttaccgtgcc ttctacaaac aacgagacac caggcgtgag atatcagtac 1440
aacgtgctgc ctatgggttg gaaaggatct cccgccatct ttcagtgtag catgaca 1497

<210> SEQ ID NO 138
<211> LENGTH: 1512
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 138
gtggccaaag aaattgtggc ctcttgcgat aagtgccagc tgaaaggaga ggctatgcac 60
ggacaggtgg attgttctcc aggaatttgg cagctggatt gtacacacct ggagggaaag 120
attattctgg tggcagtgca cgtggcatca ggatatattg aggccgaagt gattccagca 180
gaaacaggac aggagacagc ttactttctg ctcaaactgg caggtcgctg gccagtgaag 240
acaacacagg gctactttcc tgattggcag aattacacac caggaccagg aacaagatac 300
cctctgacct ttggttggtg cttcaaactg gtgcccgtga cagtgaaagc agcttgttgg 360
tgggcaggaa ttaagcagga gttcggcatc ccttacaatc ctcagtctca gggagtggtg 420
gaatctatga acaaggagct gaagaagatc atcggccagg tgagagatca ggcagaacat 480
ctgaagacag cagtgcagat ggcagtgttc atccacaact tcaagcggaa gggaggaatt 540
ggaggatata gcgcaggaga gagaatcgtg gatatcattg ccgccgctat ggcagctaga 600
gccagcgtgc tgagcggagg agaactcgat cgctgggaaa agatcagact gagaccagga 660
ggcaagaaga agtacagact gaagcacatc gtctgggctt ctagagaact ggagagattt 720
gccgtgaatc caggactgct ggaaacaagc gagggcattt ctcctagaac cctgaacgct 780
tgggtgaaag tggtggaaga aaaagccttc tctccagagg tgatccctat gtttagcgct 840
ctgtcagaag gagctacacc tcaggatctg aacaccatgc tgaacacagt gggaggacat 900
caggcagcta tgcagatgct gaaggagaca attaacgaag aagccgccga gtgggataga 960
ctgcatccag tgcacgcagg acctattgct ccaggacaga tgagagagcc tagaggaagc 1020
gatattgccg gaacaacaag cacactgcag gaacagatcg gttggatgac caataatccc 1080
cctattccag tgggcgagat ctataagcgc tggattatcc tgggcctgaa caagatcgtg 1140
agaatgtaca gccccacctc tatcctggat atcagacagg gccctaagga acctttcaga 1200
gactacgtgg acaggttcta caagacactg agagcagaac aggcatctca ggaggtgaag 1260
aattggatga ccgagacact gctggtgcag aacgccaatc cagattgcaa gacaattctg 1320
aaagccctgg gaccagcagc tacactggaa gagatgatga ccgcttgtca gggagtggga 1380
ggaccaggac ataaagctag agtgctggca gaagctatgt ctcaggcagc agctaaggag 1440
aaagtgtatc tggcttgggt gccagcccat aaaggaattg gaggaaacga gcaggtggat 1500
aaactggtgt ct 1512

<210> SEQ ID NO 139
<211> LENGTH: 1512
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 139
gtggctaagg aaattgtggc ctcttgcgac aagtgtcagc tgaaaggaga ggctatgcac 60
ggacaggtgg attgttctcc aggaatttgg cagctggatt gcacacatct ggaaggaaag 120

```
attattctgg tggcagtgca cgtggcatct ggatatatcg aggccgaggt gattccagcc    180

gaaacaggac aggaaacagc ctactttctc ctgaaactgg caggtaggtg gccagtgaag    240

acaacacagg gctacttccc agattggcag aattacaccc caggaccagg aacaagatac    300

cctctgacct ttggttggtg cttcaagctc gtcccagtga cagtgaaagc agcttgttgg    360

tgggcaggaa ttaaacagga gttcggaatc ccttacaatc ctcagtctca gggagtggtg    420

gaaagcatga acaaggagct gaagaagatc atcggacagg tgagagatca ggcagaacat    480

ctgaagacag cagtgcagat ggcagtgttc atccacaact tcaagaggaa gggcggaatt    540

ggaggatata gcgccggaga gagaatcgtg gatatcattg cagcagctat ggcagctaga    600

gcttcagtgc tgtcaggagg agaactcgat aggtgggaga agatcagact gagaccagga    660

ggcaagaaga agtacagact gaagcacatc gtgtgggctt ctagagaact ggagagattc    720

gcagtgaatc caggactgct ggaaacaagc gagggaatta gccctagaac cctgaatgct    780

tgggtgaaag tggtggaaga gaaggccttc agcccagagg tgatccctat gtttagcgct    840

ctgtcagaag gagctacacc tcaggatctg aacaccatgc tgaatacagt gggaggacat    900

caggcagcta tgcagatgct gaaggagacc atcaacgaag aagcagccga gtgggataga    960

ctgcatccag tgcacgcagg acctattgct ccaggacaga tgagagaacc tagaggaagc   1020

gatatcgccg gaacaacatc tacactgcag gaacagatcg gttggatgac caacaaccct   1080

cctattccag tgggcgagat ttacaagcgc tggattatcc tgggcctgaa taagatcgtg   1140

agaatgtaca gccctaccag cattctggac atcagacagg gacctaagga gccttttaga   1200

gactacgtgg acaggttcta caagaccctg agagcagaac aggcatctca ggaggtgaag   1260

aattggatga ccgagacact gctggtgcag aacgctaatc ccgattgcaa gaccatcctg   1320

aaagctctgg gaccagcagc tacactggaa gagatgatga cagcttgtca gggagtggga   1380

ggaccaggac ataaagctag agtgctggca gaagctatgt ctcaggcagc agctaaagag   1440

aaagtgtatc tggcttgggt gccagctcac aaaggaattg gaggaaacga gcaggtggat   1500

aaactggtga gc                                                       1512
```

<210> SEQ ID NO 140
<211> LENGTH: 1512
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 140

```
gtggccaaag agattgtggc ctcctgtgac aagtgccagc tgaaaggaga ggcaatgcat     60

ggacaggtgg attgttctcc aggaatctgg cagctggatt gcacacacct ggagggaaag    120

atcatcctgg tggcagtgca tgttgcatca ggatacattg aggcagaagt gattccagca    180

gaaacaggac aggagactgc ttactttctg ctgaaactgg caggaaggtg gccagtgaag    240

acaacacagg gttatttccc tgattggcag aactacaccc caggccctgg cacaagatac    300

cctctgacct ttggttggtg cttcaaactg gtccctgtga cagtgaaagc agcttgttgg    360

tgggcaggca tcaagcagga gtttggcatc ccttacaacc ctcagtctca gggagttgtg    420

gaatccatga acaaggagct gaagaagatc attggtcagg tgagggatca ggcagaacat    480

ctgaagacag cagtgcagat ggcagtgttc atccacaatt tcaagaggaa gggaggaatt    540

ggaggataca gtgcaggaga gagaattgtg gacatcattg cagctgcaat ggcagcaaga    600
```

gccagtgtgc tcagtggagg agaacttgac aggtgggaaa agatcagact gagaccagga 660
ggcaagaaga agtacagact gaagcacatt gtctgggctt ccagagaact ggagagattt 720
gctgtgaatc cagggctgct ggaaacaagt gagggcattt ctcccagaac tctgaatgct 780
tgggtgaagg tggtggaaga aaaagccttc tctccagagg tgatccccat gttcagtgca 840
ctgtctgaag gagccacacc tcaggacctc aacaccatgc tgaacacagt gggaggacat 900
caggcagcca tgcagatgct gaaggagacc atcaatgaag aagctgcaga gtgggacagg 960
ctgcatccag ttcatgcagg accaattgct cctggacaga tgagagagcc cagaggaagt 1020
gacattgctg gcacaaccag cacactgcag gaacagattg gttggatgac caacaatccc 1080
cccattccag tgggagagat ctacaagagg tggatcatcc ttggcctgaa caagattgtg 1140
agaatgtaca gccccacttc aatcctggac atcagacagg gccccaagga acctttcaga 1200
gactatgtgg acaggttcta caagacactg agagcagaac aggcctcaca ggaggtgaag 1260
aattggatga ctgagacact gctggtgcag aatgccaatc cagattgcaa gacaattctg 1320
aaagccctgg gtccagcagc cacactggaa gagatgatga cagcttgcca gggagtgggt 1380
ggaccaggac acaaagcaag agtgctggca gaagcaatgt ctcaggctgc agccaaggag 1440
aaagtttatc tggcttgggt cccagcgcac aaaggaattg gaggaaatga gcaggtggac 1500
aaacttgtgt cc 1512

<210> SEQ ID NO 141
<211> LENGTH: 1497
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 141
ctgtctccta gaacactgaa cgcttgggtg aaagtgatcg aggaaaaggc ctttagccca 60
gaagtgatcc ctatgtttac cgccctgtca gaaggagcta cacctcacga tctgaacacc 120
atgctgaaca caatcggagg acatcaggca gctatgcaga tgctgaagga tacaatcaac 180
gaagaagccg ccgagtggga tagagtgcat ccagtgcacg caggaccagt ggctccagga 240
cagatgagag atcctagagg aagcgatatc gcaggatcta caagcacact gcaggaacag 300
atcgcttgga tgaccaataa tccccctatt ccagtgggcg atatctacaa gcgctggatc 360
atcatgggcc tgaacaagat cgtgaggatg tacagcccag tgagcatcct ggatatcaag 420
cagggaccta aggagccttt cagagattac gtggacaggt tctacagaac actgagagcc 480
gaacaggcat ctcaggacgt gaagaattgg atgaccgaga cactgctggt gcagaacagc 540
aatcccgatt gcaagacaat cctgaaagct ctgggaccag gagctacact ggaggaaatg 600
atgagcgctt gtcagggagt gggaggacca tctcataaag ctagagtgct ggccgaagct 660
atgtgtcagg cagtgaaagc agcttgttgg tgggcaggag tgaaacagga gttcggcatc 720
ccttacaaca cccagtctca gggagtggtg gaatctatga acaacgagct gaagaagatc 780
atcggccaga tcagagacca ggcagaacat ctgaagacag cagtgcagat ggcagtgctg 840
attcacaact tcaagagaaa gggcggcatt ggagagtata gcgccggaga gagaattatc 900
gatatcatcg ccaaggagaa gatctatctg gcttgggtgc cagctcataa aggaatcgga 960
ggaaacgagc agatcgataa gctggtgtca gccgcctata tggcagctag agcttctatt 1020
ctgagcggag gaaagctcga caagtgggaa aagatcaggc tgagaccagg aggcagaaag 1080

```
aagtacaagc tgaagcatct cgtctgggct tctagagaac tggaaagatt cgctctgaat   1140

ccaggactgc tggaaacaac ccagggcttc ttccccgatt ggcagaatta caccccagga   1200

ccaggaatca gattccctct gaccttcggt tggtgtttca agctggtgcc tctggtggct   1260

aaagagattg tggcttgttg cgacaagtgt cagctgaaag gagaggctat tcacggacag   1320

gtggattgtt ctccaggagt ctggcagctg gattgtacac atctggaggg aaaagtgatt   1380

ctggtggcag tgcacgtggc atcaggatat attgaggccg aaatcatccc tacagagaca   1440

ggacaggaga cagcctactt tatcctgaag ctggcaggaa gatggccagt gacaaca      1497
```

```
<210> SEQ ID NO 142
<211> LENGTH: 1497
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 142

ctgtctccta gaacactgaa cgcttgggtg aaggtgattg aggagaaagc cttcagccca     60

gaagtgatcc ctatgtttac agccctgagc gaaggagcta cacctcacga tctgaatacc    120

atgctgaata caatcggcgg acatcaggca gccatgcaga tgctgaagga tacaatcaac    180

gaagaagcag ccgagtggga tagagtgcat ccagtgcacg caggaccagt ggctccagga    240

cagatgagag atcctagagg aagcgatatc gccggatcta catctacact gcaggaacag    300

atcgcttgga tgacaaataa ccccccctatc ccagtgggag atatctataa gcgctggatc    360

atcatgggcc tgaacaagat cgtgaggatg tacagcccag tgagcatcct ggatatcaag    420

cagggaccta aggagccttt cagagattac gtggacaggt tctacagaac cctgagagca    480

gaacaggctt ctcaggacgt gaagaattgg atgaccgaaa cactgctggt gcagaatagc    540

aaccccgatt gcaagaccat cctgaaagct ctgggaccag gagctacact ggaagaaatg    600

atgagcgctt gtcagggagt gggaggacca tctcataagg ctagagtgct ggcagaagct    660

atgtgtcagg cagtgaaagc agcttgttgg tgggcaggag tgaaacagga gtttggcatc    720

ccttacaata cccagtctca gggagtggtg gaaagcatga acaacgagct gaagaagatc    780

atcggccaga ttagagatca ggccgaacat ctgaaaacag cagtgcagat ggccgtgctg    840

atccacaatt tcaagaggaa gggcggaatt ggcgaatata gcgccggaga gagaatcatc    900

gacatcatcg ccaaggagaa gatctacctg gcttgggtgc cagctcataa aggaatcgga    960

ggaaacgagc agatcgataa actggtgtct gccgcttata tggcagctag agcttctatc   1020

ctgtcaggag gaaagctcga taagtgggaa aagatcagac tgagaccagg cggaagaaag   1080

aagtacaagc tgaagcacct cgtctgggct tctagagaac tggaaagatt cgccctgaat   1140

ccaggactgc tggaaacaac acagggattc ttccccgatt ggcagaacta cacaccagga   1200

ccaggcatca gatttcctct gacctttggt tggtgcttta aactggtgcc tctggtggct   1260

aaggagattg tggcttgttg cgacaagtgt cagctgaaag gagaggctat tcacggacag   1320

gtggattgtt ctccaggagt ctggcagctg gattgtacac acctggaggg aaaagtgatt   1380

ctggtggcag tgcacgtggc atcaggatat atcgaggccg agatcatccc tacagagaca   1440

ggacaggaaa ccgcctactt tatcctgaaa ctggcaggta ggtggccagt gacaaca      1497
```

```
<210> SEQ ID NO 143
<211> LENGTH: 1497
<212> TYPE: DNA
```

<213> ORGANISM: Artificial Sequence
<220> FEATURE:
<223> OTHER INFORMATION: Description of Artificial Sequence: Synthetic
polynucleotide

<400> SEQUENCE: 143

```
ctgagcccca gaaccctcaa tgcctgggtc aaagtgattg aggaaaaggc cttcagccca     60

gaggtgatcc ccatgttcac agccctcagt gagggggcca ccccccatga cctgaacacc    120

atgctcaaca ccattggggg ccaccaggct gccatgcaga tgctgaagga caccatcaat    180

gaggaagctg ctgagtggga cagagtccac ccagtgcatg ctggcccagt ggccccaggc    240

cagatgaggg accccagggg ctctgacatt gctggcagca ccagcaccct gcaggagcag    300

atagcctgga tgaccaacaa cccccccatc cctgtgggag acatctacaa aagatggatc    360

atcatgggcc tcaacaagat tgtcaggatg tactcccctg tgtccatcct ggacatcaag    420

cagggcccca aggaaccctt cagggactat gtggacagat tctacagaac cctgagagct    480

gagcaggcct cccaggatgt gaaaaactgg atgacagaga ccctcctggt ccagaacagc    540

aacccagact gcaagaccat cctcaaggcc ttgggcccag gagccaccct ggaagagatg    600

atgagtgcct gccagggagt tggaggcccc agccacaagg ccagagtgct ggcagaggcc    660

atgtgccagg ctgtgaaggc tgcctgctgg tgggcaggag tcaagcagga gtttggcatc    720

ccatacaaca cccagagcca gggtgtggtg gaaagcatga acaatgagct gaaaaagatc    780

attggccaga tcagagacca ggctgagcac ctgaagacag cagtgcagat ggctgtgctc    840

atccacaact tcaagaggaa aggtggcata ggggaataca gtgctgggga gaggatcatt    900

gacatcattg ccaaggagaa gatctacctg gcctgggtgc ctgcccacaa gggcattggt    960

ggcaatgagc agattgacaa gctggtctca gcagcctaca tggctgccag agcctccatc   1020

ctctcagggg gcaagctgga caagtgggag aaaatcagac tgaggcctgg tggcagaaag   1080

aagtacaagc tgaagcacct ggtgtgggcc tccagggaac tggaaagatt tgccctgaac   1140

cctggcctgc tggaaaccac ccagggcttc ttccctgact ggcagaacta caccccaggc   1200

ccaggcatca ggttcccccct gacctttggc tggtgcttca agctggtgcc cctggtggcc   1260

aaggaaatag tggcctgctg tgacaagtgc cagctgaaag gggaggccat ccatggccaa   1320

gtggactgca gccctggtgt gtggcagctg gactgcaccc acctggaagg caaggtcatc   1380

ctggttgcag tgcatgtggc cagtggctac attgaggctg agatcatccc cacagagaca   1440

ggccaggaga ctgcctactt catcctgaaa cttgcaggca ggtggcctgt gaccacc      1497
```

<210> SEQ ID NO 144
<211> LENGTH: 1497
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 144

```
atcaccaaga tccagaactt cagggtgtac tacagagaca gcagagatcc tctctggaag     60

ggaccagcta aactcctctg gaaaggagaa ggagcagtgg tgatccagga taacagcgac    120

atcaaggtgg tgcctagaag aaaggccaag atcatcaggg actacggcaa acagatggca    180

ggagacgatt gcgtggcttc tagacaggac gaagacgcag cttacgaaga ggaagaggtg    240

ggatttccag tgaaacctca ggtgcctctg agacctatga cattcaaggg agctctggat    300

ctgtctcact tcctgagaga aaagggagga ctggaaggag cagcttgggg atttaccacc    360
```

ccagacaaga agcaccagaa ggaaccacca ttcctctgga tgggatacga actgcaccca 420
gataagtgga cagtccagcc tattgtgctg ccagaaaagg actcttggac cgtgaacgat 480
atccagaagc tggtgggaaa gctgaattgg gcttctcaga tctacccagg aatcaaggtg 540
cccaagttca agctgcctat ccagaaggag acttgggaaa cttggtggac agagtattgg 600
caggctactt ggattcccga gtgggaattt gtgaacacac ctcctctggt gaagctgtgg 660
tatcagctgg aaaaggagcc tatcgtgggc gcagaaacat tttacgtgga cggagccgcc 720
aatagagaaa ccaagtttcc tcagatcact ctctggcaga gacctctggt gacaatcaag 780
atcggcggac agctgaaaga ggctctgctg gatacaggag cagacgatac cgtgctggaa 840
gaaatgaatc tgccaggtag gtggaagcct aagatgattg gcggaattgg cggcttcatc 900
aaggtgagac agtacgatca gggaacagtg ctggtgggac ctactccagt gaacatcatc 960
ggaaggaacc tgctgacaca gatcggctgt acactgaact tccctatcag ccctatcgag 1020
acagtgccag tgaaactgaa gccaggaatg gacggaccta aagtcaaaca gtggcctctg 1080
acagaggaga aaatcaaagc cctggtggag atttgtaccg agatggagaa ggagggcaag 1140
atttctaaga tcggaccaga gaacccctac aataccccag tgtttgccat caagaagaag 1200
gacagcacca agtggaggaa gctggtggat tttagggagc tgaacaagag gacacaggac 1260
ttttgggaag tgcagctggg catcccccac ccagccggac tgaaaaagaa gaagtcagtg 1320
acagtgctgg acgtgggaga tgcctatttt agcgtgcctc tggataagga cttcaggaag 1380
tacaccgcct tcacaatccc tagcatcaac aacgagaccc caggaatcag ataccagtac 1440
aacgtgctgc ctcagggttg gaaaggaagc ccagccatct ttcagtctag catgacc 1497

<210> SEQ ID NO 145
<211> LENGTH: 1497
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 145
atcaccaaga tccagaactt ccgggtgtac tacagggata gcagagatcc tctctggaag 60
ggaccagcta aactcctctg gaaaggagaa ggagcagtgg tgatccagga taatagcgac 120
atcaaggtgg tgcctagaag aaaggctaag atcatccggg actacggcaa acagatggca 180
ggagacgatt gcgtggcttc tagacaggat gaagacgcag cctacgaaga agaggaagtg 240
ggatttccag tgaaacctca ggtgcctctg agacctatga cattcaaggg agctctggac 300
ctgtctcact ttctgagaga gaagggagga ctggaaggag cagcttgggg atttaccaca 360
ccagataaga agcaccagaa ggagccacca tttctctgga tgggatacga actgcaccca 420
gataagtgga cagtccagcc tattgtgctg ccagaaaagg actcttggac agtgaacgac 480
atccagaagc tggtgggaaa gctgaattgg gcctctcaga tttacccagg aatcaaggtg 540
cccaagttta agctgcctat ccagaaggag acttgggaaa cttggtggac cgagtattgg 600
caggcaactt ggattcccga gtgggaattt gtgaacacac ctcctctggt gaagctgtgg 660
tatcagctgg aaaaggagcc tatcgtggga gccgaaacat tttacgtgga cggagcagcc 720
aacagagaga caaagttccc tcagatcact ctctggcaga gaccactggt gacaattaag 780
atcggaggac agctgaaaga agctctgctg gatacaggag cagacgatac agtgctggag 840
gaaatgaacc tgccaggtcg ctggaaacct aaaatgatcg gcggcattgg cggatttatc 900
aaggtgaggc agtacgatca gggaacagtg ctggtgggac ctacacccgt gaatattatc 960
ggaaggaatc tgctgacaca gattggctgt accctgaact tccctatcag ccctatcgaa 1020
accgtgccag tgaaactgaa accaggaatg gacggaccta aagtcaagca gtggcctctg 1080
acagaagaga agatcaaagc cctggtggag atttgtaccg agatggagaa ggagggaaag 1140
atcagcaaga tcggcccaga gaatccttac aacaccccag tgttcgccat caagaagaag 1200
gatagcacca agtggagaaa gctggtggat ttcagggagc tgaacaagag aacccaggac 1260
ttttgggaag tgcagctggg catcccccac cctgccggcc tgaagaagaa gaaaagcgtg 1320
acagtgctgg acgtgggaga cgcttatttt agcgtgcctc tggacaagga cttcagaaag 1380
tacaccgcct tcaccatccc ttctatcaat aacgagaccc caggcatcag ataccagtat 1440
aacgtgctgc ctcagggttg gaaaggaagc ccagccattt ttcagagcag catgaca 1497

<210> SEQ ID NO 146
<211> LENGTH: 1497
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 146
atcaccaaga tccagaactt cagggtctac tacagagaca gcagagatcc actctggaag 60
ggcccagcca aactcctttg gaaaggagaa ggagcagtgg tgatccagga caacagtgac 120
atcaaggtgg ttcccagaag aaaggccaag atcatcaggg actatggcaa acagatggca 180
ggagatgact gtgtggcttc cagacaggat gaagatgcag cttatgaaga ggaagaggtg 240
ggattcccag tgaaacccca ggtgcctctg aggccaatga cattcaaggg agctctggat 300
ctgtcccact tcctgagaga aaagggagga ctggaaggag cagcttgggg attcaccacc 360
ccagacaaga agcatcagaa ggaacctccc ttcctctgga tgggttatga actgcaccca 420
gacaagtgga cagtccagcc cattgtgctg ccagaaaagg attcttggac agtgaatgac 480
atccagaagc tggtgggcaa gctgaattgg gcctcccaga tctacccagg aatcaaggtg 540
cccaagttca agctccccat ccagaaggag acttgggaaa cttggtggac agagtattgg 600
caggcaactt ggattcctga gtgggaattt gtgaacaccc cccctctggt gaagctgtgg 660
tatcagctgg aaaaggagcc cattgtgggg gcagaaacat tttatgtgga tggagcagcc 720
aacagagaaa ccaagtttcc ccagatcact ctttggcaga gaccactggt gacaatcaag 780
attgggggac agctgaaaga ggctctgctg gacacaggag ctgatgacac agtgctggaa 840
gaaatgaatc tgccaggcag gtggaagccc aagatgattg gaggcattgg gggtttcatc 900
aaggtgagac agtatgacca gggaactgtg ctggtgggac ccactccagt gaacatcatt 960
ggcaggaacc tgctgacaca gattggctgc acactgaact tccccatcag ccccattgag 1020
acagtcccag tgaaactgaa gccaggaatg gatggcccaa aagtcaaaca atggcccctg 1080
acagaggaga aaatcaaagc tctggtggag atttgcacag agatggagaa ggagggcaag 1140
atctctaaga ttggcccaga gaacccatac aacactccag tgtttgcaat caagaagaag 1200
gacagcacca agtggaggaa gctggtggac ttcagggagc tcaacaagag gacacaggac 1260
ttttgggaag tgcagctggg cattccccac ccagcaggac tgaaaaagaa gaagtcagtg 1320
acagtgctgg atgtggggga tgcttatttc agtgtgcctc tggacaagga cttcaggaag 1380
tacacagcct tcacaatccc cagcatcaac aatgagaccc caggaatcag atatcagtac 1440
aatgtgctgc ctcagggttg gaaaggaagc ccagccattt tccagtcgag catgacc 1497

<210> SEQ ID NO 147
<211> LENGTH: 1479
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 147
cctaaattca gactgcctat ccagaaggag acttgggata cttggtggac cgattattgg 60
caggcaactt ggattcccga gtgggaattt accaataccc ctcctctggt gaagctgtgg 120
tatcagctgg aaacagagcc tattgccgga gtggaaacat tctacgtgga cggagcctct 180
aatagagaga ccaaggagga agtgggattt ccagtgagac ctcaggtgcc tctgagacct 240
atgacataca agggagctct ggacctgtct cactttctga aggagaaggg aggactggaa 300
ggactgcctc agattactct ctggcagaga cctatcgtga ccatcaagat cggaggacag 360
atcaaagaag ctctgctgga tacaggagca gacgatacag tgctggagga tatgaacctg 420
ccaggtaagt ggaagcctaa gatgatcggc ggaattggcg gctttatcaa ggtcaagcag 480
tacgaccaga tcaccaagct gcagaacttc agggtgtact acagggacaa cagagacccc 540
ctctggaaag gaccagctag actcctctgg aaaggagaag gagcagtggt gatccaggac 600
aatagcgaga tcaaggtggt gcctagaagg aaggtgaaga tcatcaggga ctacggaaaa 660
agaatggccg gagacgattg cgtggcagga agacaggacg aagattgggg actgacaaca 720
ccagacaaga agcaccagaa ggaccccca ttcctctgga tgggatacga actgcatcca 780
gataggtgga cagtgcagcc aattgaactg ccagagaagg agtcttggac cgtgaacgat 840
atccagaagc tgatcggcaa gctgaattgg gcttctcaga tctacgcagg aatcaaggtg 900
aagggcacag tgctgattgg acctacacca gtgaacatca tcggcagaaa cctcctgaca 960
cagctgggtt gtacactgaa tttccctatc agccctatcg atacagtgcc agtgaagctg 1020
aaaccaggaa tggacggacc tagagtcaaa cagtggcctc tgacagaaga gaagatcaag 1080
gccctgatcg agatttgcac cgagatggag aaggagggaa agatctctag gatcggccca 1140
gagaatcctt acaataccc tatcttcgcc atcaagaaga aggacggaac caagtggaga 1200
aagctggtgg atttcaggga gctgaacaag aagacccagg acttttggga ggtgcagctg 1260
ggcatccccc atccttcagg actgaagaag aagaagagcg tgacagtgct ggatatcgga 1320
gacgcttact ttagcgtgcc actggacaag gagttcagaa agtacaccgc tttcaccgtg 1380
ccttctacca ataacgagac cccaggagtg agataccagt ataacgtgct gcccatgggt 1440
tggaaaggat ctccagcaat tttcagtgt agcatgaca 1479

<210> SEQ ID NO 148
<211> LENGTH: 1479
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 148
cccaagttca ggctgcctat ccagaaagag acttgggaca cttggtggac cgattattgg 60
caggcaactt ggattcccga gtgggaattt accaacacac ctcctctggt gaagctgtgg 120

```
tatcagctgg aaacagagcc tattgccgga gtggaaacat tctacgtgga cggagccagc    180

aacagagaga ccaaggagga agtgggattt ccagtgagac ctcaggtgcc tctgagacct    240

atgacataca agggagctct ggatctgagc cactttctga aggagaaagg aggactggaa    300

ggactgcctc agattactct ctggcagaga cctatcgtga caatcaagat cggcggacag    360

atcaaggaag ctctgctgga tacaggagcc gacgatacag tgctggaaga tatgaacctg    420

ccaggcaagt ggaaacctaa gatgatcgga ggcattggcg gctttatcaa ggtgaaacag    480

tacgaccaga tcaccaagct gcagaacttc agggtgtact acagggacaa cagagacccc    540

ctctggaaag gaccagctag actgctgtgg aaaggagaag gagcagtggt gatccaggat    600

aatagcgaga tcaaggtggt gcctaggaga aaggtgaaga tcatcaggga ctacggcaag    660

agaatggcag gagacgattg cgtggcagga agacaggacg aagattgggg actgacaaca    720

ccagacaaga agcaccagaa ggacccccct ttcctctgga tgggatacga actgcatcca    780

gataggtgga cagtgcagcc aattgagctg ccagaaaagg agtcttggac agtgaacgac    840

atccagaagc tgatcggcaa gctgaattgg gcttctcaga tctacgccgg aattaaggtg    900

aagggaacag tgctgattgg acctacacca gtgaacatca tcggaagaaa cctgctgaca    960

cagctgggtt gtacactgaa cttccctatc agccctatcg ataccgtgcc agtgaaactg   1020

aaaccaggaa tggacggacc tagagtcaag cagtggcctc tgacagaaga gaagatcaag   1080

gccctgatcg agatttgcac cgagatggag aaggagggaa agatcagcag aattggcccc   1140

gagaatcctt acaacacccc tatcttcgcc atcaagaaga aggacggaac taagtggaga   1200

aagctggtgg acttcagaga gctgaacaag aagacccagg acttttggga agtgcagctg   1260

ggcatccccc atccttcagg actgaagaag aagaagagcg tgacagtgct ggacatcgga   1320

gacgcttatt ttagcgtgcc tctggataag gagttccgga aatacaccgc ctttaccgtg   1380

ccttctacca ataacgagac accaggagtg aggtaccagt ataacgtgct gccaatgggc   1440

tggaaaggat ctccagcaat ctttcagtgt agcatgaca                          1479
```

```
<210> SEQ ID NO 149
<211> LENGTH: 1479
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 149

cccaagttca ggctgcccat ccagaaagaa acctgggaca cctggtggac tgactactgg     60

caggccacct ggatcccaga gtgggagttc accaacaccc ctcccctggt gaagctgtgg    120

taccagctgg aaactgagcc catagcagga gtggaaacct tttatgtgga tggagccagc    180

aacagggaaa ccaaggaaga ggtgggcttc ccagtgaggc cccaggtgcc cctgagaccc    240

atgacctaca agggagccct ggatctgagc cacttcctga aagagaaggg gggcctggaa    300

ggcctgcccc agatcaccct gtggcagaga cccattgtga ccatcaagat tgggggccag    360

atcaaagagg ccctcctgga cactggagct gatgacacag tcctggaaga catgaacctc    420

ccaggaaagt ggaagcccaa gatgattggg ggcattggag gcttcatcaa ggtcaagcag    480

tatgaccaga tcaccaagct ccagaatttc agagtctact acagagacaa cagagacccc    540

ctgtggaaag gcccagccag acttctctgg aagggggagg gagcagtggt gatccaagac    600

aactctgaga tcaaagtggt ccccaggaga aaggtgaaga tcatcaggga ctatggcaaa    660
```

aggatggcag gggatgactg tgtggcaggc agacaggatg aggactgggg cctgaccacc 720
cctgacaaga agcaccagaa ggaccccccc ttcctgtgga tgggctatga gctgcaccca 780
gacagatgga ctgtccaacc cattgagctg cctgagaagg agagctggac agtcaatgac 840
atccagaagc tgattgggaa gctgaattgg gcctcccaga tctatgcagg catcaaggtc 900
aagggcactg tcctgattgg ccccacccct gtgaacatca taggcagaaa cctgctgacc 960
cagctgggct gcacactgaa cttccccatc agccccattg acacagtgcc tgtgaagctc 1020
aagcctggca tggatggccc cagagtgaaa cagtggccct tgacagagga aaaaatcaag 1080
gccctgattg agatctgcac tgagatggaa aaagagggca agatctcaag aattggccct 1140
gagaacccct acaacacccc catttttgcc atcaagaaaa aggatggcac aaagtggaga 1200
aagctggtgg acttcagaga gctcaacaag aagacccagg acttctggga ggtgcagctg 1260
ggcatccccc acccctctgg cctcaagaag aagaaaagtg tgactgtgct ggacattggt 1320
gatgcctact tcagtgtccc cctggacaag gaattcagga agtacacagc cttcacagtg 1380
cccagcacca acaatgagac ccctggtgtc aggtaccagt acaatgtgct gcccatgggc 1440
tggaagggca gcccagccat cttccagtgc agcatgacc 1479

<210> SEQ ID NO 150
<211> LENGTH: 1059
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 150
actgtaaagg ccgcctgttg gtgggctggg atcaaacagg agttcggaat cccatacaat 60
ccccaaagcc agggagtagt ggaatccatg aataaggagc tcaagaagat cattgggcaa 120
gtcagggacc aggctgagca cctcaagacg gccgttcaaa tggcggtatt tatccataac 180
tttaaacgca aaggcggtat tggcggttac tccgcaggtg agcggatagt tgacattatc 240
gcaataagcc ctaggacgct taacgcttgg gtcaaggtag tggaggaaaa agccttctca 300
ccggaggtca tccctatgtt tagcgccctg agcgaaggag cgacgccaca agacttgaac 360
accatgctta atacggtggg gggtcaccaa gctgcaatgc aaatgttgaa ggaaacgata 420
aacgaagagg ccgccgaatg ggacaggttg catcccgttc atgcaggtcc catagctccc 480
ggtcaaatga gggaaccacg cggatcagac atcgcgggaa cgacgtccac gttgcaggaa 540
caaattggat ggatgaccaa taaccctcct atcccagtcg gtgaaatcta taagaggtgg 600
atcatcctcg gcctcaataa aatagtgagg atgtattctc caactagcat tctggatata 660
cgccaaggcc ctaaagaacc atttcgcgat tacgtagacc gattttacaa gacactccgg 720
gctgagcagg cctcccaaga ggtaaagaat tggatgaccg aaacgttgct ggtgcagaat 780
gccaaccccg actgtaagac cattttgaag gcgcttgggc cagcagcaac actggaagag 840
atgatgactg cgtgtcaagg tgtaggtggc cccggccaca aagccagagt gttggccgag 900
gcaatgagcc aaaaagaacc cattgtagga gctgagacct tttacgttga tggcgcagct 960
aacagagaaa ctaaggcggc aaaagagaaa gtttatcttg catgggtgcc tgcgcacaaa 1020
ggaatcggcg gaaatgagca agttgataaa ctcgtaagt 1059

<210> SEQ ID NO 151
<211> LENGTH: 1074
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 151
accgtgaagg cggcgtgttg gtgggcaggg ataaagcaag aatttggcat accttataac 60
ccgcagagtc agggagttgt cgaatccatg aataaggagc ttaagaagat catcggtcag 120
gtgcgcgatc aggcagagca cctcaaaact gcggtccaaa tggccgtgtt catccacaac 180
ttcaagcgca aaggcggaat cggtggatac agtgctgggg aaaggatcgt cgatattatc 240
gccaaagagc caatcgtggg agcggaaaca ttctacgtag acggtgcggc caacagggag 300
acaaaagccg ctgcgatctc accccgaacc cttaatgctt gggtgaaggt ggtggaagaa 360
aaagccttca gtcccgaagt tatcccgatg ttctccgccc tcagtgaagg tgcaacgccg 420
caggacctta atactatgtt gaacaccgtt ggtggtcatc aggccgccat gcagatgctt 480
aaagaaacca ttaacgaaga agccgcagaa tgggacaggt tgcacccagt ccacgctggg 540
cccatcgcgc ctgggcagat gcgagagcca cgagggtccg atatcgcggg cacaacaagc 600
actttgcaag aacagattgg gtggatgact aataacccgc cgatacctgt tggggaaata 660
tataaacgct ggataattct gggactcaat aagatagtga gaatgtactc ccctacatcc 720
attcttgata tacgacaagg tccaaaagaa ccctttcgcg actacgtgga tagattttat 780
aagaccctca gggccgaaca ggcaagtcag gaggtcaaga actggatgac ggagacgctt 840
cttgttcaga atgcaaatcc cgattgcaaa actatcttga aagcgctcgg accagcagcg 900
acgctggaag aaatgatgac cgcctgccag ggcgtaggcg gcccaggtca taaagcaagg 960
gtattggcag aagcgatgag tcaagcagcg gcaaaggaga aagtatatct tgcgtgggta 1020
ccagcgcaca aagggatagg tggaaacgag caagttgata agctggtctc cctt 1074

<210> SEQ ID NO 152
<211> LENGTH: 1083
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 152
ataacgaaaa ttcagaactt tcgagtgtac tacagagata gtagagaccc gctgtggaag 60
ggcccagcta aactcctttg gaaaggtgaa ggggctgtgg tcatacagga taactcagac 120
ataaaggtcg tcccaaggag aaaagccaaa ataattagag actacggcaa gcagatggca 180
ggggatgact gtgttgcgag ccggcaggat gaggatgtcg cgaaggaaat cgtggcgagt 240
tgtgataaat gtcaactgaa gggtgaggca atgcacggcc aagtagattg cagtccaggt 300
atctggcaac tcgattgcac ccacctggag ggtaagatta tcctggtggc tgtgcatgtt 360
gcatccggct acatcgaagc tgaagtgatt ccggctgaaa cggggcagga aaccgcctac 420
ttcctgttga agttggctgg tcgatggcca gtcaagaccg gtacagtact cgttggcccg 480
acgccagtga atatcatagg tcggaacctg ctgacacaaa tcgggtgcac tcttaatttt 540
ccgatttcac ctatcgaaac cgttccagta aaactcaagc ctgggatgga tggcccgaag 600
gttaagcaat ggccactgac cgaagagaaa atcaaagcgc tcgtggagat atgtactgaa 660
atggagaaag aaggaaaaat ctctaaaatc gggccagaaa atccctataa tactccggta 720
tttgctatca aaaaaaaaga ctcaaccaag tggcgaaagc tcgttgactt ccgagagttg 780

```
aataaaagga cccaggattt ttgggaggtt cagctgggca taccgcaccc cgctggcttg    840

aaaaaaaaga agtctgttac cgtcctggat gtgggcgacg cctacttcag tgtacctctt    900

gacaaagact ttagaaagta tactgctttc acgatcccga gtataaacaa cgagactcca    960

ggaattaggt accagtacaa tgtattgccg cagggatgga agggatcacc cgcaatcttc   1020

caatctagta tgacgcaaga ggaggaggaa gtaggtttcc cagtcaaacc acaagtgccg   1080

ctc                                                                 1083
```

<210> SEQ ID NO 153
<211> LENGTH: 1095
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 153

```
attactaaaa tacaaaactt ccgagtatat tatagggata gccgggaccc tctctggaaa     60

gggcccgcga aactgctttg gaagggcgag ggcgctgttg tcatacagga caatagcgat    120

ataaaagtag tcccgcgacg caaagcaaaa ataataagag attatggaaa acaaatggcg    180

ggcgacgatt gtgtcgcctc acggcaggac gaggatgctg cagccatcgg aacagtactc    240

gtggggccaa ctcccgtcaa cataatagga cgaaatcttc tgactcaaat aggttgcacg    300

ctcaacttcc caattagccc tatagagaca gtgcccgtaa agttgaagcc tggcatggac    360

ggcccaaaag taaagcagtg gcccccttact gaagagaaga tcaaggccct ggtggagatc    420

tgtacagaga tggagaaaga agggaaaatc tccaaaatcg gtccagaaaa cccatacaac    480

acacctgttt ttgcgataaa aaaaaaggat tccaccaagt ggaggaaact ggtggatttt    540

cgagagttga ataagcgaac ccaggacttc tgggaagtac agcttgggat accacatcca    600

gcgggtctca agaaaaagaa atcagttacg gtcctcgatg ttggcgacgc gtattttagt    660

gttcctctcg ataaagattt ccgaaaatat acggcattca ccatacccag tattaacaac    720

gagacaccgg gaatcaggta tcagtataat gtacttccac aaggttggaa gggaagcccc    780

gcgatttttc agagctcaat gacggttgcc aaggagattg tagctagctg tgacaaatgt    840

cagctgaagg gcgaagcgat gcacggccag gtagattgca gccccggtat ttggcagctc    900

gactgtacac atttggaagg aaaaattata cttgtggctg tccacgttgc aagtggatac    960

atagaggcgg aggtcattcc cgcagaaact gggcaagaaa ctgcttactt tctcttgaag   1020

ttggccggta ggtggccagt gaaaacccaa gaggaagagg aggttggttt tcccgtcaaa   1080

cctcaagtcc ccctc                                                    1095
```

<210> SEQ ID NO 154
<211> LENGTH: 1053
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 154

```
ctgagcccca ggaccctgaa tgcatgggtc aaagtgattg aagagaaggc tttctctcct     60

gaagtcatcc caatgttcac agcactttct gagggggcca caccacatga tttgaacacc    120

atgctcaaca ccattggtgg tcatcaggct gctatgcaga tgctcaagga caccatcaat    180
```

gaggaagcag cagagtggga cagagtccac ccagtccatg cagggcctgt tgcaccaggg 240
caaatgaggg accccagagg ctcagacatt gcaggttcca catcaaccct tcaagaacaa 300
attgcctgga tgacaaacaa tcccccaatc ccagtggggg acatctacaa gagatggatc 360
atcatgggcc tgaacaaaat tgtgaggatg tacagccctg tgtcaattct ggacatcaag 420
caaggcccaa aagaaccttt cagggactat gttgacaggt tttacaggac cctcagggca 480
gaacaggcct cccaggatgt gaagaattgg atgacagaga cattgcttgt tcagaacagc 540
aacccagact gcaagaccat tctgaaagcc ctgggtccag gagcaaccct ggaagagatg 600
atgtcagcct gtcagggggt ggggggccca tcacacaaag ccagggtgtt ggctgaggcc 660
atgtgccaga aagaaaaaat ctatctggca tgggtgccag cccacaaggg gattggaggc 720
aatgagcaaa ttgacaagct ggtgtcaact gaacccattg ctggggtaga gactttttat 780
gtggatggtg ccagcaacag ggaaaccaag gctgtgaagg ctgcttgttg gtgggctgga 840
gtcaagcagg agtttggcat tccctacaac acccaaagcc aaggtgttgt tgaatccatg 900
aacaatgagt tgaaaaagat cataggccag atcagggatc aagctgagca tctgaaaact 960
gcagttcaga tggcagtcct gattcacaat ttcaagagaa agggagggat aggagagtac 1020
agtgcagggg aaaggatcat tgacatcatt gca 1053

<210> SEQ ID NO 155
<211> LENGTH: 1053
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 155
ctgagccccc gaaccctcaa cgcatgggtc aaggtgatcg aagagaaggc gttctctcct 60
gaagttattc ctatgtttac ggctctgtct gagggcgcca caccccatga tttgaacacg 120
atgctcaaca cgataggcgg tcatcaagcc gcgatgcaga tgctcaagga tacgatcaac 180
gaggaagctg cagagtggga ccgagttcac ccagtccatg cagggcctgt tgcaccaggg 240
caaatgcggg acccacgcgg ttcagatatt gccggttcca cgtctaccct gcaagaacaa 300
atagcgtgga tgacaaataa tccaccgatc ccggtgggcg atatatacaa gagatggatt 360
atcatgggcc tgaacaaaat agttaggatg tacagcccgg tgtcaatact tgatataaaa 420
caaggaccga aagaaccctt tcgcgactat gtagaccggt tctacaggac gcttagggca 480
gaacaggcct cccaagatgt gaagaattgg atgacagaga cattgcttgt tcagaacagc 540
aaccctgact gcaagaccat acttaaagct ctgggtccag gagccactct ggaagagatg 600
atgtcagcat gtcagggggt aggcgggcca tcacataaag cccgggtttt ggcggaagca 660
atgtgccaga aagaaaaaat ttatctggcg tgggtgcccg cccacaaggg gataggtggt 720
aacgagcaga tcgacaagct ggtctcaaca gaacctatag ctggagtaga gacgttttat 780
gtggatggtg caagcaatcg ggaaaccaag gcggtaaagg ccgcttgctg gtgggccgga 840
gtcaagcagg agttcggcat cccgtataac acccaaagtc aaggtgtcgt cgaatccatg 900
aataacgagt tgaaaaagat cataggtcaa ataagggatc aagctgaaca tctgaagacg 960
gctgttcaga tggcggtcct tatccacaac tttaagcgca aaggaggtat aggagagtac 1020
agcgcaggtg aacggataat agacattata gca 1053

<210> SEQ ID NO 156

<211> LENGTH: 1059
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 156

```
ctgtctccta gaacattgaa cgcttgggtt aaggttatag aagagaaagc cttcagtcct     60

gaggtgattc ccatgtttac cgccctgagc gagggcgcta caccacatga tctgaatacc    120

atgctgaata ctatcggggg acatcaggct gccatgcaga tgcttaaaga tacaataaat    180

gaggaggctg cagagtggga cagggtccat cctgtacacg cgggacctgt tgcgccggga    240

cagatgagag atccgcgggg gagcgatatt gcaggaagca cctcaactct tcaggagcag    300

attgcctgga tgacgaacaa ccctccgatt cctgtgggag acatttataa gaggtggata    360

attatggggt tgaacaagat agtcaggatg tattctcctg ttagcatcct ggacataaaa    420

cagggcccta aagagccttt tcgcgattat gttgacaggt tttataggac acttcgcgcg    480

gagcaagcct cccaggatgt taaaaactgg atgaccgaga cgctcctggt tcaaaacagt    540

aaccccgatt gtaagaccat ccttaaagca cttggacctg gcgctaccct ggaggaaatg    600

atgagcgcct gtcagggggt aggaggccca tcacataagg cacgggtgct cgcagaggcg    660

atgtgtcaag cggtgaaggc agcctgctgg tgggcaggtg tgaagcagga atttgggatt    720

ccttataata cacaatccca aggtgttgtc gaatctatga acaatgaact gaagaaaatt    780

atagggcaaa tccgggacca agctgagcac ctcaaaaccg cggttcaaat ggctgtactt    840

attcataatt tcaagcgcaa agggggaatc ggtgagtaca gtgctgggga acggataata    900

gatattatcg ccaccgagcc tatcgcaggt gttgaaactt tttacgtgga cggtgcatca    960

aacagagaga ccaaagcggc caaggagaag atatatttgg cctgggttcc tgctcacaag   1020

ggaattggcg gaaatgagca aattgataag ctcgtaagt                          1059
```

<210> SEQ ID NO 157
<211> LENGTH: 1092
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 157

```
gttgccaagg agattgtggc ctgctgtgac aagtgccaat tgaaggggga ggcaattcat     60

ggacaggtgg attgcagtcc aggagtctgg cagctggatt gcacacacct ggaagggaag    120

gtcatccttg ttgcagttca tgttgcctca ggatacattg aagcagagat catccccaca    180

gaaactggtc aggaaacagc ttacttcatt ctcaaactgg ctggcaggtg gccagtcacc    240

acaatcacca agcttcaaaa tttcagggtt tactacaggg acaacagaga tcctctctgg    300

aagggacctg caagacttct ttggaagggt gaaggggcag ttgtcattca ggacaacagt    360

gagatcaagg ttgttcccag gagaaaggtc aagatcatca gggactatgg gaaaaggatg    420

gcaggggatg actgtgttgc agggagacaa gatgaggatg gcactgtgct gataggcccc    480

acacctgtca acatcattgg caggaacctc ttgactcagc tgggctgcac tctcaatttt    540

cccatttccc ccattgacac agtgccagtg aaactgaagc ctggaatgga tggcccaagg    600

gtcaaacagt ggcccctgac agaggagaag atcaaggctc tcattgagat ctgcactgaa    660

atggaaaagg aaggcaagat cagcaggatt ggccctgaga acccttacaa cactcctatt    720
```

tttgcaatca agaagaagga tgggaccaag tggaggaagt tggttgactt cagggaactc 780
aacaagaaaa cacaagactt ttgggaagtc caacttggca ttccccatcc cagtgggttg 840
aaaaagaaaa agtcagtgac agtgttggac attggggatg cttatttctc agttcccctt 900
gacaaggagt tcagaaaata cacagcattc actgtgcctt ccacaaacaa tgaaacccct 960
ggggtcaggt accagtacaa tgtccttcca atgggttgga aaggcagtcc tgcaatcttt 1020
caatgcagca tgacaaaaat ccttcaagaa gaagaggaag ttggctttcc tgtgaggcct 1080
caggtccccc tt 1092

<210> SEQ ID NO 158
<211> LENGTH: 1092
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 158
gttgccaagg agatcgtggc gtgctgcgat aagtgccaat tgaaagggga ggcgattcat 60
ggacaggtcg attgtagtcc cggagtctgg cagctggatt gcactcacct ggaaggtaag 120
gtcatccttg tggctgtaca tgttgcctcc gggtatattg aagccgagat aatccctacc 180
gaaactggtc aggaaaccgc ttacttcatt ctcaaacttg ctggaaggtg gcccgttact 240
acaattacca agctgcaaaa tttcagggtg tactacaggg ataaccgcga ccctctctgg 300
aagggcccag cacgactgct ttggaagggt gagggggctg ttgttattca ggataacagt 360
gagattaagg tagtccccag gcgaaaggtt aaaataatac gggactacgg taaaagaatg 420
gcgggggatg actgtgttgc agggagacaa gacgaagacg gaacggtact tataggccca 480
actccggtaa acataattgg tagaaacctc ttgacgcagc tgggctgtac tcttaatttt 540
ccaatatcac ctattgacac tgtcccagtc aagctgaagc ctggaatgga tggacctcgg 600
gttaaacagt ggcccctcac cgaggagaag atcaaggcgc tgatcgaaat ctgcaccgaa 660
atggaaaagg aaggtaagat tagccggatc ggcccccgaga acccttataa cacgcctata 720
ttcgctatca agaagaagga cggaacaaag tggaggaagt tggttgactt ccgggaactt 780
aacaagaaaa cacaagactt ttgggaagtc caactcggca tcccacaccc aagtgggttg 840
aaaaagaaaa agtccgtaac tgtattggac ataggtgacg cttatttttc agtaccactt 900
gataaggaat ttcgaaaata cacagcgttc actgtgccgt ccacgaacaa cgaaaccccc 960
ggggtacgct accaatataa cgtactgcca atgggttgga aaggtagtcc tgcgatcttt 1020
caatgcagta tgactaaaat ccttcaagaa gaagaggaag tcggatttcc tgtgcggccc 1080
caggtccccc tg 1092

<210> SEQ ID NO 159
<211> LENGTH: 1089
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 159
gggacggtgc ttattgggcc cactccagtc aatattatcg gacgaaacct gctgactcag 60
ctgggttgca ctctcaattt ccctattagt cctatagaca cggtgcccgt aaaactcaag 120
ccaggcatgg atggtccgcg cgtgaagcaa tggcctttga ctgaagaaaa aattaaggca 180
ctcattgaga tatgtacgga gatggagaaa gaagggaaaa tctctcgaat tggaccagaa 240
aacccgtaca atactccgat ttttgcgatt aagaagaagg atggcacgaa gtggcgcaaa 300
ctcgtcgatt ttagggagct taacaagaag acccaagatt tttgggaggt ccagctgggc 360
attccgcatc cgtccggctt gaaaaagaaa aaatcagtta ctgtgcttga tataggagac 420
gcctatttta gtgtgccgtt ggacaaggaa tttcgcaaat atacagcatt taccgtccct 480
tcaacgaaca atgagactcc gggcgtacgc taccaatata atgtgttgcc tatggggtgg 540
aaggggtctc ctgcgatctt ccaatgctct atgacgatta ccaagctgca aaattttcgc 600
gtatactacc gcgacaatcg agatccattg tggaaggggc cggcgaggct cctttggaag 660
ggagaaggtg ccgtagttat ccaagataat agcgagatca aagttgtgcc ccgaagaaag 720
gtgaaaatta taagggatta cgggaagaga atggcgggag acgactgtgt tgccggtcgc 780
caagacgagg atgttgcgaa ggaaatcgtt gcgtgttgtg ataaatgtca gctgaaaggc 840
gaagcaattc acggacaggt agattgttct cctggcgtgt ggcagcttga ctgtacccat 900
ttggagggaa aagtgatcct ggtagcagtc cacgttgcca gtggctacat agaagctgag 960
ataattccta ctgagacggg acaggagacg gcttatttta ttctcaagct ggcaggcaga 1020
tggcccgtga ccaccgcggc gcaggaagag gaggaagttg gttttcccgt acgccctcag 1080
gttcccttg 1089

<210> SEQ ID NO 160
<211> LENGTH: 1173
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 160
acagtcaaag ccgcttgctg gtgggcgggc ataaagcaag aatttgggat accctataac 60
cctcaatctc aaggggtagt tgaatctatg aacaaggaac tcaaaaagat cataggacag 120
gtccgcgatc aggctgagca tttgaagacg gctgtgcaaa tggcggtttt tatccataac 180
ttcaagcgga agggtgggat cggcggagca gcaatcagtc cacgaactct taatgcttgg 240
gtgaaggttg ttgaggagaa agcgttcagt cctgaggtga tccccatgtt ctctgcactt 300
agcgaaggag caacacccca ggaccttaac acgatgttga acacagtggg gggtcatcaa 360
gccgccatgc agatgctcaa agaaactata aatgaggagg ctgccgagtg ggacagactg 420
catcctgtgc acgccggacc aatagcaccg gggcagatgc gagaaccgcg aggttccgac 480
atcgctggga ccacttctac tctgcaggag cagattggtt ggatgactaa caacccccccg 540 ataccggtgg gtgagatcta taagcgctgg atcatacttg gccttaacaa aatagttcgc 600
atgtactcac caacaagcat tctcgacatc cgacaggggc ctaaggagcc ttttcgagac 660
tatgtggata gattttataa aactttgcgg gcggagcaag catcccagga ggttaagaac 720
tggatgacag agacacttct ggtccagaat gccaaccccg actgtaaaac gatacttaaa 780
gcacttgggc cggctgcaac tctggaggaa atgatgacag cgtgtcaagg tgtgggggggt 840 cctggccata aggctcgcgt gttggcggaa gcaatgtcac aagttgccaa agaaatagtt 900
gccagttgcg acaagtgcca actcaaaggt gaagcgatgc atggacaggt ggattgctca 960
ccaggcatct ggcagcttga ctgtacacac ctggagggca agataatttt ggtcgcggtg 1020

```
catgtagcaa gtggttatat cgaagctgag gtaataccg ccgagacggg gcaagagaca   1080

gcctacttcc tcttgaagtt ggccggtcga tggccggtta agacgcaaga ggaggaagag   1140

gttggcttcc ccgttaagcc tcaagtaccg ctt                                1173
```

<210> SEQ ID NO 161
<211> LENGTH: 1179
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 161

```
gcggtgaagg ccgcatgttg gtgggcgggt gttaaacaag agttcggtat accgtacaat     60

acgcagagtc aaggagtcgt agaatctatg aataatgagc tgaaaaaaat cattgggcaa    120

attcgggacc aggctgagca tctcaaaacg gccgttcaga tggccgtcct gattcataac    180

tttaagagaa aaggcggcat aggggagctc agtccaagga ctctcaacgc ctgggtgaag    240

gttattgaag aaaaagcgtt tagcccggag gtaattccaa tgtttacagc tctcagcgag    300

ggggcgacac ctcatgatct caatacaatg ctcaatacaa tagggggggca ccaggccgct    360

atgcaaatgc tgaaagacac gatcaatgaa gaagcggctg aatgggatag agttcatcct    420

gttcatgcag gaccggtcgc cccgggacag atgagagacc cgcgcggttc cgacatagct    480

gggagcacgt ctacgttgca ggagcagatc gcttggatga ctaataatcc ccctatccct    540

gtcggtgata tttataaacg gtggattatt atgggtttga acaaaattgt gagaatgtac    600

agcccagttt ccatacttga tattaagcag gggccgaaag aaccctttag ggactatgta    660

gaccgcttct atcgcacact tagagccgag caggcgagtc aggacgtaaa gaactggatg    720

acagaaaccc tccttgtcca aaactccaat cccgattgca aaaccatttt gaaagcactc    780

ggtcctggag ccactttgga agaaatgatg tccgcgtgtc agggggtggg agggccaagc    840

cacaaagcga gagtattggc ggaggcgatg tgccaggtta ccgtagcgaa ggagatagtc    900

gcatgctgtg acaaatgcca acttaaaggc gaggcgatcc atggtcaggt tgactgcagt    960

ccgggggtat ggcaacttga ctgtacacat ttggagggta aggttattct cgttgcagtt   1020

catgtagctt caggatacat cgaggccgaa atcatcccga cggagacggg ccaagagact   1080

gcctacttca tcttgaaact ggcgggtcgc tggccggtaa ctaccgccgc ccaggaggaa   1140

gaagaagttg ggttccctgt ccgaccccaa gtgccactc                          1179
```

<210> SEQ ID NO 162
<211> LENGTH: 1173
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 162

```
acggtgaaag cggcctgttg gtgggcggga attaagcagg aatttgggat accgtataac     60

cctcaaagcc aaggcgtcgt agaatccatg aacaaagagc tgaagaagat tattggccag    120

gttcgggacc aggcagaaca ccttaaaaca gccgtgcaga tggcagtgtt catccataat    180

tttaagcgga agggcgggat tggcggagtt gcgaaggaaa ttgttgcgag ttgtgataaa    240

tgccaactta aaggggaggc aatgcacgga caagttgatt gctcacctgg catatggcag    300

ctggattgta cccaccttga gggtaaaata atcctggtgg ccgttcatgt cgcatctggc    360
```

tatatagaag cggaagtcat tccagcagag acgggtcaag aaactgctta ctttctcctt 420
aaacttgcgg gaaggtggcc tgttaaaacc gccgctatta gccccaggac gttgaatgcc 480
tgggtaaagg ttgtggagga gaaggcattc tcccctgagg taattcccat gttctcagca 540
ctgagtgaag ggctacacc tcaagatctg aacacgatgc tcaacacggt tggcggacat 600
caagcggcca tgcaaatgct caaagaaacc atcaatgaag aagcggctga gtgggaccgc 660
cttcatccag tccatgctgg cccaatcgca cctggtcaaa tgagagagcc gaggggtagt 720
gatatagccg ggacgactag cacattgcag gaacagatag ggtggatgac aaataaccct 780
cctatacctg tgggggaaat atataaacgc tggattattc tcggtctgaa caagattgtc 840
aggatgtact ccccgaccag tatccttgac ataagacaag ggcctaagga gccctttcgg 900
gactacgttg atcggttcta taagacgctt cgggccgagc aggcgtctca agaggtgaaa 960
aattggatga ctgaaacttt gctggtgcaa aatgctaacc ccgactgcaa gacaatattg 1020
aaggctctcg gtccagcagc aactttggaa gagatgatga cagcgtgtca aggcgtaggt 1080
gggccaggac acaaggctag ggtccttgca gaggctatgt ctcagcagga ggaggaagag 1140
gtaggtttcc ccgtcaagcc tcaagtccca ctc 1173

<210> SEQ ID NO 163
<211> LENGTH: 1182
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 163
cttagtccga gaactctcaa cgcttgggtc aaagtcatag aggagaaagc cttttcaccc 60
gaagtaatac ctatgttcac tgcgttgagc gagggcgcga cacctcatga cctgaatact 120
atgctgaaca ccatcggggg ccaccaagca gctatgcaga tgctgaagga cacaattaac 180
gaagaagcgg cagaatggga tagggttcac cctgtacatg ccggaccagt tgcacctggc 240
caaatgagag acccacgagg gagcgacatc gcaggctcaa ctagtaccct gcaagagcag 300
atagcgtgga tgaccaataa tcctcctatt cctgttggtg acatttacaa acgatggata 360
ataatgggcc tcaataagat cgtcagaatg tacagcccag tgagcatcct ggatataaag 420
cagggaccga aagaaccctt ccgggactat gttgaccgct tctaccggac tcttagggcg 480
gaacaggcca gccaggacgt aaaaaactgg atgactgaaa cgttgttggt tcaaaattca 540
aatccagact gcaaaaccat tctcaaagca ctcggaccag gcgctaccct ggaagagatg 600
atgtctgcct gtcaaggtgt cggggggccg agtcacaagg cacgcgtact ggcggaggcc 660
atgtgtcaac cagtagttgc caaagagatt gtcgcgtgct gtgataagtg tcagctcaaa 720
ggggaagcga tacatggaca agtagactgt agtcctggcg tgtggcagtt ggactgtacc 780
catttggagg gcaaggtaat attggtagct gtccatgtcg cgtctggtta tatcgaagca 840
gaaatcattc cgactgagac tggtcaagag acggcctact tcatactgaa acttgcaggt 900
aggtggccgg taacaacggc ggcttatgcc gtaaaagctg cttgttggtg ggctggagtc 960
aagcaagaat ttggaatccc ttacaacaca cagagtcaag gcgtcgtcga gtctatgaat 1020
aacgagctga aaaagatcat aggccaaatc agagaccaag ccgaacactt gaagacagcc 1080
gttcaaatgg cagttcttat ccacaacttc aagcgcaaag gggcatagg tgaacaggag 1140 gaggaggagg taggcttccc tgtccggccg caagtgccgc tc 1182

<210> SEQ ID NO 164
<211> LENGTH: 3084
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 164
acagtgaagg cagcttgttg gtgggccgga attaaacagg agtttggcat cccttataat 60
cctcagtctc agggagtggt ggagtctatg aacaaggagc tgaagaagat catcggccag 120
gtgagagatc aggcagaaca tctgaagaca gcagtgcaga tggccgtgtt tatccacaac 180
ttcaagagga agggcggcat tggaggatat agcgcaggag aaagaatcgt ggacatcatc 240
gccatctctc ctagaacact gaacgcttgg gtgaaagtgg tggaggagaa agcctttagc 300
ccagaagtga tccctatgtt ctcagctctg tcagaaggag ctacacctca ggatctgaac 360
accatgctga ataccgtggg aggacatcag gcagctatgc agatgctgaa ggagacaatt 420
aacgaggaag cagccgagtg ggatagactg catccagtgc acgcaggacc tattgctcca 480
ggacagatga gagagcctag aggaagcgat attgccggca caacatctac actgcaggaa 540
cagatcggtt ggatgaccaa caatcctcct atcccagtgg gcgaaatcta caaacgctgg 600
atcatcctgg gcctgaataa gatcgtgaga atgtacagcc ccacaagcat cctggatatc 660
agacagggac ctaaggaacc tttcagggat tacgtggacc ggttctacaa gacactgaga 720
gcagaacagg catctcagga ggtgaagaat tggatgaccg agacactgct ggtgcagaac 780
gctaatccag attgcaagac cattctgaaa gctctgggac cagcagctac actggaagag 840
atgatgacag cttgtcaggg agtgggagga ccaggacata aagctagagt gctggcagaa 900
gctatgtctc agatggcagc tagagcttca gtgctgtcag gaggagaact cgataggtgg 960
gagaagatca gactgagacc aggaggcaag aagaagtaca gactgaagca catcgtgtgg 1020
gcttctagag aactggagag atttgccgtg aatccaggac tcctggaaac acctccagtg 1080
gtggctaaag agattgtggc ttcttgcgat aagtgccagc tgaaaggaga ggctatgcac 1140
ggacaggtgg attgttctcc aggaatttgg cagctggatt gtacacacct ggagggaaag 1200
attattctgg tggcagtgca cgtggcatca ggatatattg aggccgaagt gattccagca 1260
gaaacaggac aggagacagc ttactttctg ctcaaactgg caggtcgctg gccagtgaaa 1320
accaaggaga aggtgtacct ggcttgggtg ccagctcata aaggaattgg cggaaacgag 1380
caggtggata aactggtgtc tacacagggc tacttcccag attggcagaa ttacacacca 1440
ggaccaggca caagatatcc tctgacattc ggttggtgtt tcaagctcgt gccagtgaga 1500
gctaaaagag ctccagtgaa gcagaccctg aatttcgatc tgctgaagct cgcaggagac 1560
gtggaatcta atccaggacc tctgtctcct agaacactga acgcttgggt gaaggtgatc 1620
gaagagaagg cctttagccc agaagtgatc cctatgttta cagccctgag cgaaggagct 1680
acacctcacg atctgaatac catgctgaac acaattggag gacatcaggc cgctatgcag 1740
atgctgaagg acaccatcaa cgaagaagca gccgagtggg atagagtgca tccagtgcac 1800
gcaggaccag tggctccagg acagatgaga gatcctagag gaagcgacat cgcaggatct 1860
acatctacac tgcaggaaca gatcgcctgg atgacaaata accccccctat cccagtggga 1920 gatatctata agcgctggat catcatgggc ctgaacaaga tcgtgaggat gtacagccca 1980
gtgtctatcc tggacatcaa gcagggacct aaggagcctt ttagagacta cgtggacaga 2040

```
ttctacagaa cactgagagc cgaacaggca tctcaggacg tgaagaattg gatgaccgag   2100
acactgctgg tgcagaacag caaccccgat tgcaagacaa tcctgaaagc cctgggacca   2160
ggagctacac tggaagagat gatgtcagct tgtcagggag tgggaggacc atctcataag   2220
gctagagtgc tggcagaagc tatgtgtcag gtggctaagg agattgtggc ttgttgcgac   2280
aagtgccagc tgaaaggaga agctatccac ggacaggtgg attgttctcc aggagtctgg   2340
cagctggatt gtacacacct ggaaggaaaa gtgattctgg tggcagtgca cgtggccagc   2400
ggctatattg aagccgagat cattcctaca gagacaggac aggagacagc ttacttcatt   2460
ctgaaactgg caggtcgctg gccagtgaca acaatggcag ctagagcttc tatcctgtca   2520
ggaggaaagc tcgataagtg ggaaaagatc agactgagac caggcggaag aaagaagtac   2580
aagctgaagc acctcgtctg ggcttctaga gaactggaaa gattcgccct gaatccaggt   2640
ctgctggaaa cagcagcagc agtgaaagca gcttgttggt gggcaggagt gaaacaggag   2700
ttcggcatcc cttacaacac ccagtctcag ggagtggtgg aatctatgaa caacgagctg   2760
aagaagatca tcggccagat cagagaccag gcagaacatc tgaagacagc agtgcagatg   2820
gcagtgctga ttcacaactt caagagaaag ggcggcattg gagagtatag cgccggagag   2880
agaatcatcg atatcattgc cacacagggc ttcttcccag attggcagaa ttacacccca   2940
ggaccaggca ttagatttcc tctgaccttc ggttggtgtt tcaaactggt gcccctgctg   3000
atcaagaagg agaagatcta cctggcttgg gtgccagctc ataaaggaat cggaggaaac   3060
gagcagatcg ataaactggt gtct                                          3084
```

<210> SEQ ID NO 165
<211> LENGTH: 3066
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 165

```
tttcctcaga tcactctctg gcagagacca ctggtgacaa tcaagatcgg aggacagctg     60
aaagaagctc tgctggatac aggagcagac gatacagtgc tggaagagat gaatctgcca    120
ggtcgctgga aacctaagat gattggaggc attggcggct ttatcaaggt gagacagtac    180
gaccaggagg aagtgggatt tccagtgaaa cctcaggtgc ctctgagacc tatgacattt    240
aagggcgctc tggacctgtc tcactttctg agagagaagg gaggactgga aggactgatc    300
cctaagttca agctgcctat ccagaaggag acttgggaaa cttggtggac agagtattgg    360
caggctactt ggattcccga gtgggaattt gtgaacacac ctcctctggt gaagctgtgg    420
tatcagctgg aaaaggagcc tattgtgggc gcagaaacat tctacgtgga cggagcagct    480
aacagagaaa ctaagtgggg attcaccacc ccagataaga agcaccagaa ggagccacca    540
tttctctgga tgggatacga actgcaccca gataagtgga cagtccagcc tattgtgctg    600
ccagaaaagg actcttggac cgtgaacgat atccagaagc tggtgggaaa gctgaattgg    660
gcttctcaga tctacccagg aatcaaggtg atcaccaaga tccagaactt cagggtgtac    720
tacagagaca gcagagatcc tctctggaag ggaccagcta aactcctctg gaaaggagaa    780
ggagcagtgg tgatccagga taacagcgac atcaaggtgg tgcctagaag aaaggccaag    840
atcatcaggg actacggcaa acagatggca ggagacgatt gcgtggcttc tagacaggac    900
gaagacggaa cagtcctggt gggacctaca ccagtgaata tcatcggcag aaatctcctg    960
```

-continued

```
acacagatcg gttgtaccct gaacttccct atcagcccta tcgagacagt gccagtgaaa   1020
ctgaagccag gaatggacgg acctaaagtc aagcagtggc ctctgacaga agagaagatc   1080
aaggccctgg tggagatttg cacagagatg gagaaggagg gaaagatcag caagatcggc   1140
ccagagaatc cttacaacac cccagtgttc gccatcaaga agaaggatag caccaagtgg   1200
agaaagctgg tggatttcag ggagctgaac aagagaaccc aggacttttg ggaagtgcag   1260
ctgggcatcc cccatccagc aggactgaag aagaagaaga gcgtgacagt gctggacgtg   1320
ggagacgctt attttagcgt gcctctggac aaggacttca gaaagtacac cgccttcacc   1380
atcccttcta tcaacaacga gaccccaggc atcagatacc agtataacgt gctgcctcag   1440
ggttggaaag gatctccagc aatcttccag agcagcatga ccagagctaa gagagctcca   1500
gtgaaacaga ccctgaactt cgatctgctc aaactggcag gagacgtgga aagcaatcca   1560
ggacctaatc tgcctcagat cacactgtgg cagagaccta ttgtgaccat caagattggc   1620
ggccagatta aagaagccct gctggataca ggagcagacg atacagtgct ggaggatatg   1680
aacctgccag gtaagtggaa gcctaagatg attggcggaa ttggcggctt tatcaaggtc   1740
aagcagtacg atcagtgggg actgacaaca ccagacaaga agcaccagaa ggacccccca   1800
ttcctctgga tgggatacga actgcatcca gataggtgga cagtgcagcc aattgaactg   1860
ccagagaagg agtcttggac cgtgaacgat atccagaagc tgatcggcaa gctgaattgg   1920
gcttctcaga tctacgcagg aattaaggtg gccgctcagg aagaagagga agtgggattt   1980
ccagtgagac ctcaggtgcc tctgagacct atgacataca agggagctct ggacctgtct   2040
cactttctga aggagaaggg aggactggaa ggaatcacca agctgcagaa tttccgggtg   2100
tactacaggg acaatagaga ccctctctgg aaaggaccag ctagactgct gtggaaagga   2160
gaaggagcag tggtgatcca ggataatagc gagatcaagg tggtgcctag gagaaaggtg   2220
aagatcatca gggactacgg caagagaatg gcaggagacg attgcgtggc aggaagacag   2280
gacgaggacc ccaagttcag actgcctatc cagaaggaga cttgggatac ttggtggacc   2340
gattattggc aggcaacttg gattcccgag tgggagttta caaataccccc tcctctggtc   2400
aagctctggt atcagctgga aacagagcct attgccggag tggaaacctt ttacgtggac   2460
ggagccagca acagagagac aaaagccgca ggaacagtgc tgattggacc taccccagtg   2520
aacatcatcg gaagaaacct gctgacacag ctgggttgta cactgaactt ccctatcagc   2580
cctattgata cagtgccagt gaagctgaaa ccaggaatgg acggacctag agtcaagcag   2640
tggcctctga cagaagagaa gatcaaggcc ctgatcgaga tttgcaccga aatggagaag   2700
gagggcaaga ttagcaggat cggcccagag aatccttaca atacccctat cttcgccatc   2760
aagaagaagg acggcaccaa gtggagaaaa ctggtggatt tcagggagct gaacaagaag   2820
acccaggact tttgggaggt gcagctgggc atcccccatc cttcaggact gaagaagaag   2880
aagagcgtga cagtgctgga cattggagac gcttacttta gcgtgccact ggacaaggag   2940
ttcagaaagt acaccgcctt cacagtgcct agcacaaata acgagacccc aggagtgaga   3000
taccagtata acgtgctgcc aatgggctgg aaaggaagcc cagctatctt tcagtgtagc   3060
atgaca                                                              3066
```

<210> SEQ ID NO 166
<211> LENGTH: 3102
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 166
gtggccaaag aaattgtggc ctcttgcgat aagtgccagc tgaaaggaga ggctatgcac 60
ggacaggtgg attgttctcc aggaatttgg cagctggatt gtacacacct ggagggaaag 120
attattctgg tggcagtgca cgtggcatca ggatatattg aggccgaagt gattccagca 180
gaaacaggac aggagacagc ttactttctg ctcaaactgg caggtcgctg gccagtgaag 240
acaacacagg gctactttcc tgattggcag aattacacac caggaccagg aacaagatac 300
cctctgacct ttggttggtg cttcaaactg gtgcccgtga cagtgaaagc agcttgttgg 360
tgggcaggaa ttaagcagga gttcggcatc ccttacaatc ctcagtctca gggagtggtg 420
gaatctatga acaaggagct gaagaagatc atcggccagg tgagagatca ggcagaacat 480
ctgaagacag cagtgcagat ggcagtgttc atccacaact tcaagcggaa gggaggaatt 540
ggaggatata gcgcaggaga gagaatcgtg gatatcattg ccgccgctat ggcagctaga 600
gccagcgtgc tgagcggagg agaactcgat cgctgggaaa agatcagact gagaccagga 660
ggcaagaaga agtacagact gaagcacatc gtctgggctt ctagagaact ggagagattt 720
gccgtgaatc caggactgct ggaaacaagc gagggcattt ctcctagaac cctgaacgct 780
tgggtgaaag tggtggaaga aaaagccttc tctccagagg tgatccctat gtttagcgct 840
ctgtcagaag gagctacacc tcaggatctg aacaccatgc tgaacacagt gggaggacat 900
caggcagcta tgcagatgct gaaggagaca attaacgaag aagccgccga gtgggataga 960
ctgcatccag tgcacgcagg acctattgct ccaggacaga tgagagagcc tagaggaagc 1020
gatattgccg gaacaacaag cacactgcag gaacagatcg gttggatgac caataatccc 1080
cctattccag tgggcgagat ctataagcgc tggattatcc tgggcctgaa caagatcgtg 1140
agaatgtaca gccccacctc tatcctggat atcagacagg gccctaagga acctttcaga 1200
gactacgtgg acaggttcta caagacactg agagcagaac aggcatctca ggaggtgaag 1260
aattggatga ccgagacact gctggtgcag aacgccaatc cagattgcaa gacaattctg 1320
aaagccctgg gaccagcagc tacactggaa gagatgatga ccgcttgtca gggagtggga 1380
ggaccaggac ataaagctag agtgctggca gaagctatgt ctcaggcagc agctaaggag 1440
aaagtgtatc tggcttgggt gccagcccat aaaggaattg gaggaaacga gcaggtggat 1500
aagctggtgt ctagagctaa gagagctcca gtgaagcaga ccctgaactt tgatctgctc 1560
aagctggcag gagacgtgga atctaatcca ggacctcatc aggctctgtc tcctagaaca 1620
ctgaacgctt gggtgaaggt gatcgaagag aaggccttta gcccagaagt gatccctatg 1680
tttacagccc tgagcgaagg agctacacct cacgatctga ataccatgct gaacacaatt 1740
ggaggacatc aggccgctat gcagatgctg aaggacacca tcaacgagga agcagcagag 1800
tgggatagag tgcatccagt gcatgcagga ccagtggctc caggacagat gagagatcct 1860
agaggaagcg atatcgcagg atctacaagc acactgcagg aacagatcgc ttggatgacc 1920
aataacccac ctatcccagt gggagacatc tacaagcgct ggatcatcat gggactgaac 1980
aagatcgtga ggatgtacag cccagtgtct atcctggata tcaagcaggg acctaaggag 2040
cctttcagag attacgtgga caggttttac agaaccctga gagccgaaca ggcatctcag 2100
gacgtgaaga attggatgac cgaaacactg ctggtgcaga atagcaaccc agattgcaag 2160
acaatcctga aagccctggg accaggagct acactggaag aaatgatgag cgcttgtcag 2220

```
ggagtgggag gaccatctca taaggctaga gtgctggcag aagctatgtg tcaggcagtg   2280

aaagcagctt gttggtgggc aggagtgaaa caggagtttg gcatccctta caacacacag   2340

tctcagggag tggtggaatc tatgaacaac gagctgaaga agatcatcgg ccagatcaga   2400

gaccaggcag aacatctgaa gacagcagtg cagatggcag tgctgattca caacttcaag   2460

agaaagggcg gcattggaga gtatagcgcc ggcgagagaa ttatcgacat catcgccaag   2520

gagaagatct atctggcttg ggtgccagcc cataaaggaa ttggaggcaa tgagcagatc   2580

gataaactgg tgtcagcagc ttatatggcc gctagagcct ctattctgag cggaggaaag   2640

ctcgataagt gggagaagat cagactgaga ccaggaggca gaaagaagta caagctgaag   2700

catctcgtct gggcttctag agaactggag agattcgctc tgaatccagg actgctggaa   2760

acaacacagg gcttcttccc cgattggcag aattacacac caggaccagg aatcagattc   2820

cctctgacct tcggttggtg ttttaagctg gtgcctctgg tggctaagga aattgtggct   2880

tgttgcgaca agtgccagct gaaaggagaa gctatccacg gacaggtgga ttgttctcca   2940

ggagtctggc agctggattg tacacacctg gagggaaaag tgattctggt ggcagtgcac   3000

gtggcatcag gatatattga ggccgagatc attcctacag aaacaggaca ggagacagcc   3060

tactttatcc tgaagctggc tggtaggtgg ccagtgacaa ca                      3102
```

```
<210> SEQ ID NO 167
<211> LENGTH: 3060
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 167
```

```
atcaccaaga tccagaactt cagggtgtac tacagagaca gcagagatcc tctctggaag     60

ggaccagcta aactcctctg gaaaggagaa ggagcagtgg tgatccagga taacagcgac    120

atcaaggtgg tgcctagaag aaaggccaag atcatcaggg actacggcaa acagatggca    180

ggagacgatt gcgtggcttc tagacaggac gaagacgcag cttacgaaga ggaagaggtg    240

ggatttccag tgaaacctca ggtgcctctg agacctatga cattcaaggg agctctggat    300

ctgtctcact tcctgagaga aaagggagga ctggaaggag cagcttgggg atttaccacc    360

ccagacaaga agcaccagaa ggaaccacca ttcctctgga tgggatacga actgcaccca    420

gataagtgga cagtccagcc tattgtgctg ccagaaaagg actcttggac cgtgaacgat    480

atccagaagc tggtgggaaa gctgaattgg gcttctcaga tctacccagg aatcaaggtg    540

cccaagttca agctgcctat ccagaaggag acttgggaaa cttggtggac agagtattgg    600

caggctactt ggattcccga gtgggaattt gtgaacacac ctcctctggt gaagctgtgg    660

tatcagctgg aaaaggagcc tatcgtgggc gcagaaacat tttacgtgga cggagccgcc    720

aatagagaaa ccaagtttcc tcagatcact ctctggcaga gacctctggt gacaatcaag    780

atcggcggac agctgaaaga ggctctgctg gatacaggag cagacgatac cgtgctggaa    840

gaaatgaatc tgccaggtag gtggaagcct aagatgattg gcggaattgg cggcttcatc    900

aaggtgagac agtacgatca gggaacagtg ctggtgggac ctactccagt gaacatcatc    960

ggaaggaacc tgctgacaca gatcggctgt acactgaact tccctatcag ccctatcgag   1020

acagtgccag tgaaactgaa gccaggaatg gacggaccta aagtcaaaca gtggcctctg   1080

acagaggaga aaatcaaagc cctggtggag atttgtaccg agatggagaa ggagggcaag   1140
```

-continued atttctaaga tcggaccaga gaacccctac aataccccag tgtttgccat caagaagaag 1200
gacagcacca agtggaggaa gctggtggat tttagggagc tgaacaagag gacacaggac 1260
ttttgggaag tgcagctggg catcccccac ccagccggac tgaaaaagaa gaagtcagtg 1320
acagtgctgg acgtgggaga tgcctatttt agcgtgcctc tggataagga cttcaggaag 1380
tacaccgcct tcacaatccc tagcatcaac aacgagaccc caggaatcag ataccagtac 1440
aacgtgctgc ctcagggttg gaaaggatct ccagccatct ttcagagcag catgacaaga 1500
gccaagagag ctccagtgaa gcagaccctg aatttcgatc tgctgaagct cgcaggagac 1560
gtggaatcta atccaggacc tcccaagttc agactgccta ttcagaagga gacttgggac 1620
acttggtgga ccgattattg gcaggcaact tggattcccg agtgggagtt cacaaataca 1680
cctcctctgg tcaagctctg gtatcagctg gaaacagagc ctatcgcagg agtggaaaca 1740
ttctacgtgg acggagcttc taacagagag accaaggagg aggtgggatt tccagtgaga 1800
cctcaggtgc ctctgagacc tatgacatac aagggagccc tggatctgtc tcactttctg 1860
aaggagaaag gcggactgga aggactgcct cagattactc tctggcagag gcctattgtg 1920
acaatcaaga tcggcggaca gatcaaagaa gccctgctgg atacaggagc agacgataca 1980
gtgctggagg atatgaacct gccaggcaag tggaaaccta agatgatcgg aggaatcggc 2040
ggatttatca aggtgaagca gtacgaccag atcaccaagc tgcagaactt cagggtgtac 2100
tacagagaca acagagaccc tctctggaaa ggaccagcta gactcctctg gaaaggagaa 2160
ggagcagtgg tgatccagga taatagcgag atcaaggtgg tgcctaggag aaaggtgaag 2220
atcatccggg actacggcaa aagaatggca ggagacgatt gcgtggcagg aagacaggac 2280
gaagattggg gactgacaac cccagataag aagcaccaga aggacccccc attcctctgg 2340
atgggatacg aactgcatcc agataggtgg acagtgcagc caattgaact gccagaaaag 2400
gagtcttgga cagtgaacga catccagaag ctgatcggca agctgaattg ggcttctcag 2460
atctacgccg gaattaaggt gaagggaaca gtgctgattg gacctacacc agtgaacatc 2520
atcgggagaa acctgctgac acagctgggt tgtacactga acttccctat cagccctatc 2580
gatacagtgc cagtgaaact gaagccagga atggacggac ctagagtgaa acagtggcct 2640
ctgacagaag agaagatcaa ggccctgatc gagatttgta cagagatgga gaaggagggc 2700
aagatctcta gaattggccc agagaacccc tacaataccc ctatctttgc catcaagaag 2760
aaggacggca ccaagtggag aaagctggtg gatttcaggg agctgaacaa gaagacccag 2820
gacttttggg aagtgcagct gggcatcccc caccctagcg gactgaaaaa gaagaagagc 2880
gtgaccgtgc tggatattgg agacgcctat tttagcgtgc cactggataa ggagttcaga 2940
aagtacaccg cctttaccgt gccttctacc aataacgaga caccaggagt gagataccag 3000
tacaacgtgc tgcctatggg ttggaaggga tcaccagcca tctttcagtg tagcatgaca 3060

<210> SEQ ID NO 168
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 168

Gln Asn Leu Gln Gly Gln Met Val His Gln Ala Ile Ser Pro Arg Thr
1 5 10 15

Leu Asn Ala Trp Val Lys Val Val Lys Ala Phe 20 25

<210> SEQ ID NO 169
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 169

Gln Asn Leu Gln Gly Gln Met Val His Gln Ala Ile Ser Pro Arg Thr
1 5 10 15

Leu Asn Ala Trp Val Lys Val Glu Lys Ala Phe
20 25

<210> SEQ ID NO 170
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 170

Gln Asn Leu Gln Gly Gln Met Val His Gln Ala Ile Ser Pro Arg Thr
1 5 10 15

Leu Asn Ala Trp Val Lys Ile Val Lys Ala Phe
20 25

<210> SEQ ID NO 171
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 171

Gln Asn Ile Gln Gly Gln Met Val His Gln Ala Ile Ser Pro Arg Thr
1 5 10 15

Leu Asn Ala Trp Val Lys Ile Glu Lys Ala Phe
20 25

<210> SEQ ID NO 172
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 172

Gln Asn Ile Gln Gly Gln Met Val His Gln Ala Ile Ser Pro Arg Thr
1 5 10 15

Leu Asn Ala Trp Val Lys Val Val Lys Ala Phe
20 25

<210> SEQ ID NO 173
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 173

Pro Asn Ile Gln Gly Gln Met Val His Gln Ala Ile Ser Pro Arg Thr
1 5 10 15

Leu Asn Ala Trp Val Lys Ile Val Lys Ala Phe
20 25

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 174

Gln Asn Leu Gln Gly Gln Met Val His
1 5

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 175

Gln Asn Ile Gln Gly Gln Met Val His
1 5

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 176

Pro Asn Ile Gln Gly Gln Met Val His
1 5

<210> SEQ ID NO 177
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 177

Ala Ile Ile Ile Ile Ile Ile Ile Ile Lys
1 5 10

<210> SEQ ID NO 178
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 178

Gly Ile Ile Ile Ile Ile Ile Ile Ile His
1 5 10

<210> SEQ ID NO 179
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Gly Ile Ile Ile Ile Ile Ile Ile Ile Arg
1               5                   10

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gly Ile Ile Ile Ile Ile Ile Ile Ile
1               5

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ala Ile Ile Ile Ile Ile Ile Ile Ile
1               5

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ile Ile Ile Ile Ile Ile Ile Ile Lys
1               5

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ile Ile Ile Ile Ile Ile Ile Ile His
1               5

<210> SEQ ID NO 184
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

-continued

Ile Ile Ile Ile Ile Ile Ile Ile Arg
1 5

<210> SEQ ID NO 185
<211> LENGTH: 9
<212> TYPE: PRT
<213> ORGANISM: Human immunodeficiency virus

<400> SEQUENCE: 185

His Pro Pro Gln Ala Gly Pro Val Ala
1 5

<210> SEQ ID NO 186
<211> LENGTH: 9
<212> TYPE: PRT
<213> ORGANISM: Homo sapiens

<400> SEQUENCE: 186

Val Pro Leu Gln Ala Gly Pro Val Gln
1 5

<210> SEQ ID NO 187
<211> LENGTH: 9
<212> TYPE: PRT
<213> ORGANISM: Homo sapiens

<400> SEQUENCE: 187

Met Pro Gly Gln Ala Gly Pro Val Gly
1 5

<210> SEQ ID NO 188
<211> LENGTH: 9
<212> TYPE: PRT
<213> ORGANISM: Homo sapiens

<400> SEQUENCE: 188

Gln Tyr Arg Gln Ala Gly Pro Val Ile
1 5

<210> SEQ ID NO 189
<211> LENGTH: 69
<212> TYPE: PRT
<213> ORGANISM: Human immunodeficiency virus 1

<400> SEQUENCE: 189

Thr Val Lys Ala Ala Cys Trp Trp Ala Gly Ile Lys Gln Glu Phe Gly
1 5 10 15

Ile Pro Tyr Asn Thr Gln Ser Gln Gly Val Val Glu Ser Met Asn Asn
20 25 30

Glu Leu Lys Lys Ile Ile Gly Gln Ile Arg Asp Gln Ala Glu His Leu
35 40 45

Lys Thr Ala Val Gln Met Ala Val Leu Ile His Asn Phe Lys Arg Lys
50 55 60

Gly Gly Ile Gly Glu
65

<210> SEQ ID NO 190
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 190

Ala Ile Ile Ile Ile Ile Ile Ile Ser
1 5

<210> SEQ ID NO 191
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 191

Met Ile Ile Ile Ile Ile Ile Ile Ile
1 5

<210> SEQ ID NO 192
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 192

Ile Ile Ile Ile Ile Ile Ile Ser Lys
1 5

<210> SEQ ID NO 193
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 193

Ala Ile Ile Ile Ile Ile Ile Ile Ser Lys
1 5 10

<210> SEQ ID NO 194
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 194

Met Ile Ile Ile Ile Ile Ile Ile Ile Arg
1 5 10

<210> SEQ ID NO 195
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 195

Gly Ile Ile Ile Ile Ile Ile Ile Ile Lys
1 5 10

<210> SEQ ID NO 196
<211> LENGTH: 10

<212> TYPE: PRT
<213> ORGANISM: Artificial Sequence
<220> FEATURE:
<223> OTHER INFORMATION: Description of Artificial Sequence: Synthetic peptide

<400> SEQUENCE: 196

Ala Ile Ile Ile Ile Ile Ile Ile Ile His
1               5                   10

<210> SEQ ID NO 197
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 197

Tyr Met Asp Asp
1

<210> SEQ ID NO 198
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 198

Lys Ile Leu Gln Glu Glu
1               5

<210> SEQ ID NO 199
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 199

Ala Ala Gln Glu Glu
1               5

<210> SEQ ID NO 200
<211> LENGTH: 734
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 200

Thr Val Lys Ala Ala Cys Trp Trp Ala Gly Ile Lys Gln Glu Phe Gly
1               5                   10                  15

Ile Pro Tyr Asn Pro Gln Ser Gln Gly Val Val Glu Ser Met Asn Lys
            20                  25                  30

Glu Leu Lys Lys Ile Ile Gly Gln Val Arg Asp Gln Ala Glu His Leu
        35                  40                  45

Lys Thr Ala Val Gln Met Ala Val Phe Ile His Asn Phe Lys Arg Lys
    50                  55                  60

Gly Gly Ile Gly Gly Tyr Ser Ala Gly Glu Arg Ile Val Asp Ile Ile
65                  70                  75                  80

```
Ala Ile Ser Pro Arg Thr Leu Asn Ala Trp Val Lys Val Val Glu Glu
                85                  90                  95

Lys Ala Phe Ser Pro Glu Val Ile Pro Met Phe Ser Ala Leu Ser Glu
            100                 105                 110

Gly Ala Thr Pro Gln Asp Leu Asn Thr Met Leu Asn Thr Val Gly Gly
        115                 120                 125

His Gln Ala Ala Met Gln Met Leu Lys Glu Thr Ile Asn Glu Glu Ala
    130                 135                 140

Ala Glu Trp Asp Arg Leu His Pro Val His Ala Gly Pro Ile Ala Pro
145                 150                 155                 160

Gly Gln Met Arg Glu Pro Arg Gly Ser Asp Ile Ala Gly Thr Thr Ser
                165                 170                 175

Thr Leu Gln Glu Gln Ile Gly Trp Met Thr Asn Asn Pro Pro Ile Pro
            180                 185                 190

Val Gly Glu Ile Tyr Lys Arg Trp Ile Ile Leu Gly Leu Asn Lys Ile
        195                 200                 205

Val Arg Met Tyr Ser Pro Thr Ser Ile Leu Asp Ile Arg Gln Gly Pro
    210                 215                 220

Lys Glu Pro Phe Arg Asp Tyr Val Asp Arg Phe Tyr Lys Thr Leu Arg
225                 230                 235                 240

Ala Glu Gln Ala Ser Gln Glu Val Lys Asn Trp Met Thr Glu Thr Leu
                245                 250                 255

Leu Val Gln Asn Ala Asn Pro Asp Cys Lys Thr Ile Leu Lys Ala Leu
            260                 265                 270

Gly Pro Ala Ala Thr Leu Glu Glu Met Met Thr Ala Cys Gln Gly Val
        275                 280                 285

Gly Gly Pro Gly His Lys Ala Arg Val Leu Ala Glu Ala Met Ser Gln
    290                 295                 300

Lys Glu Pro Ile Val Gly Ala Glu Thr Phe Tyr Val Asp Gly Ala Ala
305                 310                 315                 320

Asn Arg Glu Thr Lys Ala Ala Lys Glu Lys Val Tyr Leu Ala Trp Val
                325                 330                 335

Pro Ala His Lys Gly Ile Gly Gly Asn Glu Gln Val Asp Lys Leu Val
            340                 345                 350

Ser Arg Ala Lys Arg Ala Pro Val Lys Gln Thr Leu Asn Phe Asp Leu
        355                 360                 365

Leu Lys Leu Ala Gly Asp Val Glu Ser Asn Pro Gly Pro Leu Ser Pro
    370                 375                 380

Arg Thr Leu Asn Ala Trp Val Lys Val Ile Glu Glu Lys Ala Phe Ser
385                 390                 395                 400

Pro Glu Val Ile Pro Met Phe Thr Ala Leu Ser Glu Gly Ala Thr Pro
                405                 410                 415

His Asp Leu Asn Thr Met Leu Asn Thr Ile Gly Gly His Gln Ala Ala
            420                 425                 430

Met Gln Met Leu Lys Asp Thr Ile Asn Glu Glu Ala Ala Glu Trp Asp
        435                 440                 445

Arg Val His Pro Val His Ala Gly Pro Val Ala Pro Gly Gln Met Arg
    450                 455                 460

Asp Pro Arg Gly Ser Asp Ile Ala Gly Ser Thr Ser Thr Leu Gln Glu
465                 470                 475                 480

Gln Ile Ala Trp Met Thr Asn Asn Pro Pro Ile Pro Val Gly Asp Ile
                485                 490                 495

Tyr Lys Arg Trp Ile Ile Met Gly Leu Asn Lys Ile Val Arg Met Tyr
```

```
            500                 505                 510

Ser Pro Val Ser Ile Leu Asp Ile Lys Gln Gly Pro Lys Glu Pro Phe
        515                 520                 525

Arg Asp Tyr Val Asp Arg Phe Tyr Arg Thr Leu Arg Ala Glu Gln Ala
    530                 535                 540

Ser Gln Asp Val Lys Asn Trp Met Thr Glu Thr Leu Leu Val Gln Asn
545                 550                 555                 560

Ser Asn Pro Asp Cys Lys Thr Ile Leu Lys Ala Leu Gly Pro Gly Ala
                565                 570                 575

Thr Leu Glu Glu Met Met Ser Ala Cys Gln Gly Val Gly Gly Pro Ser
            580                 585                 590

His Lys Ala Arg Val Leu Ala Glu Ala Met Cys Gln Ala Val Lys Ala
        595                 600                 605

Ala Cys Trp Trp Ala Gly Val Lys Gln Glu Phe Gly Ile Pro Tyr Asn
    610                 615                 620

Thr Gln Ser Gln Gly Val Val Glu Ser Met Asn Asn Glu Leu Lys Lys
625                 630                 635                 640

Ile Ile Gly Gln Ile Arg Asp Gln Ala Glu His Leu Lys Thr Ala Val
                645                 650                 655

Gln Met Ala Val Leu Ile His Asn Phe Lys Arg Lys Gly Gly Ile Gly
            660                 665                 670

Glu Tyr Ser Ala Gly Glu Arg Ile Ile Asp Ile Ile Ala Thr Glu Pro
        675                 680                 685

Ile Ala Gly Val Glu Thr Phe Tyr Val Asp Gly Ala Ser Asn Arg Glu
    690                 695                 700

Thr Lys Ala Ala Lys Glu Lys Ile Tyr Leu Ala Trp Val Pro Ala His
705                 710                 715                 720

Lys Gly Ile Gly Gly Asn Glu Gln Ile Asp Lys Leu Val Ser
                725                 730


<210> SEQ ID NO 201
<211> LENGTH: 757
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Ile Thr Lys Ile Gln Asn Phe Arg Val Tyr Tyr Arg Asp Ser Arg Asp
1               5                   10                  15

Pro Leu Trp Lys Gly Pro Ala Lys Leu Leu Trp Lys Gly Glu Gly Ala
            20                  25                  30

Val Val Ile Gln Asp Asn Ser Asp Ile Lys Val Val Pro Arg Arg Lys
        35                  40                  45

Ala Lys Ile Ile Arg Asp Tyr Gly Lys Gln Met Ala Gly Asp Asp Cys
    50                  55                  60

Val Ala Ser Arg Gln Asp Glu Asp Ala Ala Ala Ile Gly Thr Val Leu
65                  70                  75                  80

Val Gly Pro Thr Pro Val Asn Ile Ile Gly Arg Asn Leu Leu Thr Gln
                85                  90                  95

Ile Gly Cys Thr Leu Asn Phe Pro Ile Ser Pro Ile Glu Thr Val Pro
            100                 105                 110

Val Lys Leu Lys Pro Gly Met Asp Gly Pro Lys Val Lys Gln Trp Pro
        115                 120                 125
```

-continued

```
Leu Thr Glu Glu Lys Ile Lys Ala Leu Val Glu Ile Cys Thr Glu Met
    130                 135                 140

Glu Lys Glu Gly Lys Ile Ser Lys Ile Gly Pro Glu Asn Pro Tyr Asn
145                 150                 155                 160

Thr Pro Val Phe Ala Ile Lys Lys Lys Asp Ser Thr Lys Trp Arg Lys
                165                 170                 175

Leu Val Asp Phe Arg Glu Leu Asn Lys Arg Thr Gln Asp Phe Trp Glu
            180                 185                 190

Val Gln Leu Gly Ile Pro His Pro Ala Gly Leu Lys Lys Lys Lys Ser
        195                 200                 205

Val Thr Val Leu Asp Val Gly Asp Ala Tyr Phe Ser Val Pro Leu Asp
    210                 215                 220

Lys Asp Phe Arg Lys Tyr Thr Ala Phe Thr Ile Pro Ser Ile Asn Asn
225                 230                 235                 240

Glu Thr Pro Gly Ile Arg Tyr Gln Tyr Asn Val Leu Pro Gln Gly Trp
                245                 250                 255

Lys Gly Ser Pro Ala Ile Phe Gln Ser Ser Met Thr Val Ala Lys Glu
            260                 265                 270

Ile Val Ala Ser Cys Asp Lys Cys Gln Leu Lys Gly Glu Ala Met His
        275                 280                 285

Gly Gln Val Asp Cys Ser Pro Gly Ile Trp Gln Leu Asp Cys Thr His
    290                 295                 300

Leu Glu Gly Lys Ile Ile Leu Val Ala Val His Val Ala Ser Gly Tyr
305                 310                 315                 320

Ile Glu Ala Glu Val Ile Pro Ala Glu Thr Gly Gln Glu Thr Ala Tyr
                325                 330                 335

Phe Leu Leu Lys Leu Ala Gly Arg Trp Pro Val Lys Thr Gln Glu Glu
            340                 345                 350

Glu Glu Val Gly Phe Pro Val Lys Pro Gln Val Pro Leu Arg Ala Lys
        355                 360                 365

Arg Ala Pro Val Lys Gln Thr Leu Asn Phe Asp Leu Leu Lys Leu Ala
    370                 375                 380

Gly Asp Val Glu Ser Asn Pro Gly Pro Val Ala Lys Glu Ile Val Ala
385                 390                 395                 400

Cys Cys Asp Lys Cys Gln Leu Lys Gly Glu Ala Ile His Gly Gln Val
                405                 410                 415

Asp Cys Ser Pro Gly Val Trp Gln Leu Asp Cys Thr His Leu Glu Gly
            420                 425                 430

Lys Val Ile Leu Val Ala Val His Val Ala Ser Gly Tyr Ile Glu Ala
        435                 440                 445

Glu Ile Ile Pro Thr Glu Thr Gly Gln Glu Thr Ala Tyr Phe Ile Leu
    450                 455                 460

Lys Leu Ala Gly Arg Trp Pro Val Thr Thr Ile Thr Lys Leu Gln Asn
465                 470                 475                 480

Phe Arg Val Tyr Tyr Arg Asp Asn Arg Asp Pro Leu Trp Lys Gly Pro
                485                 490                 495

Ala Arg Leu Leu Trp Lys Gly Glu Gly Ala Val Val Ile Gln Asp Asn
            500                 505                 510

Ser Glu Ile Lys Val Val Pro Arg Arg Lys Val Lys Ile Ile Arg Asp
        515                 520                 525

Tyr Gly Lys Arg Met Ala Gly Asp Asp Cys Val Ala Gly Arg Gln Asp
    530                 535                 540

Glu Asp Gly Thr Val Leu Ile Gly Pro Thr Pro Val Asn Ile Ile Gly
```

545 550 555 560

Arg Asn Leu Leu Thr Gln Leu Gly Cys Thr Leu Asn Phe Pro Ile Ser
565 570 575

Pro Ile Asp Thr Val Pro Val Lys Leu Lys Pro Gly Met Asp Gly Pro
580 585 590

Arg Val Lys Gln Trp Pro Leu Thr Glu Glu Lys Ile Lys Ala Leu Ile
595 600 605

Glu Ile Cys Thr Glu Met Glu Lys Glu Gly Lys Ile Ser Arg Ile Gly
610 615 620

Pro Glu Asn Pro Tyr Asn Thr Pro Ile Phe Ala Ile Lys Lys Lys Asp
625 630 635 640

Gly Thr Lys Trp Arg Lys Leu Val Asp Phe Arg Glu Leu Asn Lys Lys
645 650 655

Thr Gln Asp Phe Trp Glu Val Gln Leu Gly Ile Pro His Pro Ser Gly
660 665 670

Leu Lys Lys Lys Lys Ser Val Thr Val Leu Asp Ile Gly Asp Ala Tyr
675 680 685

Phe Ser Val Pro Leu Asp Lys Glu Phe Arg Lys Tyr Thr Ala Phe Thr
690 695 700

Val Pro Ser Thr Asn Asn Glu Thr Pro Gly Val Arg Tyr Gln Tyr Asn
705 710 715 720

Val Leu Pro Met Gly Trp Lys Gly Ser Pro Ala Ile Phe Gln Cys Ser
725 730 735

Met Thr Lys Ile Leu Gln Glu Glu Glu Glu Val Gly Phe Pro Val Arg
740 745 750

Pro Gln Val Pro Leu
755

<210> SEQ ID NO 202
<211> LENGTH: 746
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 202

Thr Val Lys Ala Ala Cys Trp Trp Ala Gly Ile Lys Gln Glu Phe Gly
1 5 10 15

Ile Pro Tyr Asn Pro Gln Ser Gln Gly Val Val Glu Ser Met Asn Lys
20 25 30

Glu Leu Lys Lys Ile Ile Gly Gln Val Arg Asp Gln Ala Glu His Leu
35 40 45

Lys Thr Ala Val Gln Met Ala Val Phe Ile His Asn Phe Lys Arg Lys
50 55 60

Gly Gly Ile Gly Gly Tyr Ser Ala Gly Glu Arg Ile Val Asp Ile Ile
65 70 75 80

Ala Ile Ser Pro Arg Thr Leu Asn Ala Trp Val Lys Val Val Glu Glu
85 90 95

Lys Ala Phe Ser Pro Glu Val Ile Pro Met Phe Ser Ala Leu Ser Glu
100 105 110

Gly Ala Thr Pro Gln Asp Leu Asn Thr Met Leu Asn Thr Val Gly Gly
115 120 125

His Gln Ala Ala Met Gln Met Leu Lys Glu Thr Ile Asn Glu Glu Ala
130 135 140

-continued

```
Ala Glu Trp Asp Arg Leu His Pro Val His Ala Gly Pro Ile Ala Pro
145                 150                 155                 160

Gly Gln Met Arg Glu Pro Arg Gly Ser Asp Ile Ala Gly Thr Thr Ser
                165                 170                 175

Thr Leu Gln Glu Gln Ile Gly Trp Met Thr Asn Asn Pro Pro Ile Pro
            180                 185                 190

Val Gly Glu Ile Tyr Lys Arg Trp Ile Ile Leu Gly Leu Asn Lys Ile
        195                 200                 205

Val Arg Met Tyr Ser Pro Thr Ser Ile Leu Asp Ile Arg Gln Gly Pro
    210                 215                 220

Lys Glu Pro Phe Arg Asp Tyr Val Asp Arg Phe Tyr Lys Thr Leu Arg
225                 230                 235                 240

Ala Glu Gln Ala Ser Gln Glu Val Lys Asn Trp Met Thr Glu Thr Leu
                245                 250                 255

Leu Val Gln Asn Ala Asn Pro Asp Cys Lys Thr Ile Leu Lys Ala Leu
            260                 265                 270

Gly Pro Ala Ala Thr Leu Glu Glu Met Met Thr Ala Cys Gln Gly Val
        275                 280                 285

Gly Gly Pro Gly His Lys Ala Arg Val Leu Ala Glu Ala Met Ser Gln
    290                 295                 300

Lys Glu Pro Ile Val Gly Ala Glu Thr Phe Tyr Val Asp Gly Ala Ala
305                 310                 315                 320

Asn Arg Glu Thr Lys Ala Ala Lys Glu Lys Val Tyr Leu Ala Trp Val
                325                 330                 335

Pro Ala His Lys Gly Ile Gly Gly Asn Glu Gln Val Asp Lys Leu Val
            340                 345                 350

Ser Arg Ala Lys Arg Ala Pro Val Lys Gln Thr Leu Asn Phe Asp Leu
        355                 360                 365

Leu Lys Leu Ala Gly Asp Val Glu Ser Asn Pro Gly Pro Ile Thr Lys
    370                 375                 380

Ile Gln Asn Phe Arg Val Tyr Tyr Arg Asp Ser Arg Asp Pro Leu Trp
385                 390                 395                 400

Lys Gly Pro Ala Lys Leu Leu Trp Lys Gly Glu Gly Ala Val Val Ile
                405                 410                 415

Gln Asp Asn Ser Asp Ile Lys Val Val Pro Arg Arg Lys Ala Lys Ile
            420                 425                 430

Ile Arg Asp Tyr Gly Lys Gln Met Ala Gly Asp Asp Cys Val Ala Ser
        435                 440                 445

Arg Gln Asp Glu Asp Ala Ala Ala Ile Gly Thr Val Leu Val Gly Pro
    450                 455                 460

Thr Pro Val Asn Ile Ile Gly Arg Asn Leu Leu Thr Gln Ile Gly Cys
465                 470                 475                 480

Thr Leu Asn Phe Pro Ile Ser Pro Ile Glu Thr Val Pro Val Lys Leu
                485                 490                 495

Lys Pro Gly Met Asp Gly Pro Lys Val Lys Gln Trp Pro Leu Thr Glu
            500                 505                 510

Glu Lys Ile Lys Ala Leu Val Glu Ile Cys Thr Glu Met Glu Lys Glu
        515                 520                 525

Gly Lys Ile Ser Lys Ile Gly Pro Glu Asn Pro Tyr Asn Thr Pro Val
    530                 535                 540

Phe Ala Ile Lys Lys Lys Asp Ser Thr Lys Trp Arg Lys Leu Val Asp
545                 550                 555                 560

Phe Arg Glu Leu Asn Lys Arg Thr Gln Asp Phe Trp Glu Val Gln Leu
```

565 570 575

Gly Ile Pro His Pro Ala Gly Leu Lys Lys Lys Lys Ser Val Thr Val
580 585 590

Leu Asp Val Gly Asp Ala Tyr Phe Ser Val Pro Leu Asp Lys Asp Phe
595 600 605

Arg Lys Tyr Thr Ala Phe Thr Ile Pro Ser Ile Asn Asn Glu Thr Pro
610 615 620

Gly Ile Arg Tyr Gln Tyr Asn Val Leu Pro Gln Gly Trp Lys Gly Ser
625 630 635 640

Pro Ala Ile Phe Gln Ser Ser Met Thr Val Ala Lys Glu Ile Val Ala
645 650 655

Ser Cys Asp Lys Cys Gln Leu Lys Gly Glu Ala Met His Gly Gln Val
660 665 670

Asp Cys Ser Pro Gly Ile Trp Gln Leu Asp Cys Thr His Leu Glu Gly
675 680 685

Lys Ile Ile Leu Val Ala Val His Val Ala Ser Gly Tyr Ile Glu Ala
690 695 700

Glu Val Ile Pro Ala Glu Thr Gly Gln Glu Thr Ala Tyr Phe Leu Leu
705 710 715 720

Lys Leu Ala Gly Arg Trp Pro Val Lys Thr Gln Glu Glu Glu Glu Val
725 730 735

Gly Phe Pro Val Lys Pro Gln Val Pro Leu
740 745

<210> SEQ ID NO 203
<211> LENGTH: 745
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 203

Leu Ser Pro Arg Thr Leu Asn Ala Trp Val Lys Val Ile Glu Glu Lys
1 5 10 15

Ala Phe Ser Pro Glu Val Ile Pro Met Phe Thr Ala Leu Ser Glu Gly
20 25 30

Ala Thr Pro His Asp Leu Asn Thr Met Leu Asn Thr Ile Gly Gly His
35 40 45

Gln Ala Ala Met Gln Met Leu Lys Asp Thr Ile Asn Glu Glu Ala Ala
50 55 60

Glu Trp Asp Arg Val His Pro Val His Ala Gly Pro Val Ala Pro Gly
65 70 75 80

Gln Met Arg Asp Pro Arg Gly Ser Asp Ile Ala Gly Ser Thr Ser Thr
85 90 95

Leu Gln Glu Gln Ile Ala Trp Met Thr Asn Asn Pro Pro Ile Pro Val
100 105 110

Gly Asp Ile Tyr Lys Arg Trp Ile Ile Met Gly Leu Asn Lys Ile Val
115 120 125

Arg Met Tyr Ser Pro Val Ser Ile Leu Asp Ile Lys Gln Gly Pro Lys
130 135 140

Glu Pro Phe Arg Asp Tyr Val Asp Arg Phe Tyr Arg Thr Leu Arg Ala
145 150 155 160

Glu Gln Ala Ser Gln Asp Val Lys Asn Trp Met Thr Glu Thr Leu Leu
165 170 175

-continued

```
Val Gln Asn Ser Asn Pro Asp Cys Lys Thr Ile Leu Lys Ala Leu Gly
            180                 185                 190

Pro Gly Ala Thr Leu Glu Glu Met Met Ser Ala Cys Gln Gly Val Gly
        195                 200                 205

Gly Pro Ser His Lys Ala Arg Val Leu Ala Glu Ala Met Cys Gln Ala
    210                 215                 220

Val Lys Ala Ala Cys Trp Trp Ala Gly Val Lys Gln Glu Phe Gly Ile
225                 230                 235                 240

Pro Tyr Asn Thr Gln Ser Gln Gly Val Val Glu Ser Met Asn Asn Glu
                245                 250                 255

Leu Lys Lys Ile Ile Gly Gln Ile Arg Asp Gln Ala Glu His Leu Lys
            260                 265                 270

Thr Ala Val Gln Met Ala Val Leu Ile His Asn Phe Lys Arg Lys Gly
        275                 280                 285

Gly Ile Gly Glu Tyr Ser Ala Gly Glu Arg Ile Ile Asp Ile Ile Ala
    290                 295                 300

Thr Glu Pro Ile Ala Gly Val Glu Thr Phe Tyr Val Asp Gly Ala Ser
305                 310                 315                 320

Asn Arg Glu Thr Lys Ala Ala Lys Glu Lys Ile Tyr Leu Ala Trp Val
                325                 330                 335

Pro Ala His Lys Gly Ile Gly Gly Asn Glu Gln Ile Asp Lys Leu Val
            340                 345                 350

Ser Arg Ala Lys Arg Ala Pro Val Lys Gln Thr Leu Asn Phe Asp Leu
        355                 360                 365

Leu Lys Leu Ala Gly Asp Val Glu Ser Asn Pro Gly Pro Val Ala Lys
    370                 375                 380

Glu Ile Val Ala Cys Cys Asp Lys Cys Gln Leu Lys Gly Glu Ala Ile
385                 390                 395                 400

His Gly Gln Val Asp Cys Ser Pro Gly Val Trp Gln Leu Asp Cys Thr
                405                 410                 415

His Leu Glu Gly Lys Val Ile Leu Val Ala Val His Val Ala Ser Gly
            420                 425                 430

Tyr Ile Glu Ala Glu Ile Ile Pro Thr Glu Thr Gly Gln Glu Thr Ala
        435                 440                 445

Tyr Phe Ile Leu Lys Leu Ala Gly Arg Trp Pro Val Thr Thr Ile Thr
    450                 455                 460

Lys Leu Gln Asn Phe Arg Val Tyr Tyr Arg Asp Asn Arg Asp Pro Leu
465                 470                 475                 480

Trp Lys Gly Pro Ala Arg Leu Leu Trp Lys Gly Glu Gly Ala Val Val
                485                 490                 495

Ile Gln Asp Asn Ser Glu Ile Lys Val Val Pro Arg Arg Lys Val Lys
            500                 505                 510

Ile Ile Arg Asp Tyr Gly Lys Arg Met Ala Gly Asp Asp Cys Val Ala
        515                 520                 525

Gly Arg Gln Asp Glu Asp Gly Thr Val Leu Ile Gly Pro Thr Pro Val
    530                 535                 540

Asn Ile Ile Gly Arg Asn Leu Leu Thr Gln Leu Gly Cys Thr Leu Asn
545                 550                 555                 560

Phe Pro Ile Ser Pro Ile Asp Thr Val Pro Val Lys Leu Lys Pro Gly
                565                 570                 575

Met Asp Gly Pro Arg Val Lys Gln Trp Pro Leu Thr Glu Glu Lys Ile
            580                 585                 590

Lys Ala Leu Ile Glu Ile Cys Thr Glu Met Glu Lys Glu Gly Lys Ile
```

```
        595                 600                 605

Ser Arg Ile Gly Pro Glu Asn Pro Tyr Asn Thr Pro Ile Phe Ala Ile
    610                 615                 620

Lys Lys Lys Asp Gly Thr Lys Trp Arg Lys Leu Val Asp Phe Arg Glu
625                 630                 635                 640

Leu Asn Lys Lys Thr Gln Asp Phe Trp Glu Val Gln Leu Gly Ile Pro
                645                 650                 655

His Pro Ser Gly Leu Lys Lys Lys Lys Ser Val Thr Val Leu Asp Ile
            660                 665                 670

Gly Asp Ala Tyr Phe Ser Val Pro Leu Asp Lys Glu Phe Arg Lys Tyr
        675                 680                 685

Thr Ala Phe Thr Val Pro Ser Thr Asn Asn Glu Thr Pro Gly Val Arg
    690                 695                 700

Tyr Gln Tyr Asn Val Leu Pro Met Gly Trp Lys Gly Ser Pro Ala Ile
705                 710                 715                 720

Phe Gln Cys Ser Met Thr Lys Ile Leu Gln Glu Glu Glu Glu Val Gly
                725                 730                 735

Phe Pro Val Arg Pro Gln Val Pro Leu
            740                 745


<210> SEQ ID NO 204
<211> LENGTH: 716
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Thr Val Lys Ala Ala Cys Trp Trp Ala Gly Ile Lys Gln Glu Phe Gly
1               5                   10                  15

Ile Pro Tyr Asn Pro Gln Ser Gln Gly Val Val Glu Ser Met Asn Lys
            20                  25                  30

Glu Leu Lys Lys Ile Ile Gly Gln Val Arg Asp Gln Ala Glu His Leu
        35                  40                  45

Lys Thr Ala Val Gln Met Ala Val Phe Ile His Asn Phe Lys Arg Lys
    50                  55                  60

Gly Gly Ile Gly Gly Tyr Ser Ala Gly Glu Arg Ile Val Asp Ile Ile
65                  70                  75                  80

Ala Ile Ser Pro Arg Thr Leu Asn Ala Trp Val Lys Val Val Glu Glu
                85                  90                  95

Lys Ala Phe Ser Pro Glu Val Ile Pro Met Phe Ser Ala Leu Ser Glu
            100                 105                 110

Gly Ala Thr Pro Gln Asp Leu Asn Thr Met Leu Asn Thr Val Gly Gly
        115                 120                 125

His Gln Ala Ala Met Gln Met Leu Lys Glu Thr Ile Asn Glu Glu Ala
    130                 135                 140

Ala Glu Trp Asp Arg Leu His Pro Val His Ala Gly Pro Ile Ala Pro
145                 150                 155                 160

Gly Gln Met Arg Glu Pro Arg Gly Ser Asp Ile Ala Gly Thr Thr Ser
                165                 170                 175

Thr Leu Gln Glu Gln Ile Gly Trp Met Thr Asn Asn Pro Pro Ile Pro
            180                 185                 190

Val Gly Glu Ile Tyr Lys Arg Trp Ile Ile Leu Gly Leu Asn Lys Ile
        195                 200                 205
```

-continued

```
Val Arg Met Tyr Ser Pro Thr Ser Ile Leu Asp Ile Arg Gln Gly Pro
    210                 215                 220

Lys Glu Pro Phe Arg Asp Tyr Val Asp Arg Phe Tyr Lys Thr Leu Arg
225                 230                 235                 240

Ala Glu Gln Ala Ser Gln Glu Val Lys Asn Trp Met Thr Glu Thr Leu
                245                 250                 255

Leu Val Gln Asn Ala Asn Pro Asp Cys Lys Thr Ile Leu Lys Ala Leu
            260                 265                 270

Gly Pro Ala Ala Thr Leu Glu Glu Met Met Thr Ala Cys Gln Gly Val
        275                 280                 285

Gly Gly Pro Gly His Lys Ala Arg Val Leu Ala Glu Ala Met Ser Gln
    290                 295                 300

Lys Glu Pro Ile Val Gly Ala Glu Thr Phe Tyr Val Asp Gly Ala Ala
305                 310                 315                 320

Asn Arg Glu Thr Lys Val Ala Lys Glu Ile Val Ala Ser Cys Asp Lys
                325                 330                 335

Cys Gln Leu Lys Gly Glu Ala Met His Gly Gln Val Asp Cys Ser Pro
            340                 345                 350

Gly Ile Trp Gln Leu Asp Cys Thr His Leu Glu Gly Lys Ile Ile Leu
        355                 360                 365

Val Ala Val His Val Ala Ser Gly Tyr Ile Glu Ala Glu Val Ile Pro
    370                 375                 380

Ala Glu Thr Gly Gln Glu Thr Ala Tyr Phe Leu Leu Lys Leu Ala Gly
385                 390                 395                 400

Arg Trp Pro Val Lys Thr Lys Glu Lys Val Tyr Leu Ala Trp Val Pro
                405                 410                 415

Ala His Lys Gly Ile Gly Gly Asn Glu Gln Val Asp Lys Leu Val Ser
            420                 425                 430

Gln Glu Glu Glu Glu Val Gly Phe Pro Val Lys Pro Gln Val Pro Leu
        435                 440                 445

Ile Thr Lys Ile Gln Asn Phe Arg Val Tyr Tyr Arg Asp Ser Arg Asp
    450                 455                 460

Pro Leu Trp Lys Gly Pro Ala Lys Leu Leu Trp Lys Gly Glu Gly Ala
465                 470                 475                 480

Val Val Ile Gln Asp Asn Ser Asp Ile Lys Val Val Pro Arg Arg Lys
                485                 490                 495

Ala Lys Ile Ile Arg Asp Tyr Gly Lys Gln Met Ala Gly Asp Asp Cys
            500                 505                 510

Val Ala Ser Arg Gln Asp Glu Asp Ala Ala Ala Ile Gly Thr Val Leu
        515                 520                 525

Val Gly Pro Thr Pro Val Asn Ile Ile Gly Arg Asn Leu Leu Thr Gln
    530                 535                 540

Ile Gly Cys Thr Leu Asn Phe Pro Ile Ser Pro Ile Glu Thr Val Pro
545                 550                 555                 560

Val Lys Leu Lys Pro Gly Met Asp Gly Pro Lys Val Lys Gln Trp Pro
                565                 570                 575

Leu Thr Glu Glu Lys Ile Lys Ala Leu Val Glu Ile Cys Thr Glu Met
            580                 585                 590

Glu Lys Glu Gly Lys Ile Ser Lys Ile Gly Pro Glu Asn Pro Tyr Asn
        595                 600                 605

Thr Pro Val Phe Ala Ile Lys Lys Lys Asp Ser Thr Lys Trp Arg Lys
    610                 615                 620

Leu Val Asp Phe Arg Glu Leu Asn Lys Arg Thr Gln Asp Phe Trp Glu
```

```
625                 630                 635                 640

Val Gln Leu Gly Ile Pro His Pro Ala Gly Leu Lys Lys Lys Lys Ser
                645                 650                 655

Val Thr Val Leu Asp Val Gly Asp Ala Tyr Phe Ser Val Pro Leu Asp
            660                 665                 670

Lys Asp Phe Arg Lys Tyr Thr Ala Phe Thr Ile Pro Ser Ile Asn Asn
        675                 680                 685

Glu Thr Pro Gly Ile Arg Tyr Gln Tyr Asn Val Leu Pro Gln Gly Trp
    690                 695                 700

Lys Gly Ser Pro Ala Ile Phe Gln Ser Ser Met Thr
705                 710                 715


<210> SEQ ID NO 205
<211> LENGTH: 715
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Leu Ser Pro Arg Thr Leu Asn Ala Trp Val Lys Val Ile Glu Glu Lys
1               5                   10                  15

Ala Phe Ser Pro Glu Val Ile Pro Met Phe Thr Ala Leu Ser Glu Gly
            20                  25                  30

Ala Thr Pro His Asp Leu Asn Thr Met Leu Asn Thr Ile Gly Gly His
        35                  40                  45

Gln Ala Ala Met Gln Met Leu Lys Asp Thr Ile Asn Glu Glu Ala Ala
    50                  55                  60

Glu Trp Asp Arg Val His Pro Val His Ala Gly Pro Val Ala Pro Gly
65                  70                  75                  80

Gln Met Arg Asp Pro Arg Gly Ser Asp Ile Ala Gly Ser Thr Ser Thr
                85                  90                  95

Leu Gln Glu Gln Ile Ala Trp Met Thr Asn Asn Pro Pro Ile Pro Val
            100                 105                 110

Gly Asp Ile Tyr Lys Arg Trp Ile Ile Met Gly Leu Asn Lys Ile Val
        115                 120                 125

Arg Met Tyr Ser Pro Val Ser Ile Leu Asp Ile Lys Gln Gly Pro Lys
    130                 135                 140

Glu Pro Phe Arg Asp Tyr Val Asp Arg Phe Tyr Arg Thr Leu Arg Ala
145                 150                 155                 160

Glu Gln Ala Ser Gln Asp Val Lys Asn Trp Met Thr Glu Thr Leu Leu
                165                 170                 175

Val Gln Asn Ser Asn Pro Asp Cys Lys Thr Ile Leu Lys Ala Leu Gly
            180                 185                 190

Pro Gly Ala Thr Leu Glu Glu Met Met Ser Ala Cys Gln Gly Val Gly
        195                 200                 205

Gly Pro Ser His Lys Ala Arg Val Leu Ala Glu Ala Met Cys Gln Val
    210                 215                 220

Ala Lys Glu Ile Val Ala Cys Cys Asp Lys Cys Gln Leu Lys Gly Glu
225                 230                 235                 240

Ala Ile His Gly Gln Val Asp Cys Ser Pro Gly Val Trp Gln Leu Asp
                245                 250                 255

Cys Thr His Leu Glu Gly Lys Val Ile Leu Val Ala Val His Val Ala
            260                 265                 270
```

-continued

```
Ser Gly Tyr Ile Glu Ala Glu Ile Ile Pro Thr Glu Thr Gly Gln Glu
        275                 280                 285

Thr Ala Tyr Phe Ile Leu Lys Leu Ala Gly Arg Trp Pro Val Thr Thr
    290                 295                 300

Lys Glu Lys Ile Tyr Leu Ala Trp Val Pro Ala His Lys Gly Ile Gly
305                 310                 315                 320

Gly Asn Glu Gln Ile Asp Lys Leu Val Ser Thr Glu Pro Ile Ala Gly
                325                 330                 335

Val Glu Thr Phe Tyr Val Asp Gly Ala Ser Asn Arg Glu Thr Lys Ile
            340                 345                 350

Thr Lys Leu Gln Asn Phe Arg Val Tyr Tyr Arg Asp Asn Arg Asp Pro
        355                 360                 365

Leu Trp Lys Gly Pro Ala Arg Leu Leu Trp Lys Gly Glu Gly Ala Val
    370                 375                 380

Val Ile Gln Asp Asn Ser Glu Ile Lys Val Val Pro Arg Arg Lys Val
385                 390                 395                 400

Lys Ile Ile Arg Asp Tyr Gly Lys Arg Met Ala Gly Asp Asp Cys Val
                405                 410                 415

Ala Gly Arg Gln Asp Glu Asp Ala Val Lys Ala Ala Cys Trp Trp Ala
            420                 425                 430

Gly Val Lys Gln Glu Phe Gly Ile Pro Tyr Asn Thr Gln Ser Gln Gly
        435                 440                 445

Val Val Glu Ser Met Asn Asn Glu Leu Lys Lys Ile Ile Gly Gln Ile
    450                 455                 460

Arg Asp Gln Ala Glu His Leu Lys Thr Ala Val Gln Met Ala Val Leu
465                 470                 475                 480

Ile His Asn Phe Lys Arg Lys Gly Gly Ile Gly Glu Tyr Ser Ala Gly
                485                 490                 495

Glu Arg Ile Ile Asp Ile Ile Ala Gln Glu Glu Glu Glu Val Gly Phe
            500                 505                 510

Pro Val Arg Pro Gln Val Pro Leu Gly Thr Val Leu Ile Gly Pro Thr
        515                 520                 525

Pro Val Asn Ile Ile Gly Arg Asn Leu Leu Thr Gln Leu Gly Cys Thr
    530                 535                 540

Leu Asn Phe Pro Ile Ser Pro Ile Asp Thr Val Pro Val Lys Leu Lys
545                 550                 555                 560

Pro Gly Met Asp Gly Pro Arg Val Lys Gln Trp Pro Leu Thr Glu Glu
                565                 570                 575

Lys Ile Lys Ala Leu Ile Glu Ile Cys Thr Glu Met Glu Lys Glu Gly
            580                 585                 590

Lys Ile Ser Arg Ile Gly Pro Glu Asn Pro Tyr Asn Thr Pro Ile Phe
        595                 600                 605

Ala Ile Lys Lys Lys Asp Gly Thr Lys Trp Arg Lys Leu Val Asp Phe
    610                 615                 620

Arg Glu Leu Asn Lys Lys Thr Gln Asp Phe Trp Glu Val Gln Leu Gly
625                 630                 635                 640

Ile Pro His Pro Ser Gly Leu Lys Lys Lys Lys Ser Val Thr Val Leu
                645                 650                 655

Asp Ile Gly Asp Ala Tyr Phe Ser Val Pro Leu Asp Lys Glu Phe Arg
            660                 665                 670

Lys Tyr Thr Ala Phe Thr Val Pro Ser Thr Asn Asn Glu Thr Pro Gly
        675                 680                 685

Val Arg Tyr Gln Tyr Asn Val Leu Pro Met Gly Trp Lys Gly Ser Pro
```

690 695 700

Ala Ile Phe Gln Cys Ser Met Thr Lys Ile Leu
705 710 715

<210> SEQ ID NO 206
<211> LENGTH: 1030
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 206

Met Thr Val Lys Ala Ala Cys Trp Trp Ala Gly Ile Lys Gln Glu Phe
1 5 10 15

Gly Ile Pro Tyr Asn Pro Gln Ser Gln Gly Val Val Glu Ser Met Asn
20 25 30

Lys Glu Leu Lys Lys Ile Ile Gly Gln Val Arg Asp Gln Ala Glu His
35 40 45

Leu Lys Thr Ala Val Gln Met Ala Val Phe Ile His Asn Phe Lys Arg
50 55 60

Lys Gly Gly Ile Gly Gly Tyr Ser Ala Gly Glu Arg Ile Val Asp Ile
65 70 75 80

Ile Ala Ile Ser Pro Arg Thr Leu Asn Ala Trp Val Lys Val Val Glu
85 90 95

Glu Lys Ala Phe Ser Pro Glu Val Ile Pro Met Phe Ser Ala Leu Ser
100 105 110

Glu Gly Ala Thr Pro Gln Asp Leu Asn Thr Met Leu Asn Thr Val Gly
115 120 125

Gly His Gln Ala Ala Met Gln Met Leu Lys Glu Thr Ile Asn Glu Glu
130 135 140

Ala Ala Glu Trp Asp Arg Leu His Pro Val His Ala Gly Pro Ile Ala
145 150 155 160

Pro Gly Gln Met Arg Glu Pro Arg Gly Ser Asp Ile Ala Gly Thr Thr
165 170 175

Ser Thr Leu Gln Glu Gln Ile Gly Trp Met Thr Asn Asn Pro Pro Ile
180 185 190

Pro Val Gly Glu Ile Tyr Lys Arg Trp Ile Ile Leu Gly Leu Asn Lys
195 200 205

Ile Val Arg Met Tyr Ser Pro Thr Ser Ile Leu Asp Ile Arg Gln Gly
210 215 220

Pro Lys Glu Pro Phe Arg Asp Tyr Val Asp Arg Phe Tyr Lys Thr Leu
225 230 235 240

Arg Ala Glu Gln Ala Ser Gln Glu Val Lys Asn Trp Met Thr Glu Thr
245 250 255

Leu Leu Val Gln Asn Ala Asn Pro Asp Cys Lys Thr Ile Leu Lys Ala
260 265 270

Leu Gly Pro Ala Ala Thr Leu Glu Glu Met Met Thr Ala Cys Gln Gly
275 280 285

Val Gly Gly Pro Gly His Lys Ala Arg Val Leu Ala Glu Ala Met Ser
290 295 300

Gln Met Ala Ala Arg Ala Ser Val Leu Ser Gly Gly Glu Leu Asp Arg
305 310 315 320

Trp Glu Lys Ile Arg Leu Arg Pro Gly Gly Lys Lys Lys Tyr Arg Leu
325 330 335

-continued

```
Lys His Ile Val Trp Ala Ser Arg Glu Leu Glu Arg Phe Ala Val Asn
            340                 345                 350

Pro Gly Leu Leu Glu Thr Pro Pro Val Val Ala Lys Glu Ile Val Ala
        355                 360                 365

Ser Cys Asp Lys Cys Gln Leu Lys Gly Glu Ala Met His Gly Gln Val
    370                 375                 380

Asp Cys Ser Pro Gly Ile Trp Gln Leu Asp Cys Thr His Leu Glu Gly
385                 390                 395                 400

Lys Ile Ile Leu Val Ala Val His Val Ala Ser Gly Tyr Ile Glu Ala
                405                 410                 415

Glu Val Ile Pro Ala Glu Thr Gly Gln Glu Thr Ala Tyr Phe Leu Leu
            420                 425                 430

Lys Leu Ala Gly Arg Trp Pro Val Lys Thr Lys Glu Lys Val Tyr Leu
        435                 440                 445

Ala Trp Val Pro Ala His Lys Gly Ile Gly Gly Asn Glu Gln Val Asp
    450                 455                 460

Lys Leu Val Ser Thr Gln Gly Tyr Phe Pro Asp Trp Gln Asn Tyr Thr
465                 470                 475                 480

Pro Gly Pro Gly Thr Arg Tyr Pro Leu Thr Phe Gly Trp Cys Phe Lys
                485                 490                 495

Leu Val Pro Val Arg Ala Lys Arg Ala Pro Val Lys Gln Thr Leu Asn
            500                 505                 510

Phe Asp Leu Leu Lys Leu Ala Gly Asp Val Glu Ser Asn Pro Gly Pro
        515                 520                 525

Met Leu Ser Pro Arg Thr Leu Asn Ala Trp Val Lys Val Ile Glu Glu
    530                 535                 540

Lys Ala Phe Ser Pro Glu Val Ile Pro Met Phe Thr Ala Leu Ser Glu
545                 550                 555                 560

Gly Ala Thr Pro His Asp Leu Asn Thr Met Leu Asn Thr Ile Gly Gly
                565                 570                 575

His Gln Ala Ala Met Gln Met Leu Lys Asp Thr Ile Asn Glu Glu Ala
            580                 585                 590

Ala Glu Trp Asp Arg Val His Pro Val His Ala Gly Pro Val Ala Pro
        595                 600                 605

Gly Gln Met Arg Asp Pro Arg Gly Ser Asp Ile Ala Gly Ser Thr Ser
    610                 615                 620

Thr Leu Gln Glu Gln Ile Ala Trp Met Thr Asn Asn Pro Pro Ile Pro
625                 630                 635                 640

Val Gly Asp Ile Tyr Lys Arg Trp Ile Ile Met Gly Leu Asn Lys Ile
                645                 650                 655

Val Arg Met Tyr Ser Pro Val Ser Ile Leu Asp Ile Lys Gln Gly Pro
            660                 665                 670

Lys Glu Pro Phe Arg Asp Tyr Val Asp Arg Phe Tyr Arg Thr Leu Arg
        675                 680                 685

Ala Glu Gln Ala Ser Gln Asp Val Lys Asn Trp Met Thr Glu Thr Leu
    690                 695                 700

Leu Val Gln Asn Ser Asn Pro Asp Cys Lys Thr Ile Leu Lys Ala Leu
705                 710                 715                 720

Gly Pro Gly Ala Thr Leu Glu Glu Met Met Ser Ala Cys Gln Gly Val
                725                 730                 735

Gly Gly Pro Ser His Lys Ala Arg Val Leu Ala Glu Ala Met Cys Gln
            740                 745                 750

Val Ala Lys Glu Ile Val Ala Cys Cys Asp Lys Cys Gln Leu Lys Gly
```

755 760 765

Glu Ala Ile His Gly Gln Val Asp Cys Ser Pro Gly Val Trp Gln Leu
770 775 780

Asp Cys Thr His Leu Glu Gly Lys Val Ile Leu Val Ala Val His Val
785 790 795 800

Ala Ser Gly Tyr Ile Glu Ala Glu Ile Ile Pro Thr Glu Thr Gly Gln
805 810 815

Glu Thr Ala Tyr Phe Ile Leu Lys Leu Ala Gly Arg Trp Pro Val Thr
820 825 830

Thr Met Ala Ala Arg Ala Ser Ile Leu Ser Gly Gly Lys Leu Asp Lys
835 840 845

Trp Glu Lys Ile Arg Leu Arg Pro Gly Gly Arg Lys Lys Tyr Lys Leu
850 855 860

Lys His Leu Val Trp Ala Ser Arg Glu Leu Glu Arg Phe Ala Leu Asn
865 870 875 880

Pro Gly Leu Leu Glu Thr Ala Ala Ala Val Lys Ala Ala Cys Trp Trp
885 890 895

Ala Gly Val Lys Gln Glu Phe Gly Ile Pro Tyr Asn Thr Gln Ser Gln
900 905 910

Gly Val Val Glu Ser Met Asn Asn Glu Leu Lys Lys Ile Ile Gly Gln
915 920 925

Ile Arg Asp Gln Ala Glu His Leu Lys Thr Ala Val Gln Met Ala Val
930 935 940

Leu Ile His Asn Phe Lys Arg Lys Gly Gly Ile Gly Glu Tyr Ser Ala
945 950 955 960

Gly Glu Arg Ile Ile Asp Ile Ile Ala Thr Gln Gly Phe Phe Pro Asp
965 970 975

Trp Gln Asn Tyr Thr Pro Gly Pro Gly Ile Arg Phe Pro Leu Thr Phe
980 985 990

Gly Trp Cys Phe Lys Leu Val Pro Leu Leu Ile Lys Lys Glu Lys Ile
995 1000 1005

Tyr Leu Ala Trp Val Pro Ala His Lys Gly Ile Gly Gly Asn Glu
1010 1015 1020

Gln Ile Asp Lys Leu Val Ser
1025 1030

<210> SEQ ID NO 207
<211> LENGTH: 1023
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 207

Met Phe Pro Gln Ile Thr Leu Trp Gln Arg Pro Leu Val Thr Ile Lys
1 5 10 15

Ile Gly Gly Gln Leu Lys Glu Ala Leu Leu Asp Thr Gly Ala Asp Asp
20 25 30

Thr Val Leu Glu Glu Met Asn Leu Pro Gly Arg Trp Lys Pro Lys Met
35 40 45

Ile Gly Gly Ile Gly Gly Phe Ile Lys Val Arg Gln Tyr Asp Gln Glu
50 55 60

Glu Val Gly Phe Pro Val Lys Pro Gln Val Pro Leu Arg Pro Met Thr
65 70 75 80

-continued

Phe Lys Gly Ala Leu Asp Leu Ser His Phe Leu Arg Glu Lys Gly Gly
                85                  90                  95

Leu Glu Gly Leu Ile Pro Lys Phe Lys Leu Pro Ile Gln Lys Glu Thr
            100                 105                 110

Trp Glu Thr Trp Trp Thr Glu Tyr Trp Gln Ala Thr Trp Ile Pro Glu
        115                 120                 125

Trp Glu Phe Val Asn Thr Pro Pro Leu Val Lys Leu Trp Tyr Gln Leu
    130                 135                 140

Glu Lys Glu Pro Ile Val Gly Ala Glu Thr Phe Tyr Val Asp Gly Ala
145                 150                 155                 160

Ala Asn Arg Glu Thr Lys Trp Gly Phe Thr Thr Pro Asp Lys Lys His
                165                 170                 175

Gln Lys Glu Pro Pro Phe Leu Trp Met Gly Tyr Glu Leu His Pro Asp
            180                 185                 190

Lys Trp Thr Val Gln Pro Ile Val Leu Pro Glu Lys Asp Ser Trp Thr
        195                 200                 205

Val Asn Asp Ile Gln Lys Leu Val Gly Lys Leu Asn Trp Ala Ser Gln
    210                 215                 220

Ile Tyr Pro Gly Ile Lys Val Ile Thr Lys Ile Gln Asn Phe Arg Val
225                 230                 235                 240

Tyr Tyr Arg Asp Ser Arg Asp Pro Leu Trp Lys Gly Pro Ala Lys Leu
                245                 250                 255

Leu Trp Lys Gly Glu Gly Ala Val Val Ile Gln Asp Asn Ser Asp Ile
            260                 265                 270

Lys Val Val Pro Arg Arg Lys Ala Lys Ile Ile Arg Asp Tyr Gly Lys
        275                 280                 285

Gln Met Ala Gly Asp Asp Cys Val Ala Ser Arg Gln Asp Glu Asp Gly
    290                 295                 300

Thr Val Leu Val Gly Pro Thr Pro Val Asn Ile Ile Gly Arg Asn Leu
305                 310                 315                 320

Leu Thr Gln Ile Gly Cys Thr Leu Asn Phe Pro Ile Ser Pro Ile Glu
                325                 330                 335

Thr Val Pro Val Lys Leu Lys Pro Gly Met Asp Gly Pro Lys Val Lys
            340                 345                 350

Gln Trp Pro Leu Thr Glu Glu Lys Ile Lys Ala Leu Val Glu Ile Cys
        355                 360                 365

Thr Glu Met Glu Lys Glu Gly Lys Ile Ser Lys Ile Gly Pro Glu Asn
    370                 375                 380

Pro Tyr Asn Thr Pro Val Phe Ala Ile Lys Lys Lys Asp Ser Thr Lys
385                 390                 395                 400

Trp Arg Lys Leu Val Asp Phe Arg Glu Leu Asn Lys Arg Thr Gln Asp
                405                 410                 415

Phe Trp Glu Val Gln Leu Gly Ile Pro His Pro Ala Gly Leu Lys Lys
            420                 425                 430

Lys Lys Ser Val Thr Val Leu Asp Val Gly Asp Ala Tyr Phe Ser Val
        435                 440                 445

Pro Leu Asp Lys Asp Phe Arg Lys Tyr Thr Ala Phe Thr Ile Pro Ser
    450                 455                 460

Ile Asn Asn Glu Thr Pro Gly Ile Arg Tyr Gln Tyr Asn Val Leu Pro
465                 470                 475                 480

Gln Gly Trp Lys Gly Ser Pro Ala Ile Phe Gln Ser Ser Met Thr Arg
                485                 490                 495

Ala Lys Arg Ala Pro Val Lys Gln Thr Leu Asn Phe Asp Leu Leu Lys

-continued

```
            500                 505                 510

Leu Ala Gly Asp Val Glu Ser Asn Pro Gly Pro Met Leu Pro Gln Ile
        515                 520                 525

Thr Leu Trp Gln Arg Pro Ile Val Thr Ile Lys Ile Gly Gly Gln Ile
    530                 535                 540

Lys Glu Ala Leu Leu Asp Thr Gly Ala Asp Asp Thr Val Leu Glu Asp
545                 550                 555                 560

Met Asn Leu Pro Gly Lys Trp Lys Pro Lys Met Ile Gly Gly Ile Gly
                565                 570                 575

Gly Phe Ile Lys Val Lys Gln Tyr Asp Gln Trp Gly Leu Thr Thr Pro
            580                 585                 590

Asp Lys Lys His Gln Lys Asp Pro Pro Phe Leu Trp Met Gly Tyr Glu
        595                 600                 605

Leu His Pro Asp Arg Trp Thr Val Gln Pro Ile Glu Leu Pro Glu Lys
    610                 615                 620

Glu Ser Trp Thr Val Asn Asp Ile Gln Lys Leu Ile Gly Lys Leu Asn
625                 630                 635                 640

Trp Ala Ser Gln Ile Tyr Ala Gly Ile Lys Val Ala Ala Gln Glu Glu
                645                 650                 655

Glu Glu Val Gly Phe Pro Val Arg Pro Gln Val Pro Leu Arg Pro Met
            660                 665                 670

Thr Tyr Lys Gly Ala Leu Asp Leu Ser His Phe Leu Lys Glu Lys Gly
        675                 680                 685

Gly Leu Glu Gly Ile Thr Lys Leu Gln Asn Phe Arg Val Tyr Tyr Arg
    690                 695                 700

Asp Asn Arg Asp Pro Leu Trp Lys Gly Pro Ala Arg Leu Leu Trp Lys
705                 710                 715                 720

Gly Glu Gly Ala Val Val Ile Gln Asp Asn Ser Glu Ile Lys Val Val
                725                 730                 735

Pro Arg Arg Lys Val Lys Ile Ile Arg Asp Tyr Gly Lys Arg Met Ala
            740                 745                 750

Gly Asp Asp Cys Val Ala Gly Arg Gln Asp Glu Asp Pro Lys Phe Arg
        755                 760                 765

Leu Pro Ile Gln Lys Glu Thr Trp Asp Thr Trp Trp Thr Asp Tyr Trp
    770                 775                 780

Gln Ala Thr Trp Ile Pro Glu Trp Glu Phe Thr Asn Thr Pro Pro Leu
785                 790                 795                 800

Val Lys Leu Trp Tyr Gln Leu Glu Thr Glu Pro Ile Ala Gly Val Glu
                805                 810                 815

Thr Phe Tyr Val Asp Gly Ala Ser Asn Arg Glu Thr Lys Ala Ala Gly
            820                 825                 830

Thr Val Leu Ile Gly Pro Thr Pro Val Asn Ile Ile Gly Arg Asn Leu
        835                 840                 845

Leu Thr Gln Leu Gly Cys Thr Leu Asn Phe Pro Ile Ser Pro Ile Asp
    850                 855                 860

Thr Val Pro Val Lys Leu Lys Pro Gly Met Asp Gly Pro Arg Val Lys
865                 870                 875                 880

Gln Trp Pro Leu Thr Glu Glu Lys Ile Lys Ala Leu Ile Glu Ile Cys
                885                 890                 895

Thr Glu Met Glu Lys Glu Gly Lys Ile Ser Arg Ile Gly Pro Glu Asn
            900                 905                 910

Pro Tyr Asn Thr Pro Ile Phe Ala Ile Lys Lys Lys Asp Gly Thr Lys
        915                 920                 925
```

```
Trp Arg Lys Leu Val Asp Phe Arg Glu Leu Asn Lys Lys Thr Gln Asp
    930                 935                 940

Phe Trp Glu Val Gln Leu Gly Ile Pro His Pro Ser Gly Leu Lys Lys
945                 950                 955                 960

Lys Lys Ser Val Thr Val Leu Asp Ile Gly Asp Ala Tyr Phe Ser Val
                965                 970                 975

Pro Leu Asp Lys Glu Phe Arg Lys Tyr Thr Ala Phe Thr Val Pro Ser
            980                 985                 990

Thr Asn Asn Glu Thr Pro Gly Val  Arg Tyr Gln Tyr Asn  Val Leu Pro
        995                 1000                 1005

Met Gly  Trp Lys Gly Ser Pro  Ala Ile Phe Gln Cys  Ser Met Thr
    1010                 1015                 1020


<210> SEQ ID NO 208
<211> LENGTH: 1023
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Met Thr Val Lys Ala Ala Cys Trp Trp Ala Gly Ile Lys Gln Glu Phe
1               5                   10                  15

Gly Ile Pro Tyr Asn Pro Gln Ser Gln Gly Val Val Glu Ser Met Asn
            20                  25                  30

Lys Glu Leu Lys Lys Ile Ile Gly Gln Val Arg Asp Gln Ala Glu His
        35                  40                  45

Leu Lys Thr Ala Val Gln Met Ala Val Phe Ile His Asn Phe Lys Arg
    50                  55                  60

Lys Gly Gly Ile Gly Gly Tyr Ser Ala Gly Glu Arg Ile Val Asp Ile
65                  70                  75                  80

Ile Ala Ile Ser Pro Arg Thr Leu Asn Ala Trp Val Lys Val Val Glu
                85                  90                  95

Glu Lys Ala Phe Ser Pro Glu Val Ile Pro Met Phe Ser Ala Leu Ser
            100                 105                 110

Glu Gly Ala Thr Pro Gln Asp Leu Asn Thr Met Leu Asn Thr Val Gly
        115                 120                 125

Gly His Gln Ala Ala Met Gln Met Leu Lys Glu Thr Ile Asn Glu Glu
    130                 135                 140

Ala Ala Glu Trp Asp Arg Leu His Pro Val His Ala Gly Pro Ile Ala
145                 150                 155                 160

Pro Gly Gln Met Arg Glu Pro Arg Gly Ser Asp Ile Ala Gly Thr Thr
                165                 170                 175

Ser Thr Leu Gln Glu Gln Ile Gly Trp Met Thr Asn Asn Pro Pro Ile
            180                 185                 190

Pro Val Gly Glu Ile Tyr Lys Arg Trp Ile Ile Leu Gly Leu Asn Lys
        195                 200                 205

Ile Val Arg Met Tyr Ser Pro Thr Ser Ile Leu Asp Ile Arg Gln Gly
    210                 215                 220

Pro Lys Glu Pro Phe Arg Asp Tyr Val Asp Arg Phe Tyr Lys Thr Leu
225                 230                 235                 240

Arg Ala Glu Gln Ala Ser Gln Glu Val Lys Asn Trp Met Thr Glu Thr
                245                 250                 255

Leu Leu Val Gln Asn Ala Asn Pro Asp Cys Lys Thr Ile Leu Lys Ala
```

-continued

```
            260                 265                 270

Leu Gly Pro Ala Ala Thr Leu Glu Glu Met Met Thr Ala Cys Gln Gly
        275                 280                 285

Val Gly Gly Pro Gly His Lys Ala Arg Val Leu Ala Glu Ala Met Ser
    290                 295                 300

Gln Met Ala Ala Arg Ala Ser Val Leu Ser Gly Gly Glu Leu Asp Arg
305                 310                 315                 320

Trp Glu Lys Ile Arg Leu Arg Pro Gly Gly Lys Lys Lys Tyr Arg Leu
                325                 330                 335

Lys His Ile Val Trp Ala Ser Arg Glu Leu Glu Arg Phe Ala Val Asn
            340                 345                 350

Pro Gly Leu Leu Glu Thr Pro Pro Val Val Ala Lys Glu Ile Val Ala
        355                 360                 365

Ser Cys Asp Lys Cys Gln Leu Lys Gly Glu Ala Met His Gly Gln Val
    370                 375                 380

Asp Cys Ser Pro Gly Ile Trp Gln Leu Asp Cys Thr His Leu Glu Gly
385                 390                 395                 400

Lys Ile Ile Leu Val Ala Val His Val Ala Ser Gly Tyr Ile Glu Ala
                405                 410                 415

Glu Val Ile Pro Ala Glu Thr Gly Gln Glu Thr Ala Tyr Phe Leu Leu
            420                 425                 430

Lys Leu Ala Gly Arg Trp Pro Val Lys Thr Lys Glu Lys Val Tyr Leu
        435                 440                 445

Ala Trp Val Pro Ala His Lys Gly Ile Gly Gly Asn Glu Gln Val Asp
    450                 455                 460

Lys Leu Val Ser Thr Gln Gly Tyr Phe Pro Asp Trp Gln Asn Tyr Thr
465                 470                 475                 480

Pro Gly Pro Gly Thr Arg Tyr Pro Leu Thr Phe Gly Trp Cys Phe Lys
                485                 490                 495

Leu Val Pro Val Arg Ala Lys Arg Ala Pro Val Lys Gln Thr Leu Asn
            500                 505                 510

Phe Asp Leu Leu Lys Leu Ala Gly Asp Val Glu Ser Asn Pro Gly Pro
        515                 520                 525

Met Phe Pro Gln Ile Thr Leu Trp Gln Arg Pro Leu Val Thr Ile Lys
    530                 535                 540

Ile Gly Gly Gln Leu Lys Glu Ala Leu Leu Asp Thr Gly Ala Asp Asp
545                 550                 555                 560

Thr Val Leu Glu Glu Met Asn Leu Pro Gly Arg Trp Lys Pro Lys Met
                565                 570                 575

Ile Gly Gly Ile Gly Gly Phe Ile Lys Val Arg Gln Tyr Asp Gln Glu
            580                 585                 590

Glu Val Gly Phe Pro Val Lys Pro Gln Val Pro Leu Arg Pro Met Thr
        595                 600                 605

Phe Lys Gly Ala Leu Asp Leu Ser His Phe Leu Arg Glu Lys Gly Gly
    610                 615                 620

Leu Glu Gly Leu Ile Pro Lys Phe Lys Leu Pro Ile Gln Lys Glu Thr
625                 630                 635                 640

Trp Glu Thr Trp Trp Thr Glu Tyr Trp Gln Ala Thr Trp Ile Pro Glu
                645                 650                 655

Trp Glu Phe Val Asn Thr Pro Pro Leu Val Lys Leu Trp Tyr Gln Leu
            660                 665                 670

Glu Lys Glu Pro Ile Val Gly Ala Glu Thr Phe Tyr Val Asp Gly Ala
        675                 680                 685
```

```
Ala Asn Arg Glu Thr Lys Trp Gly Phe Thr Thr Pro Asp Lys Lys His
    690                 695                 700

Gln Lys Glu Pro Pro Phe Leu Trp Met Gly Tyr Glu Leu His Pro Asp
705                 710                 715                 720

Lys Trp Thr Val Gln Pro Ile Val Leu Pro Glu Lys Asp Ser Trp Thr
                725                 730                 735

Val Asn Asp Ile Gln Lys Leu Val Gly Lys Leu Asn Trp Ala Ser Gln
            740                 745                 750

Ile Tyr Pro Gly Ile Lys Val Ile Thr Lys Ile Gln Asn Phe Arg Val
        755                 760                 765

Tyr Tyr Arg Asp Ser Arg Asp Pro Leu Trp Lys Gly Pro Ala Lys Leu
    770                 775                 780

Leu Trp Lys Gly Glu Gly Ala Val Val Ile Gln Asp Asn Ser Asp Ile
785                 790                 795                 800

Lys Val Val Pro Arg Arg Lys Ala Lys Ile Ile Arg Asp Tyr Gly Lys
                805                 810                 815

Gln Met Ala Gly Asp Asp Cys Val Ala Ser Arg Gln Asp Glu Asp Gly
            820                 825                 830

Thr Val Leu Val Gly Pro Thr Pro Val Asn Ile Ile Gly Arg Asn Leu
        835                 840                 845

Leu Thr Gln Ile Gly Cys Thr Leu Asn Phe Pro Ile Ser Pro Ile Glu
    850                 855                 860

Thr Val Pro Val Lys Leu Lys Pro Gly Met Asp Gly Pro Lys Val Lys
865                 870                 875                 880

Gln Trp Pro Leu Thr Glu Glu Lys Ile Lys Ala Leu Val Glu Ile Cys
                885                 890                 895

Thr Glu Met Glu Lys Glu Gly Lys Ile Ser Lys Ile Gly Pro Glu Asn
            900                 905                 910

Pro Tyr Asn Thr Pro Val Phe Ala Ile Lys Lys Lys Asp Ser Thr Lys
        915                 920                 925

Trp Arg Lys Leu Val Asp Phe Arg Glu Leu Asn Lys Arg Thr Gln Asp
    930                 935                 940

Phe Trp Glu Val Gln Leu Gly Ile Pro His Pro Ala Gly Leu Lys Lys
945                 950                 955                 960

Lys Lys Ser Val Thr Val Leu Asp Val Gly Asp Ala Tyr Phe Ser Val
                965                 970                 975

Pro Leu Asp Lys Asp Phe Arg Lys Tyr Thr Ala Phe Thr Ile Pro Ser
            980                 985                 990

Ile Asn Asn Glu Thr Pro Gly Ile  Arg Tyr Gln Tyr Asn  Val Leu Pro
        995                 1000                1005

Gln Gly  Trp Lys Gly Ser Pro  Ala Ile Phe Gln Ser  Ser Met Thr
    1010                 1015                 1020
```

<210> SEQ ID NO 209
<211> LENGTH: 1030
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 209

```
Met Leu Ser Pro Arg Thr Leu Asn Ala Trp Val Lys Val Ile Glu Glu
1               5                   10                  15

Lys Ala Phe Ser Pro Glu Val Ile Pro Met Phe Thr Ala Leu Ser Glu
```

-continued

```
            20                  25                  30

Gly Ala Thr Pro His Asp Leu Asn Thr Met Leu Asn Thr Ile Gly Gly
        35                  40                  45

His Gln Ala Ala Met Gln Met Leu Lys Asp Thr Ile Asn Glu Glu Ala
    50                  55                  60

Ala Glu Trp Asp Arg Val His Pro Val His Ala Gly Pro Val Ala Pro
65                  70                  75                  80

Gly Gln Met Arg Asp Pro Arg Gly Ser Asp Ile Ala Gly Ser Thr Ser
                85                  90                  95

Thr Leu Gln Glu Gln Ile Ala Trp Met Thr Asn Asn Pro Pro Ile Pro
            100                 105                 110

Val Gly Asp Ile Tyr Lys Arg Trp Ile Ile Met Gly Leu Asn Lys Ile
        115                 120                 125

Val Arg Met Tyr Ser Pro Val Ser Ile Leu Asp Ile Lys Gln Gly Pro
    130                 135                 140

Lys Glu Pro Phe Arg Asp Tyr Val Asp Arg Phe Tyr Arg Thr Leu Arg
145                 150                 155                 160

Ala Glu Gln Ala Ser Gln Asp Val Lys Asn Trp Met Thr Glu Thr Leu
                165                 170                 175

Leu Val Gln Asn Ser Asn Pro Asp Cys Lys Thr Ile Leu Lys Ala Leu
            180                 185                 190

Gly Pro Gly Ala Thr Leu Glu Glu Met Met Ser Ala Cys Gln Gly Val
        195                 200                 205

Gly Gly Pro Ser His Lys Ala Arg Val Leu Ala Glu Ala Met Cys Gln
    210                 215                 220

Val Ala Lys Glu Ile Val Ala Cys Cys Asp Lys Cys Gln Leu Lys Gly
225                 230                 235                 240

Glu Ala Ile His Gly Gln Val Asp Cys Ser Pro Gly Val Trp Gln Leu
                245                 250                 255

Asp Cys Thr His Leu Glu Gly Lys Val Ile Leu Val Ala Val His Val
            260                 265                 270

Ala Ser Gly Tyr Ile Glu Ala Glu Ile Ile Pro Thr Glu Thr Gly Gln
        275                 280                 285

Glu Thr Ala Tyr Phe Ile Leu Lys Leu Ala Gly Arg Trp Pro Val Thr
    290                 295                 300

Thr Met Ala Ala Arg Ala Ser Ile Leu Ser Gly Gly Lys Leu Asp Lys
305                 310                 315                 320

Trp Glu Lys Ile Arg Leu Arg Pro Gly Gly Arg Lys Lys Tyr Lys Leu
                325                 330                 335

Lys His Leu Val Trp Ala Ser Arg Glu Leu Glu Arg Phe Ala Leu Asn
            340                 345                 350

Pro Gly Leu Leu Glu Thr Ala Ala Ala Val Lys Ala Ala Cys Trp Trp
        355                 360                 365

Ala Gly Val Lys Gln Glu Phe Gly Ile Pro Tyr Asn Thr Gln Ser Gln
    370                 375                 380

Gly Val Val Glu Ser Met Asn Asn Glu Leu Lys Lys Ile Ile Gly Gln
385                 390                 395                 400

Ile Arg Asp Gln Ala Glu His Leu Lys Thr Ala Val Gln Met Ala Val
                405                 410                 415

Leu Ile His Asn Phe Lys Arg Lys Gly Gly Ile Gly Glu Tyr Ser Ala
            420                 425                 430

Gly Glu Arg Ile Ile Asp Ile Ile Ala Thr Gln Gly Phe Phe Pro Asp
        435                 440                 445
```

-continued

```
Trp Gln Asn Tyr Thr Pro Gly Pro Gly Ile Arg Phe Pro Leu Thr Phe
    450                 455                 460

Gly Trp Cys Phe Lys Leu Val Pro Leu Leu Ile Lys Lys Glu Lys Ile
465                 470                 475                 480

Tyr Leu Ala Trp Val Pro Ala His Lys Gly Ile Gly Gly Asn Glu Gln
                485                 490                 495

Ile Asp Lys Leu Val Ser Arg Ala Lys Arg Ala Pro Val Lys Gln Thr
            500                 505                 510

Leu Asn Phe Asp Leu Leu Lys Leu Ala Gly Asp Val Glu Ser Asn Pro
        515                 520                 525

Gly Pro Met Leu Pro Gln Ile Thr Leu Trp Gln Arg Pro Ile Val Thr
    530                 535                 540

Ile Lys Ile Gly Gly Gln Ile Lys Glu Ala Leu Leu Asp Thr Gly Ala
545                 550                 555                 560

Asp Asp Thr Val Leu Glu Asp Met Asn Leu Pro Gly Lys Trp Lys Pro
                565                 570                 575

Lys Met Ile Gly Gly Ile Gly Gly Phe Ile Lys Val Lys Gln Tyr Asp
            580                 585                 590

Gln Trp Gly Leu Thr Thr Pro Asp Lys Lys His Gln Lys Asp Pro Pro
        595                 600                 605

Phe Leu Trp Met Gly Tyr Glu Leu His Pro Asp Arg Trp Thr Val Gln
    610                 615                 620

Pro Ile Glu Leu Pro Glu Lys Glu Ser Trp Thr Val Asn Asp Ile Gln
625                 630                 635                 640

Lys Leu Ile Gly Lys Leu Asn Trp Ala Ser Gln Ile Tyr Ala Gly Ile
                645                 650                 655

Lys Val Ala Ala Gln Glu Glu Glu Glu Val Gly Phe Pro Val Arg Pro
            660                 665                 670

Gln Val Pro Leu Arg Pro Met Thr Tyr Lys Gly Ala Leu Asp Leu Ser
        675                 680                 685

His Phe Leu Lys Glu Lys Gly Gly Leu Glu Gly Ile Thr Lys Leu Gln
    690                 695                 700

Asn Phe Arg Val Tyr Tyr Arg Asp Asn Arg Asp Pro Leu Trp Lys Gly
705                 710                 715                 720

Pro Ala Arg Leu Leu Trp Lys Gly Glu Gly Ala Val Val Ile Gln Asp
                725                 730                 735

Asn Ser Glu Ile Lys Val Val Pro Arg Arg Lys Val Lys Ile Ile Arg
            740                 745                 750

Asp Tyr Gly Lys Arg Met Ala Gly Asp Asp Cys Val Ala Gly Arg Gln
        755                 760                 765

Asp Glu Asp Pro Lys Phe Arg Leu Pro Ile Gln Lys Glu Thr Trp Asp
    770                 775                 780

Thr Trp Trp Thr Asp Tyr Trp Gln Ala Thr Trp Ile Pro Glu Trp Glu
785                 790                 795                 800

Phe Thr Asn Thr Pro Pro Leu Val Lys Leu Trp Tyr Gln Leu Glu Thr
                805                 810                 815

Glu Pro Ile Ala Gly Val Glu Thr Phe Tyr Val Asp Gly Ala Ser Asn
            820                 825                 830

Arg Glu Thr Lys Ala Ala Gly Thr Val Leu Ile Gly Pro Thr Pro Val
        835                 840                 845

Asn Ile Ile Gly Arg Asn Leu Leu Thr Gln Leu Gly Cys Thr Leu Asn
    850                 855                 860
```

-continued

```
Phe Pro Ile Ser Pro Ile Asp Thr Val Pro Val Lys Leu Lys Pro Gly
865                 870                 875                 880

Met Asp Gly Pro Arg Val Lys Gln Trp Pro Leu Thr Glu Glu Lys Ile
                885                 890                 895

Lys Ala Leu Ile Glu Ile Cys Thr Glu Met Glu Lys Glu Gly Lys Ile
            900                 905                 910

Ser Arg Ile Gly Pro Glu Asn Pro Tyr Asn Thr Pro Ile Phe Ala Ile
        915                 920                 925

Lys Lys Lys Asp Gly Thr Lys Trp Arg Lys Leu Val Asp Phe Arg Glu
    930                 935                 940

Leu Asn Lys Lys Thr Gln Asp Phe Trp Glu Val Gln Leu Gly Ile Pro
945                 950                 955                 960

His Pro Ser Gly Leu Lys Lys Lys Lys Ser Val Thr Val Leu Asp Ile
                965                 970                 975

Gly Asp Ala Tyr Phe Ser Val Pro Leu Asp Lys Glu Phe Arg Lys Tyr
            980                 985                 990

Thr Ala Phe Thr Val Pro Ser Thr  Asn Asn Glu Thr Pro  Gly Val Arg
        995                 1000                1005

Tyr Gln  Tyr Asn Val Leu Pro  Met Gly Trp Lys Gly  Ser Pro Ala
    1010                1015                1020

Ile Phe  Gln Cys Ser Met Thr
    1025                1030
```

<210> SEQ ID NO 210
<211> LENGTH: 2202
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 210

```
acggtgaagg ctgcgtgttg gtgggccggc ataaaacaag aatttggaat accatacaat     60

ccacaatctc aaggcgttgt ggaatccatg aataaagaat tgaaaaaaat tatcgggcaa    120

gttcgagacc aggctgagca tctcaaaacg gccgtacaga tggcggtgtt tattcacaac    180

ttcaaaagaa aaggaggaat cggtggttac agtgcaggcg aacgaatagt tgacattata    240

gcgatatctc ctcggactct gaatgcgtgg gtaaaggtag tcgaggagaa agcatttagc    300

cccgaagtca tccccatgtt ttcagccctt tcagagggcg ctacaccaca ggatctgaat    360

accatgctga acacagtagg ggggcaccaa gcggcgatgc agatgctgaa ggagacaata    420

aatgaggagg cggcggaatg ggatagattg catcccgtcc acgcggggcc gatagcgcct    480

ggccagatga gggagccacg aggttccgac atcgcgggaa caacctcaac cctgcaggaa    540

caaatagggt ggatgacgaa taaccctcct attccagttg gtgaaattta taaacgatgg    600

ataatactcg gtctcaataa aatagtaagg atgtattctc cgacaagcat acttgacatc    660

agacaggggc cgaaagaacc tttccgcgat tatgtggaca gattctacaa aacgctcagg    720

gccgaacagg ccagccaaga ggttaaaaac tggatgactg aaaccctgct ggtccagaat    780

gctaaccccg actgcaagac aatcttgaag gcacttgggc cggccgcaac gttggaagaa    840

atgatgacgg cttgtcaagg ggttggcggt ccgggccata aggcccgagt cctggcagaa    900

gctatgagtc agaaagaacc aatagttgga gccgaaacat tctacgtcga cggtgctgca    960

aatcgcgaga cgaaggctgc taaggaaaag gtctatctgg cgtgggttcc ggcacacaag   1020

ggcataggcg ggaatgagca agtcgacaaa ttggtctcac gagctaaacg cgccccggtt   1080
```

-continued

```
aaacaaaccc tgaacttcga cttgcttaaa ctcgcagggg acgttgaatc aaatccgggc   1140
ccacttagtc cccgaacgct gaacgcatgg gtaaaagtaa tagaagagaa agcgttttcc   1200
ccggaggtta ttcccatgtt tacagccctc agcgagggcg cgacgccaca tgatctcaac   1260
acaatgctta acacgattgg ggggcatcag gctgcgatgc aaatgctcaa ggatacgata   1320
aacgaagagg ccgcagaatg ggaccgagta catccggtcc acgccgggcc cgtcgcacca   1380
ggacagatgc gagacccccg agggtcagac atcgccggtt ctacgtcaac cttgcaagaa   1440
caaattgcat ggatgactaa caatccacct atccccgtgg gagatatcta taagagatgg   1500
atcatcatgg ggcttaataa aatagtcagg atgtattcac cagtttcaat tcttgatatt   1560
aaacagggtc ctaaggagcc ctttcgagat tatgtggata ggttttatag aacccttcgc   1620
gcagaacagg cttcacaaga cgtcaaaaat tggatgacag aaactcttct cgtacagaat   1680
tcaaacccgg attgtaagac gatcttgaaa gcactcggtc cgggtgccac gttggaagag   1740
atgatgtcag cctgccaagg ggtgggtggc ccaagccata aggccagggt attggcagag   1800
gcaatgtgtc aagctgtcaa ggcagcatgc tggtgggctg gcgtaaagca ggaattcggc   1860
ataccgtaca atacacagtc acaaggtgtt gtcgagagta tgaataatga acttaaaaaa   1920
atcataggac agatccgaga tcaagctgaa catctgaaga ctgctgtaca aatggcagtg   1980
cttatacata acttcaaacg caagggagga attggggagt attcagcggg agagcggatt   2040
attgatatca tagcaaccga acccatagcg ggcgtcgaga ctttctatgt ggacggagcc   2100
agcaataggg agactaaggc ggcgaaagaa aagatttatc tggcatgggt tccggctcat   2160
aaggggatcg gaggcaatga gcagattgac aaactggtat cc                      2202
```

<210> SEQ ID NO 211
<211> LENGTH: 2235
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 211

```
ttgagccccc gaacccttaa cgcctgggtg aaggtaattg aggaaaaagc tttttcaccc     60
gaagtgatcc cgatgtttac agcactgtct gaaggtgcaa ccccacacga tctcaacact    120
atgctcaata ccataggggg ccaccaagca gcgatgcaga tgctcaaaga taccattaac    180
gaggaagcgg ccgagtggga cagggtacac cccgtgcatg ccggacctgt cgccccgggt    240
caaatgcgag atccacgcgg aagtgatatc gctgggagta cgtccaccct ccaagaacaa    300
atcgcgtgga tgacaaataa tcctcctatc cccgtaggag atatttataa aaggtggatt    360
atcatggggc ttaataaaat cgttcgaatg tatagtcctg tctcaatact ggacatcaaa    420
caaggcccaa aagaaccatt cagggactac gttgacagat tctatcgcac actccgagcg    480
gaacaagcaa gccaggacgt caaaaattgg atgaccgaga cgttgcttgt acaaaatagc    540
aaccccgact gtaaaacgat actcaaagcc ttggggccag gcgcgacctt ggaggagatg    600
atgtccgctt gtcagggagt aggcggacca tcacacaaag cacgcgtttt ggcggaagct    660
atgtgtcagg cggtaaaggc agcctgttgg tgggctggag tcaaacaaga atttggcatc    720
ccctataata cacagtccca gggtgtcgtc gagtctatga ataatgagct gaagaaaatc    780
attgggcaga taagagacca agccgaacat cttaaaacgg ctgtccaaat ggcggttttg    840
atccataatt ttaagcgaaa aggggggatt ggtgagtact cagcaggaga gagaatcata    900
```

```
gacatcatag caacagaacc aattgctggt gtcgagactt tttacgtaga tggggcgagc    960
aatagggaaa ctaaagcagc gaaggaaaag atttacctcg cgtgggtacc ggcccacaag   1020
ggaatcggcg ggaacgagca aatcgataaa cttgtatcca gagccaaacg ggctccagta   1080
aaacagacac tcaatttcga tcttttgaag cttgctggag acgttgagag caatcctggg   1140
ccggtagcaa aggagattgt agcttgttgc gacaagtgcc agttgaaggg tgaagcgata   1200
cacggtcagg tcgattgctc tccgggagtt tggcaacttg actgtaccca tctcgagggc   1260
aaagttatcc tcgtagctgt gcatgtagca tcaggatata tagaggccga gatcattccg   1320
acggaaacgg gtcaagaaac tgcttacttc attctcaaac ttgccgggcg gtggccagtc   1380
acaactatca cgaaactcca aaactttcga gtttactata gggacaatcg agacccactg   1440
tggaaaggac ctgccaggct tctgtggaaa ggggagggtg ccgttgtcat acaggataac   1500
tccgagataa aagttgtgcc aaggcgaaaa gttaagatta ttcgggatta cgggaaacgc   1560
atggcagggg atgactgcgt tgcggggcga caagatgagg atggtactgt acttattggc   1620
ccaacacccg tgaacattat aggacggaat ctgctgacac agttggggtg tacgctcaac   1680
tttccgataa gtccgataga tacggttccg gtaaagctga agcccggcat ggatggtccg   1740
cgcgtgaagc aatggccact cacagaagag aaaatcaaag ctttgataga aatctgcacc   1800
gaaatggaaa aagaggggaa gatcagcagg atcggcccgg agaatcctta caacacccct   1860
atttcgcga ttaagaaaaa agatggtaca aaatggagga aactcgttga ttttcgggag    1920
ctcaacaaga aaacgcaaga cttctgggag gtccagcttg gcatacccca cccctctgga   1980
cttaaaaaga aaaaaagcgt aaccgtactt gatattggtg acgcgtattt ctccgttccc   2040
ttggataaag aatttaggaa gtacacggcc tttactgtcc cctccactaa caacgaaact   2100
ccgggcgtgc gatatcaata taatgtgctt ccgatgggat ggaaaggctc accagcgatt   2160
tttcaatgca gtatgaccaa gattcttcag gaagaagagg aagtggggtt tccggtaaga   2220
ccacaggtgc ccctc                                                    2235
```

<210> SEQ ID NO 212
<211> LENGTH: 2238
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 212

```
acggttaagg cggcgtgttg gtgggcgggg ataaagcaag agttcggaat cccatataat     60
ccacaatccc aaggtgtggt ggaaagcatg aacaaggaat tgaagaagat tataggacaa    120
gtcagagatc aggccgagca tctgaaaact gcagttcaga tggctgtgtt catccacaat    180
tttaaacgca aaggaggaat tggtggatat agcgctggcg agaggattgt agacattatt    240
gccatatcac ctcgcactct gaacgcctgg gtgaaggttg ttgaagaaaa ggctttttca    300
ccggaggtaa tcccaatgtt cagtgctctt agcgaggggg caactccgca ggaccttaat    360
acaatgttga acactgtagg gggacatcaa gccgctatgc aaatgctgaa ggagacgatt    420
aacgaggaag ctgcggaatg ggatagactt caccccgtcc acgctggacc tattgcaccg    480
ggacagatgc gcgaaccaag aggttccgat atagcgggaa caactagcac actccaggaa    540
cagataggat ggatgaccaa caaccctccg ataccagtag gcgaaatcta caagcgctgg    600
ataatattgg ggctgaacaa aatcgtcagg atgtacagcc caacttcaat attggacatt    660
```

cgccaaggac ctaaagagcc gttccgggat tacgtggata ggttttacaa gactttgcga 720
gctgaacaag ccagtcaaga ggtgaaaaac tggatgaccg agactctgct cgtccaaaat 780
gctaatccag attgcaaaac aatacttaag gcactgggtc ccgccgcaac gctcgaggag 840
atgatgactg cctgccaagg tgtcggtggt ccgggtcaca aagcacgagt cctggcggaa 900
gccatgtctc agaaagagcc tatagtgggt gccgagacgt tctacgttga tggagccgct 960
aatcgagaga cgaaagcggc caaggaaaag gtgtatctcg cttgggtgcc tgctcataag 1020
ggcatcggag gtaatgaaca agttgataaa ctggtgagtc gggcgaagcg cgcaccagta 1080
aagcagaccc ttaatttcga tttgctcaaa ctcgctggtg atgtcgaatc taaccccggt 1140
ccgattacaa aaatccagaa ttttagggtt tactatcgag attcccgaga tccactctgg 1200
aaaggccccg cgaaattgct ctggaagggc gaaggggctg tagtaattca agacaattct 1260
gatatcaagg tagtccctcg gaggaaagct aaaataatac gagactatgg aaaacagatg 1320
gcgggggatg actgtgtagc aagccggcaa gatgaagacg cggcagctat aggaacagtg 1380
ctggtggggc cgaccccgt aaacattatc ggcaggaatc tgttgacgca aataggttgt 1440
acgctcaatt ttcctatctc accgatcgaa acggtgcccg tcaagttgaa gccgggcatg 1500
gacggcccaa aggtaaaaca atggcccttg acggaggaga aaatcaaagc tcttgtcgaa 1560
atctgtaccg aaatggaaaa ggaaggtaag ataagtaaaa tcggaccaga aaacccgtat 1620
aacactccag ttttcgcgat aaagaagaaa gactccacaa agtggagaaa acttgtagat 1680
ttcagggagc tgaataaaag gacccaggat tttgggaag tccagttggg cataccacat 1740
cccgcggggc tcaaaaagaa gaagtcagtc acggtactcg acgttggcga cgcatatttc 1800
tctgttccgc tcgataagga cttcagaaaa tataccgctt tcactattcc aagtatcaac 1860
aatgaaactc ccgggatacg ctatcaatac aacgttctgc cacagggatg gaaggggagt 1920
ccggctattt ttcagtcttc aatgacagtg gcaaaagaga tcgttgcaag ctgtgataaa 1980
tgccaactga aaggtgaggc catgcacgga caggttgact gctctcccgg gatatggcag 2040
ctggattgca cgcatttgga gggtaagata attctcgtcg cggtccacgt ggctagtggc 2100
tacatcgagg ccgaagtaat ccccgcagag acgggccaag aaactgcgta cttcctcctg 2160
aagctggcag gacgatggcc tgtcaaaaca caggaggaag aagaagtggg attcccggtt 2220
aagccccagg ttccgctg 2238

<210> SEQ ID NO 213
<211> LENGTH: 2235
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 213
cttagcccac ggacacttaa tgcatgggtc aaggtgattg aggagaaggc gttttcccca 60
gaggtgatcc caatgttcac agccctctct gagggcgcaa cacctcacga cctgaataca 120
atgctcaaca ctatcggagg gcaccaagca gccatgcaaa tgctgaaaga caccatcaac 180
gaggaggctg ctgagtggga tcgagtacac cctgtacacg cggggccggt tgctcctggt 240
caaatgaggg atccccgcgg ctccgacata gccggctcaa caagcactct gcaggaacag 300
atagcatgga tgaccaacaa cccccctatt cccgtagggg acatttacaa gaggtggatt 360
ataatgggtc tgaacaagat cgtacgaatg tattcaccgg tcagcatact tgatataaaa 420

```
caaggcccga aagaaccttt cagggactat gtcgatcgat tttaccgcac gctgcgcgcc    480

gagcaggcct cccaggacgt gaagaactgg atgactgaaa cactgcttgt gcaaaattca    540

aatccagatt gtaaaaccat acttaaggct cttggtccgg gggctaccct ggaagagatg    600

atgagcgcgt gtcaaggggt aggaggtcct tctcacaagg ccagggtttt ggctgaagct    660

atgtgccagg ccgttaaggc ggcctgttgg tgggcaggag tcaagcaaga attcggcatc    720

ccctacaaca cgcaatcaca gggtgtcgtt gaatcaatga acaacgagct gaaaaaaatt    780

ataggtcaaa tacgcgatca agcggaacat cttaagaccg cagtgcagat ggctgtgctt    840

atacataatt tcaagcgaaa aggaggcatc ggagaatact cagccggaga aagaatcatc    900

gacattatcg caacggagcc aatcgccggt gtggaaacgt tctatgtaga cggagcatca    960

aatagggaaa cgaaggccgc caaggagaaa atttatctgg cgtgggtccc ggcccacaag   1020

ggaattggcg gcaatgaaca gatcgacaag cttgtttctc gggctaaacg ggctcccgtt   1080

aagcagacgc tcaacttcga tcttctcaag ctggccggtg atgtcgagag caatccgggg   1140

ccggtagcta aggaaatcgt cgcttgttgt gataaatgtc aacttaaggg tgaagcaatt   1200

catggccaag ttgactgttc accgggagta tggcaactcg attgtaccca tctcgaagga   1260

aaagtcatct tggttgcagt gcacgtagct tctggctaca ttgaagcgga gattatcccg   1320

acagagaccg ggcaggagac cgcttatttt atcctcaagc tcgcaggacg atggcccgtc   1380

actactatca cgaagctcca aaattttaga gtgtactacc gcgataacag agatcctttg   1440

tggaaaggcc ccgccagact tttgtggaag ggtgagggag cggtggttat tcaggacaat   1500

tctgagataa aagttgtacc ccgacggaag gtcaagataa ttagagatta tggtaaaagg   1560

atggcgggcg acgactgtgt agctggaagg caggatgagg acggcacagt gctgattggc   1620

ccgacgcccg taaacattat cggtcgcaac cttctcaccc agctggggtg cactttgaat   1680

ttcccgattt ccccgattga tactgttcca gtaaagctca aacccgggat ggacggccca   1740

cgagtaaaac aatggccatt gacagaggag aagattaagg cgcttatcga aatatgtact   1800

gaaatggaga aggaagggaa aattagtcgg atagggcctg agaatcccta caacacgccc   1860

atttttgcta tcaagaagaa agatggcacc aagtggcgga agctggtcga ttttcgggaa   1920

cttaacaaga aaacacaaga cttctgggaa gtacagcttg ggatcccgca cccgtcagga   1980

ttgaagaaga aaaagagcgt cacggtactc gacataggcg acgcttactt ctcagttccg   2040

ctggacaaag agttcagaaa atatacagct ttcacggtac cctccactaa caatgagaca   2100

cctggagttc gctaccagta caatgtgctt ccaatgggat ggaagggctc accggctatt   2160

ttccaatgct ctatgactaa aatacttcaa gaggaagaag aggttgggtt tcccgtcaga   2220

ccgcaggttc cactt                                                    2235
```

<210> SEQ ID NO 214
<211> LENGTH: 2148
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 214

```
acggtgaaag cagcttgctg gtgggcgggg atcaaacagg agtttggaat accttataat     60

cctcaatcac agggggttgt cgaaagcatg aacaaggagc tcaagaagat catcggacag    120

gtgcgcgatc aggctgaaca tcttaagacc gcagttcaga tggcagtctt tattcacaat    180
```

```
tttaaacgga aaggaggtat aggtggctac agcgcgggcg agcgcattgt agatattata    240
gcgatttctc cgcggacgct gaatgcatgg gttaaagtag ttgaagagaa ggccttttct    300
cccgaagtaa tacccatgtt cagtgcactg tctgaaggtg ctactcctca ggatctcaac    360
acgatgctca acacggtcgg tgggcatcag gcagcaatgc agatgctgaa ggaaacgata    420
aacgaggagg cagcagaatg ggatcgactg cacccagtac acgcaggccc tatagcccca    480
ggtcaaatgc gggaaccaag aggtagtgat atagctggga ctacctcaac gttgcaggag    540
caaattggtt ggatgacgaa taatcctcct ataccagttg gcgaaatata caaaagatgg    600
attatcttgg gactgaataa aatcgtgcga atgtattctc cgacctctat actggacatt    660
cgacagggac caaaagagcc gttccgcgac tacgtcgatc ggttttataa aactttgcgg    720
gccgaacagg caagccagga ggtaaagaac tggatgacag agaccctgtt ggtgcaaaat    780
gcgaaccctg attgcaagac catactgaaa gcactcgggc cagctgccac ccttgaggaa    840
atgatgacag cttgccaggg tgtggggggg ccggggcata aagcacgcgt cctcgccgaa    900
gccatgtcac agaaagaacc aattgtgggt gccgaaactt tttacgtgga cggcgcagcc    960
aaccgagaga ctaaagtggc taaagagata gttgcatcat gtgataagtg ccaattgaaa   1020
ggtgaggcca tgcacggtca ggtagattgt tcacctggta tatggcagtt ggactgtact   1080
caccttgaag gaaagattat cctggtcgcg gtacacgtcg catccggtta tatagaggcg   1140
gaagttatac ctgcggagac tggtcaagaa actgcctact tccttcttaa attggctggt   1200
cgatggccag taaaaactaa agagaaagtg taccttgcgt gggttccagc ccacaagggt   1260
ataggaggaa atgagcaagt agacaaactc gtaagccaag aggaagaaga agtgggtttc   1320
ccagttaagc cacaggtacc cctcattacc aaaatacaga atttccgggt ttattatcgc   1380
gattcaaggg accccctgtg gaaaggtcca gcaaaactgc tgtggaaggg cgaaggggca   1440
gttgttatac aagacaactc agatatcaag gtcgtgccaa gacgcaaagc taaaattata   1500
agggattatg gtaaacagat ggctggagac gactgcgtgg ccagcagaca agacgaggat   1560
gcagctgcaa ttggaacagt cctggtcgga ccaactcccg ttaacatcat aggtagaaac   1620
ttgctcactc aaatcggatg cacacttaat tttccgattt cacctatcga gaccgttccc   1680
gttaagctga aacctgggat ggacggtccc aaggtgaagc aatggccctt gactgaggaa   1740
aagataaagg cgttggtaga gatctgcacc gaaatggaga aggaaggcaa gatatctaag   1800
atcgggccag aaaacccata taatacacct gtcttcgcga taaaaaaaaa ggactctact   1860
aaatggagaa aactggtcga cttcagagag cttaataagc gaactcaaga cttttgggaa   1920
gtgcagcttg gtatacctca ccctgctggt ctgaagaaga aaaaatctgt tactgttctt   1980
gatgtcggtg acgcatactt cagtgtgccc ctcgataaag atttcaggaa atacaccgcg   2040
ttcactatac ccagcattaa taacgagacc cccgggatac gctaccaata caatgtcctc   2100
ccccagggct ggaaagggtc tccagcaatt tttcagtcat caatgacg                2148
```

<210> SEQ ID NO 215
<211> LENGTH: 2145
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 215

```
ttgtcccctc ggacgctcaa tgcatgggtt aaagttatcg aggagaaggc cttcagtccc     60
```

```
gaggttatac ctatgttcac cgctctgtct gaaggagcaa cgccccatga tctcaatact    120
atgctcaata caattggagg tcaccaagcg gctatgcaaa tgctcaaaga taccattaat    180
gaggaggctg ctgaatggga tagggtccac ccagttcatg ccggaccggt ggctccggga    240
cagatgcgcg acccccgggg gtcagacatc gccggaagta cctctactct gcaggaacaa    300
attgcatgga tgacaaataa tccacctatt ccggtcggag acatctacaa acgatggatc    360
ataatgggtc tcaacaagat agtccggatg tatagtccgg taagtatact cgacatcaag    420
caaggcccta aggagccgtt ccgggattac gtagaccgat tctaccggac gctcagagcc    480
gaacaggcct cccaagatgt taagaactgg atgaccgaaa cgttgttggt tcaaaattcc    540
aatcctgatt gcaaaacgat actcaaagct cttggtcctg gtgcaacact ggaggaaatg    600
atgtcagcct gccaaggggt cggcgggcct tcacacaaag caagggtttt ggcggaggca    660
atgtgccaag tagcgaagga aatagtggcc tgttgtgaca aatgtcagct gaaaggagag    720
gcaatacatg gacaagttga ctgttctccc ggtgtgtggc aactcgactg tacccacttg    780
gaaggaaaag ttatactggt ggccgttcac gtcgcgtctg gctacatcga ggctgagatc    840
atacctacag agaccgggca ggagaccgcg tacttcatcc ttaagctcgc gggccgctgg    900
ccagtcacga ctaaagagaa aatttatctg gcgtgggtac ccgcgcataa aggtattggc    960
ggcaatgaac aaatagacaa attggtatca acagagccga ttgcaggagt cgaaacattc   1020
tatgttgatg gtgcgtcaaa cagggaaacg aagataacaa agttgcaaaa ctttcgagtc   1080
tactatcgcg acaatcggga tcccctctgg aagggcccag caaggttgct gtggaagggc   1140
gagggagcag tagtcattca agacaacagt gagattaagg tagttccgcg acggaaggtc   1200
aaaataatac gggattacgg caaaaggatg gcaggggatg attgcgtggc tgggcgccag   1260
gatgaggacg ctgtcaaagc cgcgtgttgg tgggcagggg ttaagcagga gttcggaata   1320
ccatacaaca cccagtctca aggagttgtt gaaagcatga acaatgagct taaaaaaata   1380
atcggacaaa taagggatca ggccgaacac ttgaagacag cagttcagat ggccgtgctg   1440
atccataact tcaaacggaa gggcggcata ggagaatact ccgcaggcga gagaataatc   1500
gacattatag ctcaagaaga agaggaagtc ggctttcctg tacgacctca ggtccctctt   1560
ggtacggtgt tgatagggcc gacccccgtc aacatcatcg gtcggaacct gcttacacaa   1620
cttggttgca ctcttaactt tcctatttcc cccatagata ccgtcccagt caagttgaag   1680
ccggggatgg atggcccgcg cgtcaagcag tggcccctga ctgaagaaaa gattaaagct   1740
ctgattgaaa tatgcacaga aatggaaaaa gagggtaaga tcagcagaat cggtccagaa   1800
aatccctata acacgccgat attcgccatt aagaagaagg acggaacaaa gtggcggaaa   1860
ctcgtcgatt ttagggagct gaataagaaa acgcaggatt tctgggaagt tcaacttggc   1920
atacctcacc cctctggtct taaaaaaaaa aagtcagtca ccgttctcga cattggggac   1980
gcgtattttt ccgttccgct cgacaaagag tttcggaagt acacggcgtt cacggtacct   2040
tctacaaaca atgaaacccc cggggtcagg tatcagtata atgtgctgcc aatggggtgg   2100
aagggtagcc ctgctatttt tcaatgctca atgacaaaga tcctt                   2145
```

<210> SEQ ID NO 216
<211> LENGTH: 3090
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 216
atgacagtaa aagcggcttg ctggtgggcg ggtattaagc aagagtttgg tatcccctac 60
aacccccagt cccaaggagt cgtcgagtct atgaacaaag aactgaagaa gatcattggg 120
caggtgcgcg atcaggctga gcacttgaaa acagcggtcc agatggctgt gtttatccat 180
aactttaaga ggaagggggg gatagggggc tattcagcag gggagagaat tgtagacatc 240
atcgccatat cccctcgaac gctcaatgcg tgggttaaag tagttgagga aaaggcattt 300
agtcctgaag tcatcccaat gtttagcgca ctttccgagg gcgctacgcc ccaggacctg 360
aataccatgc ttaacaccgt tgggggccac caggcggcca tgcagatgct caaggaaact 420
attaacgagg aggcggcgga gtgggatcgg ctgcaccctg tccacgcagg accgatcgcc 480
ccggggcaaa tgagagaacc cagaggttct gatattgctg gaactactag tactcttcag 540
gagcaaatcg ggtggatgac taataaccca ccaattcccg taggtgaaat ttacaagaga 600
tggatcatac tgggcttgaa caaaatagtc cgaatgtata gtcccacctc aatcctcgac 660
atccggcaag gaccgaagga gcctttccgc gactatgtgg atcgctttta taagactctg 720
cgagcagaac aagcatcaca agaggttaaa aactggatga ccgaaacact cttggtgcag 780
aacgcaaatc ccgactgcaa aaccatcctg aaggcattgg gccctgcagc aactttggag 840
gagatgatga ctgcatgtca aggcgtagga gggcccggcc ataaagccag agttttggca 900
gaggctatgt ctcaaatggc ggcacgagct tcagttctgt caggggcgcga acttgatcgg 960
tgggaaaaga tacggcttcg gcccggaggc aagaaaaagt acaggctgaa gcacatagta 1020
tgggcgtccc gcgaactgga gaggtttgca gtgaaccccg gcctgctcga gacgcccccg 1080
gtggttgcta aagaaatagt cgcctcttgt gataaatgcc aactcaaggg agaagctatg 1140
catggccagg ttgactgctc accgggtata tggcagctgg attgtacaca tttggaaggt 1200
aaaatcatac tcgttgctgt gcatgtagca agcgggtata ttgaggcgga agtaattccg 1260
gcggaaaccg ggcaagaaac tgcctatttc cttcttaaac tcgcggggcg gtggccggtt 1320
aagaccaagg agaaagtcta tctcgcatgg gttccggccc ataaaggcat cggcggtaat 1380
gaacaagtag ataaactcgt tagcactcaa ggatattttc cggattggca gaattataca 1440
cccggacctg gtacaagata tcccttgacg ttcggatggt gtttcaagct cgtcccagtc 1500
cgcgctaaaa gagcaccagt aaagcagacc ttgaacttcg acttgctcaa gcttgctggg 1560
gatgtcgaaa gtaaccccgg cccgatgttg tcccccagga ctttgaatgc atgggtcaaa 1620
gtgattgagg agaaggcctt ctcccccgaa gttattccga tgtttaccgc gcttagtgaa 1680
ggggccacac ctcatgatct gaatacgatg cttaacacta taggggggtca ccaggcagcg 1740
atgcaaatgc tgaaggatac catcaatgaa gaagcagctg aatgggacag ggtacatcca 1800
gtgcatgcag gaccggttgc acccggacaa atgcgcgacc cgcgaggttc cgacatcgcg 1860
gggtcaacgt ccaccctgca agaacaaatt gcatggatga ccaataatcc ccctatccca 1920
gtgggcgaca tatataagcg ctggataatc atgggtctca ataaaattgt aaggatgtat 1980
agtccggtgt caatcctgga cataaagcaa ggtcccaagg aaccgtttcg cgactatgta 2040
gacagatttt atcgaacgct gagagccgag caagcgagcc aggatgtcaa aaactggatg 2100
accgaaacac ttctcgttca gaattcaaac ccggattgta agacaatact taaggcgctc 2160
ggtcccgggg cgacccttga agagatgatg tctgcttgtc aaggtgttgg gggtccatcc 2220
cacaaagctc gcgtcctggc ggaagcaatg tgccaagtcg ccaaagaaat cgtcgcgtgc 2280
tgtgacaagt gccaactcaa gggtgaggcg atccatgggc aagtggactg tagtccaggc 2340
gtatggcaat tggactgtac gcatctcgaa gggaaggtga tcttggtggc cgtccatgtg 2400
gcgagcggat atattgaagc cgaaatcatc cctaccgaaa cgggacaaga aacggcgtat 2460
ttcattttga aactggcggg tcggtggccg gtcaccacca tggccgcgcg agcgagcata 2520
cttagcgggg gtaaattgga caagtgggag aagatccggc ttcggcccgg gggtcggaaa 2580
aaatataagc tgaagcacct ggtctgggca tcacgagaac tggagcggtt cgcacttaat 2640
ccagggttgc ttgaaaccgc agccgcggtg aaggccgcct gctggtgggc gggagtaaag 2700
caggagttcg gaattcctta caacacgcag agccaaggtg tagtggaaag catgaacaat 2760
gagcttaaga aaatcattgg tcagatcaga gaccaagcgg aacacctcaa gacagctgtg 2820
caaatggctg tacttattca caacttcaag agaaaaggcg gtataggaga atatagcgcg 2880
ggggaaagaa taatagacat catcgctact caagggtttt tccccgactg gcagaattat 2940
acacctggcc ccggtatacg gtttccactt actttcggct ggtgtttcaa gttggtgcct 3000
ctcctgataa aaaaggagaa aatatatctt gcgtgggtgc ctgcacacaa aggtataggc 3060
ggtaacgaac aaatcgacaa attggttagc 3090

<210> SEQ ID NO 217
<211> LENGTH: 3069
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 217
atgttccccc agattacact gtggcagcga cctctggtca ccatcaagat tgggggacag 60
cttaaggaag cgctgcttga cactggtgct gatgacactg tactggagga gatgaatctc 120
ccgggtcgct ggaagcctaa aatgataggc ggtatcgggg ggttcattaa ggtcaggcag 180
tacgaccaag aagaggtcgg attcccggta aagccacaag tgcctcttcg cccgatgacg 240
ttcaagggtg cgttggacct cagccacttt cttcgagaaa agggcggact ggaaggtctg 300
atacctaaat ttaagctccc tattcagaag gaaacatggg agacatggtg gacggagtat 360
tggcaggcga catggatccc cgagtgggaa tttgtaaaca ccccgccact cgtaaaactc 420
tggtaccaac tggaaaagga acccatcgtc ggtgctgaaa ccttctacgt cgatggtgcg 480
gctaataggg aaacgaagtg gggtttcact accccagaca aaaaacatca aaaagaacca 540
ccctttctct ggatgggata tgaattgcat cccgataaat ggaccgtgca acccatcgtt 600
ctgccggaaa aggacagctg gaccgttaat gatattcaga agcttgttgg gaaactcaac 660
tgggcttccc aaatttaccc gggaataaag gtgataacga aaattcagaa ttttagggtg 720
tactataggg actcacgcga tcctctttgg aaaggtccag caaagttgtt gtggaaaggt 780
gagggggctg tcgtcatcca agacaatagt gatattaagg tcgtgcctag aagaaaggca 840
aagattatta gggattacgg caagcagatg gctggtgacg actgtgttgc aagtcgccaa 900
gacgaagatg gcacggtgtt ggtcgggccc acaccagtaa acattatagg ccgaaatctg 960
cttactcaaa tcggatgtac tcttaatttt ccgatctccc ctatagaaac ggttcctgta 1020
aaattgaaac ctggaatgga tggtccgaaa gttaaacagt ggccgctcac cgaggaaaag 1080
attaaagcgc ttgtcgagat ctgtactgaa atggaaaaag aaggaaagat ctccaaaata 1140
gggccagaaa atccgtacaa tactccagtc tttgctataa agaagaagga ttctacgaag 1200

-continued tggaggaagc tggtagactt tcgcgagctc aacaaacgca cgcaagattt ttgggaagtc 1260
cagttgggca tccctcatcc agctggactc aagaaaaaaa aatccgtcac agtattggat 1320
gtgggcgacg cctacttttc agtgccattg gacaaagatt ttcgaaaata caccgcgttc 1380
acaattccta gtatcaataa cgagactccc ggaataaggt accagtacaa cgtgctccct 1440
caagggtgga aaggttctcc cgcgatattt cagtccagta tgactcgcgc gaaacgagct 1500
ccagttaaac agaccctcaa ctttgatttg ttgaagcttg ctggggatgt tgagagtaat 1560
ccaggcccta tgctgccgca aatcacactc tggcaaaggc cgatagtgac cattaaaatt 1620
ggcgggcaga tcaaggaggc attgcttgat acgggagcag acgatacagt gttggaggac 1680
atgaacctgc ccggaaaatg gaaaccaaag atgatcggtg ggattggcgg tttcataaag 1740
gtcaagcagt atgaccagtg ggtctgaca accccctgaca aaaaacatca gaaggatccc 1800
ccctttcttt ggatgggtta tgagttgcat ccagatcgct ggacggtgca gcctattgag 1860
cttccggaaa aggagtcttg gacagttaat gatattcaaa aacttattgg gaaattgaat 1920
tgggccagcc agatatacgc aggtataaaa gttgcggcgc aggaggagga agaagtgggg 1980
ttccccgtcc gaccccaggt gccgctcaga ccaatgacgt ataaaggtgc gttggatctg 2040
agtcattttt tgaaggaaaa aggcgggttg gaaggcatta ccaaactcca aaacttccgg 2100
gtgtattatc gggacaacag agatccactc tggaagggtc ccgcaagatt gctttggaag 2160
ggagaaggag cagttgttat acaagacaac tccgaaatta aggtagtgcc tagacggaag 2220
gttaaaatta ttagggacta cggaaaacgg atggcggggg atgactgcgt cgcgggccgc 2280
caggacgagg acccgaaatt ccgcctgcct atacaaaagg agacgtggga cacgtggtgg 2340
acagactact ggcaagcaac gtggatcccg gaatgggaat ttactaacac acctcctttg 2400
gtgaaactct ggtatcaact cgagacggag ccgattgcag gggtcgagac attttacgtc 2460
gatggagcat ccaataggga aactaaagca gctggtacag ttctgatagg tccgaccccg 2520
gtgaatataa taggcaggaa tctcctcaca caacttggct gcactttgaa tttcccaatt 2580
tccccaattg acaccgtacc cgtaaagttg aagcctggaa tggacggacc acgagtgaag 2640
cagtggcctc tcacggaaga aaagatcaaa gcgcttattg aaatttgtac agaaatggag 2700
aaggagggta aaatctccag gataggtcct gaaaacccgt acaacacgcc catcttcgct 2760
atcaaaaaaa aagatggaac gaaatggcgc aagctggtgg acttcagaga acttaacaaa 2820
aagacgcagg atttttggga agtccagttg ggaatccctc acccgagcgg acttaaaaaa 2880
aagaaaagtg tcacagttct tgatataggc gacgcttatt tttccgtccc acttgacaag 2940
gaatttagga agtacacggc gtttacagtg ccatcaacga acaacgaaac cccgggggtg 3000
cgctaccagt acaacgtact gccaatggga tggaaaggtt cacccgcaat ctttcaatgc 3060
tcaatgact 3069

<210> SEQ ID NO 218
<211> LENGTH: 3069
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 218
atgacggtaa aggcagcatg ctggtgggca ggtataaaac aggaattcgg cattccgtat 60
aacccacaaa gtcaaggagt tgtcgagtcc atgaacaaag aattgaaaaa gataattggt 120

-continued

```
caagtgcgag accaagcaga acacctgaaa accgcggttc aaatggccgt gtttatacac    180
aactttaaga gaaaaggggg catcgggggc tactccgcgg gtgaacgcat agtcgatata    240
atagccatct cccctcgcac tctcaacgca tgggtgaaag tcgtagagga gaaagctttc    300
tcacctgaag taattccgat gtttagtgca ctgagtgaag gcgctacgcc tcaagatctg    360
aacacgatgc ttaataccgt cggggggtcac caagccgcga tgcagatgtt gaaggaaaca    420
ataaatgagg aagcagcaga gtgggacaga cttcacccgg tccacgcggg accaatcgca    480
ccaggacaaa tgcgagaacc gagaggtagt gacatcgccg gaacaacctc caccctccag    540
gaacagattg gttggatgac aaataatcct ccgatacccg tcggtgagat ctacaaacgc    600
tggatcatcc tgggtcttaa caagatcgta cggatgtaca gcccaaccag tatccttgac    660
attaggcagg gaccgaagga gccgtttcgc gactacgtcg atcggtttta caagacgctt    720
agagcggaac aagcgtcaca ggaagttaaa aattggatga cagaaacctt gcttgtccag    780
aatgctaatc ccgattgcaa aactattctg aaggcactgg gtcctgcggc gactttggag    840
gagatgatga cggcctgtca aggtgttgga ggccctggtc ataaggcacg agtcctggct    900
gaagcaatgt ctcaaatggc ggctagagcc tctgtgctgt ccggagggga gcttgaccgc    960
tgggaaaaga tccgattgcg accaggtggg aaaaagaagt acaggctcaa gcatattgtg   1020
tgggcatcac gggaacttga gcgcttcgca gtcaatcctg gacttcttga aacgccaccg   1080
gtggtcgcta aagagatcgt tgcgagctgt gataaatgtc aacttaaagg cgaggctatg   1140
catggccagg tcgactgtag cccgggcatc tggcagctgg attgcactca cctggagggt   1200
aagatcattc tcgtggcggt ccatgttgcc agtggctaca ttgaggcgga ggtgattcct   1260
gcggaaactg gtcaggagac agcctatttc ttgctgaagc tcgcgggacg ctggcctgtc   1320
aaaactaagg aaaaggttta tttggcctgg gttcccgcac ataaaggaat tggtggcaat   1380
gaacaggtag acaaacttgt aagtactcag ggatattttc ccgattggca gaattacact   1440
ccagggccgg ggactaggta ccctttgaca tttggttggt gttttaagct tgtgcctgtt   1500
cgggcgaaga gggcgccagt caaacagact ctgaatttcg acctgctgaa gctggcagga   1560
gacgtcgagt ccaaccctgg tcctatgttc ccacagatta ctctgtggca gcgcccgctt   1620
gtgactatta aaatcggcgg acaactcaaa gaggcactcc ttgacaccgg agcggacgac   1680
acggtgctgg aagaaatgaa cttgcccggc cggtggaagc caaagatgat cggaggtatc   1740
ggcggcttta taaaggtgcg ccagtatgac caagaagaag tcggcttccc agtaaagcct   1800
caagttccac tgagacctat gacttttaag ggtgcgcttg atctgtcaca cttcctccga   1860
gagaaaggcg gcttggaggg ccttattccc aagttcaagt tgcctattca aaaagaaacg   1920
tgggagacgt ggtggactga atattggcag gcgacctgga tccctgaatg ggagttcgtg   1980
aacacacccc cactcgttaa actctggtat cagttggaaa aggaacccat cgtgggcgcc   2040
gagacatttt acgtcgatgg tgccgctaac agagagacca agtgggggtt tacaacgcct   2100
gacaagaagc accagaagga gcccccctttc ctttggatgg gatatgagtt gcacccccgac   2160
aaatggaccg tgcaaccgat tgtcttgcct gagaaagact cttggacagt gaacgatatc   2220
caaaaacttg tgggaaaatt gaattgggca agccaaatct acccagggat aaaggtaatc   2280
actaagattc aaaacttccg agtatactac cgagacagca gagatccctt gtggaaaggt   2340
cctgcgaaac tgctctggaa aggcgaggga gctgtggtca ttcaggacaa ctcagacatc   2400
aaagtagtcc cacgccgcaa agcgaaaatc atacgcgact atggcaaaca aatggcaggt   2460
gatgattgtg tggcgagtcg acaagatgag gatggtaccg ttctggtcgg gccgacacct   2520
```

```
gttaatatta taggacgcaa tttgttgaca caaatcggct gcactcttaa cttcccgata   2580
agtcccatcg agacagtgcc agttaaattg aagccaggga tggacggtcc taaggttaag   2640
cagtggcccc tcactgaaga aaaaatcaag gctctcgtgg aaatttgcac tgagatggag   2700
aaggagggca aaatctccaa gataggtcca gagaacccat ataatacgcc ggtatttgca   2760
atcaaaaaaa aggacagcac aaagtggcga aagctggttg actttcgaga gctgaacaag   2820
cggacgcagg acttttggga agtccaattg ggaataccgc atcccgctgg attgaaaaaa   2880
aaaaagagcg taacagtcct cgatgtaggt gatgcatact tcagtgtccc actcgataaa   2940
gattttagaa agtacactgc ttttacgatt ccatccatta acaacgagac tcccggtatt   3000
cgatatcaat acaatgtact cccacaaggt tggaaaggct cacctgcgat cttccaaagt   3060
agcatgact                                                          3069
```

<210> SEQ ID NO 219
<211> LENGTH: 3090
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 219

```
atgttgtctc ctagaactct gaatgcttgg gtaaaggtga tcgaagaaaa ggcattctca     60
cccgaggtta tccctatgtt tactgcgttg agcgaaggcg caacacccca tgatctgaac    120
acaatgctga atacaatcgg cggacatcaa gctgctatgc aaatgcttaa ggacaccatc    180
aatgaggagg cagccgagtg ggatcgcgtt catccagtcc acgctgggcc cgttgcgcct    240
ggtcagatga gggacccacg aggatccgac atcgcaggga gcaccagtac actccaagag    300
cagattgcat ggatgacgaa caatccacca atacctgtcg gtgacattta caaaaggtgg    360
attattatgg gcttgaacaa aattgtacgg atgtatagcc cggtgagcat actggacatt    420
aaacagggtc caaaagaacc ctttcgagat tacgttgaca gattttatag gacactgagg    480
gcggaacaag cgtctcaaga cgttaaaaac tggatgacag aaacgctgct tgtacagaat    540
tccaacccag actgcaaaac tatactgaaa gcgctcggtc ccggtgcgac acttgaggaa    600
atgatgagcg catgccaggg cgtcggaggg ccgtctcaca aggcccgcgt gttggcggaa    660
gctatgtgcc aggtggctaa ggagatagta gcatgttgtg ataaatgtca gcttaaaggt    720
gaagctatac atgggcaggt ggattgtagc ccgggtgtat ggcagctgga ctgtactcat    780
ctggaaggaa aggtaatact tgtcgcagtt catgtcgcga gcggatacat tgaagctgaa    840
atcattccta cggagacggg ccaagagaca gcttacttca tacttaaact tgctgggcga    900
tggccggtga caactatggc ggcgcgcgct tcaattttga gtggtggaaa gttggacaag    960
tgggagaaga ttagactcag acccggaggg agaaagaagt ataaactgaa acatctggtt   1020
tgggcttcac gcgaacttga acggtttgct ctcaaccccg ggctgctcga aactgctgct   1080
gctgtaaagg ccgcttgttg gtgggcgggg gtaaagcagg aattcggaat tccatataac   1140
actcaaagcc agggagtagt ggaatccatg aataatgaac ttaagaagat aattggacag   1200
attcgcgatc aggctgaaca tctcaagacg gccgtacaaa tggcagtatt gattcataac   1260
tttaaacgga agggcggcat aggagagtat tctgcgggag aacgcataat agatataatt   1320
gcgactcagg ggttctttcc ggattggcag aactatacgc cggggccagg cattaggttc   1380
cccctcacgt ttggatggtg tttcaagttg gtaccgttgc tcattaaaaa agaaaaaatc   1440
```

```
tacctggcct gggtcccggc gcacaagggt atagggggga acgagcaaat tgataagctc   1500
gtgtcaaggg cgaagcgcgc gccagtcaaa cagaccttga atttcgacct ccttaagctc   1560
gctggagacg tcgaatccaa ccctggcccg atgctgccac aaatcacatt gtggcaacga   1620
cccattgtaa caataaaaat cgggggccag atcaaagaag cgctgcttga caccggcgcc   1680
gacgatacag tcctcgagga tatgaatttg ccaggcaaat ggaagccgaa gatgattggc   1740
ggcattggcg gctttattaa ggttaaacag tatgatcagt ggggattgac cactcccgat   1800
aagaagcatc agaaagatcc gccttttctg tggatggggt acgaactgca ccctgatcga   1860
tggacggtcc agccgataga gctgccggaa aaagaatcat ggaccgtgaa tgatattcaa   1920
aaactgatcg gaaaactcaa ttgggcgtcc cagatatatg ctggcatcaa agttgcagca   1980
caagaagagg aagaggtagg tttcccggtt cggccgcaag ttcccttgcg accgatgaca   2040
tacaagggcg cattggacct ttctcacttc ctcaaggaaa agggcggttt ggagggcatc   2100
actaaacttc agaatttcag agtctactat agagataaca gggacccatt gtggaagggc   2160
cccgctcgac ttctctggaa aggggaggga gcggttgtaa ttcaagacaa cagtgaaatt   2220
aaggtcgtcc cacgacggaa ggttaaaata attcgcgact atggcaagcg aatggcggga   2280
gacgactgtg tagcaggacg acaagacgag gacccaaagt ttagattgcc gatccagaaa   2340
gagacatggg atacgtggtg gacggactat tggcaggcca cctggatacc agaatgggag   2400
tttacaaaca ctcctccact cgtgaaattg tggtatcaac ttgagaccga gcccatagct   2460
ggtgtagaga cgttttacgt tgacggtgct agcaacaggg aaacaaaggc cgctggaacc   2520
gtgctcatcg gtcctactcc tgtgaacata attggacgaa atttgttgac ccagctggga   2580
tgcaccctca atttccccat tagcccaata gataccgtac cagtcaagct taagcctggt   2640
atggacggtc cgcgagttaa gcaatggcca cttactgagg agaaaatcaa ggcactcatc   2700
gagatctgca ccgaaatgga gaaggagggc aaaataagca ggattggtcc cgagaatcca   2760
tataatacgc cgatcttcgc gataaaaaag aaggacggca ccaaatggcg aaaactggtt   2820
gacttccggg agcttaacaa aaaaactcag gatttttggg aagttcaact cgggatccca   2880
cacccgtctg gtcttaaaaa aaaaaaaagc gtaacagtcc ttgacatcgg cgatgcctac   2940
tttagcgtgc ctctcgataa ggagttcaga aaatacacgg ctttcactgt accaagcaca   3000
aacaatgaga ctcctggggt cagataccag tacaatgtcc ttcccatggg gtggaaagga   3060
agccccgcaa tattccagtg ctcaatgacg                                    3090
```

```
<210> SEQ ID NO 220
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Ile Ser Pro Arg Thr Leu Asn Ala Trp Val Lys Val Val Glu Glu Lys
1               5                   10                  15

Ala Phe Ser Pro Glu Val Ile Pro Met Phe Ser Ala Leu Ser Glu Gly
            20                  25                  30

Ala Thr Pro Gln Asp Leu Asn Thr Met Leu Asn Thr Val Gly Gly His
        35                  40                  45

Gln Ala Ala Met Gln Met Leu Lys Glu Thr Ile Asn Glu Glu Ala Ala
    50                  55                  60
```

-continued

Glu Trp Asp Arg Leu His Pro Val His Ala Gly Pro Ile Ala Pro Gly
65 70 75 80

Gln Met Arg Glu Pro Arg Gly Ser Asp Ile Ala Gly Thr Thr Ser Thr
85 90 95

Leu Gln Glu Gln Ile Gly Trp Met Thr Asn Asn Pro Pro Ile Pro Val
100 105 110

Gly Glu Ile Tyr Lys Arg Trp Ile Ile Leu Gly Leu Asn Lys Ile Val
115 120 125

Arg Met Tyr Ser Pro Thr Ser Ile Leu Asp Ile Arg Gln Gly Pro Lys
130 135 140

Glu Pro Phe Arg Asp Tyr Val Asp Arg Phe Tyr Lys Thr Leu Arg Ala
145 150 155 160

Glu Gln Ala Ser Gln Glu Val Lys Asn Trp Met Thr Glu Thr Leu Leu
165 170 175

Val Gln Asn Ala Asn Pro Asp Cys Lys Thr Ile Leu Lys Ala Leu Gly
180 185 190

Pro Ala Ala Thr Leu Glu Glu Met Met Thr Ala Cys Gln Gly Val Gly
195 200 205

Gly Pro Gly His Lys Ala Arg Val Leu Ala Glu Ala Met Ser Gln Pro
210 215 220

Pro Val Val Ala Lys Glu Ile Val Ala Ser Cys Asp Lys Cys Gln Leu
225 230 235 240

Lys Gly Glu Ala Met His Gly Gln Val Asp Cys Ser Pro Gly Ile Trp
245 250 255

Gln Leu Asp Cys Thr His Leu Glu Gly Lys Ile Ile Leu Val Ala Val
260 265 270

His Val Ala Ser Gly Tyr Ile Glu Ala Glu Val Ile Pro Ala Glu Thr
275 280 285

Gly Gln Glu Thr Ala Tyr Phe Leu Leu Lys Leu Ala Gly Arg Trp Pro
290 295 300

Val Lys Thr Met Ala Ala Arg Ala Ser Val Leu Ser Gly Gly Glu Leu
305 310 315 320

Asp Arg Trp Glu Lys Ile Arg Leu Arg Pro Gly Gly Lys Lys Lys Tyr
325 330 335

Arg Leu Lys His Ile Val Trp Ala Ser Arg Glu Leu Glu Arg Phe Ala
340 345 350

Val Asn Pro Gly Leu Leu Glu Thr Ala Ala Thr Val Lys Ala Ala Cys
355 360 365

Trp Trp Ala Gly Ile Lys Gln Glu Phe Gly Ile Pro Tyr Asn Pro Gln
370 375 380

Ser Gln Gly Val Val Glu Ser Met Asn Lys Glu Leu Lys Lys Ile Ile
385 390 395 400

Gly Gln Val Arg Asp Gln Ala Glu His Leu Lys Thr Ala Val Gln Met
405 410 415

Ala Val Phe Ile His Asn Phe Lys Arg Lys Gly Gly Ile Gly Gly Tyr
420 425 430

Ser Ala Gly Glu Arg Ile Val Asp Ile Ile Ala Thr Gln Gly Tyr Phe
435 440 445

Pro Asp Trp Gln Asn Tyr Thr Pro Gly Pro Gly Thr Arg Tyr Pro Leu
450 455 460

Thr Phe Gly Trp Cys Phe Lys Leu Val Pro Val Lys Glu Lys Val Tyr
465 470 475 480

```
Leu Ala Trp Val Pro Ala His Lys Gly Ile Gly Gly Asn Glu Gln Val
                485                 490                 495

Asp Lys Leu Val Ser
            500


<210> SEQ ID NO 221
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Phe Pro Gln Ile Thr Leu Trp Gln Arg Pro Leu Val Thr Ile Lys Ile
1               5                   10                  15

Gly Gly Gln Leu Lys Glu Ala Leu Leu Asp Thr Gly Ala Asp Asp Thr
            20                  25                  30

Val Leu Glu Glu Met Asn Leu Pro Gly Arg Trp Lys Pro Lys Met Ile
        35                  40                  45

Gly Gly Ile Gly Gly Phe Ile Lys Val Arg Gln Tyr Asp Gln Trp Gly
    50                  55                  60

Phe Thr Thr Pro Asp Lys Lys His Gln Lys Glu Pro Pro Phe Leu Trp
65                  70                  75                  80

Met Gly Tyr Glu Leu His Pro Asp Lys Trp Thr Val Gln Pro Ile Val
                85                  90                  95

Leu Pro Glu Lys Asp Ser Trp Thr Val Asn Asp Ile Gln Lys Leu Val
            100                 105                 110

Gly Lys Leu Asn Trp Ala Ser Gln Ile Tyr Pro Gly Ile Lys Val Ala
        115                 120                 125

Ala Gln Glu Glu Glu Glu Val Gly Phe Pro Val Lys Pro Gln Val Pro
    130                 135                 140

Leu Arg Pro Met Thr Phe Lys Gly Ala Leu Asp Leu Ser His Phe Leu
145                 150                 155                 160

Arg Glu Lys Gly Gly Leu Glu Gly Leu Ile Ile Thr Lys Ile Gln Asn
                165                 170                 175

Phe Arg Val Tyr Tyr Arg Asp Ser Arg Asp Pro Leu Trp Lys Gly Pro
            180                 185                 190

Ala Lys Leu Leu Trp Lys Gly Glu Gly Ala Val Val Ile Gln Asp Asn
        195                 200                 205

Ser Asp Ile Lys Val Val Pro Arg Arg Lys Ala Lys Ile Ile Arg Asp
    210                 215                 220

Tyr Gly Lys Gln Met Ala Gly Asp Asp Cys Val Ala Ser Arg Gln Asp
225                 230                 235                 240

Glu Asp Pro Lys Phe Lys Leu Pro Ile Gln Lys Glu Thr Trp Glu Thr
                245                 250                 255

Trp Trp Thr Glu Tyr Trp Gln Ala Thr Trp Ile Pro Glu Trp Glu Phe
            260                 265                 270

Val Asn Thr Pro Pro Leu Val Lys Leu Trp Tyr Gln Leu Glu Lys Glu
        275                 280                 285

Pro Ile Val Gly Ala Glu Thr Phe Tyr Val Asp Gly Ala Ala Asn Arg
    290                 295                 300

Glu Thr Lys Ala Ala Gly Thr Val Leu Val Gly Pro Thr Pro Val Asn
305                 310                 315                 320

Ile Ile Gly Arg Asn Leu Leu Thr Gln Ile Gly Cys Thr Leu Asn Phe
                325                 330                 335
```

Pro Ile Ser Pro Ile Glu Thr Val Pro Val Lys Leu Lys Pro Gly Met
            340                 345                 350

Asp Gly Pro Lys Val Lys Gln Trp Pro Leu Thr Glu Glu Lys Ile Lys
        355                 360                 365

Ala Leu Val Glu Ile Cys Thr Glu Met Glu Lys Glu Gly Lys Ile Ser
    370                 375                 380

Lys Ile Gly Pro Glu Asn Pro Tyr Asn Thr Pro Val Phe Ala Ile Lys
385                 390                 395                 400

Lys Lys Asp Ser Thr Lys Trp Arg Lys Leu Val Asp Phe Arg Glu Leu
                405                 410                 415

Asn Lys Arg Thr Gln Asp Phe Trp Glu Val Gln Leu Gly Ile Pro His
            420                 425                 430

Pro Ala Gly Leu Lys Lys Lys Lys Ser Val Thr Val Leu Asp Val Gly
        435                 440                 445

Asp Ala Tyr Phe Ser Val Pro Leu Asp Lys Asp Phe Arg Lys Tyr Thr
    450                 455                 460

Ala Phe Thr Ile Pro Ser Ile Asn Asn Glu Thr Pro Gly Ile Arg Tyr
465                 470                 475                 480

Gln Tyr Asn Val Leu Pro Gln Gly Trp Lys Gly Ser Pro Ala Ile Phe
                485                 490                 495

Gln Ser Ser Met Thr
            500

<210> SEQ ID NO 222
<211> LENGTH: 1030
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Ile Ser Pro Arg Thr Leu Asn Ala Trp Val Lys Val Val Glu Glu Lys
1               5                   10                  15

Ala Phe Ser Pro Glu Val Ile Pro Met Phe Ser Ala Leu Ser Glu Gly
            20                  25                  30

Ala Thr Pro Gln Asp Leu Asn Thr Met Leu Asn Thr Val Gly Gly His
        35                  40                  45

Gln Ala Ala Met Gln Met Leu Lys Glu Thr Ile Asn Glu Glu Ala Ala
    50                  55                  60

Glu Trp Asp Arg Leu His Pro Val His Ala Gly Pro Ile Ala Pro Gly
65                  70                  75                  80

Gln Met Arg Glu Pro Arg Gly Ser Asp Ile Ala Gly Thr Thr Ser Thr
                85                  90                  95

Leu Gln Glu Gln Ile Gly Trp Met Thr Asn Asn Pro Pro Ile Pro Val
            100                 105                 110

Gly Glu Ile Tyr Lys Arg Trp Ile Ile Leu Gly Leu Asn Lys Ile Val
        115                 120                 125

Arg Met Tyr Ser Pro Thr Ser Ile Leu Asp Ile Arg Gln Gly Pro Lys
    130                 135                 140

Glu Pro Phe Arg Asp Tyr Val Asp Arg Phe Tyr Lys Thr Leu Arg Ala
145                 150                 155                 160

Glu Gln Ala Ser Gln Glu Val Lys Asn Trp Met Thr Glu Thr Leu Leu
                165                 170                 175

Val Gln Asn Ala Asn Pro Asp Cys Lys Thr Ile Leu Lys Ala Leu Gly

-continued

```
            180                 185                 190

Pro Ala Ala Thr Leu Glu Glu Met Met Thr Ala Cys Gln Gly Val Gly
        195                 200                 205

Gly Pro Gly His Lys Ala Arg Val Leu Ala Glu Ala Met Ser Gln Pro
    210                 215                 220

Pro Val Val Ala Lys Glu Ile Val Ala Ser Cys Asp Lys Cys Gln Leu
225                 230                 235                 240

Lys Gly Glu Ala Met His Gly Gln Val Asp Cys Ser Pro Gly Ile Trp
                245                 250                 255

Gln Leu Asp Cys Thr His Leu Glu Gly Lys Ile Ile Leu Val Ala Val
            260                 265                 270

His Val Ala Ser Gly Tyr Ile Glu Ala Glu Val Ile Pro Ala Glu Thr
        275                 280                 285

Gly Gln Glu Thr Ala Tyr Phe Leu Leu Lys Leu Ala Gly Arg Trp Pro
    290                 295                 300

Val Lys Thr Met Ala Ala Arg Ala Ser Val Leu Ser Gly Gly Glu Leu
305                 310                 315                 320

Asp Arg Trp Glu Lys Ile Arg Leu Arg Pro Gly Gly Lys Lys Lys Tyr
                325                 330                 335

Arg Leu Lys His Ile Val Trp Ala Ser Arg Glu Leu Glu Arg Phe Ala
            340                 345                 350

Val Asn Pro Gly Leu Leu Glu Thr Ala Ala Thr Val Lys Ala Ala Cys
        355                 360                 365

Trp Trp Ala Gly Ile Lys Gln Glu Phe Gly Ile Pro Tyr Asn Pro Gln
    370                 375                 380

Ser Gln Gly Val Val Glu Ser Met Asn Lys Glu Leu Lys Lys Ile Ile
385                 390                 395                 400

Gly Gln Val Arg Asp Gln Ala Glu His Leu Lys Thr Ala Val Gln Met
                405                 410                 415

Ala Val Phe Ile His Asn Phe Lys Arg Lys Gly Gly Ile Gly Gly Tyr
            420                 425                 430

Ser Ala Gly Glu Arg Ile Val Asp Ile Ile Ala Thr Gln Gly Tyr Phe
        435                 440                 445

Pro Asp Trp Gln Asn Tyr Thr Pro Gly Pro Gly Thr Arg Tyr Pro Leu
    450                 455                 460

Thr Phe Gly Trp Cys Phe Lys Leu Val Pro Val Lys Glu Lys Val Tyr
465                 470                 475                 480

Leu Ala Trp Val Pro Ala His Lys Gly Ile Gly Gly Asn Glu Gln Val
                485                 490                 495

Asp Lys Leu Val Ser Arg Ala Lys Arg Ala Pro Val Lys Gln Thr Leu
            500                 505                 510

Asn Phe Asp Leu Leu Lys Leu Ala Gly Asp Val Glu Ser Asn Pro Gly
        515                 520                 525

Pro Phe Pro Gln Ile Thr Leu Trp Gln Arg Pro Leu Val Thr Ile Lys
    530                 535                 540

Ile Gly Gly Gln Leu Lys Glu Ala Leu Leu Asp Thr Gly Ala Asp Asp
545                 550                 555                 560

Thr Val Leu Glu Glu Met Asn Leu Pro Gly Arg Trp Lys Pro Lys Met
                565                 570                 575

Ile Gly Gly Ile Gly Gly Phe Ile Lys Val Arg Gln Tyr Asp Gln Trp
            580                 585                 590

Gly Phe Thr Thr Pro Asp Lys Lys His Gln Lys Glu Pro Pro Phe Leu
        595                 600                 605
```

```
Trp Met Gly Tyr Glu Leu His Pro Asp Lys Trp Thr Val Gln Pro Ile
    610                 615                 620

Val Leu Pro Glu Lys Asp Ser Trp Thr Val Asn Asp Ile Gln Lys Leu
625                 630                 635                 640

Val Gly Lys Leu Asn Trp Ala Ser Gln Ile Tyr Pro Gly Ile Lys Val
                645                 650                 655

Ala Ala Gln Glu Glu Glu Glu Val Gly Phe Pro Val Lys Pro Gln Val
            660                 665                 670

Pro Leu Arg Pro Met Thr Phe Lys Gly Ala Leu Asp Leu Ser His Phe
        675                 680                 685

Leu Arg Glu Lys Gly Gly Leu Glu Gly Leu Ile Ile Thr Lys Ile Gln
    690                 695                 700

Asn Phe Arg Val Tyr Tyr Arg Asp Ser Arg Asp Pro Leu Trp Lys Gly
705                 710                 715                 720

Pro Ala Lys Leu Leu Trp Lys Gly Glu Gly Ala Val Val Ile Gln Asp
                725                 730                 735

Asn Ser Asp Ile Lys Val Val Pro Arg Arg Lys Ala Lys Ile Ile Arg
            740                 745                 750

Asp Tyr Gly Lys Gln Met Ala Gly Asp Asp Cys Val Ala Ser Arg Gln
        755                 760                 765

Asp Glu Asp Pro Lys Phe Lys Leu Pro Ile Gln Lys Glu Thr Trp Glu
    770                 775                 780

Thr Trp Trp Thr Glu Tyr Trp Gln Ala Thr Trp Ile Pro Glu Trp Glu
785                 790                 795                 800

Phe Val Asn Thr Pro Pro Leu Val Lys Leu Trp Tyr Gln Leu Glu Lys
                805                 810                 815

Glu Pro Ile Val Gly Ala Glu Thr Phe Tyr Val Asp Gly Ala Ala Asn
            820                 825                 830

Arg Glu Thr Lys Ala Ala Gly Thr Val Leu Val Gly Pro Thr Pro Val
        835                 840                 845

Asn Ile Ile Gly Arg Asn Leu Leu Thr Gln Ile Gly Cys Thr Leu Asn
    850                 855                 860

Phe Pro Ile Ser Pro Ile Glu Thr Val Pro Val Lys Leu Lys Pro Gly
865                 870                 875                 880

Met Asp Gly Pro Lys Val Lys Gln Trp Pro Leu Thr Glu Glu Lys Ile
                885                 890                 895

Lys Ala Leu Val Glu Ile Cys Thr Glu Met Glu Lys Glu Gly Lys Ile
            900                 905                 910

Ser Lys Ile Gly Pro Glu Asn Pro Tyr Asn Thr Pro Val Phe Ala Ile
        915                 920                 925

Lys Lys Lys Asp Ser Thr Lys Trp Arg Lys Leu Val Asp Phe Arg Glu
    930                 935                 940

Leu Asn Lys Arg Thr Gln Asp Phe Trp Glu Val Gln Leu Gly Ile Pro
945                 950                 955                 960

His Pro Ala Gly Leu Lys Lys Lys Lys Ser Val Thr Val Leu Asp Val
                965                 970                 975

Gly Asp Ala Tyr Phe Ser Val Pro Leu Asp Lys Asp Phe Arg Lys Tyr
            980                 985                 990

Thr Ala Phe Thr Ile Pro Ser Ile  Asn Asn Glu Thr Pro  Gly Ile Arg
        995                 1000                1005

Tyr Gln  Tyr Asn Val Leu Pro  Gln Gly Trp Lys Gly  Ser Pro Ala
    1010                1015                1020
```

Ile Phe Gln Ser Ser Met Thr
1025 1030

<210> SEQ ID NO 223
<211> LENGTH: 1028
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 223

Leu Ser Pro Arg Thr Leu Asn Ala Trp Val Lys Val Ile Glu Glu Lys
1 5 10 15

Ala Phe Ser Pro Glu Val Ile Pro Met Phe Thr Ala Leu Ser Glu Gly
20 25 30

Ala Thr Pro His Asp Leu Asn Thr Met Leu Asn Thr Ile Gly Gly His
35 40 45

Gln Ala Ala Met Gln Met Leu Lys Asp Thr Ile Asn Glu Glu Ala Ala
50 55 60

Glu Trp Asp Arg Val His Pro Val His Ala Gly Pro Val Ala Pro Gly
65 70 75 80

Gln Met Arg Asp Pro Arg Gly Ser Asp Ile Ala Gly Ser Thr Ser Thr
85 90 95

Leu Gln Glu Gln Ile Ala Trp Met Thr Asn Asn Pro Pro Ile Pro Val
100 105 110

Gly Asp Ile Tyr Lys Arg Trp Ile Ile Met Gly Leu Asn Lys Ile Val
115 120 125

Arg Met Tyr Ser Pro Val Ser Ile Leu Asp Ile Lys Gln Gly Pro Lys
130 135 140

Glu Pro Phe Arg Asp Tyr Val Asp Arg Phe Tyr Arg Thr Leu Arg Ala
145 150 155 160

Glu Gln Ala Ser Gln Asp Val Lys Asn Trp Met Thr Glu Thr Leu Leu
165 170 175

Val Gln Asn Ser Asn Pro Asp Cys Lys Thr Ile Leu Lys Ala Leu Gly
180 185 190

Pro Gly Ala Thr Leu Glu Glu Met Met Ser Ala Cys Gln Gly Val Gly
195 200 205

Gly Pro Ser His Lys Ala Arg Val Leu Ala Glu Ala Met Cys Gln Val
210 215 220

Ala Lys Glu Ile Val Ala Cys Cys Asp Lys Cys Gln Leu Lys Gly Glu
225 230 235 240

Ala Ile His Gly Gln Val Asp Cys Ser Pro Gly Val Trp Gln Leu Asp
245 250 255

Cys Thr His Leu Glu Gly Lys Val Ile Leu Val Ala Val His Val Ala
260 265 270

Ser Gly Tyr Ile Glu Ala Glu Ile Ile Pro Thr Glu Thr Gly Gln Glu
275 280 285

Thr Ala Tyr Phe Ile Leu Lys Leu Ala Gly Arg Trp Pro Val Thr Thr
290 295 300

Met Ala Ala Arg Ala Ser Ile Leu Ser Gly Gly Lys Leu Asp Lys Trp
305 310 315 320

Glu Lys Ile Arg Leu Arg Pro Gly Gly Arg Lys Lys Tyr Lys Leu Lys
325 330 335

His Leu Val Trp Ala Ser Arg Glu Leu Glu Arg Phe Ala Leu Asn Pro
340 345 350

-continued

```
Gly Leu Leu Glu Thr Ala Ala Ala Val Lys Ala Ala Cys Trp Trp Ala
        355                 360                 365

Gly Val Lys Gln Glu Phe Gly Ile Pro Tyr Asn Thr Gln Ser Gln Gly
    370                 375                 380

Val Val Glu Ser Met Asn Asn Glu Leu Lys Lys Ile Ile Gly Gln Ile
385                 390                 395                 400

Arg Asp Gln Ala Glu His Leu Lys Thr Ala Val Gln Met Ala Val Leu
                405                 410                 415

Ile His Asn Phe Lys Arg Lys Gly Gly Ile Gly Glu Tyr Ser Ala Gly
            420                 425                 430

Glu Arg Ile Ile Asp Ile Ile Ala Thr Gln Gly Phe Phe Pro Asp Trp
        435                 440                 445

Gln Asn Tyr Thr Pro Gly Pro Gly Ile Arg Phe Pro Leu Thr Phe Gly
    450                 455                 460

Trp Cys Phe Lys Leu Val Pro Leu Leu Ile Lys Lys Glu Lys Ile Tyr
465                 470                 475                 480

Leu Ala Trp Val Pro Ala His Lys Gly Ile Gly Gly Asn Glu Gln Ile
                485                 490                 495

Asp Lys Leu Val Ser Arg Ala Lys Arg Ala Pro Val Lys Gln Thr Leu
            500                 505                 510

Asn Phe Asp Leu Leu Lys Leu Ala Gly Asp Val Glu Ser Asn Pro Gly
        515                 520                 525

Pro Leu Pro Gln Ile Thr Leu Trp Gln Arg Pro Ile Val Thr Ile Lys
    530                 535                 540

Ile Gly Gly Gln Ile Lys Glu Ala Leu Leu Asp Thr Gly Ala Asp Asp
545                 550                 555                 560

Thr Val Leu Glu Asp Met Asn Leu Pro Gly Lys Trp Lys Pro Lys Met
                565                 570                 575

Ile Gly Gly Ile Gly Gly Phe Ile Lys Val Lys Gln Tyr Asp Gln Trp
            580                 585                 590

Gly Leu Thr Thr Pro Asp Lys Lys His Gln Lys Asp Pro Pro Phe Leu
        595                 600                 605

Trp Met Gly Tyr Glu Leu His Pro Asp Arg Trp Thr Val Gln Pro Ile
    610                 615                 620

Glu Leu Pro Glu Lys Glu Ser Trp Thr Val Asn Asp Ile Gln Lys Leu
625                 630                 635                 640

Ile Gly Lys Leu Asn Trp Ala Ser Gln Ile Tyr Ala Gly Ile Lys Val
                645                 650                 655

Ala Ala Gln Glu Glu Glu Glu Val Gly Phe Pro Val Arg Pro Gln Val
            660                 665                 670

Pro Leu Arg Pro Met Thr Tyr Lys Gly Ala Leu Asp Leu Ser His Phe
        675                 680                 685

Leu Lys Glu Lys Gly Gly Leu Glu Gly Ile Thr Lys Leu Gln Asn Phe
    690                 695                 700

Arg Val Tyr Tyr Arg Asp Asn Arg Asp Pro Leu Trp Lys Gly Pro Ala
705                 710                 715                 720

Arg Leu Leu Trp Lys Gly Glu Gly Ala Val Val Ile Gln Asp Asn Ser
                725                 730                 735

Glu Ile Lys Val Val Pro Arg Arg Lys Val Lys Ile Ile Arg Asp Tyr
            740                 745                 750

Gly Lys Arg Met Ala Gly Asp Asp Cys Val Ala Gly Arg Gln Asp Glu
        755                 760                 765
```

```
Asp Pro Lys Phe Arg Leu Pro Ile Gln Lys Glu Thr Trp Asp Thr Trp
    770                 775                 780

Trp Thr Asp Tyr Trp Gln Ala Thr Trp Ile Pro Glu Trp Glu Phe Thr
785                 790                 795                 800

Asn Thr Pro Pro Leu Val Lys Leu Trp Tyr Gln Leu Glu Thr Glu Pro
                805                 810                 815

Ile Ala Gly Val Glu Thr Phe Tyr Val Asp Gly Ala Ser Asn Arg Glu
            820                 825                 830

Thr Lys Ala Ala Gly Thr Val Leu Ile Gly Pro Thr Pro Val Asn Ile
        835                 840                 845

Ile Gly Arg Asn Leu Leu Thr Gln Leu Gly Cys Thr Leu Asn Phe Pro
    850                 855                 860

Ile Ser Pro Ile Asp Thr Val Pro Val Lys Leu Lys Pro Gly Met Asp
865                 870                 875                 880

Gly Pro Arg Val Lys Gln Trp Pro Leu Thr Glu Glu Lys Ile Lys Ala
                885                 890                 895

Leu Ile Glu Ile Cys Thr Glu Met Glu Lys Glu Gly Lys Ile Ser Arg
            900                 905                 910

Ile Gly Pro Glu Asn Pro Tyr Asn Thr Pro Ile Phe Ala Ile Lys Lys
        915                 920                 925

Lys Asp Gly Thr Lys Trp Arg Lys Leu Val Asp Phe Arg Glu Leu Asn
    930                 935                 940

Lys Lys Thr Gln Asp Phe Trp Glu Val Gln Leu Gly Ile Pro His Pro
945                 950                 955                 960

Ser Gly Leu Lys Lys Lys Lys Ser Val Thr Val Leu Asp Ile Gly Asp
                965                 970                 975

Ala Tyr Phe Ser Val Pro Leu Asp Lys Glu Phe Arg Lys Tyr Thr Ala
            980                 985                 990

Phe Thr Val Pro Ser Thr Asn Asn  Glu Thr Pro Gly Val  Arg Tyr Gln
        995                 1000                1005

Tyr Asn  Val Leu Pro Met Gly  Trp Lys Gly Ser Pro  Ala Ile Phe
    1010                1015                1020

Gln Cys  Ser Met Thr
    1025
```

<210> SEQ ID NO 224
<211> LENGTH: 1021
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 224

```
Thr Val Lys Ala Ala Cys Trp Trp Ala Gly Ile Lys Gln Glu Phe Gly
1               5                   10                  15

Ile Pro Tyr Asn Pro Gln Ser Gln Gly Val Val Glu Ser Met Asn Lys
            20                  25                  30

Glu Leu Lys Lys Ile Ile Gly Gln Val Arg Asp Gln Ala Glu His Leu
        35                  40                  45

Lys Thr Ala Val Gln Met Ala Val Phe Ile His Asn Phe Lys Arg Lys
    50                  55                  60

Gly Gly Ile Gly Gly Tyr Ser Ala Gly Glu Arg Ile Val Asp Ile Ile
65                  70                  75                  80

Ala Ile Ser Pro Arg Thr Leu Asn Ala Trp Val Lys Val Val Glu Glu
                85                  90                  95
```

-continued

```
Lys Ala Phe Ser Pro Glu Val Ile Pro Met Phe Ser Ala Leu Ser Glu
            100                 105                 110

Gly Ala Thr Pro Gln Asp Leu Asn Thr Met Leu Asn Thr Val Gly Gly
        115                 120                 125

His Gln Ala Ala Met Gln Met Leu Lys Glu Thr Ile Asn Glu Glu Ala
    130                 135                 140

Ala Glu Trp Asp Arg Leu His Pro Val His Ala Gly Pro Ile Ala Pro
145                 150                 155                 160

Gly Gln Met Arg Glu Pro Arg Gly Ser Asp Ile Ala Gly Thr Thr Ser
                165                 170                 175

Thr Leu Gln Glu Gln Ile Gly Trp Met Thr Asn Asn Pro Pro Ile Pro
            180                 185                 190

Val Gly Glu Ile Tyr Lys Arg Trp Ile Ile Leu Gly Leu Asn Lys Ile
        195                 200                 205

Val Arg Met Tyr Ser Pro Thr Ser Ile Leu Asp Ile Arg Gln Gly Pro
    210                 215                 220

Lys Glu Pro Phe Arg Asp Tyr Val Asp Arg Phe Tyr Lys Thr Leu Arg
225                 230                 235                 240

Ala Glu Gln Ala Ser Gln Glu Val Lys Asn Trp Met Thr Glu Thr Leu
                245                 250                 255

Leu Val Gln Asn Ala Asn Pro Asp Cys Lys Thr Ile Leu Lys Ala Leu
            260                 265                 270

Gly Pro Ala Ala Thr Leu Glu Glu Met Met Thr Ala Cys Gln Gly Val
        275                 280                 285

Gly Gly Pro Gly His Lys Ala Arg Val Leu Ala Glu Ala Met Ser Gln
    290                 295                 300

Met Ala Ala Arg Ala Ser Val Leu Ser Gly Gly Glu Leu Asp Arg Trp
305                 310                 315                 320

Glu Lys Ile Arg Leu Arg Pro Gly Gly Lys Lys Lys Tyr Arg Leu Lys
                325                 330                 335

His Ile Val Trp Ala Ser Arg Glu Leu Glu Arg Phe Ala Val Asn Pro
            340                 345                 350

Gly Leu Leu Glu Thr Pro Pro Val Val Ala Lys Glu Ile Val Ala Ser
        355                 360                 365

Cys Asp Lys Cys Gln Leu Lys Gly Glu Ala Met His Gly Gln Val Asp
    370                 375                 380

Cys Ser Pro Gly Ile Trp Gln Leu Asp Cys Thr His Leu Glu Gly Lys
385                 390                 395                 400

Ile Ile Leu Val Ala Val His Val Ala Ser Gly Tyr Ile Glu Ala Glu
                405                 410                 415

Val Ile Pro Ala Glu Thr Gly Gln Glu Thr Ala Tyr Phe Leu Leu Lys
            420                 425                 430

Leu Ala Gly Arg Trp Pro Val Lys Thr Lys Glu Lys Val Tyr Leu Ala
        435                 440                 445

Trp Val Pro Ala His Lys Gly Ile Gly Gly Asn Glu Gln Val Asp Lys
    450                 455                 460

Leu Val Ser Thr Gln Gly Tyr Phe Pro Asp Trp Gln Asn Tyr Thr Pro
465                 470                 475                 480

Gly Pro Gly Thr Arg Tyr Pro Leu Thr Phe Gly Trp Cys Phe Lys Leu
                485                 490                 495

Val Pro Val Arg Ala Lys Arg Ala Pro Val Lys Gln Thr Leu Asn Phe
            500                 505                 510
```

```
Asp Leu Leu Lys Leu Ala Gly Asp Val Glu Ser Asn Pro Gly Pro Phe
        515                 520                 525

Pro Gln Ile Thr Leu Trp Gln Arg Pro Leu Val Thr Ile Lys Ile Gly
    530                 535                 540

Gly Gln Leu Lys Glu Ala Leu Leu Asp Thr Gly Ala Asp Asp Thr Val
545                 550                 555                 560

Leu Glu Glu Met Asn Leu Pro Gly Arg Trp Lys Pro Lys Met Ile Gly
                565                 570                 575

Gly Ile Gly Gly Phe Ile Lys Val Arg Gln Tyr Asp Gln Glu Glu Val
            580                 585                 590

Gly Phe Pro Val Lys Pro Gln Val Pro Leu Arg Pro Met Thr Phe Lys
        595                 600                 605

Gly Ala Leu Asp Leu Ser His Phe Leu Arg Glu Lys Gly Gly Leu Glu
    610                 615                 620

Gly Leu Ile Pro Lys Phe Lys Leu Pro Ile Gln Lys Glu Thr Trp Glu
625                 630                 635                 640

Thr Trp Trp Thr Glu Tyr Trp Gln Ala Thr Trp Ile Pro Glu Trp Glu
                645                 650                 655

Phe Val Asn Thr Pro Pro Leu Val Lys Leu Trp Tyr Gln Leu Glu Lys
            660                 665                 670

Glu Pro Ile Val Gly Ala Glu Thr Phe Tyr Val Asp Gly Ala Ala Asn
        675                 680                 685

Arg Glu Thr Lys Trp Gly Phe Thr Thr Pro Asp Lys Lys His Gln Lys
    690                 695                 700

Glu Pro Pro Phe Leu Trp Met Gly Tyr Glu Leu His Pro Asp Lys Trp
705                 710                 715                 720

Thr Val Gln Pro Ile Val Leu Pro Glu Lys Asp Ser Trp Thr Val Asn
                725                 730                 735

Asp Ile Gln Lys Leu Val Gly Lys Leu Asn Trp Ala Ser Gln Ile Tyr
            740                 745                 750

Pro Gly Ile Lys Val Ile Thr Lys Ile Gln Asn Phe Arg Val Tyr Tyr
        755                 760                 765

Arg Asp Ser Arg Asp Pro Leu Trp Lys Gly Pro Ala Lys Leu Leu Trp
    770                 775                 780

Lys Gly Glu Gly Ala Val Val Ile Gln Asp Asn Ser Asp Ile Lys Val
785                 790                 795                 800

Val Pro Arg Arg Lys Ala Lys Ile Ile Arg Asp Tyr Gly Lys Gln Met
                805                 810                 815

Ala Gly Asp Asp Cys Val Ala Ser Arg Gln Asp Glu Asp Gly Thr Val
            820                 825                 830

Leu Val Gly Pro Thr Pro Val Asn Ile Ile Gly Arg Asn Leu Leu Thr
        835                 840                 845

Gln Ile Gly Cys Thr Leu Asn Phe Pro Ile Ser Pro Ile Glu Thr Val
    850                 855                 860

Pro Val Lys Leu Lys Pro Gly Met Asp Gly Pro Lys Val Lys Gln Trp
865                 870                 875                 880

Pro Leu Thr Glu Glu Lys Ile Lys Ala Leu Val Glu Ile Cys Thr Glu
                885                 890                 895

Met Glu Lys Glu Gly Lys Ile Ser Lys Ile Gly Pro Glu Asn Pro Tyr
            900                 905                 910

Asn Thr Pro Val Phe Ala Ile Lys Lys Lys Asp Ser Thr Lys Trp Arg
        915                 920                 925

Lys Leu Val Asp Phe Arg Glu Leu Asn Lys Arg Thr Gln Asp Phe Trp
```

```
    930                 935                 940

Glu Val Gln Leu Gly Ile Pro His Pro Ala Gly Leu Lys Lys Lys Lys
945                 950                 955                 960

Ser Val Thr Val Leu Asp Val Gly Asp Ala Tyr Phe Ser Val Pro Leu
                965                 970                 975

Asp Lys Asp Phe Arg Lys Tyr Thr Ala Phe Thr Ile Pro Ser Ile Asn
            980                 985                 990

Asn Glu Thr Pro Gly Ile Arg Tyr  Gln Tyr Asn Val Leu  Pro Gln Gly
        995                 1000                 1005

Trp Lys  Gly Ser Pro Ala Ile  Phe Gln Ser Ser Met  Thr
    1010                 1015                 1020


<210> SEQ ID NO 225
<211> LENGTH: 3090
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 225

atttctcctc ggacgctgaa tgcatgggtg aaggtagtgg aggaaaaggc attttcacca     60

gaagtcattc cgatgttctc cgcgctctcc gagggtgcta cgccacagga cttgaatacg    120

atgctgaata ccgttggtgg ccatcaggcg gcgatgcaga tgttgaagga gacaattaac    180

gaagaagccg ccgaatggga cagattgcac ccggtgcatg cggggccaat agctcctggc    240

cagatgcgcg agcctagggg ttctgacatt gctggtacaa caagtaccct tcaggagcag    300

attggttgga tgacgaataa ccctcccata cctgttggcg agatctataa gcgctggatt    360

atacttgggc tgaataagat agtccgaatg tattctccca cctctattct ggatattcgg    420

caaggaccta aggagccgtt tagagactac gtagaccggt tttacaaaac cctgcgggcg    480

gaacaagctt ctcaggaagt caaaaattgg atgactgaga ccttgctcgt ccagaatgcg    540

aacccggact gtaaaacaat actcaaagcg ctgggccccg ctgcaaccct ggaagaaatg    600

atgacggctt gtcagggagt aggaggcccc ggacataagg cacgagtgtt ggcagaagcc    660

atgagccagc cgcctgtcgt cgcgaaagaa atcgtcgctt cttgcgacaa atgtcagctg    720

aagggggagg cgatgcacgg tcaagttgat tgctctcccg gtatttggca attggactgt    780

acccaccttg aaggcaaaat tattctggtt gcagtgcacg tagcatccgg ttacatcgaa    840

gctgaagtga tacccgcaga gacaggccag gagacggctt atttcctcct taagcttgcg    900

ggtcggtggc ccgtaaagac catggctgct cgggcatctg tcctctccgg tggtgaactc    960

gaccgatggg aaaagattcg attgcgcccc ggaggaaaga agaaatatag gctgaaacat   1020

attgtgtggg catcacggga acttgagcga tttgcggtaa acccaggcct tttggaaaca   1080

gctgcaactg tgaaagcggc ttgctggtgg gcggggataa aacaggagtt tggtatcccg   1140

tacaatcccc aatctcaggg ggtagtagaa agcatgaaca aagaattgaa aaaaataatt   1200

ggccaggttc gcgaccaagc cgagcacctc aagaccgctg tacagatggc tgtatttatt   1260

cacaacttca agcggaaggg cggaatagga ggatatagcg caggggaaag gattgttgat   1320

attattgcaa cacaaggtta ctttcctgac tggcaaaact acacaccggg ccctggcacg   1380

cgctatcccc ttacgttcgg ttggtgcttc aagctggtgc cggtaaaaga aaaagtttat   1440

ttggcatggg ttcctgcaca taaaggaata gggggtaacg aacaagttga caaactcgtc   1500

agccgcgcta aaagagcccc agtcaagcag accctgaatt ttgacctgct taaattggct   1560
```

-continued

```
ggggacgtcg agagtaaccc gggacccttc ccacaaatta cactctggca gcgaccactg   1620

gtaacaatca aaataggggg acaattgaaa gaagcactcc tggatacggg cgcggacgat   1680

acagtcctgg aggaaatgaa tctccccggc cgctggaaac ctaagatgat agggggggatc  1740

ggtggattta ttaaagtgcg gcagtacgat caatggggtt ttacgacacc tgacaagaaa   1800

catcaaaagg agccgccatt tctttggatg ggttatgagc ttcatccgga taaatggact   1860

gttcagccga ttgtcctccc cgagaaggat agttggactg tgaacgacat ccagaagctg   1920

gtcgggaaac ttaattgggc cagtcaaata tatccaggta ttaaagttgc cgcacaagaa   1980

gaggaggaag tagggttccc cgtgaaaccg caagtccctc tccggcccat gacctttaag   2040

ggcgctctcg acctgtccca tttcctccgc gaaaaggggg gtttggaagg cttgatcatt   2100

accaagattc aaaacttcag ggtctattat cgagacagtc gcgatcccct ttggaaagga   2160

cctgcgaaac ttctttggaa aggagaagga gccgtggtaa ttcaggataa ttctgacata   2220

aaggtcgtcc cacgccgaaa agcgaagatt ataagagatt atggcaagca gatggccggg   2280

gatgattgtg tcgcaagtag acaggatgaa gaccctaaat tcaagcttcc aatccagaag   2340

gaaacgtggg agacatggtg gaccgagtat tggcaagcta cttggatccc agaatgggaa   2400

tttgtgaaca ctcccccact cgtaaagctg tggtaccagc ttgaaaaaga acctatagtc   2460

ggggcggaga cgttctatgt agacggcgcc gctaatcgag agacaaaagc agcaggcacg   2520

gtactggtag gcccgacccc tgtcaacatc attggacgaa atctgttgac ccagattggg   2580

tgtaccctta actttcccat ttcaccaata gagaccgtcc cggttaaact gaaaccgggt   2640

atggatggtc ccaaagtaaa acagtggcca cttaccgagg agaagattaa ggcactcgtt   2700

gaaatatgta cagaaatgga aaaagagggg aaaatctcta aaattggccc tgaaaatccg   2760

tacaacactc cggtattcgc cataaaaaag aaggactcta ccaagtggcg caaactcgtg   2820

gactttagag aactgaataa aaggacccag gacttttggg aagtccagct gggtattcct   2880

caccccgctg gtctcaagaa aaagaaaagt gtcactgtct tggatgttgg agatgcgtac   2940

ttttcagtac ctcttgataa agattttcga aagtataccg cgtttaccat tccctccata   3000

aataacgaaa caccggggat caggtatcaa tataacgtgc ttccacaagg ctggaagggt   3060

tcaccggcta ttttccaatc ttctatgacg                                    3090
```

<210> SEQ ID NO 226
<211> LENGTH: 3090
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 226

```
atgctttcac cgagaacctt gaacgcgtgg gttaaagtaa tcgaagagaa ggcatttagc     60

ccggaggtaa tccccatgtt taccgcactt tccgaaggtg ctacacccca cgacctgaat    120

acaatgttga atactattgg cggccaccaa gctgccatgc agatgcttaa ggacactatt    180

aacgaggaag ccgccgaatg ggatcgcgtt caccctgttc acgcgggtcc agtcgcacca    240

ggacaaatgc gagaccctcg gggtctgac atcgcaggat caactagtac attgcaggaa     300

cagattgctt ggatgaccaa taaccctccg atcccggtag gtgacattta taaacggtgg    360

atcatcatgg gattgaacaa aatagtccga atgtacagtc cagtgagtat tcttgacatt    420

aaacagggac caaaggagcc gttccgggac tacgttgacc ggttttacag gaccctgaga    480
```

-continued

```
gccgaacagg cttcccagga tgtgaaaaac tggatgacag agaccctgct tgttcagaat    540
tcaaatcctg actgtaaaac gattctgaag gcactcggtc ccggcgccac gctggaggaa    600
atgatgtcag cttgtcaggg agtaggagga ccttctcata aggcacgcgt ccttgcagag    660
gccatgtgcc aagtcgcgaa agagatcgtg gcctgttgtg acaagtgcca acttaaggga    720
gaagccatcc atgggcaggt cgattgttct ccgggcgttt ggcaattgga ctgcacgcac    780
ttggagggta aggtgattct tgttgccgtt catgtcgcaa gcggttacat tgaagcggag    840
attatcccaa ctgagaccgg ccaagagact gcatatttca tccttaaact ggcgggaaga    900
tggccggtca cgactatggc tgcacgagca tccatactgt ctgggggaaa gctcgacaag    960
tgggagaaga ttcgacttag gcctggagga agaaaaaagt ataagttgaa acatcttgtt   1020
tgggcatcac gagaacttga acggtttgct ctgaatccgg gattgcttga aaccgccgcg   1080
gctgtaaagg cagcatgttg gtgggctggt gtcaaacaag agttcggtat tccctataac   1140
acccaaagtc aaggcgtcgt agaatccatg aacaatgaac ttaagaaaat tatcggacaa   1200
atccgggacc aagcggaaca cctcaaaact gctgtccaga tggcagttct gattcataac   1260
tttaaaagaa aggggggat aggggagtat tctgcaggtg aacgaattat agacataatt   1320
gccacacaag ggtttttcc agattggcaa aattatacac cgggccctgg gataagattc   1380
ccgctcacct tcggctggtg cttcaaactg gtacccttgc tgatcaagaa agagaagatc   1440
tatcttgctt gggtgccagc ccataaaggg atcgggggta acgaacaaat cgataagctg   1500
gtgtctagag ctaaacgggc tcccgtaaaa cagaccttga acttcgatct gcttaaattg   1560
gcaggggacg tggaaagcaa ccccgggcca atgctgcccc agataacact ttggcaacgc   1620
cccatcgtga caatcaagat cggtggccaa attaaggaag cactcttgga cacgggagca   1680
gacgacactg tgctggagga tatgaacctg ccgggcaagt ggaaaccaaa gatgatcggg   1740
ggcattggcg ggttcataaa ggttaaacag tacgaccaat gggggttgac aacgcctgat   1800
aagaagcatc aaaaagatcc cccatttttg tggatgggtt atgaacttca cccggacagg   1860
tggaccgttc agccgataga gctcccagaa aaggagtctt ggacagttaa tgacatacag   1920
aaacttattg gcaaacttaa ctgggcttca cagatttatg ccggcatcaa agtcgccgcc   1980
caggaagaag aagaggtagg ttttcccgta cgacctcagg ttcctcttcg gcctatgacc   2040
tataagggtg cgcttgatct ttctcacttc cttaaagaaa aaggaggtct ggaaggtatc   2100
acgaaacttc agaattttcg ggtgtattac cgggacaaca gagacccgct ttggaagggg   2160
ccggctaggc ttctgtggaa aggcgaggga gcggtagtta tccaggataa ctctgagata   2220
aaggtagtac cccgacggaa ggtaaagatc atcagagact acggcaagag gatggctgga   2280
gacgactgtg tggccgggcg acaggatgaa gatcctaaat tcaggctgcc aatccaaaaa   2340
gagacgtggg acacatggtg gaccgattat tggcaggcta cgtggatccc cgaatgggag   2400
tttaccaata ctccgccact cgtgaagctt tggtaccaat tggagacaga gcctatagcc   2460
ggcgttgaga ccttctacgt ggatggggcc agcaacagag aaaccaaagc ggccggaacg   2520
gtcctgatcg gtcccacacc tgttaacatc atagggcgca atctgcttac gcaattgggg   2580
tgcacattga attttccaat atcccctatt gataccgtgc cggttaaatt gaagccgggt   2640
atggacgggc ctcgggtcaa gcagtggccc ctgaccgaag aaaagatcaa agccctgatt   2700
gagatctgca cggaaatgga aaaagagggc aagattagtc gcatcggccc ggagaaccca   2760
tacaatactc ctatttttgc aattaaaaaa aaggacggaa caaagtggag gaaacttgta   2820
```

-continued gatttcagag agcttaataa gaaaactcag gacttctggg aggtccaact cggtattccg 2880
catccctccg gacttaagaa gaaaaagtca gtaaccgtct tggatatagg ggacgcttat 2940
ttttcagtgc ccctcgataa agaatttcgc aaatacacgg cgtttactgt gccatctact 3000
aataacgaaa cgccaggcgt gagatatcaa tacaacgtcc ttcctatggg ctggaagggt 3060
tcacccgcaa tttttcagtg ctccatgacc 3090

<210> SEQ ID NO 227
<211> LENGTH: 1029
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 227

Leu Ser Pro Arg Thr Leu Asn Ala Trp Val Lys Val Ile Glu Glu Lys
1 5 10 15

Ala Phe Ser Pro Glu Val Ile Pro Met Phe Thr Ala Leu Ser Glu Gly
20 25 30

Ala Thr Pro His Asp Leu Asn Thr Met Leu Asn Thr Ile Gly Gly His
35 40 45

Gln Ala Ala Met Gln Met Leu Lys Asp Thr Ile Asn Glu Glu Ala Ala
50 55 60

Glu Trp Asp Arg Val His Pro Val His Ala Gly Pro Val Ala Pro Gly
65 70 75 80

Gln Met Arg Asp Pro Arg Gly Ser Asp Ile Ala Gly Ser Thr Ser Thr
85 90 95

Leu Gln Glu Gln Ile Ala Trp Met Thr Asn Asn Pro Pro Ile Pro Val
100 105 110

Gly Asp Ile Tyr Lys Arg Trp Ile Ile Met Gly Leu Asn Lys Ile Val
115 120 125

Arg Met Tyr Ser Pro Val Ser Ile Leu Asp Ile Lys Gln Gly Pro Lys
130 135 140

Glu Pro Phe Arg Asp Tyr Val Asp Arg Phe Tyr Arg Thr Leu Arg Ala
145 150 155 160

Glu Gln Ala Ser Gln Asp Val Lys Asn Trp Met Thr Glu Thr Leu Leu
165 170 175

Val Gln Asn Ser Asn Pro Asp Cys Lys Thr Ile Leu Lys Ala Leu Gly
180 185 190

Pro Gly Ala Thr Leu Glu Glu Met Met Ser Ala Cys Gln Gly Val Gly
195 200 205

Gly Pro Ser His Lys Ala Arg Val Leu Ala Glu Ala Met Cys Gln Val
210 215 220

Ala Lys Glu Ile Val Ala Cys Cys Asp Lys Cys Gln Leu Lys Gly Glu
225 230 235 240

Ala Ile His Gly Gln Val Asp Cys Ser Pro Gly Val Trp Gln Leu Asp
245 250 255

Cys Thr His Leu Glu Gly Lys Val Ile Leu Val Ala Val His Val Ala
260 265 270

Ser Gly Tyr Ile Glu Ala Glu Ile Ile Pro Thr Glu Thr Gly Gln Glu
275 280 285

Thr Ala Tyr Phe Ile Leu Lys Leu Ala Gly Arg Trp Pro Val Thr Thr
290 295 300

-continued

```
Met Ala Ala Arg Ala Ser Ile Leu Ser Gly Gly Lys Leu Asp Lys Trp
305                 310                 315                 320

Glu Lys Ile Arg Leu Arg Pro Gly Gly Arg Lys Lys Tyr Lys Leu Lys
                325                 330                 335

His Leu Val Trp Ala Ser Arg Glu Leu Glu Arg Phe Ala Leu Asn Pro
            340                 345                 350

Gly Leu Leu Glu Thr Ala Ala Ala Val Lys Ala Ala Cys Trp Trp Ala
        355                 360                 365

Gly Val Lys Gln Glu Phe Gly Ile Pro Tyr Asn Thr Gln Ser Gln Gly
    370                 375                 380

Val Val Glu Ser Met Asn Asn Glu Leu Lys Lys Ile Ile Gly Gln Ile
385                 390                 395                 400

Arg Asp Gln Ala Glu His Leu Lys Thr Ala Val Gln Met Ala Val Leu
                405                 410                 415

Ile His Asn Phe Lys Arg Lys Gly Gly Ile Gly Glu Tyr Ser Ala Gly
            420                 425                 430

Glu Arg Ile Ile Asp Ile Ile Ala Thr Gln Gly Phe Phe Pro Asp Trp
        435                 440                 445

Gln Asn Tyr Thr Pro Gly Pro Gly Ile Arg Phe Pro Leu Thr Phe Gly
    450                 455                 460

Trp Cys Phe Lys Leu Val Pro Leu Leu Ile Lys Lys Glu Lys Ile Tyr
465                 470                 475                 480

Leu Ala Trp Val Pro Ala His Lys Gly Ile Gly Gly Asn Glu Gln Ile
                485                 490                 495

Asp Lys Leu Val Ser Arg Ala Lys Arg Ala Pro Val Lys Gln Thr Leu
            500                 505                 510

Asn Phe Asp Leu Leu Lys Leu Ala Gly Asp Val Glu Ser Asn Pro Gly
        515                 520                 525

Pro Met Leu Pro Gln Ile Thr Leu Trp Gln Arg Pro Ile Val Thr Ile
    530                 535                 540

Lys Ile Gly Gly Gln Ile Lys Glu Ala Leu Leu Asp Thr Gly Ala Asp
545                 550                 555                 560

Asp Thr Val Leu Glu Asp Met Asn Leu Pro Gly Lys Trp Lys Pro Lys
                565                 570                 575

Met Ile Gly Gly Ile Gly Gly Phe Ile Lys Val Lys Gln Tyr Asp Gln
            580                 585                 590

Trp Gly Leu Thr Thr Pro Asp Lys Lys His Gln Lys Asp Pro Pro Phe
        595                 600                 605

Leu Trp Met Gly Tyr Glu Leu His Pro Asp Arg Trp Thr Val Gln Pro
    610                 615                 620

Ile Glu Leu Pro Glu Lys Glu Ser Trp Thr Val Asn Asp Ile Gln Lys
625                 630                 635                 640

Leu Ile Gly Lys Leu Asn Trp Ala Ser Gln Ile Tyr Ala Gly Ile Lys
                645                 650                 655

Val Ala Ala Gln Glu Glu Glu Glu Val Gly Phe Pro Val Arg Pro Gln
            660                 665                 670

Val Pro Leu Arg Pro Met Thr Tyr Lys Gly Ala Leu Asp Leu Ser His
        675                 680                 685

Phe Leu Lys Glu Lys Gly Gly Leu Glu Gly Ile Thr Lys Leu Gln Asn
    690                 695                 700

Phe Arg Val Tyr Tyr Arg Asp Asn Arg Asp Pro Leu Trp Lys Gly Pro
705                 710                 715                 720

Ala Arg Leu Leu Trp Lys Gly Glu Gly Ala Val Val Ile Gln Asp Asn
```

-continued

```
                725                 730                 735

Ser Glu Ile Lys Val Val Pro Arg Arg Lys Val Lys Ile Ile Arg Asp
            740                 745                 750

Tyr Gly Lys Arg Met Ala Gly Asp Asp Cys Val Ala Gly Arg Gln Asp
        755                 760                 765

Glu Asp Pro Lys Phe Arg Leu Pro Ile Gln Lys Glu Thr Trp Asp Thr
    770                 775                 780

Trp Trp Thr Asp Tyr Trp Gln Ala Thr Trp Ile Pro Glu Trp Glu Phe
785                 790                 795                 800

Thr Asn Thr Pro Pro Leu Val Lys Leu Trp Tyr Gln Leu Glu Thr Glu
                805                 810                 815

Pro Ile Ala Gly Val Glu Thr Phe Tyr Val Asp Gly Ala Ser Asn Arg
            820                 825                 830

Glu Thr Lys Ala Ala Gly Thr Val Leu Ile Gly Pro Thr Pro Val Asn
        835                 840                 845

Ile Ile Gly Arg Asn Leu Leu Thr Gln Leu Gly Cys Thr Leu Asn Phe
    850                 855                 860

Pro Ile Ser Pro Ile Asp Thr Val Pro Val Lys Leu Lys Pro Gly Met
865                 870                 875                 880

Asp Gly Pro Arg Val Lys Gln Trp Pro Leu Thr Glu Glu Lys Ile Lys
                885                 890                 895

Ala Leu Ile Glu Ile Cys Thr Glu Met Glu Lys Glu Gly Lys Ile Ser
            900                 905                 910

Arg Ile Gly Pro Glu Asn Pro Tyr Asn Thr Pro Ile Phe Ala Ile Lys
        915                 920                 925

Lys Lys Asp Gly Thr Lys Trp Arg Lys Leu Val Asp Phe Arg Glu Leu
    930                 935                 940

Asn Lys Lys Thr Gln Asp Phe Trp Glu Val Gln Leu Gly Ile Pro His
945                 950                 955                 960

Pro Ser Gly Leu Lys Lys Lys Lys Ser Val Thr Val Leu Asp Ile Gly
                965                 970                 975

Asp Ala Tyr Phe Ser Val Pro Leu Asp Lys Glu Phe Arg Lys Tyr Thr
            980                 985                 990

Ala Phe Thr Val Pro Ser Thr Asn  Asn Glu Thr Pro Gly  Val Arg Tyr
        995                 1000                 1005

Gln Tyr  Asn Val Leu Pro Met  Gly Trp Lys Gly Ser  Pro Ala Ile
    1010                 1015                 1020

Phe Gln  Cys Ser Met Thr
    1025


<210> SEQ ID NO 228
<211> LENGTH: 507
<212> TYPE: PRT
<213> ORGANISM: SIVsme543

<400> SEQUENCE: 228

Met Gly Ala Arg Asn Ser Val Leu Ser Gly Lys Lys Ala Asp Glu Leu
1               5                   10                  15

Glu Lys Ile Arg Leu Arg Pro Asn Gly Lys Lys Lys Tyr Met Leu Lys
            20                  25                  30

His Val Val Trp Ala Ala Asn Glu Leu Asp Arg Phe Gly Leu Ala Glu
        35                  40                  45

Ser Leu Leu Asp Asn Lys Glu Gly Cys Gln Lys Ile Leu Ser Val Leu
    50                  55                  60
```

```
Ala Pro Leu Val Pro Thr Gly Ser Glu Asn Leu Lys Ser Leu Tyr Asn
65                  70                  75                  80

Thr Val Cys Val Ile Trp Cys Ile His Ala Glu Glu Lys Val Lys His
                85                  90                  95

Thr Glu Glu Ala Lys Gln Ile Val Gln Arg His Leu Val Val Glu Thr
            100                 105                 110

Gly Thr Ala Asp Lys Met Pro Ala Thr Ser Arg Pro Thr Ala Pro Pro
        115                 120                 125

Ser Gly Arg Gly Gly Asn Tyr Pro Val Gln Gln Val Gly Gly Asn Tyr
    130                 135                 140

Val His Leu Pro Leu Ser Pro Arg Thr Leu Asn Ala Trp Val Lys Leu
145                 150                 155                 160

Val Glu Glu Lys Lys Phe Gly Ala Glu Val Val Pro Gly Phe Gln Ala
                165                 170                 175

Leu Ser Glu Gly Cys Thr Pro Tyr Asp Ile Asn Gln Met Leu Asn Cys
            180                 185                 190

Val Gly Glu His Gln Ala Ala Met Gln Ile Ile Arg Glu Ile Ile Asn
        195                 200                 205

Glu Glu Ala Ala Asp Trp Asp Leu Gln His Pro Gln Pro Gly Pro Leu
    210                 215                 220

Pro Ala Gly Gln Leu Arg Glu Pro Arg Gly Ser Asp Ile Ala Gly Thr
225                 230                 235                 240

Thr Ser Thr Val Glu Glu Gln Ile Gln Trp Met Tyr Arg Gln Gln Asn
                245                 250                 255

Pro Ile Pro Val Gly Asn Ile Tyr Arg Arg Trp Ile Gln Leu Gly Leu
            260                 265                 270

Gln Lys Cys Val Arg Met Tyr Asn Pro Thr Asn Ile Leu Asp Val Lys
        275                 280                 285

Gln Gly Pro Lys Glu Pro Phe Gln Ser Tyr Val Asp Arg Phe Tyr Lys
    290                 295                 300

Ser Leu Arg Ala Glu Gln Thr Asp Pro Ala Val Lys Asn Trp Met Thr
305                 310                 315                 320

Gln Thr Leu Leu Ile Gln Asn Ala Asn Pro Asp Cys Lys Leu Val Leu
                325                 330                 335

Lys Gly Leu Gly Met Asn Pro Thr Leu Glu Glu Met Leu Thr Ala Cys
            340                 345                 350

Gln Gly Ile Gly Gly Pro Gly Gln Lys Ala Arg Leu Met Ala Glu Ala
        355                 360                 365

Leu Lys Glu Ala Leu Arg Pro Asp Gln Leu Pro Phe Ala Ala Val Gln
    370                 375                 380

Gln Lys Gly Gln Arg Arg Thr Ile Lys Cys Trp Asn Cys Gly Lys Glu
385                 390                 395                 400

Gly His Ser Ala Arg Gln Cys Arg Ala Pro Arg Arg Gln Gly Cys Trp
                405                 410                 415

Gly Cys Gly Lys Thr Gly His Val Met Ala Lys Cys Pro Glu Arg Gln
            420                 425                 430

Ala Gly Phe Leu Gly Phe Gly Pro Trp Gly Lys Lys Pro Arg Asn Phe
        435                 440                 445

Pro Met Ala Gln Met Pro Gln Gly Leu Thr Pro Thr Ala Pro Pro Glu
    450                 455                 460

Asp Pro Ala Val Asp Leu Leu Lys Asn Tyr Met Lys Met Gly Arg Lys
465                 470                 475                 480

Gln Arg Glu Asn Arg Glu Arg Pro Tyr Lys Glu Val Thr Glu Asp Leu
```

```
                485                 490                 495

Leu His Leu Asn Ser Leu Phe Gly Glu Asp Gln
            500                 505


<210> SEQ ID NO 229
<211> LENGTH: 531
<212> TYPE: PRT
<213> ORGANISM: SIVsme543

<400> SEQUENCE: 229

Pro Gln Phe Ser Leu Trp Arg Arg Pro Val Val Thr Ala Tyr Ile Glu
1               5                   10                  15

Glu Gln Pro Val Glu Val Leu Leu Ala Asp Asp Ser Ile Val Thr Gly
            20                  25                  30

Ile Glu Leu Gly Pro Asn Tyr Thr Pro Lys Ile Val Gly Gly Ile Gly
        35                  40                  45

Gly Phe Ile Asn Thr Lys Glu Tyr Lys Asp Val Lys Ile Lys Val Leu
    50                  55                  60

Gly Lys Val Ile Lys Gly Thr Ile Met Thr Gly Asp Thr Pro Ile Asn
65                  70                  75                  80

Ile Phe Gly Arg Asn Leu Leu Thr Ala Met Gly Met Ser Leu Asn Phe
                85                  90                  95

Pro Ile Ala Lys Val Glu Pro Ile Lys Val Thr Leu Lys Pro Gly Lys
            100                 105                 110

Glu Gly Pro Lys Leu Arg Gln Trp Pro Leu Ser Lys Glu Lys Ile Ile
        115                 120                 125

Ala Leu Arg Glu Ile Cys Glu Lys Met Glu Lys Asp Gly Gln Leu Glu
    130                 135                 140

Glu Ala Pro Pro Thr Asn Pro Tyr Asn Thr Pro Thr Phe Ala Ile Lys
145                 150                 155                 160

Lys Lys Asp Lys Asn Lys Trp Arg Met Leu Ile Asp Phe Arg Glu Leu
                165                 170                 175

Asn Lys Val Thr Gln Asp Phe Thr Glu Val Gln Leu Gly Ile Pro His
            180                 185                 190

Pro Ala Gly Leu Ala Lys Arg Arg Arg Ile Thr Val Leu Asp Val Gly
        195                 200                 205

Asp Ala Tyr Phe Ser Ile Pro Leu Asp Glu Glu Phe Arg Gln Tyr Thr
    210                 215                 220

Ala Phe Thr Leu Pro Ser Val Asn Asn Ala Glu Pro Gly Lys Arg Tyr
225                 230                 235                 240

Ile Tyr Lys Val Leu Pro Gln Gly Trp Lys Gly Ser Pro Ala Ile Phe
                245                 250                 255

Gln Tyr Thr Met Arg Asn Val Leu Glu Pro Phe Arg Lys Ala Asn Pro
            260                 265                 270

Asp Val Thr Leu Ile Gln Ile Leu Ile Ala Ser Asp Arg Thr Asp Leu
        275                 280                 285

Glu His Asp Arg Val Val Leu Gln Leu Lys Glu Leu Leu Asn Gly Ile
    290                 295                 300

Gly Phe Ser Thr Pro Glu Glu Lys Phe Gln Lys Asp Pro Pro Phe Gln
305                 310                 315                 320

Trp Met Gly Tyr Glu Leu Trp Pro Thr Lys Trp Lys Leu Gln Lys Ile
                325                 330                 335

Glu Leu Pro Gln Arg Glu Thr Trp Thr Val Asn Asp Ile Gln Lys Leu
            340                 345                 350
```

```
Val Gly Val Leu Asn Trp Ala Ala Gln Ile Tyr Pro Gly Ile Lys Thr
        355                 360                 365

Lys His Leu Cys Arg Leu Ile Arg Gly Lys Met Thr Leu Thr Glu Glu
    370                 375                 380

Val Gln Trp Thr Glu Met Ala Glu Ala Glu Tyr Glu Glu Asn Lys Ile
385                 390                 395                 400

Ile Leu Ser Gln Glu Gln Glu Gly Cys Tyr Tyr Gln Glu Gly Lys Pro
                405                 410                 415

Ile Glu Ala Thr Val Ile Lys Ser Gln Asp Asn Gln Trp Ser Tyr Lys
            420                 425                 430

Ile His Gln Glu Asp Lys Val Leu Lys Val Gly Lys Phe Ala Lys Val
        435                 440                 445

Lys Asn Thr His Thr Asn Gly Val Arg Leu Leu Ala His Val Val Gln
    450                 455                 460

Lys Ile Gly Lys Glu Ala Leu Val Ile Trp Gly Glu Val Pro Lys Phe
465                 470                 475                 480

His Leu Pro Val Glu Arg Glu Ile Trp Glu Gln Trp Trp Thr Asp Tyr
                485                 490                 495

Trp Gln Val Thr Trp Ile Pro Asp Trp Asp Phe Val Ser Thr Pro Pro
            500                 505                 510

Leu Val Arg Leu Val Phe Asn Leu Val Lys Glu Pro Ile Gln Gly Ala
        515                 520                 525

Glu Thr Phe
    530


<210> SEQ ID NO 230
<211> LENGTH: 409
<212> TYPE: PRT
<213> ORGANISM: SIVsme543

<400> SEQUENCE: 230

Tyr Val Asp Gly Ser Cys Asn Arg Gln Ser Arg Glu Gly Lys Ala Gly
1               5                   10                  15

Tyr Val Thr Asp Arg Gly Arg Asp Lys Ala Lys Leu Leu Glu Gln Thr
            20                  25                  30

Thr Asn Gln Gln Ala Leu Glu Ala Phe Tyr Leu Ala Leu Ala Asp Ser
        35                  40                  45

Gly Pro Lys Ala Asn Ile Ile Val Asp Ser Gln Tyr Val Met Gly Ile
    50                  55                  60

Val Ala Gly Gln Pro Thr Glu Ser Glu Ser Arg Leu Val Asn Gln Ile
65                  70                  75                  80

Ile Glu Glu Met Ile Lys Lys Glu Ala Ile Tyr Val Ala Trp Val Pro
                85                  90                  95

Ala His Lys Gly Ile Gly Gly Asn Gln Glu Val Asp His Leu Val Ser
            100                 105                 110

Gln Gly Ile Arg Gln Val Leu Phe Leu Glu Lys Ile Glu Pro Ala Gln
        115                 120                 125

Glu Glu His Glu Lys Tyr His Ser Asn Val Lys Glu Leu Val Phe Lys
    130                 135                 140

Phe Gly Ile Pro Arg Leu Val Ala Lys Gln Ile Val Asp Thr Cys Asp
145                 150                 155                 160

Arg Cys His Gln Lys Gly Glu Ala Ile His Gly Gln Val Asn Ala Glu
                165                 170                 175

Leu Gly Thr Trp Gln Met Cys Thr His Leu Glu Gly Lys Ile Ile Ile
            180                 185                 190
```

Val Ala Val His Val Ala Ser Gly Phe Ile Glu Ala Glu Val Ile Pro
195 200 205

Gln Glu Thr Gly Arg Gln Thr Ala Leu Phe Leu Leu Lys Leu Ala Gly
210 215 220

Arg Trp Pro Ile Thr His Leu His Thr Asn Gly Ala Asn Phe Thr Ser
225 230 235 240

Gln Glu Val Lys Met Val Ala Trp Trp Ala Gly Ile Glu Gln Thr Phe
245 250 255

Gly Val Pro Tyr Asn Pro Gln Ser Gln Gly Val Val Ala Met Asn His
260 265 270

His Leu Lys Thr Gln Ile Asp Arg Ile Arg Glu Gln Ala Asn Ser Val
275 280 285

Glu Thr Ile Val Leu Met Ala Val His Cys Met Asn Phe Lys Arg Arg
290 295 300

Gly Gly Ile Gly Asp Met Thr Pro Ala Glu Arg Leu Val Asn Met Ile
305 310 315 320

Thr Thr Glu Gln Glu Ile Gln Phe Gln Gln Ser Lys Asn Ser Lys Phe
325 330 335

Lys Asn Phe Arg Val Tyr Tyr Arg Glu Gly Arg Asp Gln Leu Trp Arg
340 345 350

Gly Pro Gly Glu Leu Leu Trp Lys Gly Glu Gly Ala Val Ile Leu Lys
355 360 365

Val Gly Thr Glu Ile Lys Val Val Pro Arg Arg Lys Ala Lys Ile Ile
370 375 380

Lys Asp Tyr Gly Gly Gly Lys Glu Leu Asp Ser Gly Ser His Leu Glu
385 390 395 400

Asp Thr Gly Glu Ala Arg Glu Val Ala
405

<210> SEQ ID NO 231
<211> LENGTH: 650
<212> TYPE: PRT
<213> ORGANISM: SIVsme543

<400> SEQUENCE: 231

Met Gly Cys Leu Gly Asn Gln Leu Leu Ile Ala Leu Leu Leu Val Ser
1 5 10 15

Val Leu Glu Ile Cys Cys Val Gln Tyr Val Thr Val Phe Tyr Gly Val
20 25 30

Pro Ala Trp Lys Asn Ala Thr Ile Pro Leu Phe Cys Ala Thr Arg Asn
35 40 45

Arg Asp Thr Trp Gly Thr Thr Gln Cys Leu Pro Asp Asn Asp Asp Tyr
50 55 60

Ser Glu Leu Ala Val Asn Ile Thr Glu Ala Phe Asp Ala Trp Asn Asn
65 70 75 80

Thr Val Thr Glu Gln Ala Ile Glu Asp Val Trp Asn Leu Phe Glu Thr
85 90 95

Ser Ile Lys Pro Cys Val Lys Leu Thr Pro Leu Cys Ile Ala Met Arg
100 105 110

Cys Asn Lys Thr Glu Thr Asp Arg Trp Gly Leu Thr Gly Arg Ala Glu
115 120 125

Thr Thr Thr Thr Ala Lys Ser Thr Thr Ser Thr Thr Thr Thr Thr Val
130 135 140

Thr Pro Lys Val Ile Asn Glu Gly Asp Ser Cys Ile Lys Asn Asn Ser

```
               145                 150                 155                 160
Cys Ala Gly Leu Glu Gln Glu Pro Met Ile Gly Cys Lys Phe Asn Met
                165                 170                 175
Thr Gly Leu Lys Arg Asp Lys Lys Ile Glu Tyr Asn Glu Thr Trp Tyr
                180                 185                 190
Ser Arg Asp Leu Ile Cys Glu Gln Pro Ala Asn Gly Ser Glu Ser Lys
                195                 200                 205
Cys Tyr Met Gln His Cys Asn Thr Ser Val Ile Gln Glu Ser Cys Asp
    210                 215                 220
Lys His Tyr Trp Asp Ala Ile Arg Phe Arg Tyr Cys Ala Pro Pro Gly
225                 230                 235                 240
Tyr Ala Leu Leu Arg Cys Asn Asp Ser Asn Tyr Ser Gly Phe Ala Pro
                245                 250                 255
Lys Cys Ser Lys Val Val Val Ser Ser Cys Thr Arg Met Met Glu Thr
                260                 265                 270
Gln Thr Ser Thr Trp Phe Gly Phe Asn Gly Thr Arg Ala Glu Asn Arg
                275                 280                 285
Thr Tyr Ile Tyr Trp His Gly Asn Ser Asn Arg Thr Ile Ile Ser Leu
    290                 295                 300
Asn Lys Tyr Tyr Asn Leu Thr Met Lys Cys Arg Arg Pro Gly Asn Lys
305                 310                 315                 320
Thr Val Leu Pro Val Thr Ile Met Ser Gly Leu Val Phe His Ser Gln
                325                 330                 335
Pro Ile Asn Glu Arg Pro Lys Gln Ala Trp Cys Arg Phe Gly Gly Asn
                340                 345                 350
Trp Ser Glu Ala Ile Gln Glu Val Lys Glu Thr Leu Val Lys His Pro
    355                 360                 365
Arg Tyr Thr Gly Thr Asn Asp Thr Arg Lys Ile Asn Leu Thr Ala Pro
    370                 375                 380
Ala Gly Gly Asp Pro Glu Val Thr Phe Met Trp Thr Asn Cys Arg Gly
385                 390                 395                 400
Glu Phe Leu Tyr Cys Lys Met Asn Trp Phe Leu Asn Trp Val Glu Asp
                405                 410                 415
Arg Asp Gln Asn Ser Asn Arg Trp Lys Gln Gln Lys Lys Pro Glu Gln
                420                 425                 430
Gln Lys Arg Asn Tyr Val Pro Cys His Ile Arg Gln Ile Ile Asn Thr
                435                 440                 445
Trp His Lys Val Gly Lys Asn Val Tyr Leu Pro Pro Arg Glu Gly Asp
    450                 455                 460
Leu Thr Cys Asn Ser Thr Val Thr Ser Leu Ile Ala Glu Ile Asp Trp
465                 470                 475                 480
Ile Asn Asn Asn Glu Thr Asn Ile Thr Met Ser Ala Glu Val Ala Glu
                485                 490                 495
Leu Tyr Arg Leu Glu Leu Gly Asp Tyr Lys Leu Val Glu Ile Thr Pro
                500                 505                 510
Ile Gly Leu Ala Pro Thr Asp Val Arg Arg Ser Leu Thr Leu Ser Ala
                515                 520                 525
Gln Ser Arg Thr Leu Leu Ala Gly Ile Val Gln Gln Gln Gln Gln Leu
    530                 535                 540
Leu Asp Val Val Lys Arg Gln His Glu Leu Leu Arg Leu Thr Val Trp
545                 550                 555                 560
Gly Thr Lys Asn Leu Gln Thr Arg Val Thr Ala Ile Glu Lys Tyr Leu
                565                 570                 575
```

-continued

```
Lys Asp Gln Ala Gln Leu Asn Asp Ser Leu Val Pro Asn Trp Asp Asn
            580                 585                 590

Met Thr Trp Gln Glu Trp Glu Gly Lys Val Asp Phe Leu Glu Ala Asn
        595                 600                 605

Ile Thr Gln Leu Leu Glu Glu Ala Gln Ile Gln Gln Glu Lys Asn Met
    610                 615                 620

Tyr Glu Leu Gln Lys Leu Asn Ser Trp Asp Ile Phe Gly Asn Trp Phe
625                 630                 635                 640

Asp Leu Thr Ser Trp Ile Arg Tyr Ile Gln
                645                 650
```

HIV VACCINES AND METHODS OF USING

CROSS-REFERENCE TO RELATED APPLICATIONS

This application claims the benefit under 35 U.S.C. § 119(e) of U.S. Provisional Application No. 63/137,521, filed on Jan. 14, 2021; U.S. Provisional Application No. 63/149,820, filed on Feb. 16, 2021 and U.S. Provisional Application No. 63/170,900, filed on Apr. 5, 2021, which are hereby incorporated herein by reference in their entireties for all purposes.

SEQUENCE LISTING

The instant application contains a Sequence Listing which has been submitted electronically in ASCII format and is hereby incorporated by reference in its entirety. Said ASCII copy, created on Dec. 12, 2021 is named 1355-US-NP.txt and is 508,767 bytes in size.

BACKGROUND

HIV remains one of the leading causes of mobility and mortality globally, with over 38 million infected globally and 690,000 deaths in 2019 (UNAIDS. Fact Sheet—World AIDS Day 2020. unaidsorg/en/resources/fact-sheet. 2020). The last three decades have seen significant improvements in therapeutics for HIV. The development of highly active anti-retroviral therapy has improved survival for people living with HIV, and reduced morbidity from HIV related immunosuppression and opportunistic infections (Johnson, et al., *PLoS Med.* 2013; 10(4):e1001418; May, et al., *AIDS.* (2014) 28(8):1193-202; Rodger, et al., *AIDS.* (2013) 27(6): 973-9; Samji, et al., *PLoS One.* (2013) 8(12):e81355). In recent years antiretroviral treatment (ART) regimens have been simplified to once daily pills with longer acting oral and injectable therapeutics on the horizon (Swindells, et al., *N Engl J Med.* (2020) 382(12):1112-23; Orkin, et al., *N Engl J Med.* (2020) 382(12):1124-35; Link, et al., *Nature.* (2020) 584(7822):614-8). Despite these advances in therapeutics, to date there has only been two well documented examples of cure, both of which required severe immunosuppression and bone marrow transplantation (Gupta, et al., *Lancet HIV.* (2020) 7(5):e340-e7; Hutter, et al., *N Engl J Med.* (2009) 360(7):692-8). Unlike many self-limited infectious diseases, the HIV virus integrates itself into its host genome, and establishes latency in resting memory CD4+ T cells (Eisele, et al., *Immunity.* (2012) 37(3):377-88). These cells form the HIV latent reservoir that cannot be cleared by standard antiretroviral therapy. Reservoir cells are also protected from immune surveillance and clearance mechanisms, as they do not express viral antigens enabling them to evade recognition and clearance by cytotoxic T cells. The reservoir is long-lived and despite detectable reductions in the size of the reservoir, viral rebound is observed following discontinuation of ART (Henrich, et al., *Ann Intern Med.* (2014) 161(5):319-27; Henrich, et al., *J Infect Dis.* (2013) 207(11): 1694-702). Activating the reservoir with latency reversing agents will need to be coupled with an effective mechanism to stimulate cytotoxic T cells and eliminate the infected reservoir cells (Ait-Ammar, et al., *Front Microbiol.* (2019) 10:3060; Mothe, et al., *Front Immunol.* (2020) 11:823; Fidler, et al., *Lancet.* (2020) 395(10227):888-98). A therapeutic vaccine designed to generate antigen specific effector T cell responses can be an additional component of an HIV cure strategy.

T cell vaccines hold significant promise in therapeutic areas such as oncology. High levels of tumor infiltrating CD8+ lymphocytes are associated with better prognosis in some cancers, leading to significant interest in developing vaccines that can induce tumor specific cytotoxic CD8+ T cells. Although previous approaches have had limited success (Rosenberg, et al., *Nature Medicine.* (2004) 10(9):909-15), the use of novel delivery platforms, improved techniques in antigen discovery and immune modulation hold some promise (Ott, et al., *Nature.* (2017) 547(7662):217-21). Similarly, T cells play an important role in the control of HIV viremia. Antigen specific T cells that arise in acute HIV infection are responsible for driving the initial drop in viremia (Borrow, et al., *J Virol.* (1994) 68(9):6103-10; Koup, et al., *J Virol.* (1994) 68(7):4650-5). HIV infected human long-term non-progressers or elite controllers are characterized by having strong effective antigen specific T cell responses. In SIV infection (a non-human primate model of human HIV infection) antigen specific T cells either generated naturally or through vaccination have been associated with viral control (Schmitz, et al., *Science.* (1999) 283 (5403):857-60; Jin, et al., *J Exp Med.* (1999) 189(6):991-8). Despite this data, T-cells vaccines for prevention have had limited success in inducing T cell responses of limited breadth or efficacy (Buchbinder, et al., *Lancet.* (2008) 372 (9653):1881-93; Janes, et al., *J Infect Dis.* (2013) 208(8): 1231-9; Excler, et al., *Curr Opin HIV AIDS.* (2016) 11(6): 607-13). Therapeutic vaccine trials with T cell vaccines have also shown limited efficacy (Mothe, et al., *Front Immunol.* (2020) 11:823; Colby, et al., *Nature Medicine.* (2020) 26(4): 498-501). These trials have used viral vectors such as adenoviruses (human and chimpanzee) as well as modified vaccinia Ankara (MVA) virus and with full length viral antigens or shorter constructs (Barouch, et al., *Lancet.* (2018) 392(10143):232-43; Mothe, et al., *EClinical Medicine.* (2019) 11:65-80). Data from these studies suggest that following vaccination the breadth of antigen specific T cells generated is low. Although these vaccine-induced T cells secrete IFN-γ in standard ELISpot assays the demonstrated lack of efficacy suggests that these T cells may not have full cytotoxic activity.

Immunogen design is a component of any therapeutic HIV vaccine to generate the right antigen specific response, targeted at a conserved region and with cytotoxic activity. Natural infection has demonstrated that the immune response will tend to focus on highly immunodominant variable regions within HIV for example in HIV envelope or Nef, or variable regions in HIV Gag (Addo, et al. *J Virol.* (2003) 77(3):2081-92; Betts, et al., *J Virol.* 2001; 75(24): 11983-91). These responses generate T cells from which the virus can rapidly escape without a fitness cost (Liu, et al., *J Virol.* (2006) 80(19):9519-29). An effective HIV vaccine will need to avoid these regions and drive the establishment of de novo responses that focus the immune response to conserved regions of the virus where conservation is required to maintain viral function.

Previous HIV vaccines have primarily focused on designing immunogens that provide universal coverage by addressing global HIV viral diversity and have generated full length sequences or have adapted algorithms to generate constructs of conserved regions (Korber, et al., *Hum Vaccin Immunother.* (2020) 16(3):713-722; Fischer, et al., *Nature Medicine.* (2007) 13(1):100-6). All of these approaches have primarily evaluated consensus sequences assessing inter patient variability to determine regions of conservation, and concatenated to provide global sequence coverage. However, within an HIV infected individual there are several circulating quasispecies. Some of these viral quasispecies are generated as a result of T cell driven pressure and reflect pre-existing escape route for the virus should a T cell response directed at it emerge (Liu, et al., *J Virol.* (2006) 80(19):9519-29; Korber, et al., 2020, supra; Price, et al., *Proc Natl Acad Sci USA.* (1997) 94(5):1890-5). That the targeting of conserved regions by previous vaccines did not consider quasispecies together with identification of highly conserved immunogenic regions, may in part explain their limited efficacy (Hanke, et al., *Expert Rev Vaccines.* (2019) 18(10):1029-41).

SUMMARY

Provided are fusion polypeptides comprising a plurality of polypeptide segments of one or more human immunodeficiency virus-1 (HIV-1) proteins encoded by two or more HIV genes selected from gag, pol and nef. In some embodiments, the plurality of polypeptide segments comprises or consists of polypeptide segments encoded by HIV-1 genes pol and nef, and does not comprise polypeptide segments encoded by HIV-1 genes env, tat, rev, vpr, vif and/or vpu. In some embodiments, the plurality of polypeptide segments comprises or consists of polypeptide segments encoded by HIV-1 genes gag, pol and nef, and does not comprise polypeptide segments encoded by HIV-1 genes env, tat, rev, vpr, vif and/or vpu. In some embodiments, the plurality polypeptide segments are derived from conserved regions in a population of viral proteome sequences. In some embodiments, the conserved regions are greater than 80%, 81%, 82%, 83%, 84%, 85%, 86%, 87%, 88%, 89%, 90%, 91%, 92%, 93%, 94%, 95%, 96%, 97%, 98% or 99% conserved amongst HIV-1 species in interpatient populations. In some embodiments, the conserved regions are conserved amongst one or more of HIV-1 clades A-K, e.g., one or more of clades A, B, C, D and G, or recombinant forms of one or more of HIV-1 clades A-K, and combinations thereof. In some embodiments, the fusion polypeptides comprise at least 4 and up to 6 polypeptide segments, e.g., 4, 5 or 6 polypeptide segments. In some embodiments, each polypeptide segment is at least 10 amino acids in length, and up to about 225 amino acids in length, e.g. from at least 10 amino acids in length up to 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220 or 225 amino acids in length. In some embodiments, the full-length of the fusion polypeptide comprises at least about 330 amino acids and up to about 505 amino acids (without a signal peptide) or up to about 550 amino acids (including a signal peptide), e.g., at least about 330 amino acids and up to about 335, 340, 345, 350, 355, 360, 365, 370, 375, 380, 385, 390, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545 or 550 amino acids. In some embodiments, the full-length of the fusion polypeptide is no longer than 550 amino acids (with a signal peptide) or no longer than 505 amino acids (without a signal peptide), e.g., no longer than 545, 540, 535, 530, 525, 520, 515, 510, 505, 500, 495, 490, 485, 480, 475, 470, 465, 460, 455, 450, 445, 440, 435, 430, 425, 420, 415, 410, 405, 400, 390, 385, 380, 375, 370, 365, 360, 355, 350, 345, 340, 335 or 330 amino acids. In some embodiments, the full-length of the fusion polypeptide comprises at least 350 amino acids and up to 385 amino acids, e.g., at least 350 amino acids and up to 365 amino acids. In some embodiments, the full-length of the fusion polypeptide comprises at least 390 amino acids and up to 395 amino acids. In some embodiments, each polypeptide segment comprises or consists of one or more predicted T cell epitopes. In some embodiments, the fusion polypeptide comprises three or more predicted T cell epitopes, e.g., four, five, six or more predicted T cell epitopes. In some embodiments, the fusion polypeptide comprises one or more polypeptide segments that bind to or are presented by one or more human HLA class I alleles (e.g. 1, 2, 3, 4, 5 or 6 alleles), e.g. within a single subject or amongst multiple patients. In some embodiments, the fusion polypeptide comprises one or more polypeptide segments that bind to or are presented by at least by a human A*0201 HLA class I molecule. In some embodiments, the fusion polypeptide comprises one or more polypeptide segments that are intracellularly processed and presented by one or more human HLA class II alleles (e.g. 1, 2, 3, 4, 5 or 6 alleles), e.g. within a single subject. In some embodiments, one or more of the polypeptide segments is abutted or fused to an adjacent segment. In some embodiments, one or more of the polypeptide segments is joined to an adjacent segment by one or more peptide linkers. In some embodiments, the one or more peptide linkers is selected from one or more of a polyalanine, a polyglycine, Gln-Glu-Glu (QEE), Lysine (L), Isoleucine (I), Leu-Ile (LI), Lys-Ile-Leu (KIL), Leu-Ile-Lys (LIK), Pro-Pro-Val (PPV), Ser-Glu-Gly (SEG), a cleavable linker, a flexible linker, a rigid linker, and combinations thereof. In some embodiments, the flexible linker is selected from Gln-Glu-Glu (QEE) (SEQ ID NO: 51), Lysine (L), Isoleucine (I), Leu-Ile (LI), Lys-Ile-Leu (KIL) (SEQ ID NO: 52), Leu-Ile-Lys (LIK) (SEQ ID NO: 53), Pro-Pro-Val (PPV) (SEQ ID NO: 54) and Ser-Glu-Gly (SEG) (SEQ ID NO:55). In some embodiments, the flexible linker comprises a polyalanine linker or a polyglycine linker, e.g., comprising or consisting of 2 or 3 contiguous alanine residues, e.g. AA, AAA (SEQ ID NO: 48), AAY (SEQ ID NO: 49) or AAX, wherein X is any amino acid (e.g. A, C, D, E, F, G, H, I, K, L, M, N, P, Q, R, S, T, V, Y) (SEQ ID NO: 50). In some embodiments, the flexible linker comprises or consists of GG, GGS (SEQ ID NO: 57), GSG (SEQ ID NO: 58) or GGGS (SEQ ID NO: 59). In some embodiments, the cleavable linker is selected from a 2A cleavable peptide (e.g. foot-and-mouth disease virus (F2A), equine rhinitis A virus (E2A), porcine teschovirus-1 (P2A) and Thosea asigna virus (T2A)), a furin recognition/cleavage sequence (e.g. RAKR (SEQ ID NO: 60), REKR (SEQ ID NO: 61) and RRKR (SEQ ID NO: 62)), and combinations, derivatives or variants thereof. In some embodiments, the cleavable linker comprises or consists of a furin recognition/cleavage site selected from RAKR (SEQ ID NO: 60), REKR (SEQ ID NO: 61) and RRKR (SEQ ID NO: 62). In some embodiments, the cleavable linker comprises or consists of the amino acid sequence that is at least 90%, 91%, 92%, 93%, 94%, 95%, 96%, 97%, 98% or at least 99% identical to ATNFSLLKQAGDVEENPGP (SEQ ID NO: 63), APVKQTLNFDLLKLAGDVESNPGP (SEQ ID NO: 64), RAKRAPVKQTLNFDLLKLAGDVESNPGP (SEQ ID NO: 65), QCTNYALLKLAGDVESNPGP (SEQ ID NO: 66), or EGRGSLLTCGDVEENPGP (SEQ ID NO: 67), or comprises or consists of the amino acid sequence of ATNFSLLKQAGDVEENPGP (SEQ ID NO: 63), APVKQTLNFDLLKLAGDVESNPGP (SEQ ID NO: 64), RAKRAPVKQTLNFDLLKLAGDVESNPGP (SEQ ID NO: 65), QCTNYALLKLAGDVESNPGP (SEQ ID NO: 66), or EGRGSLLTCGDVEENPGP (SEQ ID NO: 67). In some embodiments, the fusion polypeptide comprises two, three, four, five, six, or more, of the polypeptide segments comprising or consisting of amino acid residues corresponding to Gag 1-53; Gag 147-369; Pol 56-117; Pol 129-320; Pol 367-431 Pol 542-606; Pol 586-606; Pol 683-708, Pol 747-827; Pol 840-909; Pol 840-920; Pol 932-1003; Nef 64-76; Nef 64-99 or Nef 117-148, wherein the Gag, Pol and Nef amino acid position numbers correspond to SEQ ID NOs: 1, 2 and 3, respectively. In some embodiments, the fusion polypeptide does not comprise any polypeptide segments corresponding to Gag 54-146; Gag 370-500; Pol 1-55; Pol 118-128; Pol 321-366; Pol 432-541; Pol 607-682; Pol 709-746; Pol 828-839; Pol 921-931; Nef 1-63; Nef 100-116 and Nef 149-206, or fragments or subsequences thereof, wherein the Gag, Pol and Nef amino acid position numbers correspond to SEQ ID NOs: 1, 2 and 3, respectively. In some embodiments, the fusion polypeptide does not comprise any polypeptide segments having an amino acid sequence of any one of SEQ ID NOs: 35-47, or fragments or subsequences thereof, or an amino acid sequence at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 35-47, or fragments or subsequences thereof. In some embodiments, the fusion polypeptide comprises two, three, four, five, six, or more, polypeptide segments selected from SEQ ID NOs: 4-33. In some embodiments, the fusion polypeptide comprises or consists of the following polypeptide segments, wherein the Gag, Pol and Nef amino acid position numbers correspond to SEQ ID NOs: 1, 2 and 3, respectively: (a) amino acid residues corresponding to: Gag 1-53; Gag 147-369; Pol 683-708 and Nef 117-148; (b) amino acid residues corresponding to: Pol 56-117; Pol 129-320; Pol 367-431 and Nef 64-99; (c) amino acid residues corresponding to: Pol 542-606; Pol 747-827; Pol 840-920; Pol 932-1003 and Nef 64-99; (d) amino acid residues corresponding to: Gag 1-53; Gag 147-369; Pol 683-708; Pol 747-827; Pol 840-920 and Nef 117-148; (e) amino acid residues corresponding to: Pol 56-117; Pol 129-320; Pol 367-431; Pol 542-606; Pol 932-1003 and Nef 64-99; (f) amino acid residues corresponding to: Gag 147-369, Pol 586-606, Pol 683-708 and Pol 840-920; (g) amino acid residues corresponding to: Pol 129-320, Pol 747-827, Pol 932-1003 and Nef 64-76; or (h) amino acid residues corresponding to: Gag:147-369, Pol 747-827, Pol 840-909 and Nef 64-76. In some embodiments, the fusion polypeptide comprises or consists of the following polypeptide segments: (a) SEQ ID NOs: 4, 6, 18 and 32, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 4, 6, 18 and 32, respectively; (b) SEQ ID NOs: 5, 7, 19 and 33, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 5, 7, 19 and 33, respectively; (c) SEQ ID NOs: 8, 10, 12 and 30 or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 8, 10, 12 and 30, respectively; (d) SEQ ID NOs: 9, 11, 13 and 31, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 9, 11, 13 and 31, respectively; (e) SEQ ID NOs: 14, 20, 24, 26 and 30, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 14, 20, 24, 26 and 30, respectively; (f) SEQ ID NOs: 15, 21, 25, 27 and 31, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 15, 21, 25, 27 and 31, respectively; (g) SEQ ID NOs: 4, 6, 18, 20, 24 and 32, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 4, 6, 18, 20, 24 and 32, respectively; (h) SEQ ID NOs: 5, 7, 19, 21, 25 and 33, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 5, 7, 19, 21, 25 and 33, respectively; (i) SEQ ID NOs: 8, 10, 12, 14, 26 and 30, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 8, 10, 12, 14, 26 and 30, respectively; (j) SEQ ID NOs: 9, 11, 13, 15, 27 and 31, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 9, 11, 13, 15, 27 and 31, respectively; (k) SEQ ID NOs: 6, 16, 18 and 24, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 6, 16, 18 and 24, respectively; (1) SEQ ID NOs: 7, 17, 19 and 25, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 7, 17, 19 and 25, respectively; (m) SEQ ID NOs: 10, 20, 26 and 28, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 10, 20, 26 and 28, respectively; (n) SEQ ID NOs: 11, 21, 27 and 29, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 11, 21, 27 and 29, respectively; (o) SEQ ID NOs: 6, 20, 22 and 28, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 6, 20, 22 and 28, respectively; (p) SEQ ID NOs: 7, 21, 23 and 29, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 7, 21, 23 and 29, respectively; (q) SEQ ID NOs: 6, 16, 18 and 24, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 6, 16, 18 and 24, respectively; (r) SEQ ID NOs: 7, 17, 19 and 25, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 7, 17, 19 and 25, respectively; (s) SEQ ID NOs: 10, 20, 26 and 28, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 10, 20, 26 and 28, respectively; or (t) SEQ ID NOs: 11, 21, 27 and 29, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 11, 21, 27 and 29, respectively. In some embodiments, the fusion polypeptide comprises or consists of the following polypeptide segments in sequential order, from N-terminus to C-terminus, optionally joined or connected by one or more linkers: SEQ ID NOs: 6, 4, 18 and 32, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 6, 4, 18 and 32, respectively; SEQ ID NOs: 7, 5, 33 and 19, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 7, 5, 33 and 19, respectively; SEQ ID NOs: 12, 30, 8 and 10, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 12, 30, 8 and 10, respectively; SEQ ID NOs: 9, 31, 13 and 11, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 9, 31, 13 and 11, respectively; SEQ ID NOs: 14, 26, 20, 30 and 24, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 14, 26, 20, 30 and 24, respectively; SEQ ID NOs: 15, 31, 21, 27 and 25, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 15, 31, 21, 27 and 25, respectively; SEQ ID NOs: 32, 18, 4 and 6, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 32, 18, 4 and 6, respectively; SEQ ID NOs: 7, 33, 5 and 19, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 7, 33, 5 and 19, respectively; SEQ ID NOs: 8, 30, 12 and 10, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 8, 30, 12 and 10, respectively; SEQ ID NOs: 13, 31, 9 and 11, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 13, 31, 9 and 11, respectively; SEQ ID NOs: 26, 30, 14, 20 and 24, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 26, 30, 14, 20 and 24, respectively; SEQ ID NOs: 31, 27, 15, 25 and 21, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 31, 27, 15, 25 and 21, respectively; SEQ ID NOs: 24, 6, 4, 20, 18 and 32, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 24, 6, 4, 20, 18 and 32, respectively; SEQ ID NOs: 6, 20, 4, 24, 32 and 18, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 6, 20, 4, 24, 32 and 18, respectively; SEQ ID NOs: 7, 21, 5, 25, 33 and 19, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 7, 21, 5, 25, 33 and 19, respectively; SEQ ID NOs: 8, 30, 14, 12, 26 and 10, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 8, 30, 14, 12, 26 and 10, respectively; SEQ ID NOs: 8, 12, 30, 26, 14 and 10, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 8, 12, 30, 26, 14 and 10, respectively; SEQ ID NOs: 9, 13, 31, 27, 15 and 11, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 9, 13, 31, 27, 15 and 11, respectively; SEQ ID NOs: 20, 32, 24, 4, 6 and 18, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 20, 32, 24, 4, 6 and 18, respectively; SEQ ID NOs: 7, 25, 19, 5, 33 and 21, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 7, 25, 19, 5, 33 and 21, respectively; SEQ ID NOs: 26, 30, 12, 14, 8 and 10, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 26, 30, 12, 14, 8 and 10, respectively; SEQ ID NOs: 15, 31, 9, 27, 13 and 11, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 15, 31, 9, 27, 13 and 11, respectively; SEQ ID NOs: 24, 6, 16 and 18, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 24, 6, 16 and 18, respectively; SEQ ID NOs: 7, 19, 17 and 25, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 7, 19, 17 and 25, respectively; SEQ ID NOs: 24, 16, 6 and 18, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 24, 16, 6 and 18, respectively; SEQ ID NOs: 7, 25, 17 and 19, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 7, 25, 17 and 19, respectively; SEQ ID NOs: 26, 20, 10 and 28, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 26, 20, 10 and 28, respectively; SEQ ID NOs: 21, 27, 11 and 29, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 21, 27, 11 and 29, respectively; SEQ ID NOs: 26, 10, 20 and 28, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 26, 10, 20 and 28, respectively; SEQ ID NOs: 11, 27, 21 and 29, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 11, 27, 21 and 29, respectively; SEQ ID NOs: 22, 6, 20 and 28, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 22, 6, 20 and 28, respectively; SEQ ID NOs: 23, 7, 21 and 29, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 23, 7, 21 and 29, respectively; SEQ ID NOs: 22, 20, 6 and 28, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 22, 20, 6 and 28, respectively; or SEQ ID NOs: 7, 21, 23 and 29, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 7, 21, 23 and 29, respectively. In some embodiments, the fusion polypeptide comprises or consists of an amino acid sequence of any one of SEQ ID NOs: 70-101, 105-112, 200-209, 222-223 and 227, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70-101, 105-112, 200-209, 222-223 and 227. In some embodiments, the fusion polypeptide comprises or consists of an amino acid sequence of any one of SEQ ID NOs: 82-83, 85-87, 98-101, 209 and 222-223, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82-83, 85-87, 98-101, 209 and 222-223.

Further provided are compound fusion polypeptides comprising at least a first fusion polypeptide and a second fusion polypeptide, the first and second fusion polypeptides being independently selected from the fusion polypeptides as described above and herein. In some embodiments, the compound fusion polypeptide comprises or consists of the following first fusion polypeptide and second fusion polypeptide, optionally joined or connected by one or more linkers: SEQ ID NOs: 70 and 71, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70 and 71, respectively; SEQ ID NOs: 72 and 73, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 72 and 73, respectively; SEQ ID NOs: 74 and 75, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 74 and 75, respectively; SEQ ID NOs: 76 and 77, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 76 and 77, respectively; SEQ ID NOs: 78 and 79, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 78 and 79, respectively; SEQ ID NOs: 80 and 81, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 80 and 81, respectively; SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively; SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively; SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively; SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively; SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively; SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively; SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively; SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively; SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively; SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 88, respectively; SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively; SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively; SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively; SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively; SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively; SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively; SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively; SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively; SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively; SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively; SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively; or SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively. In some embodiments, the compound fusion polypeptide comprises or consists of the following first fusion polypeptide and second fusion polypeptide in sequential order, from N-terminus to C-terminus, optionally joined or connected by one or more linkers: SEQ ID NOs: 70 and 71, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70 and 71, respectively; SEQ ID NOs: 71 and 70, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 71 and 70, respectively; SEQ ID NOs: 72 and 73, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 72 and 73, respectively; SEQ ID NOs: 73 and 72, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 73 and 72, respectively; SEQ ID NOs: 74 and 75, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 74 and 75, respectively; SEQ ID NOs: 75 and 74, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 75 and 74, respectively; SEQ ID NOs: 76 and 77, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 76 and 77, respectively; SEQ ID NOs: 77 and 76, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 77 and 76, respectively; SEQ ID NOs: 78 and 79, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 78 and 79, respectively; SEQ ID NOs: 79 and 78, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 79 and 78, respectively; SEQ ID NOs: 80 and 81, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 80 and 81, respectively; SEQ ID NOs: 81 and 80, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 81 and 80, respectively; SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively; SEQ ID NOs: 83 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 82, respectively; SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively; SEQ ID NOs: 85 and 84, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 84, respectively; SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively; SEQ ID NOs: 87 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 86, respectively; SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively; SEQ ID NOs: 89 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 89 and 88, respectively; SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively; SEQ ID NOs: 85 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 82, SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; SEQ ID NOs: 86 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 82, SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively; SEQ ID NOs:

88 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 82, respectively; SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively; SEQ ID NOs: 87 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 83, respectively; SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively; SEQ ID NOs: 87 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 85, respectively; SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively; SEQ ID NOs: 87 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 88, respectively; SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 84, respectively; SEQ ID NOs: 88 and 84, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 84, respectively; SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively; SEQ ID NOs: 89 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 89 and 85, respectively; SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively; SEQ ID NOs: 101 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 85, respectively; SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively; SEQ ID NOs: 91 and 90, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 91 and 90, respectively; SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively; SEQ ID NOs: 93 and 92, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 93 and 92, respectively; SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively; SEQ ID NOs: 95 and 94, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 94, respectively; SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively; SEQ ID NOs: 97 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 97 and 96, respectively; SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively; SEQ ID NOs: 96 and 94, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 94, respectively; SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively; SEQ ID NOs: 97 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 97 and 95, respectively; SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively; SEQ ID NOs: 221 and 220, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 221 and 220, respectively; SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; SEQ ID NOs: 100 and 98, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 98, respectively; SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively; SEQ ID NOs: 101 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 99, respectively; SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively; SEQ ID NOs:

99 and 98, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 98, respectively; SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively; or SEQ ID NOs: 101 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 100, respectively. In some embodiments, the first fusion polypeptide and the second fusion polypeptide are joined or connected by a cleavable linker. In some embodiments, the first fusion polypeptide and the second fusion polypeptide are joined or connected by a cleavable linker selected from a 2A cleavable peptide (e.g. foot-and-mouth disease virus (F2A), equine rhinitis A virus (E2A), porcine teschovirus-1 (P2A) and Thosea asigna virus (T2A)), a furin recognition/cleavage sequence (e.g. RAKR (SEQ ID NO: 60), REKR (SEQ ID NO: 61) and RRKR (SEQ ID NO: 62)), and combinations, derivatives or variants thereof. In some embodiments, the first fusion polypeptide and the second fusion polypeptide are joined or connected by a furin recognition/cleavage site selected from RAKR (SEQ ID NO: 60), REKR (SEQ ID NO: 61) and RRKR (SEQ ID NO: 62). In some embodiments, the first fusion polypeptide and the second fusion polypeptide are joined or connected by a 2A cleavable peptide comprising or consisting of the amino acid sequence of ATNFSLLKQAGDVEENPGP (SEQ ID NO: 63), APVKQTLNFDLLKLAGDVESNPGP (SEQ ID NO: 64), RAKRAPVKQTLNFDLLKLAGDVESNPGP (SEQ ID NO: 65), QCTNYALLKLAGDVESNPGP (SEQ ID NO: 66), or EGRGSLLTCGDVEENPGP (SEQ ID NO: 67, or having an amino acid sequence that is at least 90%, 91%, 92%, 93%, 94%, 95%, 96%, 97%, 98% or at least 99% identical to ATNFSLLKQAGDVEENPGP (SEQ ID NO: 63), APVKQTLNFDLLKLAGDVESNPGP (SEQ ID NO: 64), RAKRAPVKQTLNFDLLKLAGDVESNPGP (SEQ ID NO: 65), QCTNYALLKLAGDVESNPGP (SEQ ID NO: 66), or EGRGSLLTCGDVEENPGP (SEQ ID NO: 67. In some embodiments, the compound fusion polypeptide comprises or consists of an amino acid sequence of any one of SEQ ID NOs: 105-112, 200-209, 222-223 and 227, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 105-112, 200-209, 222-223 and 227. In some embodiments, the compound fusion polypeptide comprises or consists of an amino acid sequence of any one of SEQ ID NOs: 209, 222 and 223, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 209, 222 and 223.

With respect to further embodiments of the fusion polypeptides and the compound fusion polypeptides, in some embodiments, the fusion polypeptide or the compound fusion polypeptide further comprises an N-terminal signal peptide or leader sequence. In some embodiments, the signal peptide or leader sequence is from a source protein selected from a serum protein, a cytokine, a chemokine, a chaperone protein, an invariant protein, and a protein that directs proteins to the lysosomal compartment. In some embodiments, the signal peptide or leader sequence is from a source protein selected from colony stimulating factor 2 (CSF2, GM-CSF), tissue type plasminogen activator (PLAT, t-PA), C-C motif chemokine ligand 7 (CCL7, MCP-3), C-X-C motif chemokine ligand 10 (CXCL10, IP-10), catenin beta 1 (CTNNB1), CD74 (p33; DHLAG; HLADG; Ia-GAMMA, invariant chain), serum albumin (ALB), polyubiquitin B/C (UBB/UBC), calreticulin (CALR), vesicular stomatitis virus G protein (VSV-G), lysosomal associated membrane protein 1 (LAMP-1) and lysosomal associated membrane protein 2 (LAMP-2). In some embodiments, the signal peptide or leader sequence is selected from an amino acid sequence of any one of SEQ ID NOs: 115-126, or an amino acid sequence that is at least 95%, 96%, 97%, 98%, or 99% identical to any one of SEQ ID NOs: 115-126. In some embodiments, the fusion polypeptide and/or the compound fusion polypeptide are recombinantly produced or chemically synthesized. In some embodiments, the fusion polypeptide and/or the compound fusion polypeptide are capable of inducing, promoting or stimulating an immune response in a human. In some embodiments, the fusion polypeptide and/or the compound fusion polypeptide are capable of inducing, promoting or stimulating an immune response against HIV-1 in a human. In some embodiments, the fusion polypeptide and/or the compound fusion polypeptide are capable of inducing, promoting or stimulating proliferation and/or activation of one or more cell types selected from monocyte-derived dendritic cells (DCs), CD8+ T cells and CD4+ T cells.

Further provided are polynucleotides encoding one or more fusion polypeptides or compound fusion polypeptide, as described above and herein. In some embodiments, the polynucleotide comprises cDNA, mRNA, self-amplifying RNA (SAM, saRNA), self-replicating RNA, or self-amplifying replicon RNA (RepRNA). In some embodiments, the polynucleotide comprises self-replicating or self-amplifying alphavirus replicons. In some embodiments, the polynucleotide comprises a nucleic acid sequence of any one of SEQ ID NOs: 130-167, 210-219 and 225-226, or that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 130-167, 210-219 and 225-226. In some embodiments, the polynucleotide comprises a nucleic acid sequence of any one of SEQ ID NOs: 139, 140, 142, 143, 145, 146, 148, 149, 150, 152, 155, 158, 225 and 226, or that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139, 140, 142, 143, 145, 146, 148, 149, 150, 152, 155, 158, 225 and 226. Further provided are expression cassettes comprising one or more polynucleotides described herein operably linked to one or more regulatory sequences, e.g., a promoter. In some embodiments, the polynucleotide is operably linked to and under the control of a constitutive promoter. In some embodiments, the promoter is selected from a CMV promoter, a CAG promoter and an EF1a promoter.

Further provided are lipoplexes, e.g., lipid nanoparticles (LNPs) comprising one or more polynucleotides described herein, e.g., encoding one or more polypeptides having an amino acid sequence of any one of SEQ ID NOs: 70-101, 105-112, 200-209, 222-223 and 227, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70-101, 105-112, 200-209, 222-223 and 227, e.g., one or more polynucleotides comprising a nucleic acid sequence of any one of SEQ ID NOs: 130-167, 210-219 and 225-226, or that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 130-167, 210-219 and 225-226. In some embodiments, the lipoplexes, e.g., lipid nanoparticles (LNPs) comprise one or more polynucleotides described herein, e.g., encoding one or more polypeptides having an amino acid sequence of any one of SEQ ID NOs: 82-83, 85-87, 98-101, 209 and 222-223, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82-83, 85-87, 98-101, 209 and 222-223, e.g., one or more polynucleotides comprising a nucleic acid sequence of any one of SEQ ID NOs: 139, 140, 142, 143, 145, 146, 148, 149, 150, 152, 155, 158, 225 and 226, or that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139, 140, 142, 143, 145, 146, 148, 149, 150, 152, 155, 158, 225 and 226.

Further provided are vectors comprising one or more polynucleotides or one or more expression cassette, described herein. In some embodiments, the vector comprises or consists of one or more polynucleotides encoding one or more fusion polypeptides comprising the following polypeptide segments comprising in sequential order, from N-terminus to C terminus, optionally joined or connected by one or more linkers: SEQ ID NOs: 6, 4, 16 and 26, and SEQ ID NOs: 7, 5, 27 and 17; SEQ ID NOs: 12, 24, 8 and 10, and SEQ ID NOs: 9, 25, 13 and 11; SEQ ID NOs: 14, 22, 18, 24 and 20, and SEQ ID NOs: 15, 25, 19, 23 and 21; SEQ ID NOs: 26, 16, 4 and 6, and SEQ ID NOs: 7, 27, 5 and 17; SEQ ID NOs: 8, 24, 12 and 10, and SEQ ID NOs: 13, 25, 9 and 11; SEQ ID NOs: 22, 24, 14, 18 and 20, and SEQ ID NOs: 25, 23, 15, 21 and 19; SEQ ID NOs: 20, 6, 4, 18, 16 and 26, and SEQ ID NOs: 7, 19, 5, 21, 27 and 17; SEQ ID NOs: 8, 24, 14, 12, 22 and 10, and SEQ ID NOs: 9, 13, 25, 23, 15 and 11; SEQ ID NOs: 18, 26, 20, 4, 6 and 16, and SEQ ID NOs: 7, 21, 17, 5, 27 and 19; SEQ ID NOs: 22, 24, 12, 14, 8 and 10, and SEQ ID NOs: 15, 25, 9, 23, 13 and 11; SEQ ID NOs: 24, 6, 4, 20, 18 and 32, and SEQ ID NOs: 8, 30, 14, 12, 26 and 10; SEQ ID NOs: 24, 6, 4, 20, 18 and 32, and SEQ ID NOs: 7, 21, 5, 25, 33 and 19; SEQ ID NOs: 24, 6, 4, 20, 18 and 32, and SEQ ID NOs: 8, 30, 14, 12, 26 and 10; SEQ ID NOs: 8, 30, 14, 12, 26 and 10, and SEQ ID NOs: 9, 13, 31, 27, 15 and 11; SEQ ID NOs: 6, 20, 4, 24, 32 and 18, and SEQ ID NOs: 8, 12, 30, 26, 14 and 10; SEQ ID NOs: 7, 21, 5, 25, 33 and 19 and SEQ ID NOs: 9, 13, 31, 27, 15 and 11; SEQ ID NOs: 20, 32, 24, 4, 6 and 18, and SEQ ID NOs: 26, 30, 12, 14, 8 and 10; SEQ ID NOs: 7, 25, 19, 5, 33 and 21, and SEQ ID NOs: 15, 31, 9, 27, 13 and 11; SEQ ID NOs: 24, 6, 16 and 18, and SEQ ID NOs: 26, 20, 10 and 28; SEQ ID NOs: 24, 6, 16 and 18, and SEQ ID NOs: 26, 10, 20 and 28; SEQ ID NOs: 24, 6, 16 and 18, and SEQ ID NOs: 7, 25, 17 and 19; SEQ ID NOs: 7, 19, 17 and 25, and SEQ ID NOs: 21, 27, 11 and 29; SEQ ID NOs: 24, 16, 6 and 18, and SEQ ID NOs: 27, 11, 21 and 29; SEQ ID NOs: 7, 25, 17 and 19, and SEQ ID NOs: 11, 27, 21 and 29; SEQ ID NOs: 7, 25, 17 and 19, and SEQ ID NOs: 21, 27, 11 and 29; SEQ ID NOs: 22, 6, 20 and 28, and SEQ ID NOs: 23, 7, 21 and 29; SEQ ID NOs: 22, 20, 6 and 28, and SEQ ID NOs: 7, 21, 23 and 29; SEQ ID NOs: 26, 10, 20 and 28, and SEQ ID NOs: 21, 27, 11 and 29; SEQ ID NOs: 22, 6, 16, 20, 18, 28, 26 and 10; or SEQ ID NOs: 7, 21, 19, 17, 27, 25, 29 and 11. In some embodiments, the vector comprises one or more polynucleotides encoding one or more fusion polypeptides comprising or consisting of an amino acid sequence of any one of SEQ ID NOs: 70-101, 105-112, 200-209, 222-223 and 227, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70-101, 105-112, 200-209, 222-223 and 227. In some embodiments, the vector comprises one or more polynucleotides encoding one or more fusion polypeptides comprising or consisting of an amino acid sequence of any one of SEQ ID NOs: 82-83, 85-87, 98-101, 209 and 222-223, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82-83, 85-87, 98-101, 209 and 222-223. In some embodiments, the vector comprises one or more polynucleotides encoding the following first fusion polypeptide and second fusion polypeptide, optionally joined or connected by one or more linkers: SEQ ID NOs: 70 and 71, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70 and 71, respectively; SEQ ID NOs: 72 and 73, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 72 and 73, respectively; SEQ ID NOs: 74 and 75, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 74 and 75, respectively; SEQ ID NOs: 76 and 77, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 76 and 77, respectively; SEQ ID NOs: 78 and 79, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 78 and 79, respectively; SEQ ID NOs: 80 and 81, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 80 and 81, respectively; SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively; SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively; SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively; SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively; SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively; SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively; SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively; SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively; SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively; SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 88, respectively; SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively; SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively; SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively; SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively; SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively; SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively; SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively; SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively; SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively; SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively; SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively; or SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively. In some embodiments, the vector comprises one or more polynucleotides encoding the following first fusion polypeptide and second fusion polypeptide in sequential order, from N-terminus to C-terminus, optionally joined or connected by one or more linkers: SEQ ID NOs: 70 and 71, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70 and 71, respectively; SEQ ID NOs: 71 and 70, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 71 and 70, respectively; SEQ ID NOs: 72 and 73, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 72 and 73, respectively; SEQ ID NOs: 73 and 72, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 73 and 72, respectively; SEQ ID NOs: 74 and 75, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 74 and 75, respectively; SEQ ID NOs: 75 and 74, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 75 and 74, respectively; SEQ ID NOs: 76 and 77, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 76 and 77, respectively; SEQ ID NOs: 77 and 76, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 77 and 76, respectively; SEQ ID NOs: 78 and 79, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 78 and 79, respectively; SEQ ID NOs: 79 and 78, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 79 and 78, respectively; SEQ ID NOs: 80 and 81, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 80 and 81, respectively; SEQ ID NOs: 81 and 80, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 81 and 80, respectively; SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively; SEQ ID NOs: 83 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 82, respectively; SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively; SEQ ID NOs: 85 and 84, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 84, respectively; SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively; SEQ ID NOs: 87 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 86, respectively; SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively; SEQ ID NOs: 89 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 89 and 88, respectively; SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively; SEQ ID NOs: 85 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 82, respectively; SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; SEQ ID NOs: 86 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 82, respectively; SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively; SEQ ID NOs: 88 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 82, respectively; SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively; SEQ ID NOs: 87 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 83, respectively; SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively; SEQ ID NOs: 87 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 85, respectively; SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively; SEQ ID NOs: 87 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 88, respectively; SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 84, respectively; SEQ ID NOs: 88 and 84, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 84, respectively; SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively; SEQ ID NOs: 89 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 89 and 85, respectively; SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively; SEQ ID NOs: 101 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 85, respectively; SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively; SEQ ID NOs: 91 and 90, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 91 and 90, respectively; SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively; SEQ ID NOs: 93 and 92, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 93 and 92, respectively; SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively; SEQ ID NOs: 95 and 94, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 94, respectively; SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively; SEQ ID NOs: 97 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 97 and 96, respectively; SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively; SEQ ID NOs: 96 and 94, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 94, respectively; SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively; SEQ ID NOs: 97 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 97 and 95, respectively; SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively; SEQ ID NOs: 221 and 220, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 221 and 220, respectively; SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; SEQ ID NOs: 100 and 98, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 98, respectively; SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively; SEQ ID NOs: 101 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 99, respectively; SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively; SEQ ID NOs: 99 and 98, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 98, respectively; SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively; or SEQ ID NOs: 101 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 100, respectively. In some embodiments, the vector comprises one or more polynucleotides encoding the following first fusion polypeptide and second fusion polypeptide, optionally joined or connected by one or more linkers: SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively. In some embodiments, the vector comprises one or more polynucleotides encoding the following first fusion polypeptide and second fusion polypeptide, optionally joined or connected by one or more linkers: SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively. In some embodiments, the vector comprises one or more polynucleotides encoding the following first fusion polypeptide and second fusion polypeptide, optionally joined or connected by one or more linkers: SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively. In some embodiments, the vector comprises one or more polynucleotides encoding the following first fusion polypeptide and second fusion polypeptide, optionally joined or connected by one or more linkers: SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively. In some embodiments, the vector comprises one or more polynucleotides encoding the following first fusion polypeptide and second fusion polypeptide, optionally joined or connected by one or more linkers: SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively. In some embodiments, the vector comprises one or more polynucleotides encoding the following first fusion polypeptide and second fusion polypeptide, optionally joined or connected by one or more linkers: SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively. In some embodiments, the vector comprises one or more polynucleotides encoding the following first fusion polypeptide and second fusion polypeptide, optionally joined or connected by one or more linkers: SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively. In some embodiments, the vector comprises one or more polynucleotides encoding the following first fusion polypeptide and second fusion polypeptide, optionally joined or connected by one or more linkers: SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively. In some embodiments, the vector comprises one or more polynucleotides encoding the following first fusion polypeptide and second fusion polypeptide, optionally joined or connected by one or more linkers: SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively. In some embodiments, the vector comprises one or more polynucleotides encoding the following first fusion polypeptide and second fusion polypeptide, optionally joined or connected by one or more linkers: SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively. In some embodiments, the vector comprises one or more polynucleotides encoding the following first fusion polypeptide and second fusion polypeptide, optionally joined or connected by one or more linkers: SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 88, respectively. In some embodiments, the vector comprises one or more polynucleotides encoding the following first fusion polypeptide and second fusion polypeptide, optionally joined or connected by one or more linkers: SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively. In some embodiments, the vector comprises one or more polynucleotides encoding the following first fusion polypeptide and second fusion polypeptide, optionally joined or connected by one or more linkers: SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively. In some embodiments, the vector comprises one or more polynucleotides encoding the following first fusion polypeptide and second fusion polypeptide, optionally joined or connected by one or more linkers: SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively. In some embodiments, the vector comprises one or more polynucleotides encoding the following first fusion polypeptide and second fusion polypeptide, optionally joined or connected by one or more linkers: SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively. In some embodiments, the vector comprises one or more polynucleotides encoding the following first fusion polypeptide and second fusion polypeptide, optionally joined or connected by one or more linkers: SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively. In some embodiments, the vector comprises one or more polynucleotides encoding the following first fusion polypeptide and second fusion polypeptide, optionally joined or connected by one or more linkers: SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively. In some embodiments, the vector comprises one or more polynucleotides encoding the following first fusion polypeptide and second fusion polypeptide, optionally joined or connected by one or more linkers: SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively. In some embodiments, the vector comprises one or more polynucleotides encoding the following first fusion polypeptide and second fusion polypeptide, optionally joined or connected by one or more linkers: SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively. In some embodiments, the vector comprises one or more polynucleotides encoding the following first fusion polypeptide and second fusion polypeptide, optionally joined or connected by one or more linkers: SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively. In some embodiments, the vector comprises one or more polynucleotides encoding the following first fusion polypeptide and second fusion polypeptide, optionally joined or connected by one or more linkers: SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively. In some embodiments, the vector comprises one or more polynucleotides encoding the following first fusion polypeptide and second fusion polypeptide, optionally joined or connected by one or more linkers: SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively. In some embodiments, the vector comprises one or more polynucleotides encoding the following first fusion polypeptide and second fusion polypeptide, optionally joined or connected by one or more linkers: SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively. In some embodiments, the vector comprises one or more polynucleotides encoding the following first fusion polypeptide and second fusion polypeptide, optionally joined or connected by one or more linkers: SEQ ID NOs:100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively. In some embodiments, the vector comprises a polynucleotide encoding a compound fusion polypeptide comprising or consisting of an amino acid sequence of any one of SEQ ID NOs: 105-112, 200-209, 222-223 and 227, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 105-112, 200-209, 222-223 and 227. In some embodiments, the vector comprises a polynucleotide encoding a compound fusion polypeptide comprising or consisting of an amino acid sequence of any one of SEQ ID NOs: 209, 222 and 223, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 209, 222 and 223. In some embodiments, the first and second fusion polypeptides do not comprise any polypeptide segments corresponding to Gag 54-146; Gag 370-500; Pol 1-55; Pol 118-128; Pol 321-366; Pol 432-541; Pol 607-682; Pol 709-746; Pol 828-839; Pol 921-931; Nef 1-63; Nef 100-116 and Nef 149-206, or fragments or subsequences thereof, wherein the Gag, Pol and Nef amino acid position numbers correspond to SEQ ID NOs: 1, 2 and 3, respectively. In some embodiments, the first and second fusion polypeptides do not comprise any polypeptide segments having an amino acid sequence of SEQ ID NOs: 35-47, or fragments or subsequences thereof, or an amino acid sequence at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 35-47, or fragments or subsequences thereof. In some embodiments, the vector comprises a polynucleotide comprising or consisting of a nucleic acid sequence of any one of SEQ ID NOs: 130-167, 210-219 and 225-226, or a nucleic acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 130-167, 210-219 and 225-226. In some embodiments, the vector comprises a polynucleotide comprising or consisting of a nucleic acid sequence of any one of SEQ ID NOs: 139, 140, 142, 143, 145, 146, 148, 149, 150, 152, 155, 158, 225 and 226, or a nucleic acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139, 140, 142, 143, 145, 146, 148, 149, 150, 152, 155, 158, 225 and 226. In some embodiments, the following first polynucleotide and second polynucleotide: SEQ ID NOs: 130 and 132, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 130 and 132, respectively; SEQ ID NOs: 130 and 134, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 130 and 134, respectively; SEQ ID NOs: 131 and 133, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 131 and 133, respectively; SEQ ID NOs: 131 and 135, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 131 and 135, respectively; SEQ ID NOs: 132 and 136, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 132 and 136, respectively; SEQ ID NOs: 133 and 135, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 133 and 135, respectively; SEQ ID NOs: 133 and 137, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 133 and 137, respectively; SEQ ID NOs: 134 and 136, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 134 and 136, respectively; SEQ ID NOs: 135 and 137, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 135 and 137, respectively; SEQ ID NOs: 138 and 141, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 138 and 141, respectively; SEQ ID NOs: 138 and 144, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 138 and 144, respectively; SEQ ID NOs: 139 and 142, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 142, respectively; SEQ ID NOs: 139 and 145, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 145, respectively; SEQ ID NOs: 140 and 146, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 140 and 146, respectively; SEQ ID NOs: 142 and 148, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 142 and 148, respectively; SEQ ID NOs: 143 and 149, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 143 and 149, respectively; SEQ ID NOs: 145 and 148, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 145 and 148, respectively; SEQ ID NOs: 150 and 152, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively; SEQ ID NOs: 150 and 155, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 155, respectively; SEQ ID NOs: 151 and 153, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 151 and 153, respectively; SEQ ID NOs: 151 and 156, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 151 and 156, respectively; SEQ ID NOs: 152 and 158, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 152 and 158, respectively; SEQ ID NOs: 153 and 159, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 153 and 159, respectively; SEQ ID NOs: 154 and 157, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 154 and 157, respectively; SEQ ID NOs: 155 and 158, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 155 and 158, respectively; SEQ ID NOs: 156 and 159, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 156 and 159, respectively; SEQ ID NOs: 160 and 161, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 160 and 161, respectively; SEQ ID NOs: 162 and 163, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 162 and 163, respectively; SEQ ID NOs: 164 and 165, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 164 and 165, respectively; SEQ ID NOs: 166 and 167, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 166 and 167, respectively; SEQ ID NOs: 210 and 211, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 210 and 211, respectively; SEQ ID NOs: 212 and 213, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 212 and 213, respectively; SEQ ID NOs: 214 and 215, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 214 and 215, respectively; SEQ ID NOs: 216 and 217, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 216 and 217, respectively; SEQ ID NOs: 218 and 219, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 218 and 219, respectively; SEQ ID NOs: 218 and 226, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 218 and 226, respectively; or SEQ ID NOs: 225 and 226, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 225 and 226, respectively. In some embodiments, the vector comprises the following first polynucleotide and second polynucleotide: (a) a first polynucleotide comprising SEQ ID NOs: 130 or SEQ ID NO: 131, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 130 or SEQ ID NO: 131, respectively, and (b) a second polynucleotide comprising SEQ ID NO: 134 or SEQ ID NO: 135, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 134 or SEQ ID NO: 135. In some embodiments, the vector comprises the following first polynucleotide and second polynucleotide: (a) a first polynucleotide comprising SEQ ID NO: 132 or SEQ ID NO: 133, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 132 or SEQ ID NO: 133, respectively, and (b) a second polynucleotide comprising SEQ ID NO: 136 or SEQ ID NO: 137, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 136 or SEQ ID NO: 137. In some embodiments, the vector comprises the following first polynucleotide and second polynucleotide: (a) a first polynucleotide comprising SEQ ID NO: 139, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 139, respectively, and (b) a second polynucleotide comprising SEQ ID NO: 145, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 145. In some embodiments, the vector comprises the following first polynucleotide and second polynucleotide: (a) a first polynucleotide comprising SEQ ID NO: 142, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 142, respectively, and (b) a second polynucleotide comprising SEQ ID NO: 148, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 148. In some embodiments, the vector comprises the following first polynucleotide and second polynucleotide: (a) a first polynucleotide comprising SEQ ID NO: 140, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 140, respectively, and (b) a second polynucleotide comprising SEQ ID NO: 146, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 146. In some embodiments, the vector comprises the following first polynucleotide and second polynucleotide: (a) a first polynucleotide comprising SEQ ID NO: 143, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 143, respectively, and (b) a second polynucleotide comprising SEQ ID NO: 149, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 149. In some embodiments, the vector comprises the following first polynucleotide and second polynucleotide: (a) a first polynucleotide comprising SEQ ID NO: 150, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 150, respectively, and (b) a second polynucleotide comprising SEQ ID NO: 152, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 152. In some embodiments, the vector comprises the following first polynucleotide and second polynucleotide: (a) a first polynucleotide comprising SEQ ID NO: 151, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 151, respectively, and (b) a second polynucleotide comprising SEQ ID NO: 153, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 153. In some embodiments, the vector comprises the following first polynucleotide and second polynucleotide: (a) a first polynucleotide comprising SEQ ID NO: 154, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 154, respectively, and (b) a second polynucleotide comprising SEQ ID NO: 157, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 157. In some embodiments, the vector comprises the following first polynucleotide and second polynucleotide: (a) a first polynucleotide comprising SEQ ID NO: 155, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 155, respectively, and (b) a second polynucleotide comprising SEQ ID NO: 158, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 158. In some embodiments, the vector comprises the following first polynucleotide and second polynucleotide: (a) a first polynucleotide comprising SEQ ID NO: 156, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 156, respectively, and (b) a second polynucleotide comprising SEQ ID NO: 159, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 159. In some embodiments, the vector comprises the following first polynucleotide and second polynucleotide: (a) a first polynucleotide comprising SEQ ID NO: 160, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 160, respectively, and (b) a second polynucleotide comprising SEQ ID NO: 161, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 161. In some embodiments, the vector comprises the following first polynucleotide and second polynucleotide: (a) a first polynucleotide comprising SEQ ID NO: 162, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 162, respectively, and (b) a second polynucleotide comprising SEQ ID NO: 163, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 163. In some embodiments, the vector comprises the following first polynucleotide and second polynucleotide: (a) a first polynucleotide comprising SEQ ID NO: 164, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 164, respectively, and (b) a second polynucleotide comprising SEQ ID NO: 165, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 165. In some embodiments, the vector comprises the following first polynucleotide and second polynucleotide: (a) a first polynucleotide comprising SEQ ID NO: 166, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 166, respectively, and (b) a second polynucleotide comprising SEQ ID NO: 167, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 167. In some embodiments, the vector comprises the following first polynucleotide and second polynucleotide: (a) a first polynucleotide comprising SEQ ID NO: 210, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 210, and (b) a second polynucleotide comprising SEQ ID NO: 211, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 211. In some embodiments, the vector comprises the following first polynucleotide and second polynucleotide: (a) a first polynucleotide comprising SEQ ID NO: 212, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 212, and (b) a second polynucleotide comprising SEQ ID NO: 213, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 213. In some embodiments, the vector comprises the following first polynucleotide and second polynucleotide: (a) a first polynucleotide comprising SEQ ID NO: 214, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 214, and (b) a second polynucleotide comprising SEQ ID NO: 215, or a polynucleotide that is at least 80%, 81%, 82%, 83%, 84%, 85%8, 86%, 87%, 88%, 89%, 90%, 91%, 92%, 93%, 94%, 95%, 96%, 97%, 98% or 99% identical to SEQ ID NO: 215. In some embodiments, the vector comprises the following first polynucleotide and second polynucleotide: (a) a first polynucleotide comprising SEQ ID NO: 216, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 216, and (b) a second polynucleotide comprising SEQ ID NO: 217, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 217. In some embodiments, the vector comprises the following first polynucleotide and second polynucleotide: (a) a first polynucleotide comprising SEQ ID NO: 218, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 218, and (b) a second polynucleotide comprising SEQ ID NO: 219, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 219. In some embodiments, the vector comprises the following first polynucleotide and second polynucleotide: (a) a first polynucleotide comprising SEQ ID NO: 218, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 218, and (b) a second polynucleotide comprising SEQ ID NO: 226, or a polynucleotide that is at least 80%, 81%, 82%, 83%, 84%, 85%8, 86%, 87%, 88%, 89%, 90%, 91%, 92%, 93%, 94%, 95%, 96%, 97%, 98% or 99% identical to SEQ ID NO: 226. In some embodiments, the vector comprises the following first polynucleotide and second polynucleotide: (a) a first polynucleotide comprising SEQ ID NO: 225, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 225, and (b) a second polynucleotide comprising SEQ ID NO: 226, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 226. In some embodiments, the first polynucleotide encoding the first fusion polypeptide and the second polynucleotide encoding the second fusion polypeptide are in a single open reading frame. In some embodiments, the first polynucleotide encoding the first fusion polypeptide is in a first open reading frame and the second polynucleotide encoding the second fusion polypeptide is in a second open reading frame. In some embodiments, the first polynucleotide encoding the first fusion polypeptide and the second polynucleotide encoding the second fusion polypeptide are in a single expression cassette. In some embodiments, the first polynucleotide encoding the first fusion polypeptide is in a first expression cassette and the second polynucleotide encoding the second fusion polypeptide is in a second expression cassette. In some embodiments, the vector is a plasmid vector, a bacterial vector or a viral vector. In some embodiments, the vector is a viral vector. In some embodiments, the viral vector is a DNA virus or an RNA virus. In some embodiments, the viral vector is replication defective, replication deficient, replication attenuated or replication competent. In some embodiments, the viral vector is from a virus selected from adenovirus, adeno-associated virus, arenavirus, alphavirus, poxvirus, cytomegalovirus, rhabdovirus, vesicular stomatitis virus, flavivirus, maraba virus and vaccinia virus. In some embodiments, the viral vector is from a virus from a taxonomical family selected from Adenoviridae, Arenaviridae, Herpesviridae (e.g. Cytomegalovirus), Poxviridae (e.g. Vaccinia virus, e.g. modified vaccinia Ankara (MVA)), Flaviviridae (e.g. Yellow fever virus), Rhabdoviridae (e.g. Vesiculovirus, e.g. Maraba vesiculovirus), Togaviridae (e.g., Alphavirus, e.g., Venezuelan equine encephalitis virus). In some embodiments, the viral vector is an arenavirus vector selected from Lymphocytic choriomeningitis mammarenavirus (LCMV), Cali mammarenavirus (a.k.a., Pichinde mammarenavirus or Pichinde arenavirus), Guanarito virus (GTOV), Junin virus (JUNV), Lassa virus (LASV), Lujo virus (LUJV), Machupo virus (MACV), Sabia virus (SABV), and Whitewater Arroyo virus (WWAV). In some embodiments, the viral vector is an arenavirus vector selected from Lymphocytic choriomeningitis mammarenavirus (LCMV) or Cali mammarenavirus (a.k.a. Pichinde mammarenavirus or Pichinde arenavirus). In some embodiments, the arenavirus vector comprises a bi-segmented genome. In some embodiments, the arenavirus vector comprises a tri-segmented genome. In some embodiments, the viral vector is a human adenovirus or a simian adenovirus (e.g., a chimpanzee adenovirus, a gorilla adenovirus or a rhesus adenovirus). In some embodiments, the viral vector is an adenovirus vector selected from adenovirus serotype 5 (Ad5), adenovirus serotype 26 (Ad26), adenovirus serotype 34 (Ad34), adenovirus serotype 35 (Ad35), adenovirus serotype 48 (Ad48), chimpanzee adenovirus (e.g. ChAd3 (AdC3), ChAd5 (AdC5), ChAd6 (AdC6), ChAd7 (AdC7), ChAd8 (AdC8), ChAd9 (AdC9), ChAd10 (AdC10), ChAd11 (AdC11), ChAd17 (AdC17), ChAd16 (AdC16), ChAd19 (AdC19), ChAd20 (AdC20), ChAd22 (AdC22), ChAd24 (AdC24), ChAdY25, ChAd26 (AdC26), ChAd28 (AdC28), ChAd30 (AdC30), ChAd31 (AdC31), ChAd37 (AdC37), ChAd38 (AdC38), ChAd43 (AdC43), ChAd44 (AdC44), ChAd55 (AdC55), ChAd63 (AdC63), ChAdV63, ChAd68 (AdC68), ChAd73 (AdC73), ChAd82 (AdC82), ChAd83 (AdC83), ChAd143 (AdC143), ChAd144 (AdC144), ChAd145 (AdC145), ChAd147 (AdC147)), gorilla adenovirus (e.g. GC44, GC45, GC46) and rhesus adenovirus (e.g., RhAd51, RhAd52, RhAd53, RhAd54, RhAd55, RhAd56, RhAd57, RhAd58, RhAd59, RhAd60, RhAd61, RhAd62, RhAd63, RhAd64, RhAd65, RhAd66).

Further provided are host cells comprising one or more polynucleotides, one or more expression cassettes, or one or more vectors, as described herein. In some embodiments, the one or more polynucleotides are not integrated into the host cell genome, e.g., are episomal. In some embodiments, the one or more polynucleotides are integrated into the host cell genome. In some embodiments, the host cell is a mammalian cell, e.g., a human cell. In various embodiments, the host cell can be in vitro or in vivo.

Further provided are immunogenic compositions. In various embodiments, the immunogenic compositions comprise one or more of the fusion polypeptides or compound fusion polypeptides, one or more polynucleotides, or one or more vectors, as described herein, and a pharmaceutically acceptable carrier. In some embodiments, the immunogenic composition comprises two or more of the fusion polypeptides or compound fusion polypeptides, two or more polynucleotides, two or more vectors, as described herein. In some embodiments, the one or more polynucleotides are DNA, cDNA, mRNA, or self-replicating RNA. In some embodiments, the immunogenic composition comprises a first fusion polypeptide and a second fusion polypeptide, or one or more vectors comprising one or more polynucleotides encoding the first and second fusion polypeptides, the first and second polypeptides comprising the following polypeptide segments, in sequential order, from N-terminus to C terminus, optionally joined or connected by one or more linkers: SEQ ID NOs: 6, 4, 16 and 26, and SEQ ID NOs: 7, 5, 27 and 17; SEQ ID NOs: 12, 24, 8 and 10, and SEQ ID NOs: 9, 25, 13 and 11; SEQ ID NOs: 14, 22, 18, 24 and 20, and SEQ ID NOs: 15, 25, 19, 23 and 21; SEQ ID NOs: 26, 16, 4 and 6, and SEQ ID NOs: 7, 27, 5 and 17; SEQ ID NOs: 8, 24, 12 and 10, and SEQ ID NOs: 13, 25, 9 and 11; SEQ ID NOs: 22, 24, 14, 18 and 20, and SEQ ID NOs: 25, 23, 15, 21 and 19; SEQ ID NOs: 20, 6, 4, 18, 16 and 26, and SEQ ID NOs: 7, 19, 5, 21, 27 and 17; SEQ ID NOs: 8, 24, 14, 12, 22 and 10, and SEQ ID NOs: 9, 13, 25, 23, 15 and 11; SEQ ID NOs: 18, 26, 20, 4, 6 and 16, and SEQ ID NOs: 7, 21, 17, 5, 27 and 19; SEQ ID NOs: 22, 24, 12, 14, 8 and 10, and SEQ ID NOs: 15, 25, 9, 23, 13 and 11; SEQ ID NOs: 24, 6, 4, 20, 18 and 32, and SEQ ID NOs: 8, 30, 14, 12, 26 and 10; SEQ ID NOs: 24, 6, 4, 20, 18 and 32, and SEQ ID NOs: 7, 21, 5, 25, 33 and 19; SEQ ID NOs: 24, 6, 4, 20, 18 and 32, and SEQ ID NOs: 8, 30, 14, 12, 26 and 10; SEQ ID NOs: 8, 30, 14, 12, 26 and 10, and SEQ ID NOs: 9, 13, 31, 27, 15 and 11; SEQ ID NOs: 6, 20, 4, 24, 32 and 18, and SEQ ID NOs: 8, 12, 30, 26, 14 and 10; SEQ ID NOs: 7, 21, 5, 25, 33 and 19 and SEQ ID NOs: 9, 13, 31, 27, 15 and 11; SEQ ID NOs: 20, 32, 24, 4, 6 and 18, and SEQ ID NOs: 26, 30, 12, 14, 8 and 10; SEQ ID NOs: 7, 25, 19, 5, 33 and 21, and SEQ ID NOs: 15, 31, 9, 27, 13 and 11; SEQ ID NOs: 24, 6, 16 and 18, and SEQ ID NOs: 26, 20, 10 and 28; SEQ ID NOs: 24, 6, 16 and 18, and SEQ ID NOs: 26, 10, 20 and 28; SEQ ID NOs: 24, 6, 16 and 18, and SEQ ID NOs: 7, 25, 17 and 19; SEQ ID NOs: 7, 19, 17 and 25, and SEQ ID NOs: 21, 27, 11 and 29; SEQ ID NOs: 24, 16, 6 and 18, and SEQ ID NOs: 27, 11, 21 and 29; SEQ ID NOs: 7, 25, 17 and 19, and SEQ ID NOs: 11, 27, 21 and 29; SEQ ID NOs: 7, 25, 17 and 19, and SEQ ID NOs: 21, 27, 11 and 29; SEQ ID NOs: 22, 6, 20 and 28, and SEQ ID NOs: 23, 7, 21 and 29; SEQ ID NOs: 22, 20, 6 and 28, and SEQ ID NOs: 7, 21, 23 and 29; SEQ ID NOs: 26, 10, 20 and 28, and SEQ ID NOs: 21, 27, 11 and 29; SEQ ID NOs: 22, 6, 16, 20, 18, 28, 26 and 10; or SEQ ID NOs: 7, 21, 19, 17, 27, 25, 29 and 11. In some embodiments, the immunogenic composition comprises one or more fusion polypeptides, or one or more vectors comprising one or more polynucleotides encoding one or more fusion polypeptides, comprising or consisting of an amino acid sequence of any one of SEQ ID NOs: 70-101, 105-112, 200-209, 222-223 and 227, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70-101, 105-112, 200-209, 222-223 and 227. In some embodiments, the immunogenic composition comprises one or more fusion polypeptides, or one or more vectors comprising one or more polynucleotides encoding one or more fusion polypeptides, comprising or consisting of an amino acid sequence of any one of SEQ ID NOs: 82-83, 85-87, 98-101, 209 and 222-223, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82-83, 85-87, 98-101, 209 and 222-223. In some embodiments, the immunogenic composition comprises the following first fusion polypeptide and second fusion polypeptide, one or more polynucleotides, or one or more vectors or one or more lipoplexes (e.g., LNPs) comprising one or more polynucleotides encoding the following first fusion polypeptide and second fusion polypeptide, optionally joined or connected by one or more linkers: SEQ ID NOs: 70 and 71, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70 and 71, respectively; SEQ ID NOs: 72 and 73, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 72 and 73, respectively; SEQ ID NOs: 74 and 75, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 74 and 75, respectively; SEQ ID NOs: 76 and 77, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 76 and 77, respectively; SEQ ID NOs: 78 and 79, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 78 and 79, respectively; SEQ ID NOs: 80 and 81, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 80 and 81, respectively; SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively; SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively; SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively; SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively; SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively; SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively; SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively; SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively; SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively; SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 88, respectively; SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively; SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively; SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively; SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively; SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively; SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively; SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively; SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively; SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively; SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively; SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively; or SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively. In some embodiments, the immunogenic composition comprises the following first fusion polypeptide and second fusion polypeptide, one or more polynucleotides, or one or more vectors or one or more lipoplexes (e.g., LNPs) comprising one or more polynucleotides encoding the following first fusion polypeptide and second fusion polypeptide, in sequential order, from N-terminus to C-terminus, optionally joined or connected by one or more linkers: SEQ ID NOs: 70 and 71, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70 and 71, respectively; SEQ ID NOs: 71 and 70, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 71 and 70, respectively; SEQ ID NOs: 72 and 73, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 72 and 73, respectively; SEQ ID NOs: 73 and 72, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 73 and 72, respectively; SEQ ID NOs: 74 and 75, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 74 and 75, respectively; SEQ ID NOs: 75 and 74, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 75 and 74, respectively; SEQ ID NOs: 76 and 77, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 76 and 77, respectively; SEQ ID NOs: 77 and 76, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 77 and 76, respectively; SEQ ID NOs: 78 and 79, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 78 and 79, respectively; SEQ ID NOs: 79 and 78, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 79 and 78, respectively; SEQ ID NOs: 80 and 81, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 80 and 81, respectively; SEQ ID NOs: 81 and 80, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 81 and 80, respectively; SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively; SEQ ID NOs: 83 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 82, respectively; SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively; SEQ ID NOs: 85 and 84, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 84, respectively; SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively; SEQ ID NOs: 87 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 86, respectively; SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively; SEQ ID NOs: 89 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 89 and 88, respectively; SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively; SEQ ID NOs: 85 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 82, respectively; SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; SEQ ID NOs: 86 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 82, respectively; SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively; SEQ ID NOs: 88 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 82, respectively; SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively; SEQ ID NOs: 87 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 83, respectively; SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively; SEQ ID NOs: 87 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 85, respectively; SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively; SEQ ID NOs: 87 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 88, respectively; SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 84, respectively; SEQ ID NOs: 88 and 84, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 84, respectively; SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively; SEQ ID NOs: 89 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 89 and 85, respectively; SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively; SEQ ID NOs: 101 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 85, respectively; SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively; SEQ ID NOs: 91 and 90, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 91 and 90, respectively; SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively; SEQ ID NOs: 93 and 92, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 93 and 92, respectively; SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively; SEQ ID NOs: 95 and 94, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 94, respectively; SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively; SEQ ID NOs: 97 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 97 and 96, respectively; SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively; SEQ ID NOs: 96 and 94, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 94, respectively; SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively; SEQ ID NOs: 97 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 97 and 95, respectively; SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively; SEQ ID NOs: 221 and 220, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 221 and 220, respectively; SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; SEQ ID NOs: 100 and 98, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 98, respectively; SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively; SEQ ID NOs: 101 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 99, respectively; SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively; SEQ ID NOs: 99 and 98, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 98, respectively; SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively; or SEQ ID NOs: 101 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 100, respectively. In some embodiments, the immunogenic composition comprises first and second polynucleotides, first and second viral vectors or first and second lipoplexes (e.g., LNPs) comprising one or more polynucleotides encoding the following first fusion polypeptide and second fusion polypeptide, optionally joined or connected by one or more linkers: (a) a first polynucleotide or first viral vector or first lipoplex (e.g., LNP) comprising one or more polynucleotides encoding a first fusion polypeptide and a second fusion polypeptide comprising SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively, and (b) a second polynucleotide or second viral vector or second lipoplex (e.g., LNP) comprising one or more polynucleotides encoding a first fusion polypeptide and a second fusion polypeptide comprising SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively. In some embodiments, the immunogenic composition comprises first and second polynucleotides or first and second viral vectors or first and second lipoplexes (e.g., LNPs) comprising one or more polynucleotides encoding the following first fusion polypeptide and second fusion polypeptide, optionally joined or connected by one or more linkers: (a) a first polynucleotide or first viral vector or first lipoplex (e.g., LNP) comprising one or more polynucleotides encoding a first fusion polypeptide and a second fusion polypeptide comprising SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively, and (b) a second polynucleotide or second viral vector or second lipoplex (e.g., LNP) comprising one or more polynucleotides encoding a first fusion polypeptide and a second fusion polypeptide comprising SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively. In some embodiments, the immunogenic composition comprises first and second polynucleotides or first and second viral vectors or first and second lipoplexes (e.g., LNPs) comprising one or more polynucleotides encoding the following first fusion polypeptide and second fusion polypeptide, optionally joined or connected by one or more linkers: (a) a first polynucleotide or first viral vector or first lipoplex (e.g., LNP) comprising one or more polynucleotides encoding a first fusion polypeptide and a second fusion polypeptide comprising SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively, and (b) a second polynucleotide or second viral vector or second lipoplex (e.g., LNP) comprising one or more polynucleotides encoding a first fusion polypeptide and a second fusion polypeptide comprising SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively. In some embodiments, the immunogenic composition comprises first and second viral vectors or first and second lipoplexes (e.g., LNPs) comprising one or more polynucleotides encoding the following first fusion polypeptide and second fusion polypeptide, optionally joined or connected by one or more linkers: (a) a first polynucleotide or first viral vector or first lipoplex (e.g., LNP) comprising one or more polynucleotides encoding a first fusion polypeptide and a second fusion polypeptide comprising SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively, and (b) a second polynucleotide or second viral vector or second lipoplex (e.g., LNP) comprising one or more polynucleotides encoding a first fusion polypeptide and a second fusion polypeptide comprising SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively. In some embodiments, the immunogenic composition comprises first and second viral vectors or first and second lipoplexes (e.g., LNPs) comprising one or more polynucleotides encoding the following first fusion polypeptide and second fusion polypeptide, optionally joined or connected by one or more linkers: (a) a first polynucleotide or first viral vector or first lipoplex (e.g., LNP) comprising one or more polynucleotides encoding a first fusion polypeptide and a second fusion polypeptide comprising SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively, and (b) a second polynucleotide or second viral vector or second lipoplex (e.g., LNP) comprising one or more polynucleotides encoding a first fusion polypeptide and a second fusion polypeptide comprising SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively. In some embodiments, the immunogenic composition comprises first and second polynucleotides or first and second viral vectors or first and second lipoplexes (e.g., LNPs) comprising one or more polynucleotides encoding the following first fusion polypeptide and second fusion polypeptide, optionally joined or connected by one or more linkers: (a) a first polynucleotide or first viral vector or first lipoplex (e.g., LNP) comprising one or more polynucleotides encoding a first fusion polypeptide and a second fusion polypeptide comprising SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 88, respectively, and (b) a second polynucleotide or second viral vector or second lipoplex (e.g., LNP) comprising one or more polynucleotides encoding a first fusion polypeptide and a second fusion polypeptide comprising SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively. In some embodiments, the immunogenic composition comprises first and second polynucleotides or first and second viral vectors or first and second lipoplexes (e.g., LNPs) comprising one or more polynucleotides encoding the following first fusion polypeptide and second fusion polypeptide, optionally joined or connected by one or more linkers: (a) a first polynucleotide or first viral vector or first lipoplex (e.g., LNP) comprising one or more polynucleotides encoding a first fusion polypeptide and a second fusion polypeptide comprising SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively, and (b) a second polynucleotide or second viral vector or second lipoplex (e.g., LNP) comprising one or more polynucleotides encoding a first fusion polypeptide and a second fusion polypeptide comprising SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively. In some embodiments, the immunogenic composition comprises a viral vector or a lipoplex (e.g., LNP) comprising one or more polynucleotides encoding the following first fusion polypeptide and second fusion polypeptide, optionally joined or connected by one or more linkers, SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively. In some embodiments, the immunogenic composition comprises a viral vector or a lipoplex (e.g., LNP) comprising one or more polynucleotides encoding the following first fusion polypeptide and second fusion polypeptide, optionally joined or connected by one or more linkers, SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively. In some embodiments, the composition comprises first and second viral vectors or first and second lipoplexes (e.g., LNPs) comprising one or more polynucleotides encoding the following first fusion polypeptide and second fusion polypeptide, optionally joined or connected by one or more linkers: (a) a first polynucleotide or first viral vector or first lipoplex (e.g., LNP) comprising one or more polynucleotides encoding a first fusion polypeptide and a second fusion polypeptide comprising SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively, and (b) a second polynucleotide or second viral vector or second lipoplex (e.g., LNP) comprising one or more polynucleotides encoding a first fusion polypeptide and a second fusion polypeptide comprising SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively. In some embodiments, the immunogenic composition comprises first and second polynucleotides or first and second viral vectors or first and second lipoplexes (e.g., LNPs) comprising one or more polynucleotides encoding the following first fusion polypeptide and second fusion polypeptide, optionally joined or connected by one or more linkers: (a) a first polynucleotide or first viral vector or first lipoplex (e.g., LNP) comprising one or more polynucleotides encoding a first fusion polypeptide and a second fusion polypeptide comprising SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively, and (b) a second polynucleotide or second viral vector or second lipoplex (e.g., LNP) comprising one or more polynucleotides encoding a first fusion polypeptide and a second fusion polypeptide comprising SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively. In some embodiments, the immunogenic composition comprises first and second polynucleotides or first and second viral vectors or first and second lipoplexes (e.g., LNPs) comprising one or more polynucleotides encoding the following first fusion polypeptide and second fusion polypeptide, optionally joined or connected by one or more linkers: (a) a first polynucleotide or first viral vector or first lipoplex (e.g., LNP) comprising one or more polynucleotides encoding a first fusion polypeptide and a second fusion polypeptide comprising SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively, and (b) a second polynucleotide or second viral vector or second lipoplex (e.g., LNP) comprising one or more polynucleotides encoding a first fusion polypeptide and a second fusion polypeptide comprising SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively. In some embodiments, the immunogenic composition comprises first and second polynucleotides or first and second viral vectors or first and second lipoplexes (e.g., LNPs) comprising one or more polynucleotides encoding the following first fusion polypeptide and second fusion polypeptide, optionally joined or connected by one or more linkers: (a) a first polynucleotide or first viral vector or first lipoplex (e.g., LNP) comprising one or more polynucleotides encoding a first fusion polypeptide and a second fusion polypeptide comprising SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively, and (b) a second polynucleotide or second viral vector or second lipoplex (e.g., LNP) comprising one or more polynucleotides encoding a first fusion polypeptide and a second fusion polypeptide comprising SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively. In some embodiments, the immunogenic composition comprises a viral vector or a lipoplex (e.g., LNP) comprising one or more polynucleotides encoding a first fusion polypeptide and a second fusion polypeptide, optionally joined or connected by one or more linkers, comprising SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively. In some embodiments, the immunogenic composition comprises a viral vector or a lipoplex (e.g., LNP) comprising one or more polynucleotides encoding a first fusion polypeptide and a second fusion polypeptide, optionally joined or connected by one or more linkers, comprising SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively. In some embodiments, the immunogenic composition comprises a viral vector or a lipoplex (e.g., LNP) comprising one or more polynucleotides encoding a first fusion polypeptide and a second fusion polypeptide, optionally joined or connected by one or more linkers, comprising SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively. In some embodiments, the immunogenic composition comprises a viral vector or a lipoplex (e.g., LNP) comprising one or more polynucleotides encoding a first fusion polypeptide and a second fusion polypeptide, optionally joined or connected by one or more linkers, comprising SEQ ID NOs: 87 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 88, respectively. In some embodiments, the immunogenic composition comprises a viral vector or a lipoplex (e.g., LNP) comprising one or more polynucleotides encoding a first fusion polypeptide and a second fusion polypeptide, optionally joined or connected by one or more linkers, comprising SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively. In some embodiments, the immunogenic composition comprises a viral vector or a lipoplex (e.g., LNP) comprising one or more polynucleotides encoding a first fusion polypeptide and a second fusion polypeptide, optionally joined or connected by one or more linkers, comprising SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively. In some embodiments, the immunogenic composition comprises a viral vector or a lipoplex (e.g., LNP) comprising one or more polynucleotides encoding a first fusion polypeptide and a second fusion polypeptide, optionally joined or connected by one or more linkers, comprising SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively. In some embodiments, the immunogenic composition comprises a viral vector or a lipoplex (e.g., LNP) comprising one or more polynucleotides encoding a first fusion polypeptide and a second fusion polypeptide, optionally joined or connected by one or more linkers, comprising SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively. In some embodiments, the immunogenic composition comprises a first viral vector or a lipoplex (e.g., LNP) comprising a first polynucleotide encoding a first polypeptide comprising SEQ ID NO: 200, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 200, and a second viral vector or a lipoplex (e.g., LNP) comprising a second polynucleotide encoding a second polypeptide comprising SEQ ID NO: 201, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 201. In some embodiments, the immunogenic composition comprises a first viral vector or a lipoplex (e.g., LNP) comprising a first polynucleotide encoding a first polypeptide comprising SEQ ID NO: 202, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 202, and a second viral vector or a lipoplex (e.g., LNP) comprising a second polynucleotide encoding a second polypeptide comprising SEQ ID NO: 203, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 203. In some embodiments, the immunogenic composition comprises a first viral vector or a lipoplex (e.g., LNP) comprising a first polynucleotide encoding a first polypeptide comprising SEQ ID NO: 203, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 203, and a second viral vector or a lipoplex (e.g., LNP) comprising a second polynucleotide encoding a second polypeptide comprising SEQ ID NO: 204, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 204. In some embodiments, the immunogenic composition comprises a first viral vector or a lipoplex (e.g., LNP) comprising a first polynucleotide encoding a first polypeptide comprising SEQ ID NO: 105, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 105, and a second viral vector or a lipoplex (e.g., LNP) comprising a second polynucleotide encoding a second polypeptide comprising SEQ ID NO: 107, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 107. In some embodiments, the immunogenic composition comprises a first viral vector or a lipoplex (e.g., LNP) comprising a first polynucleotide encoding a first polypeptide comprising SEQ ID NO: 206, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 206, and a second viral vector or a lipoplex (e.g., LNP) comprising a second polynucleotide encoding a second polypeptide comprising SEQ ID NO: 207, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 207. In some embodiments, the immunogenic composition comprises a first viral vector or a lipoplex (e.g., LNP) comprising a first polynucleotide encoding a first polypeptide comprising SEQ ID NO: 208, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 208, and a second viral vector or a lipoplex (e.g., LNP) comprising a second polynucleotide encoding a second polypeptide comprising SEQ ID NO: 209 or SEQ ID NO: 227, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 209 or SEQ ID NO: 227. In some embodiments, the immunogenic composition comprises a first viral vector or a lipoplex (e.g., LNP) comprising a first polynucleotide encoding a first polypeptide comprising SEQ ID NO: 222, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 222, and a second viral vector or a lipoplex (e.g., LNP) comprising a second polynucleotide encoding a second polypeptide comprising SEQ ID NO: 209 or SEQ ID NO: 227, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 209 or SEQ ID NO: 227. In some embodiments, the immunogenic composition comprises a first viral vector or a lipoplex (e.g., LNP) comprising a first polynucleotide encoding a first polypeptide comprising SEQ ID NO: 222, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 222, and a second viral vector or a lipoplex (e.g., LNP) comprising a second polynucleotide encoding a second polypeptide comprising SEQ ID NO: 223, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 223. In some embodiments, the immunogenic composition comprises a polynucleotide comprising or consisting of a nucleic acid sequence of any one of SEQ ID NOs: 130-167, 210-219 and 225-226, or a nucleic acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 130-167, 210-219 and 225-226. In some embodiments, the immunogenic composition comprises a polynucleotide comprising or consisting of a nucleic acid sequence of any one of SEQ ID NOs: 139, 140, 142, 143, 145, 146, 148, 149, 150, 152, 155, 158, 225 and 226, or a nucleic acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139, 140, 142, 143, 145, 146, 148, 149, 150, 152, 155, 158, 225 and 226. In some embodiments, the immunogenic composition comprises the following first polynucleotide and second polynucleotide, or one or more vectors comprising the following first polynucleotide and second polynucleotide: SEQ ID NOs: 130 and 132, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 130 and 132, respectively; SEQ ID NOs: 130 and 134, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 130 and 134, respectively; SEQ ID NOs: 131 and 133, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 131 and 133, respectively; SEQ ID NOs: 131 and 135, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 131 and 135, respectively; SEQ ID NOs: 132 and 136, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 132 and 136, respectively; SEQ ID NOs: 133 and 135, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 133 and 135, respectively; SEQ ID NOs: 133 and 137, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 133 and 137, respectively; SEQ ID NOs: 134 and 136, or polynucleotides that are at least 80%, 81%, 82%, 83%, 84%, 85%8, 86%, 87%, 88%, 89%, 90%, 91%, 92%, 93%, 94%, 95%, 96%, 97%, 98% or 99% identical to any one of SEQ ID NOs: 134 and 136, respectively; SEQ ID NOs: 135 and 137, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 135 and 137, respectively; SEQ ID NOs: 138 and 141, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 138 and 141, respectively; SEQ ID NOs: 138 and 144, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 138 and 144, respectively; SEQ ID NOs: 139 and 142, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 142, respectively; SEQ ID NOs: 139 and 145, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 145, respectively; SEQ ID NOs: 140 and 146, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 140 and 146, respectively; SEQ ID NOs: 142 and 148, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 142 and 148, respectively; SEQ ID NOs: 143 and 149, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 143 and 149, respectively; SEQ ID NOs: 145 and 148, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 145 and 148, respectively; SEQ ID NOs: 150 and 152, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively; SEQ ID NOs: 150 and 155, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 155, respectively; SEQ ID NOs: 151 and 153, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 151 and 153, respectively; SEQ ID NOs: 151 and 156, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 151 and 156, respectively; SEQ ID NOs: 152 and 158, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 152 and 158, respectively; SEQ ID NOs: 153 and 159, or polynucleotides that are at least 80%, 81%, 82%, 83%, 84%, 85%8, 86%, 87%, 88%, 89%, 90%, 91%, 92%, 93%, 94%, 95%, 96%, 97%, 98% or 99% identical to any one of SEQ ID NOs: 153 and 159, respectively; SEQ ID NOs: 154 and 157, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 154 and 157, respectively; SEQ ID NOs: 155 and 158, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 155 and 158, respectively; SEQ ID NOs: 156 and 159, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 156 and 159, respectively; SEQ ID NOs: 160 and 161, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 160 and 161, respectively; SEQ ID NOs: 162 and 163, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 162 and 163, respectively; SEQ ID NOs: 164 and 165, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 164 and 165, respectively; SEQ ID NOs: 166 and 167, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 166 and 167, respectively; SEQ ID NOs: 210 and 211, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 210 and 211, respectively; SEQ ID NOs: 212 and 213, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 212 and 213, respectively; SEQ ID NOs: 214 and 215, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 214 and 215, respectively; SEQ ID NOs: 216 and 217, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 216 and 217, respectively; SEQ ID NOs: 218 and 219, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 218 and 219, respectively; SEQ ID NOs: 218 and 226, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 218 and 226, respectively; or SEQ ID NOs: 225 and 226, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 225 and 226, respectively. In some embodiments, the immunogenic composition comprises first and second polynucleotides or first and second viral vectors or first and second lipoplexes (e.g., LNPs) comprising the following first polynucleotide and second polynucleotide: (a) a first vector or first lipoplex (e.g., LNP) comprising first and second polynucleotides comprising SEQ ID NOs: 131 and 135, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 131 and 135, respectively, and (b) a second vector or second lipoplex (e.g., LNP) comprising first and second polynucleotides comprising SEQ ID NOs: 133 and 137, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 133 and 137, respectively. In some embodiments, the immunogenic composition comprises first and second polynucleotides or first and second viral vectors or first and second lipoplexes (e.g., LNPs) comprising the following first polynucleotide and second polynucleotide: (a) a first vector or first lipoplex (e.g., LNP) comprising first and second polynucleotides comprising SEQ ID NOs: 139 and 145, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 145, respectively, and (b) a second vector or second lipoplex (e.g., LNP) comprising first and second polynucleotides comprising SEQ ID NOs: 142 and 148, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 142 and 148, respectively. In some embodiments, the immunogenic composition comprises first and second polynucleotides or first and second viral vectors or first and second lipoplexes (e.g., LNPs) comprising the following first polynucleotide and second polynucleotide: (a) a first vector or first lipoplex (e.g., LNP) comprising first and second polynucleotides comprising SEQ ID NOs: 140 and 146, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 140 and 146, respectively, and (b) a second vector or second lipoplex (e.g., LNP) comprising first and second polynucleotides comprising SEQ ID NOs: 143 and 149, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 143 and 149, respectively. In some embodiments, the first and second viral vectors of such an immunogenic composition are Lymphocytic choriomeningitis mammarenavirus (LCMV) viral vectors. In some embodiments, the immunogenic composition comprises first and second polynucleotides or first and second viral vectors or first and second lipoplexes (e.g., LNPs) comprising the following first polynucleotide and second polynucleotide: (a) a first vector or first lipoplex (e.g., LNP) comprising first and second polynucleotides comprising SEQ ID NOs: 150 and 152, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively, and (b) a second vector or second lipoplex (e.g., LNP) comprising first and second polynucleotides comprising SEQ ID NOs: 154 and 157 or SEQ ID NOs: 155 and 158, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 154 and 157 or SEQ ID NOs: 155 and 158, respectively. In some embodiments, the first and second viral vectors of such an immunogenic composition are Cali mammarenavirus (a.k.a. Pichinde mammarenavirus or Pichinde arenavirus) viral vectors. In some embodiments, the immunogenic composition comprises first and second polynucleotides or first and second viral vectors or first and second lipoplexes (e.g., LNPs) comprising the following first polynucleotide and second polynucleotide: (a) a first vector or first lipoplex (e.g., LNP) comprising first and second polynucleotides comprising SEQ ID NOs: 151 and 153, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 151 and 153, respectively, and (b) a second vector or second lipoplex (e.g., LNP) comprising first and second polynucleotides comprising SEQ ID NOs: 156 and 159, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 156 and 159, respectively. In some embodiments, the immunogenic composition comprises first and second polynucleotides or first and second viral vectors or first and second lipoplexes (e.g., LNPs) comprising one or more polynucleotides: (a) the first viral vector or first lipoplex (e.g., LNP) comprising a polynucleotide of SEQ ID NO: 160, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 160, respectively, and (b) the second viral vector or second lipoplex (e.g., LNP) comprising a polynucleotide of SEQ ID NO: 161, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 161, respectively. In some embodiments, the immunogenic composition comprises first and second polynucleotides or first and second viral vectors or first and second lipoplexes (e.g., LNPs) comprising one or more polynucleotides: (a) the first viral vector or first lipoplex (e.g., LNP) comprising a polynucleotide of SEQ ID NO: 162, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 162, respectively, and (b) the second viral vector or second lipoplex (e.g., LNP) comprising a polynucleotide of SEQ ID NO: 163, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 163, respectively. In some embodiments, the immunogenic composition comprises first and second polynucleotides or first and second viral vectors or first and second lipoplexes (e.g., LNPs) comprising one or more polynucleotides: (a) the first viral vector or first lipoplex (e.g., LNP) comprising a polynucleotide of SEQ ID NO: 164, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 164, respectively, and (b) the second viral vector or second lipoplex (e.g., LNP) comprising a polynucleotide of SEQ ID NO: 165, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 165, respectively. In some embodiments, the immunogenic composition comprises first and second polynucleotides or first and second viral vectors or first and second lipoplexes (e.g., LNPs) comprising one or more polynucleotides: (a) the first viral vector or first lipoplex (e.g., LNP) comprising a polynucleotide of SEQ ID NO: 166, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 166, respectively, and (b) the second viral vector or second lipoplex (e.g., LNP) comprising a polynucleotide of SEQ ID NO: 167, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 167, respectively. In some embodiments, the immunogenic composition comprises first and second polynucleotides or first and second viral vectors or first and second lipoplexes (e.g., LNPs) comprising one or more polynucleotides: (a) the first viral vector or first lipoplex (e.g., LNP) comprising a polynucleotide of SEQ ID NO: 210, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 210, and (b) the second viral vector or second lipoplex (e.g., LNP) comprising a polynucleotide of SEQ ID NO: 211, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 211. In some embodiments, the immunogenic composition comprises first and second polynucleotides or first and second viral vectors or first and second lipoplexes (e.g., LNPs) comprising one or more polynucleotides: (a) the first viral vector or first lipoplex (e.g., LNP) comprising a polynucleotide of SEQ ID NO: 212, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 212, and (b) the second viral vector or second lipoplex (e.g., LNP) comprising a polynucleotide of SEQ ID NO: 213, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 213. In some embodiments, the immunogenic composition comprises first and second polynucleotides or first and second viral vectors or first and second lipoplexes (e.g., LNPs) comprising one or more polynucleotides: (a) the first viral vector or first lipoplex (e.g., LNP) comprising a polynucleotide of SEQ ID NO: 214, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 214, and (b) the second viral vector or second lipoplex (e.g., LNP) comprising a polynucleotide of SEQ ID NO: 215, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 215. In some embodiments, the immunogenic composition comprises first and second polynucleotides or first and second viral vectors or first and second lipoplexes (e.g., LNPs) comprising one or more polynucleotides: (a) the first viral vector or first lipoplex (e.g., LNP) comprising a polynucleotide of SEQ ID NO: 216, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 216, and (b) the second viral vector or second lipoplex (e.g., LNP) comprising a polynucleotide of SEQ ID NO: 217, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 217. In some embodiments, the immunogenic composition comprises first and second polynucleotides or first and second viral vectors or first and second lipoplexes (e.g., LNPs) comprising one or more polynucleotides: (a) the first viral vector or first lipoplex (e.g., LNP) comprising a polynucleotide of SEQ ID NO: 218, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 218, and (b) the second viral vector or second lipoplex (e.g., LNP) comprising a polynucleotide of SEQ ID NO: 219, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 219. In some embodiments, the immunogenic composition comprises first and second polynucleotides or first and second viral vectors or first and second lipoplexes (e.g., LNPs) comprising one or more polynucleotides: (a) the first viral vector or first lipoplex (e.g., LNP) comprising a polynucleotide of SEQ ID NO: 218, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 218, and (b) the second viral vector or second lipoplex (e.g., LNP) comprising a polynucleotide of SEQ ID NO: 226, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 226. In some embodiments, the immunogenic composition comprises first and second polynucleotides or first and second viral vectors or first and second lipoplexes (e.g., LNPs) comprising one or more polynucleotides: (a) the first viral vector or first lipoplex (e.g., LNP) comprising a polynucleotide of SEQ ID NO: 225, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 225, and (b) the second viral vector or second lipoplex (e.g., LNP) comprising a polynucleotide of SEQ ID NO: 226, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 226. In some embodiments, the immunogenic composition comprises a compound fusion polypeptide, a vector or a lipoplex (e.g., LNP) comprising a polynucleotide encoding a compound fusion polypeptide, the compound fusion polypeptide comprising or consisting of an amino acid sequence of any one of SEQ ID NOs: 105-112, 200-209, 222-223 and 227, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 105-112, 200-209, 222-223 and 227. In some embodiments, the immunogenic composition comprises a compound fusion polypeptide, a vector or a lipoplex (e.g., LNP) comprising a polynucleotide encoding a compound fusion polypeptide, the compound fusion polypeptide comprising or consisting of an amino acid sequence of any one of SEQ ID NOs: 209, 222 and 223, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 209, 222 and 223. In some embodiments, the one or more fusion polypeptides do not comprise any polypeptide segments corresponding to Gag 54-146; Gag 370-500; Pol 1-55; Pol 118-128; Pol 321-366; Pol 432-541; Pol 607-682; Pol 709-746; Pol 828-839; Pol 921-931; Nef 1-63; Nef 100-116 and Nef 149-206, or fragments or subsequences thereof, wherein the Gag, Pol and Nef amino acid position numbers correspond to SEQ ID NOs: 1, 2 and 3, respectively. In some embodiments, the one or more fusion polypeptides do not comprise any polypeptide segments having an amino acid sequence of SEQ ID NOs: 35-47, or fragments or subsequences thereof, or an amino acid sequence at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 35-47, or fragments or subsequences thereof. In various embodiments of the immunogenic compositions, the first and second viral vectors can be Lymphocytic choriomeningitis mammarenavirus (LCMV) viral vectors, Cali mammarenavirus (a.k.a. Pichinde mammarenavirus or Pichinde arenavirus) viral vectors or adenoviral vectors, e.g., chimpanzee adenoviral vectors (ChAds). In some embodiments, the immunogenic composition comprises a single vector comprising one or more polynucleotides encoding first and second fusion polypeptides. In some embodiments, the immunogenic composition further comprises one or more of an adjuvant, a detergent, a micelle-forming agent, and an oil. In some embodiments, the immunogenic composition is formulated for administration via a route selected from intravenous, intramuscular, intradermal, subcutaneous, intranodal and mucosal (e.g. buccal, intranasal, intrarectal, intravaginal). In some embodiments, the immunogenic composition is formulated as a liquid, a suspension or an emulsion. In some embodiments, the immunogenic composition is lyophilized.

Further provided are kits comprising one or more unitary doses of one or more of the fusion polypeptides, one or more compound fusion polypeptides, one or more polynucleotides, one or more vectors, or one or more immunogenic compositions, as described herein. In some embodiments, the kit comprises two or more of the fusion polypeptides, two or more compound fusion polypeptides, two or more polynucleotides, two or more vectors, or two or more immunogenic compositions, as described herein. In some embodiments, the one or more unitary doses are in a single container. In some embodiments, one or more unitary doses are in two or more separate containers. In some embodiments, the kit comprises one or more containers selected from vials, ampules and pre-loaded syringes. In some embodiments, the kit comprises one or more containers comprising the one or more fusion polypeptides, one or more polynucleotides or one or more vectors in an aqueous solution. In some embodiments, the one or more unitary doses are the same. In some embodiments, the one or more unitary doses are the different. In some embodiments, the kit comprises one or more unitary doses of one or more viral vectors and the unitary doses are in the range of about $10^3$ to about $10^{12}$ viral focus forming units (FFU) or plaque forming units (PFU) or infectious units (IU) or viral particles (vp), e.g. from about $10^4$ to about $10^7$ viral FFU or PFU or IU or vp, e.g. from about $10^3$ to about $10^4$, $10^5$, $10^6$, $10^7$, $10^8$, $10^9$, $10^{10}$, $10^{11}$, $10^{12}$, $10^{13}$, $10^{14}$ or $10^{15}$ viral FFU or PFU or IU or vp. In some embodiments, the kit comprises a first fusion polypeptide and a second fusion polypeptide, or one or more vectors comprising one or more polynucleotides encoding the first and second fusion polypeptides, the first and second polypeptides comprising the following polypeptide segments, in sequential order, from N-terminus to C terminus, optionally joined or connected by one or more linkers: SEQ ID NOs: 6, 4, 16 and 26, and SEQ ID NOs: 7, 5, 27 and 17; SEQ ID NOs: 12, 24, 8 and 10, and SEQ ID NOs: 9, 25, 13 and 11; SEQ ID NOs: 14, 22, 18, 24 and 20, and SEQ ID NOs: 15, 25, 19, 23 and 21; SEQ ID NOs: 26, 16, 4 and 6, and SEQ ID NOs: 7, 27, 5 and 17; SEQ ID NOs: 8, 24, 12 and 10, and SEQ ID NOs: 13, 25, 9 and 11; SEQ ID NOs: 22, 24, 14, 18 and 20, and SEQ ID NOs: 25, 23, 15, 21 and 19; SEQ ID NOs: 20, 6, 4, 18, 16 and 26, and SEQ ID NOs: 7, 19, 5, 21, 27 and 17; SEQ ID NOs: 8, 24, 14, 12, 22 and 10, and SEQ ID NOs: 9, 13, 25, 23, 15 and 11; SEQ ID NOs: 18, 26, 20, 4, 6 and 16, and SEQ ID NOs: 7, 21, 17, 5, 27 and 19; SEQ ID NOs: 22, 24, 12, 14, 8 and 10, and SEQ ID NOs: 15, 25, 9, 23, 13 and 11; SEQ ID NOs: 24, 6, 4, 20, 18 and 32, and SEQ ID NOs: 8, 30, 14, 12, 26 and 10; SEQ ID NOs: 24, 6, 4, 20, 18 and 32, and SEQ ID NOs: 7, 21, 5, 25, 33 and 19; SEQ ID NOs: 24, 6, 4, 20, 18 and 32, and SEQ ID NOs: 8, 30, 14, 12, 26 and 10; SEQ ID NOs: 8, 30, 14, 12, 26 and 10, and SEQ ID NOs: 9, 13, 31, 27, 15 and 11; SEQ ID NOs: 6, 20, 4, 24, 32 and 18, and SEQ ID NOs: 8, 12, 30, 26, 14 and 10; SEQ ID NOs: 7, 21, 5, 25, 33 and 19 and SEQ ID NOs: 9, 13, 31, 27, 15 and 11; SEQ ID NOs: 20, 32, 24, 4, 6 and 18, and SEQ ID NOs: 26, 30, 12, 14, 8 and 10; SEQ ID NOs: 7, 25, 19, 5, 33 and 21, and SEQ ID NOs: 15, 31, 9, 27, 13 and 11; SEQ ID NOs: 24, 6, 16 and 18, and SEQ ID NOs: 26, 20, 10 and 28; SEQ ID NOs: 24, 6, 16 and 18, and SEQ ID NOs: 26, 10, 20 and 28; SEQ ID NOs: 24, 6, 16 and 18, and SEQ ID NOs: 7, 25, 17 and 19; SEQ ID NOs: 7, 19, 17 and 25, and SEQ ID NOs: 21, 27, 11 and 29; SEQ ID NOs: 24, 16, 6 and 18, and SEQ ID NOs: 27, 11, 21 and 29; SEQ ID NOs: 7, 25, 17 and 19, and SEQ ID NOs: 11, 27, 21 and 29; SEQ ID NOs: 7, 25, 17 and 19, and SEQ ID NOs: 21, 27, 11 and 29; SEQ ID NOs: 22, 6, 20 and 28, and SEQ ID NOs: 23, 7, 21 and 29; SEQ ID NOs: 22, 20, 6 and 28, and SEQ ID NOs: 7, 21, 23 and 29; SEQ ID NOs: 26, 10, 20 and 28, and SEQ ID NOs: 21, 27, 11 and 29; SEQ ID NOs: 22, 6, 16, 20, 18, 28, 26 and 10; or SEQ ID NOs: 7, 21, 19, 17, 27, 25, 29 and 11. In some embodiments, the kit comprises one or more fusion polypeptides, one or more vectors, or one or more lipoplexes (LNPs), comprising one or more polynucleotides encoding one or more fusion polypeptides, comprising or consisting of an amino acid sequence of any one of SEQ ID NOs: 70-101, 105-112, 200-209, 222-223 and 227, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70-101, 105-112, 200-209, 222-223 and 227. In some embodiments, the kit comprises one or more fusion polypeptides, one or more vectors, or one or more lipoplexes (LNPs), comprising one or more polynucleotides encoding one or more fusion polypeptides, comprising or consisting of an amino acid sequence of any one of SEQ ID NOs: 82-83, 85-87, 98-101, 209 and 222-223, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82-83, 85-87, 98-101, 209 and 222-223. In some embodiments, the kit comprises the following first fusion polypeptide and second fusion polypeptide, or one or more vectors comprising one or more polynucleotides encoding the following first fusion polypeptide and second fusion polypeptide, optionally joined or connected by one or more linkers: SEQ ID NOs: 70 and 71, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70 and 71, respectively; SEQ ID NOs: 72 and 73, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 72 and 73, respectively; SEQ ID NOs: 74 and 75, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 74 and 75, respectively; SEQ ID NOs: 76 and 77, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 76 and 77, respectively; SEQ ID NOs: 78 and 79, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 78 and 79, respectively; SEQ ID NOs: 80 and 81, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 80 and 81, respectively; SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively; SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively; SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively; SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively; SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively; SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively; SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively; SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively; SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively; SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 88, respectively; SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively; SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively; SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively; SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively; SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively; SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively; SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively; SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively; SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively; SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively; SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively; or SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively. In some embodiments, the kit comprises the following first fusion polypeptide and second fusion polypeptide, one or more vectors, or one or more lipoplexes (e.g., LNPs), comprising one or more polynucleotides encoding the following first fusion polypeptide and second fusion polypeptide, in sequential order, from N-terminus to C-terminus, optionally joined or connected by one or more linkers: SEQ ID NOs: 70 and 71, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70 and 71, respectively; SEQ ID NOs: 71 and 70, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 71 and 70, respectively; SEQ ID NOs: 72 and 73, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 72 and 73, respectively; SEQ ID NOs: 73 and 72, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 73 and 72, respectively; SEQ ID NOs: 74 and 75, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 74 and 75, respectively; SEQ ID NOs: 75 and 74, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 75 and 74, respectively; SEQ ID NOs: 76 and 77, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 76 and 77, respectively; SEQ ID NOs: 77 and 76, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 77 and 76, respectively; SEQ ID NOs: 78 and 79, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 78 and 79, respectively; SEQ ID NOs: 79 and 78, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 79 and 78, respectively; SEQ ID NOs: 80 and 81, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 80 and 81, respectively; SEQ ID NOs: 81 and 80, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 81 and 80, respectively; SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively; SEQ ID NOs: 83 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 82, respectively; SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively; SEQ ID NOs: 85 and 84, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 84, respectively; SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively; SEQ ID NOs: 87 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 86, respectively; SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively; SEQ ID NOs: 89 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 89 and 88, respectively; SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively; SEQ ID NOs: 85 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 82, respectively; SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; SEQ ID NOs: 86 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 82, respectively; SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively; SEQ ID NOs: 88 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 82, respectively; SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively; SEQ ID NOs: 87 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 83, respectively; SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively; SEQ ID NOs: 87 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 85, respectively; SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively; SEQ ID NOs: 87 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 88, respectively; SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 84, respectively; SEQ ID NOs: 88 and 84, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 84, respectively; SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively; SEQ ID NOs: 89 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 89 and 85, respectively; SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively; SEQ ID NOs: 101 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 85, respectively; SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively; SEQ ID NOs: 91 and 90, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 91 and 90, respectively; SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively; SEQ ID NOs: 93 and 92, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 93 and 92, respectively; SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively; SEQ ID NOs: 95 and 94, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 94, respectively; SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively; SEQ ID NOs: 97 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 97 and 96, respectively; SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively; SEQ ID NOs: 96 and 94, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 94, respectively; SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively; SEQ ID NOs: 97 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 97 and 95, respectively; SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively; SEQ ID NOs: 221 and 220, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 221 and 220, respectively; SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; SEQ ID NOs: 100 and 98, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 98, respectively; SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively; SEQ ID NOs: 101 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 99, respectively; SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively; SEQ ID NOs: 99 and 98, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 98, respectively; SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively; or SEQ ID NOs: 101 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 100, respectively. In some embodiments, the kit comprises first, second, third and fourth viral vectors or lipoplexes (e.g., LNPs) comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding a first fusion polypeptide and a second fusion polypeptide comprising SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively; (b) a second viral vector or lipoplex (e.g., LNP) comprising one or more polynucleotides encoding a first fusion polypeptide and a second fusion polypeptide comprising SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively; (c) a third viral vector or lipoplex (e.g., LNP) comprising one or more polynucleotides encoding a first fusion polypeptide and a second fusion polypeptide comprising SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively; and (d) a fourth viral vector or lipoplex (e.g., LNP) comprising one or more polynucleotides encoding a first fusion polypeptide and a second fusion polypeptide comprising SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively. In some embodiments, the kit comprises first and second viral vectors or lipoplexes (e.g., LNPs) comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding a first fusion polypeptide and a second fusion polypeptide comprising SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively, and (b) a second viral vector or lipoplex (e.g., LNP) comprising one or more polynucleotides encoding a first fusion polypeptide and a second fusion polypeptide comprising SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively. In some embodiments, the kit comprises first and second viral vectors or lipoplexes (e.g., LNPs) comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding a first fusion polypeptide and a second fusion polypeptide comprising SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively, and (b) a second viral vector or lipoplex (e.g., LNP) comprising one or more polynucleotides encoding a first fusion polypeptide and a second fusion polypeptide comprising SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively. In some embodiments, the kit comprises first and second viral vectors or lipoplexes (e.g., LNPs) comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding a first fusion polypeptide and a second fusion polypeptide comprising SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively, and (b) a second viral vector or lipoplex (e.g., LNP) comprising one or more polynucleotides encoding a first fusion polypeptide and a second fusion polypeptide comprising SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively. In some embodiments, the kit comprises first and second viral vectors or lipoplexes (e.g., LNPs) comprising one or more polynucleotides encoding the following first fusion polypeptide and second fusion polypeptide, optionally joined or connected by one or more linkers: (a) a first viral vector or lipoplex (e.g., LNP) comprising a polynucleotide encoding a fusion polypeptide comprising SEQ ID NO: 200, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 200, and (b) a second viral vector or lipoplex (e.g., LNP) comprising a polynucleotide encoding a fusion polypeptide comprising SEQ ID NO: 201, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 201. In some embodiments, the kit comprises first and second viral vectors or lipoplexes (e.g., LNPs) comprising one or more polynucleotides encoding the following first fusion polypeptide and second fusion polypeptide, optionally joined or connected by one or more linkers: (a) a first viral vector or lipoplex (e.g., LNP) comprising a polynucleotide encoding a fusion polypeptide comprising SEQ ID NO: 202, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 202, and (b) a second viral vector or lipoplex (e.g., LNP) comprising a polynucleotide encoding a fusion polypeptide comprising SEQ ID NO: 203, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 203. In some embodiments, the kit comprises first and second viral vectors or lipoplexes (e.g., LNPs) comprising one or more polynucleotides encoding the following first fusion polypeptide and second fusion polypeptide, optionally joined or connected by one or more linkers: (a) a first viral vector or lipoplex (e.g., LNP) comprising a polynucleotide encoding a fusion polypeptide comprising SEQ ID NO: 204, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 204, and (b) a second viral vector or lipoplex (e.g., LNP) comprising a polynucleotide encoding a fusion polypeptide comprising SEQ ID NO: 205, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 205. In some embodiments, the kit comprises first and second viral vectors or lipoplexes (e.g., LNPs) comprising one or more polynucleotides encoding the following first fusion polypeptide and second fusion polypeptide, optionally joined or connected by one or more linkers: (a) a first viral vector or lipoplex (e.g., LNP) comprising a polynucleotide encoding a fusion polypeptide comprising SEQ ID NO: 105 or 206, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 105 or 206, respectively, and (b) a second viral vector or lipoplex (e.g., LNP) comprising a polynucleotide encoding a fusion polypeptide comprising SEQ ID NO: 107 or 207, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 107 or 207, respectively. In some embodiments, the kit comprises first and second viral vectors or lipoplexes (e.g., LNPs) comprising one or more polynucleotides encoding the following first fusion polypeptide and second fusion polypeptide, optionally joined or connected by one or more linkers: (a) a first viral vector or lipoplex (e.g., LNP) comprising a polynucleotide encoding a fusion polypeptide comprising SEQ ID NO: 208, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 208, and (b) a second viral vector or lipoplex (e.g., LNP) comprising a polynucleotide encoding a fusion polypeptide comprising SEQ ID NO: 209 or SEQ ID NO: 227, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 209 or SEQ ID NO: 227. In some embodiments, the kit comprises first and second viral vectors or lipoplexes (e.g., LNPs) comprising one or more polynucleotides encoding the following first fusion polypeptide and second fusion polypeptide, optionally joined or connected by one or more linkers: (a) a first viral vector or lipoplex (e.g., LNP) comprising a polynucleotide encoding a fusion polypeptide comprising SEQ ID NO: 222, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 222, and (b) a second viral vector or lipoplex (e.g., LNP) comprising a polynucleotide encoding a fusion polypeptide comprising SEQ ID NO: 209 or SEQ ID NO: 227, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 209 or SEQ ID NO: 227. In some embodiments, the kit comprises first and second viral vectors or lipoplexes (e.g., LNPs) comprising one or more polynucleotides encoding the following first fusion polypeptide and second fusion polypeptide, optionally joined or connected by one or more linkers: (a) a first viral vector or lipoplex (e.g., LNP) comprising a polynucleotide encoding a fusion polypeptide comprising SEQ ID NO: 222, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 222, and (b) a second viral vector or lipoplex (e.g., LNP) comprising a polynucleotide encoding a fusion polypeptide comprising SEQ ID NO: 223, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 223. In some embodiments, the kit comprises first, second, third and fourth viral vectors or lipoplexes (e.g., LNPs) comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding a first fusion polypeptide and a second fusion polypeptide comprising SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; (b) a second viral vector or lipoplex (e.g., LNP) comprising one or more polynucleotides encoding a first fusion polypeptide and a second fusion polypeptide comprising SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively; (c) a third viral vector or lipoplex (e.g., LNP) comprising one or more polynucleotides encoding a first fusion polypeptide and a second fusion polypeptide comprising SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 88, respectively; and (d) a fourth viral vector or lipoplex (e.g., LNP) comprising one or more polynucleotides encoding a first fusion polypeptide and a second fusion polypeptide comprising SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively. In some embodiments, the kit comprises first, second, third and fourth viral vectors or lipoplexes (e.g., LNPs) comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding a first fusion polypeptide and a second fusion polypeptide comprising SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; (b) a second viral vector or lipoplex (e.g., LNP) comprising one or more polynucleotides encoding a first fusion polypeptide and a second fusion polypeptide comprising SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively; (c) a third viral vector or lipoplex (e.g., LNP) comprising one or more polynucleotides encoding a first fusion polypeptide and a second fusion polypeptide comprising SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; and (d) a fourth viral vector or lipoplex (e.g., LNP) comprising one or more polynucleotides encoding a first fusion polypeptide and a second fusion polypeptide comprising SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively. In some embodiments, the kit comprises first, second, third and fourth viral vectors or lipoplexes (e.g., LNPs) comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding a first fusion polypeptide and a second fusion polypeptide comprising SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; (b) a second viral vector or lipoplex (e.g., LNP) comprising one or more polynucleotides encoding a first fusion polypeptide and a second fusion polypeptide comprising SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively; (c) a third viral vector or lipoplex (e.g., LNP) comprising one or more polynucleotides encoding a first fusion polypeptide and a second fusion polypeptide comprising SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; and (d) a fourth viral vector or lipoplex (e.g., LNP) comprising one or more polynucleotides encoding a first fusion polypeptide and a second fusion polypeptide comprising SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively. In some embodiments, the kit comprises first and second viral vectors or lipoplexes (e.g., LNPs) comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding a first fusion polypeptide and a second fusion polypeptide comprising SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively, and (b) a second viral vector or lipoplex (e.g., LNP) comprising one or more polynucleotides encoding a first fusion polypeptide and a second fusion polypeptide comprising SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively. In some embodiments, the kit comprises first and second viral vectors or lipoplexes (e.g., LNPs) comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding the following first fusion polypeptide and second fusion polypeptide comprising SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively, and (b) a second viral vector or lipoplex (e.g., LNP) comprising one or more polynucleotides encoding the following first fusion polypeptide and second fusion polypeptide comprising SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively. In some embodiments, the kit comprises first and second viral vectors or lipoplexes (e.g., LNPs) comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding the following first fusion polypeptide and second fusion polypeptide comprising SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively, and (b) a second viral vector or lipoplex (e.g., LNP) comprising one or more polynucleotides encoding the following first fusion polypeptide and second fusion polypeptide comprising SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively. In some embodiments, the kit comprises first and second viral vectors or lipoplexes (e.g., LNPs) comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding the following first fusion polypeptide and second fusion polypeptide comprising SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively, and (b) a second viral vector or lipoplex (e.g., LNP) comprising one or more polynucleotides encoding the following first fusion polypeptide and second fusion polypeptide comprising SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively. In some embodiments, the kit comprises first and second viral vectors or lipoplexes (e.g., LNPs) comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding a first fusion polypeptide and a second fusion polypeptide comprising SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively, and (b) a second viral vector or lipoplex (e.g., LNP) comprising one or more polynucleotides encoding a first fusion polypeptide and a second fusion polypeptide comprising SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively. In some embodiments, the kit comprises first, second, third and fourth viral vectors or lipoplexes (e.g., LNPs) comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding a first fusion polypeptide and a second fusion polypeptide comprising SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively; (b) a second viral vector or lipoplex (e.g., LNP) comprising one or more polynucleotides encoding a first fusion polypeptide and a second fusion polypeptide comprising SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively; (c) a third viral vector or lipoplex (e.g., LNP) comprising one or more polynucleotides encoding a first fusion polypeptide and a second fusion polypeptide comprising SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; and (d) a fourth viral vector or lipoplex (e.g., LNP) comprising one or more polynucleotides encoding a first fusion polypeptide and a second fusion polypeptide comprising SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively. In some embodiments, the kit comprises first, second, third and fourth viral vectors or lipoplexes (e.g., LNPs) comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding a first fusion polypeptide and a second fusion polypeptide comprising SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively; (b) a second viral vector or lipoplex (e.g., LNP) comprising one or more polynucleotides encoding a first fusion polypeptide and a second fusion polypeptide comprising SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively; (c) a third viral vector or lipoplex (e.g., LNP) comprising one or more polynucleotides encoding a first fusion polypeptide and a second fusion polypeptide comprising SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively; and (d) a fourth viral vector or lipoplex (e.g., LNP) comprising one or more polynucleotides encoding a first fusion polypeptide and a second fusion polypeptide comprising SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively. In various embodiments of the kits, the viral vectors are Lymphocytic choriomeningitis mammarenavirus (LCMV) viral vectors, Cali mammarenavirus (a.k.a. Pichinde mammarenavirus or Pichinde arenavirus) viral vectors or adenoviral vectors, e.g., chimpanzee adenoviral vectors (ChAds). In some embodiments, the kit comprises a polynucleotide comprising or consisting of a nucleic acid sequence of any one of SEQ ID NOs: 130-167, 210-219 and 225-226, or a nucleic acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 130-167, 210-219 and 225-226. In some embodiments, the kit comprises a polynucleotide comprising or consisting of a nucleic acid sequence of any one of SEQ ID NOs: 139, 140, 142, 143, 145, 146, 148, 149, 150, 152, 155, 158, 225 and 226, or a nucleic acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139, 140, 142, 143, 145, 146, 148, 149, 150, 152, 155, 158, 225 and 226. In some embodiments, the kit comprises the following first polynucleotide and second polynucleotide, one or more vectors, or one or more lipoplexes (e.g., LNPs) comprising the following first polynucleotide and second polynucleotide: SEQ ID NOs: 130 and 132, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 130 and 132, respectively; SEQ ID NOs: 130 and 134, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 130 and 134, respectively; SEQ ID NOs: 131 and 133, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 131 and 133, respectively; SEQ ID NOs: 131 and 135, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 131 and 135, respectively; SEQ ID NOs: 132 and 136, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 132 and 136, respectively; SEQ ID NOs: 133 and 135, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 133 and 135, respectively; SEQ ID NOs: 133 and 137, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 133 and 137, respectively; SEQ ID NOs: 134 and 136, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 134 and 136, respectively; SEQ ID NOs: 135 and 137, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 135 and 137, respectively; SEQ ID NOs: 138 and 141, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 138 and 141, respectively; SEQ ID NOs: 138 and 144, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 138 and 144, respectively; SEQ ID NOs: 139 and 142, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 142, respectively; SEQ ID NOs: 139 and 145, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 145, respectively; SEQ ID NOs: 140 and 146, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 140 and 146, respectively; SEQ ID NOs: 142 and 148, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 142 and 148, respectively; SEQ ID NOs: 143 and 149, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 143 and 149, respectively; SEQ ID NOs: 145 and 148, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 145 and 148, respectively; SEQ ID NOs: 150 and 152, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively; SEQ ID NOs: 150 and 155, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 155, respectively; SEQ ID NOs: 151 and 153, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 151 and 153, respectively; SEQ ID NOs: 151 and 156, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 151 and 156, respectively; SEQ ID NOs: 152 and 158, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 152 and 158, respectively; SEQ ID NOs: 153 and 159, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 153 and 159, respectively; SEQ ID NOs: 154 and 157, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 154 and 157, respectively; SEQ ID NOs: 155 and 158, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 155 and 158, respectively; SEQ ID NOs: 156 and 159, or polynucleotides that are at least 80%, 81%, 82%, 83%, 84%, 85%8, 86%, 87%, 88%, 89%, 90%, 91%, 92%, 93%, 94%, 95%, 96%, 97%, 98% or 99% identical to any one of SEQ ID NOs: 156 and 159, respectively; SEQ ID NOs: 160 and 161, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 160 and 161, respectively; SEQ ID NOs: 162 and 163, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 162 and 163, respectively; SEQ ID NOs: 164 and 165, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 164 and 165, respectively; SEQ ID NOs: 166 and 167, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 166 and 167, respectively; SEQ ID NOs: 210 and 211, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 210 and 211, respectively; SEQ ID NOs: 212 and 213, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 212 and 213, respectively; SEQ ID NOs: 214 and 215, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 214 and 215, respectively; SEQ ID NOs: 216 and 217, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 216 and 217, respectively; SEQ ID NOs: 218 and 219, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 218 and 219, respectively; SEQ ID NOs: 218 and 226, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 218 and 226, respectively; or SEQ ID NOs: 225 and 226, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 225 and 226, respectively. In some embodiments, the kit comprises first and second viral vectors or lipoplexes (e.g., LNPs) comprising the following first polynucleotide and second polynucleotide: (a) a first vector or lipoplex (e.g., LNP) comprising first and second polynucleotides comprising SEQ ID NOs: 131 and 135, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 131 and 135, respectively, and (b) a second vector or lipoplex (e.g., LNP) comprising first and second polynucleotides comprising SEQ ID NOs: 133 and 137, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 133 and 137, respectively. In some embodiments, the kit comprises first and second viral vectors or lipoplexes (e.g., LNPs) comprising the following first polynucleotide and second polynucleotide: (a) a first vector or lipoplex (e.g., LNP) comprising first and second polynucleotides comprising SEQ ID NOs: 139 and 145, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 145, respectively, and (b) a second vector or lipoplex (e.g., LNP) comprising first and second polynucleotides comprising SEQ ID NOs: 143 and 149, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 145, respectively. In some embodiments, the kit comprises first, second, third and fourth viral vectors or lipoplexes (e.g., LNPs), each vector or lipoplex (e.g., LNP) comprising first and second polynucleotides: (a) a first viral vector or lipoplex (e.g., LNP) comprising first and second polynucleotides comprising SEQ ID NOs: 131 and 135, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 131 and 135, respectively; (b) a second viral vector or lipoplex (e.g., LNP) comprising first and second polynucleotides comprising SEQ ID NOs: 133 and 137, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 133 and 137, respectively; (c) a third viral vector or lipoplex (e.g., LNP) comprising first and second polynucleotides comprising SEQ ID NOs: 139 and 145, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 145, respectively; and (d) a fourth viral vector or lipoplex (e.g., LNP) comprising first and second polynucleotides comprising SEQ ID NOs: 142 and 148, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 142 and 148, respectively. In some embodiments, the kit comprises first and second viral vectors or lipoplexes (e.g., LNPs) comprising the following first polynucleotide and second polynucleotide: (a) a first vector or lipoplex (e.g., LNP) comprising first and second polynucleotides comprising SEQ ID NOs: 140 and 146, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 140 and 146, respectively, and (b) a second vector or lipoplex (e.g., LNP) comprising first and second polynucleotides comprising SEQ ID NOs: 143 and 149, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 143 and 149, respectively. In some embodiments, the first and second viral vectors are Lymphocytic choriomeningitis mammarenavirus (LCMV) viral vectors. In some embodiments, the kit comprises first and second viral vectors or lipoplexes (e.g., LNPs) comprising the following first polynucleotide and second polynucleotide: (a) a first vector or lipoplex (e.g., LNP) comprising first and second polynucleotides comprising SEQ ID NOs: 150 and 152, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively, and (b) a second vector or lipoplex (e.g., LNP) comprising first and second polynucleotides comprising SEQ ID NOs: 154 and 157 or SEQ ID NOs: 155 and 158, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 154 and 157 or SEQ ID NOs: 155 and 158, respectively. In some embodiments, the first and second viral vectors are Cali mammarenavirus (a.k.a. Pichinde mammarenavirus or Pichinde arenavirus) viral vectors. In some embodiments, the kit comprises first, second, third and fourth viral vectors or lipoplexes (e.g., LNPs), each vector or lipoplex (e.g., LNP) comprising first and second polynucleotides: (a) a first viral vector or lipoplex (e.g., LNP) comprising first and second polynucleotides comprising SEQ ID NOs: 140 and 146, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 140 and 146, respectively; (b) a second viral vector or lipoplex (e.g., LNP) comprising first and second polynucleotides comprising SEQ ID NOs: 143 and 149, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 143 and 149, respectively; (c) a third viral vector or lipoplex (e.g., LNP) comprising first and second polynucleotides comprising SEQ ID NOs: 150 and 152, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively; and (d) a fourth viral vector or lipoplex (e.g., LNP) comprising first and second polynucleotides comprising SEQ ID NOs: 154 and 157 or SEQ ID NOs: 155 and 158, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 154 and 157 or SEQ ID NOs: 155 and 158, respectively. In some embodiments, the kit comprises first, second, third and fourth viral vectors or lipoplexes (e.g., LNPs), each vector or lipoplex (e.g., LNP) comprising first and second polynucleotides: (a) a first viral vector or lipoplex (e.g., LNP) comprising first and second polynucleotides comprising SEQ ID NOs: 150 and 152, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively; (b) a second viral vector or lipoplex (e.g., LNP) comprising first and second polynucleotides comprising SEQ ID NOs: 155 and 158, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 155 and 158, respectively; (c) a third viral vector or lipoplex (e.g., LNP) comprising first and second polynucleotides comprising SEQ ID NOs: 151 and 153, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 151 and 153, respectively; and (d) a fourth viral vector or lipoplex (e.g., LNP) comprising first and second polynucleotides comprising SEQ ID NOs: 156 and 159, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 156 and 159, respectively. In various embodiments, one or more of the first, second, third and fourth vectors are adenoviral vectors. In some embodiments, the kit comprises first and second viral vectors or lipoplexes (e.g., LNPs) comprising the following first polynucleotide and second polynucleotide: (a) a first vector or lipoplex (e.g., LNP) comprising first and second polynucleotides comprising SEQ ID NOs: 160 and 161, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 160 and 161, respectively, and (b) a second vector or lipoplex (e.g., LNP) comprising first and second polynucleotides comprising SEQ ID NOs: 162 and 163, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 162 and 163, respectively. In some embodiments, the kit comprises first and second viral vectors comprising the following first polynucleotide and second polynucleotide: (a) a first vector or lipoplex (e.g., LNP) comprising first and second polynucleotides comprising SEQ ID NOs: 164 and 165, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 164 and 165, respectively, and (b) a second vector or lipoplex (e.g., LNP) comprising first and second polynucleotides comprising SEQ ID NOs: 166 and 167, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 166 and 167, respectively. In some embodiments, the kit comprises (a) a first vector or lipoplex (e.g., LNP) comprising a first polynucleotide comprising SEQ ID NO: 210, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 210, and (b) a second vector or lipoplex (e.g., LNP) comprising a second polynucleotide comprising SEQ ID NO: 211, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 211. In some embodiments, the kit comprises (a) a first vector or lipoplex (e.g., LNP) comprising a first polynucleotide comprising SEQ ID NO: 212, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 212, and (b) a second vector or lipoplex (e.g., LNP) comprising a second polynucleotide comprising SEQ ID NO: 213, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 213. In some embodiments, the kit comprises (a) a first vector or lipoplex (e.g., LNP) comprising a first polynucleotide comprising SEQ ID NO: 214, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 214, and (b) a second vector or lipoplex (e.g., LNP) comprising a second polynucleotide comprising SEQ ID NO: 215, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 215. In some embodiments, the kit comprises (a) a first vector or lipoplex (e.g., LNP) comprising a first polynucleotide comprising SEQ ID NO: 216, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 216, and (b) a second vector or lipoplex (e.g., LNP) comprising a second polynucleotide comprising SEQ ID NO: 217, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 217. In some embodiments, the kit comprises (a) a first vector or lipoplex (e.g., LNP) comprising a first polynucleotide comprising SEQ ID NO: 218, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 218, and (b) a second vector or lipoplex (e.g., LNP) comprising a second polynucleotide comprising SEQ ID NO: 219, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 219. In some embodiments, the kit comprises (a) a first vector or lipoplex (e.g., LNP) comprising a first polynucleotide comprising SEQ ID NO: 218, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 218, and (b) a second vector or lipoplex (e.g., LNP) comprising a second polynucleotide comprising SEQ ID NO: 226, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 226. In some embodiments, the kit comprises (a) a first vector or lipoplex (e.g., LNP) comprising a first polynucleotide comprising SEQ ID NO: 225, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 225, and (b) a second vector or lipoplex (e.g., LNP) comprising a second polynucleotide comprising SEQ ID NO: 226, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 226. In some embodiments, the kit comprises a compound fusion polypeptide, a vector, or a lipoplex (e.g., LNP) comprising a polynucleotide encoding a compound fusion polypeptide, the compound fusion polypeptide comprising or consisting of an amino acid sequence of any one of SEQ ID NOs: 105-112, 200-

209, 222-223 and 227, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 105-112, 200-209, 222-223 and 227. In some embodiments, the kit comprises a compound fusion polypeptide, a vector, or a lipoplex (e.g., LNP) comprising a polynucleotide encoding a compound fusion polypeptide, the compound fusion polypeptide comprising or consisting of an amino acid sequence of any one of SEQ ID NOs: 209, 222 and 223, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 209, 222 and 223. In some embodiments, the one or more fusion polypeptides do not comprise any polypeptide segments corresponding to Gag 54-146; Gag 370-500; Pol 1-55; Pol 118-128; Pol 321-366; Pol 432-541; Pol 607-682; Pol 709-746; Pol 828-839; Pol 921-931; Nef 1-63; Nef 100-116 and Nef 149-206, or fragments or subsequences thereof, wherein the Gag, Pol and Nef amino acid position numbers correspond to SEQ ID NOs: 1, 2 and 3, respectively. In some embodiments, the one or more fusion polypeptides do not comprise any polypeptide segments having an amino acid sequence of SEQ ID NOs: 35-47, or fragments or subsequences thereof, or an amino acid sequence at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 35-47, or fragments or subsequences thereof. In some embodiments, the kit further comprises one or more unitary doses of one or more additional therapeutic agents. In some embodiments, the kit comprises one or more agents that activate latent HIV, e.g., one or more latency reversing agents (LRAs). In some embodiments, the kit comprises one or more LRAs selected from agonists or activators of one or more toll-like receptors (TLRs), histone deacetylase (HDAC) inhibitors, proteasome inhibitors, protein kinase C (PKC) activators, Smyd2 inhibitors, BET-bromodomain 4 (BRD4) inhibitors, ionomycin, inhibitor of apoptosis proteins (IAP) antagonists, and second mitochondria-derived activator of caspases (SMAC) mimetics. In some embodiments, the kit comprises one or more agonists or activators of one or more toll-like receptors (TLRs). In some embodiments, the TLR agonist or activator is selected from a TLR2 agonist, a TLR3 agonist, a TLR4 agonist, a TLR5 agonist, a TLR7 agonist, a TLR8 agonist and a TLR9 agonist. In some embodiments, the TLR7 agonist is selected from GS 9620 (vesatolimod), R848 (Resiquimod), DS-0509, LHC-165 and TMX-101 (imiquimod), and/or wherein the TLR8 agonist is selected from GS-9688 (Selgantolimod), R848 (Resiquimod) and NKTR-262 (dual TLR7/TLR8 agonist). In some embodiments, the kit comprises one or more interleukin receptor agonists of an interleukin selected from IL-2, IL-7, IL-12 and IL-15. In some embodiments, the kit comprises one or more cytokines selected from IL-2, IL-7, IL-12, IL-15, and variants thereof. In some embodiments, the kit comprises one or more innate immune activators. In some embodiments, the one or more innate immune activators comprises an agonist of a receptor selected from fms related tyrosine kinase 3 (FLT3), stimulator of interferon genes (STING) receptor, DExD/H-box helicase 58 (DDX58; a.k.a., RIG-I), nucleotide binding oligomerization domain containing 2 (NOD2). In some embodiments, the kit comprises an agonist of fms related tyrosine kinase 3 (FLT3). In some embodiments, the kit comprises one or more antagonists or inhibitors of an inhibitory immune checkpoint protein or receptor and/or one or more activators or agonists of a stimulatory immune checkpoint protein or receptor. In some embodiments, the one or more immune checkpoint proteins or receptors are selected from: CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript IE (RAETIE; ULBP4); retinoic acid early transcript 1G (RAETIG; ULBP5); retinoic acid early transcript 1L (RAET1L; ULBP6); lymphocyte activating 3 (CD223); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); and SLAM family member 7 (SLAMF7). In some embodiments, the kit comprises one or more blockers or inhibitors of one or more T-cell inhibitory immune checkpoint proteins or receptors. In some embodiments, the T-cell inhibitory immune checkpoint proteins or receptors are selected from CD274 (CD274, PDL1, PD-L1); programmed cell death 1 ligand 2 (PDCD1LG2, PD-L2, CD273); programmed cell death 1

(PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In some embodiments, the kit comprises one or more agonists or activators of one or more T-cell stimulatory immune checkpoint proteins or receptors. In some embodiments the T-cell stimulatory immune checkpoint proteins or receptors are selected from CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); Poliovirus receptor (PVR) cell adhesion molecule (PVR, CD155). In some embodiments, the kit comprises one or more blockers or inhibitors of one or more NK-cell inhibitory immune checkpoint proteins or receptors. In some embodiments, the NK-cell inhibitory immune checkpoint proteins or receptors are selected from killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94). In some embodiments, the kit comprises one or more agonists or activators of one or more NK-cell stimulatory immune checkpoint proteins or receptors. In some embodiments, the NK-cell stimulatory immune checkpoint proteins or receptors are selected from CD16, CD226 (DNAM-1); killer cell lectin like receptor K1 (KLRK1, NKG2D, CD314); and SLAM family member 7 (SLAMF7). In some embodiments, the one or more immune checkpoint inhibitors comprises a proteinaceous inhibitor of PD-L1 (CD274), PD-1 (PDCD1) or CTLA4. In some embodiments, the kit comprises and antibody that binds to CTLA4. In some embodiments, the proteinaceous or antibody inhibitor of CTLA4 is selected from ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4) and AK-104 (CTLA4/PD-1). In some embodiments, the proteinaceous inhibitor of PD-L1 (CD274) or PD-1 (PDCD1) is selected from pembrolizumab, nivolumab, cemiplimab, pidilizumab, AMP-224, MEDI0680 (AMP-514), spartalizumab, atezolizumab, avelumab, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/Tim-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), and INBRX-105 (4-1BB/PDL1). In some embodiments, the one or more immune checkpoint inhibitors comprises a small molecule inhibitor of CD274 (PDL1, PD-L1), programmed cell death 1 (PDCD1, PD1, PD-1) or CTLA4. In some embodiments, the small molecule inhibitor of CD274 or PDCD1 is selected from GS-4224, GS-4416, INCB086550 and MAX10181. In some embodiments, the small molecule inhibitor of CTLA4 comprises BPI-002. In some embodiments, the kit further comprises one or more antiviral agents. In some embodiments, the one or more antiviral agents are selected from HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors and capsid inhibitors.

Further provided are methods for eliciting an immune response to human immunodeficiency virus (HIV) in a subject in need thereof, comprising administering to the subject a fusion polypeptide, a compound fusion polypeptide, a polynucleotide, a vector, a lipoplex (e.g., LNP) or an immunogenic composition, as described herein. Also provided are methods of treating or preventing human immunodeficiency virus (HIV) in a subject in need thereof, comprising administering to the subject a fusion polypeptide, a compound fusion polypeptide, a vector, a lipoplex (e.g., LNP) or an immunogenic composition, as described herein. In some embodiments the method entails administering a single vector comprising one or more polynucleotides encoding a first fusion polypeptide and a second fusion polypeptide. In some embodiments, two or more fusion polypeptides, two or more compound fusion polypeptides, two or more polynucleotides encoding the fusion polypeptides, two or more viral expression vectors comprising polynucleotides encoding the fusion polypeptides, two or more lipoplexes (e.g., LNPs) or two or more immunogenic compositions, as described herein, are administered to the subject simultaneously or concurrently. In some embodiments, two or more fusion polypeptides, or two or more polynucleotides or two or more viral expression vectors encoding the fusion polypeptides, are in the form of a bivalent antigen composition. In some embodiments, the method entails administering a first fusion polypeptide and a second fusion polypeptide, one or more polynucleotides encoding the first and second fusion polypeptides, one or more vectors comprising one or more polynucleotides encoding the first and second fusion polypeptides, or one or more lipoplexes (e.g., LNPs), the first and second polypeptides comprising the following polypeptide segments, in sequential order, from N-terminus to C terminus, optionally joined or connected by one or more linkers: SEQ ID NOs: 6, 4, 16 and 26, and SEQ ID NOs: 7, 5, 27 and 17; SEQ ID NOs: 12, 24, 8 and 10, and SEQ ID NOs: 9, 25, 13 and 11; SEQ ID NOs: 14, 22, 18, 24 and 20, and SEQ ID NOs: 15, 25, 19, 23 and 21; SEQ ID NOs: 26, 16, 4 and 6, and SEQ ID NOs: 7, 27, 5 and 17; SEQ ID NOs: 8, 24, 12 and 10, and SEQ ID NOs: 13, 25, 9 and 11; SEQ ID NOs: 22, 24, 14, 18 and 20, and SEQ ID NOs: 25, 23, 15, 21 and 19; SEQ ID NOs: 20, 6, 4, 18, 16 and 26, and SEQ ID NOs: 7, 19, 5, 21, 27 and 17; SEQ ID NOs: 8, 24, 14, 12, 22 and 10, and SEQ ID NOs: 9, 13, 25, 23, 15 and 11; SEQ ID NOs: 18, 26, 20, 4, 6 and 16, and SEQ ID NOs: 7, 21, 17, 5, 27 and 19; SEQ ID NOs: 22, 24, 12, 14, 8 and 10, and SEQ ID NOs: 15, 25, 9, 23, 13 and 11; SEQ ID NOs: 24, 6, 4, 20, 18 and 32, and SEQ ID NOs: 8, 30, 14, 12, 26 and 10; SEQ ID NOs: 24, 6, 4, 20, 18 and 32, and SEQ ID NOs: 7, 21, 5, 25, 33 and 19; SEQ ID NOs: 24, 6, 4, 20, 18 and 32, and SEQ ID NOs: 8, 30, 14, 12, 26 and 10; SEQ ID NOs: 8, 30, 14, 12, 26 and 10, and SEQ ID NOs: 9, 13, 31, 27, 15 and 11; SEQ ID NOs: 6, 20, 4, 24, 32 and 18, and SEQ ID NOs: 8, 12, 30, 26, 14 and 10; SEQ ID NOs: 7, 21, 5, 25, 33 and 19 and SEQ ID NOs: 9, 13, 31, 27, 15 and 11; SEQ ID NOs: 20, 32, 24, 4, 6 and 18, and SEQ ID NOs: 26, 30, 12, 14, 8 and 10; SEQ ID NOs: 7, 25, 19, 5, 33 and 21, and SEQ ID NOs: 15, 31, 9, 27, 13 and 11; SEQ ID NOs: 24, 6, 16 and 18, and SEQ ID NOs: 26, 20, 10 and 28; SEQ ID NOs: 24, 6, 16 and 18, and SEQ ID NOs: 26, 10, 20 and 28; SEQ ID NOs: 24, 6, 16 and 18, and SEQ ID NOs: 7, 25, 17 and 19; SEQ ID NOs: 7, 19, 17 and 25, and SEQ ID NOs: 21, 27, 11 and 29; SEQ ID NOs: 24, 16, 6 and 18, and SEQ ID NOs: 27, 11, 21 and 29; SEQ ID NOs: 7, 25, 17 and 19, and SEQ ID NOs: 11, 27, 21 and 29; SEQ ID NOs: 7, 25, 17 and 19, and SEQ ID NOs: 21, 27, 11 and 29; SEQ ID NOs: 22, 6, 20 and 28, and SEQ ID NOs: 23, 7, 21 and 29; SEQ ID NOs: 22, 20, 6 and 28, and SEQ ID NOs: 7, 21, 23 and 29; SEQ ID NOs: 26, 10, 20 and 28, and SEQ ID NOs: 21, 27, 11 and 29; SEQ ID NOs: 22, 6, 16, 20, 18, 28, 26 and 10; or SEQ ID NOs: 7, 21, 19, 17, 27, 25, 29 and 11. In some embodiments, the method entails administering one or more fusion polypeptides, one or more polynucleotides encoding one or more fusion polypeptides, one or more vectors comprising one or more polynucleotides encoding one or more fusion polypeptides, one or more lipoplexes (e.g., LNPs), the one or more fusion polypeptides comprising or consisting of an amino acid sequence of any one of SEQ ID NOs: 70-101, 105-112, 200-209, 222-223 and 227, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70-101, 105-112, 200-209, 222-223 and 227. In some embodiments, the method entails administering one or more fusion polypeptides, one or more polynucleotides encoding one or more fusion polypeptides, one or more vectors comprising one or more polynucleotides encoding one or more fusion polypeptides, one or more lipoplexes (e.g., LNPs), the one or more fusion polypeptides comprising or consisting of an amino acid sequence of any one of SEQ ID NOs: 82-83, 85-87, 98-101, 209 and 222-223, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82-83, 85-87, 98-101, 209 and 222-223. In some embodiments, the method entails administering the following first fusion polypeptide and second fusion polypeptide, one or more polynucleotides, one or more vectors or one or more lipoplexes (e.g., LNPs), comprising one or more polynucleotides encoding the following first fusion polypeptide and second fusion polypeptide, optionally joined or connected by one or more linkers: SEQ ID NOs: 70 and 71, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70 and 71, respectively; SEQ ID NOs: 72 and 73, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 72 and 73, respectively; SEQ ID NOs: 74 and 75, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 74 and 75, respectively; SEQ ID NOs: 76 and 77, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 76 and 77, respectively; SEQ ID NOs: 78 and 79, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 78 and 79, respectively; SEQ ID NOs: 80 and 81, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 80 and 81, respectively; SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively; SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively; SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively; SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively; SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively; SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively; SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively; SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively; SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively; SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 88, respectively; SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively; SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively; SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively; SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively; SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively; SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively; SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively; SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively; SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively; SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively; SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively; or SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively. In some embodiments, the method entails administering the following first fusion polypeptide and second fusion polypeptide, one or more vectors, or one or more lipoplexes (e.g., LNPs), comprising one or more polynucleotides encoding the following first fusion polypeptide and second fusion polypeptide, in sequential order, from N-terminus to C-terminus, optionally joined or connected by one or more linkers: SEQ ID NOs: 70 and 71, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70 and 71, respectively; SEQ ID NOs: 71 and 70, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 71 and 70, respectively; SEQ ID NOs: 72 and 73, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 72 and 73, respectively; SEQ ID NOs: 73 and 72, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 73 and 72, respectively; SEQ ID NOs: 74 and 75, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 74 and 75, respectively; SEQ ID NOs: 75 and 74, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 75 and 74, respectively; SEQ ID NOs: 76 and 77, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 76 and 77, respectively; SEQ ID NOs: 77 and 76, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 77 and 76, respectively; SEQ ID NOs: 78 and 79, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 78 and 79, respectively; SEQ ID NOs: 79 and 78, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 79 and 78, respectively; SEQ ID NOs: 80 and 81, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 80 and 81, respectively; SEQ ID NOs: 81 and 80, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 81 and 80, respectively; SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively; SEQ ID NOs: 83 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 82, respectively; SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively; SEQ ID NOs: 85 and 84, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 84, respectively; SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively; SEQ ID NOs: 87 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 86, respectively; SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively; SEQ ID NOs: 89 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 89 and 88, respectively; SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively; SEQ ID NOs: 85 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 82, respectively; SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; SEQ ID NOs: 86 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 82, respectively; SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively; SEQ ID NOs: 88 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 82, respectively; SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively; SEQ ID NOs: 87 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 83, respectively; SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively; SEQ ID NOs: 87 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 85, respectively; SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively; SEQ ID NOs: 87 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 88, respectively; SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 84, respectively; SEQ ID NOs: 88 and 84, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 84, respectively; SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively; SEQ ID NOs: 89 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 89 and 85, respectively; SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively; SEQ ID NOs: 101 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 85, respectively; SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively; SEQ ID NOs: 91 and 90, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 91 and 90, respectively; SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively; SEQ ID NOs: 93 and 92, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 93 and 92, respectively; SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively; SEQ ID NOs: 95 and 94, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 94, respectively; SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively; SEQ ID NOs: 97 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 97 and 96, respectively; SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively;

SEQ ID NOs: 96 and 94, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 94, respectively; SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively; SEQ ID NOs: 97 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 97 and 95, respectively; SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively; SEQ ID NOs: 221 and 220, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 221 and 220, respectively; SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; SEQ ID NOs: 100 and 98, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 98, respectively; SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively; SEQ ID NOs: 101 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 99, respectively; SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively; SEQ ID NOs: 99 and 98, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 98, respectively; SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively; or SEQ ID NOs: 101 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 100, respectively. In some embodiments, the method entails administering first and second viral vectors or first and second lipoplexes (e.g., LNPs) comprising one or more polynucleotides encoding the following first fusion polypeptide and second fusion polypeptide, optionally joined or connected by one or more linkers: (a) a first polynucleotide or first viral vector or first lipoplex (e.g., LNP) comprising one or more polynucleotides encoding the following first fusion polypeptide and second fusion polypeptide comprising SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively, and (b) a second polynucleotide or second viral vector or second lipoplex (e.g., LNP) comprising one or more polynucleotides encoding the following first fusion polypeptide and second fusion polypeptide comprising SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively. In some embodiments, the method entails administering first and second viral vectors or first and second lipoplexes (e.g., LNPs) comprising one or more polynucleotides encoding the following first fusion polypeptide and second fusion polypeptide, optionally joined or connected by one or more linkers: (a) a first polynucleotide or first viral vector or first lipoplex (e.g., LNP) comprising one or more polynucleotides encoding the following first fusion polypeptide and second fusion polypeptide comprising SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively, and (b) a second polynucleotide or second viral vector or second lipoplex (e.g., LNP) comprising one or more polynucleotides encoding the following first fusion polypeptide and second fusion polypeptide comprising SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively. In some embodiments, the method entails administering first and second viral vectors or first and second lipoplexes (e.g., LNPs) comprising one or more polynucleotides encoding the following first fusion polypeptide and second fusion polypeptide, optionally joined or connected by one or more linkers: (a) a first polynucleotide or first viral vector or first lipoplex (e.g., LNP) comprising one or more polynucleotides encoding the following first fusion polypeptide and second fusion polypeptide comprising SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively, and (b) a second polynucleotide or second viral vector or second lipoplex (e.g., LNP) comprising one or more polynucleotides encoding the following first fusion polypeptide and second fusion polypeptide comprising SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively. In some embodiments, the method entails administering first and second viral vectors or first and second lipoplexes (e.g., LNPs) comprising one or more polynucleotides encoding the following first fusion polypeptide and second fusion polypeptide, optionally joined or connected by one or more linkers: (a) a first polynucleotide or first viral vector or first lipoplex (e.g., LNP) comprising one or more polynucleotides encoding the following first fusion polypeptide and second fusion polypeptide comprising SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively, and (b) a second polynucleotide or second viral vector or second lipoplex (e.g., LNP) comprising one or more polynucleotides encoding the following first fusion polypeptide and second fusion polypeptide comprising SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively. In some embodiments, the method entails administering first and second viral vectors or first and second lipoplexes (e.g., LNPs) comprising one or more polynucleotides encoding the following first fusion polypeptide and second fusion polypeptide, optionally joined or connected by one or more linkers: (a) a first polynucleotide or first viral vector or first lipoplex (e.g., LNP) comprising one or more polynucleotides encoding the following first fusion polypeptide and second fusion polypeptide comprising SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively, and (b) a second polynucleotide or second viral vector or second lipoplex (e.g., LNP) comprising one or more polynucleotides encoding the following first fusion polypeptide and second fusion polypeptide comprising SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively. In some embodiments, the method entails administering first and second viral vectors or first and second lipoplexes (e.g., LNPs) comprising one or more polynucleotides encoding the following first fusion polypeptide and second fusion polypeptide, optionally joined or connected by one or more linkers: (a) a first polynucleotide or first viral vector or first lipoplex (e.g., LNP) comprising one or more polynucleotides encoding the following first fusion polypeptide and second fusion polypeptide comprising SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 88, respectively, and (b) a second polynucleotide or second viral vector or second lipoplex (e.g., LNP) comprising one or more polynucleotides encoding the following first fusion polypeptide and second fusion polypeptide comprising SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively. In some embodiments, the method entails administering first and second viral vectors or first and second lipoplexes (e.g., LNPs) comprising one or more polynucleotides encoding the following first fusion polypeptide and second fusion polypeptide, optionally joined or connected by one or more linkers: (a) a first polynucleotide or first viral vector or first lipoplex (e.g., LNP) comprising one or more polynucleotides encoding the following first fusion polypeptide and second fusion polypeptide comprising SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively, and (b) a second polynucleotide or second viral vector or second lipoplex (e.g., LNP) comprising one or more polynucleotides encoding the following first fusion polypeptide and second fusion polypeptide comprising SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively. In some embodiments, the method entails administering first and second viral vectors or first and second lipoplexes (e.g., LNPs) comprising one or more polynucleotides encoding the following first fusion polypeptide and second fusion polypeptide, optionally joined or connected by one or more linkers: (a) a first polynucleotide or first viral vector or first lipoplex (e.g., LNP) comprising one or more polynucleotides encoding the following first fusion polypeptide and second fusion polypeptide comprising SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively, and (b) a second polynucleotide or second viral vector or second lipoplex (e.g., LNP) comprising one or more polynucleotides encoding the following first fusion polypeptide and second fusion polypeptide comprising SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively. In some embodiments, the method entails administering first and second viral vectors or first and second lipoplexes (e.g., LNPs) comprising one or more polynucleotides encoding the following first fusion polypeptide and second fusion polypeptide, optionally joined or connected by one or more linkers: (a) a first polynucleotide or first viral vector or first lipoplex (e.g., LNP) comprising one or more polynucleotides encoding the following first fusion polypeptide and second fusion polypeptide comprising SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively, and (b) a second polynucleotide or second viral vector or second lipoplex (e.g., LNP) comprising one or more polynucleotides encoding the following first fusion polypeptide and second fusion polypeptide comprising SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively. In some embodiments, the method entails administering first and second viral vectors or first and second lipoplexes (e.g., LNPs) comprising one or more polynucleotides encoding the following first fusion polypeptide and second fusion polypeptide, optionally joined or connected by one or more linkers: (a) a first polynucleotide or first viral vector or first lipoplex (e.g., LNP) comprising one or more polynucleotides encoding the following first fusion polypeptide and second fusion polypeptide comprising SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively, and (b) a second polynucleotide or second viral vector or second lipoplex (e.g., LNP) comprising one or more polynucleotides encoding the following first fusion polypeptide and second fusion polypeptide comprising SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively. In some embodiments, the method entails administering first and second viral vectors or first and second lipoplexes (e.g., LNPs) comprising one or more polynucleotides encoding the following first fusion polypeptide and second fusion polypeptide, optionally joined or connected by one or more linkers: (a) a first polynucleotide or first viral vector or first lipoplex (e.g., LNP) comprising one or more polynucleotides encoding the following first fusion polypeptide and second fusion polypeptide comprising SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively, and (b) a second polynucleotide or second viral vector or second lipoplex (e.g., LNP) comprising one or more polynucleotides encoding the following first fusion polypeptide and second fusion polypeptide comprising SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively. In some embodiments, the method entails administering first and second viral vectors or first and second lipoplexes (e.g., LNPs) comprising first and second polynucleotides encoding the following first fusion polypeptide and second fusion polypeptide: (a) a first polynucleotide or first viral vector or first lipoplex (e.g., LNP) comprising a polynucleotide encoding a first fusion polypeptide comprising SEQ ID NO: 200, that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 200, and (b) a second polynucleotide or second viral vector or second lipoplex (e.g., LNP) comprising a polynucleotide encoding a second fusion polypeptide comprising SEQ ID NO: 201, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 201. In some embodiments, the method entails administering first and second viral vectors or first and second lipoplexes (e.g., LNPs) comprising first and second polynucleotides encoding the following first fusion polypeptide and second fusion polypeptide: (a) a first polynucleotide or first viral vector or first lipoplex (e.g., LNP) comprising a polynucleotide encoding a first fusion polypeptide comprising SEQ ID NO: 202, that is at least 80%, 81%, 82%, 83%, 84%, 85%8, 86%, 87%, 88%, 89%, 90%, 91%, 92%, 93%, 94%, 95%, 96%, 97%, 98% or 99% identical to SEQ ID NO: 202, and (b) a second polynucleotide or second viral vector or second lipoplex (e.g., LNP) comprising a polynucleotide encoding a second fusion polypeptide comprising SEQ ID NO: 203, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 203. In some embodiments, the method entails administering first and second viral vectors or first and second lipoplexes (e.g., LNPs) comprising first and second polynucleotides encoding the following first fusion polypeptide and second fusion polypeptide: (a) a first polynucleotide or first viral vector or first lipoplex (e.g., LNP) comprising a polynucleotide encoding a first fusion polypeptide comprising SEQ ID NO: 204, that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 204, and (b) a second polynucleotide or second viral vector or second lipoplex (e.g., LNP) comprising a polynucleotide encoding a second fusion polypeptide comprising SEQ ID NO: 205, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 205. In some embodiments, the method entails administering first and second viral vectors or first and second lipoplexes (e.g., LNPs) comprising first and second polynucleotides encoding the following first fusion polypeptide and second fusion polypeptide: (a) a first polynucleotide or first viral vector or first lipoplex (e.g., LNP) comprising a polynucleotide encoding a first fusion polypeptide comprising SEQ ID NO: 105, that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 105, and (b) a second polynucleotide or second viral vector or second lipoplex (e.g., LNP) comprising a polynucleotide encoding a second fusion polypeptide comprising SEQ ID NO: 107, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 107. In some embodiments, the method entails administering first and second viral vectors or first and second lipoplexes (e.g., LNPs) comprising first and second polynucleotides encoding the following first fusion polypeptide and second fusion polypeptide: (a) a first polynucleotide or first viral vector or first lipoplex (e.g., LNP) comprising a polynucleotide encoding a first fusion polypeptide comprising SEQ ID NO: 206, that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 206, and (b) a second polynucleotide or second viral vector or second lipoplex (e.g., LNP) comprising a polynucleotide encoding a second fusion polypeptide comprising SEQ ID NO: 207, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 207. In some embodiments, the method entails administering first and second viral vectors or first and second lipoplexes (e.g., LNPs) comprising first and second polynucleotides encoding the following first fusion polypeptide and second fusion polypeptide: (a) a first polynucleotide or first viral vector or first lipoplex (e.g., LNP) comprising a polynucleotide encoding a first fusion polypeptide comprising SEQ ID NO: 208, that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 208, and (b) a second polynucleotide or second viral vector or second lipoplex (e.g., LNP) comprising a polynucleotide encoding a second fusion polypeptide comprising SEQ ID NO: 209 or SEQ ID NO: 227, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 209 or SEQ ID NO: 227. In some embodiments, the method entails administering first and second viral vectors or first and second lipoplexes (e.g., LNPs) comprising first and second polynucleotides encoding the following first fusion polypeptide and second fusion polypeptide: (a) a first polynucleotide or first viral vector or first lipoplex (e.g., LNP) comprising a polynucleotide encoding a first fusion polypeptide comprising SEQ ID NO: 222, that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 222, and (b) a second polynucleotide or second viral vector or second lipoplex (e.g., LNP) comprising a polynucleotide encoding a second fusion polypeptide comprising SEQ ID NO: 209 or SEQ ID NO: 227, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 209 or SEQ ID NO: 227. In some embodiments, the method entails administering first and second viral vectors or first and second lipoplexes (e.g., LNPs) comprising first and second polynucleotides encoding the following first fusion polypeptide and second fusion polypeptide: (a) a first polynucleotide or first viral vector or first lipoplex (e.g., LNP) comprising a polynucleotide encoding a first fusion polypeptide comprising SEQ ID NO: 222, that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 222, and (b) a second polynucleotide or second viral vector or second lipoplex (e.g., LNP) comprising a polynucleotide encoding a second fusion polypeptide comprising SEQ ID NO: 223, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 223. In some embodiments, the method entails administering a viral vector or a lipoplex (e.g., LNP) comprising one or more polynucleotides encoding the following first fusion polypeptide and second fusion polypeptide, optionally joined or connected by one or more linkers: SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively. In some embodiments, the method entails administering a viral vector or a lipoplex (e.g., LNP) comprising one or more polynucleotides encoding the following first fusion polypeptide and second fusion polypeptide, optionally joined or connected by one or more linkers: SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively. In various embodiments, the first and second viral vectors are Lymphocytic choriomeningitis mammarenavirus (LCMV) viral vectors, Cali mammarenavirus (a.k.a. Pichinde mammarenavirus or Pichinde arenavirus) viral vectors or adenoviral vectors, e.g., chimpanzee adenoviral vectors (ChAds). In some embodiments, the first and second viral vectors or first and second lipoplexes (e.g., LNPs) are co-administered concurrently. In some embodiments, the methods entail administering the following first polynucleotide and second polynucleotide, one or more vectors, or one or more lipoplexes (e.g., LNPs) comprising the following first polynucleotide and second polynucleotide: SEQ ID NOs: 130 and 132, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 130 and 132, respectively; SEQ ID NOs: 130 and 134, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 130 and 134, respectively; SEQ ID NOs: 131 and 133, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 131 and 133, respectively; SEQ ID NOs: 131 and 135, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 131 and 135, respectively; SEQ ID NOs: 132 and 136, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 132 and 136, respectively; SEQ ID NOs: 133 and 135, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 133 and 135, respectively; SEQ ID NOs: 133 and 137, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 133 and 137, respectively; SEQ ID NOs: 134 and 136, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 134 and 136, respectively; SEQ ID NOs: 135 and 137, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 135 and 137, respectively; SEQ ID NOs: 138 and 141, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 138 and 141, respectively; SEQ ID NOs: 138 and 144, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 138 and 144, respectively; SEQ ID NOs: 139 and 142, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 142, respectively; SEQ ID NOs: 139 and 145, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 145, respectively; SEQ ID NOs: 140 and 146, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 140 and 146, respectively; SEQ ID NOs: 142 and 148, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 142 and 148, respectively; SEQ ID NOs: 143 and 149, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 143 and 149, respectively; SEQ ID NOs: 145 and 148, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 145 and 148, respectively; SEQ ID NOs: 150 and 152, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively; SEQ ID NOs: 150 and 155, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 155, respectively; SEQ ID NOs: 151 and 153, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 151 and 153, respectively; SEQ ID NOs: 151 and 156, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 151 and 156, respectively; SEQ ID NOs: 152 and 158, or polynucleotides that are at least 80%, 81%, 82%, 83%, 84%, 85%8, 86%, 87%, 88%, 89%, 90%, 91%, 92%, 93%, 94%, 95%, 96%, 97%, 98% or 99% identical to any one of SEQ ID NOs: 152 and 158, respectively; SEQ ID NOs: 153 and 159, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 153 and 159, respectively; SEQ ID NOs: 154 and 157, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 154 and 157, respectively; SEQ ID NOs: 155 and 158, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 155 and 158, respectively; SEQ ID NOs: 156 and 159, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 156 and 159, respectively; SEQ ID NOs: 160 and 161, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 160 and 161, respectively; SEQ ID NOs: 162 and 163, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 162 and 163, respectively; SEQ ID NOs: 164 and 165, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 164 and 165, respectively; SEQ ID NOs: 166 and 167, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 166 and 167, respectively; SEQ ID NOs: 210 and 211, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 210 and 211, respectively; SEQ ID NOs: 212 and 213, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 212 and 213, respectively; SEQ ID NOs: 214 and 215, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 214 and 215, respectively; SEQ ID NOs: 216 and 217, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 216 and 217, respectively; SEQ ID NOs: 218 and 219, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 218 and 219, respectively; SEQ ID NOs: 218 and 226, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 218 and 226, respectively; or SEQ ID NOs: 225 and 226, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 225 and 226, respectively. In some embodiments, the method entails administering first and second viral vectors, or first and second lipoplexes (e.g., LNPs), comprising the following first polynucleotide and second polynucleotide: (a) a first vector or lipoplex (e.g., LNP) comprising first and second polynucleotides comprising SEQ ID NOs: 140 and 146, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 140 and 146, respectively, and (b) a second vector or lipoplex (e.g., LNP) comprising first and second polynucleotides comprising SEQ ID NOs: 143 and 149, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 143 and 149, respectively, wherein the first and second viral vectors are Lymphocytic choriomeningitis mammarenavirus (LCMV) viral vectors. In some embodiments, the method entails administering first and second viral vectors, or first and second lipoplexes (e.g., LNPs), comprising the following first polynucleotide and second polynucleotide: (a) a first vector or lipoplex (e.g., LNP) comprising first and second polynucleotides comprising SEQ ID NOs: 150 and 152, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively, and (b) a second vector or lipoplex (e.g., LNP) comprising first and second polynucleotides comprising SEQ ID NOs: 154 and 157 or SEQ ID NOs: 155 and 158, or polynucleotides that are at least 80%, 81%, 82%, 83%, 84%, 85%8, 86%, 87%, 88%, 89%, 90%, 91%, 92%, 93%, 94%, 95%, 96%, 97%, 98% or 99% identical to any one of SEQ ID NOs: 154 and 157 or SEQ ID NOs: 155 and 158, respectively, wherein the first and second viral vectors are Cali mammarenavirus (a.k.a. Pichinde mammarenavirus or Pichinde arenavirus) viral vectors. In some embodiments, the method entails administering a compound fusion polypeptide, a vector, or a lipoplex (e.g., LNP) comprising a polynucleotide encoding a compound fusion polypeptide, the compound fusion polypeptide comprising or consisting of an amino acid sequence of any one of SEQ ID NOs: 105-112, 200-209, 222-223 and 227, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 105-112, 200-209, 222-223 and 227. In some embodiments, the method entails administering a compound fusion polypeptide, a vector, or a lipoplex (e.g., LNP) comprising a polynucleotide encoding a compound fusion polypeptide, the compound fusion polypeptide comprising or consisting of an amino acid sequence of any one of SEQ ID NOs: 209, 222 and 223, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 209, 222 and 223. In some embodiments, the methods entail administering a polynucleotide (e.g., in a vector, in a lipoplex (e.g., LNP)) comprising or consisting of a nucleic acid sequence of any one of SEQ ID NOs: 130-167, 210-219 and 225-226, or a nucleic acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 130-167, 210-219 and 225-226. In some embodiments, the methods entail administering a polynucleotide (e.g., in a vector, in a lipoplex (e.g., LNP)) comprising or consisting of a nucleic acid sequence of any one of SEQ ID NOs: 139, 140, 142, 143, 145, 146, 148, 149, 150, 152, 155, 158, 225 and 226, or a nucleic sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139, 140, 142, 143, 145, 146, 148, 149, 150, 152, 155, 158, 225 and 226. In some embodiments, the method entails administering: (a) a first vector or lipoplex (e.g., LNP) comprising a first polynucleotide comprising SEQ ID NO: 210, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 210, and (b) a second vector or lipoplex (e.g., LNP) comprising a second polynucleotide comprising SEQ ID NO: 211, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 211. In some embodiments, the method entails administering: (a) a first vector or lipoplex (e.g., LNP) comprising a first polynucleotide comprising SEQ ID NO: 212, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 212, and (b) a second vector or lipoplex (e.g., LNP) comprising a second polynucleotide comprising SEQ ID NO: 213, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 213. In some embodiments, the method entails administering: (a) a first vector or lipoplex (e.g., LNP) comprising a first polynucleotide comprising SEQ ID NO: 214, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 214, and (b) a second vector or lipoplex (e.g., LNP) comprising a second polynucleotide comprising SEQ ID NO: 215, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 215. In some embodiments, the method entails administering: (a) a first vector or lipoplex (e.g., LNP) comprising a first polynucleotide comprising SEQ ID NO: 216, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 216, and (b) a second vector or lipoplex (e.g., LNP) comprising a second polynucleotide comprising SEQ ID NO: 217, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 217. In some embodiments, the method entails administering: (a) a first vector or lipoplex (e.g., LNP) comprising a first polynucleotide comprising SEQ ID NO: 218, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 218, and (b) a second vector or lipoplex (e.g., LNP) comprising a second polynucleotide comprising SEQ ID NO: 219, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 219. In some embodiments, the method entails administering: (a) a first vector or lipoplex (e.g., LNP) comprising a first polynucleotide comprising SEQ ID NO: 218, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 218, and (b) a second vector or lipoplex (e.g., LNP) comprising a second polynucleotide comprising SEQ ID NO: 226, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 226. In some embodiments, the method entails administering: (a) a first vector or lipoplex (e.g., LNP) comprising a first polynucleotide comprising SEQ ID NO: 225, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 225, and (b) a second vector or lipoplex (e.g., LNP) comprising a second polynucleotide comprising SEQ ID NO: 226, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 226. In some embodiments, the one or more fusion polypeptides do not comprise any polypeptide segments corresponding to Gag 54-146; Gag 370-500; Pol 1-55; Pol 118-128; Pol 321-366; Pol 432-541; Pol 607-682; Pol 709-746; Pol 828-839; Pol 921-931; Nef 1-63; Nef 100-116 and Nef 149-206, or fragments or subsequences thereof, wherein the Gag, Pol and Nef amino acid position numbers correspond to SEQ ID NOs: 1, 2 and 3, respectively. In some embodiments, the one or more fusion polypeptides do not comprise any polypeptide segments having an amino acid sequence of SEQ ID NOs: 35-47, or fragments or subsequences thereof, or an amino acid sequence at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 35-47, or fragments or subsequences thereof. In some embodiments, the subject is infected with HIV-1, is suspected of being infected with HIV-1, or is at risk of being infected with HIV-1. In some embodiments, the subject is chronically infected with HIV-1. In some embodiments, the subject is acutely infected with HIV-1. In some embodiments, the subject has an HIV-1 infection of Fiebig stage IV or earlier, e.g. Fiebig stage III, Fiebig stage II or Fiebig stage I. In some embodiments, the fusion polypeptide, the compound fusion polypeptide, the polynucleotide, the vector, the lipoplex (e.g., LNP) or the immunogenic composition is administered via a route selected from intravenous, intramuscular, intradermal, subcutaneous, intranodal and mucosal (e.g. buccal, intranasal, intrarectal, intravaginal). In some embodiments, the method entails administering from about $10^3$ to about $10^{12}$ viral focus forming units (FFU) or plaque forming units (PFU) or infectious units (IU) or viral particles (vp), e.g. from about $10^4$ to about $10^7$ viral FFU or PFU or IU or vp, e.g. from about $10^3$ to about $10^4$, $10^5$, $10^6$, $10^7$, $10^8$, $10^9$, $10^{10}$, $10^{11}$, $10^{12}$, $10^{13}$, $10^{14}$ or $10^{15}$ viral FFU or PFU or IU or vp, per administration. In some embodiments, the methods comprise a prime-boost regimen comprising administering a priming composition at a first time point and administering one or more boosting compositions at one or more subsequent time points. In some embodiments, the methods comprise repeating the prime-boost regimen one or more iterations. In some embodiments, the administrations of the priming composition and the one or more boosting compositions are spaced at least 1 week, 2 weeks, 3 weeks or 1 month apart, e.g., at least 2, 3, 4, 5, 6, 7, 8, 9, 10, 11 or 12 months apart. In some embodiments, the priming composition and the boosting composition comprise the same immunogenic composition. In some embodiments, the priming composition and the boosting composition comprise different immunogenic compositions. In some embodiments, the priming composition and the boosting composition comprise the same one or more fusion polypeptides and same viral expression vector. In some embodiments, the priming composition and the boosting composition comprise different fusion polypeptides and/or different viral expression vectors. In some embodiments, the methods comprise priming with a first viral expression vector, and boosting with a second viral expression vector. In some embodiments, the prime-boost regimen comprises: (a) Priming with one or more viral expression vectors and boosting with one or more polynucleotides, wherein the one or more polynucleotides comprise DNA, cDNA, mRNA or self-replicating RNA; (b) Priming with one or more polynucleotides, wherein the one or more polynucleotides comprise DNA, cDNA, mRNA or self-replicating RNA, and boosting with one or more viral expression vectors; (c) Priming with one or more viral expression vectors, and boosting with one or more viral expression vectors, wherein the one or more viral expression vectors in the priming composition and the one or more viral expression vectors in the boosting composition are from identical, related or unrelated taxonomical families; (d) Priming with one or more replication-deficient viral expression vectors and boosting with one or more replication-deficient viral expression vectors, wherein the one or more replication-deficient viral expression vectors in the priming composition and the one or more replication-deficient viral expression vectors in the boosting composition are from identical, related or unrelated taxonomical families; (e) Priming with one or more replication-attenuated viral expression vectors and boosting with one or more replication-attenuated viral expression vectors, wherein the one or more replication-attenuated viral expression vectors in the priming composition and the one or more replication-attenuated viral expression vectors in the boosting composition are from identical, related or unrelated taxonomical families; (f) Priming with one or more replication-deficient viral expression vectors and boosting with one or more replication-attenuated viral expression vectors; (g) Priming with one or more replication-attenuated viral expression vectors and boosting with one or more replication-deficient viral expression vectors; (h) Priming with one or more Lymphocytic choriomeningitis mammarenavirus (LCMV) viral expression vectors and boosting with one or more Pichinde mammarenavirus viral expression vectors; (i) Priming with one or more Pichinde mammarenavirus viral expression vectors and boosting with one or more Lymphocytic choriomeningitis mammarenavirus (LCMV) viral expression vectors; (j) Priming with one or more replication deficient Pichinde mammarenavirus viral expression vectors and boosting with one or more replication deficient Lymphocytic choriomeningitis mammarenavirus (LCMV) viral expression vectors; (k) Priming with one or more replication deficient Lymphocytic choriomeningitis mammarenavirus (LCMV) viral expression vectors and boosting with one or more replication deficient Pichinde mammarenavirus viral expression vectors; (l) Priming with one or more arenavirus viral expression vectors and boosting with one or more adenovirus viral expression vectors; (m) Priming with one or more adenovirus viral expression vectors and boosting with boosting composition comprising one or more arenavirus viral expression vectors; (n) Priming with one or more adenovirus viral expression vectors and boosting with boosting composition comprising one or more RNA molecules (e.g., mRNA, self-amplifying or self-replicating RNA); (o) Priming with one or more RNA molecules (e.g., mRNA, self-amplifying or self-replicating RNA) and boosting with boosting composition comprising one or more adenovirus viral expression vectors; (p) Priming with one or more chimpanzee adenoviral (ChAd) expression vectors and boosting with boosting composition comprising one or more self-amplifying or self-replicating RNA (saRNA or samRNA); (q) Priming with one or more self-amplifying or self-replicating RNA (saRNA or samRNA) and boosting with boosting composition comprising one or more chimpanzee adenoviral (ChAd) expression vectors; (r) Priming with one or more poxvirus viral expression vectors and boosting with one or more arenavirus viral expression vectors; (s) Priming with one or more arenavirus viral expression vectors and boosting with boosting composition comprising one or more poxvirus viral expression vectors; (t) Priming with one or more poxvirus viral expression vectors and boosting with one or more adenovirus viral expression vectors; or (u) Priming with one or more adenovirus viral expression vectors and boosting with boosting composition comprising one or more poxvirus viral expression vectors. In some embodiments, the prime-boost regimen comprises: (1) Priming with an immunogenic composition comprising the following first fusion polypeptide and second fusion polypeptide, one or more vectors, or one or more lipoplexes (e.g., LNPs) comprising one or more polynucleotides encoding the following first fusion polypeptide and second fusion polypeptide, optionally joined or connected by one or more linkers: SEQ ID NOs: 70 and 71, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70 and 71, respectively; SEQ ID NOs: 72 and 73, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 72 and 73, respectively; SEQ ID NOs: 74 and 75, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 74 and 75, respectively; SEQ ID NOs: 76 and 77, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 76 and 77, respectively; SEQ ID NOs: 78 and 79, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 78 and 79, respectively; SEQ ID NOs: 80 and 81, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 80 and 81, respectively; SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively; SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively; SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively; SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively; SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively; SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively; SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively; SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively; SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively; SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 88, respectively; SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively; SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively; SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively; SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively; SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively; SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively; SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively; SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively; SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively; SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively; SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively; or SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively; and (2) Boosting with an immunogenic composition comprising the following first fusion polypeptide and second fusion polypeptide, one or more vectors, or one or more lipoplexes (e.g., LNPs) comprising one or more polynucleotides encoding the following first fusion polypeptide and second fusion polypeptide, optionally joined or connected by one or more linkers: SEQ ID NOs: 70 and 71, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70 and 71, respectively; SEQ ID NOs: 72 and 73, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 72 and 73, respectively; SEQ ID NOs: 74 and 75, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 74 and 75, respectively; SEQ ID NOs: 76 and 77, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 76 and 77, respectively; SEQ ID NOs: 78 and 79, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 78 and 79, respectively; SEQ ID NOs: 80 and 81, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 80 and 81, respectively; SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively; SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively; SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively; SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively; SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively; SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively; SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively; SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively; SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively; SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 88, respectively; SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively; SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively; SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively; SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively; SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively; SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively; SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively; SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively; SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively; SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively; SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively; or SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively. In some embodiments, the prime-boost regimen comprises: (1) Priming with an immunogenic composition comprising the following first fusion polypeptide and second fusion polypeptide, one or more vectors, one or more lipoplexes (e.g., LNPs), comprising one or more polynucleotides encoding the following first fusion polypeptide and second fusion polypeptide, optionally joined or connected by one or more linkers: (a) SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively; (b) SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively; (c) SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively; (d) SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively; and/or (e) SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively; and (2) Boosting with an immunogenic composition comprising the following first fusion polypeptide and second fusion polypeptide, one or more vectors, or one or more lipoplexes (e.g., LNPs), comprising one or more polynucleotides encoding the following first fusion polypeptide and second fusion polypeptide, optionally joined or connected by one or more linkers: (a) SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively; (b) SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively; (c) SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; and/or (d) SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively. In some embodiments, the prime-boost regimen comprises: (1) Priming with an immunogenic composition comprising first and second viral vectors, or first and second lipoplexes (e.g., LNPs), comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding first fusion polypeptide and second fusion polypeptides comprising SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively or one or more polynucleotides encoding first fusion polypeptide and second fusion polypeptides comprising SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively; and (b) a second viral vector or lipoplex (e.g., LNP) comprising one or more polynucleotides encoding first fusion polypeptide and second fusion polypeptides comprising SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively; and (2) Boosting with an immunogenic composition comprising first and second viral vectors, or first and second lipoplexes (e.g., LNPs), comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding first fusion polypeptide and second fusion polypeptides comprising SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; and (b) a second viral vector or lipoplex (e.g., LNP) comprising one or more polynucleotides encoding first fusion polypeptide and second fusion polypeptides comprising SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively. In some embodiments, the prime-boost regimen comprises: (1) Priming with an immunogenic composition comprising a viral vector or a lipoplex (e.g., LNP) comprising one or more polynucleotides encoding first fusion polypeptide and second fusion polypeptides, optionally joined or connected by one or more linkers, comprising SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively; and (2) Boosting with an immunogenic composition comprising a viral vector or a lipoplex (e.g., LNP) comprising one or more polynucleotides encoding first fusion polypeptide and second fusion polypeptides, optionally joined or connected by one or more linkers, comprising SEQ ID NOs: 87 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 88, respectively. In some embodiments, the prime-boost regimen comprises: priming and boosting with an immunogenic composition comprising a first viral vector or a lipoplex (e.g., LNP) comprising one or more polynucleotides encoding first fusion polypeptide and second fusion polypeptides, optionally joined or connected by one or more linkers, comprising SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively; and a second viral vector or a lipoplex (e.g., LNP) comprising one or more polynucleotides encoding first fusion polypeptide and second fusion polypeptides, optionally joined or connected by one or more linkers, comprising SEQ ID NOs: 87 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 88, respectively. In some embodiments, the prime-boost regimen comprises: (1) Priming with an immunogenic composition comprising a viral vector or a lipoplex (e.g., LNP) comprising one or more polynucleotides encoding first fusion polypeptide and second fusion polypeptides, optionally joined or connected by one or more linkers, comprising SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively; and (2) Boosting with an immunogenic composition comprising a viral vector or a lipoplex (e.g., LNP) comprising one or more polynucleotides encoding first fusion polypeptide and second fusion polypeptides, optionally joined or connected by one or more linkers, comprising SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively. In some embodiments, the prime-boost regimen comprises: priming and boosting with an immunogenic composition comprising a first viral vector or a lipoplex (e.g., LNP) comprising one or more polynucleotides encoding first fusion polypeptide and second fusion polypeptides, optionally joined or connected by one or more linkers, comprising SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively; and a second viral vector or a lipoplex (e.g., LNP) comprising one or more polynucleotides encoding first fusion polypeptide and second fusion polypeptides, optionally joined or connected by one or more linkers, comprising SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively. In some embodiments, the prime-boost regimen comprises: (1) Priming with an immunogenic composition comprising a viral vector or a lipoplex (e.g., LNP) comprising one or more polynucleotides encoding first fusion polypeptide and second fusion polypeptides, optionally joined or connected by one or more linkers, comprising SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively; and (2) Boosting with an immunogenic composition comprising a viral vector or a lipoplex (e.g., LNP) comprising one or more polynucleotides encoding first fusion polypeptide and second fusion polypeptides, optionally joined or connected by one or more linkers, comprising SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively. In some embodiments, the prime-boost regimen comprises: priming and boosting with an immunogenic composition comprising a first viral vector or a lipoplex (e.g., LNP) comprising one or more polynucleotides encoding first fusion polypeptide and second fusion polypeptides, optionally joined or connected by one or more linkers, comprising SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively; and a second viral vector or a lipoplex (e.g., LNP) comprising one or more polynucleotides encoding first fusion polypeptide and second fusion polypeptides, optionally joined or connected by one or more linkers, comprising SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively.

In some embodiments, the prime-boost regimen comprises: (1) Priming with an immunogenic composition comprising a viral vector or a lipoplex (e.g., LNP) comprising one or more polynucleotides encoding first fusion polypeptide and second fusion polypeptides, optionally joined or connected by one or more linkers, comprising SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively; and (2) Boosting with an immunogenic composition comprising a viral vector or a lipoplex (e.g., LNP) comprising one or more polynucleotides encoding first fusion polypeptide and second fusion polypeptides, optionally joined or connected by one or more linkers, comprising SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively. In some embodiments, the prime-boost regimen comprises: (1) Priming with an immunogenic composition comprising a viral vector or a lipoplex (e.g., LNP) comprising one or more polynucleotides encoding first fusion polypeptide and second fusion polypeptides, optionally joined or connected by one or more linkers, comprising SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively; and (2) Boosting with an immunogenic composition comprising a viral vector or a lipoplex (e.g., LNP) comprising one or more polynucleotides encoding first fusion polypeptide and second fusion polypeptides, optionally joined or connected by one or more linkers, comprising SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively. In some embodiments, the prime-boost regimen comprises: priming and boosting with an immunogenic composition comprising a first viral vector or a lipoplex (e.g., LNP) comprising one or more polynucleotides encoding first fusion polypeptide and second fusion polypeptides, optionally joined or connected by one or more linkers, comprising SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively; and a second viral vector or a lipoplex (e.g., LNP) comprising one or more polynucleotides encoding first fusion polypeptide and second fusion polypeptides, optionally joined or connected by one or more linkers, comprising SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively. In some embodiments, the prime-boost regimen comprises: priming and boosting with an immunogenic composition comprising a first viral vector or a lipoplex (e.g., LNP) comprising one or more polynucleotides encoding first fusion polypeptide and second fusion polypeptides, optionally joined or connected by one or more linkers, comprising SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively; and a second viral vector or a lipoplex (e.g., LNP) comprising one or more polynucleotides encoding first fusion polypeptide and second fusion polypeptides, optionally joined or connected by one or more linkers, comprising SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively. In some embodiments, the prime-boost regimen comprises: (1) Priming with an immunogenic composition comprising a viral vector or a lipoplex (e.g., LNP) comprising one or more polynucleotides encoding first fusion polypeptide and second fusion polypeptides, optionally joined or connected by one or more linkers, comprising SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively; and (2) Boosting with an immunogenic composition comprising a viral vector or a lipoplex (e.g., LNP) comprising one or more polynucleotides encoding first fusion polypeptide and second fusion polypeptides, optionally joined or connected by one or more linkers, comprising SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively. In some embodiments, the prime-boost regimen comprises: (1) Priming with an immunogenic composition comprising a viral vector or a lipoplex (e.g., LNP) comprising a polynucleotide encoding a compound fusion polypeptide comprising SEQ ID NO: 105, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 105, respectively; and (2) Boosting with an immunogenic composition comprising a viral vector or a lipoplex (e.g., LNP) comprising a polynucleotide encoding a compound fusion polypeptide comprising SEQ ID NO: 109, or a compound fusion polypeptide that is at least 80%, 81%, 82%, 83%, 84%, 85%8, 86%, 87%, 88%, 89%, 90%, 91%, 92%, 93%, 94%, 95%, 96%, 97%, 98% or 99% identical to SEQ ID NO: 109, respectively. In some embodiments, the prime-boost regimen comprises: (1) Priming with an immunogenic composition comprising a viral vector or a lipoplex (e.g., LNP) comprising a polynucleotide encoding a compound fusion polypeptide comprising SEQ ID NO: 105 or 206, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 105 or 206, respectively; and (2) Boosting with an immunogenic composition comprising a viral vector or a lipoplex (e.g., LNP) comprising a polynucleotide encoding a compound fusion polypeptide comprising SEQ ID NO: 107 or 207, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 107 or 207, respectively. In some embodiments, the prime-boost regimen comprises: priming and boosting with an immunogenic composition comprising a first viral vector or a lipoplex (e.g., LNP) comprising a polynucleotide encoding a first fusion polypeptide comprising SEQ ID NO: 105, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 105, respectively; and a second viral vector or a lipoplex (e.g., LNP) comprising a polynucleotide encoding a second fusion polypeptide, comprising SEQ ID NO: 107, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 107, respectively. In some embodiments, the prime-boost regimen comprises: priming and boosting with an immunogenic composition comprising a first viral vector or a lipoplex (e.g., LNP) comprising a polynucleotide encoding a first fusion polypeptide comprising SEQ ID NO: 206, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 206, respectively; and a second viral vector or a lipoplex (e.g., LNP) comprising a polynucleotide encoding a second fusion polypeptide, comprising SEQ ID NO: 207, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 207, respectively. In some embodiments, the prime-boost regimen comprises: (1) Priming with an immunogenic composition comprising a viral vector or a lipoplex (e.g., LNP) comprising a polynucleotide encoding a compound fusion polypeptide comprising SEQ ID NO: 208, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 208, respectively; and (2) Boosting with an immunogenic composition comprising a viral vector or a lipoplex (e.g., LNP) comprising a polynucleotide encoding a compound fusion polypeptide comprising SEQ ID NO: 209 or SEQ ID NO: 227, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 209 or SEQ ID NO: 227, respectively. In some embodiments, the prime-boost regimen comprises: (1) Priming with an immunogenic composition comprising a viral vector or a lipoplex (e.g., LNP) comprising a polynucleotide encoding a compound fusion polypeptide comprising SEQ ID NO: 222, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 222, respectively; and (2) Boosting with an immunogenic composition comprising a viral vector or a lipoplex (e.g., LNP) comprising a polynucleotide encoding a compound fusion polypeptide comprising SEQ ID NO: 209 or SEQ ID NO: 227, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 209 or SEQ ID NO: 227, respectively. In some embodiments, the prime-boost regimen comprises: (1) Priming with an immunogenic composition comprising a viral vector or a lipoplex (e.g., LNP) comprising a polynucleotide encoding a compound fusion polypeptide comprising SEQ ID NO: 222, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 222, respectively; and (2) Boosting with an immunogenic composition comprising a viral vector or a lipoplex (e.g., LNP) comprising a polynucleotide encoding a compound fusion polypeptide comprising SEQ ID NO: 223, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 223, respectively. In some embodiments, the prime-boost regimen comprises: priming and boosting with an immunogenic composition comprising a first viral vector or a lipoplex (e.g., LNP) comprising a polynucleotide encoding a first fusion polypeptide comprising SEQ ID NO: 208, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 208, respectively; and a second viral vector or a lipoplex (e.g., LNP) comprising a polynucleotide encoding a second fusion polypeptide, comprising SEQ ID NO: 209 or SEQ ID NO: 227, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 209 or SEQ ID NO: 227, respectively. In some embodiments, the prime-boost regimen comprises: priming and boosting with an immunogenic composition comprising a first viral vector or a lipoplex (e.g., LNP) comprising a polynucleotide encoding a first fusion polypeptide comprising SEQ ID NO: 222, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 222, respectively; and a second viral vector or a lipoplex (e.g., LNP) comprising a polynucleotide encoding a second fusion polypeptide, comprising SEQ ID NO: 209 or SEQ ID NO: 227, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 209 or SEQ ID NO: 227, respectively. In some embodiments, the prime-boost regimen comprises: priming and boosting with an immunogenic composition comprising a first viral vector or a lipoplex (e.g., LNP) comprising a polynucleotide encoding a first fusion polypeptide comprising SEQ ID NO: 222, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 222, respectively; and a second viral vector or a lipoplex (e.g., LNP) comprising a polynucleotide encoding a second fusion polypeptide, comprising SEQ ID NO: 223, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 223, respectively. In some embodiments, the prime-boost regimen comprises: (1) Priming with an immunogenic composition comprising a viral vector or a lipoplex (e.g., LNP) comprising one or more polynucleotides encoding first fusion polypeptide and second fusion polypeptides, optionally joined or connected by one or more linkers, comprising SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively; and (2) Boosting with an immunogenic composition comprising a viral vector or a lipoplex (e.g., LNP) comprising one or more polynucleotides encoding first fusion polypeptide and second fusion polypeptides, optionally joined or connected by one or more linkers, comprising SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively. In some embodiments, the prime-boost regimen comprises: (1) Priming with an immunogenic composition comprising a viral vector or a lipoplex (e.g., LNP) comprising a polynucleotide encoding a compound fusion polypeptide comprising SEQ ID NO: 107, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 107, respectively; and (2) Boosting with an immunogenic composition comprising a viral vector or a lipoplex (e.g., LNP) comprising a polynucleotide encoding a compound fusion polypeptide comprising SEQ ID NO: 111, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 111, respectively. In some embodiments, the prime-boost regimen comprises: (1) Priming with an immunogenic composition comprising a viral vector or a lipoplex (e.g., LNP) comprising a polynucleotide encoding a compound fusion polypeptide comprising SEQ ID NO: 200, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 200, respectively; and (2) Boosting with an immunogenic composition comprising a viral vector or a lipoplex (e.g., LNP) comprising a polynucleotide encoding a compound fusion polypeptide comprising SEQ ID NO: 201, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 201, respectively. In some embodiments, the prime-boost regimen comprises: priming and boosting with an immunogenic composition comprising a first viral vector or a lipoplex (e.g., LNP) comprising a polynucleotide encoding a first fusion polypeptide comprising SEQ ID NO: 200, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 200; and a second viral vector or a lipoplex (e.g., LNP) comprising a polynucleotide encoding a second fusion polypeptide, comprising SEQ ID NO: 201, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 201. In some embodiments, the prime-boost regimen comprises: (1) Priming with an immunogenic composition comprising a viral vector or a lipoplex (e.g., LNP) comprising a polynucleotide encoding a compound fusion polypeptide comprising SEQ ID NO: 202, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 202; and (2) Boosting with an immunogenic composition comprising a viral vector or a lipoplex (e.g., LNP) comprising a polynucleotide encoding a compound fusion polypeptide comprising SEQ ID NO: 203, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 203. In some embodiments, the prime-boost regimen comprises: priming and boosting with an immunogenic composition comprising a first viral vector or a lipoplex (e.g., LNP) comprising a polynucleotide encoding a first fusion polypeptide comprising SEQ ID NO: 202, or a fusion polypeptide that is at least 80%, 81%, 82%, 83%, 84%, 85%8, 86%, 87%, 88%, 89%, 90%, 91%, 92%, 93%, 94%, 95%, 96%, 97%, 98% or 99% identical to SEQ ID NO: 202; and a second viral vector or a lipoplex (e.g., LNP) comprising a polynucleotide encoding a second fusion polypeptide, comprising SEQ ID NO: 203, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 203. In some embodiments, the prime-boost regimen comprises: (1) Priming with an immunogenic composition comprising a viral vector or a lipoplex (e.g., LNP) comprising a polynucleotide encoding a compound fusion polypeptide comprising SEQ ID NO: 204, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 204; and (2) Boosting with an immunogenic composition comprising a viral vector or a lipoplex (e.g., LNP) comprising a polynucleotide encoding a compound fusion polypeptide comprising SEQ ID NO: 205, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 205. In some embodiments, the prime-boost regimen comprises: priming and boosting with an immunogenic composition comprising a first viral vector or a lipoplex (e.g., LNP) comprising a polynucleotide encoding a first fusion polypeptide comprising SEQ ID NO: 204, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 204; and a second viral vector or a lipoplex (e.g., LNP) comprising a polynucleotide encoding a second fusion polypeptide, comprising SEQ ID NO: 205, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 205. In some embodiments, the prime-boost regimen comprises: (1) Priming with an immunogenic composition comprising first and second viral vectors, or first and second lipoplexes (e.g., LNPs), comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding first fusion polypeptide and second fusion polypeptides comprising SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively; and (b) a second viral vector or lipoplex (e.g., LNP) comprising one or more polynucleotides encoding first fusion polypeptide and second fusion polypeptides comprising SEQ ID NOs:86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively; and (2) Boosting with an immunogenic composition comprising first and second viral vectors, or first and second lipoplexes (e.g., LNPs), comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding first fusion polypeptide and second fusion polypeptides comprising SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively; and (b) a second viral vector or lipoplex (e.g., LNP) comprising one or more polynucleotides encoding first fusion polypeptide and second fusion polypeptides comprising SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively. In some embodiments, the prime-boost regimen comprises: (1) Priming with an immunogenic composition comprising first and second viral vectors, or first and second lipoplexes (e.g., LNPs), comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding first fusion polypeptide and second fusion polypeptides comprising SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; and (b) a second viral vector or lipoplex (e.g., LNP) comprising one or more polynucleotides encoding first fusion polypeptide and second fusion polypeptides comprising SEQ ID NOs:83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively; and (2) Boosting with an immunogenic composition comprising first and second viral vectors, or first and second lipoplexes (e.g., LNPs), comprising one or more polynucleotides encoding the following first fusion polypeptide and second fusion polypeptide, optionally joined or connected by one or more linkers: (a) a first viral vector comprising one or more polynucleotides encoding first fusion polypeptide and second fusion polypeptides comprising SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 88, respectively; and (b) a second viral vector comprising one or more polynucleotides encoding first fusion polypeptide and second fusion polypeptides comprising SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively. In some embodiments, the prime-boost regimen comprises: (1) Priming with an immunogenic composition comprising first and second viral vectors, or first and second lipoplexes (e.g., LNPs), comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding first fusion polypeptide and second fusion polypeptides comprising SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; and (b) a second viral vector or lipoplex (e.g., LNP) comprising one or more polynucleotides encoding first fusion polypeptide and second fusion polypeptides comprising SEQ ID NOs:83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively; and (2) Boosting with an immunogenic composition comprising first and second viral vectors, or first and second lipoplexes (e.g., LNPs), comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding first fusion polypeptide and second fusion polypeptides comprising SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; and (b) a second viral vector or lipoplex (e.g., LNP) comprising one or more polynucleotides encoding first fusion polypeptide and second fusion polypeptides comprising SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively. In some embodiments, the prime-boost regimen comprises: (1) Priming with an immunogenic composition comprising first and second viral vectors, or first and second lipoplexes (e.g., LNPs), comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding first fusion polypeptide and second fusion polypeptides comprising SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; and (b) a second viral vector or lipoplex (e.g., LNP) comprising one or more polynucleotides encoding first fusion polypeptide and second fusion polypeptides comprising SEQ ID NOs:83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively; and (2) Boosting with an immunogenic composition comprising first and second viral vectors, or first and second lipoplexes (e.g., LNPs), comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding first fusion polypeptide and second fusion polypeptides comprising SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; and (b) a second viral vector or lipoplex (e.g., LNP) comprising one or more polynucleotides encoding first fusion polypeptide and second fusion polypeptides comprising SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively. In some embodiments, the prime-boost regimen comprises: (1) Priming with an immunogenic composition comprising first and second viral vectors, or first and second lipoplexes (e.g., LNPs), comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding first fusion polypeptide and second fusion polypeptides comprising SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; and (b) a second viral vector or lipoplex (e.g., LNP) comprising one or more polynucleotides encoding first fusion polypeptide and second fusion polypeptides comprising SEQ ID NOs:99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively; and (2) Boosting with an immunogenic composition comprising first and second viral vectors, or first and second lipoplexes (e.g., LNPs), comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding first fusion polypeptide and second fusion polypeptides comprising SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; and (b) a second viral vector or lipoplex (e.g., LNP) comprising one or more polynucleotides encoding first fusion polypeptide and second fusion polypeptides comprising SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively. In some embodiments, the prime-boost regimen comprises: (1) Priming with an immunogenic composition comprising first and second viral vectors, or first and second lipoplexes (e.g., LNPs), comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding first fusion polypeptide and second fusion polypeptides comprising SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; and (b) a second viral vector or lipoplex (e.g., LNP) comprising one or more polynucleotides encoding first fusion polypeptide and second fusion polypeptides comprising SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively; and (2) Boosting with an immunogenic composition comprising first and second viral vectors, or first and second lipoplexes (e.g., LNPs), comprising one or more polynucleotides encoding the following first fusion polypeptide and second fusion polypeptide, optionally joined or connected by one or more linkers: (a) a first viral vector or lipoplex (e.g., LNP) comprising one or more polynucleotides encoding first fusion polypeptide and second fusion polypeptides comprising SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; and (b) a second viral vector or lipoplex (e.g., LNP) comprising one or more polynucleotides encoding first fusion polypeptide and second fusion polypeptides comprising SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively. In some embodiments, the prime-boost regimen comprises: (1) Priming with an immunogenic composition comprising a viral vector or lipoplex (e.g., LNP) comprising one or more polynucleotides encoding the following first fusion polypeptide and second fusion polypeptide, optionally joined or connected by one or more linkers: SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively; and (2) Boosting with an immunogenic composition comprising a viral vector or lipoplex (e.g., LNP) comprising one or more polynucleotides encoding the following first fusion polypeptide and second fusion polypeptide, optionally joined or connected by one or more linkers: SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively. In some embodiments, the prime-boost regimen comprises: (1) Priming with an immunogenic composition comprising first and second viral vectors, or first and second lipoplexes (e.g., LNPs), comprising the following polynucleotides: (a) a first viral vector or lipoplex (e.g., LNP) comprising first and second polynucleotides comprising SEQ ID NOs: 131 and 135, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 131 and 135, respectively; and (b) a second viral vector or lipoplex (e.g., LNP) comprising first and second polynucleotides comprising SEQ ID NOs: 133 and 137, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 133 and 137, respectively; and (2) Boosting with an immunogenic composition comprising first and second viral vectors, or first and second lipoplexes (e.g., LNPs), comprising the following polynucleotides: (a) a first viral vector or lipoplex (e.g., LNP) comprising first and second polynucleotides comprising SEQ ID NOs: 139 and 145, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 145, respectively; and (b) a second viral vector or lipoplex (e.g., LNP) comprising first and second polynucleotides comprising SEQ ID NOs: 142 and 148, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 142 and 148, respectively. In some embodiments, the prime-boost regimen comprises: (1) Priming with an immunogenic composition comprising first and second viral vectors, or first and second lipoplexes (e.g., LNPs), comprising the following polynucleotides: (a) a first viral vector or lipoplex (e.g., LNP) comprising first and second polynucleotides comprising SEQ ID NOs: 140 and 146, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 140 and 146, respectively; and (b) a second viral vector or lipoplex (e.g., LNP) comprising first and second polynucleotides comprising SEQ ID NOs: 143 and 149, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 143 and 149, respectively; and (2) Boosting with an immunogenic composition comprising first and second viral vectors, or first and second lipoplexes (e.g., LNPs), comprising the following polynucleotides: (a) a first viral vector or lipoplex (e.g., LNP) comprising first and second polynucleotides comprising SEQ ID NOs: 150 and 152, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively; and (b) a second viral vector or lipoplex (e.g., LNP) comprising first and second polynucleotides comprising SEQ ID NOs: 154 and 157 or SEQ ID NOs: 155 and 158, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 154 and 157 or SEQ ID NOs: 155 and 158, respectively. In some embodiments, the prime-boost regimen comprises: (1) Priming with an immunogenic composition comprising first and second viral vectors, or first and second lipoplexes (e.g., LNPs), comprising the following polynucleotides: (a) a first viral vector or lipoplex (e.g., LNP) comprising first and second polynucleotides comprising SEQ ID NOs: 150 and 152, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively; and (b) a second viral vector or lipoplex (e.g., LNP) comprising first and second polynucleotides comprising SEQ ID NOs: 154 and 157 or SEQ ID NOs: 155 and 158, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 154 and 157 or SEQ ID NOs: 155 and 158, respectively; and (2) Boosting with an immunogenic composition comprising first and second viral vectors, or first and second lipoplexes (e.g., LNPs), comprising the following polynucleotides: (a) a first viral vector or lipoplex (e.g., LNP) comprising first and second polynucleotides comprising SEQ ID NOs: 140 and 146, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 140 and 146, respectively; and (b) a second viral vector or lipoplex (e.g., LNP) comprising first and second polynucleotides comprising SEQ ID NOs: 143 and 149, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 143 and 149, respectively. In some embodiments, the prime-boost regimen comprises: (1) Priming with an immunogenic composition comprising first and second viral vectors, or first and second lipoplexes (e.g., LNPs), comprising the following polynucleotides: (a) a first viral vector or lipoplex (e.g., LNP) comprising first and second polynucleotides comprising SEQ ID NOs: 150 and 152, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively; and (b) a second viral vector or lipoplex (e.g., LNP) comprising first and second polynucleotides comprising SEQ ID NOs: 155 and 158, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 155 and 158, respectively; and (2) Boosting with an immunogenic composition comprising first and second viral vectors, or first and second lipoplexes (e.g., LNPs), comprising the following polynucleotides: (a) a first viral vector or lipoplex (e.g., LNP) comprising first and second polynucleotides comprising SEQ ID NOs: 151 and 153, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 151 and 153, respectively; and (b) a second viral vector or lipoplex (e.g., LNP) comprising first and second polynucleotides comprising SEQ ID NOs: 156 and 159, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 156 and 159, respectively. In some embodiments, the prime-boost regimen comprises: (1) Priming with an immunogenic composition comprising first and second viral vectors, or first and second lipoplexes (e.g., LNPs), comprising the following polynucleotides: (a) a first viral vector or lipoplex (e.g., LNP) comprising first and second polynucleotides comprising SEQ ID NOs: 150 and 152, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively; and (b) a second viral vector or lipoplex (e.g., LNP) comprising first and second polynucleotides comprising SEQ ID NOs: 155 and 158, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 155 and 158, respectively; and (2) Boosting with an immunogenic composition comprising first and second viral vectors, or first and second lipoplexes (e.g., LNPs), comprising the following polynucleotides: (a) a first viral vector or lipoplex (e.g., LNP) comprising first and second polynucleotides comprising SEQ ID NOs: 139 and 145, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 145 respectively; and (b) a second viral vector or lipoplex (e.g., LNP) comprising first and second polynucleotides comprising SEQ ID NOs: 142 and 148, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 142 and 148, respectively. In some embodiments, the prime-boost regimen comprises: (1) Priming with an immunogenic composition comprising a first viral vector or lipoplex (e.g., LNP) comprising first and second polynucleotides comprising SEQ ID NOs: 160 and 161, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 160 and 161, respectively; and (2) Boosting with an immunogenic composition comprising a second viral vector or lipoplex (e.g., LNP) comprising first and second polynucleotides comprising SEQ ID NOs: 162 and 163, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 162 and 163, respectively. In some embodiments, the prime-boost regimen comprises: (1) Priming with an immunogenic composition comprising a first viral vector or lipoplex (e.g., LNP) comprising first and second polynucleotides comprising SEQ ID NOs: 164 and 165, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 164 and 165, respectively; and (2) Boosting with an immunogenic composition comprising a second viral vector or lipoplex (e.g., LNP) comprising first and second polynucleotides comprising SEQ ID NOs: 166 and 167, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 166 and 167, respectively. In some embodiments, the viral vectors in the priming composition are Lymphocytic choriomeningitis mammarenavirus (LCMV) viral vectors and the viral vectors in the boosting composition are Cali mammarenavirus (a.k.a. Pichinde mammarenavirus or Pichinde arenavirus) viral vectors. In various embodiments, the viral vectors in the priming composition are Cali mammarenavirus (a.k.a. Pichinde mammarenavirus or Pichinde arenavirus) viral vectors and the viral vectors in the boosting composition are Lymphocytic choriomeningitis mammarenavirus (LCMV) viral vectors. In some embodiments, the prime-boost regimen comprises: priming and boosting with an immunogenic composition comprising a first viral vector or lipoplex (e.g., LNP) comprising a first polynucleotide comprising SEQ ID NO: 210, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 210; and a second viral vector or lipoplex (e.g., LNP) comprising a second polynucleotide comprising SEQ ID NO: 211, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 211. In some embodiments, the prime-boost regimen comprises: priming and boosting with an immunogenic composition comprising a first viral vector or lipoplex (e.g., LNP) comprising a first polynucleotide comprising SEQ ID NO: 212, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 212; and a second viral vector or lipoplex (e.g., LNP) comprising a second polynucleotide comprising SEQ ID NO: 213, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 213. In some embodiments, the prime-boost regimen comprises: priming and boosting with an immunogenic composition comprising a first viral vector or lipoplex (e.g., LNP) comprising a first polynucleotide comprising SEQ ID NO: 214, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 214; and a second viral vector or lipoplex (e.g., LNP) comprising a second polynucleotide comprising SEQ ID NO: 215, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 215. In some embodiments, the prime-boost regimen comprises: priming and boosting with an immunogenic composition comprising a first viral vector or lipoplex (e.g., LNP) comprising a first polynucleotide comprising SEQ ID NO: 216, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 216; and a second viral vector or lipoplex (e.g., LNP) comprising a second polynucleotide comprising SEQ ID NO: 217, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 217. In some embodiments, the prime-boost regimen comprises: priming and boosting with an immunogenic composition comprising a first viral vector or lipoplex (e.g., LNP) comprising a first polynucleotide comprising SEQ ID NO: 218, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 218; and a second viral vector or lipoplex (e.g., LNP) comprising a second polynucleotide comprising SEQ ID NO: 219, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 219. In some embodiments, the prime-boost regimen comprises: priming and boosting with an immunogenic composition comprising a first viral vector or lipoplex (e.g., LNP) comprising a first polynucleotide comprising SEQ ID NO: 218, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 218; and a second viral vector or lipoplex (e.g., LNP) comprising a second polynucleotide comprising SEQ ID NO: 226, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 226. In some embodiments, the prime-boost regimen comprises: priming and boosting with an immunogenic composition comprising a first viral vector or lipoplex (e.g., LNP) comprising a first polynucleotide comprising SEQ ID NO: 225, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 225; and a second viral vector or lipoplex (e.g., LNP) comprising a second polynucleotide comprising SEQ ID NO: 226, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 226. In some embodiments, the viral vector(s) in the priming composition and the viral vector(s) in the boosting composition are adenoviral vectors, e.g., chimpanzee adenoviral vectors (ChAds). In some embodiments, the viral vectors in the priming composition and the viral vectors in the boosting composition are replication deficient. In some embodiments, the viral vectors in the priming composition and the viral vectors in the boosting composition are replication attenuated. In some embodiments, the subject is not receiving antiretroviral therapy (ART) or ART is discontinued prior to administration of the one or more compositions. In some embodiments, ART is discontinued after one or more administrations of the compositions. In some embodiments, the methods entail administering to the subject one or more additional therapeutic agents, e.g. two, three, four, or more additional therapeutic agents. In some embodiments, the methods entail co-administering one or more agents that activate latent HIV, e.g., one or more latency reversing agents (LRAs). In some embodiments, the one or more LRAs are selected from agonists or activators of one or more toll-like receptors (TLRs), histone deacetylase (HDAC) inhibitors, proteasome inhibitors, protein kinase C (PKC) activators, Smyd2 inhibitors, BET-bromodomain 4 (BRD4)

inhibitors, ionomycin, inhibitor of apoptosis proteins (IAP) antagonists, and second mitochondria-derived activator of caspases (SMAC) mimetics. In some embodiments, the methods entail co-administering one or more agonists or activators of one or more toll-like receptors (TLRs). In some embodiments, the TLR agonist or activator is selected from a TLR2 agonist, a TLR3 agonist, a TLR4 agonist, a TLR5 agonist, a TLR7 agonist, a TLR8 agonist and a TLR9 agonist. In some embodiments, the TLR7 agonist is selected from GS 9620 (vesatolimod), R848 (Resiquimod), DS-0509, LHC-165 and TMX-101 (imiquimod), and/or wherein the TLR8 agonist is selected from GS-9688 (Selgantolimod), R848 (Resiquimod) and NKTR-262 (dual TLR7/TLR8 agonist). In some embodiments, the methods entail co-administering one or more interleukin receptor agonists of an interleukin selected from IL-2, IL-7, IL-12 and IL-15. In some embodiments, the methods entail co-administering one or more cytokines selected from IL-2, IL-7, IL-12, IL-15, and variants thereof. In some embodiments, the methods entail co-administering one or more innate immune activators. In some embodiments, the one or more innate immune activators comprises an agonist of a receptor selected from fms related tyrosine kinase 3 (FLT3), stimulator of interferon genes (STING) receptor, DExD/H-box helicase 58 (DDX58; a.k.a., RIG-I), nucleotide binding oligomerization domain containing 2 (NOD2). In some embodiments, the methods entail co-administering an agonist of fms related tyrosine kinase 3 (FLT3). In some embodiments, the methods entail co-administering one or more antagonists or inhibitors of an inhibitory immune checkpoint protein or receptor and/or one or more activators or agonists of a stimulatory immune checkpoint protein or receptor. In some embodiments, the one or more immune checkpoint proteins or receptors are selected from: CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAETIE; ULBP4); retinoic acid early transcript 1G (RAETIG; ULBP5); retinoic acid early transcript 1L (RAET1L; ULBP6); lymphocyte activating 3 (CD223); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); and SLAM family member 7 (SLAMF7). In some embodiments, the methods entail co-administering one or more blockers or inhibitors of one or more T-cell inhibitory immune checkpoint proteins or receptors. In some embodiments, the T-cell inhibitory immune checkpoint proteins or receptors are selected from CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In some embodiments, the methods entail co-administering one or more agonists or activators of one or more T-cell stimulatory immune checkpoint proteins or receptors. In some embodiments, the T-cell stimulatory immune checkpoint proteins or receptors are selected from CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); Poliovirus receptor (PVR) cell adhesion molecule (PVR, CD155). In some embodiments, the methods entail co-administering one or more blockers or inhibitors of one or more NK-cell inhibitory immune checkpoint proteins or receptors. In some embodiments, the NK-cell inhibitory immune checkpoint proteins or receptors are selected from killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94). In some embodiments, the methods entail co-administering one or more agonists or activators of one or more NK-cell stimulatory immune checkpoint proteins or receptors. In some embodiments, the NK-cell stimulatory immune checkpoint proteins or receptors are selected from CD16, CD226 (DNAM-1); killer cell lectin like receptor K1 (KLRK1, NKG2D, CD314); and SLAM family member 7 (SLAMF7). In some embodiments, the one or more immune checkpoint inhibitors comprises a proteinaceous inhibitor of PD-L1 (CD274), PD-1 (PDCD1) or CTLA4. In some embodiments, the methods entail co-administering an antibody that binds to CTLA4. In some embodiments, the proteinaceous or antibody inhibitor of CTLA4 is selected from ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4) and AK-104 (CTLA4/PD-1). In some embodiments, the proteinaceous inhibitor of PD-L1 (CD274) or PD-1 (PDCD1) is selected from pembrolizumab, nivolumab, cemiplimab, pidilizumab, AMP-224, MEDI0680 (AMP-514), spartalizumab, atezolizumab, avelumab, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), and INBRX-105 (4-1BB/PDL1). In some embodiments, the one or more immune checkpoint inhibitors comprises a small molecule inhibitor of CD274 (PDL1, PD-L1), programmed cell death 1 (PDCD1, PD1, PD-1) or CTLA4. In some embodiments, the small molecule inhibitor of CD274 or PDCD1 is selected from GS-4224, GS-4416, INCB086550 and MAX10181. In some embodiments, the small molecule inhibitor of CTLA4 comprises BPI-002. In some embodiments, the methods further comprise administering to the subject one or more antiviral agents. In some embodiments, the one or more antiviral agents are selected from HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors and capsid inhibitors. In some embodiments, the methods further comprise administering to the subject one or more anti-HIV antibodies or antigen-binding fragments thereof. In some embodiments, the one or more anti-HIV antibodies or antigen-binding fragments thereof binds to HIV gp120. In some embodiments, the anti-HIV antibody or antigen-binding fragment thereof comprises a broadly neutralizing antibody. In some embodiments, the one or more anti-HIV antibodies or antigen-binding fragments thereof that bind, inhibit, and/or neutralize HIV, compete with or comprise VH and VL variable domains of a broadly neutralizing antibody (bNAb) against HIV. In some embodiments, one or more anti-HIV antibodies or antigen-binding fragments thereof that bind, inhibit, and/or neutralize HIV, bind to an epitope or region of gp120 selected from: (i) third variable loop (V3) and/or high mannose patch comprising a N332 oligomannose glycan; (ii) CD4 binding site (CD4bs); (iii) second variable loop (V2) and/or Env trimer apex; (iv) gp120/gp41 interface; or (v) silent face of gp120. In some embodiments, the antibody or antigen-binding fragment thereof that binds, inhibits, and/or neutralizes HIV, binds to an epitope or region of gp120 in the third variable loop (V3) and/or high mannose patch comprising a N332 oligomannose glycan and competes with or comprises VH and VL regions from an antibody selected from GS-9722, PGT-121, PGT-121.414, PGT-122, PGT-123, PGT-124, PGT-125, PGT-126, PGT-128, PGT-130, PGT-133, PGT-134, PGT-135, PGT-136, PGT-137, PGT-138, PGT-139, 10-1074, 10-1074-J, GS-2872, VRC24, 2G12, BG18, 354BG8, 354BG18, 354BG42, 354BG33, 354BG129, 354BG188, 354BG411, 354BG426, DH270.1, DH270.6, PGDM12, VRC41.01, PGDM21, PCDN-33A, BF520.1 and VRC29.03. In some embodiments, the antibody or antigen-binding fragment thereof binds to an epitope or region of gp120 in the CD4 binding site (CD4bs) and competes with or comprises VH and VL regions from an antibody selected from b12, F105, VRC01, VRC07, VRC07-523, VRC03, VRC06, VRC06b01 VRC08, VRC0801, NIH45-46, GS-9723, GS-5423, 3BNC117, 3BNC60, VRC-PG04, PGV04; CH103, 44-VRC13.01, 1NC9, 12A12, N6, N49-P7, NC-Cowl, IOMA, CH235 and CH235.12, N49P6, N49P7, N49P11, N49P9 and N60P25. In some embodiments, the antibody or antigen-binding fragment thereof that binds, inhibits, and/or neutralizes HIV, binds to an epitope or region of gp120 in the second variable loop (V2) and/or Env trimer apex and competes with or comprises VH and VL regions from an antibody selected from PG9, PG16, PGC14, PGG14, PGT-142, PGT-143, PGT-144, PGT-145, CH01, CH59, PGDM1400, CAP256, CAP256-VRC26.08, CAP256-VRC26.09, CAP256-VRC26.25, PCT64-24E and VRC38.01. In some embodiments, the antibody or antigen-binding fragment binds to an epitope or region of gp120 in the gp120/gp41 interface and competes with or comprises VH and VL regions from an antibody selected from PGT-151, CAP248-2B, 35022, 8ANC195, ACS202, VRC34 and VRC34.01. In some embodiments, the antibody or antigen-binding fragment thereof that binds, inhibits, and/or neutralizes HIV, binds to an epitope or region of the gp120 silent face and competes with or comprises VH and VL regions from antibody selected from VRC-PG05 and SF12. In some embodiments, the antibody or antigen-binding fragment thereof that binds, inhibits, and/or neutralizes HIV, binds to an epitope or region of gp41 in the membrane proximal region (MPER). In some embodiments, the antibody or antigen-binding fragment thereof that binds, inhibits, and/or neutralizes HIV, binds to an epitope or region of gp41 in the membrane proximal region (MPER) and competes with or comprises VH and VL regions from an antibody selected from 10E8, 10E8v4, 10E8-5R-100cF, 4E10, DH511.11P, 2F5, 7b2, and LN01. In some embodiments, the antibody or antigen-binding fragment thereof that binds, inhibits, and/or neutralizes HIV, binds to an epitope or region of the gp41 fusion peptide and competes with or comprises VH and VL regions from an antibody selected from VRC34 and ACS202. In some embodiments of the methods, after one or more administrations of the one or more fusion polypeptides, compound fusion polypeptides, polynucleotides, vectors, lipoplexes (e.g., LNPS) or immunogenic compositions, optionally in combination with one or more additional therapeutic agents, the subject does not exhibit symptoms of HIV or AIDS in the absence of anti-retroviral treatment (ART) for at least 3 months, at least 6 months, at least 1 year, at least 2 years, at least 3 years, or more. In some embodiments of the methods, after one or more administrations of the one or more fusion polypeptides, compound fusion polypeptides, polynucleotides, vectors, lipoplexes (e.g., LNPS) or immunogenic compositions, optionally in combination with one or more additional therapeutic agents, the subject has a viral load copies/ml blood of less than 500, e.g. less than 400, less than 300, less than 200, less than 100, less than 50, in the absence of anti-retroviral treatment (ART) for at least 3 months, at least 6 months, at least 1 year, at least 2 years, at least 3 years, or more.

Further provided are methods of designing a fusion polypeptide that is capable of eliciting an immune response against one or more viral target antigens, the method comprising: (a) identifying in silico one or more regions of sequence conservation in a population of polypeptide sequences encoded by a viral gene, the population from an interpatient virus population; (b) identifying in silico the two most prevalent polypeptide sequences from the one or more conserved regions identified in step a), and generating multivalent polypeptide segments from the conserved regions; and (c) arranging the polypeptide segments to reduce or avoid the creation of deleterious epitopes at junctions between polypeptide segments. In some embodiments, step (c) comprises reducing or eliminating junctional 9-mers that bind to a specific HLA allele with a predicted IC50 value of less than about 1000 nM or having a percentile rank within the top 5% in a population of polypeptide segments. Further provided are methods of designing a fusion polypeptide that is capable of eliciting an immune response against one or more viral target antigens, the method comprising: (a) identifying in silico one or more regions of sequence conservation in a first population of polypeptide sequences encoded by a viral gene, the first population from an interpatient virus population; (b) optionally, identifying in silico the two most prevalent polypeptide sequences from the one or more conserved regions identified in step a); and (c) arranging the retained polypeptide segments into one or more contiguous fusion polypeptides, such that the junctions connecting the polypeptide segments avoid or reduce creating epitopes capable of binding human MHC class I or human MHC class II molecules, e.g., with a predicted binding affinity IC50 value of less than about 1000 nM or having a percentile rank within the top 5% in a population of polypeptide segments. In some embodiments, step (c) comprises reducing or eliminating viral polypeptide 9-mers that have at least 55% (5 of 9 amino acid residues), e.g., at least 65% (6 of 9 amino acid residues), e.g., at least 75% (7 of 9 amino acid residues), e.g., at least 85% (8 of 9 amino acid residues), amino acid sequence identity to a human protein. In some embodiments, the multivalent polypeptide segments are bivalent polypeptide segments. In some embodiments, the fusion polypeptide design method further comprises the step of identifying variant subsequences within one or more regions of sequence conservation in an intrapatient population of polypeptide sequences encoded by a viral gene, e.g., using deep sequencing data. In some embodiments, the fusion polypeptide design method further comprises the step of identifying conserved regions of a polypeptide encoded by a viral gene, such that at least 70% of the variant subsequences within the one or more regions of sequence conservation in the intrapatient population are within the bivalent polypeptide segments. In some embodiments, the fusion polypeptide design method further comprises the step of shortening the length of the fusion polypeptide, e.g., by at least 10%, 15%, 20%, 25%, 30%, or more, retaining polypeptide segment subsequences comprising epitopes (i) predicted in silico, and (ii) confirmed in vitro. Further provided are methods for producing a multivalent antigen, the method comprising constructing, in silico, a set of multivalent amino acid sequences within structurally conserved regions of a population of viral proteome sequences by a method comprising: (a) aligning the population of viral proteome sequences; (b) creating, for each sequence in the alignment, a set of 9-amino acid subsequences ("9-mers") starting with the N-terminal amino acid, each subsequence overlapping the preceding subsequence by eight amino acids such that each sequence of length 1 in the alignment contains (1-8) 9-mers; (c) calculating a frequency for each unique 9-mer starting at a position i in each sequence of the alignment and identifying the two or more most common unique 9-mers at each position; (c)(1) wherein frequency is calculated as the number of times the unique 9-mer occurs at position i in the alignment divided by the total number of sequences in the alignment; (d) calculating a multivalent conservation for each position by summing the proportion of sequences in the alignment containing either of the two or more most common unique 9-mers; (e) creating an alignment of conserved regions by extracting the sequences in the alignment having a multivalent conservation of greater than 80% or greater than 90%; (f) determining a frequency for each pair of unique 9-mers at each position in the alignment of conserved regions; (g) connecting 9-mer pairs in adjacent positions of the alignment of conserved regions that share an overlap of eight amino acids; (h) creating a directed acyclic graph in which each 9-mer pair is a node and the edges between adjacent nodes are formed from the connected 9-mer pairs in the adjacent positions with the weight of each edge equal to the frequency of the downstream 9-mer pair, (h)(1) adding a source node and connecting it with all of the nodes in the first position, (h)(2) adding a sink node and connecting it with all of the nodes in the last position, and (h)(3) negating all of the weights; (i) finding an optimal path in the directed acyclic graph from the source node to the sink node where the optimal path is defined in terms of the sum of the frequencies of all 9-mer pairs in the directed acyclic graph; (j) building a multivalent antigen by connecting two or more 9-mers in adjacent positions within the optimal multivalent 9-mer path if they share an overlap of eight amino acids, thereby creating two or more sequences of connected 9-mers which together form the multivalent antigen; and (k) optionally, rearranging the polypeptide segments to reduce or avoid the creation of deleterious epitopes at junctions between polypeptide segments. In some embodiments, the multivalent conservation is bivalent conservation and wherein the multivalent antigen is a bivalent antigen. In some embodiments, in step (a) the conserved regions are further defined by performing one or more of the following steps: (i) removing segments of fewer than 35 amino acids in length, e.g., from 9 amino acids to 10, 15, 20, 25, 30 or 35 amino acids in length; (ii) removing segments determined to have less than 90% multivalent (e.g., bivalent) conservation; (iii) removing segments determined to be weakly immunogenic or non-immunogenic, e.g., as demonstrated in in vitro or in vivo; and/or (iv) including additional segments determined to be immunogenic, e.g., as demonstrated in in vitro or in vivo. In some embodiments, the step of rearranging the peptide segments to reduce or avoid creation of deleterious epitopes is performed by a method comprising one or more of in silico HLA binding analysis and human proteome cross-recognition analysis. In some embodiments, the fusion polypeptide design method further comprises the step of inserting a linker sequence between one or more adjacent segments. In some embodiments, the fusion polypeptide design method further comprises improving the multivalent (e.g., bivalent) antigen produced in step (h) by removing junctional 9-mers that bind to a specific HLA allele with a predicted IC50 value of less than about 1000 nM or having a percentile rank within the top 5% in a population of polypeptide segments. In some embodiments, the method further comprises improving the multivalent (e.g., bivalent) antigen produced in step (h) by removing 9-mers that have at least 55% (5 of 9 amino acid residues), e.g., at least 65% (6 of 9 amino acid residues), e.g., at least 75% (7 of 9 amino acid residues), e.g., at least 85% (8 of 9 amino acid residues), amino acid sequence identity with human peptides or that have the same T cell receptor (TCR) facing residues with human proteins. In some embodiments, the fusion polypeptide design method further comprises the step of rearranging the polypeptide segments to reduce or avoid the creation of deleterious epitopes at junctions between polypeptide segments. In some embodiments, the step of rearranging the peptide segments to reduce or avoid creation of deleterious epitopes is performed by a method comprising one or more of in silico HLA binding analysis and human proteome cross-recognition analysis. In some embodiments, the fusion polypeptide design method further comprises the step of identifying variant subsequences within one or more regions of sequence conservation in an intrapatient population of polypeptide sequences encoded by a viral gene, e.g., using deep sequencing data. In some embodiments, the fusion polypeptide design method further comprises the step of identifying conserved regions of a polypeptide encoded by a viral gene, such that at least 70% of the variant subsequences within the one or more regions of sequence conservation in the intrapatient population are within the bivalent polypeptide segments. In some embodiments, the fusion polypeptide design method further comprises the step of shortening the length of the fusion polypeptide, e.g., by at least 10%, 15%, 20%, 25%, 30%, or more, retaining polypeptide segment subsequences comprising epitopes (i) predicted in silico, and (ii) confirmed in vitro. With respect to the fusion polypeptide design methods, in some embodiments, the one or more viral target antigens are from a mammalian virus, e.g., a human virus. In some embodiments, the one or more viral target antigens are from a virus selected from human immunodeficiency virus (HIV), hepatitis B virus (HBV), human papillomavirus (HPV), herpes simplex virus (HSV), Ebola virus, Zika virus and Chikungunya virus. In some embodiments, the interpatient virus population is from a population of patients who have not received antiretroviral therapy (ART). In some embodiments, the interpatient virus population is from a population of patients who have received antiretroviral therapy (ART). Further provided are fusion polypeptides made according to the fusion polypeptide design methods, described herein, wherein the fusion polypeptide elicits an immune response against a virus in a mammal, e.g., a human.

BRIEF DESCRIPTION OF THE DRAWINGS

FIG. 2 illustrates a representative methodology of a population-based vaccine construct approach.

FIG. 4A illustrates how "bivalent conservation" can be determined based on the prevalence of the two most common 9-mers among all considered viral sequences in a population. FIG. 4A discloses the sequences corresponding to Patients 1-10 as SEQ ID NOS 168-169, 169-170, 169, 169, 171-172 and 172-173, respectively, in order of appearance. FIG. 4A also discloses "QNLQGQMVH" as SEQ ID NO: 174, "QNIQGQMVH" as SEQ ID NO: 175 and "PNIQGQMVH" as SEQ ID NO: 176. FIG. 4B illustrates how the conserved regions are identified based on the "bivalent conservation" distribution across 9-mer positions. HIV-1 Gag p24 was used as the representative protein.

FIG. 5A illustrates unique 9-mers extracted from aligned natural sequences. FIG. 5A discloses SEQ ID NOs 177-183, respectively, in order of columns. FIG. 5B illustrates a directed acyclic graph built based on 9-mer pair nodes and their connection. FIG. 5B discloses "GIIIIIIII" as SEQ ID NO: 180, "AIIIIIIII" as SEQ ID NO: 181, "IIIIIIIIK" as SEQ ID NO: 182, "IIIIIIIIH" as SEQ ID NO: 183 and "IIIIIIIIR" as SEQ ID NO: 184. FIG. 5C illustrates how 9-mers in connected 9-mer pairs are connected. When there are two options available for the connection, the ultimate connection is determined by the prevalence of each connection in naturally occurring sequences. FIG. 5C discloses "GIIIIIIII" as SEQ ID NO: 180, "AIIIIIIII" as SEQ ID NO: 181, "IIIIIIIIK" as SEQ ID NO: 182 and "IIIIIIIIH" as SEQ ID NO: 183.

FIG. 6 illustrates the results of human proteome cross-recognition analysis. FIG. 6 discloses SEQ ID NOs 185-188, respectively, in order of columns.

FIG. 9 provides a flow diagram illustrating the basic methodology of the approach for designing the fusion proteins of immunogen version 2 (e.g., SEQ ID NOs: 82-89). A set of 9-mers is selected from conserved regions and combined to form the fusion polypeptides of immunogen version 2, a subset of immunogen version 1. The sequences and gene regions included in immunogen version 2 are provided in Table E.

FIG. 13 provides a flow diagram illustrating the basic methodology of the approach for designing the fusion proteins of immunogen version 3 (e.g., SEQ ID NOs: 90-93). A set of 9-mers is selected from conserved regions and combined to form the fusion polypeptides of immunogen version 3, a subset of immunogen version 1. The sequences and gene regions included in immunogen version 3 are provided in Table E.

FIG. 16 illustrates polypeptide segments encoded by the HIV-1 Gag gene used in the fusion polypeptide constructs described herein. The Gag HIV-1 HXB2 reference polypeptide (SEQ ID NO: 1) sequence is underlined. Amino acid residues corresponding to Gag HIV-1 HXB2 reference polypeptide residues 54-146 and 370-500, and subsequences and fragments thereof, are not included in the herein described polypeptide segments. FIG. 16 discloses SEQ ID NOs 1 and 4-7, respectively, in order of appearance.

FIGS. 17A-17C illustrate polypeptide segments encoded by the HIV-1 Pol gene used in the fusion polypeptide constructs described herein. The Pol HIV-1 HXB2 reference polypeptide (SEQ ID NO: 2) sequence is underlined. Amino acid residues corresponding to Pol HIV-1 HXB2 reference polypeptide residues 1-55, 118-128, 321-366, 432-541, 607-682, 709-746, 828-839 and 921-931, and subsequences and fragments thereof, are not included in the herein described polypeptide segments. FIG. 17A-17C discloses SEQ ID NOs 2, 8-21, 24-25, 189, 23 and 26-27, respectively, in order of appearance.

FIG. 18 illustrates polypeptide segments encoded by the HIV-1 Nef gene used in the fusion polypeptide constructs described herein. The Nef HIV-1 HXB2 reference polypeptide, having a tryptophan (W) at position 124 (SEQ ID NO: 3) sequence is underlined. Amino acid residues corresponding to Nef HIV-1 HXB2 reference polypeptide residues 1-63, 100-116 and 149-206, and subsequences and fragments thereof, are not included in the herein described polypeptide segments. FIG. 18 discloses SEQ ID NOs 3, 30-31, 28-29 and 32-33, respectively, in order of appearance.

FIG. 19 discloses "AAA" as SEQ ID NO: 48 and "AAY" as SEQ ID NO: 49.

FIG. 20B illustrates representative moDC transduction efficiency using GFP expressing Ad5 viral vectors at MOI of 500 in N=36 human donors at day 3 post-transduction. Proportion of cells expressing GFP by flow cytometry is shown on the y-axis. The x-axis represents vaccine immunogen constructs of conserved regions of SEQ ID NOs: 105, 107, 109 and 111 (■) or empty vector control (▲) at multiplicity of infection (MOI) of 500, or untransduced (●). Transduction efficiency was determined by evaluation of percent GFP expression of transduced moDCs by flow cytometry (N=36). The amino acid sequences are provided in Table F.

FIG. 21 discloses "AAA" as SEQ ID NO:

48, "QEE" as SEQ ID NO: 51, "KILQEE" as SEQ ID NO: 198 and "AAQEE" as SEQ ID NO: 199.

Figure 22B:
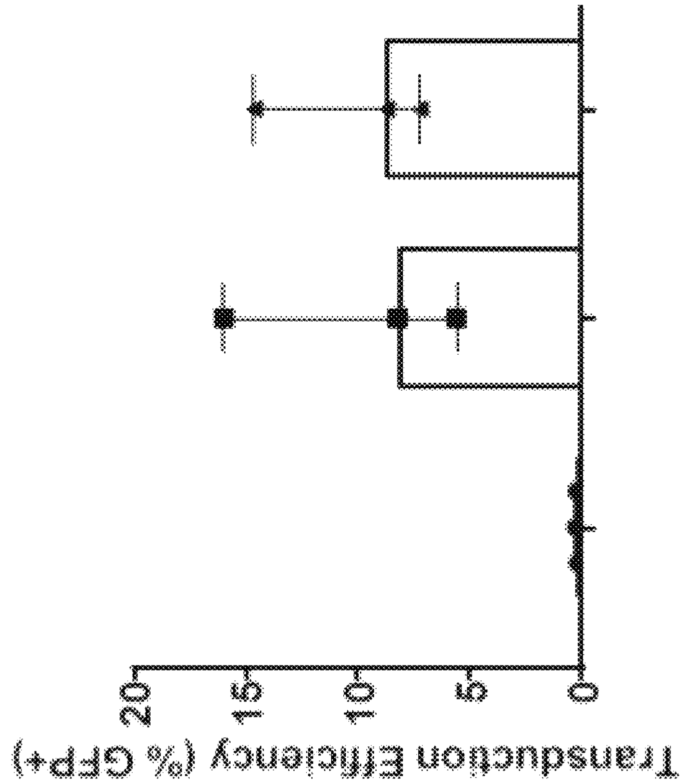
Figure 22A:
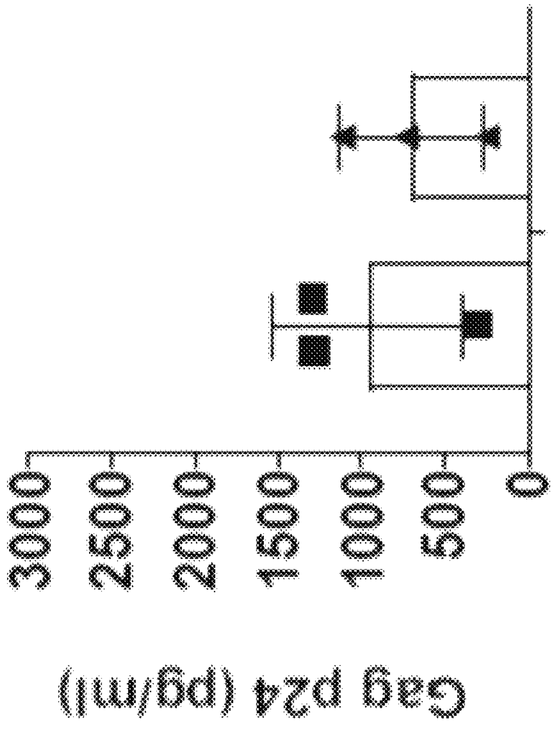

FIGS. 22A-22B. Ad5 vectors expressing compound fusion polypeptides of SEQ ID NO: 82-89 were used to transduce moDCs to evaluate expression of the transgene and transduction efficiency. Expression efficiency was assessed by Gag p24 ELISA (N=2) (FIG. 22A). The y-axis represents Gag p24 concentration (pg/ml) detected in moDC lysates at day 3 post transduction with Ad5 vectors expressing compound fusion polypeptides of SEQ ID NOs: 82-89 (■) or empty vector control (▲) at multiplicity of infection (MOI) of 500. FIG. 22B illustrates representative moDC transduction efficiency using GFP expressing Ad5 viral vectors at MOI of 500 in N=3 human donors at day 3 post-transduction. Proportion of cells expressing GFP by flow cytometry is shown on the y-axis. The x-axis represents vaccine immunogen constructs of conserved regions of SEQ ID NOs: 82-89 (■) or empty vector control (▲) at multiplicity of infection (MOI) of 500, or untransduced (●). The amino acid sequences are provided in Table E.

Figure 23:
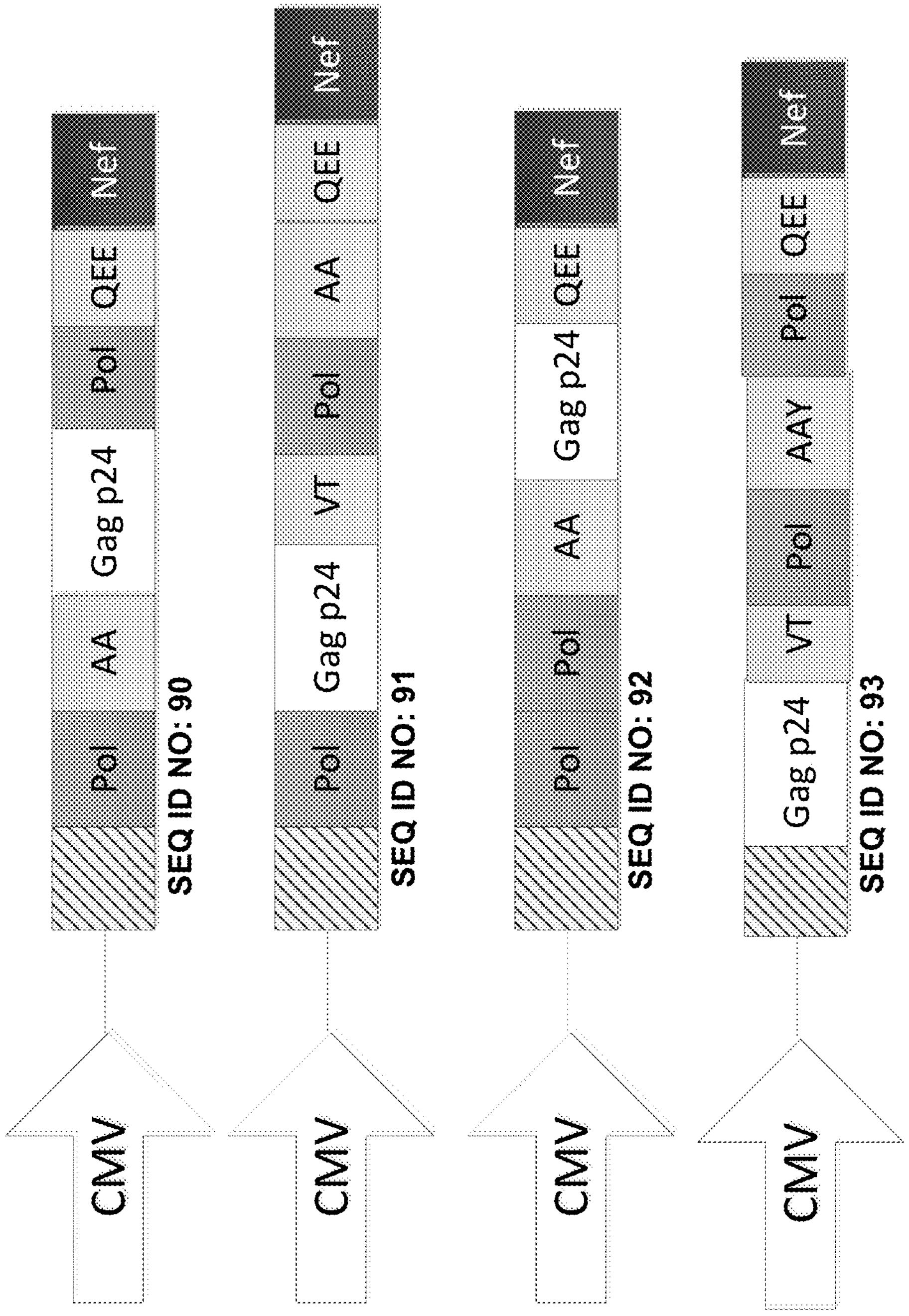

FIG. 23 illustrates a schematic representation of fusion polypeptides containing HIV-1 immunogen version 3 fusion polypeptides (SEQ ID NOs: 90-93). All four vectors were used for transduction of moDCs in CD8+ T cell priming assays and are collectively labeled as "post vaccination" in assays using these sequences. FIG. 23 discloses "QEE" as SEQ ID NO: 51, "AAQEE" as SEQ ID NO: 199 and "AAY" as SEQ ID NO: 49.

Figure 24:
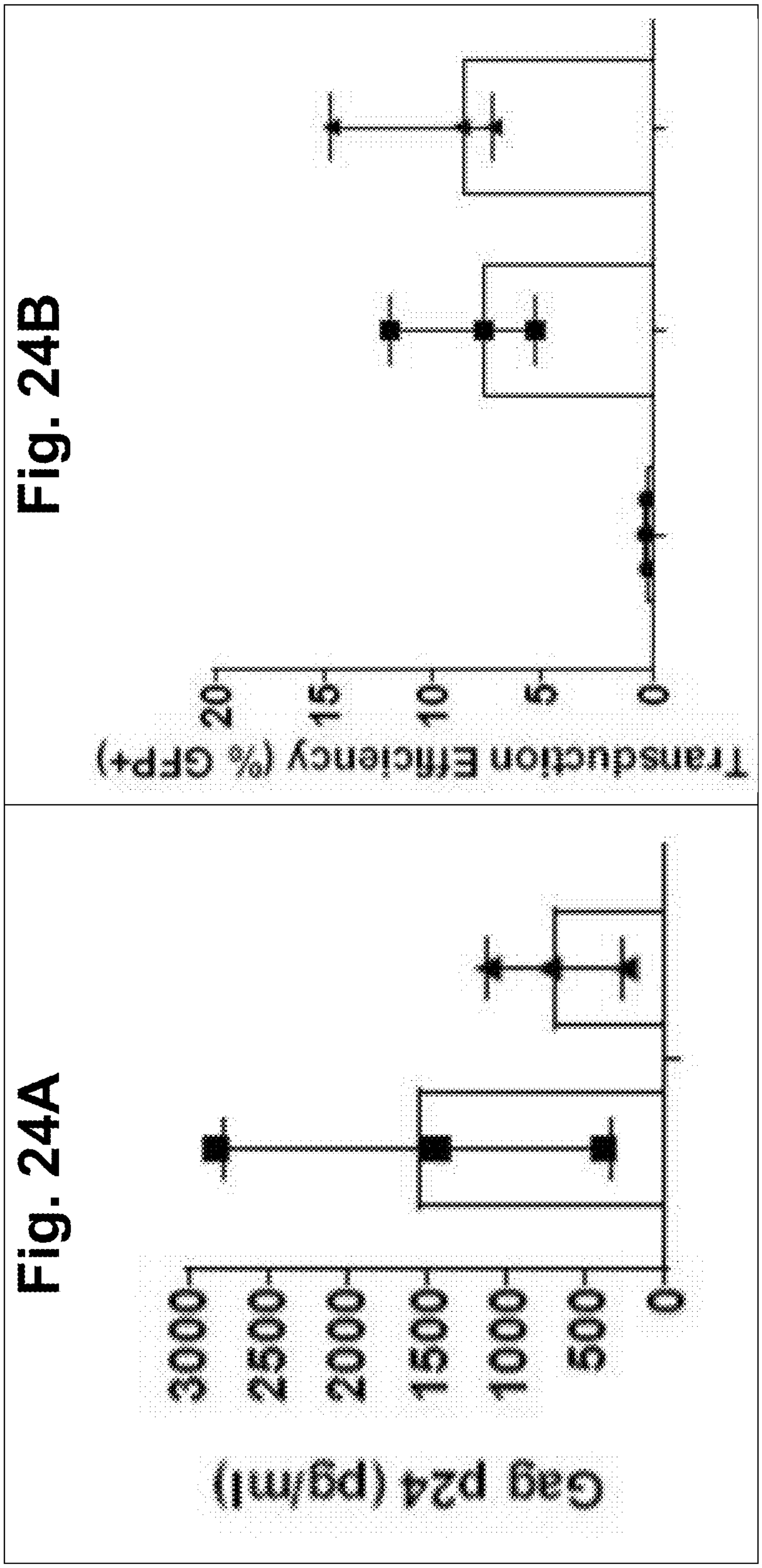

FIGS. 24A-24B. Ad5 vectors expressing compound fusion polypeptides of SEQ ID NO: 90-93 were used to transduce moDCs to evaluate expression of the transgene and transduction efficiency. Expression efficiency was assessed by Gag p24 ELISA (N=2) (FIG. 24A). The y-axis represents Gag p24 concentration (pg/ml) detected in moDC lysates at day 3 post transduction with Ad5 vectors expressing compound fusion polypeptides of SEQ ID NOs: 82-89 (■) or empty vector control (▲) at multiplicity of infection (MOI) of 500. FIG. 24B illustrates representative moDC transduction efficiency using GFP expressing Ad5 viral vectors at MOI of 500 in N=3 human donors at day 3 post-transduction. Proportion of cells expressing GFP by flow cytometry is shown on the y-axis. The x-axis represents vaccine immunogen constructs of conserved regions of SEQ ID NOs: 90-93 (■) or empty vector control (▲) at multiplicity of infection (MOI) of 500, or untransduced (●). The amino acid sequences are provided in Table E.

Figure 25:
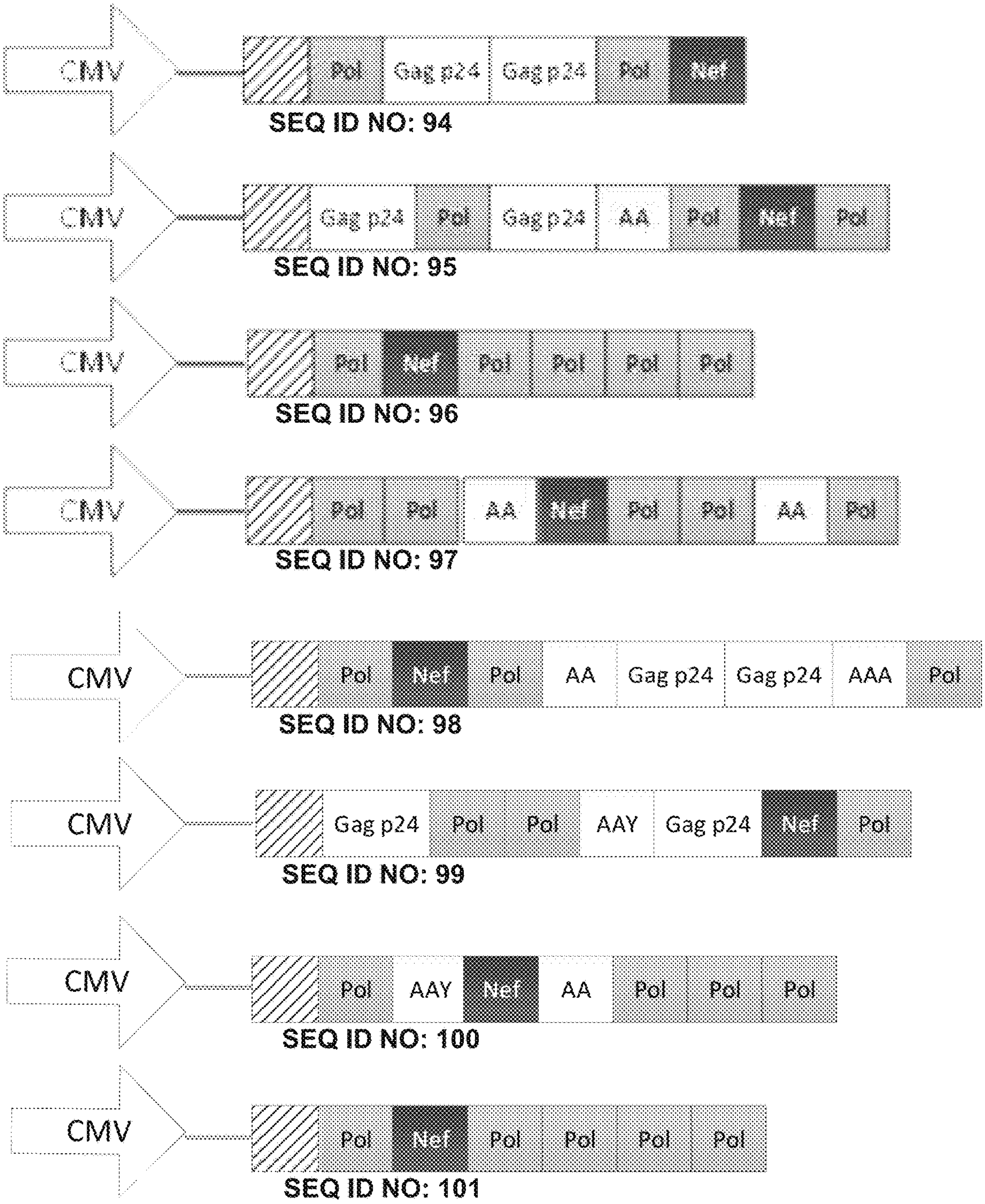

FIG. 25 illustrates a schematic representation of fusion polypeptides containing HIV-1 immunogen version 1 fusion polypeptide sequences. The fusion polypeptides of SEQ ID NOs: 94 and 95 represent bivalent sequences within HIV-1 Gag, Pol and Nef; SEQ ID NOs: 96 and 97 represent bivalent sequences within HIV-1 Pol and Nef. The fusion polypeptides of SEQ ID NOs: 94-97 can be combined to form a priming sequence. The fusion polypeptides of SEQ ID NOs: 98 and 99 represent bivalent sequences within HIV-1 Gag, Pol and Nef. The fusion polypeptides of SEQ ID NOs: 100 and 101 represent bivalent sequences within HIV-1 Pol and Nef. The fusion polypeptides of SEQ ID NOs: 98-101 can be combined to form a boosting sequence that can be used following priming with the fusion polypeptides of SEQ ID NOs: 94-97. Bivalent sequences are designed to cover >80% of inter patient diversity in viral sequences, and gene segments used to generate the polypeptide fusion constructs are rearranged in order to minimize creation of de novo epitopes that react with the human protein and to minimize boosting of junctional responses in prime boost sequences. FIG. 25 discloses "AAA" as SEQ ID NO: 48 and "AAY" as SEQ ID NO: 49.

Figure 26:
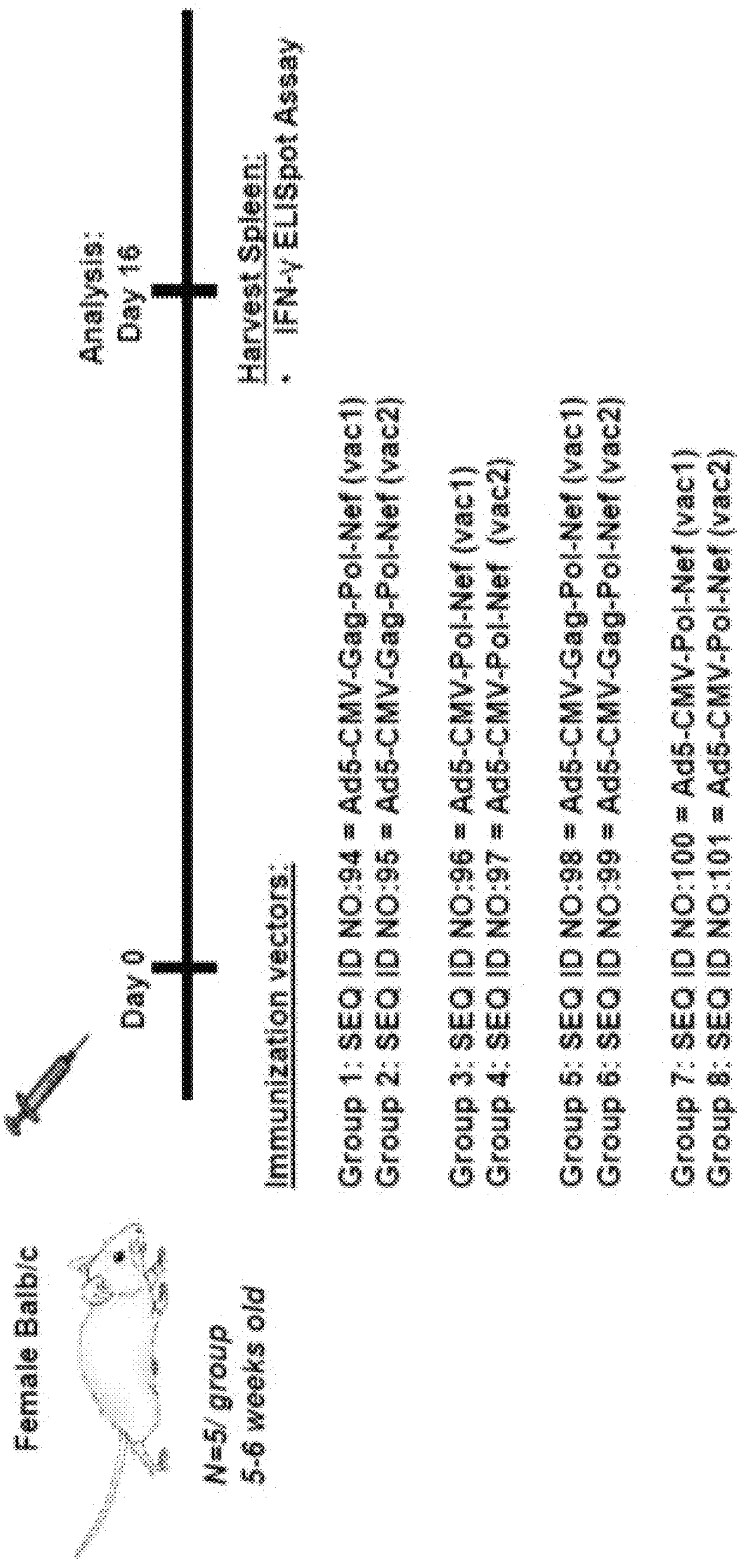

FIG. 26 illustrates immunization schedule in Balb/c mice. Mice were immunized intramuscularly (IM) in right and left quadriceps at $1\times10^9$ PFU with Ad5 vectors expressing HIV-1 fusion polypeptide sequences as indicated. Splenocytes were collected at day 16 after immunization and responses against HIV Gag, Pol and Nef antigens were measured by IFN-γ ELISpot Assay.

Figure 27A:
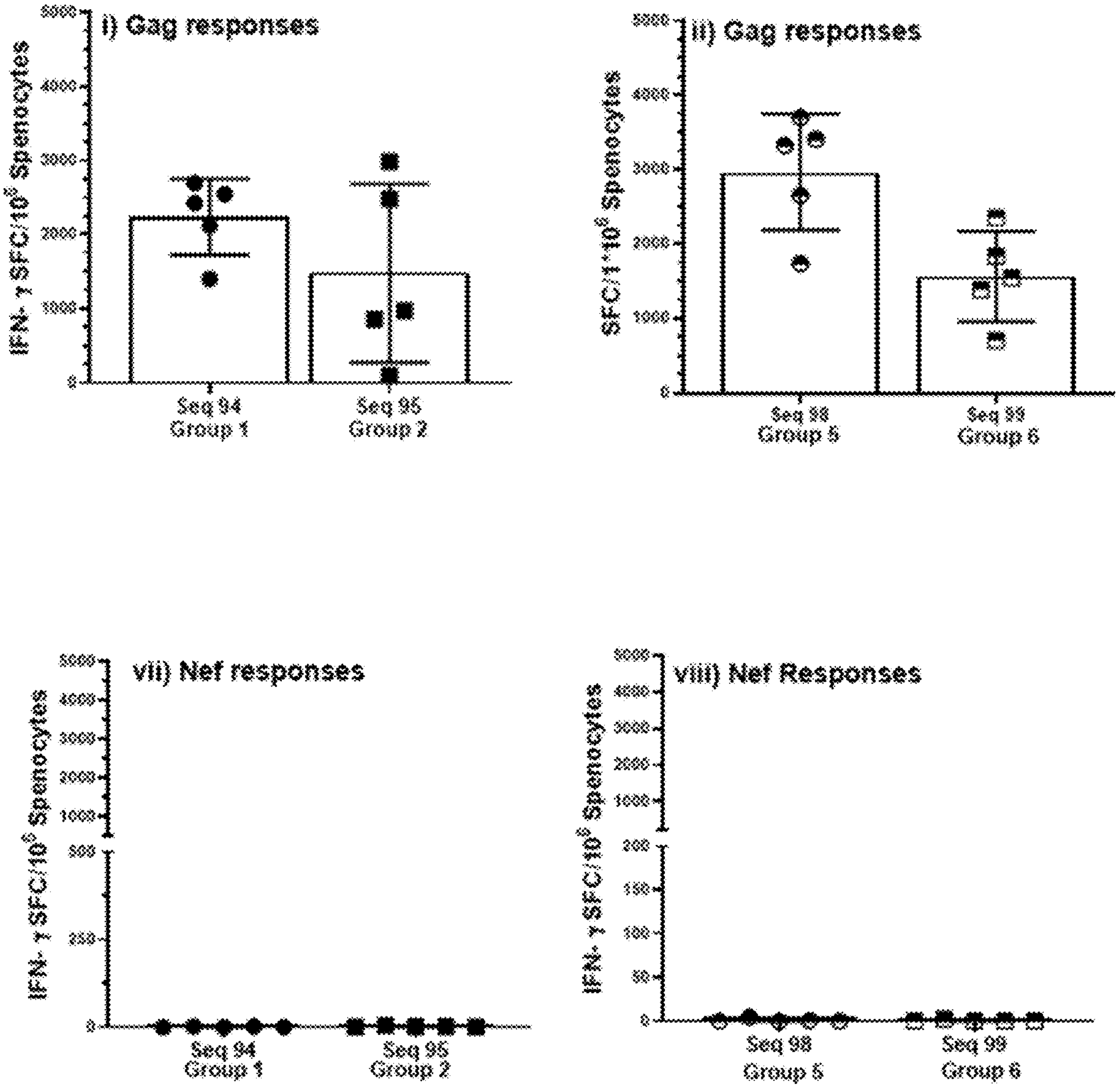
Figure 27B:
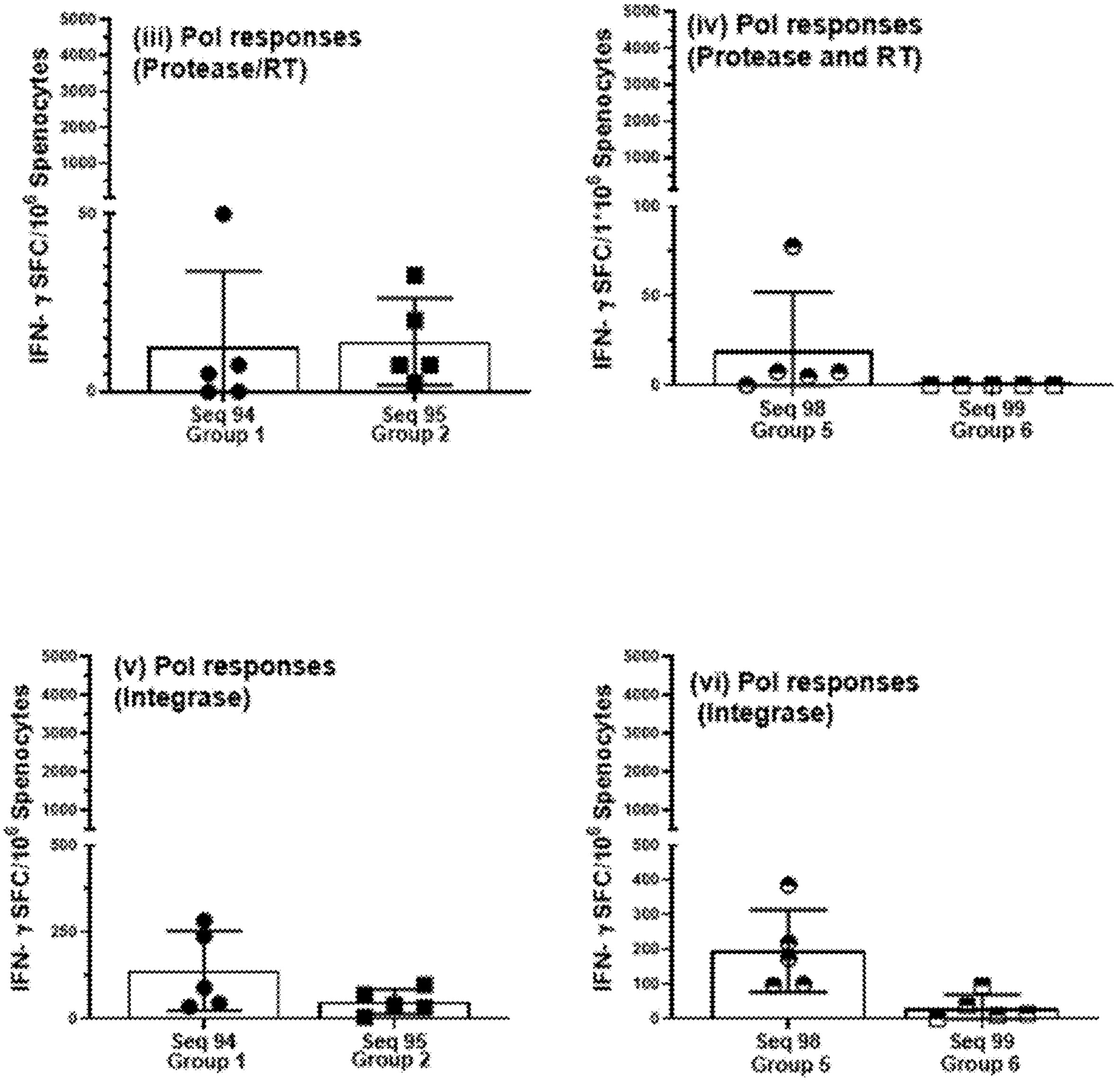

FIGS. 27A-B illustrate results of immunogenicity testing in Balb/c mice by IFN-γ ELISpot with peptide stimulation with either HIV-1 Gag (i and ii), Nef (vii and viii) (FIG. 27A), Pol (protease/RT) (iii and iv), or Pol (integrase) (v and vi) (FIG. 27B) peptides. The fusion polypeptides of SEQ ID NOs: 94-95 (Seq 94, Seq 95) were used as bivalent priming sequences. The fusion polypeptides of SEQ ID NOs: 98-99 (Seq 98, Seq 99) were used as boosting sequences. The Y-axis represents magnitude of IFN-γ responses against the specific peptide pool stimulus as number of spot forming colonies (SFC) per $10^6$ splenocytes. Peptide specific values were obtained by subtracting no peptide stimulated control to exclude nonspecific responses. The X-axis indicates the individual vaccine constructs used for in vivo priming against which peptide specific responses were studied. All vectors were immunogenic inducing robust responses to HIV-1 Gag responses, with weaker but detectable responses to Pol proteins (Protease, RT and integrase). No responses were detected to HIV-Nef in this model likely due to previously described immunodominance patterns for HIV-1 Gag epitopes in Balb/c mice and reflecting the lack of Nef epitopes that can be presented in Balb/c mice.

Figure 28:
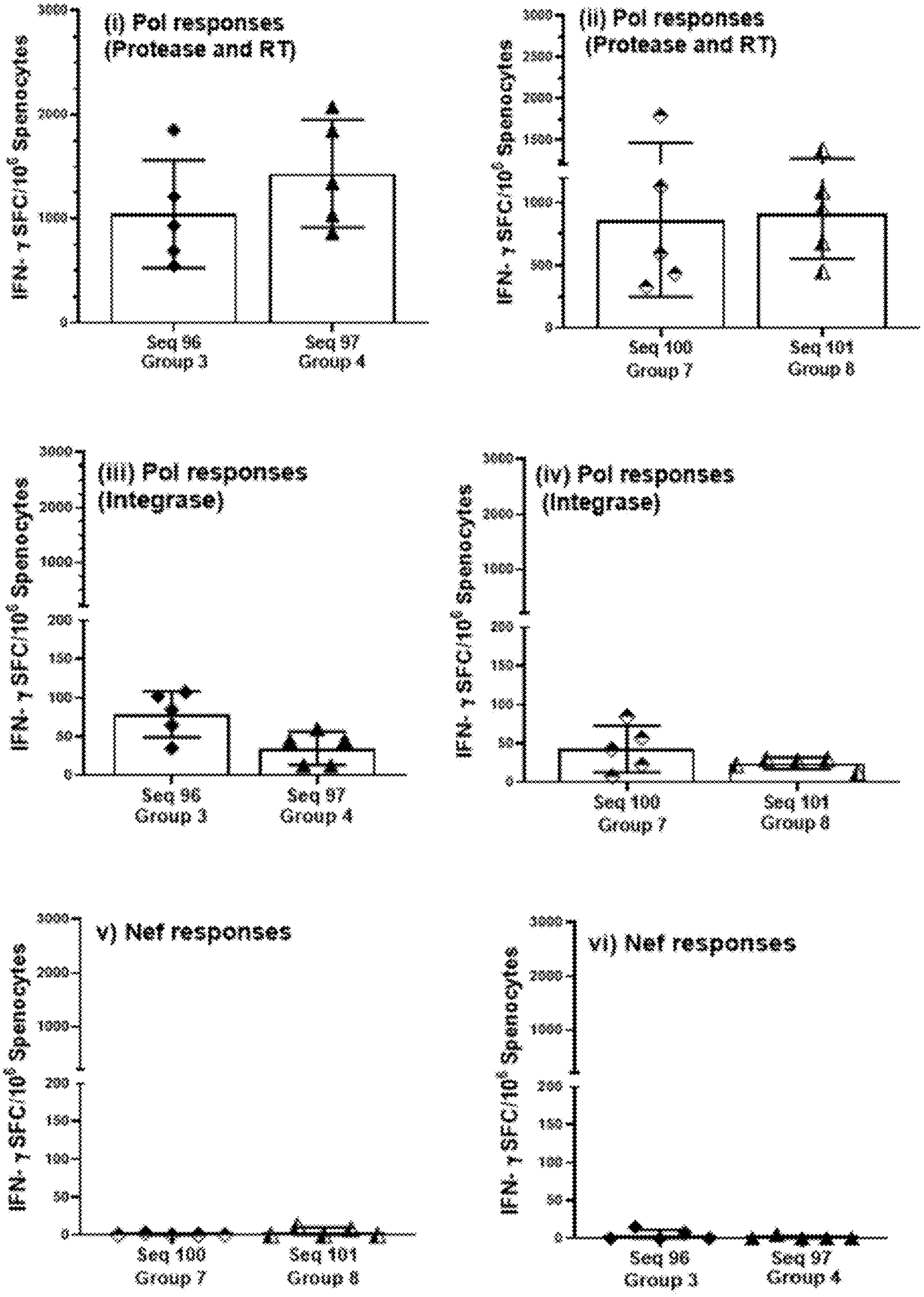

FIG. 28 illustrates results of immunogenicity testing in Balb/c mice by IFN-γ ELISpot with peptide stimulation with either HIV-1 Pol (protease/RT) (i and ii), Pol (integrase) (iii and iv) or Nef (v and vi) peptides. The fusion polypeptides of SEQ ID NOs: 96-97 (Seq 96, Seq 97) were used as bivalent priming sequences. The fusion polypeptides of SEQ ID NOs: 100-101 (Seq 100, Seq 101) were used as boosting sequences. The Y axis represents magnitude of IFN-γ responses against the specific peptide pool stimulus as number of spot forming colonies (SFC) per $10^6$ Splenocytes. Peptide specific values were obtained by subtracting no peptide stimulated control to exclude nonspecific responses. The X-axis indicates the individual vaccine constructs used for in vivo priming against which peptide specific responses were studied. All vectors were immunogenic inducing robust responses to HIV-1 Pol, particularly protease and RT peptides with weaker responses detected to integrase peptides. No responses were detected to HIV-Nef in this model likely due to previously described immunodominance patterns for HIV-1 Gag epitopes in Balb/c mice and reflecting the lack of Nef epitopes that can be presented in Balb/c mice.

Figure 29:
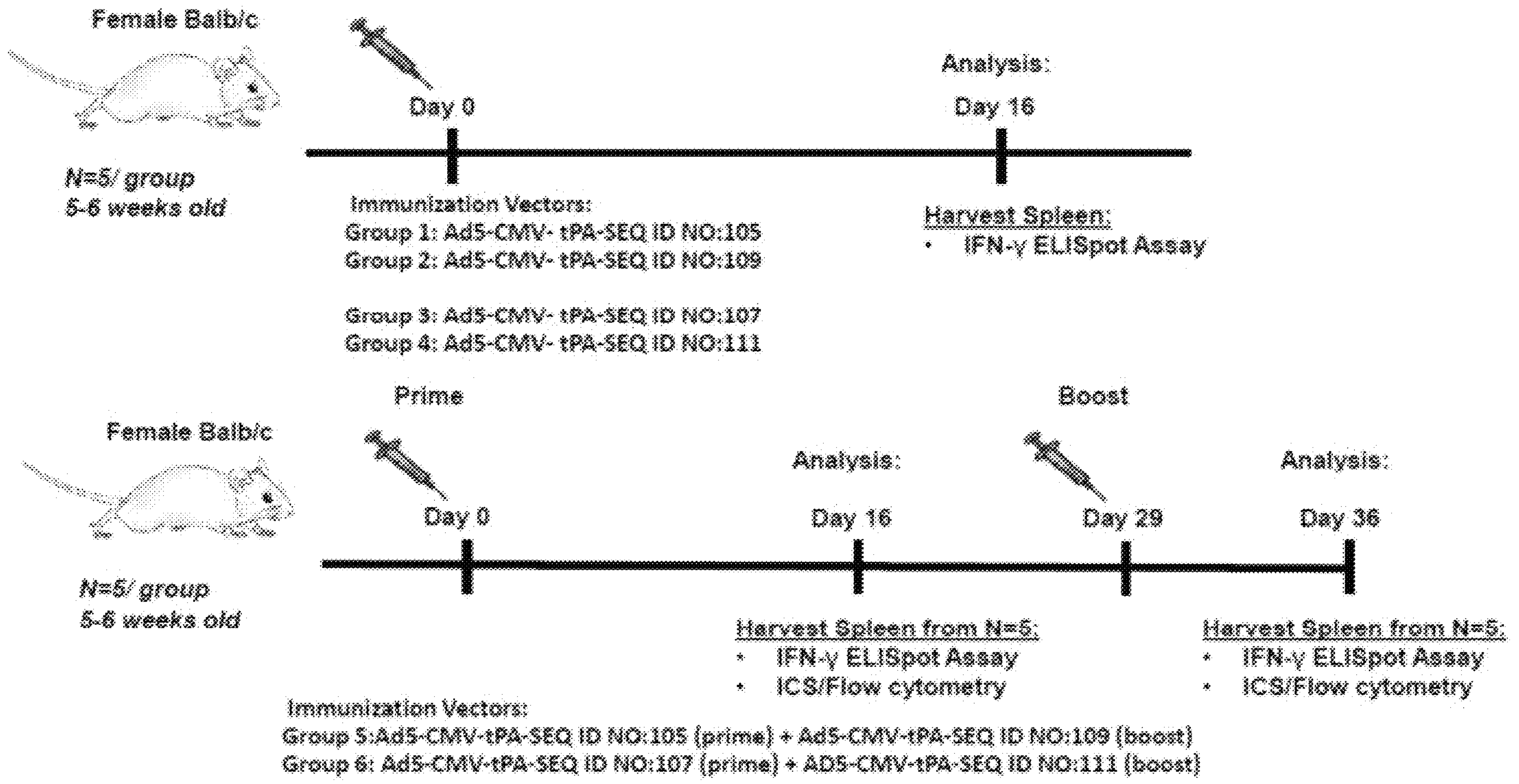

FIG. 29 illustrates a representative immunization schedule in Balb/c mice. Mice were immunized I.M. in right and left quadriceps at $1\times10^9$ PFU with Ad5 vectors expressing HIV-1 sequences as indicated. Individual vectors (i) were tested for immunogenicity as a single dose to prime the response with spleens harvested on Day 16 for analysis. Combination vectors (ii) were tested in a homologous vector prime-boost schedule, with boosting on Day 29 and spleens harvested for analysis on Day 36. Responses against Gag, Pol and Nef antigens were measured by IFN-γ ELISpot Assay and ICS/Flow cytometry.

Figure 30A:
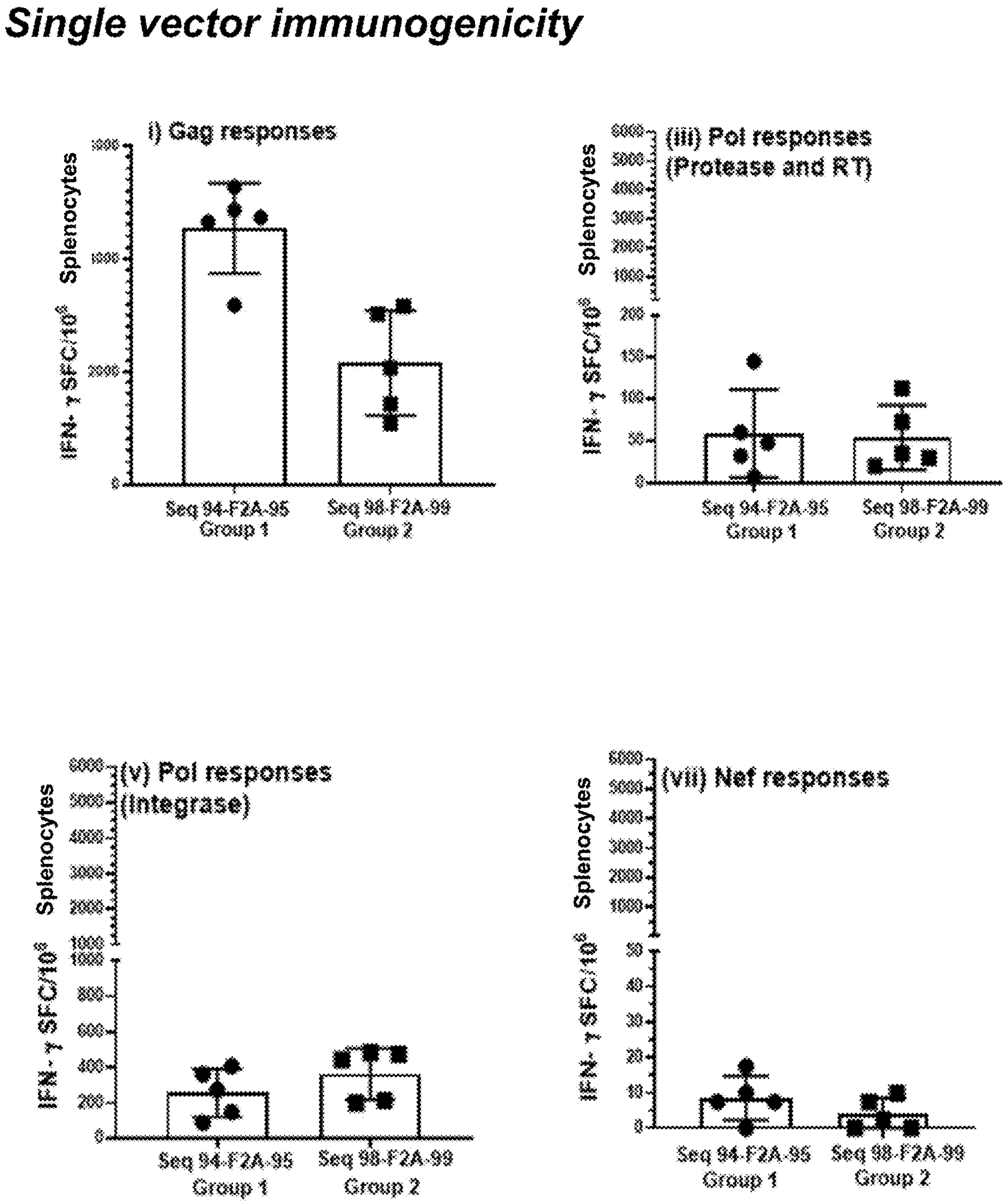
Figure 30B:
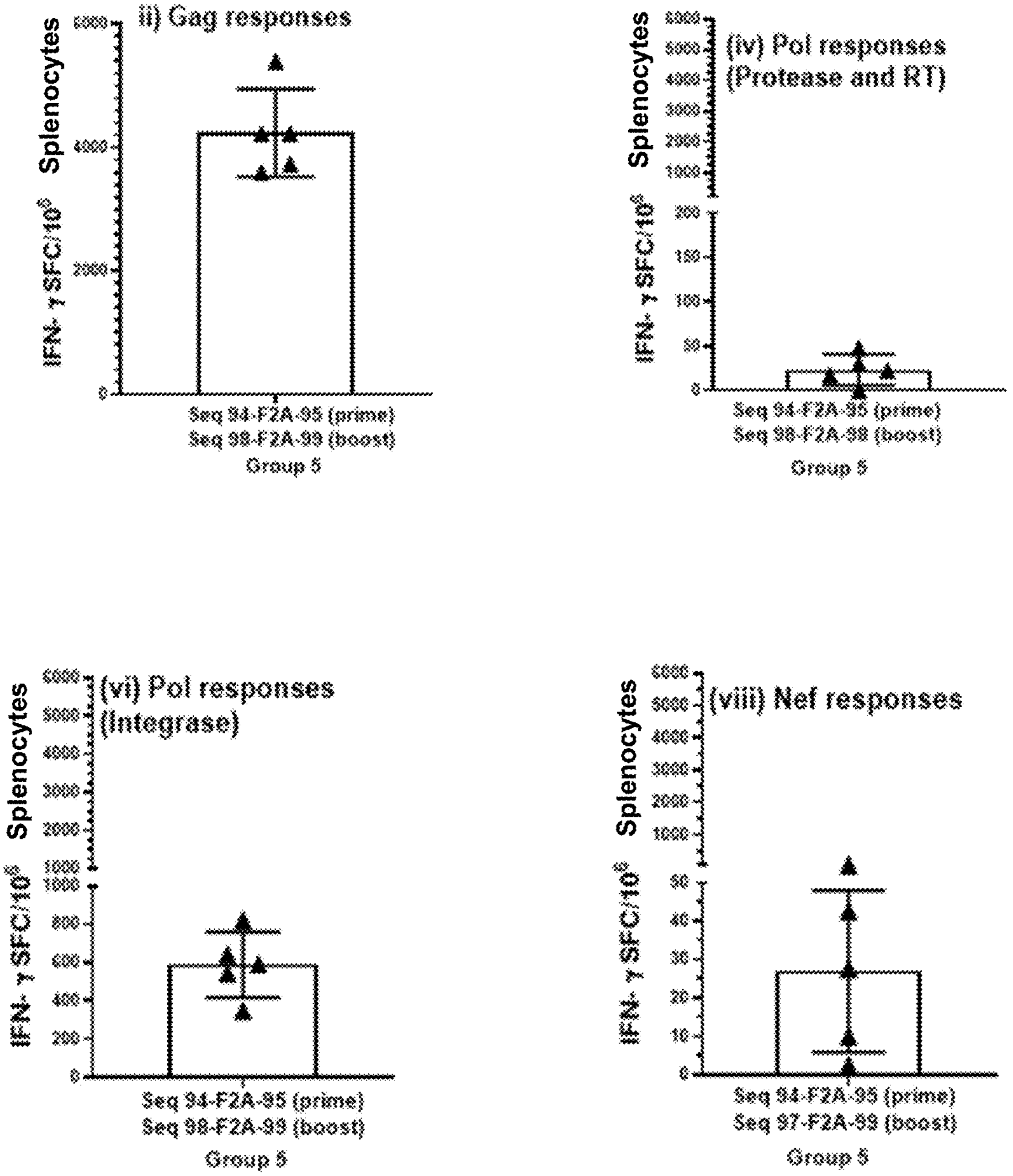

FIGS. 30A-30B illustrate immunogenicity assessed following immunization either by single Ad5 vector prime alone (A) or in a homologous Ad5 vector prime-boost combination (B). Seq 94-F2A-95 (tPA-SEQ ID NO: 105)

and Seq 98-F2A-99 (tPA-SEQ ID NO: 109) were used as a prime-boost pair. Vectors were tested for immunogenicity in Balb/c mice by IFN-γ ELISpot with peptide stimulation with either HIV-1 Gag, (i) and (ii); Pol (protease/RT, (iii) and (iv); Pol (integrase, (v) and (vi); or Nef (vii and viii) peptides. The Y axis represents magnitude of IFN-γ responses against the specific peptide pool stimulus as number of spot forming colonies (SFC) per $10^6$ Splenocytes. Peptide specific values were obtained by subtracting no peptide stimulated control to exclude nonspecific responses. The X-axis indicates the individual vaccine constructs used for in vivo priming against which peptide specific responses were studied. All vectors were immunogenic inducing robust responses to HIV-1 Gag responses, with weaker but detectable responses to Pol proteins (protease, RT and integrase). No responses were detected to HIV-Nef in this model likely due to previously described immunodominance patterns for HIV-1 Gag epitopes in Balb/c mice and reflecting the lack of Nef epitopes that can be presented in Balb/c mice. Responses were enhanced by homologous boosting with Ad5 vectors expressing the boost sequence.

Figure 31A:
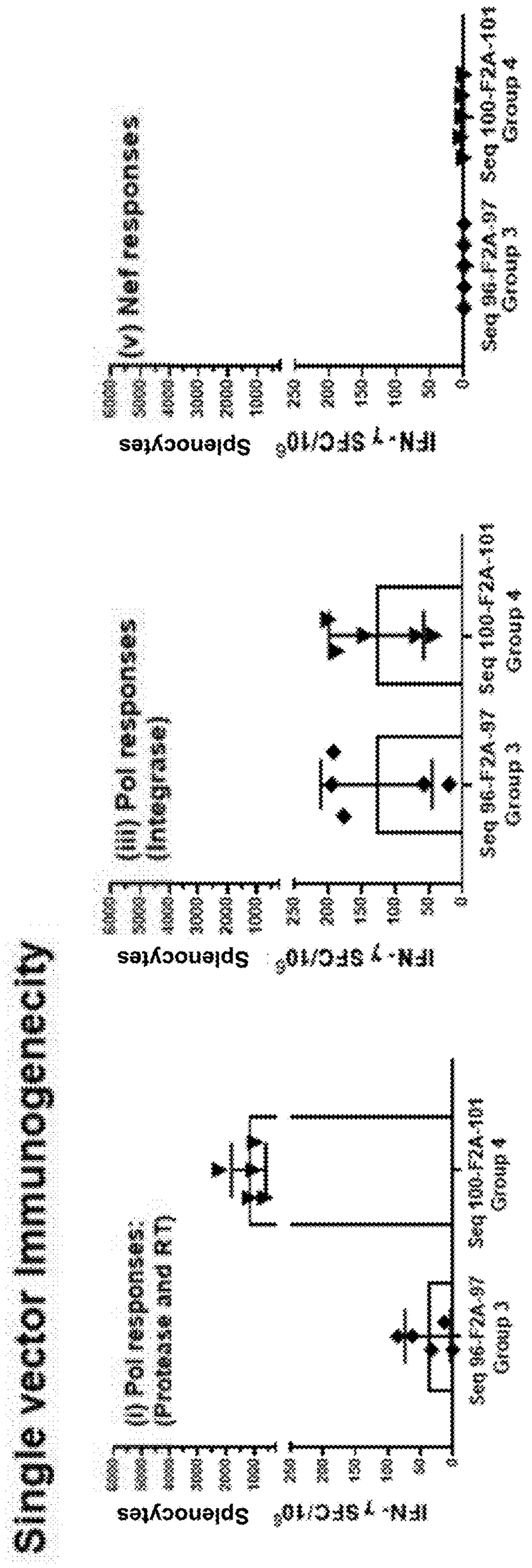
Figure 31B:
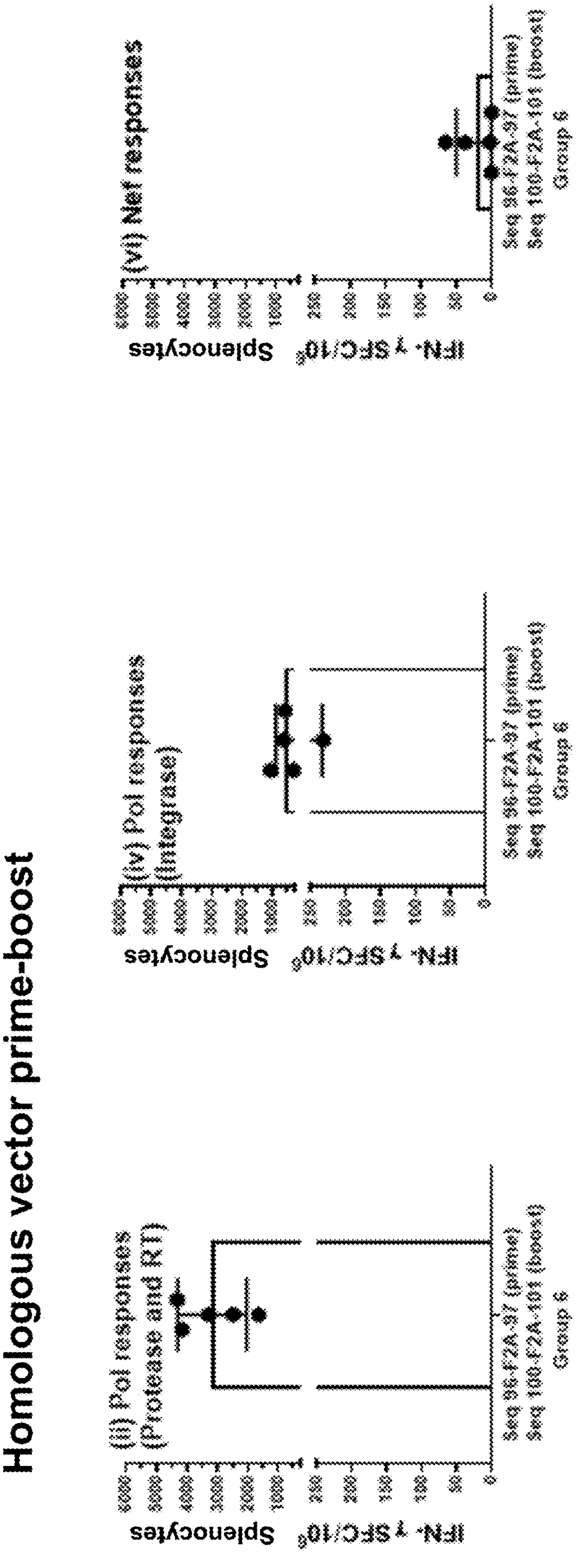

FIGS. 31A-31B illustrate immunogenicity is assessed following immunization either by single Ad5 vector prime alone or in a homologous Ad5 vector prime-boost combination. Seq 96-F2A-97 (tPA-SEQ ID NO: 107) and Seq 100-F2A-101 (tPA-SEQ ID NO: 111) were used as a prime boost pair. Vectors were tested for immunogenicity in Balb/c mice by IFN-γ ELISpot with peptide stimulation with either HIV-1 Pol (protease/RT, (i) and (ii); Pol (integrase, (iii) and (iv); or Nef (v and vi) peptides. The Y-axis represents magnitude of IFN-γ responses against the specific peptide pool stimulus as number of spot forming colonies (SFC) per $10^6$ Splenocytes. Peptide specific values were obtained by subtracting no peptide stimulated control to exclude nonspecific responses. The X-axis indicates the individual vaccine constructs used for in vivo priming against which peptide specific responses were studied. All vectors were immunogenic inducing robust responses to HIV-1 Pol, particularly Protease and RT peptides, with weaker responses detected to integrase peptides. The responses observed to the Protease and RT were weaker than previously observed by Seq 96 and Seq 97 when not combined. The immunogenicity responses were boosted in sequential dosing with Seq 96-F2A-97 and Seq 100-F2A-101, however. No responses were detected to HIV-Nef in this model likely due to previously described immunodominance patterns for HIV-1 Gag epitopes in Balb/c mice and reflecting the lack of Nef epitopes that can be presented in Balb/c mice.

Figure 32A:
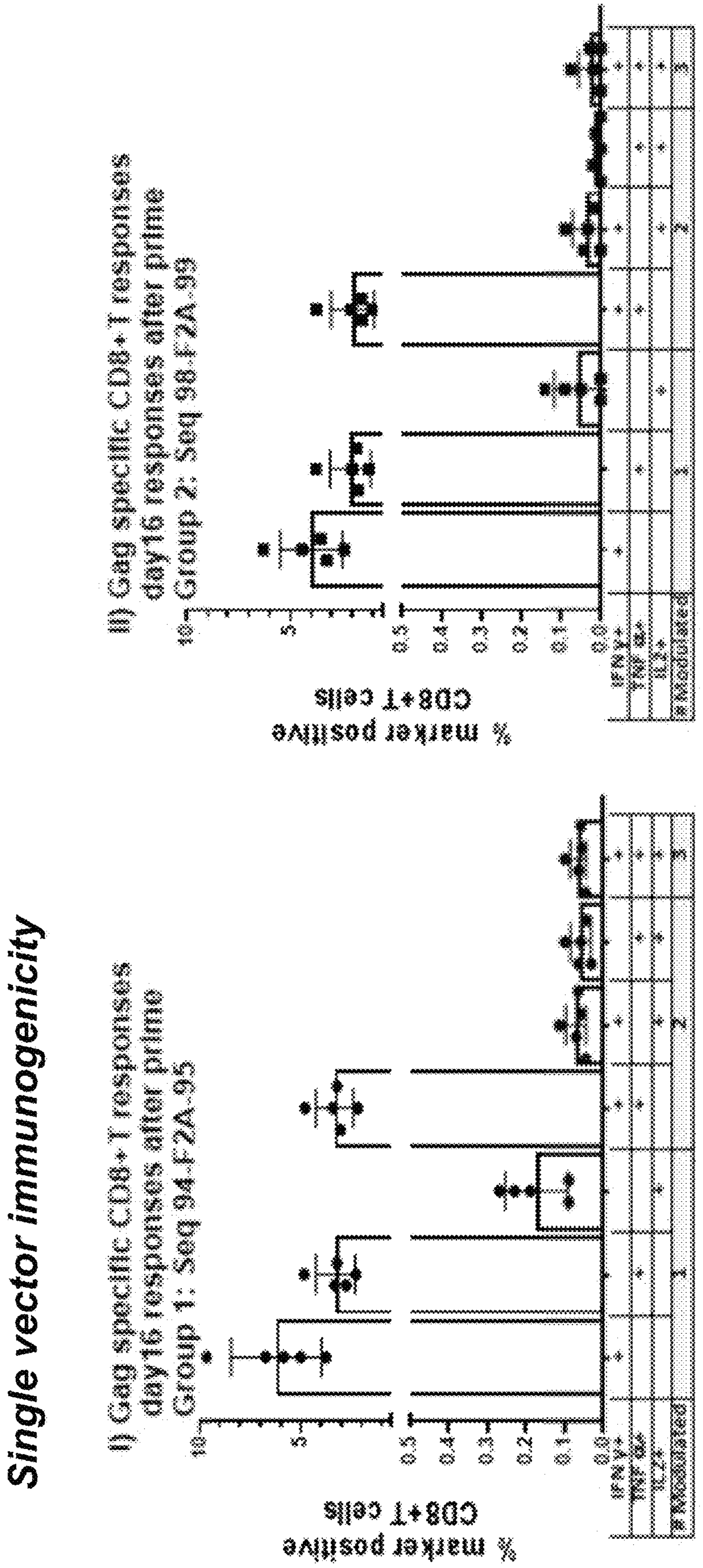
Figure 32B:
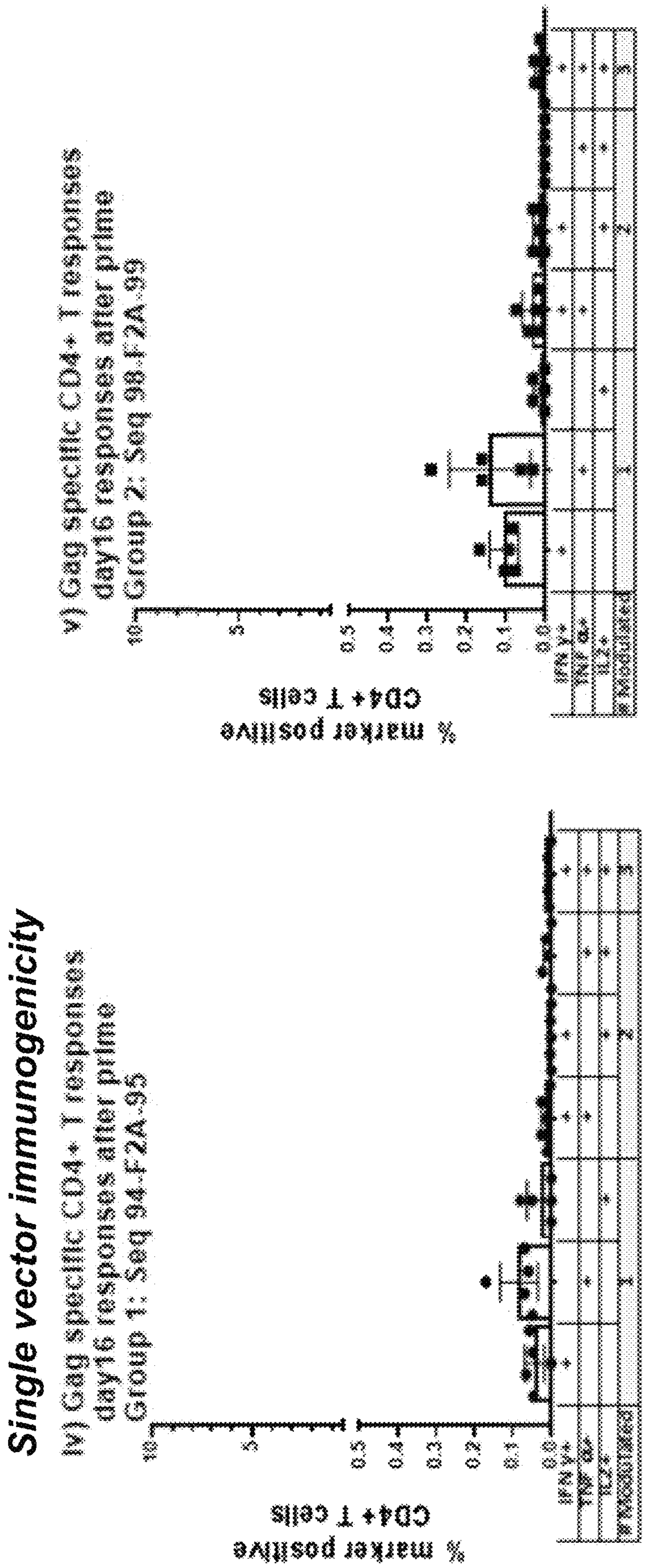
Figure 32C:
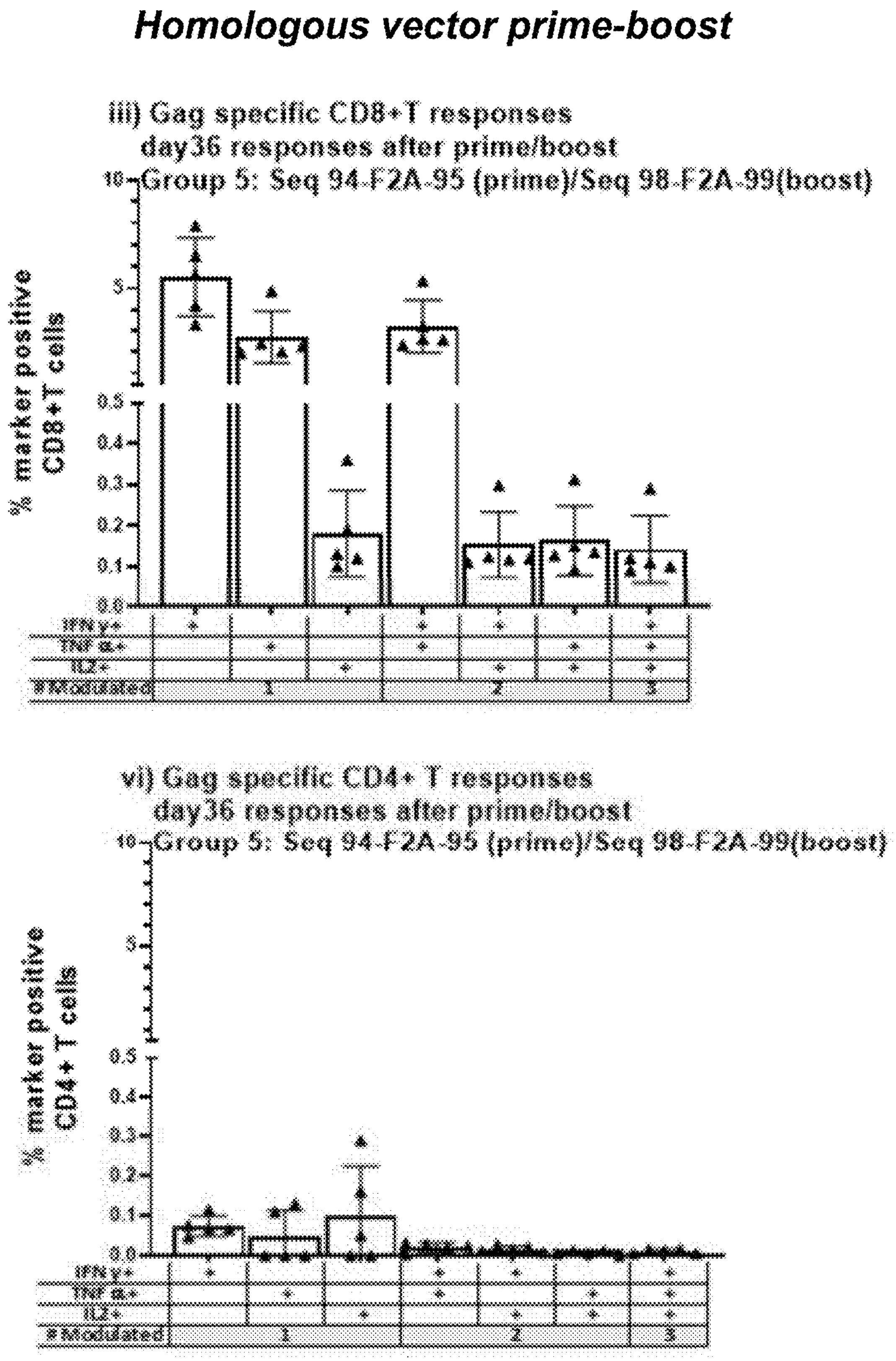

FIGS. 32A-32C illustrate HIV-1 Gag immunogenicity by intracellular cytokine staining (ICS) following vaccination with single vectors, Seq 94-F2A-95 (tPA-SEQ ID NO:105) or Seq 98-F2A-99 (tPA-SEQ ID NO: 109), as well as homologous prime-boost. The Y axis represents proportion of CD8+ (FIG. 32A i, ii and FIG. 32C iii) or CD4+ (FIG. 32B iv, v and FIG. 32C vi) T cells exhibiting HIV-Gag specific responses by expressing cytokines IFN-γ, IL-2 and TNF-α, either as individual cytokines or combination of cytokines, as shown on X axis. HIV-Gag specific values were obtained by subtracting no peptide stimulated control to exclude nonspecific responses. Strong CD4+ and CD8+ T cell responses were generated in response to vaccination, with demonstrated polyfunctionality most robust in CD8+ T cells. Homologous prime-boost enhanced polyfunctionality of the CD8+ T cell responses.

Figure 33A:
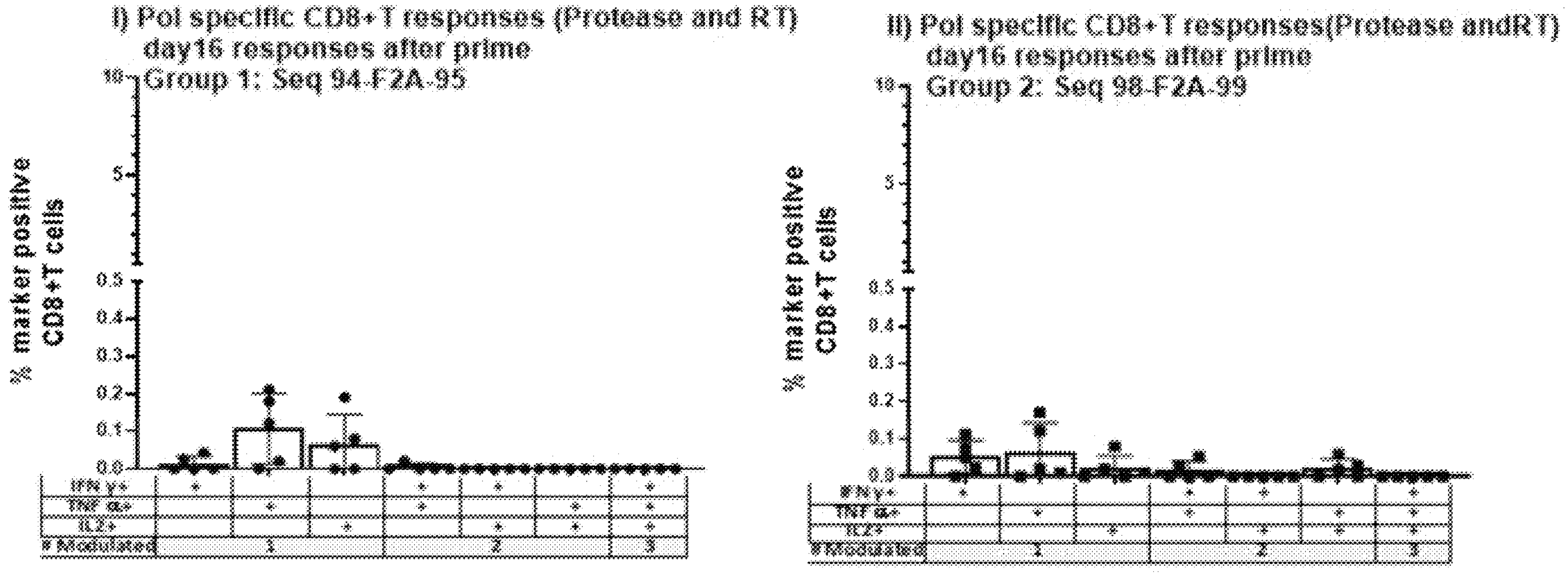
Figure 33B:
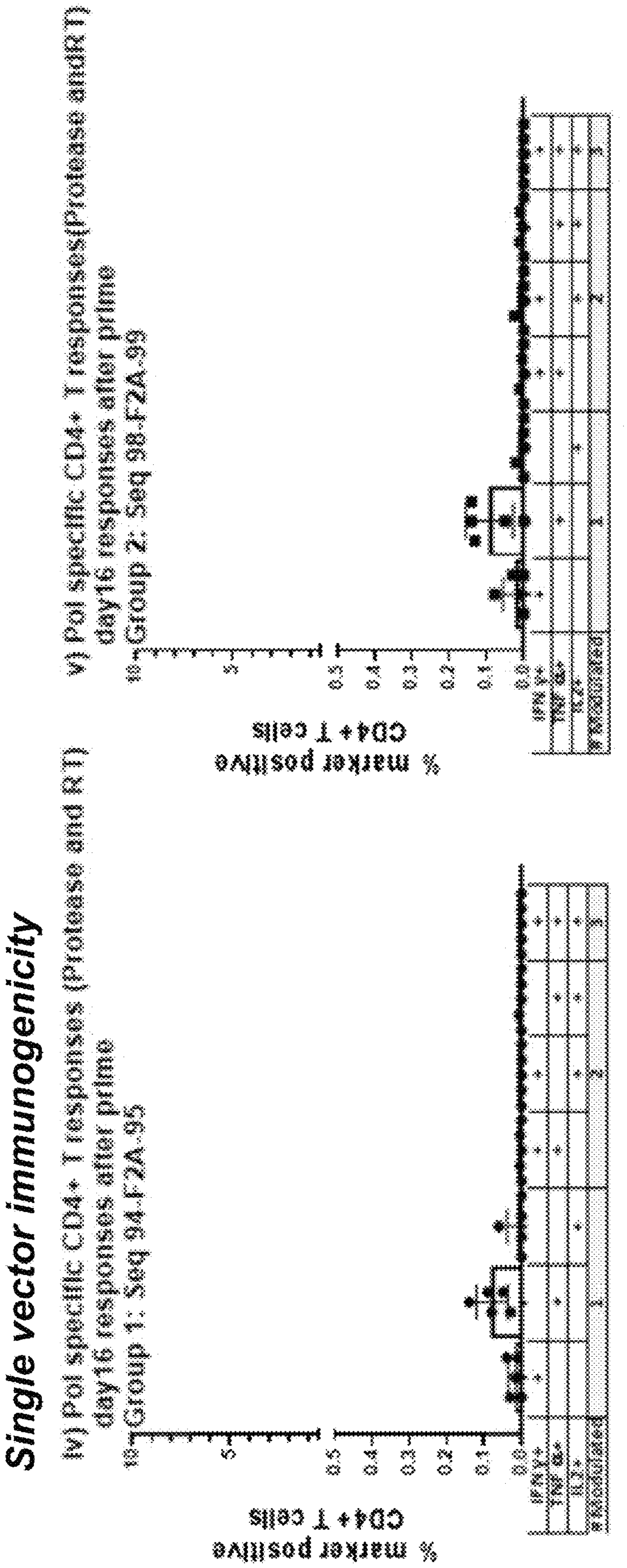

FIGS. 33A-33C illustrate HIV-1 Pol (protease and RT) immunogenicity by ICS following vaccination with single vectors, Seq 94-F2A-95 (tPA-SEQ ID NO: 105) or Seq 98-F2A-99 (tPA-SEQ ID NO: 109), as well as homologous prime-boost. The Y axis represents proportion of CD8+ (FIG. 33A i, ii and FIG. 33C iii) or CD4+ (FIG. 33B iv, v and FIG. 33C vi) T cells exhibiting HIV-Pol (protease and RT) specific responses by expressing cytokines IFN-γ, IL-2 and TNF-α, either as individual cytokines or combination of cytokines, as shown on X-axis. HIV-Pol (Protease and RT) specific values were obtained by subtracting no peptide stimulated control to exclude nonspecific responses. CD4+ and CD8+ T cell responses were generated in response to vaccination. Responses are weaker than Gag responses and tend to be monofunctional, with limited boosting.

Figure 34A:
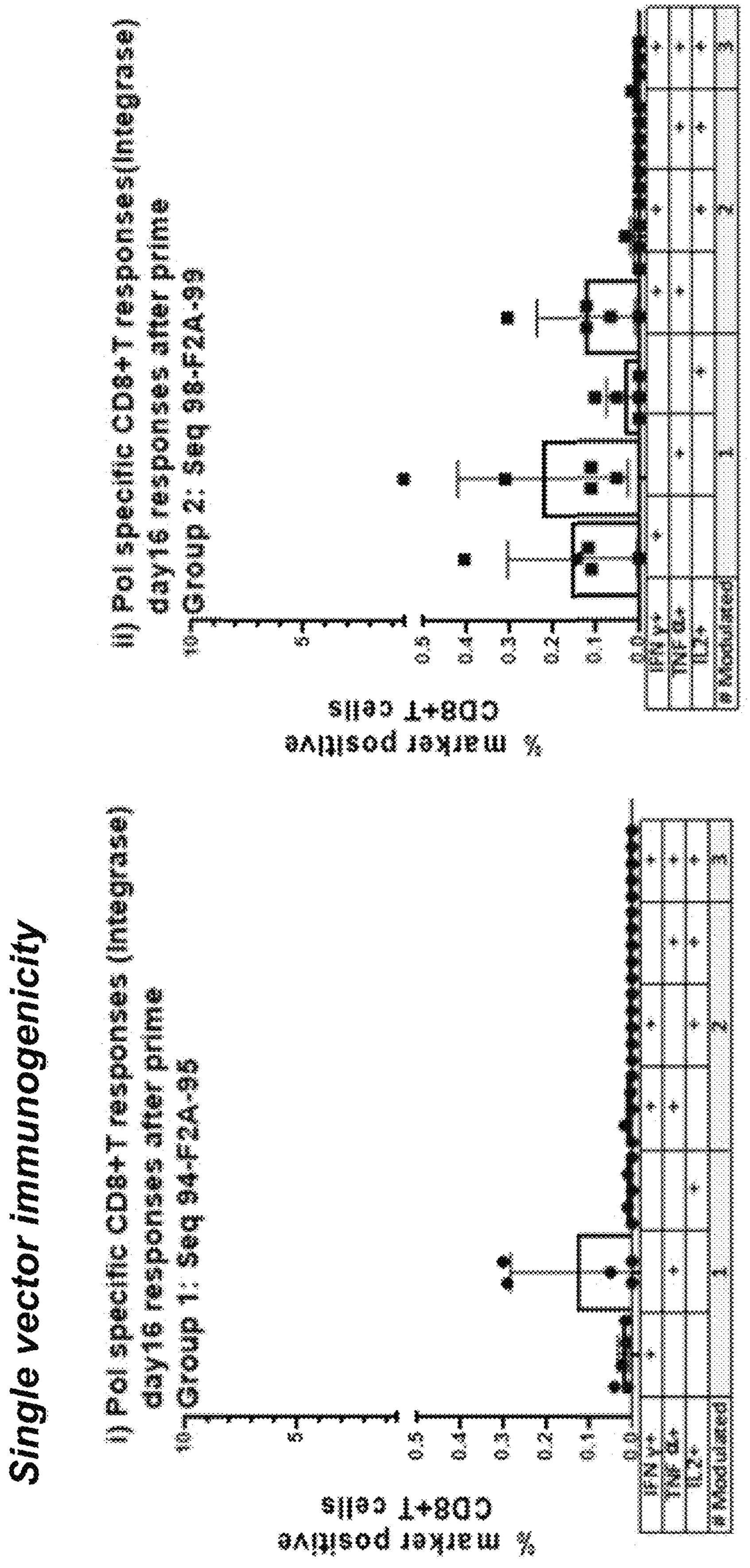
Figure 34B:
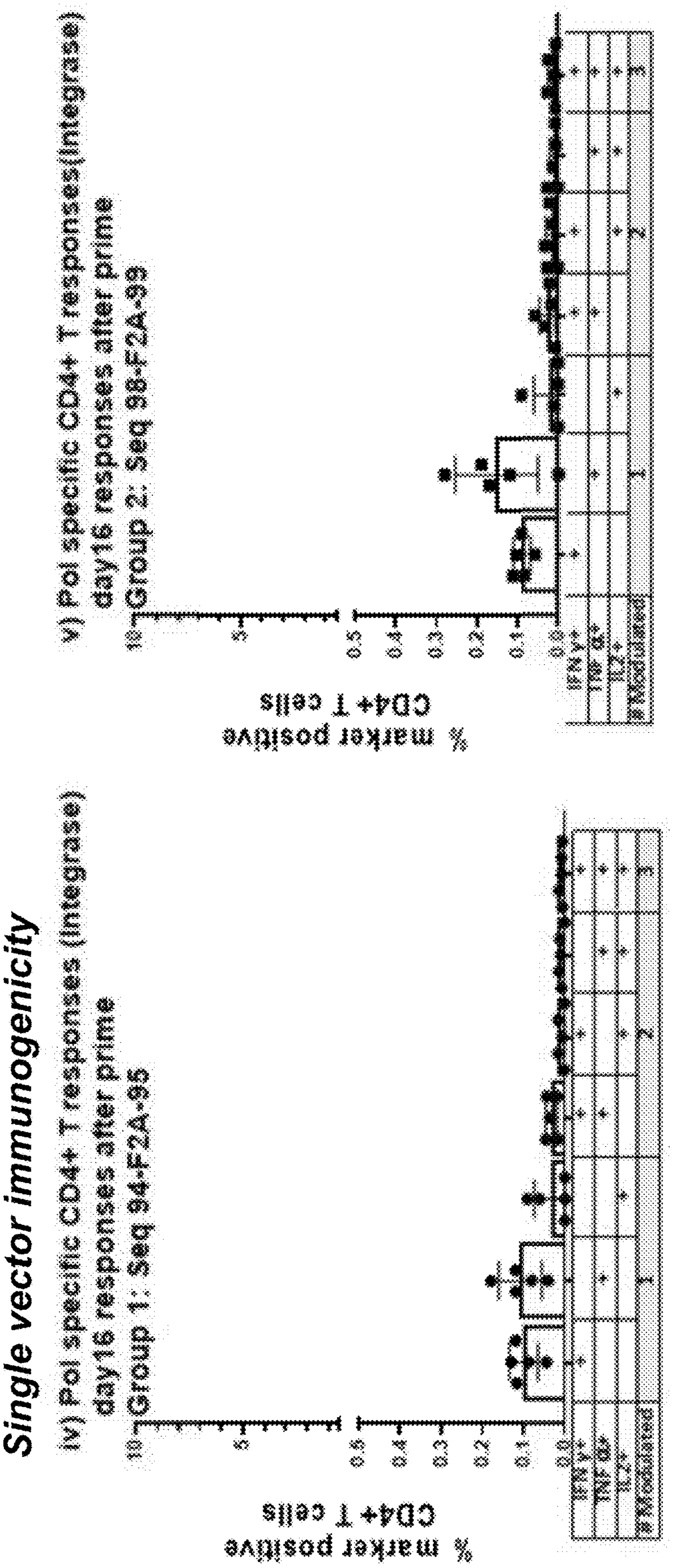

FIGS. 34A-34C illustrate HIV-1 Pol (integrase) immunogenicity by ICS following vaccination with single vectors, Seq 94-F2A-95 (tPA-SEQ ID NO: 105) or Seq 98-F2A-99 (tPA-SEQ ID NO: 109), as well as homologous prime-boost. The Y-axis represents proportion of CD8+ (FIG. 34A i, ii and FIG. 34C iii) or CD4+ (FIG. 34B iv, v and FIG. 34C vi) T cells exhibiting HIV-Pol (integrase) specific responses by expressing cytokines IFN-γ, IL-2 and TNF-α, either as individual cytokines or combination of cytokines, as shown on the X-axis. HIV-Pol (integrase) specific values were obtained by subtracting no peptide stimulated control to exclude nonspecific responses. CD4+ and CD8+ T cell responses were generated in response to vaccination. Responses are weaker than Gag responses and tend to be monofunctional, with limited boosting.

Figure 35A:
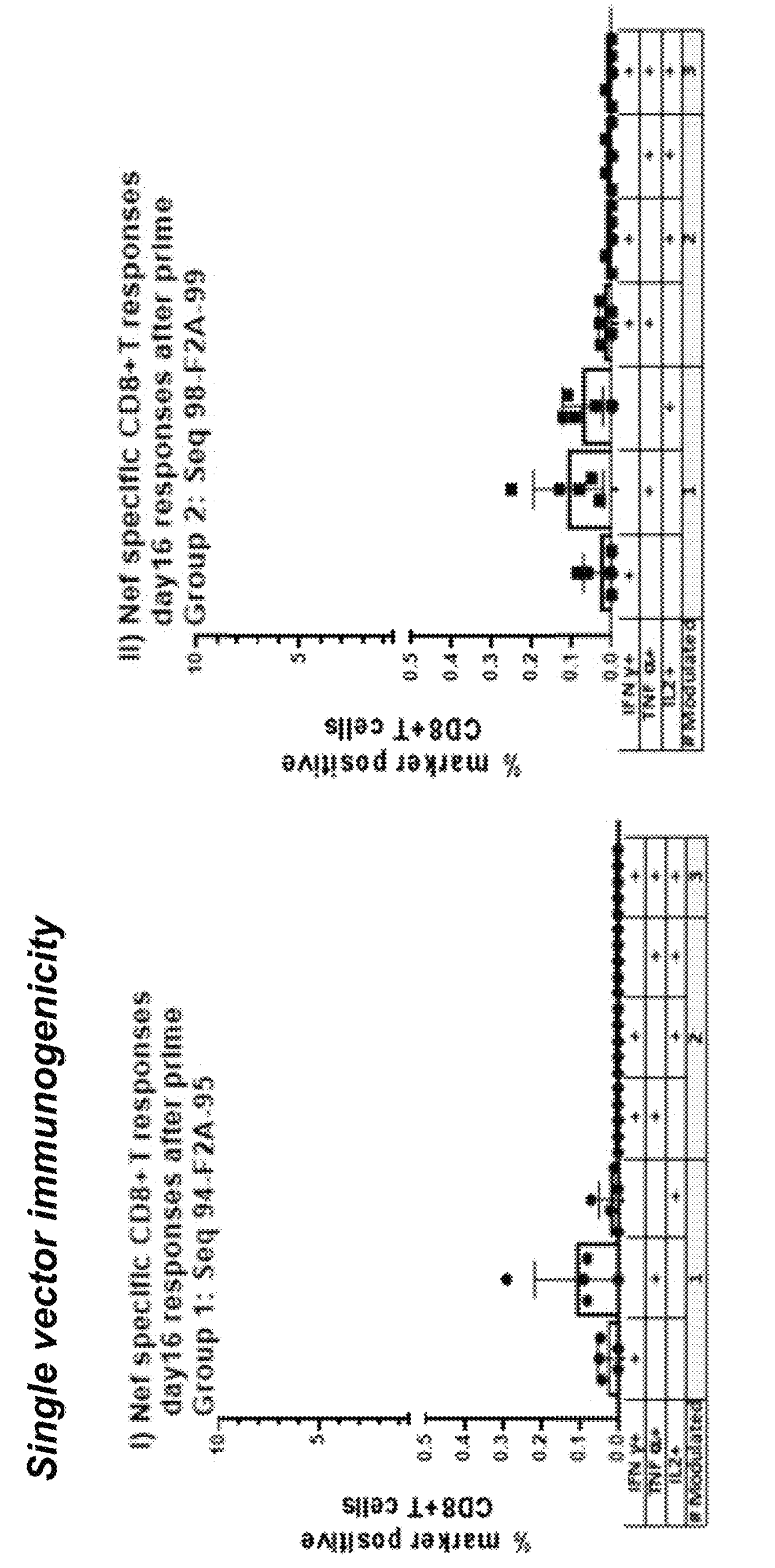
Figure 35B:
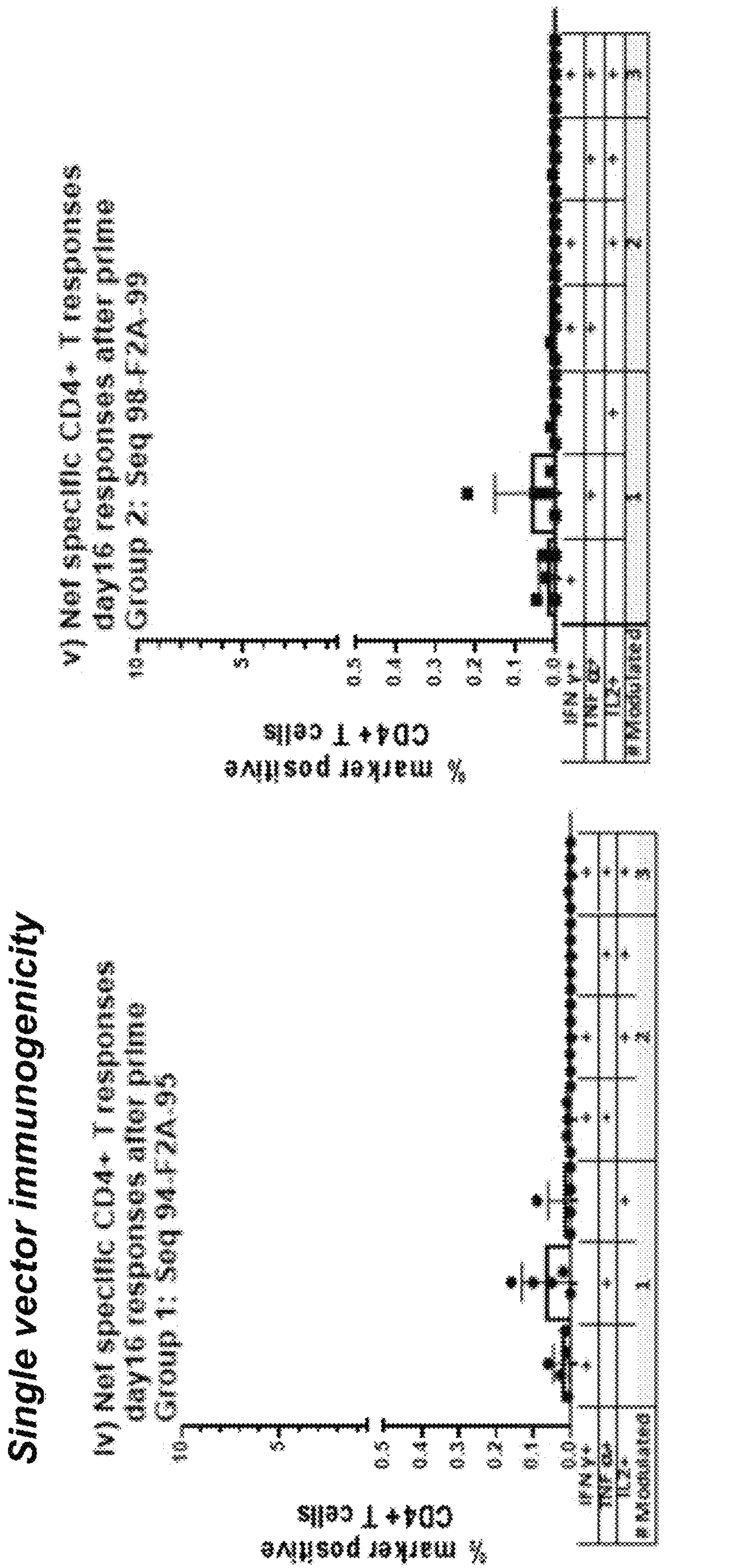

FIGS. 35A-35C illustrate HIV-1 Nef immunogenicity by ICS following vaccination with single vectors, Seq 94-F2A-95 (tPA-SEQ ID NO:105) or Seq 98-F2A-99 (tPA-SEQ ID NO: 109), as well as homologous prime boost. The Y-axis represents proportion of CD8+ (FIG. 35A i, ii and FIG. 35C iii) or CD4+ (FIG. 35B iv, v and FIG. 35C vi) T cells exhibiting HIV-Nef specific responses by expressing cytokines IFN-γ, IL-2 and TNF-α, either as individual cytokines or combination of cytokines, as shown on the X-axis. HIV-1 Nef specific values were obtained by subtracting no peptide stimulated control to exclude nonspecific responses. Very low proportion of CD4+ and CD8+ T cell responses were generated in response to vaccination. Responses are weaker than Gag responses and tend to be monofunctional, with limited boosting.

Figure 36A:
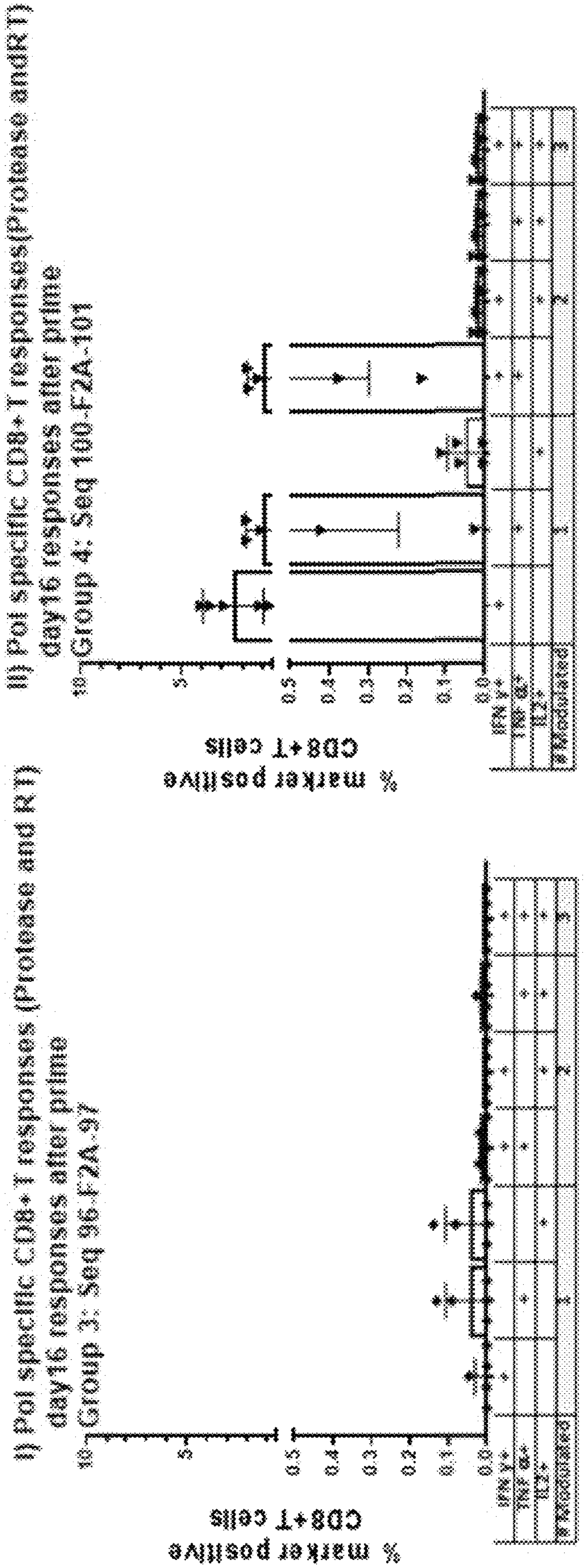
Figure 36B:
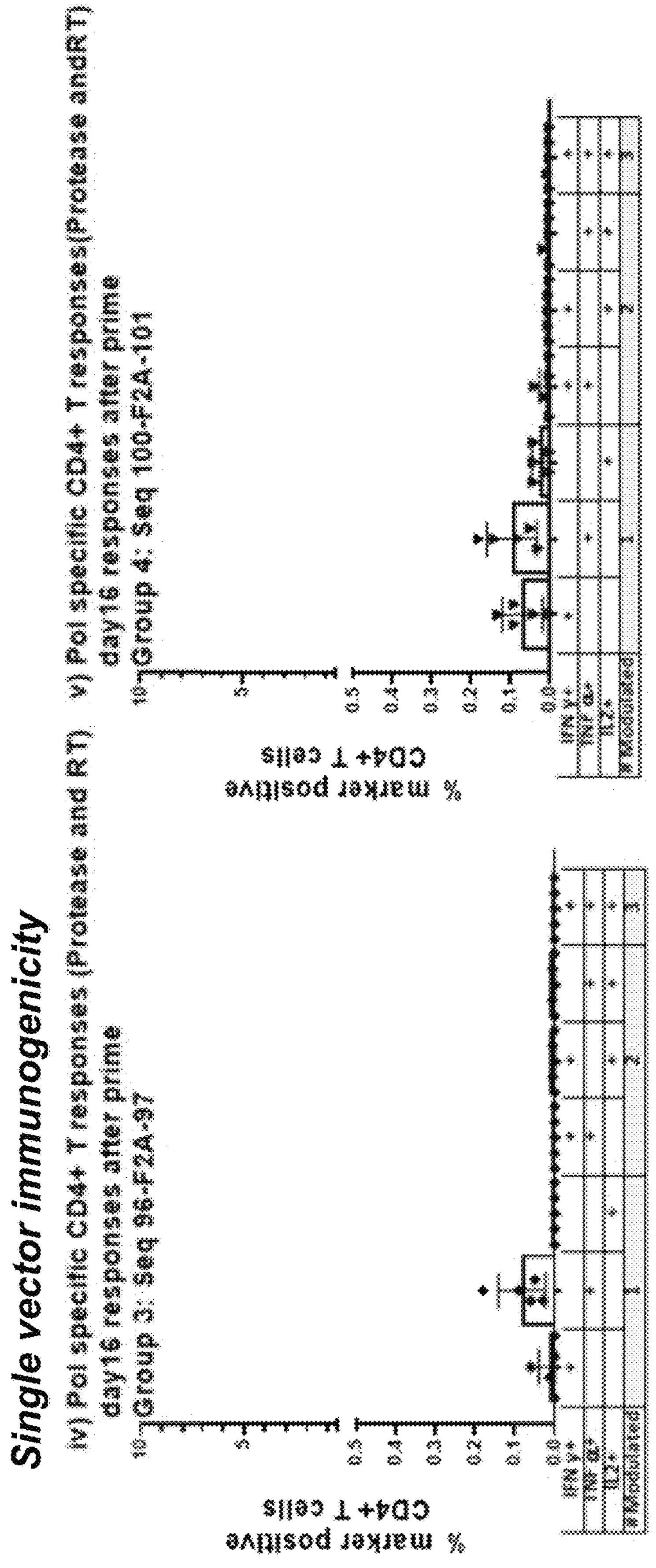

FIGS. 36A-36C illustrate HIV-1 Pol (protease and RT) immunogenicity by ICS following vaccination with single vectors, Seq 96-F2A-97 (tPA-SEQ ID NO: 107) and Seq 100-F2A-101 (tPA-SEQ ID NO: 111), as well as homologous vector prime-boost. The Y-axis represents proportion of CD8+ (FIG. 36A i, ii and FIG. 36C iii) or CD4+ (FIG. 36B iv, v and FIG. 36C vi) T cells exhibiting HIV-Pol (protease and RT) specific responses by expressing cytokines IFN-γ, IL-2 and TNF-α, either as individual cytokines or combination of cytokines, as shown on X-axis. HIV-1 Pol (protease and RT) specific values were obtained by subtracting no peptide stimulated control to exclude nonspecific responses. CD4+ and CD8+ responses were generated in response to vaccination. Seq 100-F2A-101 (tPA-SEQ ID NO: 111) demonstrated strong immunogenicity with polyfunctionality (≥2 cytokines produced). Homologous vector prime-boost with the vectors expressing the fusion polypeptides enhanced both CD4+ and CD8+ T cell responses.

Figure 37A:
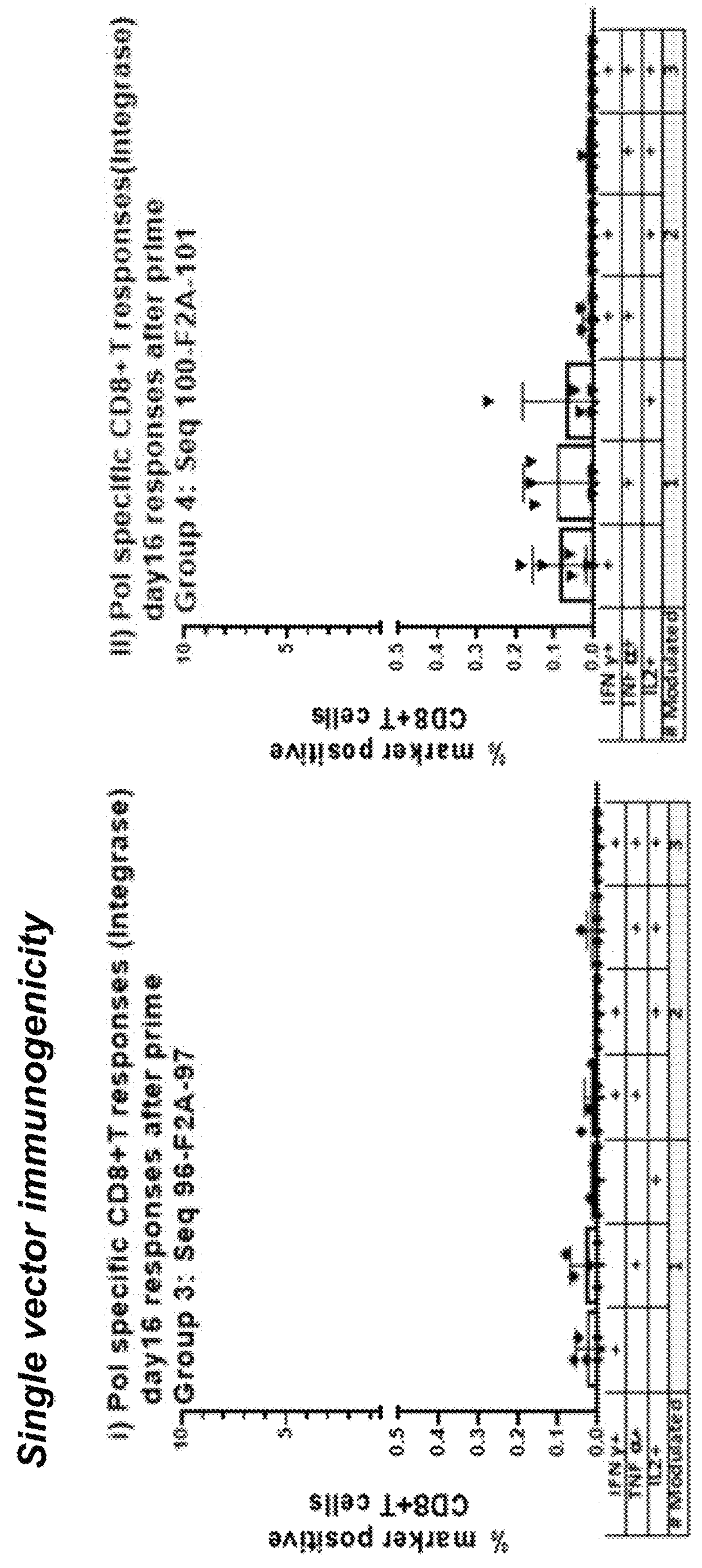
Figure 37B:
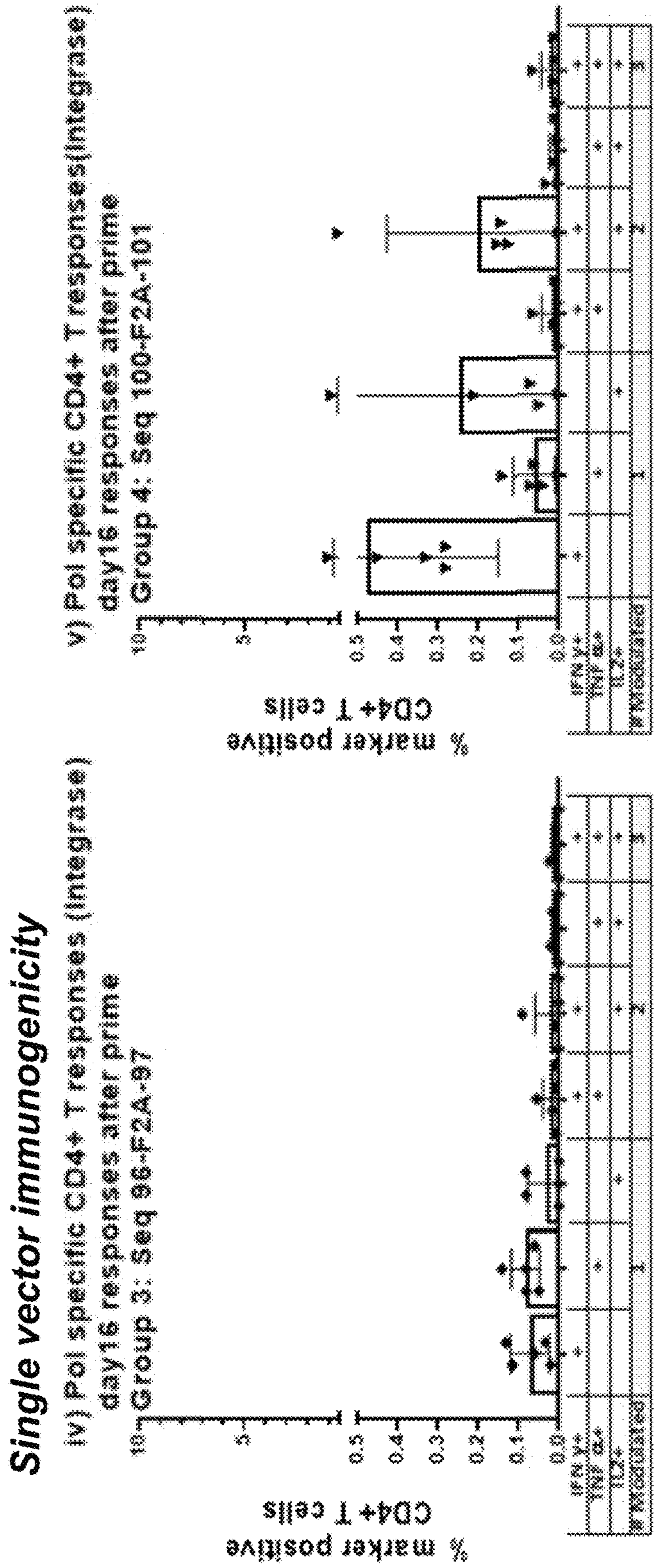
Figure 37C:
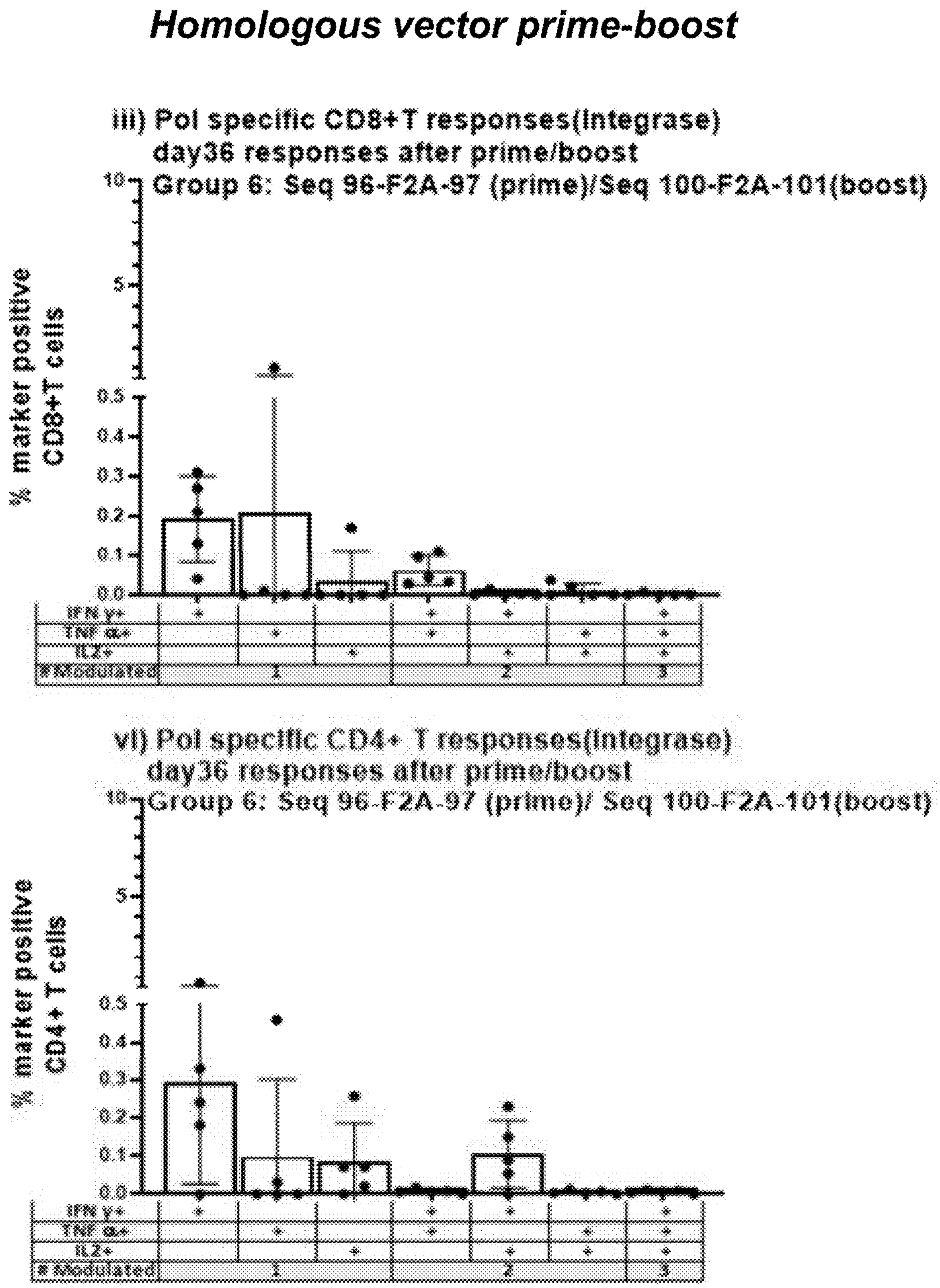

FIGS. 37A-37C illustrate HIV-1 Pol (Integrase) immunogenicity by ICS following vaccination with single vectors, Seq 96-F2A-97 (tPA-SEQ ID NO: 107) and Seq 100-F2A-101 (tPA-SEQ ID NO: 111), as well as homologous vector prime boost. The Y-axis represents proportion of CD8+ (FIG. 37A i, ii and FIG. 37C iii) or CD4+ (FIG. 37B iv, v and FIG. 37C vi) T cells exhibiting HIV-Pol (integrase) specific responses by expressing cytokines IFN-γ, IL-2 and TNF-α, either as individual cytokines or combination of cytokines, as shown on X-axis. HIV-1 Pol (integrase) specific values were obtained by subtracting no peptide stimulated control to exclude nonspecific responses. CD4+ and CD8+ responses were generated in response to vaccination. Seq 100-F2A-101 (tPA-SEQ ID NO: 111) demonstrated strong immunogenicity with polyfunctionality (≥2 cytokines produced). Homologous vector prime-boost with the vectors expressing the fusion polypeptides enhanced both CD4+ and CD8+ T cell responses.

Figure 38A:
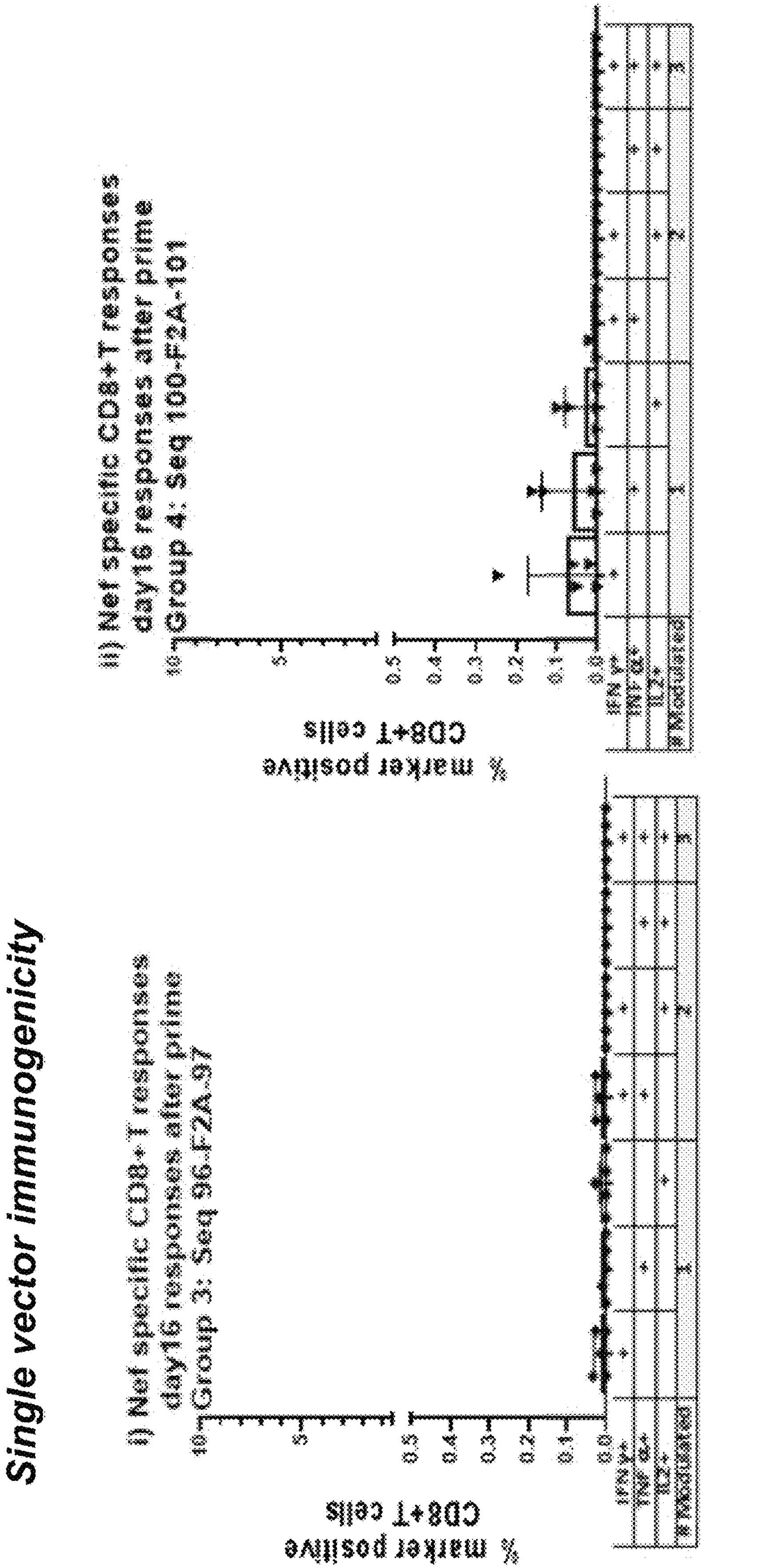
Figure 38B:
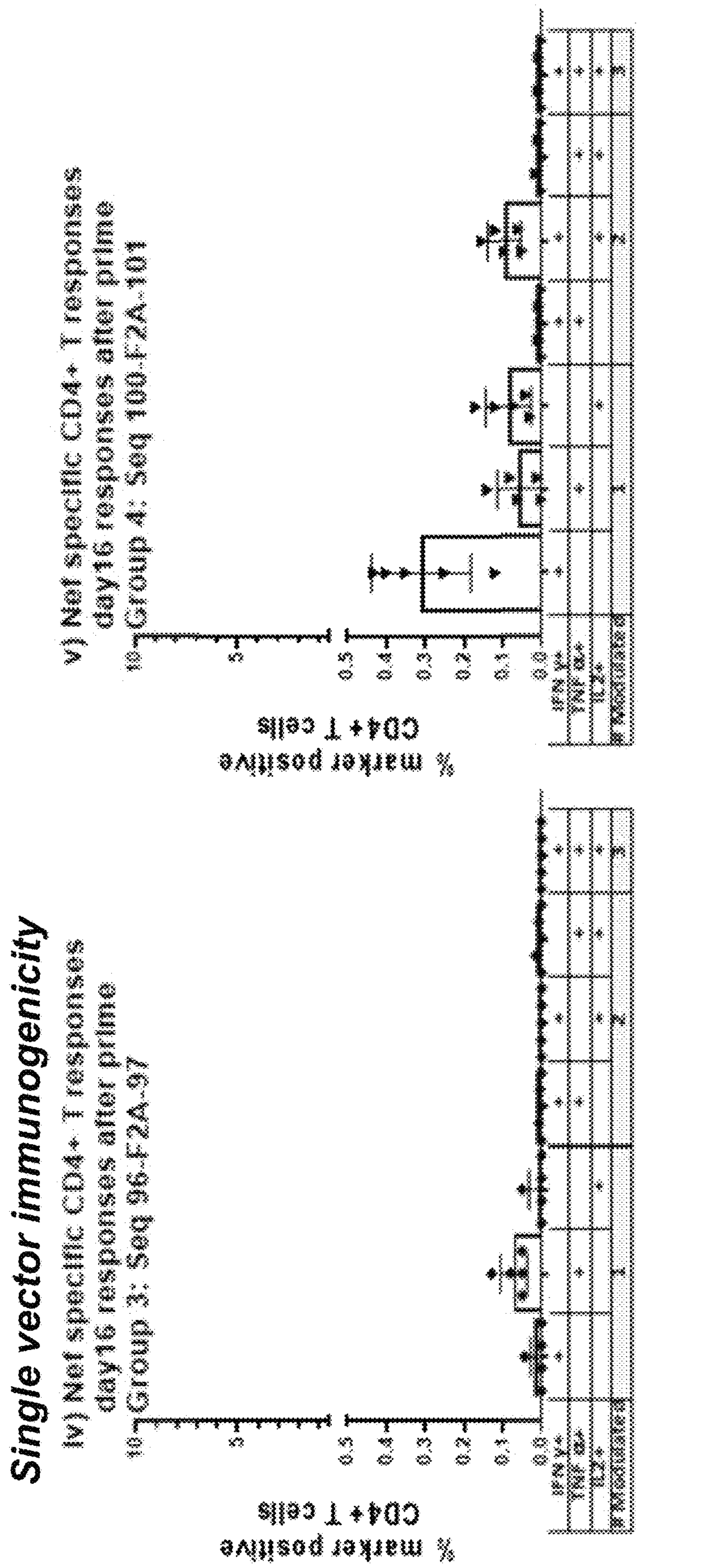

FIGS. 38A-38C illustrate HIV-1 Nef Immunogenicity by ICS following vaccination with single vectors, Seq 96-F2A-97 (tPA-SEQ ID NO: 107) and Seq 100-F2A-101 (tPA-SEQ ID NO: 111), as well as homologous vector prime boost. The Y axis represents proportion of CD8+ FIG. 38A i, ii and FIG. 38C iii) or CD4+ (FIG. 38B iv, v and FIG. 38C vi) T cells exhibiting HIV-Nef specific responses by expressing cytokines IFN-γ, IL-2 and TNF-α, either as individual cytokines or combination of cytokines, as shown on X-axis. HIV-1 Nef specific values were obtained by subtracting no peptide stimulated control to exclude nonspecific responses. Low levels of CD4+ and CD8+ T cell responses were generated in response to vaccination and more responses were seen with CD4 T cells. Seq 100-F2A-101 (tPA-SEQ ID NO: 111) demonstrated and induced mostly monokine production. Homologous vector prime-boost with the vectors expressing the fusion polypeptides enhanced both CD4+ and CD8+ T cell responses.

Figure 39:
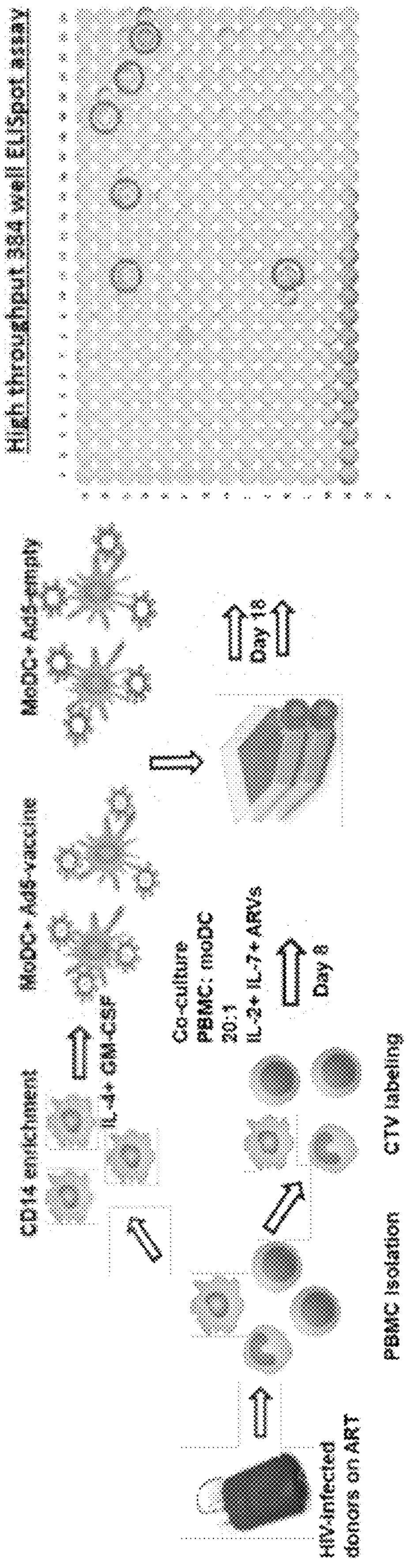

FIG. 39 provides a schematic of a protocol established for moDC-T cell priming assays for testing immunogenicity of all conserved regions vaccine constructs followed by individual epitope mapping using 384-well ELISpot assays.

Figure 40:
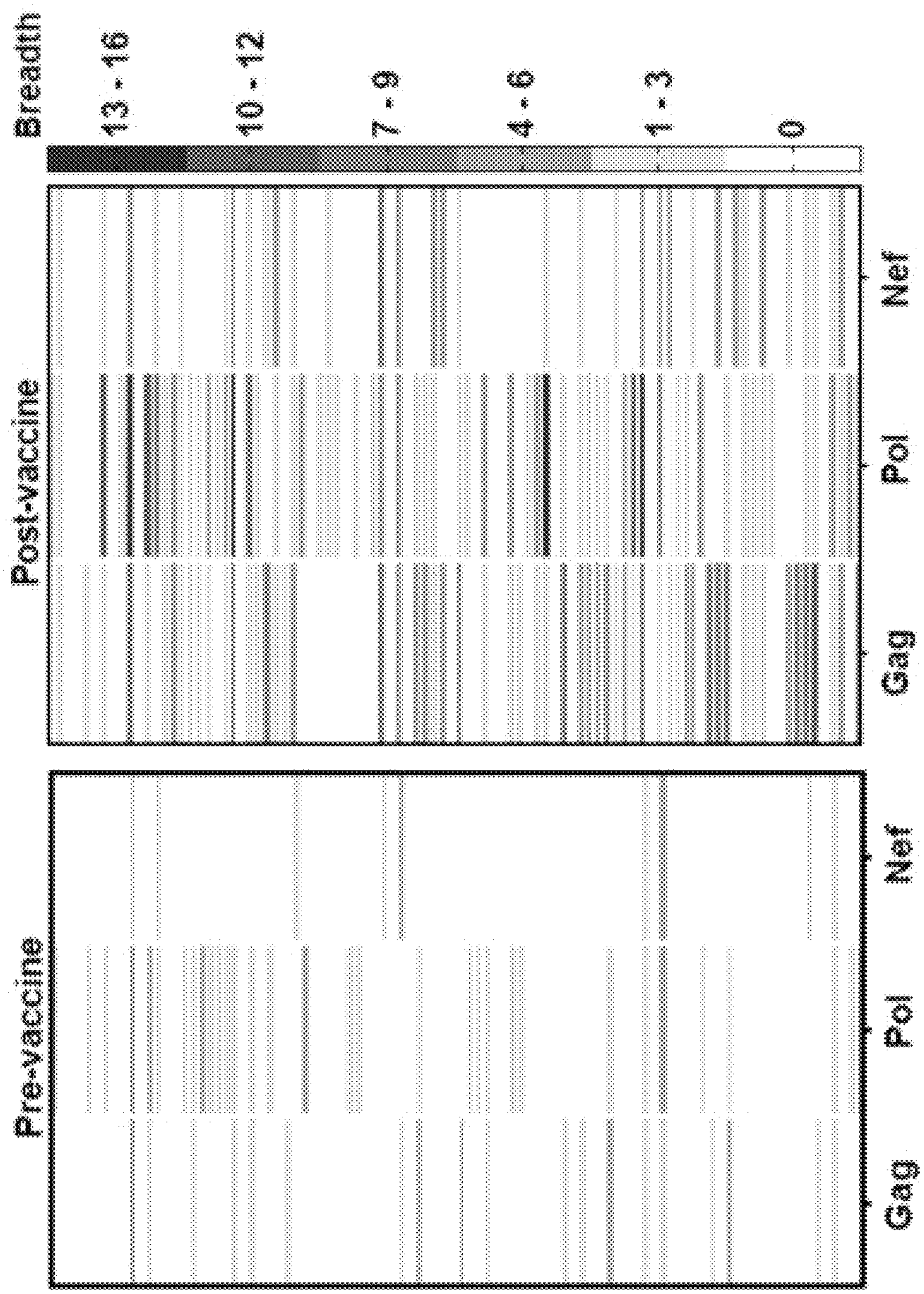

FIG. 40 provides a summary of breadth of responses in ex vivo analysis of PBMCs from N=93 participants following in vitro priming with moDCs. Heat map representing the breadth of T cell responses to Gag, Pol and Nef conserved antigens following in vitro priming with moDCs transduced with Ad5-empty vector MOI 500 (pre-vaccine) or Ad5 viral vectors expressing SEQ ID NOs:105, 107, 109 and 111, each at MOI=500 (post-vaccine). Each matched row in the heat map represents responses from a single participant and breadth of responses are categorized as 0, 1-3, 4-6, 7-9, 10-12 or 13-16. Positive ELISpot responses were defined as >3-fold background levels as described in detail in Example 9.

Figure 41:
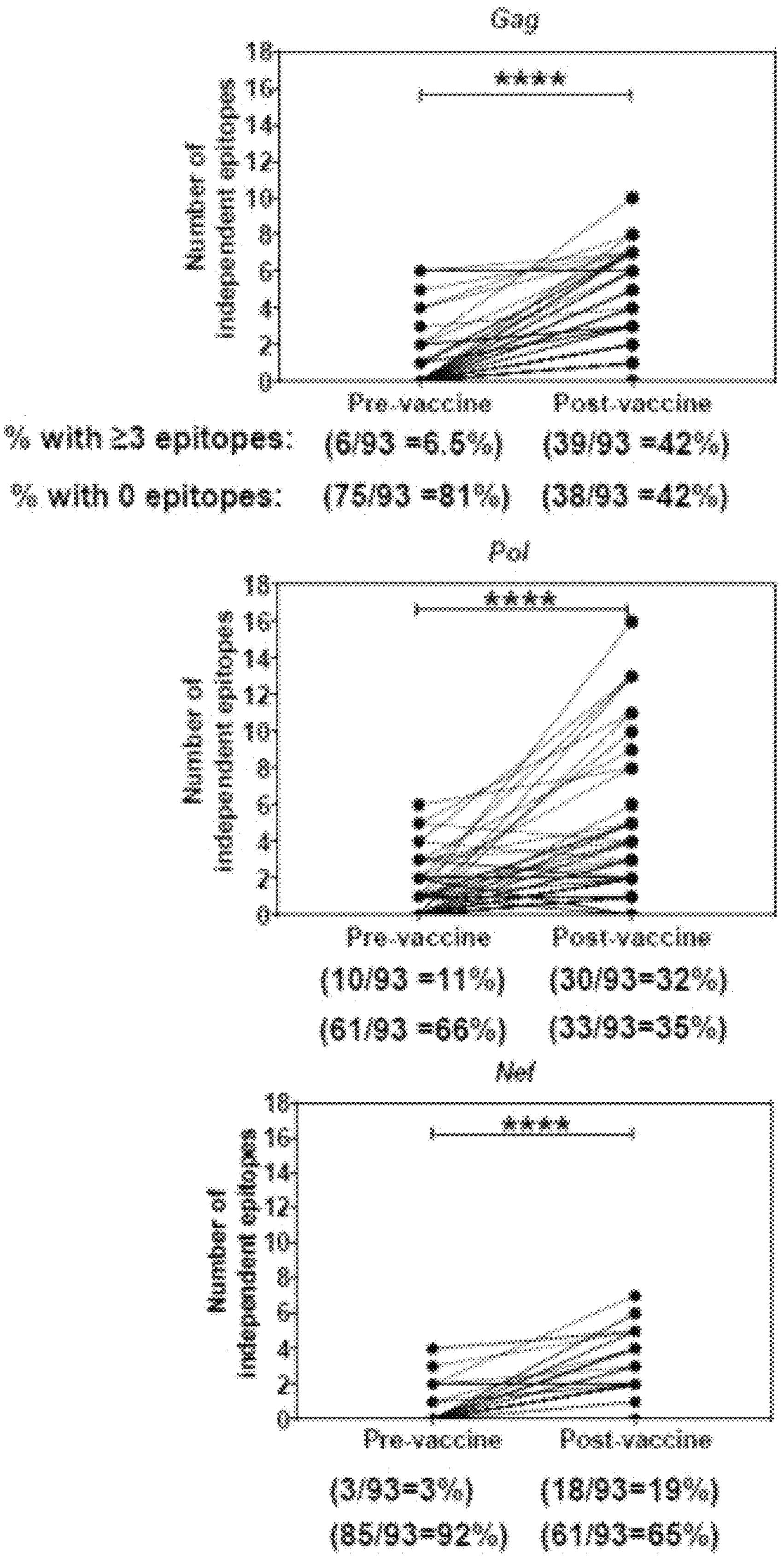

FIG. 41 illustrates characterization of the breadth of immune responses targeted to HIV-1 Gag, Pol and Nef antigens post priming with moDCs transduced with Ad5 viral vectors expressing empty vectors (pre-vaccine) or conserved regions vaccines (SEQ ID NOs: 105, 107, 109 and 111, each at MOI=500 (post vaccine) in N=93 participants. Also enumerated is the fraction of participants that exhibited responses to ≥3 or 0 epitopes in each antigen following in vitro priming with vaccine immunogen sequences. Positive ELISpot responses were defined as >3-fold background levels. Each point represents one donor. Wilcoxon matched pairs signed rank test ****p<0.0001.

Figure 42:
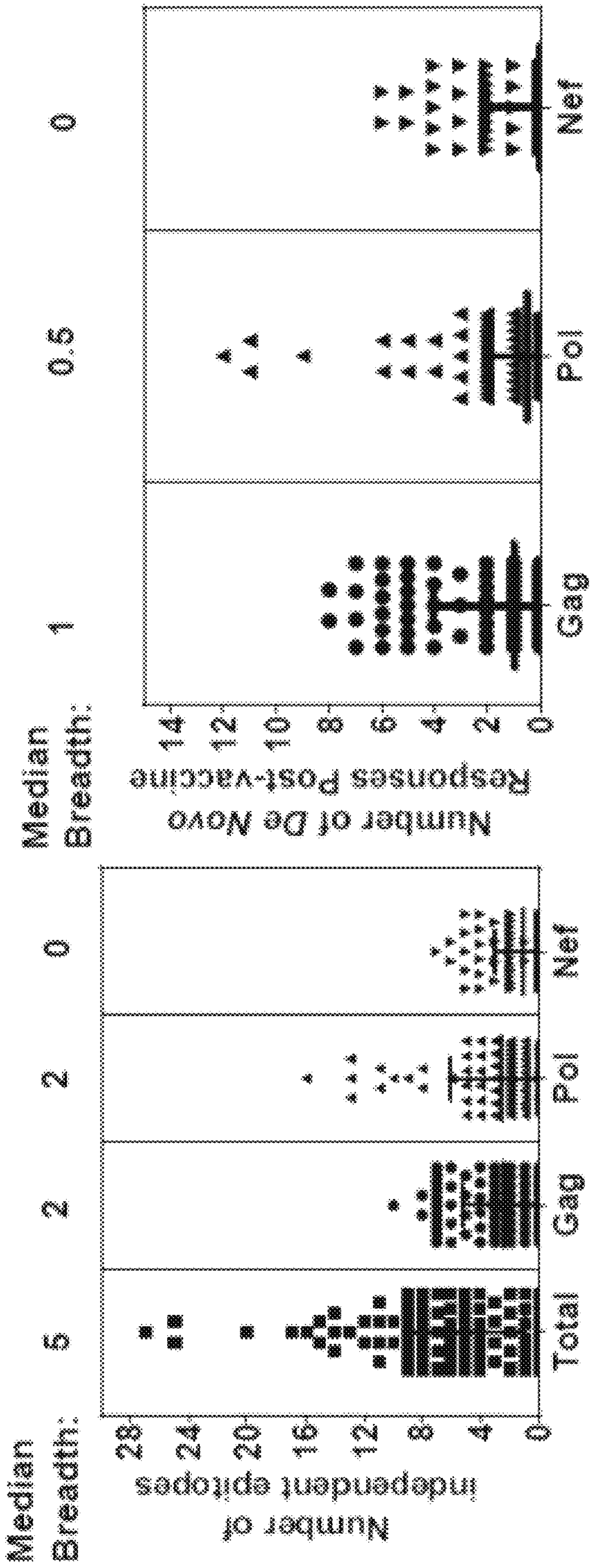

FIG. 42 illustrates breadth of responses to Gag (●), Pol (▲) and Nef (▼) defined as number of de novo recognized peptides (excluding pre-existing baseline responses) assessed by IFN-γ ELISpot assay on day 10 following co-culture of PBMCs with Ad5 vaccine vector transduced autologous moDCs expressing conserved regions constructs (SEQ ID NOs: 105, 107, 109 and 111, each at MOI=500). Each point represents one donor. Median with interquartile range are shown.

Figure 43A:
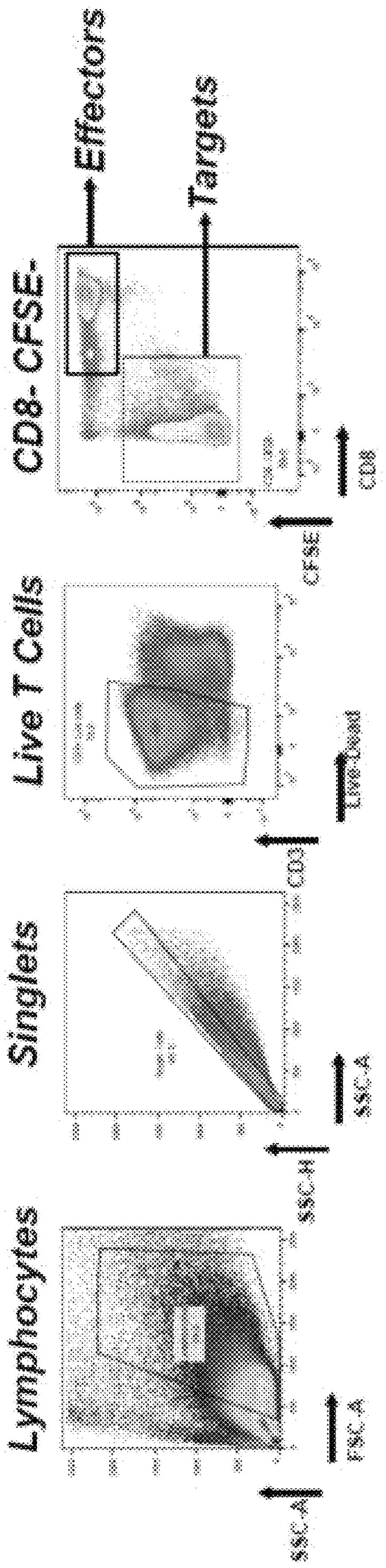
Figure 43B:
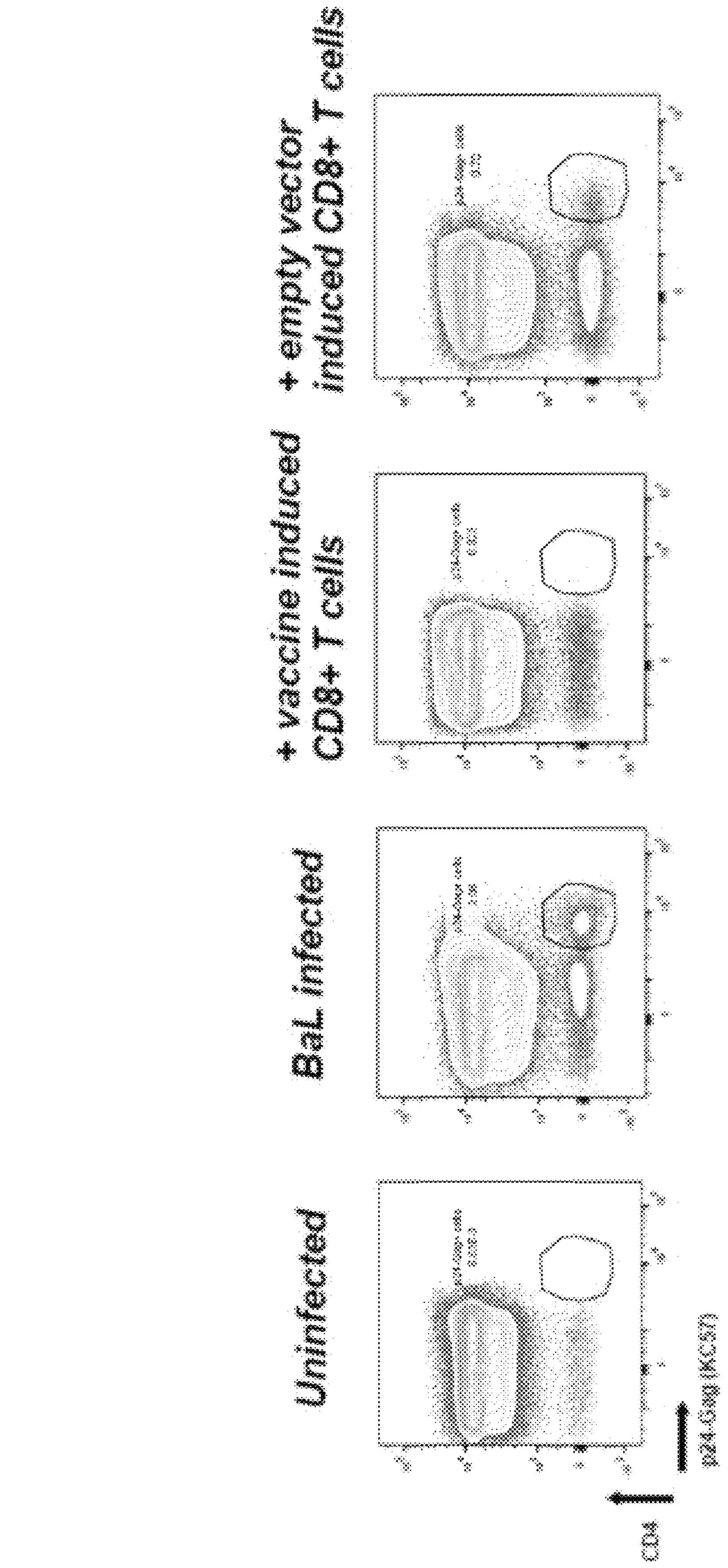

FIGS. 43A-43B illustrate results of an in vitro HIV-1 viral inhibition assay staining for Gag-p24 within target cells. Autologous CD4+ T cells were infected in vitro with HIV-1 BaL, cultured alone or in the presence of vaccine or empty vector primed CFSE labeled CD8+ T cells for 3 days and analyzed for infection using flow cytometry. Representative flow cytometry plots illustrating the gating strategy to define Gag p24+ infected CD4+ T cells (HIV-1 Gag+ cells with down-regulated surface CD4 expression) within target cells (CFSE-CD8− cells).

Figure 44A:
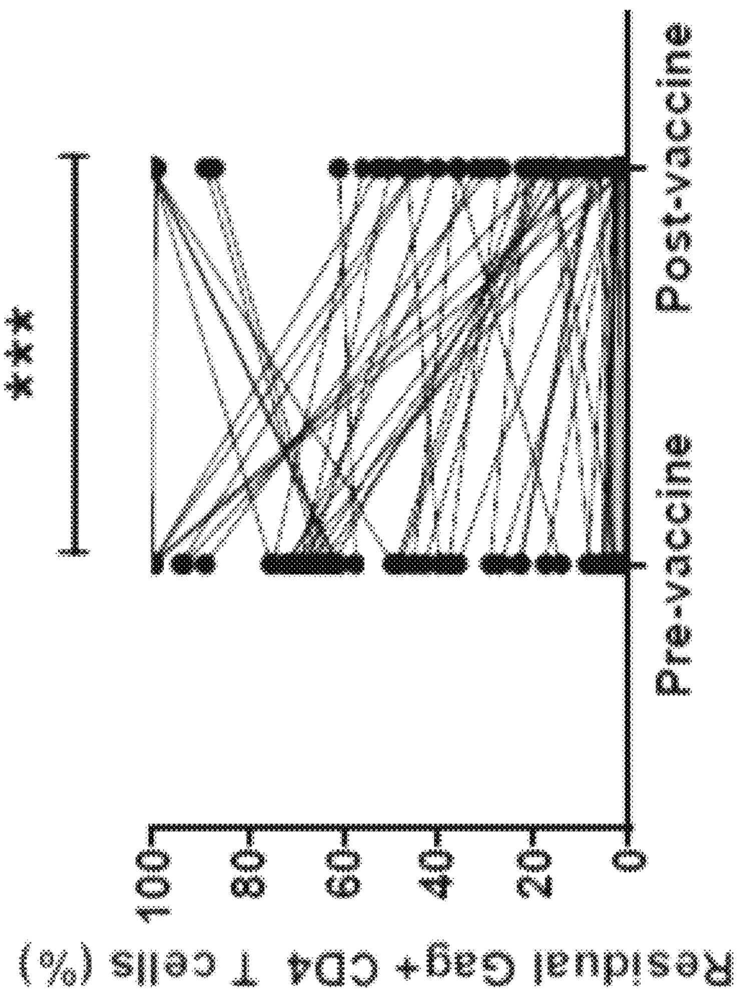
Figure 44B:
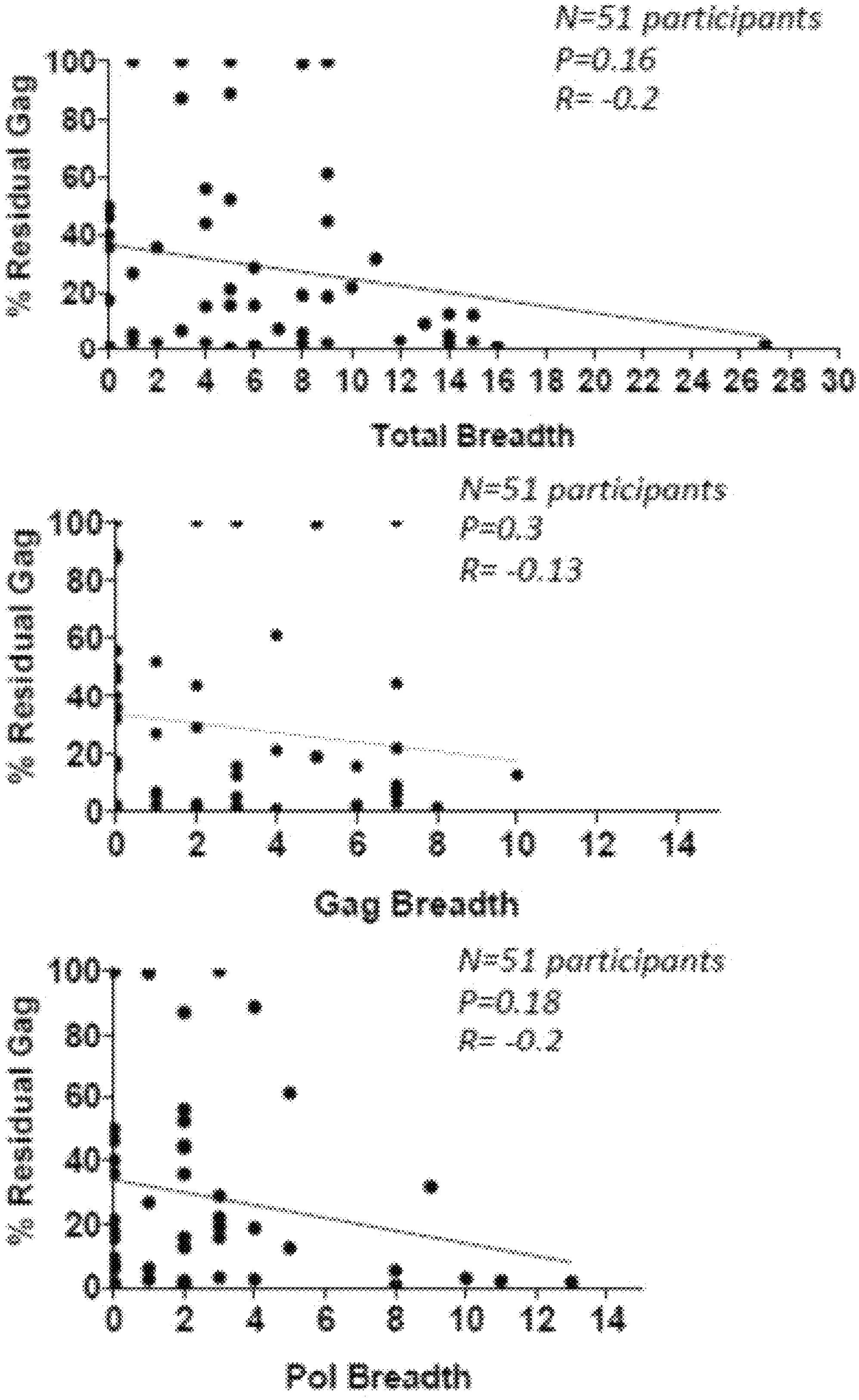

FIGS. 44A-44B illustrate fraction of residual HIV-1 Gag+ CD4− T cells after 3 days of co-culture with enriched CD8+ T cells obtained after priming with vaccine (SEQ ID NOs: 105, 107, 109 and 111, or empty vector control each at MOI=500 for N=51 participants normalized to infected CD4+ T cells cultured without CD8+ T cells. Each condition was completed in technical duplicates or triplicates depending on cell availability. Also illustrated correlation between % residual Gag+ cells (FIG. 44A) and breadth of total, Gag and Pol responses (FIG. 44B). Correlations evaluated by 2-sided Spearman rank-correlation tests without Bonferroni adjustments.

Figure 45A:
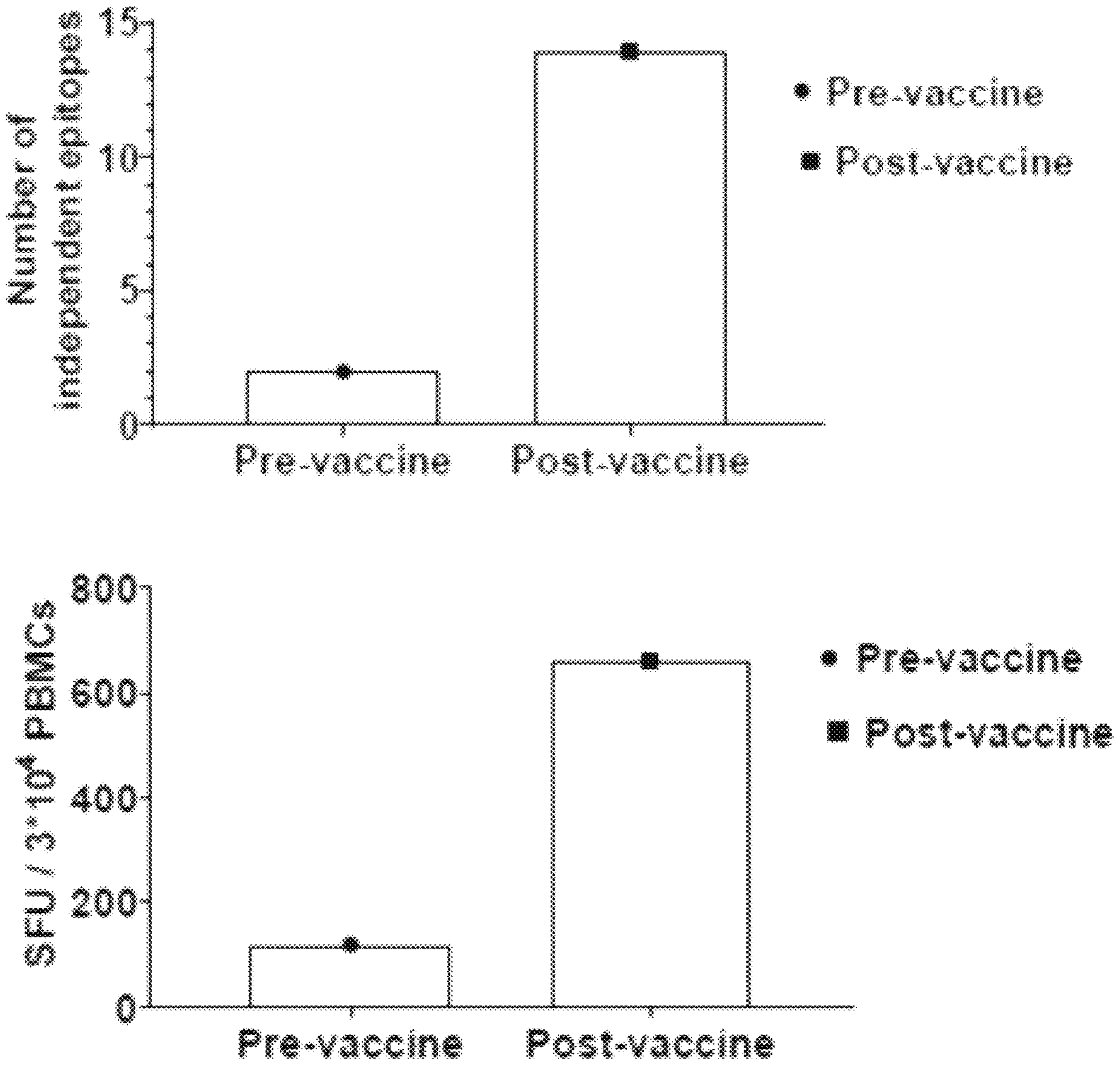
Figure 45B:
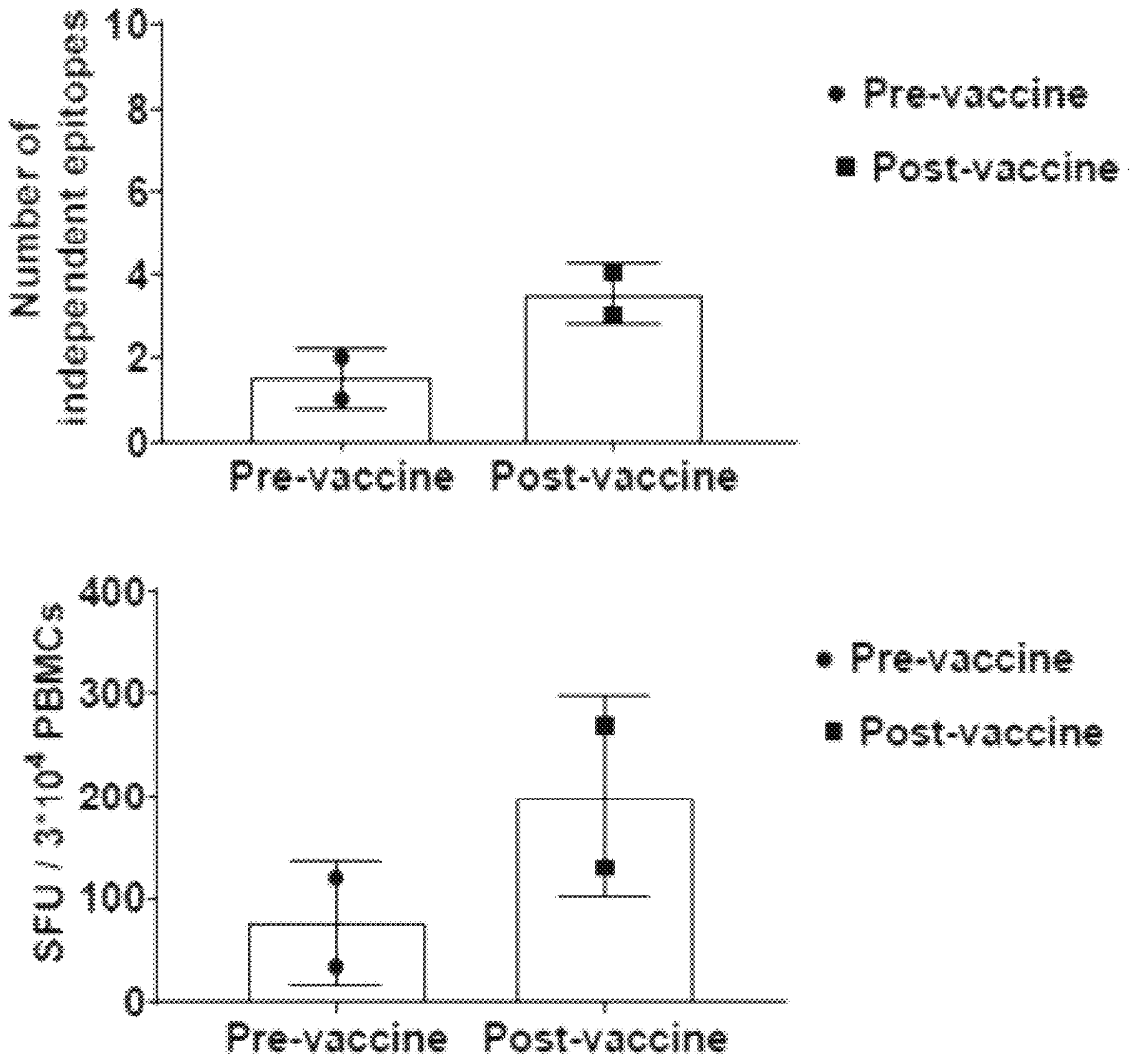

FIGS. 45A-45B illustrates breadth of responses to Gag, Pol and Nef assessed by IFN-γ ELISpot assay on day 10 following co-culture of PBMCs with Ad5 vaccine vector transduced autologous moDCs expressing conserved regions constructs, SEQ ID NO: 82-89 (FIG. 45A) and SEQ ID NO: 90-93 (FIG. 45B), each at MOI=500). Each point represents one donor. Median with interquartile range are shown.

Figure 46:
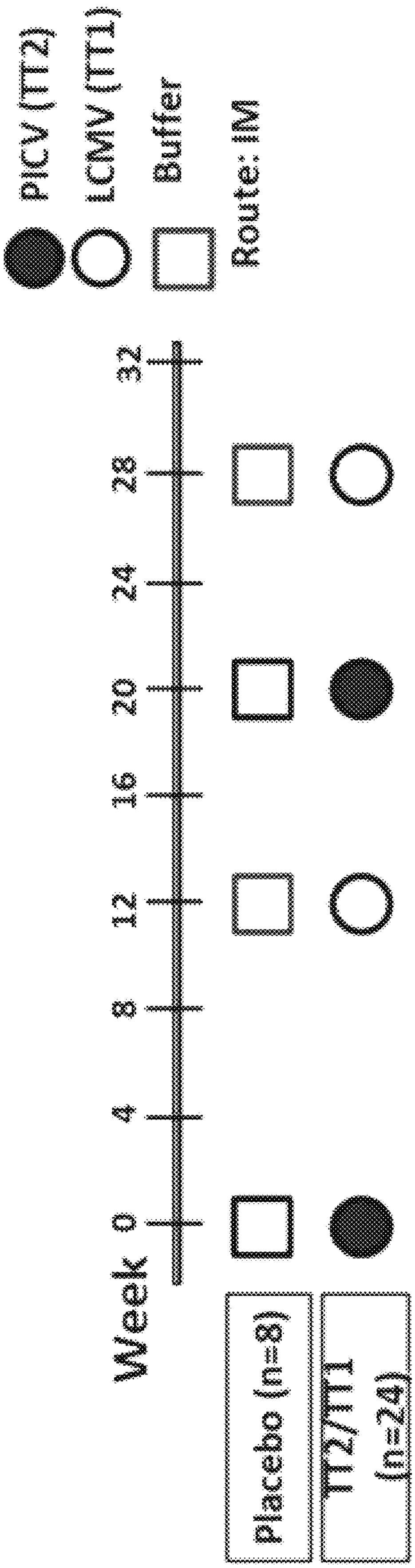

FIG. 46 provides a schematic of immunization schedule prime-boost with arenavirus vectors in non-human primates (NHPs). Indian-origin healthy rhesus macaques were immunized via intramuscular (I.M.) route with the arenavirus vectors. The Gag and Env expressing vectors (TT2 (replication attenuated Pichinde) and TT1 (replication attenuated LCMV)) were administered on the left quadricep whereas the Pol expressing vectors (TT2 and TT1) were administered on the right quadricep. The doses administered are as below: 1×10$^6$ replication competent virus particles (RCV) of TT2 Gag, Env and Poll/Pol 2 vectors, 4×10$^6$ RCV of TT1 Gag, Env, and 2×10$^6$ RCV of TT1 Poll/Pol 2. In the placebo group, NHPs were administered placebo buffer solution composed of 10 mM HEPES, 150 mM NaCl, 20 mM Glycine and 0.1% macaque serum albumin. Responses against Gag, Env and Pol antigens were measured by IFN-γ ELISpot Assay.

Figure 47A:
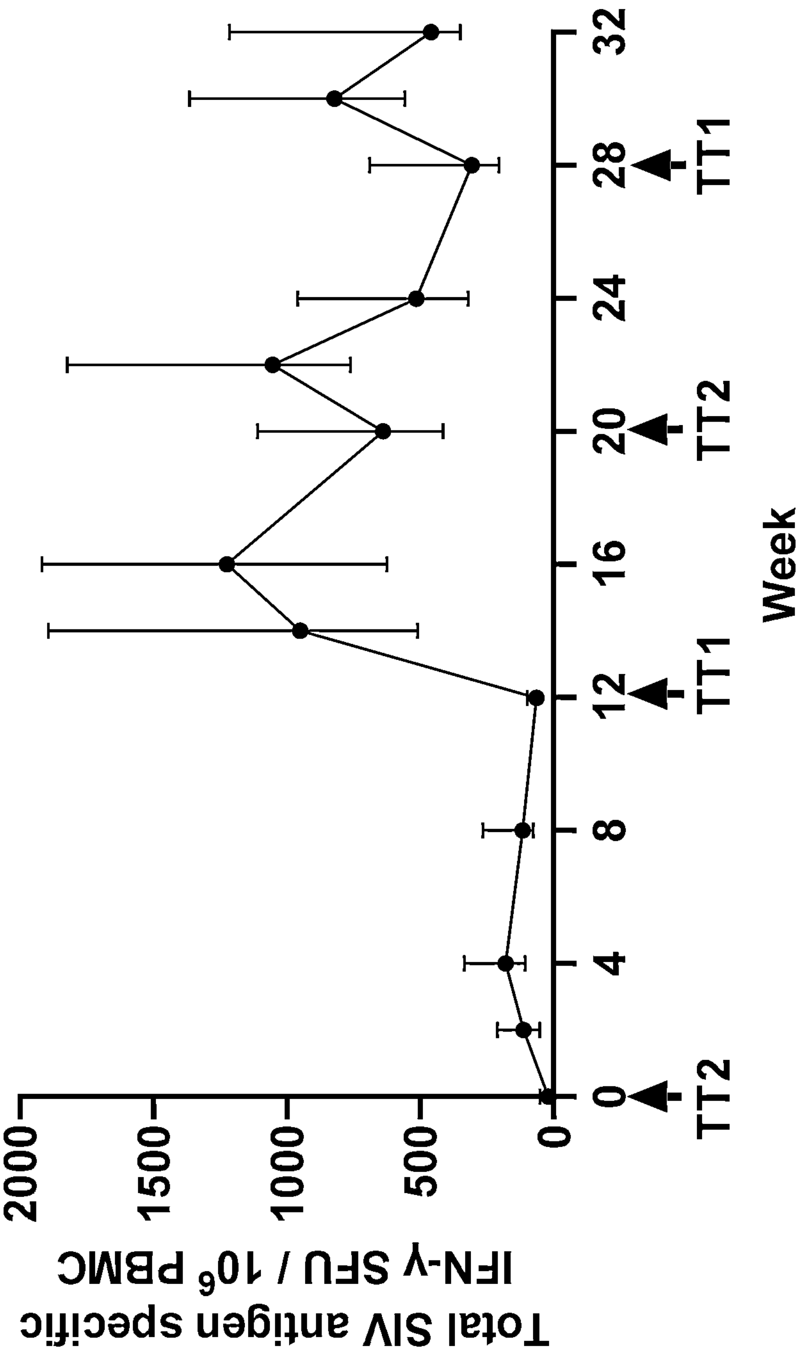
Figure 47B:
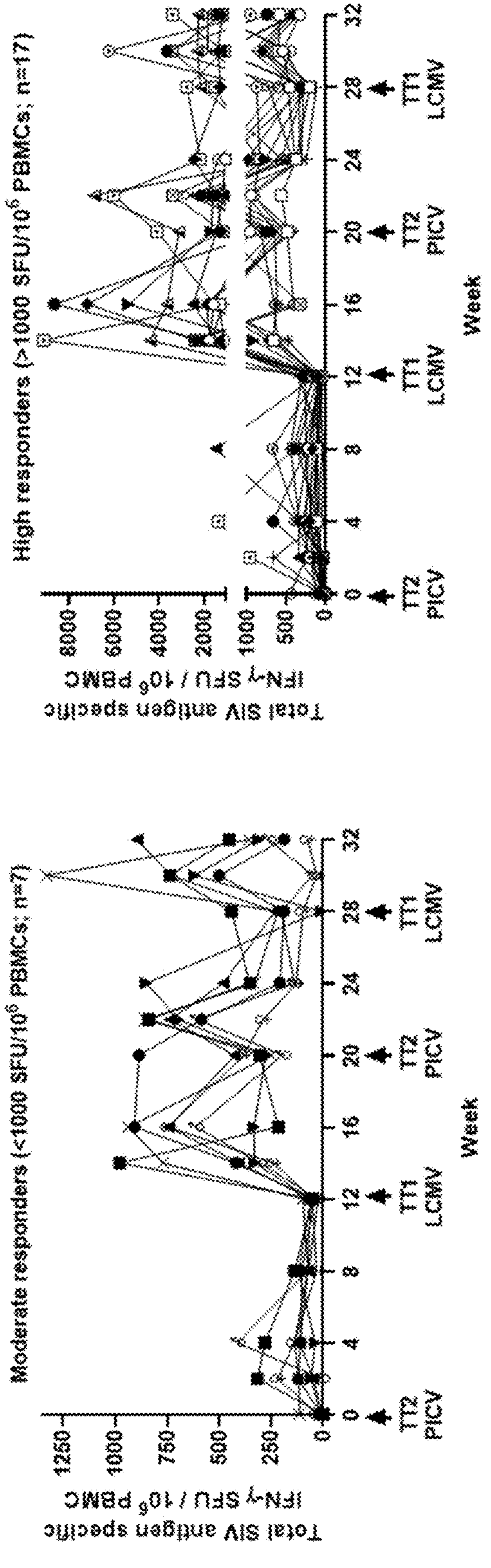

FIGS. 47A-47B. 47A. Time course of total responses to Gag, Env and Pol was assessed by IFN-γ ELISpot on PBMCs isolated from NHP peripheral blood at two four-week intervals post 1st vaccine dose up to week 32. Median with interquartile range are shown. 47B. The NHP responses in FIG. 47A were classified as moderate or high responders depending on whether the magnitude of peak IFN-γ-ELISpot responses was below or above 1000 SFU/10$^6$ PBMCs, respectively. Each line represents one animal that received the arenavirus vaccine vector. Peak response after each immunization remains constant with subsequent boosting.

FIGS. 48A-48D illustrate magnitude of total responses (A) to Gag (B), Env (C) and Pol (D) assessed by IFN-γ ELISpot on PBMCs isolated from NHP peripheral blood at two weeks post vaccine doses 1, 2, 3 and 4. Threshold for positive response is indicated by dotted line and set to observing at least 50 SFU/10$^6$ PBMCs for Gag, Env and Pol and to 150 SFU/$10^6$ PBMCs for the total SIV-specific response. Each symbol represents one NHP. Median with interquartile range are shown. After four doses of the heterologous vaccine, a positive response to Gag, Env and Pol is observed in at least 21 of 24 NHPs (response rate greater or equal to 87.5%). The magnitude of the Gag and Pol responses observed after doses 2 (TT1) and 3 (TT2) remained stable with each subsequent vaccine boost.

FIGS. 49A-49D illustrate the breadth of total SIV (A), Gag (B), Env (C) and Pol (D)-specific IFN-γ responses at 2 weeks post vaccine boost dose 2 (triangles), dose 3 (squares) and dose 4 (diamond). Statistical analysis by Wilcoxon matched-pairs signed rank test was performed. Data are represented as median±interquartile range (IQR).

Figure 50A:
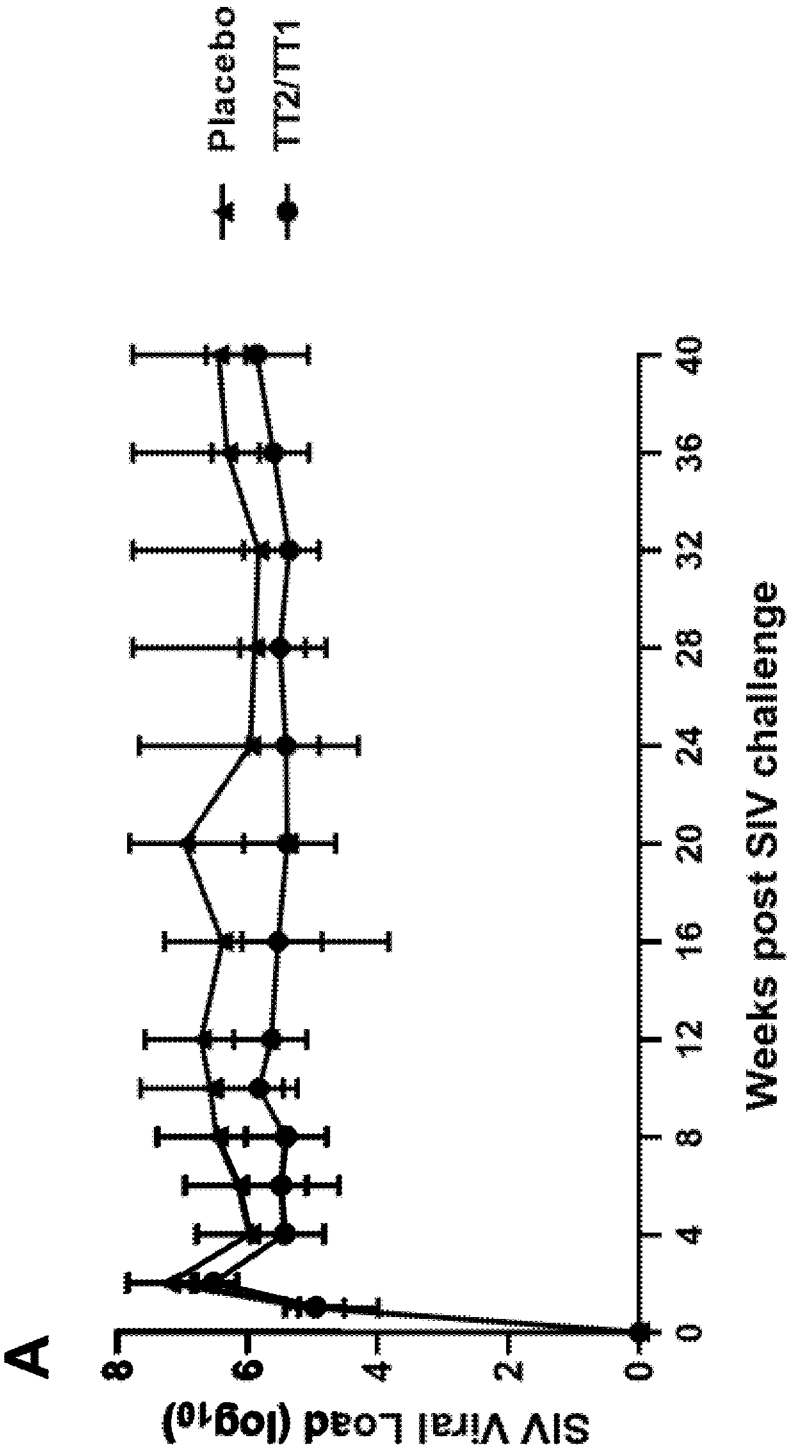

FIGS. 50A-50C illustrate (A) Time course of plasma SIV viral load over weeks 0-40 post challenge; (B) Peak viral load at week 2 post challenge; (C) Setpoint viral load measured over weeks 10-40 post challenge. Placebo group is shown as closed triangles and TT2/TT1 vaccine group in closed circles. Data are represented as median±SEM. * $p<0.05$ and ** $p<0.01$ in B and C by Mann-Whitney t-test. Median viral load (VL) is indicated above each group in figures B and C.

Figure 51:
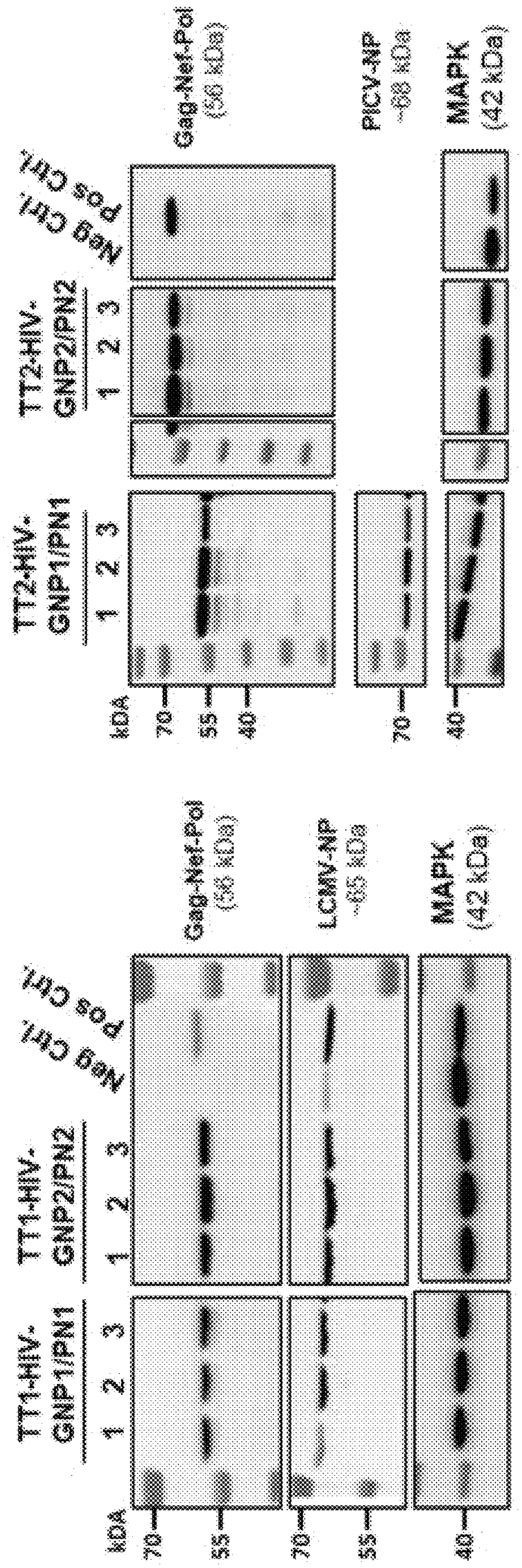

FIG. 51 illustrates an immunoblot analysis of replication-attenuated arenavirus vectors. Transgene expression of Gag/Nef/Pol fusion polypeptides from stock material (p1) of replication-attenuated-LCMV and replication-attenuated-PICV vectors, was determined by immunoblot staining of the Gag epitope p24 (mAb anti HIV1 p24; Abcam). Whole cell lysates of three biological replicates (1, 2, 3) were analyzed. TT1=replication-attenuated-LCMV; TT2=replication-attenuated-PICV. GNP=Gag/Nef/Pol; PN=Pol/Nef. TT1-HIV-GNP1/PN1 (SEQ ID NOs: 98 and 100); TT1-HIV-GNP2/PN2 (SEQ ID NOs: 99 and 101); TT2-HIV-GNP1/PN1 (SEQ ID NOs: 82 and 86); TT2-HIV-GNP2/PN2 (SEQ ID NOs: 83 and 87).

Figure 52:
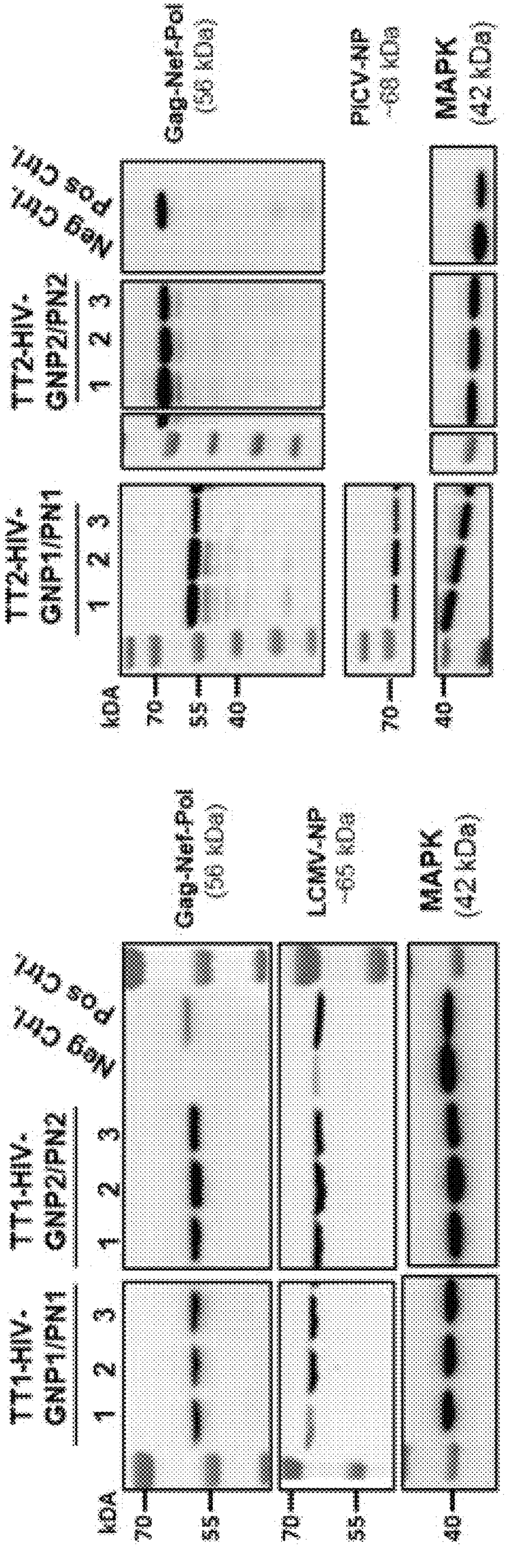

FIG. 52 illustrates immunoblot analysis of replication-attenuated arenavirus vectors. Transgene expression Gag/Nef/Pol from stock material (p1) of replication attenuated-LCMV and replication attenuated-PICV HIV Immunogen 1 vectors, was determined by immunoblot staining of the Gag epitope p24 (mAb anti HIV1 p24; Abcam). Whole cell lysates of three biological replicates (1, 2, 3) were analyzed. TT1=replication attenuated-LCMV; TT2=replication attenuated-PICV. GNP=Gag/Nef/Pol; PN=Pol/Nef.

Figure 53:
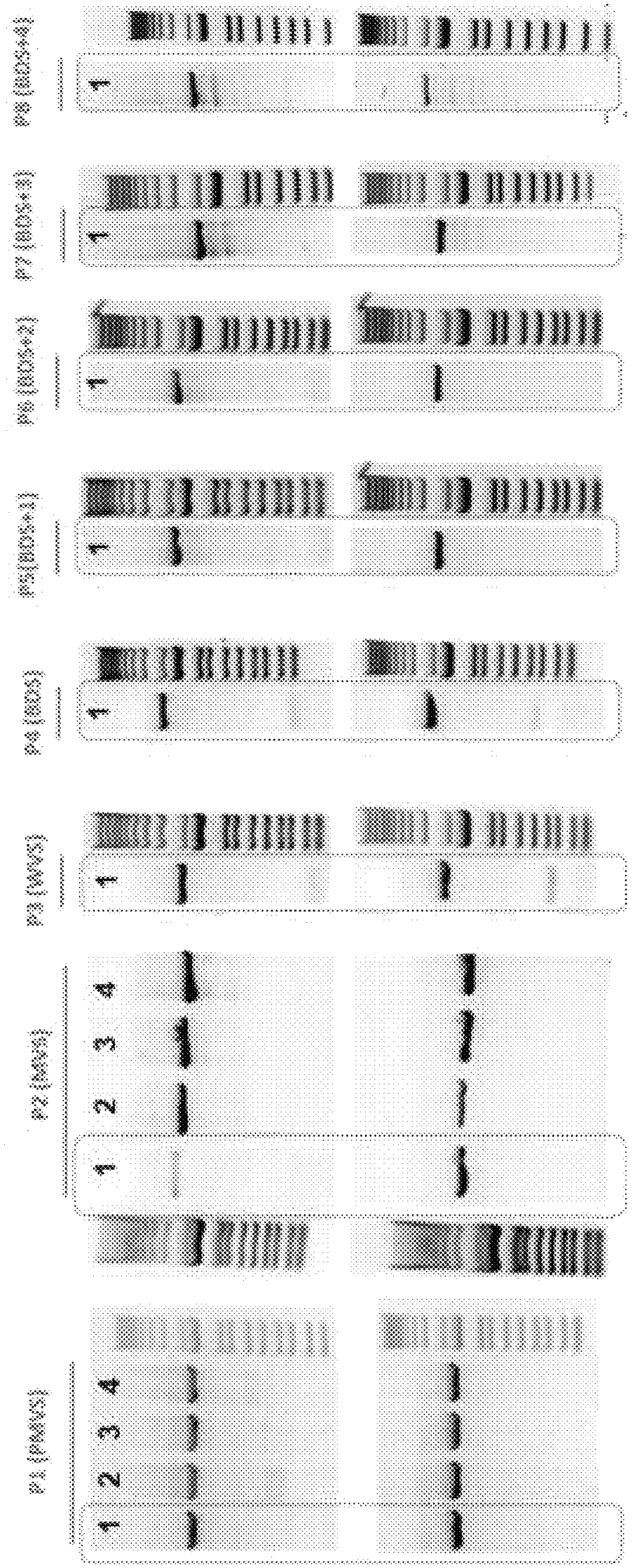

FIG. 53 illustrates transgene stability analysis of TT1-HIV-GNP1/PN1 (having transgenes encoding fusion polypeptides of SEQ ID NOs: 98 and 100). Shown are transgene PCR results for 4 biological replicates (1-4) and for indicated passaging levels. The last passage showing ≥50% full length transgene was visually assessed.

Figure 54:
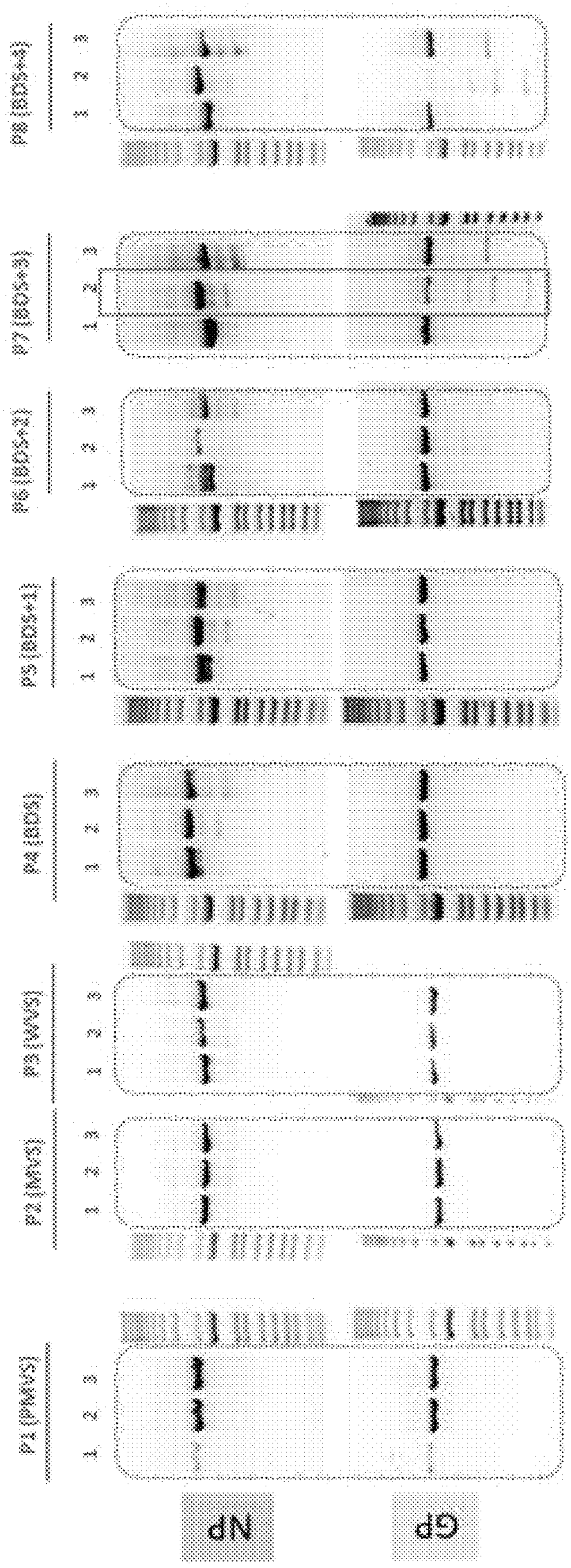

FIG. 54 illustrates transgene stability analysis of TT1-HIV-GNP2/PN2 (having transgenes encoding fusion polypeptides of SEQ ID NOs: 99 and 101). Shown are transgene PCR results for 3 biological replicates (1-3) and for indicated passaging levels. The last passage showing ≥50% full length transgene was visually assessed.

Figure 55:
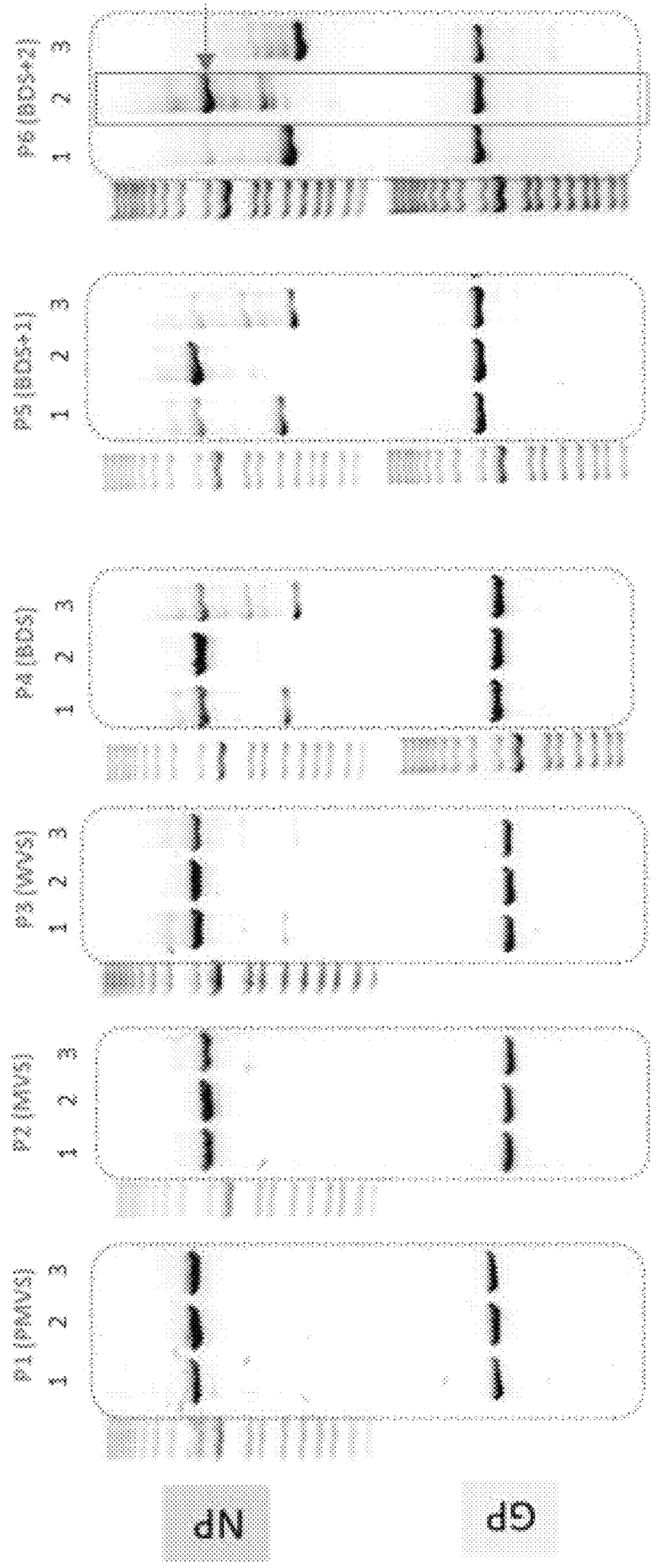

FIG. 55 illustrates transgene stability analysis of TT2-HIV-GNP1/PN1 (having transgenes encoding fusion polypeptides SEQ ID NOs: 94 and 95). Shown are transgene PCR results for 3 biological replicates (1-3) and for indicated passaging levels. The last passage showing ≥50% full length transgene was visually assessed.

Figure 56:
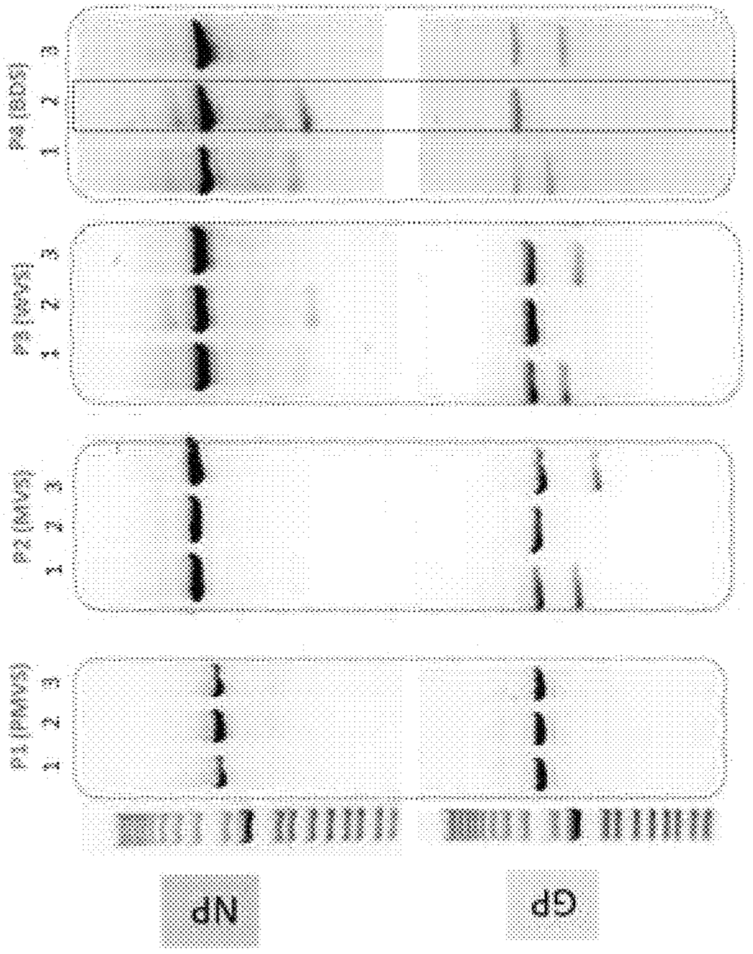

FIG. 56 illustrates transgene Stability analysis of TT2-HIV-GNP2/PN2 (having transgenes encoding fusion polypeptides SEQ ID NOs: 95 and 97). Shown are transgene PCR results for 3 biological replicates (1-3) and for indicated passaging levels. Passaging was discontinued at passage level 4. The (presumably) last passage showing ≥50% full length transgene was visually assessed.

Figure 57:
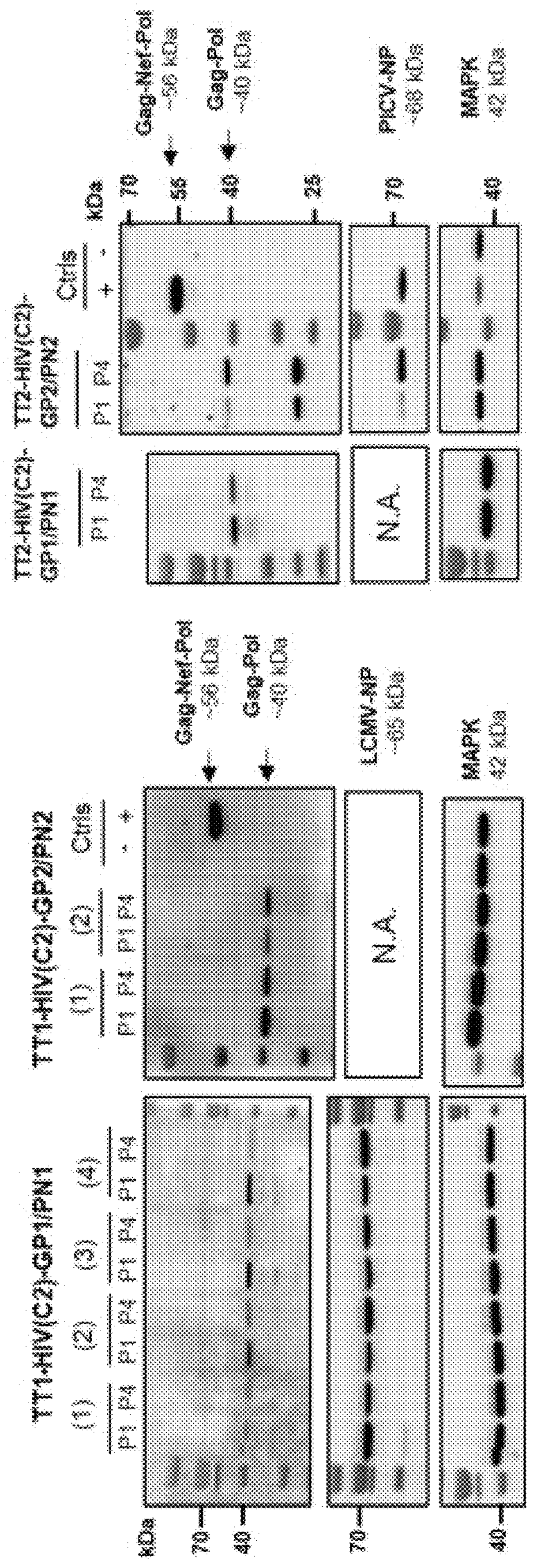

FIG. 57 illustrates immunoblot analysis of replication-attenuated arenavirus vectors. Transgene expression Gag/Pol from stock material (P1) and BDS-equivalent passage (P4) of replication-attenuated-LCMV and replication-attenuated-PICV HIV Immunogen 2 vectors, was determined by immunoblot staining of the Gag epitope p24 (mAb anti HIV1 p24; Abcam). Whole cell lysates of biological replicates (1, 2, 3, 4 for TT1-HIV(C2)-GP1/PN1; 1, 2 for TT1-HIV(C2)-GP2/PN2) or representative samples (TT2-HIV(C2)-GP1/PN1 and TT2-HIV(C2)-GP2/PN2) were analyzed. TT1=replication-attenuated-LCMV; TT2=replication-attenuated-PICV. GP=Gag/Pol; PN=Pol/Nef Ctrls=positive (+) control represents TT1-HIV Immunogen 2 or TT2-HIV Immunogen 2 infected cell lysates; negative (−) control represents uninfected cells.

Figure 58:
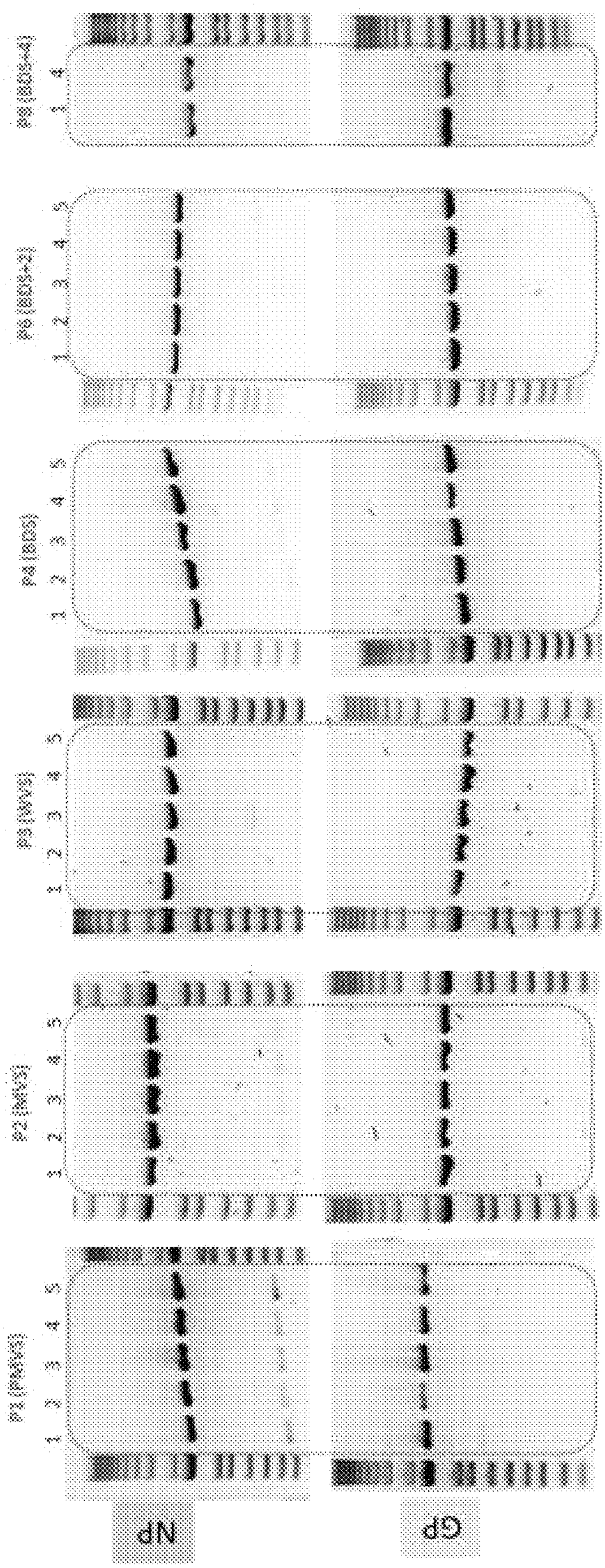

FIG. 58 illustrates transgene stability analysis of TT1-HIV(C2)-GP1/PN1. A Shown are transgene PCR results for 5 biological replicates (1-5) and for indicated passaging levels. The expected size of the full-length PCR product is 1359 bp (LCMV-GP1 NP-Segment) and 1366 bp (LCMV-PN1 GP-Segment), respectively. The last passage showing ≥50% full length transgene was visually assessed.

Figure 59:
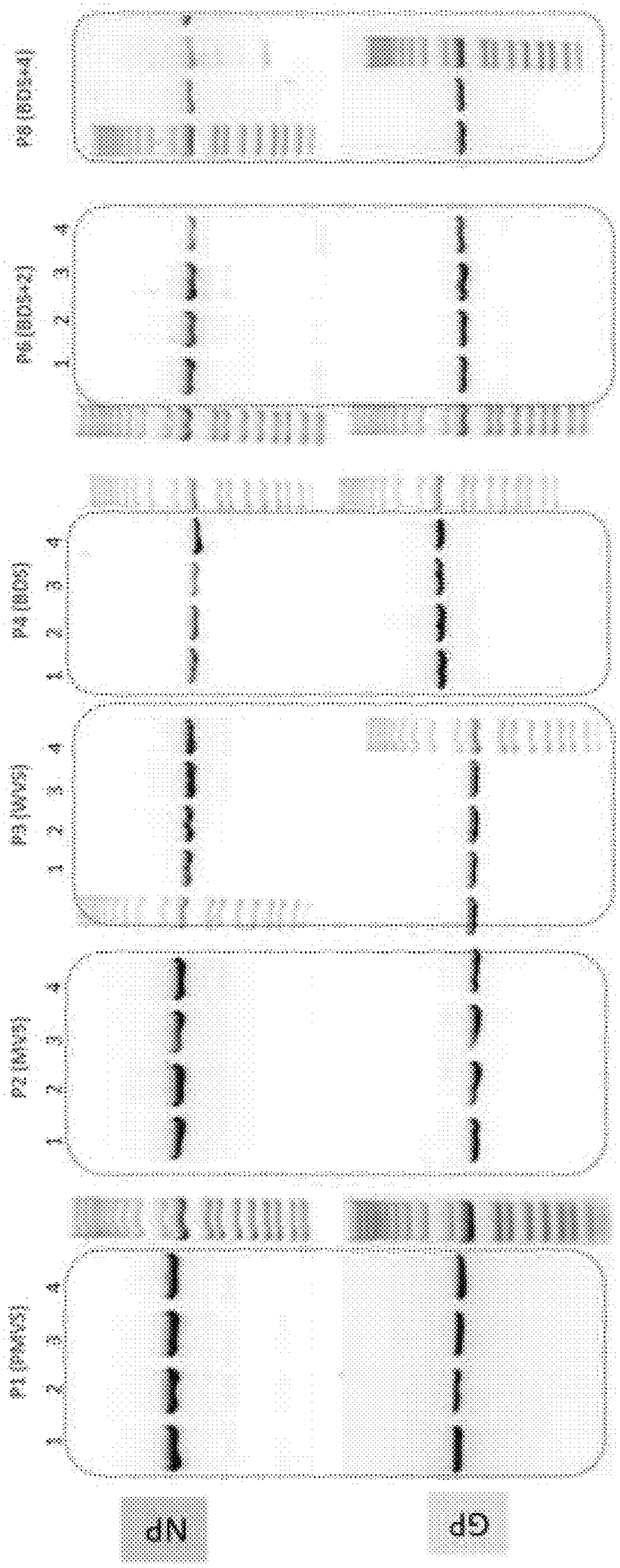

FIG. 59 illustrates transgene stability analysis of TT1-HIV(C2)-GNP2/PN2. A Shown are transgene PCR results for 4 biological replicates (1-4) and for indicated passaging levels. The expected size of the full-length PCR product is 1344 bp (LCMV-GP2 NP-Segment) and 1364 bp (LCMV-PN2 GP-Segment), respectively. The last passage showing ≥50% full length transgene was visually assessed.

Figure 60:
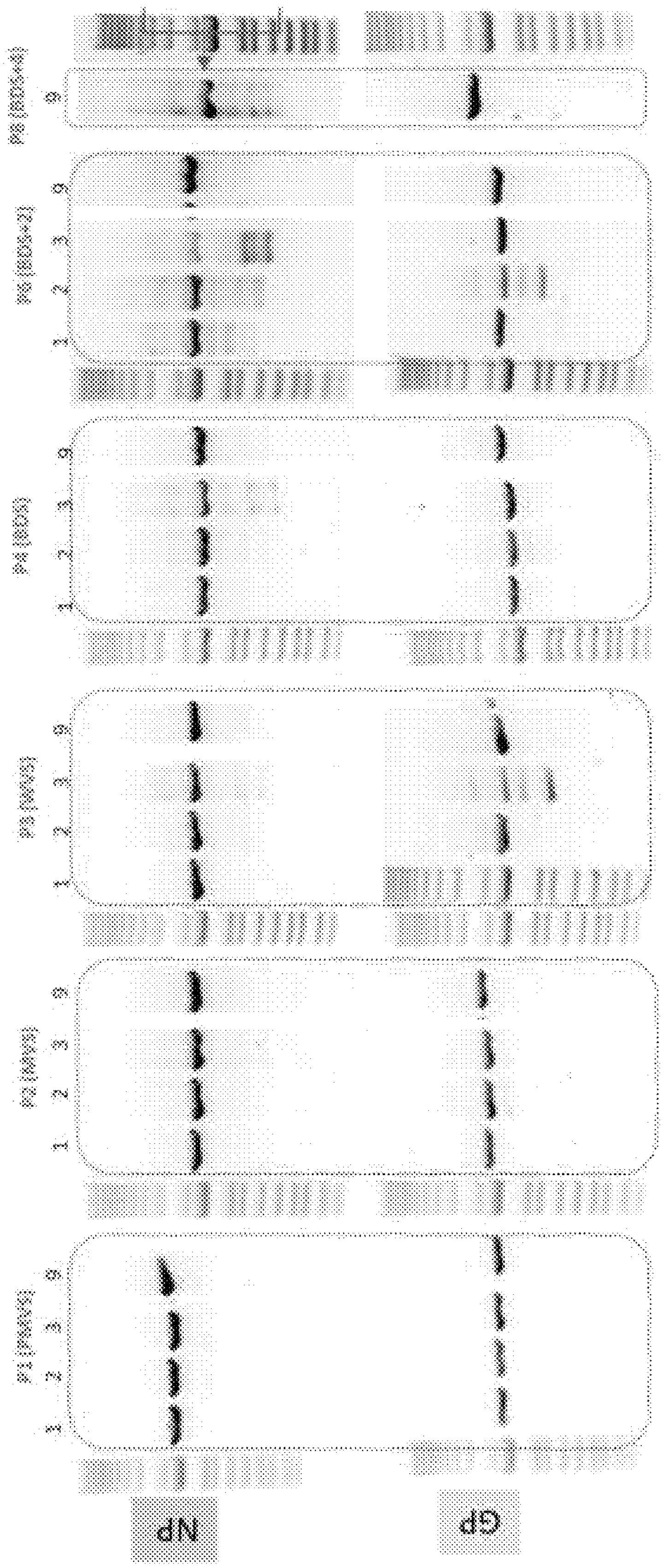

FIG. 60 illustrates transgene stability analysis of TT2-HIV(C2)-GP1/PN1. A Shown are transgene PCR results for 4 biological replicates (1-3 and 9) and for indicated passaging levels. The expected size of the full-length PCR product is 1456 bp (PICV-GP1 NP-Segment) and 1496 bp (PICV-PN1 GP-Segment), respectively. The last passage showing ≥50% full-length transgene was visually assessed.

Figure 61:
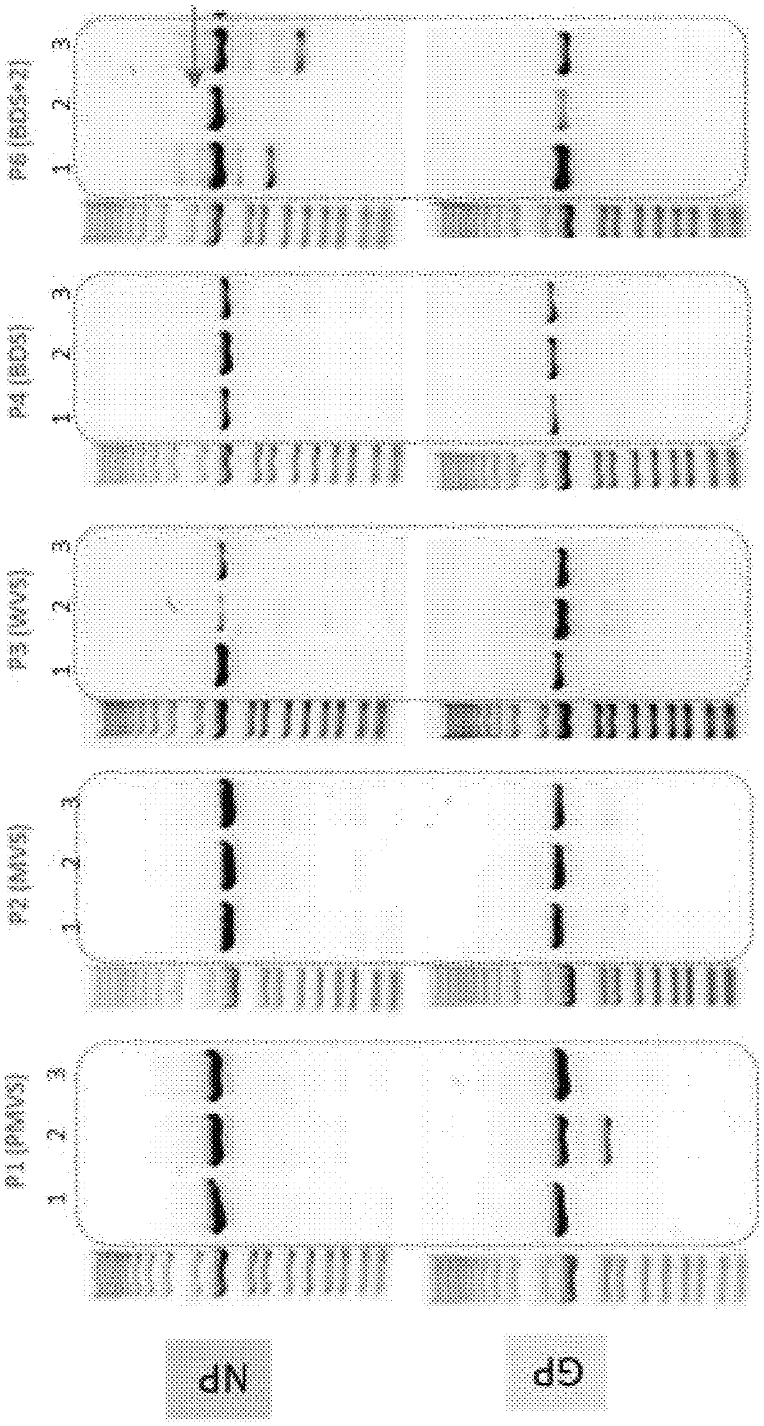

FIG. 61 illustrates transgene stability analysis of TT2-HIV(C2)-GP2/PN2. Shown are transgene PCR results for 3 biological replicates (1-3) and for indicated passaging levels. The expected size of the full-length PCR product is 1450 bp (PICV-GP2 NP-Segment) and 1505 bp (PICV-PN2 GP-Segment), respectively. Passaging was discontinued at passage level 6. The (presumably) last passage showing ≥50% full length transgene was visually assessed.

Figure 62:
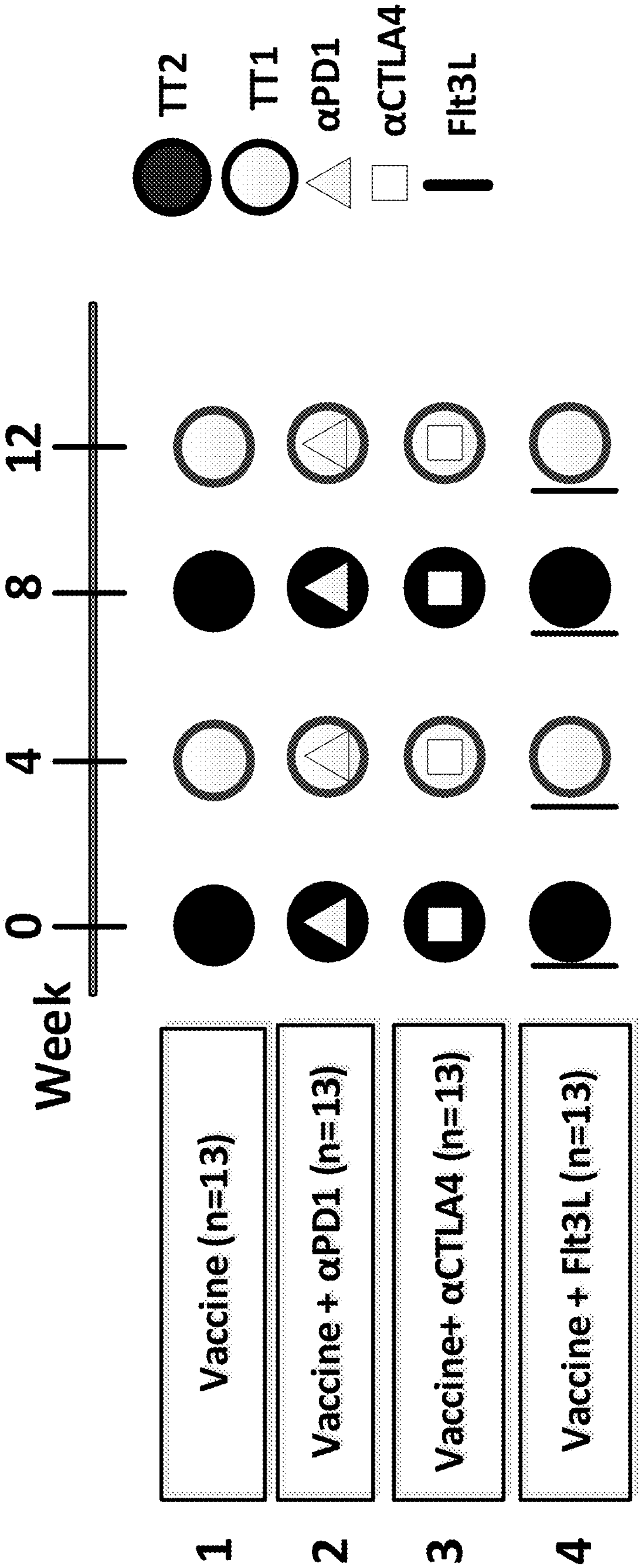

FIG. 62 illustrates a schematic of non-human primate study evaluating combination of TT2/TT1 vaccine replication-attenuated PICV/LCMV arenavirus prime-boost scheme in combination with immune modulators. Each group had 13 rhesus macaques. Vaccine refers to alternating dosing of TT2 (closed circles) and TT1 (open circles). Checkpoint inhibitors αPD1 antibody (triangle) and αCTLA4 antibody (square) were administered immediately after the vaccine. FLT3L-Fc FLT3 agonist (black line) was administered one week before each vaccine dosing.

Figure 63:
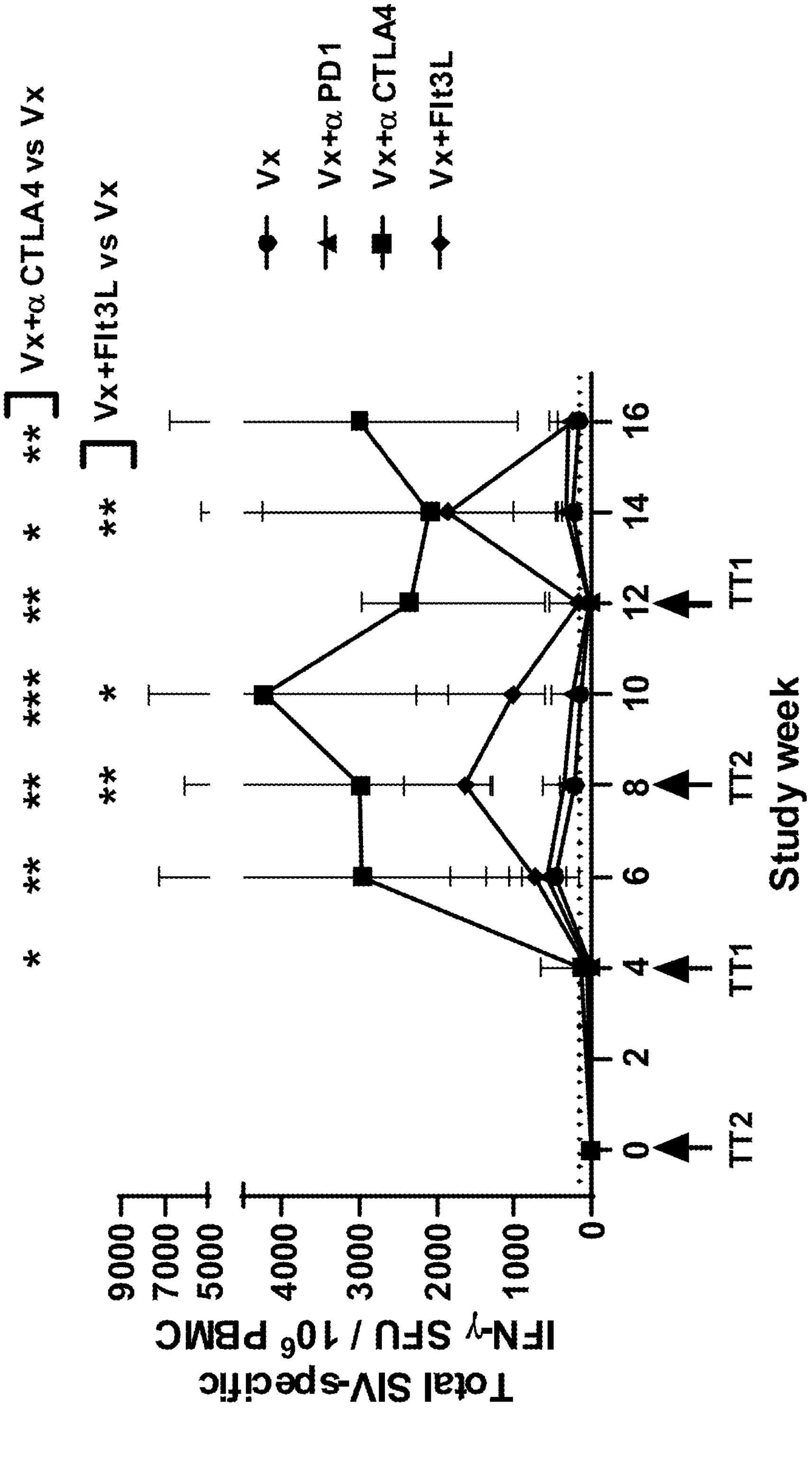

FIG. 63 illustrates the kinetics of total responses to Gag, Env and Pol was assessed by IFN-γ ELISpot in PBMCs isolated from NHP peripheral blood at two week intervals post 1st vaccine dose up to week 16. Median with interquartile range are shown. Statistical analysis by two-way ANOVA with repeated measures and Dunnett's post-test was performed. * $p<0.05$,  $p<0.01$, * $p<0.001$ for comparison of combination group with vaccine alone.

FIGS. 64A-D illustrates the breadth of (A) total SIV, (B) Gag, (C) Env and (D) Pol-specific IFN-γ responses at 2 weeks post last vaccine dose in PBMCs. Vector (Vx) only group in circles, Vx+αPD1 in triangles, Vx+αCTLA4 in squares and Vx+Flt3L in diamonds. Statistical analysis by Kruskal-Wallis test with Dunn's post-test was performed. Data are represented as median±IQR. * $p<0.05$,  $p<0.01$, * $p<0.001$, **** $p<0.0001$.

DETAILED DESCRIPTION

1. Introduction

Herein is described an antiviral vaccine immune design approach that incorporates intra-patient diversity by using deep sequence data to evaluate viral quasispecies and determine the level of viral diversity within an individual. We developed an algorithm that considers both the interpatient as well as intrapatient viral diversity in the design of the vaccine immunogen, as well as immunogenicity of vaccine sequences. Understanding host viral diversity and antigen processing and presentation and T cell priming not only ensures that a vaccine immunogen generates a large number of antigen specific T cells, but also generates antigen specific T cells with cytotoxic activity. In the design of the antiviral vaccine immunogen we have combined computational in silico analysis of viral sequences and binding specificities with in vitro experimental immunology. We established an in vitro vaccine trial model that has enabled us to identify conserved regions that generate the strongest response across a large population. The approach has enabled us to identify novel epitopes within the conserved region that had previously not been recognized. This immunogenicity data has enabled the development of highly conserved, highly immunogenic vaccine immunogens that can be delivered to a broad population.

Provided herein are fusion polypeptides comprising a plurality of polypeptide or peptide segments and related compositions, including immunogenic compositions and pharmaceutical compositions, as well as methods for making the fusion polypeptides and methods for their use to elicit an immunogenic response to a human immunodeficiency virus (HIV-1) in a subject in need thereof. As used herein, an "immunogen" is a substance, such as an antigen, that elicits an immune response or is capable of eliciting an immune response. Also provided are polynucleotides encoding the fusion polypeptides described herein, as well as vectors comprising same.

Provided herein are fusion polypeptides designed to induce an antiviral immune response. The vaccine constructs described herein were designed to provide mathematically-determined improved coverage of predicted T cell epitopes ("PTE") using the most highly conserved predicted epitopes within a source set of viral proteome sequences. As a paradigm for the methods of designing antiviral immunogens, fusion polypeptides encoded at least two of the HIV-1 genes gag, pol and nef were used. The fusion polypeptides and methods described herein both retain the positional information of the PTE's within the source set of sequences and construct a bivalent set of sequences to improve coverage of conserved PTEs. Accordingly, described herein are multivalent, e.g., bivalent, vaccine constructs that advantageously improve or increase highly conserved PTEs that are most likely to be highly similar to conserved epitopes in the naturally occurring sequences in proteins expressed by viral species amongst a population of patients and within an individual patient, due to both the retained positional information. In addition, the use of only highly conserved PTE sequences amongst HIV-1 species in interpatient populations reduces the likelihood of escape mutants because the highly conserved sequences are more likely to contribute viral structure and function.

Further provided are computational approaches for designing antiviral vaccine immunogens for a highly variable virus, such as HIV-1. The antiviral immunogens can be designed to provide coverage at an individual level, for a group of individuals with a defined set of HLA alleles, or for broad population coverage. In the herein described vaccine immunogen design methods, we define a computational approach for targeting conserved regions within a vaccine sequence using bulk population sequences, e.g., from public databases and internally developed databases. Further, using individual patient deep sequence data we define sequence variability for each potential T cell epitope within the conserved regions. Moreover, we identify regions that may serve as actual epitopes based on likelihood of presentation by the individual host's set of HLA alleles. The likelihood of binding to host HLA defined by publicly available and internally-developed databases, was used to develop deep learning models that model peptide binding per allele. This can be coupled with in-silico, published and/or experimental in-vitro T cell priming data that can define the potential impact of antigen variants in modulating TCR recognition or identify a peptide as an escape variant. This data is used to design a set of peptide immunogens that contain the epitopes and associated epitope variants. The epitope sequences are concatenated or connected in series into a single fusion polypeptide, either directly fused or linked via a linker sequence. Peptide segments are joined in a computationally determined sequential order from N-terminus to C-terminus that reduces or eliminates the creation of junctional epitopes that may mimic human self-antigens and have undesirable effects (e.g., eliciting an autoimmune response or a tolerogenic response).

Unlike similar graph-based approaches to vaccine design, the approaches described herein build segments of connected PTE's using only adjacent PTE's that are also adjacent in the natural sequences. In addition, the present methods first build a bivalent construct consisting of two polypeptides matched to improve or increase coverage at each PTE position in the viral proteome. The bivalent construct itself may be used as a vaccine, as in the constructs described in Examples 1 and 2 below. The bivalent constructs designed by analysis of population-based sequences (e.g., interpatient diversity) identifies population-based conserved sequences that may contribute to viral structure.

The methods described herein can begin with the identification of conserved region bivalent sequences, using a process referred to herein as the "Conservation Analysis" or "Conservation Algorithm." The methods further can comprise a step of building a bivalent vaccine construct having maximal epitope coverage while retaining the positional information of the PTE's from the natural sequences, using a process referred to referred to herein as a "Conserved Walking Algorithm" or "CWA."

2. Fusion Polypeptides Useful to Promote Immune Response Against Human Immunodeficiency Virus-1 (HIV-1)

Provided herein are fusion polypeptides comprising a plurality of polypeptide or peptide segments encoded by one or more HIV-1 genes. A 'segment' of a fusion polypeptide described herein is a contiguous sequence of at least 25 amino acids with respect to a reference sequence, for example HIV-1 HXB2 reference sequences for Gag, Pol and Nef polypeptides, provided herein as SEQ ID NOs: 1-3, respectively. The polypeptides described herein are 'fusion' polypeptides in the sense that they are assembled from connected or concatenated polypeptide or peptide segments of two or more HIV-1 proteins, e.g., at least Pol and Nef. With respect to the HIV-1 protein reference sequences, the polypeptide or peptide segments may correspond to discontinuous sequences of the same HIV-1 protein or different HIV-1 proteins. Generally, the fusion polypeptides are non-naturally occurring, and can be synthetic or recombinantly produced.

In various embodiments, immunogenic polypeptides or fusion polypeptides described herein, and/or the polynucleotides encoding such polypeptides, are provided in isolated form. This means that the polypeptide or polynucleotide is at least 50% w/w pure of interfering proteins, cellular and other contaminants arising from its production or purification but does not exclude the possibility that the agent is combined with an excess of pharmaceutical acceptable carrier(s) or other vehicle intended to facilitate its use. The term "isolated," when applied to a polypeptide or polynucleotide, as described herein, denotes that the polypeptide or polynucleotide is essentially free of cellular components with which it is associated in the natural state. It can be, for example, in a homogeneous state and may be in either a dry or aqueous solution. Purity and homogeneity can be determined using known methods, e.g., analytical chemistry techniques such as polyacrylamide gel electrophoresis, column chromatography, thin layer chromatography, or high-performance liquid chromatography (HPLC) analysis. A protein that is the predominant species present in a preparation is substantially purified. An "isolated" or "purified" polypeptide or polynucleotide is substantially free of other cellular material, or culture medium when produced by recombinant techniques, or chemical precursors or other chemicals when chemically synthesized. In various embodiments, purified polypeptides and/or polynucleotides are at least 60%, 70%, 75%, 80%, 85%, 90%, 91%, 92%, 93%, 94%, 95%, 96%, 97%, 98%, 99%, or 100% (w/w), separated from, purified of, or free of interfering proteins and contaminants from production or purification. Often an immunogenic polypeptides or fusion polypeptides described herein, and/or the polynucleotides encoding such polypeptides, is the predominant macromolecular species remaining after its purification.

a. Polypeptide Segments

With respect to the HIV-1 genes encoding the polypeptide segments used to assemble the herein described fusion polypeptides, in various embodiments, the fusion polypeptides comprise a plurality of polypeptide segments of one or more human immunodeficiency virus-1 (HIV-1) proteins encoded by one or more, e.g. two or more, three or more, HIV-1 genes selected from Gag, Pol and Nef. In some embodiments, the plurality of polypeptide segments is comprised of only polypeptide segments encoded by HIV-1 genes pol and nef e.g., does not comprise polypeptide segments encoded by HIV-1 genes gag, env, tat, rev, vpr, vif and vpu. In some embodiments, the plurality of polypeptide segments is comprised of only polypeptide segments encoded by HIV-1 genes gag, pol and nef and does not comprise polypeptide segments encoded by HIV-1 genes env, tat, rev, vpr, vif and vpu.

With respect to the number of polypeptide segments assembled, connected, linked or concatenated into a single fusion polypeptide, in various embodiments, the fusion polypeptides are comprised of at least 4 and up to 6 polypeptide segments, e.g., 4, 5 or 6 polypeptide segments. As appropriate, the polypeptide segments can be arranged in the same order or according to a different order than in the naturally occurring proteins. In various embodiments, the fusion polypeptides comprise from 1 to 4 Pol polypeptide segments, from 1 to 2 Nef polypeptide segments, and optionally, from 1 to 3 Gag polypeptide segments.

With respect to the regions of the polypeptides encoded by an HIV-1 gene selected as polypeptide segments to include in the fusion polypeptides, in various embodiments, the polypeptide segments are derived from conserved regions in a population of viral proteome sequences. In some embodiments, the conserved regions are greater than 80%, e.g., greater than 81%, 82%, 83%, 84%, 85%, 86%, 87%, 88%, 89%, 90%, 91%, 92%, 93%, 94%, 95%, 96%, 97%, 98% or 99% conserved amongst HIV-1 species, e.g., as determined in interpatient populations. As used herein, conserved regions in a polypeptide encoded by an HIV-1 gene refers to the percentage of sequences in a population of sequences containing identical amino acid segments or subsequences e.g., segments 9 amino acids in length or 9-mers as the most prevalent one in a predetermined amino acid segment or subsequence position, where an amino acid segment or subsequence position is determined with respect to a reference sequence, e.g., HIV-1 HXB2 polypeptide sequences, e.g., SEQ ID NOs: 1-3. The start and end positions of the HIV polypeptides identified herein are with respect to HIV-1 HXB2 reference polypeptides, GenBank Accession No. K03455 (ncbi.nlm.nih.gov/nuccore/K03455), provided herein as SEQ ID NOs: 1-3 and identified in Table A. As used herein, numbering of a given amino acid polymer or nucleic acid polymer "corresponds to", is "corresponding to" or is "relative to" the numbering of a selected or reference amino acid polymer or nucleic acid polymer when the position of any given polymer component (e.g., amino acid, nucleotide, also referred to generically as a "residue") is designated by reference to the same or to an equivalent position (e.g., based on an optimal alignment or a consensus sequence) in the selected amino acid or nucleic acid polymer, rather than by the actual numerical position of the component in the given polymer. In various embodiments, the conserved regions are conserved amongst one or more of HIV-1 clades within Group M, e.g., one or more of HIV-1 clades A-K, e.g., one or more of clades A, B, C, D and G, e.g., amongst HIV-1 Group M, clade B, and recombinant forms thereof, e.g., CRF01_AE.

TABLE A

HIV-1 HXB2 reference sequences

| SEQ ID NO: | gene | Amino acid sequence of encoded protein |
|---|---|---|
| 1 | gag | MGARASVLSGGELDRWEKIRLRPGGKKKYKLKHIVWASRELERFAVNPGLLETSEG<br>CRQILGQLQPSLQTGSEELRSLYNTVATLYCVHQRIEIKDTKEALDKIEEEQNKSK<br>KKAQQAAADTGHSNQVSQNYPIVQNIQGQMVHQAISPRTLNAWVKVVEEKAFSPEV<br>IPMFSALSEGATPQDLNTMLNTVGGHQAAMQMLKETINEEAAEWDRVHPVHAGPIA<br>PGQMREPRGSDIAGTTSTLQEQIGWMTNNPPIPVGEIYKRWIILGLNKIVRMYSPT |

TABLE A-continued

| HIV-1 HXB2 reference sequences | | |
|---|---|---|
| SEQ ID NO: | gene | Amino acid sequence of encoded protein |
| | | SILDIRQGPKEPFRDYVDRFYKTLRAEQASQEVKNWMTETLLVQNANPDCKTILKALGPAATLEEMMTACQGVGGPGHKARVLAEAMSQVTNSATIMMQRGNERNQRKIVKCFNCGKEGHTARNCRAPRKKGCWKCGKEGHQMKDCTERQANFLGKIWPSYKGRPGNFLQSRPEPTAPPEESFRSGVETTTPPQKQEPIDKELYPLISLRSLFGNDPSSQ |
| 2 | pol | FFREDLAFLQGKAREFSSEQTRANSPTRRELQVWGRDNNSPSEAGADRQGTVSFNFPQVTLWQRPLVTIKIGGQLKEALLDTGADDTVLEEMSLPGRWKPKMIGGIGGFIKVRQYDQILIEICGHKAIGTVLVGPTPVNIIGRNLLTQIGCTLNFPISPIETVPVKLKPGMDGPKVKQWPLTEEKIKALVEICTEMEKEGKISKIGPENPYNTPVFAIKKKDSTKWRKLVDFRELNKRTQDFWEVQLGIPHPAGLKKKKSVTVLDVGDAYFSVPLDEDFRKYTAFTIPSINNETPGIRYQYNVLPQGWKGSPAIFQSSMTKILEPFRKQNPDIVIYQYMDDLYVGSDLEIGQHRTKIEELRQHLLRWGLTTPDKKHQKEPPFLWMGYELHPDKWTVQPIVLPEKDSWTVNDIQKLVGKLNWASQIYPGIKVRQLCKLLRGTKALTEVIPLTEEAELELAENREILKEPVHGVYYDPSKDLIAEIQKQGQGQWTYQIYQEPFKNLKTGKYARMRGAHTNDVKQLTEAVQKITTESIVIWGKTPKFKLPIQKETWETWWTEYWQATWIPEWEEVNTPPLVKLWYQLEKEPIVGAETFYVDGAANRETKLGKAGYVTNRGRQKVVTLTDTTNQKTELQAIYLALQDSGLEVNIVTDSQYALGIIQAQPDQSESELVNQIIEQLIKKEKVYLAWVPAHKGIGGNEQVDKLVSAGIRKVLFLDGIDKAQDEHEKYHSNWRAMASDFNLPPVVAKEIVASCDKCQLKGEAMHGQVDCSPGIWQLDCTHLEGKVILVAVHVASGYIEAEVIPAETGQETAYFLLKLAGRWPVKIIHTDNGSNFTGATVRAACWWAGIKQEFGIPYNPQSQGVVESMNKELKKIIGQVRDQAEHLKTAVQMAVFIHNFKRKGGIGGYSAGERIVDIIATDIQTKELQKQITKIQNFRVYYRDSRNPLWKGPAKLLWKGEGAVVIQDNSDIKVVPRRKAKIIRDYGKQMAGDDCVASRQDED |
| 3 | nef | MGGKWSKSSVIGWPTVRERMRRAEPAADRVGAASRDLEKHGAITSSNTAATNAACAWLEAQEEEEVGFPVTPQVPLRPMTYKAAVDLSHFLKEKGGLEGLIHSQRRQDILDLWIYHTQGYFPDWQNYTPGPGVRYPLTFGWCYKLVPVEPDKIEEANKGENTSLLHPVSLHGMDDPEREVLEWRFDSRLAFHHVARELHPEYFKNC |

In some embodiments, the plurality of polypeptide segments comprises at least 4 polypeptide segments, e.g., at least 4, 5, 6 or more, polypeptide segments selected from SEQ ID NOs: 4-33, e.g., polypeptide segments identified in Table B.

TABLE B

| polypeptide segments in HIV-1 fusion polypeptides | | | | | |
|---|---|---|---|---|---|
| SEQ ID NO: | Gene | Start | End | Length (aa) | Sequence |
| 4 | gag | 1 | 53 | 53 | MAARASVLSGGELDRWEKIRLRPGGKKKYRLKHIVWASRELERFAVNPGLLET |
| 5 | gag | 1 | 53 | 53 | MAARASILSGGKLDKWEKIRLRPGGRKKYKLKHLVWASRELERFALNPGLLET |
| 6 | gag | 147 | 369 | 223 | ISPRTLNAWVKVVEEKAFSPEVIPMFSALSEGATPQDLNTMLNTVGGHQAAMQMLKETINEEAAEWDRLHPVHAGPIAPGQMREPRGSDIAGTTSTLQEQIGWMTNNPPIPVGEIYKRWIILGLNKIVRMYSPTSILDIRQGPKEPFRDYVDRFYKTLRAEQASQEVKNWMTETLLVQNANPDCKTILKALGPAATLEEMMTACQGVGGPGHKARVLAEAMSQ |
| 7 | gag | 147 | 369 | 223 | LSPRTLNAWVKVIEEKAFSPEVIPMFTALSEGATPHDLNTMLNTIGGHQAAMQMLKDTINEEAAEWDRVHPVHAGPVAPGQMRDPRGSDIAGSTSTLQEQIAWMTNNPPIPVGDIYKRWIIMGLNKIVRMYSPVSILDIKQGPKEPERDYVDRFYRTLRAEQASQDVKNWMTETLLVQNSNPDCKTILKALGPGATLEEMMSACQGVGGPSHKARVLAEAMCQ |
| 8 | pol | 56 | 117 | 62 | FPQITLWQRPLVTIKIGGQLKEALLDTGADDTVLEEMNLPGRWKPKMIGGIGGFIKVRQYDQ |
| 9 | pol | 56 | 117 | 62 | LPQITLWQRPIVTIKIGGQIKEALLDTGADDTVLEDMNLPGKWKPKMIGGIGGFIKVKQYDQ |

TABLE B-continued polypeptide segments in HIV-1 fusion polypeptides

| SEQ ID NO: | Gene | Start | End | Length (aa) | Sequence |
|---|---|---|---|---|---|
| 10 | pol | 129 | 320 | 192 | GTVLVGPTPVNIIGRNLLTQIGCTLNFPISPIE TVPVKLKPGMDGPKVKQWPLTEEKIKALVEICT EMEKEGKISKIGPENPYNTPVFAIKKKDSTKWR KLVDFRELNKRTQDFWEVQLGIPHPAGLKKKKS VTVLDVGDAYFSVPLDKDFRKYTAFTIPSINNE TPGIRYQYNVLPQGWKGSPAIFQSSMT |
| 11 | pol | 129 | 320 | 192 | GTVLIGPTPVNIIGRNLLTQLGCTLNFPISPID TVPVKLKPGMDGPRVKQWPLTEEKIKALIEICT EMEKEGKISRIGPENPYNTPIFAIKKKDGTKWR KLVDFRELNKKTQDFWEVQLGIPHPSGLKKKKS VTVLDIGDAYFSVPLDKEFRKYTAFTVPSTNNE TPGVRYQYNVLPMGWKGSPAIFQCSMT |
| 12 | pol | 367 | 431 | 65 | WGFTTPDKKHQKEPPFLWMGYELHPDKWTVQPI VLPEKDSWTVNDIQKLVGKLNWASQIYPGIKV |
| 13 | pol | 367 | 431 | 65 | WGLTTPDKKHQKDPPFLWMGYELHPDRWTVQPI ELPEKESWTVNDIQKLIGKLNWASQIYAGIKV |
| 14 | pol | 542 | 606 | 65 | PKFKLPIQKETWETWWTEYWQATWIPEWEFVNT PPLVKLWYQLEKEPIVGAETFYVDGAANRETK |
| 15 | pol | 542 | 606 | 65 | PKFRLPIQKETWDTWWIDYWQATWIPEWEFTNT PPLVKLWYQLETEPIAGVETFYVDGASNRETK |
| 16 | pol | 586 | 606 | 21 | KEPIVGAETFYVDGAANRETK |
| 17 | pol | 586 | 606 | 21 | TEPIAGVETFYVDGASNRETK |
| 18 | pol | 683 | 708 | 26 | KEKVYLAWVPAHKGIGGNEQVDKLVS |
| 19 | pol | 683 | 708 | 26 | KEKIYLAWVPAHKGIGGNEQIDKLVS |
| 20 | pol | 747 | 827 | 81 | VAKEIVASCDKCQLKGEAMHGQVDCSPGIWQLD CTHLEGKIILVAVHVASGYIEAEVIPAETGQET AYFLLKLAGRWPVKT |
| 21 | pol | 747 | 827 | 81 | VAKEIVACCDKCQLKGEAIHGQVDCSPGVWQLD CTHLEGKVILVAVHVASGYIEAEIIPTETGQET AYFILKLAGRWPVTT |
| 22 | pol | 840 | 909 | 69 | TVKAACWWAGIKQEFGIPYNPQSQGVVESMNKE LKKIIGQVRDQAEHLKTAVQMAVFIHNFKRKGG IGG |
| 23 | pol | 840 | 909 | 69 | AVKAACWWAGVKQEFGIPYNTQSQGVVESMNNE LKKIIGQIRDQAEHLKTAVQMAVLIHNFKRKGG IGE |
| 24 | pol | 840 | 920 | 81 | TVKAACWWAGIKQEFGIPYNPQSQGVVESMNKE LKKIIGQVRDQAEHLKTAVQMAVFIHNFKRKGG IGGYSAGERIVDIIA |
| 25 | pol | 840 | 920 | 81 | AVKAACWWAGVKQEFGIPYNTQSQGVVESMNNE LKKIIGQIRDQAEHLKTAVQMAVLIHNFKRKGG IGEYSAGERIIDIIA |
| 26 | pol | 932 | 1003 | 72 | ITKIQNFRVYYRDSRDPLWKGPAKLLWKGEGAV VIQDNSDIKVVPRRKAKIIRDYGKQMAGDDCVA SRQDED |
| 27 | pol | 932 | 1003 | 72 | ITKLQNFRVYYRDNRDPLWKGPARLLWKGEGAV VIQDNSEIKVVPRRKVKIIRDYGKRMAGDDCVA GRQDED |
| 28 | nef | 64 | 76 | 13 | EEVGFPVKPQVPL |
| 29 | nef | 64 | 76 | 13 | EEVGFPVRPQVPL |
| 30 | nef | 64 | 99 | 36 | EEVGFPVKPQVPLRPMTFKGALDLSHFLREKGG LEG |

TABLE B-continued polypeptide segments in HIV-1 fusion polypeptides

| SEQ ID NO: | Gene | Start | End | Length (aa) | Sequence |
|---|---|---|---|---|---|
| 31 | nef | 64 | 99 | 36 | EEVGFPVRPQVPLRPMTYKGALDLSHFLKEKGG LEG |
| 32 | nef | 117 | 148 | 32 | TQGYFPDWQNYTPGPGTRYPLTFGWCFKLVPV |
| 33 | nef | 117 | 148 | 32 | TQGFFPDWQNYTPGPGIRFPLTFGWCFKLVPL |

In various embodiments, the fusion polypeptide comprises two, three, four, five, six, or more, of the polypeptide segments comprising or consisting of amino acid residues corresponding to Gag 1-53; Gag 147-369; Pol 56-117; Pol 129-320; Pol 367-431 Pol 542-606; Pol 586-606; Pol 683-708, Pol 747-827; Pol 840-909; Pol 840-920; Pol 932-1003; Nef 64-76; Nef 64-99 or Nef 117-148, wherein the Gag, Pol and Nef amino acid position numbers correspond to HIV-1 HXB2 reference sequences, as set forth in SEQ ID NOs: 1, 2 and 3, respectively. In some embodiments, the fusion polypeptide comprises two, three, four, five, six, or more, polypeptide segments selected from SEQ ID NOs: 4-33.

In some embodiments, the fusion polypeptide comprises or consists of the following polypeptide segments, wherein the Gag, Pol and Nef amino acid position numbers correspond to SEQ ID NOs: 1, 2 and 3, respectively:

a) amino acid residues corresponding to: Gag 1-53; Gag 147-369; Pol 683-708 and Nef 117-148;
b) amino acid residues corresponding to: Pol 56-117; Pol 129-320; Pol 367-431 and Nef 64-99;
c) amino acid residues corresponding to: Pol 542-606; Pol 747-827; Pol 840-920; Pol 932-1003 and Nef 64-99;
d) amino acid residues corresponding to: Gag 1-53; Gag 147-369; Pol 683-708; Pol 747-827; Pol 840-920 and Nef 117-148;
e) amino acid residues corresponding to: Pol 56-117; Pol 129-320; Pol 367-431; Pol 542-606; Pol 932-1003 and Nef 64-99;
f) amino acid residues corresponding to: Gag 147-369, Pol 586-606, Pol 683-708 and Pol 840-920;
g) amino acid residues corresponding to: Pol 129-320, Pol 747-827, Pol 932-1003 and Nef 64-76; or
h) amino acid residues corresponding to: Gag: 147-369, Pol 747-827, Pol 840-909 and Nef 64-76.

In some embodiments, the fusion polypeptide comprises or consists of the following polypeptide segments:

a) SEQ ID NOs: 4, 6, 18 and 32, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 4, 6, 18 and 32, respectively;
b) SEQ ID NOs: 5, 7, 19 and 33, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 5, 7, 19 and 33, respectively;
c) SEQ ID NOs: 8, 10, 12 and 30 or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 8, 10, 12 and 30, respectively;
d) SEQ ID NOs: 9, 11, 13 and 31, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 9, 11, 13 and 31, respectively;
e) SEQ ID NOs: 14, 20, 24, 26 and 30, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 14, 20, 24, 26 and 30, respectively;
f) SEQ ID NOs: 15, 21, 25, 27 and 31, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 15, 21, 25, 27 and 31, respectively;
g) SEQ ID NOs: 4, 6, 18, 20, 24 and 32, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 4, 6, 18, 20, 24 and 32, respectively;
h) SEQ ID NOs: 5, 7, 19, 21, 25 and 33, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 5, 7, 19, 21, 25 and 33, respectively;
i) SEQ ID NOs: 8, 10, 12, 14, 26 and 30, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 8, 10, 12, 14, 26 and 30, respectively;
j) SEQ ID NOs: 9, 11, 13, 15, 27 and 31, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 9, 11, 13, 15, 27 and 31, respectively;
k) SEQ ID NOs: 6, 16, 18 and 24, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 6, 16, 18 and 24, respectively;
l) SEQ ID NOs: 7, 17, 19 and 25, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 7, 17, 19 and 25, respectively;
m) SEQ ID NOs: 10, 20, 26 and 28, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 10, 20, 26 and 28, respectively;
n) SEQ ID NOs: 11, 21, 27 and 29, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 11, 21, 27 and 29, respectively;

o) SEQ ID NOs: 6, 20, 22 and 28, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 6, 20, 22 and 28, respectively;

p) SEQ ID NOs: 7, 21, 23 and 29, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 7, 21, 23 and 29, respectively;

q) SEQ ID NOs: 6, 16, 18 and 24, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 6, 16, 18 and 24, respectively;

r) SEQ ID NOs: 7, 17, 19 and 25, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 7, 17, 19 and 25, respectively;

s) SEQ ID NOs: 10, 20, 26 and 28, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 10, 20, 26 and 28, respectively; or t) SEQ ID NOs: 11, 21, 27 and 29, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 11, 21, 27 and 29, respectively.

Modifications may be made in the structure of the fusion polypeptides and polynucleotides encoding such fusion polypeptides, described herein, and still obtain a functional molecule that encodes a variant or derivative polypeptide with desirable (e.g., immunogenic) characteristics. When it is desired to alter the amino acid sequence of a polypeptide to create an equivalent, or even an improved, variant or portion of a fusion polypeptide described herein, one skilled in the art will typically change one or more of the codons of the encoding DNA sequence.

For example, certain amino acids may be substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the polypeptide sequences of the disclosed fusion polypeptides, or corresponding DNA sequences that encode such fusion polypeptides without appreciable loss of their biological utility or activity.

In many instances, a polypeptide variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, WI), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J. (1990) Unified Approach to Alignment and Phylogenes pp. 626-645 Methods in Enzymology vol. 183, Academic Press, Inc., San Diego, CA; Higgins, D. G. and Sharp, P. M. (1989) CABIOS 5: 151-153; Myers, E. W. and Muller W. (1988) CABIOS 4:11-17; Robinson, E. D. (1971) Comb. Theor 77: 105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, CA; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, WI), or by inspection.

One example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides described herein. Software for performing BLAST analyses is publicly available through the National Center for Biotechnology Information (blast.ncbi.nlm.nih.gov/Blast.cgi).

In one illustrative example, cumulative scores can be calculated using, for nucleotide sequences, the parameters M (reward score for a pair of matching residues; always $>0$) and N (penalty score for mismatching residues; always $<0$). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a word length (W) of 11, and expectation (E) of 10, and the BLOSUM62 scoring matrix (see Henikoff and Henikoff (1989) Proc. Natl. Acad. Sci. USA 89: 10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

A "polypeptide variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences described herein and evaluating one or more biological activities of the polypeptide as described herein and/or using any of a number of techniques well known in the art. The term "variant" may also refer to any naturally occurring or engineered molecule comprising one or more nucleotide or amino acid mutations.

In some embodiments, the fusion polypeptide comprises or consists of the following polypeptide segments in sequential order, from N-terminus to C-terminus, optionally joined or connected by one or more linkers:

a) SEQ ID NOs: 6, 4, 18 and 32, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 6, 4, 18 and 32, respectively;
b) SEQ ID NOs: 7, 5, 33 and 19, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 7, 5, 33 and 19, respectively;
c) SEQ ID NOs: 12, 30, 8 and 10, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 12, 30, 8 and 10, respectively;
d) SEQ ID NOs: 9, 31, 13 and 11, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 9, 31, 13 and 11, respectively;
e) SEQ ID NOs: 14, 26, 20, 30 and 24, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 14, 26, 20, 30 and 24, respectively;
f) SEQ ID NOs: 15, 31, 21, 27 and 25, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 15, 31, 21, 27 and 25, respectively;
g) SEQ ID NOs: 32, 18, 4 and 6, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 32, 18, 4 and 6, respectively;
h) SEQ ID NOs: 7, 33, 5 and 19, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 7, 33, 5 and 19, respectively;
i) SEQ ID NOs: 8, 30, 12 and 10, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 8, 30, 12 and 10, respectively;
j) SEQ ID NOs: 13, 31, 9 and 11, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 13, 31, 9 and 11, respectively;
k) SEQ ID NOs: 26, 30, 14, 20 and 24, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 26, 30, 14, 20 and 24, respectively;
l) SEQ ID NOs: 31, 27, 15, 25 and 21, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 31, 27, 15, 25 and 21, respectively;
m) SEQ ID NOs: 24, 6, 4, 20, 18 and 32, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 24, 6, 4, 20, 18 and 32, respectively;
n) SEQ ID NOs: 6, 20, 4, 24, 32 and 18, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 6, 20, 4, 24, 32 and 18, respectively;
o) SEQ ID NOs: 7, 21, 5, 25, 33 and 19, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 7, 21, 5, 25, 33 and 19, respectively;
p) SEQ ID NOs: 8, 30, 14, 12, 26 and 10, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 8, 30, 14, 12, 26 and 10, respectively;
q) SEQ ID NOs: 8, 12, 30, 26, 14 and 10, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 8, 12, 30, 26, 14 and 10, respectively;
r) SEQ ID NOs: 9, 13, 31, 27, 15 and 11, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 9, 13, 31, 27, 15 and 11, respectively;
s) SEQ ID NOs: 20, 32, 24, 4, 6 and 18, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 20, 32, 24, 4, 6 and 18, respectively;

t) SEQ ID NOs: 7, 25, 19, 5, 33 and 21, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 7, 25, 19, 5, 33 and 21, respectively;

u) SEQ ID NOs: 26, 30, 12, 14, 8 and 10, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 26, 30, 12, 14, 8 and 10, respectively;

v) SEQ ID NOs: 15, 31, 9, 27, 13 and 11, or sequence segments that are at least 80%, 81%, 82%, 83%, 84%, 85%8, 86%, 87%, 88%, 89%, 90%, 91%, 92%, 93%, 94%, 95%, 96%, 97%, 98% or 99% identical to SEQ ID NOs: 15, 31, 9, 27, 13 and 11, respectively;

w) SEQ ID NOs: 24, 6, 16 and 18, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 24, 6, 16 and 18, respectively;

x) SEQ ID NOs: 7, 19, 17 and 25, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 7, 19, 17 and 25, respectively;

y) SEQ ID NOs: 24, 16, 6 and 18, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 24, 16, 6 and 18, respectively;

z) SEQ ID NOs: 7, 25, 17 and 19, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 7, 25, 17 and 19, respectively;

aa) SEQ ID NOs: 26, 20, 10 and 28, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 26, 20, 10 and 28, respectively;

bb) SEQ ID NOs: 21, 27, 11 and 29, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 21, 27, 11 and 29, respectively;

cc) SEQ ID NOs: 26, 10, 20 and 28, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 26, 10, 20 and 28, respectively;

dd) SEQ ID NOs: 11, 27, 21 and 29, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 11, 27, 21 and 29, respectively;

ee) SEQ ID NOs: 22, 6, 20 and 28, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 22, 6, 20 and 28, respectively;

ff) SEQ ID NOs: 23, 7, 21 and 29, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 23, 7, 21 and 29, respectively;

gg) SEQ ID NOs: 22, 20, 6 and 28, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 22, 20, 6 and 28, respectively; or hh) SEQ ID NOs: 7, 21, 23 and 29, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 7, 21, 23 and 29, respectively.

Generally, the fusion polypeptides do not comprise any polypeptide segments corresponding to Gag 54-146; Gag 370-500; Pol 1-55; Pol 118-128; Pol 321-366; Pol 432-541; Pol 607-682; Pol 709-746; Pol 828-839; Pol 921-931; Nef 1-63; Nef 100-116 and Nef 149-206, or fragments or subsequences thereof, wherein the Gag, Pol and Nef amino acid position numbers correspond to SEQ ID NOs: 1, 2 and 3, respectively. Generally, the fusion polypeptides do not comprise any polypeptide segments having an amino acid sequence of SEQ ID NOs: 35-47, provided in Table C, or fragments or subsequences thereof, or an amino acid sequence at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 35-47, or fragments or subsequences thereof.

TABLE C polypeptide segments NOT in present HIV-1 fusion polypeptides

| SEQ ID NO: | Gene | Start | End | Sequence |
|---|---|---|---|---|
| 35 | Gag | 54 | 146 | EGCRQILGQLQPSLQTGSEELRSLYNTVATLYCVHQRIE IKDTKEALDKIEEEQNKSKKKAQQAAADTGHSNQVSQNY PIVQNIQGQMVHQA |
| 36 | Gag | 370 | 500 | VTNSATIMMQRGNERNQRKIVKCFNCGKEGHTARNCRAP RKKGCWKCGKEGHQMKDCTERQANFLGKIWPSYKGRPGN FLQSRPEPTAPPEESFRSGVETTTPPQKQEPIDKELYPL TSLRSLFGNDPSSQ |
| 37 | Pol | 1 | 55 | FFREDLAFLQGKAREFSSEQTRANSPTRRELQVWGRDNN SPSEAGADRQGTVSFN |
| 38 | Pol | 118 | 128 | ILIEICGHKAI |

TABLE C-continued polypeptide segments NOT in present HIV-1 fusion polypeptides

| SEQ ID NO: | Gene | Start | End | Sequence |
|---|---|---|---|---|
| 39 | Pol | 321 | 366 | KILEPFRKQNPDIVIYQYMDDLYVGSDLEIGQHRTKIEE LRQHLLR |
| 40 | Pol | 432 | 541 | QLCKLLRGTKALTEVIPLTEEAELELAENREILKEPVHG VYYDPSKDLIAEIQKQGQGQWTYQIYQEPFKNLKTGKYA RMRGAHTNDVKQLTEAVQKITTESIVIWGKT |
| 41 | Pol | 607 | 682 | GKAGYVTNRGRQKVVTLTDTTNQKTELQAIYLALQDSGL EVNIVTDSQYALGIIQAQPDQSESELVNQIIEQLIK |
| 42 | Pol | 709 | 746 | AGIRKVLFLDGIDKAQDEHEKYHSNWRAMASDFNLPPV |
| 43 | Pol | 828 | 839 | IHTDNGSNFTGA |
| 44 | Pol | 921 | 931 | TDIQTKELQKQ |
| 45 | Nef | 1 | 63 | MGGKWSKSSVIGWPTVRERMRRAEPAADRVGAASRDLEK HGAITSSNTAATNAACAWLEAQEE |
| 46 | Nef | 100 | 116 | LIHSQRRQDILDLWIYH |
| 47 | Nef | 149 | 206 | PDKIEEANKGENTSLLHPVSLHGMDDPEREVLEWRFDSR LAFHHVARELHPEYFKNC |

With respect to the range of lengths of the individual polypeptide or peptide segments, in various embodiments, each polypeptide segment is at least 25 amino acids in length, and up to about 230 amino acids in length, e.g. from at least 25 amino acids in length up to 26, 27, 28, 29, 30, 31, 32, 33, 34, 35, 36, 37, 38, 39, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225 or 230 amino acids in length.

With respect to the length of the full-length fusion polypeptide, in various embodiments, in some embodiments, the full-length of the fusion polypeptide comprises at least about 330 amino acids and up to about 550 amino acids, e.g., at least about 330 amino acids and up to about 335, 340, 345, 350, 355, 360, 365, 370, 375, 380, 385, 390, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545 or 550 amino acids in length. In some embodiments, the full-length of the fusion polypeptide is no longer than 550 amino acids, e.g. no longer than 545, 540, 535, 530, 525, 520, 515, 510, 505, 500, 495, 490, 485, 480, 475, 470, 465, 460, 455, 450, 445, 440, 435, 430, 425, 420, 415, 410, 405, 400, 390, 385, 380, 375, 370, 365, 360, 355, 350, 345, 340, 335 or 330 amino acids in length. In various embodiments, in the absence of a signal or leader sequence, the full-length of the fusion polypeptide comprises at least about 330 amino acids and up to about 505 amino acids, e.g., at least about 330 amino acids and up to about 335, 340, 345, 350, 355, 360, 365, 370, 375, 380, 385, 390, 400, 405, 410, 415, 420, 425, 430, 435, 440, 445, 450, 455, 460, 465, 470, 475, 480, 485, 490, 495, 500, 505 amino acids in length. amino acids in length. In various embodiments, in the absence of a signal or leader sequence, the full-length of the fusion polypeptide is no longer than 505 amino acids, e.g. no longer than 505, 500, 495, 490, 485, 480, 475, 470, 465, 460, 455, 450, 445, 440, 435, 430, 425, 420, 415, 410, 405, 400, 390, 385, 380, 375, 370, 365, 360, 355, 350, 345, 340, 335 or 330 amino acids in length. In various embodiments, in the presence of a signal or leader sequence, the full-length of the fusion polypeptide comprises at least about 350 amino acids and up to about 550 amino acids, e.g., at least about 350 amino acids and up to about 355, 360, 365, 370, 375, 380, 385, 390, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545 or 550 amino acids in length. In various embodiments, in the absence of a signal or leader sequence, the full-length of the fusion polypeptide is no longer than 550 amino acids, e.g. no longer than 545, 540, 535, 530, 525, 520, 515, 510, 505, 500, 495, 490, 485, 480, 475, 470, 465, 460, 455, 450, 445, 440, 435, 430, 425, 420, 415, 410, 405, 400, 390, 385, 380, 375, 370, 365, 360, 355 or 350 amino acids in length. The inclusion of a signal or leader peptide sequence is described in further detail below.

Generally, the fusion polypeptides are immunogenic, in that they are capable of eliciting an immune response in a human, e.g., against HIV-1. In some embodiments, the fusion polypeptides, optionally in combination with one or more additional therapeutic agents, e.g., as described herein, are capable of eliciting a protective or a therapeutically effective immune response in a human against HIV-1, e.g., capable of either preventing HIV-1 infection in an uninfected individual, or in therapeutic contexts, capable of eliciting an immune response sufficient to induce immune mediated control of HIV-1 or eradicate HIV-1 in an infected individual. The immunogenicity of the fusion polypeptides can be evaluated and demonstrated, in in vitro and in vivo assays, as described herein. For example, immunogenicity of the fusion polypeptides can be demonstrated by an in vitro assay, including CD4+ and/or CD8+ T-cell activation (e.g., including cytokine expression and target killing assays) or proliferation assays. The T-cells can be activated by exposure to antigen presenting cells (APCs) (such as dendritic cells, e.g., monocyte-derived dendritic cells) that have been transfected with a polynucleotide encoding the fusion polypeptide. Such assays are known in the art and described herein. The immunogenicity of the fusion polypeptides can also be demonstrated in in vivo animal models, for example, by administering to mice, e.g., BALB/c or BL6, or transgenic for one or more human HLA molecules (available from Jackson Laboratories or Taconic), or non-human primates, and evaluating CD4+ and/or CD8+ T-cell activation (e.g., including serum cytokine levels) or proliferation. In various embodiments, one, two, three, or more, of each polypeptide segment comprises or consists of one or more predicted T cell epitopes, e.g., as computationally or experimentally determined. In some embodiments, the fusion polypeptide comprises one or more polypeptide segments that bind to or are presented by one or more human HLA class I and/or class II alleles (e.g. 1, 2, 3, 4, 5 or 6 alleles), e.g. within a single subject or amongst multiple subjects.

Concatenating Polypeptide Segments

As appropriate, the one or more of the polypeptide segments can be directly abutted or fused to an adjacent segment, or can be joined, connected or linked to an adjacent segment by one or more peptide linkers. In various embodiments, the one or more peptide linkers is selected from one or more of a polyalanine linker, a polyglycine linker, a cleavable linker, a flexible linker, a rigid linker, a Nef linking sequence, and combinations thereof, e.g., within a linker or within a full-length fusion polypeptide. Illustrative fusion protein linkers that can be used in the present fusion polypeptides to connect one or more polypeptide segments are described, e.g., in Chen, et al., *Adv Drug Deliv Rev.* (2013) 65(10): 1357-1369. In some embodiments, the polyalanine linker comprises or consists of 2 or 3 contiguous alanine residues, e.g. AA, AAA (SEQ ID NO: 48), AAY (SEQ ID NO: 49) or AAX, wherein X is any amino acid (e.g., A, C, D, E, F, G, H, I, K, L, M, N, P, Q, R, S, T, V, Y) (SEQ ID NO: 50). In some embodiments, a polyglycine linker is used, e.g., GGS (SEQ ID NO: 57), GSG (SEQ ID NO: 58) or GGGS (SEQ ID NO: 59). In some embodiments, the cleavable linker is selected from a 2A cleavable peptide. Illustrative 2A cleavable peptides that can be used in the present fusion polypeptides to connect one or more polypeptide segments are described, e.g., in Donnelly, et al., *J. Gen. Virol* (2001), 82, 1027-1041 and Chng, et al., mAbs (2015) 7:2, 403-412. Illustrative cleavable peptides that can be used to link one or more polypeptide segments include without limitation 2A cleavage sequences (e.g., foot-and-mouth disease virus (F2A), equine rhinitis A virus (E2A), porcine teschovirus-1 (P2A) and Thosea asigna virus (T2A)), and furin recognition/cleavage sequences (e.g. RAKR (SEQ ID NO: 60), REKR (SEQ ID NO: 61), RRKR (SEQ ID NO: 62)). In certain embodiments, a furin recognition/cleavage sequence (e.g., RAKR (SEQ ID NO: 60), REKR (SEQ ID NO: 61), RRKR (SEQ ID NO: 62)) is combined or fused with a 2A cleavable peptide (e.g., foot-and-mouth disease virus (F2A), equine rhinitis A virus (E2A), porcine teschovirus-1 (P2A) and Thosea asigna virus (T2A)) in a single linker. See, e.g., Chng, et al., mAbs (2015) 7:2, 403-412. In various embodiments, the 2A cleavable linker comprises or consists of the amino acid sequence that is at least 90%, 91%, 92%, 93%, 94%, 95%, 96%, 97%, 98% or at least 99% identical to ATNFSLLKQAGDVEENPGP (SEQ ID NO: 63), APVKQTLNFDLLKLAGDVESNPGP (SEQ ID NO: 64), RAKRAPVKQTLNFDLLKLAGDVESNPGP (SEQ ID NO: 65), QCTNYALLKLAGDVESNPGP (SEQ ID NO: 66), or EGRGSLLTCGDVEENPGP (SEQ ID NO: 67), or comprises or consists of the amino acid sequence of ATNFSLLKQAGDVEENPGP (SEQ ID NO: 63), APVKQTLNFDLLKLAGDVESNPGP (SEQ ID NO: 64), RAKRAPVKQTLNFDLLKLAGDVESNPGP (SEQ ID NO: 65), QCTNYALLKLAGDVESNPGP (SEQ ID NO: 66), or EGRGSLLTCGDVEENPGP (SEQ ID NO: 67). As appropriate, in certain embodiments, a furin recognition/cleavage sequence can be positioned either at the N-terminus or the C-terminus of a 2A linker. In some embodiments, the cleavable linker comprises or consists of a furin recognition/cleavage site selected from RAKR (SEQ ID NO: 60), REKR (SEQ ID NO: 61) and RRKR (SEQ ID NO: 62). REKR (SEQ ID NO: 61) is a naturally occurring cleavable linker in HIV and SIV envelope glycoprotein precursor (Bahbouhi, et al., *Biochem. J.* (2002) 366, 863-872). Illustrative linkers that can be used to link or connect one or more polypeptide segments in a fusion polypeptide are provided in Table D.

TABLE D illustrative linkers

| SEQ ID NO: | NAME | SEQUENCE |
|---|---|---|
| | poly-alanine (2) | AA |
| 48 | poly-alanine (3) | AAA |
| 49 | poly-alanine-Tyr | AAY |
| 50 | poly-alanine-Xaa | AAX (X = any amino acid) |
| 51 | Gln-Glu-Glu | QEE |
| | Glu-Glu | EE |
| | Isoleucine | I |
| | Lysine | K |
| | Leu-Ile | LI |
| 52 | Lys-Ile-Leu | KIL |
| 53 | Leu-Ile-Lys | LIK |
| 54 | Pro-Pro-Val | PPV |
| 55 | Ser-Glu-Gly | SEG |
| | poly-glycine (2) | GG |
| 57 | poly-glycine | GGS |
| 58 | poly-glycine | GSG |
| 59 | Gly3Ser | GGGS |
| 60 | furin recognition site | RAKR |
| 61 | furin recognition site | REKR |
| 62 | furin recognition site | RRKR |
| 63 | P2A | ATNFSLLKQAGDVEENPGP |
| 64 | F2A | APVKQTLNFDLLKLAGDVESNPGP |
| 65 | F2A + N-terminal furin recognition site | RAKRAPVKQTLNFDLLKLAGDVESNPGP |
| 66 | E2A | QCTNYALLKLAGDVESNPGP |
| 67 | T2A | EGRGSLLTCGDVEENPGP |

Illustrative fusion polypeptides, without signal sequences, which have been designed and assembled according to the herein described methods, are provided in Table E. Table E discloses “AAA” as SEQ ID NO: 48, “LIK” as SEQ ID NO: 53, “AAY” as SEQ ID NO: 49, “SEG” as SEQ ID NO: 55, “QEE” as SEQ ID NO: 51, “KIL” as SEQ ID NO: 52 and “PPV” as SEQ ID NO: 54.

In some embodiments, the fusion polypeptide comprises or consists of an amino acid sequence of any one of SEQ ID NOs: 70-101, 105-112, 200-209, 222-223 and 227, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70-101, 105-112, 200-209, 222-223 and 227. In some embodiments, the fusion polypeptide comprises or consists of an amino acid sequence of any one of SEQ ID NOs: 82-83, 85-87, 98-101, 209 and 222-223, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82-83, 85-87, 98-101, 209 and 222-223. In some embodiments, the fusion polypeptide comprises or consists of an amino acid sequence of SEQ ID NO: 82, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 82. In some embodiments, the fusion polypeptide comprises or consists of an amino acid sequence of SEQ ID NO: 83, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 83. In some embodiments, the fusion polypeptide comprises or consists of an amino acid sequence of SEQ ID NO: 85, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 85. In some embodiments, the fusion polypeptide comprises or consists of an amino acid sequence of SEQ ID NO: 86, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 86. In some embodiments, the fusion polypeptide comprises or consists of an amino acid sequence of SEQ ID NO: 87, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 87. In some embodiments, the fusion polypeptide comprises or consists of an amino acid sequence of SEQ ID NO: 98, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 98. In some embodiments, the fusion polypeptide comprises or consists of an amino acid sequence of SEQ ID NO: 99, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 99. In some embodiments, the fusion polypeptide comprises or consists of an amino acid sequence of SEQ ID NO: 100, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 100. In some embodiments, the fusion polypeptide comprises or consists of an amino acid sequence of SEQ ID NO: 101, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 101. In some embodiments, the fusion polypeptide comprises or consists of an amino acid sequence of SEQ ID NO: 209, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 209. In some embodiments, the fusion polypeptide comprises or consists of an amino acid sequence of SEQ ID NO: 222, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 222. In some embodiments, the fusion polypeptide comprises or consists of an amino acid sequence of SEQ ID NO: 223, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 223. In some embodiments, the fusion polypeptide comprises or consists of an amino acid sequence of SEQ ID NO: 227, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 227. As appropriate or desired, the fusion polypeptide can have an N-terminal methionine residue.

TABLE E

Illustrative Fusion Polypeptides

| SEQ ID NO: | Polypeptide segments (N-term to C-term) | Length (aa) | Amino Acid Sequence |
|---|---|---|---|
| 70 | Gag: 147-369<br>Gag: 1-53<br>AAA<br>Pol: 683-708<br>Nef: 117-148 | 337 | ISPRTLNAWVKVVEEKAFSPEVIPMFSALSEGATPQDLNTMLNTVGGHQAAMQMLKETINE<br>EAAEWDRLHPVHAGPIAPGQMREPRGSDIAGTTSTLQEQIGWMTNNPPIPVGEIYKRWIIL<br>GLNKIVRMYSPTSILDIRQGPKEPFRDYVDRFYKTLRAEQASQEVKNWMTETLLVQNANPD<br>CKTILKALGPAATLEEMMTACQGVGGPGHKARVLAEAMSQMAARASVLSGGELDRWEKIRL<br>RPGGKKKYRLKHIVWASRELERFAVNPGLLETAAAKEKVYLAWVPAHKGIGGNEQVDKLVS<br>TQGYFPDWQNYTPGPGTRYPLTFGWCFKLVPV |
| 71 | Gag: 147-369<br>AA<br>Gag: 1-53<br>Nef: 117-148<br>LIK<br>Pol: 683-708 | 339 | LSPRTLNAWVKVIEEKAFSPEVIPMFTALSEGATPHDLNTMLNTIGGHQAAMQMLKDTINE<br>EAAEWDRVHPVHAGPVAPGQMRDPRGSDIAGSTSTLQEQIAWMTNNPPIPVGDIYKRWIIM<br>GLNKIVRMYSPVSILDIKQGPKEPFRDYVDRFYRTLRAEQASQDVKNWMTETLLVQNSNPD<br>CKTILKALGPGATLEEMMSACQGVGGPSHKARVLAEAMCQAAMAARASILSGGKLDKWEKI<br>RLRPGGRKKYKLKHLVWASRELERFALNPGLLETTQGFFPDWQNYTPGPGIRFPLTFGWCF<br>KLVPLLIKKEKIYLAWVPAHKGIGGNEQIDKLVS |
| 72 | Pol: 367-431<br>AA | 360 | WGFTTPDKKHQKEPPFLWMGYELHPDKWTVQPIVLPEKDSWTVNDIQKLVGKLNWASQIYP<br>GIKVAAQEEEEVGFPVKPQVPLRPMTFKGALDLSHFLREKGGLEGFPQITLWQRPLVTIKI |

TABLE E-continued

Illustrative Fusion Polypeptides

| SEQ ID NO: | Polypeptide segments (N-term to C-term) | Length (aa) | Amino Acid Sequence |
|---|---|---|---|
| | QEE | | GGQLKEALLDTGADDTVLEEMNLPGRWKPKMIGGIGGFIKVRQYDQGTVLVGPTPVNIIGR |
| | Nef: 64-99 | | NLLTQIGCTLNFPISPIETVPVKLKPGMDGPKVKQWPLTEEKIKALVEICTEMEKEGKISK |
| | Pol: 56-117 | | IGPENPYNTPVFAIKKKDSTKWRKLVDFRELNKRTQDFWEVQLGIPHPAGLKKKKSVTVLD |
| | Pol: 129-320 | | VGDAYFSVPLDKDFRKYTAFTIPSINNETPGIRYQYNVLPQGWKGSPAIFQSSMT |
| 73 | Pol: 56-117 | 356 | LPQITLWQRPIVTIKIGGQIKEALLDTGADDTVLEDMNLPGKWKPKMIGGIGGFIKVKQYD |
| | Nef: 64-99 | | QEEVGFPVRPQVPLRPMTYKGALDLSHFLKEKGGLEGWGLTTPDKKHQKDPPFLWMGYELH |
| | Pol: 367-431 | | PDRWTVQPIELPEKESWTVNDIQKLIGKLNWASQIYAGIKVKGTVLIGPTPVNIIGRNLLT |
| | K | | QLGCTLNFPISPIDTVPVKLKPGMDGPRVKQWPLTEEKIKALIEICTEMEKEGKISRIGPE |
| | Pol: 129-320 | | NPYNTPIFAIKKKDGTKWRKLVDFRELNKKTQDFWEVQLGIPHPSGLKKKKSVTVLDIGDA |
| | | | YFSVPLDKEFRKYTAFTVPSTNNETPGVRYQYNVLPMGWKGSPAIFQCSMT |
| 74 | Pol: 542-606 | 335 | PKFKLPIQKETWETWWTEYWQATWIPEWEFVNTPPLVKLWYQLEKEPIVGAETFYVDGAAN |
| | Pol: 932-1003 | | RETKITKIQNFRVYYRDSRDPLWKGPAKLLWKGEGAVVIQDNSDIKVVPRRKAKIIRDYGK |
| | Pol: 747-827 | | QMAGDDCVASRQDEDVAKEIVASCDKCQLKGEAMHGQVDCSPGIWQLDCTHLEGKIILVAV |
| | Nef: 64-99 | | HVASGYIEAEVIPAETGQETAYFLLKLAGRWPVKTEEVGFPVKPQVPLRPMTFKGALDLSH |
| | Pol: 840-920 | | FLREKGGLEGTVKAACWWAGIKQEFGIPYNPQSQGVVESMNKELKKIIGQVRDQAEHLKTA |
| | | | VQMAVFIHNFKRKGGIGGYSAGERIVDIIA |
| 75 | Pol: 542-606 | 335 | PKFRLPIQKETWDTWWTDYWQATWIPEWEFTNTPPLVKLWYQLETEPIAGVETFYVDGASN |
| | Nef: 64-99 | | RETKEEVGFPVRPQVPLRPMTYKGALDLSHFLKEKGGLEGVAKEIVACCDKCQLKGEAIHG |
| | Pol: 747-827 | | QVDCSPGVWQLDCTHLEGKVILVAVHVASGYIEAEIIPTETGQETAYFILKLAGRWPVTTI |
| | Pol: 932-1003 | | TKLQNFRVYYRDNRDPLWKGPARLLWKGEGAVVIQDNSEIKVVPRRKVKIIRDYGKRMAGD |
| | Pol: 840-920 | | DCVAGRQDEDAVKAACWWAGVKQEFGIPYNTQSQGVVESMNNELKKIIGQIRDQAEHLKTA |
| | | | VQMAVLIHNFKRKGGIGEYSAGERIIDIIA |
| 76 | Nef: 117-148 | 340 | TQGYFPDWQNYTPGPGTRYPLTFGWCFKLVPVKEKVYLAWVPAHKGIGGNEQVDKLVSAAY |
| | Pol: 683-708 | | MAARASVLSGGELDRWEKIRLRPGGKKKYRLKHIVWASRELERFAVNPGLLETSEGISPRT |
| | AY | | LNAWVKVVEEKAFSPEVIPMFSALSEGATPQDLNTMLNTVGGHQAAMQMLKETINEEAAEW |
| | Gag: 1-53 | | DRLHPVHAGPIAPGQMREPRGSDIAGTTSTLQEQIGWMTNNPPIPVGEIYKRWIILGLNKI |
| | SEG | | VRMYSPTSILDIRQGPKEPFRDYVDRFYKTLRAEQASQEVKNWMTETLLVQNANPDCKTIL |
| | Gag: 147-369 | | KALGPAATLEEMMTACQGVGGPGHKARVLAEAMSQ |
| 77 | Gag: 147-369 | 334 | LSPRTLNAWVKVIEEKAFSPEVIPMFTALSEGATPHDLNTMLNTIGGHQAAMQMLKDTINE |
| | Nef: 117-148 | | EAAEWDRVHPVHAGPVAPGQMRDPRGSDIAGSTSTLQEQIAWMTNNPPIPVGDIYKRWIIM |
| | Gag: 1-53 | | GLNKIVRMYSPVSILDIKQGPKEPFRDYVDRFYRTLRAEQASQDVKNWMTETLLVQNSNPD |
| | Pol: 683-708 | | CKTILKALGPGATLEEMMSACQGVGGPSHKARVLAEAMCQTQGFFPDWQNYTPGPGIRFPL |
| | | | TFGWCFKLVPLMAARASILSGGKLDKWEKIRLRPGGRKKYKLKHLVWASRELERFALNPGL |
| | | | LETKEKIYLAWVPAHKGIGGNEQIDKLVS |
| 78 | Pol: 56-117 | 360 | FPQITLWQRPLVTIKIGGQLKEALLDTGADDTVLEEMNLPGRWKPKMIGGIGGFIKVRQYD |
| | AAY | | QAAYEEVGFPVKPQVPLRPMTFKGALDLSHFLREKGGLEGAAWGFTTPDKKHQKEPPFLWM |
| | Nef: 64-99 | | GYELHPDKWTVQPIVLPEKDSWTVNDIQKLVGKLNWASQIYPGIKVGTVLVGPTPVNIIGR |
| | AA | | NLLTQIGCTLNFPISPIETVPVKLKPGMDGPKVKQWPLTEEKIKALVEICTEMEKEGKISK |
| | Pol: 367-431 | | IGPENPYNTPVFAIKKKDSTKWRKLVDFRELNKRTQDFWEVQLGIPHPAGLKKKKSVTVLD |
| | Pol: 129-320 | | VGDAYFSVPLDKDFRKYTAFTIPSINNETPGIRYQYNVLPQGWKGSPAIFQSSMT |
| 79 | Pol: 367-431 | 358 | WGLTTPDKKHQKDPPFLWMGYELHPDRWTVQPIELPEKESWTVNDIQKLIGKLNWASQIYA |
| | Nef: 64-99 | | GIKVEEVGFPVRPQVPLRPMTYKGALDLSHFLKEKGGLEGLPQITLWQRPIVTIKIGGQIK |
| | Pol: 56-117 | | EALLDTGADDTVLEDMNLPGKWKPKMIGGIGGFIKVKQYDQAAAGTVLIGPTPVNIIGRNL |
| | AAA | | LTQLGCTLNFPISPIDTVPVKLKPGMDGPRVKQWPLTEEKIKALIEICTEMEKEGKISRIG |
| | Pol: 129-320 | | PENPYNTPIFAIKKKDGTKWRKLVDFRELNKKTQDFWEVQLGIPHPSGLKKKKSVTVLDIG |
| | | | DAYFSVPLDKEFRKYTAFTVPSTNNETPGVRYQYNVLPMGWKGSPAIFQCSMT |
| 80 | Pol: 932-1003 | 342 | ITKIQNFRVYYRDSRDPLWKGPAKLLWKGEGAVVIQDNSDIKVVPRRKAKIIRDYGKQMAG |
| | AAY | | DDCVASRQDEDAAYEEEEVGFPVKPQVPLRPMTFKGALDLSHFLREKGGLEGLIPKFKLPI |
| | EE | | QKETWETWWTEYWQATWIPEWEFVNTPPLVKLWYQLEKEPIVGAETFYVDGAANRETKVAK |
| | Nef: 64-99 | | EIVASCDKCQLKGEAMHGQVDCSPGIWQLDCTHLEGKIILVAVHVASGYIEAEVIPAETGQ |
| | LI | | ETAYFLLKLAGRWPVKTTVKAACWWAGIKQEFGIPYNPQSQGVVESMNKELKKIIGQVRDQ |
| | Pol: 542-606 | | AEHLKTAVQMAVFIHNFKRKGGIGGYSAGERIVDIIA |
| | Pol: 747-827 | | |
| | Pol: 840-920 | | |
| 81 | Nef: 64-99 | 335 | EEVGFPVRPQVPLRPMTYKGALDLSHFLKEKGGLEGITKLQNFRVYYRDNRDPLWKGPARL |
| | Pol: 932-1003 | | LWKGEGAVVIQDNSEIKVVPRRKVKIIRDYGKRMAGDDCVAGRQDEDPKFRLPIQKETWDT |
| | Pol: 542-606 | | WWITYWQATWIPEWEFTNTPPLVKLWYQLETEPIAGVETFYVDGASNRETKAVKAACWWAG |
| | Pol: 840-920 | | VKQEFGIPYNTQSQGVVESMNNELKKIIGQIRDQAEHLKTAVQMAVLIHNFKRKGGIGEYS |
| | Pol: 747-827 | | AGERIIDIIAVAKEIVACCDKCQLKGEAIHGQVDCSPGVWQLDCTHLEGKVILVAVHVASG |
| | | | YIEAEIIPTETGQETAYFILKLAGRWPVTT |
| 82 | Pol: 840-920 | 353 | TVKAACWWAGIKQEFGIPYNPQSQGVVESMNKELKKIIGQVRDQAEHLKTAVQMAVFIHNF |
| | Gag: 147-369 | | KRKGGIGGYSAGERIVDIIAISPRTLNAWVKVVEEKAFSPEVIPMFSALSEGATPQDLNTM |
| | Pol: 586-606 | | LNTVGGHQAAMQMLKETINEEAAEWDRLHPVHAGPIAPGQMREPRGSDIAGTTSTLQEQIG |

TABLE E-continued

Illustrative Fusion Polypeptides

| SEQ ID NO: | Polypeptide segments (N-term to C-term) | Length (aa) | Amino Acid Sequence |
|---|---|---|---|
| | AA<br>Pol: 683-708 | | WMTNNPPIPVGEIYKRWIILGLNKIVRMYSPTSILDIRQGPKEPFRDYVDRFYKTLRAEQA<br>SQEVKNWMTETLLVQNANPDCKTILKALGPAATLEEMMTACQGVGGPGHKARVLAEAMSQK<br>EPIVGAETFYVDGAANRETKAAKEKVYLAWVPAHKGIGGNEQVDKLVS |
| 83 | Gag: 147-369<br>Pol: 683-708<br>Pol: 586-606<br>Pol: 840-920 | 351 | LSPRTLNAWVKVIEEKAFSPEVIPMFTALSEGATPHDLNTMLNTIGGHQAAMQMLKDTINE<br>EAAEWDRVHPVHAGPVAPGQMRDPRGSDIAGSTSTLQEQIAWMTNNPPIPVGDIYKRWIIM<br>GLNKIVRMYSPVSILDIKQGPKEPFRDYVDRFYRTLRAEQASQDVKNWMTETLLVQNSNPD<br>CKTILKALGPGATLEEMMSACQGVGGPSHKARVLAEAMCQKEKIYLAWVPAHKGIGGNEQI<br>DKLVSTEPIAGVETFYVDGASNRETKAVKAACWWAGVKQEFGIPYNTQSQGVVESMNNELK<br>KIIGQIRDQAEHLKTAVQMAVLIHNFKRKGGIGEYSAGERIIDIIA |
| 84 | Pol: 840-920<br>Pol: 586-606<br>AAA<br>Gag: 147-369<br>AAA<br>Pol: 683-708 | 358 | TVKAACWWAGIKQEFGIPYNPQSQGVVESMNKELKKIIGQVRDQAEHLKTAVQMAVFIHNF<br>KRKGGIGGYSAGERIVDIIAKEPIVGAETFYVDGAANRETKAAISPRTLNAWVKVVEEKA<br>FSPEVIPMFSALSEGATPQDLNTMLNTVGGHQAAMQMLKETINEEAAEWDRLHPVHAGPIA<br>PGQMREPRGSDIAGTTSTLQEQIGWMTNNPPIPVGEIYKRWIILGLNKIVRMYSPTSILDI<br>RQGPKEPFRDYVDRFYKTLRAEQASQEVKNWMTETLLVQNANPDCKTILKALGPAATLEEM<br>MTACQGVGGPGHKARVLAEAMSQAAAKEKVYLAWVPAHKGIGGNEQVDKLVSL |
| 85 | Gag: 147-369<br>Pol: 840-920<br>Pol: 586-606<br>AA<br>Pol: 683-708 | 353 | LSPRTLNAWVKVIEEKAFSPEVIPMFTALSEGATPHDLNTMLNTIGGHQAAMQMLKDTINE<br>EAAEWDRVHPVHAGPVAPGQMRDPRGSDIAGSTSTLQEQIAWMTNNPPIPVGDIYKRWIIM<br>GLNKIVRMYSPVSILDIKQGPKEPFRDYVDRFYRTLRAEQASQDVKNWMTETLLVQNSNPD<br>CKTILKALGPGATLEEMMSACQGVGGPSHKARVLAEAMCQAVKAACWWAGVKQEFGIPYNT<br>QSQGVVESMNNELKKIIGQIRDQAEHLKTAVQMAVLIHNFKRKGGIGEYSAGERIIDIIAT<br>EPIAGVETFYVDGASNRETKAAKEKIYLAWVPAHKGIGGNEQIDKLVS |
| 86 | Pol: 932-1003<br>Pol: 747-827<br>Pol: 129-320<br>QEE<br>Nef: 64-76 | 361 | ITKIQNFRVYYRDSRDPLWKGPAKLLWKGEGAVVIQDNSDIKVVPRRKAKIIRDYGKQMAG<br>DDCVASRQDEDVAKEIVASCDKCQLKGEAMHGQVDCSPGIWQLDCTHLEGKIILVAVHVAS<br>GYIEAEVIPAETGQETAYFLLKLAGRWPVKTGTVLVGPTPVNIIGRNLLTQIGCTLNFPIS<br>PIETVPVKLKPGMDGPKVKQWPLTEEKIKALVEICTEMEKEGKISKIGPENPYNTPVFAIK<br>KKDSTKWRKLVDFRELNKRTQDFWEVQLGIPHPAGLKKKKSVTVLDVGDAYFSVPLDKDFR<br>KYTAFTIPSINNETPGIRYQYNVLPQGWKGSPAIFQSSMTQEEEEVGFPVKPQVPL |
| 87 | Pol: 747-827<br>Pol: 932-1003<br>Pol: 129-320<br>KIL<br>QEE<br>Nef: 64-76 | 364 | VAKEIVACCDKCQLKGEAIHGQVDCSPGVWQLDCTHLEGKVILVAVHVASGYIEAEIIPTE<br>TGQETAYFILKLAGRWPVTTITKLQNFRVYYRDNRDPLWKGPARLLWKGEGAVVIQDNSEI<br>KVVPRRKVKIIRDYGKRMAGDDCVAGRQDEDGTVLIGPTPVNIIGRNLLTQLGCTLNFPIS<br>PIDTVPVKLKPGMDGPRVKQWPLTEEKIKALIEICTEMEKEGKISRIGPENPYNTPIFAIK<br>KKDGTKWRKLVDFRELNKKTQDFWEVQLGIPHPSGLKKKKSVTVLDIGDAYFSVPLDKEFR<br>KYTAFTVPSTNNETPGVRYQYNVLPMGWKGSPAIFQCSMTKILQEEEEVGFPVRPQVPL |
| 88 | Pol: 932-1003<br>AAA<br>I<br>Pol: 129-320<br>Pol: 747-827<br>QEE<br>Nef: 64-76 | 365 | ITKIQNFRVYYRDSRDPLWKGPAKLLWKGEGAVVIQDNSDIKVVPRRKAKIIRDYGKQMAG<br>DDCVASRQDEDAAAIGTVLVGPTPVNIIGRNLLTQIGCTLNFPISPIETVPVKLKPGMDGP<br>KVKQWPLTEEKIKALVEICTEMEKEGKISKIGPENPYNTPVFAIKKKDSTKWRKLVDFREL<br>NKRTQDFWEVQLGIPHPAGLKKKKSVTVLDVGDAYFSVPLDKDFRKYTAFTIPSINNETPG<br>IRYQYNVLPQGWKGSPAIFQSSMTVAKEIVASCDKCQLKGEAMHGQVDCSPGIWQLDCTHL<br>EGKIILVAVHVASGYIEAEVIPAETGQETAYFLLKLAGRWPVKTQEEEEVGFPVKPQVPL |
| 89 | Pol: 129-320<br>Pol: 932-1003<br>Pol: 747-827<br>AA<br>QEE<br>Nef: 64-76 | 363 | GTVLIGPTPVNIIGRNLLTQLGCTLNFPISPIDTVPVKLKPGMDGPRVKQWPLTEEKIKAL<br>IEICTEMEKEGKISRIGPENPYNTPIFAIKKKDGTKWRKLVDFRELNKKTQDFWEVQLGIP<br>HPSGLKKKKSVTVLDIGDAYFSVPLDKEFRKYTAFTVPSTNNETPGVRYQYNVLPMGWKGS<br>PAIFQCSMTITKLQNFRVYYRDNRDPLWKGPARLLWKGEGAVVIQDNSEIKVVPRRKVKII<br>RDYGKRMAGDDCVAGRQDEDVAKEIVACCDKCQLKGEAIHGQVDCSPGVWQLDCTHLEGKV<br>ILVAVHVASGYIEAEIIPTETGQETAYFILKLAGRWPVTTAAQEEEEVGFPVRPQVPL |
| 90 | Pol: 840-909<br>AA<br>Gag: 147-369<br>Pol: 747-827<br>QEE<br>Nef: 64-76 | 391 | TVKAACWWAGIKQEFGIPYNPQSQGVVESMNKELKKIIGQVRDQAEHLKTAVQMAVFIHNF<br>KRKGGIGGAAISPRTLNAWVKVVEEKAFSPEVIPMFSALSEGATPQDLNTMLNTVGGHQAA<br>MQMLKETINEEAAEWDRLHPVHAGPIAPGQMREPRGSDIAGTTSTLQEQIGWMTNNPPIPV<br>GEIYKRWIILGLNKIVRMYSPTSILDIRQGPKEPFRDYVDRFYKTLRAEQASQEVKNWMTE<br>TLLVQNANPDCKTILKALGPAATLEEMMTACQGVGGPGHKARVLAEAMSQVAKEIVASCDK<br>CQLKGEAMHGQVDCSPGIWQLDCTHLEGKIILVAVHVASGYIEAEVIPAETGQETAYFLLK<br>LAGRWPVKTQEEEEVGFPVKPQVPL |
| 91 | Pol: 840-909<br>Gag: 147-369<br>VT<br>Pol: 747-827<br>AA<br>QEE<br>Nef: 64-76 | 393 | AVKAACWWAGVKQEFGIPYNTQSQGVVESMNNELKKIIGQIRDQAEHLKTAVQMAVLIHNF<br>KRKGGIGELSPRTLNAWVKVIEEKAFSPEVIPMFTALSEGATPHDLNTMLNTIGGHQAAMQ<br>MLKDTINEEAAEWDRVHPVHAGPVAPGQMRDPRGSDIAGSTSTLQEQIAWMTNNPPIPVGD<br>IYKRWIIMGLNKIVRMYSPVSILDIKQGPKEPFRDYVDRFYRTLRAEQASQDVKNWMTETL<br>LVQNSNPDCKTILKALGPGATLEEMMSACQGVGGPSHKARVLAEAMCQVTVAKEIVACCDK<br>CQLKGEAIHGQVDCSPGVWQLDCTHLEGKVILVAVHVASGYIEAEIIPTETGQETAYFILK<br>LAGRWPVTTAAQEEEEVGFPVRPQVPL |
| 92 | Pol: 840-909<br>Pol: 747-827<br>AA | 391 | TVKAACWWAGIKQEFGIPYNPQSQGVVESMNKELKKIIGQVRDQAEHLKTAVQMAVFIHNF<br>KRKGGIGGVAKEIVASCDKCQLKGEAMHGQVDCSPGIWQLDCTHLEGKIILVAVHVASGYI<br>EAEVIPAETGQETAYFLLKLAGRWPVKTAAISPRTLNAWVKVVEEKAFSPEVIPMFSALSE |

TABLE E-continued

Illustrative Fusion Polypeptides

| SEQ ID NO: | Polypeptide segments (N-term to C-term) | Length (aa) | Amino Acid Sequence |
|---|---|---|---|
| | Gag: 147-369 | | GATPQDLNTMLNTVGGHQAAMQMLKETINEEAAEWDRLHPVHAGPIAPGQMREPRGSDIAG |
| | QEE | | TTSTLQEQIGWMTNNPPIPVGEIYKRWIILGLNKIVRMYSPTSILDIRQGPKEPFRDYVDR |
| | Nef: 64-76 | | FYKTLRAEQASQEVKNWMTETLLVQNANPDCKTILKALGPAATLEEMMTACQGVGGPGHKA |
| | | | RVLAEAMSQQEEEEVGFPVKPQVPL |
| 93 | Gag: 147-369 | 394 | LSPRTLNAWVKVIEEKAFSPEVIPMFTALSEGATPHDLNTMLNTIGGHQAAMQMLKDTINE |
| | PV | | EAAEWDRVHPVHAGPVAPGQMRDPRGSDIAGSTSTLQEQIAWMTNNPPIPVGDIYKRWIIM |
| | Pol: 747-827 | | GLNKIVRMYSPVSILDIKQGPKEPFRDYVDRFYRTLRAEQASQDVKNWMTETLLVQNSNPD |
| | AAY | | CKTILKALGPGATLEEMMSACQGVGGPSHKARVLAEAMCQPVVAKEIVACCDKCQLKGEAI |
| | Pol: 840-909 | | HGQVDCSPGVWQLDCTHLEGKVILVAVHVASGYIEAEIIPTETGQETAYFILKLAGRWPVT |
| | QEE | | TAAYAVKAACWWAGVKQEFGIPYNTQSQGVVESMNNELKKIIGQIRDQAEHLKTAVQMAVL |
| | Nef: 64-76 | | IHNFKRKGGIGEQEEEEVGFPVRPQVPL |
| 94 | Pol: 840-920 | 499 | TVKAACWWAGIKQEFGIPYNPQSQGVVESMNKELKKIIGQVRDQAEHLKTAVQMAVFIHNF |
| | Gag: 147-369 | | KRKGGIGGYSAGERIVDIIAISPRTLNAWVKVVEEKAFSPEVIPMFSALSEGATPQDLNTM |
| | Gag: 1-53 | | LNTVGGHQAAMQMLKETINEEAAEWDRLHPVHAGPIAPGQMREPRGSDIAGTTSTLQEQIG |
| | PPV | | WMTNNPPIPVGEIYKRWIILGLNKIVRMYSPTSILDIRQGPKEPFRDYVDRFYKTLRAEQA |
| | Pol: 747-827 | | SQEVKNWMTETLLVQNANPDCKTILKALGPAATLEEMMTACQGVGGPGHKARVLAEAMSQM |
| | Pol: 683-708 | | AARASVLSGGELDRWEKIRLRPGGKKKYRLKHIVWASRELERFAVNPGLLETPPVVAKEIV |
| | Nef: 117-148 | | ASCDKCQLKGEAMHGQVDCSPGIWQLDCTHLEGKIILVAVHVASGYIEAEVIPAETGQETA |
| | | | YFLLKLAGRWPVKTKEKVYLAWVPAHKGIGGNEQVDKLVSTQGYFPDWQNYTPGPGTRYPL |
| | | | TFGWCFKLVPV |
| 95 | Gag: 147-369 | 501 | LSPRTLNAWVKVIEEKAFSPEVIPMFTALSEGATPHDLNTMLNTIGGHQAAMQMLKDTINE |
| | Pol: 747-827 | | EAAEWDRVHPVHAGPVAPGQMRDPRGSDIAGSTSTLQEQIAWMTNNPPIPVGDIYKRWIIM |
| | Gag: 1-53 | | GLNKIVRMYSPVSILDIKQGPKEPFRDYVDRFYRTLRAEQASQDVKNWMTETLLVQNSNPD |
| | AA | | CKTILKALGPGATLEEMMSACQGVGGPSHKARVLAEAMCQVAKEIVACCDKCQLKGEAIHG |
| | Pol: 840-920 | | QVDCSPGVWQLDCTHLEGKVILVAVHVASGYIEAEIIPTETGQETAYFILKLAGRWPVTTM |
| | Nef: 117-148 | | AARASILSGGKLDKWEKIRLRPGGRKKYKLKHLVWASRELERFALNPGLLETAAAVKAACW |
| | LIK | | WAGVKQEFGIPYNTQSQGVVESMNNELKKIIGQIRDQAEHLKTAVQMAVLIHNFKRKGGIG |
| | Pol: 683-708 | | EYSAGERIIDIIATQGFFPDWQNYTPGPGIRFPLTFGWCFKLVPLLIKKEKIYLAWVPAHK |
| | | | GIGGNEQIDKLVS |
| 220 | Gag: 147-369 | 501 | ISPRTLNAWVKVVEEKAFSPEVIPMFSALSEGATPQDLNTMLNTVGGHQAAMQMLKETINE |
| | Pol: 747-827 | | EAAEWDRLHPVHAGPIAPGQMREPRGSDIAGTTSTLQEQIGWMTNNPPIPVGEIYKRWIIL |
| | Gag: 1-53 | | GLNKIVRMYSPTSILDIRQGPKEPFRDYVDRFYKTLRAEQASQEVKNWMTETLLVQNANPD |
| | AA | | CKTILKALGPAATLEEMMTACQGVGGPGHKARVLAEAMSQPPVVAKEIVASCDKCQLKGEA |
| | Pol: 840-920 | | MHGQVDCSPGIWQLDCTHLEGKIILVAVHVASGYIEAEVIPAETGQETAYFLLKLAGRWPV |
| | Nef: 117-148 | | KTMAARASVLSGGELDRWEKIRLRPGGKKKYRLKHIVWASRELERFAVNPGLLETAATVKA |
| | LIK | | ACWWAGIKQEFGIPYNPQSQGVVESMNKELKKIIGQVRDQAEHLKTAVQMAVFIHNFKRKG |
| | Pol: 683-708 | | GIGGYSAGERIVDIIATQGYFPDWQNYTPGPGTRYPLTFGWCFKLVPVKEKVYLAWVPAHK |
| | | | GIGGNEQVDKLVS |
| 96 | Pol: 56-117 | 494 | FPQITLWQRPLVTIKIGGQLKEALLDTGADDTVLEEMNLPGRWKPKMIGGIGGFIKVRQYD |
| | Nef: 64-99 | | QEEVGFPVKPQVPLRPMTFKGALDLSHFLREKGGLEGLIPKFKLPIQKETWETWWTEYWQA |
| | LI | | TWIPEWEFVNTPPLVKLWYQLEKEPIVGAETFYVDGAANRETKWGFTTPDKKHQKEPPFLW |
| | Pol: 542-606 | | MGYELHPDKWTVQPIVLPEKDSWTVNDIQKLVGKLNWASQIYPGIKVITKIQNFRVYYRDS |
| | Pol: 367-431 | | RDPLWKGPAKLLWKGEGAVVIQDNSDIKVVPRRKAKIIRDYGKQMAGDDCVASRQDEDGTV |
| | Pol: 932-1003 | | LVGPTPVNIIGRNLLTQIGCTLNFPISPIETVPVKLKPGMDGPKVKQWPLTEEKIKALVEI |
| | Pol: 129-320 | | CTEMEKEGKISKIGPENPYNTPVFAIKKKDSTKWRKLVDFRELNKRTQDFWEVQLGIPHPA |
| | | | GLKKKKSVTVLDVGDAYFSVPLDKDFRKYTAFTIPSINNETPGIRYQYNVLPQGWKGSPAI |
| | | | FQSSMT |
| 97 | Pol: 56-117 | 499 | LPQITLWQRPIVTIKIGGQIKEALLDTGADDTVLEDMNLPGKWKPKMIGGIGGFIKVKQYD |
| | Pol: 367-431 | | QWGLTTPDKKHQKDPPFLWMGYELHPDRWTVQPIELPEKESWTVNDIQKLIGKLNWASQIY |
| | AA | | AGIKVAAQEEEEVGFPVRPQVPLRPMTYKGALDLSHFLKEKGGLEGITKLQNFRVYYRDNR |
| | QEE | | DPLWKGPARLLWKGEGAVVIQDNSEIKVVPRRKVKIIRDYGKRMAGDDCVAGRQDEDPKFR |

TABLE E-continued

Illustrative Fusion Polypeptides

| SEQ ID NO: | Polypeptide segments (N-term to C-term) | Length (aa) | Amino Acid Sequence |
|---|---|---|---|
| | Nef: 64-99<br>Pol: 932-1003<br>Pol: 542-606<br>AA<br>Pol: 129-320 | | LPIQKETWDTWWTDYWQATWIPEWEFTNTPPLVKLWYQLETEPIAGVETFYVDGASNRETK<br>AAGTVLIGPTPVNIIGRNLLTQLGCTLNFPISPIDTVPVKLKPGMDGPRVKQWPLTEEKIK<br>ALIEICTEMEKEGKISRIGPENPYNTPIFAIKKKDGTKWRKLVDFRELNKKTQDFWEVQLG<br>IPHPSGLKKKKSVTVLDIGDAYFSVPLDKEFRKYTAFTVPSTNNETPGVRYQYNVLPMGWK<br>GSPAIFQCSMT |
| 221 | Pol: 56-117<br>Pol: 367-431<br>AA<br>QEE<br>Nef: 64-99<br>Pol: 932-1003<br>Pol: 542-606<br>AA<br>Pal: 129-320 | 501 | FPQITLWQRPLVTIKIGGQLKEALLDTGADDTVLEEMNLPGRWKPKMIGGIGGFIKVRQYD<br>QWGFTTPDKKHQKEPPFLWMGYELHPDKWTVQPIVLPEKDSWTVNDIQKLVGKLNWASQIY<br>PGIKVAAQEEEEVGFPVKPQVPLRPMTFKGALDLSHFLREKGGLEGLIITKIQNFRVYYRD<br>SRDPLWKGPAKLLWKGEGAVVIQDNSDIKVVPRRKAKIIRDYGKQMAGDDCVASRQDEDPK<br>FKLPIQKETWETWWTEYWQATWIPEWEFVNTPPLVKLWYQLEKEPIVGAETFYVDGAANRE<br>TKAAGTVLVGPTPVNIIGRNLLTQIGCTLNFPISPIETVPVKLKPGMDGPKVKQWPLTEEK<br>IKALVEICTEMEKEGKISKIGPENPYNTPVFAIKKKDSTKWRKLVDFRELNKRTQDFWEVQ<br>LGIPHPAGLKKKKSVTVLDVGDAYFSVPLDKDFRKYTAFTIPSINNETPGIRYQYNVLPQG<br>WKGSPAIFQSSMT |
| 98 | Pol: 747-827<br>Nef: 117-148<br>Pol: 840-920<br>AA<br>Gag: 1-53<br>SEG<br>Gag: 147-369<br>AAA<br>Pol: 683-708 | 504 | VAKEIVASCDKCQLKGEAMHGQVDCSPGIWQLDCTHLEGKIILVAVHVASGYIEAEVIPAE<br>TGQETAYFLLKLAGRWPVKTTQGYFPDWQNYTPGPGTRYPLTFGWCFKLVPVTVKAACWWA<br>GIKQEFGIPYNPQSQGVVESMNKELKKIIGQVRDQAEHLKTAVQMAVFIHNFKRKGGIGGY<br>SAGERIVDIIAAAMAARASVLSGGELDRWEKIRLRPGGKKKYRLKHIVWASRELERFAVNP<br>GLLETSEGISPRTLNAWVKVVEEKAFSPEVIPMFSALSEGATPQDLNTMLNTVGGHQAAMQ<br>MLKETINEEAAEWDRLHPVHAGPIAPGQMREPRGSDIAGTTSTLQEQIGWMTNNPPIPVGE<br>IYKRWIILGLNKIVRMYSPTSILDIRQGPKEPFRDYVDRFYKTLRAEQASQEVKNWMTETL<br>LVQNANPDCKTILKALGPAATLEEMMTACQGVGGPGHKARVLAEAMSQAAAKEKVYLAWVP<br>AHKGIGGNEQVDKLVS |
| 99 | Gag: 147-369<br>Pol: 840-920<br>Pol: 683-708<br>AAY<br>Gag: 1-53<br>Nef: 117-148<br>Pol: 747-827 | 499 | LSPRTLNAWVKVIEEKAFSPEVIPMFTALSEGATPHDLNTMLNTIGGHQAAMQMLKDTINE<br>EAAEWDRVHPVHAGPVAPGQMRDPRGSDIAGSTSTLQEQIAWMTNNPPIPVGDIYKRWIIM<br>GLNKIVRMYSPVSILDIKQGPKEPFRDYVDRFYRTLRAEQASQDVKNWMTETLLVQNSNPD<br>CKTILKALGPGATLEEMMSACQGVGGPSHKARVLAEAMCQAVKAACWWAGVKQEFGIPYNT<br>QSQGVVESMNNELKKIIGQIRDQAEHLKTAVQMAVLIHNFKRKGGIGEYSAGERIIDIIAK<br>EKIYLAWVPAHKGIGGNEQIDKLVSAAYMAARASILSGGKLDKWEKIRLRPGGRKKYKLKH<br>LVWASRELERFALNPGLLETTQGFFPDWQNYTPGPGIRFPLTFGWCFKLVPLVAKEIVACC<br>DKCQLKGEAIHGQVDCSPGVWQLDCTHLEGKVILVAVHVASGYIEAEIIPTETGQETAYFI<br>LKLAGRWPVTT |
| 100 | Pol: 932-1003<br>AAY<br>EE<br>Nef: 64-99<br>AA<br>Pol: 367-431<br>Pol: 542-606<br>Pol: 56-117<br>Pol: 129-320 | 499 | ITKIQNFRVYYRDSRDPLWKGPAKLLWKGEGAVVIQDNSDIKVVPRRKAKIIRDYGKQMAG<br>DDCVASRQDEDAAYEEEEVGFPVKPQVPLRPMTFKGALDLSHFLREKGGLEGAAWGFTTPD<br>KKHQKEPPFLWMGYELHPDKWTVQPIVLPEKDSWTVNDIQKLVGKLNWASQIYPGIKVPKF<br>KLPIQKETWETWWTEYWQATWIPEWEFVNTPPLVKLWYQLEKEPIVGAETFYVDGAANRET<br>KFPQITLWQRPLVTIKIGGQLKEALLDTGADDTVLEEMNLPGRWKPKMIGGIGGFIKVRQY<br>DQGTVLVGPTPVNIIGRNLLTQIGCTLNFPISPIETVPVKLKPGMDGPKVKQWPLTEEKIK<br>ALVEICTEMEKEGKISKIGPENPYNTPVFAIKKKDSTKWRKLVDFRELNKRTQDFWEVQLG<br>IPHPAGLKKKKSVTVLDVGDAYFSVPLDKDFRKYTAFTIPSINNETPGIRYQYNVLPQGWK<br>GSPAIFQSSMT |
| 101 | Pol: 542-606<br>Nef: 64-99<br>Pol: 56-117<br>Pol: 932-1003<br>Pol: 367-431<br>K<br>Pol: 129-320 | 493 | PKFRLPIQKETWDTWWTDYWQATWIPEWEFTNTPPLVKLWYQLETEPIAGVETFYVDGASN<br>RETKEEVGFPVRPQVPLRPMTYKGALDLSHFLKEKGGLEGLPQITLWQRPIVTIKIGGQIK<br>EALLDTGADDTVLEDMNLPGKWKPKMIGGIGGFIKVKQYDQITKLQNFRVYYRDNRDPLWK<br>GPARLLWKGEGAVVIQDNSEIKVVPRRKVKIIRDYGKRMAGDDCVAGRQDEDWGLTTPDKK<br>HQKDPPFLWMGYELHPDRWTVQPIELPEKESWTVNDIQKLIGKLNWASQIYAGIKVKGTVL<br>IGPTPVNIIGRNLLTQLGCTLNFPISPIDTVPVKLKPGMDGPRVKQWPLTEEKIKALIEIC<br>TEMEKEGKISRIGPENPYNTPIFAIKKKDGTKWRKLVDFRELNKKTQDFWEVQLGIPHPSG<br>LKKKKSVTVLDIGDAYFSVPLDKEFRKYTAFTVPSTNNETPGVRYQYNVLPMGWKGSPAIF<br>QCSMT |

Compound Fusion Polypeptides

In various embodiments, provided are compound fusion polypeptides comprising two or more fusion polypeptides, as described herein. Such compound fusion polypeptides can be delivered in viral vectors that can express a polypeptide having at least about 750 amino acids in length, e.g., at least about 800, 850, 900, 950, 1000, 1050, 1100 amino acids in length, or longer. As appropriate, the two or more fusion polypeptides can be directly fused, or joined or connected by one or more linkers. In some embodiments, provided are compound fusion polypeptides comprising at least a first fusion polypeptide and a second fusion polypeptide, as described herein, the first and second fusion polypeptides optionally joined or connected by one or more linkers, as described herein, e.g., a cleavable linker such as a 2A cleavable peptide linker.

In various embodiments, the first fusion polypeptide and the second fusion polypeptide in the compound fusion polypeptide comprises the same polypeptide segments, e.g., same amino acid residue position ranges. In some embodiments, the first fusion polypeptide and the second fusion polypeptide in the compound fusion polypeptide are bivalent. For example, in some embodiments, the first fusion polypeptide and the second fusion polypeptide comprise or consist of the following polypeptide segments, wherein the Gag, Pol and Nef amino acid position numbers correspond to SEQ ID NOs: 1, 2 and 3, respectively:

a) amino acid residues corresponding to: Gag 1-53; Gag 147-369; Pol 683-708 and Nef 117-148;

b) amino acid residues corresponding to: Pol 56-117; Pol 129-320; Pol 367-431 and Nef 64-99;

c) amino acid residues corresponding to: Pol 542-606; Pol 747-827; Pol 840-920; Pol 932-1003 and Nef 64-99;

d) amino acid residues corresponding to: Gag 1-53; Gag 147-369; Pol 683-708; Pol 747-827; Pol 840-920 and Nef 117-148;

e) amino acid residues corresponding to: Pol 56-117; Pol 129-320; Pol 367-431; Pol 542-606; Pol 932-1003 and Nef 64-99;

f) amino acid residues corresponding to: Gag 147-369, Pol 586-606, Pol 683-708 and Pol 840-920;

g) amino acid residues corresponding to: Pol 129-320, Pol 747-827, Pol 932-1003 and Nef 64-76; or h) amino acid residues corresponding to: Gag:147-369, Pol 747-827, Pol 840-909 and Nef 64-76.

In various embodiments, the first fusion polypeptide and the second fusion polypeptide in the compound fusion polypeptide comprises different polypeptide segments, e.g., same amino acid residue position ranges. In some embodiments, the first fusion polypeptide and the second fusion polypeptide are bivalent. For example, in some embodiments, the compound fusion polypeptide (inclusive of the first fusion polypeptide and the second fusion polypeptide) comprises or consists of the following polypeptide segments, wherein the Gag, Pol and Nef amino acid position numbers correspond to SEQ ID NOs: 1, 2 and 3, respectively:

a) amino acid residues corresponding to: Gag 147-369, Pol 129-320, Pol 586-606, Pol 683-708, Pol 747-827, Pol 840-920, Pol 932-1003 and Nef 64-76; or b) Gag 1-53, Gag 147-369, Pol 56-117, Pol 129-320, Pol 367-431, Pol 542-606, Pol 683-708, Pol 747-827, Pol 840-920, Pol 932-1003, Nef 64-99 and Nef 117-148.

In some embodiments, the compound fusion polypeptide comprises the following polypeptide segments comprising in sequential order, from N-terminus to C-terminus, optionally joined or connected by one or more linkers:

a) SEQ ID NOs: 6, 4, 16 and 26, and SEQ ID NOs: 7, 5, 27 and 17, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 6, 4, 16 and 26, and SEQ ID NOs: 7, 5, 27 and 17, respectively;

b) SEQ ID NOs: 12, 24, 8 and 10, and SEQ ID NOs: 9, 25, 13 and 11, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 12, 24, 8 and 10, and SEQ ID NOs: 9, 25, 13 and 11, respectively;

c) SEQ ID NOs: 14, 22, 18, 24 and 20, and SEQ ID NOs: 15, 25, 19, 23 and 21, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 14, 22, 18, 24 and 20, and SEQ ID NOs: 15, 25, 19, 23 and 21, respectively;

d) SEQ ID NOs: 26, 16, 4 and 6, and SEQ ID NOs: 7, 27, 5 and 17, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 26, 16, 4 and 6, and SEQ ID NOs: 7, 27, 5 and 17, respectively;

e) SEQ ID NOs: 8, 24, 12 and 10, and SEQ ID NOs: 13, 25, 9 and 11, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 8, 24, 12 and 10, and SEQ ID NOs: 13, 25, 9 and 11, respectively;

f) SEQ ID NOs: 24, 6, 16 and 18, and SEQ ID NOs: 7, 25, 17 and 19, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 24, 6, 16 and 18, and SEQ ID NOs: 7, 25, 17 and 19, respectively;

g) SEQ ID NOs: 26, 10, 20 and 28, and SEQ ID NOs: 21, 27, 11 and 29, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 26, 10, 20 and 28, and SEQ ID NOs: 21, 27, 11 and 29, respectively;

h) SEQ ID NOs: 24, 6, 16 and 18, and SEQ ID NOs: 26, 10, 20 and 28, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 24, 6, 16 and 18, and SEQ ID NOs: 26, 10, 20 and 28, respectively;

i) SEQ ID NOs: 7, 25, 17 and 19, and SEQ ID NOs: 21, 27, 11 and 29, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 7, 25, 17 and 19, and SEQ ID NOs: 21, 27, 11 and 29, respectively;

j) SEQ ID NOs: 22, 6, 16, 20, 18, 28, 26 and 10, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 22, 6, 16, 20, 18, 28, 26 and 10, respectively;

k) SEQ ID NOs: 7, 21, 19, 17, 27, 25, 29 and 11, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 7, 21, 19, 17, 27, 25, 29 and 11, respectively;

l) SEQ ID NOs: 22, 24, 14, 18 and 20, and SEQ ID NOs: 25, 23, 15, 21 and 19, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 22, 24, 14, 18 and 20, and SEQ ID NOs: 25, 23, 15, 21 and 19, respectively;

m) SEQ ID NOs: 20, 6, 4, 18, 16 and 26, and SEQ ID NOs: 7, 19, 5, 21, 27 and 17, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 20, 6, 4, 18, 16 and 26, and SEQ ID NOs: 7, 19, 5, 21, 27 and 17, respectively;

n) SEQ ID NOs: 8, 24, 14, 12, 22 and 10, and SEQ ID NOs: 9, 13, 25, 23, 15 and 11, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 8, 24, 14, 12, 22 and 10, and SEQ ID NOs: 9, 13, 25, 23, 15 and 11, respectively;

o) SEQ ID NOs: 18, 26, 20, 4, 6 and 16, and SEQ ID NOs: 7, 21, 17, 5, 27 and 19, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 18, 26, 20, 4, 6 and 16, SEQ ID NOs: 7, 21, 17, 5, 27 and 19, respectively;

p) SEQ ID NOs: 24, 6, 4, 20, 18, and 32, and SEQ ID NOs: 7, 21, 5, 25, 33 and 19, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 24, 6, 4, 20, 18, and 32, SEQ ID NOs: 7, 21, 5, 25, 33 and 19, respectively;

q) SEQ ID NOs: 6, 20, 4, 24, 32, 18, and SEQ ID NOs: 8, 12, 30, 26, 14 and 10, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 6, 20, 4, 24, 32, 18, and SEQ ID NOs: 8, 12, 30, 26, 14 and 10, respectively;

r) SEQ ID NOs: 8, 30, 14, 12, 26, and 10, and SEQ ID NOs: 9, 13, 31, 27, 15 and 11, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 8, 30, 14, 12, 26, and 10, SEQ ID NOs: 9, 13, 31, 27, 15 and 11, respectively;

s) SEQ ID NOs: 24, 6, 4, 20, 18 and 32, and SEQ ID NOs: 8, 30, 14, 12, 26 and 10, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 24, 6, 4, 20, 18 and 32, and SEQ ID NOs: 8, 30, 14, 12, 26 and 10, respectively;

t) SEQ ID NOs: 6, 20, 4, 24, 32, 18, and SEQ ID NOs: 8, 12, 30, 26, 14 and 10, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 6, 20, 4, 24, 32, 18, and SEQ ID NOs: 8, 12, 30, 26, 14 and 10, respectively; or u) SEQ ID NOs: 7, 21, 5, 25, 33 and 19, and SEQ ID NOs: 9, 13, 31, 27, 15 and 11, or sequence segments that are at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 7, 21, 5, 25, 33 and 19, and SEQ ID NOs: 9, 13, 31, 27, 15 and 11, respectively.

In various embodiments, the compound fusion polypeptide comprises or consists of the following first fusion polypeptide and second fusion polypeptide, optionally joined or connected by one or more linkers:

SEQ ID NOs: 70 and 71, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70 and 71, respectively;

SEQ ID NOs: 72 and 73, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 72 and 73, respectively;

SEQ ID NOs: 74 and 75, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 74 and 75, respectively;

SEQ ID NOs: 76 and 77, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 76 and 77, respectively;

SEQ ID NOs: 78 and 79, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 78 and 79, respectively;

SEQ ID NOs: 80 and 81, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 80 and 81, respectively;

SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively;

SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively;

SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively;

SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively;

SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively;

SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively;

SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively;

SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively;

SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively;

SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively;

SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 88, respectively;

SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively;

SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively;

SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively;

SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively;

SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively;

SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively;

SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively;

SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively;

SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively;

SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively;

SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively;

SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively; or SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively.

In various embodiments, the compound fusion polypeptide comprises or consists of the following first fusion polypeptide and second fusion polypeptide in sequential order, from N-terminus to C-terminus, optionally joined or connected by one or more linkers:

SEQ ID NOs: 70 and 71, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70 and 71, respectively;

SEQ ID NOs: 71 and 70, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 71 and 70, respectively;

SEQ ID NOs: 72 and 73, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 72 and 73, respectively;

SEQ ID NOs: 73 and 72, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 73 and 72, respectively;

SEQ ID NOs: 74 and 75, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 74 and 75, respectively;

SEQ ID NOs: 75 and 74, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 75 and 74, respectively;

SEQ ID NOs: 76 and 77, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 76 and 77, respectively;

SEQ ID NOs: 77 and 76, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 77 and 76, respectively;

SEQ ID NOs: 78 and 79, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 78 and 79, respectively;

SEQ ID NOs: 79 and 78, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 79 and 78, respectively;

SEQ ID NOs: 80 and 81, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 80 and 81, respectively;

SEQ ID NOs: 81 and 80, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 81 and 80, respectively;

SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively;

SEQ ID NOs: 83 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 82, respectively;

SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively;

SEQ ID NOs: 85 and 84, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 84, respectively;

SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively;

SEQ ID NOs: 87 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 86, respectively;

SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively;

SEQ ID NOs: 89 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 89 and 88, respectively;

SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively;

SEQ ID NOs: 85 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 82, respectively;

SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively;

SEQ ID NOs: 86 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 82, respectively;

SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively;

SEQ ID NOs: 88 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 82, respectively;

SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively;

SEQ ID NOs: 87 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 83, respectively;

SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively;

SEQ ID NOs: 87 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 85, respectively;

SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively;

SEQ ID NOs: 87 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 88, respectively;

SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 84, respectively;

SEQ ID NOs: 88 and 84, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 84, respectively;

SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively;

SEQ ID NOs: 89 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 89 and 85, respectively;

SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively;

SEQ ID NOs: 101 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 85, respectively;

SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively;

SEQ ID NOs: 91 and 90, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 91 and 90, respectively;

SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively;

SEQ ID NOs: 93 and 92, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 93 and 92, respectively;

SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively;

SEQ ID NOs: 95 and 94, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 94, respectively;

SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively;

SEQ ID NOs: 97 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 97 and 96, respectively;

SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively;

SEQ ID NOs: 96 and 94, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 94, respectively;

SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively;

SEQ ID NOs: 97 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 97 and 95, respectively;

SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively;

SEQ ID NOs: 221 and 220, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 221 and 220, respectively;

SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively;

SEQ ID NOs: 100 and 98, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 98, respectively;

SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively;

SEQ ID NOs: 101 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 99, respectively;

SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively;

SEQ ID NOs: 99 and 98, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 98, respectively;

SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively; or SEQ ID NOs: 101 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 100, respectively.

In some embodiments of the compound fusion polypeptide, the first fusion polypeptide and the second fusion polypeptide are joined or connected by a cleavable linker. In various embodiments, the first fusion polypeptide and the second fusion polypeptide are joined or connected by a cleavable linker selected from a 2A cleavable peptide (e.g. foot-and-mouth disease virus (F2A), equine rhinitis A virus (E2A), porcine teschovirus-1 (P2A) and Thosea asigna virus (T2A)), a furin recognition/cleavage sequence (e.g. RAKR (SEQ ID NO: 60), REKR (SEQ ID NO: 61), RRKR (SEQ ID NO: 62)), and combinations, derivatives or variants thereof. In some embodiments, the first fusion polypeptide and the second fusion polypeptide are joined or connected by a furin recognition/cleavage site selected from RAKR (SEQ ID NO: 60), REKR (SEQ ID NO: 61) and RRKR (SEQ ID NO: 62). In some embodiments, the first fusion polypeptide and the second fusion polypeptide are joined or connected by a 2A cleavable peptide comprising or consisting of the amino acid sequence of ATNFSLLKQAGD- VEENPGP (SEQ ID NO: 63), APVKQTLNFDLLKLAGD-VESNPGP (SEQ ID NO: 64), RAKRAPVKQTLNFDLLKLAGDVESNPGP (SEQ ID NO: 65), QCTNYALLKLAGDVESNPGP (SEQ ID NO: 66), or EGRGSLLTCGDVEENPGP (SEQ ID NO: 67), or having an amino acid sequence that is at least 90%, 91%, 92%, 93%, 94%, 95%, 96%, 97%, 98% or at least 99% identical to ATNFSLLKQAGDVEENPGP (SEQ ID NO: 63), APVKQTLNFDLLKLAGDVESNPGP (SEQ ID NO: 64), RAKRAPVKQTLNFDLLKLAGDVESNPGP (SEQ ID NO: 65), QCTNYALLKLAGDVESNPGP (SEQ ID NO: 66), or EGRGSLLTCGDVEENPGP (SEQ ID NO: 67).

Illustrative compound fusion polypeptides, without signal sequences, which have been designed and assembled according to the herein described methods, are provided in Table F. Table F discloses "AAA" as SEQ ID NO: 48, "LIK" as SEQ ID NO: 53, "AAY" as SEQ ID NO: 49, "SEG" as SEQ ID NO: 55, "QEE" as SEQ ID NO: 51, "RAKR" as SEQ ID NO: 60 and "PPV" as SEQ ID NO: 54.

In some embodiments, the compound fusion polypeptide comprises or consists of an amino acid sequence of any one of SEQ ID NOs: 105-112, 200-209, 222-223 and 227, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 105-112, 200-209, 222-223 and 227. In some embodiments, the compound fusion polypeptide comprises or consists of an amino acid sequence of any one of SEQ ID NOs: 209, 222 and 223, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 209, 222 and 223. In some embodiments, the compound fusion polypeptide comprises or consists of an amino acid sequence of SEQ ID NO: 209, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 209. In some embodiments, the compound fusion polypeptide comprises or consists of an amino acid sequence of SEQ ID NO: 222, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 222. In some embodiments, the compound fusion polypeptide comprises or consists of an amino acid sequence of SEQ ID NO: 223, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 223. In some embodiments, the compound fusion polypeptide comprises or consists of an amino acid sequence of SEQ ID NO: 227, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 227. As appropriate or desired, the compound fusion polypeptide can have an N-terminal methionine residue.

TABLE F

Illustrative Compound Fusion Polypeptides

| SEQ ID NO: | Polypeptide segments | Length (aa) | Amino Acid Sequence |
|---|---|---|---|
| 105 | Pol:840-920<br>Gag:147-369<br>Gag:1-53<br>PPV<br>Pol:747-827<br>Pol:683-708<br>Nef:117-148<br>RAKR<br>F2A linker<br>Gag:147-369<br>Pol:747-827<br>Gag:1-53<br>AA<br>Pol:840-920<br>Nef:117-148<br>LIK<br>Pol:683-708 | 1028 | TVKAACWWAGIKQEFGIPYNPQSQGVVESMNKELKKIIGQVRDQAEHLKTAVQMAVFIH<br>NFKRKGGIGGYSAGERIVDIIAISPRTLNAWVKVVEEKAFSPEVIPMFSALSEGATPQD<br>LNTMLNTVGGHQAAMQMLKETINEEAAEWDRLHPVHAGPIAPGQMREPRGSDIAGTTST<br>LQEQIGWMTNNPPIPVGEIYKRWIILGLNKIVRMYSPTSILDIRQGPKEPFRDYVDRFY<br>KTLRAEQASQEVKNWMTETLLVQNANPDCKTILKALGPAATLEEMMTACQGVGGPGHKA<br>RVLAEAMSQMAARASVLSGGELDRWEKIRLRPGGKKKYRLKHIVWASRELERFAVNPGL<br>LETPPVVAKEIVASCDKCQLKGEAMHGQVDCSPGIWQLDCTHLEGKIILVAVHVASGYI<br>EAEVIPAETGQETAYFLLKLAGRWPVKTKEKVYLAWVPAHKGIGGNEQVDKLVSTQGYF<br>PDWQNYTPGPGTRYPLTFGWCFKLVPVRAKRAPVKQTLNFDLLKLAGDVESNPGPLSPR<br>TLNAWVKVIEEKAFSPEVIPMFTALSEGATPHDLNTMLNTIGGHQAAMQMLKDTINEEA<br>AEWDRVHPVHAGPVAPGQMRDPRGSDIAGSTSTLQEQIAWMTNNPPIPVGDIYKRWIIM<br>GLNKIVRMYSPVSILDIKQGPKEPFRDYVDRFYRTLRAEQASQDVKNWMTETLLVQNSN<br>PDCKTILKALGPGATLEEMMSACQGVGGPSHKARVLAEAMCQVAKEIVACCDKCQLKGE<br>AIHGQVDCSPGVWQLDCTHLEGKVILVAVHVASGYIEAEIIPTETGQETAYFILKLAGR<br>WPVTTMAARASILSGGKLDKWEKIRLRPGGRKKYKLKHLVWASRELERFALNPGLLETA<br>AAVKAACWWAGVKQEFGIPYNTQSQGVVESMNNELKKIIGQIRDQAEHLKTAVQMAVLI<br>HNFKRKGGIGEYSAGERIIDIIATQGFFPDWQNYTPGPGIRFPLTFGWCFKLVPLLIKK<br>EKIYLAWVPAHKGIGGNEQIDKLVS |
| 206 | M<br>Pol:840-920<br>Gag:147-369<br>Gag:1-53<br>PPV<br>Pol:747-827<br>Pol:683-708<br>Nef:117-148<br>RAKR<br>F2A linker<br>M<br>Gag:147-369<br>Pol:747-827<br>Gag:1-53<br>AA<br>Pol:840-920<br>Nef:117-148<br>LIK<br>Pol:683-708 | 1030 | MTVKAACWWAGIKQEFGIPYNPQSQGVVESMNKELKKIIGQVRDQAEHLKTAVQMAVFI<br>HNFKRKGGIGGYSAGERIVDIIAISPRTLNAWVKVVEEKAFSPEVIPMFSALSEGATPQ<br>DLNTMLNTVGGHQAAMQMLKETINEEAAEWDRLHPVHAGPIAPGQMREPRGSDIAGTTS<br>TLQEQIGWMTNNPPIPVGEIYKRWIILGLNKIVRMYSPTSILDIRQGPKEPFRDYVDRF<br>YKTLRAEQASQEVKNWMTETLLVQNANPDCKTILKALGPAATLEEMMTACQGVGGPGHK<br>ARVLAEAMSQMAARASVLSGGELDRWEKIRLRPGGKKKYRLKHIVWASRELERFAVNPG<br>LLETPPVVAKEIVASCDKCQLKGEAMHGQVDCSPGIWQLDCTHLEGKIILVAVHVASGY<br>IEAEVIPAETGQETAYFLLKLAGRWPVKTKEKVYLAWVPAHKGIGGNEQVDKLVSTQGY<br>FPDWQNYTPGPGTRYPLTFGWCFKLVPVRAKRAPVKQTLNFDLLKLAGDVESNPGPMLS<br>PRTLNAWVKVIEEKAFSPEVIPMFTALSEGATPHDLNTMLNTIGGHQAAMQMLKDTINE<br>EAAEWDRVHPVHAGPVAPGQMRDPRGSDIAGSTSTLQEQIAWMTNNPPIPVGDIYKRWI<br>IMGLNKIVRMYSPVSILDIKQGPKEPFRDYVDRFYRTLRAEQASQDVKNWMTETLLVQN<br>SNPDCKTILKALGPGATLEEMMSACQGVGGPSHKARVLAEAMCQVAKEIVACCDKCQLK<br>GEAIHGQVDCSPGVWQLDCTHLEGKVILVAVHVASGYIEAEIIPTETGQETAYFILKLA<br>GRWPVTTMAARASILSGGKLDKWEKIRLRPGGRKKYKLKHLVWASRELERFALNPGLLE<br>TAAAVKAACWWAGVKQEFGIPYNTQSQGVVESMNNELKKIIGQIRDQAEHLKTAVQMAV<br>LIHNFKRKGGIGEYSAGERIIDIIATQGFFPDWQNYTPGPGIRFPLTFGWCFKLVPLLI<br>KKEKIYLAWVPAHKGIGGNEQIDKLVS |

TABLE F-continued

Illustrative Compound Fusion Polypeptides

| SEQ ID NO: | Polypeptide segments | Length (aa) | Amino Acid Sequence |
|---|---|---|---|
| 106 | Gag:147-369 | 1028 | LSPRTLNAWVKVIEEKAFSPEVIPMFTALSEGATPHDLNTMLNTIGGHQAAMQMLKDTI |
| | Pol:747-827 | | NEEAAEWDRVHPVHAGPVAPGQMRDPRGSDIAGSTSTLQEQIAWMTNNPPIPVGDIYKR |
| | Gag:1-53 | | WIIMGLNKIVRMYSPVSILDIKQGPKEPFRDYVDRFYRTLRAEQASQDVKNWMTETLLV |
| | AA | | QNSNPDCKTILKALGPGATLEEMMSACQGVGGPSHKARVLAEAMCQVAKEIVACCDKCQ |
| | Pol:840-920 | | LKGEAIHGQVDCSPGVWQLDCTHLEGKVILVAVHVASGYIEAEIIPTETGQETAYFILK |
| | Nef:117-148 | | LAGRWPVTTMAARASILSGGKLDKWEKIRLRPGGRKKYKLKHLVWASRELERFALNPGL |
| | LIK | | LETAAAVKAACWWAGVKQEFGIPYNTQSQGVVESMNNELKKIIGQIRDQAEHLKTAVQM |
| | Pol:683-708 | | AVLIHNFKRKGGIGEYSAGERIIDIIATQGFFPDWQNYTPGPGIRFPLTFGWCFKLVPL |
| | RAKR | | LIKKEKIYLAWVPAHKGIGGNEQIDKLVSRAKRAPVKQTLNFDLLKLAGDVESNPGPTV |
| | F2A linker | | KAACWWAGIKQEFGIPYNPQSQGVVESMNKELKKIIGQVRDQAEHLKTAVQMAVFIHNF |
| | Pol:840-920 | | KRKGGIGGYSAGERIVDIIAISPRTLNAWVKVVEEKAFSPEVIPMFSALSEGATPQDLN |
| | Gag:147-369 | | TMLNTVGGHQAAMQMLKETINEEAAEWDRLHPVHAGPIAPGQMREPRGSDIAGTTSTLQ |
| | Gag:1-53 | | EQIGWMTNNPPIPVGEIYKRWIILGLNKIVRMYSPTSILDIRQGPKEPFRDYVDRFYKT |
| | PPV | | LRAEQASQEVKNWMTETLLVQNANPDCKTILKALGPAATLEEMMTACQGVGGPGHKARV |
| | Pol:747-827 | | LAEAMSQMAARASVLSGGELDRWEKIRLRPGGKKKYRLKHIVWASRELERFAVNPGLLE |
| | Pol:683-708 | | TPPVVAKEIVASCDKCQLKGEAMHGQVDCSPGIWQLDCTHLEGKIILVAVHVASGYIEA |
| | Nef:117-148 | | EVIPAETGQETAYFLLKLAGRWPVKTKEKVYLAWVPAHKGIGGNEQVDKLVSTQGYFPD |
| | | | WQNYTPGPGTRYPLTFGWCFKLVPV |
| 107 | Pol:56-117 | 1022 | FPQITLWQRPLVTIKIGGQLKEALLDTGADDTVLEEMNLPGRWKPKMIGGIGGFIKVRQ |
| | Nef:64-99 | | YDQEEVGFPVKPQVPLRPMTFKGALDLSHFLREKGGLEGLIPKFKLPIQKETWETWWTE |
| | LI | | YWQATWIPEWEFVNTPPLVKLWYQLEKEPIVGAETFYVDGAANRETKWGFTTPDKKHQK |
| | Pol:542-606 | | EPPFLWMGYELHPDKWTVQPIVLPEKDSWTVNDIQKLVGKLNWASQTYPGIKVITKIQN |
| | Pol:367-431 | | FRVYYRDSRDPLWKGPAKLLWKGEGAVVIQDNSDIKVVPRRKAKIIRDYGKQMAGDDCV |
| | Pol:932-1003 | | ASRQDEDGTVLVGPTPVNIIGRNLLTQIGCTLNFPISPIETVPVKLKPGMDGPKVKQWP |
| | Pol:129-320 | | LTEEKIKALVEICTEMEKEGKISKIGPENPYNTPVFAIKKKDSTKWRKLVDFRELNKRT |
| | RAKR | | QDFWEVQLGIPHPAGLKKKKSVTVLDVGDAYFSVPLDKDFRKYTAFTIPSINNETPGIR |
| | F2A linker | | YQYNVLPQGWKGSPAIFQSSMTRAKRAPVKQTLNFDLLKLAGDVESNPGPNLPQITLWQ |
| | Pol:56-117 | | RPIVTIKIGGQIKEALLDTGADDTVLEDMNLPGKWKPKMIGGIGGFIKVKQYDQWGLTT |
| | Pol:367-431 | | PDKKHQKDPPFLWMGYELHPDRWTVQPIELPEKESWTVNDIQKLIGKLNWASQIYAGIK |
| | AA | | VAAQEEEEVGFPVRPQVPLRPMTYKGALDLSHFLKEKGGLEGITKLQNFRVYYRDNRDP |
| | QEE | | LWKGPARLLWKGEGAVVIQDNSEIKVVPRRKVKIIRDYGKRMAGDDCVAGRQDEDPKFR |
| | Nef:64-99 | | LPIQKETWDTWWTDYWQATWIPEWEFTNTPPLVKLWYQLETEPIAGVETFYVDGASNRE |
| | Pol:932-1003 | | TKAAGTVLIGPTPVNIIGRNLLTQLGCTLNFPISPIDTVPVKLKPGMDGPRVKQWPLTE |
| | Pol:542-606 | | EKIKALIEICTEMEKEGKISRIGPENPYNTPIFAIKKKDGTKWRKLVDFRELNKKTQDF |
| | AA | | WEVQLGIPHPSGLKKKKSVTVLDIGDAYFSVPLDKEFRKYTAFTVPSTNNETPGVRYQY |
| | Pol:129-320 | | NVLPMGWKGSPAIFQCSMT |
| 207 | M | 1023 | MFPQITLWQRPLVTIKIGGQLKEALLDTGADDTVLEEMNLPGRWKPKMIGGIGGFIKVR |
| | Pol:56-117 | | QYDQEEVGFPVKPQVPLRPMTFKGALDLSHFLREKGGLEGLIPKFKLPIQKETWETWWT |
| | Nef:64-99 | | EYWQATWIPEWEFVNTPPLVKLWYQLEKEPIVGAETFYVDGAANRETKWGFTTPDKKHQ |
| | LI | | KEPPFLWMGYELHPDKWTVQPIVLPEKDSWTVNDIQKLVGKLNWASQIYPGIKVITKIQ |
| | Pol:542-606 | | NFRVYYRDSRDPLWKGPAKLLWKGEGAVVIQDNSDIKVVPRRKAKIIRDYGKQMAGDDC |
| | Pol:367-431 | | VASRQDEDGTVLVGPTPVNIIGRNLLTQIGCTLNFPISPIETVPVKLKPGMDGPKVKQW |
| | Pol:932-1003 | | PLTEEKIKALVEICTEMEKEGKISKIGPENPYNTPVFAIKKKDSTKWRKLVDFRELNKR |
| | Pol:129-320 | | TQDFWEVQLGIPHPAGLKKKKSVTVLDVGDAYFSVPLDKDFRKYTAFTIPSINNETPGI |
| | RAKR | | RYQYNVLPQGWKGSPAIFQSSMTRAKRAPVKQTLNFDLLKLAGDVESNPGPMLPQITLW |
| | F2A linker | | QRPIVTIKIGGQIKEALLDTGADDTVLEDMNLPGKWKPKMIGGIGGFIKVKQYDQWGLT |
| | M | | TPDKKHQKDPPFLWMGYELHPDRWTVQPIELPEKESWTVNDIQKLIGKLNWASQIYAGI |
| | Pol:56-117 | | KVAAQEEEEVGFPVRPQVPLRPMTYKGALDLSHFLKEKGGLEGITKLQNFRVYYRDNRD |
| | Pol:367-431 | | PLWKGPARLLWKGEGAVVIQDNSEIKVVPRRKVKIIRDYGKRMAGDDCVAGRQDEDPKF |
| | AA | | RLPIQKETWDTWWTDYWQATWIPEWEFTNTPPLVKLWYQLETEPIAGVETFYVDGASNR |
| | QEE | | ETKAAGTVLIGPTPVNIIGRNLLTQLGCTLNFPISPIDTVPVKLKPGMDGPRVKQWPLT |
| | Nef:64-99 | | EEKIKALIEICTEMEKEGKISRIGPENPYNTPIFAIKKKDGTKWRKLVDFRELNKKTQD |
| | Pol:932-1003 | | FWEVQLGIPHPSGLKKKKSVTVLDIGDAYFSVPLDKEFRKYTAFTVPSTNNETPGVRYQ |
| | Pol:542-606 | | YNVLPMGWKGSPAIFQCSMT |
| | AA | | |
| | Pol:129-320 | | |
| 108 | Pol:56-117 | 1022 | LPQITLWQRPIVTIKIGGQIKEALLDTGADDTVLEDMNLPGKWKPKMIGGIGGFIKVKQ |
| | Pol:367-431 | | YDQWGLTTPDKKHQKDPPFLWMGYELHPDRWTVQPIELPEKESWTVNDIQKLIGKLNWA |
| | AA | | SQIYAGIKVAAQEEEEVGFPVRPQVPLRPMTYKGALDLSHFLKEKGGLEGITKLQNFRV |
| | QEE | | YYRDNRDPLWKGPARLLWKGEGAVVIQDNSEIKVVPRRKVKIIRDYGKRMAGDDCVAGR |
| | Nef:64-99 | | QDEDPKFRLPIQKETWDTWWTDYWQATWIPEWEFTNTPPLVKLWYQLETEPIAGVETFY |
| | Pol:932-1003 | | VDGASNRETKAAGTVLIGPTPVNIIGRNLLTQLGCTLNFPISPIDTVPVKLKPGMDGPR |
| | Pol:542-606 | | VKQWPLTEEKIKALIEICTEMEKEGKISRIGPENPYNTPIFAIKKKDGTKWRKLVDFRE |
| | AA | | LNKKTQDFWEVQLGIPHPSGLKKKKSVTVLDIGDAYFSVPLDKEFRKYTAFTVPSTNNE |
| | Pol:129-320 | | TPGVRYQYNVLPMGWKGSPAIFQCSMTRAKRAPVKQTLNFDLLKLAGDVESNPGPFPQI |
| | RAKR | | TLWQRPLVTIKIGGQLKEALLDTGADDTVLEEMNLPGRWKPKMIGGIGGFIKVRQYDQE |
| | F2A linker | | EVGFPVKPQVPLRPMTFKGALDLSHFLREKGGLEGLIPKFKLPIQKETWETWWTEYWQA |
| | Pol:56-117 | | TWIPEWEFVNTPPLVKLWYQLEKEPIVGAETFYVDGAANRETKWGFTTPDKKHQKEPPF |
| | Nef:64-99 | | LWMGYELHPDKWTVQPIVLPEKDSWTVNDIQKLVGKLNWASQIYPGIKVITKIQNFRVY |
| | LI | | YRDSRDPLWKGPAKLLWKGEGAVVIQDNSDIKVVPRRKAKIIRDYGKQMAGDDCVASRQ |
| | Pol:542-606 | | DEDGTVLVGPTPVNIIGRNLLTQIGCTLNFPISPIETVPVKLKPGMDGPKVKQWPLTEE |
| | Pol:367-431 | | KIKALVEICTEMEKEGKISKIGPENPYNTPVFAIKKKDSTKWRKLVDFRELNKRTQDFW |

TABLE F-continued

Illustrative Compound Fusion Polypeptides

| SEQ ID NO: | Polypeptide segments | Length (aa) | Amino Acid Sequence |
|---|---|---|---|
| | Pol:932-1003<br>Pol:129-320 | | EVQLGIPHPAGLKKKKSVTVLDVGDAYFSVPLDKDFRKYTAFTIPSINNETPGIRYQYN<br>VLPQGWKGSPAIFQSSMT |
| 109 | Pol:747-827<br>Nef:117-148<br>Pol:840-920<br>AA<br>Gag:1-53<br>SEG<br>Gag:147-369<br>AAA<br>Pol:683-708<br>RAKR<br>F2A linker<br>Gag:147-369<br>Pol:840-920<br>Pol:683-708<br>AAY<br>Gag:1-53<br>Nef:117-148<br>Pol:747-827 | 1034 | VAKEIVASCDKCQLKGEAMHGQVDCSPGIWQLDCTHLEGKIILVAVHVASGYIEAEVIP<br>AETGQETAYFLLKLAGRWPVKTTQGYFPDWQNYTPGPGTRYPLTFGWCFKLVPVTVKAA<br>CWWAGIKQEFGIPYNPQSQGVVESMNKELKKIIGQVRDQAEHLKTAVQMAVFIHNFKRK<br>GGIGGYSAGERIVDIIAAAMAARASVLSGGELDRWEKIRLRPGGKKKYRLKHIVWASRE<br>LERFAVNPGLLETSEGISPRTLNAWVKVVEEKAFSPEVIPMFSALSEGATPQDLNTMLN<br>TVGGHQAAMQMLKETINEEAAEWDRLHPVHAGPIAPGQMREPRGSDIAGTTSTLQEQIG<br>WMTNNPPIPVGEIYKRWIILGLNKIVRMYSPTSILDIRQGPKEPFRDYVDRFYKTLRAE<br>QASQEVKNWMTETLLVQNANPDCKTILKALGPAATLEEMMTACQGVGGPGHKARVLAEA<br>MSQAAAKEKVYLAWVPAHKGIGGNEQVDKLVSRAKRAPVKQTLNFDLLKLAGDVESNPG<br>PHQALSPRTLNAWVKVIEEKAFSPEVIPMFTALSEGATPHDLNTMLNTIGGHQAAMQML<br>KDTINEEAAEWDRVHPVHAGPVAPGQMRDPRGSDIAGSTSTLQEQIAWMTNNPPIPVGD<br>IYKRWIIMGLNKIVRMYSPVSILDIKQGPKEPFRDYVDRFYRTLRAEQASQDVKNWMTE<br>TLLVQNSNPDCKTILKALGPGATLEEMMSACQGVGGPSHKARVLAEAMCQAVKAACWWA<br>GVKQEFGIPYNTQSQGVVESMNNELKKIIGQIRDQAEHLKTAVQMAVLIHNFKRKGGIG<br>EYSAGERIIDIIAKEKIYLAWVPAHKGIGGNEQIDKLVSAAYMAARASILSGGKLDKWE<br>KIRLRPGGRKKYKLKHLVWASRELERFALNPGLLETTQGFFPDWQNYTPGPGIRFPLTF<br>GWCFKLVPLVAKEIVACCDKCQLKGEAIHGQVDCSPGVWQLDCTHLEGKVILVAVHVAS<br>GYIEAEIIPTETGQETAYFILKLAGRWPVTT |
| 110 | Gag:147-369<br>Pol:840-920<br>Pol:683-708<br>AAY<br>Gag:1-53<br>Nef:117-148<br>Pol:747-827<br>RAKR<br>F2A linker<br>Pol:747-827<br>Nef:117-148<br>Pol:840-920<br>AA<br>Gag:1-53<br>SEG<br>Gag:147-369<br>AAA<br>Pol:683-708 | 1031 | LSPRTLNAWVKVIEEKAFSPEVIPMFTALSEGATPHDLNTMLNTIGGHQAAMQMLKDTI<br>NEEAAEWDRVHPVHAGPVAPGQMRDPRGSDIAGSTSTLQEQIAWMTNNPPIPVGDIYKR<br>WIIMGLNKIVRMYSPVSILDIKQGPKEPFRDYVDRFYRTLRAEQASQDVKNWMTETLLV<br>QNSNPDCKTILKALGPGATLEEMMSACQGVGGPSHKARVLAEAMCQAVKAACWWAGVKQ<br>EFGIPYNTQSQGVVESMNNELKKIIGQIRDQAEHLKTAVQMAVLIHNFKRKGGIGEYSA<br>GERIIDIIAKEKIYLAWVPAHKGIGGNEQIDKLVSAAYMAARASILSGGKLDKWEKIRL<br>RPGGRKKYKLKHLVWASRELERFALNPGLLETTQGFFPDWQNYTPGPGIRFPLTFGWCF<br>KLVPLVAKEIVACCDKCQLKGEAIHGQVDCSPGVWQLDCTHLEGKVILVAVHVASGYIE<br>AEIIPTETGQETAYFILKLAGRWPVTTRAKRAPVKQTLNFDLLKLAGDVESNPGPVAKE<br>IVASCDKCQLKGEAMHGQVDCSPGIWQLDCTHLEGKIILVAVHVASGYIEAEVIPAETG<br>QETAYFLLKLAGRWPVKTTQGYFPDWQNYTPGPGTRYPLTFGWCFKLVPVTVKAACWWA<br>GIKQEFGIPYNPQSQGVVESMNKELKKIIGQVRDQAEHLKTAVQMAVFIHNFKRKGGIG<br>GYSAGERIVDIIAAAMAARASVLSGGELDRWEKIRLRPGGKKKYRLKHIVWASRELERF<br>AVNPGLLETSEGISPRTLNAWVKVVEEKAFSPEVIPMFSALSEGATPQDLNTMLNTVGG<br>HQAAMQMLKETINEEAAEWDRLHPVHAGPIAPGQMREPRGSDIAGTTSTLQEQIGWMTN<br>NPPIPVGEIYKRWIILGLNKIVRMYSPTSILDIRQGPKEPFRDYVDRFYKTLRAEQASQ<br>EVKNWMTETLLVQNANPDCKTILKALGPAATLEEMMTACQGVGGPGHKARVLAEAMSQA<br>AAKEKVYLAWVPAHKGIGGNEQVDKLVS |
| 111 | Pol:932-1003<br>AAY<br>EE<br>Nef:64-99<br>AA<br>Pol:367-431<br>Pol:542-606<br>Pol:56-117<br>Pol:129-320<br>RAKR<br>F2A linker<br>Pol:542-606<br>Nef:64-99<br>Pol:56-117<br>Pol:932-1003<br>Pol:367-431<br>K<br>Pol:129-320 | 1020 | ITKIQNFRVYYRDSRDPLWKGPAKLLWKGEGAVVIQDNSDIKVVPRRKAKIIRDYGKQM<br>AGDDCVASRQDEDAAYEEEEVGFPVKPQVPLRPMTFKGALDLSHFLREKGGLEGAAWGF<br>TTPDKKHQKEPPFLWMGYELHPDKWTVQPIVLPEKDSWTVNDIQKLVGKLNWASQIYPG<br>IKVPKFKLPIQKETWETWWTEYWQATWIPEWEFVNTPPLVKLWYQLEKEPIVGAETFYV<br>DGAANRETKFPQITLWQRPLVTIKIGGQLKEALLDTGADDTVLEEMNLPGRWKPKMIGG<br>IGGFIKVRQYDQGTVLVGPTPVNIIGRNLLTQIGCTLNFPISPIETVPVKLKPGMDGPK<br>VKQWPLTEEKIKALVEICTEMEKEGKISKIGPENPYNTPVFAIKKKDSTKWRKLVDFRE<br>LNKRTQDFWEVQLGIPHPAGLKKKKSVTVLDVGDAYFSVPLDKDFRKYTAFTIPSINNE<br>TPGIRYQYNVLPQGWKGSPAIFQSSMTRAKRAPVKQTLNFDLLKLAGDVESNPGPPKFR<br>LPIQKETWDTWWTDYWQATWIPEWEFTNTPPLVKLWYQLETEPIAGVETFYVDGASNRE<br>TKEEVGFPVRPQVPLRPMTYKGALDLSHFLKEKGGLEGLPQITLWQRPIVTIKIGGQIK<br>EALLDTGADDTVLEDMNLPGKWKPKMIGGIGGFIKVKQYDQITKLQNFRVYYRDNRDPL<br>WKGPARLLWKGEGAVVIQDNSEIKVVPRRKVKIIRDYGKRMAGDDCVAGRQDEDWGLTT<br>PDKKHQKDPPFLWMGYELHPDRWTVQPIELPEKESWTVNDIQKLIGKLNWASQIYAGIK<br>VKGTVLIGPTPVNIIGRNLLTQLGCTLNFPISPIDTVPVKLKPGMDGPRVKQWPLTEEK<br>IKALIEICTEMEKEGKISRIGPENPYNTPIFAIKKKDGTKWRKLVDFRELNKKTQDFWE<br>VQLGIPHPSGLKKKKSVTVLDIGDAYFSVPLDKEFRKYTAFTVPSTNNETPGVRYQYNV<br>LPMGWKGSPAIFQCSMT |
| 112 | Pol:542-606<br>Nef:64-99<br>Pol:56-117<br>Pol:932-1003<br>Pol:367-431<br>K<br>Pol:129-320<br>RAKR<br>F2A linker<br>Pol:932-1003<br>AAY<br>EE<br>Nef:64-99<br>AA<br>Pol:367-431 | 1020 | PKFRLPIQKETWDTWWTDYWQATWIPEWEFTNTPPLVKLWYQLETEPIAGVETFYVDGA<br>SNRETKEEVGFPVRPQVPLRPMTYKGALDLSHFLKEKGGLEGLPQITLWQRPIVTIKIG<br>GQIKEALLDTGADDTVLEDMNLPGKWKPKMIGGIGGFIKVKQYDQITKLQNFRVYYRDN<br>RDPLWKGPARLLWKGEGAVVIQDNSEIKVVPRRKVKIIRDYGKRMAGDDCVAGRQDEDW<br>GLTTPDKKHQKDPPFLWMGYELHPDRWTVQPIELPEKESWTVNDIQKLIGKLNWASQIY<br>AGIKVKGTVLIGPTPVNIIGRNLLTQLGCTLNFPISPIDTVPVKLKPGMDGPRVKQWPL<br>TEEKIKALIEICTEMEKEGKISRIGPENPYNTPIFAIKKKDGTKWRKLVDFRELNKKTQ<br>DFWEVQLGIPHPSGLKKKKSVTVLDIGDAYFSVPLDKEFRKYTAFTVPSTNNETPGVRY<br>QYNVLPMGWKGSPAIFQCSMTRAKRAPVKQTLNFDLLKLAGDVESNPGPITKIQNFRVY<br>YRDSRDPLWKGPAKLLWKGEGAVVIQDNSDIKVVPRRKAKIIRDYGKQMAGDDCVASRQ<br>DEDAAYEEEEVGFPVKPQVPLRPMTFKGALDLSHFLREKGGLEGAAWGFTTPDKKHQKE<br>PPFLWMGYELHPDKWTVQPIVLPEKDSWTVNDIQKLVGKLNWASQIYPGIKVPKFKLPI<br>QKETWETWWTEYWQATWIPEWEFVNTPPLVKLWYQLEKEPIVGAETFYVDGAANRETKF<br>PQITLWQRPLVTIKIGGQLKEALLDTGADDTVLEEMNLPGRWKPKMIGGIGGFIKVRQY<br>DQGTVLVGPTPVNIIGRNLLTQIGCTLNFPISPIETVPVKLKPGMDGPKVKQWPLTEEK |

TABLE F-continued

Illustrative Compound Fusion Polypeptides

| SEQ ID NO: | Polypeptide segments | Length (aa) | Amino Acid Sequence |
|---|---|---|---|
| | Pol:542-606 | | IKALVEICTEMEKEGKISKIGPENPYNTPVFAIKKKDSTKWRKLVDFRELNKRTQDFWE |
| | Pol:56-117 | | VQLGIPHPAGLKKKKSVTVLDVGDAYFSVPLDKDFRKYTAFTIPSINNETPGIRYQYNV |
| | Pol:129-320 | | LPQGWKGSPAIFQSSMT |
| 208 | M | 1023 | MTVKAACWWAGIKQEFGIPYNPQSQGVVESMNKELKKIIGQVRDQAEHLKTAVQMAVFI |
| | Pol:840-920 | | HNFKRKGGIGGYSAGERIVDIIAISPRTLNAWVKVVEEKAFSPEVIPMFSALSEGATPQ |
| | Gag:147-369 | | DLNTMLNTVGGHQAAMQMLKETINEEAAEWDRLHPVHAGPIAPGQMREPRGSDIAGTTS |
| | Gag:1-53 | | TLQEQIGWMTNNPPIPVGEIYKRWIILGLNKIVRMYSPTSILDIRQGPKEPFRDYVDRF |
| | PPV | | YKTLRAEQASQEVKNWMTETLLVQNANPDCKTILKALGPAATLEEMMTACQGVGGPGHK |
| | Pol:747-827 | | ARVLAEAMSQMAARASVLSGGELDRWEKIRLRPGGKKKYRLKHIVWASRELERFAVNPG |
| | Pol:683-708 | | LLETPPVVAKEIVASCDKCQLKGEAMHGQVDCSPGIWQLDCTHLEGKIILVAVHVASGY |
| | Nef:117-148 | | IEAEVIPAETGQETAYFLLKLAGRWPVKTKEKVYLAWVPAHKGIGGNEQVDKLVSTQGY |
| | RAKR | | FPDWQNYTPGPGTRYPLTFGWCFKLVPVRAKRAPVKQTLNFDLLKLAGDVESNPGPMFP |
| | F2A linker | | QITLWQRPLVTIKIGGQLKEALLDTGADDTVLEEMNLPGRWKPKMIGGIGGFIKVRQYD |
| | M | | QEEVGFPVKPQVPLRPMTFKGALDLSHFLREKGGLEGLIPKFKLPIQKETWETWWTEYW |
| | Pol:56-117 | | QATWIPEWEFVNTPPLVKLWYQLEKEPIVGAETFYVDGAANRETKWGFTTPDKKHQKEP |
| | Nef:64-99 | | PFLWMGYELHPDKWTVQPIVLPEKDSWTVNDIQKLVGKLNWASQIYPGIKVITKIQNFR |
| | LI | | VYYRDSRDPLWKGPAKLLWKGEGAVVIQDNSDIKVVPRRKAKIIRDYGKQMAGDDCVAS |
| | Pol:542-606 | | RQDEDGTVLVGPTPVNIIGRNLLTQIGCTLNFPISPIETVPVKLKPGMDGPKVKQWPLT |
| | Pol:367-431 | | EEKIKALVEICTEMEKEGKISKIGPENPYNTPVFAIKKKDSTKWRKLVDFRELNKRTQD |
| | Pol:932-1003 | | FWEVQLGIPHPAGLKKKKSVTVLDVGDAYFSVPLDKDFRKYTAFTIPSINNETPGIRYQ |
| | Pol:129-320 | | YNVLPQGWKGSPAIFQSSMT |
| 224 | Pol:840-920 | 1021 | TVKAACWWAGIKQEFGIPYNPQSQGVVESMNKELKKIIGQVRDQAEHLKTAVQMAVFIH |
| | Gag:147-369 | | NFKRKGGIGGYSAGERIVDIIAISPRTLNAWVKVVEEKAFSPEVIPMFSALSEGATPQD |
| | Gag:1-53 | | LNTMLNTVGGHQAAMQMLKETINEEAAEWDRLHPVHAGPIAPGQMREPRGSDIAGTTST |
| | PPV | | LQEQIGWMTNNPPIPVGEIYKRWIILGLNKIVRMYSPTSILDIRQGPKEPFRDYVDRFY |
| | Pol:747-827 | | KTLRAEQASQEVKNWMTETLLVQNANPDCKTILKALGPAATLEEMMTACQGVGGPGHKA |
| | Pol:683-708 | | RVLAEAMSQMAARASVLSGGELDRWEKIRLRPGGKKKYRLKHIVWASRELERFAVNPGL |
| | Nef:117-148 | | LETPPVVAKEIVASCDKCQLKGEAMHGQVDCSPGIWQLDCTHLEGKIILVAVHVASGYI |
| | RAKR | | EAEVIPAETGQETAYFLLKLAGRWPVKTKEKVYLAWVPAHKGIGGNEQVDKLVSTQGYF |
| | F2A linker | | PDWQNYTPGPGTRYPLTFGWCFKLVPVRAKRAPVKQTLNFDLLKLAGDVESNPGPFPQI |
| | Pol:56-117 | | TLWQRPLVTIKIGGQLKEALLDTGADDTVLEEMNLPGRWKPKMIGGIGGFIKVRQYDQE |
| | Nef:64-99 | | EVGFPVKPQVPLRPMTFKGALDLSHFLREKGGLEGLIPKFKLPIQKETWETWWTEYWQA |
| | LI | | TWIPEWEFVNTPPLVKLWYQLEKEPIVGAETFYVDGAANRETKWGFTTPDKKHQKEPPF |
| | Pol:542-606 | | LWMGYELHPDKWTVQPIVLPEKDSWTVNDIQKLVGKLNWASQIYPGIKVITKIQNFRVY |
| | Pol:367-431 | | YRDSRDPLWKGPAKLLWKGEGAVVIQDNSDIKVVPRRKAKIIRDYGKQMAGDDCVASRQ |
| | Pol:932-1003 | | DEDGTVLVGPTPVNIIGRNLLTQIGCTLNFPISPIETVPVKLKPGMDGPKVKQWPLTEE |
| | Pol:129-320 | | KIKALVEICTEMEKEGKISKIGPENPYNTPVFAIKKKDSTKWRKLVDFRELNKRTQDFW |
| | | | EVQLGIPHPAGLKKKKSVTVLDVGDAYFSVPLDKDFRKYTAFTIPSINNETPGIRYQYN |
| | | | VLPQGWKGSPAIFQSSMT |
| 209 | M | 1030 | MLSPRTLNAWVKVIEEKAFSPEVIPMFTALSEGATPHDLNTMLNTIGGHQAAMQMLKDT |
| | Gag:147-369 | | INEEAAEWDRVHPVHAGPVAPGQMRDPRGSDIAGSTSTLQEQIAWMTNNPPIPVGDIYK |
| | Pol:747-827 | | RWIIMGLNKIVRMYSPVSILDIKQGPKEPFRDYVDRFYRTLRAEQASQDVKNWMTETLL |
| | Gag:1-53 | | VQNSNPDCKTILKALGPGATLEEMMSACQGVGGPSHKARVLAEAMCQVAKEIVACCDKC |
| | AA | | QLKGEAIHGQVDCSPGVWQLDCTHLEGKVILVAVHVASGYIEAEIIPTETGQETAYFIL |
| | Pol:840-920 | | KLAGRWPVTTMAARASILSGGKLDKWEKIRLRPGGRKKYKLKHLVWASRELERFALNPG |
| | Nef:117-148 | | LLETAAAVKAACWWAGVKQEFGIPYNTQSQGVVESMNNELKKIIGQIRDQAEHLKTAVQ |
| | LIK | | MAVLIHNFKRKGGIGEYSAGERIIDIIATQGFFPDWQNYTPGPGIRFPLTFGWCFKLVP |
| | Pol:683-708 | | LLIKKEKIYLAWVPAHKGIGGNEQIDKLVSRAKRAPVKQTLNFDLLKLAGDVESNPGPM |
| | RAKR | | LPQITLWQRPIVTIKIGGQIKEALLDTGADDTVLEDMNLPGKWKPKMIGGIGGFIKVKQ |
| | F2A linker | | YDQWGLTTPDKKHQKDPPFLWMGYELHPDRWTVQPIELPEKESWTVNDIQKLIGKLNWA |
| | M | | SQIYAGIKVAAQEEEEVGFPVRPQVPLRPMTYKGALDLSHFLKEKGGLEGITKLQNFRV |
| | Pol:56-117 | | YYRDNRDPLWKGPARLLWKGEGAVVIQDNSEIKVVPRRKVKIIRDYGKRMAGDDCVAGR |
| | Pol:367-431 | | QDEDPKFRLPIQKETWDTWWTDYWQATWIPEWEFTNTPPLVKLWYQLETEPIAGVETFY |
| | AA | | VDGASNRETKAAGTVLIGPTPVNIIGRNLLTQLGCTLNFPISPIDTVPVKLKPGMDGPR |
| | QEE | | VKQWPLTEEKIKALIEICTEMEKEGKISRIGPENPYNTPIFAIKKKDGTKWRKLVDFRE |
| | Nef:64-99 | | LNKKTQDFWEVQLGIPHPSGLKKKKSVTVLDIGDAYFSVPLDKEFRKYTAFTVPSTNNE |
| | Pol:932-1003 | | TPGVRYQYNVLPMGWKGSPAIFQCSMT |
| | Pol:542-606 | | |
| | AA | | |
| | Pol:129-320 | | |
| 227 | Gag:147-369 | 1029 | LSPRTLNAWVKVIEEKAFSPEVIPMFTALSEGATPHDLNTMLNTIGGHQAAMQMLKDTI |
| | Pol:747-827 | | NEEAAEWDRVHPVHAGPVAPGQMRDPRGSDIAGSTSTLQEQIAWMTNNPPIPVGDIYKR |
| | Gag:1-53 | | WIIMGLNKIVRMYSPVSILDIKQGPKEPFRDYVDRFYRTLRAEQASQDVKNWMTETLLV |
| | AA | | QNSNPDCKTILKALGPGATLEEMMSACQGVGGPSHKARVLAEAMCQVAKEIVACCDKCQ |
| | Pol:840-920 | | LKGEAIHGQVDCSPGVWQLDCTHLEGKVILVAVHVASGYIEAEIIPTETGQETAYFILK |
| | Nef:117-148 | | LAGRWPVTTMAARASILSGGKLDKWEKIRLRPGGRKKYKLKHLVWASRELERFALNPGL |
| | LIK | | LETAAAVKAACWWAGVKQEFGIPYNTQSQGVVESMNNELKKIIGQIRDQAEHLKTAVQM |
| | Pol:683-708 | | AVLIHNFKRKGGIGEYSAGERIIDIIATQGFFPDWQNYTPGPGIRFPLTFGWCFKLVPL |
| | RAKR | | LIKKEKIYLAWVPAHKGIGGNEQIDKLVSRAKRAPVKQTLNFDLLKLAGDVESNPGPML |
| | F2A linker | | PQITLWQRPIVTIKIGGQIKEALLDTGADDTVLEDMNLPGKWKPKMIGGIGGFIKVKQY |
| | M | | DQWGLTTPDKKHQKDPPFLWMGYELHPDRWTVQPIELPEKESWTVNDIQKLIGKLNWAS |

TABLE F-continued

Illustrative Compound Fusion Polypeptides

| SEQ ID NO: | Polypeptide segments | Length (aa) | Amino Acid Sequence |
|---|---|---|---|
| | Pol:56-117<br>Pol:367-431<br>AA<br>QEE<br>Nef:64-99<br>Pol:932-1003<br>Pol:542-606<br>AA<br>Pol:129-320 | | QIYAGIKVAAQEEEEVGFPVRPQVPLRPMTYKGALDLSHFLKEKGGLEGITKLQNFRVY<br>YRDNRDPLWKGPARLLWKGEGAVVIQDNSEIKVVPRRKVKIIRDYGKRMAGDDCVAGRQ<br>DEDPKFRLPIQKETWDTWWTDYWQATWIPEWEFTNTPPLVKLWYQLETEPIAGVETFYV<br>DGASNRETKAAGTVLIGPTPVNIIGRNLLTQLGCTLNFPISPIDTVPVKLKPGMDGPRV<br>KQWPLTEEKIKALIEICTEMEKEGKISRIGPENPYNTPIFAIKKKDGTKWRKLVDFREL<br>NKKTQDFWEVQLGIPHPSGLKKKKSVTVLDIGDAYFSVPLDKEFRKYTAFTVPSTNNET<br>PGVRYQYNVLPMGWKGSPAIFQCSMT |
| 223 | Gag:147-369<br>Pol:747-827<br>Gag:1-53<br>AA<br>Pol:840-920<br>Nef:117-148<br>LIK<br>Pol:683-708<br>RAKR<br>F2A linker<br>Pol:56-117<br>Pol:367-431<br>AA<br>QEE<br>Nef:64-99<br>Pol:932-1003<br>Pol:542-606<br>AA<br>Pol:129-320 | 1028 | LSPRTLNAWVKVIEEKAFSPEVIPMFTALSEGATPHDLNTMLNTIGGHQAAMQMLKDTI<br>NEEAAEWDRVHPVHAGPVAPGQMRDPRGSDIAGSTSTLQEQIAWMTNNPPIPVGDIYKR<br>WIIMGLNKIVRMYSPVSILDIKQGPKEPFRDYVDRFYRTLRAEQASQDVKNWMTETLLV<br>QNSNPDCKTILKALGPGATLEEMMSACQGVGGPSHKARVLAEAMCQVAKEIVACCDKCQ<br>LKGEAIHGQVDCSPGVWQLDCTHLEGKVILVAVHVASGYIEAEIIPTETGQETAYFILK<br>LAGRWPVTTMAARASILSGGKLDKWEKIRLRPGGRKKYKLKHLVWASRELERFALNPGL<br>LETAAAVKAACWWAGVKQEFGIPYNTQSQGVVESMNNELKKIIGQIRDQAEHLKTAVQM<br>AVLIHNFKRKGGIGEYSAGERIIDIIATQGFFPDWQNYTPGPGIRFPLTFGWCFKLVPL<br>LIKKEKIYLAWVPAHKGIGGNEQIDKLVSRAKRAPVKQTLNFDLLKLAGDVESNPGPLP<br>QITLWQRPIVTIKIGGQIKEALLDTGADDTVLEDMNLPGKWKPKMIGGIGGFIKVKQYD<br>QWGLTTPDKKHQKDPPFLWMGYELHPDRWTVQPIELPEKESWTVNDIQKLIGKLNWASQ<br>IYAGIKVAAQEEEEVGFPVRPQVPLRPMTYKGALDLSHFLKEKGGLEGITKLQNFRVYY<br>RDNRDPLWKGPARLLWKGEGAVVIQDNSEIKVVPRRKVKIIRDYGKRMAGDDCVAGRQD<br>EDPKFRLPIQKETWDTWWTDYWQATWIPEWEFTNTPPLVKLWYQLETEPIAGVETFYVD<br>GASNRETKAAGTVLIGPTPVNIIGRNLLTQLGCTLNFPISPIDTVPVKLKPGMDGPRVK<br>QWPLTEEKIKALIEICTEMEKEGKISRIGPENPYNTPIFAIKKKDGTKWRKLVDFRELN<br>KKTQDFWEVQLGIPHPSGLKKKKSVTVLDIGDAYFSVPLDKEFRKYTAFTVPSTNNETP<br>GVRYQYNVLPMGWKGSPAIFQCSMT |
| 222 | Gag:147-369<br>Pol:747-827<br>Gag:1-53<br>AA<br>Pol:840-920<br>Nef:117-148<br>LIK<br>Pol:683-708<br>F2A<br>Pol:56-117<br>Pol:367-431<br>AA<br>QEE<br>Nef:64-99<br>Pol:932-1003<br>Pol:542-606<br>AA<br>Pol:129-320 | 1030 | ISPRTLNAWVKVVEEKAFSPEVIPMFSALSEGATPQDLNTMLNTVGGHQAAMQMLKETI<br>NEEAAEWDRLHPVHAGPIAPGQMREPRGSDIAGTTSTLQEQIGWMTNNPPIPVGEIYKR<br>WIILGLNKIVRMYSPTSILDIRQGPKEPFRDYVDRFYKTLRAEQASQEVKNWMTETLLV<br>QNANPDCKTILKALGPAATLEEMMTACQGVGGPGHKARVLAEAMSQPPVVAKEIVASCD<br>KCQLKGEAMHGQVDCSPGIWQLDCTHLEGKIILVAVHVASGYIEAEVIPAETGQETAYF<br>LLKLAGRWPVKTMAARASVLSGGELDRWEKIRLRPGGKKKYRLKHIVWASRELERFAVN<br>PGLLETAATVKAACWWAGIKQEFGIPYNPQSQGVVESMNKELKKIIGQVRDQAEHLKTA<br>VQMAVFIHNFKRKGGIGGYSAGERIVDIIATQGYFPDWQNYTPGPGTRYPLTFGWCFKL<br>VPVKEKVYLAWVPAHKGIGGNEQVDKLVSRAKRAPVKQTLNFDLLKLAGDVESNPGPFP<br>QITLWQRPLVTIKIGGQLKEALLDTGADDTVLEEMNLPGRWKPKMIGGIGGFIKVRQYD<br>QWGFTTPDKKHQKEPPFLWMGYELHPDKWTVQPIVLPEKDSWTVNDIQKLVGKLNWASQ<br>IYPGIKVAAQEEEEVGFPVKPQVPLRPMTFKGALDLSHFLREKGGLEGLIITKIQNFRV<br>YYRDSRDPLWKGPAKLLWKGEGAVVIQDNSDIKVVPRRKAKIIRDYGKQMAGDDCVASR<br>QDEDPKFKLPIQKETWETWWTEYWQATWIPEWEFVNTPPLVKLWYQLEKEPIVGAETFY<br>VDGAANRETKAAGTVLVGPTPVNIIGRNLLTQIGCTLNFPISPIETVPVKLKPGMDGPK<br>VKQWPLTEEKIKALVEICTEMEKEGKISKIGPENPYNTPVFAIKKKDSTKWRKLVDFRE<br>LNKRTQDFWEVQLGIPHPAGLKKKKSVTVLDVGDAYFSVPLDKDFRKYTAFTIPSINNE<br>TPGIRYQYNVLPQGWKGSPAIFQSSMT |
| 200 | Pol:840-920<br>Gag:147-369<br>Pol:586-606<br>AA<br>Pol:683-708<br>RAKR<br>F2A linker<br>Gag:147-369<br>Pol:840-920<br>Pol:586-606<br>AA<br>Pol:683-708 | 735 | TVKAACWWAGIKQEFGIPYNPQSQGVVESMNKELKKIIGQVRDQAEHLKTAVQMAVFIH<br>NFKRKGGIGGYSAGERIVDIIAISPRTLNAWVKVVEEKAFSPEVIPMFSALSEGATPQD<br>LNTMLNTVGGHQAAMQMLKETINEEAAEWDRLHPVHAGPIAPGQMREPRGSDIAGTTST<br>LQEQIGWMTNNPPIPVGEIYKRWIILGLNKIVRMYSPTSILDIRQGPKEPFRDYVDRFY<br>KTLRAEQASQEVKNWMTETLLVQNANPDCKTILKALGPAATLEEMMTACQGVGGPGHKA<br>RVLAEAMSQKEPIVGAETFYVDGAANRETKAAKEKVYLAWVPAHKGIGGNEQVDKLVSR<br>AKRAPVKQTLNFDLLKLAGDVESNPGPLSPRTLNAWVKVIEEKAFSPEVIPMFTALSEG<br>ATPHDLNTMLNTIGGHQAAMQMLKDTINEEAAEWDRVHPVHAGPVAPGQMRDPRGSDIA<br>GSTSTLQEQIAWMTNNPPIPVGDIYKRWIIMGLNKIVRMYSPVSILDIKQGPKEPFRDY<br>VDRFYRTLRAEQASQDVKNWMTETLLVQNSNPDCKTILKALGPGATLEEMMSACQGVGG<br>PSHKARVLAEAMCQAVKAACWWAGVKQEFGIPYNTQSQGVVESMNNELKKIIGQIRDQA<br>EHLKTAVQMAVLIHNFKRKGGIGEYSAGERIIDIIATEPIAGVETFYVDGASNRETKAA<br>KEKIYLAWVPAHKGIGGNEQIDKLVS |
| 201 | Pol:932-1003<br>AAA<br>I<br>Pol:129-320<br>Pol:747-827<br>QEE<br>Nef:64-76<br>RAKR<br>F2A linker<br>Pol:747-827<br>Pol:932-1003<br>Pol:129-320 | 758 | ITKIQNFRVYYRDSRDPLWKGPAKLLWKGEGAVVIQDNSDIKVVPRRKAKIIRDYGKQM<br>AGDDCVASRQDEDAAAIGTVLVGPTPVNIIGRNLLTQIGCTLNFPISPIETVPVKLKPG<br>MDGPKVKQWPLTEEKIKALVEICTEMEKEGKISKIGPENPYNTPVFAIKKKDSTKWRKL<br>VDFRELNKRTQDFWEVQLGIPHPAGLKKKKSVTVLDVGDAYFSVPLDKDFRKYTAFTIP<br>SINNETPGIRYQYNVLPQGWKGSPAIFQSSMTVAKEIVASCDKCQLKGEAMHGQVDCSP<br>GIWQLDCTHLEGKIILVAVHVASGYIEAEVIPAETGQETAYFLLKLAGRWPVKTQEEEE<br>VGFPVKPQVPLRAKRAPVKQTLNFDLLKLAGDVESNPGPVAKEIVACCDKCQLKGEAIH<br>GQVDCSPGVWQLDCTHLEGKVILVAVHVASGYIEAEIIPTETGQETAYFILKLAGRWPV<br>TTITKLQNFRVYYRDNRDPLWKGPARLLWKGEGAVVIQDNSEIKVVPRRKVKIIRDYGK<br>RMAGDDCVAGRQDEDGTVLIGPTPVNIIGRNLLTQLGCTLNFPISPIDTVPVKLKPGMD<br>GPRVKQWPLTEEKIKALIEICTEMEKEGKISRIGPENPYNTPIFAIKKKDGTKWRKLVD<br>FRELNKKTQDFWEVQLGIPHPSGLKKKKSVTVLDIGDAYFSVPLDKEFRKYTAFTVPST |

TABLE F-continued

Illustrative Compound Fusion Polypeptides

| SEQ ID NO: | Polypeptide segments | Length (aa) | Amino Acid Sequence |
|---|---|---|---|
| | KIL<br>QEE<br>Nef:64-76 | | NNETPGVRYQYNVLPMGWKGSPAIFQCSMTKILQEEEEVGFPVRPQVPL |
| 202 | Pol:840-920<br>Gag:147-369<br>Pol:586-606<br>AA<br>Pol:683-708<br>RAKR<br>F2A linker<br>Pol:932-1003<br>AAA<br>I<br>Pol:129-320<br>Pol:747-827<br>QEE<br>Nef:64-76 | 747 | TVKAACWWAGIKQEFGIPYNPQSQGVVESMNKELKKIIGQVRDQAEHLKTAVQMAVFIHNFKRKGGIGGYSAGERIVDIIAISPRTLNAWVKVVEEKAFSPEVIPMFSALSEGATPQDLNTMLNTVGGHQAAMQMLKETINEEAAEWDRLHPVHAGPIAPGQMREPRGSDIAGTTSTLQEQIGWMTNNPPIPVGEIYKRWIILGLNKIVRMYSPTSILDIRQGPKEPFRDYVDRFYKTLRAEQASQEVKNWMTETLLVQNANPDCKTILKALGPAATLEEMMTACQGVGGPGHKARVLAEAMSQKEPIVGAETFYVDGAANRETKAAKEKVYLAWVPAHKGIGGNEQVDKLVSRAKRAPVKQTLNFDLLKLAGDVESNPGPITKIQNFRVYYRDSRDPLWKGPAKLLWKGEGAVVIQDNSDIKVVPRRKAKIIRDYGKQMAGDDCVASRQDEDAAAIGTVLVGPTPVNIIGRNLLTQIGCTLNFPISPIETVPVKLKPGMDGPKVKQWPLTEEKIKALVEICTEMEKEGKISKIGPENPYNTPVFAIKKKDSTKWRKLVDFRELNKRTQDFWEVQLGIPHPAGLKKKKSVTVLDVGDAYFSVPLDKDFRKYTAFTIPSINNETPGIRYQYNVLPQGWKGSPAIFQSSMTVAKEIVASCDKCQLKGEAMHGQVDCSPGIWQLDCTHLEGKIILVAVHVASGYIEAEVIPAETGQETAYFLLKLAGRWPVKTQEEEEVGFPVKPQVPL |
| 203 | Gag:147-369<br>Pol:840-920<br>Pol:586-606<br>AA<br>Pol:683-708<br>RAKR<br>F2A linker<br>Pol:747-827<br>Pol:932-1003<br>Pol:129-320<br>KIL<br>QEE<br>Nef:64-76 | 746 | LSPRTLNAWVKVIEEKAFSPEVIPMFTALSEGATPHDLNTMLNTIGGHQAAMQMLKDTINEEAAEWDRVHPVHAGPVAPGQMRDPRGSDIAGSTSTLQEQIAWMTNNPPIPVGDIYKRWIIMGLNKIVRMYSPVSILDIKQGPKEPFRDYVDRFYRTLRAEQASQDVKNWMTETLLVQNSNPDCKTILKALGPGATLEEMMSACQGVGGPSHKARVLAEAMCQAVKAACWWAGVKQEFGIPYNTQSQGVVESMNNELKKIIGQIRDQAEHLKTAVQMAVLIHNFKRKGGIGEYSAGERIIDIIATEPIAGVETFYVDGASNRETKAAKEKIYLAWVPAHKGIGGNEQIDKLVSRAKRAPVKQTLNFDLLKLAGDVESNPGPVAKEIVACCDKCQLKGEAIHGQVDCSPGVWQLDCTHLEGKVILVAVHVASGYIEAEIIPTETGQETAYFILKLAGRWPVTTITKLQNFRVYYRDNRDPLWKGPARLLWKGEGAVVIQDNSEIKVVPRRKVKIIRDYGKRMAGDDCVAGRQDEDGTVLIGPTPVNIIGRNLLTQLGCTLNFPISPIDTVPVKLKPGMDGPRVKQWPLTEEKIKALIEICTEMEKEGKISRIGPENPYNTPIFAIKKKDGTKWRKLVDFRELNKKTQDFWEVQLGIPHPSGLKKKKSVTVLDIGDAYFSVPLDKEFRKYTAFTVPSTNNETPGVRYQYNVLPMGWKGSPAIFQCSMTKILQEEEEVGFPVRPQVPL |
| 204 | Pol:840-920<br>Gag:147-369<br>Pol:586-606<br>Pol:747-827<br>Pol:683-708<br>Nef:64-76<br>Pol:932-1003<br>AAA<br>Pol:129-320 | 717 | TVKAACWWAGIKQEFGIPYNPQSQGVVESMNKELKKIIGQVRDQAEHLKTAVQMAVFIHNFKRKGGIGGYSAGERIVDIIAISPRTLNAWVKVVEEKAFSPEVIPMFSALSEGATPQDLNTMLNTVGGHQAAMQMLKETINEEAAEWDRLHPVHAGPIAPGQMREPRGSDIAGTTSTLQEQIGWMTNNPPIPVGEIYKRWIILGLNKIVRMYSPTSILDIRQGPKEPFRDYVDRFYKTLRAEQASQEVKNWMTETLLVQNANPDCKTILKALGPAATLEEMMTACQGVGGPGHKARVLAEAMSQKEPIVGAETFYVDGAANRETKVAKEIVASCDKCQLKGEAMHGQVDCSPGIWQLDCTHLEGKIILVAVHVASGYIEAEVIPAETGQETAYFLLKLAGRWPVKTKEKVYLAWVPAHKGIGGNEQVDKLVSQEEEEVGFPVKPQVPLITKIQNFRVYYRDSRDPLWKGPAKLLWKGEGAVVIQDNSDIKVVPRRKAKIIRDYGKQMAGDDCVASRQDEDAAAIGTVLVGPTPVNIIGRNLLTQIGCTLNFPISPIETVPVKLKPGMDGPKVKQWPLTEEKIKALVEICTEMEKEGKISKIGPENPYNTPVFAIKKKDSTKWRKLVDFRELNKRTQDFWEVQLGIPHPAGLKKKKSVTVLDVGDAYFSVPLDKDFRKYTAFTIPSINNETPGIRYQYNVLPQGWKGSPAIFQSSMT |
| 205 | Gag:147-369<br>Pol:747-827<br>Pol:683-708<br>Pol:586-606<br>Pol:932-1003<br>Pol:840-920<br>Nef:64-76<br>Pol:129-320 | 716 | LSPRTLNAWVKVIEEKAFSPEVIPMFTALSEGATPHDLNTMLNTIGGHQAAMQMLKDTINEEAAEWDRVHPVHAGPVAPGQMRDPRGSDIAGSTSTLQEQIAWMTNNPPIPVGDIYKRWIIMGLNKIVRMYSPVSILDIKQGPKEPFRDYVDRFYRTLRAEQASQDVKNWMTETLLVQNSNPDCKTILKALGPGATLEEMMSACQGVGGPSHKARVLAEAMCQVAKEIVACCDKCQLKGEAIHGQVDCSPGVWQLDCTHLEGKVILVAVHVASGYIEAEIIPTETGQETAYFILKLAGRWPVTTKEKIYLAWVPAHKGIGGNEQIDKLVSTEPIAGVETFYVDGASNRETKITKLQNFRVYYRDNRDPLWKGPARLLWKGEGAVVIQDNSEIKVVPRRKVKIIRDYGKRMAGDDCVAGRQDEDAVKAACWWAGVKQEFGIPYNTQSQGVVESMNNELKKIIGQIRDQAEHLKTAVQMAVLIHNFKRKGGIGEYSAGERIIDIIAQEEEEVGFPVRPQVPLGTVLIGPTPVNIIGRNLLTQLGCTLNFPISPIDTVPVKLKPGMDGPRVKQWPLTEEKIKALIEICTEMEKEGKISRIGPENPYNTPIFAIKKKDGTKWRKLVDFRELNKKTQDFWEVQLGIPHPSGLKKKKSVTVLDIGDAYFSVPLDKEFRKYTAFTVPSTNNETPGVRYQYNVLPMGWKGSPAIFQCSMTKIL |

Signal or Leader Sequences

In various embodiments, the fusion polypeptides and/or compound fusion polypeptides comprise a signal sequence or signal peptide, e.g., to direct intracellular trafficking of the fusion polypeptide or compound fusion polypeptide to a proteasomal or lysosomal compartment. In various embodiments, fusion polypeptide or compound fusion polypeptide comprises a signal sequence at the N-terminus and/or the C-terminus. In some embodiments, the fusion polypeptide or compound fusion polypeptide comprises an N-terminal signal peptide or leader sequence. In various embodiments, the signal peptide or leader sequence is from a source protein selected from a serum protein, a cytokine, a chemokine, a chaperone protein, an invariant protein, and a protein that directs proteins to the lysosomal compartment. In some embodiments, the signal peptide or leader sequence is from a source protein selected from colony stimulating factor 2 (CSF2, GM-CSF), tissue type plasminogen activator (PLAT, t-PA), C-C motif chemokine ligand 7 (CCL7, MCP-3), C-X-C motif chemokine ligand 10 (CXCL10, IP-10), catenin beta 1 (CTNNB1), CD74 (p33; DHLAG; HLADG; Ia-GAMMA, invariant chain), serum albumin (ALB), polyubiquitin B/C (UBB/UBC), calreticulin (CALR), vesicular stomatitis virus G protein (VSV-G), lysosomal associated membrane protein 1 (LAMP-1) and lysosomal associated membrane protein 2 (LAMP-2). In certain embodiments, the fusion polypeptide comprises N-terminal and C-terminal signal sequences from LAMP-1, e.g., SEQ ID NOs: 125 and 126, respectively. In various embodiments, the signal peptide or leader sequence is selected from an amino acid sequence of any one of SEQ ID NOs: 115-126, or a nucleic acid sequence that is at least 95%, 96%, 97%, 98%, or 99% identical to any one of SEQ ID NOs: 115-126. Illustrative signal sequences that can be used in the present fusion polypeptides and compound fusion polypeptides are provided in Table G.

TABLE G signal sequences

| SEQ ID NO: | source protein name | SEQUENCE |
|---|---|---|
| 115 | CD74 | MHRRRSRSCREDQKPV |
| 116 | VSV-G | MKCLLYLAFLFIGVNC |
| 117 | albumin | KWVTFISLLELESSAYS |
| 118 | calreticulin | MLLSVPLLLGLLGLAVA |
| 119 | CSF2, GM-CSF | MWLQSLLLLGTVACSISV |
| 120 | CXCL10, IP-10 | MNQTAILICCLIFLTLSGIQG |
| 121 | PLAT, t-PA | MDAMKRGLCCVLLLCGAVEVSAR |
| 122 | β-catenin | MRKAAVSHWQQQSYLDSGIHSGATTTAPSLS |
| 123 | ubiquitin | MQIFVKTLTGKTITLEVEPSDTIENVKAKIQ DKEGIPPDQQRLIFAGKQLEDGRTLSDYNIQ KESTLHLVLRLRGG |
| 124 | CCL7, MCP-3 | MKASAALLCLLLTAAAFSPQGLA |
| 125 | LAMP-1 N-terminal | MAPRSARRPLLLLLLLLLLGLMHCASAAMEM VKNGNGTACIMANFSAAFSVNYDTKSGPKNM TLDLPSDATVVLNRSSCGKENTSDPSLVIAF GRGHTLTLNFTRNATRYSVQLMSFVYNLSDT HLFPNASSKEIKTVESITDIRADIDKKYRCV SGTQVHMNNVTVTLHDATIQAYLSNSSFSRG ETRCEQDRPSPTTAPPAPPSPSPSPVPKSPS VDKYNVSGTNGTCLLASMGLQLNLTYERKDN TTVTRLLNINPNKTSASGSCGAHLVTLELHS EGTTVLLFQFGMNASSSRFELQGIQLNTILP DARDPAFKAANGSLRALQATVGNSYKCNAEE HVRVTKAFSVNIFKVWVQAFKVEGGQFGSVE ECLLDENSLEDI |
| 126 | LAMP-1 C-terminal | GSEFTLIPIAVGGALAGLVIVLIAYLVGRKR SHAGYQTI |

3. Polynucleotides Encoding the Fusion Polypeptides or Compound Fusion Polypeptides Provided are polynucleotides encoding the fusion polypeptides or the compound fusion polypeptides, described herein, vectors comprising such polynucleotides, and host cells (e.g., human cells, mammalian cells, yeast cells, plant cells, insect cells, bacterial cells, e.g., *E. coli*) comprising such polynucleotides or expression vectors. Provided herein are polynucleotides comprising nucleotide sequence(s) encoding any of the fusion polypeptides or compound fusion polypeptides provided herein, as well as expression cassettes and vector(s) comprising such polynucleotide sequences, e.g., expression vectors for their efficient expression in host cells, e.g., mammalian cells. In various embodiments, the polynucleotide is a DNA, a cDNA, an mRNA, a self-amplifying RNA (SAM), a self-replicating RNA, or a self-amplifying replicon RNA (RepRNA). In some embodiments, the polynucleotide comprises an alphavirus self-replicating or self-amplifying replicon RNA (RepRNA). Self-replicating RNA and self-amplifying replicon RNA as modes of vaccine delivery are described, e.g., by Ballesteros-Briones, et al., *Curr Opin Virol.* (2020) 44:145-153; Bloom, et al., *Gene Ther.* (2020) 22:1-13; Lundstrom, *Int. J. Mol. Sci.* (2020) 21:5130; Moyo, et al., *Mol Ther Methods Clin Dev.* (2018) 12:32-46; Tews, et al., *Methods Mol Biol.* (2017) 1499:15-35; Démoulins, et al., *Methods Mol Biol.* (2017) 1499:37-75; Englezou, et al., *Mol Ther Nucleic Acids.* (2018) 12:118-134; McCollough, et al., *Vaccines* (Basel). (2014) 2(4):735-54; and McCollough, et al., *Mol Ther Nucleic Acids.* (2014) 3:e173.

The terms "polynucleotide" and "nucleic acid molecule" interchangeably refer to a polymeric form of nucleotides and includes both sense and anti-sense strands of RNA, cDNA, genomic DNA, and synthetic forms and mixed polymers of the above. As used herein, the term nucleic acid molecule may be interchangeable with the term polynucleotide. In some embodiments, a nucleotide refers to a ribonucleotide, deoxynucleotide or a modified form of either type of nucleotide, and combinations thereof. The terms also include without limitation, single- and double-stranded forms of DNA. In addition, a polynucleotide, e.g., a cDNA or mRNA, may include either or both naturally occurring and modified nucleotides linked together by naturally occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analogue, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). The above term is also intended to include any topological conformation, including single-stranded, double-stranded, partially duplexed, triplex, hairpinned, circular and padlocked conformations. A reference to a nucleic acid sequence encompasses its complement unless otherwise specified. Thus, a reference to a nucleic acid molecule having a particular sequence should be understood to encompass its complementary strand, with its complementary sequence. The term also includes codon-biased polynucleotides for improved expression in a desired viral expression vector or host cell.

A "substitution," as used herein, denotes the replacement of one or more amino acids or nucleotides by different amino acids or nucleotides, respectively.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location. "Isolated nucleic acid" encoding a polypeptide segment or a fusion polypeptide or a compound fusion polypeptide refers to one or more nucleic acid molecules encoding such polypeptide segments or fusion polypeptides or compound fusion polypeptides, including such nucleic acid molecule(s) in a single vector or separate vectors, and such nucleic acid molecule(s) present at one or more locations in a host cell.

A "polynucleotide variant," as the term is used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences described herein and evaluating one or more biological activities of the encoded polypeptide as described herein and/or using any of a number of techniques well known in the art.

In some embodiments, the nucleic acid molecule is codon-biased to enhance expression in a desired host cell, e.g., in human cells, mammalian cells, yeast cells, plant cells, insect cells, or bacterial cells, e.g., *E. coli* cells. Accordingly, provided are polynucleotides encoding a fusion polypeptide or a compound fusion polypeptide, described herein, wherein the polynucleotides are codon-biased, comprise replacement heterologous signal sequences, and/or have mRNA instability elements eliminated. Methods to generate codon-biased nucleic acids can be carried out by adapting the methods described in, e.g., U.S. Pat. Nos. 5,965,726; 6,174,666; 6,291,664; 6,414,132; and 6,794,498. Preferred codon usage for expression of the fusion polypeptides or compound fusion polypeptides comprising HIV-1 polypeptide segments from desired viral expression vectors and/or in desired host cells is provided, e.g., at kazusa.or.jp/codon/; and genscript.com/tools/codon-frequency-table.

In some embodiments, the polynucleotide encoding a fusion polypeptide or a compound fusion polypeptide, as described herein, which has a nucleic acid sequence of any one of SEQ ID NOs: 130-167, 210-219 and 225-226, or is at least 80%, at least 85%, at least 90%, at least 91%, at least 92%, at least 93%, at least 94%, at least 95%, at least 96%, at least 97%, at least 98%, at least 99% identical, or 100% identical to a nucleic acid sequence selected from SEQ ID NOs: 130-167, 210-219 and 225-226, as provided in Table H. In some embodiments, the polynucleotide encoding a fusion polypeptide or a compound fusion polypeptide, as described herein, which has a nucleic acid sequence of any one of SEQ ID NOs: 139, 140, 142, 143, 145, 146, 148, 149, 150, 152, 155, 158, 225 and 226, or is at least 80%, at least 85%, at least 90%, at least 91%, at least 92%, at least 93%, at least 94%, at least 95%, at least 96%, at least 97%, at least 98%, at least 99% identical, or 100% identical to a nucleic acid sequence selected from SEQ ID NOs: 139, 140, 142, 143, 145, 146, 148, 149, 150, 152, 155, 158, 225 and 226, as provided in Table H. Table H discloses "AAA" as SEQ ID NO: 48, "LIK" as SEQ ID NO: 53, "AAY" as SEQ ID NO: 49, "SEG" as SEQ ID NO: 55, "QEE" as SEQ ID NO: 51, "RAKR" as SEQ ID NO: 60, "KIL" as SEQ ID NO: 52 and "PPV" as SEQ ID NO: 54. In some embodiments, the polynucleotide encoding a fusion polypeptide or a compound fusion polypeptide, as described herein, which has a nucleic acid sequence of SEQ ID NO: 139, or a nucleic acid sequence that is at least 80%, at least 85%, at least 90%, at least 91%, at least 92%, at least 93%, at least 94%, at least 95%, at least 96%, at least 97%, at least 98%, at least 99% identical, or 100% identical to SEQ ID NO: 139. In some embodiments, the polynucleotide encoding a fusion polypeptide or a compound fusion polypeptide, as described herein, which has a nucleic acid sequence of SEQ ID NO: 142, or a nucleic acid sequence that is at least 80%, at least 85%, at least 90%, at least 91%, at least 92%, at least 93%, at least 94%, at least 95%, at least 96%, at least 97%, at least 98%, at least 99% identical, or 100% identical to SEQ ID NO: 142. In some embodiments, the polynucleotide encoding a fusion polypeptide or a compound fusion polypeptide, as described herein, which has a nucleic acid sequence of SEQ ID NO: 145, or a nucleic acid sequence that is at least 80%, at least 85%, at least 90%, at least 91%, at least 92%, at least 93%, at least 94%, at least 95%, at least 96%, at least 97%, at least 98%, at least 99% identical, or 100% identical to SEQ ID NO: 145. In some embodiments, the polynucleotide encoding a fusion polypeptide or a compound fusion polypeptide, as described herein, which has a nucleic acid sequence of SEQ ID NO: 148, or a nucleic acid sequence that is at least 80%, at least 85%, at least 90%, at least 91%, at least 92%, at least 93%, at least 94%, at least 95%, at least 96%, at least 97%, at least 98%, at least 99% identical, or 100% identical to SEQ ID NO: 148. In some embodiments, the polynucleotide encoding a fusion polypeptide or a compound fusion polypeptide, as described herein, which has a nucleic acid sequence of SEQ ID NO: 150, or a nucleic acid sequence that is at least 80%, at least 85%, at least 90%, at least 91%, at least 92%, at least 93%, at least 94%, at least 95%, at least 96%, at least 97%, at least 98%, at least 99% identical, or 100% identical to SEQ ID NO: 150. In some embodiments, the polynucleotide encoding a fusion polypeptide or a compound fusion polypeptide, as described herein, which has a nucleic acid sequence of SEQ ID NO: 152, or a nucleic acid sequence that is at least 80%, at least 85%, at least 90%, at least 91%, at least 92%, at least 93%, at least 94%, at least 95%, at least 96%, at least 97%, at least 98%, at least 99% identical, or 100% identical to SEQ ID NO: 152. In some embodiments, the polynucleotide encoding a fusion polypeptide or a compound fusion polypeptide, as described herein, which has a nucleic acid sequence of SEQ ID NO: 155, or a nucleic acid sequence that is at least 80%, at least 85%, at least 90%, at least 91%, at least 92%, at least 93%, at least 94%, at least 95%, at least 96%, at least 97%, at least 98%, at least 99% identical, or 100% identical to SEQ ID NO: 155. In some embodiments, the polynucleotide encoding a fusion polypeptide or a compound fusion polypeptide, as described herein, which has a nucleic acid sequence of SEQ ID NO: 158, or a nucleic acid sequence that is at least 80%, at least 85%, at least 90%, at least 91%, at least 92%, at least 93%, at least 94%, at least 95%, at least 96%, at least 97%, at least 98%, at least 99% identical, or 100% identical to SEQ ID NO: 158. In some embodiments, the polynucleotide encoding a fusion polypeptide or a compound fusion polypeptide, as described herein, which has a nucleic acid sequence of SEQ ID NO: 225, or a nucleic acid sequence that is at least 80%, at least 85%, at least 90%, at least 91%, at least 92%, at least 93%, at least 94%, at least 95%, at least 96%, at least 97%, at least 98%, at least 99% identical, or 100% identical to SEQ ID NO: 225. In some embodiments, the polynucleotide encoding a fusion polypeptide or a compound fusion polypeptide, as described herein, which has a nucleic acid sequence of SEQ ID NO: 226, or a nucleic acid sequence that is at least 80%, at least 85%, at least 90%, at least 91%, at least 92%, at least 93%, at least 94%, at least 95%, at least 96%, at least 97%, at least 98%, at least 99% identical, or 100% identical to SEQ ID NO: 226.

TABLE H

Illustrative Polynucleotides Encoding Fusion Polypeptides

| SEQ ID NO: | Encoded Polypeptide Segments | Nucleic Acid Sequences |
|---|---|---|
| 130 | Pol:840-920 | ACAGTGAAGGCAGCTTGTTGGTGGGCCGGAATTAAACAGGAGTTTGGCATCCCTTATAATCCTCAGTCTCAG |
| | Gag:147-369 | GGAGTGGTGGAGTCTATGAACAAGGAGCTGAAGAAGATCATCGGCCAGGTGAGAGATCAGGCAGAACATCTG |
| | Gag:1-53 | AAGACAGCAGTGCAGATGGCCGTGTTTATCCACAACTTCAAGAGGAAGGGCGGCATTGGAGGATATAGCGCA |
| | PPV | GGAGAAAGAATCGTGGACATCATCGCCATCTCTCCTAGAACACTGAACGCTTGGGTGAAAGTGGTGGAGGAG |
| | Pol:747-827 | AAAGCCTTTAGCCCAGAAGTGATCCCTATGTTCTCAGCTCTGTCAGAAGGAGCTACACCTCAGGATCTGAAC |
| | Pol:683-708 | ACCATGCTGAATACCGTGGGAGGACATCAGGCAGCTATGCAGATGCTGAAGGAGACAATTAACGAGGAAGCA |
| | Nef:117-148 | GCCGAGTGGGATAGACTGCATCCAGTGCACGCAGGACCTATTGCTCCAGGACAGATGAGAGAGCCTAGAGGA |
| | | AGCGATATTGCCGGCACAACATCTACACTGCAGGAACAGATCGGTTGGATGACCAACAATCCTCCTATCCCA |
| | | GTGGGCGAAATCTACAAACGCTGGATCATCCTGGGCCTGAATAAGATCGTGAGAATGTACAGCCCCACAAGC |
| | | ATCCTGGATATCAGACAGGGACCTAAGGAACCTTTCAGGGATTACGTGGACCGGTTCTACAAGACACTGAGA |
| | | GCAGAACAGGCATCTCAGGAGGTGAAGAATTGGATGACCGAGACACTGCTGGTGCAGAACGCTAATCCAGAT |
| | | TGCAAGACCATTCTGAAAGCTCTGGGACCAGCAGCTACACTGGAAGAGATGATGACAGCTTGTCAGGGAGTG |
| | | GGAGGACCAGGACATAAAGCTAGAGTGCTGGCAGAAGCTATGTCTCAGATGGCAGCTAGAGCTTCAGTGCTG |
| | | TCAGGAGGAGAACTCGATAGGTGGGAGAAGATCAGACTGAGACCAGGAGGCAAGAAGAAGTACAGACTGAAG |
| | | CACATCGTGTGGGCTTCTAGAGAACTGGAGAGATTTGCCGTGAATCCAGGACTCCTGGAAACACCTCCAGTG |
| | | GTGGCTAAAGAGATTGTGGCTTCTTGCGATAAGTGCCAGCTGAAAGGAGAGGCTATGCACGGACAGGTGGAT |
| | | TGTTCTCCAGGAATTTGGCAGCTGGATTGTACACACCTGGAGGGAAAGATTATTCTGGTGGCAGTGCACGTG |
| | | GCATCAGGATATATTGAGGCCGAAGTGATTCCAGCAGAAACAGGACAGGAGACAGCTTACTTTCTGCTCAAA |
| | | CTGGCAGGTCGCTGGCCAGTGAAAACCAAGGAGAAGGTGTACCTGGCTTGGGTGCCAGCTCATAAAGGAATT |
| | | GGCGGAAACGAGCAGGTGGATAAACTGGTGTCTACACAGGGCTACTTCCCAGATTGGCAGAATTACACACCA |
| | | GGACCAGGCACAAGATATCCTCTGACATTCGGTTGGTGTTTCAAGCTGGTGCCCGTG |
| 131 | Pol:840-920 | ACAGTGAAAGCAGCTTGTTGGTGGGCAGGAATCAAGCAGGAGTTTGGCATCCCTTACAATCCTCAGTCTCAG |
| | Gag:147-369 | GGAGTGGTGGAATCTATGAACAAGGAGCTGAAGAAGATCATCGGCCAGGTGAGAGATCAGGCAGAACATCTG |
| | Gag:1-53 | AAGACAGCAGTGCAGATGGCAGTGTTTATCCACAATTTCAAGAGAAAGGGCGGCATTGGCGGATATAGCGCC |
| | PPV | GGAGAGAGAATCGTGGATATCATCGCCATCTCTCCTAGAACACTGAACGCTTGGGTGAAAGTGGTGGAAGAG |
| | Pol:747-827 | AAAGCCTTCTCTCCAGAGGTGATCCCTATGTTTAGCGCTCTGTCAGAAGGAGCTACACCTCAGGATCTGAAT |
| | Pol:683-708 | ACCATGCTGAATACCGTGGGCGGACATCAGGCAGCTATGCAGATGCTGAAAGAGACAATCAACGAAGAAGCA |
| | Nef:117-148 | GCCGAGTGGGATAGACTGCATCCAGTGCACGCAGGACCTATTGCTCCAGGACAGATGAGAGAACCTAGAGGA |
| | | TCAGACATTGCCGGAACAACATCTACACTGCAGGAGCAGATCGGTTGGATGACAAACAACCCTCCAATCCCA |
| | | GTGGGAGAGATCTACAAGAGATGGATCATCCTGGGCCTGAATAAGATCGTGAGAATGTACAGCCCCACAAGC |
| | | ATCCTGGATATCAGACAGGGACCTAAGGAGCCTTTCAGAGATTACGTGGACAGGTTCTACAAGACCCTGAGA |
| | | GCAGAACAGGCTTCTCAGGAGGTGAAAAATTGGATGACCGAAACACTGCTGGTGCAGAACGCTAATCCCGAT |
| | | TGCAAGACCATCCTGAAAGCTCTGGGACCAGCAGCTACACTGGAAGAGATGATGACAGCTTGTCAGGGAGTG |
| | | GGAGGACCAGGACATAAAGCTAGAGTGCTGGCAGAAGCTATGTCTCAGATGGCAGCTAGAGCTTCAGTGCTG |
| | | TCAGGAGGAGAACTCGATAGATGGGAAAAGATCAGACTGAGACCAGGAGGAAAGAAGAAGTACAGGCTGAAG |
| | | CACATCGTCTGGGCTTCTAGAGAACTGGAGAGATTTGCCGTGAATCCAGGACTCCTGGAAACACCTCCAGTG |
| | | GTGGCTAAAGAGATTGTGGCTTCTTGCGACAAGTGTCAGCTGAAAGGAGAGGCTATGCACGGACAGGTGGAT |
| | | TGTTCTCCAGGAATTTGGCAGCTGGATTGCACACATCTGGAAGGAAAGATTATTCTGGTGGCAGTGCACGTG |
| | | GCATCTGGATATATCGAGGCCGAGGTGATTCCAGCCGAAACAGGACAGGAAACAGCCTACTTTCTCCTGAAA |
| | | CTGGCAGGTAGGTGGCCAGTGAAGACAAAGGAGAAGGTGTACCTGGCTTGGGTGCCAGCCCATAAAGGAATT |
| | | GGAGGCAATGAGCAGGTGGATAAACTGGTGTCAACACAGGGCTACTTCCCAGATTGGCAGAATTACACCCCA |
| | | GGACCAGGAACAAGATATCCTCTGACATTCGGTTGGTGCTTTAAACTGGTGCCCGTG |
| 132 | Gag:147-369 | CTGTCTCCTAGAACACTGAACGCTTGGGTGAAGGTGATCGAAGAGAAGGCCTTTAGCCCAGAAGTGATCCCT |
| | Pol:747-827 | ATGTTCACAGCTCTGTCAGAAGGAGCTACACCTCATGACCTGAACACCATGCTGAATACCATCGGAGGACAT |
| | Gag:1-53 | CAGGCAGCTATGCAGATGCTGAAGGATACCATCAACGAAGAAGCAGCCGAGTGGGATAGAGTGCATCCAGTG |
| | AA | CACGCAGGACCAGTGGCTCCAGGACAGATGAGAGATCCTAGAGGAAGCGATATTGCCGGCTCTACATCTACA |
| | Pol:840-920 | CTGCAGGAACAGATCGCTTGGATGACCAACAATCCTCCTATCCCAGTGGGCGATATCTACAAACGCTGGATC |
| | Nef:117-148 | ATCATGGGCCTGAACAAGATCGTGAGGATGTACAGCCCAGTGTCTATCCTGGATATCAAGCAGGGCCCTAAA |
| | LIK | GAACCTTTCAGGGATTACGTGGACCGGTTCTACAGAACACTGAGAGCAGAACAGGCCTCACAGGATGTGAAG |
| | Pol:683-708 | AATTGGATGACCGAGACACTGCTGGTGCAGAACAGCAACCCCGATTGCAAGACCATTCTGAAAGCTCTGGGA |
| | | CCAGGAGCTACACTGGAAGAGATGATGTCAGCTTGTCAGGGAGTGGGAGGACCATCTCATAAAGCTAGAGTG |
| | | CTGGCCGAAGCTATGTGTCAGGTGGCTAAAGAGATCGTGGCTTGTTGCGACAAGTGTCAGCTGAAAGGAGAG |
| | | GCTATTCACGGACAGGTGGATTGTTCTCCAGGAGTCTGGCAGCTGGATTGTACACACCTGGAGGGAAAGGTG |
| | | ATTCTGGTGGCAGTGCACGTGGCATCAGGATATATTGAGGCCGAGATCATTCCTACAGAAACAGGACAGGAG |
| | | ACCGCTTACTTCATCCTGAAACTGGCAGGTAGGTGGCCAGTGACAACAATGGCAGCTAGAGCTTCTATCCTG |
| | | AGCGGAGGAAAACTCGACAAGTGGGAGAAGATCAGACTGAGACCAGGAGGCAGAAAGAAGTACAAGCTGAAG |
| | | CATCTCGTCTGGGCTTCTAGAGAGCTGGAAAGATTCGCTCTGAATCCAGGTCTGCTGGAAACAGCAGCAGCA |
| | | GTGAAAGCAGCTTGTTGGTGGGCAGGAGTGAAACAGGAATTTGGCATCCCTTACAATACACAGTCTCAGGGA |
| | | GTGGTGGAGAGCATGAACAACGAGCTGAAGAAGATCATCGGCCAGATCAGAGATCAGGCAGAACATCTGAAG |
| | | ACAGCAGTGCAGATGGCAGTGCTGATCCACAACTTCAAGAGGAAGGGCGGAATCGGAGAATATAGCGCCGGC |
| | | GAGAGAATTATCGATATCATCGCCACACAGGGCTTTTTCCCAGATTGGCAGAACTATACACCAGGACCAGGA |
| | | ATCAGGTTCCCTCTGACATTCGGTTGGTGTTTCAAGCTGGTGCCTCTGCTGATCAAGAAGGAGAAAATCTAT |
| | | CTGGCTTGGGTGCCAGCTCACAAAGGAATTGGCGGAAACGAGCAGATCGATAAGCTGGTGTCT |
| 133 | Gag:147-369 | CTGTCTCCTAGAACACTGAACGCTTGGGTGAAGGTGATTGAGGAGAAAGCCTTCAGCCCAGAAGTGATCCCT |
| | Pol:747-827 | ATGTTTACAGCCCTGAGCGAAGGAGCTACACCTCACGATCTGAATACCATGCTGAATACAATCGGCGGACAT |
| | Gag:1-53 | CAGGCAGCCATGCAGATGCTGAAGGATACAATCAACGAAGAAGCAGCCGAGTGGGATAGAGTGCATCCAGTG |
| | AA | CACGCAGGACCAGTGGCTCCAGGACAGATGAGAGATCCTAGAGGAAGCGATATCGCCGGATCTACATCTACA |
| | Pol:840-920 | CTGCAGGAACAGATCGCTTGGATGACAAATAACCCCCCTATCCCAGTGGGAGATATCTATAAGCGCTGGATC |
| | Nef:117-148 | ATCATGGGCCTGAACAAGATCGTGAGGATGTACAGCCCAGTGAGCATCCTGGATATCAAGCAGGGACCTAAG |
| | LIK | GAGCCTTTCAGAGATTACGTGGACAGGTTCTACAGAACCCTGAGAGCAGAACAGGCTTCTCAGGACGTGAAG |
| | Pol:683-708 | AATTGGATGACCGAAACACTGCTGGTGCAGAATAGCAACCCCGATTGCAAGACCATCCTGAAAGCTCTGGGA |

TABLE H-continued

Illustrative Polynucleotides Encoding Fusion Polypeptides

| SEQ ID NO: | Encoded Polypeptide Segments | Nucleic Acid Sequences |
|---|---|---|
| | | CCAGGAGCTACACTGGAAGAAATGATGAGCGCTTGTCAGGGAGTGGGAGGACCATCTCATAAGGCTAGAGTG |
| | | CTGGCAGAAGCTATGTGTCAGGTGGCTAAGGAGATTGTGGCTTGTTGCGACAAGTGTCAGCTGAAAGGAGAG |
| | | GCTATTCACGGACAGGTGGATTGTTCTCCAGGAGTCTGGCAGCTGGATTGTACACATCTGGAGGGAAAAGTG |
| | | ATTCTGGTGGCAGTGCACGTGGCATCAGGATATATTGAGGCCGAAATCATCCCTACAGAGACAGGACAGGAG |
| | | ACAGCCTACTTTATCCTGAAACTGGCAGGCAGATGGCCAGTGACAACAATGGCAGCTAGAGCTTCTATCCTG |
| | | AGCGGAGGAAAGCTGGATAAGTGGGAAAAGATCAGACTGAGACCAGGAGGAAGGAAGAAGTACAAGCTGAAG |
| | | CACCTGGTCTGGGCTTCTAGAGAACTGGAAAGATTCGCCCTGAATCCAGGTCTGCTGGAAACAGCAGCAGCA |
| | | GTGAAAGCAGCTTGTTGGTGGGCAGGAGTGAAACAGGAGTTCGGAATCCCCTACAACACACAGTCTCAGGGA |
| | | GTGGTGGAATCTATGAACAACGAGCTGAAGAAGATCATCGGCCAGATCAGAGACCAGGCCGAACATCTGAAG |
| | | ACAGCAGTGCAGATGGCAGTGCTGATTCACAATTTCAAGAGAAAGGGCGGCATCGGAGAGTATAGCGCCGGA |
| | | GAGAGAATCATCGATATCATCGCTACACAGGGCTTCTTCCCCGATTGGCAGAATTACACCCCAGGCCCAGGC |
| | | ATTAGATTCCCTCTGACATTCGGTTGGTGCTTCAAACTGGTGCCTCTGCTGATCAAGAAGGAGAAGATCTAC |
| | | CTGGCTTGGGTGCCAGCTCATAAAGGAATCGGAGGAAACGAGCAGATCGATAAGCTGGTGTCT |
| 134 | Pol:56-117 | TTTCCTCAGATCACTCTCTGGCAGAGACCACTGGTGACAATCAAGATCGGAGGACAGCTGAAAGAAGCTCTG |
| | Nef:64-99 | CTGGATACAGGAGCAGACGATACAGTGCTGGAAGAGATGAATCTGCCAGGTCGCTGGAAACCTAAGATGATT |
| | LI | GGAGGCATTGGCGGCTTTATCAAGGTGAGACAGTACGACCAGGAGGAAGTGGGATTTCCAGTGAAACCTCAG |
| | Pol:542-606 | GTGCCTCTGAGACCTATGACATTTAAGGGCGCTCTGGACCTGTCTCACTTTCTGAGAGAGAAGGGAGGACTG |
| | Pol:367-431 | GAAGGACTGATCCCTAAGTTCAAGCTGCCTATCCAGAAGGAGACTTGGGAAACTTGGTGGACAGAGTATTGG |
| | Pol:932-1003 | CAGGCTACTTGGATTCCCGAGTGGGAATTTGTGAACACACCTCCTCTGGTGAAGCTGTGGTATCAGCTGGAA |
| | Pol:129-320 | AAGGAGCCTATTGTGGGCGCAGAAACATTCTACGTGGACGGAGCAGCTAACAGAGAAACTAAGTGGGGATTC |
| | | ACCACCCCAGATAAGAAGCACCAGAAGGAGCCACCATTTCTCTGGATGGGATACGAACTGCACCCAGATAAG |
| | | TGGACAGTCCAGCCTATTGTGCTGCCAGAAAAGGACTCTTGGACCGTGAACGATATCCAGAAGCTGGTGGGA |
| | | AAGCTGAATTGGGCTTCTCAGATCTACCCAGGAATCAAGGTGATCACCAAGATCCAGAACTTCAGGGTGTAC |
| | | TACAGAGACAGCAGAGATCCTCTCTGGAAGGGACCAGCTAAACTCCTCTGGAAAGGAGAAGGAGCAGTGGTG |
| | | ATCCAGGATAACAGCGACATCAAGGTGGTGCCTAGAAGAAAGGCCAAGATCATCAGGGACTACGGCAAACAG |
| | | ATGGCAGGAGACGATTGCGTGGCTTCTAGACAGGACGAAGACGGAACAGTCCTGGTGGGACCTACACCAGTG |
| | | AATATCATCGGCAGAAATCTCCTGACACAGATCGGTTGTACCCTGAACTTCCCTATCAGCCCTATCGAGACA |
| | | GTGCCAGTGAAACTGAAGCCAGGAATGGACGGACCTAAAGTCAAGCAGTGGCCTCTGACAGAAGAGAAGATC |
| | | AAGGCCCTGGTGGAGATTTGCACAGAGATGGAGAAGGAGGGAAAGATCAGCAAGATCGGCCCAGAGAATCCT |
| | | TACAACACCCCAGTGTTCGCCATCAAGAAGAAGGATAGCACCAAGTGGAGAAAGCTGGTGGATTTCAGGGAG |
| | | CTGAACAAGAGAACCCAGGACTTTTGGGAAGTGCAGCTGGGCATCCCCCATCCAGCAGGACTGAAGAAGAAG |
| | | AAGAGCGTGACAGTGCTGGACGTGGGAGACGCTTATTTTAGCGTGCCTCTGGACAAGGACTTCAGAAAGTAC |
| | | ACCGCCTTCACCATCCCTTCTATCAACAACGAGACCCCAGGCATCAGATACCAGTATAACGTGCTGCCTCAG |
| | | GGTTGGAAAGGATCTCCAGCAATCTTTCAGTCTAGCATGACC |
| 135 | Pol:56-117 | TTCCCTCAGATTACTCTCTGGCAGAGGCCACTGGTGACAATTAAGATCGGAGGACAGCTGAAAGAAGCTCTG |
| | Nef:64-99 | CTGGATACAGGAGCAGACGATACAGTGCTGGAGGAAATGAACCTGCCAGGTCGCTGGAAACCTAAAATGATC |
| | LI | GGAGGAATCGGCGGCTTTATTAAGGTGAGACAGTACGATCAGGAGGAAGTGGGATTTCCAGTGAAACCTCAG |
| | Pol:542-606 | GTGCCTCTGAGACCTATGACATTTAAGGGCGCTCTGGATCTGAGCCACTTTCTGAGAGAGAAAGGAGGACTG |
| | Pol:367-431 | GAAGGACTGATCCCTAAGTTCAAGCTGCCCATCCAGAAGGAGACTTGGGAAACTTGGTGGACCGAGTATTGG |
| | Pol:932-1003 | CAGGCAACTTGGATTCCCGAGTGGGAATTTGTGAACACACCTCCTCTGGTGAAGCTGTGGTATCAGCTGGAA |
| | Pol:129-320 | AAGGAGCCTATCGTGGGAGCCGAAACATTTTACGTGGACGGAGCAGCCAACAGAGAAACTAAGTGGGGATTC |
| | | ACCACCCCAGATAAGAAGCACCAGAAAGAGCCTCCCTTTCTCTGGATGGGATACGAACTGCACCCAGATAAG |
| | | TGGACAGTCCAGCCTATTGTGCTGCCAGAAAAGGACTCTTGGACAGTGAACGACATCCAGAAGCTGGTGGGA |
| | | AAGCTGAATTGGGCCTCTCAGATTTACCCAGGAATCAAGGTGATCACCAAGATCCAGAACTTCAGGGTGTAC |
| | | TACAGGGATAGCAGAGATCCTCTCTGGAAGGGACCAGCTAAACTCCTCTGGAAAGGAGAAGGAGCAGTGGTG |
| | | ATCCAGGATAATAGCGACATCAAGGTGGTGCCTAGAAGAAAGGCTAAGATCATCCGGGACTACGGCAAACAG |
| | | ATGGCAGGAGACGATTGCGTGGCTTCTAGACAGGATGAAGACGGAACAGTCCTGGTGGGACCTACACCAGTG |
| | | AACATCATCGGCAGAAACCTGCTGACACAGATCGGTTGTACCCTGAACTTCCCTATCTCTCCTATCGAAACA |
| | | GTGCCAGTGAAGCTGAAGCCAGGAATGGACGGACCTAAAGTCAAGCAGTGGCCTCTGACAGAAGAGAAGATC |
| | | AAGGCTCTGGTGGAGATTTGCACCGAAATGGAGAAGGAGGGCAAGATCAGCAAGATCGGACCAGAGAATCCT |
| | | TACAATACCCCAGTGTTCGCCATCAAGAAGAAGGACAGCACCAAGTGGAGAAAGCTGGTGGATTTCAGGGAA |
| | | CTGAACAAGAGGACCCAGGACTTTTGGGAAGTGCAGCTGGGCATCCCCCATCCAGCAGGACTGAAGAAGAAG |
| | | AAGAGCGTGACAGTGCTGGACGTGGGAGACGCTTATTTTAGCGTGCCTCTGGACAAGGACTTCAGAAAGTAC |
| | | ACCGCCTTCACCATCCCTAGCATCAATAACGAGACCCCAGGCATCAGATACCAGTATAACGTGCTGCCACAG |
| | | GGCTGGAAAGGATCTCCAGCAATCTTTCAGAGCTCTATGACA |
| 136 | Pol:56-117 | CTGCCTCAGATTACCCTGTGGCAGAGACCTATCGTGACCATCAAGATCGGAGGACAGATCAAAGAAGCTCTG |
| | Pol:367-431 | CTGGATACAGGAGCAGACGATACAGTGCTGGAGGATATGAACCTGCCAGGTAAGTGGAAGCCTAAGATGATC |
| | AA | GGCGGAATTGGCGGCTTTATCAAGGTCAAGCAGTACGATCAGTGGGGACTGACAACACCAGACAAGAAGCAC |
| | QEE | CAGAAGGACCCCCCTTTCCTCTGGATGGGATACGAACTGCATCCAGATAGGTGGACAGTGCAGCCAATTGAG |
| | Nef:64-99 | CTGCCAGAAAAGGAGTCTTGGACAGTGAACGACATCCAGAAGCTGATCGGCAAGCTGAATTGGGCTTCTCAG |
| | Pol:932-1003 | ATCTACGCCGGAATTAAGGTGGCAGCTCAGGAAGAAGAAGAAGTGGGATTTCCAGTGAGACCTCAGGTGCCT |
| | Pol:542-606 | CTGAGACCTATGACATACAAGGGAGCTCTGGATCTGAGCCACTTTCTGAAAGAGAAGGGAGGACTGGAGGGA |
| | AA | ATTACCAAGCTGCAGAACTTCAGGGTGTACTACAGGGACAACAGAGATCCTCTGTGGAAAGGACCAGCTAGA |
| | Pol:129-320 | CTCCTCTGGAAAGGAGAAGGAGCAGTGGTGATTCAGGACAATAGCGAGATCAAGGTGGTGCCTAGAAGAAAG |
| | | GTGAAGATCATCCGGGACTACGGCAAAAGAATGGCAGGAGACGATTGCGTGGCAGGAAGACAGGACGAGGAC |
| | | CCCAAATTCAGACTGCCTATCCAGAAGGAGACTTGGGACACTTGGTGGACAGATTATTGGCAGGCAACTTGG |
| | | ATTCCCGAGTGGGAATTTACCAATACCCCTCCTCTGGTCAAGCTCTGGTATCAGCTGGAAACAGAGCCTATC |
| | | GCAGGAGTGGAAACATTCTACGTGGACGGAGCCTCTAATAGAGAGACAAAAGCCGCAGGAACAGTGCTGATT |
| | | GGACCTACACCAGTGAACATCATCGGGAGAAACCTGCTGACACAGCTGGGTTGTACACTGAACTTCCCTATC |
| | | AGCCCTATCGATACAGTGCCAGTGAAACTGAAGCCAGGAATGGACGGACCTAGAGTGAAACAGTGGCCTCTG |
| | | ACAGAAGAGAAGATCAAGGCCCTGATCGAGATTTGTACAGAGATGGAGAAGGAGGGCAAGATCTCTAGAATT |

TABLE H-continued

Illustrative Polynucleotides Encoding Fusion Polypeptides

| SEQ ID NO: | Encoded Polypeptide Segments | Nucleic Acid Sequences |
|---|---|---|
| | | GGCCCAGAGAACCCCTACAATACCCCTATCTTTGCCATCAAGAAGAAGGACGGCACCAAGTGGAGAAAGCTG |
| | | GTGGATTTCAGGGAGCTGAACAAGAAGACCCAGGACTTTTGGGAAGTGCAGCTGGGCATCCCCCACCCTAGC |
| | | GGACTGAAAAAGAAGAAGAGCGTGACCGTGCTGGATATTGGAGACGCCTATTTTAGCGTGCCACTGGATAAG |
| | | GAGTTCAGAAAGTACACCGCCTTTACCGTGCCTTCTACCAATAACGAGACACCAGGAGTGAGATACCAGTAC |
| | | AACGTGCTGCCTATGGGTTGGAAGGGATCACCAGCCATCTTTCAGTGTAGCATGACA |
| 137 | Pol:56-117 | CTGCCTCAGATTACTCTCTGGCAGAGGCCTATTGTGACAATCAAGATCGGCGGACAGATCAAAGAAGCCCTG |
| | Pol:367-431 | CTGGATACAGGAGCAGACGATACAGTGCTGGAGGATATGAACCTGCCAGGCAAGTGGAAACCTAAGATGATC |
| | AA | GGAGGAATCGGCGGATTTATCAAGGTGAAGCAGTACGATCAGTGGGGACTGACAACACCAGATAAGAAGCAC |
| | QEE | CAGAAGGACCCCCCATTCCTGTGGATGGGATACGAACTGCATCCAGATAGGTGGACAGTGCAGCCAATCGAA |
| | Nef:64-99 | CTGCCAGAAAAGGAGTCTTGGACCGTGAACGACATCCAGAAACTGATCGGCAAGCTGAATTGGGCCAGCCAG |
| | Pol:932-1003 | ATTTACGCCGGAATCAAAGTGGCAGCTCAGGAAGAAGAGGAAGTGGGATTTCCAGTGAGACCTCAGGTGCCT |
| | Pol:542-606 | CTGAGACCTATGACATACAAAGGCGCTCTGGATCTGAGCCACTTTCTGAAAGAGAAGGGAGGACTGGAGGGA |
| | AA | ATTACAAAGCTGCAGAACTTCCGGGTGTACTACAGAGACAACAGAGACCCTCTCTGGAAAGGACCAGCTAGA |
| | Pol:129-320 | CTCCTCTGGAAAGGAGAAGGAGCAGTGGTGATCCAGGATAATAGCGAGATCAAGGTGGTGCCTAGGAGAAAG |
| | | GTGAAGATCATCAGGGATTACGGCAAAAGAATGGCCGGAGACGATTGCGTGGCAGGAAGACAGGACGAAGAT |
| | | CCCAAGTTCAGACTGCCTATCCAGAAGGAGACTTGGGACACTTGGTGGACCGATTATTGGCAGGCAACTTGG |
| | | ATTCCCGAGTGGGAATTTACCAACACACCTCCTCTGGTGAAGCTGTGGTATCAGCTGGAAACAGAGCCTATT |
| | | GCCGGAGTGGAAACATTCTACGTGGACGGAGCCAGCAACAGAGAGACAAAAGCCGCCGGAACAGTGCTGATT |
| | | GGACCTACACCCGTGAATATCATCGGAAGAAATCTGCTGACACAGCTGGGTTGTACCCTGAATTTCCCTATC |
| | | AGCCCCATCGATACAGTGCCAGTGAAACTGAAGCCAGGAATGGACGGACCTAGAGTCAAACAGTGGCCTCTG |
| | | ACAGAAGAGAAGATCAAGGCCCTGATCGAGATTTGTACCGAGATGGAGAAGGAGGGAAAGATCAGCAGAATC |
| | | GGCCCAGAGAATCCTTACAACACCCCCATCTTCGCCATCAAGAAGAAAGACGGAACCAAGTGGAGAAAGCTG |
| | | GTGGATTTCAGGGAGCTGAACAAGAAGACCCAGGACTTTTGGGAAGTGCAGCTGGGCATCCCCCACCCTAGC |
| | | GGCCTGAAGAAGAAAAAGAGCGTGACAGTGCTGGACATTGGAGACGCTTATTTCAGCGTGCCACTGGATAAG |
| | | GAGTTCAGAAAGTACACCGCCTTTACCGTGCCTTCTACAAACAACGAGACACCAGGCGTGAGATATCAGTAC |
| | | AACGTGCTGCCTATGGGTTGGAAAGGATCTCCCGCCATCTTTCAGTGTAGCATGACA |
| 138 | Pol:747-827 | GTGGCCAAAGAAATTGTGGCCTCTTGCGATAAGTGCCAGCTGAAAGGAGAGGCTATGCACGGACAGGTGGAT |
| | Nef:117-148 | TGTTCTCCAGGAATTTGGCAGCTGGATTGTACACACCTGGAGGGAAAGATTATTCTGGTGGCAGTGCACGTG |
| | Pol:840-920 | GCATCAGGATATATTGAGGCCGAAGTGATTCCAGCAGAAACAGGACAGGAGACAGCTTACTTTCTGCTCAAA |
| | AA | CTGGCAGGTCGCTGGCCAGTGAAGACAACACAGGGCTACTTTCCTGATTGGCAGAATTACACACCAGGACCA |
| | Gag:1-53 | GGAACAAGATACCCTCTGACCTTTGGTTGGTGCTTCAAACTGGTGCCCGTGACAGTGAAAGCAGCTTGTTGG |
| | SEG | TGGGCAGGAATTAAGCAGGAGTTCGGCATCCCTTACAATCCTCAGTCTCAGGGAGTGGTGGAATCTATGAAC |
| | Gag:147-369 | AAGGAGCTGAAGAAGATCATCGGCCAGGTGAGAGATCAGGCAGAACATCTGAAGACAGCAGTGCAGATGGCA |
| | AAA | GTGTTCATCCACAACTTCAAGCGGAAGGGAGGAATTGGAGGATATAGCGCAGGAGAGAGAATCGTGGATATC |
| | Pol:683-708 | ATTGCCGCCGCTATGGCAGCTAGAGCCAGCGTGCTGAGCGGAGGAGAACTCGATCGCTGGGAAAAGATCAGA |
| | | CTGAGACCAGGAGGCAAGAAGAAGTACAGACTGAAGCACATCGTCTGGGCTTCTAGAGAACTGGAGAGATTT |
| | | GCCGTGAATCCAGGACTGCTGGAAACAAGCGAGGGCATTTCTCCTAGAACCCTGAACGCTTGGGTGAAAGTG |
| | | GTGGAAGAAAAAGCCTTCTCTCCAGAGGTGATCCCTATGTTTAGCGCTCTGTCAGAAGGAGCTACACCTCAG |
| | | GATCTGAACACCATGCTGAACACAGTGGGAGGACATCAGGCAGCTATGCAGATGCTGAAGGAGACAATTAAC |
| | | GAAGAAGCCGCCGAGTGGGATAGACTGCATCCAGTGCACGCAGGACCTATTGCTCCAGGACAGATGAGAGAG |
| | | CCTAGAGGAAGCGATATTGCCGGAACAACAAGCACACTGCAGGAACAGATCGGTTGGATGACCAATAATCCC |
| | | CCTATTCCAGTGGGCGAGATCTATAAGCGCTGGATTATCCTGGGCCTGAACAAGATCGTGAGAATGTACAGC |
| | | CCCACCTCTATCCTGGATATCAGACAGGGCCCTAAGGAACCTTTCAGAGACTACGTGGACAGGTTCTACAAG |
| | | ACACTGAGAGCAGAACAGGCATCTCAGGAGGTGAAGAATTGGATGACCGAGACACTGCTGGTGCAGAACGCC |
| | | AATCCAGATTGCAAGACAATTCTGAAAGCCCTGGGACCAGCAGCTACACTGGAAGAGATGATGACCGCTTGT |
| | | CAGGGAGTGGGAGGACCAGGACATAAAGCTAGAGTGCTGGCAGAAGCTATGTCTCAGGCAGCAGCTAAGGAG |
| | | AAAGTGTATCTGGCTTGGGTGCCAGCCCATAAAGGAATTGGAGGAAACGAGCAGGTGGATAAACTGGTGTCT |
| 139 | Pol:747-827 | GTGGCTAAGGAAATTGTGGCCTCTTGCGACAAGTGTCAGCTGAAAGGAGAGGCTATGCACGGACAGGTGGAT |
| | Nef:117-148 | TGTTCTCCAGGAATTTGGCAGCTGGATTGCACACATCTGGAAGGAAAGATTATTCTGGTGGCAGTGCACGTG |
| | Pol:840-920 | GCATCTGGATATATCGAGGCCGAGGTGATTCCAGCCGAAACAGGACAGGAAACAGCCTACTTTCTCCTGAAA |
| | AA | CTGGCAGGTAGGTGGCCAGTGAAGACAACACAGGGCTACTTCCCAGATTGGCAGAATTACACCCCAGGACCA |
| | Gag:1-53 | GGAACAAGATACCCTCTGACCTTTGGTTGGTGCTTCAAGCTCGTCCCAGTGACAGTGAAAGCAGCTTGTTGG |
| | SEG | TGGGCAGGAATTAAACAGGAGTTCGGAATCCCTTACAATCCTCAGTCTCAGGGAGTGGTGGAAAGCATGAAC |
| | Gag:147-369 | AAGGAGCTGAAGAAGATCATCGGACAGGTGAGAGATCAGGCAGAACATCTGAAGACAGCAGTGCAGATGGCA |
| | AAA | GTGTTCATCCACAACTTCAAGAGGAAGGGCGGAATTGGAGGATATAGCGCCGGAGAGAGAATCGTGGATATC |
| | Pol:683-708 | ATTGCAGCAGCTATGGCAGCTAGAGCTTCAGTGCTGTCAGGAGGAGAACTCGATAGGTGGGAGAAGATCAGA |
| | | CTGAGACCAGGAGGCAAGAAGAAGTACAGACTGAAGCACATCGTGTGGGCTTCTAGAGAACTGGAGAGATTC |
| | | GCAGTGAATCCAGGACTGCTGGAAACAAGCGAGGGAATTAGCCCTAGAACCCTGAATGCTTGGGTGAAAGTG |
| | | GTGGAAGAGAAGGCCTTCAGCCCAGAGGTGATCCCTATGTTTAGCGCTCTGTCAGAAGGAGCTACACCTCAG |
| | | GATCTGAACACCATGCTGAATACAGTGGGAGGACATCAGGCAGCTATGCAGATGCTGAAGGAGACCATCAAC |
| | | GAAGAAGCAGCCGAGTGGGATAGACTGCATCCAGTGCACGCAGGACCTATTGCTCCAGGACAGATGAGAGAA |
| | | CCTAGAGGAAGCGATATCGCCGGAACAACATCTACACTGCAGGAACAGATCGGTTGGATGACCAACAACCCT |
| | | CCTATTCCAGTGGGCGAGATTTACAAGCGCTGGATTATCCTGGGCCTGAATAAGATCGTGAGAATGTACAGC |
| | | CCTACCAGCATTCTGGACATCAGACAGGGACCTAAGGAGCCTTTTAGAGACTACGTGGACAGGTTCTACAAG |
| | | ACCCTGAGAGCAGAACAGGCATCTCAGGAGGTGAAGAATTGGATGACCGAGACACTGCTGGTGCAGAACGCT |
| | | AATCCCGATTGCAAGACCATCCTGAAAGCTCTGGGACCAGCAGCTACACTGGAAGAGATGATGACAGCTTGT |
| | | CAGGGAGTGGGAGGACCAGGACATAAAGCTAGAGTGCTGGCAGAAGCTATGTCTCAGGCAGCAGCTAAAGAG |
| | | AAAGTGTATCTGGCTTGGGTGCCAGCTCACAAAGGAATTGGAGGAAACGAGCAGGTGGATAAACTGGTGAGC |
| 140 | Pol:747-827 | GTGGCCAAAGAGATTGTGGCCTCCTGTGACAAGTGCCAGCTGAAAGGAGAGGCAATGCATGGACAGGTGGAT |
| | Nef:117-148 | TGTTCTCCAGGAATCTGGCAGCTGGATTGCACACACCTGGAGGGAAAGATCATCCTGGTGGCAGTGCATGTT |

TABLE H-continued

Illustrative Polynucleotides Encoding Fusion Polypeptides

| SEQ ID NO: | Encoded Polypeptide Segments | Nucleic Acid Sequences |
|---|---|---|
| | Pol:840-920 | GCATCAGGATACATTGAGGCAGAAGTGATTCCAGCAGAAACAGGACAGGAGACTGCTTACTTTCTGCTGAAA |
| | AA | CTGGCAGGAAGGTGGCCAGTGAAGACAACACAGGGTTATTTCCCTGATTGGCAGAACTACACCCCAGGCCCT |
| | Gag:1-53 | GGCACAAGATACCCTCTGACCTTTGGTTGGTGCTTCAAACTGGTCCCTGTGACAGTGAAAGCAGCTTGTTGG |
| | SEG | TGGGCAGGCATCAAGCAGGAGTTTGGCATCCCTTACAACCCTCAGTCTCAGGGAGTTGTGGAATCCATGAAC |
| | Gag:147-369 | AAGGAGCTGAAGAAGATCATTGGTCAGGTGAGGGATCAGGCAGAACATCTGAAGACAGCAGTGCAGATGGCA |
| | AAA | GTGTTCATCCACAATTTCAAGAGGAAGGGAGGAATTGGAGGATACAGTGCAGGAGAGAGAATTGTGGACATC |
| | Pol:683-708 | ATTGCAGCTGCAATGGCAGCAAGAGCCAGTGTGCTCAGTGGAGGAGAACTTGACAGGTGGGAAAAGATCAGA |
| | | CTGAGACCAGGAGGCAAGAAGAAGTACAGACTGAAGCACATTGTCTGGGCTTCCAGAGAACTGGAGAGATTT |
| | | GCTGTGAATCCAGGGCTGCTGGAAACAAGTGAGGGCATTTCTCCCAGAACTCTGAATGCTTGGGTGAAGGTG |
| | | GTGGAAGAAAAAGCCTTCTCTCCAGAGGTGATCCCCATGTTCAGTGCACTGTCTGAAGGAGCCACACCTCAG |
| | | GACCTCAACACCATGCTGAACACAGTGGGAGGACATCAGGCAGCCATGCAGATGCTGAAGGAGACCATCAAT |
| | | GAAGAAGCTGCAGAGTGGGACAGGCTGCATCCAGTTCATGCAGGACCAATTGCTCCTGGACAGATGAGAGAG |
| | | CCCAGAGGAAGTGACATTGCTGGCACAACCAGCACACTGCAGGAACAGATTGGTTGGATGACCAACAATCCC |
| | | CCCATTCCAGTGGGAGAGATCTACAAGAGGTGGATCATCCTTGGCCTGAACAAGATTGTGAGAATGTACAGC |
| | | CCCACTTCAATCCTGGACATCAGACAGGGCCCCAAGGAACCTTTCAGAGACTATGTGGACAGGTTCTACAAG |
| | | ACACTGAGAGCAGAACAGGCCTCACAGGAGGTGAAGAATTGGATGACTGAGACACTGCTGGTGCAGAATGCC |
| | | AATCCAGATTGCAAGACAATTCTGAAAGCCCTGGGTCCAGCAGCCACACTGGAAGAGATGATGACAGCTTGC |
| | | CAGGGAGTGGGTGGACCAGGACACAAAGCAAGAGTGCTGGCAGAAGCAATGTCTCAGGCTGCAGCCAAGGAG |
| | | AAAGTTTATCTGGCTTGGGTCCCAGCGCACAAAGGAATTGGAGGAAATGAGCAGGTGGACAAACTTGTGTCC |
| 141 | Gag:147-369 | CTGTCTCCTAGAACACTGAACGCTTGGGTGAAAGTGATCGAGGAAAAGGCCTTTAGCCCAGAAGTGATCCCT |
| | Pol:840-920 | ATGTTTACCGCCCTGTCAGAAGGAGCTACACCTCACGATCTGAACACCATGCTGAACACAATCGGAGGACAT |
| | Pol:683-708 | CAGGCAGCTATGCAGATGCTGAAGGATACAATCAACGAAGAAGCCGCCGAGTGGGATAGAGTGCATCCAGTG |
| | AAY | CACGCAGGACCAGTGGCTCCAGGACAGATGAGAGATCCTAGAGGAAGCGATATCGCAGGATCTACAAGCACA |
| | Gag:1-53 | CTGCAGGAACAGATCGCTTGGATGACCAATAATCCCCCTATTCCAGTGGGCGATATCTACAAGCGCTGGATC |
| | Nef:117-148 | ATCATGGGCCTGAACAAGATCGTGAGGATGTACAGCCCAGTGAGCATCCTGGATATCAAGCAGGGACCTAAG |
| | Pol:747-827 | GAGCCTTTCAGAGATTACGTGGACAGGTTCTACAGAACACTGAGAGCCGAACAGGCATCTCAGGACGTGAAG |
| | | AATTGGATGACCGAGACACTGCTGGTGCAGAACGCAATCCCGATTGCAAGACAATCCTGAAAGCTCTGGGA |
| | | CCAGGAGCTACACTGGAGGAAATGATGAGCGCTTGTCAGGGAGTGGGAGGACCATCTCATAAAGCTAGAGTG |
| | | CTGGCCGAAGCTATGTGTCAGGCAGTGAAAGCAGCTTGTTGGTGGGCAGGAGTGAAACAGGAGTTCGGCATC |
| | | CCTTACAACACCCAGTCTCAGGGAGTGGTGGAATCTATGAACAACGAGCTGAAGAAGATCATCGGCCAGATC |
| | | AGAGACCAGGCAGAACATCTGAAGACAGCAGTGCAGATGGCAGTGCTGATTCACAACTTCAAGAGAAAGGGC |
| | | GGCATTGGAGAGTATAGCGCCGGAGAGAGAATTATCGATATCATCGCCAAGGAGAAGATCTATCTGGCTTGG |
| | | GTGCCAGCTCATAAAGGAATCGGAGGAAACGAGCAGATCGATAAGCTGGTGTCAGCCGCCTATATGGCAGCT |
| | | AGAGCTTCTATTCTGAGCGGAGGAAAGCTCGACAAGTGGGAAAAGATCAGGCTGAGACCAGGAGGCAGAAAG |
| | | AAGTACAAGCTGAAGCATCTCGTCTGGGCTTCTAGAGAACTGGAAAGATTCGCTCTGAATCCAGGACTGCTG |
| | | GAAACAACCCAGGGCTTCTTCCCCGATTGGCAGAATTACACCCCAGGACCAGGAATCAGATTCCCTCTGACC |
| | | TTCGGTTGGTGTTTCAAGCTGGTGCCTCTGGTGGCTAAAGAGATTGTGGCTTGTTGCGACAAGTGTCAGCTG |
| | | AAAGGAGAGGCTATTCACGGACAGGTGGATTGTTCTCCAGGAGTCTGGCAGCTGGATTGTACACATCTGGAG |
| | | GGAAAAGTGATTCTGGTGGCAGTGCACGTGGCATCAGGATATATTGAGGCCGAAATCATCCCTACAGAGACA |
| | | GGACAGGAGACAGCCTACTTTATCCTGAAGCTGGCAGGAAGATGGCCAGTGACAACA |
| 142 | Gag:147-369 | CTGTCTCCTAGAACACTGAACGCTTGGGTGAAGGTGATTGAGGAGAAAGCCTTCAGCCCAGAAGTGATCCCT |
| | Pol:840-920 | ATGTTTACAGCCCTGAGCGAAGGAGCTACACCTCACGATCTGAATACCATGCTGAATACAATCGGCGGACAT |
| | Pol:683-708 | CAGGCAGCCATGCAGATGCTGAAGGATACAATCAACGAAGAAGCAGCCGAGTGGGATAGAGTGCATCCAGTG |
| | AAY | CACGCAGGACCAGTGGCTCCAGGACAGATGAGAGATCCTAGAGGAAGCGATATCGCCGGATCTACATCTACA |
| | Gag:1-53 | CTGCAGGAACAGATCGCTTGGATGACAAATAACCCCCCTATCCCAGTGGGAGATATCTATAAGCGCTGGATC |
| | Nef:117-148 | ATCATGGGCCTGAACAAGATCGTGAGGATGTACAGCCCAGTGAGCATCCTGGATATCAAGCAGGGACCTAAG |
| | Pol:747-827 | GAGCCTTTCAGAGATTACGTGGACAGGTTCTACAGAACCCTGAGAGCAGAACAGGCTTCTCAGGACGTGAAG |
| | | AATTGGATGACCGAAACACTGCTGGTGCAGAATAGCAACCCCGATTGCAAGACCATCCTGAAAGCTCTGGGA |
| | | CCAGGAGCTACACTGGAAGAAATGATGAGCGCTTGTCAGGGAGTGGGAGGACCATCTCATAAGGCTAGAGTG |
| | | CTGGCAGAAGCTATGTGTCAGGCAGTGAAAGCAGCTTGTTGGTGGGCAGGAGTGAAACAGGAGTTTGGCATC |
| | | CCTTACAATACCCAGTCTCAGGGAGTGGTGGAAAGCATGAACAACGAGCTGAAGAAGATCATCGGCCAGATT |
| | | AGAGATCAGGCCGAACATCTGAAAACAGCAGTGCAGATGGCCGTGCTGATCCACAATTTCAAGAGGAAGGGC |
| | | GGAATTGGCGAATATAGCGCCGGAGAGAGAATCATCGACATCATCGCCAAGGAGAAGATCTACCTGGCTTGG |
| | | GTGCCAGCTCATAAAGGAATCGGAGGAAACGAGCAGATCGATAAACTGGTGTCTGCCGCTTATATGGCAGCT |
| | | AGAGCTTCTATCCTGTCAGGAGGAAAGCTCGATAAGTGGGAAAAGATCAGACTGAGACCAGGCGGAAGAAAG |
| | | AAGTACAAGCTGAAGCACCTCGTCTGGGCTTCTAGAGAACTGGAAAGATTCGCCCTGAATCCAGGACTGCTG |
| | | GAAACAACACAGGGATTCTTCCCCGATTGGCAGAACTACACACCAGGACCAGGCATCAGATTTCCTCTGACC |
| | | TTTGGTTGGTGCTTTAAACTGGTGCCTCTGGTGGCTAAGGAGATTGTGGCTTGTTGCGACAAGTGTCAGCTG |
| | | AAAGGAGAGGCTATTCACGGACAGGTGGATTGTTCTCCAGGAGTCTGGCAGCTGGATTGTACACACCTGGAG |
| | | GGAAAAGTGATTCTGGTGGCAGTGCACGTGGCATCAGGATATATCGAGGCCGAGATCATCCCTACAGAGACA |
| | | GGACAGGAAACCGCCTACTTTATCCTGAAACTGGCAGGTAGGTGGCCAGTGACAACA |
| 143 | Gag:147-369 | CTGAGCCCCAGAACCCTCAATGCCTGGGTCAAAGTGATTGAGGAAAAGGCCTTCAGCCCAGAGGTGATCCCC |
| | Pol:840-920 | ATGTTCACAGCCCTCAGTGAGGGGGCCACCCCCCATGACCTGAACACCATGCTCAACACCATTGGGGGCCAC |
| | Pol:683-708 | CAGGCTGCCATGCAGATGCTGAAGGACACCATCAATGAGGAAGCTGCTGAGTGGGACAGAGTCCACCCAGTG |
| | AAY | CATGCTGGCCCAGTGGCCCCAGGCCAGATGAGGGACCCCAGGGGCTCTGACATTGCTGGCAGCACCAGCACC |
| | Gag:1-53 | CTGCAGGAGCAGATAGCCTGGATGACCAACAACCCCCCCATCCCTGTGGGAGACATCTACAAAAGATGGATC |
| | Nef:117-148 | ATCATGGGCCTCAACAAGATTGTCAGGATGTACTCCCCTGTGTCCATCCTGGACATCAAGCAGGGCCCCAAG |
| | Pol:747-827 | GAACCCTTCAGGGACTATGTGGACAGATTCTACAGAACCCTGAGAGCTGAGCAGGCCTCCCAGGATGTGAAA |
| | | AACTGGATGACAGAGACCCTCCTGGTCCAGAACGCAACCCAGACTGCAAGACCATCCTCAAGGCCTTGGGC |
| | | CCAGGAGCCACCCTGGAAGAGATGATGAGTGCCTGCCAGGGAGTTGGAGGCCCCAGCCACAAGGCCAGAGTG |
| | | CTGGCAGAGGCCATGTGCCAGGCTGTGAAGGCTGCCTGCTGGTGGGCAGGAGTCAAGCAGGAGTTTGGCATC |

TABLE H-continued

Illustrative Polynucleotides Encoding Fusion Polypeptides

| SEQ ID NO: | Encoded Polypeptide Segments | Nucleic Acid Sequences |
|---|---|---|
| | | CCATACAACACCCAGAGCCAGGGTGTGGTGGAAAGCATGAACAATGAGCTGAAAAAGATCATTGGCCAGATC<br>AGAGACCAGGCTGAGCACCTGAAGACAGCAGTGCAGATGGCTGTGCTCATCCACAACTTCAAGAGGAAAGGT<br>GGCATAGGGGAATACAGTGCTGGGGAGAGGATCATTGACATCATTGCCAAGGAGAAGATCTACCTGGCCTGG<br>GTGCCTGCCCACAAGGGCATTGGTGGCAATGAGCAGATTGACAAGCTGGTCTCAGCAGCCTACATGGCTGCC<br>AGAGCCTCCATCCTCTCAGGGGGCAAGCTGGACAAGTGGGAGAAAATCAGACTGAGGCCTGGTGGCAGAAAG<br>AAGTACAAGCTGAAGCACCTGGTGTGGGCCTCCAGGGAACTGGAAAGATTTGCCCTGAACCCTGGCCTGCTG<br>GAAACCACCCAGGGCTTCTTCCCTGACTGGCAGAACTACACCCCAGGCCCAGGCATCAGGTTCCCCCTGACC<br>TTTGGCTGGTGCTTCAAGCTGGTGCCCCTGGTGGCCAAGGAAATAGTGGCCTGCTGTGACAAGTGCCAGCTG<br>AAAGGGGAGGCCATCCATGGCCAAGTGGACTGCAGCCCTGGTGTGTGGCAGCTGGACTGCACCCACCTGGAA<br>GGCAAGGTCATCCTGGTTGCAGTGCATGTGGCCAGTGGCTACATTGAGGCTGAGATCATCCCCACAGAGACA<br>GGCCAGGAGACTGCCTACTTCATCCTGAAACTTGCAGGCAGGTGGCCTGTGACCACC |
| 144 | Pol:932-1003<br>AAY<br>EE<br>Nef:64-99<br>AA<br>Pol:367-431<br>Pol:542-606<br>Pol:56-117<br>Pol:129-320 | ATCACCAAGATCCAGAACTTCAGGGTGTACTACAGAGACAGCAGAGATCCTCTCTGGAAGGGACCAGCTAAA<br>CTCCTCTGGAAAGGAGAAGGAGCAGTGGTGATCCAGGATAACAGCGACATCAAGGTGGTGCCTAGAAGAAAG<br>GCCAAGATCATCAGGGACTACGGCAAACAGATGGCAGGAGACGATTGCGTGGCTTCTAGACAGGACGAAGAC<br>GCAGCTTACGAAGAGGAAGAGGTGGGATTTCCAGTGAAACCTCAGGTGCCTCTGAGACCTATGACATTCAAG<br>GGAGCTCTGGATCTGTCTCACTTCCTGAGAGAAAAGGGAGGACTGGAAGGAGCAGCTTGGGGATTTACCACC<br>CCAGACAAGAAGCACCAGAAGGAACCACCATTCCTCTGGATGGGATACGAACTGCACCCAGATAAGTGGACA<br>GTCCAGCCTATTGTGCTGCCAGAAAAGGACTCTTGGACCGTGAACGATATCCAGAAGCTGGTGGGAAAGCTG<br>AATTGGGCTTCTCAGATCTACCCAGGAATCAAGGTGCCCAAGTTCAAGCTGCCTATCCAGAAGGAGACTTGG<br>GAAACTTGGTGGACAGAGTATTGGCAGGCTACTTGGATTCCCGAGTGGGAATTTGTGAACACACCTCCTCTG<br>GTGAAGCTGTGGTATCAGCTGGAAAAGGAGCCTATCGTGGGCGCAGAAACATTTTACGTGGACGGAGCCGCC<br>AATAGAGAAACCAAGTTTCCTCAGATCACTCTCTGGCAGAGACCTCTGGTGACAATCAAGATCGGCGGACAG<br>CTGAAAGAGGCTCTGCTGGATACAGGAGCAGACGATACCGTGCTGGAAGAAATGAATCTGCCAGGTAGGTGG<br>AAGCCTAAGATGATTGGCGGAATTGGCGGCTTCATCAAGGTGAGACAGTACGATCAGGGAACAGTGCTGGTG<br>GGACCTACTCCAGTGAACATCATCGGAAGGAACCTGCTGACACAGATCGGCTGTACACTGAACTTCCCTATC<br>AGCCCTATCGAGACAGTGCCAGTGAAACTGAAGCCAGGAATGGACGGACCTAAAGTCAAACAGTGGCCTCTG<br>ACAGAGGAGAAAATCAAAGCCCTGGTGGAGATTTGTACCGAGATGGAGAAGGAGGGCAAGATTTCTAAGATC<br>GGACCAGAGAACCCCTACAATACCCCAGTGTTTGCCATCAAGAAGAAGGACAGCACCAAGTGGAGGAAGCTG<br>GTGGATTTTAGGGAGCTGAACAAGAGGACACAGGACTTTTGGGAAGTGCAGCTGGGCATCCCCCACCCAGCC<br>GGACTGAAAAAGAAGAAGTCAGTGACAGTGCTGGACGTGGGAGATGCCTATTTTAGCGTGCCTCTGGATAAG<br>GACTTCAGGAAGTACACCGCCTTCACAATCCCTAGCATCAACAACGAGACCCCAGGAATCAGATACCAGTAC<br>AACGTGCTGCCTCAGGGTTGGAAAGGAAGCCCAGCCATCTTTCAGTCTAGCATGACC |
| 145 | Pol:932-1003<br>AAY<br>EE<br>Nef:64-99<br>AA<br>Pol:367-431<br>Pol:542-606<br>Pol:56-117<br>Pol:129-320 | ATCACCAAGATCCAGAACTTCCGGGTGTACTACAGGGATAGCAGAGATCCTCTCTGGAAGGGACCAGCTAAA<br>CTCCTCTGGAAAGGAGAAGGAGCAGTGGTGATCCAGGATAATAGCGACATCAAGGTGGTGCCTAGAAGAAAG<br>GCTAAGATCATCCGGGACTACGGCAAACAGATGGCAGGAGACGATTGCGTGGCTTCTAGACAGGATGAAGAC<br>GCAGCCTACGAAGAAGAGGAAGTGGGATTTCCAGTGAAACCTCAGGTGCCTCTGAGACCTATGACATTCAAG<br>GGAGCTCTGGACCTGTCTCACTTTCTGAGAGAGAAGGGAGGACTGGAAGGAGCAGCTTGGGGATTTACCACA<br>CCAGATAAGAAGCACCAGAAGGAGCCACCATTTCTCTGGATGGGATACGAACTGCACCCAGATAAGTGGACA<br>GTCCAGCCTATTGTGCTGCCAGAAAAGGACTCTTGGACAGTGAACGACATCCAGAAGCTGGTGGGAAAGCTG<br>AATTGGGCCTCTCAGATTTACCCAGGAATCAAGGTGCCCAAGTTTAAGCTGCCTATCCAGAAGGAGACTTGG<br>GAAACTTGGTGGACCGAGTATTGGCAGGCAACTTGGATTCCCGAGTGGGAATTTGTGAACACACCTCCTCTG<br>GTGAAGCTGTGGTATCAGCTGGAAAAGGAGCCTATCGTGGGAGCCGAAACATTTTACGTGGACGGAGCAGCC<br>AACAGAGAGACAAAGTTCCCTCAGATCACTCTCTGGCAGAGACCACTGGTGACAATTAAGATCGGAGGACAG<br>CTGAAAGAAGCTCTGCTGGATACAGGAGCAGACGATACAGTGCTGGAGGAAATGAACCTGCCAGGTCGCTGG<br>AAACCTAAAATGATCGGCGGCATTGGCGGATTTATCAAGGTGAGGCAGTACGATCAGGGAACAGTGCTGGTG<br>GGACCTACACCCGTGAATATTATCGGAAGGAATCTGCTGACACAGATTGGCTGTACCCTGAACTTCCCTATC<br>AGCCCTATCGAAACCGTGCCAGTGAAACTGAAACCAGGAATGGACGGACCTAAAGTCAAGCAGTGGCCTCTG<br>ACAGAAGAGAAGATCAAAGCCCTGGTGGAGATTTGTACCGAGATGGAGAAGGAGGGAAAGATCAGCAAGATC<br>GGCCCAGAGAATCCTTACAACACCCCAGTGTTCGCCATCAAGAAGAAGGATAGCACCAAGTGGAGAAAGCTG<br>GTGGATTTCAGGGAGCTGAACAAGAGAACCCAGGACTTTTGGGAAGTGCAGCTGGGCATCCCCCACCCTGCC<br>GGCCTGAAGAAGAAGAAAAGCGTGACAGTGCTGGACGTGGGAGACGCTTATTTTAGCGTGCCTCTGGACAAG<br>GACTTCAGAAAGTACACCGCCTTCACCATCCCTTCTATCAATAACGAGACCCCAGGCATCAGATACCAGTAT<br>AACGTGCTGCCTCAGGGTTGGAAAGGAAGCCCAGCCATTTTTCAGAGCAGCATGACA |
| 146 | Pol:932-1003<br>AAY<br>EE<br>Nef:64-99<br>AA<br>Pol:367-431<br>Pol:542-606<br>Pol:56-117<br>Pol:129-320 | ATCACCAAGATCCAGAACTTCAGGGTCTACTACAGAGACAGCAGAGATCCACTCTGGAAGGGCCCAGCCAAA<br>CTCCTTTGGAAAGGAGAAGGAGCAGTGGTGATCCAGGACAACAGTGACATCAAGGTGGTTCCCAGAAGAAAG<br>GCCAAGATCATCAGGGACTATGGCAAACAGATGGCAGGAGATGACTGTGTGGCTTCCAGACAGGATGAAGAT<br>GCAGCTTATGAAGAGGAAGAGGTGGGATTCCCAGTGAAACCCCAGGTGCCTCTGAGGCCAATGACATTCAAG<br>GGAGCTCTGGATCTGTCCCACTTCCTGAGAGAAAAGGGAGGACTGGAAGGAGCAGCTTGGGGATTCACCACC<br>CCAGACAAGAAGCATCAGAAGGAACCTCCCTTCCTCTGGATGGGTTATGAACTGCACCCAGACAAGTGGACA<br>GTCCAGCCCATTGTGCTGCCAGAAAAGGATTCTTGGACAGTGAATGACATCCAGAAGCTGGTGGGCAAGCTG<br>AATTGGGCCTCCCAGATCTACCCAGGAATCAAGGTGCCCAAGTTCAAGCTCCCCATCCAGAAGGAGACTTGG<br>GAAACTTGGTGGACAGAGTATTGGCAGGCAACTTGGATTCCTGAGTGGGAATTTGTGAACACCCCCCCTCTG<br>GTGAAGCTGTGGTATCAGCTGGAAAAGGAGCCCATTGTGGGGGCAGAAACATTTTATGTGGATGGAGCAGCC<br>AACAGAGAAACCAAGTTTCCCCAGATCACTCTTTGGCAGAGACCACTGGTGACAATCAAGATTGGGGGACAG<br>CTGAAAGAGGCTCTGCTGGACACAGGAGCTGATGACACAGTGCTGGAAGAAATGAATCTGCCAGGCAGGTGG<br>AAGCCCAAGATGATTGGAGGCATTGGGGGTTTCATCAAGGTGAGACAGTATGACCAGGGAACTGTGCTGGTG<br>GGACCCACTCCAGTGAACATCATTGGCAGGAACCTGCTGACACAGATTGGCTGCACACTGAACTTCCCCATC<br>AGCCCCATTGAGACAGTCCCAGTGAAACTGAAGCCAGGAATGGATGGCCCAAAAGTCAAACAATGGCCCCTG<br>ACAGAGGAGAAAATCAAAGCTCTGGTGGAGATTTGCACAGAGATGGAGAAGGAGGGCAAGATCTCTAAGATT<br>GGCCCAGAGAACCCATACAACACTCCAGTGTTTGCAATCAAGAAGAAGGACAGCACCAAGTGGAGGAAGCTG<br>GTGGACTTCAGGGAGCTCAACAAGAGGACACAGGACTTTTGGGAAGTGCAGCTGGGCATTCCCCACCCAGCA |

TABLE H-continued

Illustrative Polynucleotides Encoding Fusion Polypeptides

| SEQ ID NO: | Encoded Polypeptide Segments | Nucleic Acid Sequences |
|---|---|---|
| | | GGACTGAAAAAGAAGAAGTCAGTGACAGTGCTGGATGTGGGGGATGCTTATTTCAGTGTGCCTCTGGACAAG |
| | | GACTTCAGGAAGTACACAGCCTTCACAATCCCCAGCATCAACAATGAGACCCCAGGAATCAGATATCAGTAC |
| | | AATGTGCTGCCTCAGGGTTGGAAAGGAAGCCCAGCCATTTTCCAGTCGAGCATGACC |
| 147 | Pol:542-606 | CCTAAATTCAGACTGCCTATCCAGAAGGAGACTTGGGATACTTGGTGGACCGATTATTGGCAGGCAACTTGG |
| | Nef:64-99 | ATTCCCGAGTGGGAATTTACCAATACCCCTCCTCTGGTGAAGCTGTGGTATCAGCTGGAAACAGAGCCTATT |
| | Pol:56-117 | GCCGGAGTGGAAACATTCTACGTGGACGGAGCCTCTAATAGAGAGACCAAGGAGGAAGTGGGATTTCCAGTG |
| | Pol:932-1003 | AGACCTCAGGTGCCTCTGAGACCTATGACATACAAGGGAGCTCTGGACCTGTCTCACTTTCTGAAGGAGAAG |
| | Pol:367-431 | GGAGGACTGGAAGGACTGCCTCAGATTACTCTCTGGCAGAGACCTATCGTGACCATCAAGATCGGAGGACAG |
| | K | ATCAAAGAAGCTCTGCTGGATACAGGAGCAGACGATACAGTGCTGGAGGATATGAACCTGCCAGGTAAGTGG |
| | Pol:129-320 | AAGCCTAAGATGATCGGCGGAATTGGCGGCTTTATCAAGGTCAAGCAGTACGACCAGATCACCAAGCTGCAG |
| | | AACTTCAGGGTGTACTACAGGGACAACAGAGACCCCCTCTGGAAAGGACCAGCTAGACTCCTCTGGAAAGGA |
| | | GAAGGAGCAGTGGTGATCCAGGACAATAGCGAGATCAAGGTGGTGCCTAGAAGGAAGGTGAAGATCATCAGG |
| | | GACTACGGAAAAAGAATGGCCGGAGACGATTGCGTGGCAGGAAGACAGGACGAAGATTGGGGACTGACAACA |
| | | CCAGACAAGAAGCACCAGAAGGACCCCCCATTCCTCTGGATGGGATACGAACTGCATCCAGATAGGTGGACA |
| | | GTGCAGCCAATTGAACTGCCAGAGAAGGAGTCTTGGACCGTGAACGATATCCAGAAGCTGATCGGCAAGCTG |
| | | AATTGGGCTTCTCAGATCTACGCAGGAATCAAGGTGAAGGGCACAGTGCTGATTGGACCTACACCAGTGAAC |
| | | ATCATCGGCAGAAACCTCCTGACACAGCTGGGTTGTACACTGAATTTCCCTATCAGCCCTATCGATACAGTG |
| | | CCAGTGAAGCTGAAACCAGGAATGGACGGACCTAGAGTCAAACAGTGGCCTCTGACAGAAGAGAAGATCAAG |
| | | GCCCTGATCGAGATTTGCACCGAGATGGAGAAGGAGGGAAAGATCTCTAGGATCGGCCCAGAGAATCCTTAC |
| | | AATACCCCTATCTTCGCCATCAAGAAGAAGGACGGAACCAAGTGGAGAAAGCTGGTGGATTTCAGGGAGCTG |
| | | AACAAGAAGACCCAGGACTTTTGGGAGGTGCAGCTGGGCATCCCCCATCCTTCAGGACTGAAGAAGAAGAAG |
| | | AGCGTGACAGTGCTGGATATCGGAGACGCTTACTTTAGCGTGCCACTGGACAAGGAGTTCAGAAAGTACACC |
| | | GCTTTCACCGTGCCTTCTACCAATAACGAGACCCCAGGAGTGAGATACCAGTATAACGTGCTGCCCATGGGT |
| | | TGGAAAGGATCTCCAGCAATTTTTCAGTGTAGCATGACA |
| 148 | Pol:542-606 | CCCAAGTTCAGGCTGCCTATCCAGAAAGAGACTTGGGACACTTGGTGGACCGATTATTGGCAGGCAACTTGG |
| | Nef:64-99 | ATTCCCGAGTGGGAATTTACCAACACACCTCCTCTGGTGAAGCTGTGGTATCAGCTGGAAACAGAGCCTATT |
| | Pol:56-117 | GCCGGAGTGGAAACATTCTACGTGGACGGAGCCAGCAACAGAGAGACCAAGGAGGAAGTGGGATTTCCAGTG |
| | Pol:932-1003 | AGACCTCAGGTGCCTCTGAGACCTATGACATACAAGGGAGCTCTGGATCTGAGCCACTTTCTGAAGGAGAAA |
| | Pol:367-431 | GGAGGACTGGAAGGACTGCCTCAGATTACTCTCTGGCAGAGACCTATCGTGACAATCAAGATCGGCGGACAG |
| | K | ATCAAGGAAGCTCTGCTGGATACAGGAGCCGACGATACAGTGCTGGAAGATATGAACCTGCCAGGCAAGTGG |
| | Pol:129-320 | AAACCTAAGATGATCGGAGGCATTGGCGGCTTTATCAAGGTGAAACAGTACGACCAGATCACCAAGCTGCAG |
| | | AACTTCAGGGTGTACTACAGGGACAACAGAGACCCCCTCTGGAAAGGACCAGCTAGACTGCTGTGGAAAGGA |
| | | GAAGGAGCAGTGGTGATCCAGGATAATAGCGAGATCAAGGTGGTGCCTAGGAGAAAGGTGAAGATCATCAGG |
| | | GACTACGGCAAGAGAATGGCAGGAGACGATTGCGTGGCAGGAAGACAGGACGAAGATTGGGGACTGACAACA |
| | | CCAGACAAGAAGCACCAGAAGGACCCCCCTTTCCTCTGGATGGGATACGAACTGCATCCAGATAGGTGGACA |
| | | GTGCAGCCAATTGAGCTGCCAGAAAAGGAGTCTTGGACAGTGAACGACATCCAGAAGCTGATCGGCAAGCTG |
| | | AATTGGGCTTCTCAGATCTACGCCGGAATTAAGGTGAAGGGAACAGTGCTGATTGGACCTACACCAGTGAAC |
| | | ATCATCGGAAGAAACCTGCTGACACAGCTGGGTTGTACACTGAACTTCCCTATCAGCCCTATCGATACCGTG |
| | | CCAGTGAAACTGAAACCAGGAATGGACGGACCTAGAGTCAAGCAGTGGCCTCTGACAGAAGAGAAGATCAAG |
| | | GCCCTGATCGAGATTTGCACCGAGATGGAGAAGGAGGGAAAGATCAGCAGAATTGGCCCCGAGAATCCTTAC |
| | | AACACCCCTATCTTCGCCATCAAGAAGAAGGACGGAACTAAGTGGAGAAAGCTGGTGGACTTCAGAGAGCTG |
| | | AACAAGAAGACCCAGGACTTTTGGGAAGTGCAGCTGGGCATCCCCCATCCTTCAGGACTGAAGAAGAAGAAG |
| | | AGCGTGACAGTGCTGGACATCGGAGACGCTTATTTTAGCGTGCCTCTGGATAAGGAGTTCCGGAAATACACC |
| | | GCCTTTACCGTGCCTTCTACCAATAACGAGACACCAGGAGTGAGGTACCAGTATAACGTGCTGCCAATGGGC |
| | | TGGAAAGGATCTCCAGCAATCTTTCAGTGTAGCATGACA |
| 149 | Pol:542-606 | CCCAAGTTCAGGCTGCCCATCCAGAAAGAAACCTGGGACACCTGGTGGACTGACTACTGGCAGGCCACCTGG |
| | Nef:64-99 | ATCCCAGAGTGGGAGTTCACCAACACCCCTCCCCTGGTGAAGCTGTGGTACCAGCTGGAAACTGAGCCCATA |
| | Pol:56-117 | GCAGGAGTGGAAACCTTTTATGTGGATGGAGCCAGCAACAGGGAAACCAAGGAAGAGGTGGGCTTCCCAGTG |
| | Pol:932-1003 | AGGCCCCAGGTGCCCCTGAGACCCATGACCTACAAGGGAGCCCTGGATCTGAGCCACTTCCTGAAAGAGAAG |
| | Pol:367-431 | GGGGGCCTGGAAGGCCTGCCCCAGATCACCCTGTGGCAGAGACCCATTGTGACCATCAAGATTGGGGGCCAG |
| | K | ATCAAAGAGGCCCTCCTGGACACTGGAGCTGATGACACAGTCCTGGAAGACATGAACCTCCCAGGAAAGTGG |
| | Pol:129-320 | AAGCCCAAGATGATTGGGGGCATTGGAGGCTTCATCAAGGTCAAGCAGTATGACCAGATCACCAAGCTCCAG |
| | | AATTTCAGAGTCTACTACAGAGACAACAGAGACCCCCTGTGGAAAGGCCCAGCCAGACTTCTCTGGAAGGGG |
| | | GAGGGAGCAGTGGTGATCCAAGACAACTCTGAGATCAAAGTGGTCCCCAGGAGAAAGGTGAAGATCATCAGG |
| | | GACTATGGCAAAAGGATGGCAGGGGATGACTGTGTGGCAGGCAGACAGGATGAGGACTGGGGCCTGACCACC |
| | | CCTGACAAGAAGCACCAGAAGGACCCCCCCTTCCTGTGGATGGGCTATGAGCTGCACCCAGACAGATGGACT |
| | | GTCCAACCCATTGAGCTGCCTGAGAAGGAGAGCTGGACAGTCAATGACATCCAGAAGCTGATTGGGAAGCTG |
| | | AATTGGGCCTCCCAGATCTATGCAGGCATCAAGGTCAAGGGCACTGTCCTGATTGGCCCCACCCCTGTGAAC |
| | | ATCATAGGCAGAAACCTGCTGACCCAGCTGGGCTGCACACTGAACTTCCCCATCAGCCCCATTGACACAGTG |
| | | CCTGTGAAGCTCAAGCCTGGCATGGATGGCCCCAGAGTGAAACAGTGGCCCTTGACAGAGGAAAAAATCAAG |
| | | GCCCTGATTGAGATCTGCACTGAGATGGAAAAAGAGGGCAAGATCTCAAGAATTGGCCCTGAGAACCCCTAC |
| | | AACACCCCCATTTTTGCCATCAAGAAAAAGGATGGCACAAAGTGGAGAAAGCTGGTGGACTTCAGAGAGCTC |
| | | AACAAGAAGACCCAGGACTTCTGGGAGGTGCAGCTGGGCATCCCCCACCCCTCTGGCCTCAAGAAGAAGAAA |
| | | AGTGTGACTGTGCTGGACATTGGTGATGCCTACTTCAGTGTCCCCCTGGACAAGGAATTCAGGAAGTACACA |
| | | GCCTTCACAGTGCCCAGCACCAACAATGAGACCCCTGGTGTCAGGTACCAGTACAATGTGCTGCCCATGGGC |
| | | TGGAAGGGCAGCCCAGCCATCTTCCAGTGCAGCATGACC |
| 150 | Pol:840-920 | ACTGTAAAGGCCGCCTGTTGGTGGGCTGGGATCAAACAGGAGTTCGGAATCCCATACAATCCCCAAAGCCAG |
| | Gag:147-369 | GGAGTAGTGGAATCCATGAATAAGGAGCTCAAGAAGATCATTGGGCAAGTCAGGGACCAGGCTGAGCACCTC |
| | Pol:586-606 | AAGACGGCCGTTCAAATGGCGGTATTTATCCATAACTTTAAACGCAAAGGCGGTATTGGCGGTTACTCCGCA |
| | AA | GGTGAGCGGATAGTTGACATTATCGCAATAAGCCCTAGGACGCTTAACGCTTGGGTCAAGGTAGTGGAGGAA |

TABLE H-continued

| Illustrative Polynucleotides Encoding Fusion Polypeptides | | |
|---|---|---|
| SEQ ID NO: | Encoded Polypeptide Segments | Nucleic Acid Sequences |
| | Pol:683-708 | AAAGCCTTCTCACCGGAGGTCATCCCTATGTTTAGCGCCCTGAGCGAAGGAGCGACGCCACAAGACTTGAAC<br>ACCATGCTTAATACGGTGGGGGTCACCAAGCTGCAATGCAAATGTTGAAGGAAACGATAAACGAAGAGGCC<br>GCCGAATGGGACAGGTTGCATCCCGTTCATGCAGGTCCCATAGCTCCCGGTCAAATGAGGGAACCACGCGGA<br>TCAGACATCGCGGGAACGACGTCCACGTTGCAGGAACAAATTGGATGGATGACCAATAACCCTCCTATCCCA<br>GTCGGTGAAATCTATAAGAGGTGGATCATCCTCGGCCTCAATAAAATAGTGAGGATGTATTCTCCAACTAGC<br>ATTCTGGATATACGCCAAGGCCCTAAAGAACCATTTCGCGATTACGTAGACCGATTTTACAAGACACTCCGG<br>GCTGAGCAGGCCTCCCAAGAGGTAAAGAATTGGATGACCGAAACGTTGCTGGTGCAGAATGCCAACCCCGAC<br>TGTAAGACCATTTTGAAGGCGCTTGGGCCAGCAGCAACACTGGAAGAGATGATGACTGCGTGTCAAGGTGTA<br>GGTGGCCCCGGCCACAAAGCCAGAGTGTTGGCCGAGGCAATGAGCCAAAAAGAACCCATTGTAGGAGCTGAG<br>ACCTTTTACGTTGATGGCGCAGCTAACAGAGAAACTAAGGCGGCAAAAGAGAAAGTTTATCTTGCATGGGTG<br>CCTGCGCACAAAGGAATCGGCGGAAATGAGCAAGTTGATAAACTCGTAAGT |
| 151 | Pol:840-920<br>Pol:586-606<br>AAA<br>Gag:147-369<br>AAA<br>Pol:683-708 | ACCGTGAAGGCGGCGTGTTGGTGGGCAGGGATAAAGCAAGAATTTGGCATACCTTATAACCCGCAGAGTCAG<br>GGAGTTGTCGAATCCATGAATAAGGAGCTTAAGAAGATCATCGGTCAGGTGCGCGATCAGGCAGAGCACCTC<br>AAAACTGCGGTCCAAATGGCCGTGTTCATCCACAACTTCAAGCGCAAAGGCGGAATCGGTGGATACAGTGCT<br>GGGGAAAGGATCGTCGATATTATCGCCAAAGAGCCAATCGTGGGAGCGGAAACATTCTACGTAGACGGTGCG<br>GCCAACAGGGAGACAAAAGCCGCTGCGATCTCACCCCGAACCCTTAATGCTTGGGTGAAGGTGGTGGAAGAA<br>AAAGCCTTCAGTCCCGAAGTTATCCCGATGTTCTCCGCCCTCAGTGAAGGTGCAACGCCGCAGGACCTTAAT<br>ACTATGTTGAACACCGTTGGTGGTCATCAGGCCGCCATGCAGATGCTTAAAGAAACCATTAACGAAGAAGCC<br>GCAGAATGGGACAGGTTGCACCCAGTCCACGCTGGGCCCATCGCGCCTGGGCAGATGCGAGAGCCACGAGGG<br>TCCGATATCGCGGGCACAACAAGCACTTTGCAAGAACAGATTGGGTGGATGACTAATAACCCGCCGATACCT<br>GTTGGGGAAATATATAAACGCTGGATAATTCTGGGACTCAATAAGATAGTGAGAATGTACTCCCCTACATCC<br>ATTCTTGATATACGACAAGGTCCAAAAGAACCCTTTCGCGACTACGTGGATAGATTTTATAAGACCCTCAGG<br>GCCGAACAGGCAAGTCAGGAGGTCAAGAACTGGATGACGGAGACGCTTCTTGTTCAGAATGCAAATCCCGAT<br>TGCAAAACTATCTTGAAAGCGCTCGGACCAGCAGCGACGCTGGAAGAAATGATGACCGCCTGCCAGGGCGTA<br>GGCGGCCCAGGTCATAAAGCAAGGGTATTGGCAGAAGCGATGAGTCAAGCAGCGGCAAAGGAGAAAGTATAT<br>CTTGCGTGGGTACCAGCGCACAAAGGGATAGGTGGAAACGAGCAAGTTGATAAGCTGGTCTCCCTT |
| 152 | Pol:932-1003<br>Pol:747-827<br>Pol:129-320<br>QEE<br>Nef:64-76 | ATAACGAAAATTCAGAACTTTCGAGTGTACTACAGAGATAGTAGAGACCCGCTGTGGAAGGGCCCAGCTAAA<br>CTCCTTTGGAAAGGTGAAGGGGCTGTGGTCATACAGGATAACTCAGACATAAAGGTCGTCCCAAGGAGAAAA<br>GCCAAAATAATTAGAGACTACGGCAAGCAGATGGCAGGGGATGACTGTGTTGCGAGCCGGCAGGATGAGGAT<br>GTCGCGAAGGAAATCGTGGCGAGTTGTGATAAATGTCAACTGAAGGGTGAGGCAATGCACGGCCAAGTAGAT<br>TGCAGTCCAGGTATCTGGCAACTCGATTGCACCCACCTGGAGGGTAAGATTATCCTGGTGGCTGTGCATGTT<br>GCATCCGGCTACATCGAAGCTGAAGTGATTCCGGCTGAAACGGGGCAGGAAACCGCCTACTTCCTGTTGAAG<br>TTGGCTGGTCGATGGCCAGTCAAGACCGGTACAGTACTCGTTGGCCCGACGCCAGTGAATATCATAGGTCGG<br>AACCTGCTGACACAAATCGGGTGCACTCTTAATTTTCCGATTTCACCTATCGAAACCGTTCCAGTAAAACTC<br>AAGCCTGGGATGGATGGCCCGAAGGTTAAGCAATGGCCACTGACCGAAGAGAAAATCAAAGCGCTCGTGGAG<br>ATATGTACTGAAATGGAGAAAGAAGGAAAAATCTCTAAAATCGGGCCAGAAAATCCCTATAATACTCCGGTA<br>TTTGCTATCAAAAAAAAAGACTCAACCAAGTGGCGAAAGCTCGTTGACTTCCGAGAGTTGAATAAAAGGACC<br>CAGGATTTTTGGGAGGTTCAGCTGGGCATACCGCACCCCGCTGGCTTGAAAAAAAAGAAGTCTGTTACCGTC<br>CTGGATGTGGGCGACGCCTACTTCAGTGTACCTCTTGACAAAGACTTTAGAAAGTATACTGCTTTCACGATC<br>CCGAGTATAAACAACGAGACTCCAGGAATTAGGTACCAGTACAATGTATTGCCGCAGGGATGGAAGGGATCA<br>CCCGCAATCTTCCAATCTAGTATGACGCAAGAGGAGGAGGAAGTAGGTTTCCCAGTCAAACCACAAGTGCCG<br>CTC |
| 153 | Pol:932-1003<br>Pol:747-827<br>Pol:129-320<br>QEE<br>Nef:64-76 | ATTACTAAAATACAAAACTTCCGAGTATATTATAGGGATAGCCGGGACCCTCTCTGGAAAGGGCCCGCGAAA<br>CTGCTTTGGAAGGGCGAGGGCGCTGTTGTCATACAGGACAATAGCGATATAAAAGTAGTCCCGCGACGCAAA<br>GCAAAAATAATAAGAGATTATGGAAAACAAATGGCGGGCGACGATTGTGTCGCCTCACGGCAGGACGAGGAT<br>GCTGCAGCCATCGGAACAGTACTCGTGGGGCCAACTCCCGTCAACATAATAGGACGAAATCTTCTGACTCAA<br>ATAGGTTGCACGCTCAACTTCCCAATTAGCCCTATAGAGACAGTGCCCGTAAAGTTGAAGCCTGGCATGGAC<br>GGCCCAAAAGTAAAGCAGTGGCCCCTTACTGAAGAGAAGATCAAGGCCCTGGTGGAGATCTGTACAGAGATG<br>GAGAAAGAAGGGAAAATCTCCAAAATCGGTCCAGAAAACCCATACAACACACCTGTTTTTGCGATAAAAAAA<br>AAGGATTCCACCAAGTGGAGGAAACTGGTGGATTTTCGAGAGTTGAATAAGCGAACCCAGGACTTCTGGGAA<br>GTACAGCTTGGGATACCACATCCAGCGGGTCTCAAGAAAAAGAAATCAGTTACGGTCCTCGATGTTGGCGAC<br>GCGTATTTTAGTGTTCCTCTCGATAAAGATTTCCGAAAATATACGGCATTCACCATACCCAGTATTAACAAC<br>GAGACACCGGGAATCAGGTATCAGTATAATGTACTTCCACAAGGTTGGAAGGGAAGCCCCGCGATTTTTCAG<br>AGCTCAATGACGGTTGCCAAGGAGATTGTAGCTAGCTGTGACAAATGTCAGCTGAAGGGCGAAGCGATGCAC<br>GGCCAGGTAGATTGCAGCCCCGGTATTTGGCAGCTCGACTGTACACATTTGGAAGGAAAAATTATACTTGTG<br>GCTGTCCACGTTGCAAGTGGATACATAGAGGCGGAGGTCATTCCCGCAGAAACTGGGCAAGAAACTGCTTAC<br>TTTCTCTTGAAGTTGGCCGGTAGGTGGCCAGTGAAAACCCAAGAGGAAGAGGAGGTTGGTTTTCCCGTCAAA<br>CCTCAAGTCCCCCTC |
| 154 | Gag:147-369<br>Pol:683-708<br>Pol:586-606<br>Pol:840-920 | CTGAGCCCCAGGACCCTGAATGCATGGGTCAAAGTGATTGAAGAGAAGGCTTTCTCTCCTGAAGTCATCCCA<br>ATGTTCACAGCACTTTCTGAGGGGGCCACACCACATGATTTGAACACCATGCTCAACACCATTGGTGGTCAT<br>CAGGCTGCTATGCAGATGCTCAAGGACACCATCAATGAGGAAGCAGCAGAGTGGGACAGAGTCCACCCAGTC<br>CATGCAGGGCCTGTTGCACCAGGGCAAATGAGGGACCCCAGAGGCTCAGACATTGCAGGTTCCACATCAACC<br>CTTCAAGAACAAATTGCCTGGATGACAAACAATCCCCCAATCCCAGTGGGGGACATCTACAAGAGATGGATC<br>ATCATGGGCCTGAACAAAATTGTGAGGATGTACAGCCCTGTGTCAATTCTGGACATCAAGCAAGGCCCAAAA<br>GAACCTTTCAGGGACTATGTTGACAGGTTTTACAGGACCCTCAGGGCAGAACAGGCCTCCCAGGATGTGAAG<br>AATTGGATGACAGAGACATTGCTTGTTCAGAACAGCAACCCAGACTGCAAGACCATTCTGAAAGCCCTGGGT<br>CCAGGAGCAACCCTGGAAGAGATGATGTCAGCCTGTCAGGGGGTGGGGGGCCATCACACAAAGCCAGGGTG<br>TTGGCTGAGGCCATGTGCCAGAAAGAAAAAATCTATCTGGCATGGGTGCCAGCCCACAAGGGGATTGGAGGC<br>AATGAGCAAATTGACAAGCTGGTGTCAACTGAACCCATTGCTGGGGTAGAGACTTTTTATGTGGATGGTGCC<br>AGCAACAGGGAAACCAAGGCTGTGAAGGCTGCTTGTTGGTGGGCTGGAGTCAAGCAGGAGTTTGGCATTCCC |

TABLE H-continued

Illustrative Polynucleotides Encoding Fusion Polypeptides

| SEQ ID NO: | Encoded Polypeptide Segments | Nucleic Acid Sequences |
|---|---|---|
| | | TACAACACCCAAAGCCAAGGTGTTGTTGAATCCATGAACAATGAGTTGAAAAAGATCATAGGCCAGATCAGG<br>GATCAAGCTGAGCATCTGAAAACTGCAGTTCAGATGGCAGTCCTGATTCACAATTTCAAGAGAAAGGGAGGG<br>ATAGGAGAGTACAGTGCAGGGGAAAGGATCATTGACATCATTGCA |
| 155 | Gag:147-369<br>Pol:683-708<br>Pol:586-606<br>Pol:840-920 | CTGAGCCCCCGAACCCTCAACGCATGGGTCAAGGTGATCGAAGAGAAGGCGTTCTCTCCTGAAGTTATTCCT<br>ATGTTTACGGCTCTGTCTGAGGGCGCCACACCCCATGATTTGAACACGATGCTCAACACGATAGGCGGTCAT<br>CAAGCCGCGATGCAGATGCTCAAGGATACGATCAACGAGGAAGCTGCAGAGTGGGACCGAGTTCACCCAGTC<br>CATGCAGGGCCTGTTGCACCAGGGCAAATGCGGGACCCACGCGGTTCAGATATTGCCGGTTCCACGTCTACC<br>CTGCAAGAACAAATAGCGTGGATGACAAATAATCCACCGATCCCGGTGGGCGATATATACAAGAGATGGATT<br>ATCATGGGCCTGAACAAAATAGTTAGGATGTACAGCCCGGTGTCAATACTTGATATAAAACAAGGACCGAAA<br>GAACCCTTTCGCGACTATGTAGACCGGTTCTACAGGACGCTTAGGGCAGAACAGGCCTCCCAAGATGTGAAG<br>AATTGGATGACAGAGACATTGCTTGTTCAGAACAGCAACCCTGACTGCAAGACCATACTTAAAGCTCTGGGT<br>CCAGGAGCCACTCTGGAAGAGATGATGTCAGCATGTCAGGGGGTAGGCGGGCCATCACATAAAGCCCGGGTT<br>TTGGCGGAAGCAATGTGCCAGAAAGAAAAAATTTATCTGGCGTGGGTGCCCGCCCACAAGGGGATAGGTGGT<br>AACGAGCAGATCGACAAGCTGGTCTCAACAGAACCTATAGCTGGAGTAGAGACGTTTTATGTGGATGGTGCA<br>AGCAATCGGGAAACCAAGGCGGTAAAGGCCGCTTGCTGGTGGGCCGGAGTCAAGCAGGAGTTCGGCATCCCG<br>TATAACACCCAAAGTCAAGGTGTCGTCGAATCCATGAATAACGAGTTGAAAAAGATCATAGGTCAAATAAGG<br>GATCAAGCTGAACATCTGAAGACGGCTGTTCAGATGGCGGTCCTTATCCACAACTTTAAGCGCAAAGGAGGT<br>ATAGGAGAGTACAGCGCAGGTGAACGGATAATAGACATTATAGCA |
| 156 | Gag:147-369<br>Pol:840-920<br>Pol:586-606<br>AA<br>Pol:683-708 | CTGTCTCCTAGAACATTGAACGCTTGGGTTAAGGTTATAGAAGAGAAAGCCTTCAGTCCTGAGGTGATTCCC<br>ATGTTTACCGCCCTGAGCGAGGGCGCTACACCACATGATCTGAATACCATGCTGAATACTATCGGGGGACAT<br>CAGGCTGCCATGCAGATGCTTAAAGATACAATAAATGAGGAGGCTGCAGAGTGGGACAGGGTCCATCCTGTA<br>CACGCGGGACCTGTTGCGCCGGGACAGATGAGAGATCCGCGGGGGAGCGATATTGCAGGAAGCACCTCAACT<br>CTTCAGGAGCAGATTGCCTGGATGACGAACAACCCTCCGATTCCTGTGGGAGACATTTATAAGAGGTGGATA<br>ATTATGGGGTTGAACAAGATAGTCAGGATGTATTCTCCTGTTAGCATCCTGGACATAAAACAGGGCCCTAAA<br>GAGCCTTTTCGCGATTATGTTGACAGGTTTTATAGGACACTTCGCGCGGAGCAAGCCTCCCAGGATGTTAAA<br>AACTGGATGACCGAGACGCTCCTGGTTCAAAACAGTAACCCCGATTGTAAGACCATCCTTAAAGCACTTGGA<br>CCTGGCGCTACCCTGGAGGAAATGATGAGCGCCTGTCAGGGGGTAGGAGGCCCATCACATAAGGCACGGGTG<br>CTCGCAGAGGCGATGTGTCAAGCGGTGAAGGCAGCCTGCTGGTGGGCAGGTGTGAAGCAGGAATTTGGGATT<br>CCTTATAATACACAATCCCAAGGTGTTGTCGAATCTATGAACAATGAACTGAAGAAAATTATAGGGCAAATC<br>CGGGACCAAGCTGAGCACCTCAAAACCGCGGTTCAAATGGCTGTACTTATTCATAATTTCAAGCGCAAAGGG<br>GGAATCGGTGAGTACAGTGCTGGGGAACGGATAATAGATATTATCGCCACCGAGCCTATCGCAGGTGTTGAA<br>ACTTTTTACGTGGACGGTGCATCAAACAGAGAGACCAAAGCGGCCAAGGAGAAGATATATTTGGCCTGGGTT<br>CCTGCTCACAAGGGAATTGGCGGAAATGAGCAAATTGATAAGCTCGTAAGT |
| 157 | Pol:747-827<br>Pol:932-1003<br>Pol:129-320<br>KIL<br>QEE<br>Nef:64-76 | GTTGCCAAGGAGATTGTGGCCTGCTGTGACAAGTGCCAATTGAAGGGGGAGGCAATTCATGGACAGGTGGAT<br>TGCAGTCCAGGAGTCTGGCAGCTGGATTGCACACACCTGGAAGGGAAGGTCATCCTTGTTGCAGTTCATGTT<br>GCCTCAGGATACATTGAAGCAGAGATCATCCCCACAGAAACTGGTCAGGAAACAGCTTACTTCATTCTCAAA<br>CTGGCTGGCAGGTGGCCAGTCACCACAATCACCAAGCTTCAAAATTTCAGGGTTTACTACAGGGACAACAGA<br>GATCCTCTCTGGAAGGGACCTGCAAGACTTCTTTGGAAGGGTGAAGGGGCAGTTGTCATTCAGGACAACAGT<br>GAGATCAAGGTTGTTCCCAGGAGAAAGGTCAAGATCATCAGGGACTATGGAAAAGGATGGCAGGGGATGAC<br>TGTGTTGCAGGGAGACAAGATGAGGATGGCACTGTGCTGATAGGCCCCACACCTGTCAACATCATTGGCAGG<br>AACCTCTTGACTCAGCTGGGCTGCACTCTCAATTTTCCCATTTCCCCCATTGACACAGTGCCAGTGAAACTG<br>AAGCCTGGAATGGATGGCCCAAGGGTCAAACAGTGGCCCCTGACAGAGGAGAAGATCAAGGCTCTCATTGAG<br>ATCTGCACTGAAATGGAAAAGGAAGGCAAGATCAGCAGGATTGGCCCTGAGAACCCTTACAACACTCCTATT<br>TTTGCAATCAAGAAGAAGGATGGGACCAAGTGGAGGAAGTTGGTTGACTTCAGGGAACTCAACAAGAAAACA<br>CAAGACTTTTGGGAAGTCCAACTTGGCATTCCCCATCCCAGTGGGTTGAAAAAGAAAAAGTCAGTGACAGTG<br>TTGGACATTGGGGATGCTTATTTCTCAGTTCCCCTTGACAAGGAGTTCAGAAAATACACAGCATTCACTGTG<br>CCTTCCACAAACAATGAAACCCCTGGGGTCAGGTACCAGTACAATGTCCTTCCAATGGGTTGGAAAGGCAGT<br>CCTGCAATCTTTCAATGCAGCATGACAAAAATCCTTCAAGAAGAAGAGGAAGTTGGCTTTCCTGTGAGGCCT<br>CAGGTCCCCCTT |
| 158 | Pol:747-827<br>Pol:932-1003<br>Pol:129-320<br>KIL<br>QEE<br>Nef:64-76 | GTTGCCAAGGAGATCGTGGCGTGCTGCGATAAGTGCCAATTGAAAGGGGAGGCGATTCATGGACAGGTCGAT<br>TGTAGTCCCGGAGTCTGGCAGCTGGATTGCACTCACCTGGAAGGTAAGGTCATCCTTGTGGCTGTACATGTT<br>GCCTCCGGGTATATTGAAGCCGAGATAATCCCTACCGAAACTGGTCAGGAAACCGCTTACTTCATTCTCAAA<br>CTTGCTGGAAGGTGGCCCGTTACTACAATTACCAAGCTGCAAAATTTCAGGGTGTACTACAGGGATAACCGC<br>GACCCTCTCTGGAAGGGCCCAGCACGACTGCTTTGGAAGGGTGAGGGGGCTGTTGTTATTCAGGATAACAGT<br>GAGATTAAGGTAGTCCCCAGGCGAAAGGTTAAAATAATACGGGACTACGGTAAAAGAATGGCGGGGGATGAC<br>TGTGTTGCAGGGAGACAAGACGAAGACGGAACGGTACTTATAGGCCCAACTCCGGTAAACATAATTGGTAGA<br>AACCTCTTGACGCAGCTGGGCTGTACTCTTAATTTTCCAATATCACCTATTGACACTGTCCCAGTCAAGCTG<br>AAGCCTGGAATGGATGGACCTCGGGTTAAACAGTGGCCCCTCACCGAGGAGAAGATCAAGGCGCTGATCGAA<br>ATCTGCACCGAAATGGAAAAGGAAGGTAAGATTAGCCGGATCGGCCCCGAGAACCCTTATAACACGCCTATA<br>TTCGCTATCAAGAAGAAGGACGGAACAAAGTGGAGGAAGTTGGTTGACTTCCGGGAACTTAACAAGAAAACA<br>CAAGACTTTTGGGAAGTCCAACTCGGCATCCCACACCCAAGTGGGTTGAAAAAGAAAAAGTCCGTAACTGTA<br>TTGGACATAGGTGACGCTTATTTTTCAGTACCACTTGATAAGGAATTTCGAAAATACACAGCGTTCACTGTG<br>CCGTCCACGAACAACGAAACCCCCGGGGTACGCTACCAATATAACGTACTGCCAATGGGTTGGAAAGGTAGT<br>CCTGCGATCTTTCAATGCAGTATGACTAAAATCCTTCAAGAAGAAGAGGAAGTCGGATTTCCTGTGCGGCCC<br>CAGGTCCCCCTG |
| 159 | Pol:129-320<br>Pol:932-1003<br>Pol:747-827<br>AA | GGGACGGTGCTTATTGGGCCCACTCCAGTCAATATTATCGGACGAAACCTGCTGACTCAGCTGGGTTGCACT<br>CTCAATTTCCCTATTAGTCCTATAGACACGGTGCCCGTAAAACTCAAGCCAGGCATGGATGGTCCGCGCGTG<br>AAGCAATGGCCTTTGACTGAAGAAAAAATTAAGGCACTCATTGAGATATGTACGGAGATGGAGAAAGAAGGG<br>AAAATCTCTCGAATTGGACCAGAAAACCCGTACAATACTCCGATTTTTGCGATTAAGAAGAAGGATGGCACG |

TABLE H-continued

Illustrative Polynucleotides Encoding Fusion Polypeptides

| SEQ ID NO: | Encoded Polypeptide Segments | Nucleic Acid Sequences |
|---|---|---|
| | QEE | AAGTGGCGCAAACTCGTCGATTTTAGGGAGCTTAACAAGAAGACCCAAGATTTTTGGGAGGTCCAGCTGGGC |
| | Nef:64-76 | ATTCCGCATCCGTCCGGCTTGAAAAAGAAAAAATCAGTTACTGTGCTTGATATAGGAGACGCCTATTTTAGT |
| | | GTGCCGTTGGACAAGGAATTTCGCAAATATACAGCATTTACCGTCCCTTCAACGAACAATGAGACTCCGGGC |
| | | GTACGCTACCAATATAATGTGTTGCCTATGGGGTGGAAGGGGTCTCCTGCGATCTTCCAATGCTCTATGACG |
| | | ATTACCAAGCTGCAAAATTTTCGCGTATACTACCGCGACAATCGAGATCCATTGTGGAAGGGGCCGGCGAGG |
| | | CTCCTTTGGAAGGGAGAAGGTGCCGTAGTTATCCAAGATAATAGCGAGATCAAAGTTGTGCCCCGAAGAAAG |
| | | GTGAAAATTATAAGGGATTACGGGAAGAGAATGGCGGGAGACGACTGTGTTGCCGGTCGCCAAGACGAGGAT |
| | | GTTGCGAAGGAAATCGTTGCGTGTTGTGATAAATGTCAGCTGAAAGGCGAAGCAATTCACGGACAGGTAGAT |
| | | TGTTCTCCTGGCGTGTGGCAGCTTGACTGTACCCATTTGGAGGGAAAAGTGATCCTGGTAGCAGTCCACGTT |
| | | GCCAGTGGCTACATAGAAGCTGAGATAATTCCTACTGAGACGGGACAGGAGACGGCTTATTTTATTCTCAAG |
| | | CTGGCAGGCAGATGGCCCGTGACCACCGCGGCGCAGGAAGAGGAGGAAGTTGGTTTTCCCGTACGCCCTCAG |
| | | GTTCCCTTG |
| 160 | Pol:840-909 | ACAGTCAAAGCCGCTTGCTGGTGGGCGGGCATAAAGCAAGAATTTGGGATACCCTATAACCCTCAATCTCAA |
| | AA | GGGGTAGTTGAATCTATGAACAAGGAACTCAAAAAGATCATAGGACAGGTCCGCGATCAGGCTGAGCATTTG |
| | Gag:147-369 | AAGACGGCTGTGCAAATGGCGGTTTTTATCCATAACTTCAAGCGGAAGGGTGGGATCGGCGGAGCAGCAATC |
| | Pol:747-827 | AGTCCACGAACTCTTAATGCTTGGGTGAAGGTTGTTGAGGAGAAAGCGTTCAGTCCTGAGGTGATCCCCATG |
| | QEE | TTCTCTGCACTTAGCGAAGGAGCAACACCCCAGGACCTTAACACGATGTTGAACACAGTGGGGGGTCATCAA |
| | Nef:64-76 | GCCGCCATGCAGATGCTCAAAGAAACTATAAATGAGGAGGCTGCCGAGTGGGACAGACTGCATCCTGTGCAC |
| | | GCCGGACCAATAGCACCGGGGCAGATGCGAGAACCGCGAGGTTCCGACATCGCTGGGACCACTTCTACTCTG |
| | | CAGGAGCAGATTGGTTGGATGACTAACAACCCCCCGATACCGGTGGGTGAGATCTATAAGCGCTGGATCATA |
| | | CTTGGCCTTAACAAAATAGTTCGCATGTACTCACCAACAAGCATTCTCGACATCCGACAGGGGCCTAAGGAG |
| | | CCTTTTCGAGACTATGTGGATAGATTTTATAAAACTTTGCGGGCGGAGCAAGCATCCCAGGAGGTTAAGAAC |
| | | TGGATGACAGAGACACTTCTGGTCCAGAATGCCAACCCCGACTGTAAAACGATACTTAAAGCACTTGGGCCG |
| | | GCTGCAACTCTGGAGGAAATGATGACAGCGTGTCAAGGTGTGGGGGGTCCTGGCCATAAGGCTCGCGTGTTG |
| | | GCGGAAGCAATGTCACAAGTTGCCAAAGAAATAGTTGCCAGTTGCGACAAGTGCCAACTCAAAGGTGAAGCG |
| | | ATGCATGGACAGGTGGATTGCTCACCAGGCATCTGGCAGCTTGACTGTACACACCTGGAGGGCAAGATAATT |
| | | TTGGTCGCGGTGCATGTAGCAAGTGGTTATATCGAAGCTGAGGTAATACCCGCCGAGACGGGGCAAGAGACA |
| | | GCCTACTTCCTCTTGAAGTTGGCCGGTCGATGGCCGGTTAAGACGCAAGAGGAGGAAGAGGTTGGCTTCCCC |
| | | GTTAAGCCTCAAGTACCGCTT |
| 161 | Pol:840-909 | GCGGTGAAGGCCGCATGTTGGTGGGCGGGTGTTAAACAAGAGTTCGGTATACCGTACAATACGCAGAGTCAA |
| | Gag:147-369 | GGAGTCGTAGAATCTATGAATAATGAGCTGAAAAAAATCATTGGGCAAATTCGGGACCAGGCTGAGCATCTC |
| | VT | AAAACGGCCGTTCAGATGGCCGTCCTGATTCATAACTTTAAGAGAAAAGGCGGCATAGGGGGAGCTCAGTCCA |
| | Pol:747-827 | AGGACTCTCAACGCCTGGGTGAAGGTTATTGAAGAAAAAGCGTTTAGCCCGGAGGTAATTCCAATGTTTACA |
| | AA | GCTCTCAGCGAGGGGGCGACACCTCATGATCTCAATACAATGCTCAATACAATAGGGGGGCACCAGGCCGCT |
| | QEE | ATGCAAATGCTGAAAGACACGATCAATGAAGAAGCGGCTGAATGGGATAGAGTTCATCCTGTTCATGCAGGA |
| | Nef:64-76 | CCGGTCGCCCCGGGACAGATGAGAGACCCGCGCGGTTCCGACATAGCTGGGAGCACGTCTACGTTGCAGGAG |
| | | CAGATCGCTTGGATGACTAATAATCCCCCTATCCCTGTCGGTGATATTTATAAACGGTGGATTATTATGGGT |
| | | TTGAACAAAATTGTGAGAATGTACAGCCCAGTTTCCATACTTGATATTAAGCAGGGGCCGAAAGAACCCTTT |
| | | AGGGACTATGTAGACCGCTTCTATCGCACACTTAGAGCCGAGCAGGCGAGTCAGGACGTAAAGAACTGGATG |
| | | ACAGAAACCCTCCTTGTCCAAAACTCCAATCCCGATTGCAAAACCATTTTGAAAGCACTCGGTCCTGGAGCC |
| | | ACTTTGGAAGAAATGATGTCCGCGTGTCAGGGGGTGGGAGGGCCAAGCCACAAAGCGAGAGTATTGGCGGAG |
| | | GCGATGTGCCAGGTTACCGTAGCGAAGGAGATAGTCGCATGCTGTGACAAATGCCAACTTAAAGGCGAGGCG |
| | | ATCCATGGTCAGGTTGACTGCAGTCCGGGGGTATGGCAACTTGACTGTACACATTTGGAGGGTAAGGTTATT |
| | | CTCGTTGCAGTTCATGTAGCTTCAGGATACATCGAGGCCGAAATCATCCCGACGGAGACGGGCCAAGAGACT |
| | | GCCTACTTCATCTTGAAACTGGCGGGTCGCTGGCCGGTAACTACCGCCGCCCAGGAGGAAGAAGAAGTTGGG |
| | | TTCCCTGTCCGACCCCAAGTGCCACTC |
| 162 | Pol:840-909 | ACGGTGAAAGCGGCCTGTTGGTGGGCGGGAATTAAGCAGGAATTTGGGATACCGTATAACCCTCAAAGCCAA |
| | Pol:747-827 | GGCGTCGTAGAATCCATGAACAAAGAGCTGAAGAAGATTATTGGCCAGGTTCGGGACCAGGCAGAACACCTT |
| | AA | AAAACAGCCGTGCAGATGGCAGTGTTCATCCATAATTTTAAACGGAAGGGCGGGATTGGCGGAGTTGCGAAG |
| | Gag:147-369 | GAAATTGTTGCGAGTTGTGATAAATGCCAACTTAAAGGGGAGGCAATGCACGGACAAGTTGATTGCTCACCT |
| | QEE | GGCATATGGCAGCTGGATTGTACCCACCTTGAGGGTAAAATAATCCTGGTGGCCGTTCATGTCGCATCTGGC |
| | Nef:64-76 | TATATAGAAGCGGAAGTCATTCCAGCAGAGACGGGTCAAGAAACTGCTTACTTTCTCCTTAAACTTGCGGGA |
| | | AGGTGGCCTGTTAAAACCGCCGCTATTAGCCCCAGGACGTTGAATGCCTGGGTAAAGGTTGTGGAGGAGAAG |
| | | GCATTCTCCCCTGAGGTAATTCCCATGTTCTCAGCACTGAGTGAAGGGGCTACACCTCAAGATCTGAACACG |
| | | ATGCTCAACACGGTTGGCGGACATCAAGCGGCCATGCAAATGCTCAAAGAAACCATCAATGAAGAAGCGGCT |
| | | GAGTGGGACCGCCTTCATCCAGTCCATGCTGGCCCAATCGCACCTGGTCAAATGAGAGAGCCGAGGGGTAGT |
| | | GATATAGCCGGGACGACTAGCACATTGCAGGAACAGATAGGGTGGATGACAAATAACCCTCCTATACCTGTG |
| | | GGGGAAATATATAAACGCTGGATTATTCTCGGTCTGAACAAGATTGTCAGGATGTACTCCCCGACCAGTATC |
| | | CTTGACATAAGACAAGGGCCTAAGGAGCCCTTTCGGGACTACGTTGATCGGTTCTATAAGACGCTTCGGGCC |
| | | GAGCAGGCGTCTCAAGAGGTGAAAAATTGGATGACTGAAACTTTGCTGGTGCAAAATGCTAACCCCGACTGC |
| | | AAGACAATATTGAAGGCTCTCGGTCCAGCAGCAACTTTGGAAGAGATGATGACAGCGTGTCAAGGCGTAGGT |
| | | GGGCCAGGACACAAGGCTAGGGTCCTTGCAGAGGCTATGTCTCAGCAGGAGGAGGAAGAGGTAGGTTTCCCC |
| | | GTCAAGCCTCAAGTCCCACTC |
| 163 | Gag:147-369 | CTTAGTCCGAGAACTCTCAACGCTTGGGTCAAAGTCATAGAGGAGAAAGCCTTTTCACCCGAAGTAATACCT |
| | PV | ATGTTCACTGCGTTGAGCGAGGGCGCGACACCTCATGACCTGAATACTATGCTGAACACCATCGGGGGCCAC |
| | Pol:747-827 | CAAGCAGCTATGCAGATGCTGAAGGACACAATTAACGAAGAAGCGGCAGAATGGGATAGGGTTCACCCTGTA |
| | AAY | CATGCCGGACCAGTTGCACCTGGCCAAATGAGAGACCCACGAGGGAGCGACATCGCAGGCTCAACTAGTACC |
| | Pol:840-909 | CTGCAAGAGCAGATAGCGTGGATGACCAATAATCCTCCTATTCCTGTTGGTGACATTTACAAACGATGGATA |
| | QEE | ATAATGGGCCTCAATAAGATCGTCAGAATGTACAGCCCAGTGAGCATCCTGGATATAAAGCAGGGACCGAAA |
| | Nef:64-76 | GAACCCTTCCGGGACTATGTTGACCGCTTCTACCGGACTCTTAGGGCGGAACAGGCCAGCCAGGACGTAAAA |

TABLE H-continued

Illustrative Polynucleotides Encoding Fusion Polypeptides

| SEQ ID NO: | Encoded Polypeptide Segments | Nucleic Acid Sequences |
|---|---|---|
| | | AACTGGATGACTGAAACGTTGTTGGTTCAAAATTCAAATCCAGACTGCAAAACCATTCTCAAAGCACTCGGA |
| | | CCAGGCGCTACCCTGGAAGAGATGATGTCTGCCTGTCAAGGTGTCGGGGGGCCGAGTCACAAGGCACGCGTA |
| | | CTGGCGGAGGCCATGTGTCAACCAGTAGTTGCCAAAGAGATTGTCGCGTGCTGTGATAAGTGTCAGCTCAAA |
| | | GGGGAAGCGATACATGGACAAGTAGACTGTAGTCCTGGCGTGTGGCAGTTGGACTGTACCCATTTGGAGGGC |
| | | AAGGTAATATTGGTAGCTGTCCATGTCGCGTCTGGTTATATCGAAGCAGAAATCATTCCGACTGAGACTGGT |
| | | CAAGAGACGGCCTACTTCATACTGAAACTTGCAGGTAGGTGGCCGGTAACAACGGCGGCTTATGCCGTAAAA |
| | | GCTGCTTGTTGGTGGGCTGGAGTCAAGCAAGAATTTGGAATCCCTTACAACACACAGAGTCAAGGCGTCGTC |
| | | GAGTCTATGAATAACGAGCTGAAAAAGATCATAGGCCAAATCAGAGACCAAGCCGAACACTTGAAGACAGCC |
| | | GTTCAAATGGCAGTTCTTATCCACAACTTCAAGCGCAAAGGGGGCATAGGTGAACAGGAGGAGGAGGAGGTA |
| | | GGCTTCCCTGTCCGGCCGCAAGTGCCGCTC |
| 164 | Pol:840-920 | ACAGTGAAGGCAGCTTGTTGGTGGGCCGGAATTAAACAGGAGTTTGGCATCCCTTATAATCCTCAGTCTCAG |
| | Gag:147-369 | GGAGTGGTGGAGTCTATGAACAAGGAGCTGAAGAAGATCATCGGCCAGGTGAGAGATCAGGCAGAACATCTG |
| | Gag:1-53 | AAGACAGCAGTGCAGATGGCCGTGTTTATCCACAACTTCAAGAGGAAGGGCGGCATTGGAGGATATAGCGCA |
| | PPV | GGAGAAAGAATCGTGGACATCATCGCCATCTCTCCTAGAACACTGAACGCTTGGGTGAAAGTGGTGGAGGAG |
| | Pol:747-827 | AAAGCCTTTAGCCCAGAAGTGATCCCTATGTTCTCAGCTCTGTCAGAAGGAGCTACACCTCAGGATCTGAAC |
| | Pol:683-708 | ACCATGCTGAATACCGTGGGAGGACATCAGGCAGCTATGCAGATGCTGAAGGAGACAATTAACGAGGAAGCA |
| | Nef:117-148 | GCCGAGTGGGATAGACTGCATCCAGTGCACGCAGGACCTATTGCTCCAGGACAGATGAGAGAGCCTAGAGGA |
| | RAKR | AGCGATATTGCCGGCACAACATCTACACTGCAGGAACAGATCGGTTGGATGACCAACAATCCTCCTATCCCA |
| | F2A linker | GTGGGCGAAATCTACAAACGCTGGATCATCCTGGGCCTGAATAAGATCGTGAGAATGTACAGCCCCACAAGC |
| | Gag:147-369 | ATCCTGGATATCAGACAGGGACCTAAGGAACCTTTCAGGGATTACGTGGACCGGTTCTACAAGACACTGAGA |
| | Pol:747-827 | GCAGAACAGGCATCTCAGGAGGTGAAGAATTGGATGACCGAGACACTGCTGGTGCAGAACGCTAATCCAGAT |
| | Gag:1-53 | TGCAAGACCATTCTGAAAGCTCTGGGACCAGCAGCTACACTGGAAGAGATGATGACAGCTTGTCAGGGAGTG |
| | AA | GGAGGACCAGGACATAAAGCTAGAGTGCTGGCAGAAGCTATGTCTCAGATGGCAGCTAGAGCTTCAGTGCTG |
| | Pol:840-920 | TCAGGAGGAGAACTCGATAGGTGGGAGAAGATCAGACTGAGACCAGGAGGCAAGAAGAAGTACAGACTGAAG |
| | Nef:117-148 | CACATCGTGTGGGCTTCTAGAGAACTGGAGAGATTTGCCGTGAATCCAGGACTCCTGGAAACACCTCCAGTG |
| | LIK | GTGGCTAAAGAGATTGTGGCTTCTTGCGATAAGTGCCAGCTGAAAGGAGAGGCTATGCACGGACAGGTGGAT |
| | Pol:683-708 | TGTTCTCCAGGAATTTGGCAGCTGGATTGTACACACCTGGAGGGAAAGATTATTCTGGTGGCAGTGCACGTG |
| | | GCATCAGGATATATTGAGGCCGAAGTGATTCCAGCAGAAACAGGACAGGAGACAGCTTACTTTCTGCTCAAA |
| | | CTGGCAGGTCGCTGGCCAGTGAAAACCAAGGAGAAGGTGTACCTGGCTTGGGTGCCAGCTCATAAAGGAATT |
| | | GGCGGAAACGAGCAGGTGGATAAACTGGTGTCTACACAGGGCTACTTCCCAGATTGGCAGAATTACACACCA |
| | | GGACCAGGCACAAGATATCCTCTGACATTCGGTTGGTGTTTCAAGCTCGTGCCAGTGAGAGCTAAAAGAGCT |
| | | CCAGTGAAGCAGACCCTGAATTTCGATCTGCTGAAGCTCGCAGGAGACGTGGAATCTAATCCAGGACCTCTG |
| | | TCTCCTAGAACACTGAACGCTTGGGTGAAGGTGATCGAAGAGAAGGCCTTTAGCCCAGAAGTGATCCCTATG |
| | | TTTACAGCCCTGAGCGAAGGAGCTACACCTCACGATCTGAATACCATGCTGAACACAATTGGAGGACATCAG |
| | | GCCGCTATGCAGATGCTGAAGGACACCATCAACGAAGAAGCAGCCGAGTGGGATAGAGTGCATCCAGTGCAC |
| | | GCAGGACCAGTGGCTCCAGGACAGATGAGAGATCCTAGAGGAAGCGACATCGCAGGATCTACATCTACACTG |
| | | CAGGAACAGATCGCCTGGATGACAAATAACCCCCCTATCCCAGTGGGAGATATCTATAAGCGCTGGATCATC |
| | | ATGGGCCTGAACAAGATCGTGAGGATGTACAGCCCAGTGTCTATCCTGGACATCAAGCAGGGACCTAAGGAG |
| | | CCTTTTAGAGACTACGTGGACAGATTCTACAGAACACTGAGAGCCGAACAGGCATCTCAGGACGTGAAGAAT |
| | | TGGATGACCGAGACACTGCTGGTGCAGAACAGCAACCCCGATTGCAAGACAATCCTGAAAGCCCTGGGACCA |
| | | GGAGCTACACTGGAAGAGATGATGTCAGCTTGTCAGGGAGTGGGAGGACCATCTCATAAGGCTAGAGTGCTG |
| | | GCAGAAGCTATGTGTCAGGTGGCTAAGGAGATTGTGGCTTGTTGCGACAAGTGCCAGCTGAAAGGAGAAGCT |
| | | ATCCACGGACAGGTGGATTGTTCTCCAGGAGTCTGGCAGCTGGATTGTACACACCTGGAAGGAAAAGTGATT |
| | | CTGGTGGCAGTGCACGTGGCCAGCGGCTATATTGAAGCCGAGATCATTCCTACAGAGACAGGACAGGAGACA |
| | | GCTTACTTCATTCTGAAACTGGCAGGTCGCTGGCCAGTGACAACAATGGCAGCTAGAGCTTCTATCCTGTCA |
| | | GGAGGAAAGCTCGATAAGTGGGAAAAGATCAGACTGAGACCAGGCGGAAGAAAGAAGTACAAGCTGAAGCAC |
| | | CTCGTCTGGGCTTCTAGAGAACTGGAAAGATTCGCCCTGAATCCAGGTCTGCTGGAAACAGCAGCAGCAGTG |
| | | AAAGCAGCTTGTTGGTGGGCAGGAGTGAAACAGGAGTTCGGCATCCCTTACAACACCCAGTCTCAGGGAGTG |
| | | GTGGAATCTATGAACAACGAGCTGAAGAAGATCATCGGCCAGATCAGAGACCAGGCAGAACATCTGAAGACA |
| | | GCAGTGCAGATGGCAGTGCTGATTCACAACTTCAAGAGAAAGGGCGGCATTGGAGAGTATAGCGCCGGAGAG |
| | | AGAATCATCGATATCATTGCCACACAGGGCTTCTTCCCAGATTGGCAGAATTACACCCCAGGACCAGGCATT |
| | | AGATTTCCTCTGACCTTCGGTTGGTGTTTCAAACTGGTGCCCCTGCTGATCAAGAAGGAGAAGATCTACCTG |
| | | GCTTGGGTGCCAGCTCATAAAGGAATCGGAGGAAACGAGCAGATCGATAAACTGGTGTCT |
| 165 | Pol:56-117 | TTTCCTCAGATCACTCTCTGGCAGAGACCACTGGTGACAATCAAGATCGGAGGACAGCTGAAAGAAGCTCTG |
| | Nef:64-99 | CTGGATACAGGAGCAGACGATACAGTGCTGGAAGAGATGAATCTGCCAGGTCGCTGGAAACCTAAGATGATT |
| | LI | GGAGGCATTGGCGGCTTTATCAAGGTGAGACAGTACGACCAGGAGGAAGTGGGATTTCCAGTGAAACCTCAG |
| | Pol:542-606 | GTGCCTCTGAGACCTATGACATTTAAGGGCGCTCTGGACCTGTCTCACTTTCTGAGAGAGAAGGGAGGACTG |
| | Pol:367-431 | GAAGGACTGATCCCTAAGTTCAAGCTGCCTATCCAGAAGGAGACTTGGGAAACTTGGTGGACAGAGTATTGG |
| | Pol:932-1003 | CAGGCTACTTGGATTCCCGAGTGGGAATTTGTGAACACACCTCCTCTGGTGAAGCTGTGGTATCAGCTGGAA |
| | Pol:129-320 | AAGGAGCCTATTGTGGGCGCAGAAACATTCTACGTGGACGGAGCAGCTAACAGAGAAACTAAGTGGGGATTC |
| | RAKR | ACCACCCCAGATAAGAAGCACCAGAAGGAGCCACCATTTCTCTGGATGGGATACGAACTGCACCCAGATAAG |
| | F2A linker | TGGACAGTCCAGCCTATTGTGCTGCCAGAAAAGGACTCTTGGACCGTGAACGATATCCAGAAGCTGGTGGGA |
| | Pol:56-117 | AAGCTGAATTGGGCTTCTCAGATCTACCCAGGAATCAAGGTGATCACCAAGATCCAGAACTTCAGGGTGTAC |
| | Pol:367-431 | TACAGAGACAGCAGAGATCCTCTCTGGAAGGGACCAGCTAAACTCCTCTGGAAAGGAGAAGGAGCAGTGGTG |
| | AA | ATCCAGGATAACAGCGACATCAAGGTGGTGCCTAGAAGAAAGGCCAAGATCATCAGGGACTACGGCAAACAG |
| | QEE | ATGGCAGGAGACGATTGCGTGGCTTCTAGACAGGACGAAGACGGAACAGTCCTGGTGGGACCTACACCAGTG |
| | Nef:64-99 | AATATCATCGGCAGAAATCTCCTGACACAGATCGGTTGTACCCTGAACTTCCCTATCAGCCCTATCGAGACA |
| | Pol:932-1003 | GTGCCAGTGAAACTGAAGCCAGGAATGGACGGACCTAAAGTCAAGCAGTGGCCTCTGACAGAAGAGAAGATC |
| | Pol:542-606 | AAGGCCCTGGTGGAGATTTGCACAGAGATGGAGAAGGAGGGAAAGATCAGCAAGATCGGCCCAGAGAATCCT |
| | AA | TACAACACCCCAGTGTTCGCCATCAAGAAGAAGGATAGCACCAAGTGGAGAAAGCTGGTGGATTTCAGGGAG |
| | Pol:129-320 | CTGAACAAGAGAACCCAGGACTTTTGGGAAGTGCAGCTGGGCATCCCCCATCCAGCAGGACTGAAGAAGAAG |
| | | AAGAGCGTGACAGTGCTGGACGTGGGAGACGCTTATTTAGCGTGCCTCTGGACAAGGACTTCAGAAAGTAC |

TABLE H-continued

Illustrative Polynucleotides Encoding Fusion Polypeptides

| SEQ ID NO: | Encoded Polypeptide Segments | Nucleic Acid Sequences |
|---|---|---|
| | | ACCGCCTTCACCATCCCTTCTATCAACAACGAGACCCCAGGCATCAGATACCAGTATAACGTGCTGCCTCAG |
| | | GGTTGGAAAGGATCTCCAGCAATCTTCCAGAGCAGCATGACCAGAGCTAAGAGAGCTCCAGTGAAACAGACC |
| | | CTGAACTTCGATCTGCTCAAACTGGCAGGAGACGTGGAAAGCAATCCAGGACCTAATCTGCCTCAGATCACA |
| | | CTGTGGCAGAGACCTATTGTGACCATCAAGATTGGCGGCCAGATTAAAGAAGCCCTGCTGGATACAGGAGCA |
| | | GACGATACAGTGCTGGAGGATATGAACCTGCCAGGTAAGTGGAAGCCTAAGATGATTGGCGGAATTGGCGGC |
| | | TTTATCAAGGTCAAGCAGTACGATCAGTGGGGACTGACAACACCAGACAAGAAGCACCAGAAGGACCCCCCA |
| | | TTCCTCTGGATGGGATACGAACTGCATCCAGATAGGTGGACAGTGCAGCCAATTGAACTGCCAGAGAAGGAG |
| | | TCTTGGACCGTGAACGATATCCAGAAGCTGATCGGCAAGCTGAATTGGGCTTCTCAGATCTACGCAGGAATT |
| | | AAGGTGGCCGCTCAGGAAGAAGAGGAAGTGGGATTTCCAGTGAGACCTCAGGTGCCTCTGAGACCTATGACA |
| | | TACAAGGGAGCTCTGGACCTGTCTCACTTTCTGAAGGAGAAGGGAGGACTGGAAGGAATCACCAAGCTGCAG |
| | | AATTTCCGGGTGTACTACAGGGACAATAGAGACCCTCTCTGGAAAGGACCAGCTAGACTGCTGTGGAAAGGA |
| | | GAAGGAGCAGTGGTGATCCAGGATAATAGCGAGATCAAGGTGGTGCCTAGGAGAAAGGTGAAGATCATCAGG |
| | | GACTACGGCAAGAGAATGGCAGGAGACGATTGCGTGGCAGGAAGACAGGACGAGGACCCCAAGTTCAGACTG |
| | | CCTATCCAGAAGGAGACTTGGGATACTTGGTGGACCGATTATTGGCAGGCAACTTGGATTCCCGAGTGGGAG |
| | | TTTACAAATACCCCTCCTCTGGTCAAGCTCTGGTATCAGCTGGAAACAGAGCCTATTGCCGGAGTGGAAACC |
| | | TTTTACGTGGACGGAGCCAGCAACAGAGAGACAAAAGCCGCAGGAACAGTGCTGATTGGACCTACCCCAGTG |
| | | AACATCATCGGAAGAAACCTGCTGACACAGCTGGGTTGTACACTGAACTTCCCTATCAGCCCTATTGATACA |
| | | GTGCCAGTGAAGCTGAAACCAGGAATGGACGGACCTAGAGTCAAGCAGTGGCCTCTGACAGAAGAGAAGATC |
| | | AAGGCCCTGATCGAGATTTGCACCGAAATGGAGAAGGAGGGCAAGATTAGCAGGATCGGCCCAGAGAATCCT |
| | | TACAATACCCCTATCTTCGCCATCAAGAAGAAGGACGGCACCAAGTGGAGAAAACTGGTGGATTTCAGGGAG |
| | | CTGAACAAGAAGACCCAGGACTTTTGGGAGGTGCAGCTGGGCATCCCCCATCCTTCAGGACTGAAGAAGAAG |
| | | AAGAGCGTGACAGTGCTGGACATTGGAGACGCTTACTTTAGCGTGCCACTGGACAAGGAGTTCAGAAAGTAC |
| | | ACCGCCTTCACAGTGCCTAGCACAAATAACGAGACCCCAGGAGTGAGATACCAGTATAACGTGCTGCCAATG |
| | | GGCTGGAAAGGAAGCCCAGCTATCTTTCAGTGTAGCATGACA |
| 166 | Pol:747-827 | GTGGCCAAAGAAATTGTGGCCTCTTGCGATAAGTGCCAGCTGAAAGGAGAGGCTATGCACGGACAGGTGGAT |
| | Nef:117-148 | TGTTCTCCAGGAATTTGGCAGCTGGATTGTACACACCTGGAGGGAAAGATTATTCTGGTGGCAGTGCACGTG |
| | Pol:840-920 | GCATCAGGATATATTGAGGCCGAAGTGATTCCAGCAGAAACAGGACAGGAGACAGCTTACTTTCTGCTCAAA |
| | AA | CTGGCAGGTCGCTGGCCAGTGAAGACAACACAGGGCTACTTTCCTGATTGGCAGAATTACACACCAGGACCA |
| | Gag:1-53 | GGAACAAGATACCCTCTGACCTTTGGTTGGTGCTTCAAACTGGTGCCCGTGACAGTGAAAGCAGCTTGTTGG |
| | SEG | TGGGCAGGAATTAAGCAGGAGTTCGGCATCCCTTACAATCCTCAGTCTCAGGGAGTGGTGGAATCTATGAAC |
| | Gag:147-369 | AAGGAGCTGAAGAAGATCATCGGCCAGGTGAGAGATCAGGCAGAACATCTGAAGACAGCAGTGCAGATGGCA |
| | AAA | GTGTTCATCCACAACTTCAAGCGGAAGGGAGGAATTGGAGGATATAGCGCAGGAGAGAGAATCGTGGATATC |
| | Pol:683-708 | ATTGCCGCCGCTATGGCAGCTAGAGCCAGCGTGCTGAGCGGAGGAGAACTCGATCGCTGGGAAAAGATCAGA |
| | RAKR | CTGAGACCAGGAGGCAAGAAGAAGTACAGACTGAAGCACATCGTCTGGGCTTCTAGAGAACTGGAGAGATTT |
| | F2A linker | GCCGTGAATCCAGGACTGCTGGAAACAAGCGAGGGCATTTCTCCTAGAACCCTGAACGCTTGGGTGAAAGTG |
| | Gag:147-369 | GTGGAAGAAAAAGCCTTCTCTCCAGAGGTGATCCCTATGTTTAGCGCTCTGTCAGAAGGAGCTACACCTCAG |
| | Pol:840-920 | GATCTGAACACCATGCTGAACACAGTGGGAGGACATCAGGCAGCTATGCAGATGCTGAAGGAGACAATTAAC |
| | Pol:683-708 | GAAGAAGCCGCCGAGTGGGATAGACTGCATCCAGTGCACGCAGGACCTATTGCTCCAGGACAGATGAGAGAG |
| | AAY | CCTAGAGGAAGCGATATTGCCGGAACAACAAGCACACTGCAGGAACAGATCGGTTGGATGACCAATAATCCC |
| | Gag:1-53 | CCTATTCCAGTGGGCGAGATCTATAAGCGCTGGATTATCCTGGGCCTGAACAAGATCGTGAGAATGTACAGC |
| | Nef:117-148 | CCCACCTCTATCCTGGATATCAGACAGGGCCCTAAGGAACCTTTCAGAGACTACGTGGACAGGTTCTACAAG |
| | Pol:747-827 | ACACTGAGAGCAGAACAGGCATCTCAGGAGGTGAAGAATTGGATGACCGAGACACTGCTGGTGCAGAACGCC |
| | | AATCCAGATTGCAAGACAATTCTGAAAGCCCTGGGACCAGCAGCTACACTGGAAGAGATGATGACCGCTTGT |
| | | CAGGGAGTGGGAGGACCAGGACATAAAGCTAGAGTGCTGGCAGAAGCTATGTCTCAGGCAGCAGCTAAGGAG |
| | | AAAGTGTATCTGGCTTGGGTGCCAGCCCATAAAGGAATTGGAGGAAACGAGCAGGTGGATAAGCTGGTGTCT |
| | | AGAGCTAAGAGAGCTCCAGTGAAGCAGACCCTGAACTTTGATCTGCTCAAGCTGGCAGGAGACGTGGAATCT |
| | | AATCCAGGACCTCATCAGGCTCTGTCTCCTAGAACACTGAACGCTTGGGTGAAGGTGATCGAAGAGAAGGCC |
| | | TTTAGCCCAGAAGTGATCCCTATGTTTACAGCCCTGAGCGAAGGAGCTACACCTCACGATCTGAATACCATG |
| | | CTGAACACAATTGGAGGACATCAGGCCGCTATGCAGATGCTGAAGGACACCATCAACGAGGAAGCAGCAGAG |
| | | TGGGATAGAGTGCATCCAGTGCATGCAGGACCAGTGGCTCCAGGACAGATGAGAGATCCTAGAGGAAGCGAT |
| | | ATCGCAGGATCTACAAGCACACTGCAGGAACAGATCGCTTGGATGACCAATAACCCACCTATCCCAGTGGGA |
| | | GACATCTACAAGCGCTGGATCATCATGGGACTGAACAAGATCGTGAGGATGTACAGCCCAGTGTCTATCCTG |
| | | GATATCAAGCAGGGACCTAAGGAGCCTTTCAGAGATTACGTGGACAGGTTTTACAGAACCCTGAGAGCCGAA |
| | | CAGGCATCTCAGGACGTGAAGAATTGGATGACCGAAACACTGCTGGTGCAGAATAGCAACCCAGATTGCAAG |
| | | ACAATCCTGAAAGCCCTGGGACCAGGAGCTACACTGGAAGAAATGATGAGCGCTTGTCAGGGAGTGGGAGGA |
| | | CCATCTCATAAGGCTAGAGTGCTGGCAGAAGCTATGTGTCAGGCAGTGAAAGCAGCTTGTTGGTGGGCAGGA |
| | | GTGAAACAGGAGTTTGGCATCCCTTACAACACACAGTCTCAGGGAGTGGTGGAATCTATGAACAACGAGCTG |
| | | AAGAAGATCATCGGCCAGATCAGAGACCAGGCAGAACATCTGAAGACAGCAGTGCAGATGGCAGTGCTGATT |
| | | CACAACTTCAAGAGAAAGGGCGGCATTGGAGAGTATAGCGCCGGCGAGAGAATTATCGACATCATCGCCAAG |
| | | GAGAAGATCTATCTGGCTTGGGTGCCAGCCCATAAAGGAATTGGAGGCAATGAGCAGATCGATAAACTGGTG |
| | | TCAGCAGCTTATATGGCCGCTAGAGCCTCTATTCTGAGCGGAGGAAAGCTCGATAAGTGGGAGAAGATCAGA |
| | | CTGAGACCAGGAGGCAGAAAGAAGTACAAGCTGAAGCATCTCGTCTGGGCTTCTAGAGAACTGGAGAGATTC |
| | | GCTCTGAATCCAGGACTGCTGGAAACAACACAGGGCTTCTTCCCCGATTGGCAGAATTACACACCAGGACCA |
| | | GGAATCAGATTCCCTCTGACCTTCGGTTGGTGTTTTAAGCTGGTGCCTCTGGTGGCTAAGGAAATTGTGGCT |
| | | TGTTGCGACAAGTGCCAGCTGAAAGGAGAAGCTATCCACGGACAGGTGGATTGTTCTCCAGGAGTCTGGCAG |
| | | CTGGATTGTACACACCTGGAGGGAAAAGTGATTCTGGTGGCAGTGCACGTGGCATCAGGATATATTGAGGCC |
| | | GAGATCATTCCTACAGAAACAGGACAGGAGACAGCCTACTTTATCCTGAAGCTGGCTGGTAGGTGGCCAGTG |
| | | ACAACA |
| 167 | Pol:932-1003 | ATCACCAAGATCCAGAACTTCAGGGTGTACTACAGAGACAGCAGAGATCCTCTCTGGAAGGGACCAGCTAAA |
| | AAY | CTCCTCTGGAAAGGAGAAGGAGCAGTGGTGATCCAGGATAACAGCGACATCAAGGTGGTGCCTAGAAGAAAG |
| | EE | GCCAAGATCATCAGGGACTACGGCAAACAGATGGCAGGAGACGATTGCGTGGCTTCTAGACAGGACGAAGAC |
| | Nef:64-99 | GCAGCTTACGAAGAGGAAGAGGTGGGATTTCCAGTGAAACCTCAGGTGCCTCTGAGACCTATGACATTCAAG |

TABLE H-continued

Illustrative Polynucleotides Encoding Fusion Polypeptides

| SEQ ID NO: | Encoded Polypeptide Segments | Nucleic Acid Sequences |
|---|---|---|
| | AA | GGAGCTCTGGATCTGTCTCACTTCCTGAGAGAAAAGGGAGGACTGGAAGGAGCAGCTTGGGGATTTACCACC |
| | Pol:367-431 | CCAGACAAGAAGCACCAGAAGGAACCACCATTCCTCTGGATGGGATACGAACTGCACCCAGATAAGTGGACA |
| | Pol:542-606 | GTCCAGCCTATTGTGCTGCCAGAAAAGGACTCTTGGACCGTGAACGATATCCAGAAGCTGGTGGGAAAGCTG |
| | Pol:56-117 | AATTGGGCTTCTCAGATCTACCCAGGAATCAAGGTGCCCAAGTTCAAGCTGCCTATCCAGAAGGAGACTTGG |
| | Pol:129-320 | GAAACTTGGTGGACAGAGTATTGGCAGGCTACTTGGATTCCCGAGTGGGAATTTGTGAACACACCTCCTCTG |
| | RAKR | GTGAAGCTGTGGTATCAGCTGGAAAAGGAGCCTATCGTGGGCGCAGAAACATTTTACGTGGACGGAGCCGCC |
| | F2A linker | AATAGAGAAACCAAGTTTCCTCAGATCACTCTCTGGCAGAGACCTCTGGTGACAATCAAGATCGGCGGACAG |
| | Pol:542-606 | CTGAAAGAGGCTCTGCTGGATACAGGAGCAGACGATACCGTGCTGGAAGAAATGAATCTGCCAGGTAGGTGG |
| | Nef:64-99 | AAGCCTAAGATGATTGGCGGAATTGGCGGCTTCATCAAGGTGAGACAGTACGATCAGGGAACAGTGCTGGTG |
| | Pol:56-117 | GGACCTACTCCAGTGAACATCATCGGAAGGAACCTGCTGACACAGATCGGCTGTACACTGAACTTCCCTATC |
| | Pol:932-1003 | AGCCCTATCGAGACAGTGCCAGTGAAACTGAAGCCAGGAATGGACGGACCTAAAGTCAAACAGTGGCCTCTG |
| | Pol:367-431 | ACAGAGGAGAAAATCAAAGCCCTGGTGGAGATTTGTACCGAGATGGAGAAGGAGGGCAAGATTTCTAAGATC |
| | K | GGACCAGAGAACCCCTACAATACCCCAGTGTTTGCCATCAAGAAGAAGGACAGCACCAAGTGGAGGAAGCTG |
| | Pol:129-320 | GTGGATTTTAGGGAGCTGAACAAGAGGACACAGGACTTTTGGGAAGTGCAGCTGGGCATCCCCCACCCAGCC |
| | | GGACTGAAAAAGAAGAAGTCAGTGACAGTGCTGGACGTGGGAGATGCCTATTTTAGCGTGCCTCTGGATAAG |
| | | GACTTCAGGAAGTACACCGCCTTCACAATCCCTAGCATCAACAACGAGACCCCAGGAATCAGATACCAGTAC |
| | | AACGTGCTGCCTCAGGGTTGGAAAGGATCTCCAGCCATCTTTCAGAGCAGCATGACAAGAGCCAAGAGAGCT |
| | | CCAGTGAAGCAGACCCTGAATTTCGATCTGCTGAAGCTCGCAGGAGACGTGGAATCTAATCCAGGACCTCCC |
| | | AAGTTCAGACTGCCTATTCAGAAGGAGACTTGGGACACTTGGTGGACCGATTATTGGCAGGCAACTTGGATT |
| | | CCCGAGTGGGAGTTCACAAATACACCTCCTCTGGTCAAGCTCTGGTATCAGCTGGAAACAGAGCCTATCGCA |
| | | GGAGTGGAAACATTCTACGTGGACGGAGCTTCTAACAGAGAGACCAAGGAGGAGGTGGGATTTCCAGTGAGA |
| | | CCTCAGGTGCCTCTGAGACCTATGACATACAAGGGAGCCCTGGATCTGTCTCACTTTCTGAAGGAGAAAGGC |
| | | GGACTGGAAGGACTGCCTCAGATTACTCTCTGGCAGAGGCCTATTGTGACAATCAAGATCGGCGGACAGATC |
| | | AAAGAAGCCCTGCTGGATACAGGAGCAGACGATACAGTGCTGGAGGATATGAACCTGCCAGGCAAGTGGAAA |
| | | CCTAAGATGATCGGAGGAATCGGCGGATTTATCAAGGTGAAGCAGTACGACCAGATCACCAAGCTGCAGAAC |
| | | TTCAGGGTGTACTACAGAGACAACAGAGACCCTCTCTGGAAAGGACCAGCTAGACTCCTCTGGAAAGGAGAA |
| | | GGAGCAGTGGTGATCCAGGATAATAGCGAGATCAAGGTGGTGCCTAGGAGAAAGGTGAAGATCATCCGGGAC |
| | | TACGGCAAAAGAATGGCAGGAGACGATTGCGTGGCAGGAAGACAGGACGAAGATTGGGGACTGACAACCCCA |
| | | GATAAGAAGCACCAGAAGGACCCCCCATTCCTCTGGATGGGATACGAACTGCATCCAGATAGGTGGACAGTG |
| | | CAGCCAATTGAACTGCCAGAAAAGGAGTCTTGGACAGTGAACGACATCCAGAAGCTGATCGGCAAGCTGAAT |
| | | TGGGCTTCTCAGATCTACGCCGGAATTAAGGTGAAGGGAACAGTGCTGATTGGACCTACACCAGTGAACATC |
| | | ATCGGGAGAAACCTGCTGACACAGCTGGGTTGTACACTGAACTTCCCTATCAGCCCTATCGATACAGTGCCA |
| | | GTGAAACTGAAGCCAGGAATGGACGGACCTAGAGTGAAACAGTGGCCTCTGACAGAAGAGAAGATCAAGGCC |
| | | CTGATCGAGATTTGTACAGAGATGGAGAAGGAGGGCAAGATCTCTAGAATTGGCCCAGAGAACCCCTACAAT |
| | | ACCCCTATCTTTGCCATCAAGAAGAAGGACGGCACCAAGTGGAGAAAGCTGGTGGATTTCAGGGAGCTGAAC |
| | | AAGAAGACCCAGGACTTTTGGGAAGTGCAGCTGGGCATCCCCCACCCTAGCGGACTGAAAAAGAAGAAGAGC |
| | | GTGACCGTGCTGGATATTGGAGACGCCTATTTTAGCGTGCCACTGGATAAGGAGTTCAGAAAGTACACCGCC |
| | | TTTACCGTGCCTTCTACCAATAACGAGACACCAGGAGTGAGATACCAGTACAACGTGCTGCCTATGGGTTGG |
| | | AAGGGATCACCAGCCATCTTTCAGTGTAGCATGACA |
| 210 | Pol:840-920 | ACGGTGAAGGCTGCGTGTTGGTGGGCCGGCATAAAACAAGAATTTGGAATACCATACAATCCACAATCTCAA |
| | Gag:147-369 | GGCGTTGTGGAATCCATGAATAAAGAATTGAAAAAAATTATCGGGCAAGTTCGAGACCAGGCTGAGCATCTC |
| | Pol:586-606 | AAAACGGCCGTACAGATGGCGGTGTTTATTCACAACTTCAAAAGAAAAGGAGGAATCGGTGGTTACAGTGCA |
| | AA | GGCGAACGAATAGTTGACATTATAGCGATATCTCCTCGGACTCTGAATGCGTGGGTAAAGGTAGTCGAGGAG |
| | Pol:683-708 | AAAGCATTTAGCCCCGAAGTCATCCCCATGTTTTCAGCCCTTTCAGAGGGCGCTACACCACAGGATCTGAAT |
| | RAKR | ACCATGCTGAACACAGTAGGGGGGCACCAAGCGGCGATGCAGATGCTGAAGGAGACAATAAATGAGGAGGCG |
| | F2A linker | GCGGAATGGGATAGATTGCATCCCGTCCACGCGGGGCCGATAGCGCCTGGCCAGATGAGGGAGCCACGAGGT |
| | Gag:147-369 | TCCGACATCGCGGGAACAACCTCAACCCTGCAGGAACAAATAGGGTGGATGACGAATAACCCTCCTATTCCA |
| | Pol:840-920 | GTTGGTGAAATTTATAAACGATGGATAATACTCGGTCTCAATAAAATAGTAAGGATGTATTCTCCGACAAGC |
| | Pol:586-606 | ATACTTGACATCAGACAGGGGCCGAAAGAACCTTTCCGCGATTATGTGGACAGATTCTACAAAACGCTCAGG |
| | AA | GCCGAACAGGCCAGCCAAGAGGTTAAAAACTGGATGACTGAAACCCTGCTGGTCCAGAATGCTAACCCCGAC |
| | Pol:683-708 | TGCAAGACAATCTTGAAGGCACTTGGGCCGGCCGCAACGTTGGAAGAAATGATGACGGCTTGTCAAGGGGTT |
| | | GGCGGTCCGGGCCATAAGGCCCGAGTCCTGGCAGAAGCTATGAGTCAGAAAGAACCAATAGTTGGAGCCGAA |
| | | ACATTCTACGTCGACGGTGCTGCAAATCGCGAGACGAAGGCTGCTAAGGAAAAGGTCTATCTGGCGTGGGTT |
| | | CCGGCACACAAGGGCATAGGCGGGAATGAGCAAGTCGACAAATTGGTCTCACGAGCTAAACGCGCCCCGGTT |
| | | AAACAAACCCTGAACTTCGACTTGCTTAAACTCGCAGGGGACGTTGAATCAAATCCGGGCCCACTTAGTCCC |
| | | CGAACGCTGAACGCATGGGTAAAAGTAATAGAAGAGAAAGCGTTTTCCCCGGAGGTTATTCCCATGTTTACA |
| | | GCCCTCAGCGAGGGCGCGACGCCACATGATCTCAACACAATGCTTAACACGATTGGGGGGCATCAGGCTGCG |
| | | ATGCAAATGCTCAAGGATACGATAAACGAAGAGGCCGCAGAATGGGACCGAGTACATCCGGTCCACGCCGGG |
| | | CCCGTCGCACCAGGACAGATGCGAGACCCCCGAGGGTCAGACATCGCCGGTTCTACGTCAACCTTGCAAGAA |
| | | CAAATTGCATGGATGACTAACAATCCACCTATCCCCGTGGGAGATATCTATAAGAGATGGATCATCATGGGG |
| | | CTTAATAAAATAGTCAGGATGTATTCACCAGTTTCAATTCTTGATATTAAACAGGGTCCTAAGGAGCCCTTT |
| | | CGAGATTATGTGGATAGGTTTTATAGAACCCTTCGCGCAGAACAGGCTTCACAAGACGTCAAAAATTGGATG |
| | | ACAGAAACTCTTCTCGTACAGAATTCAAACCCGGATTGTAAGACGATCTTGAAAGCACTCGGTCCGGGTGCC |
| | | ACGTTGGAAGAGATGATGTCAGCCTGCCAAGGGGTGGGTGGCCCAAGCCATAAGGCCAGGGTATTGGCAGAG |
| | | GCAATGTGTCAAGCTGTCAAGGCAGCATGCTGGTGGGCTGGCGTAAAGCAGGAATTCGGCATACCGTACAAT |
| | | ACACAGTCACAAGGTGTTGTCGAGAGTATGAATAATGAACTTAAAAAAATCATAGGACAGATCCGAGATCAA |
| | | GCTGAACATCTGAAGACTGCTGTACAAATGGCAGTGCTTATACATAACTTCAAACGCAAGGGAGGAATTGGG |
| | | GAGTATTCAGCGGGAGAGCGGATTATTGATATCATAGCAACCGAACCCATAGCGGGCGTCGAGACTTTCTAT |
| | | GTGGACGGAGCCAGCAATAGGGAGACTAAGGCGGCGAAAGAAAAGATTTATCTGGCATGGGTTCCGGCTCAT |
| | | AAGGGGATCGGAGGCAATGAGCAGATTGACAAACTGGTATCC |
| 211 | Pol:932-1003 | TTGAGCCCCCGAACCCTTAACGCCTGGGTGAAGGTAATTGAGGAAAAAGCTTTTTCACCCGAAGTGATCCCG |
| | AAA | ATGTTTACAGCACTGTCTGAAGGTGCAACCCCACACGATCTCAACACTATGCTCAATACCATAGGGGGCCAC |

TABLE H-continued

Illustrative Polynucleotides Encoding Fusion Polypeptides

| SEQ ID NO: | Encoded Polypeptide Segments | Nucleic Acid Sequences |
|---|---|---|
| | I | CAAGCAGCGATGCAGATGCTCAAAGATACCATTAACGAGGAAGCGGCCGAGTGGGACAGGGTACACCCCGTG |
| | Pol:129-320 | CATGCCGGACCTGTCGCCCCGGGTCAAATGCGAGATCCACGCGGAAGTGATATCGCTGGGAGTACGTCCACC |
| | Pol:747-827 | CTCCAAGAACAAATCGCGTGGATGACAAATAATCCTCCTATCCCCGTAGGAGATATTTATAAAAGGTGGATT |
| | QEE | ATCATGGGGCTTAATAAAATCGTTCGAATGTATAGTCCTGTCTCAATACTGGACATCAAACAAGGCCCAAAA |
| | Nef:64-76 | GAACCATTCAGGGACTACGTTGACAGATTCTATCGCACACTCCGAGCGGAACAAGCAAGCCAGGACGTCAAA |
| | RAKR | AATTGGATGACCGAGACGTTGCTTGTACAAAATAGCAACCCCGACTGTAAAACGATACTCAAAGCCTTGGGG |
| | F2A linker | CCAGGCGCGACCTTGGAGGAGATGATGTCCGCTTGTCAGGGAGTAGGCGGACCATCACACAAAGCACGCGTT |
| | Pol:747-827 | TTGGCGGAAGCTATGTGTCAGGCGGTAAAGGCAGCCTGTTGGTGGGCTGGAGTCAAACAAGAATTTGGCATC |
| | Pol:932-1003 | CCCTATAATACACAGTCCCAGGGTGTCGTCGAGTCTATGAATAATGAGCTGAAGAAAATCATTGGGCAGATA |
| | Pol:129-320 | AGAGACCAAGCCGAACATCTTAAAACGGCTGTCCAAATGGCGGTTTTGATCCATAATTTTAAGCGAAAAGGG |
| | KIL | GGGATTGGTGAGTACTCAGCAGGAGAGAGAATCATAGACATCATAGCAACAGAACCAATTGCTGGTGTCGAG |
| | QEE | ACTTTTTACGTAGATGGGGCGAGCAATAGGGAAACTAAAGCAGCGAAGGAAAAGATTTACCTCGCGTGGGTA |
| | Nef:64-76 | CCGGCCCACAAGGGAATCGGCGGGAACGAGCAAATCGATAAACTTGTATCCAGAGCCAAACGGGCTCCAGTA |
| | | AAACAGACACTCAATTTCGATCTTTTGAAGCTTGCTGGAGACGTTGAGAGCAATCCTGGGCCGGTAGCAAAG |
| | | GAGATTGTAGCTTGTTGCGACAAGTGCCAGTTGAAGGGTGAAGCGATACACGGTCAGGTCGATTGCTCTCCG |
| | | GGAGTTTGGCAACTTGACTGTACCCATCTCGAGGGCAAAGTTATCCTCGTAGCTGTGCATGTAGCATCAGGA |
| | | TATATAGAGGCCGAGATCATTCCGACGGAAACGGGTCAAGAAACTGCTTACTTCATTCTCAAACTTGCCGGG |
| | | CGGTGGCCAGTCACAACTATCACGAAACTCCAAAACTTTCGAGTTTACTATAGGGACAATCGAGACCCACTG |
| | | TGGAAAGGACCTGCCAGGCTTCTGTGGAAAGGGGAGGGTGCCGTTGTCATACAGGATAACTCCGAGATAAAA |
| | | GTTGTGCCAAGGCGAAAAGTTAAGATTATTCGGGATTACGGGAAACGCATGGCAGGGGATGACTGCGTTGCG |
| | | GGGCGACAAGATGAGGATGGTACTGTACTTATTGGCCCAACACCCGTGAACATTATAGGACGGAATCTGCTG |
| | | ACACAGTTGGGGTGTACGCTCAACTTTCCGATAAGTCCGATAGATACGGTTCCGGTAAAGCTGAAGCCCGGC |
| | | ATGGATGGTCCGCGCGTGAAGCAATGGCCACTCACAGAAGAGAAAATCAAAGCTTTGATAGAAATCTGCACC |
| | | GAAATGGAAAAAGAGGGGAAGATCAGCAGGATCGGCCCGGAGAATCCTTACAACACCCCTATTTTCGCGATT |
| | | AAGAAAAAAGATGGTACAAAATGGAGGAAACTCGTTGATTTTCGGGAGCTCAACAAGAAAACGCAAGACTTC |
| | | TGGGAGGTCCAGCTTGGCATACCCCACCCCTCTGGACTTAAAAAGAAAAAAAGCGTAACCGTACTTGATATT |
| | | GGTGACGCGTATTTCTCCGTTCCCTTGGATAAAGAATTTAGGAAGTACACGGCCTTTACTGTCCCCTCCACT |
| | | AACAACGAAACTCCGGGCGTGCGATATCAATATAATGTGCTTCCGATGGGATGGAAAGGCTCACCAGCGATT |
| | | TTTCAATGCAGTATGACCAAGATTCTTCAGGAAGAAGAGGAAGTGGGGTTTCCGGTAAGACCACAGGTGCCC |
| | | CTC |
| 212 | Pol:840-920 | ACGGTTAAGGCGGCGTGTTGGTGGGCGGGGATAAAGCAAGAGTTCGGAATCCCATATAATCCACAATCCCAA |
| | Gag:147-369 | GGTGTGGTGGAAAGCATGAACAAGGAATTGAAGAAGATTATAGGACAAGTCAGAGATCAGGCCGAGCATCTG |
| | Pol:586-606 | AAAACTGCAGTTCAGATGGCTGTGTTCATCCACAATTTTAAACGCAAAGGAGGAATTGGTGGATATAGCGCT |
| | AA | GGCGAGAGGATTGTAGACATTATTGCCATATCACCTCGCACTCTGAACGCCTGGGTGAAGGTTGTTGAAGAA |
| | Pol:683-708 | AAGGCTTTTTCACCGGAGGTAATCCCAATGTTCAGTGCTCTTAGCGAGGGGGCAACTCCGCAGGACCTTAAT |
| | RAKR | ACAATGTTGAACACTGTAGGGGGACATCAAGCCGCTATGCAAATGCTGAAGGAGACGATTAACGAGGAAGCT |
| | F2A linker | GCGGAATGGGATAGACTTCACCCCGTCCACGCTGGACCTATTGCACCGGGACAGATGCGCGAACCAAGAGGT |
| | Pol:932-1003 | TCCGATATAGCGGGAACAACTAGCACACTCCAGGAACAGATAGGATGGATGACCAACAACCCTCCGATACCA |
| | AAA | GTAGGCGAAATCTACAAGCGCTGGATAATATTGGGGCTGAACAAAATCGTCAGGATGTACAGCCCAACTTCA |
| | I | ATATTGGACATTCGCCAAGGACCTAAAGAGCCGTTCCGGGATTACGTGGATAGGTTTTACAAGACTTTGCGA |
| | Pol:129-320 | GCTGAACAAGCCAGTCAAGAGGTGAAAAACTGGATGACCGAGACTCTGCTCGTCCAAAATGCTAATCCAGAT |
| | Pol:747-827 | TGCAAAACAATACTTAAGGCACTGGGTCCCGCCGCAACGCTCGAGGAGATGATGACTGCCTGCCAAGGTGTC |
| | QEE | GGTGGTCCGGGTCACAAAGCACGAGTCCTGGCGGAAGCCATGTCTCAGAAAGAGCCTATAGTGGGTGCCGAG |
| | Nef:64-76 | ACGTTCTACGTTGATGGAGCCGCTAATCGAGAGACGAAAGCGGCCAAGGAAAAGGTGTATCTCGCTTGGGTG |
| | | CCTGCTCATAAGGGCATCGGAGGTAATGAACAAGTTGATAAACTGGTGAGTCGGGCGAAGCGCGCACCAGTA |
| | | AAGCAGACCCTTAATTTCGATTTGCTCAAACTCGCTGGTGATGTCGAATCTAACCCCGGTCCGATTACAAAA |
| | | ATCCAGAATTTTAGGGTTTACTATCGAGATTCCCGAGATCCACTCTGGAAAGGCCCCGCGAAATTGCTCTGG |
| | | AAGGGCGAAGGGGCTGTAGTAATTCAAGACAATTCTGATATCAAGGTAGTCCCTCGGAGGAAAGCTAAAATA |
| | | ATACGAGACTATGGAAAACAGATGGCGGGGGATGACTGTGTAGCAAGCCGGCAAGATGAAGACGCGGCAGCT |
| | | ATAGGAACAGTGCTGGTGGGGCCGACCCCCGTAAACATTATCGGCAGGAATCTGTTGACGCAAATAGGTTGT |
| | | ACGCTCAATTTTCCTATCTCACCGATCGAAACGGTGCCCGTCAAGTTGAAGCCGGGCATGGACGGCCCAAAG |
| | | GTAAAACAATGGCCCTTGACGGAGGAGAAAATCAAAGCTCTTGTCGAAATCTGTACCGAAATGGAAAAGGAA |
| | | GGTAAGATAAGTAAAATCGGACCAGAAAACCCGTATAACACTCCAGTTTTCGCGATAAAGAAGAAAGACTCC |
| | | ACAAAGTGGAGAAAACTTGTAGATTTCAGGGAGCTGAATAAAAGGACCCAGGATTTTTGGGAAGTCCAGTTG |
| | | GGCATACCACATCCCGCGGGGCTCAAAAAGAAGAAGTCAGTCACGGTACTCGACGTTGGCGACGCATATTTC |
| | | TCTGTTCCGCTCGATAAGGACTTCAGAAAATATACCGCTTTCACTATTCCAAGTATCAACAATGAAACTCCC |
| | | GGGATACGCTATCAATACAACGTTCTGCCACAGGGATGGAAGGGGAGTCCGGCTATTTTTCAGTCTTCAATG |
| | | ACAGTGGCAAAAGAGATCGTTGCAAGCTGTGATAAATGCCAACTGAAAGGTGAGGCCATGCACGGACAGGTT |
| | | GACTGCTCTCCCGGGATATGGCAGCTGGATTGCACGCATTTGGAGGGTAAGATAATTCTCGTCGCGGTCCAC |
| | | GTGGCTAGTGGCTACATCGAGGCCGAAGTAATCCCCGCAGAGACGGGCCAAGAAACTGCGTACTTCCTCCTG |
| | | AAGCTGGCAGGACGATGGCCTGTCAAAACACAGGAGGAAGAAGAAGTGGGATTCCCGGTTAAGCCCCAGGTT |
| | | CCGCTG |
| 213 | Gag:147-369 | CTTAGCCCACGGACACTTAATGCATGGGTCAAGGTGATTGAGGAGAAGGCGTTTTCCCCAGAGGTGATCCCA |
| | Pol:840-920 | ATGTTCACAGCCCTCTCTGAGGGCGCAACACCTCACGACCTGAATACAATGCTCAACACTATCGGAGGGCAC |
| | Pol:586-606 | CAAGCAGCCATGCAAATGCTGAAAGACACCATCAACGAGGAGGCTGCTGAGTGGGATCGAGTACACCCTGTA |
| | AA | CACGCGGGGCCGGTTGCTCCTGGTCAAATGAGGGATCCCCGCGGCTCCGACATAGCCGGCTCAACAAGCACT |
| | Pol:683-708 | CTGCAGGAACAGATAGCATGGATGACCAACAACCCCCCTATTCCCGTAGGGGACATTTACAAGAGGTGGATT |
| | RAKR | ATAATGGGTCTGAACAAGATCGTACGAATGTATTCACCGGTCAGCATACTTGATATAAAACAAGGCCCGAAA |
| | F2A linker | GAACCTTTCAGGGACTATGTCGATCGATTTTACCGCACGCTGCGCGCCGAGCAGGCCTCCCAGGACGTGAAG |
| | Pol:747-827 | AACTGGATGACTGAAACACTGCTTGTGCAAAATTCAAATCCAGATTGTAAAACCATACTTAAGGCTCTTGGT |
| | Pol:932-1003 | CCGGGGGCTACCCTGGAAGAGATGATGAGCGCGTGTCAAGGGGTAGGAGGTCCTTCTCACAAGGCCAGGGTT |
| | Pol:129-320 | TTGGCTGAAGCTATGTGCCAGGCCGTTAAGGCGGCCTGTTGGTGGGCAGGAGTCAAGCAAGAATTCGGCATC |

TABLE H-continued

Illustrative Polynucleotides Encoding Fusion Polypeptides

| SEQ ID NO: | Encoded Polypeptide Segments | Nucleic Acid Sequences |
|---|---|---|
| | KIL | CCCTACAACACGCAATCACAGGGTGTCGTTGAATCAATGAACAACGAGCTGAAAAAAATTATAGGTCAAATA |
| | QEE | CGCGATCAAGCGGAACATCTTAAGACCGCAGTGCAGATGGCTGTGCTTATACATAATTTCAAGCGAAAAGGA |
| | Nef:64-76 | GGCATCGGAGAATACTCAGCCGGAGAAAGAATCATCGACATTATCGCAACGGAGCCAATCGCCGGTGTGGAA |
| | | ACGTTCTATGTAGACGGAGCATCAAATAGGGAAACGAAGGCCGCCAAGGAGAAAATTTATCTGGCGTGGGTC |
| | | CCGGCCCACAAGGGAATTGGCGGCAATGAACAGATCGACAAGCTTGTTTCTCGGGCTAAACGGGCTCCCGTT |
| | | AAGCAGACGCTCAACTTCGATCTTCTCAAGCTGGCCGGTGATGTCGAGAGCAATCCGGGGCCGGTAGCTAAG |
| | | GAAATCGTCGCTTGTTGTGATAAATGTCAACTTAAGGGTGAAGCAATTCATGGCCAAGTTGACTGTTCACCG |
| | | GGAGTATGGCAACTCGATTGTACCCATCTCGAAGGAAAAGTCATCTTGGTTGCAGTGCACGTAGCTTCTGGC |
| | | TACATTGAAGCGGAGATTATCCCGACAGAGACCGGGCAGGAGACCGCTTATTTTATCCTCAAGCTCGCAGGA |
| | | CGATGGCCCGTCACTACTATCACGAAGCTCCAAAATTTTAGAGTGTACTACCGCGATAACAGAGATCCTTTG |
| | | TGGAAAGGCCCCGCCAGACTTTTGTGGAAGGGTGAGGGAGCGGTGGTTATTCAGGACAATTCTGAGATAAAA |
| | | GTTGTACCCCGACGGAAGGTCAAGATAATTAGAGATTATGGTAAAAGGATGGCGGGCGACGACTGTGTAGCT |
| | | GGAAGGCAGGATGAGGACGGCACAGTGCTGATTGGCCCGACGCCCGTAAACATTATCGGTCGCAACCTTCTC |
| | | ACCCAGCTGGGGTGCACTTTGAATTTCCCGATTTCCCCGATTGATACTGTTCCAGTAAAGCTCAAACCCGGG |
| | | ATGGACGGCCCACGAGTAAAACAATGGCCATTGACAGAGGAGAAGATTAAGGCGCTTATCGAAATATGTACT |
| | | GAAATGGAGAAGGAAGGGAAAATTAGTCGGATAGGGCCTGAGAATCCCTACAACACGCCCATTTTTGCTATC |
| | | AAGAAGAAAGATGGCACCAAGTGGCGGAAGCTGGTCGATTTTCGGGAACTTAACAAGAAAACACAAGACTTC |
| | | TGGGAAGTACAGCTTGGGATCCCGCACCCGTCAGGATTGAAGAAGAAAAAGAGCGTCACGGTACTCGACATA |
| | | GGCGACGCTTACTTCTCAGTTCCGCTGGACAAAGAGTTCAGAAAATATACAGCTTTCACGGTACCCTCCACT |
| | | AACAATGAGACACCTGGAGTTCGCTACCAGTACAATGTGCTTCCAATGGGATGGAAGGGCTCACCGGCTATT |
| | | TTCCAATGCTCTATGACTAAAATACTTCAAGAGGAAGAAGAGGTTGGGTTTCCCGTCAGACCGCAGGTTCCA |
| | | CTT |
| 214 | Pol:840-920 | ACGGTGAAAGCAGCTTGCTGGTGGGCGGGGATCAAACAGGAGTTTGGAATACCTTATAATCCTCAATCACAG |
| | Gag:147-369 | GGGGTTGTCGAAAGCATGAACAAGGAGCTCAAGAAGATCATCGGACAGGTGCGCGATCAGGCTGAACATCTT |
| | Pol:586-606 | AAGACCGCAGTTCAGATGGCAGTCTTTATTCACAATTTTAAACGGAAAGGAGGTATAGGTGGCTACAGCGCG |
| | Pol:747-827 | GGCGAGCGCATTGTAGATATTATAGCGATTTCTCCGCGGACGCTGAATGCATGGGTTAAAGTAGTTGAAGAG |
| | Pol:683-708 | AAGGCCTTTTCTCCCGAAGTAATACCCATGTTCAGTGCACTGTCTGAAGGTGCTACTCCTCAGGATCTCAAC |
| | Nef:64-76 | ACGATGCTCAACACGGTCGGTGGGCATCAGGCAGCAATGCAGATGCTGAAGGAAACGATAAACGAGGAGGCA |
| | Pol:932-1003 | GCAGAATGGGATCGACTGCACCCAGTACACGCAGGCCCTATAGCCCCAGGTCAAATGCGGGAACCAAGAGGT |
| | AAA | AGTGATATAGCTGGGACTACCTCAACGTTGCAGGAGCAAATTGGTTGGATGACGAATAATCCTCCTATACCA |
| | Pol:129-320 | GTTGGCGAAATATACAAAAGATGGATTATCTTGGGACTGAATAAAATCGTGCGAATGTATTCTCCGACCTCT |
| | | ATACTGGACATTCGACAGGGACCAAAAGAGCCGTTCCGCGACTACGTCGATCGGTTTTATAAAACTTTGCGG |
| | | GCCGAACAGGCAAGCCAGGAGGTAAAGAACTGGATGACAGAGACCCTGTTGGTGCAAAATGCGAACCCTGAT |
| | | TGCAAGACCATACTGAAAGCACTCGGGCCAGCTGCCACCCTTGAGGAAATGATGACAGCTTGCCAGGGTGTG |
| | | GGGGGGCCGGGGCATAAAGCACGCGTCCTCGCCGAAGCCATGTCACAGAAAGAACCAATTGTGGGTGCCGAA |
| | | ACTTTTTACGTGGACGGCGCAGCCAACCGAGAGACTAAAGTGGCTAAAGAGATAGTTGCATCATGTGATAAG |
| | | TGCCAATTGAAAGGTGAGGCCATGCACGGTCAGGTAGATTGTTCACCTGGTATATGGCAGTTGGACTGTACT |
| | | CACCTTGAAGGAAAGATTATCCTGGTCGCGGTACACGTCGCATCCGGTTATATAGAGGCGGAAGTTATACCT |
| | | GCGGAGACTGGTCAAGAAACTGCCTACTTCCTTCTTAAATTGGCTGGTCGATGGCCAGTAAAAACTAAAGAG |
| | | AAAGTGTACCTTGCGTGGGTTCCAGCCCACAAGGGTATAGGAGGAAATGAGCAAGTAGACAAACTCGTAAGC |
| | | CAAGAGGAAGAAGAAGTGGGTTTCCCAGTTAAGCCACAGGTACCCCTCATTACCAAAATACAGAATTTCCGG |
| | | GTTTATTATCGCGATTCAAGGGACCCCCTGTGGAAAGGTCCAGCAAAACTGCTGTGGAAGGGCGAAGGGGCA |
| | | GTTGTTATACAAGACAACTCAGATATCAAGGTCGTGCCAAGACGCAAAGCTAAAATTATAAGGGATTATGGT |
| | | AAACAGATGGCTGGAGACGACTGCGTGGCCAGCAGACAAGACGAGGATGCAGCTGCAATTGGAACAGTCCTG |
| | | GTCGGACCAACTCCCGTTAACATCATAGGTAGAAACTTGCTCACTCAAATCGGATGCACACTTAATTTTCCG |
| | | ATTTCACCTATCGAGACCGTTCCCGTTAAGCTGAAACCTGGGATGGACGGTCCCAAGGTGAAGCAATGGCCC |
| | | TTGACTGAGGAAAAGATAAAGGCGTTGGTAGAGATCTGCACCGAAATGGAGAAGGAAGGCAAGATATCTAAG |
| | | ATCGGGCCAGAAAACCCATATAATACACCTGTCTTCGCGATAAAAAAAAAGGACTCTACTAAATGGAGAAAA |
| | | CTGGTCGACTTCAGAGAGCTTAATAAGCGAACTCAAGACTTTTGGGAAGTGCAGCTTGGTATACCTCACCCT |
| | | GCTGGTCTGAAGAAGAAAAAATCTGTTACTGTTCTTGATGTCGGTGACGCATACTTCAGTGTGCCCCTCGAT |
| | | AAAGATTTCAGGAAATACACCGCGTTCACTATACCCAGCATTAATAACGAGACCCCCGGGATACGCTACCAA |
| | | TACAATGTCCTCCCCCAGGGCTGGAAAGGGTCTCCAGCAATTTTTCAGTCATCAATGACG |
| 215 | Gag:147-369 | TTGTCCCCTCGGACGCTCAATGCATGGGTTAAAGTTATCGAGGAGAAGGCCTTCAGTCCCGAGGTTATACCT |
| | Pol:747-827 | ATGTTCACCGCTCTGTCTGAAGGAGCAACGCCCCATGATCTCAATACTATGCTCAATACAATTGGAGGTCAC |
| | Pol:683-708 | CAAGCGGCTATGCAAATGCTCAAAGATACCATTAATGAGGAGGCTGCTGAATGGGATAGGGTCCACCCAGTT |
| | Pol:586-606 | CATGCCGGACCGGTGGCTCCGGGACAGATGCGCGACCCCCGGGGGTCAGACATCGCCGGAAGTACCTCTACT |
| | Pol:932-1003 | CTGCAGGAACAAATTGCATGGATGACAAATAATCCACCTATTCCGGTCGGAGACATCTACAAACGATGGATC |
| | Pol:840-920 | ATAATGGGTCTCAACAAGATAGTCCGGATGTATAGTCCGGTAAGTATACTCGACATCAAGCAAGGCCCTAAG |
| | Nef:64-76 | GAGCCGTTCCGGGATTACGTAGACCGATTCTACCGGACGCTCAGAGCCGAACAGGCCTCCCAAGATGTTAAG |
| | Pol:129-320 | AACTGGATGACCGAAACGTTGTTGGTTCAAAATTCCAATCCTGATTGCAAAACGATACTCAAAGCTCTTGGT |
| | | CCTGGTGCAACACTGGAGGAAATGATGTCAGCCTGCCAAGGGGTCGGCGGGCCTTCACACAAAGCAAGGGTT |
| | | TTGGCGGAGGCAATGTGCCAAGTAGCGAAGGAAATAGTGGCCTGTTGTGACAAATGTCAGCTGAAAGGAGAG |
| | | GCAATACATGGACAAGTTGACTGTTCTCCCGGTGTGTGGCAACTCGACTGTACCCACTTGGAAGGAAAAGTT |
| | | ATACTGGTGGCCGTTCACGTCGCGTCTGGCTACATCGAGGCTGAGATCATACCTACAGAGACCGGGCAGGAG |
| | | ACCGCGTACTTCATCCTTAAGCTCGCGGGCCGCTGGCCAGTCACGACTAAAGAGAAAATTTATCTGGCGTGG |
| | | GTACCCGCGCATAAAGGTATTGGCGGCAATGAACAAATAGACAAATTGGTATCAACAGAGCCGATTGCAGGA |
| | | GTCGAAACATTCTATGTTGATGGTGCGTCAAACAGGGAAACGAAGATAACAAAGTTGCAAAACTTTCGAGTC |
| | | TACTATCGCGACAATCGGGATCCCCTCTGGAAGGGCCCAGCAAGGTTGCTGTGGAAGGGCGAGGGAGCAGTA |
| | | GTCATTCAAGACAACAGTGAGATTAAGGTAGTTCCGCGACGGAAGGTCAAAATAATACGGGATTACGGCAAA |
| | | AGGATGGCAGGGGATGATTGCGTGGCTGGGCGCCAGGATGAGGACGCTGTCAAAGCCGCGTGTTGGTGGGCA |
| | | GGGGTTAAGCAGGAGTTCGGAATACCATACAACACCCAGTCTCAAGGAGTTGTTGAAAGCATGAACAATGAG |
| | | CTTAAAAAAATAATCGGACAAATAAGGGATCAGGCCGAACACTTGAAGACAGCAGTTCAGATGGCCGTGCTG |

TABLE H-continued

Illustrative Polynucleotides Encoding Fusion Polypeptides

| SEQ ID NO: | Encoded Polypeptide Segments | Nucleic Acid Sequences |
|---|---|---|
| | | ATCCATAACTTCAAACGGAAGGGCGGCATAGGAGAATACTCCGCAGGCGAGAGAATAATCGACATTATAGCT |
| | | CAAGAAGAAGAGGAAGTCGGCTTTCCTGTACGACCTCAGGTCCCTCTTGGTACGGTGTTGATAGGGCCGACC |
| | | CCCGTCAACATCATCGGTCGGAACCTGCTTACACAACTTGGTTGCACTCTTAACTTTCCTATTTCCCCATA |
| | | GATACCGTCCCAGTCAAGTTGAAGCCGGGGATGGATGGCCCGCGCGTCAAGCAGTGGCCCCTGACTGAAGAA |
| | | AAGATTAAAGCTCTGATTGAAATATGCACAGAAATGGAAAAAGAGGGTAAGATCAGCAGAATCGGTCCAGAA |
| | | AATCCCTATAACACGCCGATATTCGCCATTAAGAAGAAGGACGGAACAAAGTGGCGGAAACTCGTCGATTTT |
| | | AGGGAGCTGAATAAGAAAACGCAGGATTTCTGGGAAGTTCAACTTGGCATACCTCACCCCTCTGGTCTTAAA |
| | | AAAAAAAAGTCAGTCACCGTTCTCGACATTGGGGACGCGTATTTTTCCGTTCCGCTCGACAAAGAGTTTCGG |
| | | AAGTACACGGCGTTCACGGTACCTTCTACAAACAATGAAACCCCCGGGGTCAGGTATCAGTATAATGTGCTG |
| | | CCAATGGGGTGGAAGGGTAGCCCTGCTATTTTTCAATGCTCAATGACAAAGATCCTT |
| 216 | M | ATGACAGTAAAAGCGGCTTGCTGGTGGGCGGGTATTAAGCAAGAGTTTGGTATCCCCTACAACCCCCAGTCC |
| | Pol:840-920 | CAAGGAGTCGTCGAGTCTATGAACAAAGAACTGAAGAAGATCATTGGGCAGGTGCGCGATCAGGCTGAGCAC |
| | Gag:147-369 | TTGAAAACAGCGGTCCAGATGGCTGTGTTTATCCATAACTTTAAGAGGAAGGGGGGGATAGGGGGCTATTCA |
| | Gag:1-53 | GCAGGGGAGAGAATTGTAGACATCATCGCCATATCCCCTCGAACGCTCAATGCGTGGGTTAAAGTAGTTGAG |
| | PPV | GAAAAGGCATTTAGTCCTGAAGTCATCCCAATGTTTAGCGCACTTTCCGAGGGCGCTACGCCCCAGGACCTG |
| | Pol:747-827 | AATACCATGCTTAACACCGTTGGGGGCCACCAGGCGGCCATGCAGATGCTCAAGGAAACTATTAACGAGGAG |
| | Pol:683-708 | GCGGCGGAGTGGGATCGGCTGCACCCTGTCCACGCAGGACCGATCGCCCCGGGGCAAATGAGAGAACCCAGA |
| | Nef:117-148 | GGTTCTGATATTGCTGGAACTACTAGTACTCTTCAGGAGCAAATCGGGTGGATGACTAATAACCCACCAATT |
| | RAKR | CCCGTAGGTGAAATTTACAAGAGATGGATCATACTGGGCTTGAACAAAATAGTCCGAATGTATAGTCCCACC |
| | F2A linker | TCAATCCTCGACATCCGGCAAGGACCGAAGGAGCCTTTCCGCGACTATGTGGATCGCTTTTATAAGACTCTG |
| | M | CGAGCAGAACAAGCATCACAAGAGGTTAAAAACTGGATGACCGAAACACTCTTGGTGCAGAACGCAAATCCC |
| | Gag:147-369 | GACTGCAAAACCATCCTGAAGGCATTGGGCCCTGCAGCAACTTTGGAGGAGATGATGACTGCATGTCAAGGC |
| | Pol:747-827 | GTAGGAGGGCCCGGCCATAAAGCCAGAGTTTTGGCAGAGGCTATGTCTCAAATGGCGGCACGAGCTTCAGTT |
| | Gag:1-53 | CTGTCAGGGGGCGAACTTGATCGGTGGGAAAAGATACGGCTTCGGCCCGGAGGCAAGAAAAAGTACAGGCTG |
| | AA | AAGCACATAGTATGGGCGTCCCGCGAACTGGAGAGGTTTGCAGTGAACCCCGGCCTGCTCGAGACGCCCCCG |
| | Pol:840-920 | GTGGTTGCTAAAGAAATAGTCGCCTCTTGTGATAAATGCCAACTCAAGGGAGAAGCTATGCATGGCCAGGTT |
| | Nef:117-148 | GACTGCTCACCGGGTATATGGCAGCTGGATTGTACACATTTGGAAGGTAAAATCATACTCGTTGCTGTGCAT |
| | LIK | GTAGCAAGCGGGTATATTGGAGGCGGAAGTAATTCCGGCGGAAACCGGGCAAGAAACTGCCTATTTCCTTCTT |
| | Pol:683-708 | AAACTCGCGGGGCGGTGGCCGGTTAAGACCAAGGAGAAAGTCTATCTCGCATGGGTTCCGGCCCATAAAGGC |
| | | ATCGGCGGTAATGAACAAGTAGATAAACTCGTTAGCACTCAAGGATATTTTCCGGATTGGCAGAATTATACA |
| | | CCCGGACCTGGTACAAGATATCCCTTGACGTTCGGATGGTGTTTCAAGCTCGTCCCAGTCCGCGCTAAAAGA |
| | | GCACCAGTAAAGCAGACCTTGAACTTCGACTTGCTCAAGCTTGCTGGGGATGTCGAAAGTAACCCCGGCCCG |
| | | ATGTTGTCCCCCAGGACTTTGAATGCATGGGTCAAAGTGATTGAGGAGAAGGCCTTCTCCCCCGAAGTTATT |
| | | CCGATGTTTACCGCGCTTAGTGAAGGGGCCACACCTCATGATCTGAATACGATGCTTAACACTATAGGGGGT |
| | | CACCAGGCAGCGATGCAAATGCTGAAGGATACCATCAATGAAGAAGCAGCTGAATGGGACAGGGTACATCCA |
| | | GTGCATGCAGGACCGGTTGCACCCGGACAAATGCGCGACCCGCGAGGTTCCGACATCGCGGGGTCAACGTCC |
| | | ACCCTGCAAGAACAAATTGCATGGATGACCAATAATCCCCCTATCCCAGTGGGCGACATATATAAGCGCTGG |
| | | ATAATCATGGGTCTCAATAAAATTGTAAGGATGTATAGTCCGGTGTCAATCCTGGACATAAAGCAAGGTCCC |
| | | AAGGAACCGTTTCGCGACTATGTAGACAGATTTTATCGAACGCTGAGAGCCGAGCAAGCGAGCCAGGATGTC |
| | | AAAAACTGGATGACCGAAACACTTCTCGTTCAGAATTCAAACCCCGGATTGTAAGACAATACTTAAGGCGCTC |
| | | GGTCCCGGGGCGACCCTTGAAGAGATGATGTCTGCTTGTCAAGGTGTTGGGGGTCCATCCCACAAAGCTCGC |
| | | GTCCTGGCGGAAGCAATGTGCCAAGTCGCCAAAGAAATCGTCGCGTGCTGTGACAAGTGCCAACTCAAGGGT |
| | | GAGGCGATCCATGGGCAAGTGGACTGTAGTCCAGGCGTATGGCAATTGGACTGTACGCATCTCGAAGGGAAG |
| | | GTGATCTTGGTGGCCGTCCATGTGGCGAGCGGATATATTGAAGCCGAAATCATCCCTACCGAAACGGGACAA |
| | | GAAACGGCGTATTTCATTTTGAAACTGGCGGGTCGGTGGCCGGTCACCACCATGGCCGCGCGAGCGAGCATA |
| | | CTTAGCGGGGGTAAATTGGACAAGTGGGAGAAGATCCGGCTTCGGCCCGGGGGTCGGAAAAAATATAAGCTG |
| | | AAGCACCTGGTCTGGGCATCACGAGAACTGGAGCGGTTCGCACTTAATCCAGGGTTGCTTGAAACCGCAGCC |
| | | GCGGTGAAGGCCGCCTGCTGGTGGGCGGGAGTAAAGCAGGAGTTCGGAATTCCTTACAACACGCAGAGCCAA |
| | | GGTGTAGTGGAAAGCATGAACAATGAGCTTAAGAAAATCATTGGTCAGATCAGAGACCAAGCGGAACACCTC |
| | | AAGACAGCTGTGCAAATGGCTGTACTTATTCACAACTTCAAGAGAAAAGGCGGTATAGGAGAATATAGCGCG |
| | | GGGGAAAGAATAATAGACATCATCGCTACTCAAGGGTTTTTCCCCGACTGGCAGAATTATACACCTGGCCCC |
| | | GGTATACGGTTTCCACTTACTTTCGGCTGGTGTTTCAAGTTGGTGCCTCTCCTGATAAAAAAGGAGAAAATA |
| | | TATCTTGCGTGGGTGCCTGCACACAAAGGTATAGGCGGTAACGAACAAATCGACAAATTGGTTAGC |
| 217 | M | ATGTTCCCCCAGATTACACTGTGGCAGCGACCTCTGGTCACCATCAAGATTGGGGGACAGCTTAAGGAAGCG |
| | Pol:56-117 | CTGCTTGACACTGGTGCTGATGACACTGTACTGGAGGAGATGAATCTCCCGGGTCGCTGGAAGCCTAAAATG |
| | Nef:64-99 | ATAGGCGGTATCGGGGGGTTCATTAAGGTCAGGCAGTACGACCAAGAAGAGGTCGGATTCCCGGTAAAGCCA |
| | LI | CAAGTGCCTCTTCGCCCGATGACGTTCAAGGGTGCGTTGGACCTCAGCCACTTTCTTCGAGAAAAGGGCGGA |
| | Pol:542-606 | CTGGAAGGTCTGATACCTAAATTTAAGCTCCCTATTCAGAAGGAAACATGGGAGACATGGTGGACGGAGTAT |
| | Pol:367-431 | TGGCAGGCGACATGGATCCCCGAGTGGGAATTTGTAAACACCCCGCCACTCGTAAAACTCTGGTACCAACTG |
| | Pol:932-1003 | GAAAAGGAACCCATCGTCGGTGCTGAAACCTTCTACGTCGATGGTGCGGCTAATAGGGAAACGAAGTGGGGT |
| | Pol:129-320 | TTCACTACCCCAGACAAAAAACATCAAAAGAACCACCCCTTTCTCTGGATGGGATATGAATTGCATCCCGAT |
| | RAKR | AAATGGACCGTGCAACCCATCGTTCTGCCGGAAAAGGACAGCTGGACCGTTAATGATATTCAGAAGCTTGTT |
| | F2A linker | GGGAAACTCAACTGGGCTTCCCAAATTTACCCGGGAATAAAGGTGATAACGAAAATTCAGAATTTTAGGGTG |
| | M_ | TACTATAGGGACTCACGCGATCCTCTTTGGAAAGGTCCAGCAAAGTTGTTGTGGAAAGGTGAGGGGGCTGTC |
| | Pol:56-117 | GTCATCCAAGACAATAGTGATATTAAGGTCGTGCCTAGAAGAAAGGCAAAGATTATTAGGGATTACGGCAAG |
| | Pol:367-431 | CAGATGGCTGGTGACGACTGTGTTGCAAGTCGCCAAGACGAAGATGGCACGGTGTTGGTCGGGCCCACACCA |
| | AA | GTAAACATTATAGGCCGAAATCTGCTTACTCAAATCGGATGTACTCTTAATTTTCCGATCTCCCCTATAGAA |
| | QEE | ACGGTTCCTGTAAAATTGAAACCTGGAATGGATGGTCCGAAAGTTAAACAGTGGCCGCTCACCGAGGAAAAG |
| | Nef:64-99 | ATTAAAGCGCTTGTCGAGATCTGTACTGAAATGGAAAAAGAAGGAAAGATCTCCAAAATAGGGCCAGAAAAT |
| | Pol:932-1003 | CCGTACAATACTCCAGTCTTTGCTATAAAGAAGAAGGATTCTACGAAGTGGAGGAAGCTGGTAGACTTTCGC |
| | Pol:542-606 | GAGCTCAACAAACGCACGCAAGATTTTTGGGAAGTCCAGTTGGGCATCCCTCATCCAGCTGGACTCAAGAAA |
| | AA | AAAAAATCCGTCACAGTATTGGATGTGGGCGACGCCTACTTTTCAGTGCCATTGGACAAAGATTTTCGAAAA |

TABLE H-continued

Illustrative Polynucleotides Encoding Fusion Polypeptides

| SEQ ID NO: | Encoded Polypeptide Segments | Nucleic Acid Sequences |
|---|---|---|
| | Pol:129-320 | TACACCGCGTTCACAATTCCTAGTATCAATAACGAGACTCCCGGAATAAGGTACCAGTACAACGTGCTCCCT<br>CAAGGGTGGAAAGGTTCTCCCGCGATATTTCAGTCCAGTATGACTCGCGCGAAACGAGCTCCAGTTAAACAG<br>ACCCTCAACTTTGATTTGTTGAAGCTTGCTGGGGATGTTGAGAGTAATCCAGGCCCTATGCTGCCGCAAATC<br>ACACTCTGGCAAAGGCCGATAGTGACCATTAAAATTGGCGGGCAGATCAAGGAGGCATTGCTTGATACGGGA<br>GCAGACGATACAGTGTTGGAGGACATGAACCTGCCCGGAAAATGGAAACCAAAGATGATCGGTGGGATTGGC<br>GGTTTCATAAAGGTCAAGCAGTATGACCAGTGGGGTCTGACAACCCCTGACAAAAAACATCAGAAGGATCCC<br>CCCTTTCTTTGGATGGGTTATGAGTTGCATCCAGATCGCTGGACGGTGCAGCCTATTGAGCTTCCGGAAAAG<br>GAGTCTTGGACAGTTAATGATATTCAAAAACTTATTGGGAAATTGAATTGGGCCAGCCAGATATACGCAGGT<br>ATAAAAGTTGCGGCGCAGGAGGAGGAAGAAGTGGGGTTCCCCGTCCGACCCCAGGTGCCGCTCAGACCAATG<br>ACGTATAAAGGTGCGTTGGATCTGAGTCATTTTTTGAAGGAAAAAGGCGGGTTGGAAGGCATTACCAAACTC<br>CAAAACTTCCGGGTGTATTATCGGGACAACAGAGATCCACTCTGGAAGGGTCCCGCAAGATTGCTTTGGAAG<br>GGAGAAGGAGCAGTTGTTATACAAGACAACTCCGAAATTAAGGTAGTGCCTAGACGGAAGGTTAAAATTATT<br>AGGGACTACGGAAAACGGATGGCGGGGATGACTGCGTCGCGGGCCGCCAGGACGAGGACCCGAAATTCCGC<br>CTGCCTATACAAAAGGAGACGTGGGACACGTGGTGGACAGACTACTGGCAAGCAACGTGGATCCCGGAATGG<br>GAATTTACTAACACACCTCCTTTGGTGAAACTCTGGTATCAACTCGAGACGGAGCCGATTGCAGGGGTCGAG<br>ACATTTTACGTCGATGGAGCATCCAATAGGGAAACTAAAGCAGCTGGTACAGTTCTGATAGGTCCGACCCCG<br>GTGAATATAATAGGCAGGAATCTCCTCACACAACTTGGCTGCACTTTGAATTTCCCAATTTCCCCAATTGAC<br>ACCGTACCCGTAAAGTTGAAGCCTGGAATGGACGGACCACGAGTGAAGCAGTGGCCTCTCACGGAAGAAAAG<br>ATCAAAGCGCTTATTGAAATTTGTACAGAAATGGAGAAGGAGGGTAAAATCTCCAGGATAGGTCCTGAAAAC<br>CCGTACAACACGCCCATCTTCGCTATCAAAAAAAAAGATGGAACGAAATGGCGCAAGCTGGTGGACTTCAGA<br>GAACTTAACAAAAAGACGCAGGATTTTTGGGAAGTCCAGTTGGGAATCCCTCACCCGAGCGGACTTAAAAAA<br>AAGAAAAGTGTCACAGTTCTTGATATAGGCGACGCTTATTTTTCCGTCCCACTTGACAAGGAATTTAGGAAG<br>TACACGGCGTTTACAGTGCCATCAACGAACAACGAAACCCCGGGGGTGCGCTACCAGTACAACGTACTGCCA<br>ATGGGATGGAAAGGTTCACCCGCAATCTTTCAATGCTCAATGACT |
| 218 | M<br>Pol:840-920<br>Gag:147-369<br>Gag:1-53<br>PPV<br>Pol:747-827<br>Pol:683-708<br>Nef:117-148<br>RAKR<br>F2A linker<br>M<br>Pol:56-117<br>Nef:64-99<br>LI<br>Pol:542-606<br>Pol:367-431<br>Pol:932-1003<br>Pol:129-320 | ATGACGGTAAAGGCAGCATGCTGGTGGGCAGGTATAAAACAGGAATTCGGCATTCCGTATAACCCACAAAGT<br>CAAGGAGTTGTCGAGTCCATGAACAAAGAATTGAAAAAGATAATTGGTCAAGTGCGAGACCAAGCAGAACAC<br>CTGAAAACCGCGGTTCAAATGGCCGTGTTTATACACAACTTTAAGAGAAAAGGGGGCATCGGGGGCTACTCC<br>GCGGGTGAACGCATAGTCGATATAATAGCCATCTCCCCTCGCACTCTCAACGCATGGGTGAAAGTCGTAGAG<br>GAGAAAGCTTTCTCACCTGAAGTAATTCCGATGTTTAGTGCACTGAGTGAAGGCGCTACGCCTCAAGATCTG<br>AACACGATGCTTAATACCGTCGGGGGTCACCAAGCCGCGATGCAGATGTTGAAGGAAACAATAAATGAGGAA<br>GCAGCAGAGTGGGACAGACTTCACCCGGTCCACGCGGGACCAATCGCACCAGGACAAATGCGAGAACCGAGA<br>GGTAGTGACATCGCCGGAACAACCTCCACCCTCCAGGAACAGATTGGTTGGATGACAAATAATCCTCCGATA<br>CCCGTCGGTGAGATCTACAAACGCTGGATCATCCTGGGTCTTAACAAGATCGTACGGATGTACAGCCCAACC<br>AGTATCCTTGACATTAGGCAGGGACCGAAGGAGCCGTTTCGCGACTACGTCGATCGGTTTTACAAGACGCTT<br>AGAGCGGAACAAGCGTCACAGGAAGTTAAAAATTGGATGACAGAAACCTTGCTTGTCCAGAATGCTAATCCC<br>GATTGCAAAACTATTCTGAAGGCACTGGGTCCTGCGGCGACTTTGGAGGAGATGATGACGGCCTGTCAAGGT<br>GTTGGAGGCCCTGGTCATAAGGCACGAGTCCTGGCTGAAGCAATGTCTCAAATGGCGGCTAGAGCCTCTGTG<br>CTGTCCGGAGGGGGAGCTTGACCGCTGGGAAAAGATCCGATTGCGACCAGGTGGGAAAAAGAAGTACAGGCTC<br>AAGCATATTGTGTGGGCATCACGGGAACTTGAGCGCTTCGCAGTCAATCCTGGACTTCTTGAAACGCCACCG<br>GTGGTCGCTAAAGAGATCGTTGCGAGCTGTGATAAATGTCAACTTAAAGGCGAGGCTATGCATGGCCAGGTC<br>GACTGTAGCCCGGGCATCTGGCAGCTGGATTGCACTCACCTGGAGGGTAAGATCATTCTCGTGGCGGTCCAT<br>GTTGCCAGTGGCTACATTGAGGCGGAGGTGATTCCTGCGGAAACTGGTCAGGAGACAGCCTATTTCTTGCTG<br>AAGCTCGCGGGACGCTGGCCTGTCAAAACTAAGGAAAAGGTTTATTGGCCTGGGTTCCCGCACATAAAGGA<br>ATTGGTGGCAATGAACAGGTAGACAAACTTGTAAGTACTCAGGGATATTTTCCCGATTGGCAGAATTACACT<br>CCAGGGCCGGGGACTAGGTACCCTTTGACATTTGGTTGGTGTTTTAAGCTTGTGCCTGTTCGGGCGAAGAGG<br>GCGCCAGTCAAACAGACTCTGAATTTCGACCTGCTGAAGCTGGCAGGAGACGTCGAGTCCAACCCTGGTCCT<br>ATGTTCCCACAGATTACTCTGTGGCAGCGCCCGCTTGTGACTATTAAAATCGGCGGACAACTCAAAGAGGCA<br>CTCCTTGACACCGGAGCGGACGACACGGTGCTGGAAGAAATGAACTTGCCCGGCCGGTGGAAGCCAAAGATG<br>ATCGGAGGTATCGGCGGCTTTATAAAGGTGCGCCAGTATGACCAAGAAGAAGTCGGCTTCCCAGTAAAGCCT<br>CAAGTTCCACTGAGACCTATGACTTTTAAGGGTGCGCTTGATCTGTCACACTTCCTCCGAGAGAAAGGCGGC<br>TTGGAGGGCCTTATTCCCAAGTTCAAGTTGCCTATTCAAAAAGAAACGTGGGAGACGTGGTGGACTGAATAT<br>TGGCAGGCGACCTGGATCCCTGAATGGGAGTTCGTGAACACACCCCCACTCGTTAAACTCTGGTATCAGTTG<br>GAAAAGGAACCCATCGTGGGCGCCGAGACATTTTACGTCGATGGTGCCGCTAACAGAGAGACCAAGTGGGGG<br>TTTACAACGCCTGACAAGAAGCACCAGAAGGAGCCCCCTTTCCTTTGGATGGGATATGAGTTGCACCCCGAC<br>AAATGGACCGTGCAACCGATTGTCTTGCCTGAGAAAGACTCTTGGACAGTGAACGATATCCAAAAACTTGTG<br>GGAAAATTGAATTGGGCAAGCCAAATCTACCCAGGGATAAAGGTAATCACTAAGATTCAAAACTTCCGAGTA<br>TACTACCGAGACAGCAGAGATCCCTTGTGGAAAGGTCCTGCGAAACTGCTCTGGAAAGGCGAGGGAGCTGTG<br>GTCATTCAGGACAACTCAGACATCAAAGTAGTCCCACGCCGCAAAGCGAAAATCATACGCGACTATGGCAAA<br>CAAATGGCAGGTGATGATTGTGTGGCGAGTCGACAAGATGAGGATGGTACCGTTCTGGTCGGGCCGACACCT<br>GTTAATATTATAGGACGCAATTTGTTGACACAAATCGGCTGCACTCTTAACTTCCCGATAAGTCCCATCGAG<br>ACAGTGCCAGTTAAATTGAAGCCAGGGATGGACGGTCCTAAGGTTAAGCAGTGGCCCCTCACTGAAGAAAAA<br>ATCAAGGCTCTCGTGGAAATTTGCACTGAGATGGAGAAGGAGGGCAAAATCTCCAAGATAGGTCCAGAGAAC<br>CCATATAATACGCCGGTATTTGCAATCAAAAAAAAGGACAGCACAAAGTGGCGAAAGCTGGTTGACTTTCGA<br>GAGCTGAACAAGCGGACGCAGGACTTTTGGGAAGTCCAATTGGGAATACCGCATCCCGCTGGATTGAAAAAA<br>AAAAAGAGCGTAACAGTCCTCGATGTAGGTGATGCATACTTCAGTGTCCCACTCGATAAAGATTTTAGAAAG<br>TACACTGCTTTTACGATTCCATCCATTAACAACGAGACTCCCGGTATTCGATATCAATACAATGTACTCCCA<br>CAAGGTTGGAAAGGCTCACCTGCGATCTTCCAAAGTAGCATGACT |
| 219 | M<br>Gag:147-369<br>Pol:747-827<br>Gag:1-53<br>AA | ATGTTGTCTCCTAGAACTCTGAATGCTTGGGTAAAGGTGATCGAAGAAAAGGCATTCTCACCCGAGGTTATC<br>CCTATGTTTACTGCGTTGAGCGAAGGCGCAACACCCCATGATCTGAACACAATGCTGAATACAATCGGCGGA<br>CATCAAGCTGCTATGCAAATGCTTAAGGACACCATCAATGAGGAGGCAGCCGAGTGGGATCGCGTTCATCCA<br>GTCCACGCTGGGCCCGTTGCGCCTGGTCAGATGAGGGACCCACGAGGATCCGACATCGCAGGAGCACCAGT<br>ACACTCCAAGAGCAGATTGCATGGATGACGAACAATCCACCAATACCTGTCGGTGACATTTACAAAAGGTGG |

TABLE H-continued

Illustrative Polynucleotides Encoding Fusion Polypeptides

| SEQ ID NO: | Encoded Polypeptide Segments | Nucleic Acid Sequences |
|---|---|---|
| | Pol:840-920 | ATTATTATGGGCTTGAACAAAATTGTACGGATGTATAGCCCGGTGAGCATACTGGACATTAAACAGGGTCCA |
| | Nef:117-148 | AAAGAACCCTTTCGAGATTACGTTGACAGATTTTATAGGACACTGAGGGCGGAACAAGCGTCTCAAGACGTT |
| | LIK | AAAAACTGGATGACAGAAACGCTGCTTGTACAGAATTCCAACCCAGACTGCAAAACTATACTGAAAGCGCTC |
| | Pol:683-708 | GGTCCCGGTGCGACACTTGAGGAAATGATGAGCGCATGCCAGGGCGTCGGAGGGCCGTCTCACAAGGCCCGC |
| | RAKR | GTGTTGGCGGAAGCTATGTGCCAGGTGGCTAAGGAGATAGTAGCATGTTGTGATAAATGTCAGCTTAAAGGT |
| | F2A linker | GAAGCTATACATGGGCAGGTGGATTGTAGCCCGGGTGTATGGCAGCTGGACTGTACTCATCTGGAAGGAAAG |
| | M | GTAATACTTGTCGCAGTTCATGTCGCGAGCGGATACATTGAAGCTGAAATCATTCCTACGGAGACGGGCCAA |
| | Pol:56-117 | GAGACAGCTTACTTCATACTTAAACTTGCTGGGCGATGGCCGGTGACAACTATGGCGGCGCGCGCTTCAATT |
| | Pol:367-431 | TTGAGTGGTGGAAAGTTGGACAAGTGGGAGAAGATTAGACTCAGACCCGGAGGGAGAAAGAAGTATAAACTG |
| | AA | AAACATCTGGTTTGGGCTTCACGCGAACTTGAACGGTTTGCTCTCAACCCCGGGCTGCTCGAAACTGCTGCT |
| | QEE | GCTGTAAAGGCCGCTTGTTGGTGGGCGGGGGTAAAGCAGGAATTCGGAATTCCATATAACACTCAAAGCCAG |
| | Nef:64-99 | GGAGTAGTGGAATCCATGAATAATGAACTTAAGAAGATAATTGGACAGATTCGCGATCAGGCTGAACATCTC |
| | Pol:932-1003 | AAGACGGCCGTACAAATGGCAGTATTGATTCATAACTTTAAACGGAAGGGCGGCATAGGAGAGTATTCTGCG |
| | Pol:542-606 | GGAGAACGCATAATAGATATAATTGCGACTCAGGGGTTCTTTCCGGATTGGCAGAACTATACGCCGGGGCCA |
| | AA | GGCATTAGGTTCCCCCTCACGTTTGGATGGTGTTTCAAGTTGGTACCGTTGCTCATTAAAAAAGAAAAAATC |
| | Pol:129-320 | TACCTGGCCTGGGTCCCGGCGCACAAGGGTATAGGGGGGAACGAGCAAATTGATAAGCTCGTGTCAAGGGCG |
| | | AAGCGCGCGCCAGTCAAACAGACCTTGAATTTCGACCTCCTTAAGCTCGCTGGAGACGTCGAATCCAACCCT |
| | | GGCCCGATGCTGCCACAAATCACATTGTGGCAACGACCCATTGTAACAATAAAAATCGGGGGCCAGATCAAA |
| | | GAAGCGCTGCTTGACACCGGCGCCGACGATACAGTCCTCGAGGATATGAATTTGCCAGGCAAATGGAAGCCG |
| | | AAGATGATTGGCGGCATTGGCGGCTTTATTAAGGTTAAACAGTATGATCAGTGGGGATTGACCACTCCCGAT |
| | | AAGAAGCATCAGAAAGATCCGCCTTTTCTGTGGATGGGGTACGAACTGCACCCTGATCGATGGACGGTCCAG |
| | | CCGATAGAGCTGCCGGAAAAAGAATCATGGACCGTGAATGATATTCAAAAACTGATCGGAAAACTCAATTGG |
| | | GCGTCCCAGATATATGCTGGCATCAAAGTTGCAGCACAAGAAGAGGAAGAGGTAGGTTTCCCGGTTCGGCCG |
| | | CAAGTTCCCTTGCGACCGATGACATACAAGGGCGCATTGGACCTTTCTCACTTCCTCAAGGAAAAGGGCGGT |
| | | TTGGAGGGCATCACTAAACTTCAGAATTTCAGAGTCTACTATAGAGATAACAGGGACCCATTGTGGAAGGGC |
| | | CCCGCTCGACTTCTCTGGAAAGGGGAGGGAGCGGTTGTAATTCAAGACAACAGTGAAATTAAGGTCGTCCCA |
| | | CGACGGAAGGTTAAAATAATTCGCGACTATGGCAAGCGAATGGCGGGAGACGACTGTGTAGCAGGACGACAA |
| | | GACGAGGACCCAAAGTTTAGATTGCCGATCCAGAAAGAGACATGGGATACGTGGTGGACGGACTATTGGCAG |
| | | GCCACCTGGATACCAGAATGGGAGTTTACAAACACTCCTCCACTCGTGAAATTGTGGTATCAACTTGAGACC |
| | | GAGCCCATAGCTGGTGTAGAGACGTTTTACGTTGACGGTGCTAGCAACAGGGAAACAAAGGCCGCTGGAACC |
| | | GTGCTCATCGGTCCTACTCCTGTGAACATAATTGGACGAAATTTGTTGACCCAGCTGGGATGCACCCTCAAT |
| | | TTCCCCATTAGCCCAATAGATACCGTACCAGTCAAGCTTAAGCCTGGTATGGACGGTCCGCGAGTTAAGCAA |
| | | TGGCCACTTACTGAGGAGAAAATCAAGGCACTCATCGAGATCTGCACCGAAATGGAGAAGGAGGGCAAAATA |
| | | AGCAGGATTGGTCCCGAGAATCCATATAATACGCCGATCTTCGCGATAAAAAAGAAGGACGGCACCAAATGG |
| | | CGAAAACTGGTTGACTTCCGGGAGCTTAACAAAAAAACTCAGGATTTTTGGGAAGTTCAACTCGGGATCCCA |
| | | CACCCGTCTGGTCTTAAAAAAAAAAAAAGCGTAACAGTCCTTGACATCGGCGATGCCTACTTTAGCGTGCCT |
| | | CTCGATAAGGAGTTCAGAAAATACACGGCTTTCACTGTACCAAGCACAAACAATGAGACTCCTGGGGTCAGA |
| | | TACCAGTACAATGTCCTTCCCATGGGGTGGAAAGGAAGCCCCGCAATATTCCAGTGCTCAATGACG |
| 226 | M | ATGCTTTCACCGAGAACCTTGAACGCGTGGGTTAAAGTAATCGAAGAGAAGGCATTTAGCCCGGAGGTAATC |
| | Gag:147-369 | CCCATGTTTACCGCACTTTCCGAAGGTGCTACACCCCACGACCTGAATACAATGTTGAATACTATTGGCGGC |
| | Pol:747-827 | CACCAAGCTGCCATGCAGATGCTTAAGGACACTATTAACGAGGAAGCCGCCGAATGGGATCGCGTTCACCCT |
| | Gag:1-53 | GTTCACGCGGGTCCAGTCGCACCAGGACAAATGCGAGACCCTCGGGGGTCTGACATCGCAGGATCAACTAGT |
| | AA | ACATTGCAGGAACAGATTGCTTGGATGACCAATAACCCTCCGATCCCGGTAGGTGACATTTATAAACGGTGG |
| | Pol:840-920 | ATCATCATGGGATTGAACAAAATAGTCCGAATGTACAGTCCAGTGAGTATTCTTGACATTAAACAGGGACCA |
| | Nef:117-148 | AAGGAGCCGTTCCGGGACTACGTTGACCGGTTTTACAGGACCCTGAGAGCCGAACAGGCTTCCCAGGATGTG |
| | LIK | AAAAACTGGATGACAGAGACCCTGCTTGTTCAGAATTCAAATCCTGACTGTAAAACGATTCTGAAGGCACTC |
| | Pol:683-708 | GGTCCCGGCGCCACGCTGGAGGAAATGATGTCAGCTTGTCAGGGAGTAGGAGGACCTTCTCATAAGGCACGC |
| | F2A | GTCCTTGCAGAGGCCATGTGCCAAGTCGCGAAAGAGATCGTGGCCTGTTGTGACAAGTGCCAACTTAAGGGA |
| | M | GAAGCCATCCATGGGCAGGTCGATTGTTCTCCGGGCGTTTGGCAATTGGACTGCACGCACTTGGAGGGTAAG |
| | Pol:56-117 | GTGATTCTTGTTGCCGTTCATGTCGCAAGCGGTTACATTGAAGCGGAGATTATCCCAACTGAGACCGGCCAA |
| | Pol:367-431 | GAGACTGCATATTTCATCCTTAAACTGGCGGGAAGATGGCCGGTCACGACTATGGCTGCACGAGCATCCATA |
| | AA | CTGTCTGGGGAAAGCTCGACAAGTGGGAGAAGATTCGACTTAGGCCTGGAGGAAGAAAAAAGTATAAGTTG |
| | QEE | AAACATCTTGTTTGGGCATCACGAGAACTTGAACGGTTTGCTCTGAATCCGGGATTGCTTGAAACCGCCGCG |
| | Nef:64-99 | GCTGTAAAGGCAGCATGTTGGTGGGCTGGTGTCAAACAAGAGTTCGGTATTCCCTATAACACCCAAAGTCAA |
| | Pol:932-1003 | GGCGTCGTAGAATCCATGAACAATGAACTTAAGAAAATTATCGGACAAATCCGGGACCAAGCGGAACACCTC |
| | Pol:542-60 | AAAACTGCTGTCCAGATGGCAGTTCTGATTCATAACTTTAAAAGAAAGGGGGGGATAGGGGAGTATTCTGCA |
| | AA | GGTGAACGAATTATAGACATAATTGCCACACAAGGGTTTTTTCCAGATTGGCAAAATTATACACCGGGCCCT |
| | Pol:129-320 | GGGATAAGATTCCCGCTCACCTTCGGCTGGTGCTTCAAACTGGTACCCTTGCTGATCAAGAAAGAGAAGATC |
| | | TATCTTGCTTGGGTGCCAGCCCATAAAGGGATCGGGGGTAACGAACAAATCGATAAGCTGGTGTCTAGAGCT |
| | | AAACGGGCTCCCGTAAAACAGACCTTGAACTTCGATCTGCTTAAATTGGCAGGGGACGTGGAAAGCAACCCC |
| | | GGGCCAATGCTGCCCCAGATAACACTTTGGCAACGCCCCATCGTGACAATCAAGATCGGTGGCCAAATTAAG |
| | | GAAGCACTCTTGGACACGGGAGCAGACGACACTGTGCTGGAGGATATGAACCTGCCGGGCAAGTGGAAACCA |
| | | AAGATGATCGGGGGCATTGGCGGGTTCATAAAGGTTAAACAGTACGACCAATGGGGGTTGACAACGCCTGAT |
| | | AAGAAGCATCAAAAAGATCCCCCATTTTTGTGGATGGGTTATGAACTTCACCCGGACAGGTGGACCGTTCAG |
| | | CCGATAGAGCTCCCAGAAAAGGAGTCTTGGACAGTTAATGACATACAGAAACTTATTGGCAAACTTAACTGG |
| | | GCTTCACAGATTTATGCCGGCATCAAAGTCGCCGCCCAGGAAGAAGAAGAGGTAGGTTTTCCCGTACGACCT |
| | | CAGGTTCCTCTTCGGCCTATGACCTATAAGGGTGCGCTTGATCTTTCTCACTTCCTTAAAGAAAAAGGAGGT |
| | | CTGGAAGGTATCACGAAACTTCAGAATTTTCGGGTGTATTACCGGGACAACAGAGACCCGCTTTGGAAGGGG |
| | | CCGGCTAGGCTTCTGTGGAAAGGCGAGGGAGCGGTAGTTATCCAGGATAACTCTGAGATAAAGGTAGTACCC |
| | | CGACGGAAGGTAAAGATCATCAGAGACTACGGCAAGAGGATGGCTGGAGACGACTGTGTGGCCGGGCGACAG |
| | | GATGAAGATCCTAAATTCAGGCTGCCAATCCAAAAAGAGACGTGGGACACATGGTGGACCGATTATTGGCAG |
| | | GCTACGTGGATCCCCGAATGGGAGTTTACCAATACTCCGCCACTCGTGAAGCTTTGGTACCAATTGGAGACA |
| | | GAGCCTATAGCCGGCGTTGAGACCTTCTACGTGGATGGGGCCAGCAACAGAGAAACCAAAGCGGCCGGAACG |

TABLE H-continued

Illustrative Polynucleotides Encoding Fusion Polypeptides

| SEQ ID NO: | Encoded Polypeptide Segments | Nucleic Acid Sequences |
|---|---|---|
| | | GTCCTGATCGGTCCCACACCTGTTAACATCATAGGGCGCAATCTGCTTACGCAATTGGGGTGCACATTGAAT<br>TTTCCAATATCCCCTATTGATACCGTGCCGGTTAAATTGAAGCCGGGTATGGACGGGCCTCGGGTCAAGCAG<br>TGGCCCCTGACCGAAGAAAAGATCAAAGCCCTGATTGAGATCTGCACGGAAATGGAAAAAGAGGGCAAGATT<br>AGTCGCATCGGCCCGGAGAACCCATACAATACTCCTATTTTTGCAATTAAAAAAAAGGACGGAACAAAGTGG<br>AGGAAACTTGTAGATTTCAGAGAGCTTAATAAGAAAACTCAGGACTTCTGGGAGGTCCAACTCGGTATTCCG<br>CATCCCTCCGGACTTAAGAAGAAAAAGTCAGTAACCGTCTTGGATATAGGGGACGCTTATTTTTCAGTGCCC<br>CTCGATAAAGAATTTCGCAAATACACGGCGTTTACTGTGCCATCTACTAATAACGAAACGCCAGGCGTGAGA<br>TATCAATACAACGTCCTTCCTATGGGCTGGAAGGGTTCACCCGCAATTTTTCAGTGCTCCATGACC |
| 225 | Gag:147-369<br>Pol:747-827<br>Gag:1-53<br>AA<br>Pol:840-920<br>Nef:117-148<br>LIK<br>Pol:683-708<br>F2A<br>Pol:56-117<br>Pol:367-431<br>AA<br>QEE<br>Nef:64-99<br>Pol:932-1003<br>Pol:542-606<br>AA<br>Pol:129-320 | ATTTCTCCTCGGACGCTGAATGCATGGGTGAAGGTAGTGGAGGAAAAGGCATTTTCACCAGAAGTCATTCCG<br>ATGTTCTCCGCGCTCTCCGAGGGTGCTACGCCACAGGACTTGAATACGATGCTGAATACCGTTGGTGGCCAT<br>CAGGCGGCGATGCAGATGTTGAAGGAGACAATTAACGAAGAAGCCGCCGAATGGGACAGATTGCACCCGGTG<br>CATGCGGGGCCAATAGCTCCTGGCCAGATGCGCGAGCCTAGGGGTTCTGACATTGCTGGTACAACAAGTACC<br>CTTCAGGAGCAGATTGGTTGGATGACGAATAACCCTCCCATACCTGTTGGCGAGATCTATAAGCGCTGGATT<br>ATACTTGGGCTGAATAAGATAGTCCGAATGTATTCTCCCACCTCTATTCTGGATATTCGGCAAGGACCTAAG<br>GAGCCGTTTAGAGACTACGTAGACCGGTTTTACAAAACCCTGCGGGCGGAACAAGCTTCTCAGGAAGTCAAA<br>AATTGGATGACTGAGACCTTGCTCGTCCAGAATGCGAACCCGGACTGTAAAACAATACTCAAAGCGCTGGGC<br>CCCGCTGCAACCCTGGAAGAAATGATGACGGCTTGTCAGGGAGTAGGAGGCCCCGGACATAAGGCACGAGTG<br>TTGGCAGAAGCCATGAGCCAGCCGCCTGTCGTCGCGAAAGAAATCGTCGCTTCTTGCGACAAATGTCAGCTG<br>AAGGGGGAGGCGATGCACGGTCAAGTTGATTGCTCTCCCGGTATTTGGCAATTGGACTGTACCCACCTTGAA<br>GGCAAAATTATTCTGGTTGCAGTGCACGTAGCATCCGGTTACATCGAAGCTGAAGTGATACCCGCAGAGACA<br>GGCCAGGAGACGGCTTATTTCCTCCTTAAGCTTGCGGGTCGGTGGCCCGTAAAGACCATGGCTGCTCGGGCA<br>TCTGTCCTCTCCGGTGGTGAACTCGACCGATGGGAAAAGATTCGATTGCGCCCCGGAGGAAAGAAGAAATAT<br>AGGCTGAAACATATTGTGTGGGCATCACGGGAACTTGAGCGATTTGCGGTAAACCCAGGCCTTTTGGAAACA<br>GCTGCAACTGTGAAAGCGGCTTGCTGGTGGGCGGGGATAAAACAGGAGTTTGGTATCCCGTACAATCCCCAA<br>TCTCAGGGGGTAGTAGAAAGCATGAACAAAGAATTGAAAAAAATAATTGGCCAGGTTCGCGACCAAGCCGAG<br>CACCTCAAGACCGCTGTACAGATGGCTGTATTTATTCACAACTTCAAGCGGAAGGGCGGAATAGGAGGATAT<br>AGCGCAGGGGAAAGGATTGTTGATATTATTGCAACACAAGGTTACTTTCCTGACTGGCAAAACTACACACCG<br>GGCCCTGGCACGCGCTATCCCCTTACGTTCGGTTGGTGCTTCAAGCTGGTGCCGGTAAAAGAAAAAGTTTAT<br>TTGGCATGGGTTCCTGCACATAAAGGAATAGGGGGTAACGAACAAGTTGACAAACTCGTCAGCCGCGCTAAA<br>AGAGCCCCAGTCAAGCAGACCCTGAATTTTGACCTGCTTAAATTGGCTGGGGACGTCGAGAGTAACCCGGGA<br>CCCTTCCCACAAATTACACTCTGGCAGCGACCACTGGTAACAATCAAAATAGGGGGACAATTGAAAGAAGCA<br>CTCCTGGATACGGGCGCGGACGATACAGTCCTGGAGGAAATGAATCTCCCCGGCCGCTGGAAACCTAAGATG<br>ATAGGGGGGATCGGTGGATTTATTAAAGTGCGGCAGTACGATCAATGGGGTTTTACGACACCTGACAAGAAA<br>CATCAAAAGGAGCCGCCATTTCTTTGGATGGGTTATGAGCTTCATCCGGATAAATGGACTGTTCAGCCGATT<br>GTCCTCCCCGAGAAGGATAGTTGGACTGTGAACGACATCCAGAAGCTGGTCGGGAAACTTAATTGGGCCAGT<br>CAAATATATCCAGGTATTAAAGTTGCCGCACAAGAAGAGGAGGAAGTAGGGTTCCCCGTGAAACCGCAAGTC<br>CCTCTCCGGCCCATGACCTTTAAGGGCGCTCTCGACCTGTCCCATTTCCTCCGCGAAAAGGGGGGTTTGGAA<br>GGCTTGATCATTACCAAGATTCAAAACTTCAGGGTCTATTATCGAGACAGTCGCGATCCCCTTTGGAAAGGA<br>CCTGCGAAACTTCTTTGGAAAGGAGAAGGAGCCGTGGTAATTCAGGATAATTCTGACATAAAGGTCGTCCCA<br>CGCCGAAAAGCGAAGATTATAAGAGATTATGGCAAGCAGATGGCCGGGGATGATTGTGTCGCAAGTAGACAG<br>GATGAAGACCCTAAATTCAAGCTTCCAATCCAGAAGGAAACGTGGGAGACATGGTGGACCGAGTATTGGCAA<br>GCTACTTGGATCCCAGAATGGGAATTTGTGAACACTCCCCCACTCGTAAAGCTGTGGTACCAGCTTGAAAAA<br>GAACCTATAGTCGGGGCGGAGACGTTCTATGTAGACGGCGCCGCTAATCGAGAGACAAAAGCAGCAGGCACG<br>GTACTGGTAGGCCCGACCCCTGTCAACATCATTGGACGAAATCTGTTGACCCAGATTGGGTGTACCCTTAAC<br>TTTCCCATTTCACCAATAGAGACCGTCCCGGTTAAACTGAAACCGGGTATGGATGGTCCCAAAGTAAAACAG<br>TGGCCACTTACCGAGGAGAAGATTAAGGCACTCGTTGAAATATGTACAGAAATGGAAAAAGAGGGGAAAATC<br>TCTAAAATTGGCCCTGAAAATCCGTACAACACTCCGGTATTCGCCATAAAAAAGAAGGACTCTACCAAGTGG<br>CGCAAACTCGTGGACTTTAGAGAACTGAATAAAGGACCCAGGACTTTTGGGAAGTCCAGCTGGGTATTCCT<br>CACCCCGCTGGTCTCAAGAAAAAGAAAAGTGTCACTGTCTTGGATGTTGGAGATGCGTACTTTTCAGTACCT<br>CTTGATAAAGATTTTCGAAAGTATACCGCGTTTACCATTCCCTCCATAAATAACGAAACACCGGGGATCAGG<br>TATCAATATAACGTGCTTCCACAAGGCTGGAAGGGTTCACCGGCTATTTTCCAATCTTCTATGACG |

As appropriate, in certain embodiments, the 3'-end of the polynucleotide encoding the fusion polypeptides or compound fusion polypeptides described herein comprises one or multiple tandem stop codons, e.g., two or more tandem TAG ("amber"), TAA ("ochre") or TGA ("opal" or "umber") stop codons. The multiple tandem stop codons can be the same or different.

As appropriate, in certain embodiments, the 3'-end of the polynucleotide encoding the fusion polypeptides or compound fusion polypeptides described herein does not comprise a poly A sequence. As appropriate, in certain embodiments, the 3'-end of the polynucleotide encoding the fusion polypeptides or compound fusion polypeptides described herein comprises a poly A sequence.

Further provided are expression cassettes, comprising a polynucleotide encoding a fusion polypeptide or a compound fusion polypeptide, as described herein, operably linked to one or more regulatory sequences, e.g., a promoter. In some embodiments, the polynucleotide is operably linked to and under the control of a constitutive promoter or an inducible promoter. In some embodiments, the promoter is selected from cytomegalovirus major immediate-early (CMV), the CMV enhancer fused to the chicken beta-actin promoter (CAG), human elongation factor-1α (HEF-1α), mouse cytomegalovirus (mouse CMV), Chinese hamster elongation factor-1α (CHEF-1α), and phosphoglycerate kinase (PGK). In some embodiments, the promoter is a native promoter of the viral expression vector, e.g., an arenavirus vector promoter, an adenovirus vector promoter, etc.

Further provided are methods for making a fusion polypeptide or compound fusion polypeptide, pharmaceutical composition, immunogenic composition or vaccine composition comprising same. In some implementations, the methods comprise constructing the fusion polypeptides or compound fusion polypeptides using peptide synthesis. In some implementations, the methods comprise constructing, using synthetic or recombinant DNA technology, polynucleotides encoding each of the polypeptides of the bivalent antigen and expressing the polypeptides from an expression vector. In some implementations, the methods may further comprise inserting the polynucleotides into one or more vectors and expressing the encoded polypeptides in a cell.

4. Vectors and Host Cells

Further provided are vectors comprising one or more polynucleotides encoding one or more of the fusion polypeptides or compound fusion polypeptides, described herein, or an expression cassette comprising such polynucleotides. A vector can be of any type, for example, a recombinant vector such as an expression vector. Vectors include without limitation, plasmids, cosmids, bacterial artificial chromosomes (BAC) and yeast artificial chromosomes (YAC) and vectors derived from bacteriophages or plant or animal (including human) viruses. Vectors can comprise an origin of replication recognized by the proposed host cell and in the case of expression vectors, promoter and other regulatory regions recognized by the host cell. In additional embodiments, a vector comprises one or more polynucleotides encoding one or more fusion polypeptides or one or more compound fusion polypeptides, as described herein, operably linked to a promoter and optionally additional regulatory elements. Certain vectors are capable of autonomous replication in a host into which they are introduced (e.g., vectors having a bacterial origin of replication can replicate in bacteria). Other vectors can be integrated into the genome of a host upon introduction into the host, and thereby are replicated along with the host genome. Vectors include without limitation, those suitable for recombinant production of the fusion polypeptides and/or compound fusion polypeptides, disclosed herein.

The term “vector,” as used herein, refers to a nucleic acid molecule capable of propagating another nucleic acid to which it is linked. The term includes the vector as a self-replicating nucleic acid structure as well as the vector incorporated into the genome of a host cell into which it has been introduced. Some vectors are suitable for delivering the nucleic acid molecule or polynucleotide of the present application. Certain vectors are capable of directing the expression of nucleic acids to which they are operatively linked. Such vectors are referred to herein as expression vectors.

The term “operably linked” refers to two or more nucleic acid sequence elements that are usually physically linked and are in a functional relationship with each other. For instance, a promoter is operably linked to a coding sequence if the promoter is able to initiate or regulate the transcription or expression of a coding sequence, in which case, the coding sequence should be understood as being “under the control of” the promoter.

The choice of the vector is dependent on the recombinant procedures followed and the host used. Introduction of vectors into host cells can be effected by inter alia calcium phosphate transfection, DEAE-dextran-mediated transfection, lipofectamine transfection, electroporation, virus infection, or via administration to a subject, as described herein. Vectors may be autonomously replicating or may replicate together with the chromosome into which they have been integrated. In certain embodiments, the vectors contain one or more selection markers. The choice of the markers may depend on the host cells of choice. These include without limitation, kanamycin, neomycin, puromycin, hygromycin, zeocin, thymidine kinase gene from Herpes simplex virus (HSV-TK), and dihydrofolate reductase gene from mouse (dhfr). Vectors comprising one or more nucleic acid molecules encoding the fusion polypeptides or compound fusion polypeptides, described herein, operably linked to one or more nucleic acid molecules encoding proteins or peptides that can be used to isolate the fusion polypeptides or compound fusion polypeptides, are also contemplated. These proteins or peptides include without limitation, glutathione-S-transferase, maltose binding protein, metal-binding polyhistidine, green fluorescent protein, luciferase and beta-galactosidase.

In various embodiments, the vector comprises one or more polynucleotides encoding one or more fusion polypeptides comprising or consisting of an amino acid sequence of any one of SEQ ID NOs: 70-101, 105-112, 200-209, 222-223 and 227, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70-101, 105-112, 200-209, 222-223 and 227. In various embodiments, the vector comprises one or more polynucleotides encoding one or more fusion polypeptides comprising or consisting of an amino acid sequence of any one of SEQ ID NOs: 82-83, 85-87, 98-101, 209 and 222-223, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82-83, 85-87, 98-101, 209 and 222-223.

In various embodiments, the vector comprises a polynucleotide encoding a fusion polypeptide comprising or consisting of an amino acid sequence of SEQ ID NO: 82, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:82. In various embodiments, the vector comprises a polynucleotide encoding a fusion polypeptide comprising or consisting of an amino acid sequence of SEQ ID NO: 83, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:83. In various embodiments, the vector comprises a polynucleotide encoding a fusion polypeptide comprising or consisting of an amino acid sequence of SEQ ID NO: 85, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:85. In various embodiments, the vector comprises a polynucleotide encoding a fusion polypeptide comprising or consisting of an amino acid sequence of SEQ ID NO: 86, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:86. In various embodiments, the vector comprises a polynucleotide encoding a fusion polypeptide comprising or consisting of an amino acid sequence of SEQ ID NO: 87, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:87. In various embodiments, the vector comprising a polynucleotide encoding one or more of the foregoing fusion polypeptides is a Cali mammarenavirus (a.k.a., Pichinde mammarenavirus or Pichinde arenavirus.

In various embodiments, the vector comprises a polynucleotide encoding a fusion polypeptide comprising or consisting of an amino acid sequence of SEQ ID NO: 85, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:85. In various embodiments, the vector comprises a polynucleotide encoding a fusion polypeptide comprising or consisting of an amino acid sequence of SEQ ID NO: 98, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:98. In various embodiments, the vector comprises a polynucleotide encoding a fusion polypeptide comprising or consisting of an amino acid sequence of SEQ ID NO: 99, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:99. In various embodiments, the vector comprises a polynucleotide encoding a fusion polypeptide comprising or consisting of an amino acid sequence of SEQ ID NO: 100, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 100. In various embodiments, the vector comprises a polynucleotide encoding a fusion polypeptide comprising or consisting of an amino acid sequence of SEQ ID NO: 101, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 101. In various embodiments, the vector comprising a polynucleotide encoding one or more of the foregoing fusion polypeptides is a Lymphocytic choriomeningitis mammarenavirus (LCMV).

In various embodiments, the vector comprises a polynucleotide encoding a fusion polypeptide comprising or consisting of an amino acid sequence of SEQ ID NO: 209, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 209. In various embodiments, the vector comprises a polynucleotide encoding a fusion polypeptide comprising or consisting of an amino acid sequence of SEQ ID NO: 222, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 222. In various embodiments, the vector comprises a polynucleotide encoding a fusion polypeptide comprising or consisting of an amino acid sequence of SEQ ID NO: 223, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 223. In various embodiments, the vector comprises a polynucleotide encoding a fusion polypeptide comprising or consisting of an amino acid sequence of SEQ ID NO: 227, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 227.

In various embodiments, the vector comprises one or more polynucleotides encoding the following first fusion polypeptide and second fusion polypeptide, optionally joined or connected by one or more linkers:

- SEQ ID NOs: 70 and 71, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70 and 71, respectively;
- SEQ ID NOs: 72 and 73, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 72 and 73, respectively;
- SEQ ID NOs: 74 and 75, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 74 and 75, respectively;
- SEQ ID NOs: 76 and 77, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 76 and 77, respectively;
- SEQ ID NOs: 78 and 79, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 78 and 79, respectively;
- SEQ ID NOs: 80 and 81, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 80 and 81, respectively;
- SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively;
- SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively;
- SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively;
- SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively;
- SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively;
- SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively;
- SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively;
- SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively;
- SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively;

SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively;

SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 88, respectively;

SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively;

SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively;

SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively;

SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively;

SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively;

SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively;

SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively;

SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively;

SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively;

SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively;

SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively;

SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively; or SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively.

In various embodiments, the vector comprises one or more polynucleotides encoding the following first fusion polypeptide and second fusion polypeptide, optionally joined or connected by one or more linkers: SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively.

In various embodiments, the vector comprises one or more polynucleotides encoding the following first fusion polypeptide and second fusion polypeptide, optionally joined or connected by one or more linkers: SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively.

In various embodiments, the vector comprises one or more polynucleotides encoding the following first fusion polypeptide and second fusion polypeptide, optionally joined or connected by one or more linkers: SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively.

In various embodiments, the vector comprises one or more polynucleotides encoding the following first fusion polypeptide and second fusion polypeptide, optionally joined or connected by one or more linkers: SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively.

In various embodiments, the vector comprises one or more polynucleotides encoding the following first fusion polypeptide and second fusion polypeptide, optionally joined or connected by one or more linkers: SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively.

In various embodiments, the vector comprises one or more polynucleotides encoding the following first fusion polypeptide and second fusion polypeptide, optionally joined or connected by one or more linkers: SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively.

In various embodiments, the vector comprises one or more polynucleotides encoding the following first fusion polypeptide and second fusion polypeptide, optionally joined or connected by one or more linkers: SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively.

In various embodiments, the vector comprises one or more polynucleotides encoding the following first fusion polypeptide and second fusion polypeptide, optionally joined or connected by one or more linkers: SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively.

In various embodiments, the vector comprises one or more polynucleotides encoding the following first fusion polypeptide and second fusion polypeptide, optionally joined or connected by one or more linkers: SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively.

In various embodiments, the vector comprises one or more polynucleotides encoding the following first fusion polypeptide and second fusion polypeptide, optionally joined or connected by one or more linkers: SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively.

In various embodiments, the vector comprises one or more polynucleotides encoding the following first fusion polypeptide and second fusion polypeptide, optionally joined or connected by one or more linkers: SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 88, respectively.

In various embodiments, the vector comprises one or more polynucleotides encoding the following first fusion polypeptide and second fusion polypeptide, optionally joined or connected by one or more linkers: SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively.

In various embodiments, the vector comprises one or more polynucleotides encoding the following first fusion polypeptide and second fusion polypeptide, optionally joined or connected by one or more linkers: SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively.

In various embodiments, the vector comprises one or more polynucleotides encoding the following first fusion polypeptide and second fusion polypeptide, optionally joined or connected by one or more linkers: SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively.

In various embodiments, the vector comprises one or more polynucleotides encoding the following first fusion polypeptide and second fusion polypeptide, optionally joined or connected by one or more linkers: SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively.

In various embodiments, the vector comprises one or more polynucleotides encoding the following first fusion polypeptide and second fusion polypeptide, optionally joined or connected by one or more linkers: SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively.

In various embodiments, the vector comprises one or more polynucleotides encoding the following first fusion polypeptide and second fusion polypeptide, optionally joined or connected by one or more linkers: SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively.

In various embodiments, the vector comprises one or more polynucleotides encoding the following first fusion polypeptide and second fusion polypeptide, optionally joined or connected by one or more linkers: SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively.

In various embodiments, the vector comprises one or more polynucleotides encoding the following first fusion polypeptide and second fusion polypeptide, optionally joined or connected by one or more linkers: SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively.

In various embodiments, the vector comprises one or more polynucleotides encoding the following first fusion polypeptide and second fusion polypeptide, optionally joined or connected by one or more linkers: SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively.

In various embodiments, the vector comprises one or more polynucleotides encoding the following first fusion polypeptide and second fusion polypeptide, optionally joined or connected by one or more linkers: SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively.

In various embodiments, the vector comprises one or more polynucleotides encoding the following first fusion polypeptide and second fusion polypeptide, optionally joined or connected by one or more linkers: SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively.

In various embodiments, the vector comprises one or more polynucleotides encoding the following first fusion polypeptide and second fusion polypeptide, optionally joined or connected by one or more linkers: SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively.

In various embodiments, the vector comprises one or more polynucleotides encoding the following first fusion polypeptide and second fusion polypeptide, optionally joined or connected by one or more linkers: SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively.

In various embodiments, the vector comprises a polynucleotide encoding a compound fusion polypeptide comprising SEQ ID NO: 105 or 206, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 105 or 206.

In various embodiments, the vector comprises a polynucleotide encoding a compound fusion polypeptide comprising SEQ ID NO: 107 or 207, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 107 or 207.

In various embodiments, the vector comprises a polynucleotide encoding a compound fusion polypeptide comprising SEQ ID NO: 109, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 109.

In various embodiments, the vector comprises a polynucleotide encoding a compound fusion polypeptide comprising SEQ ID NO: 111, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 111.

In various embodiments, the vector comprises a polynucleotide encoding a compound fusion polypeptide comprising SEQ ID NO: 200, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 200.

In various embodiments, the vector comprises a polynucleotide encoding a compound fusion polypeptide comprising SEQ ID NO: 201, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 201.

In various embodiments, the vector comprises a polynucleotide encoding a compound fusion polypeptide comprising SEQ ID NO: 202, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 202.

In various embodiments, the vector comprises a polynucleotide encoding a compound fusion polypeptide comprising SEQ ID NO: 203, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 203.

In various embodiments, the vector comprises a polynucleotide encoding a compound fusion polypeptide comprising SEQ ID NO: 204, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 204.

In various embodiments, the vector comprises a polynucleotide encoding a compound fusion polypeptide comprising SEQ ID NO: 205, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 205.

In various embodiments, the vector comprises a polynucleotide encoding a compound fusion polypeptide comprising SEQ ID NO: 208, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 208.

In various embodiments, the vector comprises a polynucleotide encoding a compound fusion polypeptide comprising SEQ ID NO: 209, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 209.

In various embodiments, the vector comprises a polynucleotide encoding a compound fusion polypeptide comprising SEQ ID NO: 222, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 222.

In various embodiments, the vector comprises a polynucleotide encoding a compound fusion polypeptide comprising SEQ ID NO: 223, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 223.

In various embodiments, the vector comprises a polynucleotide encoding a compound fusion polypeptide comprising SEQ ID NO: 227, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 227.

In some embodiments, the vector comprises a polynucleotide encoding a fusion polypeptide or a compound fusion polypeptide, as described herein, which has a nucleic acid sequence of any one of SEQ ID NOs: 130-167, 210-219 and 225-226, or a nucleic acid sequence that is at least 80%, at least 85%, at least 90%, at least 91%, at least 92%, at least 93%, at least 94%, at least 95%, at least 96%, at least 97%, at least 98%, at least 99% identical, or 100% identical to a nucleic acid sequence selected from SEQ ID NOs: 130-167, 210-219 and 225-226. In some embodiments, the vector comprises a polynucleotide encoding a fusion polypeptide or a compound fusion polypeptide, as described herein, which has a nucleic acid sequence of any one of SEQ ID NOs: 139, 140, 142, 143, 145, 146, 148, 149, 150, 152, 155, 158, 225 and 226, or a nucleic acid sequence that is at least 80%, at least 85%, at least 90%, at least 91%, at least 92%, at least 93%, at least 94%, at least 95%, at least 96%, at least 97%, at least 98%, at least 99% identical, or 100% identical to a nucleic acid sequence selected from SEQ ID NOs: 139, 140, 142, 143, 145, 146, 148, 149, 150, 152, 155, 158, 225 and 226.

In some embodiments, the vector comprises a polynucleotide encoding a fusion polypeptide or a compound fusion polypeptide, as described herein, which has a nucleic acid sequence of SEQ ID NO: 139, or a nucleic acid sequence that is at least 80%, at least 85%, at least 90%, at least 91%, at least 92%, at least 93%, at least 94%, at least 95%, at least 96%, at least 97%, at least 98%, at least 99% identical, or 100% identical to a nucleic acid sequence of SEQ ID NO: 139. In some embodiments, the vector comprises a polynucleotide encoding a fusion polypeptide or a compound fusion polypeptide, as described herein, which has a nucleic acid sequence of SEQ ID NO: 142, or a nucleic acid sequence that is at least 80%, at least 85%, at least 90%, at least 91%, at least 92%, at least 93%, at least 94%, at least 95%, at least 96%, at least 97%, at least 98%, at least 99% identical, or 100% identical to a nucleic acid sequence of SEQ ID NO: 142. In some embodiments, the vector comprises a polynucleotide encoding a fusion polypeptide or a compound fusion polypeptide, as described herein, which has a nucleic acid sequence of SEQ ID NO: 145, or a nucleic acid sequence that is at least 80%, at least 85%, at least 90%, at least 91%, at least 92%, at least 93%, at least 94%, at least 95%, at least 96%, at least 97%, at least 98%, at least 99% identical, or 100% identical to a nucleic acid sequence of SEQ ID NO: 145. In some embodiments, the vector comprises a polynucleotide encoding a fusion polypeptide or a compound fusion polypeptide, as described herein, which has a nucleic acid sequence of SEQ ID NO: 148, or a nucleic acid sequence that is at least 80%, at least 85%, at least 90%, at least 91%, at least 92%, at least 93%, at least 94%, at least 95%, at least 96%, at least 97%, at least 98%, at least 99% identical, or 100% identical to a nucleic acid sequence of SEQ ID NO: 148. In various embodiments, the vector comprising one or more of the foregoing polynucleotides is a Lymphocytic choriomeningitis mammarenavirus (LCMV).

In some embodiments, the vector comprises a polynucleotide encoding a fusion polypeptide or a compound fusion polypeptide, as described herein, which has a nucleic acid sequence of SEQ ID NO: 150, or a nucleic acid sequence that is at least 80%, at least 85%, at least 90%, at least 91%, at least 92%, at least 93%, at least 94%, at least 95%, at least 96%, at least 97%, at least 98%, at least 99% identical, or 100% identical to a nucleic acid sequence of SEQ ID NO: 150. In some embodiments, the vector comprises a polynucleotide encoding a fusion polypeptide or a compound fusion polypeptide, as described herein, which has a nucleic acid sequence of SEQ ID NO: 152, or a nucleic acid sequence that is at least 80%, at least 85%, at least 90%, at least 91%, at least 92%, at least 93%, at least 94%, at least 95%, at least 96%, at least 97%, at least 98%, at least 99% identical, or 100% identical to a nucleic acid sequence of SEQ ID NO: 152. In some embodiments, the vector comprises a polynucleotide encoding a fusion polypeptide or a compound fusion polypeptide, as described herein, which has a nucleic acid sequence of SEQ ID NO: 155, or a nucleic acid sequence that is at least 80%, at least 85%, at least 90%, at least 91%, at least 92%, at least 93%, at least 94%, at least 95%, at least 96%, at least 97%, at least 98%, at least 99% identical, or 100% identical to a nucleic acid sequence of SEQ ID NO: 155. In some embodiments, the vector comprises a polynucleotide encoding a fusion polypeptide or a compound fusion polypeptide, as described herein, which has a nucleic acid sequence of SEQ ID NO: 158, or a nucleic acid sequence that is at least 80%, at least 85%, at least 90%, at least 91%, at least 92%, at least 93%, at least 94%, at least 95%, at least 96%, at least 97%, at least 98%, at least 99% identical, or 100% identical to a nucleic acid sequence of SEQ ID NO: 158. In various embodiments, the vector comprising one or more of the foregoing polynucleotides is a Cali mammarenavirus (a.k.a., Pichinde mammarenavirus or Pichinde arenavirus).

In some embodiments, the vector comprises a polynucleotide encoding a fusion polypeptide or a compound fusion polypeptide, as described herein, which has a nucleic acid sequence of SEQ ID NO: 225, or a nucleic acid sequence that is at least 80%, at least 85%, at least 90%, at least 91%, at least 92%, at least 93%, at least 94%, at least 95%, at least 96%, at least 97%, at least 98%, at least 99% identical, or 100% identical to a nucleic acid sequence of SEQ ID NO: 225. In some embodiments, the vector comprises a polynucleotide encoding a fusion polypeptide or a compound fusion polypeptide, as described herein, which has a nucleic acid sequence of SEQ ID NO: 226, or a nucleic acid sequence that is at least 80%, at least 85%, at least 90%, at least 91%, at least 92%, at least 93%, at least 94%, at least 95%, at least 96%, at least 97%, at least 98%, at least 99% identical, or 100% identical to a nucleic acid sequence of SEQ ID NO: 226.

In various embodiments, the vector comprises the following first polynucleotide and second polynucleotide:

SEQ ID NOs: 130 and 132, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 130 and 132, respectively;

SEQ ID NOs: 130 and 134, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 130 and 134, respectively;

SEQ ID NOs: 131 and 133, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 131 and 133, respectively;

SEQ ID NOs: 131 and 135, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 131 and 135, respectively;

SEQ ID NOs: 132 and 136, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 132 and 136, respectively;

SEQ ID NOs: 133 and 135, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 133 and 135, respectively;

SEQ ID NOs: 133 and 137, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 133 and 137, respectively;

SEQ ID NOs: 134 and 136, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 134 and 136, respectively;

SEQ ID NOs: 135 and 137, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 135 and 137, respectively;

SEQ ID NOs: 138 and 141, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 138 and 141, respectively;

SEQ ID NOs: 138 and 144, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 138 and 144, respectively;

SEQ ID NOs: 139 and 142, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 142, respectively;

SEQ ID NOs: 139 and 145, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 145, respectively;

SEQ ID NOs: 140 and 146, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 140 and 146, respectively;

SEQ ID NOs: 142 and 148, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 142 and 148, respectively;

SEQ ID NOs: 143 and 149, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 143 and 149, respectively;

SEQ ID NOs: 145 and 148, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 145 and 148, respectively;

SEQ ID NOs: 150 and 152, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively;

SEQ ID NOs: 150 and 155, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 155, respectively;

SEQ ID NOs: 151 and 153, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 151 and 153, respectively;

SEQ ID NOs: 151 and 156, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 151 and 156, respectively;

SEQ ID NOs: 152 and 158, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 152 and 158, respectively;

SEQ ID NOs: 153 and 159, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 153 and 159, respectively;

SEQ ID NOs: 154 and 157, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 154 and 157, respectively;

SEQ ID NOs: 155 and 158, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 155 and 158, respectively;

SEQ ID NOs: 156 and 159, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 156 and 159, respectively;

SEQ ID NOs: 160 and 161, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 160 and 161, respectively;

SEQ ID NOs: 162 and 163, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 162 and 163, respectively;

SEQ ID NOs: 164 and 165, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 164 and 165, respectively;

SEQ ID NOs: 166 and 167, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 166 and 167, respectively;

SEQ ID NOs: 210 and 211, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 210 and 211, respectively;

SEQ ID NOs: 212 and 213, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 212 and 213, respectively;

SEQ ID NOs: 214 and 215, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 214 and 215, respectively;

SEQ ID NOs: 216 and 217, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 216 and 217, respectively;

SEQ ID NOs: 218 and 219, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 218 and 219, respectively;

SEQ ID NOs: 218 and 226, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 218 and 226, respectively; or SEQ ID NOs: 225 and 226, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 225 and 226, respectively.

In various embodiments, the vector comprises the following first polynucleotide and second polynucleotide:

a) a first polynucleotide comprising SEQ ID NO: 130 or SEQ ID NO: 131, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 130 or SEQ ID NO: 131, respectively, and b) a second polynucleotide comprising SEQ ID NO: 134 or SEQ ID NO: 135, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 134 or SEQ ID NO: 135.

In various embodiments, the vector comprises the following first polynucleotide and second polynucleotide:

a) a first polynucleotide comprising SEQ ID NO: 132 or SEQ ID NO: 133, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 132 or SEQ ID NO: 133, respectively, and b) a second polynucleotide comprising SEQ ID NO: 136 or SEQ ID NO: 137, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 136 or SEQ ID NO: 137.

In various embodiments, the vector comprises the following first polynucleotide and second polynucleotide:

a) a first polynucleotide comprising SEQ ID NO: 139, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 139, respectively, and b) a second polynucleotide comprising SEQ ID NO: 145, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 145.

In various embodiments, the vector comprises the following first polynucleotide and second polynucleotide:

a) a first polynucleotide comprising SEQ ID NO: 140, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 140, respectively, and b) a second polynucleotide comprising SEQ ID NO: 146, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 146.

In various embodiments, the vector comprises the following first polynucleotide and second polynucleotide:

a) a first polynucleotide comprising SEQ ID NO: 142, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 142, respectively, and b) a second polynucleotide comprising SEQ ID NO: 148, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 148.

In various embodiments, the vector comprises the following first polynucleotide and second polynucleotide:

a) a first polynucleotide comprising SEQ ID NO: 143, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 143, respectively, and b) a second polynucleotide comprising SEQ ID NO: 149, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 149.

In various embodiments, the vector comprises the following first polynucleotide and second polynucleotide:

a) a first polynucleotide comprising SEQ ID NO: 150, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 150, respectively, and b) a second polynucleotide comprising SEQ ID NO: 152, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 152.

In various embodiments, the vector comprises the following first polynucleotide and second polynucleotide:

a) a first polynucleotide comprising SEQ ID NO: 151, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 151, respectively, and b) a second polynucleotide comprising SEQ ID NO: 153, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 153.

In various embodiments, the vector comprises the following first polynucleotide and second polynucleotide:

a) a first polynucleotide comprising SEQ ID NO: 154, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 154, respectively, and b) a second polynucleotide comprising SEQ ID NO: 157, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 157.

In various embodiments, the vector comprises the following first polynucleotide and second polynucleotide:

a) a first polynucleotide comprising SEQ ID NO: 155, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 155, respectively, and b) a second polynucleotide comprising SEQ ID NO: 158, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 158.

In various embodiments, the vector comprises the following first polynucleotide and second polynucleotide:

a) a first polynucleotide comprising SEQ ID NO: 156, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 156, respectively, and b) a second polynucleotide comprising SEQ ID NO: 159, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 159.

In various embodiments, the vector comprises the following first polynucleotide and second polynucleotide:

a) a first polynucleotide comprising SEQ ID NO: 160, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 160, respectively, and b) a second polynucleotide comprising SEQ ID NO: 161, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 161.

In various embodiments, the vector comprises the following first polynucleotide and second polynucleotide:

a) a first polynucleotide comprising SEQ ID NO: 162, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 162, respectively, and b) a second polynucleotide comprising SEQ ID NO: 163, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 163.

In various embodiments, the vector comprises the following first polynucleotide and second polynucleotide:

a) a first polynucleotide comprising SEQ ID NO: 164, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 164, respectively, and b) a second polynucleotide comprising SEQ ID NO: 165, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 165.

In various embodiments, the vector comprises the following first polynucleotide and second polynucleotide:

a) a first polynucleotide comprising SEQ ID NO: 166, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 166, respectively, and b) a second polynucleotide comprising SEQ ID NO: 167, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 167.

In various embodiments, the vector comprises the following first polynucleotide and second polynucleotide:

a) a first polynucleotide comprising SEQ ID NO: 210, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 210, and b) a second polynucleotide comprising SEQ ID NO: 211, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 211.

In various embodiments, the vector comprises the following first polynucleotide and second polynucleotide:

a) a first polynucleotide comprising SEQ ID NO: 212, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 212, and b) a second polynucleotide comprising SEQ ID NO: 213, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 213.

In various embodiments, the vector comprises the following first polynucleotide and second polynucleotide:

a) a first polynucleotide comprising SEQ ID NO: 214, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 214, and b) a second polynucleotide comprising SEQ ID NO: 215, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 215.

In various embodiments, the vector comprises the following first polynucleotide and second polynucleotide:

a) a first polynucleotide comprising SEQ ID NO: 216, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 216, and b) a second polynucleotide comprising SEQ ID NO: 217, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 217.

In various embodiments, the vector comprises the following first polynucleotide and second polynucleotide:

a) a first polynucleotide comprising SEQ ID NO: 218, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 218, and b) a second polynucleotide comprising SEQ ID NO: 219, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 219.

In various embodiments, the vector comprises the following first polynucleotide and second polynucleotide:

a) a first polynucleotide comprising SEQ ID NO: 218, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 218, and b) a second polynucleotide comprising SEQ ID NO: 226, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 226.

In various embodiments, the vector comprises the following first polynucleotide and second polynucleotide:

a) a first polynucleotide comprising SEQ ID NO: 225, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 225, and b) a second polynucleotide comprising SEQ ID NO: 226, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 226.

In various embodiments, the vector comprises a polynucleotide comprising SEQ ID NO: 225, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 225.

In various embodiments, the vector comprises a polynucleotide comprising SEQ ID NO: 226, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 226.

In other embodiments, the vector that is used is pcDNA™3.1+ (ThermoFisher, MA).

In some embodiments, the vector is viral vector. As appropriate, the viral vector can be a DNA virus or an RNA virus, including a self-replicating RNA virus. Self-replicating RNA viruses include Alphaviruses, and are described, e.g., in Lundstrom, *Molecules*. (2018) 23(12). pii: E3310 (PMID: 30551668); and Ljungberg, et al., *Expert Rev Vaccines*. (2015) 14(2):177-94). Additional alphaviruses of use as viral vectors are described, e.g., in WO 2020/097393 and WO 2018/208856. In various embodiments, the viral vector is from a virus selected from adenovirus, adeno-associated virus, arenavirus, alphavirus, self-replicating alphavirus, poxvirus, cytomegalovirus, rhabdovirus, vesicular stomatitis virus, flavivirus, maraba virus and vaccinia virus. In some embodiments, the viral vector is from a viral family selected from: Adenoviridae (e.g., Adenovirus, adeno-associated virus), Arenaviridae (e.g., lymphocytic choriomeningitis mammarenavirus, Cali mammarenavirus (a.k.a., Pichinde mammarenavirus), Poxviridae (e.g., Vaccinia virus), Herpesviridae (e.g., Cytomegalovirus, Herpesvirus, e.g., HSV-1), Parvoviridae (e.g., Parvovirus H1), Poxviridae (e.g. Vaccinia virus, e.g. modified vaccinia Ankara (MVA)), Flaviviridae (e.g. Yellow fever virus), Reoviridae (e.g., Reovirus), Picornaviridae (e.g., Coxsackievirus, Seneca Valley Virus, Poliovirus), Paramyxoviridae (e.g., Measles virus, Newcastle disease virus (NDV)), Rhabdoviridae (e.g., Vesiculovirus, including Maraba vesiculovirus and Vesicular stomatitis virus (VSV)), Togaviridae (e.g., Alphavirus, e.g., Venezuelan equine encephalitis virus, e.g., self-replicating Alphavirus; Sindbis virus), Enteroviridae (e.g., Echovirus). Illustrative modified vaccinia viral vectors of use for expressing the present fusion polypeptides and/or compound fusion polypeptides are described, e.g., in WO 2019/134049.

In some embodiments, the viral expression vector is an arenavirus vector selected from Lymphocytic choriomeningitis mammarenavirus (LCMV)(NCBI:txid11623), Cali mammarenavirus (a.k.a., Pichinde mammarenavirus or Pichinde arenavirus) (NCBI:txid2169993), Guanarito virus (GTOV) (NCBI:txid45219), Argentinian mammarenavirus (a.k.a., Junin virus (JUNV))(NCBI:txid2169991), Lassa virus (LASV)(NCBI:txid11620), Lujo virus (LUJV)(NCBI:txid649188), Machupo virus (MACV)(NCBI:txid11628), Brazilian mammarenavirus (a.k.a., Sabia virus (SABV)) (NCBI:txid2169992), and Whitewater Arroyo virus (WWAV)(NCBI:txid46919). In some embodiments, the viral expression vector is an arenavirus vector selected from Lymphocytic choriomeningitis mammarenavirus (LCMV) or Cali mammarenavirus (a.k.a., Pichinde mammarenavirus or Pichinde arenavirus). Illustrative arenavirus vectors that can be used as delivery and expression vehicles for the herein described fusion polypeptides are described, e.g., in WO 2009/083210; WO 2015/183895; WO 2016/075250; WO 2017/198726; and U.S. Pat. No. 9,943,585.

In some embodiments, the viral expression vector is an adenovirus vector, e.g., from a human adenovirus or a simian adenovirus (e.g., a chimpanzee adenovirus, a gorilla adenovirus or a rhesus monkey adenovirus). In various embodiments, the adenovirus vector is selected from adenovirus serotype 5 (Ad5), adenovirus serotype 26 (Ad26), adenovirus serotype 34 (Ad34), adenovirus serotype 35 (Ad35), adenovirus serotype 48 (Ad48), chimpanzee adenovirus (e.g. ChAd3 (AdC3), ChAd5 (AdC5), ChAd6 (AdC6), ChAd7 (AdC7), ChAd8 (AdC8), ChAd9 (AdC9), ChAd10 (AdC10), ChAd11 (AdC11), ChAd17 (AdC17), ChAd16 (AdC16), ChAd19 (AdC19), ChAd20 (AdC20), ChAd22 (AdC22), ChAd24 (AdC24), ChAdY25, ChAd26 (AdC26), ChAd28 (AdC28), ChAd30 (AdC30), ChAd31 (AdC31), ChAd37 (AdC37), ChAd38 (AdC38), ChAd43 (AdC43), ChAd44 (AdC44), ChAd55 (AdC55), ChAd63 (AdC63), ChAdV63, ChAd68 (AdC68), ChAd73 (AdC73), ChAd82 (AdC82), ChAd83 (AdC83), ChAd143 (AdC143), ChAd144 (AdC144), ChAd145 (AdC145), ChAd147 (AdC147)), gorilla adenovirus (e.g. GC44, GC45, GC46) and rhesus adenovirus (e.g., RhAd51, RhAd52, RhAd53, RhAd54, RhAd55, RhAd56, RhAd57, RhAd58, RhAd59, RhAd60, RhAd61, RhAd62, RhAd63, RhAd64, RhAd65, RhAd66). Illustrative Chimpanzee, Gorilla and Rhesus monkey adenovirus vectors that can be used as delivery and expression vehicles for the herein described fusion polypeptides and/or compound fusion polypeptides are described, e.g., in WO 2019/076880; WO 2019/076877; Andrabi et al., (2019) *Cell Reports* 27:2426-2441; Guo, et al., *Hum Vaccin Immunother*. (2018) 14(7):1679-1685; Abbink, et al., *J Virol*. (2015) 89(3):1512-22; Abbink, et al., *J Virol*. (2018) 92(6). pii: e01924-17, and in WO 2020/243719A1 and WO 2018/098362A1.

In various embodiments, the viral expression vector is incapable of replication (i.e., replication defective or replication deficient), has reduced or diminished capacity for replication, e.g., in comparison to a wild-type viral vector (i.e., replication attenuated) or is replication competent.

Further provided are host cells comprising one or more polynucleotides encoding one or more of the fusion polypeptides or compound fusion polypeptides, or one or more vectors expressing the fusion polypeptides or compound fusion polypeptides, as described herein. Any of a variety of host cells can be used. In one embodiment, a host cell is a prokaryotic cell, for example, *E. coli*. In another embodiment, a host cell is a eukaryotic cell, for example, a yeast cell, a plant cell, an insect cell, a mammalian cell, such as a Chinese Hamster Ovary (CHO)-based or CHO-origin cell line (e.g., CHO-S, CHO DG44, ExpiCHO™, CHOZN® ZFN-modified GS−/− CHO cell line, CHO-K1, CHO-K1a), COS cells, BHK cells, NSO cells or Bowes melanoma cells. Examples of human host cells are, inter alia, HeLa, 911, AT1080, A549 and HEK293 (e.g., HEK293E, HEK293F, HEK293H, HEK293T, Expi293™) In addition, the fusion polypeptides and/or compound fusion polypeptides can be expressed in a yeast cell such as *Pichia* (see, e.g., Powers et al., *J Immunol Methods*. 251:123-35 (2001)), *Hanseula*, or *Saccharomyces*.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As appropriate, the host cells can be stably or transiently transfected with one or more polynucleotides encoding one or more fusion polypeptides or compound fusion polypeptides, as described herein. As appropriate, the host cells can be infected with one or more vectors expressing one or more fusion polypeptides or compound fusion polypeptides, as described herein. In some embodiments, the host cells are capable of being infected with and propagating one or more replication attenuated or replication competent vectors expressing one or more fusion polypeptides or compound fusion polypeptides, as described herein. Illustrative cells useful for infecting with and/or propagating viral vectors include without limitation BHK-21, A549, Vero and HEK293 (e.g., HEK293E, HEK293F, HEK293H, HEK293T, Expi293™) cells. In certain embodiments, the host cells express the Coxsackievirus and adenovirus receptor (CAR), e.g., MDCK, Caco-2 or Calu-3 host cells. In certain embodiments, the polynucleotides integrate into the genome of the host cell.

5. Pharmaceutical Compositions/Immunogenic Compositions

Provided are pharmaceutical compositions or immunogenic compositions comprising one or more of the fusion polypeptides or compound fusion polypeptides, as described herein, or a polynucleotide encoding one or more of the fusion polypeptides or compound fusion polypeptides, as described herein, or a viral expression vector comprising one or more of such polynucleotides, and a pharmaceutically acceptable diluent, carrier or excipient. Generally, the pharmaceutical compositions described herein are immunogenic. In certain embodiments, the pharmaceutical composition comprises a therapeutically effective amount of the one or more fusion polypeptides or compound fusion polypeptides, or one or more polynucleotides encoding one or more of the fusion polypeptides or compound fusion polypeptides, or one or more viral expression vectors containing one or more of the polynucleotides encoding one or more of the fusion polypeptides or compound fusion polypeptides.

Various pharmaceutically acceptable diluents, carriers, and excipients, and techniques for the preparation and use of pharmaceutical compositions or immunogenic compositions will be known to those of skill in the art in light of the present disclosure. Illustrative pharmaceutical compositions/immunogenic compositions and pharmaceutically acceptable diluents, carriers, and excipients are also described in, e.g., Loyd V. Allen Jr (Editor), "Remington: The Science and Practice of Pharmacy," $22^{nd}$ Edition, 2012, Pharmaceutical Press; Brunton, Knollman and Hilal-Dandan, "Goodman and Gilman's The Pharmacological Basis of Therapeutics," 13th Edition, 2017, McGraw-Hill Education/Medical; McNally and Hastedt (Editors), "Protein Formulation and Delivery, 2nd Edition, 2007, CRC Press; Banga, "Therapeutic Peptides and Proteins: Formulation, Processing, and Delivery Systems," 3rd Edition, 2015, CRC Press; Lars Hovgaard, Frokjaer and van de Weert (Editors), "Pharmaceutical Formulation Development of Peptides and Proteins," 2nd Edition, 2012, CRC Press; Carpenter and Manning (Editors), "Rational Design of Stable Protein Formulations: Theory and Practice," 2002, Springer (Pharmaceutical Biotechnology (Book 13)); Meyer (Editor), "Therapeutic Protein Drug Products: Practical Approaches to Formulation in the Laboratory, Manufacturing, and the Clinic, 2012, Woodhead Publishing.

In certain embodiments, the polynucleotides or vectors are formulated into a lipoplex, e.g., a lipid nanoparticle (LNP). As used herein, a "lipoplex" refers to cationic liposomes that are nonviral (synthetic) lipid carriers of one or more polynucleotides, e.g., RNA, DNA. For example, in some embodiments where the fusion polypeptides and/or compound fusion polypeptides are expressed from self-replicating or self-amplifying RNA molecules, the self-replicating or self-amplifying RNA can be formulated into LNPs. As used herein, the term "lipid nanoparticle" refers to one or more spherical nanoparticles with an average diameter of between about 10 to about 1000 nanometers, and which comprise a solid lipid core matrix that can solubilize lipophilic molecules. In certain embodiments, the lipid core is stabilized by surfactants (e.g., emulsifiers), and can comprise one or more of triglycerides (e.g., tristearin), diglycerides (e.g., glycerol bahenate), monoglycerides (e.g., glycerol monostearate), fatty acids (e.g., stearic acid), steroids (e.g., cholesterol), and waxes (e.g., cetyl palmitate), including combinations thereof. Lipid nanoparticles are described, for example, in Petrilli et al., Curr Pharm Biotechnol. 15:847-55, 2014; and U.S. Pat. Nos. 6,217,912; 6,881,421; 7,402,573; 7,404,969; 7,550,441; 7,727,969; 8,003,621; 8,691,750; 8,871,509; 9,017,726; 9,173,853; 9,220,779; 9,227,917; and 9,278,130, each of which is incorporated by reference in its entirety. In one embodiment, a self-replicating or self-amplifying RNA (saRNA) molecule encoding one or more of the fusion polypeptides or compound fusion polypeptides described herein is formulated or condensed into polyethylenimine (PEI)-polyplex delivery vehicles, e.g., as described in Moyo, et al., *Mol Ther Methods Clin Dev*. (2018) 12:32-46; Blakney, et al., *Gene Therapy* (2019) 26:363-372; Démoulins, et al., *Nanomedicine*. (2016) April; 12(3):711-722 and Démoulins, et al., *J Control Release*. (2017) 266:256-271, which can be nanoparticulate.

In embodiments where the fusion polypeptides or compound fusion polypeptides are expressed from a viral expression vector, the viral expression vector can be formulated for the desired route of administration, e.g., as an isotonic pharmaceutically acceptable aqueous solution for intravenous, intramuscular, subcutaneous, intradermal or intranodal administration. In some embodiments, the viral expression vector can be formulated for mucosal, e.g., buccal or intra-rectal delivery. Illustrative formulations for viral expression vectors that can be used in the herein described pharmaceutical compositions/immunogenic compositions and methods are described, e.g., in Manfredsson and Benskey, editors, "Viral Vectors for Gene Therapy: Methods and Protocols (Methods in Molecular Biology)," 2019, Book 1937 in Methods in Molecular Biology Series, Humana Press; WO 2017/013169 (formulation of Adenoviral vectors in an aqueous mixture or freeze dried composition in the presence of amorphous sugar and low salt concentration); and Kumru, et al., *J Pharm Sci*. (2018) November; 107(11):2764-3374 (aqueous formulations buffered in Tris and containing proline, lactose, and mannitol as stabilizing additives). Formulation of arenavirus vectors is described, e.g., in WO 2009/083210; WO 2016/075250 and WO 2017/198726. In certain embodiments, the viral expression vectors are delivered via microneedle-mediated delivery, e.g., as described in Zaric, et al., *Expert Opin Drug Deliv*. (2017) October; 14(10):1177-1187. Intranodal delivery of mRNA vaccines are described, e.g., in Jong, et al., *Vaccines* (Basel). (2019) 7(4):209; Leal, et al., *AIDS*. (2018) 32(17):2533-2545; de Jong, et al., *Trials*. (2019) 20(1):361; and Joe, et al., *J Transl Med*. (2019) 17(1):242.

In some embodiments, each carrier, diluent or excipient is "acceptable" in the sense of being compatible with the other ingredients of the pharmaceutical composition/immunogenic composition and not injurious to the subject. Often, the pharmaceutically acceptable carrier is an aqueous pH-buffered solution. Some examples of materials which can serve as pharmaceutically-acceptable carriers, diluents or excipients include: water; buffers, e.g., a buffer having a pKa in the range of about 6.0 to about 8.0, e.g., a physiologically acceptable buffer, e.g., selected from phosphate, carbonate, bicarbonate, citrate, maleate, glycine-glycine, HEPES, HEPPSO, HEPPS, imidazole, BICINE, TRICINE, Tris, and BIS-Tris; sugars, such as lactose, trehalose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Hank's solution, Ringer's solution; ethyl alcohol; phosphate buffer solutions; amino acids (e.g., charged amino acids, including without limitation, aspartate, asparagine, glutamate, glutamine, histidine, arginine, lysine); and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

In one particular formulation, an arenavirus vector (e.g., a LCMV or Pichinde mammarenavirus vector (PICV)) described herein is formulated in an isotonic aqueous solution comprising a biologically compatible buffer having a pKa in the range of about 6.0 to about 8.0 (e.g., HEPES and NaCl), at a neutral or near-neutral pH and a non-ionic surfactant (e.g., PLURONIC® F68 (a.k.a., poloxamer 188)). In one particular formulation, an arenavirus vector (e.g., a LCMV or Pichinde mammarenavirus vector) described herein is formulated in an isotonic aqueous solution comprising HEPES buffer at pH 7.4, NaCl, and PLURONIC® F68 (a.k.a., poloxamer 188). Schleiss, et al. (*Clin Vaccine Immunol.* 2017 Jan. 5; 24(1):e00300-16) describes an LCMV formulating LCMV vectors in a diluent of 25 mM HEPES, 150 mM NaCl, 0.01% PLURONIC® F68; pH 7.4), which can be used to formulate the herein described arenavirus vectors. A final concentration of 10% sorbitol was added before freezing below −60° C.

The formulation of and delivery methods of pharmaceutical compositions or immunogenic compositions will generally be adapted according to the site and the disease to be treated. Exemplary formulations include without limitation, those suitable for parenteral administration, e.g., intravenous, intra-arterial, intramuscular, subcutaneous or intranodal administration, including formulations encapsulated in micelles, liposomes or drug-release capsules (active agents incorporated within a biocompatible coating designed for slow-release); ingestible formulations; formulations for topical use, such as creams, ointments and gels; and other formulations such as inhalants, aerosols and sprays. In some embodiments, the pharmaceutical compositions or immunogenic compositions are formulated for parenteral, e.g., intravenous, subcutaneous, intranodal or oral administration. In some embodiments, the pharmaceutical compositions or immunogenic compositions are formulated for mucosal, e.g., buccal, intrarectal and/or intravaginal administration. In some embodiments, for intrarectal administration, the pharmaceutical composition or immunogenic composition can be formulated as a suppository or as an enema. In some embodiments, for intravaginal administration, the pharmaceutical composition or immunogenic composition can be formulated as a pessary.

In certain embodiments, pharmaceutical compositions/immunogenic compositions are sterile. In certain embodiments, the pharmaceutical composition or immunogenic composition has a pH in the range of 4.5 to 8.5, 4.5 to 6.5, 6.5 to 8.5, or a pH of about 5.0, about 5.5, about 6.0, about 6.5, about 7.0, about 7.5, about 8.0 or about 8.5. In one embodiment, the pharmaceutical composition/immunogenic composition has an osmolarity in the range of 240-260 or 250-330 mOsmol/L. In certain embodiments, the pharmaceutical composition/immunogenic composition is isotonic or near isotonic.

In some embodiments, the pharmaceutical compositions or immunogenic compositions are liquids or solids. In some embodiments, the pharmaceutical composition or immunogenic composition comprises an aqueous solution. In some embodiments, the pharmaceutical composition or immunogenic composition is lyophilized or is a frozen liquid.

In some embodiments, the pharmaceutical composition or immunogenic composition further comprises one or more additional therapeutic agents, e.g., a second therapeutic agent, or second and third therapeutic agents, for use in combination therapies, as described herein.

In certain embodiments, the pharmaceutical composition or immunogenic composition further comprises an adjuvant. Illustrative adjuvants that can be co-formulated or co-administered with the herein described fusion polypeptides or compound fusion polypeptides, polynucleotides encoding such fusion polypeptides or compound fusion polypeptides, and vectors expressing such fusion polypeptides or compound fusion polypeptides, include without limitation cytokines, chemokines, immune costimulatory molecules, toll-like receptor agonists, second mitochondria-derived activator of caspases (SMAC) mimetics or inhibitors of immune suppressive pathways (e.g., immune checkpoint inhibitors), as described herein, and in Li, et al., *Curr Issues Mol Biol.* (2017) 22:17-40. Other adjuvants that can be co-formulated or co-administered with the herein described fusion polypeptides or compound fusion polypeptides, polynucleotides encoding such fusion polypeptides or compound fusion polypeptides, and vectors expressing such fusion polypeptides or compound fusion polypeptides, include without limitation mineral salts (e.g., aluminum salts (e.g., alum), calcium phosphate, incomplete Freunds's adjuvant), lipid particles (e.g., MF59, cochleates, virus-like particles), microparticles (e.g., virosomes, polylactic acid (PLA), poly [lactide-coglycolide] (PLG)), immune potentiators (e.g., dsRNA:Poly(I:C), Poly-IC:LC, Monophosphoryl lipid A (MPL), LPS, Flagellin, Imidazoquinolines: imiquimod (R837), resiquimod (848), CpG oligodeoxynucleotides (ODN), Muramyl dipeptide (MDP), Saponins (QS-21)), and mucosal adjuvants (e.g., Cholera toxin (CT), Heat-labile enterotoxin (LTK3 and LTR72), Chitosan). Adjuvants that can be co-formulated or co-administered with the herein described fusion polypeptides, polynucleotides encoding such fusion polypeptides and vectors expressing such fusion polypeptides are summarized in Apostólico, et al., *J Immunol Res.* (2016) 2016:1459394.

In some embodiments, the pharmaceutical compositions or immunogenic compositions comprise two or more fusion polypeptides and/or compound fusion polypeptides, two or more polynucleotides encoding such fusion polypeptides and/or compound fusion polypeptides, or two or more vectors expressing such fusion polypeptides and/or compound fusion polypeptides. In various embodiments, the pharmaceutical compositions or immunogenic compositions comprise a first fusion polypeptide and a second fusion polypeptide that are bivalent, or one or more vectors comprising one or more polynucleotides encoding the bivalent first and second fusion polypeptides. In some embodiments, the pharmaceutical compositions or immunogenic compositions comprise a first fusion polypeptide and a second fusion polypeptide, or one or more vectors comprising one or more polynucleotides encoding the first and second fusion polypeptides, the first and second polypeptides comprising the following polypeptide segments, in sequential order, from N-terminus to C terminus, optionally joined or connected by one or more linkers:

- SEQ ID NOs: 6, 4, 16 and 26, and SEQ ID NOs: 7, 5, 27 and 17;
- SEQ ID NOs: 12, 24, 8 and 10, and SEQ ID NOs: 9, 25, 13 and 11;
- SEQ ID NOs: 14, 22, 18, 24 and 20, and SEQ ID NOs: 15, 25, 19, 23 and 21;
- SEQ ID NOs: 26, 16, 4 and 6, and SEQ ID NOs: 7, 27, 5 and 17;
- SEQ ID NOs: 8, 24, 12 and 10, and SEQ ID NOs: 13, 25, 9 and 11;
- SEQ ID NOs: 22, 24, 14, 18 and 20, and SEQ ID NOs: 25, 23, 15, 21 and 19;
- SEQ ID NOs: 20, 6, 4, 18, 16 and 26, and SEQ ID NOs: 7, 19, 5, 21, 27 and 17;
- SEQ ID NOs: 8, 24, 14, 12, 22 and 10, and SEQ ID NOs: 9, 13, 25, 23, 15 and 11;
- SEQ ID NOs: 18, 26, 20, 4, 6 and 16, and SEQ ID NOs: 7, 21, 17, 5, 27 and 19;
- SEQ ID NOs: 22, 24, 12, 14, 8 and 10, and SEQ ID NOs: 15, 25, 9, 23, 13 and 11;
- SEQ ID NOs: 24, 6, 4, 20, 18 and 32, and SEQ ID NOs: 8, 30, 14, 12, 26 and 10;
- SEQ ID NOs: 24, 6, 4, 20, 18 and 32, and SEQ ID NOs: 7, 21, 5, 25, 33 and 19;
- SEQ ID NOs: 24, 6, 4, 20, 18 and 32, and SEQ ID NOs: 8, 30, 14, 12, 26 and 10;
- SEQ ID NOs: 8, 30, 14, 12, 26 and 10, and SEQ ID NOs: 9, 13, 31, 27, 15 and 11;
- SEQ ID NOs: 6, 20, 4, 24, 32 and 18 and SEQ ID NOs: 8, 12, 30, 26, 14 and 10;
- SEQ ID NOs: 7, 21, 5, 25, 33 and 19 and SEQ ID NOs: 9, 13, 31, 27, 15 and 11;
- SEQ ID NOs: 20, 32, 24, 4, 6 and 18, and SEQ ID NOs: 26, 30, 12, 14, 8 and 10;
- SEQ ID NOs: 7, 25, 19, 5, 33 and 21, and SEQ ID NOs: 15, 31, 9, 27, 13 and 11;
- SEQ ID NOs: 24, 6, 16 and 18, and SEQ ID NOs: 26, 20, 10 and 28;
- SEQ ID NOs: 24, 6, 16 and 18, and SEQ ID NOs: 26, 10, 20 and 28;
- SEQ ID NOs: 24, 6, 16 and 18, and SEQ ID NOs: 7, 25, 17 and 19;
- SEQ ID NOs: 7, 19, 17 and 25, and SEQ ID NOs: 21, 27, 11 and 29;
- SEQ ID NOs: 24, 16, 6 and 18, and SEQ ID NOs: 27, 11, 21 and 29;
- SEQ ID NOs: 7, 25, 17 and 19, and SEQ ID NOs: 11, 27, 21 and 29;
- SEQ ID NOs: 7, 25, 17 and 19, and SEQ ID NOs: 21, 27, 11 and 29;
- SEQ ID NOs: 22, 6, 20 and 28, and SEQ ID NOs: 23, 7, 21 and 29;
- SEQ ID NOs: 22, 20, 6 and 28, and SEQ ID NOs: 7, 21, 23 and 29;
- SEQ ID NOs: 26, 10, 20 and 28, and SEQ ID NOs: 21, 27, 11 and 29;
- SEQ ID NOs: 22, 6, 16, 20, 18, 28, 26 and 10; or
- SEQ ID NOs: 7, 21, 19, 17, 27, 25, 29 and 11.

In some embodiments, the pharmaceutical composition or immunogenic composition comprises one or more, e.g., two or more, fusion polypeptides, or one or more, e.g., two or more, vectors comprising one or more polynucleotides encoding one or more, e.g., two or more, fusion polypeptides, comprising or consisting of an amino acid sequence of any one of SEQ ID NOs: 70-101, 105-112, 200-209, 222-223 and 227, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70-101, 105-112, 200-209, 222-223 and 227. In some embodiments, the pharmaceutical composition or immunogenic composition comprises one or more, e.g., two or more, fusion polypeptides, or one or more, e.g., two or more, vectors comprising one or more polynucleotides encoding one or more, e.g., two or more, fusion polypeptides, comprising or consisting of an amino acid sequence of any one of SEQ ID NOs: 82-83, 85-87, 98-101, 209 and 222-223, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82-83, 85-87, 98-101, 209 and 222-223.

In some embodiments, the pharmaceutical compositions or immunogenic compositions comprise the following first fusion polypeptide and second fusion polypeptide, or one or more vectors comprising one or more polynucleotides encoding the following first fusion polypeptide and second fusion polypeptide, optionally joined or connected by one or more linkers:

- SEQ ID NOs: 70 and 71, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70 and 71, respectively;
- SEQ ID NOs: 72 and 73, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 72 and 73, respectively;
- SEQ ID NOs: 74 and 75, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 74 and 75, respectively;
- SEQ ID NOs: 76 and 77, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 76 and 77, respectively;
- SEQ ID NOs: 78 and 79, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 78 and 79, respectively;
- SEQ ID NOs: 80 and 81, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 80 and 81, respectively;
- SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively;

SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively;

SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively;

SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively;

SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively;

SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively;

SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively;

SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively;

SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively;

SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively;

SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 88, respectively;

SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively;

SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively;

SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively;

SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively;

SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively;

SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively;

SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively;

SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively;

SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively;

SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively;

SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively;

SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively; or SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively.

In some embodiments, the pharmaceutical compositions or immunogenic compositions comprise a compound fusion polypeptide or a vector comprising a polynucleotide encoding a compound fusion polypeptide, the compound fusion polypeptide comprising or consisting of an amino acid sequence of any one of SEQ ID NOs: 105-112, 200-209, 222-223 and 227, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 105-112, 200-209, 222-223 and 227. In some embodiments, the pharmaceutical compositions or immunogenic compositions comprise a compound fusion polypeptide or a vector comprising a polynucleotide encoding a compound fusion polypeptide, the compound fusion polypeptide comprising or consisting of an amino acid sequence of any one of SEQ ID NOs: 209, 222 and 223, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 209, 222 and 223. In some embodiments, the pharmaceutical compositions or immunogenic compositions comprise a compound fusion polypeptide or a vector comprising a polynucleotide encoding a compound fusion polypeptide, the compound fusion polypeptide comprising or consisting of an amino acid sequence of SEQ ID NO: 209, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 209. In some embodiments, the pharmaceutical compositions or immunogenic compositions comprise a compound fusion polypeptide or a vector comprising a polynucleotide encoding a compound fusion polypeptide, the compound fusion polypeptide comprising or consisting of an amino acid sequence of SEQ ID NO: 222, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 222. In some embodiments, the pharmaceutical compositions or immunogenic compositions comprise a compound fusion polypeptide or a vector comprising a polynucleotide encoding a compound fusion polypeptide, the compound fusion polypeptide comprising or consisting of an amino acid sequence of SEQ ID NO: 223, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 223. In some embodiments, the pharmaceutical compositions or immunogenic compositions comprise a compound fusion polypeptide or a vector comprising a polynucleotide encoding a compound fusion polypeptide, the compound fusion polypeptide comprising or consisting of an amino acid sequence of SEQ ID NO: 227, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 227.

In some embodiments, the pharmaceutical compositions or immunogenic compositions comprise the following first fusion polypeptide and second fusion polypeptide, or one or more vectors comprising one or more polynucleotides encoding the following first fusion polypeptide and second fusion polypeptide, in sequential order, from N-terminus to C-terminus, optionally joined or connected by one or more linkers:

- SEQ ID NOs: 70 and 71, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70 and 71, respectively;
- SEQ ID NOs: 71 and 70, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 71 and 70, respectively;
- SEQ ID NOs: 72 and 73, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 72 and 73, respectively;
- SEQ ID NOs: 73 and 72, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 73 and 72, respectively;
- SEQ ID NOs: 74 and 75, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 74 and 75, respectively;
- SEQ ID NOs: 75 and 74, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 75 and 74, respectively;
- SEQ ID NOs: 76 and 77, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 76 and 77, respectively;
- SEQ ID NOs: 77 and 76, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 77 and 76, respectively;
- SEQ ID NOs: 78 and 79, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 78 and 79, respectively;
- SEQ ID NOs: 79 and 78, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 79 and 78, respectively;
- SEQ ID NOs: 80 and 81, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 80 and 81, respectively;
- SEQ ID NOs: 81 and 80, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 81 and 80, respectively;
- SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively;
- SEQ ID NOs: 83 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 82, respectively;
- SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively;
- SEQ ID NOs: 85 and 84, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 84, respectively;
- SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively;
- SEQ ID NOs: 87 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 86, respectively;

SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively;

SEQ ID NOs: 89 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 89 and 88, respectively;

SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively;

SEQ ID NOs: 85 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 82, respectively;

SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively;

SEQ ID NOs: 86 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 82, respectively;

SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively;

SEQ ID NOs: 88 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 82, respectively;

SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively;

SEQ ID NOs: 87 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 83, respectively;

SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively;

SEQ ID NOs: 87 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 85, respectively;

SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively;

SEQ ID NOs: 87 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 88, respectively;

SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 84, respectively;

SEQ ID NOs: 88 and 84, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 84, respectively;

SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively;

SEQ ID NOs: 89 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 89 and 85, respectively;

SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively;

SEQ ID NOs: 101 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 85, respectively;

SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively;

SEQ ID NOs: 91 and 90, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 91 and 90, respectively;

SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively;

SEQ ID NOs: 93 and 92, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 93 and 92, respectively;

SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively;

SEQ ID NOs: 95 and 94, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 94, respectively;

SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively;

SEQ ID NOs: 97 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 97 and 96, respectively;

SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively;

SEQ ID NOs: 96 and 94, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 94, respectively;

SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively;

SEQ ID NOs: 97 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 97 and 95, respectively;

SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively;

SEQ ID NOs: 221 and 220, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 221 and 220, respectively;

SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively;

SEQ ID NOs: 100 and 98, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 98, respectively;

SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively;

SEQ ID NOs: 101 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 99, respectively;

SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively;

SEQ ID NOs: 99 and 98, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 98, respectively;

SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively; or SEQ ID NOs: 101 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 100, respectively.

In various embodiments, the immunogenic composition or pharmaceutical composition comprises first and second viral vectors comprising one or more polynucleotides encoding the following first fusion polypeptide and second fusion polypeptide, optionally joined or connected by one or more linkers:

a) a first viral vector comprising one or more polynucleotides encoding a first fusion polypeptide and a second fusion polypeptide comprising SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively, and b) a second viral vector comprising one or more polynucleotides encoding a first fusion polypeptide and a second fusion polypeptide comprising SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively.

In various embodiments, the immunogenic composition or pharmaceutical composition comprises first and second viral vectors comprising one or more polynucleotides encoding the following first fusion polypeptide and second fusion polypeptide, optionally joined or connected by one or more linkers:

a) a first viral vector comprising one or more polynucleotides encoding a first fusion polypeptide and a second fusion polypeptide comprising SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively, and b) a second viral vector comprising one or more polynucleotides encoding a first fusion polypeptide and a second fusion polypeptide comprising SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively.

In various embodiments, the immunogenic composition or pharmaceutical composition comprises first and second viral vectors comprising one or more polynucleotides encoding the following first fusion polypeptide and second fusion polypeptide, optionally joined or connected by one or more linkers:

a) a first viral vector comprising one or more polynucleotides encoding a first fusion polypeptide and a second fusion polypeptide comprising SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively, and b) a second viral vector comprising one or more polynucleotides encoding a first fusion polypeptide and a second fusion polypeptide comprising SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively.

In various embodiments, the immunogenic composition or pharmaceutical composition comprises first and second viral vectors comprising one or more polynucleotides encoding the following first fusion polypeptide and second fusion polypeptide, optionally joined or connected by one or more linkers:

a) a first viral vector comprising one or more polynucleotides encoding a first fusion polypeptide and a second fusion polypeptide comprising SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively, and b) a second viral vector comprising one or more polynucleotides encoding a first fusion polypeptide and a second fusion polypeptide comprising SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively.

In various embodiments, the immunogenic composition or pharmaceutical composition comprises first and second viral vectors comprising one or more polynucleotides encoding the following first fusion polypeptide and second fusion polypeptide, optionally joined or connected by one or more linkers:

a) a first viral vector comprising one or more polynucleotides encoding a first fusion polypeptide and a second fusion polypeptide comprising SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively, and b) a second viral vector comprising one or more polynucleotides encoding a first fusion polypeptide and a second fusion polypeptide comprising SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively.

In various embodiments, the immunogenic composition or pharmaceutical composition comprises first and second viral vectors comprising one or more polynucleotides encoding the following first fusion polypeptide and second fusion polypeptide, optionally joined or connected by one or more linkers:

a) a first viral vector comprising one or more polynucleotides encoding a first fusion polypeptide and a second fusion polypeptide comprising SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 88, respectively, and b) a second viral vector comprising one or more polynucleotides encoding a first fusion polypeptide and a second fusion polypeptide comprising SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively.

In various embodiments, the immunogenic composition or pharmaceutical composition comprises a viral vector or a lipoplex (e.g., LNP) comprising one or more polynucleotides encoding a first fusion polypeptide and a second fusion polypeptide, optionally joined or connected by one or more linkers, comprising SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively.

In various embodiments, the immunogenic composition or pharmaceutical composition comprises a viral vector or a lipoplex (e.g., LNP) comprising one or more polynucleotides encoding a first fusion polypeptide and a second fusion polypeptide, optionally joined or connected by one or more linkers, comprising SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively.

In various embodiments, the immunogenic composition or pharmaceutical composition comprises a viral vector or a lipoplex (e.g., LNP) comprising one or more polynucleotides encoding a first fusion polypeptide and a second fusion polypeptide, optionally joined or connected by one or more linkers, comprising SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively.

In various embodiments, the immunogenic composition or pharmaceutical composition comprises a viral vector or a lipoplex (e.g., LNP) comprising one or more polynucleotides encoding a first fusion polypeptide and a second fusion polypeptide, optionally joined or connected by one or more linkers, comprising SEQ ID NOs: 87 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 88, respectively.

In various embodiments, the immunogenic composition or pharmaceutical composition comprises a viral vector comprising one or more polynucleotides encoding the following first fusion polypeptide and second fusion polypeptide, optionally joined or connected by one or more linkers, SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively.

In various embodiments, the immunogenic composition or pharmaceutical composition comprises a viral vector comprising one or more polynucleotides encoding the following first fusion polypeptide and second fusion polypeptide, optionally joined or connected by one or more linkers, SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively.

In various embodiments, the immunogenic composition or pharmaceutical composition comprises first and second viral vectors comprising one or more polynucleotides encoding the following first fusion polypeptide and second fusion polypeptide, optionally joined or connected by one or more linkers:

a) the first viral vector comprising one or more polynucleotides encoding a first fusion polypeptide and a second fusion polypeptide comprising SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively, and b) the second viral vector comprising one or more polynucleotides encoding a first fusion polypeptide and a second fusion polypeptide comprising SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively.

In various embodiments, the immunogenic composition or pharmaceutical composition comprises first and second viral vectors comprising one or more polynucleotides encoding the following first fusion polypeptide and second fusion polypeptide, optionally joined or connected by one or more linkers:

a) the first viral vector comprising one or more polynucleotides encoding a first fusion polypeptide and a second fusion polypeptide comprising SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively, and b) the second viral vector comprising one or more polynucleotides encoding a first fusion polypeptide and a second fusion polypeptide comprising SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively.

In various embodiments, the immunogenic composition or pharmaceutical composition comprises a viral vector comprising one or more polynucleotides encoding a first fusion polypeptide and a second fusion polypeptide comprising SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively.

In various embodiments, the immunogenic composition or pharmaceutical composition comprises a viral vector comprising one or more polynucleotides encoding a first fusion polypeptide and a second fusion polypeptide comprising SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively.

In various embodiments, the immunogenic composition or pharmaceutical composition comprises first and second viral vectors comprising one or more polynucleotides encoding the following first fusion polypeptide and second fusion polypeptide, optionally joined or connected by one or more linkers:

a) the first viral vector comprising one or more polynucleotides encoding a first fusion polypeptide and a second fusion polypeptide comprising SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively, and b) the second viral vector comprising one or more polynucleotides encoding a first fusion polypeptide and a second fusion polypeptide comprising SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively.

In various embodiments, the immunogenic composition or pharmaceutical composition comprises first and second viral vectors comprising one or more polynucleotides encoding the following first fusion polypeptide and second fusion polypeptide, optionally joined or connected by one or more linkers:

a) the first viral vector comprising one or more polynucleotides encoding a first fusion polypeptide and a second fusion polypeptide comprising SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively, and b) the second viral vector comprising one or more polynucleotides encoding a first fusion polypeptide and a second fusion polypeptide comprising SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively.

In various embodiments, the immunogenic composition or pharmaceutical composition comprises a viral vector comprising one or more polynucleotides encoding a first fusion polypeptide and a second fusion polypeptide comprising SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively.

In various embodiments, the immunogenic composition or pharmaceutical composition comprises a viral vector comprising one or more polynucleotides encoding a first fusion polypeptide and a second fusion polypeptide comprising SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively.

In various embodiments, the immunogenic composition or pharmaceutical composition comprises a viral vector comprising a polynucleotide encoding a compound fusion polypeptide comprising SEQ ID NO: 105 or 206, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 105 or 206.

In various embodiments, the immunogenic composition or pharmaceutical composition comprises a viral vector comprising a polynucleotide encoding a compound fusion polypeptide comprising SEQ ID NO: 107 or 207, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 107 or 207.

In various embodiments, the immunogenic composition or pharmaceutical composition comprises a viral vector comprising a polynucleotide encoding a compound fusion polypeptide comprising SEQ ID NO: 109, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 109.

In various embodiments, the immunogenic composition or pharmaceutical composition comprises a viral vector comprising a polynucleotide encoding a compound fusion polypeptide comprising SEQ ID NO: 111, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 111.

In various embodiments, the immunogenic composition or pharmaceutical composition comprises a viral vector comprising a polynucleotide encoding a compound fusion polypeptide comprising SEQ ID NO: 200, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 200.

In various embodiments, the immunogenic composition or pharmaceutical composition comprises a viral vector comprising a polynucleotide encoding a compound fusion polypeptide comprising SEQ ID NO: 201, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 201.

In various embodiments, the immunogenic composition or pharmaceutical composition comprises a viral vector comprising a polynucleotide encoding a compound fusion polypeptide comprising SEQ ID NO: 202, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 202.

In various embodiments, the immunogenic composition or pharmaceutical composition comprises a viral vector comprising a polynucleotide encoding a compound fusion polypeptide comprising SEQ ID NO: 203, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 203.

In various embodiments, the immunogenic composition or pharmaceutical composition comprises a viral vector comprising a polynucleotide encoding a compound fusion polypeptide comprising SEQ ID NO: 204, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 204.

In various embodiments, the immunogenic composition or pharmaceutical composition comprises a viral vector comprising a polynucleotide encoding a compound fusion polypeptide comprising SEQ ID NO: 205, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 205.

In various embodiments, the immunogenic composition or pharmaceutical composition comprises a viral vector comprising a polynucleotide encoding a compound fusion polypeptide comprising SEQ ID NO: 208, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 208.

In various embodiments, the immunogenic composition or pharmaceutical composition comprises a viral vector comprising a polynucleotide encoding a compound fusion polypeptide comprising SEQ ID NO: 209, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 209.

In various embodiments, the immunogenic composition or pharmaceutical composition comprises a viral vector comprising a polynucleotide encoding a compound fusion polypeptide comprising SEQ ID NO: 222, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 222.

In various embodiments, the immunogenic composition or pharmaceutical composition comprises a viral vector comprising a polynucleotide encoding a compound fusion polypeptide comprising SEQ ID NO: 223, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 223.

In various embodiments, the immunogenic composition or pharmaceutical composition comprises a viral vector comprising a polynucleotide encoding a compound fusion polypeptide comprising SEQ ID NO: 227, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 227.

In various embodiments, the immunogenic composition or pharmaceutical composition comprises a first viral vector or a lipoplex (e.g., LNP) comprising a first polynucleotide encoding a first polypeptide comprising SEQ ID NO: 200, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 200, and a second viral vector or a lipoplex (e.g., LNP) comprising a second polynucleotide encoding a second polypeptide comprising SEQ ID NO: 201, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 201.

In various embodiments, the immunogenic composition or pharmaceutical composition comprises a first viral vector or a lipoplex (e.g., LNP) comprising a first polynucleotide encoding a first polypeptide comprising SEQ ID NO: 202, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 202, and a second viral vector or a lipoplex (e.g., LNP) comprising a second polynucleotide encoding a second polypeptide comprising SEQ ID NO: 203, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 203.

In various embodiments, the immunogenic composition or pharmaceutical composition comprises a first viral vector or a lipoplex (e.g., LNP) comprising a first polynucleotide encoding a first polypeptide comprising SEQ ID NO: 204, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 204, and a second viral vector or a lipoplex (e.g., LNP) comprising a second polynucleotide encoding a second polypeptide comprising SEQ ID NO: 205, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 205.

In various embodiments, the immunogenic composition or pharmaceutical composition comprises a first viral vector or a lipoplex (e.g., LNP) comprising a first polynucleotide encoding a first polypeptide comprising SEQ ID NO: 105, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 105, and a second viral vector or a lipoplex (e.g., LNP) comprising a second polynucleotide encoding a second polypeptide comprising SEQ ID NO: 107, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 107.

In various embodiments, the immunogenic composition or pharmaceutical composition comprises a first viral vector or a lipoplex (e.g., LNP) comprising a first polynucleotide encoding a first polypeptide comprising SEQ ID NO: 206, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 206, and a second viral vector or a lipoplex (e.g., LNP) comprising a second polynucleotide encoding a second polypeptide comprising SEQ ID NO: 207, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 207.

In various embodiments, the immunogenic composition or pharmaceutical composition comprises a first viral vector or a lipoplex (e.g., LNP) comprising a first polynucleotide encoding a first polypeptide comprising SEQ ID NO: 208, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 208, and a second viral vector or a lipoplex (e.g., LNP) comprising a second polynucleotide encoding a second polypeptide comprising SEQ ID NO: 209 or SEQ ID NO: 227, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 209 or SEQ ID NO: 227.

In various embodiments, the immunogenic composition or pharmaceutical composition comprises a first viral vector or a lipoplex (e.g., LNP) comprising a first polynucleotide encoding a first polypeptide comprising SEQ ID NO: 222, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 222, and a second viral vector or a lipoplex (e.g., LNP) comprising a second polynucleotide encoding a second polypeptide comprising SEQ ID NO: 209 or SEQ ID NO: 227, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 209 or SEQ ID NO: 227.

In various embodiments, the immunogenic composition or pharmaceutical composition comprises a first viral vector or a lipoplex (e.g., LNP) comprising a first polynucleotide encoding a first polypeptide comprising SEQ ID NO: 222, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 222, and a second viral vector or a lipoplex (e.g., LNP) comprising a second polynucleotide encoding a second polypeptide comprising SEQ ID NO: 223, or a polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 223.

In some embodiments, the pharmaceutical compositions or immunogenic compositions comprise a polynucleotide comprising or consisting of a nucleic acid sequence of any one of SEQ ID NOs: 130-167, 210-219 and 225-226, or a nucleic acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 130-167, 210-219 and 225-226. In some embodiments, the pharmaceutical compositions or immunogenic compositions comprise a polynucleotide comprising or consisting of a nucleic acid sequence of any one of SEQ ID NOs: 139, 140, 142, 143, 145, 146, 148, 149, 150, 152, 155, 158, 225 and 226, or a nucleic acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139, 140, 142, 143, 145, 146, 148, 149, 150, 152, 155, 158, 225 and 226.

In some embodiments, the pharmaceutical compositions or immunogenic compositions comprise the following first polynucleotide and second polynucleotide, or one or more vectors comprising the following first polynucleotide and second polynucleotide, the first and second polynucleotides comprising or consisting of, respectively:

SEQ ID NOs: 130 and 132, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 130 and 132, respectively;

SEQ ID NOs: 130 and 134, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 130 and 134, respectively;

SEQ ID NOs: 131 and 133, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 131 and 133, respectively;

SEQ ID NOs: 131 and 135, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 131 and 135, respectively;

SEQ ID NOs: 132 and 136, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 132 and 136, respectively;

SEQ ID NOs: 133 and 135, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 133 and 135, respectively;

SEQ ID NOs: 133 and 137, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 133 and 137, respectively;

SEQ ID NOs: 134 and 136, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 134 and 136, respectively;

SEQ ID NOs: 135 and 137, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 135 and 137, respectively;

SEQ ID NOs: 138 and 141, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 138 and 141, respectively;

SEQ ID NOs: 138 and 144, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 138 and 144, respectively;

SEQ ID NOs: 139 and 142, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 142, respectively;

SEQ ID NOs: 139 and 145, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 145, respectively;

SEQ ID NOs: 140 and 146, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 140 and 146, respectively;

SEQ ID NOs: 142 and 148, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 142 and 148, respectively;

SEQ ID NOs: 143 and 149, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 143 and 149, respectively;

SEQ ID NOs: 145 and 148, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 145 and 148, respectively;

SEQ ID NOs: 150 and 152, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively;

SEQ ID NOs: 150 and 155, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 155, respectively;

SEQ ID NOs: 151 and 153, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 151 and 153, respectively;

SEQ ID NOs: 151 and 156, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 151 and 156, respectively;

SEQ ID NOs: 152 and 158, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 152 and 158, respectively;

SEQ ID NOs: 153 and 159, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 153 and 159, respectively;

SEQ ID NOs: 154 and 157, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 154 and 157, respectively;

SEQ ID NOs: 155 and 158, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 155 and 158, respectively;

SEQ ID NOs: 156 and 159, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 156 and 159, respectively;

SEQ ID NOs: 160 and 161, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 160 and 161, respectively;

SEQ ID NOs: 162 and 163, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 162 and 163, respectively;

SEQ ID NOs: 164 and 165, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 164 and 165, respectively;

SEQ ID NOs: 166 and 167, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 166 and 167, respectively;

SEQ ID NOs: 210 and 211, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 210 and 211, respectively;

SEQ ID NOs: 212 and 213, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 212 and 213, respectively;

SEQ ID NOs: 214 and 215, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 214 and 215, respectively;

SEQ ID NOs: 216 and 217, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 216 and 217, respectively;

SEQ ID NOs: 218 and 219, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 218 and 219, respectively;

SEQ ID NOs: 218 and 226, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 218 and 226, respectively; or SEQ ID NOs: 225 and 226, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 225 and 226, respectively.

In various embodiments, the immunogenic composition or pharmaceutical composition comprises first and second viral vectors comprising one or more polynucleotides:

a) the first viral vector comprising first and second polynucleotides of SEQ ID NOs: 131 and 135, or first and second polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 131 and 135, respectively, and b) the second viral vector comprising first and second polynucleotides of SEQ ID NOs: 133 and 137, or first and second polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 133 and 137, respectively.

In various embodiments, the immunogenic composition or pharmaceutical composition comprises first and second viral vectors comprising one or more polynucleotides:

a) the first viral vector comprising first and second polynucleotides of SEQ ID NOs: 139 and 145, or first and second polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 145, respectively, and b) the second viral vector comprising first and second polynucleotides of SEQ ID NOs: 142 and 148, or first and second polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 142 and 148, respectively.

In various embodiments, the immunogenic composition or pharmaceutical composition comprises first and second viral vectors comprising one or more polynucleotides:

a) the first viral vector comprising first and second polynucleotides of SEQ ID NOs: 140 and 146, or first and second polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 140 and 146, respectively, and b) the second viral vector comprising first and second polynucleotides of SEQ ID NOs: 143 and 149, or first and second polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 143 and 149, respectively.

In various embodiments, the immunogenic composition or pharmaceutical composition comprises first and second viral vectors comprising one or more polynucleotides:

a) the first viral vector comprising first and second polynucleotides of SEQ ID NOs: 150 and 152, or first and second polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively, and b) the second viral vector comprising first and second polynucleotides of SEQ ID NOs: 154 and 157, or first and second polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 154 and 157, respectively.

In various embodiments, the immunogenic composition or pharmaceutical composition comprises first and second viral vectors comprising one or more polynucleotides:

a) the first viral vector comprising first and second polynucleotides of SEQ ID NOs: 150 and 152, or first and second polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively, and b) the second viral vector comprising first and second polynucleotides of SEQ ID NOs: 155 and 158, or first and second polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 155 and 158, respectively.

In various embodiments, the immunogenic composition or pharmaceutical composition comprises first and second viral vectors comprising one or more polynucleotides:

a) the first viral vector comprising first and second polynucleotides of SEQ ID NOs: 151 and 153, or first and second polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 151 and 153, respectively, and b) the second viral vector comprising first and second polynucleotides of SEQ ID NOs: 156 and 159, or first and second polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 156 and 159, respectively.

In various embodiments, the immunogenic composition or pharmaceutical composition comprises first and second viral vectors comprising one or more polynucleotides:

a) the first viral vector comprising a polynucleotide of SEQ ID NO: 160, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 160, respectively, and b) the second viral vector comprising a polynucleotide of SEQ ID NO: 161, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 161, respectively.

In various embodiments, the immunogenic composition or pharmaceutical composition comprises first and second viral vectors comprising one or more polynucleotides:

a) the first viral vector comprising a polynucleotide of SEQ ID NO: 162, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 162, respectively, and b) the second viral vector comprising a polynucleotide of SEQ ID NO: 163, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 163, respectively.

In various embodiments, the immunogenic composition or pharmaceutical composition comprises first and second viral vectors comprising one or more polynucleotides:

a) the first viral vector comprising a polynucleotide of SEQ ID NO: 164, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 164, respectively, and b) the second viral vector comprising a polynucleotide of SEQ ID NO: 165, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 165, respectively.

In various embodiments, the immunogenic composition or pharmaceutical composition comprises first and second viral vectors comprising one or more polynucleotides:

a) the first viral vector comprising a polynucleotide of SEQ ID NO: 166, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 166, respectively, and b) the second viral vector comprising a polynucleotide of SEQ ID NO: 167, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 167, respectively.

In various embodiments, the immunogenic composition or pharmaceutical composition comprises first and second viral vectors comprising one or more polynucleotides:

a) the first viral vector comprising a polynucleotide of SEQ ID NO: 210, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 210, and b) the second viral vector comprising a polynucleotide of SEQ ID NO: 211, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 211.

In various embodiments, the immunogenic composition or pharmaceutical composition comprises first and second viral vectors comprising one or more polynucleotides:

a) the first viral vector comprising a polynucleotide of SEQ ID NO: 212, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 212, and b) the second viral vector comprising a polynucleotide of SEQ ID NO: 213, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 213.

In various embodiments, the immunogenic composition or pharmaceutical composition comprises first and second viral vectors comprising one or more polynucleotides:

a) the first viral vector comprising a polynucleotide of SEQ ID NO: 214, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 214, and b) the second viral vector comprising a polynucleotide of SEQ ID NO: 215, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 215.

In various embodiments, the immunogenic composition or pharmaceutical composition comprises first and second viral vectors comprising one or more polynucleotides:

a) the first viral vector comprising a polynucleotide of SEQ ID NO: 216, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 216, and b) the second viral vector comprising a polynucleotide of SEQ ID NO: 217, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 217.

In various embodiments, the immunogenic composition or pharmaceutical composition comprises first and second viral vectors comprising one or more polynucleotides:

a) the first viral vector comprising a polynucleotide of SEQ ID NO: 218, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 218, and b) the second viral vector comprising a polynucleotide of SEQ ID NO: 219, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 219.

In various embodiments, the immunogenic composition or pharmaceutical composition comprises first and second viral vectors comprising one or more polynucleotides:

a) the first viral vector comprising a polynucleotide of SEQ ID NO: 218, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 218, and b) the second viral vector comprising a polynucleotide of SEQ ID NO: 226, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 226.

In various embodiments, the immunogenic composition or pharmaceutical composition comprises first and second viral vectors comprising one or more polynucleotides:

a) the first viral vector comprising a polynucleotide of SEQ ID NO: 225, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 225, and b) the second viral vector comprising a polynucleotide of SEQ ID NO: 226, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 226.

In various embodiments of the pharmaceutical compositions or immunogenic compositions, the one or more fusion polypeptides do not comprise any polypeptide segments corresponding to Gag 54-146; Gag 370-500; Pol 1-55; Pol 118-128; Pol 321-366; Pol 432-541; Pol 607-682; Pol 709-746; Pol 828-839; Pol 921-931; Nef 1-63; Nef 100-116 and Nef 149-206, or fragments or subsequences thereof, wherein the Gag, Pol and Nef amino acid position numbers correspond to SEQ ID NOs: 1, 2 and 3, respectively. In various embodiments of the pharmaceutical compositions or immunogenic compositions, the one or more fusion polypeptides do not comprise any polypeptide segments having an amino acid sequence of SEQ ID NOs: 35-47, or fragments or subsequences thereof, or an amino acid sequence at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 35-47, or fragments or subsequences thereof.

6. Methods of Treatment

Further provided are methods for treating or preventing an HIV infection or a related disease or disorder in a subject in need thereof (e.g., a human subject), comprising providing to a subject in need thereof an effective amount of one or more fusion polypeptides or compound fusion polypeptides, as described herein, or one or more polynucleotides encoding one or more fusion polypeptides or compound fusion polypeptides, as described herein, or one or more vectors expressing one or more fusion polypeptides or compound fusion polypeptides, as described herein. As used herein, the term “subject” refers to a mammal. The mammal can be any mammal, for example, a human, a non-human primate, a rodent (e.g., mouse, rat, guinea pig), a dog, a cat, or a domesticated animal such as a cow, a horse, a goat, a camel, a sheep or a pig. The term “patient” refers to a human subject. As used herein, the term “effective amount” in the context of the administration of a therapy to a subject refers to the amount of a therapy that achieves a desired prophylactic or therapeutic effect. The polynucleotide may be present in a vector, e.g., a viral vector, as described herein. In some embodiments, the related disease or disorder is caused by infection with HIV. In other embodiments, it is acquired immune deficiency syndrome (AIDS). In certain embodiments, the subject is a virologically suppressed HIV-infected mammal, while in other embodiments, the subject is a treatment-naïve HIV-infected mammal or a treatment experienced HIV-infected subject that is not virologically suppressed. In certain embodiments, a treatment-naïve subject has a viral load between <50 copies/mL and $10^8$ copies/ml. In certain embodiments, a virologically suppressed subject has a viral load <50 copies/ml. In another embodiment, the subject is a mammal, e.g., a human. In certain embodiments, the subject has been diagnosed with an HIV, e.g., HIV-1 or HIV-2, infection or a related disease or disorder, e.g., AIDS, or is considered at risk for developing an HIV, e.g., HIV-1 or HIV-2, infection or a related disease or disorder, e.g., AIDS. Subjects at risk for HIV-related diseases or disorders include patients who have come into contact with an infected person or who have been exposed to HIV in some other way. Administration of a prophylactic agent can occur prior to the manifestation of symptoms characteristic of HIV-related disease or disorder, such that a disease or disorder is prevented or, alternatively, delayed in its progression.

In some embodiments, the subject is chronically infected with HIV-1. In some embodiments, the subject is acutely infected with HIV-1, e.g., has an HIV-1 infection of Fiebig stage IV or earlier, e.g. Fiebig stage III, Fiebig stage II or Fiebig stage I. In some embodiments, the subject is not receiving antiretroviral therapy (ART) or ART is discontinued prior to administration of the one or more compositions. In some embodiments, ART is discontinued after one or more administrations of the compositions. In some embodiments, ART is administered concurrently with administration of one or more fusion polypeptides or compound fusion polypeptides, as described herein, or one or more polynucleotides encoding one or more fusion polypeptides or compound fusion polypeptides, as described herein, or one or more vectors expressing one or more fusion polypeptides or compound fusion polypeptides, as described herein.

Also provided are methods for preventing or inhibiting an increase in HIV virus titer, virus replication, virus proliferation or an amount of an HIV viral DNA, HIV proviral DNA, or HIV viral protein in a subject (e.g., a human subject). In one embodiment, the method entails providing to the subject in need thereof an amount of an one or more fusion polypeptides or compound fusion polypeptides, as described herein, or one or more polynucleotides encoding one or more fusion polypeptides or compound fusion polypeptides, as described herein, or one or more vectors expressing one or more fusion polypeptides or compound fusion polypeptides, as described herein, effective to prevent an increase in HIV titer, virus replication, or an amount of an HIV protein of one or more HIV strains or isolates in the subject. In certain embodiments, the method further comprises measuring an amount of HIV viral or proviral DNA or protein at one or more time points, e.g., before and after the subject in provided with one or more fusion polypeptides or compound fusion polypeptides, as described herein, or one or more polynucleotides encoding one or more fusion polypeptides or compound fusion polypeptides, as described herein, or one or more vectors expressing one or more fusion polypeptides or compound fusion polypeptides, as described herein. Methods and biomarkers for determining an amount of HIV viral or proviral DNA or protein in a subject are known and available in the art, and described for example, in Siliciano, J. D. et al., Curr Opin. HIV AIDS, 5(6):491-7 (2010), and Rouzioux, C. et al., Curr Opin HIV AIDS, 8(3):170-5 (2013).

In some embodiments, one or more fusion polypeptides or compound fusion polypeptides or compound fusion polypeptides, as described herein, or one or more polynucleotides encoding one or more fusion polypeptides or compound fusion polypeptides, as described herein, or one or more vectors expressing one or more fusion polypeptides or compound fusion polypeptides, as described herein, may be used in, for example, methods of inhibiting certain viruses such as HIV isolates described herein, prophylactic inhibiting or preventing infections of certain viruses such as HIV isolates described herein, detection of certain viruses such as HIV isolates described herein in a sample, inhibiting certain viruses such as HIV isolates described herein, or diagnosis of certain viruses such as HIV isolates described herein.

For in vivo treatment of mammalian subject, e.g., humans, the subject may be administered or provided a pharmaceutical composition comprising one or more fusion polypeptides or compound fusion polypeptides, as described herein, or one or more polynucleotides encoding one or more fusion polypeptides or compound fusion polypeptides, as described herein, or one or more vectors expressing one or more fusion polypeptides or compound fusion polypeptides, as described herein. When used for in vivo therapy, the one or more fusion polypeptides or compound fusion polypeptides, as described herein, or one or more polynucleotides encoding one or more fusion polypeptides or compound fusion polypeptides, as described herein, or one or more vectors expressing one or more fusion polypeptides or compound fusion polypeptides, as described herein, are typically administered or provided to the patient in therapeutically effective amounts (i.e., amounts that eliminate or reduce the patient's viral burden and/or viral reservoir). The one or more fusion polypeptides or compound fusion polypeptides, as described herein, or one or more polynucleotides encoding one or more fusion polypeptides or compound fusion polypeptides, as described herein, or one or more vectors expressing one or more fusion polypeptides or compound fusion polypeptides, as described herein, are administered or provided to a mammalian subject, e.g., a human, in accord with known methods, such as, but not limited to, intravenous administration, e.g., as a bolus or by continuous infusion over a period of time, by intramuscular, intraperitoneal, intracerebrospinal, subcutaneous, intranodal, intraarticular, intrasynovial, intrathecal, oral, topical, or inhalation routes. The one or more fusion polypeptides or compound fusion polypeptides, as described herein, or one or more polynucleotides encoding one or more fusion polypeptides or compound fusion polypeptides, as described herein, or one or more vectors expressing one or more fusion polypeptides or compound fusion polypeptides, as described herein, may be administered parenterally, when possible, at the target cell site, or intravenously. In one embodiment, administration of the one or more fusion polypeptides or compound fusion polypeptides, as described herein, or one or more polynucleotides encoding one or more fusion polypeptides or compound fusion polypeptides, as described herein, or one or more vectors expressing one or more fusion polypeptides or compound fusion polypeptides, as described herein, to the subject is via an intravenous route. In another embodiment, administration of the one or more fusion polypeptides or compound fusion polypeptides, as described herein, or one or more polynucleotides encoding one or more fusion polypeptides or compound fusion polypeptides, as described herein, or one or more vectors expressing one or more fusion polypeptides or compound fusion polypeptides, as described herein, to the subject is via a subcutaneous route. In additional embodiments, pharmaceutical compositions of the disclosure are administered to a subject systemically, parenterally, or locally (e.g., mucosally, including buccal, intrarectal and/or intravaginal routes).

In certain embodiments, the present disclosure provides a method for treating an HIV infection, comprising administering to a human subject in need thereof a therapeutically effective amount of one or more fusion polypeptides or compound fusion polypeptides, as described herein, or one or more polynucleotides encoding one or more fusion polypeptides or compound fusion polypeptides, as described herein, or one or more vectors expressing one or more fusion polypeptides or compound fusion polypeptides, as described herein. In some embodiments, the present disclosure provides a method for preventing an HIV infection, comprising administering to a human subject in need thereof a therapeutically effective amount of one or more fusion polypeptides or compound fusion polypeptides, as described herein, or one or more polynucleotides encoding one or more fusion polypeptides or compound fusion polypeptides, as described herein, or one or more vectors expressing one or more fusion polypeptides or compound fusion polypeptides, as described herein.

In various embodiments, the method entails administering first and second bivalent fusion polypeptides, or first and second polynucleotides (e.g., first and second expression cassettes, first and second open reading frames) encoding the first and second fusion polypeptides, respectively, or a single viral expression vector comprising first and second polynucleotides (e.g., first and second expression cassettes, first and second open reading frames) encoding the first and second fusion polypeptides, respectively, wherein the first and second fusion polypeptides are bivalent fusion polypeptides. In certain embodiments, the single viral expression vector has a bi-segmented genome. In certain embodiments, the single viral expression vector has a tri-segmented genome. In various embodiments, the method entails administering a single compound fusion polypeptide, or a single polynucleotide (e.g., single expression cassette, single open reading frame) encoding the compound fusion polypeptide, or single viral expression vector comprising a polynucleotide encoding the compound fusion polypeptide, wherein the compound fusion polypeptide comprises bivalent fusion polypeptides.

In some embodiments, the methods entail administering to the subject: a first fusion polypeptide and a second fusion polypeptide, or one or more vectors comprising one or more polynucleotides encoding the first and second fusion polypeptides, the first and second polypeptides comprising the following polypeptide segments, in sequential order, from N-terminus to C-terminus, optionally joined or connected by one or more linkers:

SEQ ID NOs: 6, 4, 16 and 26, and SEQ ID NOs: 7, 5, 27 and 17;
SEQ ID NOs: 12, 24, 8 and 10, and SEQ ID NOs: 9, 25, 13 and 11;
SEQ ID NOs: 14, 22, 18, 24 and 20, and SEQ ID NOs: 15, 25, 19, 23 and 21;
SEQ ID NOs: 26, 16, 4 and 6, and SEQ ID NOs: 7, 27, 5 and 17;
SEQ ID NOs: 8, 24, 12 and 10, and SEQ ID NOs: 13, 25, 9 and 11;
SEQ ID NOs: 22, 24, 14, 18 and 20, and SEQ ID NOs: 25, 23, 15, 21 and 19;
SEQ ID NOs: 20, 6, 4, 18, 16 and 26, and SEQ ID NOs: 7, 19, 5, 21, 27 and 17;
SEQ ID NOs: 8, 24, 14, 12, 22 and 10, and SEQ ID NOs: 9, 13, 25, 23, 15 and 11;

SEQ ID NOs: 18, 26, 20, 4, 6 and 16, and SEQ ID NOs: 7, 21, 17, 5, 27 and 19;

SEQ ID NOs: 22, 24, 12, 14, 8 and 10, and SEQ ID NOs: 15, 25, 9, 23, 13 and 11;

SEQ ID NOs: 24, 6, 4, 20, 18 and 32, and SEQ ID NOs: 8, 30, 14, 12, 26 and 10;

SEQ ID NOs: 24, 6, 4, 20, 18 and 32, and SEQ ID NOs: 7, 21, 5, 25, 33 and 19;

SEQ ID NOs: 24, 6, 4, 20, 18 and 32, and SEQ ID NOs: 8, 30, 14, 12, 26 and 10;

SEQ ID NOs: 8, 30, 14, 12, 26 and 10, and SEQ ID NOs: 9, 13, 31, 27, 15 and 11;

SEQ ID NOs: 7, 21, 5, 25, 33 and 19 and SEQ ID NOs: 9, 13, 31, 27, 15 and 11;

SEQ ID NOs: 20, 32, 24, 4, 6 and 18, and SEQ ID NOs: 26, 30, 12, 14, 8 and 10;

SEQ ID NOs: 6, 20, 4, 24, 32, and 18, and SEQ ID NOs: 8, 12, 30, 26, 14 and 10;

SEQ ID NOs: 7, 25, 19, 5, 33 and 21, and SEQ ID NOs: 15, 31, 9, 27, 13 and 11;

SEQ ID NOs: 24, 6, 16 and 18, and SEQ ID NOs: 26, 20, 10 and 28;

SEQ ID NOs: 24, 6, 16 and 18, and SEQ ID NOs: 26, 10, 20 and 28;

SEQ ID NOs: 24, 6, 16 and 18, and SEQ ID NOs: 7, 25, 17 and 19;

SEQ ID NOs: 7, 19, 17 and 25, and SEQ ID NOs: 21, 27, 11 and 29;

SEQ ID NOs: 24, 16, 6 and 18, and SEQ ID NOs: 27, 11, 21 and 29;

SEQ ID NOs: 7, 25, 17 and 19, and SEQ ID NOs: 11, 27, 21 and 29;

SEQ ID NOs: 7, 25, 17 and 19, and SEQ ID NOs: 21, 27, 11 and 29;

SEQ ID NOs: 22, 6, 20 and 28, and SEQ ID NOs: 23, 7, 21 and 29;

SEQ ID NOs: 22, 20, 6 and 28, and SEQ ID NOs: 7, 21, 23 and 29;

SEQ ID NOs: 26, 10, 20 and 28, and SEQ ID NOs: 21, 27, 11 and 29;

SEQ ID NOs: 22, 6, 16, 20, 18, 28, 26 and 10; or

SEQ ID NOs: 7, 21, 19, 17, 27, 25, 29 and 11.

In some embodiments, the methods entail administering to the subject: one or more fusion polypeptides, or one or more vectors comprising one or more polynucleotides encoding one or more fusion polypeptides, comprising or consisting of an amino acid sequence of any one of SEQ ID NOs: 70-101, 105-112, 200-209, 222-223 and 227, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70-101, 105-112, 200-209, 222-223 and 227. In some embodiments, the methods entail administering to the subject: one or more fusion polypeptides, or one or more vectors comprising one or more polynucleotides encoding one or more fusion polypeptides, comprising or consisting of an amino acid sequence of any one of SEQ ID NOs: 82-83, 85-87, 98-101, 209 and 222-223, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82-83, 85-87, 98-101, 209 and 222-223.

In some embodiments, the methods entail administering to the subject: the following first fusion polypeptide and second fusion polypeptide, or one or more vectors comprising one or more polynucleotides encoding the following first fusion polypeptide and second fusion polypeptide, optionally joined or connected by one or more linkers:

SEQ ID NOs: 70 and 71, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70 and 71, respectively;

SEQ ID NOs: 72 and 73, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 72 and 73, respectively;

SEQ ID NOs: 74 and 75, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 74 and 75, respectively;

SEQ ID NOs: 76 and 77, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 76 and 77, respectively;

SEQ ID NOs: 78 and 79, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 78 and 79, respectively;

SEQ ID NOs: 80 and 81, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 80 and 81, respectively;

SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively;

SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively;

SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively;

SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively;

SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively;

SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively;

SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively;

SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively;

SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively;

SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively;

SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 88, respectively;

SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively;

SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively;

SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively;

SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively;

SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively;

SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively;

SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively;

SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively;

SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively;

SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively;

SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively;

SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively; or SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively.

In some embodiments, the methods entail administering to the subject first and second viral vectors comprising one or more polynucleotides encoding the following first fusion polypeptide and second fusion polypeptide, optionally joined or connected by one or more linkers: (a) a first viral vector comprising one or more polynucleotides encoding the following first fusion polypeptide and second fusion polypeptide comprising SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively, and (b) a second viral vector comprising one or more polynucleotides encoding the following first fusion polypeptide and second fusion polypeptide comprising SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively.

In some embodiments, the methods entail administering to the subject first and second viral vectors comprising one or more polynucleotides encoding the following first fusion polypeptide and second fusion polypeptide, optionally joined or connected by one or more linkers: (a) a first viral vector comprising one or more polynucleotides encoding the following first fusion polypeptide and second fusion polypeptide comprising SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively, and (b) a second viral vector comprising one or more polynucleotides encoding the following first fusion polypeptide and second fusion polypeptide comprising SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively.

In some embodiments, the methods entail administering to the subject first and second viral vectors comprising one or more polynucleotides encoding the following first fusion polypeptide and second fusion polypeptide, optionally joined or connected by one or more linkers: (a) a first viral vector comprising one or more polynucleotides encoding the following first fusion polypeptide and second fusion polypeptide comprising SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively, and (b) a second viral vector comprising one or more polynucleotides encoding the following first fusion polypeptide and second fusion polypeptide comprising SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively.

In some embodiments, the methods entail administering to the subject first and second viral vectors comprising one or more polynucleotides encoding the following first fusion polypeptide and second fusion polypeptide, optionally joined or connected by one or more linkers: (a) a first viral vector comprising one or more polynucleotides encoding the following first fusion polypeptide and second fusion polypeptide comprising SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively, and (b) a second viral vector comprising one or more polynucleotides encoding the following first fusion polypeptide and second fusion polypeptide comprising SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively.

In some embodiments, the methods entail administering to the subject first and second viral vectors comprising one or more polynucleotides encoding the following first fusion polypeptide and second fusion polypeptide, optionally joined or connected by one or more linkers: (a) a first viral vector comprising one or more polynucleotides encoding the following first fusion polypeptide and second fusion polypeptide comprising SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively, and (b) a second viral vector comprising one or more polynucleotides encoding the following first fusion polypeptide and second fusion polypeptide comprising SEQ ID NOs: 87 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 88, respectively.

In some embodiments, the methods entail administering to the subject first and second viral vectors comprising one or more polynucleotides encoding the following first fusion polypeptide and second fusion polypeptide, optionally joined or connected by one or more linkers: (a) a first viral vector comprising one or more polynucleotides encoding the following first fusion polypeptide and second fusion polypeptide comprising SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 88, respectively, and (b) a second viral vector comprising one or more polynucleotides encoding the following first fusion polypeptide and second fusion polypeptide comprising SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively.

In some embodiments, the methods entail administering to the subject first and second viral vectors comprising one or more polynucleotides encoding the following first fusion polypeptide and second fusion polypeptide, optionally joined or connected by one or more linkers: (a) a first viral vector comprising one or more polynucleotides encoding the following first fusion polypeptide and second fusion polypeptide comprising SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively, and (b) a second viral vector comprising one or more polynucleotides encoding the following first fusion polypeptide and second fusion polypeptide comprising SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively.

In some embodiments, the methods entail administering to the subject first and second viral vectors comprising one or more polynucleotides encoding the following first fusion polypeptide and second fusion polypeptide, optionally joined or connected by one or more linkers: (a) a first viral vector comprising one or more polynucleotides encoding the following first fusion polypeptide and second fusion polypeptide comprising SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively, and (b) a second viral vector comprising one or more polynucleotides encoding the following first fusion polypeptide and second fusion polypeptide comprising SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively.

In some embodiments, the methods entail administering to the subject first and second viral vectors comprising one or more polynucleotides encoding the following first fusion polypeptide and second fusion polypeptide, optionally joined or connected by one or more linkers: (a) a first viral vector comprising one or more polynucleotides encoding the following first fusion polypeptide and second fusion polypeptide comprising SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively, and (b) a second viral vector comprising one or more polynucleotides encoding the following first fusion polypeptide and second fusion polypeptide comprising SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively.

In some embodiments, the methods entail administering to the subject first and second viral vectors comprising one or more polynucleotides encoding the following first fusion polypeptide and second fusion polypeptide, optionally joined or connected by one or more linkers: (a) a first viral vector comprising one or more polynucleotides encoding the following first fusion polypeptide and second fusion polypeptide comprising SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively, and (b) a second viral vector comprising one or more polynucleotides encoding the following first fusion polypeptide and second fusion polypeptide comprising SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively.

In some embodiments, the methods entail administering to the subject first and second viral vectors comprising one or more polynucleotides encoding the following first fusion polypeptide and second fusion polypeptide, optionally joined or connected by one or more linkers: (a) a first viral vector comprising one or more polynucleotides encoding the following first fusion polypeptide and second fusion polypeptide comprising SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively, and (b) a second viral vector comprising one or more polynucleotides encoding the following first fusion polypeptide and second fusion polypeptide comprising SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively.

In some embodiments, the methods entail administering to the subject first and second viral vectors comprising one or more polynucleotides encoding the following first fusion polypeptide and second fusion polypeptide, optionally joined or connected by one or more linkers: (a) a first viral vector comprising one or more polynucleotides encoding the following first fusion polypeptide and second fusion polypeptide comprising SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively, and (b) a second viral vector comprising one or more polynucleotides encoding the following first fusion polypeptide and second fusion polypeptide comprising SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively.

In some embodiments, the methods entail administering first and second viral vectors or first and second lipoplexes (e.g., LNPs) comprising first and second polynucleotides encoding the following first fusion polypeptide and second fusion polypeptide: (a) a first polynucleotide or first viral vector or first lipoplex (e.g., LNP) comprising a polynucleotide encoding a first fusion polypeptide comprising SEQ ID NO: 200, that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 200, and (b) a second polynucleotide or second viral vector or second lipoplex (e.g., LNP) comprising a polynucleotide encoding a second fusion polypeptide comprising SEQ ID NO: 201, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 201.

In some embodiments, the methods entail administering first and second viral vectors or first and second lipoplexes (e.g., LNPs) comprising first and second polynucleotides encoding the following first fusion polypeptide and second fusion polypeptide: (a) a first polynucleotide or first viral vector or first lipoplex (e.g., LNP) comprising a polynucleotide encoding a first fusion polypeptide comprising SEQ ID NO: 202, that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 202, and (b) a second polynucleotide or second viral vector or second lipoplex (e.g., LNP) comprising a polynucleotide encoding a second fusion polypeptide comprising SEQ ID NO: 203, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 203.

In some embodiments, the methods entail administering first and second viral vectors or first and second lipoplexes (e.g., LNPs) comprising first and second polynucleotides encoding the following first fusion polypeptide and second fusion polypeptide: (a) a first polynucleotide or first viral vector or first lipoplex (e.g., LNP) comprising a polynucleotide encoding a first fusion polypeptide comprising SEQ ID NO: 204, that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 204, and (b) a second polynucleotide or second viral vector or second lipoplex (e.g., LNP) comprising a polynucleotide encoding a second fusion polypeptide comprising SEQ ID NO: 205, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 205.

In some embodiments, the methods entail administering first and second viral vectors or first and second lipoplexes (e.g., LNPs) comprising first and second polynucleotides encoding the following first fusion polypeptide and second fusion polypeptide: (a) a first polynucleotide or first viral vector or first lipoplex (e.g., LNP) comprising a polynucleotide encoding a first fusion polypeptide comprising SEQ ID NO: 105, that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 105, and (b) a second polynucleotide or second viral vector or second lipoplex (e.g., LNP) comprising a polynucleotide encoding a second fusion polypeptide comprising SEQ ID NO: 107, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 107.

In some embodiments, the methods entail administering first and second viral vectors or first and second lipoplexes (e.g., LNPs) comprising first and second polynucleotides encoding the following first fusion polypeptide and second fusion polypeptide: (a) a first polynucleotide or first viral vector or first lipoplex (e.g., LNP) comprising a polynucleotide encoding a first fusion polypeptide comprising SEQ ID NO: 206, that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 206, and (b) a second polynucleotide or second viral vector or second lipoplex (e.g., LNP) comprising a polynucleotide encoding a second fusion polypeptide comprising SEQ ID NO: 207, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 207.

In some embodiments, the methods entail administering g first and second viral vectors or first and second lipoplexes (e.g., LNPs) comprising first and second polynucleotides encoding the following first fusion polypeptide and second fusion polypeptide: (a) a first polynucleotide or first viral vector or first lipoplex (e.g., LNP) comprising a polynucleotide encoding a first fusion polypeptide comprising SEQ ID NO: 208, that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 208, and (b) a second polynucleotide or second viral vector or second lipoplex (e.g., LNP) comprising a polynucleotide encoding a second fusion polypeptide comprising SEQ ID NO: 209 or SEQ ID NO: 227, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 209 or SEQ ID NO: 227.

In some embodiments, the methods entail administering g first and second viral vectors or first and second lipoplexes (e.g., LNPs) comprising first and second polynucleotides encoding the following first fusion polypeptide and second fusion polypeptide: (a) a first polynucleotide or first viral vector or first lipoplex (e.g., LNP) comprising a polynucleotide encoding a first fusion polypeptide comprising SEQ ID NO: 222, that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 222, and (b) a second polynucleotide or second viral vector or second lipoplex (e.g., LNP) comprising a polynucleotide encoding a second fusion polypeptide comprising SEQ ID NO: 209 or SEQ ID NO: 227, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 209 or SEQ ID NO: 227.

In some embodiments, the methods entail administering g first and second viral vectors or first and second lipoplexes (e.g., LNPs) comprising first and second polynucleotides encoding the following first fusion polypeptide and second fusion polypeptide: (a) a first polynucleotide or first viral vector or first lipoplex (e.g., LNP) comprising a polynucleotide encoding a first fusion polypeptide comprising SEQ ID NO: 222, that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 222, and (b) a second polynucleotide or second viral vector or second lipoplex (e.g., LNP) comprising a polynucleotide encoding a second fusion polypeptide comprising SEQ ID NO: 223, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 223.

In some embodiments, the methods entail administering to the subject a viral vector comprising one or more polynucleotides encoding the following first fusion polypeptide and second fusion polypeptide, optionally joined or connected by one or more linkers: SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively.

In some embodiments, the methods entail administering to the subject a viral vector comprising one or more polynucleotides encoding the following first fusion polypeptide and second fusion polypeptide, optionally joined or connected by one or more linkers: SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively.

In some embodiments, the methods entail administering to the subject: the following first fusion polypeptide and second fusion polypeptide, or one or more vectors comprising one or more polynucleotides encoding the following first fusion polypeptide and second fusion polypeptide, in sequential order, from N-terminus to C-terminus, optionally joined or connected by one or more linkers:

SEQ ID NOs: 70 and 71, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70 and 71, respectively;

SEQ ID NOs: 71 and 70, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 71 and 70, respectively;

SEQ ID NOs: 72 and 73, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 72 and 73, respectively;

SEQ ID NOs: 73 and 72, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 73 and 72, respectively;

SEQ ID NOs: 74 and 75, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 74 and 75, respectively;

SEQ ID NOs: 75 and 74, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 75 and 74, respectively;

SEQ ID NOs: 76 and 77, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 76 and 77, respectively;

SEQ ID NOs: 77 and 76, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 77 and 76, respectively;

SEQ ID NOs: 78 and 79, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 78 and 79, respectively;

SEQ ID NOs: 79 and 78, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 79 and 78, respectively;

SEQ ID NOs: 80 and 81, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 80 and 81, respectively;

SEQ ID NOs: 81 and 80, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 81 and 80, respectively;

SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively;

SEQ ID NOs: 83 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 82, respectively;

SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively;

SEQ ID NOs: 85 and 84, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 84, respectively;

SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively;

SEQ ID NOs: 87 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 86, respectively;

SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively;

SEQ ID NOs: 89 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 89 and 88, respectively;

SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively;

SEQ ID NOs: 85 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 82, respectively;

SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively;

SEQ ID NOs: 86 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 82, respectively;

SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively;

SEQ ID NOs: 88 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 82, respectively;

SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively;

SEQ ID NOs: 87 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 83, respectively;

SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively;

SEQ ID NOs: 87 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 85, respectively;

SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively;

SEQ ID NOs: 87 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 88, respectively;

SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 84, respectively;

SEQ ID NOs: 88 and 84, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 84, respectively;

SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively;

SEQ ID NOs: 89 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 89 and 85, respectively;

SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively;

SEQ ID NOs: 101 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 85, respectively;

SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively;

SEQ ID NOs: 91 and 90, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 91 and 90, respectively;

SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively;

SEQ ID NOs: 93 and 92, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 93 and 92, respectively;

SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively;

SEQ ID NOs: 95 and 94, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 94, respectively;

SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively;

SEQ ID NOs: 97 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 97 and 96, respectively;

SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively;

SEQ ID NOs: 96 and 94, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 94, respectively;

SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively;

SEQ ID NOs: 97 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 97 and 95, respectively;

SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively;

SEQ ID NOs: 221 and 220, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 221 and 220, respectively;

SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively;

SEQ ID NOs: 100 and 98, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 98, respectively;

SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively;

SEQ ID NOs: 101 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 99, respectively;

SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively;

SEQ ID NOs: 99 and 98, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 98, respectively;

SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively; or SEQ ID NOs: 101 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 100, respectively.

In some embodiments, the methods entail administering to the subject: a polynucleotide comprising or consisting of a nucleic acid sequence of any one of SEQ ID NOs: 130-167, 210-219 and 225-226, or a nucleic acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 130-167, 210-219 and 225-226. In some embodiments, the methods entail administering to the subject: a polynucleotide comprising or consisting of a nucleic acid sequence of any one of SEQ ID NOs: 139, 140, 142, 143, 145, 146, 148, 149, 150, 152, 155, 158, 225 and 226, or a nucleic acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139, 140, 142, 143, 145, 146, 148, 149, 150, 152, 155, 158, 225 and 226.

In some embodiments, the methods entail administering to the subject: the following first polynucleotide and second polynucleotide, or one or more vectors comprising or consisting of the following first polynucleotide and second polynucleotide:

SEQ ID NOs: 130 and 132, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 130 and 132, respectively;

SEQ ID NOs: 130 and 134, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 130 and 134, respectively;

SEQ ID NOs: 131 and 133, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 131 and 133, respectively;

SEQ ID NOs: 131 and 135, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 131 and 135, respectively;

SEQ ID NOs: 132 and 136, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 132 and 136, respectively;

SEQ ID NOs: 133 and 135, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 133 and 135, respectively;

SEQ ID NOs: 133 and 137, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 133 and 137, respectively;

SEQ ID NOs: 134 and 136, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 134 and 136, respectively;

SEQ ID NOs: 135 and 137, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 135 and 137, respectively;

SEQ ID NOs: 138 and 141, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 138 and 141, respectively;

SEQ ID NOs: 138 and 144, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 138 and 144, respectively;

SEQ ID NOs: 139 and 142, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 142, respectively;

SEQ ID NOs: 139 and 145, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 145, respectively;

SEQ ID NOs: 140 and 146, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 140 and 146, respectively;

SEQ ID NOs: 142 and 148, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 142 and 148, respectively;

SEQ ID NOs: 143 and 149, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 143 and 149, respectively;

SEQ ID NOs: 145 and 148, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 145 and 148, respectively;

SEQ ID NOs: 150 and 152, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively;

SEQ ID NOs: 150 and 155, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 155, respectively;

SEQ ID NOs: 151 and 153, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 151 and 153, respectively;

SEQ ID NOs: 151 and 156, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 151 and 156, respectively;

SEQ ID NOs: 152 and 158, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 152 and 158, respectively;

SEQ ID NOs: 153 and 159, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 153 and 159, respectively;

SEQ ID NOs: 154 and 157, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 154 and 157, respectively;

SEQ ID NOs: 155 and 158, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 155 and 158, respectively;

SEQ ID NOs: 156 and 159, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 156 and 159, respectively;

SEQ ID NOs: 160 and 161, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 160 and 161, respectively;

SEQ ID NOs: 162 and 163, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 162 and 163, respectively;

SEQ ID NOs: 164 and 165, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 164 and 165, respectively;

SEQ ID NOs: 166 and 167, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 166 and 167, respectively;

SEQ ID NOs: 210 and 211, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 210 and 211, respectively;

SEQ ID NOs: 212 and 213, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 212 and 213, respectively;

SEQ ID NOs: 214 and 215, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 214 and 215, respectively;

SEQ ID NOs: 216 and 217, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 216 and 217, respectively;

SEQ ID NOs: 218 and 219, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 218 and 219, respectively;

SEQ ID NOs: 218 and 226, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 218 and 226, respectively; or SEQ ID NOs: 225 and 226, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 225 and 226, respectively.

In some embodiments, the method entails administering: (a) a first vector or lipoplex (e.g., LNP) comprising a first polynucleotide comprising SEQ ID NO: 210, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 210, and (b) a second vector or lipoplex (e.g., LNP) comprising a second polynucleotide comprising SEQ ID NO: 211, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 211.

In some embodiments, the method entails administering: (a) a first vector or lipoplex (e.g., LNP) comprising a first polynucleotide comprising SEQ ID NO: 212, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 212, and (b) a second vector or lipoplex (e.g., LNP) comprising a second polynucleotide comprising SEQ ID NO: 213, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 213.

In some embodiments, the method entails administering: (a) a first vector or lipoplex (e.g., LNP) comprising a first polynucleotide comprising SEQ ID NO: 214, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 214, and (b) a second vector or lipoplex (e.g., LNP) comprising a second polynucleotide comprising SEQ ID NO: 215, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 215.

In some embodiments, the method entails administering: (a) a first vector or lipoplex (e.g., LNP) comprising a first polynucleotide comprising SEQ ID NO: 216, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 216, and (b) a second vector or lipoplex (e.g., LNP) comprising a second polynucleotide comprising SEQ ID NO: 217, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 217.

In some embodiments, the method entails administering: (a) a first vector or lipoplex (e.g., LNP) comprising a first polynucleotide comprising SEQ ID NO: 218, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 218, and (b) a second vector or lipoplex (e.g., LNP) comprising a second polynucleotide comprising SEQ ID NO: 219, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 219.

In some embodiments, the method entails administering: (a) a first vector or lipoplex (e.g., LNP) comprising a first polynucleotide comprising SEQ ID NO: 218, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 218, and (b) a second vector or lipoplex (e.g., LNP) comprising a second polynucleotide comprising SEQ ID NO: 226, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 226.

In some embodiments, the method entails administering: (a) a first vector or lipoplex (e.g., LNP) comprising a first polynucleotide comprising SEQ ID NO: 225, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 225, and (b) a second vector or lipoplex (e.g., LNP) comprising a second polynucleotide comprising SEQ ID NO: 226, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 226.

In some embodiments, the methods entail administering to the subject: a compound fusion polypeptide or a vector comprising a polynucleotide encoding a compound fusion polypeptide, the compound fusion polypeptide comprising or consisting of an amino acid sequence of any one of SEQ ID NOs: 105-112, 200-209, 222-223 and 227, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 105-112, 200-209, 222-223 and 227. In some embodiments, the methods entail administering to the subject: a compound fusion polypeptide or a vector comprising a polynucleotide encoding a compound fusion polypeptide, the compound fusion polypeptide comprising or consisting of an amino acid sequence of any one of SEQ ID NOs: 209, 222 and 223, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 209, 222 and 223.

In various embodiments of the methods, the one or more fusion polypeptides do not comprise any polypeptide segments corresponding to Gag 54-146; Gag 370-500; Pol 1-55; Pol 118-128; Pol 321-366; Pol 432-541; Pol 607-682; Pol 709-746; Pol 828-839; Pol 921-931; Nef 1-63; Nef 100-116 and Nef 149-206, or fragments or subsequences thereof, wherein the Gag, Pol and Nef amino acid position numbers correspond to SEQ ID NOs: 1, 2 and 3, respectively. In various embodiments of the methods, the one or more fusion polypeptides do not comprise any polypeptide segments having an amino acid sequence of SEQ ID NOs: 35-47, or fragments or subsequences thereof, or an amino acid sequence at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 35-47, or fragments or subsequences thereof.

In some embodiments, the methods entail administering one or more viral expression vectors that express one or more of the fusion polypeptides. In various embodiments, the methods entail administering from about $10^3$ to about $10^{12}$ viral focus forming units (FFU) or plaque forming units (PFU) or infectious units (IU) or viral particles (vp), e.g. from about $10^4$ to about $10^7$ viral FFU or PFU or IU or vp, e.g. from about $10^3$ to about $10^4$, $10^5$, $10^6$, $10^7$, $10^8$, $10^9$, $10^{10}$, $10^{11}$, $10^{12}$, $10^{13}$, $10^{14}$ or $10^{15}$ viral FFU or PFU or IU or vp, per administration.

In various embodiments, the methods implement a prime-boost regimen comprising administering a priming composition at a first time point and administering one or more boosting compositions at one or more subsequent time points. Generally, in a prime-boost regimen, the priming composition and the boosting composition are administered sequentially. Illustrative prime-boost regimens include prime-boost-prime-boost and prime-boost-boost-boost. In some embodiments, the administrations of the priming composition and the one or more boosting compositions are spaced at least 1 week, 2 weeks, 3 weeks or 1 month apart, e.g., at least 2, 3, 4, 5, 6, 7, 8, 9, 10, 11 or 12 months apart. In some embodiments, the priming composition and the boosting composition comprise the same immunogenic composition. In some embodiments, the priming composition and the boosting composition comprise different immunogenic compositions. In some embodiments, the priming composition and the boosting composition comprise the same one or more fusion polypeptides and same viral expression vector. In some embodiments, the priming composition and the boosting composition comprise different fusion polypeptides and the same viral expression vectors. In some embodiments, the priming composition and the boosting composition comprise the same fusion polypeptides and different viral expression vectors. In some embodiments, the methods entail priming with a first viral expression vector, and boosting with a second viral expression vector. As appropriate, a prime-boost regimen can be repeated one or more iterations.

In various embodiments, the prime-boost regimen comprises:

Priming with one or more viral expression vectors and boosting with one or more polynucleotides, wherein the one or more polynucleotides comprise DNA, cDNA, mRNA or self-replicating RNA;

Priming with one or more polynucleotides, wherein the one or more polynucleotides comprise DNA, cDNA, mRNA, self-amplifying or self-replicating RNA, and boosting with one or more viral expression vectors;

Priming with one or more viral expression vectors, and boosting with one or more viral expression vectors, wherein the one or more viral expression vectors in the priming composition and the one or more viral expression vectors in the boosting composition are from identical, related or unrelated taxonomical families;

Priming with one or more replication-deficient viral expression vectors and boosting with one or more replication-deficient viral expression vectors, wherein the one or more replication-deficient viral expression vectors in the priming composition and the one or more replication-deficient viral expression vectors in the boosting composition are from identical, related or unrelated taxonomical families;

Priming with one or more replication-attenuated viral expression vectors and boosting with one or more replication-attenuated viral expression vectors, wherein the one or more replication-attenuated viral expression vectors in the priming composition and the one or more replication-attenuated viral expression vectors in the boosting composition are from identical, related or unrelated taxonomical families;

Priming with one or more replication-deficient viral expression vectors and boosting with one or more replication-attenuated viral expression vectors;

Priming with one or more replication-attenuated viral expression vectors and boosting with one or more replication-deficient viral expression vectors;

Priming with one or more Lymphocytic choriomeningitis mammarenavirus (LCMV) viral expression vectors and boosting with one or more Pichinde mammarenavirus viral expression vectors;

Priming with one or more Pichinde mammarenavirus viral expression vectors and boosting with one or more Lymphocytic choriomeningitis mammarenavirus (LCMV) viral expression vectors;

Priming with one or more replication deficient Pichinde mammarenavirus viral expression vectors and boosting with one or more replication deficient Lymphocytic choriomeningitis mammarenavirus (LCMV) viral expression vectors;

Priming with one or more replication deficient Lymphocytic choriomeningitis mammarenavirus (LCMV) viral expression vectors and boosting with one or more replication deficient Pichinde mammarenavirus viral expression vectors;

Priming with one or more arenavirus viral expression vectors and boosting with one or more adenovirus viral expression vectors;

Priming with one or more adenovirus viral expression vectors and boosting with boosting composition comprising one or more arenavirus viral expression vectors;

- Priming with one or more adenovirus viral expression vectors and boosting with boosting composition comprising one or more RNA molecules (e.g., mRNA, self-amplifying or self-replicating RNA);
- Priming with one or more RNA molecules (e.g., mRNA, self-amplifying or self-replicating RNA) and boosting with boosting composition comprising one or more adenovirus viral expression vectors;
- Priming with one or more chimpanzee adenoviral (ChAd) expression vectors and boosting with boosting composition comprising one or more self-amplifying or self-replicating RNA (saRNA or samRNA);
- Priming with one or more self-amplifying or self-replicating RNA (saRNA or samRNA) and boosting with boosting composition comprising one or more chimpanzee adenoviral (ChAd) expression vectors;
- Priming with one or more poxvirus (e.g., Vaccinia) viral expression vectors and boosting with one or more arenavirus viral expression vectors;
- Priming with one or more arenavirus viral expression vectors and boosting with boosting composition comprising one or more poxvirus (e.g., Vaccinia) viral expression vectors;
- Priming with one or more poxvirus (e.g., Vaccinia) viral expression vectors and boosting with one or more adenovirus viral expression vectors; or
- Priming with one or more adenovirus viral expression vectors and boosting with boosting composition comprising one or more poxvirus (e.g., Vaccinia) viral expression vectors.

In some embodiments, the prime-boost regimen comprises:

1) Priming with an immunogenic composition comprising the following first fusion polypeptide and second fusion polypeptide, or one or more vectors comprising one or more polynucleotides encoding the following first fusion polypeptide and second fusion polypeptide, optionally joined or connected by one or more linkers:

- SEQ ID NOs: 70 and 71, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70 and 71, respectively;
- SEQ ID NOs: 72 and 73, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 72 and 73, respectively;
- SEQ ID NOs: 74 and 75, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 74 and 75, respectively;
- SEQ ID NOs: 76 and 77, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 76 and 77, respectively;
- SEQ ID NOs: 78 and 79, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 78 and 79, respectively;
- SEQ ID NOs: 80 and 81, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 80 and 81, respectively;
- SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively;
- SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively;
- SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively;
- SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively;
- SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively;
- SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively;
- SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively;
- SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively;
- SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively;
- SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively;
- SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 88, respectively;
- SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively;
- SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively;

SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively;

SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively;

SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively;

SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively;

SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively;

SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively;

SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively;

SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively;

SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively;

SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively; or SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively; and 2) Boosting with an immunogenic composition comprising the following first fusion polypeptide and second fusion polypeptide, or one or more vectors comprising one or more polynucleotides encoding the following first fusion polypeptide and second fusion polypeptide, optionally joined or connected by one or more linkers:

SEQ ID NOs: 70 and 71, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70 and 71, respectively;

SEQ ID NOs: 72 and 73, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 72 and 73, respectively;

SEQ ID NOs: 74 and 75, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 74 and 75, respectively;

SEQ ID NOs: 76 and 77, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 76 and 77, respectively;

SEQ ID NOs: 78 and 79, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 78 and 79, respectively;

SEQ ID NOs: 80 and 81, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 80 and 81, respectively;

SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively;

SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively;

SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively;

SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively;

SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively;

SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively;

SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively;

SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively;

SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively;

SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively;

SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 88, respectively;

SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively;

SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively;

SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively;

SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively;

SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively;

SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively;

SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively;

SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively;

SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively;

SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively;

SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively;

SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively; or SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively.

In some embodiments, the prime-boost regimen comprises:

1) Priming with an immunogenic composition comprising the following first fusion polypeptide and second fusion polypeptide, or one or more vectors comprising one or more polynucleotides encoding the following first fusion polypeptide and second fusion polypeptide, optionally joined or connected by one or more linkers:

a) SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively;

b) SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively;

c) SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively;

d) SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively; and/or e) SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively; and 2) Boosting with an immunogenic composition comprising the following first fusion polypeptide and second fusion polypeptide, or one or more vectors comprising one or more polynucleotides encoding the following first fusion polypeptide and second fusion polypeptide, optionally joined or connected by one or more linkers:

a) SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively;

b) SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively;

c) SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; and/or d) SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively.

In some embodiments, the prime-boost regimen comprises: 1) Priming with an immunogenic composition comprising first and second viral vectors comprising one or more polynucleotides encoding the following first fusion polypeptide and second fusion polypeptide, optionally joined or connected by one or more linkers:

a) a first viral vector comprising one or more polynucleotides encoding first fusion polypeptide and second fusion polypeptides comprising SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively; and b) a second viral vector comprising one or more polynucleotides encoding first fusion polypeptide and second fusion polypeptides comprising SEQ ID NOs:86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively; and 2) Boosting with an immunogenic composition comprising first and second viral vectors comprising one or more polynucleotides encoding the following first fusion polypeptide and second fusion polypeptide, optionally joined or connected by one or more linkers:

a) a first viral vector comprising one or more polynucleotides encoding first fusion polypeptide and second fusion polypeptides comprising SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively; and/or b) a second viral vector comprising one or more polynucleotides encoding first fusion polypeptide and second fusion polypeptides comprising SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively.

In some embodiments, the prime-boost regimen comprises:

1) Priming with an immunogenic composition comprising first and second viral vectors comprising one or more polynucleotides encoding the following first fusion polypeptide and second fusion polypeptide, optionally joined or connected by one or more linkers:

a) a first viral vector comprising one or more polynucleotides encoding first fusion polypeptide and second fusion polypeptides comprising SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; and b) a second viral vector comprising one or more polynucleotides encoding first fusion polypeptide and second fusion polypeptides comprising SEQ ID NOs:83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively; and 2) Boosting with an immunogenic composition comprising first and second viral vectors comprising one or more polynucleotides encoding the following first fusion polypeptide and second fusion polypeptide, optionally joined or connected by one or more linkers:

a) a first viral vector comprising one or more polynucleotides encoding first fusion polypeptide and second fusion polypeptides comprising SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 88, respectively; and/or b) a second viral vector comprising one or more polynucleotides encoding first fusion polypeptide and second fusion polypeptides comprising SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively.

In some embodiments, the prime-boost regimen comprises:

1) Priming with an immunogenic composition comprising first and second viral vectors comprising one or more polynucleotides encoding the following first fusion polypeptide and second fusion polypeptide, optionally joined or connected by one or more linkers:

a) a first viral vector comprising one or more polynucleotides encoding first fusion polypeptide and second fusion polypeptides comprising SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; and b) a second viral vector comprising one or more polynucleotides encoding first fusion polypeptide and second fusion polypeptides comprising SEQ ID NOs:83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively; and 2) Boosting with an immunogenic composition comprising first and second viral vectors comprising one or more polynucleotides encoding the following first fusion polypeptide and second fusion polypeptide, optionally joined or connected by one or more linkers:

a) a first viral vector comprising one or more polynucleotides encoding first fusion polypeptide and second fusion polypeptides comprising SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; and/or b) a second viral vector comprising one or more polynucleotides encoding first fusion polypeptide and second fusion polypeptides comprising SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively. In various embodiments of this method, the priming vectors are Cali mammarenavirus (a.k.a., Pichinde mammarenavirus or Pichinde arenavirus) and the boosting vectors are Lymphocytic choriomeningitis mammarenavirus (LCMV). In various embodiments of this method the priming vectors and boosting vectors are replication attenuated or replication competent.

In some embodiments, the prime-boost regimen comprises:

1) Priming with an immunogenic composition comprising first and second viral vectors comprising one or more polynucleotides encoding the following first fusion polypeptide and second fusion polypeptide, optionally joined or connected by one or more linkers:

a) a first viral vector comprising one or more polynucleotides encoding first fusion polypeptide and second fusion polypeptides comprising SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; and b) a second viral vector comprising one or more polynucleotides encoding first fusion polypeptide and second fusion polypeptides comprising SEQ ID NOs:83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively; and 2) Boosting with an immunogenic composition comprising first and second viral vectors comprising one or more polynucleotides encoding the following first fusion polypeptide and second fusion polypeptide, optionally joined or connected by one or more linkers:

a) a first viral vector comprising one or more polynucleotides encoding first fusion polypeptide and second fusion polypeptides comprising SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; and/or b) a second viral vector comprising one or more polynucleotides encoding first fusion polypeptide and second fusion polypeptides comprising SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively. In various embodiments of this method, the priming vectors are Cali mammarenavirus (a.k.a., Pichinde mammarenavirus or Pichinde arenavirus) and the boosting vectors are Lymphocytic choriomeningitis mammarenavirus (LCMV). In various embodiments of this method the priming vectors and boosting vectors are replication attenuated or replication competent.

In some embodiments, the prime-boost regimen comprises:

1) Priming with an immunogenic composition comprising first and second viral vectors comprising one or more polynucleotides encoding the following first fusion polypeptide and second fusion polypeptide, optionally joined or connected by one or more linkers:

a) a first viral vector comprising one or more polynucleotides encoding first fusion polypeptide and second fusion polypeptides comprising SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; and b) a second viral vector comprising one or more polynucleotides encoding first fusion polypeptide and second fusion polypeptides comprising SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively; and 2) Boosting with an immunogenic composition comprising first and second viral vectors comprising one or more polynucleotides encoding the following first fusion polypeptide and second fusion polypeptide, optionally joined or connected by one or more linkers:

a) a first viral vector comprising one or more polynucleotides encoding first fusion polypeptide and second fusion polypeptides comprising SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; and/or b) a second viral vector comprising one or more polynucleotides encoding first fusion polypeptide and second fusion polypeptides comprising SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively. In various embodiments of this method, the priming vectors are Lymphocytic choriomeningitis mammarenavirus (LCMV) and the boosting vectors are Cali mammarenavirus (a.k.a., Pichinde mammarenavirus or Pichinde arenavirus). In various embodiments of this method the priming vectors and boosting vectors are replication attenuated or replication competent.

In some embodiments, the prime-boost regimen comprises:

1) Priming with an immunogenic composition comprising first and second viral vectors comprising one or more polynucleotides encoding the following first fusion polypeptide and second fusion polypeptide, optionally joined or connected by one or more linkers:

a) a first viral vector comprising one or more polynucleotides encoding first fusion polypeptide and second fusion polypeptides comprising SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; and b) a second viral vector comprising one or more polynucleotides encoding first fusion polypeptide and second fusion polypeptides comprising SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively; and 2) Boosting with an immunogenic composition comprising first and second viral vectors comprising one or more polynucleotides encoding the following first fusion polypeptide and second fusion polypeptide, optionally joined or connected by one or more linkers:

a) a first viral vector comprising one or more polynucleotides encoding first fusion polypeptide and second fusion polypeptides comprising SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; and/or b) a second viral vector comprising one or more polynucleotides encoding first fusion polypeptide and second fusion polypeptides comprising SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively. In various embodiments of this method, the priming vectors are Lymphocytic choriomeningitis mammarenavirus (LCMV) and the boosting vectors are Cali mammarenavirus (a.k.a., Pichinde mammarenavirus or Pichinde arenavirus). In various embodiments of this method the priming vectors and boosting vectors are replication attenuated or replication competent.

In some embodiments, the prime-boost regimen comprises:

1) Priming with an immunogenic composition comprising first and second viral vectors comprising one or more polynucleotides encoding the following first fusion polypeptide and second fusion polypeptide, optionally joined or connected by one or more linkers:

a) a first viral vector comprising one or more polynucleotides encoding first fusion polypeptide and second fusion polypeptides comprising SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively, or one or more polynucleotides encoding first fusion polypeptide and second fusion polypeptides comprising SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively; and b) a second viral vector comprising one or more polynucleotides encoding first fusion polypeptide and second fusion polypeptides comprising SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively; and 2) Boosting with an immunogenic composition comprising first and second viral vectors comprising one or more polynucleotides encoding the following first fusion polypeptide and second fusion polypeptide, optionally joined or connected by one or more linkers:

a) a first viral vector comprising one or more polynucleotides encoding first fusion polypeptide and second fusion polypeptides comprising SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; and/or b) a second viral vector comprising one or more polynucleotides encoding first fusion polypeptide and second fusion polypeptides comprising SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively.

In some embodiments, the prime-boost regimen comprises:

1) Priming with an immunogenic composition comprising a viral vector comprising one or more polynucleotides encoding the following first fusion polypeptide and second fusion polypeptide, optionally joined or connected by one or more linkers: SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively; and 2) Boosting with an immunogenic composition comprising a viral vector comprising one or more polynucleotides encoding the following first fusion polypeptide and second fusion polypeptide, optionally joined or connected by one or more linkers: SEQ ID NOs: 87 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 88, respectively.

In some embodiments, the prime-boost regimen comprises: priming and boosting with an immunogenic composition comprising a first viral vector or a lipoplex (e.g., LNP) comprising one or more polynucleotides encoding first fusion polypeptide and second fusion polypeptides, optionally joined or connected by one or more linkers, comprising SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively; and a second viral vector or a lipoplex (e.g., LNP) comprising one or more polynucleotides encoding first fusion polypeptide and second fusion polypeptides, optionally joined or connected by one or more linkers, comprising SEQ ID NOs: 87 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 88, respectively.

In some embodiments, the prime-boost regimen comprises:

1) Priming with an immunogenic composition comprising a viral vector comprising one or more polynucleotides encoding the following first fusion polypeptide and second fusion polypeptide, optionally joined or connected by one or more linkers: SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively; and 2) Boosting with an immunogenic composition comprising a viral vector comprising one or more polynucleotides encoding the following first fusion polypeptide and second fusion polypeptide, optionally joined or connected by one or more linkers: SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively.

In some embodiments, the prime-boost regimen comprises: priming and boosting with an immunogenic composition comprising a first viral vector or a lipoplex (e.g., LNP) comprising one or more polynucleotides encoding first fusion polypeptide and second fusion polypeptides, optionally joined or connected by one or more linkers, comprising SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively; and a second viral vector or a lipoplex (e.g., LNP) comprising one or more polynucleotides encoding first fusion polypeptide and second fusion polypeptides, optionally joined or connected by one or more linkers, comprising SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively.

In some embodiments, the prime-boost regimen comprises:

1) Priming with an immunogenic composition comprising a viral vector comprising one or more polynucleotides encoding the following first fusion polypeptide and second fusion polypeptide, optionally joined or connected by one or more linkers: SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively; and 2) Boosting with an immunogenic composition comprising a viral vector comprising one or more polynucleotides encoding the following first fusion polypeptide and second fusion polypeptide, optionally joined or connected by one or more linkers: SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively.

In some embodiments, the prime-boost regimen comprises:

1) Priming with an immunogenic composition comprising a viral vector comprising one or more polynucleotides encoding the following first fusion polypeptide and second fusion polypeptide, optionally joined or connected by one or more linkers: SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively; and 2) Boosting with an immunogenic composition comprising a viral vector comprising one or more polynucleotides encoding the following first fusion polypeptide and second fusion polypeptide, optionally joined or connected by one or more linkers: SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively.

In some embodiments, the prime-boost regimen comprises: priming and boosting with an immunogenic composition comprising a first viral vector or a lipoplex (e.g., LNP) comprising one or more polynucleotides encoding first fusion polypeptide and second fusion polypeptides, optionally joined or connected by one or more linkers, comprising SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively; and a second viral vector or a lipoplex (e.g., LNP) comprising one or more polynucleotides encoding first fusion polypeptide and second fusion polypeptides, optionally joined or connected by one or more linkers, comprising SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively.

In some embodiments, the prime-boost regimen comprises:

1) Priming with an immunogenic composition comprising a viral vector comprising one or more polynucleotides encoding the following first fusion polypeptide and second fusion polypeptide, optionally joined or connected by one or more linkers: SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively; and 2) Boosting with an immunogenic composition comprising a viral vector comprising one or more polynucleotides encoding the following first fusion polypeptide and second fusion polypeptide, optionally joined or connected by one or more linkers: SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively.

In some embodiments, the prime-boost regimen comprises:

1) Priming with an immunogenic composition comprising a viral vector comprising one or more polynucleotides encoding the following first fusion polypeptide and second fusion polypeptide, optionally joined or connected by one or more linkers: SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively; and 2) Boosting with an immunogenic composition comprising a viral vector comprising one or more polynucleotides encoding the following first fusion polypeptide and second fusion polypeptide, optionally joined or connected by one or more linkers: SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively.

In some embodiments, the prime-boost regimen comprises: priming and boosting with an immunogenic composition comprising a first viral vector or a lipoplex (e.g., LNP) comprising one or more polynucleotides encoding first fusion polypeptide and second fusion polypeptides, optionally joined or connected by one or more linkers, comprising SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively; and a second viral vector or a lipoplex (e.g., LNP) comprising one or more polynucleotides encoding first fusion polypeptide and second fusion polypeptides, optionally joined or connected by one or more linkers, comprising SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively.

In some embodiments, the prime-boost regimen comprises: priming and boosting with an immunogenic composition comprising a first viral vector or a lipoplex (e.g., LNP) comprising one or more polynucleotides encoding first fusion polypeptide and second fusion polypeptides, optionally joined or connected by one or more linkers, comprising SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively; and a second viral vector or a lipoplex (e.g., LNP) comprising one or more polynucleotides encoding first fusion polypeptide and second fusion polypeptides, optionally joined or connected by one or more linkers, comprising SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively.

In some embodiments, the prime-boost regimen comprises:

1) Priming with an immunogenic composition comprising a viral vector comprising one or more polynucleotides encoding the following first fusion polypeptide and second fusion polypeptide, optionally joined or connected by one or more linkers: SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively; and 2) Boosting with an immunogenic composition comprising a viral vector comprising one or more polynucleotides encoding the following first fusion polypeptide and second fusion polypeptide, optionally joined or connected by one or more linkers: SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively.

In some embodiments, the prime-boost regimen comprises:

1) Priming with an immunogenic composition comprising a viral vector comprising a polynucleotide encoding a compound fusion polypeptide comprising SEQ ID NO: 105, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 105; and 2) Boosting with an immunogenic composition comprising a viral vector comprising a polynucleotide encoding a compound fusion polypeptide comprising SEQ ID NO: 109, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 109.

In some embodiments, the prime-boost regimen comprises:

1) Priming with an immunogenic composition comprising a viral vector comprising a polynucleotide encoding a compound fusion polypeptide comprising SEQ ID NO: 105 or 206, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 105 or 206; and 2) Boosting with an immunogenic composition comprising a viral vector comprising a polynucleotide encoding a compound fusion polypeptide comprising SEQ ID NO: 107 or 207, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 107 or 207.

In some embodiments, the prime-boost regimen comprises: priming and boosting with an immunogenic composition comprising a first viral vector or a lipoplex (e.g., LNP) comprising a polynucleotide encoding a first fusion polypeptide comprising SEQ ID NO: 105, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 105, respectively; and a second viral vector or a lipoplex (e.g., LNP) comprising a polynucleotide encoding a second fusion polypeptide, comprising SEQ ID NO: 107, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 107, respectively.

In some embodiments, the prime-boost regimen comprises: priming and boosting with an immunogenic composition comprising a first viral vector or a lipoplex (e.g., LNP) comprising a polynucleotide encoding a first fusion polypeptide comprising SEQ ID NO: 206, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 206, respectively; and a second viral vector or a lipoplex (e.g., LNP) comprising a polynucleotide encoding a second fusion polypeptide, comprising SEQ ID NO: 207, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 207, respectively.

In some embodiments, the prime-boost regimen comprises:

1) Priming with an immunogenic composition comprising a viral vector comprising a polynucleotide encoding a compound fusion polypeptide comprising SEQ ID NO: 208, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 208; and 2) Boosting with an immunogenic composition comprising a viral vector comprising a polynucleotide encoding a compound fusion polypeptide comprising SEQ ID NO: 209 or SEQ ID NO: 227, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 209 or SEQ ID NO: 227.

In some embodiments, the prime-boost regimen comprises:

1) Priming with an immunogenic composition comprising a viral vector comprising a polynucleotide encoding a compound fusion polypeptide comprising SEQ ID NO: 222, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 222; and 2) Boosting with an immunogenic composition comprising a viral vector comprising a polynucleotide encoding a compound fusion polypeptide comprising SEQ ID NO: 209 or SEQ ID NO: 227, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 209 or SEQ ID NO: 227.

In some embodiments, the prime-boost regimen comprises:

1) Priming with an immunogenic composition comprising a viral vector comprising a polynucleotide encoding a compound fusion polypeptide comprising SEQ ID NO: 222, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 222; and 2) Boosting with an immunogenic composition comprising a viral vector comprising a polynucleotide encoding a compound fusion polypeptide comprising SEQ ID NO: 223, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 223.

In some embodiments, the prime-boost regimen comprises: priming and boosting with an immunogenic composition comprising a first viral vector or a lipoplex (e.g., LNP) comprising a polynucleotide encoding a first fusion polypeptide comprising SEQ ID NO: 208, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 208, respectively; and a second viral vector or a lipoplex (e.g., LNP) comprising a polynucleotide encoding a second fusion polypeptide, comprising SEQ ID NO: 209 or SEQ ID NO: 227, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 209 or SEQ ID NO: 227, respectively. In various embodiments of this method, the priming composition comprises one or more ChAd vectors and the boosting composition comprises one or more self-amplifying mRNA molecules, e.g., analogous to the prime-boost regimen described in NCT04776317 and WO 2021/236854 for SARS-CoV2 vaccines, in WO 2021/203104 for infectious disease vaccines and in WO 2020/243719.

In some embodiments, the prime-boost regimen comprises: priming and boosting with an immunogenic composition comprising a first viral vector or a lipoplex (e.g., LNP) comprising a polynucleotide encoding a first fusion polypeptide comprising SEQ ID NO: 222, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 222, respectively; and a second viral vector or a lipoplex (e.g., LNP) comprising a polynucleotide encoding a second fusion polypeptide, comprising SEQ ID NO: 209 or SEQ ID NO: 227, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 209 or SEQ ID NO: 227, respectively. In various embodiments of this method, the priming composition comprises one or more ChAd vectors and the boosting composition comprises one or more self-amplifying mRNA molecules, e.g., analogous to the prime-boost regimen described in NCT04776317 and WO 2021/236854 for SARS-CoV2 vaccines, in WO 2021/203104 for infectious disease vaccines and in WO 2020/243719.

In some embodiments, the prime-boost regimen comprises: priming and boosting with an immunogenic composition comprising a first viral vector or a lipoplex (e.g., LNP) comprising a polynucleotide encoding a first fusion polypeptide comprising SEQ ID NO: 222, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 222, respectively; and a second viral vector or a lipoplex (e.g., LNP) comprising a polynucleotide encoding a second fusion polypeptide, comprising SEQ ID NO: 223, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 223, respectively. In various embodiments of this method, the priming composition comprises one or more ChAd vectors and the boosting composition comprises one or more self-amplifying mRNA molecules, e.g., analogous to the prime-boost regimen described in NCT04776317 and WO 2021/236854 for SARS-CoV2 vaccines, in WO 2021/203104 for infectious disease vaccines and in WO 2020/243719.

In some embodiments, the prime-boost regimen comprises:

1) Priming with an immunogenic composition comprising a viral vector comprising one or more polynucleotides encoding the following first fusion polypeptide and second fusion polypeptide, optionally joined or connected by one or more linkers: SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively; and 2) Boosting with an immunogenic composition comprising a viral vector comprising one or more polynucleotides encoding the following first fusion polypeptide and second fusion polypeptide, optionally joined or connected by one or more linkers: SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively.

In some embodiments, the prime-boost regimen comprises:

1) Priming with an immunogenic composition comprising a viral vector comprising a polynucleotide encoding a compound fusion polypeptide comprising SEQ ID NO: 107, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 107; and 2) Boosting with an immunogenic composition comprising a viral vector comprising a polynucleotide encoding a compound fusion polypeptide comprising SEQ ID NO: 111, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 111.

In some embodiments, the prime-boost regimen comprises:

1) Priming with an immunogenic composition comprising a viral vector comprising a polynucleotide encoding a compound fusion polypeptide comprising SEQ ID NO: 200, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 200; and 2) Boosting with an immunogenic composition comprising a viral vector comprising a polynucleotide encoding a compound fusion polypeptide comprising SEQ ID NO: 201, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 201.

In some embodiments, the prime-boost regimen comprises:

1) Priming with an immunogenic composition comprising a viral vector comprising a polynucleotide encoding a compound fusion polypeptide comprising SEQ ID NO: 202, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 202; and 2) Boosting with an immunogenic composition comprising a viral vector comprising a polynucleotide encoding a compound fusion polypeptide comprising SEQ ID NO: 203, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 203.

In some embodiments, the prime-boost regimen comprises:

1) Priming with an immunogenic composition comprising a viral vector comprising a polynucleotide encoding a compound fusion polypeptide comprising SEQ ID NO: 204, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 204; and 2) Boosting with an immunogenic composition comprising a viral vector comprising a polynucleotide encoding a compound fusion polypeptide comprising SEQ ID NO: 205, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 205.

In some embodiments, the prime-boost regimen comprises: priming and boosting with an immunogenic composition comprising a first viral vector or a lipoplex (e.g., LNP) comprising a polynucleotide encoding a first fusion polypeptide comprising SEQ ID NO: 204, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 204, respectively; and a second viral vector or a lipoplex (e.g., LNP) comprising a polynucleotide encoding a second fusion polypeptide, comprising SEQ ID NO: 205, or a fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 205, respectively.

In some embodiments, the prime-boost regimen comprises:

1) Priming with an immunogenic composition comprising first and second viral vectors comprising the following polynucleotides:

a) a first viral vector comprising first and second polynucleotides comprising SEQ ID NOs: 131 and 135, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 131 and 135, respectively; and b) a second viral vector comprising first and second polynucleotides comprising SEQ ID NOs: 133 and 137, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 133 and 137, respectively; and 2) Boosting with an immunogenic composition comprising first and second viral vectors comprising the following polynucleotides:

a) a first viral vector comprising first and second polynucleotides comprising SEQ ID NOs: 139 and 145, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 145, respectively; and b) a second viral vector comprising first and second polynucleotides comprising SEQ ID NOs: 142 and 148, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 142 and 148, respectively.

In some embodiments, the prime-boost regimen comprises:

1) Priming with an immunogenic composition comprising first and second viral vectors comprising the following polynucleotides:

a) a first viral vector comprising first and second polynucleotides comprising SEQ ID NOs: 139 and 145, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 145, respectively; and b) a second viral vector comprising first and second polynucleotides comprising SEQ ID NOs: 142 and 148, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 142 and 148, respectively; and 2) Boosting with an immunogenic composition comprising first and second viral vectors comprising the following polynucleotides:

a) a first viral vector comprising first and second polynucleotides comprising SEQ ID NOs: 131 and 135, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 131 and 135, respectively; and b) a second viral vector comprising first and second polynucleotides comprising SEQ ID NOs: 133 and 137, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 133 and 137, respectively.

In some embodiments, the prime-boost regimen comprises:

1) Priming with an immunogenic composition comprising first and second viral vectors comprising the following polynucleotides:

a) a first viral vector comprising first and second polynucleotides comprising SEQ ID NOs: 140 and 146, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 140 and 146, respectively; and b) a second viral vector comprising first and second polynucleotides comprising SEQ ID NOs: 143 and 149, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 143 and 149, respectively; and 2) Boosting with an immunogenic composition comprising first and second viral vectors comprising the following polynucleotides:

a) a first viral vector comprising first and second polynucleotides comprising SEQ ID NOs: 150 and 152, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively; and b) a second viral vector comprising first and second polynucleotides comprising SEQ ID NOs: 154 and 157 or SEQ ID NOs: 155 and 158, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 154 and 157 or SEQ ID NOs: 155 and 158, respectively. In various embodiments of this method, the priming vectors are Cali mammarenavirus (a.k.a., Pichinde mammarenavirus or Pichinde arenavirus) and the boosting vectors are Lymphocytic choriomeningitis mammarenavirus (LCMV). In various embodiments of this method the priming vectors and boosting vectors are replication attenuated or replication competent.

In some embodiments, the prime-boost regimen comprises:

1) Priming with an immunogenic composition comprising first and second viral vectors comprising the following polynucleotides:

a) a first viral vector comprising first and second polynucleotides comprising SEQ ID NOs: 150 and 152, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively; and b) a second viral vector comprising first and second polynucleotides comprising SEQ ID NOs: 154 and 157 or SEQ ID NOs: 155 and 158, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 154 and 157 or SEQ ID NOs: 155 and 158, respectively; and 2) Boosting with an immunogenic composition comprising first and second viral vectors comprising the following polynucleotides:

a) a first viral vector comprising first and second polynucleotides comprising SEQ ID NOs: 140 and 146, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 140 and 146, respectively; and b) a second viral vector comprising first and second polynucleotides comprising SEQ ID NOs: 143 and 149, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 143 and 149, respectively. In various embodiments of this method, the priming vectors are Cali mammarenavirus (a.k.a., Pichinde mammarenavirus or Pichinde arenavirus) and the boosting vectors are Lymphocytic choriomeningitis mammarenavirus (LCMV). In various embodiments of this method the priming vectors and boosting vectors are replication attenuated or replication competent.

In some embodiments, the prime-boost regimen comprises:

1) Priming with an immunogenic composition comprising first and second viral vectors comprising the following polynucleotides:

a) a first viral vector comprising first and second polynucleotides comprising SEQ ID NOs: 150 and 152, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively; and b) a second viral vector comprising first and second polynucleotides comprising SEQ ID NOs: 155 and 158, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 155 and 158, respectively; and 2) Boosting with an immunogenic composition comprising first and second viral vectors comprising the following polynucleotides:

a) a first viral vector comprising first and second polynucleotides comprising SEQ ID NOs: 151 and 153, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 151 and 153, respectively; and b) a second viral vector comprising first and second polynucleotides comprising SEQ ID NOs: 156 and 159, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 156 and 159, respectively.

In some embodiments, the prime-boost regimen comprises:

1) Priming with an immunogenic composition comprising first and second viral vectors comprising the following polynucleotides:

a) a first viral vector comprising first and second polynucleotides comprising SEQ ID NOs: 150 and 152, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively; and b) a second viral vector comprising first and second polynucleotides comprising SEQ ID NOs: 155 and 158, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 155 and 158, respectively; and 2) Boosting with an immunogenic composition comprising first and second viral vectors comprising the following polynucleotides:

a) a first viral vector comprising first and second polynucleotides comprising SEQ ID NOs: 139 and 145, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 145, respectively; and b) a second viral vector comprising first and second polynucleotides comprising SEQ ID NOs: 142 and 148, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 142 and 148, respectively. In various embodiments of this method, the priming vectors are Cali mammarenavirus (a.k.a., Pichinde mammarenavirus or Pichinde arenavirus) and the boosting vectors are Lymphocytic choriomeningitis mammarenavirus (LCMV). In various embodiments of this method the priming vectors and boosting vectors are replication attenuated or replication competent.

In some embodiments, the prime-boost regimen comprises:

1) Priming with an immunogenic composition comprising a first viral vector comprising first and second polynucleotides comprising SEQ ID NOs: 160 and 161, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 160 and 161, respectively; and 2) Boosting with an immunogenic composition comprising a second viral vector comprising first and second polynucleotides comprising SEQ ID NOs: 162 and 163, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 162 and 163, respectively.

In some embodiments, the prime-boost regimen comprises:

1) Priming with an immunogenic composition comprising a first viral vector comprising first and second polynucleotides comprising SEQ ID NOs: 164 and 165, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 164 and 165, respectively; and 2) Boosting with an immunogenic composition comprising a second viral vector comprising first and second polynucleotides comprising SEQ ID NOs: 166 and 167, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 166 and 167, respectively.

In some embodiments, the prime-boost regimen comprises: priming and boosting with an immunogenic composition comprising a first viral vector comprising a first polynucleotide comprising SEQ ID NO: 210, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 210; and a second viral vector comprising a second polynucleotide comprising SEQ ID NO: 211, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 211.

In some embodiments, the prime-boost regimen comprises: priming and boosting with an immunogenic composition comprising a first viral vector comprising a first polynucleotide comprising SEQ ID NO: 212, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 212; and a second viral vector comprising a second polynucleotide comprising SEQ ID NO: 213, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 213.

In some embodiments, the prime-boost regimen comprises: priming and boosting with an immunogenic composition comprising a first viral vector comprising a first polynucleotide comprising SEQ ID NO: 214, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 214; and a second viral vector comprising a second polynucleotide comprising SEQ ID NO: 215, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 215.

In some embodiments, the prime-boost regimen comprises: priming and boosting with an immunogenic composition comprising a first viral vector comprising a first polynucleotide comprising SEQ ID NO: 216, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 216; and a second viral vector comprising a second polynucleotide comprising SEQ ID NO: 217, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 217.

In some embodiments, the prime-boost regimen comprises: priming and boosting with an immunogenic composition comprising a first viral vector comprising a first polynucleotide comprising SEQ ID NO: 218, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 218; and a second viral vector comprising a second polynucleotide comprising SEQ ID NO: 219, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 219.

In some embodiments, the prime-boost regimen comprises: priming and boosting with an immunogenic composition comprising a first viral vector comprising a first polynucleotide comprising SEQ ID NO: 218, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 218; and a second viral vector comprising a second polynucleotide comprising SEQ ID NO: 226, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 226. In various embodiments of this method, the priming composition comprises one or more ChAd vectors and the boosting composition comprises one or more self-amplifying mRNA molecules, e.g., analogous to the prime-boost regimen described in NCT04776317 and WO 2021/236854 for SARS-CoV2 vaccines, in WO 2021/203104 for infectious disease vaccines and in WO 2020/243719.

In some embodiments, the prime-boost regimen comprises: priming and boosting with an immunogenic composition comprising a first viral vector comprising a first polynucleotide comprising SEQ ID NO: 225, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 225; and a second viral vector comprising a second polynucleotide comprising SEQ ID NO: 226, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 226. In various embodiments of this method, the priming composition comprises one or more ChAd vectors and the boosting composition comprises one or more self-amplifying mRNA molecules, e.g., analogous to the prime-boost regimen described in NCT04776317 and WO 2021/236854 for SARS-CoV2 vaccines, in WO 2021/203104 for infectious disease vaccines and in WO 2020/243719.

In some embodiments, after one or more administrations of the one or more fusion polypeptides, as described herein, or one or more polynucleotides encoding one or more fusion polypeptides, as described herein, or one or more vectors expressing one or more fusion polypeptides, as described herein, optionally with one or more additional therapeutic agents, described herein, the subject does not exhibit symptoms of HIV or AIDS in the absence of anti-retroviral treatment (ART) for at least 3 months, at least 6 months, at least 1 year, at least 2 years, at least 3 years, or more. In some embodiments, after one or more administrations of the one or more fusion polypeptides, as described herein, or one or more polynucleotides encoding one or more fusion polypeptides, as described herein, or one or more vectors expressing one or more fusion polypeptides, as described herein, optionally with one or more additional therapeutic agents, the subject has a viral load of copies/ml blood of less than 500, e.g., less than 400, less than 300, less than 200, less than 100, less than 50, in the absence of anti-retroviral treatment (ART) for at least 3 months, at least 6 months, at least 1 year, at least 2 years, at least 3 years, or more.

7. Combination Therapies

In certain embodiments, a method for treating or preventing an HIV infection in a human having or at risk of having the infection is provided, comprising administering to the human a therapeutically effective amount of one or more fusion polypeptides, or polynucleotides encoding or vectors expressing such fusion polypeptides, as disclosed herein, in combination with a therapeutically effective amount of one or more (e.g., one, two, three, one or two, or one to three) additional therapeutic agents. In one embodiment, a method for treating an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In various embodiments, of one or more fusion polypeptides, or polynucleotides encoding or vectors expressing such fusion polypeptides, as disclosed herein, are administered in combination with one or more (e.g., one, two, three, four, one or two, one to three, or one to four) additional therapeutic agents, and a pharmaceutically acceptable carrier, diluent, or excipient.

In certain embodiments, the provided are methods for treating an HIV infection, comprising administering to a patient in need thereof a therapeutically effective amount of a compound disclosed herein, or a pharmaceutically acceptable salt thereof, in combination with a therapeutically effective amount of one or more (e.g., one, two, three, one or two, or one to three) additional therapeutic agents which are suitable for treating an HIV infection.

In certain embodiments, one or more fusion polypeptides, or polynucleotides encoding or vectors expressing such fusion polypeptides, as disclosed herein, is co-formulated with one, two, three, four, or more additional therapeutic agents, and a pharmaceutically acceptable carrier. In certain embodiments, one or more fusion polypeptides, or polynucleotides encoding or vectors expressing such fusion polypeptides, as disclosed herein, or a pharmaceutically acceptable salt thereof, is combined with two additional therapeutic agents. As appropriate, the one, two, three, four, or more additional therapeutic agents can be different therapeutic agents selected from the same class of therapeutic agents, and/or they can be selected from different classes of therapeutic agents.

Administration of HIV Combination Therapy

In certain embodiments, a one or more fusion polypeptides, or polynucleotides encoding or vectors expressing such fusion polypeptides, as disclosed herein, are administered with one or more additional therapeutic agents. Co-administration of a compound disclosed herein with one or more additional therapeutic agents generally refers to simultaneous or concurrent, or sequential, administration of a compound disclosed herein and one or more additional therapeutic agents, such that therapeutically effective amounts of the compound disclosed herein and the one or more additional therapeutic agents are both present in the body of the patient. When administered sequentially, the combination may be administered in two or more administrations.

Co-administration includes administration of unit dosages of a unit dose of the one or more fusion polypeptides, or polynucleotides encoding, lipoplexes (e.g., LNPs) comprising such polynucleotides, or vectors expressing such fusion polypeptides, as disclosed herein, disclosed herein before or after administration of unit dosages of one or more additional therapeutic agents. For example, the one or more fusion polypeptides, or polynucleotides encoding, lipoplexes (e.g., LNPs) comprising such polynucleotides, or vectors expressing such fusion polypeptides, as disclosed herein, may be administered within seconds, minutes, or hours of the administration of the one or more additional therapeutic agents. In some embodiments, a unit dose of a one or more fusion polypeptides, or polynucleotides encoding or vectors expressing such fusion polypeptides, as disclosed herein, is administered first, followed within seconds or minutes by administration of a unit dose of one or more additional therapeutic agents. Alternatively, a unit dose of one or more additional therapeutic agents is administered first, followed by administration of a unit dose of a one or more fusion polypeptides, or polynucleotides encoding or vectors expressing such fusion polypeptides, as disclosed herein, within seconds or minutes. In other embodiments, a unit dose of one or more fusion polypeptides, or polynucleotides encoding, lipoplexes (e.g., LNPs) comprising such polynucleotides, or vectors expressing such fusion polypeptides, as disclosed herein, is administered first, followed, after a period of hours (e.g., 1-12 hours), by administration of a unit dose of one or more additional therapeutic agents. In yet other embodiments, a unit dose of one or more additional therapeutic agents is administered first, followed, after a period of hours (e.g., 1-12 hours), by administration of a unit dose of one or more fusion polypeptides, or polynucleotides encoding or vectors expressing such fusion polypeptides, as disclosed herein. In some embodiments, the one or more additional therapeutic agents are not co-administered, but are separately administered as part of a combination therapy regimen. In such approaches, a unit dose of one or more fusion polypeptides, or polynucleotides encoding, lipoplexes (e.g., LNPs) comprising such polynucleotides, or vectors expressing such fusion polypeptides, as disclosed herein, and the one or more additional therapeutic agents can be administered at longer time intervals, e.g., 1, 2, 3, 4, 5, 6, 7, 8, 9, 10 days or more apart.

In certain embodiments, one or more fusion polypeptides, or polynucleotides encoding or vectors expressing such fusion polypeptides, as disclosed herein, is combined or co-administered with one or more additional therapeutic agents in a unitary dosage form for simultaneous or concurrent administration to a patient, for example as an aqueous formulation for intravenous, intramuscular, intradermal, intranodal or subcutaneous administration. In certain embodiments, one or more fusion polypeptides, or polynucleotides encoding or vectors expressing such fusion polypeptides, as disclosed herein, is combined with one or more additional therapeutic agents in a unitary dosage form for simultaneous or concurrent administration to a patient, for example as an intrarectal suppository.

In certain embodiments, the one or more fusion polypeptides, or polynucleotides encoding, lipoplexes (e.g., LNPs) comprising such polynucleotides, or vectors expressing such fusion polypeptides, as disclosed herein, can be co-formulated or co-administered with one or more other compounds useful for treating HIV. In certain embodiments, the co-formulation or co-administration can comprise another active agent for treating HIV, such as anti-HIV antibodies (e.g., HIV bNAbs), bispecific antibodies, and "antibody-like" therapeutic proteins, toll-like receptor (TLR) agonists (e.g., agonists of TLR7, TLR8, and/or TLR9), an immune checkpoint inhibitor, HIV protease inhibitors, HIV non-nucleoside or non-nucleotide inhibitors of reverse transcriptase, HIV nucleoside or nucleotide inhibitors of reverse transcriptase, HIV integrase inhibitors, HIV capsid inhibitors, nucleocapsid protein 7 (NCp7) inhibitors, HIV Tat or Rev inhibitors, inhibitors of Tat-TAR-P-TEFb, HIV non-catalytic site (or allosteric) integrase inhibitors, HIV entry (fusion) inhibitors, HIV maturation inhibitors, latency reversing agents, immune-based therapies, PI3K inhibitors, gp41 inhibitors, CXCR4 inhibitors, gp120 inhibitors, CCR5 inhibitors, Nef inhibitors, latency reversing agents, HIV vaccines, cytokines, immune checkpoint inhibitors, FLT3 agonists, T cell and NK cell recruiting bispecific antibodies, chimeric T cell receptors targeting HIV antigens, pharmacokinetic enhancers, and other drugs for treating HIV, and combinations thereof.

In some embodiments, the additional therapeutic agent or agents are selected from dolutegravir, cabotegravir, islatravir, darunavir, bictegravir, elsulfavirine, rilpivirine, and lenacapavir, and combinations thereof.

In certain embodiments, the one or more active agents are suitable for once daily dosing, weekly dosing, monthly dosing, every 3 months dosing, every four months dosing, bi-annual dosing, or annual dosing, as appropriate.

In some embodiments, the one or more fusion polypeptides, or polynucleotides encoding, lipoplexes (e.g., LNPs) comprising such polynucleotides, or vectors expressing such fusion polypeptides, as disclosed herein, and the one or more additional therapeutic agents may be an anti-HIV agent. In some instances, the additional therapeutic agent can be HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, HIV capsid inhibitors, nucleocapsid protein 7 (NCp7) inhibitors, HIV Tat or Rev inhibitors, inhibitors of Tat-TAR-P-TEFb, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T-cell receptors, TCR-T, autologous T-cell therapies, engineered B cells, NK cells), latency reversing agents, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, fatty acid synthase inhibitor, HIV vif-gene modulators, Vif dimerization antagonists, HIV-1 viral infectivity factor inhibitors, HIV-1 Nef modulators, TNF alpha ligand inhibitors, HIV Nef inhibitors, Hck tyrosine kinase modulators, mixed lineage kinase-3 (MLK-3) inhibitors, HIV-1 splicing inhibitors, integrin antagonists, nucleoprotein inhibitors, splicing factor modulators, COMM domain containing protein 1 modulators, HIV ribonuclease H inhibitors, interferon (IFN) antagonists, retrocyclin modulators, CD3 antagonists, CDK-4 inhibitors, CDK-6 inhibitors, CDK-9 inhibitors, Cytochrome P450 3 inhibitors, CXCR4 modulators, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, HPK1 (MAP4K1) inhibitors, proprotein convertase PC9 stimulators, ATP dependent RNA helicase DDX3X inhibitors, reverse transcriptase priming complex inhibitors, G6PD and NADH-oxidase inhibitors, mTOR complex 1 inhibitors, mTOR complex 2 inhibitors, P-Glycoprotein modulators, RNA polymerase modulators, TAT protein inhibitors, prolylendopeptidase inhibitors, phospholipase A2 inhibitors, pharmacokinetic enhancers, HIV gene therapy, HIV vaccines, anti-HIV peptides and combinations thereof.

In some embodiments, the additional therapeutic agent is selected from combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

Combination Drugs

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with an HIV combination drug. Examples of combination drugs that can be employed with an agent of this disclosure include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; tenofovir analog; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); BIKTARVY® (bictegravir+emtricitabine+tenofovir alafenamide), DOVATO® (dolutegravir+lamivudine), TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine, lopinavir+ritonavir+abacavir+lamivudine, lamivudine, cabotegravir+rilpivirine, 3-BNC117+albuvirtide, elpida (elsulfavirine, VM-1500), and VM-1500A, lenacapavir+islatravir (oral, injectable), and dual-target HIV-1 reverse transcriptase/nucleocapsid protein 7 inhibitors.

Examples of other drugs for treating HIV that can be combined with the one or more fusion polypeptides, or polynucleotides encoding, lipoplexes (e.g., LNPs) comprising such polynucleotides, or vectors expressing such fusion polypeptides, as disclosed herein, include without limitation aspernigrin C, acemannan, alisporivir, BanLec, deferiprone, Gamimune, metenkefalin, naltrexone, Prolastin, REP 9, RPI-MN, VSSP, Hlviral, SB-728-T, 1,5-dicaffeoylquinic acid, rHIV7-shl-TAR-CCR5RZ, AAV-eCD4-Ig gene therapy, MazF gene therapy, BlockAide, bevirimat derivatives, ABBV-382, ABX-464, AG-1105, APH-0812, APH0202, bryostatin-1, bryostatin analogs, BG-HIV, BIT-225, BRII-732, BRII-778, CYT-107, CS-TATI-1, fluoro-beta-D-arabinose nucleic acid (FANA)-modified antisense oligonucleotides, FX-101, griffithsin, GSK-3739937, GSK-3739937 (long-acting), HGTV-43, HPH-116, HS-10234, hydroxychloroquine, IB-10035, IMO-3100, IND-02, JL-18008, LADAVRU, MK-1376, MK-2048, MK-4250, MK-8507, MK-8558, MK-8591, islatravir, NOV-205, OB-002H, ODE-Bn-TFV, PA-1050040 (PA-040), PC-707, PGN-007, QF-036, S-648414, SCY-635, SB-9200, SCB-719, TR-452, TEV-90110, TEV-90112, TEV-90111, TEV-90113, RN-18, DIACC-1010, Fasnall, Immuglo, 2-CLIPS peptide, HRF-4467, thrombospondin analogs, TBL-1004HI, VG-1177, xl-081, AVI-CO-004, rfhSP-D, [18F]-MC-225, URMC-099-C, RES-529, Verdinexor, IMC-Mi 13V, IML-106, antiviral fc conjugate (AVC), WP-1096, WP-1097, Gammora, ISR-CO48, ISR-48, ISR-49, MK-8527, cannabinoids, ENOB-HV-32, HiviCide-I, T-1144, VIR-576, nipamovir, Covimro, and ABBV-1882.

HIV Protease Inhibitors

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with an HIV protease inhibitor. Examples of HIV protease inhibitors that can be co-administered or combined include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, ASC-09+ritonavir, AEBL-2, DG-17, GS-1156, TMB-657 (PPL-100), T-169, BL-008, MK-8122, TMB-607, GRL-02031, and TMC-310911. Additional examples of HIV protease inhibitors are described, e.g., in U.S. Pat. No. 10,294,234 and U.S. Patent Publ. Nos. US2020030327 and US2019210978.

HIV Gag Protein Inhibitors

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with an HIV Gag protein inhibitor. Examples of HIV Gag protein inhibitors that can be combined or co-administered include, but are not limited to, HRF-10071.

HIV Ribonuclease H Inhibitors

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with an HIV ribonuclease H inhibitor. Examples of HIV ribonuclease H inhibitors that can be combined or co-administered include, but are not limited to, NSC-727447.

HIV Nef Inhibitors

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with an HIV Nef inhibitor. Examples of HIV Nef inhibitors that can be combined or co-administered include, but are not limited to, FP-1.

HIV Reverse Transcriptase Inhibitors

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with a non-nucleoside or non-nucleotide inhibitor. Examples of HIV non-nucleoside or non-nucleotide inhibitors of reverse transcriptase that can be combined or co-administered include dapivirine, delavirdine, delavirdine mesylate, doravirine, efavirenz, etravirine, lentinan, nevirapine, rilpivirine, ACC-007, ACC-008, AIC-292, F-18, KM-023, PC-1005, M1-TFV, M2-TFV, VM-1500A-LAI, PF-3450074, elsulfavirine (sustained release oral, HIV infection), doravirine+islatravir (fixed dose combination/oral tablet formulation, HIV-1 infection), elsulfavirine (long acting injectable nanosuspension, HIV infection), and elsulfavirine (VM-1500).

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with an HIV nucleoside or nucleotide inhibitor. Examples of HIV nucleoside or nucleotide inhibitors of reverse transcriptase that can be combined or co-administered include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddl), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, rovafovir etalafenamide (GS-9131), GS-9148, MK-8504, MK-8591, MK-858, VM-2500 and KP-1461.

HIV Integrase Inhibitors

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with an HIV integrase inhibitor. Examples of HIV integrase inhibitors that can be combined or co-administered include without limitation elvitegravir, elvitegravir (extended-release microcapsules), curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, PEGylated raltegravir, dolutegravir, JTK-351, bictegravir, AVX-15567, cabotegravir (long acting injectable), diketo quinolin-4-1 derivatives, integrase-LEDGF inhibitor, ledgins, M-522, M-532, MK-0536, NSC-310217, NSC-371056, NSC-48240, NSC-642710, NSC-699171, NSC-699172, NSC-699173, NSC-699174, stilbenedisulfonic acid, T169, STP-0404, VM-3500, XVIR-110, ACC-017 and cabotegravir.

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with a HIV non-catalytic site, or allosteric, integrase inhibitor (NCINI). Examples of HIV non-catalytic site, or allosteric, integrase inhibitors (NCINI) that can be combined or co-administered include CX-05045, CX-05168, and CX-14442. Additional examples of HIV capsid inhibitors include, without limitation those described in U.S. Patent Publ. Nos. US2014221356 and US2016016973.

HIV Viral Infectivity Factor Inhibitors

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with a HIV Viral Infectivity Factor Inhibitor. Examples of HIV viral infectivity factor inhibitors include, but are not limited to 2-amino-N-(2-methoxyphenyl)-6-((4-nitrophenyl)thio)benzamide derivatives and Irino-L.

HIV Entry Inhibitors

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with an HIV entry inhibitor. Examples of HIV entry (fusion) inhibitors that can be combined or co-administered include without limitation AAR-501, LBT-5001, cenicriviroc, CCR5 inhibitors, gp41 inhibitors, CD4 attachment inhibitors, gp120 inhibitors, gp160 inhibitors, and CXCR4 inhibitors.

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with a CCR5 inhibitor. Examples of CCR5 inhibitors that can be combined or co-administered include without limitation aplaviroc, vicriviroc, maraviroc, maraviroc (long acting injectable nanoemulsion), cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, thioraviroc and vMIP (Haimipu).

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with a gp41 inhibitor. Examples of gp41 inhibitors that can be combined or co-administered include without limitation albuvirtide, enfuvirtide, griffithsin (gp41/gp120/gp160 inhibitor), BMS-986197, enfuvirtide biobetter, enfuvirtide biosimilar, HIV-1 fusion inhibitors (P26-Bapc), ITV-1, ITV-2, ITV-3, ITV-4, CPT-31, C13hmAb, lipuvirtide, PIE-12 trimer and sifuvirtide.

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with a CD4 attachment inhibitor. Examples of CD4 attachment inhibitors that can be combined or co-administered include ibalizumab and CADA analogs.

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with a gp120 inhibitor. Examples of gp120 inhibitors that can be combined or co-administered include without limitation anti-HIV microbicide, Radha-108 (receptol) 3B3-PE38, BMS818251, BanLec, bentonite-based nanomedicine, fostemsavir tromethamine, IQP-0831, VVX-004, and BMS-663068.

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with a gp160 inhibitor. Examples of gp160 inhibitors that can be combined or co-administered include without limitation fangchinoline.

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with a CXCR4 inhibitor. Examples of CXCR4 inhibitors that can be combined or co-administered include plerixafor, ALT-1188, N15 peptide, and vMIP (Haimipu).

Maturation Inhibitors

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with a HIV maturation inhibitor. Examples of HIV maturation inhibitors that can be combined or co-administered include BMS-955176, GSK-3640254 and GSK-2838232.

Latency Reversing Agents

In certain embodiments, the one or more fusion polypeptides, or polynucleotides encoding, lipoplexes (e.g., LNPs)

comprising such polynucleotides, or vectors expressing such fusion polypeptides, as disclosed herein, are combined or co-administered with a latency reversing agent (LRA). Examples of latency reversing agents that can be combined or co-administered include toll-like receptor (TLR) agonists (including TLR7 agonists, e.g., GS-9620 (vesatolimod), TLR8 agonists, e.g., GS-9688 (Selgantolimod), TLR9 agonists, e.g., lefitolimod (MGN-1703)), histone deacetylase (HDAC) inhibitors, proteasome inhibitors such as velcade, protein kinase C (PKC) activators, Smyd2 inhibitors, BET-bromodomain 4 (BRD4) inhibitors (such as ZL-0580, apabetalone), ionomycin, IAP antagonists (inhibitor of apoptosis proteins, such as APG-1387, LBW-242), SMAC mimetics (including TL32711, LCL161, GDC-0917, HGS1029, AT-406, Debio-1143), PMA, SAHA (suberanilohydroxamic acid, or suberoyl, anilide, and hydroxamic acid), NIZ-985, IL-15 modulating antibodies (including IL-15, IL-15 fusion proteins, and IL-15 receptor agonists), JQ1, disulfiram, amphotericin B, and ubiquitin inhibitors such as largazole analogs, APH-0812, and GSK-343. Examples of PKC activators include, but are not limited to indolactam, prostratin, ingenol B, and DAG-lactones. Additional examples of TLR7 agonists includes but are not limited to those described in U.S. Patent No. US2010/143301. Additional examples of TLR8 agonists includes but are not limited to those described in U.S. Patent No. US2017/071944.

Histone Deacetylase (HDAC) Inhibitors

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with an inhibitor of a histone deacetylase 1, histone deacetylase 9 (HDAC9, HD7, HD7b, HD9, HDAC, HDAC7, HDAC7B, HDAC9B, HDAC9FL, HDRP, MITR; Gene ID: 9734). Examples of HDAC inhibitors include without limitation, abexinostat, ACY-241, AR-42, BEBT-908, belinostat, CKD-581, CS-055 (HIBI-8000), CT-101, CUDC-907 (fimepinostat), entinostat, givinostat, mocetinostat, panobinostat, pracinostat, quisinostat (JNJ-26481585), resminostat, ricolinostat, romidepsin, SHP-141, TMB-ADC, valproic acid (VAL-001), vorinostat, tinostamustine, remetinostat, and entinostat.

Capsid Inhibitors

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with a capsid inhibitor. Examples of capsid inhibitors that can be combined or co-administered include without limitation capsid polymerization inhibitors or capsid disrupting compounds, HIV nucleocapsid p7 (NCp7) inhibitors such as azodicarbonamide, HIV p24 capsid protein inhibitors, lenacapavir (GS-6207), GS-CA1, AVI-621, AVI-101, AVI-201, AVI-301, and AVI-CAN1-15 series, PF-3450074, HIV-1 capsid inhibitors (HIV-1 infection, Shandong University), and compounds described in (WO 2019/087016 (GSK)). Additional examples of capsid inhibitors include without limitation those described in US Patent Publ. Nos. US2018051005, US2016108030.

HIV Long-Acting Therapy

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with an HIV long-acting therapy. Examples of as long acting regimens that can be combined or co-administered include without limitation cabotegravir, rilpivirine, any integrase LA, VM-1500 LAI, maraviroc (LAI), tenofovir implant, islatravir implant, doravirine, raltegravir, and long acting dolutegravir.

Additionally encompassed as HIV long-acting therapies include anti-HIV broadly neutralizing antibodies (bNAbs), described herein, having serum half-life extended amino acid substitutions in the Fc region. Fc region amino acid substitutions that increase the half-life of an antibody have been described. For example, a "YTE mutant" (a methionine to tyrosine substitution at position 252, a serine to threonine substitution at position 254, and a threonine to glutamic acid substitution at position 256 (EU numbering)) exhibits a four-fold increased half-life relative to wild-type versions of the same antibody (Dall'Acqua, et al., J Biol Chem, 281: 23514-24 (2006); Robbie, et al., Antimicrob Agents Chemotherap., 57(12):6147-6153 (2013)). See also, U.S. Pat. No. 7,658,921. In a further example, M428L and N434S (EU numbering; "LS") substitutions can increase the pharmacokinetic half-life of the bNAb. In other embodiments, the bNAbs described herein comprise T250Q and M428L (EU numbering) mutations. In other embodiments, the bNAbs described herein comprise H433K and N434F (EU numbering) mutations. Illustrative serum half-life extended bNAbs that may be combined or co-administered with the one or more fusion polypeptides, or polynucleotides encoding, lipoplexes (e.g., LNPs) comprising such polynucleotides, or vectors expressing such fusion polypeptides, as disclosed herein, include 3BNC117-LS, 10-1074-LS, 10-1074-LS-J, GS-5423 and GS-2872.

Cytochrome P450 3 Inhibitors

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with a Cytochrome P450 3 inhibitor. Examples of Cytochrome P450 3 inhibitors include without limitation those described in U.S. Pat. No. 7,939,553.

RNA Polymerase Inhibitors

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with an RNA polymerase modulator. Examples of RNA polymerase modulators include without limitation those described in U.S. Pat. Nos. 10,065,958; and 8,008,264.

Immune Checkpoint Modulators

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of infected cells. Activation or stimulation of stimulatory immune check points can augment the effect of immune checkpoint inhibitors in infective therapeutics. In various embodiments, the immune checkpoint proteins or receptors regulate T cell responses (e.g., reviewed in Xu, et al., J Exp Clin Cancer Res. (2018) 37:110). In various embodiments, the immune checkpoint proteins or receptors regulate NK cell responses (e.g., reviewed in Davis, et al., Semin Immunol. (2017) 31:64-75 and Chiossone, et al., Nat Rev Immunol. (2018) 18(11):671-688).

Examples of immune checkpoint proteins or receptors include without limitation CD27 (NCBI Gene ID: 939), CD70 (NCBI Gene ID: 970), CD40 (NCBI Gene ID: 958), CD40LG (NCBI Gene ID: 959), CD47 (NCBI Gene ID: 961), CD48 (SLAMF2; NCBI Gene ID: 962), transmembrane and immunoglobulin domain containing 2 (TMIGD2, CD28H; NCBI Gene ID: 126259), CD84 (LY9B, SLAMF5; NCBI Gene ID: 8832), CD96 (NCBI Gene ID: 10225), CD160 (NCBI Gene ID: 11126), MS4A1 (CD20; NCBI Gene ID: 931), CD244 (SLAMF4; NCBI Gene ID: 51744); CD276 (B7H3; NCBI Gene ID: 80381); V-set domain containing T cell activation inhibitor 1 (VTCN1, B7H4; NCBI Gene ID: 79679); V-set immunoregulatory receptor (VSIR, B7H5, VISTA; NCBI Gene ID: 64115); immunoglobulin superfamily member 11 (IGSF11, VSIG3; NCBI Gene ID: 152404); natural killer cell cytotoxicity receptor 3 ligand 1 (NCR3LG1, B7H6; NCBI Gene ID: 374383); HERV-H LTR-associating 2 (HHLA2, B7H7; NCBI Gene ID: 11148); inducible T cell co-stimulator (ICOS, CD278; NCBI Gene ID: 29851); inducible T cell co-stimulator ligand (ICOSLG, B7H2; NCBI Gene ID: 23308); TNF receptor superfamily member 4 (TNFRSF4, OX40; NCBI Gene ID: 7293); TNF superfamily member 4 (TNFSF4, OX40L; NCBI Gene ID: 7292); TNFRSF8 (CD30; NCBI Gene ID: 943), TNFSF8 (CD30L; NCBI Gene ID: 944); TNFRSF10A (CD261, DR4, TRAILR1; NCBI Gene ID: 8797), TNFRSF9 (CD137; NCBI Gene ID: 3604), TNFSF9 (CD137L; NCBI Gene ID: 8744); TNFRSF10B (CD262, DR5, TRAILR2; NCBI Gene ID: 8795), TNFRSF10 (TRAIL; NCBI Gene ID: 8743); TNFRSF14 (HVEM, CD270; NCBI Gene ID: 8764), TNFSF14 (HVEML; NCBI Gene ID: 8740); CD272 (B and T lymphocyte associated (BTLA); NCBI Gene ID: 151888); TNFRSF17 (BCMA, CD269; NCBI Gene ID: 608), TNFSF13B (BAFF; NCBI Gene ID: 10673); TNFRSF18 (GITR; NCBI Gene ID: 8784), TNFSF18 (GITRL; NCBI Gene ID: 8995); MHC class I polypeptide-related sequence A (MICA; NCBI Gene ID: 100507436); MHC class I polypeptide-related sequence B (MICB; NCBI Gene ID: 4277); CD274 (CD274, PDL1, PD-L1; NCBI Gene ID: 29126); programmed cell death 1 (PDCD1, PD1, PD-1; CD279; NCBI Gene ID: 5133); cytotoxic T-lymphocyte associated protein 4 (CTLA4, CD152; NCBI Gene ID: 1493); CD80 (B7-1; NCBI Gene ID: 941), CD28 (NCBI Gene ID: 940); nectin cell adhesion molecule 2 (NECTIN2, CD112; NCBI Gene ID: 5819); CD226 (DNAM-1; NCBI Gene ID: 10666); Poliovirus receptor (PVR) cell adhesion molecule (PVR, CD155; NCBI Gene ID: 5817); PVR related immunoglobulin domain containing (PVRIG, CD112R; NCBI Gene ID: 79037); T cell immunoreceptor with Ig and ITIM domains (TIGIT; NCBI Gene ID: 201633); T cell immunoglobulin and mucin domain containing 4 (TIMD4; TIM4; NCBI Gene ID: 91937); hepatitis A virus cellular receptor 2 (HAVCR2, TIMD3, TIM3; NCBI Gene ID: 84868); galectin 9 (LGALS9; NCBI Gene ID: 3965); lymphocyte activating 3 (LAG3, CD223; NCBI Gene ID: 3902); signaling lymphocytic activation molecule family member 1 (SLAMF1, SLAM, CD150; NCBI Gene ID: 6504); lymphocyte antigen 9 (LY9, CD229, SLAMF3; NCBI Gene ID: 4063); SLAM family member 6 (SLAMF6, CD352; NCBI Gene ID: 114836); SLAM family member 7 (SLAMF7, CD319; NCBI Gene ID: 57823); UL16 binding protein 1 (ULBP1; NCBI Gene ID: 80329); UL16 binding protein 2 (ULBP2; NCBI Gene ID: 80328); UL16 binding protein 3 (ULBP3; NCBI Gene ID: 79465); retinoic acid early transcript 1E (RAETIE; ULBP4; NCBI Gene ID: 135250); retinoic acid early transcript 1G (RAETIG; ULBP5; NCBI Gene ID: 353091); retinoic acid early transcript 1L (RAET1L; ULBP6; NCBI Gene ID: 154064); killer cell lectin like receptor C1 (KLRC1, NKG2A, CD159A; NCBI Gene ID: 3821); killer cell lectin like receptor K1 (KLRK1, NKG2D, CD314; NCBI Gene ID: 22914); killer cell lectin like receptor C2 (KLRC2, CD159c, NKG2C; NCBI Gene ID: 3822); killer cell lectin like receptor C3 (KLRC3, NKG2E; NCBI Gene ID: 3823); killer cell lectin like receptor C4 (KLRC4, NKG2F; NCBI Gene ID: 8302); killer cell immunoglobulin like receptor, two Ig domains and long cytoplasmic tail 1 (KIR2DL1; NCBI Gene ID: 3802); killer cell immunoglobulin like receptor, two Ig domains and long cytoplasmic tail 2 (KIR2DL2; NCBI Gene ID: 3803); killer cell immunoglobulin like receptor, two Ig domains and long cytoplasmic tail 3 (KIR2DL3; NCBI Gene ID: 3804); killer cell immunoglobulin like receptor, three Ig domains and long cytoplasmic tail 1 (KIR3DL1, KIR, CD158E1; NCBI Gene ID: 3811) (e.g., Lirilumab (IPH2102/BMS-986015), IPH-4102); killer cell lectin like receptor D1 (KLRD1; NCBI Gene ID: 3824) and mitogen-activated protein kinase kinase kinase kinase 1 (MAP4K1, a.k.a., Hematopoietic Progenitor Kinase 1 (HPK1); NCBI Gene ID: 11184).

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with one or more blockers or inhibitors of one or more T-cell inhibitory immune checkpoint proteins or receptors. Illustrative T-cell inhibitory immune checkpoint proteins or receptors include without limitation CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CDI 12R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). Lirilumab is an illustrative antibody that binds to and blocks KIR2DL1/2L3 receptors. In various embodiments, the fusion polypeptides, polynucleotides, vectors, LNPs, immunogenic compositions and/or pharmaceutical compositions, as described herein, are combined with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4

(TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu, et al., J Exp Clin Cancer Res. (2018) 37:110.

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with one or more blockers or inhibitors of one or more NK-cell inhibitory immune checkpoint proteins or receptors. Illustrative NK-cell inhibitory immune checkpoint proteins or receptors include without limitation killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A), e.g., monalizumab (IPH2201); and killer cell lectin like receptor D1 (KLRD1, CD94). In various embodiments, the agents as described herein, are combined with one or more agonist or activators of one or more NK-cell stimulatory immune checkpoint proteins or receptors. Illustrative NK-cell stimulatory immune checkpoint proteins or receptors include without limitation CD16, CD226 (DNAM-1); CD244 (2B4, SLAMF4); killer cell lectin like receptor K1 (KLRK1, NKG2D, CD314); SLAM family member 7 (SLAMF7). See, e.g., Davis, et al., Semin Immunol. (2017) 31:64-75; Fang, et al., Semin Immunol. (2017) 31:37-54; and Chiossone, et al., Nat Rev Immunol. (2018) 18(11):671-688.

In some embodiments, the one or more immune checkpoint inhibitors comprises a proteinaceous (e.g., antibody or fragment thereof, or antibody mimetic) inhibitor of PD-L1 (CD274), PD-1 (PDCD1) or CTLA4. In some embodiments, the one or more immune checkpoint inhibitors comprises a small organic molecule inhibitor of PD-L1 (CD274), PD-1 (PDCD1) or CTLA4. In some embodiments, the small molecule inhibitor of CD274 or PDCD1 is selected from GS-4224, GS-4416, INCB086550 and MAX10181. In some embodiments, the small molecule inhibitor of CTLA4 comprises BPI-002.

Examples of inhibitors of CTLA4 that can be co-administered include without limitation ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors of PD-L1 (CD274) or PD-1 (PDCD1) that can be co-administered include without limitation pembrolizumab, nivolumab, cemiplimab, pidilizumab, AMP-224, MEDI0680 (AMP-514), spartalizumab, atezolizumab, avelumab, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181 (budigalimab), PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, GS-4224, GS-4416, INCB086550, MAX10181, as well as multi-specific inhibitors FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), and INBRX-105 (4-1BB/PDL1).

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with anti-TIGIT antibodies, such as etigilimab, BMS-986207, tiragolumab (a.k.a., MTIG-7192A; RG-6058; RO 7092284), vibostolimab (MK-7684), AGEN1307, AGEN1327, AGEN1777, COM-902, IBI-939, AB154, SGN-TGT, MG1131 and EOS884448 (EOS-448).

TNF Receptor Superfamily (TNFRSF) Member Agonists or Activators

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with one or more agonists of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Example anti-TNFRSF4 (OX40) antibodies that can be co-administered include without limitation, MEDI6469, MEDI6383, MEDI0562 (tavolixizumab), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628.

Example anti-TNFRSF5 (CD40) antibodies that can be co-administered include without limitation RG7876, SEA-CD40, APX-005M and ABBV-428.

In some embodiments, the anti-TNFRSF7 (CD27) antibody varlilumab (CDX-1127) is co-administered.

Example anti-TNFRSF9 (4-1BB, CD137) antibodies that can be co-administered include without limitation urelumab, utomilumab (PF-05082566), AGEN2373 and ADG-106.

Example anti-TNFRSF18 (GITR) antibodies that can be co-administered include without limitation, MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Bi- and Tri-Specific Natural Killer (NK)-Cell Engagers

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (4-1B). As appropriate, the anti-CD16 binding bi-specific molecules may or may not have an Fc. Illustrative bi-specific NK-cell engagers that can be co-administered target CD16 and one or more HIV-associated antigens as described herein. BiKEs and TriKEs are described, e.g., in Felices, et al., Methods Mol Biol. (2016) 1441:333-346; Fang, et al., Semin Immunol. (2017) 31:37-54. Examples of a trispecific NK cell engager (TRiKE) include OXS-3550, HIV-TriKE and CD16-IL-15-B7H3 TriKe.

Indoleamine-Pyrrole-2,3-Dioxygenase (IDO1) Inhibitors

In various embodiments, the one or more fusion polypeptides, or polynucleotides encoding, lipoplexes (e.g., LNPs) comprising such polynucleotides, or vectors expressing such fusion polypeptides, as disclosed herein, are combined with an inhibitor of indoleamine 2,3-dioxygenase 1 (IDO1; NCBI Gene ID: 3620). Examples of IDO1 inhibitors include without limitation, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, and shIDO-ST, EOS-200271, KHK-2455, LY-3381916.

Toll-Like Receptor (TLR) Agonists

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793). Example TLR7 agonists that can be co-administered include without limitation AL-034, DSP-0509, GS-9620 (vesatolimod), vesatolimod analog, LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7854, RG-7795, and the compounds disclosed in US20100143301 (Gilead Sciences), US20110098248 (Gilead Sciences), and US20090047249 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). An TLR7/TLR8 agonist that can be co-administered is NKTR-262, telratolimod and BDB-001. Example TLR8 agonists that can be co-administered include without limitation E-6887, IMO-4200, IMO-8400, IMO-9200, MCT-465, MEDI-9197, motolimod, resiquimod, GS-9688 (Selgantolimod), VTX-1463, VTX-763, 3M-051, 3M-052, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). Example TLR9 agonists that can be co-administered include without limitation AST-008 (cavrotolimod), cobitolimod, CMP-001, IMO-2055, IMO-2125, 5-540956, litenimod, MGN-1601, BB-001, BB1-006, IMO-3100, IMO-8400, IR-103, IMO-9200, agatolimod, DIMS-9054, DV-1079, DV-1179, AZD-1419, lefitolimod (MGN-1703), CYT-003, CYT-003-QbG10, tilsotolimod and PUL-042. Examples of TLR3 agonists include rintatolimod, poly-ICLC, RIBOXXON®, Apoxxim, RIBOXXIM®, IPH-33, MCT-465, MCT-475, and ND-1.1. Examples of TLR4 agonists include G-100, and GSK-1795091.

CDK Inhibitors or Antagonists

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with a CDK inhibitor or antagonist. In some embodiments, the agents described herein are combined with an inhibitor or antagonist of CDK. In some embodiments, the CDK inhibitor or antagonist is selected from VS2-370.

STING Agonists, RIG-I and NOD2 Modulators

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with a stimulator of interferon genes (STING) receptor (a.k.a, stimulator of interferon response cGAMP interactor 1 (STINGI); transmembrane protein 173 (TMEM173); NCBI Gene ID: 340061) agonist. In some embodiments, the STING receptor agonist or activator is selected from ADU-S100 (MIW-815), SB-11285, MK-1454, SR-8291, STING agonist (latent HIV), 5,6-dimethylxanthenone-4-acetic acid (DMXAA), cyclic-GAMP (cGAMP) and cyclic-di-AMP. In some embodiments, the agents described herein are combined with a RIG-I modulator such as RGT-100, or NOD2 modulator, such as SB-9200, and IR-103.

In some embodiments, the additional therapeutic agent is an agonist of DExD/H-box helicase 58 (DDX58; a.k.a., RIG-I, RIG1, RIGI, RLR-1, SGMRT2; NCBI Gene ID: 23586). Illustrative RIG-I agonists include inarigivir soproxil (SB-9200; GS-9992); SB-40, SB-44, ORI-7246, ORI-9350, ORI-7537, ORI-9020, ORI-9198, ORI-7170, RGT-100 and KIN1148, described by Hemann, et al., *J Immunol May* 1, 2016, 196 (1 Supplement) 76.1. Additional RIG-I agonists are described, e.g., in Elion, et al., *Cancer Res*. (2018) 78(21):6183-6195; and Liu, et al., *J Virol*. (2016) 90(20):9406-19. RIG-I agonists are commercially available, e.g., from Invivogen (invivogen.com). In some embodiments, the agents described herein are combined with a nucleotide binding oligomerization domain containing 2 (NOD2; NCBI Gene ID: 64127) agonist, such as inarigivir soproxil (SB-9200; GS-9992) and IR-103.

LAG-3 and TIM-3 Inhibitors

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with an anti-TIM-3 antibody, such as TSR-022, LY-3321367, MBG-453, INCAGN-2390.

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with anti-LAG-3 (Lymphocyte-activation) antibody, such as relatlimab (ONO-4482), LAG-525, MK-4280, REGN-3767, INCAGN2385.

Interleukin or Cytokine Receptor Agonists

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with an interleukin receptor agonist, such as IL-2, IL-7, IL-15, IL-10, IL-12 receptor agonists. Examples of IL-2 receptor agonists that can be co-administered include proleukin (aldesleukin, IL-2); BC-IL (Cel-Sci), pegylated IL-2 (e.g., NKTR-214); modified variants of IL-2 (e.g., THOR-707, Fc-IL-2 fusion protein), bempegaldesleukin, AIC-284, ALKS-4230, CUI-101, Neo-2/15. Examples of IL-15 receptor agonists that can be co-administered include ALT-803, NKTR-255, and hetIL-15, interleukin-15/Fc fusion protein, AM-0015, NIZ-985, SO-C101, IL-15 Synthorin (pegylated Il-15), P-22339, and an IL-15-PD-1 fusion protein N-809. Examples of IL-7 receptor agonist that can be co-administered include CYT-107.

Examples of additional immune-based therapies that can be combined or co-administered include interferon alfa; interferon alfa-2b; interferon alfa-n3; pegylated interferon alfa; interferon gamma; fms related tyrosine kinase 3 (FLT3) agonists (e.g., GS-3583, CDX-301); gepon; normferon, peginterferon alfa-2a, peginterferon alfa-2b, RPI-MN. In various embodiments, a fms related tyrosine kinase 3 (FLT3) agonists (e.g., GS-3583, CDX-301) is administered at a first time point and the one or more fusion polypeptides, or polynucleotides encoding, lipoplexes (e.g., LNPs) comprising such polynucleotides, or vectors expressing such fusion polypeptides are administered at a time point at least 6, 7, 8, 9, 10 days, e.g., 1 week, after the first time point.

In some embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with an fms related tyrosine kinase 3 (FLT3) agonist (e.g., GS-3583, CDX-301). Illustrative FLT3 agonists that can be co-administered are described, e.g., in WO 2020/263830A1. In various embodiments, the co-administration of a FLT3 agonist increases the vaccine-induced T cell response in comparison to administration of the one or more fusion polypeptides, or polynucleotides encoding, lipoplexes (e.g., LNPs) comprising such polynucleotides, or vectors expressing such fusion polypeptides in the absence of a FLT3 agonist.

Phosphatidylinositol 3-Kinase (PI3K) Inhibitors

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with a PI3K inhibitor. Examples of PI3K inhibitors that can be combined or co-administered include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

Diacylglycerol Kinase Inhibitors

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with an inhibitor of a diacylglycerol kinase (DGK), e.g., diacylglycerol kinase alpha (DGKα) and diacylglycerol kinase zeta (DGKζ). Examples of DGK inhibitors that can be combined or co-administered include ritanserin and the DGK inhibitors described in WO2020006016 and WO2020006018.

Alpha-4/Beta-7 Antagonists

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with an alpha-4/beta-7 antagonist. Examples of Integrin alpha-4/beta-7 antagonists that can be combined or co-administered include PTG-100, TRK-170, abrilumab, etrolizumab, carotegrast methyl, and vedolizumab.

HPK1/MAP4K1 Inhibitors

In certain embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with an inhibitor of mitogen-activated protein kinase kinase kinase kinase 1 (MAP4K1, a.k.a., Hematopoietic Progenitor Kinase 1 (HPK1); NCBI Gene ID: 11184). Examples of HPK1 inhibitors include, but are not limited to, ZYF-0272, and ZYF-0057.

HIV-Targeting Antibodies

Examples of HIV antibodies, bispecific antibodies, and “antibody-like” therapeutic proteins that can be combined or co-administered include DARTs®, DUOBODIES®, BITES®, XmAbs®, TandAbs®, Fab derivatives, bNAbs (broadly neutralizing HIV-1 antibodies), TMB-360, TMB-370, and those targeting HIV gp120 or gp41, antibody-Recruiting Molecules targeting HIV, anti-CD63 monoclonal antibodies, anti-GB virus C antibodies, anti-GP120/CD4, gp120 bispecific monoclonal antibody, CCR5 bispecific antibodies, anti-Nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs, ibalizumab, ibalizumab (second generation), Immuglo, MB-66, clone 3 human monoclonal antibody targeting KLIC (HIV infection). Various bNAbs may be used, as described herein.

In certain embodiments, the co-administered antibody or antigen-binding fragment thereof, or an antigen-binding molecule, is or is derived from human neutralizing antibodies (e.g., monoclonal) that target HIV-1. A "neutralizing antibody" is one that can neutralize the ability of HIV to initiate and/or perpetuate an infection in a host and/or in target cells in vitro. The disclosure provides neutralizing monoclonal human antibodies, wherein the antibody recognizes an antigen from HIV, e.g., a gp120 polypeptide. In certain embodiments, a "neutralizing antibody" may inhibit the entry of HIV-1 virus, e.g., SF162 and/or JR-CSF, with a neutralization index >1.5 or >2.0 (Kostrikis L G et al., J. Virol., 70(1): 445-458 (1996)).

In some embodiments, the co-administered antibody or antigen-binding fragment thereof, or an antigen-binding molecule, is or is derived from a human broadly neutralizing antibody (e.g., monoclonal) that target HIV-1. By "broadly neutralizing antibodies" are meant antibodies that neutralize more than one HIV-1 virus species (from diverse clades and different strains within a clade) in a neutralization assay. A broad neutralizing antibody may neutralize at least 2, 3, 4, 5, 6, 7, 8, 9 or more different strains of HIV-1, the strains belonging to the same or different clades. Illustrative broadly neutralizing antibodies (bNAbs) which can be co-administered as an additional therapeutic agent in a combination therapy are described, e.g., in U.S. Pat. Nos. 8,673,307; 9,493,549; 9,783,594; and WO 2012/154312; WO2012/158948; WO 2013/086533; WO 2013/142324; WO2014/063059; WO 2014/089152, WO 2015/048462; WO 2015/103549; WO 2015/117008; WO2016/014484; WO 2016/154003; WO 2016/196975; WO 2016/149710; WO2017/096221; WO 2017/133639; WO 2017/133640, which are hereby incorporated herein by reference in their entireties for all purposes. Illustrative bNAbs that can be co-administered include without limitation 12A12, 12A21, NIH45-46, bANC131, 8ANC134, 132530, INC9, 8ANC195, 8ANC196, 10-259, 10-303, 10-410, 10-847, 10-996, 10-1074, 10-1074-LS, 10-1074-LS-J, 10-1121, 10-1130, 10-1146, 10-1341, 10-1369, 10-1074GM, PGT-121, PGT-121.414, GS-9721, GS-9722, GS-2872. Additional examples include those described in Sajadi, et al., Cell. (2018) 173(7):1783-1795; Sajadi, et al., J Infect Dis. (2016) 213(1):156-64; Klein et al., Nature, 492(7427): 118-22 (2012), Horwitz et al., Proc Natl Acad Sci USA, 110(41): 16538-43 (2013), Scheid, et al., Science, 333: 1633-1637 (2011), Scheid, et al., Nature, 458:636-640 (2009), Eroshkin et al, Nucleic Acids Res., 42 (Database issue):Dl 133-9 (2014), Mascola et al., Immunol Rev., 254(1):225-44 (2013), such as 2F5, 4E10, M66.6, CAP206-CH12, 10E81 (all of which bind the MPER of gp41); PG9, PG16, CH01-04 (all of which bind V1V2-glycan), 2G12 (which binds to outer domain glycan); b12, HJ16, CH130-149, VRC01-03, VRC-PG04, 04b, VRC-CH30-34, 3BNC62, 3BNC89, 3BNC91, 3BNC95, 3BNC104, 3BNC117, 3BNC176, 8ANC131, GS-9723, GS-5423 (all of which bind to the CD4 binding site), which are hereby incorporated herein by reference in their entireties for all purposes.

In some embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with a broadly neutralizing antibody (bNAb)) that binds to an epitope or region of gp120 selected from: (i) the third variable loop (V3) and/or high mannose patch comprising a N332 oligomannose glycan; (ii) second variable loop (V2) and/or Env trimer apex; (iii) CD4 binding site (CD4bs); (iv) gp120/gp41 interface; or (v) silent face of gp120. The foregoing epitopes or regions of gp120 bound by broadly neutralizing antibodies are described, e.g., in McCoy, *Retrovirology* (2018) 15:70; Sok and Burton, *Nat Immunol.* 2018 19(11):1179-1188; Possas, et al., *Expert Opin Ther Pat.* 2018 July; 28(7):551-560; and Stephenson and Barouch, *Curr HIV/AIDS Rep* (2016) 13:31-37, which are hereby incorporated herein by reference in their entirety for all purposes.

In some embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with a broadly neutralizing antibody (bNAb) that binds to an epitope or region of gp120 in the third variable loop (V3) and/or high mannose patch comprising a N332 oligomannose glycan and competes with or comprises VH and VL regions from an antibody selected from GS-9722, PGT-121.60, PGT-121.66, PGT-121, PGT-121.414, PGT-122, PGT-123, PGT-124, PGT-125, PGT-126, PGT-128, PGT-130, PGT-133, PGT-134, PGT-135, PGT-136, PGT-137, PGT-138, PGT-139, 10-1074, VRC24, 2G12, BG18, 354BG8, 354BG18, 354BG42, 354BG33, 354BG129, 354BG188, 354BG411, 354BG426, DH270.1, DH270.6, PGDM12, VRC41.01, PGDM21, PCDN-33A, BF520.1 and VRC29.03. Additional broadly neutralizing antibodies that bind to gp120 in the third variable loop (V3) and/or high mannose patch comprising a N332 oligomannose glycan and which can be used as the second antibody or antigen-binding fragment thereof are described, e.g., in WO 2012/030904; WO 2014/063059; WO 2016/149698; WO 2017/106346; WO 2018/075564, WO 2018/125813 and WO 2018/237148, which are hereby incorporated herein by reference in their entireties for all purposes.

In some embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with a broadly neutralizing antibody (bNAb)) that binds to an epitope or region of gp120 in the CD4 binding site (CD4bs) and competes with or comprises CDRs and/or VH and VL regions from an antibody selected from b12, F105, VRC01, VRC07, VRC07-523, VRC03, VRC06, VRC06b01 VRC08, VRC0801, NIH45-46, GS-9723, GS-5423, 3BNC117, 3BNC60, VRC-PG04, PGV04; CH103, 44-VRC13.01, 1NC9, 12A12, N6, N49-P7, NC-Cowl, IOMA, CH235 and CH235.12, N49P6, N49P7, N49P11, N49P9 and N60P25. Additional broadly neutralizing antibodies that bind to gp120 CD4 binding site (CD4bs) and which can be used as the second antibody or antigen-binding fragment thereof are described, e.g., in WO 2012/154312, WO 2012/158948, WO 2013/090644, WO 2013/192589, WO 2018/125813, which are hereby incorporated herein by reference in their entireties for all purposes.

In some embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with a broadly neutralizing antibody (bNAb)) that binds to an epitope or region of gp120 in the second variable loop (V2) and/or Env trimer apex and competes with or comprises VH and VL regions from an antibody selected from PG9, PG16, PGC14, PGG14, PGT-142, PGT-143, PGT-144, PGT-145, CH01, CH59, PGDM1400, CAP256, CAP256-VRC26.08, CAP256-VRC26.09, CAP256-VRC26.25, PCT64-24E and VRC38.01. Additional broadly neutralizing antibodies that bind to gp120 in the second variable loop (V2) and/or Env trimer apex and which can be used as the second antibody or antigen-binding fragment thereof are described, e.g., in WO 2010/107939; WO 2012/030904; WO 2018/075564 and WO 2018/125813, which are hereby incorporated herein by reference in their entireties for all purposes.

In some embodiments the one or more fusion polypeptides, or polynucleotides encoding, lipoplexes (e.g., LNPs) comprising such polynucleotides, or vectors expressing such fusion polypeptides, as disclosed herein, are combined or co-administered with a broadly neutralizing antibody (bNAb)) that binds to an epitope or region of gp120 in the gp120/gp41 interface and competes with or comprises VH and VL regions from an antibody selected from PGT-151, CAP248-2B, 35022, 8ANC195, ACS202, VRC34 and VRC34.01. Additional broadly neutralizing antibodies that bind to gp120 in the gp120/gp41 interface and which can be used as the second antibody or antigen-binding fragment thereof are described, e.g., in WO 2011/038290; WO 2012/030904 and WO2017/079479, which are hereby incorporated herein by reference in their entireties for all purposes.

In some embodiments, the one or more fusion polypeptides, or polynucleotides encoding, lipoplexes (e.g., LNPs) comprising such polynucleotides, or vectors expressing such fusion polypeptides, as disclosed herein, combined or co-administered with a broadly neutralizing antibody (bNAb)) that binds to an epitope or region of the gp120 silent face and competes with or comprises VH and VL regions from an antibody selected from VRC-PG05 and SF12. See, e.g., Schoofs, et al., "Broad and Potent Neutralizing Antibodies Recognize the Silent Face of the HIV Envelope," *Immunity* (2019) May 14. pii: S1074-7613(19)30194-3 (PMID 31126879).

In some embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with a broadly neutralizing antibody (bNAb)) that binds to an epitope or region of gp41 in the membrane proximal region (MIPER). Additional broadly neutralizing antibodies that bind to gp41 in the MPER and which can be used as the second antibody or antigen-binding fragment thereof are described, e.g., in WO 2011/034582; WO 2011/038290; WO 2011/046623 and WO 2013/070776, which are hereby incorporated herein by reference in their entireties for all purposes.

In some embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with a broadly neutralizing antibody (bNAb)) that binds to an epitope or region of gp41 in the membrane proximal region (MPER) and competes with or comprises VH and VL regions from an antibody selected from 10E8, 10E8v4, 10E8-5R-100cF, 4E10, DH511.11P, 2F5, 7b2, and LN01.

In some embodiments, the one or more fusion polypeptides, or polynucleotides encoding, lipoplexes (e.g., LNPs) comprising such polynucleotides, or vectors expressing such fusion polypeptides, as disclosed herein, are combined or co-administered with a broadly neutralizing antibody (bNAb)) that binds to an epitope or region of the gp41 fusion peptide and competes with or comprises VH and VL regions from an antibody selected from VRC34 and ACS202.

Examples of additional antibodies that can be co-administered include bavituximab, UB-421, BF520.1, BiIA-SG, CH01, CH59, C2F5, C4E10, C2F5+C2G12+C4E10, CAP256V2LS, 3BNC117, 3BNC117-LS, 3BNC60, DH270.1, DH270.6, D1D2, 10-1074-LS, Cl3hmAb, GS-9722 (elipovimab), PGT-121.414, PGT-121.60, PGT-121.66, PGT122, PGT-123, PGT-124, PGT-125, PGT-126, PGT-151, PGT-130, PGT-133, PGT-134, PGT-135, PGT-128, PGT-136, PGT-137, PGT-138, PGT-139, MDX010 (ipilimumab), DH511, DH511-2, N6, N6LS, N49P6, N49P7, N49P7.1, N49P9, N49P11, N60P1.1, N60P25.1, N60P2.1, N60P31.1, N60P22, NIH 45-46, PGC14, PGG14, PGT-142, PGT-143, PGT-144, PGDM1400, PGDM12, PGDM21, PCDN-33A, 2Dm2m, 4Dm2m, 6Dm2m, PGDM1400, MDX010 (ipilimumab), VRC01, VRC-01-LS, A32, 7B2, 10E8, VRC-07-523, VRC07-523LS, VRC24, VRC41.01, 10E8VLS, 3810109, 10E8v4, IMC-HIV, iMabm36, eCD4-Ig, IOMA, CAP256-VRC26.25, DRVIA7, VRC-HIVMAB080-00-AB, VRC-HIVMAB060-00-AB, P2G12, VRC07, 354BG8, 354BG18, 354BG42, 354BG33, 354BG129, 354BG188, 354BG411, 354BG426, VRC29.03, CAP256, CAP256-VRC26.08, CAP256-VRC26.09, CAP256-VRC26.25, PCT64-24E and VRC38.01, PGT-151, CAP248-2B, 35022, ACS202, VRC34 and VRC34.01, 10E8, 10E8v4, 10E8-5R-100cF, 4E10, DH511.11P, 2F5, 7b2, and LN01.

Example of HIV bispecific and trispecific antibodies include MGD014, B12BiTe, BiIA-SG, TMB-bispecific, SAR-441236, VRC-01/PGDM-1400/10E8v4, 10E8.4/iMab, 10E8v4/PGT121-VRC01.

In some embodiments, the bNAbs can be expressed in vivo in the patient. Examples of in vivo delivered bNAbs include AAV8-VRC07; mRNA encoding anti-HIV antibody VRC01; and engineered B-cells encoding 3BNC117 (Hartweger et al, J. Exp. Med. 2019, 1301).

Pharmacokinetic Enhancers

In certain embodiments, the one or more fusion polypeptides, or polynucleotides encoding, lipoplexes (e.g., LNPs) comprising such polynucleotides, or vectors expressing such fusion polypeptides, as disclosed herein, are combined with a pharmacokinetic enhancer. Examples of pharmacokinetic enhancers that can be combined or co-administered include cobicistat and ritonavir.

Additional Therapeutic Agents

Examples of additional therapeutic agents that can be combined with the one or more fusion polypeptides, or polynucleotides encoding, lipoplexes (e.g., LNPs) comprising such polynucleotides, or vectors expressing such fusion polypeptides, as disclosed herein, include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

HIV Vaccines

In certain embodiments, the one or more fusion polypeptides, or polynucleotides encoding, lipoplexes (e.g., LNPs) comprising such polynucleotides, or vectors expressing such fusion polypeptides, as disclosed herein, are combined with an HIV vaccine. Examples of HIV vaccines that can be combined or co-administered include peptide vaccines, recombinant subunit protein vaccines, live vector vaccines, DNA vaccines, HIV MAG DNA vaccine, CD4-derived peptide vaccines, vaccine combinations, adenoviral vector vaccines (an adenoviral vector such as Ad5, Ad26 or Ad35), simian adenovirus (chimpanzee, gorilla, rhesus i.e. rhAd), adeno-associated virus vector vaccines, Chimpanzee adenoviral vaccines (e.g., ChAdOX1, ChAd68, ChAd3, ChAd63, ChAd83, ChAd155, ChAd157, Pan5, Pan6, Pan7, Pan9), Coxsackieviruses based vaccines, enteric virus based vaccines, Gorilla adenovirus vaccines, lentiviral vector based vaccine, arenavirus vaccines (such as LCMV, Pichinde), bi-segmented or tri-segmented arenavirus based vaccine, trimer-based HIV-1 vaccine, measles virus based vaccine, flavivirus vector based vaccines, tobacco mosaic virus vector based vaccine, Varicella-zoster virus based vaccine, Human parainfluenza virus 3 (PIV3) based vaccines, poxvirus based vaccine (modified vaccinia virus Ankara (MVA), orthopoxvirus-derived NYVAC, and avipoxvirus-derived ALVAC (canarypox virus) strains); fowlpox virus based vaccine, rhabdovirus-based vaccines, such as VSV and marabavirus; recombinant human CMV (rhCMV) based vaccine, alphavirus-based vaccines, such as semliki forest virus, venezuelan equine encephalitis virus and sindbis virus; (see Lauer, Clinical and Vaccine Immunology, 2017, DOI: 10.1128/CVI.00298-16); LNP formulated mRNA based therapeutic vaccines; LNP-formulated self-replicating RNA/self-amplifying RNA vaccines.

Examples of HIV vaccines that can be co-administered include without limitation AAVLP-HIV vaccine, AE-298p, anti-CD40.Env-gp140 vaccine, Ad4-EnvC150, BG505 SOSIP.664 gp140 adjuvanted vaccine, BG505 SOSIP.GT1.1 gp140 adjuvanted vaccine, ChAdOx1.tHIVconsv1 vaccine, CMV-MVA triplex vaccine, ChAdOx1.HTI, Chimigen HIV vaccine, ConM SOSIP.v7 gp140, ALVAC HIV (vCP1521), AIDSVAX B/E (gp120), monomeric gp120 HIV-1 subtype C vaccine, MPER-656 liposome subunit vaccine, Remune, ITV-1, Contre Vir, Ad5-ENVA-48, DCVax-001 (CDX-2401), Vacc-4x, Vacc-C5, VAC-3S, multiclade DNA recombinant adenovirus-5 (rAd5), rAd5 gag-pol env A/B/C vaccine, Pennvax-G, Pennvax-GP, Pennvax-G/MVA-CMDR, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multiHIV (FIT-06), ChAdV63.HIVconsv, gp140[delta]V2.TV1+MF-59, rVSVIN HIV-1 gag vaccine, SeV-EnvF, SeV-Gag vaccine, AT-20, DNK-4, ad35-Grin/ENV, TBC-M4, HIVAX, HIVAX-2, N123-VRC-34.01 inducing epitope-based HIV vaccine, NYVAC-HIV-PT1, NYVAC-HIV-PT4, DNA-HIV-PT123, rAAV1-PG9DP, GOVX-B11, GOVX-B21, GOVX-C55, TVI-HIV-1, Ad-4 (Ad4-env Clade C+Ad4-mGag), Paxvax, EN41-UGR7C, EN41-FPA2, ENOB-HV-11, ENOB-HV-12, PreVaxTat, AE-H, MYM-V101, CombiHIVvac, ADVAX, MYM-V201, MVA-CMDR, MagaVax, DNA-Ad5 gag/pol/nef/nev (HVTN505), MVATG-17401, ETV-01, CDX-1401, DNA and Sev vectors vaccine expressing SCaVII, rcAD26.MOS1.HIV-Env, Ad26.Mod.HIV vaccine, Ad26.Mod.HIV+MVA mosaic vaccine+gp140, AGS-004, AVX-101, AVX-201, PEP-6409, SAV-001, ThV-01, TL-01, TUTI-16, VGX-3300, VIR-1111, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines (such as DermaVir), gag-based DNA vaccine, GI-2010, gp41 HIV-1 vaccine, HIV vaccine (PIKA adjuvant), i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, rgp160 HIV vaccine, RNActive HIV vaccine, SCB-703, Tat Oyi vaccine, TBC-M4, UBI HIV gp120, Vacc-4x+romidepsin, variant gp120 polypeptide vaccine, rAd5 gag-pol env A/B/C vaccine, DNA.HTI and MVA.HTI, VRC-HIVDNA016-00-VP+VRC-HIVADV014-00-VP, INO-6145, JNJ-9220, gp145 C.6980; eOD-GT8 60mer based vaccine, PD-201401, env (A, B, C, A/E)/gag (C) DNA Vaccine, gp120 (A,B,C,A/E) protein vaccine, PDPHV-201401, Ad4-EnvCN54, EnvSeq-1 Envs HIV-1 vaccine (GLA-SE adjuvanted), HIV p24gag prime-boost plasmid DNA vaccine, HIV-1 iglb12 neutralizing VRC-01 antibody-stimulating anti-CD4 vaccine, arenavirus vector-based vaccines (VaxWave®, TheraT®), MVA-BN HIV-1 vaccine regimen, UBI HIV gp120, mRNA based prophylactic vaccines, VPI-211, multimeric HIV gp120 vaccine (Fred Hutchinson cancer center), TBL-1203HI, CH505 TF chTrimer, CD40.HIVRI.Env vaccine, Drep-HIV-PT-1, mRNA-1644, and mRNA-1574.

Birth Control (Contraceptive) Combination Therapy

In certain embodiments, the agents described herein are combined with a birth control or contraceptive regimen. Therapeutic agents used for birth control (contraceptive) that can be combined or co-administered include cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

In one embodiment, an agent disclosed herein, or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); BIKTARVY (bictegravir+emtricitabine+tenofovir alafenamide), adefovir; adefovir dipivoxil; cobicistat; emtricitabine; tenofovir; tenofovir alafenamide and elvitegravir; tenofovir alafenamide+elvitegravir (rectal formulation, HIV infection); tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; PEGylated raltegravir; raltegravir and lamivudine; lamivudine+lopinavir+ritonavir+abacavir; maraviroc; tenofovir+ emtricitabine+maraviroc, enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In some embodiments, the one or more fusion polypeptides, or polynucleotides encoding, lipoplexes (e.g., LNPs) comprising such polynucleotides, or vectors expressing such fusion polypeptides, as disclosed herein, are combined with an HIV nucleoside or nucleotide inhibitor of reverse transcriptase and an HIV non-nucleoside inhibitor of reverse transcriptase. In another specific embodiment, an agent disclosed herein, or a pharmaceutical composition thereof, is combined with an HIV nucleoside or nucleotide inhibitor of reverse transcriptase, and an HIV protease inhibiting compound. In an additional embodiment, an agent disclosed herein, or a pharmaceutical composition thereof, is combined with an HIV nucleoside or nucleotide inhibitor of reverse transcriptase, an HIV non-nucleoside inhibitor of reverse transcriptase, and a pharmacokinetic enhancer. In certain embodiments, an agent disclosed herein, or a pharmaceutical composition thereof, is combined with at least one HIV nucleoside inhibitor of reverse transcriptase, an integrase inhibitor, and a pharmacokinetic enhancer. In another embodiment, an agent disclosed herein, or a pharmaceutical composition thereof, is combined with two HIV nucleoside or nucleotide inhibitors of reverse transcriptase.

In a certain embodiment, the one or more fusion polypeptides, or polynucleotides encoding, lipoplexes (e.g., LNPs) comprising such polynucleotides, or vectors expressing such fusion polypeptides, as disclosed herein, are combined with abacavir sulfate, tenofovir, tenofovir disoproxil, tenofovir disoproxil fumarate, tenofovir disoproxil hemifumarate, tenofovir alafenamide, or tenofovir alafenamide hemifumarate.

In another embodiment, the one or more fusion polypeptides, or polynucleotides encoding, lipoplexes (e.g., LNPs) comprising such polynucleotides, or vectors expressing such fusion polypeptides, as disclosed herein, are combined with tenofovir, tenofovir disoproxil, tenofovir disoproxil fumarate, tenofovir alafenamide, or tenofovir alafenamide hemifumarate.

In yet another embodiment, the one or more fusion polypeptides, or polynucleotides encoding, lipoplexes (e.g., LNPs) comprising such polynucleotides, or vectors expressing such fusion polypeptides, as disclosed herein, are combined with a first additional therapeutic agent selected from abacavir sulfate, tenofovir, tenofovir disoproxil, tenofovir disoproxil fumarate, tenofovir alafenamide, and tenofovir alafenamide hemifumarate, and a second additional therapeutic agent selected from emtricitabine and lamivudine.

In yet another embodiment, the one or more fusion polypeptides, or polynucleotides encoding, lipoplexes (e.g., LNPs) comprising such polynucleotides, or vectors expressing such fusion polypeptides, as disclosed herein, are combined with a first additional therapeutic agent selected from dolutegravir, cabotegravir, islatravir, darunavir, bictegravir, elsulfavirine, rilpivirine, and lenacapavir, and a second additional therapeutic agent selected from emtricitabine and lamivudine.

In another embodiment, the one or more fusion polypeptides, or polynucleotides encoding, lipoplexes (e.g., LNPs) comprising such polynucleotides, or vectors expressing such fusion polypeptides, as disclosed herein, are combined with a first additional therapeutic agent selected from tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine.

the one or more fusion polypeptides, or polynucleotides encoding, lipoplexes (e.g., LNPs) comprising such polynucleotides, or vectors expressing such fusion polypeptides, as disclosed herein, are combined with a first additional therapeutic agent (a contraceptive) selected from cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

Gene Therapy and Cell Therapy

In certain embodiments, the one or more fusion polypeptides, or polynucleotides encoding, lipoplexes (e.g., LNPs) comprising such polynucleotides, or vectors expressing such fusion polypeptides, as disclosed herein, are combined with a gene or cell therapy regimen. Gene therapy and cell therapy include without limitation the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection. Examples of cell therapy include without limitation LB-1903, ENOB-HV-01, ENOB-HV-21, ENOB-HV-31, GOVX-B01, HSPCs overexpressing ALDH1 (LV-800, HIV infection), AGT103-T, and SupTI cell-based therapy. Examples of dendritic cell therapy include without limitation AGS-004. CCR5 gene editing agents include without limitation SB-728T, SB-728-HSPC. CCR5 gene inhibitors include without limitation Cal-1, and lentivirus vector CCR5 shRNA/TRIM5alpha/TAR decoy-transduced autologous CD34-positive hematopoietic progenitor cells (HIV infection/HIV-related lymphoma). In some embodiments, C34-CCR5/C34-CXCR4 expressing CD4-positive T-cells are co-administered with one or more fusion polypeptides. In some embodiments, the agents described herein are co-administered with AGT-103-transduced autologous T-cell therapy or AAV-eCD4-Ig gene therapy.

Gene Editors

In certain embodiments, the one or more fusion polypeptides, or polynucleotides encoding, lipoplexes (e.g., LNPs) comprising such polynucleotides, or vectors expressing such fusion polypeptides, as disclosed herein, are combined with a gene editor, e.g., an HIV targeted gene editor. In various embodiments, the genome editing system can be selected from: a CRISPR/Cas9 complex, a zinc finger nuclease complex, a TALEN complex, a homing endonucleases complex, and a meganuclease complex. An illustrative HIV targeting CRISPR/Cas9 system includes without limitation EBT-101.

CAR-T-Cell Therapy

In some embodiments, the agents described herein can be co-administered with a population of immune effector cells engineered to express a chimeric antigen receptor (CAR), wherein the CAR comprises an HIV antigen binding domain. The HIV antigen include an HIV envelope protein or a portion thereof, gp120 or a portion thereof, a CD4 binding site on gp120, the CD4-induced binding site on gp120, N-glycan on gp120, the V2 of gp120, the membrane proximal region on gp41. The immune effector cell is a T-cell or an NK cell. In some embodiments, the T-cell is a CD4+ T-cell, a CD8+ T-cell, or a combination thereof. Cells can be autologous or allogeneic. Examples of HIV CAR-T include A-1801, A-1902, convertible CAR-T, VC-CAR-T, CMV-N6-CART, anti-HIV duoCAR-T, anti-CD4 CART-cell therapy, CD4 CAR+C34-CXCR4+CCR5 ZFN T-cells, dual anti-CD4 CART-T cell therapy (CD4 CAR+C34-CXCR4 T-cells), anti-CD4 MicAbody antibody+anti-MicAbody CAR T-cell therapy (iNKG2D CAR, HIV infection), GP-120 CAR-T therapy, autologous hematopoietic stem cells genetically engineered to express a CD4 CAR and the C46 peptide.

TCR-T-Cell Therapy

In certain embodiments, the one or more fusion polypeptides, or polynucleotides encoding, lipoplexes (e.g., LNPs) comprising such polynucleotides, or vectors expressing such fusion polypeptides, as disclosed herein, are combined with a population of TCR-T-cells. TCR-T-cells are engineered to target HIV derived peptides present on the surface of virus-infected cells, for example ImmTAV.

B-Cell Therapy

In certain embodiments, the one or more fusion polypeptides, or polynucleotides encoding, lipoplexes (e.g., LNPs) comprising such polynucleotides, or vectors expressing such fusion polypeptides, as disclosed herein, are combined with a population of B cells genetically modified to express broadly neutralizing antibodies, such as 3BNC117 (Hartweger et al, J. Exp. Med. 2019, 1301, Moffett et al., Sci. Immunol. 4, eaax0644 (2019) 17 May 2019).

8. Kits

Further provided are kits comprising one or more unitary doses of one or more of the fusion polypeptides or compound fusion polypeptides, as described herein, or one or more polynucleotides encoding such fusion polypeptides or compound fusion polypeptides, as described herein, or one or more vectors expressing such fusion polypeptides or compound fusion polypeptides, as described herein. In some embodiments, the kit comprises two or more unitary doses of one or more of the fusion polypeptides or compound fusion polypeptides, as described herein, or two or more polynucleotides encoding such fusion polypeptides or compound fusion polypeptides, as described herein, or two or more vectors expressing such fusion polypeptides or compound fusion polypeptides, as described herein. In some embodiments, the one or more unitary doses are in a single container. In some embodiments, the one or more unitary doses are in two or more separate containers. In certain embodiments, the unitary doses can be the same or different, e.g., can comprise the same or different unitary doses, e.g., can comprise polypeptides, polynucleotides, vectors or combinations thereof.

In various embodiments, the kit comprises one or more pharmaceutical packs or one or more containers (e.g., vials, ampules, pre-loaded syringes) containing one or more of the ingredients of the pharmaceutical compositions described herein, such as one or more of the fusion polypeptides, as described herein, or one or more polynucleotides encoding such fusion polypeptides, as described herein, or one or more vectors expressing such fusion polypeptides, as described herein. In various embodiments, the kit comprises one or more containers comprising the one or more of the fusion polypeptides, as described herein, or one or more polynucleotides encoding such fusion polypeptides, as described herein, or one or more vectors expressing such fusion polypeptides, as described herein, in an aqueous solution. In various embodiments, the kit comprises one or more containers comprising the one or more of the fusion polypeptides, as described herein, or one or more polynucleotides encoding such fusion polypeptides, as described herein, or one or more vectors expressing such fusion polypeptides, as described herein, in lyophilized form.

In some embodiments, the kit comprises one or more unitary doses of one or more viral vectors capable of expressing the fusion polypeptides. In some embodiments, the unitary doses of the one or more viral vectors are in the range of about $10^3$ to about $10^{12}$ viral focus forming units (FFU) or plaque forming units (PFU) or infectious units (IU) or viral particles (vp), e.g. from about $10^4$ to about $10^7$ viral FFU or PFU or IU or vp, e.g. from about $10^3$ to about $10^4$, $10^5$, $10^6$, $10^7$, $10^8$, $10^9$, $10^{10}$, $10^{11}$, $10^{12}$, $10^{13}$, $10^{14}$ or $10^{15}$ viral FFU or PFU or IU or vp, per administration.

In some embodiments, the kit comprises a first fusion polypeptide and a second fusion polypeptide, or one or more vectors comprising one or more polynucleotides encoding the first and second fusion polypeptides, the first and second polypeptides comprising the following polypeptide segments, in sequential order, from N-terminus to C-terminus, optionally joined or connected by one or more linkers:

SEQ ID NOs: 6, 4, 16 and 26, and SEQ ID NOs: 7, 5, 27 and 17;

SEQ ID NOs: 12, 24, 8 and 10, and SEQ ID NOs: 9, 25, 13 and 11;

SEQ ID NOs: 14, 22, 18, 24 and 20, and SEQ ID NOs: 15, 25, 19, 23 and 21;

SEQ ID NOs: 26, 16, 4 and 6, and SEQ ID NOs: 7, 27, 5 and 17;

SEQ ID NOs: 8, 24, 12 and 10, and SEQ ID NOs: 13, 25, 9 and 11;

SEQ ID NOs: 22, 24, 14, 18 and 20, and SEQ ID NOs: 25, 23, 15, 21 and 19;

SEQ ID NOs: 20, 6, 4, 18, 16 and 26, and SEQ ID NOs: 7, 19, 5, 21, 27 and 17;

SEQ ID NOs: 8, 24, 14, 12, 22 and 10, and SEQ ID NOs: 9, 13, 25, 23, 15 and 11;

SEQ ID NOs: 18, 26, 20, 4, 6 and 16, and SEQ ID NOs: 7, 21, 17, 5, 27 and 19;

SEQ ID NOs: 22, 24, 12, 14, 8 and 10, and SEQ ID NOs: 15, 25, 9, 23, 13 and 11;

SEQ ID NOs: 24, 6, 4, 20, 18 and 32, and SEQ ID NOs: 8, 30, 14, 12, 26 and 10;

SEQ ID NOs: 24, 6, 4, 20, 18 and 32, and SEQ ID NOs: 7, 21, 5, 25, 33 and 19;

SEQ ID NOs: 24, 6, 4, 20, 18 and 32, and SEQ ID NOs: 8, 30, 14, 12, 26 and 10;

SEQ ID NOs: 8, 30, 14, 12, 26 and 10, and SEQ ID NOs: 9, 13, 31, 27, 15 and 11;

SEQ ID NOs: 7, 21, 5, 25, 33 and 19 and SEQ ID NOs: 9, 13, 31, 27, 15 and 11;

SEQ ID NOs: 20, 32, 24, 4, 6 and 18, and SEQ ID NOs: 26, 30, 12, 14, 8 and 10;

SEQ ID NOs: 6, 20, 4, 24, 32 and 18, and SEQ ID NOs: 8, 12, 30, 26, 14 and 10;

SEQ ID NOs: 7, 25, 19, 5, 33 and 21, and SEQ ID NOs: 15, 31, 9, 27, 13 and 11;

SEQ ID NOs: 24, 6, 16 and 18, and SEQ ID NOs: 26, 20, 10 and 28;

SEQ ID NOs: 24, 6, 16 and 18, and SEQ ID NOs: 26, 10, 20 and 28;

SEQ ID NOs: 24, 6, 16 and 18, and SEQ ID NOs: 7, 25, 17 and 19;

SEQ ID NOs: 7, 19, 17 and 25, and SEQ ID NOs: 21, 27, 11 and 29;

SEQ ID NOs: 24, 16, 6 and 18, and SEQ ID NOs: 27, 11, 21 and 29;

SEQ ID NOs: 7, 25, 17 and 19, and SEQ ID NOs: 11, 27, 21 and 29;

SEQ ID NOs: 7, 25, 17 and 19, and SEQ ID NOs: 21, 27, 11 and 29;

SEQ ID NOs: 22, 6, 20 and 28, and SEQ ID NOs: 23, 7, 21 and 29;

SEQ ID NOs: 22, 20, 6 and 28, and SEQ ID NOs: 7, 21, 23 and 29;

SEQ ID NOs: 26, 10, 20 and 28, and SEQ ID NOs: 21, 27, 11 and 29;

SEQ ID NOs: 22, 6, 16, 20, 18, 28, 26 and 10; or

SEQ ID NOs: 7, 21, 19, 17, 27, 25, 29 and 11.

In some embodiments, the kit comprises one or more fusion polypeptides, or one or more vectors comprising one or more polynucleotides encoding one or more fusion polypeptides, comprising or consisting of an amino acid sequence of any one of SEQ ID NOs: 70-101, 105-112, 200-209, 222-223 and 227, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70-101, 105-112, 200-209, 222-223 and 227. In some embodiments, the kit comprises one or more fusion polypeptides, or one or more vectors comprising one or more polynucleotides encoding one or more fusion polypeptides, comprising or consisting of an amino acid sequence of any one of SEQ ID NOs: 82-83, 85-87, 98-101, 209 and 222-223, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82-83, 85-87, 98-101, 209 and 222-223.

In some embodiments, the kit comprises the following first fusion polypeptide and second fusion polypeptide, or one or more vectors comprising one or more polynucleotides encoding the following first fusion polypeptide and second fusion polypeptide, optionally joined or connected by one or more linkers:

SEQ ID NOs: 70 and 71, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70 and 71, respectively;

SEQ ID NOs: 72 and 73, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 72 and 73, respectively;

SEQ ID NOs: 74 and 75, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 74 and 75, respectively;

SEQ ID NOs: 76 and 77, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 76 and 77, respectively;

SEQ ID NOs: 78 and 79, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 78 and 79, respectively;

SEQ ID NOs: 80 and 81, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 80 and 81, respectively;

SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively;

SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively;

SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively;

SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively;

SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively;

SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively;

SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively;

SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively;

SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively;

SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively;

SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 88, respectively;

SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively;

SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively;

SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively;

SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively;

SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively;

SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively;

SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively;

SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively;

SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively;

SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively;

SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively;

SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively; or SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively.

In some embodiments, the kit comprises first, second, third and fourth viral vectors comprising one or more polynucleotides encoding the following first fusion polypeptide and second fusion polypeptide, optionally joined or connected by one or more linkers:

a) a first viral vector comprising one or more polynucleotides encoding a first fusion polypeptide and a second fusion polypeptide comprising SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively;

b) a second viral vector comprising one or more polynucleotides encoding a first fusion polypeptide and a second fusion polypeptide comprising SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively;

c) a third viral vector comprising one or more polynucleotides encoding a first fusion polypeptide and a second fusion polypeptide comprising SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively; and d) a fourth viral vector comprising one or more polynucleotides encoding a first fusion polypeptide and a second fusion polypeptide comprising SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively.

In some embodiments, the kit comprises first and second viral vectors comprising one or more polynucleotides encoding the following first fusion polypeptide and second fusion polypeptide, optionally joined or connected by one or more linkers:

a) a first viral vector comprising one or more polynucleotides encoding a first fusion polypeptide and a second fusion polypeptide comprising SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively; and b) a second viral vector comprising one or more polynucleotides encoding a first fusion polypeptide and a second fusion polypeptide comprising SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively.

In some embodiments, the kit comprises first, second, third and fourth viral vectors comprising one or more polynucleotides encoding the following first fusion polypeptide and second fusion polypeptide, optionally joined or connected by one or more linkers:

a) a first viral vector comprising one or more polynucleotides encoding a first fusion polypeptide and a second fusion polypeptide comprising SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively;

b) a second viral vector comprising one or more polynucleotides encoding a first fusion polypeptide and a second fusion polypeptide comprising SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively;

c) a third viral vector comprising one or more polynucleotides encoding a first fusion polypeptide and a second fusion polypeptide comprising SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 88, respectively; and d) a fourth viral vector comprising one or more polynucleotides encoding a first fusion polypeptide and a second fusion polypeptide comprising SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively.

In some embodiments, the kit comprises first, second, third and fourth viral vectors comprising one or more polynucleotides encoding the following first fusion polypeptide and second fusion polypeptide, optionally joined or connected by one or more linkers:

a) a first viral vector comprising one or more polynucleotides encoding a first fusion polypeptide and a second fusion polypeptide comprising SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively;

b) a second viral vector comprising one or more polynucleotides encoding a first fusion polypeptide and a second fusion polypeptide comprising SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively;

c) a third viral vector comprising one or more polynucleotides encoding a first fusion polypeptide and a second fusion polypeptide comprising SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; and d) a fourth viral vector comprising one or more polynucleotides encoding a first fusion polypeptide and a second fusion polypeptide comprising SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively.

In some embodiments, the kit comprises first, second, third and fourth viral vectors comprising one or more polynucleotides encoding the following first fusion polypeptide and second fusion polypeptide, optionally joined or connected by one or more linkers:

a) a first viral vector comprising one or more polynucleotides encoding a first fusion polypeptide and a second fusion polypeptide comprising SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively;

b) a second viral vector comprising one or more polynucleotides encoding a first fusion polypeptide and a second fusion polypeptide comprising SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively;

c) a third viral vector comprising one or more polynucleotides encoding a first fusion polypeptide and a second fusion polypeptide comprising SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively; and d) a fourth viral vector comprising one or more polynucleotides encoding a first fusion polypeptide and a second fusion polypeptide comprising SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively.

In some embodiments, the kit comprises first and second viral vectors comprising one or more polynucleotides encoding the following first fusion polypeptide and second fusion polypeptide, optionally joined or connected by one or more linkers:

a) a first viral vector comprising one or more polynucleotides encoding a first fusion polypeptide and a second fusion polypeptide comprising SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively, and b) a second viral vector comprising one or more polynucleotides encoding a first fusion polypeptide and a second fusion polypeptide comprising SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively.

In some embodiments, the kit comprises first and second viral vectors comprising one or more polynucleotides encoding the following first fusion polypeptide and second fusion polypeptide, optionally joined or connected by one or more linkers:

a) a first viral vector comprising one or more polynucleotides encoding the following first fusion polypeptide and second fusion polypeptide comprising SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively, and b) a second viral vector comprising one or more polynucleotides encoding the following first fusion polypeptide and second fusion polypeptide comprising SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively.

In some embodiments, the kit comprises first and second viral vectors comprising one or more polynucleotides encoding the following first fusion polypeptide and second fusion polypeptide, optionally joined or connected by one or more linkers:

a) a first viral vector comprising one or more polynucleotides encoding the following first fusion polypeptide and second fusion polypeptide comprising SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively, and b) a second viral vector comprising one or more polynucleotides encoding the following first fusion polypeptide and second fusion polypeptide comprising SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively.

In some embodiments, the kit comprises first and second viral vectors comprising one or more polynucleotides encoding the following first fusion polypeptide and second fusion polypeptide, optionally joined or connected by one or more linkers:

a) a first viral vector comprising one or more polynucleotides encoding the following first fusion polypeptide and second fusion polypeptide comprising SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively, and b) a second viral vector comprising one or more polynucleotides encoding the following first fusion polypeptide and second fusion polypeptide comprising SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively.

In some embodiments, the kit comprises first and second viral vectors comprising one or more polynucleotides encoding the following first fusion polypeptide and second fusion polypeptide, optionally joined or connected by one or more linkers:

a) a first viral vector comprising one or more polynucleotides encoding a first fusion polypeptide and a second fusion polypeptide comprising SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively, and b) a second viral vector comprising one or more polynucleotides encoding a first fusion polypeptide and a second fusion polypeptide comprising SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively.

In some embodiments, the kit comprises first and second viral vectors comprising one or more polynucleotides encoding the following first fusion polypeptide and second fusion polypeptide, optionally joined or connected by one or more linkers:

a) a first viral vector comprising one or more polynucleotides encoding a first fusion polypeptide and a second fusion polypeptide comprising SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively, and b) a second viral vector comprising one or more polynucleotides encoding a first fusion polypeptide and a second fusion polypeptide comprising SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively.

In some embodiments, the kit comprises first and second viral vectors comprising polynucleotides encoding the following first compound fusion polypeptide and second compound fusion polypeptide:

a) a first viral vector comprising a polynucleotide encoding a first compound fusion polypeptide comprising SEQ ID NO: 105, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 105, and b) a second viral vector comprising a polynucleotide encoding a first compound fusion polypeptide comprising SEQ ID NO: 109, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 109.

In some embodiments, the kit comprises first and second viral vectors comprising polynucleotides encoding the following first compound fusion polypeptide and second compound fusion polypeptide:

a) a first viral vector comprising a polynucleotide encoding a first compound fusion polypeptide comprising SEQ ID NO: 107, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 107, and b) a second viral vector comprising a polynucleotide encoding a first compound fusion polypeptide comprising SEQ ID NO: 111, or a compound fusion polypeptide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 111.

In some embodiments, the kit comprises the following first fusion polypeptide and second fusion polypeptide, or one or more vectors comprising one or more polynucleotides encoding the following first fusion polypeptide and second fusion polypeptide, in sequential order, from N-terminus to C-terminus, optionally joined or connected by one or more linkers:

SEQ ID NOs: 70 and 71, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 70 and 71, respectively;

SEQ ID NOs: 71 and 70, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 71 and 70, respectively;

SEQ ID NOs: 72 and 73, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 72 and 73, respectively;

SEQ ID NOs: 73 and 72, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 73 and 72, respectively;

SEQ ID NOs: 74 and 75, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 74 and 75, respectively;

SEQ ID NOs: 75 and 74, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 75 and 74, respectively;

SEQ ID NOs: 76 and 77, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 76 and 77, respectively;

SEQ ID NOs: 77 and 76, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 77 and 76, respectively;

SEQ ID NOs: 78 and 79, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 78 and 79, respectively;

SEQ ID NOs: 79 and 78, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 79 and 78, respectively;

SEQ ID NOs: 80 and 81, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 80 and 81, respectively;

SEQ ID NOs: 81 and 80, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 81 and 80, respectively;

SEQ ID NOs: 82 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 83, respectively;

SEQ ID NOs: 83 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 82, respectively;

SEQ ID NOs: 84 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84 and 85, respectively;

SEQ ID NOs: 85 and 84, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 84, respectively;

SEQ ID NOs: 86 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 87, respectively;

SEQ ID NOs: 87 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 86, respectively;

SEQ ID NOs: 88 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 89, respectively;

SEQ ID NOs: 89 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 89 and 88, respectively;

SEQ ID NOs: 82 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 85, respectively;

SEQ ID NOs: 85 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 82, respectively;

SEQ ID NOs: 82 and 86, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 86, respectively;

SEQ ID NOs: 86 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 86 and 82, respectively;

SEQ ID NOs: 82 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 82 and 88, respectively;

SEQ ID NOs: 88 and 82, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 82, respectively;

SEQ ID NOs: 83 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 83 and 87, respectively;

SEQ ID NOs: 87 and 83, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 83, respectively;

SEQ ID NOs: 85 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 87, respectively;

SEQ ID NOs: 87 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 85, respectively;

SEQ ID NOs: 88 and 87, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 87, respectively;

SEQ ID NOs: 87 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 87 and 88, respectively;

SEQ ID NOs: 84 and 88, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 84, respectively;

SEQ ID NOs: 88 and 84, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 88 and 84, respectively;

SEQ ID NOs: 85 and 89, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 89, respectively;

SEQ ID NOs: 89 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 89 and 85, respectively;

SEQ ID NOs: 85 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 85 and 101, respectively;

SEQ ID NOs: 101 and 85, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 85, respectively;

SEQ ID NOs: 90 and 91, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 90 and 91, respectively;

SEQ ID NOs: 91 and 90, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 91 and 90, respectively;

SEQ ID NOs: 92 and 93, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 92 and 93, respectively;

SEQ ID NOs: 93 and 92, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 93 and 92, respectively;

SEQ ID NOs: 94 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 95, respectively;

SEQ ID NOs: 95 and 94, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 94, respectively;

SEQ ID NOs: 96 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 97, respectively;

SEQ ID NOs: 97 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 97 and 96, respectively;

SEQ ID NOs: 94 and 96, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 94 and 96, respectively;

SEQ ID NOs: 96 and 94, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 96 and 94, respectively;

SEQ ID NOs: 95 and 97, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 95 and 97, respectively;

SEQ ID NOs: 97 and 95, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 97 and 95, respectively;

SEQ ID NOs: 220 and 221, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 220 and 221, respectively;

SEQ ID NOs: 221 and 220, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 221 and 220, respectively;

SEQ ID NOs: 98 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 100, respectively;

SEQ ID NOs: 100 and 98, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 98, respectively;

SEQ ID NOs: 99 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 101, respectively;

SEQ ID NOs: 101 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 99, respectively;

SEQ ID NOs: 98 and 99, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 98 and 99, respectively;

SEQ ID NOs: 99 and 98, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 99 and 98, respectively;

SEQ ID NOs: 100 and 101, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 100 and 101, respectively; or SEQ ID NOs: 101 and 100, or fusion polypeptides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 101 and 100, respectively.

In some embodiments, the kit comprises a polynucleotide comprising or consisting of a nucleic acid sequence of any one of SEQ ID NOs: 130-167, 210-219 and 225-226, or a nucleic acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 130-167, 210-219 and 225-226. In some embodiments, the kit comprises a polynucleotide comprising or consisting of a nucleic acid sequence of any one of SEQ ID NOs: 139, 140, 142, 143, 145, 146, 148, 149, 150, 152, 155, 158, 225 and 226, or a nucleic acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139, 140, 142, 143, 145, 146, 148, 149, 150, 152, 155, 158, 225 and 226.

In some embodiments, the kit comprises the following first polynucleotide and second polynucleotide, or one or more vectors comprising the following first polynucleotide and second polynucleotide:

SEQ ID NOs: 130 and 132, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 130 and 132, respectively;

SEQ ID NOs: 130 and 134, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 130 and 134, respectively;

SEQ ID NOs: 131 and 133, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 131 and 133, respectively;

SEQ ID NOs: 131 and 135, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 131 and 135, respectively;

SEQ ID NOs: 132 and 136, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 132 and 136, respectively;

SEQ ID NOs: 133 and 135, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 133 and 135, respectively;

SEQ ID NOs: 133 and 137, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 133 and 137, respectively;

SEQ ID NOs: 134 and 136, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 134 and 136, respectively;

SEQ ID NOs: 135 and 137, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 135 and 137, respectively;

SEQ ID NOs: 138 and 141, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 138 and 141, respectively;

SEQ ID NOs: 138 and 144, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 138 and 144, respectively;

SEQ ID NOs: 139 and 142, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 142, respectively;

SEQ ID NOs: 139 and 145, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 145, respectively;

SEQ ID NOs: 140 and 146, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 140 and 146, respectively;

SEQ ID NOs: 142 and 148, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 142 and 148, respectively;

SEQ ID NOs: 143 and 149, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 143 and 149, respectively;

SEQ ID NOs: 145 and 148, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 145 and 148, respectively;

SEQ ID NOs: 150 and 152, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively;

SEQ ID NOs: 150 and 155, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 155, respectively;

SEQ ID NOs: 151 and 153, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 151 and 153, respectively;

SEQ ID NOs: 151 and 156, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 151 and 156, respectively;

SEQ ID NOs: 152 and 158, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 152 and 158, respectively;

SEQ ID NOs: 153 and 159, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 153 and 159, respectively;

SEQ ID NOs: 154 and 157, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 154 and 157, respectively;

SEQ ID NOs: 155 and 158, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 155 and 158, respectively;

SEQ ID NOs: 156 and 159, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 156 and 159, respectively;

SEQ ID NOs: 160 and 161, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 160 and 161, respectively;

SEQ ID NOs: 162 and 163, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 162 and 163, respectively;

SEQ ID NOs: 164 and 165, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 164 and 165, respectively;

SEQ ID NOs: 166 and 167, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 166 and 167, respectively;

SEQ ID NOs: 210 and 211, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 210 and 211, respectively;

SEQ ID NOs: 212 and 213, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 212 and 213, respectively;

SEQ ID NOs: 214 and 215, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 214 and 215, respectively;

SEQ ID NOs: 216 and 217, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 216 and 217, respectively;

SEQ ID NOs: 218 and 219, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 218 and 219, respectively;

SEQ ID NOs: 218 and 226, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 218 and 226, respectively; or SEQ ID NOs: 225 and 226, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 225 and 226, respectively.

In some embodiments, the kit comprises first and second viral vectors comprising the following first polynucleotide and second polynucleotide:

a) a first vector comprising first and second polynucleotides comprising SEQ ID NOs: 131 and 135, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 131 and 135, respectively, and b) a second vector comprising first and second polynucleotides comprising SEQ ID NOs: 133 and 137, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 133 and 137, respectively. In some embodiments, the first and second viral vectors are adenoviral vectors.

In some embodiments, the kit comprises first and second viral vectors comprising the following first polynucleotide and second polynucleotide:

a) a first vector comprising first and second polynucleotides comprising SEQ ID NOs: 139 and 145, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 145, respectively, and b) a second vector comprising first and second polynucleotides comprising SEQ ID NOs: 142 and 148, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 142 and 148, respectively. In some embodiments, the first and second viral vectors are adenoviral vectors.

In some embodiments, the kit comprises first and second viral vectors comprising the following first polynucleotide and second polynucleotide:

a) a first vector comprising first and second polynucleotides comprising SEQ ID NOs: 140 and 146, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 140 and 146, respectively, and b) a second vector comprising first and second polynucleotides comprising SEQ ID NOs: 143 and 149, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 143 and 149, respectively. In some embodiments, the first and second viral vectors are Lymphocytic choriomeningitis mammarenavirus (LCMV) viral vectors.

In some embodiments, the kit comprises first and second viral vectors comprising the following first polynucleotide and second polynucleotide:

a) a first vector comprising first and second polynucleotides comprising SEQ ID NOs: 150 and 152, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively, and b) a second vector comprising first and second polynucleotides comprising SEQ ID NOs: 154 and 157 or SEQ ID NOs: 155 and 158, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 154 and 157 or SEQ ID NOs: 155 and 158, respectively. In some embodiments, the first and second viral vectors are Cali mammarenavirus (a.k.a. Pichinde mammarenavirus or Pichinde arenavirus) viral vectors.

In some embodiments, the kit comprises first, second, third and fourth viral vectors, each vector comprising first and second polynucleotides:

a) a first viral vector comprising first and second polynucleotides comprising SEQ ID NOs: 140 and 146, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 140 and 146, respectively;

b) a second viral vector comprising first and second polynucleotides comprising SEQ ID NOs: 143 and 149, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 143 and 149, respectively;

c) a third viral vector comprising first and second polynucleotides comprising SEQ ID NOs: 150 and 152, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively; and d) a fourth viral vector comprising first and second polynucleotides comprising SEQ ID NOs: 154 and 157 or SEQ ID NOs: 155 and 158, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 154 and 157 or SEQ ID NOs: 155 and 158, respectively.

In some embodiments, the kit comprises first, second, third and fourth viral vectors, each vector comprising first and second polynucleotides:

a) a first viral vector comprising first and second polynucleotides comprising SEQ ID NOs: 150 and 152, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 150 and 152, respectively;

b) a second viral vector comprising first and second polynucleotides comprising SEQ ID NOs: 155 and 158, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 155 and 158, respectively;

c) a third viral vector comprising first and second polynucleotides comprising SEQ ID NOs: 151 and 153, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 151 and 153, respectively; and d) a fourth viral vector comprising first and second polynucleotides comprising SEQ ID NOs: 156 and 159, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 156 and 159, respectively. In some embodiments, one or more of the first, second, third and fourth viral vectors are adenoviral vectors.

In some embodiments, the kit comprises first, second, third and fourth viral vectors, each vector comprising first and second polynucleotides:

a) a first viral vector comprising first and second polynucleotides comprising SEQ ID NOs: 131 and 135, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 131 and 135, respectively;

b) a second viral vector comprising first and second polynucleotides comprising SEQ ID NOs: 133 and 137, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 133 and 137, respectively;

c) a third viral vector comprising first and second polynucleotides comprising SEQ ID NOs: 139 and 145, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 139 and 145, respectively; and d) a fourth viral vector comprising first and second polynucleotides comprising SEQ ID NOs: 142 and 148, or that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 142 and 148, respectively.

In some embodiments, the kit comprises first and second viral vectors comprising the following first polynucleotide and second polynucleotide:

a) a first vector comprising first and second polynucleotides comprising SEQ ID NOs: 160 and 161, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 160 and 161, respectively, and b) a second vector comprising first and second polynucleotides comprising SEQ ID NOs: 162 and 163, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 162 and 163, respectively.

In some embodiments, the kit comprises first and second viral vectors comprising the following first polynucleotide and second polynucleotide:

a) a first vector comprising first and second polynucleotides comprising SEQ ID NOs: 164 and 165, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 164 and 165, respectively, and b) a second vector comprising first and second polynucleotides comprising SEQ ID NOs: 166 and 167, or polynucleotides that are at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 166 and 167, respectively.

In some embodiments, the kit comprises first and second viral vectors comprising the following first polynucleotide and second polynucleotide:

a) a first vector comprising a first polynucleotides comprising SEQ ID NO: 210, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 210, and b) a second vector comprising a second polynucleotide comprising SEQ ID NO: 211, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 211.

In some embodiments, the kit comprises first and second viral vectors comprising the following first polynucleotide and second polynucleotide:

a) a first vector comprising a first polynucleotides comprising SEQ ID NO: 212, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 212, and b) a second vector comprising a second polynucleotide comprising SEQ ID NO: 213, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 213.

In some embodiments, the kit comprises first and second viral vectors comprising the following first polynucleotide and second polynucleotide:

a) a first vector comprising a first polynucleotides comprising SEQ ID NO: 214, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 214, and b) a second vector comprising a second polynucleotide comprising SEQ ID NO: 215, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 215.

In some embodiments, the kit comprises first and second viral vectors comprising the following first polynucleotide and second polynucleotide:

a) a first vector comprising a first polynucleotides comprising SEQ ID NO: 216, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 216, and b) a second vector comprising a second polynucleotide comprising SEQ ID NO: 217, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 217.

In some embodiments, the kit comprises first and second viral vectors comprising the following first polynucleotide and second polynucleotide:

a) a first vector comprising a first polynucleotides comprising SEQ ID NO: 218, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 218, and b) a second vector comprising a second polynucleotide comprising SEQ ID NO: 219, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 219.

In some embodiments, the kit comprises first and second viral vectors comprising the following first polynucleotide and second polynucleotide:

a) a first vector comprising a first polynucleotides comprising SEQ ID NO: 218, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 218, and b) a second vector comprising a second polynucleotide comprising SEQ ID NO: 226, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 226.

In some embodiments, the kit comprises first and second viral vectors comprising the following first polynucleotide and second polynucleotide:

a) a first vector comprising a first polynucleotides comprising SEQ ID NO: 225, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 225, and b) a second vector comprising a second polynucleotide comprising SEQ ID NO: 226, or a polynucleotide that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 226.

In some embodiments, the kit comprises a compound fusion polypeptide or a vector comprising a polynucleotide encoding a compound fusion polypeptide, the compound fusion polypeptide comprising or consisting of an amino acid sequence of any one of SEQ ID NOs: 105-112, 200-209, 222-223 and 227, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 105-112, 200-209, 222-223 and 227. In some embodiments, the kit comprises a compound fusion polypeptide or a vector comprising a polynucleotide encoding a compound fusion polypeptide, the compound fusion polypeptide comprising or consisting of an amino acid sequence of any one of SEQ ID NOs: 209, 222 and 223, or an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 209, 222 and 223.

In various embodiments of the kits, the one or more fusion polypeptides do not comprise any polypeptide segments corresponding to Gag 54-146; Gag 370-500; Pol 1-55; Pol 118-128; Pol 321-366; Pol 432-541; Pol 607-682; Pol 709-746; Pol 828-839; Pol 921-931; Nef 1-63; Nef 100-116 and Nef 149-206, or fragments or subsequences thereof, wherein the Gag, Pol and Nef amino acid position numbers correspond to SEQ ID NOs: 1, 2 and 3, respectively. In various embodiments of the kits, the one or more fusion polypeptides do not comprise any polypeptide segments having an amino acid sequence of SEQ ID NOs: 35-47, or fragments or subsequences thereof, or an amino acid sequence at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 35-47, or fragments or subsequences thereof.

In some embodiments, the kits further comprise one or more unitary doses of one or more additional therapeutic agents. For example, in some embodiments, the kit comprises one or more agonists or activators of one or more toll-like receptors (TLRs). In some embodiments, the TLR agonist or activator is selected from a TLR2 agonist, a TLR3 agonist, a TLR4 agonist, a TLR5 agonist, a TLR7 agonist, a TLR8 agonist and a TLR9 agonist. In some embodiments, the TLR7 agonist is selected from GS 9620 (vesatolimod), R848 (Resiquimod), DS-0509, LHC-165 and TMX-101 (imiquimod), and/or wherein the TLR8 agonist is selected from GS-9688 (Selgantolimod), R848 (Resiquimod) and NKTR-262 (dual TLR7/TLR8 agonist).

In some embodiments, the kit comprises one or more antagonists or inhibitors of an inhibitory immune checkpoint protein or receptor and/or one or more activators or agonists of a stimulatory immune checkpoint protein or receptor. In some embodiments, the one or more immune checkpoint proteins or receptors are selected from: CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript IE (RAETIE; ULBP4); retinoic acid early transcript 1G (RAETIG; ULBP5); retinoic acid early transcript 1L (RAET1L; ULBP6); lymphocyte activating 3 (CD223); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); and SLAM family member 7 (SLAMF7). In some embodiments, the kit comprises one or more blockers or inhibitors of one or more T-cell inhibitory immune checkpoint proteins or receptors. In some embodiments, the T-cell inhibitory immune checkpoint proteins or receptors are selected from CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). Lirilumab is an illustrative antibody that binds to and blocks KIR2DL1/2L3 receptors. In some embodiments, the kit comprises one or more agonists or activators of one or more T-cell stimulatory immune checkpoint proteins or receptors. In some embodiments, the T-cell stimulatory immune checkpoint proteins or receptors are selected from CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); Poliovirus receptor (PVR) cell adhesion molecule (PVR, CD155). In some embodiments, the kit comprises one or more blockers or inhibitors of one or more NK-cell inhibitory immune checkpoint proteins or receptors. In some embodiments, the NK-cell inhibitory immune checkpoint proteins or receptors are selected from killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A), e.g., monalizumab (IPH2201); and killer cell lectin like receptor D1 (KLRD1, CD94). In some embodiments, the kit comprises one or more agonists or activators of one or more NK-cell stimulatory immune checkpoint proteins or receptors. In some embodiments, the NK-cell stimulatory immune checkpoint proteins or receptors are selected from CD16, CD226 (DNAM-1); killer cell lectin like receptor K1 (KLRK1, NKG2D, CD314); and SLAM family member 7 (SLAMF7). In some embodiments, the one or more immune checkpoint inhibitors comprises a proteinaceous inhibitor of PD-L1 (CD274), PD-1 (PDCD1) or CTLA4. In some embodiments, the proteinaceous or antibody inhibitor of CTLA4 is selected from ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4) and AK-104 (CTLA4/PD-1). In various embodiments, the co-administration of a proteinaceous or antibody inhibitor of CTLA4 increases the vaccine-induced T cell response in comparison to administration of the one or more fusion polypeptides, or polynucleotides encoding, lipoplexes (e.g., LNPs) comprising such polynucleotides, or vectors expressing such fusion polypeptides in the absence of a proteinaceous or antibody inhibitor of CTLA4. In some embodiments, the proteinaceous inhibitor of PD-L1 (CD274) or PD-1 (PDCD1) is selected from pembrolizumab, nivolumab, cemiplimab, pidilizumab, AMP-224, MEDI0680 (AMP-514), spartalizumab, atezolizumab, avelumab, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/Tim-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), and INBRX-105 (4-1BB/PDL1). In some embodiments, the one or more immune checkpoint inhibitors comprises a small molecule inhibitor of CD274 (PDL1, PD-L1), programmed cell death 1 (PDCD1, PD1, PD-1) or CTLA4. In some embodiments, the small molecule inhibitor of CD274 or PDCD1 is selected from GS-4224, GS-4416, INCB086550 and MAX10181. In some embodiments, the small molecule inhibitor of CTLA4 comprises BPI-002.

In some embodiments, the kit comprises one or more antiviral agents. In some embodiments, the one or more antiviral agents are selected from HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, and capsid inhibitors.

Optionally associated with such container(s) can be a notice in the form prescribed by a governmental agency regulating the manufacture, use or sale of pharmaceuticals or biological products, which notice reflects approval by the agency of manufacture, use or sale for human administration.

9. Methods of Designing Fusion Polypeptides Useful to Promote Antiviral Immune Responses Provided are methods for designing a vaccine construct or an immunogen that is capable of eliciting an immune response in a human against one or more viral antigens. The immunogenic fusion polypeptides are designed employing a combination of computational, experiential and manual steps, and can be used to elicit an immune response against a highly variable virus. The design methods can be applied to creating an immunogen capable of inducing an immune response in a human against one or more viral antigens of a desired target virus, including without limitation human immunodeficiency virus (HIV), hepatitis B virus (HBV), human papillomavirus (HPV), herpes simplex virus (HSV), Ebola virus, Zika virus and Chikungunya virus. Generally, the immunogen design methods provide a vaccine construct designed for maximum epitope coverage of a broad-based population, referred to herein as a "population" construct or antigen. Usually, the segments comprising each of the constructs represent one or more MHC class I and/or MHC class II T cell epitopes. The population-based polypeptide segments can be combined and assembled into immunogenic fusion polypeptides.

Most of the steps can be performed in silico, but some steps can be performed manually (e.g., inclusion and/or exclusion selections of certain polypeptide sequences; selection of linker or linkers) and may incorporate information based on experimental data (e.g., experimentally determined MHC class II epitopes). The input information is a viral sequence data set (e.g., for HIV, internal and publicly available HIV population data sets). As summarized in the flow chart of FIG. 1, the vaccine design methods involve at least 2, e.g., at least 3 of the steps of:

1. Identify conserved regions. All 9 amino acid segments (9-mers) are considered in naturally occurring viral sequences as potential T-cell epitopes. 9-mer positions having a conservation of at least 80% across interpatient viral populations, are identified as conserved regions and included for further analysis.
2. Build bivalent sequences from conserved regions. This can be done by employing a graph-based algorithm. 9-mers are assembled from conserved regions to include the maximum number of naturally occurring 9-mers.
3. Arrange polypeptide segments to reduce or avoid the creation of human-recognizable neoepitopes and cross-reactivities with human proteins at junctions. This can be done by evaluating 9-mers around junctions for MHC class I binding, cross-recognition with host (e.g., human, dog, cat, horse) proteins, and checking whether there are identical or substantially identical 9-mers between multiple antigen sequences if multiple insert sequences are developed simultaneously. As used herein, "substantially identical" 9-mers have at least 5 of 9 identical amino acid residues, e.g., have at least 55% (5 of 9), e.g., at least 65% (6 of 9), e.g., at least 75% (7 of 9), e.g., at least 85% (8 of 9) identical amino acid residues.

In one aspect, these methods comprise screening a set of candidate polypeptide segments of a population/conservation-based construct for MHC peptide binding affinity. MHC binding affinity can be predicted using one or more algorithms. Exemplary predictive algorithms include NetMHC (Vita et al. Nucleic Acids Res 2015 43:D405-D412), NetMHCpan (Andreatta and Nielsen Bioinformatics 2016 32:511-517), and MHCflurry (O'Donnell et al. Cell Syst 2018 7:12-132). Other T-cell epitope prediction tools are publicly available and are described, for example in Sanchez-Trincado et al. J. Immunology Res. 2017 Article ID 2680160. Additional methods for identifying MHC binding peptides include those employing machine learning tools, for example, as described in U.S. Pat. No. 10,055,540, WO 2019/104203 and the "EDGE" tool described in Bulik-Sullivan et al. Nature Biotechnology 2019 37:55.

In some implementations, the disclosure provides methods for producing a bivalent population/conservation-based construct designed both to capture the unique diversity of a viral proteome (e.g., HIV proteome) by providing mathematically determined and improved coverage of all potential T cell epitopes and to ensure that the epitopes in each polypeptide of the pair of constructed polypeptides retain the positional information of the original input viral sequences, e.g., by retaining the same order of the polypeptide segments as found in the naturally occurring viral proteome. The epitopes of the resulting pair of polypeptides will therefore more closely resemble those of the naturally occurring viral sequences, increasing the likelihood of their eliciting a relevant T cell response.

Generally, the methods described here comprise initially providing a set of mathematically determined and improved potential T cell epitopes ("PTE") in terms of their coverage of all PTEs in a population of viral proteome sequences, using a graph-based approach. Unlike similar graph-based approaches to vaccine design, the approach described here builds segments of connected PTE's using only adjacent PTE's that are also adjacent in the natural sequences. This provides constructs that retain the positional information of the PTE's within the source set of sequences. Also, unlike other graph-based approaches, the methods described here simultaneously build a bivalent construct to provide maximal coverage of the most highly conserved PTEs in the population. The result is an initial bivalent vaccine construct that advantageously maximizes highly conserved PTEs that are most likely to be highly similar to conserved epitopes in the natural sequences. Further advantageously, the use of only the most highly conserved PTEs reduces the likelihood of escape mutants because the highly conserved sequences are more likely to be essential for viral function.

The methods described herein generally begin with the identification of a conserved region bivalent sequences, using a process referred to herein as the "Conservation Analysis" or "Conservation Algorithm". The methods further generally comprise a step of building a bivalent vaccine construct having maximal epitope coverage while retaining the positional information of the PTE's from the natural sequences, using a process referred to referred to herein as a "Conserved Walking Algorithm" or "CWA". Thus, in some implementations, an initial step in the method is identifying a set of all conserved regions in a viral proteome for a selected set of viral genes. In implementations for designing a fusion polypeptide to elicit an immune response against HIV-1, the set of HIV-1 viral genes is selected from two or more of Gag, Pol and Nef. In some implementations, the set of viral genes consists of Gag, Pol and Nef. In some implementations, the set of viral genes consists of Pol and Nef.

In accordance with the methods described here, a population of viral proteome sequences is first aligned to a reference sequence, for example, the HIV reference sequence HXB2 identified by GenBank No. Accession K03455. Reference sequences for polypeptides encoded by the Gag, Nef and Pol genes are provided herein as SEQ ID NOs: 1-3, in Table A. The initial input or 'source' population of viral proteome sequences consists of sequences obtained from naturally occurring viruses. Such sequences are publicly available, for example, from the HIV Databases maintained by the Los Alamos National Laboratory, the U.S. Dept. of Health and Human Services, and the National Institutes of Health. In some implementations of the methods described herein, the source viral sequences may consist of sequences corresponding to a specific viral group and/or clade. In some implementations, in order to improve the identification of conserved regions and sequences, the input viral sequences may be restricted to a single viral clade and/or group. In some implementations, the input viral sequences are restricted to Group M clade B sequences.

The alignment of the source viral sequences to the reference sequence may be accomplished using a multiple alignment algorithm, for example, the fast Fourier transform algorithm, MAFFT. Katoh et al. 2002 Nucleic Acids Res. 30 (14):3059-66. The base MAFFT software is publicly available and distributed, e.g., under the Berkeley Software Distribution (BSD) license.

Next, the Conservation Algorithm is applied to the aligned sequences. For each sequence in the alignment, starting from the first amino acid position, the method shifts one amino acid position at a time and creates all possible amino acid segments that are 9 amino acids in length, referred to herein as "9-mers". The algorithm thus creates, for each sequence in the alignment, a set of 9-amino acid subsequences ("9-mers") starting with the N-terminal amino acid, each subsequence overlapping the preceding subsequence by eight amino acids such that each sequence of length 1 in the alignment contains (1-8) 9-mers.

Next, for each 9-mer position, the method identifies the two most common unique 9-mers and their prevalence in the aligned set of source viral proteome sequences. Stated another way, starting at position i the two most common unique 9-mers at each position are identified based on their frequency, calculated as the number of times the unique 9-mer occurs at position i in the alignment divided by the total number of sequences in the alignment.

Computationally, each sequence of length l, contains l-8 9-mers. We define all the 9-mers starting at position i as $s_{ij}$ and frequency as $f_{ij}$, j=1, 2, 3, . . . m. In total there are m unique 9-mers at position i. Each two unique 9-mers ($s_{iu}$, $s_{iv}$) can constitute a 9-mer pair and its frequency is $f_{iu}+f_{iv}$. And each 9-mer itself can constitute a 9-mer pair as ($s_{iu}$, $s_{iv}$) and its frequency is $f_{iu}$. Thus, in total, there are m+(m−1)+(m−2)+ . . . +2+1=m*(m+1)/2 9-mer pairs at each position.

The method then calculates the bivalent conservation for each 9-mer position by summing up the proportions of aligned set of source viral proteome sequences containing either of the two most common 9-mers. To do this, a "bivalent conservation" is calculated for each position by summing the proportion of sequences in the alignment containing either of the two most common unique 9-mers. As used herein, "bivalent conservation" refers to the percentage of sequences containing exactly the same 9 amino acid segments (9-mers) as either of the two most prevalent ones in a 9-mer position.

Next, a new alignment of conserved regions is created by extracting the sequences in the alignment having a desired bivalent conservation, for example, a bivalent conservation of greater than 80% or greater than 90%, meaning that the two most common 9-mers at position i account for more than 80% or more than 90% of the 9-mers at that position in the new alignment of conserved regions. Stated another way, the method identifies the conserved regions in the new alignment as those in which the sum of the frequencies of the two most common 9-mers at each position is greater than a certain cutoff, e.g., greater than 80% or greater than 90%. Thus, the method also calculates the frequency of each pair of unique 9-mers at each position in the new alignment of conserved regions.

In some implementations, further selection criteria may be applied to the conserved regions, such as restricting to regions having greater than 90% conservation and removing short segments of less than 35 amino acids.

Using this modified set of conserved regions, certain implementations of the method apply the CWA to build bivalent sequence constructs. The CWA connects 9-mer pairs in adjacent positions of the alignment of conserved regions that share an overlap of eight amino acids.

Computationally, each 9-mer s contains 9 amino acids, we write s[x:y] to represent the amino acid subsequence from position x to y, y−x+1 amino acids in total:

$s_{iu}[2:9]==s_{i+1p}[1:8]$ and $s_{iv}[2:9]==s_{i+1q}[1:8]$ or $s_{iu}[2:9]==s_{i+1p}[1:8]$ and $s_{iv}[2:9]==s_{i+1q}[1:8]$.

Next, the algorithm builds a directed acyclic graph in which each 9-mer pair is a node and the edges between adjacent nodes are formed from the connected 9-mer pairs in the adjacent positions with the weight of each edge equal to the frequency of the downstream 9-mer pair. This directed acyclic graph is a positional De Brujin graph. Such graphs have been described in connection with assemblies of next generation sequencing data, for example as described in Ronen et al., Bioinformatics 2012 28:188-196. The method further adds a source node, connecting it with all of the nodes in the first position; and a sink node, connecting it with all of the nodes in the last position. The weights are then negated and the optimal path is found from the source node to the sink node, where the optimal path is defined as the path that has the largest sum of the frequencies of all 9-mer pairs among all the paths from the source node to the sink node. The task of finding the optimal path is performed, for example, using the Bellman-Ford algorithm. Generally, the Bellman-Ford algorithm computes the shortest paths from a single source vertex to all of the other vertices in a weighted directed graph which is made up of a set of vertices connected by edges, where the edges have a direction associated with them. The computational steps can be summarized as follows:

(4-1) Treat each 9-mer pair as a node, and build edges between adjacent nodes in Step 3;

(4-2) Adding a source node and connect it with all the nodes at the 1st position;

(4-3) Adding a sink node and connect it with all the nodes at the last position;

(4-4) Weight of each edge equals to the frequency of downstream 9-mer pair;

(4-5) Negating all the weights and finding the optimal path using the Bellman-Ford algorithm.

A further step of the method is to build bivalent vaccine sequences based on the optimal bivalent 9-mer pair path and connect two 9-mers in adjacent positions within the optimal bivalent 9-mer pair path if they share an overlap of 8 amino acids. A bivalent construct is built by connecting two 9-mers in adjacent positions within the optimal bivalent 9-mer path if they share an overlap of eight amino acids, thereby creating two sequences of connected 9-mers which together form the bivalent construct. The connected adjacent 9-mer pairs all have an 8 amino acid overlap, so they will be assembled into two sequences. For example, one 9-mer pair (AIIIIIIIS (SEQ ID NO: 190), MIIIIIIII (SEQ ID NO: 191)) can be connected with another 9-mer pair (IIIIIIISK (SEQ ID NO: 192), IIIIIIIIR (SEQ ID NO: 184)) and make two sequences (bivalent sequences): AIIIIIIISK (SEQ ID NO: 193) and MIIIIIIIIR (SEQ ID NO: 194).

Computationally, the methodology can be described as a positional De Brujin graph based bivalent vaccine sequence design algorithm comprising the following 5 basic steps:

Step 1: align all the population sequences

Step 2: for each 9-mer position, pull out all the unique 9-mers and their frequencies, and build 9-mer pair sets with frequencies. Each sequence of length l, contains l-8 9-mers. We define all the 9-mers starting at position i as $s_{ij}$ and frequency as $f_{ij}$, j=1, 2, 3, . . . m. In total there are m unique 9-mers at position i. Each two unique 9-mers ($s_{iu}$, $s_{iv}$) can constitute a 9-mer pair and its frequency is $f_{iu}+f_{iv}$. And each 9-mer itself can constitute a 9-mer pair as ($s_{iu}$, $s_{iv}$) and its frequency is $f_{iu}$. Thus, in total, there are m+(m−1)+(m−2)+ . . . +2+1=m*(m+1)/2 9-mer pairs at each position.

Step 3: connect 9-mer pairs in adjacent positions if they do not have any conflicting amino acids. As used herein, "conflicting amino acid residues" refers to different amino acid residues at overlapped positions between two 9-mers. Each 9-mer s contains 9 amino acids, we write s[x:y] to represent the amino acid subsequence from position x to y, y−x+1 amino acids in total:

$s_{iu}[2:9]==s_{i+1p}[1:8]$ and $s_{iv}[2:9]==s_{i+1q}[1:8]$ or $s_{iu}[2:9]==s_{i+1p}[1:8]$ and $s_{iv}[2:9]==s_{i+1q}[1:8]$.

Step 4: find the optimal path from the 1st 9-mer position to the last position in terms of the sum of the frequencies of all the 9-mers within the path. The basic idea is to model the maximum coverage bivalent vaccine construction problem as a classic graph theory problem where the solution is finding the minimum path in a directed acyclic graph.

Step 5: build bivalent vaccine sequences based on the optimal bivalent 9-mer pair path and connect two 9-mers in adjacent positions within the optimal bivalent 9-mer pair path if they share an overlap of 8 amino acids. Take for example the following cases:

Case 1: if $s_{iu}[2:9]=s_{i+1p}[1:8]$ and $s_{iv}[2:9]=s_{i+1q}[1:8]$, connect $s_{iu}$ with $s_{i+1p}$ and $s_{iv}$ with $s_{i+1q}$;

Case 2: if $s_{iu}[2:9]=s_{i+1q}[1:8]$ and $s_{iv}[2:9]=s_{i+1p}[1:8]$, connect $s_{iv}$ with $s_{i+1q}$ and $s_{iv}$ with $s_{i+1p}$;

Case 3: if $s_{iu}[2:9]=s_{i+1p}[1:8]$ and $s_{iv}[2:9]=s_{i+1q}[1:8]$ and $s_{iu}[2:9]=s_{i+1q}[1:8]$ and $s_{iv}[2:9]=s_{i+1p}[1:8]$, the selection of connection is based on the prevalence of the two connections in natural sequences:

Denote the prevalence of the co-existence of $s_{ix}$ and $s_{i+1y}$ in input sequences as $C_{ixy}$ If $C_{iup}+C_{ivq}>C_{iuq}+C_{ivp}$, connect $s_{iu}$ with $s_{i+1p}$ and $s_{iv}$ with $s_{i+1q}$;

If $C_{iuq}+C_{ivp}>C_{iup}+C_{ivq}$, connect $s_{iu}$ with $s_{i+1q}$ and $s_{iv}$ with $s_{i+1p}$;

If $C_{iup}+C_{ivq}=C_{iuq}+C_{ivp}$, backtrack and combine the prevalence of the co-existence of 9-mer pairs in positions i−1 and i until the $1^{st}$ position. If there is no difference between two different connections, randomly pick one.

In some implementations, the construct is further improved by performing a human proteome cross-recognition analysis, for example by a method comprising searching all of the 9-mers in the construct against a human proteome database such as UniProt to identify any 9-mers having a certain amino acid sequence identity with human peptides, e.g., at least 5 residues, or that share T cell receptor (TCR) facing residues with human proteins. Any such 9-mers may then be excluded from the construct. In some implementations, the polypeptide segments may optionally be rearranged to reduce or avoid deleterious junctional responses, for example by performing an HLA binding analysis, a human proteome cross-recognition analysis, or both, with respect to the junctional segments. Illustrative methods for reducing junction epitope presentation for neoantigens, in the context of designing anticancer vaccines, are described in WO 2019/104203. Alternatively, if multiple antigen sequences are developed, the polypeptide segments can be rearranged to avoid near-identical or identical 9-mers at junction between antigen sequences.

In some implementations, the conserved regions are further defined by performing one or more of the following steps in silico: (i) removing short polypeptide segments, e.g., polypeptide segments of 35 or fewer amino acids in length, e.g., 9-35 amino acids in length; (ii) removing segments that are weakly immunogenic or non-immunogenic in humans; (iii) removing segments that are less than 90% conserved, in certain instances, less than 80% conserved, amongst a predetermined population of sequences; (iv) including additional segments from HIV-1 proteins, e.g., Env, Gag, Nef and Pol, that are known to be immunogenic in humans (see, e.g., epitope maps at hiv.lanl.gov/content/immunology/maps/maps.html; Fischer, et al., *Nat Med.* (2007) 13(1):100-6; and Addo, et al., *J Virol*, (2003) 77(3):2081-92).

In some implementations, adjacent polypeptide segments may optionally be separated with a linker sequence, as described above. In some implementations, the linker sequence or sequences comprise a cleavable linker, optionally further comprising an additional linker sequence located adjacent to the cleavable linker. The additional linker may be another cleavable linker, a polyalanine linker, a polyglycine linker, a flexible linker, or a rigid linker, as described above and herein. In some embodiments, a furin recognition site precedes or is positioned N-terminal to a 2A cleavable linker. In a specific implementation, where the linker sequence comprises a foot-and-mouth disease virus (FMDV) cleavable peptide, FMDV 2A, or derivative thereof, the additional linker sequence may be a REKR (SEQ ID NO: 61) sequence, or derivative thereof. In some implementations, the linker is selected from a short polyalanine peptide, for example a peptide consisting of from 2 to 4 alanine residues, or having the sequence AAY (SEQ ID NO: 49) or AAX, where X is any amino acid residue (SEQ ID NO: 50).

In some implementations, the linker is inserted between each adjacent conserved region of the bivalent polypeptide. In some implementations, e.g., when no deleterious junctional epitope is created, no linker is inserted between adjacent segments of the same protein in the polypeptide. A linker can be inserted between adjacent segments of different proteins.

EXAMPLES

The following examples are offered to illustrate, but not to limit the claimed invention.

Example 1

Illustrated Implementation of the Conservation Analysis and Conserved Walking Analysis (CWA) to Generate a Bivalent Vaccine Construct This Example describes the design of population-based bivalent polypeptide constructs by a specific implementation of the Conservation Analysis and CWA to generate a bivalent vaccine construct based on conserved protein regions encoded by the HIV-1 Gag, Nef and/or Pol genes.

First, we identified a set of all conserved regions in a viral proteome for a selected set of viral genes. In this example, the set of viral genes consisted of HIV-1 Gag, Pol, and Nef.

Figure 3:
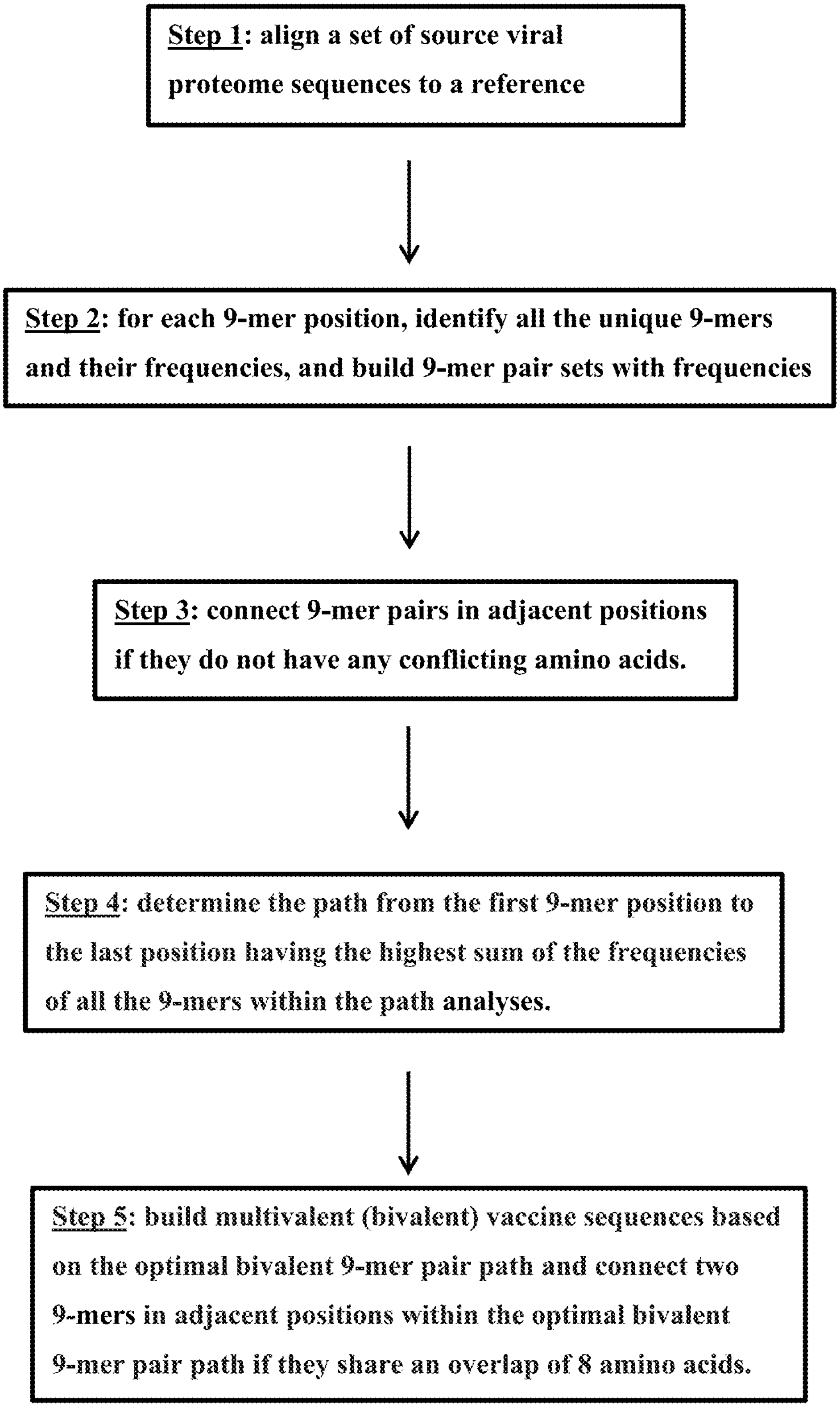
FIG. 3 illustrates the steps of the conserved walking analysis (CWA) algorithm, as described herein.

Computationally, the combination of the Conservation Algorithm and the CWA is a positional De Brujin graph based bivalent vaccine sequence design algorithm comprising the following 5 basic steps, illustrated in FIG. 3:

Step 1: Align a Set of Source Viral Proteome Sequences to a Reference Sequence.

In Step 1, a source population of viral proteome sequences was aligned to a reference sequence. In this example, the reference sequence used was the HIV-1 HXB2, identified by GenBank No. Accession K03455. The amino acid sequences of HXB2 reference polypeptides Gag, Nef and Pol are provided herein as SEQ ID NOs: 1, 2 and 3, respectively, in Table A. The source population of viral proteome sequences consists of sequences obtained from naturally occurring viruses. Such sequences are publicly available, for example, from the HIV Databases maintained by the Los Alamos National Laboratory, the U.S. Dept. of Health and Human Services, and the National Institutes of Health (hiv.lanl.gov), which was the database used for the source population of sequences in this example. For the purposes of illustration, we focused our analysis on a subset of the viral sequences, here, sequences of Group M Clade B. The alignment was performed using a multiple alignment algorithm, specifically a fast Fourier transform algorithm, MAFFT. Katoh, et al. (2002) *Nucleic Acids Res.* 30 (14):3059-66. The base MAFFT software is publicly available and distributed, e.g., under the Berkeley Software Distribution (BSD) license.

Step 2: for each 9-mer position, pull out all the unique 9-mers and their frequencies, and build 9-mer pair sets with frequencies In Step 2, we applied the Conservation Algorithm to the set of aligned sequences. For each sequence in the alignment, starting from the first amino acid of the N-terminus, the algorithm shifts one amino acid position at a time to create a set of all possible amino acid segments that are 9 amino acids in length, referred to as "9-mers." The algorithm thus created, for each sequence in the alignment, a set of 9-amino acid subsequences ("9-mers") starting with the N-terminal amino acid, each subsequence overlapping the preceding subsequence by eight amino acids such that each sequence of length l in the alignment contains (l-8) 9-mers.

Next, for each 9-mer position, the method identified the two most common unique 9-mers and their prevalence in the aligned set of source viral proteome sequences. Stated another way, starting at position i the two most common unique 9-mers at each position were identified based on their frequency, calculated as the number of times the unique 9-mer occurred at position i in the alignment divided by the total number of sequences in the alignment.

Computationally, each sequence of length l, contained l-8 9-mers. We defined all the 9-mers starting at position i as s; and frequency as $f_{ij}$, j=1, 2, 3, . . . m. In total there were m unique 9-mers at position i. Each two unique 9-mers ($s_{iu}$, $s_{iv}$) can constitute a 9-mer pair and its frequency is $f_{iu}+f_{iv}$. And each 9-mer itself can constitute a 9-mer pair as ($s_{iu}$, $s_{iu}$) and its frequency is $f_{iu}$. Thus, in total, there were m*(m+1)/2 9-mer pairs at each position.

The method then calculated the bivalent conservation for each 9-mer position by summing up the proportions of aligned set of source viral proteome sequences containing either of the two most common 9-mers. To do this, a "bivalent conservation" was calculated for each position by summing the proportion of sequences in the alignment containing either of the two most common unique 9-mers.

Next, a new alignment of conserved regions was created by extracting the sequences in the alignment having a desired bivalent conservation. In this example, we used a bivalent conservation of greater than 80% or greater than 90%, meaning that the two most common 9-mers at position i accounted for more than 80% or more than 90% of the 9-mers at that position in the new alignment of conserved regions. Stated another way, the method identified the conserved regions in the new alignment as those in which the sum of the frequencies of the two most common 9-mers at each position was greater than a certain cutoff, e.g., greater than 80% or greater than 90%. Thus, the method also calculated the frequency of each pair of unique 9-mers at each position in the new alignment of conserved regions.

Figure 4A:
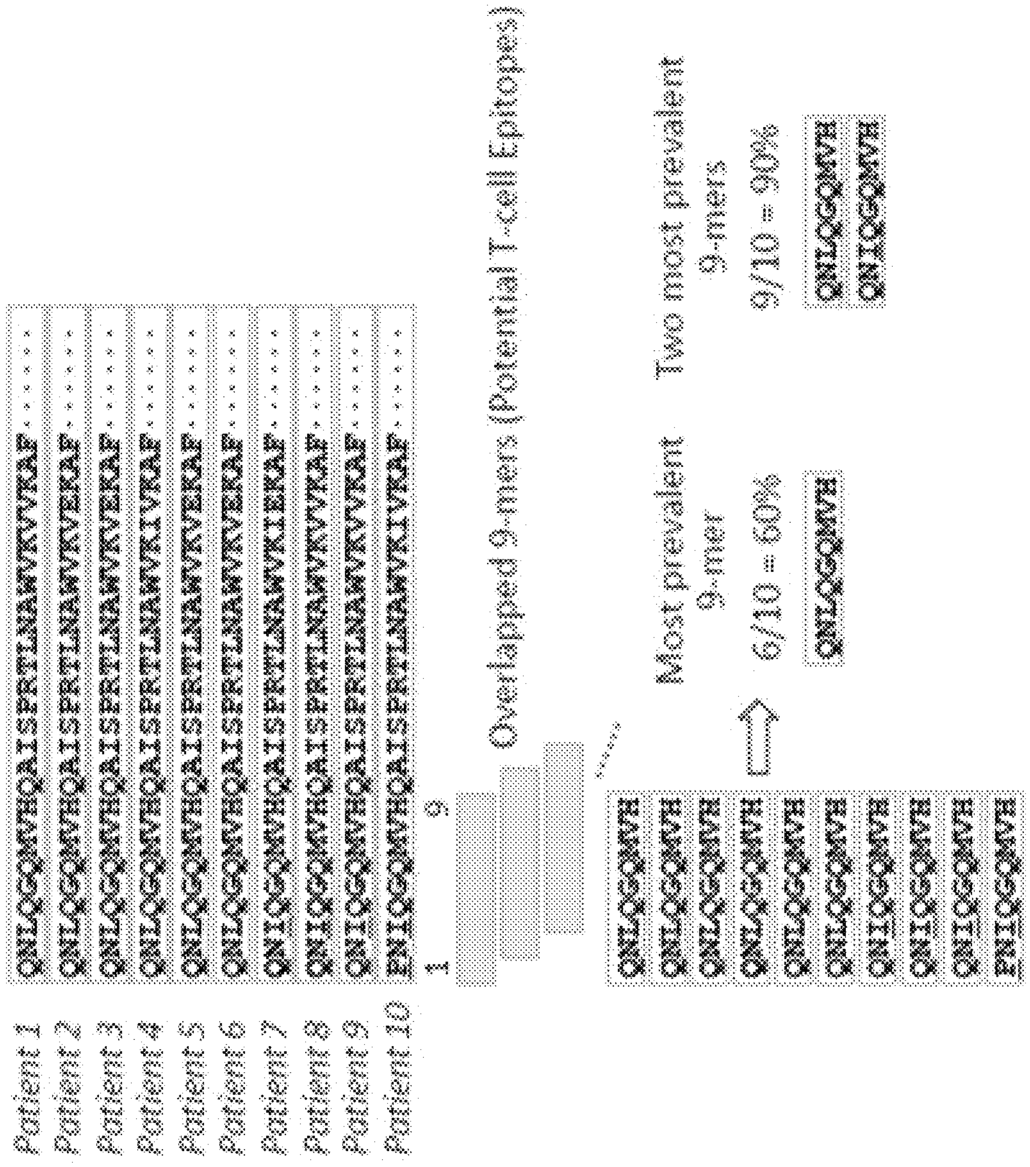
FIGS. 4A-4B.

This is illustrated graphically in FIG. 4A. FIG. 4A shows a hypothetical set of 10 input natural sequences, each having a single amino acid variation within the first 9-mer. Across the set of 10 sequences, the 9-mer having an "L" at the third amino acid position occurs 6 times, the 9-mer having an "I" at that location occurs 3 times, and the 9-mer having an "I" at that location but a different amino acid in the first position occurs once. Thus, the Conservation Algorithm selected the two most prevalent 9-mers which together account for 90% of the possible 9-mers at that position in the population of aligned sequences.

Figure 4B:
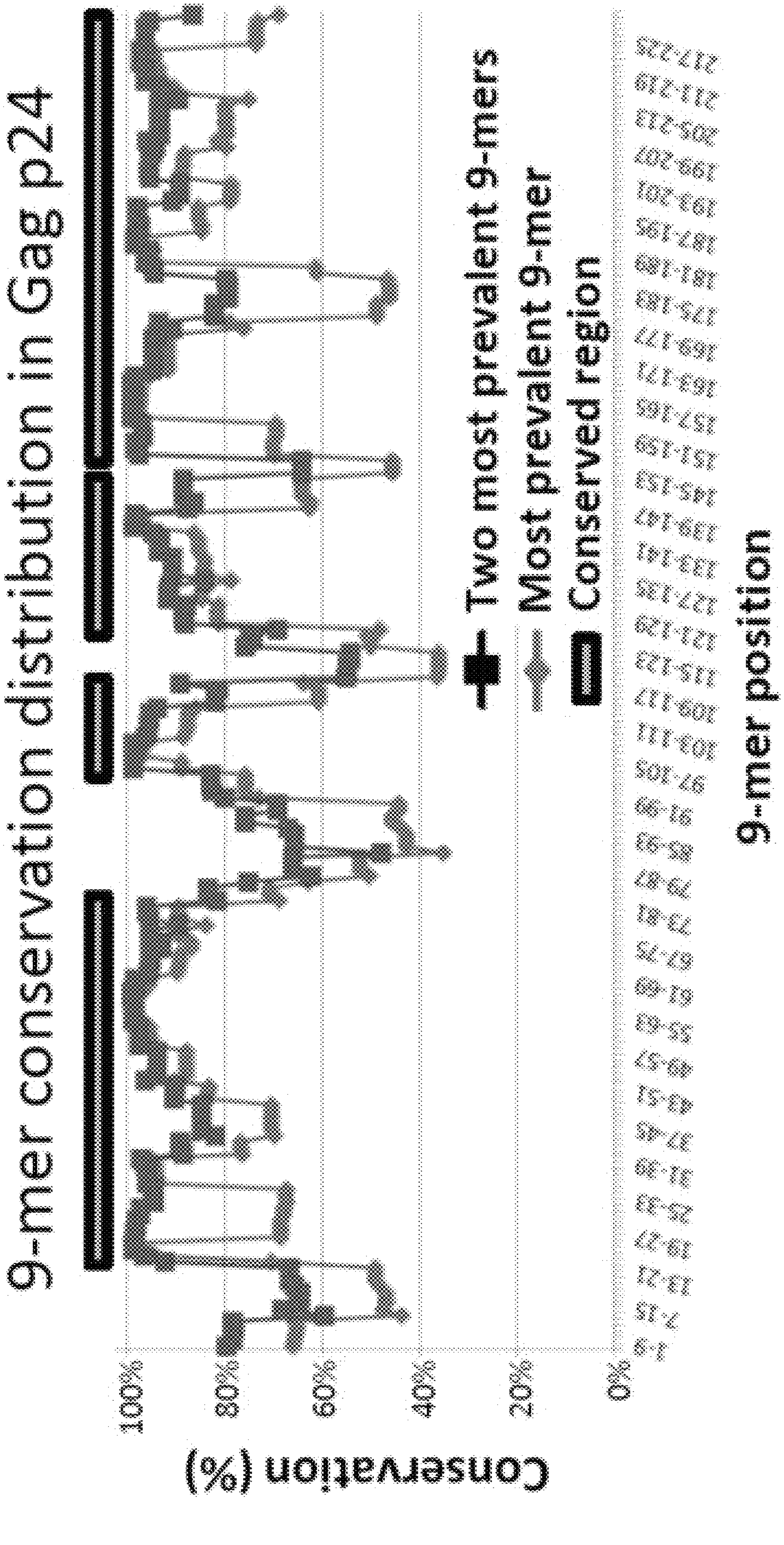

Using this analysis, the distribution of highly conserved 9-mers at each position across all of the protein sequences in the population was determined. This is illustrated graphically in FIG. 4B. The plot shows the conservation distribution for proteins encoded by the Gag gene p24 protein in 9,846 Group M Clade B input sequences obtained from the Los Alamos HIV Sequence database. The y-axis shows bivalent conservation and the x-axis shows the location of the 9-mer relative to the reference sequence, Gag p24 from HXB2. Across the top of the graph the horizontal bars depict conserved regions as those having at least 80% bivalent conservation using the two most prevalent 9-mers at each position. The dark gray line with the squares plots the bivalent conservation at each position using the two most prevalent 9-mers while the light gray line with the diamonds shows conservation using only the most prevalent 9-mer at each position. This analysis demonstrates that the use of the two most prevalent 9-mers improved the identification of structurally conserved sequences with an input population.

We next applied further selection criteria to define the conserved regions, including restricting to regions having greater than 90% bivalent conservation and removing short segments of less than 35 amino acids, e.g., segments 9-35 amino acids in length.

We also included some additional segments from certain regions having at least 80% bivalent conservation and known to be highly immunogenic, in particular, the region of Nef corresponding to amino acids 64-99 of the reference sequence HXB2_K03455 (see, e.g., epitope maps at hiv-.lanl.gov/content/immunology/maps/maps.html; Fischer, et al., *Nat Med.* (2007) 13(1):100-6; and Addo, et al., *J Virol*, (2003) 77(3):2081-92).

Step 3: Connect 9-Mer Pairs in Adjacent Positions if they do not have any Conflicting Amino Acids.

Using this modified set of conserved regions, we applied the CWA to build bivalent sequence constructs. The CWA connects 9-mer pairs in adjacent positions of the alignment of conserved regions that share an overlap of eight amino acids.

Computationally, each 9-mer s contains 9 amino acids, and s[x:y] represented the amino acid subsequence from position x to y, y−x+1 amino acids in total:

$s_{iu}[2:9]==s_{i+lp}[1:8]$ and $s_{iv}[2:9]==s_{i+lq}[1:8]$ or $s_{iu}[2:9]==s_{i+lq}[1:8]$ and $s_{iv}[2:9]==s_{i+lp}[1:8]$.

Step 4: Find the Optimal Path from the First 9-Mer Position to the Last Position in Terms of the Sum of the Frequencies of all the 9-Mers within the Path.

In Step 4, the algorithm built a directed acyclic graph in which each 9-mer pair was a node and the edges between adjacent nodes were formed from the connected 9-mer pairs in the adjacent positions with the weight of each edge equal to the frequency of the downstream 9-mer pair. This directed acyclic graph is a positional De Brujin graph. Such graphs have been described in connection with assemblies of next generation sequencing data, for example as described in Ronen et al., *Bioinformatics* (2012) 28:188-196.

In the present example, we added a source node and connected it with all of the nodes in the first position; and we added a sink node and connected it with all of the nodes in the last position. In a directed graph, a source node was a node that only has out flow and a sink node was a node that only has in flow. Here, the source node was a dummy node that connects to all the 9-mer pair nodes in the first position, and the sink node was a dummy node that connects to all the 9-mer pair nodes in the last position.

We then negate all of the weights and find the optimal path from the source node to the sink node, where the optimal path is defined in terms of the sum of the frequencies of all 9-mer pairs. The task of finding the optimal path is performed, for example, using the Bellman-Ford algorithm. Generally, the Bellman-Ford algorithm computes the shortest paths from a single source vertex to all of the other vertices in a weighted directed graph. A directed graph is one made up of a set of vertices connected by edges, where the edges have a direction associated with them.

Computationally, the basic idea was to model the maximum coverage bivalent vaccine construction problem as a classic graph theory problem where the solution was finding the minimum path in a directed acyclic graph. The computational steps are summarized as follows:

(4-1) Treat each 9-mer pair as a node, and build edges between adjacent nodes in Step 3;

(4-2) Adding a source node and connect it with all the nodes at the 1st position;

(4-3) Adding a sink node and connect it with all the nodes at the last position;

(4-4) Weight of each edge equals to the frequency of downstream 9-mer pair; and (4-5) Negating all the weights and finding the optimal path using the Bellman-Ford algorithm.

Step 5: Build Bivalent Vaccine Sequences Based on the Optimal Bivalent 9-Mer Pair Path and Connect Two 9-Mers in Adjacent Positions within the Optimal Bivalent 9-Mer Pair Path if they Share an Overlap of 8 Amino Acids.

In Step 5, a bivalent construct was built by connecting two 9-mers in adjacent positions within the optimal bivalent 9-mer path if they shared an overlap of eight amino acids, thereby creating two sequences of connected 9-mers which together form the bivalent construct. The connected adjacent 9-mer pairs all had an 8 amino acid overlap, so they were assembled into two sequences. For example, one 9-mer pair (AIIIIIIIS (SEQ ID NO: 190), MIIIIIIII (SEQ ID NO: 191)) was connected with another 9-mer pair (IIIIIIISK (SEQ ID NO: 192), IIIIIIIIR (SEQ ID NO: 184)) and made two sequences (bivalent sequences):AIIIIIIISK (SEQ ID NO: 193) and MIIIIIIIIR (SEQ ID NO: 194).

Figure 5A:
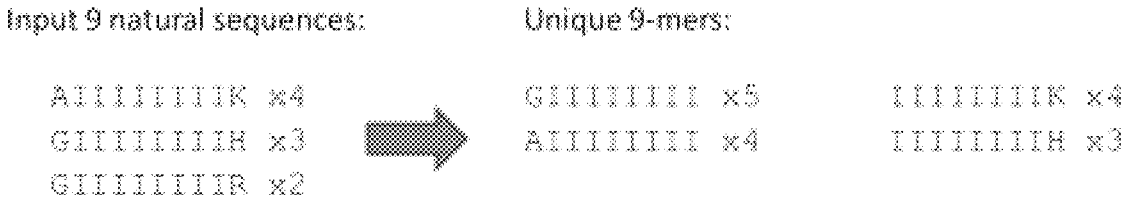
FIGS. 5A-5C.
Figure 5B:
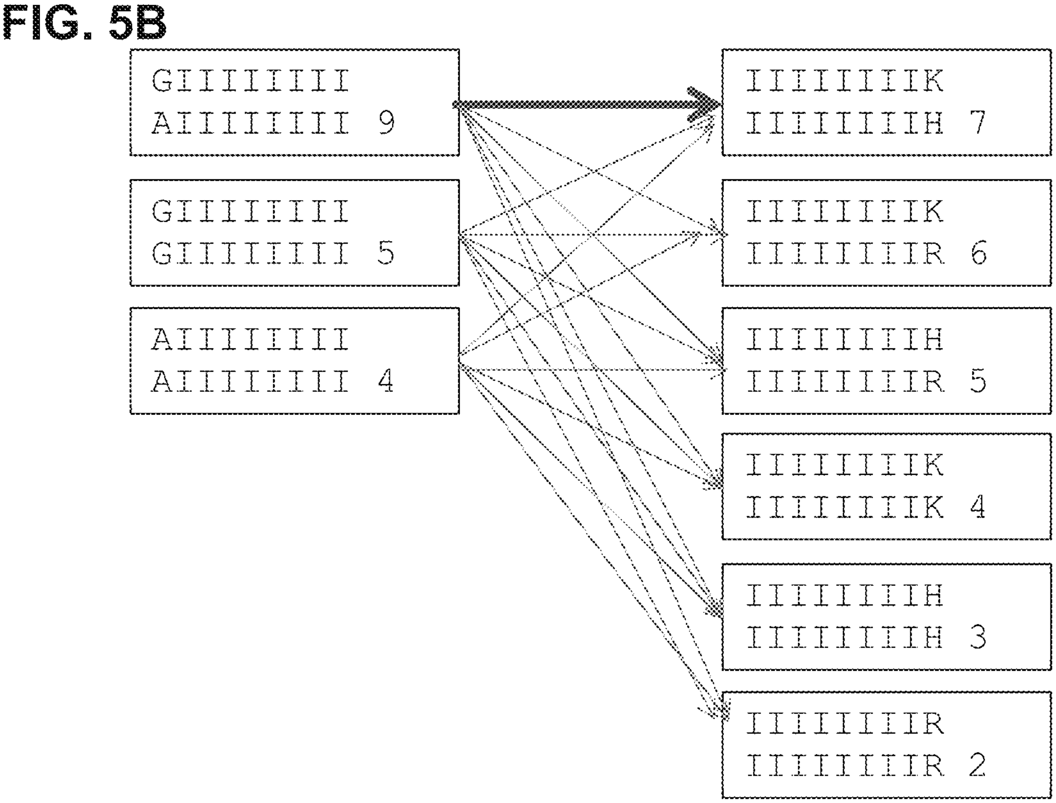
Figure 5C:
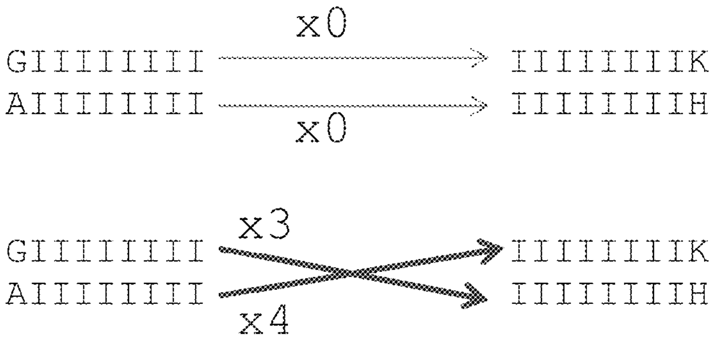

This method is illustrated graphically in FIGS. 5A-5C. FIG. 5A shows a hypothetical set of 9 source viral sequences having, at the first position, 2 unique 9-mers and at the second adjacent position 3 unique 9-mers. The frequency of each sequence is indicated to the right of the sequence as ‘times’, e.g., “×5” means that sequence occurs 5 times in the source set. FIG. 5B depicts the building of the positional De Brujin graph in which each node is one bivalent 9-mer pair. Where two bivalent 9-mer pairs in adjacent positions shared an overlap of eight amino acids they were connected to build an edge. In this manner the directed acyclic graph was created. FIG. 5C illustrates the finding of the optimal path. As noted above, the optimal path was defined in terms of the sum of the frequencies of all 9-mer pairs. This was accomplished by finding the connection between adjacent 9-mers that provided the highest conservation with reference to the input sequences. Thus, in FIG. 5C, connecting the two 9-mer pairs as shown in the top set of four pairs provided the following bivalent sequences,

```
GIIIIIIIIK (SEQ ID NO: 195) x0

AIIIIIIIIH (SEQ ID NO: 196) x0.
```

Neither of these sequences was present in the source sequences shown in FIG. 5A.

In contrast, connecting the two 9-mer pairs as shown in the bottom set of four pairs in FIG. 5C provided the following bivalent sequences,

```
GIIIIIIIIH (SEQ ID NO: 178) x3

AIIIIIIIIK (SEQ ID NO: 177) x4.
```

Each of these was present, 3 or 4 times, respectively, in the source sequences shown in FIG. 5A. Accordingly, it is these second pairs of bivalent sequences that were selected by the algorithm because it maximized conservation relative to the source sequences.

Computationally, this can be illustrated by the following exemplary cases:

Case 1: if $s_{iu}[2:9]=s_{i+1p}[1:8]$ and $s_{iv}[2:9]=s_{i+1q}[1:8]$, connect $s_{iu}$ with $s_{i+1p}$ and $s_{iv}$ with $s_{i+1q}$;

Case 2: if $s_{iu}[2:9]=s_{i+1q}[1:8]$ and $s_{iv}[2:9]=s_{i+1p}[1:8]$, connect $s_{iv}$ with $s_{i+1q}$ and $s_{iv}$ with $s_{i+1p}$;

Case 3: if $s_{iu}[2:9]=s_{i+1p}[1:8]$ and $s_{iv}[2:9]=s_{i+1q}[1:8]$ and $s_{iu}[2:9]=s_{i+1q}[1:8]$ and $s_{iv}[2:9]=s_{i+1p}[1:8]$, the selection of connection is based on the prevalence of the two connections in natural sequences:

Denote the prevalence of the co-existence of $s_{ix}$ and $s_{i+1y}$ in input sequences as $C_{ixy}$ If $C_{iup}+C_{ivq}>C_{iuq}+C_{ivp}$, connect $s_{iu}$ with $s_{i+1p}$ and $s_{iv}$ with $s_{i+1q}$;

If $C_{iuq}+C_{ivp}>C_{iup}+C_{ivq}$, connect $s_{iu}$ with $s_{i+1q}$ and $s_{iv}$ with $s_{i+1p}$;

If $C_{iup}+C_{ivq}=C_{iuq}+C_{ivp}$, backtrack and combine the prevalence of the co-existence of 9-mer pairs in positions i−1 and i until the first position. If there is no difference between two different connections, randomly pick one.

This backtrack and co-existence prevalence approach considered prevalence of peptides longer than 9 amino acids and further differentiated the present algorithm from other graph-based methods.

Next, constructed sequences from regions not adjacent to one another in the natural sequence, that is, regions which could not be joined according to the CWA as described above due to their lacking an 8 amino acid overlap, were combined using one of three different linker strategies: 1. direct fusion without any linker; 2. insert ‘AAA’ (SEQ ID NO: 48) linker between each two conserved regions; 3. direct fusion without any linker for segments within the same protein and insertion of an F2A linker between segments from different proteins.

Figure 1:
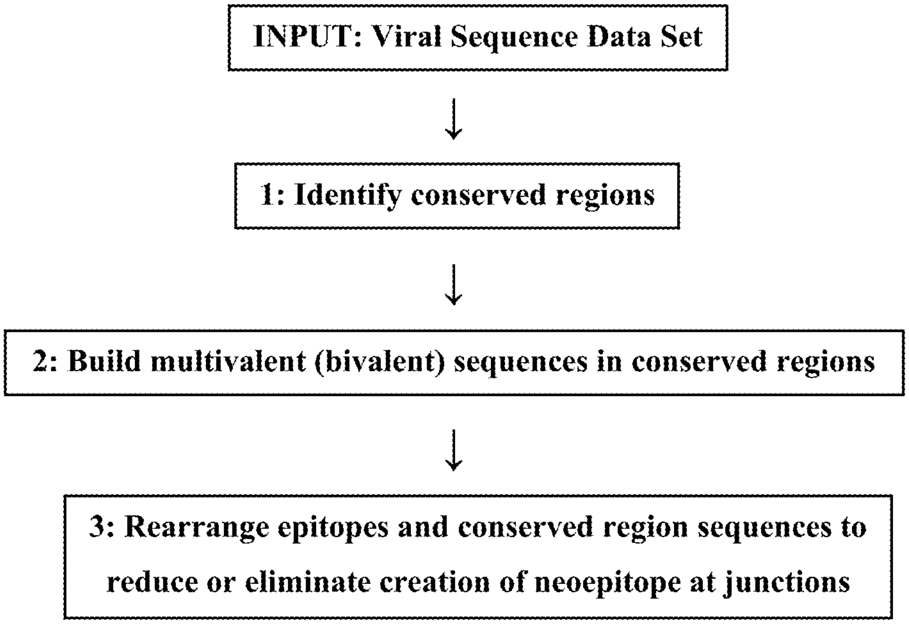
FIG. 1 illustrates a 6-step workflow for designing a fusion polypeptide to elicit an antiviral response.

An overview of the Conserved Walking Analysis (CWA) method is shown in FIGS. 1 and 2.

Example 2

Illustrated Implementation of the Conservation Analysis and Conserved Walking Analysis (CWA) Applied to Proteins Encoded by HIV-1 Genes This example describes a similar implementation based on conserved HIV-1 regions of (1) Gag, Pol and Nef or (2) Pol and Nef.

In Example 1 above, the Conservation algorithm was applied to identify a set of all candidate conserved regions in the protein coding regions of the target genes Gag, Nef and Pol. In this example, we utilized the protein coding regions of (1) Gag, Pol and Nef, (2) Pol and Nef to generate different bivalent constructs. As in Steps 1-2 of Example 1 above, we first aligned the source sequences and then applied the Conservation Algorithm to identify a set of all candidate conserved regions in the protein coding regions of the target genes, which were either from (1) Gag and Nef, Pol, or (2) Pol and Nef. As above, we then we applied further selection criteria based on conservation and known immunogenicity (see, e.g., epitope maps at hiv.lanl.gov/content/immunology/maps/maps.html and Fischer, et al., *Nat Med.* (2007) 13(1):100-6). In certain sequences including polypeptide segments encoding by the Pol gene, we excluded sequence segments including one or both of the "YMDD" motif (SEQ ID NO: 197) in reverse transcriptase and the "DTG" motif in protease, because they may affect one or both of the expression and maintenance of enzymatic activity.

Using this modified set of conserved regions, we applied the CWA to build bivalent sequence constructs, as in Steps 3-5 in Example 1.

Some polypeptide segments were connected by a polyalanine linker (e.g., AA, AAA (SEQ ID NO: 48) or AAY (SEQ ID NO: 49)), chosen for demonstration purposes because it is a small flexible linker that is unlikely to have a significant influence on protein structure. Some polypeptide segments were connected by natural short linkers (e.g., K, I, LI, EE, PPV, LIK, KIL, QEE, or SEG), chosen from the natural HIV protein sequences that flanking the conserved polypeptide segments to be fused. If we determined that it was possible to fuse polypeptide segments without creating a deleterious or undesirable junctional epitope, e.g., such as one that may stimulate T cells that may cross react to self-antigens, a fusion approach was used. If we determined that a deleterious or undesirable junctional epitope may be created, a flexible or natural short linker was inserted between polypeptide segments.

For this Example, we applied a further analysis of the junctional regions for possible presentation of deleterious epitopes and arranged the segments to reduce or avoid the creation of such junctional epitopes.

Different arrangements of peptide segments generate different junction 9-mers that can induce different junction responses. We developed a polypeptide segment arrangement tool to examine MHC binding affinities and cross-recognition with human peptides for all the junction 9-mers in each arrangement. Our internally developed polypeptide segment arrangement tool searched different arrangements of peptides and determined the best arrangement with minimal junction response based on in silico prediction results of applying the two analyses described below ((1) in-silico HLA binding analysis and (2) human proteome analysis to identify epitopes that may prime T cells that may recognize self-antigens) on the junctions of 9-mers. The junctional response score between each two adjacent segments was determined by the sum of the number of junction 9-mers that were predicted to have high binding affinities to target HLA alleles and the number of human proteins predicted to have peptides or T cell recognition motifs with any junction 9-mers. The score of each segment arrangement was determined by the sum of the junctional response scores for all the junctional regions in each segment arrangement.

1) When there were less than 15 peptide segments, our internally developed polypeptide segment arrangement tool searched all the possible arrangements and determined the best one with minimal junction response (the lowest segment arrangement score).
2) When there were at least 15 peptide segments, our internally developed polypeptide segment arrangement tool uses a 'greedy' strategy. It first created all the junctions and then started from the best junction in terms of predicted junctional response. Next, it searched for the next compatible best junction iteratively and assembled all the peptide segments.

In-silico MHC class I (human HLA) binding analysis: Antigen processing, presentation, and T cell receptor recognition are complex processes that remain incompletely understood. Intracellular and extracellular antigens are processed within endosomal compartments, and the cytoplasm by the proteasome and trafficked to endosomal compartments such as the ER where they peptide fragments interact with MHC molecules. Stable peptide-MHC complexes are trafficked to the cell surface where they can be recognized by a T cell expressing a TCR with the appropriate specificity. One of the most selective steps in antigen processing and presentation is HLA binding. HLA binding affinities can be predicted using various tools such as NetNMC or MHCflurry, or large internal datasets derived from immunopeptidome analyses and confirmed by experimental binding data as well as epitopes defined from patient samples. These tools are publicly available and are described, for example, in Lundegarrd et al., *Nucleic Acids Res.* 2008 Jul. 1; 36(Web Server issue):W509-12 and O'Donnell, et al., *Cell Systems* 2018 7:129-132. In this example we used NetNMC, version 4.0. The default settings were used for all the parameters in NetNMC, along with inputting information for peptide sequences and HLA alleles. Predicted binding affinities with an IC50 value less than 1,000 nM were considered as low binding affinities.

Human proteome cross-recognition analysis: Epitopes similar to human peptides may induce tolerogenic responses or responses that may cross-react with self-antigens. We searched all the 9-mers in our vaccine against public human protein databases (e.g., Uniprot, NCBI). If an HIV peptide 9-mer has at least a 5-residue amino acid sequence identity with a human peptide 9-mer, and both were predicted to have high binding affinities to the same alleles, they were considered as cross-conserved 9-mers. We downloaded all the human protein sequences from the UniProt database and built a tool to support efficient search of a given 9-mer against all the human protein 9-mers with up to 4 mismatches (at least 5 matches).

FIG. 6 illustrates the results of human proteome cross-recognition analysis. In this example, we searched HIV-1 peptide 9-mers over human protein databases and identified all the human protein 9-mers sharing a certain number of amino acids (at least 5 tentatively) and were predicted to have high binding affinities (e.g., IC50 of less than about 1000 nM or having a percentile rank within the top 5% in a population of polypeptide segments) to the same alleles based on the in silico MHC class I analysis described herein. Such HIV 9-mers having both substantial or high sequence identity (e.g., having at least 55% (5 of 9 amino acid residues), e.g., at least 65% (6 of 9 amino acid residues), e.g., at least 75% (7 of 9 amino acid residues), e.g., at least 85% (8 of 9 amino acid residues)) to a peptide segment of a human protein and high predicted MHC class I binding affinity were excluded because they may induce tolerogenic responses or responses that may cross-react with human self-antigens (defined herein as "deleterious epitopes").

Figure 7:
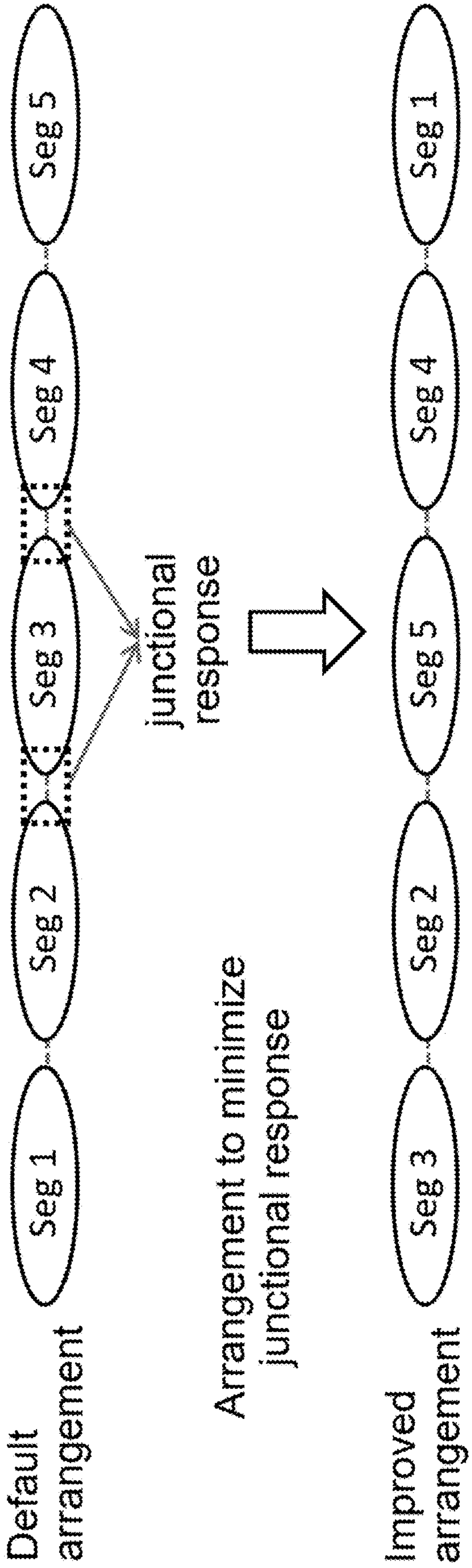
FIG. 7 illustrates how polypeptide segment arrangement analysis can reduce or eliminate possible presentation of deleterious or undesirable epitopes injunction regions.

FIG. 7 illustrates how polypeptide segment arrangement analysis can reduce or eliminate possible presentation of deleterious or undesirable epitopes injunction regions. In the illustrated default arrangement, the junction 9-mers between Seg 2 and Seg 3, and between Seg 3 and Seg 4 were predicted to produce junctional sequences that may induce tolerogenic or self-reactive responses in a human (e.g., having either high MHC binding affinity based on in silico HLA binding analysis or cross-recognition with human proteins based on human proteome cross-recognition analysis). We applied an algorithm that searched different arrangements and determined an arrangement that results in reduced or eliminated predicted junctional sequences that may induce tolerogenic or self-reactive responses in a human. Additionally, if multiple antigen sequences were developed, the polypeptide segments were also rearranged to avoid identical or nearly identical 9-mers at junction between antigen sequences.

Figure 8:
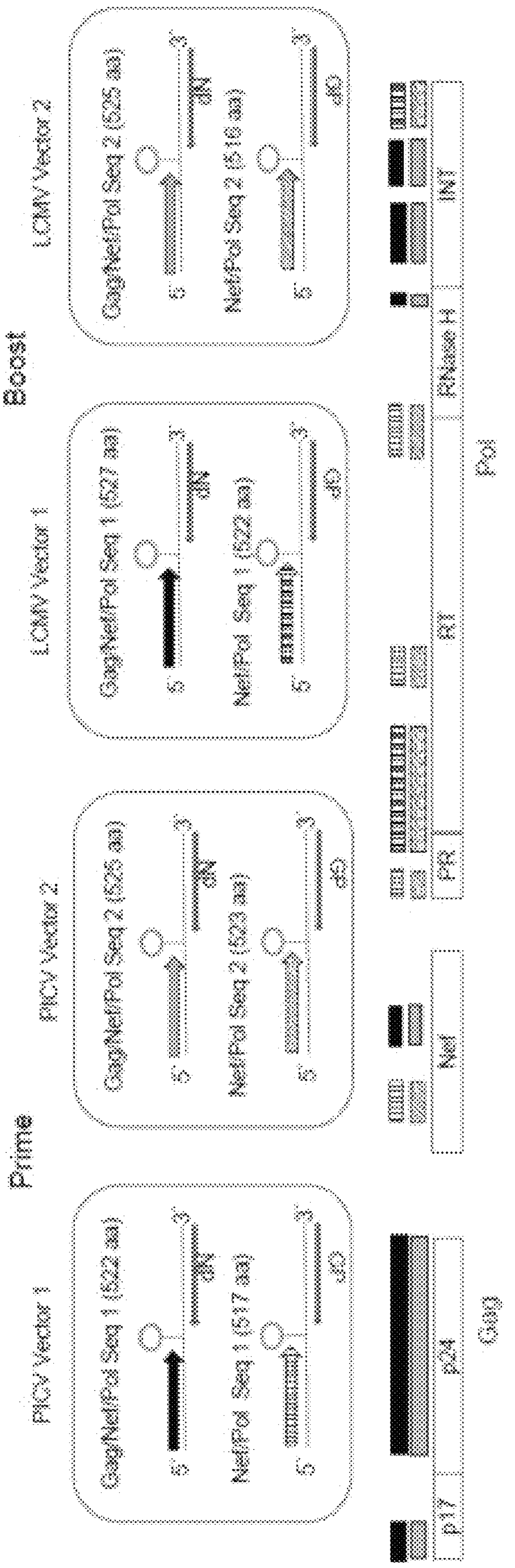
FIG. 8 provides a schematic of viral vectors containing fusion proteins of immunogen version 1 (e.g., SEQ ID NOs: 94-101). Fusion polypeptides of immunogen version 1 have twelve conserved regions within HIV-1 Gag, Pol and Nef in the range of 516 to 527 amino acids in length that have been rearranged to reduce or minimize overall junctional responses. A total of four vectors to enable a bi-valent, heterologous prime/boost vaccine regimen.

The fusion polypeptides and compound fusion polypeptides described herein are exemplary immunogenic fusion polypeptide sequences designed according to the herein described immunogen design methods. The fusion polypeptides of SEQ ID NOs: 70-101 (provided in Table E), particularly SEQ ID NOs: 94-101 (immunogen version 1), and the compound fusion polypeptides of SEQ ID NOs: 105-112, 200-209, 222-223 and 227 (provided in Table F), which have polypeptide segments encoding by the HIV-1 Gag, Nef and Pol genes, are exemplary immunogenic fusion polypeptide sequences designed according to this method. FIG. 8 provides a schematic of viral vectors containing the fusion proteins of immunogen version 1.

Example 3

Immunogen Design Improved with Deep Sequencing Analysis and Immunogenicity Data: Immunogen Version 2

In Example 1 above, the Conservation algorithm was applied to identify a set of all candidate conserved regions in the protein coding regions of the target genes Gag, Nef and Pol. In Example 2, we utilized the protein coding regions of (1) Gag, Pol and Nef, (2) Pol and Nef to generate different bivalent constructs. In this example, we describe the design of immunogen version 2 by incorporating both deep sequencing data and immunogenicity data to identify which conserved regions from immunogen version 1 to be included in shortened bivalent polypeptide constructs. For the design of this improved immunogen, as in Steps 1-2 of Example 1 above, we first aligned the source sequences and then applied the herein described conserved walking algorithm (CWA) to identify a set of all candidate conserved regions in the protein coding regions of the target genes. The target genes were Gag, Nef and Pol, and we applied the CWA to build bivalent sequences in those regions, as in Steps 3-5 of Example 1.

INTRA-patient Conservation Analysis using Deep Sequencing. In addition to the 9-mers derived from downloaded population sequences, we also analyzed viral deep sequencing data from HIV-1 subtype B chronically infected individuals to identify intra-patient diversity within those conserved regions. To identify intra-patient 9-mer variants using deep sequencing data, deep sequencing data of N=238 HIV chronically infected treatment-naïve subjects were analyzed to evaluate intra-patient diversity within conserved regions defined by CWA. To evaluate intra-patient 9-mer variants using deep sequencing data, deep sequencing reads were assembled to create subject-specific consensus sequence. Reads were aligned to subject-specific consensus sequence and then the alignment was mapped to HXB2 position coordinates based on alignment of subject-specific consensus to HXB2 reference sequence. At each 9-mer position, corresponding sequencing reads completely covering the 27 bp of the 9-mer were extracted and converted into 9-mer amino acid sequences. Only 9-mer positions with ≥1000 sequencing read depth were included in the analysis and variants were analyzed with a 1% frequency cutoff. The 9-mer variants were used to evaluate the bivalent vaccine sequences for coverage of quasispecies variants. Here we defined the intra-patient conservation of a 9-mer position as percentage of patients (Total N=238 samples) that were covered by the bivalent vaccine sequences without escape variants. High intra-patient conserved 9-mers are the 9-mers that were covered by bivalent population-based vaccine sequences without any escape variants in >70% patients. The intra-patient conservation was evaluated for the regions of Pol, Gag, and Nef that were selected based on population conservation as described in Example 1.

FIG. 10 provides a flow diagram illustrating the basic methodology of the approach for designing immunogen version 2. The fusion polypeptides of SEQ ID NOs: 82-89 are illustrative amino acid sequences designed according to this method.

Known epitopes from Los Alamos National Laboratory (LANL) database and Gilead ELISPOT Assay Identified Epitopes. To evaluate immunogenicity of the previously identified conserved regions, described CD8+ T-cell epitopes (e.g., from LANL database) and internally conducted ELISpot assays were analyzed. Any 9-mer positions in conserved regions of Pol, Gag, and Nef with >1 mapped epitope defined by ELISPOT assay or from LANL database were considered as an immunogenic region. Immunogenicity results were not limited to specific HLA alleles.

Figure 10A:
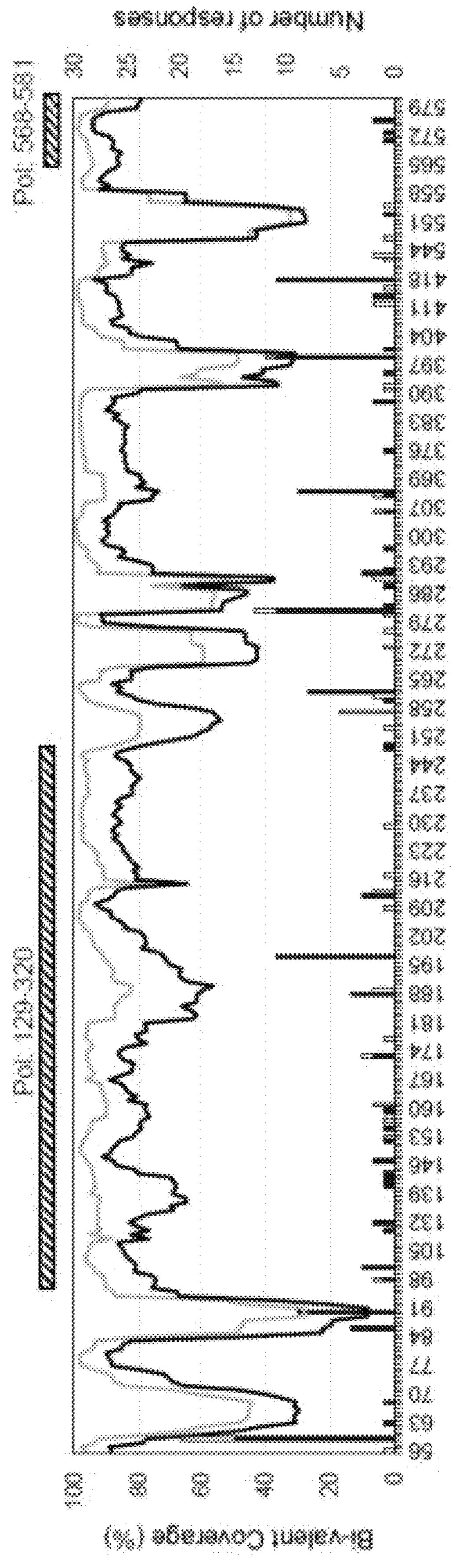
FIGS. 10A-10D illustrate the regions of HIV encoded proteins Pol (A-B), Gag (C) and Nef (D) that were selected for the immunogen version 2 by combining deep sequencing data and immunogenicity data. Solid horizontal black line=intra-patient conservation (evaluated by coverage of intra-patient 9-mer variants with bi-valent vaccine). Grey horizontal line=inter-patient conservation. Solid vertical black bars=LANL responses. White vertical bars=ELISpot responses. Horizontal bar (diagonal stripes)=regions maintained in immunogen version 2.
Figure 10B:
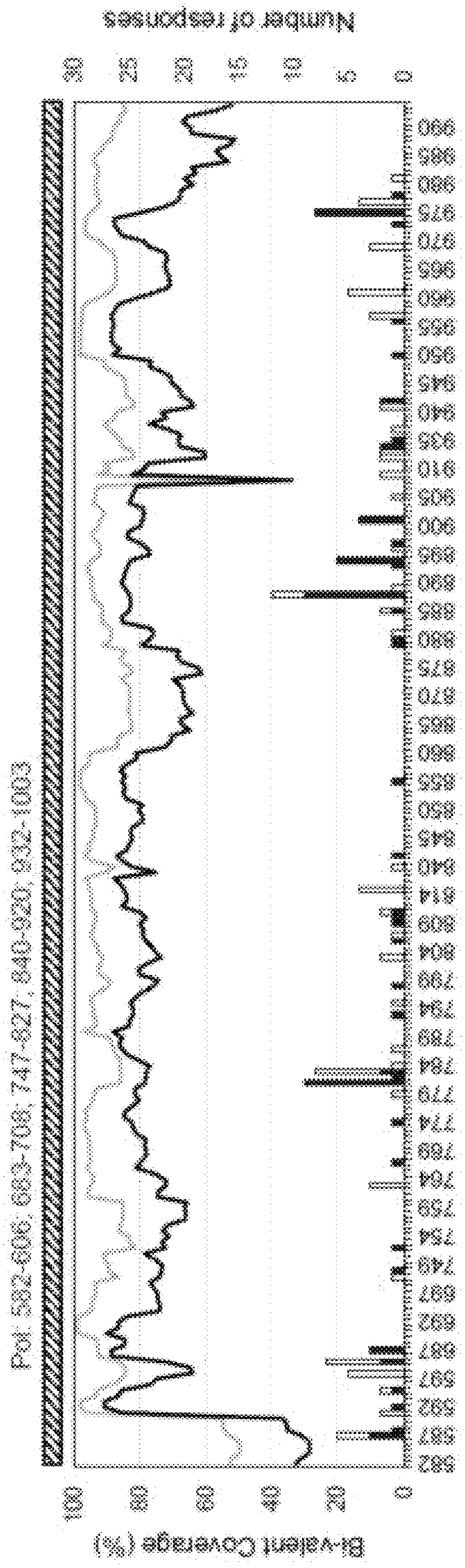
Figure 10C:
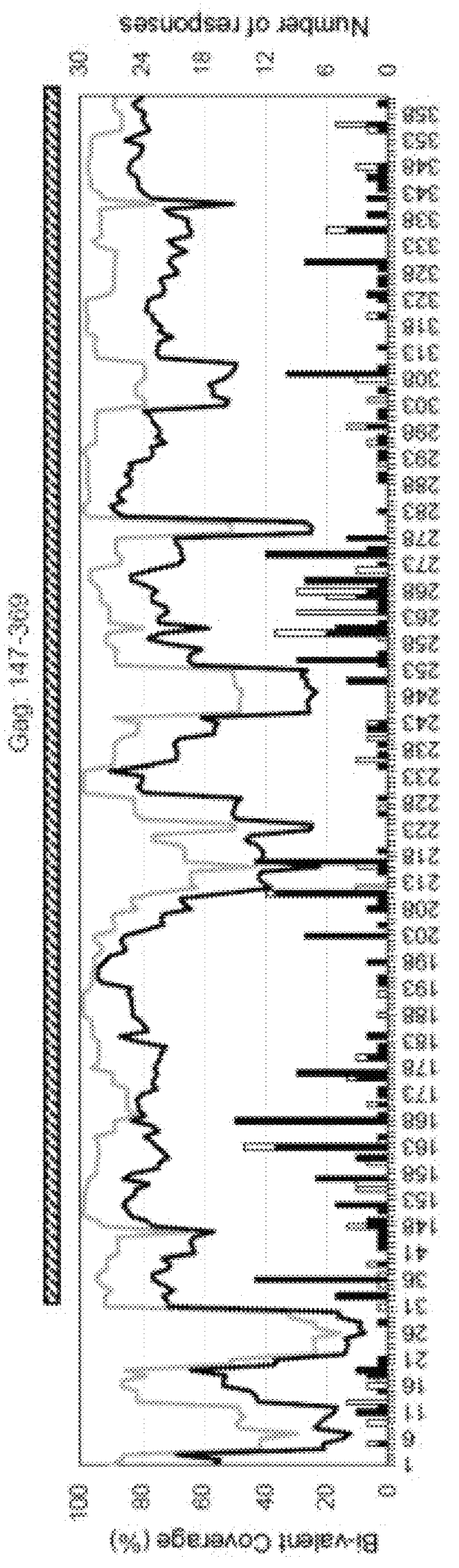
Figure 10D:
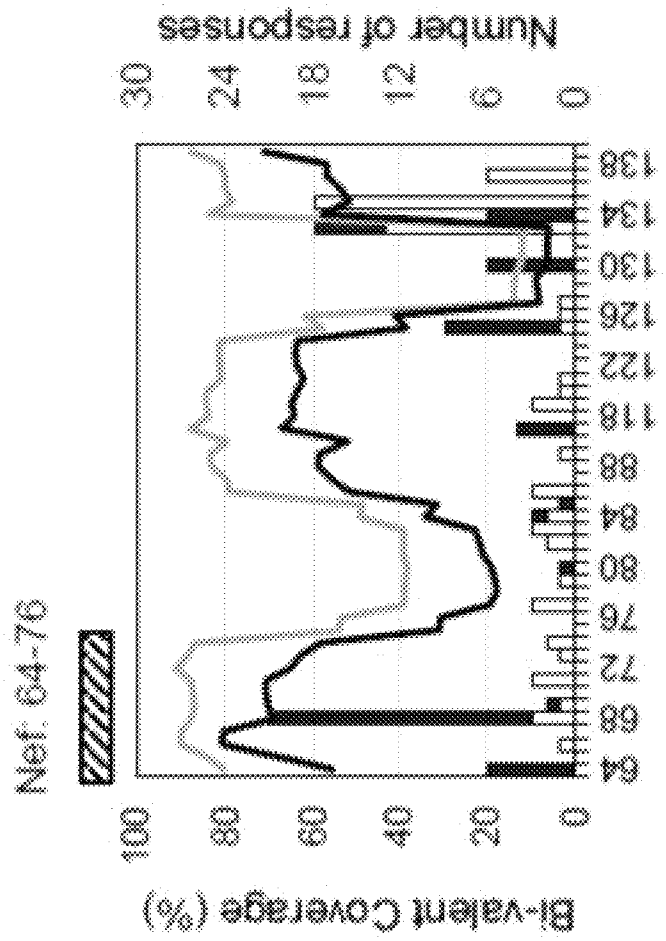

FIGS. 10A-10C illustrate the regions that were selected for immunogen version 2 by combining deep sequencing data and immunogenicity data. The intra-patient conservation is represented as the black horizontal lines for each 9-mer position in the plot. The number of epitopes overlapped at each 9-mer region is shown as stacked bar in the plot. We selected the amino acid 9-mers that have intra-patient conservation >70% and overlap with epitopes reported by LANL database or defined by ELISpot assay. After identifying the amino acid 9-mers to use for the improved immunogen, those 9-mers that were from the same viral protein and contiguous were connected (e.g., via a linker or directly fused) to form fusion amino acid segments as highlighted in the plot.

Figure 11:
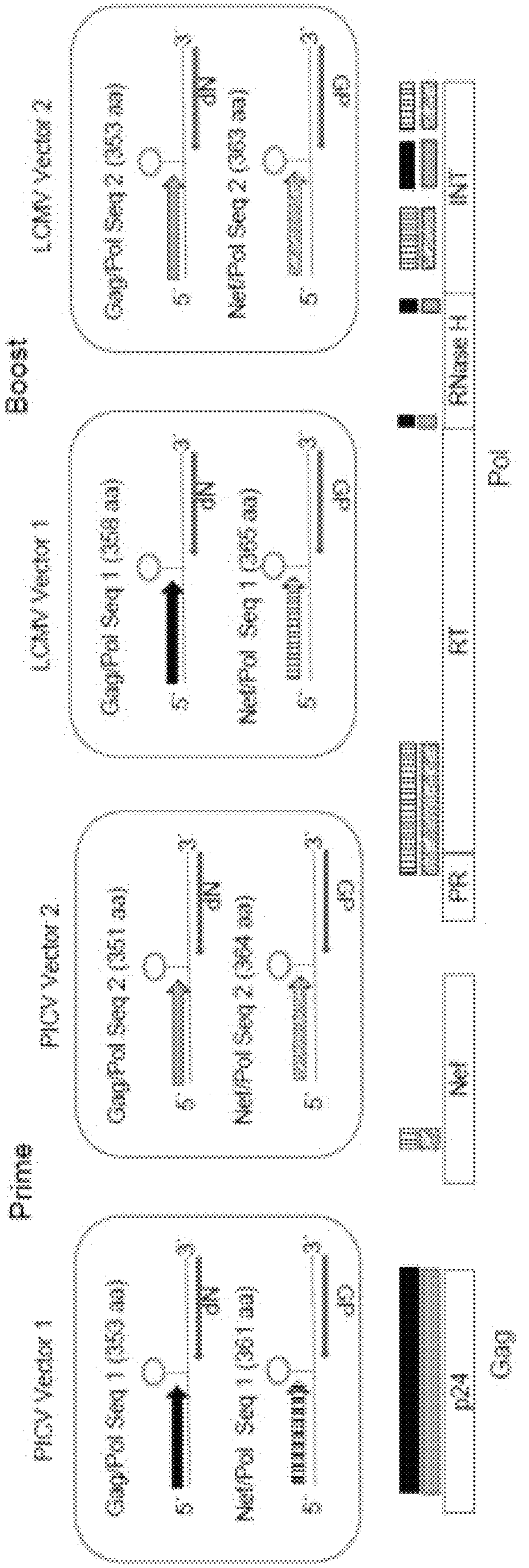
FIG. 11 provides a schematic of viral vectors containing fusion proteins of immunogen version 2 (e.g., SEQ ID NOs: 82-89). Fusion polypeptides of immunogen version 2 have eight conserved regions within HIV-1 Gag, Pol and Nef in the range of 351 to 365 amino acids in length that have been rearranged to reduce or minimize overall junctional responses. A total of four vectors to enable a bi-valent, heterologous prime/boost vaccine regimen.

We utilized the protein coding regions of (1) Gag and Pol, (2) Pol and Nef to generate different bivalent constructs. In a final step, we applied our internally developed polypeptide segment arrangement tool described in Example 2 on the segments to reduce or eliminate possible presentation of deleterious or undesirable epitopes injunction regions. We anchored Nef conserved sequence to the C-terminus of the vaccine sequence during segment rearrangement for immunogen 2, because our previous experiments showed that positioning a Nef segment on the C-terminus of the vaccine sequences was more likely to induce immune responses. FIG. 11 provides a schematic of viral vectors containing the fusion proteins of immunogen version 2 (e.g., SEQ ID NOs: 82-89).

Figure 12A:
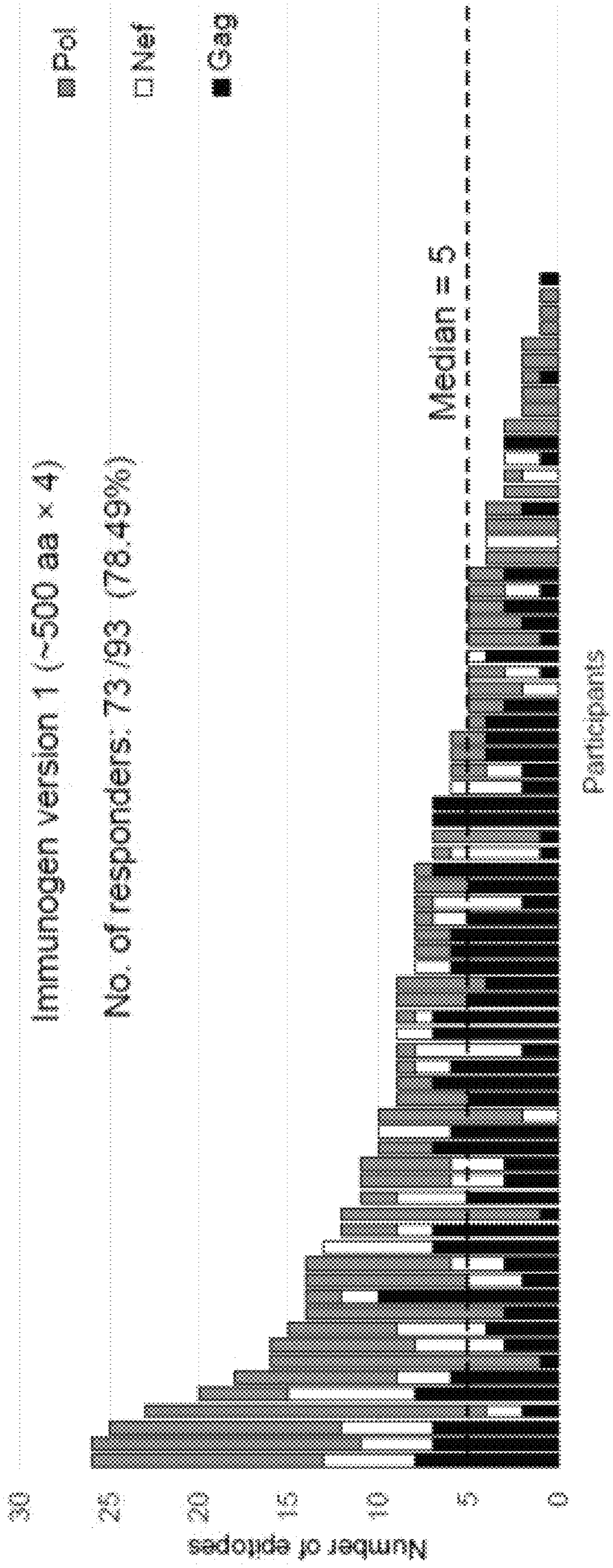
FIGS. 12A-12B illustrate that median responses remain stable with size reduction of the fusion polypeptides of immunogen version 1 to the fusion polypeptides of immunogen version 2. 12A. The ability of the fusion polypeptides of immunogen version 1 to induce T-cell responses was tested in vitro for a total of 93 donor PBMCs. The dash line shows the median number of responses recognized. Immune responses are detected in 73/93 (78.49%) participants for immunogen version 1. 12B. The fusion polypeptides of immunogen 2 were assessed in silico for the ability to induce T-cell responses in the same participants. The dash line shows the median number of responses recognized. Immune responses are detected in 71/93 (76.34%) participants for immunogen version 2.
Figure 12B:
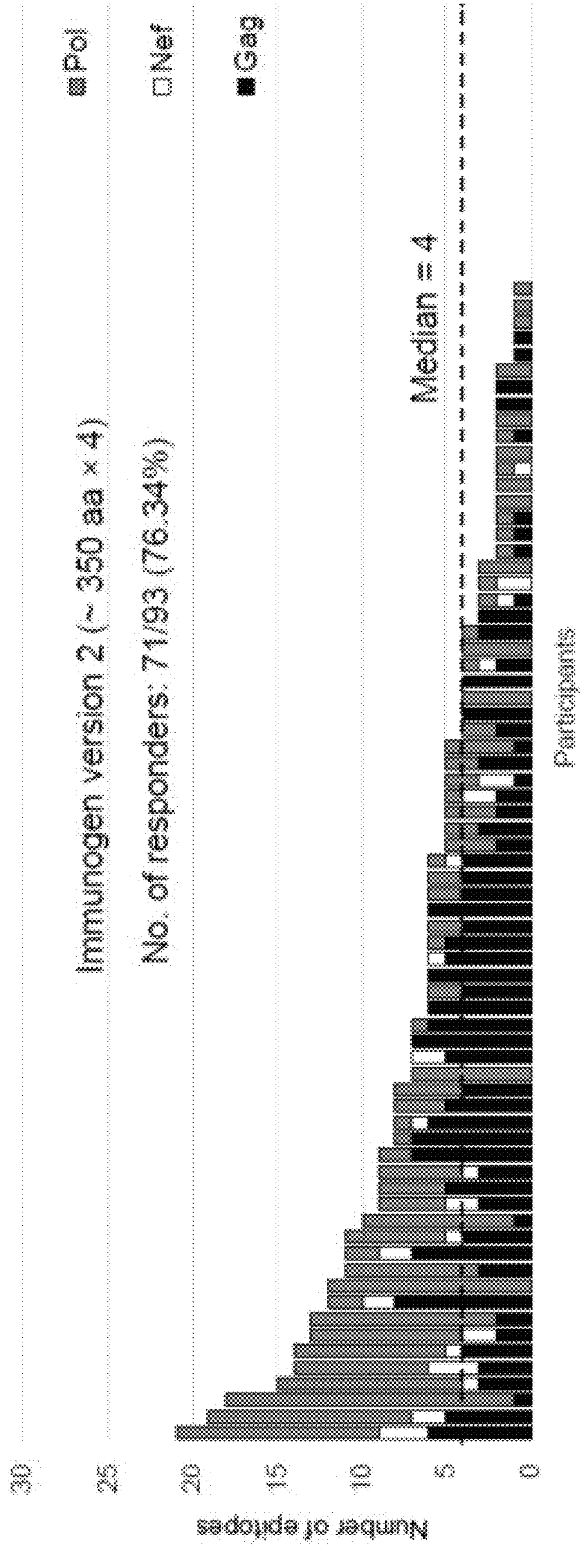
Figure 14A:
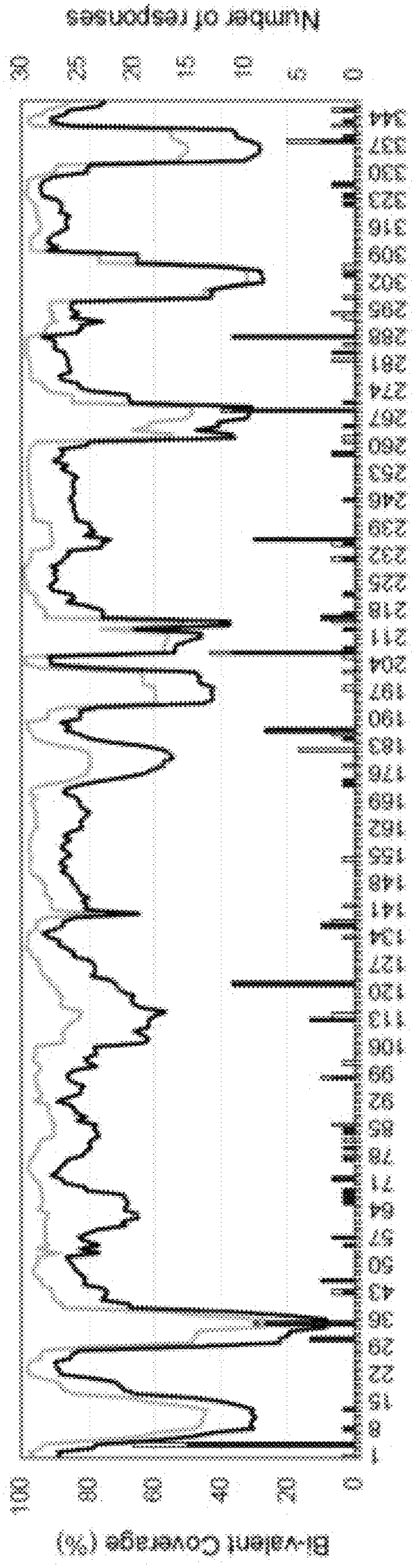
FIGS. 14A-14D illustrate the regions of HIV encoded proteins Pol (A-B), Gag (C) and Nef (D) that were selected for the immunogen version 3 by combining deep sequencing data and immunogenicity data. Solid horizontal black line=intra-patient conservation (evaluated by coverage of intra-patient 9-mer variants with bi-valent vaccine). Grey horizontal line=inter-patient conservation. Solid vertical black bars=LANL responses. Grey vertical bars=ELISpot responses. Horizontal open bar=regions maintain in improved immunogen.
Figure 14B:
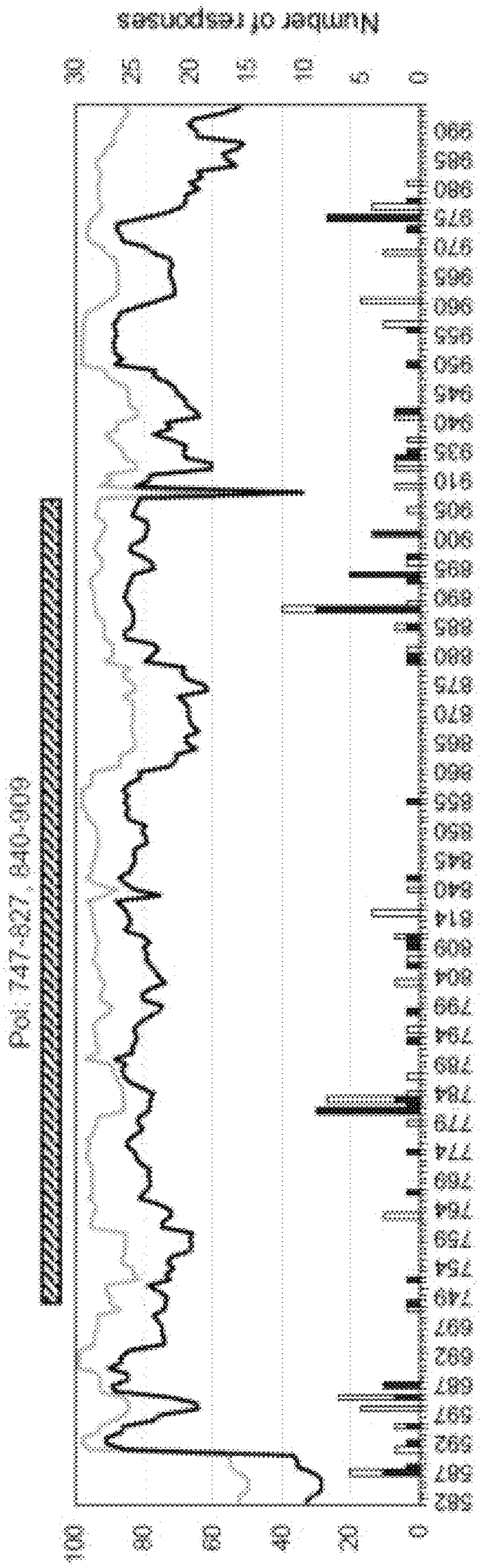
Figure 14C:
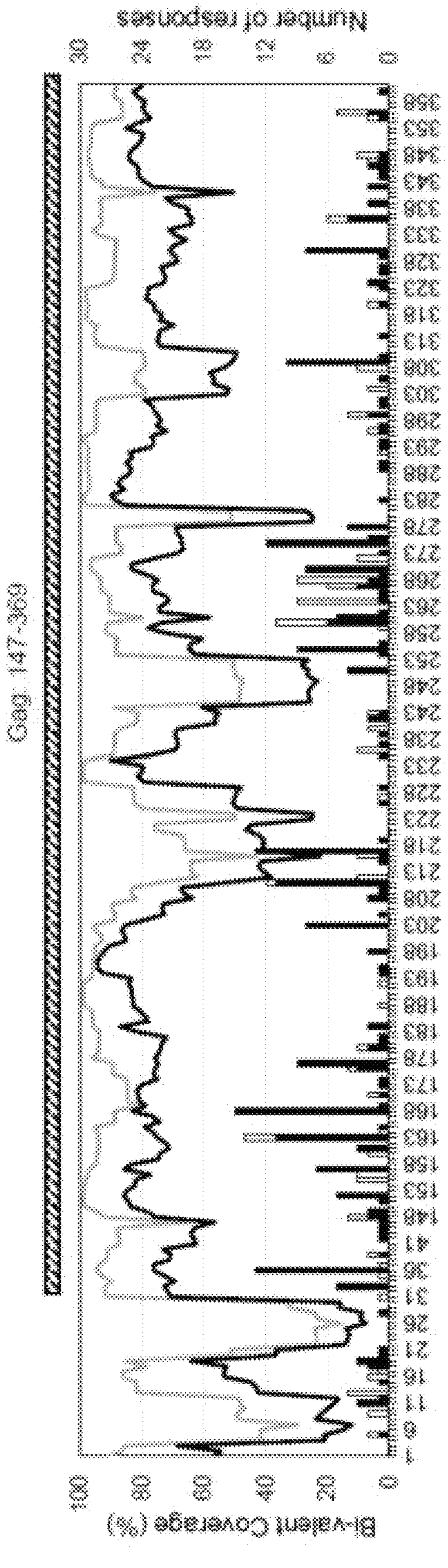
Figure 14D:
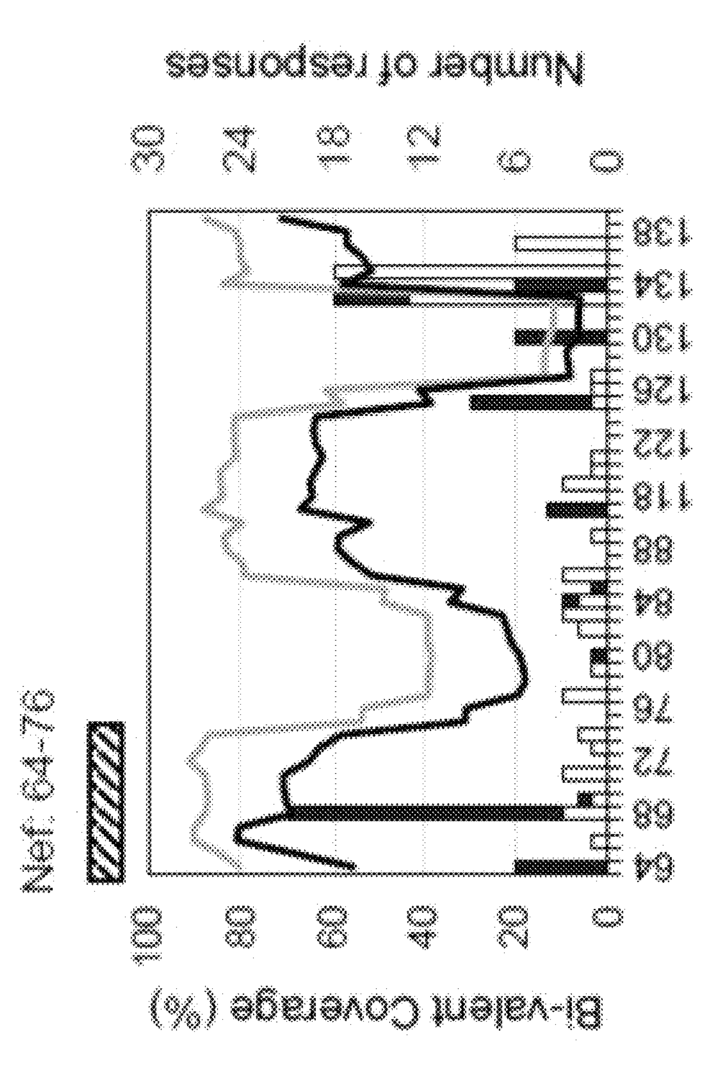

Median response and epitope density of the improved immunogen design. To assess whether the shortened immunogen is enriched with immunogenic regions, we compared the number of internally defined epitopes per sample between the fusion proteins designed according to the methods of Examples 1-2 (e.g., immunogen version 1; SEQ ID NOs: 94-101) and the fusion proteins designed according to the methods of Examples 1-3 (e.g., immunogen version 2; SEQ ID NOs: 82-89). FIGS. 12A-12B illustrate the median responses remain stable with size modification. Total of 93 samples were analyzed. We measured the median number of epitopes identified in each sample. The median number of epitopes of immunogen version 2 is 4 while the median number of epitopes of immunogen 1 is 5. Two non-responders were observed using shorter immunogen version 2. Epitope density was examined by assessing epitope rate. The epitope rate was defined as the number of in vitro clinical trial defined epitopes divided by the total potential epitopes in the immunogen. As illustrated in Table 1, the epitope rate analysis results demonstrate that we maximized the epitope density after size reduction of the fusion proteins of immunogen version 1 (516-527 amino acids in length) to the fusion proteins of immunogen version 2 (351-365 amino acids in length). The epitope rate of immunogen version 1 was maintained in immunogen version 2. We define the epitope rate as the percentage of all 9-mers that are recognized as epitopes by ELISpot assay (Total number of epitopes/the number of 9-mer positions).

TABLE 1

Epitope Rate Analysis Between Immunogen Versions 1 and 2

| | Immunogen version 1 | | | Immunogen version 2 | | |
|---|---|---|---|---|---|---|
| Gene | Number of unique epitopes | Number of 9mer positions | Epitope rate (%) | Number of unique epitopes | Number of 9mer positions | Epitope rate (%) |
| Gag | 64 | 259 | 24.71 | 53 | 215 | 24.65 |
| Nef | 13 | 50 | 26.00 | 2 | 5 | 40.00 |
| Pol | 107 | 572 | 18.71 | 84 | 419 | 20.04 |
| Total | 184 | 881 | 20.89 | 138 | 639 | 21.60 |

Example 4

Shortened Construct Suitable for Expression from Single Priming Vector and Single Boosting Vector: Immunogen Version 3

In this Example, as in Steps 1-2 of Example 1 above, we first aligned the source sequences and then applied the CWA to identify a set of all candidate conserved regions in the protein coding regions of the target genes. In this example, the target genes were Gag, Nef and Pol. We applied the CWA to build bivalent sequences in those regions, as in Steps 3-5 of Example 1.

Figure 15:
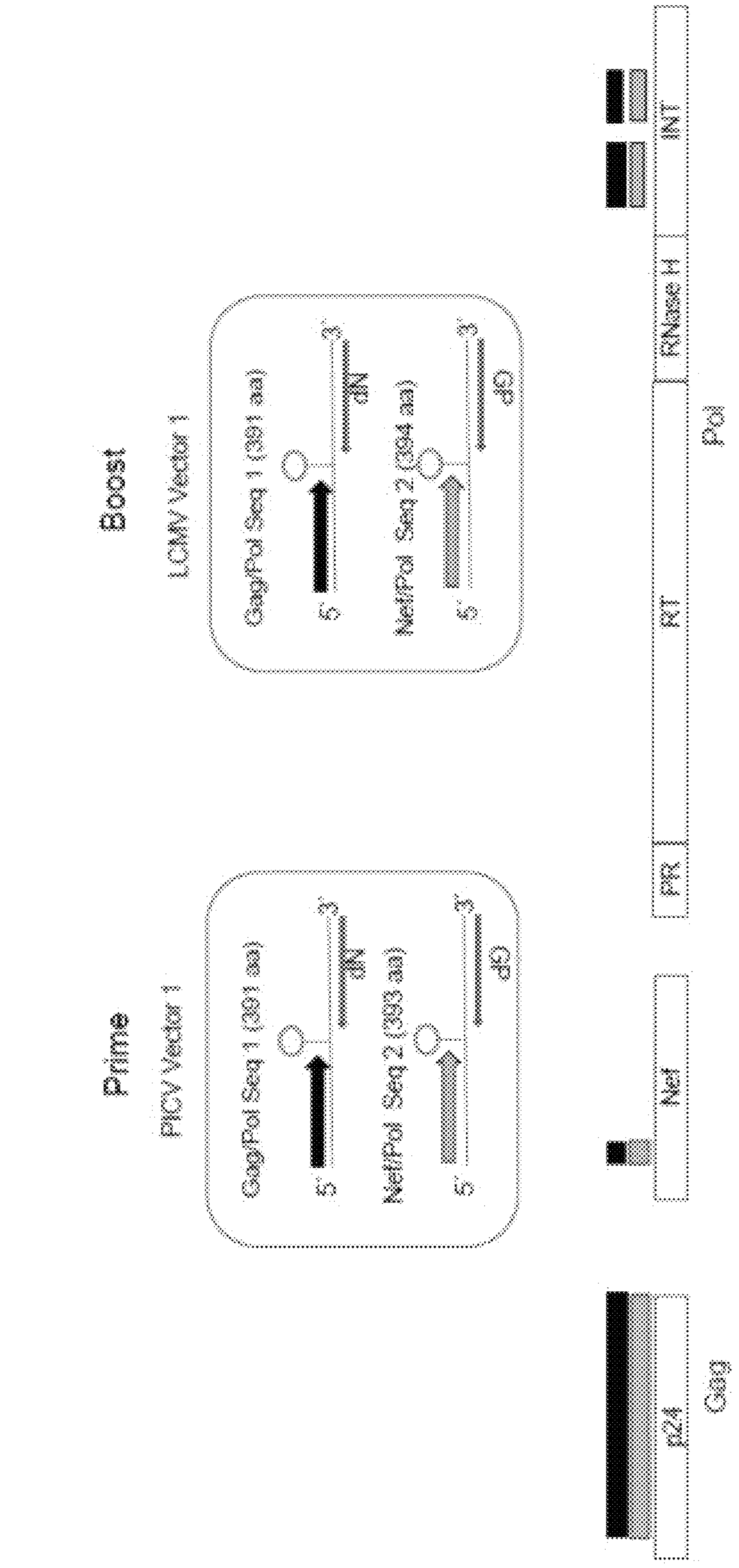
FIG. 15 provides a schematic of viral vectors containing the fusion proteins of immunogen version 3 (e.g., SEQ ID NOs: 90-93). Schematic representation of immunogen 3 version constructs. The fusion polypeptides of immunogen version 3 have four conserved regions within HIV-1 Gag, Pol and Nef in the range of 391 to 394 amino acids in length that have been rearranged to minimize overall junctional responses. A total of two vectors to enable a bi-valent, heterologous prime/boost vaccine regimen.

As Example 3 above, we applied deep sequencing and immunogenicity data to identify a subset of highly conserved and immunogenic regions within immunogen version 1 to retain in a shortened immunogen. FIG. 13 provides a flow diagram illustrating the basic methodology of the fusion polypeptides of immunogen version 3. SEQ ID NOs: 90-93 are illustrative fusion polypeptides designed according to this method. We utilized the same method described in Example 3 to design the shortened bivalent fusion polypeptides of immunogen version 3 (391-394 amino acids in length) of a length such that four fusion polypeptides could be expressed from two virus vectors (e.g., two arenavirus vectors). Immunogenicity data showed that Gag p24 and Nef segment (64-76) elicited strong immune responses, so Nef 64-76 was retained in Immunogen version 3. For Pol, as above, we identified the continuous regions in Pol that have intra-patient conservation >75% and contain multiple epitopes defined by in vitro assay. The FIGS. 14A-14D illustrate the regions selected for immunogen 3. We utilized the protein coding regions of (1) Gag and Pol, (2) Pol and Nef to generate different bivalent constructs. In a final step, we applied our internally developed polypeptide segment arrangement tool described in Example 2 on the segments to reduce or eliminate possible presentation of deleterious or undesirable epitopes injunction regions. A conserved subsequence of Nef was positioned at the C-terminus of the immunogen version 3 fusion polypeptides. FIG. 15 provides a schematic of viral vectors containing the fusion proteins of immunogen version 3 (e.g., SEQ ID NOs: 90-93).

Example 5

Viral Expression Vectors Containing Immunogenic Fusion Polypeptides in Immunogen 1

In this example, we generated viral expression vectors encoding the computationally defined polypeptide segments containing conserved regions of HIV-1 encoded by Gag, Nef and Pol genes as a transgene and confirmed expression of the transgene in mammalian cells. The polypeptide segments containing conserved regions were concatenated or connected by a variety of approaches including direct fusion, linkage of regions by the addition of a proteolytic cleavage site sequence or the addition of a flexible linker between regions Methods Evaluation of target gene expression in vitro. To improve assembly of viral vectors encoding the vaccine expression cassette, the genes were cloned into vector plasmids (ThermoFisher Scientific) containing restriction sites for cloning target genes and a GFP marker. DNA was transformed into One Shot™ TOP10 competent cells (Invitrogen, Carlsbad, CA) following manufacturer's protocol and plated onto LB agar plate supplemented with 100 μg/ml ampicillin. The plate was incubated overnight at 37° C. A single colony was picked from the plate and inoculated into a 10 ml liquid LB+ampicillin culture and shaken overnight at 37° C. at 250 rpm in an Eppendorf bench top shaker. The bacterial pellet was processed using QIAprep Spin miniprep kit (Qiagen, Germantown, MD) to obtain the plasmid DNA following manufacturer's protocol. Nucleic acid concentration was determined by reading absorbance at 280 nm using NanoDrop™2000 (Thermo Scientific). To evaluate in vitro expression, the Adenovirus serotype 5 (Ad5) expression vectors expressing a compound fusion protein of SEQ ID NO: 105, 107, 109 or 111 were used to transduce monocyte derived dendritic cells (moDCs) as outlined in Example 9 below. At day 2 post-transduction, when the viability of cells was still at >80%, they were evaluated for GFP expression by flow cytometry or pelleted. The cell lysates were evaluated for HIV-1 Gag p24 expression by ELISA.

Construction of viral expression vector containing transgene encoding fusion polypeptide variants. Ad5 vectors expressing an HIV-1 computationally defined vaccine immunogen with various approaches to linkage of conserved HIV-1 sequences, were generated by in vitro recombination using standard methods (Vector Biolabs). Expression cassettes were generated by PCR using synthetic oligonucleotides codon-biased for improved human expression (IDT), and placed under the control of the CMV promoter using standard gene cloning techniques. The immunogen version 1 compound fusion polypeptide constructs developed for this evaluation are listed in Table F and schematically depicted in FIG. 19.

Results

Figure 20B:
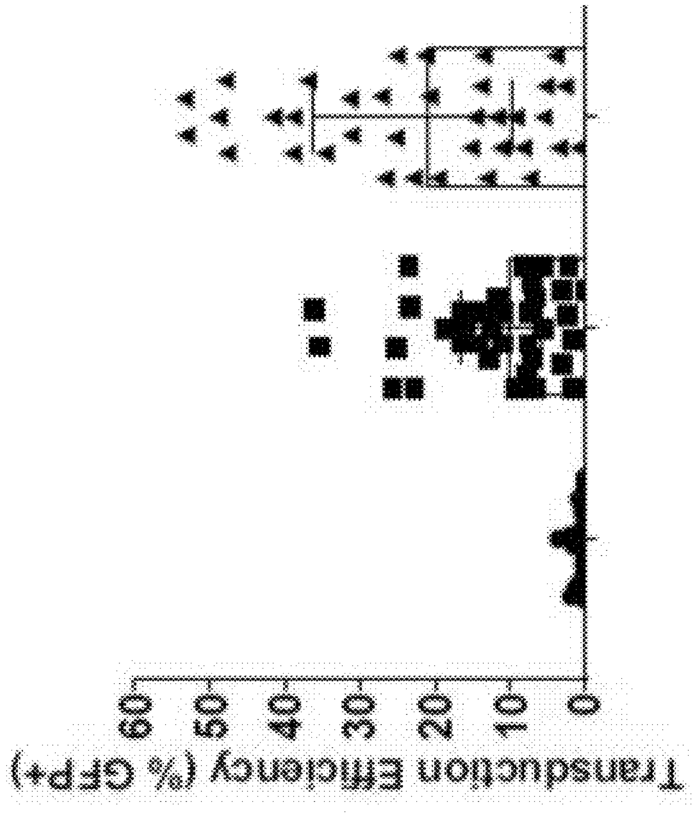
FIGS. 20A-20B. Ad5 vectors expressing compound fusion polypeptides of SEQ ID NO: 105, 107, 109 or 111 were used to transduce moDCs to evaluate expression of the transgene and transduction efficiency. Expression efficiency was assessed by Gag p24 ELISA (N=2) (FIG. 20A). The y-axis represents Gag p24 concentration (pg/ml) detected in moDC lysates at day 3 post transduction with Ad5 vectors expressing compound fusion polypeptides of SEQ ID NO: 105, 107, 109 or 111 (■) or empty vector control (▲) at multiplicity of infection (MOI) of 500.
Figure 20A:
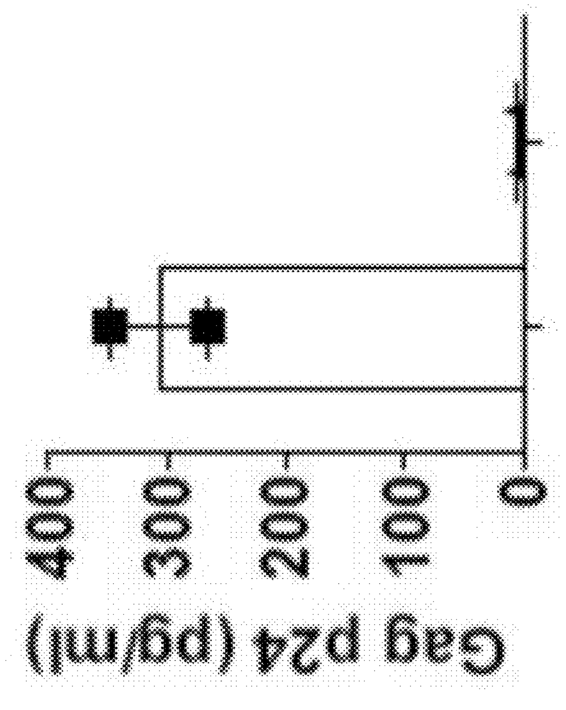

The data depicted in FIG. 20 demonstrate that all conserved region fusion polypeptide sequences were efficiently expressed (FIG. 20A) and transduced (FIG. 20B) as demonstrated by GFP expression and Gag p24 ELISA.

Example 6

Viral Expression Vectors Containing Immunogenic Fusion Polypeptides in Immunogen 2

Figure 21:
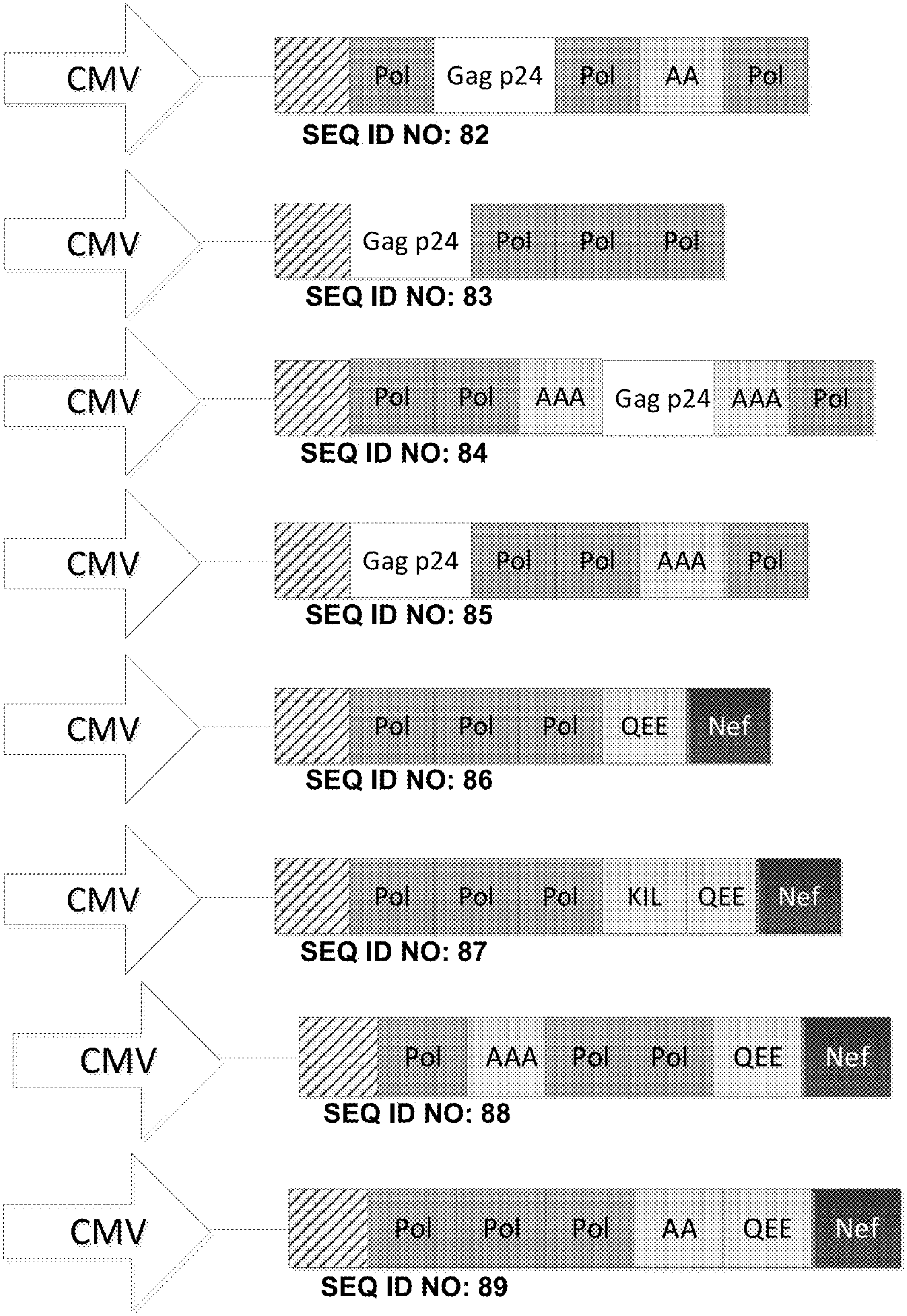
FIG. 21 illustrates a schematic representation of fusion polypeptides containing HIV-1 immunogen version 2 fusion polypeptides (SEQ ID NOs: 82-89). The depicted compound fusion polypeptides have 12 conserved regions within HIV-1 Gag, Pol and Nef that have been rearranged to minimize overall junctional responses. All eight vectors were used for transduction of moDCs in CD8+ T cell priming assays and are collectively labeled as "post vaccination" in assays using these sequences.

This example evaluates target gene expression in vitro and construction of Ad5 viral expression vectors. Similar strategy was adopted for evaluating the expression of conserved regions HIV Immunogen 2 (SEQ ID NO: 82-89) as described above in Example 5 for immunogen version 1 fusion polypeptides. The immunogen version 2 fusion polypeptide constructs are listed in Table E and schematically depicted in FIG. 21.

Results

The data depicted in FIGS. 22A-22B demonstrate that all conserved region polypeptide sequences resulted in the efficient expression (FIG. 22A) and transduction (FIG. 22B) of polynucleotides encoding the fusion polypeptides of SEQ ID NOs: 82-89.

Example 7

Viral Expression Vectors Containing Immunogenic Fusion Polypeptides in Immunogen 3

This example evaluates target gene expression in vitro and Construction of Ad5 viral expression vectors. Similar strategy was adopted for evaluating the expression of conserved regions HIV Immunogen 3 (SEQ ID NO: 90-93) as described above in Example 5 for the fusion polypeptides of immunogen version 1. The immunogen version 3 fusion polypeptide constructs are listed in Table E and schematically depicted in FIG. 23.

Results

The data depicted in FIGS. 24A-24B demonstrate that all conserved region polypeptide sequences resulted in the efficient expression (FIG. 24A) and transduction (FIG. 24B) of polynucleotides encoding the fusion polypeptides of SEQ ID NOs: 90-93.

We then tested the efficiency of these constructs in various viral vector systems to prime T cell responses in vitro and in vivo.

Example 8

In Vivo T Cell Activation Assays

In this example, we evaluated the efficacy of in vivo T cell priming by vaccine constructs in a mouse model. To do this, we immunized groups of mice with Ad5 vectors expressing computationally defined conserved regions vaccine immunogen sequences. We investigated the magnitude and functional phenotype of those responses to determine the immunogenicity of the vaccine sequences.

The vaccines were administered in a homologous (with respect to viral expression vector) prime-boost approach. Each viral Ad5 vector in the prime-boost pair had different rearrangements of the HIV gene segments encoded in the fusion polypeptide construct. This gene rearrangement reduced or eliminated the formation of junctional responses. Vectors may differ in the size of transgene that they can stably express. In the design of the vaccine immunogens two complementary fusion polypeptides of less than 600 amino acids in length each were expressed from a single viral vector. Vectors that can accommodate larger transgenes may combine two segments, e.g., using an F2A linker (described herein as "compound fusion polypeptides;" see Table F). We tested the immunogenicity of each individual fusion polypeptide sequence in a priming sequence, and again in a prime-boost sequence using vectors expressing compound fusion polypeptides with and without the F2A linker. Vectors that contained F2A linker also had an N-terminal tissue plasminogen (t-PA) signal peptide sequence (MDAMKRGLCCVLLLCGAVFVSAR (SEQ ID NO: 121)). The immunogen version 1 fusion polypeptide constructs are listed in Table E and schematically depicted in FIG. 25. The immunogen version 1 compound fusion polypeptide constructs are listed in Table F and schematically depicted in FIG. 19.

Methods

In Vivo Evaluation of Immunogenicity

Immunizations. Five or six-week-old Balb/c mice were immunized with $1\times10^9$ PFU of Ad5 vectors expressing HIV immunogens by intramuscular (I.M.) injections in both hind leg muscles. The vaccine vector was administered in 100 μl of phosphate-buffered saline (PBS) injections (50 μl per quadriceps). Mice were anesthetized with isoflurane prior to vaccine immunization. Animals were housed at the animal facility (Bioqual, Maryland) and experiments were performed according to approved IACUC protocol. A schematic of the regimen is provided in FIG. 26.

Single vector immunogenicity. Mice were randomly assigned into 8 groups and were primed with $1\times10^9$ PFU of Ad5 vectors expressing HIV immunogens (SEQ ID NOs: 94-101, schematically depicted in FIG. 25) by intramuscular (I.M.) injections in both hind leg muscles and rested for 16 days before splenocytes were harvested. Immunogenicity was evaluated by analyzing splenocytes by IFN-γ ELISpot assay as previously described (Miyahira, et al., *J Immunol Methods*, (1995) 181(1):45-54).

ELISpot Assays. Pre-coated strip ELISpot plates (Cellular Technologies Limited) were used for all ELISpot analyses. Briefly, $2\times10^5$ splenocytes from immunized animals were seeded to each well. Peptide pools having 15-mer peptides overlapping by 11 amino acid residues spanning the HIV Gag, Pol and Nef conserved regions sequences were used in IFN-γ ELISpot assays to evaluate vaccine immunogenicity. 2.5 ng/ml PMA and 250 ng/mL ionomycicn as well as 1 μg/mL ConA were used as positive controls. Plates were incubated at 37° C. in 5% $CO_2$ overnight and up to 18 hrs. After overnight stimulation, the cells were removed from the plates and the wells were washed two times in PBS prior to two washes with PBS containing 0.05% tween. Biotinylated anti-IFN-γ detection antibody was then added to the plates for 2 hours at room temperature. The plates were then washed three times with PBS containing 0.05% tween prior to the addition of streptavidin-conjugated alkaline phosphatase (AP). Wells were then washed two times with 0.05% tween-PBS and then two times with distilled water prior to the addition of the blue developer solution. The plates were then incubated at room temperature for 15 minutes before the reaction was stopped using tap water. The wells were then dried overnight and spot forming units (SFUs) were counted on an Immunospot ELISpot reader. The settings were identical for all plates and counts were expressed at SFU per $10^6$ splenocytes. A schematic of the vector variants is provided in FIG. 25, the immunization regimen is provided in FIG. 26, and the results are shown in FIGS. 27-28.

Homologous prime-boost. Mice were randomly allocated into 6 groups. Groups 1 and 2 mice were immunized with $1\times10^9$ PFU of Ad5 vectors expressing bivalent fusion polypeptides of SEQ ID NO: 105 (Seq 94-F2A-95) and SEQ ID NO: 109 (Seq 98-F2A-99) having N-terminal t-PA leader sequences, respectively, by intramuscular (i.m.) injections in both hind leg muscles and rested for 16 days before splenocytes were harvested. Groups 3 and 4 mice were immunized with $1\times10^9$ PFU of Ad5 vectors expressing bivalent fusion polypeptides of SEQ ID NO: 107 (Seq 96-F2A-97) and SEQ ID NO: 111 (Seq 100-F2A-101) having N-terminal t-PA leader sequences, respectively, by i.m. injections in both hind leg muscles and rested for 16 days before splenocytes were harvested.

Group 5 and 6 mice were immunized with 1×10$^9$ PFU of Ad5 vectors Seq-94-F2A-95 (tPA-SEQ ID NO: 105) and Seq 96-F2A-97 (tPA-SEQ ID NO: 107) expressing HIV immunogens utilized in Group 1 or 3 respectively, by i.m. injections in both hind leg muscles and rested for 29 days before homologous boost with vectors expressing the same antigens but rearranged to minimize junctional responses (Seq 98-F2A-99 (tPA-SEQ ID NO:109) and Seq 100-F2A-101 (tPA-SEQ ID NO: 111) immunogens utilized in Group 2 and 4 respectively). Immunogenicity and cellular phenotype were evaluated by analyzing splenocytes on Day 36 by ELISpot assay as previously described (Miyahira, et al., *J Immunol Methods*, (1995) 181(1):45-54), ICS by flow cytometry was conducted at day 16 after prime and day 36 after prime/boost. A schematic of the vector variants is provided in FIG. 19, the immunization regimen provided in FIG. 29 and results are shown in FIGS. 30-31.

Flow cytometry. Cell counts for prepared single-cell suspensions were determined using a hemacytometer. 1×10$^6$ cells/condition were stimulated with relevant HIV peptides in the presence of Golgi plug for a total of 6 hr (no more than 18 hrs). Washed cells were surface stained with live dead Aqua (Thermo fisher L34957) dye first and incubated with a mixture of fluorescence-conjugated anti-mouse antibodies for 20 min at 4° C. CD3 APC-Cy7 clone 17A2, CD4 PE-Cy7 clone GK 1.5, CD8 percp-Cy5.5 clone 53-6.7 were used for surface staining. After surface staining, cells were fixed and permeabilized in preparation for intracellular cytokine staining. Briefly, 1×10$^6$ cells already stained with surface antibodies were incubated with 200 μl BD cytofix/cytoperm buffer for 25 minutes on ice. Subsequently, cells were washed twice with 200 μl 1×Perm buffer each time and were then incubated with a cocktail of antibodies diluted in 100 μl of Perm buffer per 1×10$^6$ cells. A cocktail of fluorophore-conjugated anti mouse anti-IFN-γ APC clone XMG1.2, anti-IL-2 PE clone JES6-5H4 and anti-TNF-α FITC clone MP6-XT22 were used for intracellular cytokine staining. Permeabilized cells were then washed with 100 μl Perm buffer twice and immediately analyzed on MACSQUANT 10 Analyzer using MACS Quantify version 2.13 (Miltenyi Biotech) and analyzed using FlowJo software version 10.7 (TreeStar).

Results

The various viral Ad5 vector constructs expressing immunogen version 1 fusion polypeptides (SEQ ID NOs: 94-101; depicted in FIG. 25) were effective in priming a T cell response. Immunogenicity of these sequences was studied in a Balb/C mouse model by IM immunization as shown in FIG. 26.

Priming bivalent fusion polypeptides SEQ ID NOs: 94-95 and boosting bivalent fusion polypeptides SEQ ID NOs: 98-99 having HIV-1 Gag, Pol and Nef sequence segments induced robust responses to HIV-1 Gag (FIG. 27A(i and ii), with weaker but detectable responses to Pol proteins (protease, RT and integrase, (FIG. 27A(iii to vi). No responses were detected to HIV-Nef (FIG. 27A(vii and viii) in this model likely due to previously described immunodominance patterns for HIV-1 Gag epitopes in Balb/c mice and reflecting the lack of Nef epitopes that can be presented in Balb/c mice.

Priming bivalent fusion polypeptides SEQ ID NOs: 96-97 and boosting bivalent fusion polypeptides SEQ ID NOs: 100-101 having HIV-1 Pol and Nef induced robust responses to HIV-1 Pol, especially protease and RT (FIGS. 28(*i* and *ii*), with weaker responses to Pol integrase (FIGS. 28(*iii* and *iv*). Responses to HIV-Nef (FIGS. 28(*v* and *vi*) were also not seen with this set of sequences corroborating the observations from previous set of sequences (FIG. 27A(vii and viii)).

Figure 19:
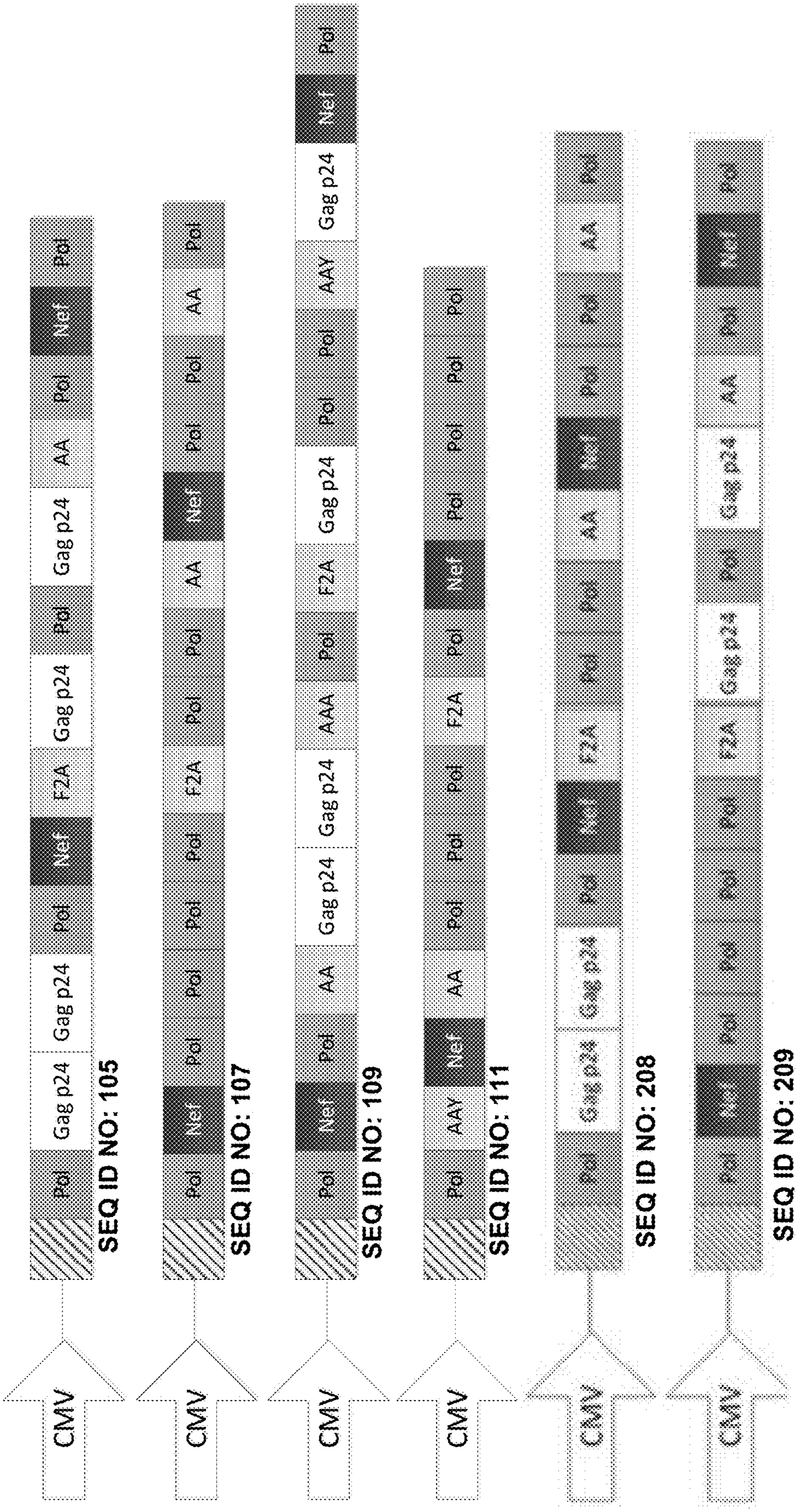
FIG. 19 illustrates a schematic representation of compound fusion polypeptides containing HIV-1 immunogen version 1 polypeptide sequences (e.g., SEQ ID NOs: 105, 107, 109, 111 and 206-209). The depicted compound fusion polypeptides have 12 conserved regions within HIV-1 Gag, Pol and Nef that have been rearranged to minimize overall junctional responses. All four vectors were used for transduction of monocyte-derived dendritic cells (moDCs) in CD8+ T cell priming assays and are collectively labeled as "post vaccination" in assays corresponding to these polypeptide sequences.

To test if combining these bivalent construct sequences designed to ensure coverage of >80% of circulating HIV-1 viral sequences into a single construct affects immunogenicity, individual sequences were combined using an F2A linker as shown in FIG. 19 (SEQ ID NOs: 105, 107, 109 and 111). The compound fusion polypeptides each had an N-terminal tPA leader sequence. Bivalent fusion polypeptide pairs, SEQ ID NOs: 94 and 95 were combined into Seq 94-F2A-95 (tPA-SEQ ID NO: 105), SEQ ID NOs: 96 and 97 were combined into Seq 96-F2A-Seq 97 (tPA-SEQ ID NO: 107), SEQ ID NOs: 98 and 99 were combined into Seq 98-F2A-Seq 99 (tPA-SEQ ID NO: 109) and SEQ ID NOs: 100 and 101 were combined into Seq 100-F2A-Seq 101 (tPA-SEQ ID NO: 111), respectively.

To test immunogenicity, these combined sequences were tested by IM immunization in Balb/C mice (FIG. 29), as single vectors in a prime only mode (FIG. 30A and in a homologous prime boost combination mode (FIG. 30B). Sequences Seq 94-F2A-95 (tPA-SEQ ID NO: 105) and Seq 98-F2A-99 (tPA-SEQ ID NO: 107) were used as bivalent fusion polypeptides having HIV-1 Gag, Pol and Nef sequence segments and were tested as prime and boost sequences in homologous vector prime boost combination mode. Seq 96-F2A-97 (tPA-SEQ ID NO: 109) and Seq 100-F2A-Seq 101 (tPA-SEQ ID NO: 111) were used as bivalent fusion polypeptides having HIV-1 Pol and Nef and were tested as prime and boost sequences in homologous vector prime-boost combination mode. The priming and boosting fusion polypeptides encode similar regions but are rearranged in order to reduce or eliminate creation of de novo epitopes that resemble epitopes from the human proteome and to reduce or eliminate boosting of junctional responses in prime boost sequences.

Combined sequences Seq 94-F2A-95 (tPA-SEQ ID NO: 105) and Seq 98-F2A-99 (tPA-SEQ ID NO: 109) when tested for immunogenicity either as single prime or in a prime/boost combination were immunogenic (FIG. 31A, responses to HIV-Gag(i), Pol (protease and RT(iii), Pol (integrase(v)) and Nef(vii) respectively and FIG. 27 HIV-1 Gag(i and ii), Pol (protease, RT and integrase(iii to vi) and Nef(vii and viii). Bivalent sequences concatenated with F2A did not inhibit their immunogenicity. Overall, responses to HIV-1 Gag were robust with weaker but detectable responses to Pol proteins (protease, RT and integrase) and minimal responses to HIV-Nef. Responses induced by priming sequence Seq 94-F2A-95 (tPA-SEQ ID NO: 105) were enhanced by boosting sequence Seq 98-F2A-99 (tPA-SEQ ID NO: 109), especially for Pol (integrase) (FIG. 30B(vi) and Nef (FIG. 30B(viii). No responses were generated to the F2A and tPA sequences.

Combined sequences Seq 96-F2A-97 (tPA-SEQ ID NO: 107) and Seq 100-F2A-101 (tPA-SEQ ID NO: 111) when tested for immunogenicity either as single prime or in a prime/boost combination were immunogenic, inducing robust responses to HIV-1 Pol, particularly protease and RT, with weaker responses detected toward integrase (FIG. 31A (i to iv). Magnitude of IFN-γ ELISpot responses induced by the combination vector Seq 96-F2A-97 (tPA-SEQ ID NO: 107) to Pol (protease and RT, FIG. 31B(i) were weaker than responses previously observed individual vectors expressing a fusion polypeptide of SEQ ID NO: 96 or 97 (FIG. 28(*i*). The responses were boosted in sequential dosing with Seq 96-F2A-97 (tPA-SEQ ID NO: 107) and Seq 100-F2A-101 (tPA-SEQ ID NO: 111) (FIG. 31B(ii). The responses induced by priming sequence Seq 96-F2A-97 (tPA-SEQ ID NO: 107) were enhanced by boosting sequence Seq 100-F2A-101 (tPA-SEQ ID NO: 111) against both Pol (integrase) (FIG. 31B(iv) and Nef (FIG. 31B(vi)).

The ability to produce cytokines is a functional measure of effector and memory CD4+ and CD8+ T cells. We evaluated the phenotypic and functional characteristics of CD4+ and CD8+ T cell responses generated following immunization with Ad5 vectors expressing compound fusion proteins of SEQ ID NOs: 105, 107, 109 or 111, using both single vector prime immunization and homologous prime/boost immunization. Responses were measured using ICS and Flow cytometry.

FIGS. 32-35 show immunogenicity against HIV-1 Gag, Pol and Nef antigens by intracellular cytokine staining (ICS) following single vector immunization with Seq 94-F2A-95 (tPA-SEQ ID NO: 105), or Seq 98-F2A-99 (tPA-SEQ ID NO: 109), and by homologous vector prime-boost immunization. The Y axis represents proportion of CD8+ (i, ii and iii) or CD4+ (iv, v and vi) T cells exhibiting HIV-1 Gag (FIG. 32), Pol (protease and RT) (FIG. 33), Pol (integrase (FIG. 34) and Nef (FIG. 35) specific responses by expressing cytokines IFN-γ, IL-2 and TNF-α, either as individual cytokines or combination of cytokines, as shown on X axis. Antigen specific values were obtained by subtracting no antigen stimulated control to exclude nonspecific responses. Strong HIV-1 Gag specific CD8+ and CD4+ T cell responses were seen in response to vaccination, with demonstrated polyfunctionality most robust in CD8+ T cells. Homologous prime-boost enhanced polyfunctionality of the CD8+ T cell responses. Even though generated, the Pol (protease, RT and integrase) specific and Nef specific CD8+ and CD4+ T cell responses produced after vaccination were weaker than Gag responses and tend to be monofunctional, with limited boosting.

FIGS. 36-38 show immunogenicity against HIV-1 Pol and Nef antigens by intracellular cytokine staining (ICS) following single vector immunization with Seq 96-F2A-97 (tPA-SEQ ID NO: 107), or Seq 100-F2A-101 (tPA-SEQ ID NO: 111), and by homologous vector prime-boost immunization. The Y axis represents proportion of CD8+ (i, ii and iii) or CD4+ (iv, v and vi) T cells exhibiting HIV-1 Pol (protease and RT) (FIG. 36), Pol (integrase (FIG. 37) and Nef (FIG. 38) specific responses by expressing cytokines IFN-γ, IL-2 and TNF-α, either as individual cytokines or combination of cytokines, as shown on X axis. Antigen specific values were obtained by subtracting no antigen stimulated control to exclude nonspecific responses. HIV-1 Pol (Protease and RT) specific CD4+ and CD8+ T cell responses were seen in response to vaccination with robust CD8+ T cell responses. Seq 100-F2A-101 (tPA-SEQ ID NO: 111) demonstrated strong immunogenicity with polyfunctionality (≥2 cytokines produced). Low levels of Pol (Integrase) and Nef specific CD4+ and CD8+ T cell responses were generated in response to vaccination and higher responses were seen with CD4+ T cells. Seq 100-F2A-101 (tPA-SEQ ID NO: 111) demonstrated and induced mostly monokine production. Homologous vector prime-boost immunization with the vectors encoding the fusion polypeptides enhanced both CD4+ and CD8+ T cell responses.

The data are consistent with the conclusion that the above tested HIV-1 bivalent sequences are immunogenic either as individual priming sequences, or when combined with an F2A linker, except for the Seq 96-F2A-Seq97 (tPA-SEQ ID NO: 107), and also in a homologous prime boost immunization. The magnitude of responses generated were antigen specific, CD4+ and CD8+ and expressed polyfunctionality.

Example 9

In Vitro Assays Demonstrating Human T Cell Activation Induced by Immunogens 1-3

In this example, we established an in vitro method for testing the efficacy of T cell priming in humans by vaccine constructs in expression vectors. The application of this method in vaccinology allows evaluation of antigen processing, presentation and priming of T cells in humans of the transgene cassette, as well as the study of immune parameters including adjuvants and immune modulators that may modify the efficacy of priming.

Methods

Monocyte purification and maturation of monocyte derived dendritic cells (moDCs). Freshly isolated or cryopreserved PBMCs were used in the moDC-based T cell stimulation assays. CD14+ monocytes were purified from PBMCS from individuals with or without HIV, and ART naïve or on ART using the EasySep human anti-CD14 positive selection antibody kit (StemCell Technologies). Flow cytometry was used to confirm the purification of the isolated CD14+ monocytes to >90% prior to the establishment of the culture. To generate immature moDCs, $2\times10^6$ purified CD14+ monocytes were cultured in 3 mL of moDC differentiation media (complete RPMI 1640 containing 10% heat inactivated fetal calf serum, 1% penicillin streptomycin/mL, 0.5 mM HEPES, 800 U/mL of GM-CSF (Miltenyi Biotec), and 1000 U of IL-4 (Miltenyi Biotec)) in 6 well culture plates. The plates were incubated at 37° C. and 5% $CO_2$ for 6 days and monitored daily to ensure adherence of monocytes. To generate mature moDCs, adherent immature moDC cultures were supplemented with recombinant soluble CD40L (0.5 μg/ml), IFN-γ (1,000 U/ml), PGE2 (5 μM), TNF-α (10 ng/ml), IL-6 (100 ng/ml) and IL-1β (10 ng/ml) with an additional 3 ml of moDC differentiation media on day 6 and incubated at 37° C. and 5% $CO_2$ for an additional 48 hrs.

On day 8, adherent mature moDCs were detached using ice-cold PBS and a cell scrapper to manually detach the moDCs. Following this procedure, unattached cells were washed using moDC differentiation media and transferred to a 50 ml centrifuge tube. The resulting cell mixture was centrifuged at 1500 rpm for 5 minutes at room temperature. Next, the supernatant was discarded and the cell pellet was resuspended in 5 ml of moDC differentiation media. A fraction of the mature moDCs were isolated and stained to characterize the differentiation phenotype of the moDCs with antiCD11c+, anti-HLA-DR+, anti-CD14-, anti-CD40+, anti-DCSIGN+, anti-CD83, anti-CD86 and anti-OX40L antibodies.

Transduction of moDCs with Adenovirus 5 (Ad5) viral vectors. The purified moDCs were harvested, washed twice in serum-free media, and re-suspended in X-Vivo 15 (Bio-Whittaker, Walkersville, MD) at $10^7$/ml. Cells were equilibrated at 37° C. in a water bath for 20-30 min before transduction. Ad5 stocks expressing vaccine immunogen or empty vector controls were thawed on ice and added to the moDC suspension at a multiplicity of infection (MOI) of 500. Cells were gently mixed and placed immediately in the 37° C. incubator. After 2 hours, warm moDC differentiation media containing GM-CSF and IL-4 were added to dilute the moDCs to a final concentration of $10^6$/ml. Transduced moDCs ($4\times10^6$) were transferred to T75 cell culture flasks and maintained at 37° C. in 5% $CO_2$ for an additional 48 h before addition of autologous PBMCs.

Co-culture of autologous PBMCs with moDCs. In experiments evaluating the immunogenicity of our conserved regions vaccines, autologous PBMCs were enumerated and $80\times10^6$ PBMCs were co-cultured with $4\times10^6$ moDCs that had been transduced with Ad5 vectors expressing vaccine immunogens or Ad5 empty vector controls. The PBMC-moDC co-cultures proceeded for a period of 10 days in the presence of IL-2 (50 U/ml), IL-7 (10 ng/ml), Efavirenz (0.1 μM) and Elvitegravir (0.1 μM). Co-cultures of moDC and PBMCs were set up at a moDC:PBMC ratio of 1:20.

IFN-γ ELISpot Assays. Pre-coated strip ELISpot plates (Cellular Technologies Limited) were used for all ELISpot analyses. Briefly, $3\times10^4$ cells from Day 10 moDC-PBMC cultures were seeded to each well. Vaccine-matched peptides consisting of 15-mers overlapping by 11 amino acids spanning the entire HIV conserved regions immunogen were assembled into 384 ELISpot plates with each individual well corresponding to an individual 15-mer peptide and used in IFN-γ ELISpot assays to evaluate vaccine immunogenicity. For positive controls, 50 ng/ml PMA (Sigma) was added. Plates were incubated at 37° C. in 5% $CO_2$ for 24 h. After 24 h stimulation, the cells were removed from the plates and the wells were washed three times in PBS prior to three washes with PBS containing 0.05% tween. Biotinylated anti-IFN-γ detection antibody was then added to the plates for 2 hours at room temperature. The plates were then washed three times with PBS containing 0.05% tween prior to the addition of streptavidin-conjugated alkaline phosphatase (AP). Wells were then washed two times with 0.05% tween-PBS and then two times with distilled water prior to the addition of the blue developer solution. The plates were then incubated at room temperature for 15 minutes before the reaction was stopped using tap water. The wells were then dried overnight and spot forming units (SFUs) were counted on an Immunospot ELISpot reader. The settings were identical for all plates and counts were expressed at SFU per $3\times10^4$ PBMCs. The SFU were calculated as number of spots in test wells minus the mean number of spots in medium control wells. Positive responses were defined as >3-fold higher SFUs compared to medium control wells and >5 spots per well ($3\times10^4$ cells). Medium control wells contained media reconstituted with a similar composition of DMSO as peptide stimulated test wells. A schematic summarizing the moDC-PBMC culture and ELISpot assay is depicted in FIG. 39.

In vitro viral inhibition assay. The capacity of vaccine-induced CD8+ T cells to suppress HIV-1 infection of autologous CD4+ T cells was evaluated to determine cytotoxicity. CD4+ T cells were isolated using negative magnetic bead selection (StemCell Technologies) from cryopreserved PBMCs, rested for 24 h and cultured in RPMI and 10% FBS. After 24 h, cultured CD4+ T cells were washed, counted and added to 50 ml conical tubes for spinoculation with HIV-1BaL at a multiplicity of infection (MOI) of 0.01. Spinoculation was performed by centrifugation at 1200 g for 2 h. After infection, CD4+ T cells were washed twice and cultured in in RPMI and 10% FBS and IL-2 (30 U/ml) for 72 h. After 72 h, CD8+ T cells were isolated at the end of the PBMC-moDC co-cultures using negative magnetic bead selection (StemCell Technologies), labeled with CFSE and counted. Meanwhile, cultured CD4+ T cells were washed, counted and plated in U-bottom 96 well plates with vaccine-induced CD8+ T cells at a 1:1 ratio in RPMI and 10% FBS. Three days post co-culture of CD4+ T cells and CD8+ T cells, cells were stained with viability dye and surface markers, followed by intracellular detection of HIV-1 Gag (Beckman Coulter) using the IC Fixation/Permeabilization kit (BD Biosciences) according to the manufacturer's protocol. Cells were incubated with a mixture of fluorescence-conjugated anti-human antibodies for 30 min at 4° C. Stained cells were washed twice using FACS buffer (PBS, 2% FCS, 0.1% $NaN_3$), acquired with an LSR II flow cytometer using FACSDiva software (BD), and analyzed using FlowJo software version 10.2 (TreeStar). For surface staining, cells were stained with anti-CD4 BV605 clone OKT4, anti-CD8 BV650 clone RPA-T8, anti CD3 AF700 clone SK7, anti-CD20 BV421 clone 2H7, Live-dead Aqua dye (ThermoFischer). For intracellular detection of p24, cells were fixed and permeabilized using Cytofix/cytoperm buffers (BD Biosciences) and stained with anti-HIV Gag p24 PE (KC57). All experiments were performed in duplicate or triplicate, depending on cell availability. Uninfected CD4+ T cells were included as negative controls and infected CD4+ T cells cultured without CD8+ T cells served as 100% infectivity controls. Productive infection was considered only when >0.1% p24 Gag+CD4− cells were detected by flow cytometry for each independent sample.

Results

In this example, we used the in vitro T cell priming assay described herein to evaluate immunogenicity and decode the CD8+ T cell responses to the vaccine immunogen (schematic provided in FIG. 39). We focused on determining the epitopes within conserved regions vaccine that induce antigen specific T cell responses and evaluated the impact of pre-existing responses on induction of de novo responses. Monocyte derived DCs were transduced with viral vectors containing a vaccine transgene were able to prime autologous vaccine antigen specific T cells in vitro. This assay can facilitate the preclinical evaluation of vaccine constructs and provides a useful tool for the identification of immunogenic regions within the conserved region vaccine across a broad repertoire of participants prior to initiation of large-scale vaccine trials.

We completed the evaluation of immunogenicity for immunogen 1 (SEQ ID NOs: 105, 107, 109 and 111) in N=93 HIV-1+ participant samples. Patient to patient variability is observed in transduction efficiency of moDCs and may reflect variability in expression of receptors to facilitate uptake of viral vectors as would be expected in a heterogeneous human population (FIGS. 40-41).

The heat map depicted in FIG. 40 summarizes the profile of the breadth of immune responses to each HIV protein in all 93 participants after in vitro priming with SEQ ID NOs: 105, 107, 109 and 111. Our data shows that in vitro vaccination resulted in induction of responses to conserved regions (≥1 epitope) in 80% (74/93) of tested samples, suggesting that vaccination re-focuses immune responses to conserved regions. Additionally, while vaccination with conserved regions vaccine boosted 25% of pre-existing detectable responses, 69% of all responses identified post vaccination were de novo T cell responses primarily to conserved Gag and Pol epitopes that were not detected in the pre-vaccine condition (Ad5-empty vector control) (FIG. 42). Vaccination also significantly enhanced the breadth of immune responses to Gag, Pol and Nef antigens (median total breadth of responses=5, median Gag breadth=2, median Pol breadth=2 and median Nef breadth=0; FIG. 40). Detailed analysis further showed that vaccination significantly enhanced the fraction of participants responding to ≥3 epitopes within each of Gag, Pol and Nef (FIG. 41). We chose to evaluate responses that were greater than 3 epitopes given the data from the STEP Trial. See, Janes, et al., *J Infect Dis* (2013) 208(8):1231-1239; ClinicalTrials.gov identifier: NCT00095576.

To determine whether vaccine-induced CD8+ T cells could eliminate HIV-1 infected cells in vitro, we performed HIV-1 viral inhibition assays. CD4+ T cells from participants were infected with HIV-1BaL and co-cultured either alone or in the presence of purified vaccine or empty vector primed CD8+ T cells. Data from 51/68 participants who demonstrated a productive infection rate with HIV-1BaL (≥0.1% p24 Gag+ cells) were used in our analysis (FIG. 43). The data in FIG. 44B shows that CD8+ T cells from 69% (N=35/51) of participants demonstrated increased suppression of HIV-1BaL in vitro in the presence of vaccine (SEQ ID NOs: 105, 107, 109 and 111) primed CD8+ T cells compared to empty vector primed CD8+ T cells. To evaluate whether there was a correlation between breadth of responses and CD8+ T cell mediated suppression of HIV-1BaL, we evaluated breadth and cytotoxicity in each participant that had demonstrated a productive infection rate with HIV-1BaL (≥0.1% p24 Gag+ cells). The data in FIG. 44B shows a lack of correlation between % residual Gag+ cells with Gag/Pol breadth which may be indicative that the quality of responses was more important.

We also evaluated immunogenicity of immunogen version 2 (SEQ ID NOs: 82-89) and immunogen version 3 (SEQ ID NOs: 90-93), using the moDC-T cell priming assay described above, in N=3 participants. The data, summarized in FIGS. 45A and 45B, show the breadth and magnitude of total, Gag, Pol and Nef immune responses to each immunogen. For immunogen version 2, in a single donor in vitro priming with the vaccine sequence resulted in expansion of the response from 2 to 14 independent epitopes; for immunogen version 3, the median breadth of the response was 3.

Example 10

Non-Human Primate (NHP) Arenavirus Vector Data

Heterologous prime-boost in non-human primates. Simian immunodeficiency virus infection in NHPs serves as a good model for evaluating HIV vaccine vector immunogenicity. To evaluate the immunogenicity of replication-competent LCMV (TT1) and replication-competent PICV (TT2) vectors in NHPs (e.g., vectors as described in WO2016075250 and WO2017198726), we developed vectors expressing full length SIV proteins Gag, Env or Pol derived from the $SIV_{sme543}$ strain. The amino acid sequences are provided in Table 2. Indian-origin healthy rhesus macaques were immunized via IM route with the arenavirus vectors. The Gag and Env expressing vectors (replication attenuated Pichinde arenavirus (TT2) and replication attenuated LCMV arenavirus (T T1)) were administered on the left quadricep whereas the Pol expressing vectors (TT2 and TT1) were administered on the right quadricep. The doses administered are as below: $1\times10^6$ RCV of TT2 Gag, $1\times10^6$ RCV of TT2 Env, $1\times10^6$ RCV of TT2 Poll/Pol 2, $4\times10^6$ RCV of TT1 Gag, $4\times10^6$ RCV of TT1 Env, and $2\times10^6$ RCV of TT1 Poll/Pol 2. In the placebo group, NHPs were administered placebo buffer solution composed of 10 mM HEPES, 150 mM NaCl, 20 mM Glycine and 0.1% macaque serum albumin.

TABLE 2 amino acid sequences of full length SIV proteins Gag, Env or Pol derived from the SIVsme543 strain

| SEQ ID NO: | SIV protein | Amino acid sequence |
|---|---|---|
| 228 | SIV GAG | MGARNSVLSGKKADELEKIRLRPNGKKKYMLKHVVWAANELDRFGLAESLLDNKEGCQKILSVLAPLVPTGSENLKSLYNTVCV<br>IWCIHAEEKVKHTEEAKQIVQRHLVVETGTADKMPATSRPTAPPSGRGGNYPVQQVGGNYVHLPLSPRTLNAWVKLVEEKKFGA<br>EVVPGFQALSEGCTPYDINQMLNCVGEHQAAMQIIREIINEEAADWDLQHPQPGPLPAGQLREPRGSDIAGTTSTVEEQIQWMY<br>RQQNPIPVGNIYRRWIQLGLQKCVRMYNPTNILDVKQGPKEPFQSYVDRFYKSLRAEQTDPAVKNWMTQTLLIQNANPDCKLVL<br>KGLGMNPTLEEMLTACQGIGGPGQKARLMAEALKEALRPDQLPFAAVQQKGQRRTIKCWNCGKEGHSARQCRAPRRQGCWGCGK<br>TGHVMAKCPERQAGFLGFGPWGKKPRNFPMAQMPQGLTPTAPPEDPAVDLLKNYMKMGRKQRENRERPYKEVTEDLLHLNSLFG<br>EDQ |
| 229 | Pol1-Protease/RT | PQFSLWRRPVVTAYIEEQPVEVLLADDSIVIGIELGPNYTPKIVGGIGGFINTKEYKDVKIKVLGKVIKGTIMIGDTPINIFGR<br>NLLTAMGMSLNFPIAKVEPIKVTLKPGKEGPKLRQWPLSKEKIIALREICEKMEKDGQLEEAPPINPYNTPTFAIKKKDKNKWR<br>MLIDFRELNKVTQDFTEVQLGIPHPAGLAKRRRITVLDVGDAYFSIPLDEEFRQYTAFTLPSVNNAEPGKRYIYKVLPQGWKGS<br>PAIFQYTMRNVLEPFRKANPDVTLIQILIASDRIDLEHDRVVLQLKELLNGIGFSTPEEKFQKDPPFQWMGYELWPTKWKLQKI<br>ELPQRETWTVNDIQKLVGVLNWAAQIYPGIKTKHLCRLIRGKMTLTEEVQWTEMAEAEYEENKIILSQEQEGCYYQEGKPIEAT<br>VIKSQDNQWSYKIHQEDKVLKVGKFAKVKNTHINGVRLLAHVVQKIGKEALVIWGEVPKFHLPVEREIWEQWWTDYWQVTWIPD<br>WDFVSTPPLVRLVFNLVKEPIQGAETF |
| 230 | Pol2-RNaseH/Integrase | YVDGSCNRQSREGKAGYVTDRGRDKAKLLEQTTNQQALEAFYLALADSGPKANIIVDSQYVMGIVAGQPTESESRLVNQIIEEM<br>IKKEAIYVAWVPAHKGIGGNQEVDHLVSQGIRQVLFLEKIEPAQEEHEKYHSNVKELVFKFGIPRLVAKQIVDTCDRCHQKGEA<br>IHGQVNAELGTWQMCTHLEGKIIIVAVHVASGFIEAEVIPQETGRQTALFLLKLAGRWPITHLHTNGANFTSQEVKMVAWWAGI<br>EQTFGVPYNPQSQGVVAMNHHLKTQIDRIREQANSVETIVLMAVHCMNFKRRGGIGDMTPAERLVNMITTEQEIQFQQSKNSKF<br>KNFRVYYREGRDQLWRGPGELLWKGEGAVILKVGTEIKVVPRRKAKIIKDYGGGKELDSGSHLEDTGEAREVA |
| 231 | SIV sm543 Env | MGCLGNQLLIALLLVSVLEICCVQYVIVFYGVPAWKNATIPLFCATRNRDTWGTTQCLPDNDDYSELAVNITEAFDAWNNTVTE<br>QAIEDVWNLFETSIKPCVKLTPLCIAMRCNKTETDRWGLTGRAETTTTAKSTTSTTTTTVTPKVINEGDSCIKNNSCAGLEQEP<br>MIGCKFNMTGLKRDKKIEYNETWYSRDLICEQPANGSESKCYMQHCNTSVIQESCDKHYWDAIRFRYCAPPGYALLRCNDSNYS<br>GFAPKCSKVVVSSCTRMMETQTSTWFGENGTRAENRTYIYWHGNSNRTIISLNKYYNLTMKCRRPGNKTVLPVTIMSGLVFHSQ<br>PINERPKQAWCRFGGNWSEAIQEVKETLVKHPRYTGTNDTRKINLTAPAGGDPEVTFMWTNCRGEFLYCKMNWFLNWVEDRDQN<br>SNRWKQQKKPEQQKRNYVPCHIRQIINTWHKVGKNVYLPPREGDLTCNSTVTSLIAEIDWINNNETNITMSAEVAELYRLELGD<br>YKLVEITPIGLAPTDVRRSLTLSAQSRTLLAGIVQQQQQLLDVVKRQHELLRLTVWGTKNLQTRVTAIEKYLKDQAQLNDSLVP<br>NWDNMTWQEWEGKVDFLEANITQLLEEAQIQQEKNMYELQKLNSWDIFGNWFDLTSWIRYIQ |

IFN-γ ELISpot Assays. Pre-coated strip ELISpot plates (MabTech) were used for all ELISpot analyses. Briefly, $2\times10^5$ PBMCs isolated from whole blood at each of the timepoints analyzed was seeded to each well. SIV smE543 peptides consisting of 15-mers overlapping by 11 amino acids spanning the SIV immunogens Gag, Env and Pol at a final concentration of 1 μg/ml were assembled into 96-well ELISpot plates. To determine breadth of responses to Gag, Env and Pol, sub-pools of 12, 16 or 23 peptides respectively were tested individually at a final concentration of 1 ug/ml. Each sub-pool had 10 peptides composed of 15-mers overlapping by 11 amino acids. Each sample was tested in duplicates. For positive controls, 5 μg/ml PHA (Sigma) was added. Medium control wells contained cell culture media reconstituted with a similar composition of DMSO as peptide stimulated test wells. Plates were incubated at 37° C. in 5% $CO_2$ for 20-24 h. After overnight stimulation, the cells were removed from the plates and the wells were washed three times in PBS prior to three washes with PBS containing 0.05% tween. Biotinylated anti-IFN-γ detection antibody was then added to the plates for 2 hours at room temperature. The plates were then washed three times with PBS containing 0.05% tween prior to the addition of streptavidin-conjugated alkaline phosphatase (AP). Wells were then washed two times with 0.05% tween-PBS and then two times with distilled water prior to the addition of the blue developer solution. The plates were then incubated at room temperature for 15 minutes before the reaction was stopped using tap water. The wells were then dried overnight and spot forming units (SFUs) were counted on an Immunospot ELISpot reader. The settings were identical for all plates and counts were expressed at SFU per $2\times10^5$ PBMCs. To determine a proper spot count using the CTL Single Color immunospot counting software, multiple parameters were normalized relative to the sample. Signal sensitivity is set to the highest value before non-specific spots begin to appear. Spot size is reduced to the point where all real spots are counted but artifacts are not. Background signal reduction is set to avoid counting artifacts. The SFU were calculated as number of spots in test wells minus the mean number of spots in medium control wells. Positive responses were defined as >3-fold higher SFUs compared to medium control wells and >50 spots per $1\times10^6$ PBMCs.

SIV Challenge and Viral Load. All animals in the study were challenged at 4 weeks post the last vaccine dose (i.e., week 32 of study) with a single intravenous (IV) inoculation of a heterologous SIV virus swarm (SIVmac251, 8.19 $TCID_{50}$). The viral sequence of the challenge virus differs from that in the vaccine sequence (SIVsme543). The estimated AID50 of the SIVmac251 challenge stock is 0.29 $TCID_{50}$ via the IV route. Post challenge, all animals were monitored for clinical and laboratory progression as well as viral load to determine peak viral load (calculated at 2 weeks post challenge) and set point viral load (calculated over weeks 10-40 post challenge). Plasma SIV viral load as copies/ml was quantified by two-step RT-PCR assay performed in duplicates.

Results

FIG. 47A shows the magnitude of SIV-specific IFN-γ responses as assessed by IFN-γ ELISpot. Boosting by TT1 results in a robust increase in response at week 14. The peak magnitude of response observed at 2 weeks post each vaccine dose is maintained with each subsequent boost.

FIG. 47B shows the categorization of the animals that received the heterologous TT2/TT1 vaccine as moderate or high responders. This is based on the magnitude of peak response post each vaccine dose being less or more than 1000 SFU/million PBMCs respectively. The majority of the animals (17 of 24) were high responders with all animals showing a positive response to at least one SIV immunogen.

FIGS. 48A-D demonstrate the magnitude of peak SIV-specific IFN-γ responses at 2 weeks post each vaccine dose. Peak Gag- and Pol-specific responses are maintained after doses 2, 3 and 4. Env-specific responses increased with each subsequent dose. After four doses of the heterologous vaccine, a positive response to Gag, Env and Pol is observed in at least 21 of 24 NHPs (response rate=87.5%).

With respect to breadth, highest total SIV-specific breadth was observed post-dose 3 compared to post-doses 2 and 4. Similarly, significantly higher Env- and Pol-specific breadth observed post-dose 3 compared to post dose 2 and 4. Gag-specific breadth is significantly high post dose 3 and 4 compared to post dose 2. These results suggest the induction of TT2/TT1 vaccine-induced breadth of responses to Gag, Env and Pol-specific immunogens at 2 weeks post each vaccine boost dose. See, FIGS. 49A-D.

With respect to SIV challenge and viral load, post-challenge, reduced viral load was observed in the TT2/TT1 group compared with the placebo group (FIG. 50A). The median peak viral load measured at 2 weeks post challenge with SIVmac251 was 6.54 log 10 SIV copies/ml in the TT2/TT1 group and 7.2 log 10 SIV copies/ml in the placebo group. A significant decrease in peak viral load ( p=0.0046, Mann-Whitney t-test) was observed in the TT2/TT1 vaccinated NHPs compared to the placebo group (FIG. 50**B). The setpoint viral load was calculated as the average SIV viral load over weeks 10-40 post challenge. The median setpoint VL was 5.5 log 10 SIV copies/ml in the TT2/TT1 group and 6.7 log 10 SIV copies/ml in the placebo group. A significant decrease of 1.2 log 10 SIV copies/ml in setpoint viral load (* p=0.0291, Mann-Whitney t-test) was observed in the TT2/TT1 vaccinated NHPs compared to the placebo group (FIG. 50C). These data demonstrate the prophylactic efficacy of heterologous TT2/TT1 prime-boost schemes of PICV/LMCV replication-attenuated arenavirus vectors encoding SIV immunogens in a SIV challenge model in NHPs.

Example 11

Replication-Attenuated Arenavirus Vectors Containing HIV-1 Immunogen Version 1 Fusion Polypeptide-Encoding Transgenes In this example, we generated replication-attenuated arenavirus-based viral vectors encoding the computationally defined polypeptide antigens containing conserved regions of HIV-1 encoded by Gag, Nef and Pol genes as a transgene. Replication-attenuated arenavirus vectors based on Pichinde Virus (PICV) and Lymphocytic choriomeningitis virus (LCMV) were generated. The polypeptide segments containing conserved regions were concatenated or connected by different approaches including direct fusion, or the addition of various flexible linkers between regions. The transgenes were segregated and encoded on both viral S-Segments (NP-Segment and GP-Segment). In a first replication-attenuated LCMV vector, the NP-Segment was replaced with a polynucleotide encoding a fusion polypeptide of SEQ ID NO: 98 and the GP-Segment was replaced with a polynucleotide encoding a fusion polypeptide of SEQ ID NO: 100. In a second replication-attenuated LCMV vector, the NP-Segment was replaced with a polynucleotide encoding a fusion polypeptide of SEQ ID NO: 99 and the GP-Segment was replaced with a polynucleotide encoding a fusion polypeptide of SEQ ID NO: 101. In a first replication-attenuated PICV vector, the NP-Segment was replaced with a polynucleotide encoding a fusion polypeptide of SEQ ID NO: 94 and the GP-Segment was replaced with a polynucleotide encoding a fusion polypeptide of SEQ ID NO: 96. In a second replication-attenuated PICV vector, the NP-Segment was replaced with a polynucleotide encoding a fusion polypeptide of SEQ ID NO: 95 and the GP-Segment was replaced with a polynucleotide encoding a fusion polypeptide of SEQ ID NO: 97. Schematics of the fusion polypeptides are provided in FIG. 25.

Methods

Construction and generation of replication-attenuated arenavirus vectors containing HIV-1 fusion polypeptide transgene polypeptide variants. Replication-attenuated arena virus vectors expressing HIV-1 computationally defined vaccine immunogens, were generated as described previously (Kallert, et al, *Nat Commun.* (2017) 8:15327; see also, WO2016075250 and WO2017198726). Briefly, cDNA sequences were synthesized and subcloned into the respective backbone plasmids. Plasmids for each viral genomic segment and plasmids expressing the viral trans-acting factors NP and L, were transfected into LCMV-GP complementing cells. Cell culture supernatant was harvested and further propagated on HEK293 suspension cells, to generated vector stock material (passage 1 (P1)). The vectors developed for this evaluation are listed in Table 3 and schematically depicted in FIG. 25.

TABLE 3

Arenavirus Vectors Encoding HIV-1 Immunogen 1 Fusion Polypeptides

| Vector Name | Arenavirus | Fusion Polypeptide (SEQ ID NOs) | Transgene (SEQ ID NOs) |
|---|---|---|---|
| TT1-HIV-GNP1/PN1 | LCMV | NP - SEQ ID NO: 98 | NP - SEQ ID NO: 140 |
| | | GP - SEQ ID NO: 100 | GP - SEQ ID NO: 146 |
| TT1-HIV-GNP2/PN2 | LCMV | NP - SEQ ID NO: 99 | NP - SEQ ID NO: 143 |
| | | GP - SEQ ID NO: 101 | GP - SEQ ID NO: 149 |
| TT2-HIV-GNP1/PN1 | PICV | NP - SEQ ID NO: 94 | NP - SEQ ID NO: 131 |
| | | GP - SEQ ID NO: 96 | GP - SEQ ID NO: 135 |
| TT2-HIV-GNP2/PN2 | PICV | NP - SEQ ID NO: 95 | NP - SEQ ID NO: 133 |
| | | GP - SEQ ID NO: 97 | GP - SEQ ID NO: 137 |

Evaluation of target gene expression by detection of the conserved region for Gag (p24). We evaluated transgene expression by detection of the conserved region for Gag (p24) either by Immunoblot or Double-Immuno staining (DI). For immunoblot analysis, infected HEK293 cells were harvested and lysed, before applying whole cell lysates to acrylamide gel electrophoresis. After blotting, membranes were incubated using either a mouse mAb [39/5.4A] to detect HIV1 p24 (Abcam (ab9071)), a rabbit pAb ERK-2 (sc-154; Santa Cruz) or antibodies for detection of successful infection (rabbit pAb anti LCMV-NP (University of Genf, Prof. Doron Merkler); mouse mAb anti PICV-NP (University of Basel; Prof. Daniel Pinschewer).

Evaluation of stable transgene integration by serial passaging of viral vectors. We evaluated transgene stability of replication-attenuated arenavirus vectors, by serial passaging of vectors stock material in HEK293 suspension cells. To this end, P1 stock material infectious titer was determined by Focus Forming Assay, and HEK293 cells were infected using a multiplicity of infection (MOI) of 0.001. Progeny virus was harvested 72 hours post infection and again titrated. Further passages were infected applying the same principle. After a maximum eight passages, virus containing supernatant samples were analyzed by transgene PCR and/or DI staining. For transgene PCR analysis, RNA from virus containing supernatant was extracted and subsequently reverse transcribed and amplified by PCR using specific HIV-transgene flanking primers. PCR products were applied to gel electrophoresis analysis to evaluate transgene PCR fragment length as an indicator of transgene stability.

Results

Evaluation of HIV-1 fusion polypeptide transgene expression by immunoblot analysis. We could verify expression of Gag/Nef/Pol antigen by immunoblot analysis of cell lysates of three replicates per vector. The results are shown in FIG. 52.

Evaluation of stable integration of HIV-1 fusion polypeptide transgene by serial passaging. To evaluate, whether HIV-1 Immunogen 1 transgenes are stably encoded in replication attenuated arenaviral vectors over several passages, we analyzed cell culture supernatant and performed transgene PCR analysis. The passage level at which the majority (≥50%) of the transgene specific band still shows the expected full-length size, was considered the last passage level with stable transgene insertion. Results are shown in Table 4 and FIGS. 53-56. Further, where applicable, supernatant samples harvested from each passaging step were applied to double-immuno staining (DI staining), to determine the ratio of HIV-1 Gag and arenavirus-NP expression. A combination of both results allowed for a more accurate assessment of transgene stability of HIV-1 Immunogen 1 transgenes.

We found that replication attenuated-LCMV HIV antigen encoding vectors to stably encoded the transgenes up to passage level 7, while replication attenuated-PICV HIV antigen encoding vectors stably encoded the transgenes to passage levels 4 and 6.

TABLE 4

Overview Table for Assessment of Transgene Genetic Stability

| Vector Name | Arenavirus | Transgene Stability Through Passage (P) |
|---|---|---|
| TT1-HIV-GNP1/PN1 | LCMV | P7 |
| TT1-HIV-GNP2/PN2 | LCMV | P7 |
| TT2-HIV-GNP1/PN1 | PICV | P6 |
| TT2-HIV-GNP2/PN2 | PICV | P4 |

P# indicates number of passages

Replication-attenuated-LCMV HIV antigen encoding vectors stably retained the transgenes encoding the fusion polypeptides SEQ ID NOs 98 and 100 (TT1-HIV-GNP1/PN1) and SEQ ID NOs: 99 and 101 (TT1-HIV-GNP2/PN2) up to passage level 7. Replication-attenuated-PICV vector TT2-HIV-GNP1/PN1 stably retained transgenes encoding fusion polypeptides SEQ ID NOs: 94 and 96 up to passage level 6 and replication attenuated-PICV vector TT2-HIV-GNP2/PN2 stably retained transgenes encoding fusion polypeptides SEQ ID NOs: 95 and 97 up to passage level 4, however.

Example 12

Replication-Attenuated Arenavirus Vectors Containing HIV-1 Immunogen Version 2 Fusion Polypeptide-Encoding Transgenes In this example, we generated replication attenuated arenavirus based viral vectors encoding shorter computationally defined polypeptide antigen HIV-1 Immunogen 2, containing conserved regions of HIV-1 including Gag, Nef and Pol genes as a transgene. Replication-attenuated arenavirus vectors based on Pichinde Virus (PICV) and Lymphocytic choriomeningitis virus (LCMV) were generated. The polypeptide segments containing conserved regions were concatenated or connected by different approaches including direct fusion, or the addition of various flexible linkers between regions. The transgenes were segregated and encoded on both viral S-Segments (NP-Segment and GP-Segment). In a first replication-attenuated LCMV vector, the NP-Segment was replaced with a polynucleotide encoding a fusion polypeptide of SEQ ID NO: 84 and the GP-Segment was replaced with a polynucleotide encoding a fusion polypeptide of SEQ ID NO: 88. In a second replication-attenuated LCMV vector, the NP-Segment was replaced with a polynucleotide encoding a fusion polypeptide of SEQ ID NO: 85 and the GP-Segment was replaced with a polynucleotide encoding a fusion polypeptide of SEQ ID NO: 89. In a first replication-attenuated PICV vector, the NP-Segment was replaced with a polynucleotide encoding a fusion polypeptide of SEQ ID NO: 82 and the GP-Segment was replaced with a polynucleotide encoding a fusion polypeptide of SEQ ID NO: 86. In a second replication-attenuated PICV vector, the NP-Segment was replaced with a polynucleotide encoding a fusion polypeptide of SEQ ID NO: 83 and the GP-Segment was replaced with a polynucleotide encoding a fusion polypeptide of SEQ ID NO: 87. Schematics of the fusion polypeptides are provided in FIG. 21.

Methods

Construction and generation of replication attenuated arenavirus vectors containing HIV-1 Immunogen 2 transgene polypeptide variants. Replication-attenuated PICV and replication-attenuated LCMV viral vectors expressing HIV-1 computationally defined vaccine immunogens, were generated as described previously (Kallert, et al, (2017) *Nat. Comm*., supra). Briefly, cDNA sequences were synthesized and subcloned into the respective backbone plasmids. Plasmids for each viral genomic segment and plasmids expressing the viral trans-acting factors NP and L, were transfected into LCMV-GP complementing cells. Cell culture supernatant was harvested and further propagated on HEK293 suspension cells, to generate vector stock material (passage 1). The vectors developed for this evaluation are listed in Table 5 and schematically depicted in FIG. 21.

TABLE 5

Arenavirus Vectors Encoding HIV-1 Immunogen 2 Fusion Polypeptides

| Vector Name | Arenavirus | Fusion Polypeptide (SEQ ID NOs) | Transgene (SEQ ID NOs) |
|---|---|---|---|
| TT1-HIV(C2)-GP1/PN1 | LCMV | NP - SEQ ID NO: 84<br>GP - SEQ ID NO: 88 | NP - SEQ ID NO: 151<br>GP - SEQ ID NO: 153 |
| TT1-HIV(C2)-GP2/PN2 | LCMV | NP - SEQ ID NO: 85<br>GP - SEQ ID NO: 89 | NP - SEQ ID NO: 156<br>GP - SEQ ID NO: 159 |
| TT2-HIV(C2)-GP1/PN1 | PICV | NP - SEQ ID NO: 82<br>GP - SEQ ID NO: 86 | NP - SEQ ID NO: 150<br>GP - SEQ ID NO: 152 |
| TT2-HIV(C2)-GP2/PN2 | PICV | NP - SEQ ID NO: 83<br>GP - SEQ ID NO: 87 | NP - SEQ ID NO: 154<br>GP - SEQ ID NO: 157 |

Evaluation of target gene expression by detection of the conserved region for Gag (p24). We evaluated transgene expression by detection of the conserved region for Gag (p24) either by Immunoblot or Double-Immunostaining (DI). For immunoblot analysis, infected HEK293 cells were harvested and lysed, before applying whole cell lysates to acrylamide gel electrophoresis. After blotting, membranes were incubated using either a mouse mAb [39/5.4A] to detect HIV1 p24 (Abcam (ab9071)), a rabbit pAb ERK-2 (sc-154; Santa Cruz) or antibodies for detection of successful infection (rabbit pAb anti LCMV-NP (University of Genf; Prof. Doron Merkler); mouse mAb anti PICV-NP (University of Basel; Prof. Daniel Pinschewer).

Evaluation of stable transgene integration by serial passaging of viral vectors. We evaluated transgene stability of replication attenuated arenavirus vectors, by serial passaging of vector stock material in HEK293 suspension cells. To this end, P1 stock material infectious titer was determined by Focus Forming Assay, and HEK293 cells were infected using a MOI 0.001. Progeny virus was harvested 72 hours post infection and again titrated. Further passages were infected applying the same principle. After a maximum of eight passages, virus containing supernatant samples were analyzed by transgene PCR and/or DI staining. For transgene PCR analysis, RNA from virus containing supernatant was extracted and subsequently reverse transcribed and amplified by PCR using specific HIV-transgene flanking primers. PCR products were applied to Gel electrophoresis analysis to evaluate transgene PCR fragment length as an indicator of transgene stability.

Results

Evaluation of HIV Immunogen 2 transgene expression by immunoblot analysis. We verified expression of Gag/Nef/Pol antigen by immunoblot analysis of cell lysates of four (TT1-HIV(C2)-GP1/PN1) or two (TT1-HIV(C2)-GP2/PN2) replicates per replication-attenuated-LCMV vector (left panel) and one representative vector stock per replication-attenuated-PICV vector (right panel). We determined antigen expression by staining of HIV-1 Gag-Pol in passage level 1 (P1) and 4 (P4). Cells infected with TT2-HIV(C2)-GP2/PN2 showed an additional band around 30 kDa size, when stained by Gag antibody. Results are shown in FIG. 57.

Evaluation of stable integration of HIV-1 Immunogen 2 transgene by serial passaging. To evaluate whether HIV-1 Immunogen 2 transgenes are stably encoded in replication attenuated arenavirus vectors over several passages, we analyzed cell culture supernatant and performed transgene PCR analysis. The passage level at which the majority (≥50%) of the transgene specific band still shows the expected full-length size, was considered the last passage level with stable transgene insertion. Results are shown in Table 6 and FIGS. 58-61. Further, where applicable, supernatant samples harvested from each passaging step were applied to double-immunostaining (DI staining), to determine the ratio of HIV-1 Gag and replication attenuated arenavirus-NP expression. A combination of both results allowed for a more accurate assessment of transgene stability of HIV-1 Immunogen 2 transgenes.

We found that replication attenuated-LCMV HIV antigen encoding vectors to stably encoded the transgenes greater than passage level 8, while replication attenuated-PICV HIV antigen encoding vectors stably encoded the transgenes to passage levels 6 and 8.

TABLE 6

Overview Table for Assessment of Transgene Genetic Stability

| Vector Name | SEQ ID NOs: | Arenavirus | Transgene Stability Through Passage (P) |
|---|---|---|---|
| TT1-HIV(C2)-GP1/PN1 | 84 and 88 | LCMV | >P8 |
| TT1-HIV(C2)-GP2/PN2 | 85 and 89 | LCMV | >P8 |
| TT2-HIV(C2)-GP1/PN1 | 82 and 86 | PICV | P8 |
| TT2-HIV(C2)-GP2/PN2 | 83 and 87 | PICV | >P6 |

P# indicates number of passages

Replication-attenuated-LCMV HIV antigen encoding vectors stably retained the transgenes encoding the fusion polypeptides SEQ ID NOs 84 and 88 (TT1-HIV(C2)-GP1/PN1) and SEQ ID NOs: 85 and 89 (TT1-HIV(C2)-GP2/PN2) greater than passage level 8. Replication-attenuated-PICV vector TT2-HIV(C2)-GP1/PN1 stably retained transgenes encoding fusion polypeptides SEQ ID NOs: 82 and 86 up to passage level 8 and replication attenuated-PICV vector TT2-HIV(C2)-GP2/PN2 stably retained transgenes encoding fusion polypeptides SEQ ID NOs: 83 and 87 greater than passage level 6, however.

Example 13

Vaccine and Immune Modulator Combinations

In non-human primates, administration of an adenoviral vector based vaccine encoding SIV immunogens in combination with checkpoint inhibitors such as αPD1 antibody has shown an increase in durability of vaccine induced T cell responses whereas combination with αCTLA4 antibody has demonstrated an increase in magnitude of T cell responses. See, Pan, et al., *Front Immunol.* (2018) 9:2415; and Loffredo, et al., Poster P55, Society for Immunotherapy of Cancer (SITC) 32nd Annual Meeting and Pre-Conference Programs; 2017, 8-12 Nov.; National Harbor, MD). FLT3L-FLT3 interaction leads to expansion and maturation of dendritic cells. Arenavirus based vectors show dendritic cell tropism (Flatz, et al., *Nat Med* (2010) 16(3):339-45). Therefore, we postulated that combining DC expansion with arenavirus vectors would enhance immunogenicity observed with the TT2/TT1 replication-attenuated PICV/LCMV arenavirus vector prime-boost scheme.

Methods

FIG. 62 provides a schematic of immunization schedule prime-boost with arenavirus vectors (TT2/TT1) in non-human primates (NHPs) in combination with immune modulators. Indian-origin healthy rhesus macaques were immunized via intramuscular (I.M.) route with the arenavirus vectors and via intravenous (I.V.) route with immune modulators with thirteen (13) NHPs in each group. The Gag and Env expressing vectors TT2 (replication-attenuated Pichinde (PICV)) and TT1 (replication-attenuated LCMV)) were administered in the left quadricep whereas the Pol expressing vectors (TT2 and TT1) were administered in the right quadricep. The doses administered are as below: $1\times10^6$ replication competent virus particles (RCV) of TT2 Gag, Env and Poll/Pol 2 vectors, $4\times10^6$ RCV of TT1 Gag, Env, and $2\times10^6$ RCV of TT1 Poll/Pol 2.

The heterologous TT2/TT1 vaccine was administered every 4 weeks for a total of 4 doses either alone (Group 1, Vaccine) or in combination with checkpoint inhibitors (0PD1 antibody in group 2, or αCTLA4 antibody in group 3, 10 mg/kg each) administered immediately after the vaccine. The FLT3L-Fc FLT3 agonist was administered 1 week before the vaccine dose (Group 4, 0.3 mg/kg).

IFN-γ ELISpot assays were performed as described in Example 10.

Results

FIG. 63 shows the magnitude of SIV-specific IFN-γ responses as assessed by IFN-γ ELISpot in peripheral blood. Addition of αCTLA4 antibody with TT2/TT1 vaccine led to a robust and sustained increase in magnitude of SIV-specific responses compared to TT2/TT1 vaccine alone ($p<0.05$ at week 4, 6, 8, 10, 12, 14 and 16; Two-way ANOVA with Dunnett's multiple comparison test). Combination with the FLT3L-Fc FLT3 agonist also led to a significant increase in magnitude of SIV-specific response post boost ($p<0.05$ at weeks 8, 10 and 14; Two-way ANOVA with Dunnett's multiple comparison test). Administration of αPD1 antibody did not have any effect on the magnitude of vaccine-induced T cell response. Both checkpoint inhibitor αCTLA4 antibody and DC agonist FLT3L-Fc induced a significant increase in peak magnitude of T cell response consistent with the conclusion that vaccine-induced responses were augmented by these immune modulators.

With respect to breadth, FIG. 64 shows that the highest total SIV-specific breadth at 2 weeks post last vaccine dose is observed in groups that received vaccine in combination with αCTLA4 antibody or FLT3L-Fc FLT3 agonist. Administration of TT2/TT1 vaccine in combination with FLT3L-Fc FLT3 agonist resulted in a significant increase in Gag, Env and Pol-specific breadth of responses. Administration of TT2/TT1 vaccine in combination with αCTLA4 antibody resulted in a significant increase in Env and Pol-specific breadth of responses. Taken together, these results are consistent with the conclusion that combination of heterologous TT2/TT1 vaccine with αCTLA4 antibody or FLT3L-Fc FLT3 agonist leads to a significant increase in breadth of SIV-specific T cell responses.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A fusion polypeptide comprising or consisting of an amino acid sequence of any one of SEQ ID NOs: 82-89, or an amino acid sequence that is at least 90%, 91%, 92%, 93%, 94%, 95%, 96%, 97%, 98% or 99% identical to any one of SEQ ID NOs: 82-89, wherein the full-length of the fusion polypeptide comprises at least 350 amino acids and up to 385 amino acids, and wherein the fusion polypeptide is capable of inducing, promoting or stimulating an immune response in a human.

2. An immunogenic composition comprising one or more of the fusion polypeptides of claim 1, and a pharmaceutically acceptable carrier.

3. The immunogenic composition of claim 2, comprising first and second viral vectors comprising one or more polynucleotides encoding the following first fusion polypeptide and second fusion polypeptide, optionally joined or connected by one or more linkers:

a) a first polynucleotide or first viral vector comprising one or more polynucleotides encoding a first fusion polypeptide and a second fusion polypeptide comprising SEQ ID NOs: 82 and 83, or fusion polypeptides that are at least 90%, 91%, 92%, 93%, 94%, 95%, 96%, 97%, 98% or 99% identical to any one of SEQ ID NOs: 82 and 83, respectively, and b) a second polynucleotide or second viral vector comprising one or more polynucleotides encoding a first fusion polypeptide and a second fusion polypeptide comprising SEQ ID NOs: 86 and 87, or fusion polypeptides that are at least 90%, 91%, 92%, 93%, 94%, 95%, 96%, 97%, 98% or 99% identical to any one of SEQ ID NOs: 86 and 87, respectively.

4. The immunogenic composition of claim 2, comprising first and second viral vectors comprising one or more polynucleotides encoding the following first fusion polypeptide and second fusion polypeptide, optionally joined or connected by one or more linkers:

a) a first polynucleotide or first viral vector comprising one or more polynucleotides encoding a first fusion polypeptide and a second fusion polypeptide comprising SEQ ID NOs: 84 and 85, or fusion polypeptides that are at least 90%, 91%, 92%, 93%, 94%, 95%, 96%, 97%, 98% or 99% identical to any one of SEQ ID NOs: 84 and 85, respectively, and b) a second polynucleotide or second viral vector comprising one or more polynucleotides encoding a first fusion polypeptide and a second fusion polypeptide comprising SEQ ID NOs: 88 and 89, or fusion polypeptides that are at least 90%, 91%, 92%, 93%, 94%, 95%, 96%, 97%, 98% or 99% identical to any one of SEQ ID NOs: 88 and 89, respectively.

5. The immunogenic composition of claim 2, comprising first and second viral vectors comprising one or more polynucleotides encoding the following first fusion polypeptide and second fusion polypeptide, optionally joined or connected by one or more linkers:

a) a first polynucleotide or first viral vector comprising one or more polynucleotides encoding a first fusion polypeptide and a second fusion polypeptide comprising SEQ ID NOs: 82 and 86, or fusion polypeptides that are at least 90%, 91%, 92%, 93%, 94%, 95%, 96%, 97%, 98% or 99% identical to any one of SEQ ID NOs: 82 and 86, respectively, and b) a second polynucleotide or second viral vector comprising one or more polynucleotides encoding a first fusion polypeptide and a second fusion polypeptide comprising SEQ ID NOs: 83 and 87, or fusion polypeptides that are at least 90%, 91%, 92%, 93%, 94%, 95%, 96%, 97%, 98% or 99% identical to any one of SEQ ID NOs: 83 and 87, respectively.

6. The immunogenic composition of claim 2, comprising first and second viral vectors comprising one or more polynucleotides encoding the following first fusion polypeptide and second fusion polypeptide, optionally joined or connected by one or more linkers:

a) a first polynucleotide or first viral vector comprising one or more polynucleotides encoding a first fusion polypeptide and a second fusion polypeptide comprising SEQ ID NOs: 82 and 85, or fusion polypeptides that are at least 90%, 91%, 92%, 93%, 94%, 95%, 96%, 97%, 98% or 99% identical to any one of SEQ ID NOs: 82 and 85, respectively, and b) a second polynucleotide or second viral vector comprising one or more polynucleotides encoding a first fusion polypeptide and a second fusion polypeptide comprising SEQ ID NOs: 88 and 87, or fusion polypeptides that are at least 90%, 91%, 92%, 93%, 94%, 95%, 96%, 97%, 98% or 99% identical to any one of SEQ ID NOs: 88 and 87, respectively.

7. The immunogenic composition of claim 2, comprising first and second viral vectors comprising one or more polynucleotides encoding the following first fusion polypeptide and second fusion polypeptide, optionally joined or connected by one or more linkers:

a) a first polynucleotide or first viral vector comprising one or more polynucleotides encoding a first fusion polypeptide and a second fusion polypeptide comprising SEQ ID NOs: 82 and 88, or fusion polypeptides that are at least 90%, 91%, 92%, 93%, 94%, 95%, 96%, 97%, 98% or 99% identical to any one of SEQ ID NOs: 82 and 88, respectively, and b) a second polynucleotide or second viral vector comprising one or more polynucleotides encoding a first fusion polypeptide and a second fusion polypeptide comprising SEQ ID NOs: 85 and 87, or fusion polypeptides that are at least 90%, 91%, 92%, 93%, 94%, 95%, 96%, 97%, 98% or 99% identical to any one of SEQ ID NOs: 85 and 87, respectively.

8. The immunogenic composition of claim 2, comprising first and second viral vectors comprising one or more polynucleotides encoding the following first fusion polypeptide and second fusion polypeptide, optionally joined or connected by one or more linkers:

a) a first polynucleotide or first viral vector comprising one or more polynucleotides encoding a first fusion polypeptide and a second fusion polypeptide comprising SEQ ID NOs: 84 and 88, or fusion polypeptides that are at least 90%, 91%, 92%, 93%, 94%, 95%, 96%, 97%, 98% or 99% identical to any one of SEQ ID NOs: 84 and 88, respectively, and b) a second polynucleotide or second viral vector comprising one or more polynucleotides encoding a first fusion polypeptide and a second fusion polypeptide comprising SEQ ID NOs: 85 and 89, or fusion polypeptides that are at least 90%, 91%, 92%, 93%, 94%, 95%, 96%, 97%, 98% or 99% identical to any one of SEQ ID NOs: 85 and 89, respectively.

9. A kit comprising one or more unitary doses of one or more of the fusion polypeptides of claim 1.

10. A method for eliciting an immune response to human immunodeficiency virus (HIV) in a subject in need thereof, comprising administering to the subject the immunogenic composition of claim 2.

11. The fusion polypeptide of claim 1, wherein the fusion polypeptide is capable of inducing, promoting or stimulating an immune response against HIV-1 in a human.

12. The fusion polypeptide of claim 1, wherein fusion polypeptide is capable of inducing, promoting or stimulating proliferation and/or activation of one or more cell types selected from monocyte-derived dendritic cells (DCs), CD8+ T cells and CD4+ T cells.

* * * * *